(12) United States Patent
Armstrong et al.

(10) Patent No.: US 11,858,918 B2
(45) Date of Patent: Jan. 2, 2024

(54) GLP-1R MODULATING COMPOUNDS

(71) Applicant: Gilead Sciences, Inc., Foster City, CA (US)

(72) Inventors: Megan K. Armstrong, San Francisco, CA (US); James S. Cassidy, San Francisco, CA (US); Elbert Chin, San Mateo, CA (US); Chienhung Chou, Dublin, CA (US); Jeromy J. Cottell, Redwood City, CA (US); Chao-I Hung, San Mateo, CA (US); Kavoos Kolahdouzan, San Francisco, CA (US); David W. Lin, Berkeley, CA (US); Michael L. Mitchell, Castro Valley, CA (US); Ezra Roberts, San Francisco, CA (US); Scott D. Schroeder, Union City, CA (US); Nathan D. Shapiro, Belmont, CA (US); James G. Taylor, Burlingame, CA (US); Rhiannon Thomas-Tran, San Jose, CA (US); Nathan E. Wright, San Diego, CA (US); Zheng-Yu Yang, Palo Alto, CA (US)

(73) Assignee: GILEAD SCIENCES, INC., Foster City, CA (US)

( * ) Notice: Subject to any disclaimer, the term of this patent is extended or adjusted under 35 U.S.C. 154(b) by 0 days.

(21) Appl. No.: 17/724,212

(22) Filed: Apr. 19, 2022

(65) Prior Publication Data
US 2023/0102927 A1 Mar. 30, 2023

Related U.S. Application Data

(60) Provisional application No. 63/286,475, filed on Dec. 6, 2021, provisional application No. 63/177,778, filed on Apr. 21, 2021.

(51) Int. Cl.
| | |
|---|---|
| *C07D 405/14* | (2006.01) |
| *A61K 31/437* | (2006.01) |
| *A61K 31/4439* | (2006.01) |
| *A61K 31/497* | (2006.01) |
| *A61K 31/506* | (2006.01) |
| *A61K 31/5377* | (2006.01) |
| *A61K 31/675* | (2006.01) |
| *C07D 401/08* | (2006.01) |
| *C07D 401/10* | (2006.01) |
| *C07D 401/14* | (2006.01) |
| *C07D 409/14* | (2006.01) |
| *C07D 417/14* | (2006.01) |
| *C07D 471/04* | (2006.01) |
| *C07D 491/048* | (2006.01) |
| *C07D 493/08* | (2006.01) |
| *C07D 493/10* | (2006.01) |
| *C07F 9/6558* | (2006.01) |

(52) U.S. Cl.
CPC .......... *C07D 405/14* (2013.01); *A61K 31/437* (2013.01); *A61K 31/4439* (2013.01); *A61K 31/497* (2013.01); *A61K 31/506* (2013.01); *A61K 31/5377* (2013.01); *A61K 31/675* (2013.01); *C07D 401/08* (2013.01); *C07D 401/10* (2013.01); *C07D 401/14* (2013.01); *C07D 409/14* (2013.01); *C07D 417/14* (2013.01); *C07D 471/04* (2013.01); *C07D 491/048* (2013.01); *C07D 493/08* (2013.01); *C07D 493/10* (2013.01); *C07F 9/65586* (2013.01)

(58) Field of Classification Search
CPC .......................... C07D 405/14; C07D 401/10; C07D 491/048; A61K 31/437
See application file for complete search history.

(56) References Cited

U.S. PATENT DOCUMENTS

| | | | |
|---|---|---|---|
| 10,543,212 | B2 | 1/2020 | Matsunaga et al. |
| 10,954,221 | B2 | 3/2021 | Zhong et al. |
| 11,702,404 | B2 | 7/2023 | Ammann |
| 2017/0035881 | A1 | 2/2017 | Lannutti et al. |
| 2018/0170908 | A1 | 6/2018 | Aspnes et al. |
| 2020/0325121 | A1 | 10/2020 | Zhong et al. |
| 2021/0023072 | A1 | 1/2021 | Freeman et al. |
| 2021/0171499 | A1 | 6/2021 | Ammann et al. |
| 2022/0177449 | A1 | 6/2022 | Brizgys et al. |
| 2022/0288030 | A1 | 9/2022 | Ammann et al. |
| 2022/0298148 | A1 | 9/2022 | Brizgys et al. |
| 2022/0306614 | A1 | 9/2022 | Brizgys et al. |
| 2023/0021705 | A1 | 1/2023 | Armstrong et al. |

FOREIGN PATENT DOCUMENTS

| | | |
|---|---|---|
| CN | 112409331 A | 2/2021 |
| CN | 113480534 A | 10/2021 |
| CN | 113493447 A | 10/2021 |
| CN | 113816948 A | 12/2021 |
| EP | 3438095 A1 | 2/2019 |

(Continued)

OTHER PUBLICATIONS

Andersen, A et al. (2018), "Glucagon-like peptide 1 in health and disease", Nat Rev Endocrinol., Jul. 14(7):390-403.

(Continued)

*Primary Examiner* — Brandon J Fetterolf
*Assistant Examiner* — Frank S. Hou
(74) *Attorney, Agent, or Firm* — Mintz, Levin, Cohn, Ferris, Glovsky and Popeo, P.C.

(57) ABSTRACT

The present disclosure provides GLP-1R agonists, and compositions, methods, and kits thereof. Such compounds are generally useful for treating a GLP-1R mediated disease or condition in a human.

18 Claims, 1 Drawing Sheet

(56) References Cited

FOREIGN PATENT DOCUMENTS

| | | |
|---|---|---|
| EP | 4057055 A1 | 9/2022 |
| WO | WO-2000/08015 A2 | 2/2000 |
| WO | WO-2003/026587 A2 | 4/2003 |
| WO | WO-2004/099192 A2 | 11/2004 |
| WO | WO-2005/014543 A1 | 2/2005 |
| WO | WO-2006/055708 A2 | 5/2006 |
| WO | WO-2006/066879 A2 | 6/2006 |
| WO | WO-2007/031791 A1 | 3/2007 |
| WO | WO-2007/115077 A2 | 10/2007 |
| WO | WO-2008/033455 A2 | 3/2008 |
| WO | WO-2010/029299 A1 | 3/2010 |
| WO | WO-2010/029300 A1 | 3/2010 |
| WO | WO-2010/046780 A2 | 4/2010 |
| WO | WO-2011/163355 A1 | 12/2011 |
| WO | WO-2013/025733 A1 | 2/2013 |
| WO | WO-2013/056679 A1 | 4/2013 |
| WO | WO-2013/186229 A1 | 12/2013 |
| WO | WO-2016/018701 A1 | 2/2016 |
| WO | WO-2016/089060 A2 | 6/2016 |
| WO | WO-2016/118638 A1 | 7/2016 |
| WO | WO-2017/161028 A1 | 9/2017 |
| WO | WO-2018/109607 A1 | 6/2018 |
| WO | WO-2018/183112 A1 | 10/2018 |
| WO | WO-2019/055540 A1 | 3/2019 |
| WO | WO-2019/239319 A1 | 12/2019 |
| WO | WO-2019/239371 A1 | 12/2019 |
| WO | WO-2020/033413 A2 | 2/2020 |
| WO | WO-2020/103815 A1 | 5/2020 |
| WO | WO-2020/207474 A1 | 10/2020 |
| WO | WO-2020/263695 A1 | 12/2020 |
| WO | WO-2021/018023 A1 | 2/2021 |
| WO | WO-2021/018026 A1 | 2/2021 |
| WO | WO-2021/081207 A1 | 4/2021 |
| WO | WO-2021/096284 A1 | 5/2021 |
| WO | WO-2021/096304 A1 | 5/2021 |
| WO | WO-2021/112538 A1 | 6/2021 |
| WO | WO-2021/154796 A1 | 8/2021 |
| WO | WO-2021/155841 A1 | 8/2021 |
| WO | WO-2021/160127 A1 | 8/2021 |
| WO | WO-2021/187886 A1 | 9/2021 |
| WO | WO-2021/191812 A1 | 9/2021 |
| WO | WO-2021/197464 A1 | 10/2021 |
| WO | WO-2021/242817 A1 | 12/2021 |
| WO | WO-2021/244645 A1 | 12/2021 |
| WO | WO-2022/040600 A1 | 2/2022 |
| WO | WO-2022/068772 A1 | 4/2022 |
| WO | WO-2022/078152 A1 | 4/2022 |
| WO | WO-2022/109182 A1 | 5/2022 |
| WO | WO-2022/111624 A1 | 6/2022 |
| WO | WO-2022/192428 A1 | 9/2022 |
| WO | WO-2022/192430 A1 | 9/2022 |
| WO | WO-2022/225914 A1 | 10/2022 |

OTHER PUBLICATIONS

Armstrong M J et al. (2016), "Liraglutide safety and efficacy in patients with non-alcoholic steatohepatitis (LEAN): a multicentre, double-blind, randomised, placebo-controlled phase 2 study", Lancet, 387(10019): 679-690.

Armstrong, M et al. (2013), "Liraglutide efficacy and action in non-alcoholic steatohepatitis (LEAN): study protocol for a phase II multicentre, double-blinded, randomised, controlled trial", BMJ Open., 3(11):e003995, pp. 1-13.

Armstrong, M J et al. (2016), "Glucagon-like peptide 1 decreases lipotoxicity in non-alcoholic steatohepatitis", Randomized Controlled Trial J Hepatol., 64(2):399-408.

Armstrong, M. J. (2017), "Glucagon-like peptide-1 analogues in nonalcoholic steatohepatitis: From bench to bedside", Review Clin Liver Dis (Hoboken), 10(2):32-35.

Ben-Shlomo, S et al. (2011), "Glucagon-like peptide-1 reduces hepatic lipogenesis via activation of AMP-activated protein kinase", J Hepatol. 54(6):1214-23.

Bernsmeier, C et al. (2014), "Glucose-Induced Glucagon-Like Peptide 1 Secretion Is Deficient in Patients with Non-Alcoholic Fatty Liver Disease", PLoS One, 9(1):e87488, 1-7.

Bueno, A B et al. (2016), "Positive Allosteric Modulation of the Glucagon-like Peptide-1 Receptor by Diverse Electrophiles", J Biol Chem, May 13, 2016; 291(20):10700-15.

Carbone L J et al. (2016), "Incretin-based therapies for the treatment of non-alcoholic fatty liver disease: A systemic review and meta-analysis", J Gastroenterol Hepatol, 31(1):23-31.

Chen D et al. (2007), "A nonpeptidic agonist of glucagon-like peptide 1 receptors with efficacy in diabetic db/db mice", Proc Natl Acad Sci USA, 104(3):943-948.

Chen, J et al. (2017), "GLP-1/GLP-1R Signaling in Regulation of Adipocyte Differentiation and Lipogenesis", Cell Physiol Biochem, 42(3):1165-1176.

Dalsgaard N B et al. (2018), "Effects of glucagon-like peptide-1 receptor agonists on cardiovascular risk factors: A narrative review of head-to-head comparisons", Diabetes Obes Metab, 20(3):508-519.

Davies, M et al. (2017), "Effect of Oral Semaglutide Compared With Placebo and Subcutaneous Semaglutide on Glycemic Control in Patients With Type 2 Diabetes: A Randomized Clinical Trial", JAMA, 318(15):1460-1470.

De Graaf C et al. (2016), "Glucagon-Like Peptide-1 and Its Class B G Protein-Coupled Receptors: A Long March to Therapeutic Successes", Pharmacol Rev., 68(4):954-1013.

Donnelly K L et al. (2005), "Sources of fatty acids stored in liver and secreted via lipoproteins in patients with nonalcoholic fatty liver disease", J Clin Invest, 115(5):1343-1351.

Edmonds, D J et al. (2013), "Oral GLP-1 Modulators for the Treatment of Diabetes", Annual Reports in Medicinal Chemistry, Chapter Nine, 48:119-130.

Eguchi Y et al. (2015), "Pilot study of liraglutide effects in non-alcoholic steatohepatitis and non-alcoholic fatty liver disease with glucose intolerance in Japanese patients (LEAN-J)", Hepatol Res, 45(3):269-278.

Gastaldelli A et al. (2016), "Exenatide improves both hepatic and adipose tissue insulin resistance: A dynamic positron emission tomography study", Hepatology, 64(6):2028-2037.

Jazayeri A et al. (2017), "Crystal structure of the GLP-1 receptor bound to a peptide agonist", Nature, 546(7657):254-258.

Jones, B et al. (2018), "Targeting GLP-1 receptor trafficking to improve agonist efficacy", Nature Communications, 9:1602, pp. 1-17.

Knudsen, L B et al. (2007), "Small-molecule agonists for the glucagon-like peptide 1 receptor", Proc Natl Acad Sci USA, 104(3):937-942.

Koole C et al. (2013), "Recent advances in understanding GLP-1R (glucagon-like peptide-1 receptor) function", Biochem Soc Trans, 41(1):172-179.

Ma H et al. (2020), "Structural insights into the activation of GLP-1R by a small molecule agonist", Cell Res 30, 1140-1142.

Mendez M et al. (2019), "Design, Synthesis and Pharmacological Evaluation of Potent Positive Allosteric Modulators of the Glucagon-like Peptide-1 Receptor (GLP-1R)", J. Med. Chem., Just Accepted Manuscript, Publication Date (Web): Oct. 9, 2019.

Nauck, M A et al. (2011), "Rapid tachyphylaxis of the glucagon-like peptide 1-induced deceleration of gastric emptying in humans", Diabetes, 60(5):1561-1565.

Nauck, M A et al. (2016), "A Phase 2, Randomized, Dose-Finding Study of the Novel Once-Weekly Human GLP-1 Analog, Semaglutide, Compared With Placebo and Open-Label Liraglutide in Patients With Type 2 Diabetes", Diabetes Care, 39(2):231-241.

Petit, J-M et al. (2017), "GLP-1 receptor agonists in NAFLD", Diabetes Metab., 43 Suppl 1:2S28-2S33.

Plisson F et al. (2017), "Helixconstraints and amino acid substitution in GLP-1 increase cAMP and insulin secretion but not beta-arrestin 2 signaling", Eur J Med Chem, 127:703-714.

Portillo-Sanchez P et al. (2016), "Treatment of Nonalcoholic Fatty Liver Disease (NAFLD) in patients with Type 2 Diabetes Mellitus", Clin Diabetes Endocrinol, 2:9.

(56) References Cited

OTHER PUBLICATIONS

Sloop K W et al. (2010), "Novel small molecule glucagon-like peptide-1 receptor agonist stimulates insulin secretion in rodents and from human islets", Diabetes, 59(12):3099-3107.
Song G et al. (2017), "Human GLP-1 receptor transmembrane domain structure in complex with allosteric modulators", Nature, 546(7657):312-315.
Svegliati-Baroni G et al. (2011), "Glucagon-like peptide-1 receptor activation stimulates hepatic lipid oxidation and restores hepatic signalling alteration induced by a high-fat diet in nonalcoholic steatohepatitis", Liver Int., 31(9):1285-1297.
Takayanagi R et al. (2018), "Evaluation of Drug Efficacy of GLP-1 Receptor Agonists and DPP-4 Inhibitors Based on Target Molecular Binding Occupancy", Biol Pharm Bull, 41(2):153-157.
Tong W et al. (2016), "Liraglutide ameliorates non-alcoholic fatty liver disease by enhancing mitochondrial architecture and promoting autophagy through the SIRT1/SIRT3-FOXO3a pathway", Hepatol Res., 46(9):933-943.
Umapathysivam M M et al. (2014), "Comparative effects of prolonged and intermittent stimulation of the glucagon-like peptide 1 receptor on gastric emptying and glycemia", Diabetes, 63(2):785-790.
Vendrell J et al. (2011), "Study of the potential association of adipose tissue GLP-1 receptor with obesity and insulin resistance", Endocrinology, 152(11):4072-4079.
Vilar-Gomez E et al. (2015), "Weight Loss Through Lifestyle Modification Significantly Reduces Features of Nonalcoholic Steatohepatitis", Gastroenterology, 149(2):367-378.e5.
Villanueva-Penacarrillo M L et al. (2001), "Effect of GLP-1 on lipid metabolism in human adipocytes", Horm Metab Res, 33(2):73-77.
VTv Therapeutics (2016), "Oral Small Molecule GLP-1 Receptor (GLP-1R) Agonists for Type 2 Diabetes (T2DM) with Negligible Nausea and Vomiting", Presentation from Keystone Symposia 2016.
Wang X-C et al. (2014), "Effects of glucagon-like peptide-1 receptor agonists on non-alcoholic fatty liver disease and inflammation", World J Gastroenterol, 20(40):14821-14830.
Wootten D et al. (2013), "Differential activation and modulation of the glucagon-like peptide-1 receptor by small molecule ligands", Mol Pharmacol, 83(4):822-834.
Wootten D et al. (2016), "A Hydrogen-Bonded Polar Network in the Core of the Glucagon-Like Peptide-1 Receptor Is a Fulcrum for Biased Agonism: Lessons from Class B Crystal Structures", Mol Pharmacol, 89(3):335-347.
Yang D et al. (2015), "Landmark studies on the glucagon subfamily of GPCRs: from small molecule modulators to a crystal structure", Acta Pharmacol Sin, 36(9):1033-42.
Intl. Search Report-Written Opinion dated Jul. 20, 2022 for Intl. Appl. No. PCT/US2022/025364.
TW Office Action dated May 23, 2023 for Application No. 111114936.

GLP-1R MODULATING COMPOUNDS

CROSS REFERENCE TO RELATED APPLICATIONS

This application claims priority to U.S. Provisional Application No. 63/177,778, filed Apr. 21, 2021, and U.S. Provisional Application No. 63/286,475, filed Dec. 6, 2021, which are incorporated herein in their entireties for all purposes.

FIELD

The present disclosure relates to compounds that bind to and act as agonists or modulators of the glucagon-like peptide-1 receptor (GLP-1R) and act as agonists or modulators of GLP-1R. The disclosure further relates to the use of the compounds for the treatment and/or prevention of diseases and/or conditions by said compounds.

BACKGROUND

Glucagon-like peptide-1 (GLP-1) is a peptide hormone that is secreted from the enteroendocrine cells in the gut in response to a meal. GLP-1 is believed to play a role in regulation of post-prandial glycemia, via directly augmenting meal-induced insulin secretion from the pancreatic beta-cells, as well as in promoting satiety by delaying the transit of food through the gut. GLP-1 mediates intracellular signaling via the GLP-1 receptor (GLP-1R) which belongs to a family of G-protein coupled receptors that are present on the cell membrane and can result in accumulation of the secondary messenger cyclic adenosine monophosphate (cAMP) upon activation. Non-alcoholic steatohepatitis (NASH) can be associated with features of metabolic syndrome, including obesity, type 2 diabetes, insulin resistance and cardiovascular disease.

GLP-1R agonists are currently being investigated in connection with diabetes, obesity, and NASH. GLP-1R agonists include peptides, such as exenatide, liraglutide, and dulaglutide, that have been approved for the management of type 2 diabetes. Such peptides are predominantly administered by subcutaneous injection. Oral GLP-1 agonists are also under investigation for treatment of type 2 diabetes. Some GLP-1R agonists, such as liraglutide, dulaglutide, and exenatide, are resistant to rapid degradation by dipeptidyl peptidase 4, resulting in longer half-lives than endogenous GLP-1.

There remains a need for compounds, such as agonists of GLP-1R, with desirable therapeutic properties, metabolic properties, and/or easy administration in the treatment of metabolic diseases and related diseases, including but not limited to NASH, obesity, and Type 2 diabetes.

SUMMARY

In one embodiment, the present disclosure provides a compound of Formula (I):

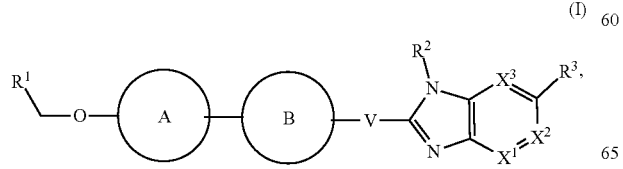

(I)

or a pharmaceutically acceptable salt thereof, wherein
$R^1$ is
i) $C_{6-10}$ aryl or 6-membered heteroaryl, each of which is optionally substituted with one to four $R^4$; or
ii) 6-membered heteroaryl, wherein the heteroaryl is fused to a 5- or 6-membered ring having zero to three heteroatoms, each independently N, O, or S, to form a fused ring system, wherein the fused ring system is optionally substituted with one to four $R^5$;
ring A is

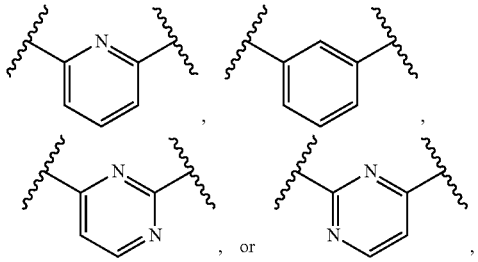

, or which are each optionally substituted with one to three $R^A$, each $R^A$ independently $C_{1-6}$ alkyl, $C_{1-6}$ haloalkyl, $C_{1-6}$ alkoxy, $C_{1-6}$ haloalkoxy, halogen, —OH, —CN, or —N($R^{10a}$)($R^{10b}$);
ring B is
(i) $C_{6-10}$ aryl or heteroaryl, which is each optionally substituted with one to four $R^B$, each $R^B$ independently $C_{1-9}$ alkyl, $C_{1-8}$ haloalkyl, $C_{1-6}$ haloalkoxy, $C_{2-6}$ alkoxyalkyl, $C_{2-6}$ alkenyl, $C_{2-6}$ alkynyl, halogen, $C_{3-10}$ cycloalkyl, heterocyclyl, $C_{6-10}$ aryl, heteroaryl, oxo, —$NO_2$, —CN, —$N_3$, —O—$R^{10a}$, —C(O)$R^{10a}$, —C(O)O—$R^{10a}$, —N($R^{10a}$)($R^{10b}$), N($R^{10a}$)$_2$($R^{10b}$)$^+$, —N($R^{10a}$)C(O)—$R^{10b}$, —N($R^{10a}$)C(O)O— $R^{10b}$, —N($R^{10a}$)C(O)N($R^{10b}$)($R^{10c}$), —N($R^{10a}$)S(O)$_2$($R^{10b}$), —N$R^{10a}$S(O)$_2$N($R^{10b}$)($R^{10c}$), —N$R^{10a}$S(O)$_2$O($R^{10b}$), —OC(O)$R^{10a}$, —OC(O)O $R^{10a}$, —OC(O)—N($R^{10a}$)($R^{10b}$), —S—$R^{10a}$, —S(O) $R^{10a}$, —S(O)(NH) $R^{10a}$, —S(O)$_2$$R^{10a}$, —S(O)$_2$N($R^{10a}$)($R^{10b}$), —S(O)(N$R^{10a}$) $R^{10b}$, or —Si($R^{10a}$)$_3$; or
(ii) $C_{6-10}$ aryl or heteroaryl, which is each fused to a 5 or 6 membered ring having zero to four heteroatoms, each independently N, O, or S, to form a fused ring system, wherein the fused ring system is optionally substituted with one to five $R^B$, each $R^B$ independently $C_{1-9}$ alkyl, $C_{1-8}$ haloalkyl, $C_{1-6}$ haloalkoxy, $C_{2-6}$ alkoxyalkyl, $C_{2-6}$ alkenyl, $C_{2-6}$ alkynyl, halogen, $C_{3-10}$ cycloalkyl, heterocyclyl, $C_{6-10}$ aryl, heteroaryl, oxo, —$NO_2$, —CN, —$N_3$, —O—$R^{10a}$, —C(O)$R^{10a}$, —C(O)O—$R^{10a}$, —N($R^{10a}$)($R^{10b}$), N($R^{10a}$)$_2$($R^{10b}$)$^+$, —N($R^{10a}$)C(O)—$R^{10b}$, —N($R^{10a}$) C(O)N($R^{10b}$)($R^{10c}$), —N($R^{10a}$)S(O)$_2$($R^{10b}$), —N$R^{10a}$S(O)$_2$N($R^{10b}$)($R^{10c}$), —N$R^{10a}$S(O)$_2$O ($R^{10b}$), —OC(O)$R^{10a}$, —OC(O)O $R^{10a}$, —OC(O)— N($R^{10a}$)($R^{10b}$), —S—$R^{10a}$, —S(O)$R^{10a}$, —S(O) (NH)$R^{10a}$, —S(O)$_2$$R^{10a}$, —S(O)$_2$N($R^{10a}$)($R^{10b}$), —S(O)(N$R^{10a}$) $R^{10b}$, or —Si($R^{10a}$)$_3$,
V is —C($R^{11a}$)($R^{11b}$)—;
$X^1$, $X^2$, and $X^3$ are each independently —C(H)=, or —C($R^8$)=;
$R^2$ is
i) $C_{3-10}$ cycloalkyl or heterocyclyl, wherein the cycloalkyl or heterocyclyl is each optionally substituted with one to four Z¹, wherein each Z¹ is independently $C_{1-6}$ alkyl, $C_{1-6}$ alkoxy, $C_{1-6}$ hydroxyalkyl, $C_{2-6}$ alkoxyalkyl, halogen, $C_{1-6}$ haloalkyl, $C_{1-6}$ haloalkoxy, oxo, —OH, —CN, $C_{1-6}$ alkyl-CN, —C(O)R$^{10a}$, —C(O)O—R$^{10a}$, —C(O)NH$_2$, —C(O)NH($C_{1-9}$ alkyl), —N(R$^{10a}$)(R$^{10b}$), —N(R$^{10a}$)C(O)O— R$^{10b}$, —N(R$^{10a}$)C(O)—R$^{10b}$, —S(O)$_2$R$^{10a}$, —S(O)$_2$($C_{1-9}$ alkyl), —O—$C_{3-6}$ cycloalkyl or heteroaryl,
wherein each —O—$C_{3-6}$ cycloalkyl or heteroaryl is optionally substituted with one to four $Z^{1a}$ groups, each $Z^{1a}$ independently $C_{1-6}$ alkyl, $C_{1-6}$ alkoxy, halogen, $C_{1-6}$ haloalkyl, or $C_{1-6}$ haloalkoxy; or

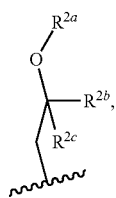

(ii)

wherein
$R^{2a}$ is $C_{1-6}$ alkyl, $C_{1-6}$ hydroxyalkyl, $C_{2-6}$ alkoxyalkyl, $C_{1-6}$ haloalkyl, $C_{1-6}$ alkyl-CN, —$C_{3-6}$ cycloalkyl or heteroaryl,
wherein each alkyl, cycloalkyl, or heteroaryl is optionally substituted with one to four groups each independently $C_{1-6}$ alkyl, $C_{1-6}$ alkoxy, halogen, $C_{1-6}$ haloalkyl, or $C_{1-6}$ haloalkoxy;
$R^{2b}$ is H, $C_{1-3}$ alkyl, $C_{1-3}$ haloalkyl; and
$R^{2c}$ is H, $C_{1-3}$ alkyl, $C_{1-3}$ haloalkyl;
$R^3$ is —C(O)OR$^{3a}$;
wherein R$^{3a}$ is H, $C_{1-4}$ alkyl-N(R$^{9a}$)(R$^{9b}$), —$C_{1-4}$ alkyl-N(R$^{9a}$)C(O)—O—$C_{1-4}$ alkyl-OP(O)(OR$^{9c}$)$_2$, $C_{1-4}$ alkyl-C(O)N(R$^{9a}$)(R$^{9b}$), —$C_{1-4}$ alkyl-O—C(O)—$C_{1-4}$ alkyl, —$C_{1-4}$ alkyl-O—C(O)—O—$C_{1-4}$ alkyl, —$C_{1-4}$ alkyl-O—C(O)—$C_{1-4}$ alkyl-N(R$^{9a}$)(R$^{9b}$), —$C_{1-4}$ alkyl-O—C(O)—$C_{1-4}$ alkyl-OP(O)(OR$^{9c}$)$_2$, —CH$_2$CH(N(R$^{9a}$)$_2$)C(O)OR$^{9b}$, —P(O)(OR$^{9c}$)$_2$, —OP(O)(OR$^{9c}$)$_2$, —CH$_2$P(O)(OR$^{9c}$)$_2$, —CH$_2$OP(O)(OR$^{9c}$)$_2$, —OCH$_2$P(O)(OR$^{9c}$)$_2$, C(O)OCH$_2$P(O)(OR$^{9c}$)$_2$, —P(O)(R$^{9c}$)(OR$^{9d}$), —OP(O)(R$^{9c}$)(OR$^{9d}$), —CH$_2$P(O)(R$^{9c}$)(OR$^{9d}$), —OCH$_2$P(O)(R$^{9c}$)(OR$^{9d}$), —C(O)OCH$_2$P(O)(R$^{9c}$)(OR$^{9d}$), —P(O)(N(R$^{9c}$)$_2$)$_2$, —OP(O)(N(R$^{9c}$)$_2$)$_2$, —CH$_2$P(O)(N(R$^{9c}$)$_2$)$_2$, —OCH$_2$P(O)(N(R$^{9c}$)$_2$)$_2$, —C(O)OCH$_2$P(O)(N(R$^{9c}$)$_2$)$_2$, —P(O)(N(R$^{9c}$)$_2$)(OR$^{9d}$), —OP(O)(N(R$^{9c}$)$_2$)(OR$^{9d}$), —CH$_2$P(O)(N(R$^{9c}$)$_2$)(OR$^{9d}$), —OCH$_2$P(O)(N(R$^{9c}$)$_2$)(OR$^{9d}$), —C(O)OCH$_2$P(O)(N(R$^{9c}$)$_2$)(OR$^{9d}$), —P(O)(R$^{9c}$)(N(R$^{9d}$)$_2$), —OP(O)(R$^{9c}$)(N(R$^{9d}$)$_2$), —CH$_2$P(O)(R$^{9c}$)(N(R$^{9d}$)$_2$), —OCH$_2$P(O)(R$^{9c}$)(N(R$^{9d}$)$_2$), —C(O)OCH$_2$P(O)(R$^{9c}$)(N(R$^{9d}$)$_2$), or $C_{1-6}$ alkyl-heterocyclyl,
wherein each alkyl or heterocyclyl is optionally substituted with one to four halogens;
each $R^4$ is independently $C_{1-6}$ alkyl, $C_{1-8}$ haloalkyl, $C_{1-6}$ haloalkoxy, $C_{2-6}$ alkoxyalkyl, $C_{2-6}$ alkenyl, halogen, $C_{3-10}$ cycloalkyl, heterocyclyl, $C_{6-10}$ aryl, heteroaryl, oxo, —NO$_2$, —CN, —N$_3$, —O—R$^{10a}$, —C(O)R$^{10a}$, —C(O)O—R$^{10a}$, —N(R$^{10a}$)(R$^{10b}$), —N(R$^{10a}$)$_2$(R$^{10b}$)$^+$, —N(R$^{10a}$)—C(O)R$^{10b}$, —N(R$^{10a}$)C(O)O(R$^{10b}$), —N(R$^{10a}$)C(O)N(R$^{10b}$)(R$^{10c}$), — N(R$^{10a}$)S(O)$_2$(R$^{10b}$), —N(R$^{10a}$)S(O)$_2$— N(R$^{10b}$)(R$^{10c}$), —N(R$^{10a}$)S(O)$_2$O(R$^{10b}$), —OC(O)R$^{10a}$, —OC(O)OR$^{10a}$, —OC(O)—N(R$^{10a}$)(R$^{10b}$), —S—R$^{10a}$, —S(O)R$^{10a}$, —S(O)(NH)R$^{10a}$, —S(O)$_2$R$^{10a}$, —S(O)$_2$N(R$^{10a}$)(R$^{10b}$), —S(O)(NR$^{10a}$)R$^{10b}$, or —Si(R$^{10a}$)$_3$,
wherein each alkyl, haloalkyl, alkenyl or aryl is optionally substituted with one to four $R^5$, and
wherein each cycloalkyl, heterocyclyl or heteroaryl is optionally substituted with one to four $R^{12}$;
each $R^5$ is independently $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —NO$_2$, —N$_3$, —CN, —O—R$^{10a}$, —C(O)—R$^{10a}$, —C(O)O—R$^{10a}$, C(O)—N(R$^{10a}$)(R$^{10b}$), —N(R$^{10a}$)(R$^{10b}$), —N(R$^{10a}$)$_2$(R$^{10b}$)$^+$, —N(RR$^{10a}$)C(O)—R$^{10b}$, —N(R$^{10a}$)C(O)O— R$^{10b}$, —N(R$^{10a}$)C(O)N(R$^{10b}$)(R$^{10c}$), —N(R$^{10a}$)S(O)$_2$(R$^{10}$), —NR$^{10a}$S(O)$_2$N(R$^{10b}$)(R$^{10c}$), —NR$^{10a}$S(O)$_2$O(R$^{10b}$), —OC(O) R$^{10a}$, —OC(O)O R$^{10a}$, —OC(O)—N(R$^{10a}$)(R$^{10b}$), —S—R$^{10a}$, —S(O)R$^{10a}$, —S(O)(NH) R$^{10a}$, —S(O)$_2$R$^{10a}$, —S(O)$_2$N(R$^{10a}$)(R$^{10b}$), —S(O)(NR$^{10a}$)R$^{10b}$, or —Si(R$^{10a}$)$_3$,
wherein each alkyl, haloalkyl, alkenyl, alkynyl, cycloalkyl, heterocyclyl, aryl, or heteroaryl is optionally substituted with one to four $R^6$;
each $R^6$ is independently $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, $C_{3-15}$ cycloalkyl, halogen, $C_{3-15}$ cycloalkyl, heterocyclyl, $C_{6-10}$ aryl, heteroaryl, oxo, —NO$_2$, —N$_3$, —CN, —O— R", —C(O)— R", —C(O)O—R$^{10a}$a, —C(O)—N(R$^{10a}$)(R$^{10b}$), —N(R$^{10a}$)(R$^{10b}$), —N(R$^{10a}$)C(O)—R$^{10b}$, —N(R$^{10a}$)C(O)O— R$^{10b}$, —N(R$^{10a}$)C(O)N(R$^{10b}$)(R$^{10c}$), —N(R$^{10a}$)S(O)$_2$(R$^{10b}$), —NR$^{10a}$S(O)$_2$N(R$^{10b}$)(R$^{10c}$), —NR$^{10a}$S(O)$_2$O(R$^{10b}$), —OC(O)R$^{10a}$, OC(O)O R$^{10a}$, —OC(O)—N(R$^{10a}$)(R$^{10b}$), —S(O)(NR$^{10a}$), —S(O) R$^{10a}$, —S(O)(NH)R$^{10a}$, —S(O)$_2$R$^{10a}$, —S(O)$_2$N(R$^{10a}$)(R$^{10b}$), —S(O)(NR$^{10a}$)R$^{10b}$, or —Si(R$^{10a}$)$_3$,
wherein each alkyl, haloalkyl, alkenyl, alkynyl, cycloalkyl, heterocyclyl, aryl, or heteroaryl is optionally substituted with one to four $R^7$;
each $R^7$ and $R^8$ is independently $C_{1-9}$ alkyl, $C_{1-6}$ alkoxy, $C_{2-6}$ alkoxyalkyl, $C_{1-8}$ haloalkyl, $C_{2-6}$ alkenyl, $C_{2-6}$ alkynyl, halogen, $C_{3-15}$ cycloalkyl, heterocyclyl, $C_{6-11}$) aryl, heteroaryl, oxo, —OH, —CN, —NO$_2$, —NH$_2$, —N$_3$, —SH, —O($C_{1-9}$ alkyl), —O($C_{1-8}$ haloalkyl), —O($C_{2-6}$ alkenyl), —O($C_{2-6}$ alkynyl), —O($C_{3-15}$ cycloalkyl), —O(heterocyclyl), —O($C_{6-10}$ aryl), —O(heteroaryl), —NH($C_{1-9}$ alkyl), —NH($C_{1-8}$ haloalkyl), —NH($C_{2-6}$ alkenyl), —NH($C_{2-6}$ alkynyl), —NH($C_{3-15}$ cycloalkyl), —NH(heterocyclyl), —NH($C_{6-10}$ aryl), —NH(heteroaryl), —N($C_{1-9}$ alkyl)$_2$, —N($C_{1-8}$ haloalkyl)$_2$, —N($C_{2-6}$ alkenyl)$_2$, —N($C_{2-6}$ alkynyl)$_2$, —N($C_{3-15}$ cycloalkyl)$_2$, —N(heterocyclyl)$_2$, —N($C_{6-10}$ aryl)$_2$, —N(heteroaryl)$_2$, —N($C_{1-9}$ alkyl)($C_{1-8}$ haloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)(heterocyclyl), —N($C_{1-9}$ alkyl)($C_{6-10}$ aryl), —N($C_{1-9}$ alkyl)(heteroaryl), —C(O)($C_{1-9}$ alkyl), —C(O)($C_{1-8}$ haloalkyl), —C(O)($C_{2-6}$ alkenyl), —C(O)($C_{2-6}$ alkynyl), —C(O)($C_{3-15}$ cycloalkyl), —C(O)(heterocyclyl), —C(O)($C_{6-10}$ aryl), —C(O)(heteroaryl), —C(O)O($C_{1-9}$ alkyl), —C(O)O($C_{1-8}$ haloalkyl), —C(O)O($C_{2-6}$ alkenyl), —C(O)O($C_{2-6}$ alkynyl), —C(O)O($C_{3-15}$ cycloalkyl), —C(O)O(heterocyclyl), —C(O)O($C_{6-10}$ aryl), —C(O)O(heteroaryl), —C(O)NH$_2$, —C(O)NH($C_{1-9}$ alkyl), —C(O)NH($C_{1-8}$ haloalkyl), —C(O)NH($C_{2-6}$ alkenyl), —C(O)NH($C_{2-6}$ alkynyl), —C(O)NH($C_{3-15}$ cycloalkyl), —C(O)NH (heterocyclyl), —C(O)NH($C_{6-10}$ aryl), —C(O)NH (heteroaryl), —C(O)N($C_{1-9}$ alkyl)$_2$, —C(O)N($C_{1-8}$ haloalkyl)$_2$, —C(O)N($C_{2-6}$ alkenyl)$_2$, —C(O)N($C_{2-6}$ alkynyl)$_2$, —C(O)N($C_{3-15}$ cycloalkyl)$_2$, —C(O)N(heterocyclyl)$_2$, —C(O)N($C_{6-10}$ aryl)$_2$, —C(O)N(heteroaryl)$_2$, —NHC(O)($C_{1-9}$ alkyl), —NHC(O)($C_{1-8}$ haloalkyl), —NHC(O)($C_{2-6}$ alkenyl), —NHC(O)($C_{2-6}$ alkynyl), —NHC(O)($C_{3-15}$ cycloalkyl), —NHC(O) (heterocyclyl), —NHC(O)($C_{6-10}$ aryl), —NHC(O)(heteroaryl), —NHC(O)O($C_{1-9}$ alkyl), —NHC(O)O($C_{1-8}$ haloalkyl), —NHC(O)O($C_{2-6}$ alkenyl), —NHC(O)O ($C_{2-6}$ alkynyl), —NHC(O)O($C_{3-15}$ cycloalkyl), —NHC(O)O(heterocyclyl), —NHC(O)O($C_{6-10}$ aryl), —NHC(O)O(heteroaryl), —NHC(O)NH($C_{1-9}$ alkyl), —NHC(O)NH($C_{1-8}$ haloalkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH(heterocyclyl), —NHC(O)NH($C_{6-10}$ aryl), —NHC(O)NH(heteroaryl), —NHS(O) ($C_{1-9}$ alkyl), —N($C_{1-9}$ alkyl)(S(O)($C_{1-9}$ alkyl), —S($C_{1-9}$ alkyl), —S($C_{1-8}$ haloalkyl), —S($C_{2-6}$ alkenyl), —S($C_{2-6}$ alkynyl), —S($C_{3-15}$ cycloalkyl), —S(heterocyclyl), —S($C_{6-10}$ aryl), —S(heteroaryl), —S(O)N($C_{1-9}$ alkyl)$_2$, —S(O)($C_{1-9}$ alkyl), —S(O)($C_{1-8}$ haloalkyl), —S(O)($C_{2-6}$ alkenyl), —S(O)($C_{2-6}$ alkynyl), —S(O)($C_{3-15}$ cycloalkyl), —S(O)(heterocyclyl), —S(O)($C_{6-10}$ aryl), —S(O)(heteroaryl), —S(O)$_2$($C_{1-9}$ alkyl), —S(O)$_2$($C_{1-8}$ haloalkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$(heterocyclyl), —S(O)$_2$($C_{6-10}$ aryl), —S(O)$_2$(heteroaryl), —S(O)(NH)($C_{1-9}$ alkyl), —S(O)$_2$NH ($C_{1-9}$ alkyl), or —S(O)$_2$N($C_{1-9}$ alkyl)$_2$, wherein each alkyl, cycloalkyl, heterocyclyl, aryl, or heteroaryl is optionally substituted with one to three $C_{1-9}$ alkyl, $C_{1-8}$ haloalkyl, halogen, —OH, —NH$_2$, CO$_2$H, —O($C_{1-9}$ alkyl), —O($C_{1-8}$ haloalkyl), —O($C_{3-15}$ cycloalkyl), —O(heterocyclyl), —O(aryl), —O(heteroaryl), —NH($C_{1-9}$ alkyl), —NH($C_{1-8}$ haloalkyl), —NH($C_{3-15}$ cycloalkyl), —NH(heterocyclyl), —NH(aryl), —NH(heteroaryl), —N($C_{1-9}$ alkyl)$_2$, —N($C_{3-15}$ cycloalkyl)$_2$, —NHC(O)($C_{1-8}$ haloalkyl), —NHC(O)($C_{3-15}$ cycloalkyl), —NHC(O)(heterocyclyl), —NHC(O) (aryl), —NHC(O)(heteroaryl), —NHC(O)O($C_{1-9}$ alkyl), —NHC(O)O($C_{1-8}$ haloalkyl), —NHC(O)O ($C_{2-6}$ alkynyl), —NHC(O)O($C_{3-15}$ cycloalkyl), —NHC(O)O(heterocyclyl), —NHC(O)O(aryl), —NHC(O)O(heteroaryl), —NHC(O)NH($C_{1-9}$ alkyl), S(O)$_2$($C_{1-9}$ alkyl), —S(O)$_2$($C_{1-8}$ haloalkyl), —S(O)$_2$($C_{3-15}$ cycloalkyl), —S(O)$_2$(heterocyclyl), —S(O)$_2$(aryl), —S(O)$_2$(heteroaryl), —S(O)(NH) ($C_{1-9}$ alkyl), —S(O)$_2$NH($C_{1-9}$ alkyl), or —S(O)$_2$N ($C_{1-9}$ alkyl)$_2$, wherein each alkyl or heterocyclyl is optionally substituted with one to four halogens;

each $R^{9a}$ and $R^{9b}$ is independently H, $C_{1-6}$ alkyl, or $C_{1-6}$ haloalkyl, or $R^{9a}$ and $R^{9b}$ together form a 6-membered heterocyclyl;

each $R^{9c}$, $R^{9d}$, $R^{10a}$, $R^{10b}$, an $R^{10c}$ is independently H, $C_{1-9}$ alkyl, $C_{2-6}$ alkenyl, $C_{2-6}$ alkynyl, $C_{3-15}$ cycloalkyl, heterocyclyl, $C_{6-10}$ aryl, or heteroaryl, wherein the alkyl, alkenyl, alkynyl, cycloalkyl, heterocyclyl, aryl, or heteroaryl is each optionally substituted with one to four $R^6$;

each $R^{11a}$ and $R^{11b}$ is independently —H, $C_{1-6}$ alkyl, oxo, or halogen;

each $R^{12}$ is $C_{1-9}$ alkyl, $C_{1-8}$ haloalkyl, $C_{2-6}$ alkenyl, $C_{2-6}$ alkynyl, halogen, oxo, —OH, —CN, —NO$_2$, —NH$_2$, —N$_3$, —SH, —O($C_{1-9}$ alkyl), —O($C_{1-8}$ haloalkyl), —O($C_{2-6}$ alkenyl), —O($C_{2-6}$ alkynyl), —O($C_{3-15}$ cycloalkyl), —O(heterocyclyl), —O($C_{6-10}$ aryl), —O(heteroaryl), —NH($C_{1-9}$ alkyl), —NH($C_{1-s}$ haloalkyl), —NH($C_{2-6}$ alkenyl), —NH($C_{2-6}$ alkynyl), —NH($C_{3-15}$ cycloalkyl), —NH(heterocyclyl), —NH ($C_{6-10}$ aryl), —NH(heteroaryl), —N($C_{1-9}$ alkyl)$_2$, —N($C_{1-8}$ haloalkyl)$_2$, —N($C_{2-6}$ alkenyl)$_2$, —N($C_{2-6}$ alkynyl)$_2$, —N($C_{3-15}$ cycloalkyl)$_2$, —N(heterocyclyl)$_2$, —N($C_{6-10}$ aryl)$_2$, —N(heteroaryl)$_2$, —N($C_{1-9}$ alkyl) ($C_{1-8}$ haloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)(heterocyclyl), —N($C_{1-9}$ alkyl)($C_{6-10}$ aryl), —N($C_{1-9}$ alkyl)(heteroaryl), —C(O) ($C_{1-9}$ alkyl), —C(O)($C_{1-8}$ haloalkyl), —C(O)($C_{2-6}$ alkenyl), —C(O)($C_{2-6}$ alkynyl), —C(O)($C_{3-15}$ cycloalkyl), —C(O)(heterocyclyl), —C(O)($C_{6-10}$ aryl), —C(O) (heteroaryl), —C(O)O($C_{1-9}$ alkyl), —C(O)O($C_{1-8}$ haloalkyl), —C(O)O($C_{2-6}$ alkenyl), —C(O)O($C_{2-6}$ alkynyl), —C(O)O($C_{3-15}$ cycloalkyl), —C(O)O(heterocyclyl), —C(O)O($C_{6-10}$ aryl), —C(O)O(heteroaryl), —C(O)NH$_2$, —C(O)NH($C_{1-9}$ alkyl), —C(O)NH($C_{1-8}$ haloalkyl), —C(O)NH($C_{2-6}$ alkenyl), —C(O)NH($C_{2-6}$ alkynyl), —C(O)NH($C_{3-15}$ cycloalkyl), —C(O)NH (heterocyclyl), —C(O)NH($C_{6-10}$ aryl), —C(O)NH(heteroaryl), —C(O)N($C_{1-9}$ alkyl)$_2$, —C(O)N($C_{1-8}$ haloalkyl)$_2$, —C(O)N($C_{2-6}$ alkenyl)$_2$, —C(O)N($C_{2-6}$ alkynyl)$_2$, —C(O)N($C_{3-15}$ cycloalkyl)$_2$, —C(O)N(heterocyclyl)$_2$, —C(O)N($C_{6-10}$ aryl)$_2$, —C(O)N(heteroaryl)$_2$, —NHC(O)($C_{1-9}$ alkyl), —NHC(O)($C_{1-8}$ haloalkyl), —NHC(O)($C_{2-6}$ alkenyl), —NHC(O)($C_{2-6}$ alkynyl), —NHC(O)($C_{3-15}$ cycloalkyl), —NHC(O) (heterocyclyl), —NHC(O)($C_{6-10}$ aryl), —NHC(O)(heteroaryl), —NHC(O)O($C_{1-9}$ alkyl), —NHC(O)O($C_{1-8}$ haloalkyl), —NHC(O)O($C_{2-6}$ alkenyl), —NHC(O)O ($C_{2-6}$ alkynyl), —NHC(O)O($C_{3-15}$ cycloalkyl), —NHC(O)O(heterocyclyl), —NHC(O)O($C_{6-10}$ aryl), —NHC(O)O(heteroaryl), —NHC(O)NH($C_{1-9}$ alkyl), —NHC(O)NH($C_{1-8}$ haloalkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH(heterocyclyl), —NHC(O)NH($C_{6-10}$ aryl), —NHC(O)NH(heteroaryl), —NHS(O) ($C_{1-9}$ alkyl), —N($C_{1-9}$ alkyl)(S(O)($C_{1-9}$ alkyl), —S($C_{1-9}$ alkyl), —S($C_{1-8}$ haloalkyl), —S($C_{2-6}$ alkenyl), —S($C_{2-6}$ alkynyl), —S($C_{3-15}$ cycloalkyl), —S(heterocyclyl), —S($C_{6-10}$ aryl), —S(heteroaryl), —S(O)N($C_{1-9}$ alkyl)$_2$, —S(O)($C_{1-9}$ alkyl), —S(O)($C_{1-8}$ haloalkyl), —S(O)($C_{2-6}$ alkenyl), —S(O)($C_{2-6}$ alkynyl), —S(O)($C_{3-15}$ cycloalkyl), —S(O)(heterocyclyl), —S(O)($C_{6-10}$ aryl), —S(O)(heteroaryl), —S(O)$_2$($C_{1-9}$ alkyl), —S(O)$_2$($C_{1-8}$ haloalkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$(heterocyclyl), —S(O)$_2$($C_{6-10}$ aryl), —S(O)$_2$ (heteroaryl), —S(O)(NH)($C_{1-9}$ alkyl), —S(O)$_2$NH ($C_{1-9}$ alkyl), or —S(O)$_2$N($C_{1-9}$ alkyl)$_2$, wherein each alkyl, cycloalkyl, heterocyclyl, aryl, or heteroaryl is optionally substituted with 1 to 3 $C_{1-9}$ alkyl, $C_{1-8}$ haloalkyl, halogen, —OH, —NH$_2$, CO$_2$H, —O($C_{1-9}$ alkyl), —O($C_{1-8}$ haloalkyl), —O($C_{3-15}$ cycloalkyl), —O(heterocyclyl), —O(aryl), —O(heteroaryl), —NH($C_{1-9}$ alkyl), —NH($C_{1-8}$ haloalkyl), —NH($C_{3-15}$ cycloalkyl), —NH(heterocyclyl), —NH(aryl), —NH(heteroaryl), —N($C_{1-9}$ alkyl)$_2$, —N($C_{3-15}$ cycloalkyl)$_2$, —NHC(O)($C_{1-8}$ haloalkyl), —NHC(O)($C_{3-15}$ cycloalkyl), —NHC(O)(heterocyclyl), —NHC(O) (aryl), —NHC(O)(heteroaryl), —NHC(O)O($C_{1-9}$ alkyl), —NHC(O)O($C_{1-8}$ haloalkyl), —NHC(O)O ($C_{2-6}$ alkynyl), —NHC(O)O($C_{3-15}$ cycloalkyl), —NHC(O)O(heterocyclyl), —NHC(O)O(aryl), —NHC(O)O(heteroaryl), —NHC(O)NH($C_{1-9}$ alkyl), S(O)$_2$($C_{1-9}$ alkyl), —S(O)$_2$($C_{1-8}$ haloalkyl), —S(O)$_2$($C_{3-15}$ cycloalkyl), —S(O)$_2$(heterocyclyl), —S(O)$_2$(aryl), —S(O)$_2$(heteroaryl), —S(O)(NH) ($C_{1-9}$ alkyl), —S(O)$_2$NH($C_{1-9}$ alkyl), or —S(O)$_2$N ($C_{1-9}$ alkyl)$_2$, wherein each alkyl or heterocyclyl is optionally substituted with one to four halogens;

wherein each heterocyclyl has three to twelve ring members and has one to four heteroatoms, each independently N, O, or S; and wherein each heteroaryl has five to twelve ring members and one to four heteroatoms, each independently N, O, or S.

The present disclosure further provides pharmaceutical compositions, methods, and uses comprising the compound of Formula (I) or pharmaceutically acceptable salts thereof. The present disclosure further provides pharmaceutical compositions, methods, and uses comprising the compound of Formula (I-A-1) or pharmaceutically acceptable salts thereof. For example, the compounds of the present disclosure are generally useful in a method of treating a GLP-1R-mediated disease or condition.

DETAILED DESCRIPTION

I. Definitions

Figure 1:
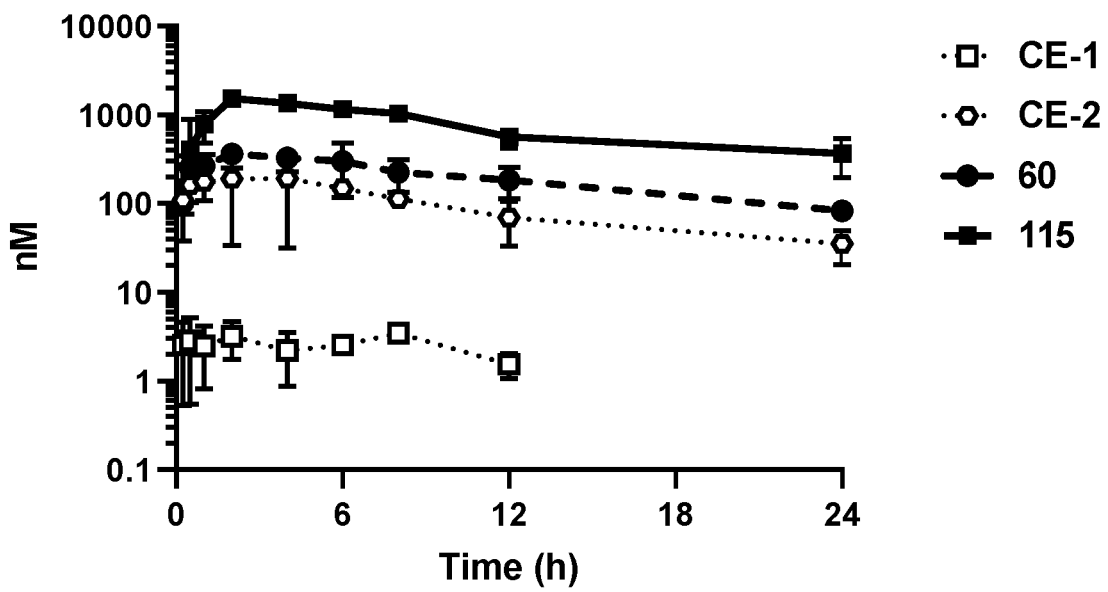
FIG. 1: Graph depicting plasma concentration as a function of time of in cynomolgus monkey.

Unless defined otherwise, all technical and scientific terms used herein have the same meaning as commonly understood by one of ordinary skill in the art. A dash at the front or end of a chemical group is a matter of convenience to indicate the point of attachment to a parent moiety; chemical groups may be depicted with or without one or more dashes without losing their ordinary meaning. A prefix such as "$C_{u-v}$" or "$C_u$-$C_v$" indicates that the following group has from u to v carbon atoms, where u and v are integers. For example, "$C_{1-6}$ alkyl" or "$C_1$-$C_6$ alkyl" indicates that the alkyl group has from 1 to 6 carbon atoms.

"Alkyl" is a monovalent or divalent linear or branched saturated hydrocarbon radical. For example, an alkyl group can have 1 to 10 carbon atoms (i.e., $C_{1-10}$ alkyl) or 1 to 8 carbon atoms (i.e., $C_{1-8}$ alkyl) or 1 to 6 carbon atoms (i.e., $C_{1-6}$ alkyl) or 1 to 4 carbon atoms (i.e., $C_{1-4}$ alkyl). Examples of alkyl groups include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$) CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$) CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$) CH$_2$CH$_2$CH$_2$CH$_3$), 3-hexyl (—CH(CH$_2$CH$_3$) (CH$_2$CH$_2$CH$_3$)), 2-methyl-2-pentyl (—C(CH$_3$)$_2$ CH$_2$CH$_2$CH$_3$), 3-methyl-2-pentyl (—CH(CH$_3$)CH(CH$_3$) CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C (CH$_3$)$_2$CH(CH$_3$)$_2$), 3,3-dimethyl-2-butyl (—CH(CH$_3$)C (CH$_3$)$_3$, and octyl (—(CH$_2$)$_7$CH$_3$). Alkyl groups can be unsubstituted or substituted.

"Alkoxy" refers to the group —O-alkyl, where alkyl is as defined above. For example, $C_{1-4}$ alkoxy refers to an —O-alkyl group having 1 to 4 carbons. Alkoxy groups can be unsubstituted or substituted.

"Alkoxyalkyl" is an alkoxy group attached to an alkyl as defined above, such that the alkyl is divalent. For example, $C_{2-6}$ alkoxyalkyl includes —CH$_2$—OMe, —CH$_2$—O-iPr, —CH$_2$—CH$_2$—OMe, —CH$_2$—CH$_2$—O—CH$_2$—CH$_3$, and —CH$_2$—CH$_2$—O-tBu. Alkoxyalkyl groups can be unsubstituted or substituted.

"Hydroxyalkyl" is a hydroxy group attached to an alkyl as defined above, such that the alkyl is divalent. For example, $C_{1-6}$ hydroxyalkyl includes —CH$_2$-0H, and —CH$_2$—CH$_2$—OH. Hydroxyalkyl groups can be unsubstituted or substituted.

"Alkenyl" is a monovalent or divalent linear or branched hydrocarbon radical with at least one carbon-carbon double bond. For example, an alkenyl group can have 2 to 8 carbon atoms (i.e., $C_{2-8}$ alkenyl) or 2 to 6 carbon atoms (i.e., $C_{2-6}$ alkenyl) or 2 to 4 carbon atoms (i.e., $C_{2-4}$ alkenyl). Examples of alkenyl groups include, but are not limited to, ethenyl (—CH═CH$_2$), allyl (—CH$_2$CH═CH$_2$), and —CH$_2$—CH═CH—CH$_3$. Alkenyl groups can be unsubstituted or substituted.

"Alkynyl" is a monovalent or divalent linear or branched hydrocarbon radical with at least one carbon-carbon triple bond. For example, an alkynyl group can have 2 to 8 carbon atoms (i.e., $C_{2-8}$ alkynyl) or 2 to 6 carbon atoms (i.e., $C_{2-6}$ alkynyl) or 2 to 4 carbon atoms (i.e., $C_{2-4}$ alkynyl). Examples of alkynyl groups include, but are not limited to, acetylenyl (—C≡CH), propargyl (—CH$_2$C≡CH), and —CH$_2$—C≡C—CH$_3$. Alkynyl groups can be unsubstituted or substituted.

"Halogen" refers to fluoro (—F), chloro (—Cl), bromo (—Br) and iodo (—I).

"Haloalkyl" is an alkyl as defined herein, wherein one or more hydrogen atoms of the alkyl are independently replaced by a halogen, which may be the same or different, such that the alkyl is divalent. The alkyl group and the halogen can be any of those described above. In some embodiments, the haloalkyl defines the number of carbon atoms in the alkyl portion, e.g., $C_{1-4}$ haloalkyl includes CF$_3$, CH$_2$F, CHF$_2$, CH$_2$CF$_3$, CH$_2$CH$_2$CF$_3$, CCl$_2$CH$_2$CH$_2$CH$_3$, and C(CH$_3$)$_2$(CF$_2$H). Haloalkyl groups can be unsubstituted or substituted.

"Haloalkoxy" is an alkoxy as defined herein, wherein one or more hydrogen atoms of the alkyl in the alkyoxy are independently replaced by a halogen, which may be the same or different, such that the alkyl is divalent. The alkoxy group and the halogen can be any of those described above. In some embodiments, the haloalkoxy defines the number of carbon atoms in the alkyl portion, e.g., $C_{1-4}$ haloalkoxy includes OCF$_3$, OCH$_2$F, OCH$_2$CF$_3$, OCH$_2$CH$_2$CF$_3$, OCCl$_2$CH$_2$CH$_2$CH$_3$, and OC(CH$_3$)$_2$(CF$_2$H). Haloalkoxy groups can be unsubstituted or substituted.

"Cycloalkyl" is a monovalent or divalent single all carbon ring or a multiple condensed all carbon ring system wherein the ring in each instance is a non-aromatic saturated or unsaturated ring. For example, in some embodiments, a cycloalkyl group has 3 to 12 carbon atoms, 3 to 10 carbon atoms, 3 to 8 carbon atoms, 3 to 6 carbon atoms, 3 to 5 carbon atoms, or 3 to 4 carbon atoms. Exemplary single ring cycloalkyl groups include cyclopropyl, cyclobutyl, cyclopentyl, cyclohexyl, cyclohexenyl, cycloheptyl, cycloheptenyl, and cyclooctyl. Cycloalkyl also includes multiple condensed ring systems (e.g., ring systems comprising 2 rings) having about 7 to 12 carbon atoms. The rings of the multiple condensed ring system can be connected to each other via fused, spiro, or bridged bonds when allowed by valency requirements. Exemplary multiple ring cycloalkyl groups include octahydropentalene, bicyclo[2. 2. 1]heptane, bicyclo [2. 2. 2]octane, bicyclo[2. 2. 2]oct-2-ene, and spiro[2. 5]octane. Cycloalkyl groups can be unsubstituted or substituted.

"Alkylcycloalkyl" refers to an alkyl as defined herein, wherein one or more hydrogen atoms of the alkyl are independently replaced by a cycloalkyl group, which may be the same or different. The alkyl group and the cycloalkyl group can be any of those described above. In some embodiments, the number of carbon atoms in the alkyl and cycloalkyl portion can be designated separately, e.g., $C_{1-6}$ alkyl-$C_{3-12}$ cycloalkyl. Alkylcycloalkyl groups can be unsubstituted or substituted.

"Aryl" as used herein refers to a monovalent or divalent single all carbon aromatic ring or a multiple condensed all carbon ring system wherein the ring is aromatic. For example, in some embodiments, an aryl group has 6 to 20 carbon atoms, 6 to 14 carbon atoms, 6 to 12 carbon atoms, or 6 to 10 carbon atoms. Aryl includes a phenyl radical. Aryl also includes multiple condensed ring systems (e.g., ring systems comprising 2, 3 or 4 rings) having about 9 to 20 carbon atoms in which multiple rings are aromatic. The rings of the multiple condensed ring system can be connected to each other via fused, spiro, or bridged bonds when allowed by valency requirements It is also understood that when reference is made to a certain atom-range membered aryl (e.g., 6-10 membered aryl), the atom range is for the total ring atoms of the aryl. For example, a 6-membered aryl would include phenyl and a 10-membered aryl would include naphthyl. Non-limiting examples of aryl groups include, but are not limited to, phenyl, naphthyl, anthracenyl, and the like. Aryl groups can be unsubstituted or substituted.

"Alkylaryl" refers to an alkyl as defined herein, wherein one or more hydrogen atoms of the alkyl are independently replaced by an aryl group, which may be the same or different. The alkyl group and the aryl group can be any of those described above, such that the alkyl is divalent. In some embodiments, an alkylaryl group has 7 to 24 carbon atoms, 7 to 16 carbon atoms, 7 to 13 carbon atoms, or 7 to 11 carbon atoms. An alkylaryl group defined by the number of carbon atoms refers to the total number of carbon atoms present in the constitutive alkyl and aryl groups combined. For example, $C_7$ alkylaryl refers to benzyl, while $C_{11}$ alkylaryl includes 1-methylnaphthyl and n-pentylphenyl. In some embodiments the number of carbon atoms in the alkyl and aryl portion can be designated separately, e.g., $C_{1-6}$ alkyl-$C_{6-10}$ aryl. Non-limiting examples of alkylaryl groups include, but are not limited to, benzyl, 2,2-dimethylphenyl, n-pentylphenyl, 1-methylnaphthyl, 2-ethylnaphthyl, and the like. Alkylaryl groups can be unsubstituted or substituted.

"Heterocyclyl" or "heterocycle" or "heterocycloalkyl" as used herein refers to a single saturated or partially unsaturated non-aromatic ring or a non-aromatic multiple ring system that has at least one heteroatom in the ring (i.e., at least one annular (i.e., ring-shaped) heteroatom selected from oxygen, nitrogen, and sulfur). Unless otherwise specified, a heterocyclyl group has from 3 to about 20 annular atoms, for example from 3 to 12 annular atoms, for example from 4 to 12 annular atoms, 4 to 10 annular atoms, or 3 to 8 annular atoms, or 3 to 6 annular atoms, or 3 to 5 annular atoms, or 4 to 6 annular atoms, or 4 to 5 annular atoms. Thus, the term includes single saturated or partially unsaturated rings (e.g., 3, 4, 5, 6 or 7-membered rings) having from about 1 to 6 annular carbon atoms and from about 1 to 3 annular heteroatoms selected from the group consisting of oxygen, nitrogen and sulfur in the ring. The rings of the multiple condensed ring system can be connected to each other via fused, spiro, or bridged bonds when allowed by valency requirements. Heterocycles include, but are not limited to, azetidine, aziridine, imidazolidine, morpholine, oxirane (epoxide), oxetane, thietane, piperazine, piperidine, pyrazolidine, piperidine, pyrrolidine, pyrrolidinone, tetrahydrofuran, tetrahydrothiophene, dihydropyridine, tetrahydropyridine, quinuclidine, 2-oxa-6-azaspiro[3. 3]heptan-6-yl, 6-oxa-1-azaspiro[3. 3]heptan-1-yl, 2-thia-6-azaspiro[3. 3]heptan-6-yl, 2,6-diazaspiro[3. 3]heptan-2-yl, 2-azabicyclo [3. 1. 0]hexan-2-yl, 3-azabicyclo[3. 1. 0]hexanyl, 2-azabicyclo[2. 1. 1]hexanyl, 2-azabicyclo[2. 2. 1]heptan-2-yl, 4-azaspiro[2. 4]heptanyl, 5-azaspiro[2. 4]heptanyl, and the like. Heterocyclyl groups can be unsubstituted or substituted.

"Alkylheterocyclyl" refers to an alkyl as defined herein, wherein one or more hydrogen atoms of the alkyl are independently replaced by a heterocyclyl group, which may be the same or different. The alkyl group and the heterocyclyl group can be any of those described above, such that the alkyl is divalent. In some embodiments, the number of atoms in the alkyl and heterocyclyl portion can be designated separately, e.g., $C_{1-6}$ alkyl-3 to 12 membered heterocyclyl having one to three heteroatoms each independently N, O, or S. Alkylheterocyclyl groups can be unsubstituted or substituted.

"Heteroaryl" refers to a single aromatic ring that has at least one atom other than carbon in the ring, wherein the atom is selected from the group consisting of oxygen, nitrogen and sulfur; "heteroaryl" also includes multiple condensed ring systems that have at least one such aromatic ring, which multiple condensed ring systems are further described below. Thus, "heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2, 3 or 4 rings) wherein a heteroaryl group, as defined above, is condensed with one or more rings selected from heteroaryls (to form for example 1,8-naphthyridinyl) and aryls (to form, for example, benzimidazolyl or indazolyl) to form the multiple condensed ring system. Thus, a heteroaryl (a single aromatic ring or multiple condensed ring system) can have about 1-20 carbon atoms and about 1-6 heteroatoms within the heteroaryl ring. For example, tetrazolyl has 1 carbon atom and 4 nitrogen heteroatoms within the ring. The rings of the multiple condensed ring system can be connected to each other via fused, spiro, or bridged bonds when allowed by valency requirements. It is to be understood that the individual rings of the multiple condensed ring system may be connected in any order relative to one another. It is to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). It also to be understood that when a reference is made to a certain atom-range membered heteroaryl (e.g., a 5 to 10 membered heteroaryl), the atom range is for the total ring atoms of the heteroaryl and includes carbon atoms and heteroatoms. It is also to be understood that the rings of the multiple condensed ring system may include an aryl ring fused to a heterocyclic ring with saturated or partially unsaturated bonds (e.g., 3, 4, 5, 6 or 7-membered rings) having from about 1 to 6 annular carbon atoms and from about 1 to 3 annular heteroatoms selected from the group consisting of oxygen, nitrogen and sulfur in the ring. For example, a 5-membered heteroaryl includes thiazolyl and a 10-membered heteroaryl includes quinolinyl. Exemplary heteroaryls include but are not limited to pyridyl, pyrrolyl, pyrazinyl, pyrimidinyl, pyridazinyl, pyrazolyl, thienyl, indolyl, imidazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, quinazolyl, benzofuranyl, benzimidazolyl, thianaphthenyl, pyrrolo[2,3-b]pyridinyl, quinazolinyl-4(3H)-one, triazolyl, and tetrazolyl. Heteroaryl groups can be unsubstituted or substituted.

"Alkylheteroaryl" refers to an alkyl as defined herein, wherein one or more hydrogen atoms of the alkyl are independently replaced by a heteroaryl group, which may be the same or different, such that the alkyl is divalent. The alkyl group and the heteroaryl group can be any of those described above. In some embodiments, the number of atoms in the alkyl and heteroaryl portion are designated separately, e.g., $C_{1-6}$ alkyl-5 to 10 membered heteroaryl having one to four heteroatoms each independently N, O, or S. Alkylheteroaryl groups can be unsubstituted or substituted.

"Oxo" as used herein refers to =O.

"Substituted" as used herein refers to wherein one or more hydrogen atoms of the group are independently replaced by one or more substituents (e.g., 1, 2, 3, or 4 or more) as indicated.

A "compound of the present disclosure" includes compounds disclosed herein, for example a compound of the present disclosure includes compounds of Formula (I), including the compounds of the Examples. In some embodiments, a "compound of the present disclosure" includes compounds of Formula (I).

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Therapeutically effective amount" or "effective amount" as used herein refers to an amount that is effective to elicit the desired biological or medical response, including the amount of a compound that, when administered to a subject for treating a disease, is sufficient to affect such treatment for the disease. The effective amount will vary depending on the compound, the disease, and its severity and the age, weight, etc., of the subject to be treated. The effective amount can include a range of amounts. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any co-administered compounds may optionally be lowered due to the combined action (e.g., additive or synergistic effects) of the compounds.

"Co-administration" as used herein refers to administration of unit dosages of the compounds disclosed herein before or after administration of unit dosages of one or more additional therapeutic agents, for example, administration of the compound disclosed herein within seconds, minutes, or hours of the administration of one or more additional therapeutic agents. For example, in some embodiments, a unit dose of a compound of the present disclosure is administered first, followed within seconds or minutes by administration of a unit dose of one or more additional therapeutic agents. Alternatively, in other embodiments, a unit dose of one or more additional therapeutic agents is administered first, followed by administration of a unit dose of a compound of the present disclosure within seconds or minutes. In some embodiments, a unit dose of a compound of the present disclosure is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound of the present disclosure. Co-administration of a compound disclosed herein with one or more additional therapeutic agents generally refers to simultaneous or sequential administration of a compound disclosed herein and one or more additional therapeutic agents, such that therapeutically effective amounts of each agent are present in the body of the subject.

Provided are also pharmaceutically acceptable salts, hydrates, solvates, tautomeric forms, polymorphs, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The compounds described herein may be prepared and/or formulated as pharmaceutically acceptable salts or when appropriate as a free base. Pharmaceutically acceptable salts are non-toxic salts of a free base form of a compound that possesses the desired pharmacological activity of the free base. These salts may be derived from inorganic or organic acids or bases. For example, a compound that contains a basic nitrogen may be prepared as a pharmaceutically acceptable salt by contacting the compound with an inorganic or organic acid. Non-limiting examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington: The Science and Practice of Pharmacy, 21st Edition, Lippincott Williams and Wilkins, Philadelphia, Pa., 2006.

Examples of "pharmaceutically acceptable salts" of the compounds disclosed herein also include salts derived from an appropriate base, such as an alkali metal (for example, sodium, potassium), an alkaline earth metal (for example, magnesium), ammonium and $N(C_1{\equiv}C_4$ alkyl)4+. Also included are base addition salts, such as sodium or potassium salts.

Provided are also compounds described herein or pharmaceutically acceptable salts, isomers, or a mixture thereof, in which from 1 to n hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds may increase resistance to metabolism, and thus may be useful for increasing the half-life of the compounds described herein or pharmaceutically acceptable salts, isomer, or a mixture thereof when administered to a mammal. See, e.g., Foster, "Deuterium Isotope Effects in Studies of Drug Metabolism", Trends Pharmacol. Sci., 5(12):524-527 (1984). Such compounds are synthesized by means well known in the art, for example by employing starting materials in which one or more hydrogen atoms have been replaced by deuterium.

Examples of isotopes that can be incorporated into the disclosed compounds also include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of Formula (I) can generally be prepared by conventional techniques known to those skilled in the art or by processes analogous to those described in the Examples as set out below using an appropriate isotopically-labeled reagent in place of the non-labeled reagent previously employed.

The compounds of the embodiments disclosed herein, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high-pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included. Where compounds are represented in their chiral form, it is understood that the embodiment encompasses, but is not limited to, the specific diastereomerically or enantiomerically enriched form. Where chirality is not specified but is present, it is understood that the embodiment is directed to either the specific diastereomerically or enantiomerically enriched form; or a racemic or scalemic mixture of such compound(s). As used herein, "scalemic mixture" is a mixture of stereoisomers at a ratio other than 1:1.

"Stereoisomer" as used herein refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are non-superimposable mirror images of one another.

"Tautomer" as used herein refers to a proton shift from one atom of a molecule to another atom of the same molecule. In some embodiments, the present disclosure includes tautomers of said compounds.

"Solvate" as used herein refers to the result of the interaction of a solvent and a compound. Solvates of salts of the compounds described herein are also provided. Hydrates of the compounds described herein are also provided.

"Hydrate" as used herein refers to a compound of the disclosure that is chemically associated with one or more molecules of water.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Prodrug" as used herein refers to a derivative of a drug that upon administration to the human body is converted to the parent drug according to some chemical or enzymatic pathway. In some embodiments, a prodrug is a biologically inactive derivative of a drug that upon administration to the human body is converted to the biologically active parent drug according to some chemical or enzymatic pathway.

"Treatment" or "treat" or "treating" as used herein refers to an approach for obtaining beneficial or desired results. For purposes of the present disclosure, beneficial or desired results include, but are not limited to, alleviation of a symptom and/or diminishment of the extent of a symptom and/or preventing a worsening of a symptom associated with a disease or condition. In one embodiment, "treatment" or "treating" includes one or more of the following: a) inhibiting the disease or condition (e.g., decreasing one or more symptoms resulting from the disease or condition, and/or diminishing the extent of the disease or condition); b) slowing or arresting the development of one or more symptoms associated with the disease or condition (e.g., stabilizing the disease or condition, delaying the worsening or progression of the disease or condition); and c) relieving the disease or condition, e.g., causing the regression of clinical symptoms, ameliorating the disease state, delaying the progression of the disease, increasing the quality of life, and/or prolonging survival. "At risk individual" as used herein refers to an individual who is at risk of developing a condition to be treated. An individual "at risk" may or may not have detectable disease or condition and may or may not have displayed detectable disease prior to the treatment of methods described herein. "At risk" denotes that an individual has one or more so-called risk factors, which are measurable parameters that correlate with development of a disease or condition and are known in the art. An individual having one or more of these risk factors has a higher probability of developing the disease or condition than an individual without these risk factor(s).

II. Compounds

In one embodiment, the present disclosure provides a compound of Formula (I):

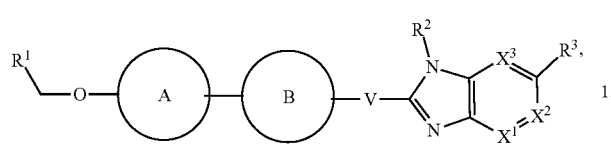

(I)

or a pharmaceutically acceptable salt thereof, wherein
$R^1$ is
  i) $C_{6-10}$ aryl or 6-membered heteroaryl, each of which is optionally substituted with one to four $R^4$; or
  ii) 6-membered heteroaryl, wherein the heteroaryl is fused to a 5- or 6-membered ring having zero to three heteroatoms, each independently N, O, or S, to form a fused ring system, wherein the fused ring system is optionally substituted with one to four $R^5$;
ring A is

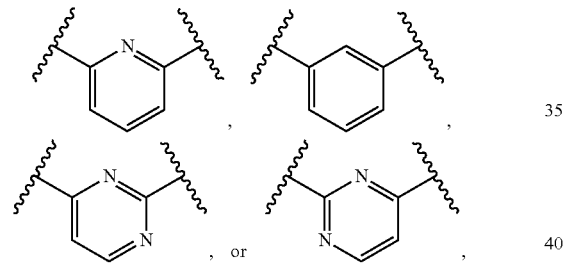

, or which are each optionally substituted with one to three $R^A$, each $R^A$ independently $C_{1-6}$ alkyl, $C_{1-6}$ haloalkyl, $C_{1-6}$ alkoxy, $C_{1-6}$ haloalkoxy, halogen, —OH, —CN, or —N($R^{10a}$)($R^{10b}$);
ring B is
  (i) $C_{6-10}$ aryl or heteroaryl, which is each optionally substituted with one to four $R^B$, each $R^B$ independently $C_{1-9}$ alkyl, $C_{1-8}$ haloalkyl, $C_{1-6}$ haloalkoxy, $C_{2-6}$ alkoxyalkyl, $C_{2-6}$ alkenyl, $C_{2-6}$ alkynyl, halogen, $C_{3-10}$ cycloalkyl, heterocyclyl, $C_{6-10}$ aryl, heteroaryl, oxo, —NO$_2$, —CN, —N$_3$, —O—$R^{10a}$, —C(O)$R^{10a}$, —C(O)O— $R^{10a}$, —N($R^{10a}$)($R^{10b}$), N($R^{10a}$)$_2$($R^{10b}$)$^+$, —N($R^{10a}$)C(O)—$R^{10b}$, —N($R^{10a}$)C(O)O— $R^{10b}$, —N($R^{10a}$)C(O)N($R^{10b}$)($R^{10c}$), —N($R^{10a}$)S(O)$_2$($R^{10b}$), —NR$^{10a}$S(O)$_2$N($R^{10b}$)($R^{10c}$), —NR$^{10a}$S(O)$_2$O($R^{10b}$), —OC(O)$R^{10a}$, —OC(O)O $R^{10a}$, —OC(O)—N($R^{10a}$)($R^{10b}$), —S—$R^{10a}$, —S(O) $R^{10a}$, —S(O)(NH)Rub, —S(O)$_2R^{10a}$, —S(O)$_2$N($R^{10a}$)($R^{10b}$), —S(O)(NR$^{10a}$) $R^{10b}$, or —Si($R^{10a}$)$_3$; or
  (ii) $C_{6-10}$ aryl or heteroaryl, which is each fused to a 5 or 6 membered ring having zero to four heteroatoms, each independently N, O, or S, to form a fused ring system, wherein the fused ring system is optionally substituted with one to five $R^B$, each $R^B$ independently $C_{1-9}$ alkyl, $C_{1-8}$ haloalkyl, $C_{1-6}$ haloalkoxy, $C_{2-6}$ alkoxyalkyl, $C_{2-6}$ alkenyl, $C_{2-6}$ alkynyl, halogen, $C_{3-10}$ cycloalkyl, heterocyclyl, $C_{6-10}$ aryl, heteroaryl, oxo, —NO$_2$, —CN, —N$_3$, —O—$R^{10a}$, —C(O)$R^{10a}$, —C(O)O— $R^{10a}$, —N($R^{10a}$)($R^{10b}$), N($R^{10a}$)$_2$($R^{10b}$)$^+$, —N($R^{10a}$)C(O)—$R^{10b}$, —N($R^{10a}$)C(O)O— $R^{10b}$, —N($R^{10a}$)C(O)N($R^{10b}$)($R^{10c}$), —N($R^{10a}$)S(O)$_2$($R^{10b}$), —NR$^{10a}$S(O)$_2$N($R^{10b}$)($R^{10c}$), —NR$^{10a}$S(O)$_2$O($R^{10b}$), —OC(O) $R^{10a}$, —OC(O)O $R^{10a}$, —OC(O)—N($R^{10a}$)($R^{10b}$), —S—$R^{10a}$, —S(O) $R^{10a}$, —S(O)(NH) $R^{10a}$, —S(O)$_2R^{10a}$, —S(O)$_2$N($R^{10a}$)($R^{10b}$), —S(O)(NR$^{10a}$) $R^{10b}$, or —Si($R^{10a}$
V is —C($R^{11a}$)($R^{11b}$)—;
$X^1$, $X^2$, and $X^3$ are each independently —C(H)=, or —C($R^8$)=;
$R^2$ is
  i) $C_{3-10}$ cycloalkyl or heterocyclyl, wherein the cycloalkyl or heterocyclyl is each optionally substituted with one to four $Z^1$, wherein each $Z^1$ is independently $C_{1-6}$ alkyl, $C_{1-6}$ alkoxy, $C_{1-6}$ hydroxyalkyl, $C_{2-6}$ alkoxyalkyl, halogen, $C_{1-6}$ haloalkyl, $C_{1-6}$ haloalkoxy, oxo, —OH, —CN, $C_{1-6}$ alkyl-CN, —C(O)$R^{10a}$, —C(O)O— $R^{10a}$, —C(O)NH$_2$, —C(O)NH($C_{1-9}$ alkyl), —N($R^{10a}$)($R^{10b}$), —N($R^{10a}$)C(O)O— $R^{10b}$, —N($R^{10a}$)C(O)—$R^{10b}$, —S(O)$_2R^{10a}$, —S(O)$_2$($C_{1-9}$ alkyl), —O—$C_{3-6}$ cycloalkyl or heteroaryl,
  wherein each —O—$C_{3-6}$ cycloalkyl or heteroaryl is optionally substituted with one to four $Z^{1a}$ groups, each $Z^{1a}$ independently $C_{1-6}$ alkyl, $C_{1-6}$ alkoxy, halogen, $C_{1-6}$ haloalkyl, or $C_{1-6}$ haloalkoxy; or

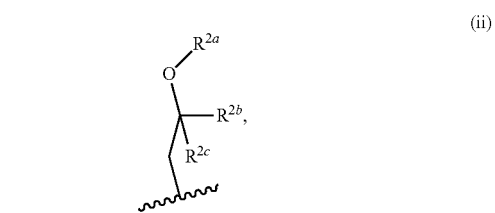

(ii)

wherein
  $R^{2a}$ is $C_{1-6}$ alkyl, $C_{1-6}$ hydroxyalkyl, $C_{2-6}$ alkoxyalkyl, $C_{1-6}$ haloalkyl, $C_{1-6}$ alkyl-CN, —$C_{3-6}$ cycloalkyl or heteroaryl,
    wherein each alkyl, cycloalkyl, or heteroaryl is optionally substituted with one to four groups each independently $C_{1-6}$ alkyl, $C_{1-6}$ alkoxy, halogen, $C_{1-6}$ haloalkyl, or $C_{1-6}$ haloalkoxy;
  $R^{2b}$ is H, $C_{1-3}$ alkyl, $C_{1-3}$ haloalkyl; and
  $R^{2c}$ is H, $C_{1-3}$ alkyl, $C_{1-3}$ haloalkyl;
$R^3$ is —C(O)O$R^{3a}$;
  wherein $R^{3a}$ is H, $C_{1-4}$ alkyl-N($R^{9a}$)($R^{9b}$), —$C_{1-4}$ alkyl-N($R^{9a}$)C(O)—O—$C_{1-4}$ alkyl-OP(O)(O$R^{9c}$)$_2$, $C_{1-4}$ alkyl-C(O)N($R^{9a}$)($R^{9b}$), —$C_{1-4}$ alkyl-O—C(O)—$C_{1-4}$ alkyl, —$C_{1-4}$ alkyl-O—C(O)—O—$C_{1-4}$alkyl, —$C_{1-4}$ alkyl-O—C(O)—$C_{1-4}$ alkyl-N($R^{9a}$)($R^{9b}$), —$C_{1-4}$ alkyl-O—C(O)—$C_{1-4}$ alkyl-OP(O)(O$R^{9c}$)$_2$, —CH$_2$CH(N($R^{9a}$)$_2$)C(O)O$R^{9b}$, —P(O)(O$R^{9c}$)$_2$, —OP(O)(O$R^{9c}$)$_2$, —CH$_2$P(O)(O$R^{9c}$)$_2$, —CH$_2$OP(O)(O$R^{9c}$)$_2$, —OCH$_2$P(O)(O$R^{9c}$)$_2$, C(O)OCH$_2$P(O)(O$R^{9c}$)$_2$, —P(O)($R^{9c}$)(O$R^{9d}$), —OP(O)($R^{9c}$)(O$R^{9d}$), —CH$_2$P(O)($R^{9c}$)(O$R^{9d}$), —OCH$_2$P(O)($R^{9c}$)(O$R^{9d}$), —C(O)OCH$_2$P(O)($R^{9c}$)(O$R^{9d}$), —P(O)(N($R^{9c}$)$_2$)$_2$, —OP(O)(N($R^{9c}$)$_2$)$_2$, —CH$_2$P(O)(N($R^{9c}$)$_2$)$_2$, —OCH$_2$P(O)(N($R^{9c}$)$_2$)$_2$, —C(O)OCH$_2$P(O)(N($R^{9c}$)$_2$)$_2$, —P(O)(N($R^{9c}$)$_2$)(O$R^{9d}$), —OP(O)(N($R^{9c}$)$_2$)(O$R^{9d}$), —CH$_2$P(O)(N($R^{9c}$)$_2$)(O$R^{9d}$), —OCH$_2$P(O)(N($R^{9c}$)$_2$)(O$R^{9d}$), —C(O)OCH$_2$P(O)(N($R^{9c}$)$_2$)(O$R^{9d}$), —P(O)($R^{9c}$)(N($R^{9d}$)$_2$), —OP(O)($R^{9c}$)(N($R^{9d}$)$_2$), —CH$_2$P(O)($R^{9c}$)(N($R^{9d}$)$_2$), —OCH$_2$P(O)($R^{9c}$)(N($R^{9d}$)$_2$), —C(O)OCH$_2$P(O)($R^9$)(N($R^{9d}$)$_2$), or C$_{1-6}$ alkyl-heterocyclyl, wherein each alkyl or heterocyclyl is optionally substituted with one to four halogens;

each $R^4$ is independently C$_{1-6}$ alkyl, C$_{1-8}$ haloalkyl, C$_{1-6}$ haloalkoxy, C$_{2-6}$ alkoxyalkyl, C$_{2-6}$ alkenyl, halogen, C$_{3-10}$ cycloalkyl, heterocyclyl, C$_{6-10}$ aryl, heteroaryl, oxo, —NO$_2$, —CN, —N$_3$, —O—$R^{10a}$, —C(O)$R^{10a}$, —C(O)O—$R^{10a}$, —N($R^{10a}$)($R^{10b}$), —N($R^{10a}$)$_2$($R^{10b}$), —N($R^{10a}$)—C(O)$R^{10b}$, —N($R^{10a}$)C(O)O($R^{10b}$), —N($R^{10a}$)C(O)N($R^{10b}$)($R^{10c}$), —N($R^{10a}$)S(O)$_2$($R^{10b}$), —N($R^{10a}$)S(O)$_2$—N($R^{10b}$)($R^{10c}$), —N($R^{10a}$)S(O)$_2$O($R^{10b}$), —OC(O)$R^{10a}$, —OC(O)O$R^{10a}$, —OC(O)—N($R^{10a}$)($R^{10b}$), —S—$R^{10a}$, —S(O)$R^{10a}$, —S(O)(NH)$R^{10a}$, —S(O)$_2$$R^{10a}$, —S(O)$_2$N($R^{10a}$)($R^{10b}$), —S(O)(N$R^{10a}$)$R^{10b}$, or —Si($R^{10a}$)$_3$ wherein each alkyl, haloalkyl, alkenyl or aryl is optionally substituted with one to four $R^5$, and wherein each cycloalkyl, heterocyclyl or heteroaryl is optionally substituted with one to four $R^{12}$;

each $R^5$ is independently C$_{1-9}$ alkyl, C$_{1-8}$ haloalkyl, C$_{1-6}$ alkoxy, C$_{1-6}$ haloalkoxy, C$_{2-6}$ alkoxyalkyl, C$_{2-6}$ alkenyl, C$_{2-6}$ alkynyl, halogen, C$_{3-15}$ cycloalkyl, heterocyclyl, C$_{6-10}$ aryl, heteroaryl, oxo, —NO$_2$, —N$_3$, —CN, —O—$R^{10a}$, —C(O)—$R^{10a}$, —C(O)O—$R^{10a}$, C(O)—N($R^{10a}$)($R^{10b}$), —N($R^{10a}$)($R^{10b}$), —N($R^{10a}$)$_2$($R^{10b}$), —N(RR$^{10a}$)C(O)—$R^{10b}$, —N($R^{10a}$)C(O)O— $R^{10b}$, —N($R^{10a}$)C(O)N($R^{10b}$)($R^{10c}$), —N($R^{10a}$)S(O)$_2$($R^{10b}$), —N$R^{10a}$S(O)$_2$N($R^{10b}$)($R^{10c}$), —N$R^{10a}$S(O)$_2$O($R^{10b}$), —OC(O) $R^{10a}$, —OC(O)O $R^{10a}$, —OC(O)—N($R^{10a}$)($R^{10b}$), —S—$R^{10a}$, —S(O) $R^{10a}$, —S(O)(NH) $R^{10a}$, —S(O)$_2$$R^{10a}$, —S(O)$_2$N($R^{10a}$)($R^{10b}$), —S(O)(N$R^{10a}$)$R^{10b}$, or —Si($R^{10a}$)$_3$ wherein each alkyl, haloalkyl, alkenyl, alkynyl, cycloalkyl, heterocyclyl, aryl, or heteroaryl is optionally substituted with one to four $R^6$;

each $R^6$ is independently C$_{1-9}$ alkyl, C$_{1-8}$ haloalkyl, C$_{1-8}$ alkoxy, C$_{1-6}$ haloalkoxy, C$_{2-6}$ alkoxyalkyl, C$_{2-6}$ alkenyl, C$_{2-6}$ alkynyl, C$_{3-15}$ cycloalkyl, halogen, C$_{3-15}$ cycloalkyl, heterocyclyl, C$_{6-10}$ aryl, heteroaryl, oxo, —NO$_2$, —N$_3$, —CN, —O— $R^{10a}$, —C(O)—$R^{10a}$, —C(O)O—$R^{10a}$, —C(O)—N($R^{10a}$)($R^{10b}$), —N($R^{10a}$)($R^{10b}$), —N($R^{10a}$)C(O)—$R^{10b}$, —N($R^{10a}$)C(O)O— $R^{10b}$, —N($R^{10a}$)C(O)N($R^{10b}$)($R^{10c}$), —N($R^{10a}$)S(O)$_2$($R^{10b}$), —N$R^{10a}$S(O)$_2$N($R^{10b}$)($R^{10c}$), —N$R^{10a}$S(O)$_2$O($R^{10b}$), —OC(O) $R^{10a}$, —OC(O)O $R^{10a}$, —OC(O)—N($R^{10a}$)($R^{10b}$), —S—$R^{10a}$, —S(O) $R^{10a}$, —S(O)(NH) $R^{10a}$, —S(O)$_2$$R^{10a}$, —S(O)$_2$N($R^{10a}$)($R^{10b}$), —S(O)(N$R^{10a}$)$R^{10b}$, or —Si($R^{10a}$)$_3$ wherein each alkyl, haloalkyl, alkenyl, alkynyl, cycloalkyl, heterocyclyl, aryl, or heteroaryl is optionally substituted with one to four $R^7$;

each $R^7$ and $R^8$ is independently C$_{1-9}$ alkyl, C$_{1-6}$ alkoxy, C$_{2-6}$ alkoxyalkyl, C$_{1-8}$ haloalkyl, C$_{2-6}$ alkenyl, C$_{2-6}$ alkynyl, halogen, C$_{3-15}$ cycloalkyl, heterocyclyl, C$_{6-10}$ aryl, heteroaryl, oxo, —OH, —CN, —NO$_2$, —NH$_2$, —N$_3$, —SH, —O(C$_{1-9}$ alkyl), —O(C$_{1-8}$ haloalkyl), —O(C$_{2-6}$ alkenyl), —O(C$_{2-6}$ alkynyl), —O(C$_{3-15}$ cycloalkyl), —O(heterocyclyl), —O(C$_{6-10}$ aryl), —O(heteroaryl), —NH(C$_{1-9}$ alkyl), —NH(C$_{1-8}$ haloalkyl), —NH(C$_{2-6}$ alkenyl), —NH(C$_{2-6}$ alkynyl), —NH(C$_{3-15}$ cycloalkyl), —NH(heterocyclyl), —NH(C$_{6-10}$ aryl), —NH(heteroaryl), —N(C$_{1-9}$ alkyl)$_2$, —N(C$_{1-8}$ haloalkyl)$_2$, —N(C$_{2-6}$ alkenyl)$_2$, —N(C$_{2-6}$ alkynyl)$_2$, —N(C$_{3-15}$ cycloalkyl)$_2$, —N(heterocyclyl)$_2$, —N(C$_{6-10}$ aryl)$_2$, —N(heteroaryl)$_2$, —N(C$_{1-9}$ alkyl)(C$_{1-8}$ haloalkyl), —N(C$_{1-9}$ alkyl)(C$_{2-6}$ alkenyl), —N(C$_{1-9}$ alkyl)(C$_{2-6}$ alkynyl), —N(C$_{1-9}$ alkyl)(C$_{3-15}$ cycloalkyl), —N(C$_{1-9}$ alkyl)(heterocyclyl), —N(C$_{1-9}$ alkyl)(C$_{6-10}$ aryl), —N(C$_{1-9}$ alkyl)(heteroaryl), —C(O)(C$_{1-9}$ alkyl), —C(O)(C$_{1-8}$ haloalkyl), —C(O)(C$_{2-6}$ alkenyl), —C(O)(C$_{2-6}$ alkynyl), —C(O)(C$_{3-15}$ cycloalkyl), —C(O)(heterocyclyl), —C(O)(C$_{6-10}$ aryl), —C(O)(heteroaryl), —C(O)O(C$_{1-9}$ alkyl), —C(O)O(C$_{1-8}$ haloalkyl), —C(O)O(C$_{2-6}$ alkenyl), —C(O)O(C$_{2-6}$ alkynyl), —C(O)O(C$_{3-15}$ cycloalkyl), —C(O)O(heterocyclyl), —C(O)O(C$_{6-10}$ aryl), —C(O)O(heteroaryl), —C(O)NH$_2$, —C(O)NH(C$_{1-9}$ alkyl), —C(O)NH(C$_{1-8}$ haloalkyl), —C(O)NH(C$_{2-6}$ alkenyl), —C(O)NH(C$_{2-6}$ alkynyl), —C(O)NH(C$_{3-15}$ cycloalkyl), —C(O)NH(heterocyclyl), —C(O)NH(C$_{6-10}$ aryl), —C(O)NH(heteroaryl), —C(O)N(C$_{1-9}$ alkyl)$_2$, —C(O)N(C$_{1-8}$ haloalkyl)$_2$, —C(O)N(C$_{2-6}$ alkenyl)$_2$, —C(O)N(C$_{2-6}$ alkynyl)$_2$, —C(O)N(C$_{3-15}$ cycloalkyl)$_2$, —C(O)N(heterocyclyl)$_2$, —C(O)N(C$_{6-10}$ aryl)$_2$, —C(O)N(heteroaryl)$_2$, —NHC(O)(C$_{1-9}$ alkyl), —NHC(O)(C$_{1-8}$ haloalkyl), —NHC(O)(C$_{2-6}$ alkenyl), —NHC(O)(C$_{2-6}$ alkynyl), —NHC(O)(C$_{3-15}$ cycloalkyl), —NHC(O)(heterocyclyl), —NHC(O)(C$_{6-10}$ aryl), —NHC(O)(heteroaryl), —NHC(O)O(C$_{1-9}$ alkyl), —NHC(O)O(C$_{1-8}$ haloalkyl), —NHC(O)O(C$_{2-6}$ alkenyl), —NHC(O)O(C$_{2-6}$ alkynyl), —NHC(O)O(C$_{3-15}$ cycloalkyl), —NHC(O)O(heterocyclyl), —NHC(O)O(C$_{6-10}$ aryl), —NHC(O)O(heteroaryl), —NHC(O)NH(C$_{1-9}$ alkyl), —NHC(O)NH(C$_{1-8}$ haloalkyl), —NHC(O)NH(C$_{2-6}$ alkenyl), —NHC(O)NH(C$_{2-6}$ alkynyl), —NHC(O)NH(C$_{3-15}$ cycloalkyl), —NHC(O)NH(heterocyclyl), —NHC(O)NH(C$_{6-10}$ aryl), —NHC(O)NH(heteroaryl), —NHS(O)(C$_{1-9}$ alkyl), —N(C$_{1-9}$ alkyl)(S(O)(C$_{1-9}$ alkyl), —S(C$_{1-9}$ alkyl), —S(C$_{1-8}$ haloalkyl), —S(C$_{2-6}$ alkenyl), —S(C$_{2-6}$ alkynyl), —S(C$_{3-15}$ cycloalkyl), —S(heterocyclyl), —S(C$_{6-10}$ aryl), —S(heteroaryl), —S(O)N(C$_{1-9}$ alkyl)$_2$, —S(O)(C$_{1-9}$ alkyl), —S(O)(C$_{1-8}$ haloalkyl), —S(O)(C$_{2-6}$ alkenyl), —S(O)(C$_{2-6}$ alkynyl), —S(O)(C$_{3-15}$ cycloalkyl), —S(O)(heterocyclyl), —S(O)(C$_{6-10}$ aryl), —S(O)(heteroaryl), —S(O)$_2$(C$_{1-9}$ alkyl), —S(O)$_2$(C$_{1-8}$ haloalkyl), —S(O)$_2$(C$_{2-6}$ alkenyl), —S(O)$_2$(C$_{2-6}$ alkynyl), —S(O)$_2$(C$_{3-15}$ cycloalkyl), —S(O)$_2$(heterocyclyl), —S(O)$_2$(C$_{6-10}$ aryl), —S(O)$_2$(heteroaryl), —S(O)(NH)(C$_{1-9}$ alkyl), —S(O)$_2$NH(C$_{1-9}$ alkyl), or —S(O)$_2$N(C$_{1-9}$ alkyl)$_2$, wherein each alkyl, cycloalkyl, heterocyclyl, aryl, or heteroaryl is optionally substituted with one to three C$_{1-9}$ alkyl, C$_{1-8}$ haloalkyl, halogen, —OH, —NH$_2$, CO$_2$H, —O(C$_{1-9}$ alkyl), —O(C$_{1-8}$ haloalkyl), —O(C$_{3-15}$ cycloalkyl), —O(heterocyclyl), —O(aryl), —O(heteroaryl), —NH(C$_{1-9}$ alkyl), —NH(C$_{1-8}$ haloalkyl), —NH(C$_{3-15}$ cycloalkyl), —NH(heterocyclyl), —NH(aryl), —NH(heteroaryl), —N(C$_{1-9}$ alkyl)$_2$, —N(C$_{3-15}$ cycloalkyl)$_2$, —NHC(O)(C$_{1-8}$ haloalkyl), —NHC(O)(C$_{3-15}$ cycloalkyl), —NHC(O)(heterocyclyl), —NHC(O)(aryl), —NHC(O)(heteroaryl), —NHC(O)O(C$_{1-9}$ alkyl), —NHC(O)O(C$_{1-8}$ haloalkyl), —NHC(O)O(C$_{2-6}$ alkynyl), —NHC(O)O(C$_{3-15}$ cycloalkyl), —NHC(O)O(heterocyclyl), —NHC(O)O(aryl), —NHC(O)O(heteroaryl), —NHC(O)NH(C$_{1-9}$ alkyl), S(O)$_2$(C$_{1-9}$ alkyl), —S(O)$_2$(C$_{1-8}$ haloalkyl), —S(O)$_2$(C$_{3-15}$ cycloalkyl), —S(O)$_2$(heterocyclyl), —S(O)$_2$(aryl), —S(O)$_2$(heteroaryl), —S(O)(NH)(C$_{1-9}$ alkyl), —S(O)$_2$NH(C$_{1-9}$ alkyl), or —S(O)$_2$N(C$_{1-9}$ alkyl)$_2$, wherein each alkyl or heterocyclyl is optionally substituted with one to four halogens;

each $R^{9a}$ and $R^{9b}$ is independently H, C$_{1-6}$ alkyl, or C$_{1-6}$ haloalkyl, or $R^{9a}$ and $R^{9b}$ together form a 6-membered heterocyclyl;

each $R^{9c}$, $R^{9d}$, $R^{10a}$, $R^{10b}$, and $R^{10c}$ is independently H, C$_{1-9}$ alkyl, C$_{2-6}$ alkenyl, C$_{2-6}$ alkynyl, C$_{3-15}$ cycloalkyl, heterocyclyl, C$_{6-10}$ aryl, or heteroaryl, wherein the alkyl, alkenyl, alkynyl, cycloalkyl, heterocyclyl, aryl, or heteroaryl is each optionally substituted with one to four $R^6$;

each $R^{11a}$ and $R^{11b}$ is independently —H, C$_{1-6}$ alkyl, oxo, or halogen;

each $R^{12}$ is C$_{1-9}$ alkyl, C$_{1-8}$ haloalkyl, C$_{2-6}$ alkenyl, C$_{2-6}$ alkynyl, halogen, oxo, —OH, —CN, —NO$_2$, —NH$_2$, —N$_3$, —SH, —O(C$_{1-9}$ alkyl), —O(C$_{1-8}$ haloalkyl), —O(C$_{2-6}$ alkenyl), —O(C$_{2-6}$ alkynyl), —O(C$_{3-15}$ cycloalkyl), —O(heterocyclyl), —O(C$_{6-10}$ aryl), —O(heteroaryl), —NH(C$_{1-9}$ alkyl), —NH(C$_{1-8}$ haloalkyl), —NH(C$_{2-6}$ alkenyl), —NH(C$_{2-6}$ alkynyl), —NH(C$_{3-15}$ cycloalkyl), —NH(heterocyclyl), —NH(C$_{6-10}$ aryl), —NH(heteroaryl), —N(C$_{1-9}$ alkyl)$_2$, —N(C$_{1-8}$ haloalkyl)$_2$, —N(C$_{2-6}$ alkenyl)$_2$, —N(C$_{2-6}$ alkynyl)$_2$, —N(C$_{3-15}$ cycloalkyl)$_2$, —N(heterocyclyl)$_2$, —N(C$_{6-10}$ aryl)$_2$, —N(heteroaryl)$_2$, —N(C$_{1-9}$ alkyl)(C$_{1-8}$ haloalkyl), —N(C$_{1-9}$ alkyl)(C$_{2-6}$ alkenyl), —N(C$_{1-9}$ alkyl)(C$_{2-6}$ alkynyl), —N(C$_{1-9}$ alkyl)(C$_{3-15}$ cycloalkyl), —N(C$_{1-9}$ alkyl)(heterocyclyl), —N(C$_{1-9}$ alkyl)(C$_{6-10}$ aryl), —N(C$_{1-9}$ alkyl)(heteroaryl), —C(O)(C$_{1-9}$ alkyl), —C(O)(C$_{1-8}$ haloalkyl), —C(O)(C$_{2-6}$ alkenyl), —C(O)(C$_{2-6}$ alkynyl), —C(O)(C$_{3-15}$ cycloalkyl), —C(O)(heterocyclyl), —C(O)(C$_{6-10}$ aryl), —C(O)(heteroaryl), —C(O)O(C$_{1-9}$ alkyl), —C(O)O(C$_{1-8}$ haloalkyl), —C(O)O(C$_{2-6}$ alkenyl), —C(O)O(C$_{2-6}$ alkynyl), —C(O)O(C$_{3-15}$ cycloalkyl), —C(O)O(heterocyclyl), —C(O)O(C$_{6-10}$ aryl), —C(O)O(heteroaryl), —C(O)NH$_2$, —C(O)NH(C$_{1-9}$ alkyl), —C(O)NH(C$_{1-8}$ haloalkyl), —C(O)NH(C$_{2-6}$ alkenyl), —C(O)NH(C$_{2-6}$ alkynyl), —C(O)NH(C$_{3-15}$ cycloalkyl), —C(O)NH(heterocyclyl), —C(O)NH(C$_{6-10}$ aryl), —C(O)NH(heteroaryl), —C(O)N(C$_{1-9}$ alkyl)$_2$, —C(O)N(C$_{1-8}$ haloalkyl)$_2$, —C(O)N(C$_{2-6}$ alkenyl)$_2$, —C(O)N(C$_{2-6}$ alkynyl)$_2$, —C(O)N(C$_{3-15}$ cycloalkyl)$_2$, —C(O)N(heterocyclyl)$_2$, —C(O)N(C$_{6-10}$ aryl)$_2$, —C(O)N(heteroaryl)$_2$, —NHC(O)(C$_{1-9}$ alkyl), —NHC(O)(C$_{1-8}$ haloalkyl), —NHC(O)(C$_{2-6}$ alkenyl), —NHC(O)(C$_{2-6}$ alkynyl), —NHC(O)(C$_{3-15}$ cycloalkyl), —NHC(O)(heterocyclyl), —NHC(O)(C$_{6-10}$ aryl), —NHC(O)(heteroaryl), —NHC(O)O(C$_{1-9}$ alkyl), —NHC(O)O(C$_{1-8}$ haloalkyl), —NHC(O)O(C$_{2-6}$ alkenyl), —NHC(O)O(C$_{2-6}$ alkynyl), —NHC(O)O(C$_{3-15}$ cycloalkyl), —NHC(O)O(heterocyclyl), —NHC(O)O(C$_{6-10}$ aryl), —NHC(O)O(heteroaryl), —NHC(O)NH(C$_{1-9}$ alkyl), —NHC(O)NH(C$_{1-8}$ haloalkyl), —NHC(O)NH(C$_{2-6}$ alkenyl), —NHC(O)NH(C$_{2-6}$ alkynyl), —NHC(O)NH(C$_{3-15}$ cycloalkyl), —NHC(O)NH(heterocyclyl), —NHC(O)NH(C$_{6-10}$ aryl), —NHC(O)NH(heteroaryl), —NHS(O)(C$_{1-9}$ alkyl), —N(C$_{1-9}$ alkyl)(S(O)(C$_{1-9}$ alkyl), —S(C$_{1-9}$ alkyl), —S(C$_{1-8}$ haloalkyl), —S(C$_{2-6}$ alkenyl), —S(C$_{2-6}$ alkynyl), —S(C$_{3-15}$ cycloalkyl), —S(heterocyclyl), —S(C$_{6-10}$ aryl), —S(heteroaryl), —S(O)N(C$_{1-9}$ alkyl)$_2$, —S(O)(C$_{1-9}$ alkyl), —S(O)(C$_{1-8}$ haloalkyl), —S(O)(C$_{2-6}$ alkenyl), —S(O)(C$_{2-6}$ alkynyl), —S(O)(C$_{3-15}$ cycloalkyl), —S(O)(heterocyclyl), —S(O)(C$_{6-10}$ aryl), —S(O)(heteroaryl), —S(O)$_2$(C$_{1-9}$ alkyl), —S(O)$_2$(C$_{1-8}$ haloalkyl), —S(O)$_2$(C$_{2-6}$ alkenyl), —S(O)$_2$(C$_{2-6}$ alkynyl), —S(O)$_2$(C$_{3-15}$), —S(O)$_2$(heterocyclyl), —S(O)$_2$(C$_{6-10}$ aryl), —S(O)$_2$(heteroaryl), —S(O)(NH)(C$_{1-9}$ alkyl), —S(O)$_2$NH(C$_{1-9}$ alkyl), or —S(O)$_2$N(C$_{1-9}$ alkyl)$_2$, wherein each alkyl, cycloalkyl, heterocyclyl, aryl, or heteroaryl is optionally substituted with 1 to 3 C$_{1-9}$ alkyl, C$_{1-8}$ haloalkyl, halogen, —OH, —NH$_2$, CO$_2$H, —O(C$_{1-9}$ alkyl), —O(C$_{1-8}$ haloalkyl), —O(C$_{3-15}$ cycloalkyl), —O(heterocyclyl), —O(aryl), —O(heteroaryl), —NH(C$_{1-9}$ alkyl), —NH(C$_{1-8}$ haloalkyl), —NH(C$_{3-15}$ cycloalkyl), —NH(heterocyclyl), —NH(aryl), —NH(heteroaryl), —N(C$_{1-9}$ alkyl)$_2$, —N(C$_{3-15}$ cycloalkyl)$_2$, —NHC(O)(C$_{1-8}$ haloalkyl), —NHC(O)(C$_{3-15}$ cycloalkyl), —NHC(O)(heterocyclyl), —NHC(O)(aryl), —NHC(O)(heteroaryl), —NHC(O)O(C$_{1-9}$ alkyl), —NHC(O)O(C$_{1-8}$ haloalkyl), —NHC(O)O(C$_{2-6}$ alkynyl), —NHC(O)O(C$_{3-15}$ cycloalkyl), —NHC(O)O(heterocyclyl), —NHC(O)O(aryl), —NHC(O)O(heteroaryl), —NHC(O)NH(C$_{1-9}$ alkyl), S(O)$_2$(C$_{1-9}$ alkyl), —S(O)$_2$(C$_{1-8}$ haloalkyl), —S(O)$_2$(C$_{3-15}$ cycloalkyl), —S(O)$_2$(heterocyclyl), —S(O)$_2$(aryl), —S(O)$_2$(heteroaryl), —S(O)(NH)(C$_{1-9}$ alkyl), —S(O)$_2$NH(C$_{1-9}$ alkyl), or —S(O)$_2$N(C$_{1-9}$ alkyl)$_2$, wherein each alkyl or heterocyclyl is optionally substituted with one to four halogens;

wherein each heterocyclyl has three to twelve ring members and has one to four heteroatoms, each independently N, O, or S; and wherein each heteroaryl has five to twelve ring members and one to four heteroatoms, each independently N, O, or S.

In some embodiments, of the compound of Formula (I), or a pharmaceutically acceptable salt thereof, $R^1$ C$_{6-10}$ aryl or 6-membered heteroaryl, each of which is optionally substituted with one to four $R^4$ In some embodiments of the compound of Formula (I), or a pharmaceutically acceptable salt thereof, $R^1$ is phenyl or 6-membered heteroaryl, each of which is optionally substituted with one to four $R^4$. In some embodiments, of the compound of Formula (I), or a pharmaceutically acceptable salt thereof, $R^1$ is

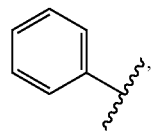 [SMILES: *c1ccccc1], optionally substituted with one to four $R^4$.

In some embodiments, of the compound of Formula (I), or a pharmaceutically acceptable salt thereof, $R^1$ is a 6-membered heteroaryl, each of which is optionally substituted with one to four $R^4$. In some embodiments, of the compound of Formula (I), or a pharmaceutically acceptable salt thereof, $R^1$ is

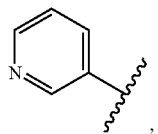

optionally substituted with one to four $R^4$.

In some embodiments, of the compound of Formula (I), or a pharmaceutically acceptable salt thereof, $R^1$ is substituted with three $R^4$. In some embodiments, of the compound of Formula (I), or a pharmaceutically acceptable salt thereof, $R^1$ is substituted with two $R^4$. In some embodiments, of the compound of Formula (I), or a pharmaceutically acceptable salt thereof, $R^1$ can be substituted with one $R^4$.

In some embodiments, of the compound of Formula (I), or a pharmaceutically acceptable salt thereof $R^1$ is 6-membered heteroaryl, wherein the heteroaryl is fused to a 5- or 6-membered ring having zero to three heteroatoms, each independently N, O, or S, to form a fused ring system, wherein the fused ring system is optionally substituted with one to four $R^5$.

In some embodiments, of the compound of Formula (I), or a pharmaceutically acceptable salt thereof, ring A is

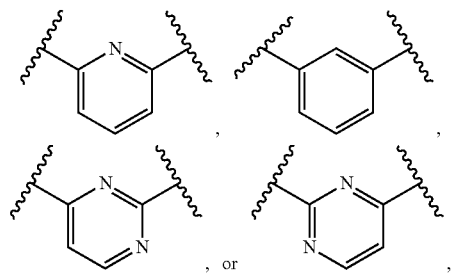

which are each optionally substituted with one to three $R^A$.

In some embodiments, of the compound of Formula (I), or a pharmaceutically acceptable salt thereof, ring A is

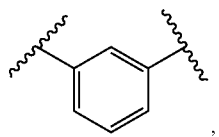 [SMILES: *c1cccc(*)c1]

which is optionally substituted with one to three $R^A$.

In some embodiments, of the compound of Formula (I), or a pharmaceutically acceptable salt thereof, ring A is

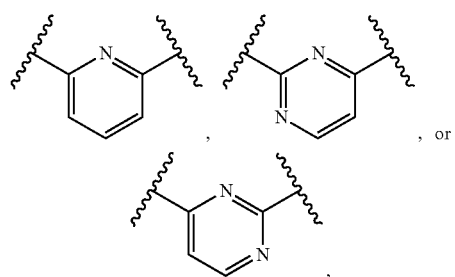

which are each optionally substituted with one to three $R^A$.

In some embodiments, of the compound of Formula (I), or a pharmaceutically acceptable salt thereof, ring A is

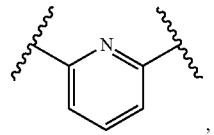

which is optionally substituted with one to three $R^A$. In some embodiments, of the compound of Formula (I), or a pharmaceutically acceptable salt thereof, ring A is

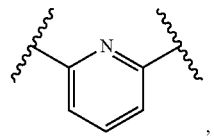

which is optionally substituted with one to three $R^A$. In some embodiments, of the compound of Formula (I), or a pharmaceutically acceptable salt thereof, ring A is

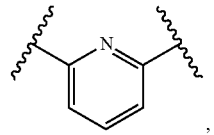 [SMILES: *c1cccc(*)n1]

which is optionally substituted with one to two $R^A$. In some embodiments, of the compound of Formula (I), or a pharmaceutically acceptable salt thereof, ring A is

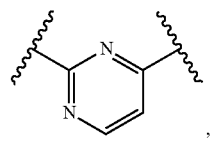 [SMILES: *c1ccnc(*)n1]

which is optionally substituted with one $R^A$.

In some embodiments, of the compound of Formula (I), or a pharmaceutically acceptable salt thereof, ring A is

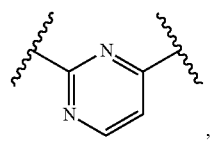 [SMILES: *c1ccnc(*)n1]

which is optionally substituted with one to three $R^A$. In some embodiments, of the compound of Formula (I), or a pharmaceutically acceptable salt thereof, ring A is

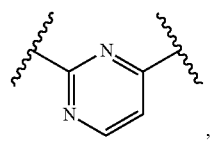 [SMILES: *c1ccnc(*)n1]

which is optionally substituted with one to two $R^A$. In some embodiments, of the compound of Formula (I), or a pharmaceutically acceptable salt thereof, ring A is

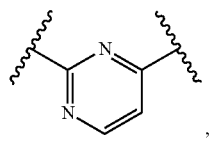, which is optionally substituted with one $R^A$.

In some embodiments of the compound of Formula (I), or a pharmaceutically acceptable salt thereof, each $R^A$ is independently $C_{1-6}$ alkyl, $C_{1-6}$ haloalkyl, $C_{1-8}$ alkoxy, $C_{1-6}$ haloalkoxy, halogen, —OH, —CN, or —N($R^{10a}$)($R^{10b}$).

In some embodiments of the compound of Formula (I), or a pharmaceutically acceptable salt thereof, ring B is $C_{6-10}$ aryl or heteroaryl, which is each optionally substituted with one to four $R^B$.

In some embodiments of the compound of Formula (I), or a pharmaceutically acceptable salt thereof, ring B is phenyl or 5 to 6 membered heteroaryl, wherein the phenyl or heteroaryl is optionally substituted with one to four $R^B$.

In some embodiments of the compound of Formula (I), or a pharmaceutically acceptable salt thereof, ring B is

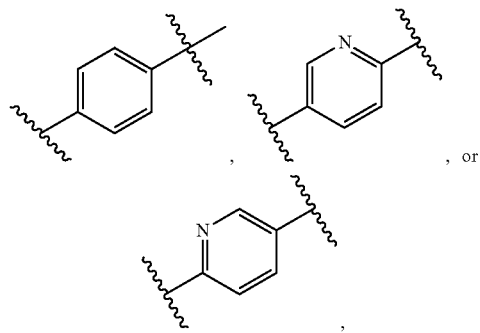, which is optionally substituted with one to four $R^B$.

In some embodiments of the compound of Formula (I), or a pharmaceutically acceptable salt thereof, ring B is

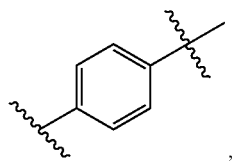 [SMILES: *c1ccc(*)cc1], which is optionally substituted with one to four $R^B$. In some embodiments of the compound of Formula (I), or a pharmaceutically acceptable salt thereof, ring B can be substituted with three $R^B$. In some embodiments of the compound of Formula (I), or a pharmaceutically acceptable salt thereof, ring B can be substituted with two $R^B$. In some embodiments of the compound of Formula (I), or a pharmaceutically acceptable salt thereof, ring B can be substituted with one $R^B$.

In some embodiments of the compound of Formula (I), or a pharmaceutically acceptable salt thereof, ring B is a phenyl or 5 to 6 membered heteroaryl, which is each fused to a 5 or 6 membered ring having zero to four heteroatoms, each independently N, O, or S, to form a fused ring system, wherein the fused ring system is optionally substituted with one to five $R^B$.

In some embodiments of the compound of Formula (I), or a pharmaceutically acceptable salt thereof, ring B is

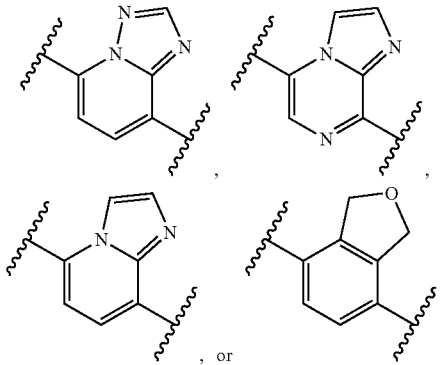, which is optionally substituted with one to five $R^B$

In some embodiments of the compound of Formula (I), or a pharmaceutically acceptable salt thereof, each $R^B$ is independently $C_{1-9}$ alkyl, $C_{1-8}$ haloalkyl, halogen, heteroaryl, oxo, or —N($R^{10a}$)($R^{10b}$).

In some embodiments of the compound of Formula (I), or a pharmaceutically acceptable salt thereof, V is $CH_2$—, —C(O)—, —C(F)$_2$—, —CH(F)—, or —CH(CH$_3$)—.

In some embodiments of the compound of Formula (I), or a pharmaceutically acceptable salt thereof $X^1$, $X^2$, and $X^3$ are each independently —CH=, —C(Br)=, —C(C≡CH$_2$CH$_2$CH$_3$)=, or —C(C≡CC(CH$_3$)(CH$_3$)(CH$_2$(OH)))=. In some embodiments of the compound of Formula (I), or a pharmaceutically acceptable salt thereof, $X^1$, $X^2$, and $X^3$ are each independently —CH=, —C(F)=, —C(Cl)=, —C(Br)=, or —C(CN)=. In some embodiments, $X^1$, $X^2$, and $X^3$ are each independently —CH= or —C(F)=. In some embodiments, two of $X^1$, $X^2$, and $X^3$ are —CH= and one is —C(F)=. In some embodiments $X^1$ is —C(F)=, and $X^2$, and $X^3$ are each —CH=. In some embodiments $X^2$ is —C(F)=, and $X^1$, and $X^3$ are each —CH=. In some embodiments $X^1$, and $X^2$ are each —CH=, and $X^3$ is —C(F)=. In some embodiments, $X^1$, $X^2$, and $X^3$ is each —CH=. In some embodiments, $X^1$, $X^2$, and $X^3$ are each independently —CH= or —C(Cl)=. In some embodiments, two of $X^1$, $X^2$, and $X^3$ are —CH= and one is —C(Cl)=. In some embodiments $X^1$ is —C(Cl)=, and $X^2$, and $X^3$ are each —CH=. In some embodiments $X^2$ is —C(Cl)=, and $X^1$, and $X^3$ are each —CH=. In some embodiments $X^1$, and $X^2$ are each —CH=, and $X^3$ is —C(Cl)=. In some embodiments, $X^1$, $X^2$, and $X^3$ is each —CH=.

In some embodiments of the compound of Formula (I), or a pharmaceutically acceptable salt thereof, $R^2$ is $C_{3-10}$ cycloalkyl or heterocyclyl, wherein the cycloalkyl or heterocyclyl is optionally substituted with one to four $Z^1$.

In some embodiments of the compound of Formula (I), or a pharmaceutically acceptable salt thereof, $R^2$ is

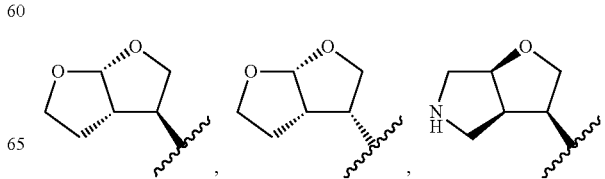,

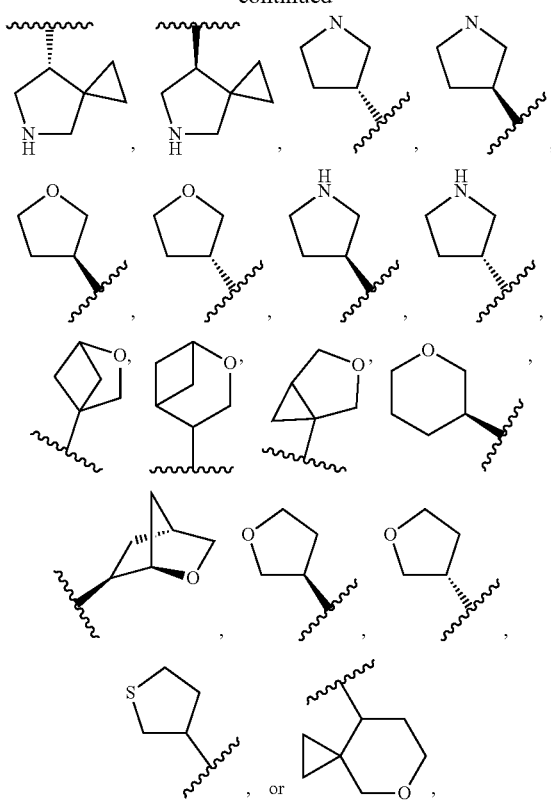

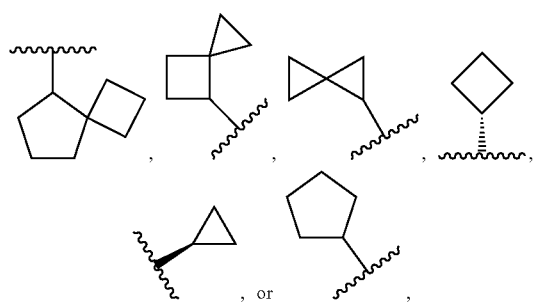

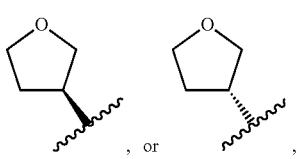 [SMILES: *[C@H]1CCOC1 ; *[C@@H]1CCOC1]

each optionally substituted with one to four $Z^1$.

In some embodiments of the compound of Formula (I), or a pharmaceutically acceptable salt thereof, $R^2$ is

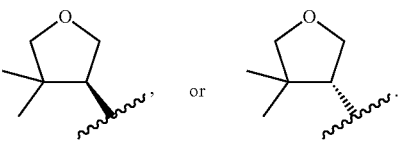

or In some embodiments of the compound of Formula (I) or a pharmaceutically acceptable salt thereof, $R^2$ is

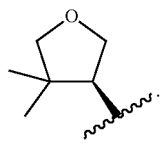 [SMILES: *[C@@H]1COCC1(C)C]

In some embodiments of the compound of Formula (I) or a pharmaceutically acceptable salt thereof, $R^2$ is

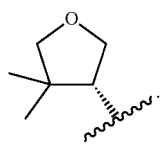 [SMILES: *[C@H]1COCC1(C)C]

In some embodiments of the compound of Formula (I), or a pharmaceutically acceptable salt thereof, $R^2$ is

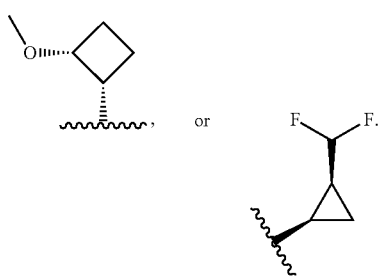

In some embodiments of the compound of Formula (I) or a pharmaceutically acceptable salt thereof, $R^2$ is

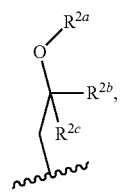

wherein
$R^{2a}$ is $C_{1-6}$ alkyl or $C_{1-6}$ haloalkyl;
$R^{2b}$ is H, or $C_{1-3}$ alkyl;
$R^{2c}$ is H, or $C_{1-3}$ alkyl; or
alternatively, $R^{2b}$ and $R^{2c}$ can bind to each other to form a ring.

In some embodiments of the compound of Formula (I) or a pharmaceutically acceptable salt thereof, $R^2$ is

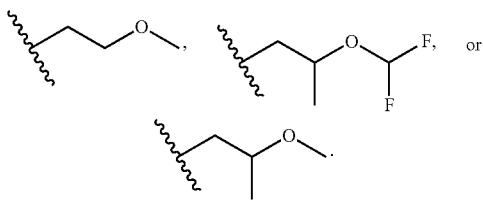

In some embodiments of the compound of Formula (I) or a pharmaceutically acceptable salt thereof, $R^2$ is

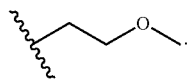

In some embodiments of the compound of Formula (I) or a pharmaceutically acceptable salt thereof, each $Z^1$ is independently $C_{1-6}$ alkyl, $C_{1-6}$ alkoxy, $C_{1-6}$ hydroxyalkyl, $C_{2-6}$ alkoxyalkyl, halogen, $C_{1-6}$ haloalkyl, $C_{1-6}$ haloalkoxy, oxo, —OH, —CN, $C_{1-6}$ alkyl-CN, —C(O)$R^{10a}$, —C(O)O—$R^{10a}$, —C(O)NH$_2$, —C(O)NH($C_{1-9}$alkyl), —N($R^{10a}$)($R^{10b}$), —N($R^{10a}$)C(O)O—$R^{10b}$, —N($R^{10a}$)C(O)—$R^{10b}$, —S(O)$_2R^{10a}$, or —S(O)$_2(C_{1-9}$ alkyl).

In some embodiments of the compound of Formula (I) or a pharmaceutically acceptable salt thereof, each $Z^1$ is independently $C_{1-6}$ alkyl, $C_{1-6}$ alkoxy, halogen, oxo, —C(O)$R^{10a}$, —C(O)O—$R^{10a}$, —C(O)NH$_2$, —C(O)NH($C_{1-9}$ alkyl), —N($R^{10a}$)($R^{10b}$), —N($R^{10a}$)C(O)O— $R^{10b}$, —N($R^{10a}$)C(O)—$R^{10b}$, —S(O)$_2R^{10a}$, or —S(O)$_2(C_{1-9}$ alkyl).

In some embodiments of the compound of Formula (I), or a pharmaceutically acceptable salt thereof, each $Z^1$ is independently $C_{1-6}$ alkyl, $C_{1-6}$ alkoxy, halogen, or $C_{1-6}$ haloalkyl.

In some embodiments of the compound of Formula (I), or a pharmaceutically acceptable salt thereof, each $Z^1$ is independently methyl, ethyl, or propyl. In some embodiments of the compound of Formula (I), or a pharmaceutically acceptable salt thereof, each $Z^1$ is independently methyl, or ethyl. In some embodiments of the compound of Formula (I), or a pharmaceutically acceptable salt thereof, each $Z^1$ is independently methyl.

In some embodiments of the compound of Formula (I), or a pharmaceutically acceptable salt thereof, $R^3$ is —C(O)OH.

In some embodiments of the compound of Formula (I), or a pharmaceutically acceptable salt thereof, each $R^4$ is independently $C_{1-9}$ alkyl, $C_{1-8}$ haloalkyl, $C_{1-6}$ haloalkoxy, $C_{2-6}$ alkoxyalkyl, halogen, $C_{3-10}$ cycloalkyl, heterocyclyl, $C_{6-10}$ aryl, heteroaryl, oxo, —NO$_2$, —CN, —N$_3$, —O—$R^{10a}$, —C(O)$R^{10a}$, —C(O)O—$R^{10}R^{10a}$, —N($R^{10a}$)($R^{10b}$), —N($R^{10a}$)$_2(R^{10b}$), —N($R^{10a}$)—C(O)$R^{10b}$, —N($R^{10a}$)S(O)$_2$—N($R^{10b}$)($R^{10c}$), —S(O)$R^{10a}$, or —S(O)(N$R^{10a}$)$R^{10b}$—S(O)$_2R^{10a}$.

In some embodiments of the compound of Formula (I), or a pharmaceutically acceptable salt thereof, each $R^4$ is independently $C_{1-9}$ alkyl, $C_{1-8}$ haloalkyl, $C_{1-6}$ haloalkoxy, $C_{2-6}$ alkoxyalkyl, halogen, $C_{3-10}$ cycloalkyl, heteroaryl, or —C(O)$R^{10a}$ In some embodiments of the compound of Formula (I), or a pharmaceutically acceptable salt thereof, each $R^4$ is independently —F, —Cl, —CN, $C_{1-9}$ alkyl, $C_{3-10}$ cycloalkyl, heterocyclyl, or —C(O)$R^{10a}$. In some embodiments of the compound of Formula (I), or a pharmaceutically acceptable salt thereof, each $R^4$ is independently —F, —Cl, —CN, or heteroaryl. In some embodiments of the compound of Formula (I), or a pharmaceutically acceptable salt thereof, each $R^4$ is independently —F, —Cl, of —CN. In some embodiments of the compound of Formula (I), or a pharmaceutically acceptable salt thereof, each $R^4$ is independently —F, —Cl, or heteroaryl. In some embodiments of the compound of Formula (I), or a pharmaceutically acceptable salt thereof, each $R^4$ heteroaryl is a pyrole, imidazole, triazole or a thiazole. In some embodiments of the compound of Formula (I), or a pharmaceutically acceptable salt thereof, each $R^4$ heteroaryl is an imidazole or a triazole. In some embodiments of the compound of Formula (I), or a pharmaceutically acceptable salt thereof, each $R^4$ heteroaryl is a triazole.

In some embodiments of the compound of Formula (I), or a pharmaceutically acceptable salt thereof, each $R^5$ is independently $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, heteroaryl, $C_{6-10}$ aryl, oxo, —N$_3$, —CN, —O—$R^{10a}$, —C(O)—$R^{10a}$, —C(O)O—$R^{10a}$, C(O)—N($R^{10a}$)($R^{10b}$), —N($R^{10a}$)($R^{10b}$), —N($R^{10a}$)$_2(R^{10b}$)$^+$, —N($R^{10a}R^{10b}$)C(O)—$R^{10b}$, —N($R^{10a}$)C(O)O—$R^{10b}$, —N($R^{10a}$)C(O)N($R^{10b}$)($R^{10c}$), or —OC(O)—N($R^{10a}$)($R^{10b}$).

In some embodiments of the compound of Formula (I), or a pharmaceutically acceptable salt thereof, each $R^5$ is independently $C_{1-9}$ alkyl, $C_{1-8}$ haloalkyl, $C_{1-6}$ alkoxy, $C_{2-6}$ alkoxyalkyl, halogen, $C_{3-15}$ cycloalkyl, heteroaryl, or —CN.

In some embodiments of the compound of Formula (I), or a pharmaceutically acceptable salt thereof, each $R^6$ is independently $C_{1-9}$ alkyl, $C_{1-6}$ alkoxy, $C_{2-6}$ alkoxyalkyl, $C_{1-8}$ haloalkyl, halogen, $C_{3-15}$ cycloalkyl, heterocyclyl, $C_{6-10}$ aryl, heteroaryl, —O($C_{1-9}$ alkyl), —O($C_{1-8}$ haloalkyl), —O($C_{2-6}$ alkenyl), —O($C_{2-6}$ alkynyl), —O($C_{3-15}$ cycloalkyl), —O(heterocyclyl), —O($C_{6-10}$ aryl), —O(heteroaryl), —NH($C_{1-9}$ alkyl), —NH($C_{1-8}$ haloalkyl), —NH($C_{2-6}$ alkenyl), —NH($C_{2-6}$ alkynyl), —NH($C_{3-15}$ cycloalkyl), —NH(heterocyclyl), —NH($C_{6-10}$ aryl), or —NH(heteroaryl).

In some embodiments of the compound of Formula (I), or a pharmaceutically acceptable salt thereof, each $R^6$ is independently $C_{1-9}$ alkyl, $C_{1-6}$ alkoxy, $C_{2-6}$ alkoxyalkyl, $C_{1-8}$ haloalkyl, $C_{3-15}$ cycloalkyl or halogen.

In some embodiments of the compound of Formula (I), or a pharmaceutically acceptable salt thereof, each $R^7$ is independently $C_{1-9}$ alkyl, $C_{1-6}$ alkoxy, $C_{2-6}$ alkoxyalkyl, $C_{1-8}$ haloalkyl, oxo, —OH, —CN, —NH$_2$, or halogen.

In some embodiments of the compound of Formula (I), or a pharmaceutically acceptable salt thereof, each $R^7$ is $C_{2-6}$ alkoxyalkyl.

In some embodiments, a compound of Formula (II) is provided:

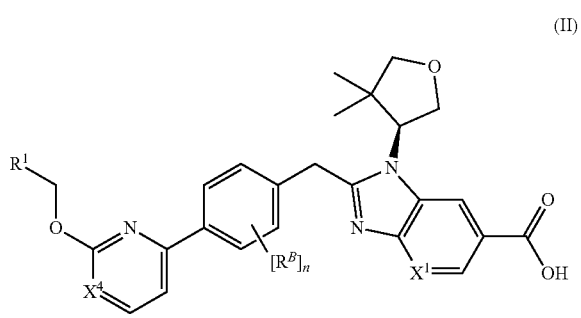

or a pharmaceutically acceptable salt thereof, wherein
$R^1$ is a phenyl or 6 membered heteroaryl optionally substituted with $R^4$;

$X^1$ is —C(H)= or —C($R^8$)=;

$X^4$ is —C(H)=, —C($R^8$)= or N;

each $R^4$ is independently halogen or —CN;

each $R^B$ is independently $C_{1-9}$ alkyl, $C_{1-8}$ haloalkyl, or halogen;

each $R^8$ is independently H or halogen; and n is 0, 1, 2, or 3.

In some embodiments, a compound of Formula (I) is a compound according to Formula (II).

In some embodiments, of a compound of Formula (II), or a pharmaceutically acceptable salt thereof, $R^1$ is phenyl, substituted with halogen or —CN.

In some embodiments, of a compound of Formula (II), or a pharmaceutically acceptable salt thereof, $R^1$ is

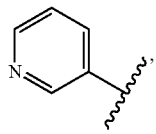

substituted with halogen or —CN.

In some embodiments, of a compound of Formula (II), or a pharmaceutically acceptable salt thereof, $R^1$ is

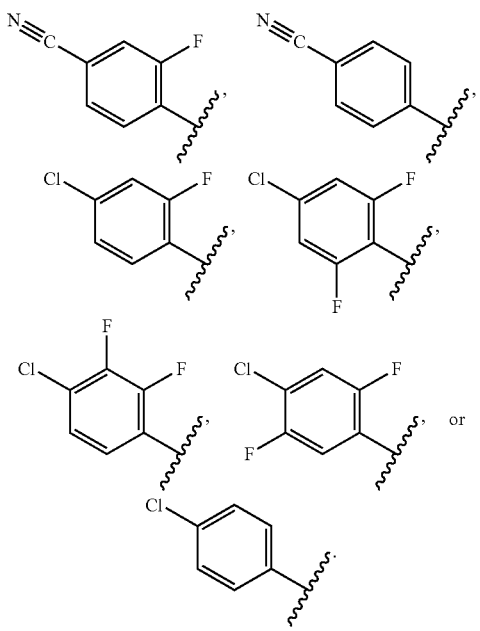

In some embodiments, a compound of Formula (III), or a pharmaceutically acceptable salt thereof, wherein $R^B$ is methyl, ethyl, F, or Cl. In some embodiments, a compound of Formula (III), or a pharmaceutically acceptable salt thereof, wherein $R^B$ is methyl or F. In some embodiments, embodiments, a compound of Formula (III), or a pharmaceutically acceptable salt thereof, wherein $R^B$ is F.

In some embodiments of a compound of Formula (II), or a pharmaceutically acceptable salt thereof, $R^8$ is F or Cl.

In some embodiments, a compound of Formula (III) is provided:

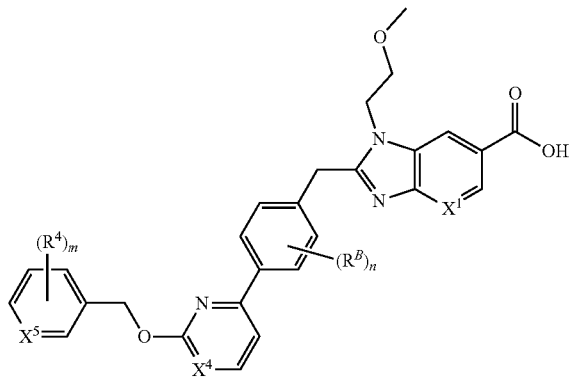

(III)

or a pharmaceutically acceptable salt thereof, wherein $X^1$ is —C(H)= or —C($R^8$)=;

$X^4$ is —C(H)=, —C($R^8$)= or N;

$X^5$ is —C(H)= or N;

each $R^B$ is independently $C_{1-9}$ alkyl, $C_{1-8}$ haloalkyl, or halogen;

each $R^4$ is independently pyrole, imidazole, triazole or a thiazole;

each $R^8$ is independently halogen;

m is 0, or 1; and n is 0, 1, 2, or 3.

In some embodiments, a compound of Formula (I) is a compound according to Formula (III).

In some embodiments, a compound of Formula (III), or a pharmaceutically acceptable salt thereof, wherein $R^B$ is methyl, ethyl, F, or Cl. In some embodiments, a compound of Formula (III), or a pharmaceutically acceptable salt thereof, wherein $R^B$ is methyl or F. In some embodiments, embodiments, a compound of Formula (III), or a pharmaceutically acceptable salt thereof, wherein $R^B$ is F.

In some embodiments, a compound of Formula (III), or a pharmaceutically acceptable salt thereof, wherein $R^4$ is imidazole or triazole. In some embodiments, a compound of Formula (III), or a pharmaceutically acceptable salt thereof, wherein $R^4$ is triazole.

In some embodiments, a compound of Formula (III), or a pharmaceutically acceptable salt thereof, wherein $R^4$ is

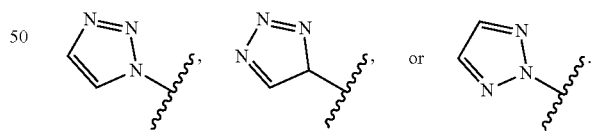

In some embodiments, a compound of Formula (III), or a pharmaceutically acceptable salt thereof, wherein $R^4$ is

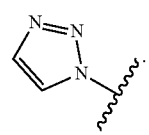 [SMILES: *n1ccnn1]

In some embodiments, the compound of Formula (I), Formula (II) or Formula (III), or pharmaceutically acceptable salt thereof, has the structure of a compound in Table 2.

Also disclosed herein are the in vivo metabolic products of the compounds described herein, to the extent such products are novel and unobvious over the prior art. Such products may result for example from the oxidation, reduction, hydrolysis, amidation, esterification and the like of the administered compound, primarily due to enzymatic processes. Accordingly, included are novel and unobvious compounds produced by a process comprising contacting a compound with a mammal for a period of time sufficient to yield a metabolic product thereof. Such products typically are identified by preparing a radiolabeled (e.g. $^{14}$C or $^{3}$H) compound, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products can be easily isolated since they are labeled (others are isolated by the use of antibodies capable of binding epitopes surviving in the metabolite). The metabolite structures are determined in conventional fashion, e.g. by MS or NMR analysis. In general, analysis of metabolites can be done in the same way as conventional drug metabolism studies well-known to those skilled in the art. The conversion products, so long as they are not otherwise found in vivo, can be useful in diagnostic assays for therapeutic dosing of the compounds even if they possess no GLP-1R activity of their own.

Recipes and methods for determining stability of compounds in surrogate gastrointestinal secretions are known. Compounds are defined herein as stable in the gastrointestinal tract where less than about 50 mole percent of the protected groups are deprotected in surrogate intestinal or gastric juice upon incubation for 1 hour at 37° C. Simply because the compounds are stable to the gastrointestinal tract does not mean that they cannot be hydrolyzed in vivo. The prodrugs typically will be stable in the digestive system but may be substantially hydrolyzed to the parental drug in the digestive lumen, liver, lung or other metabolic organ, or within cells in general. As used herein, a prodrug is understood to be a compound that is chemically designed to efficiently liberate the parent drug after overcoming biological barriers to oral delivery.

II. Methods of Preparing Compounds

The compounds of the present disclosure can be prepared by any method known in the art. The following exemplary general methods illustrate routes that may be used to obtain a compound of the present disclosure.

Scheme 1

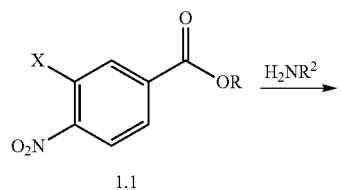
1.1

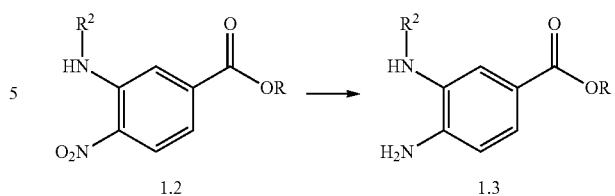

Intermediate 1.3 may be assembled by reacting an amine with Intermediate 1.1, wherein X is a halogen, and R is an alkyl, alkylaryl, or aryl, in the presence of a suitable base (e.g. DIPEA, KOtBu, etc.) to give Intermediate 1.2. Intermediate 1.2 can be converted to Intermediate 1.3 using suitable reducing conditions (e.g. $H_2$ and Pd/C, Fe and HCl, etc.).

Scheme 2

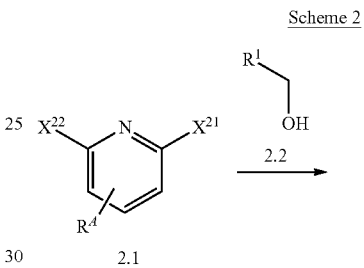
2.1

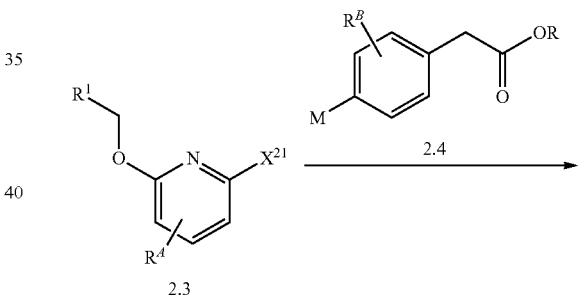
2.3

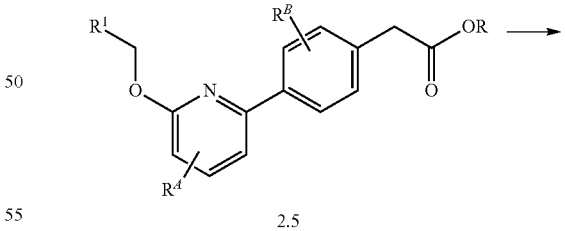
2.5

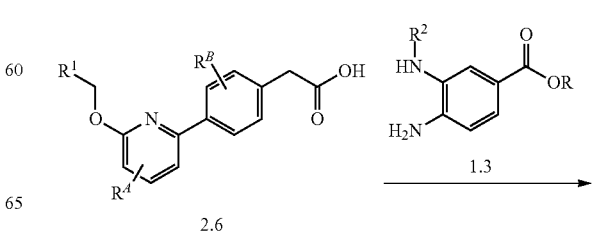
2.6

-continued

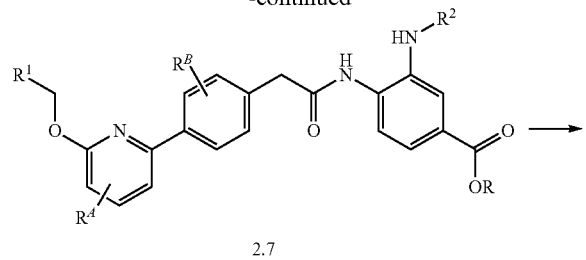

2.7

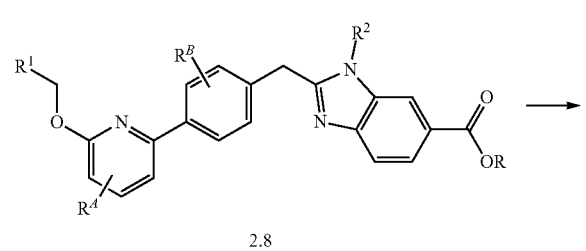

2.8

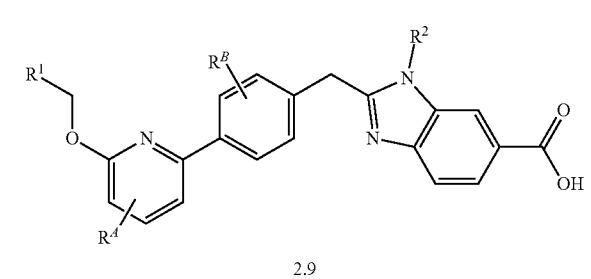

2.9

Compounds of Formula (I) having the structure of a compound of Formula 2.9 can be assembled by first coupling Intermediate 2.1, wherein $X^{21}$ and $X^{22}$ is each a leaving group, e.g., a halogen such as Cl or Br, with a heteroatom containing Intermediate 2.2 (where Y=O, NH, or S) using either a suitable base (e.g., DIPEA, KOtBu, etc.) or through metal mediated cross-coupling using a suitable palladium catalyst to give Intermediate 2.3 (Scheme 2). Intermediate 2.4 (where M=Li, MgBr, MgCl, or MgI, purchased commercially or obtained through metalation of a corresponding halide) can be combined with Intermediate 2.3 using a suitable palladium catalyst to deliver Intermediate 2.5. Following conversion to the acid Intermediate 2.6 using standard conditions (e.g. LiOH, LiI and pyridine, etc.), the Intermediate 1.3 can be added using standard amide bond forming conditions (e.g. DIPEA with HATU, etc.) to give Intermediate 2.7, which can, in turn, be converted to the corresponding benzimidazole Intermediate 2.8 under the influence of an acid catalyst (e.g. HCl, AcOH, etc.) or dehydrating agents (e.g., POCl$_3$, Tf$_2$O/triphenylphosphine oxide, etc.). This intermediate can be converted to the compound of Formula (I) using standard ester hydrolysis conditions (e.g., LiOH, LiI and pyridine, etc.).

While the above Scheme 2 is illustrated using Intermediate 2.1 as a dihalopyridine, any dihalogenated A-ring starting material can be used to obtain the analogous compound of Formula (I).

Scheme 3

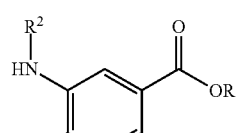

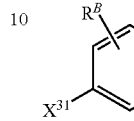

3.1

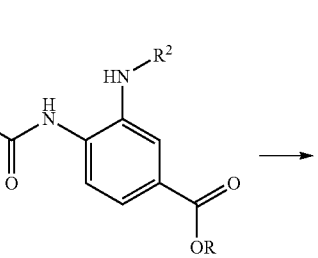

3.2

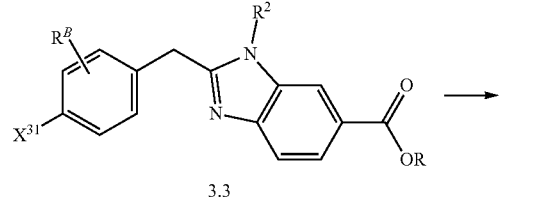

3.3

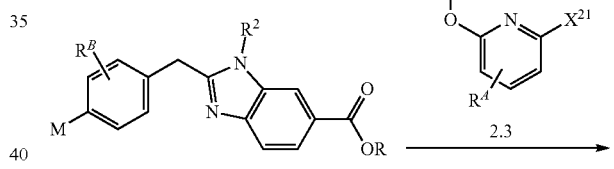

3.4

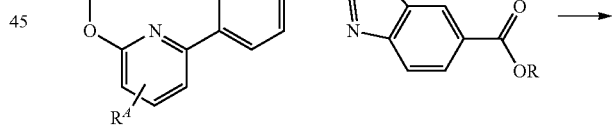

2.8

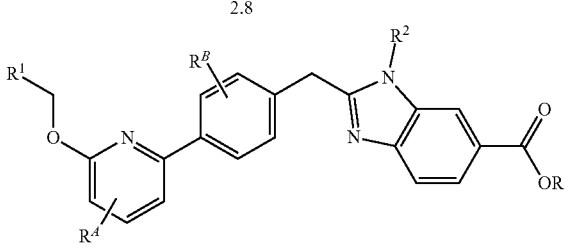

2.9

In some embodiments, a compound of Formula (I) having the structure of a compound of Formula 2.9 can be assembled first by the combination of Intermediate 3.1 (wherein X31 is Cl, Br, or I) with Intermediate 1.3 (wherein R=alkyl, alkylaryl, or aryl) under standard amide bond forming conditions, e.g. DIPEA with HATU, etc. (Scheme 3). Treatment with a suitable acid catalyst (e.g. HCl, AcOH, etc.) or dehydrating agents (e.g., POCl₃, Tf₂O/triphenylphosphine oxide, etc.) can deliver Intermediate 3.3. Halogen metal exchange of —X31 to -M can be achieved using a suitable reagent (e.g. iPrMgBr, etc.) or transition metal coupling using a suitable palladium catalyst and metal source (e.g. B2Pin2, Bu6Sn2, etc.) to give Intermediate 2.8 which can be converted to the compound of Formula (I) using standard ester hydrolysis conditions (e.g. LiOH, LiI and pyridine, etc.).

Scheme 4

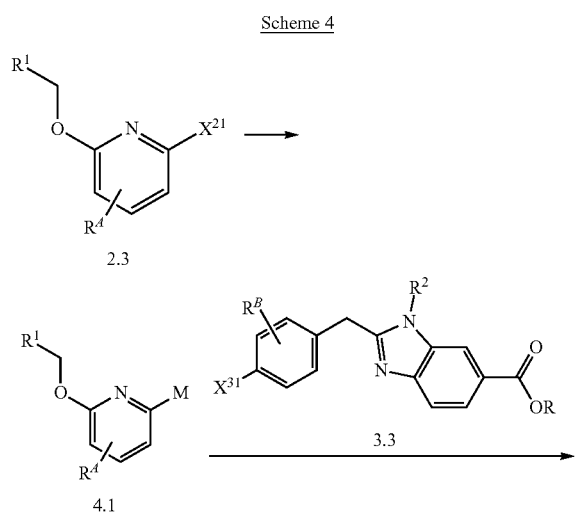

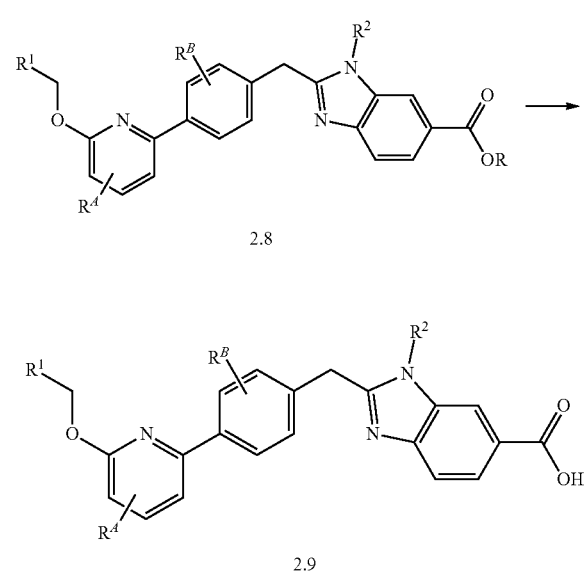

In some embodiments, a compound of Formula 2.9 can be formed by first conversion of Intermediate 2.3 to the metallated variant Intermediate 4.1 using a suitable palladium catalyst and metal source, e.g. B₂Pin₂, Bu₆Sn₂, etc. (Scheme 4). Intermediate 4.1 can be coupled to Intermediate 3.3 using a suitable palladium catalyst to deliver Intermediate 2.8 which can then be converted to the compound of Formula (I) using standard ester hydrolysis conditions, e.g. LiOH, LiI and pyridine, etc.

Scheme 5

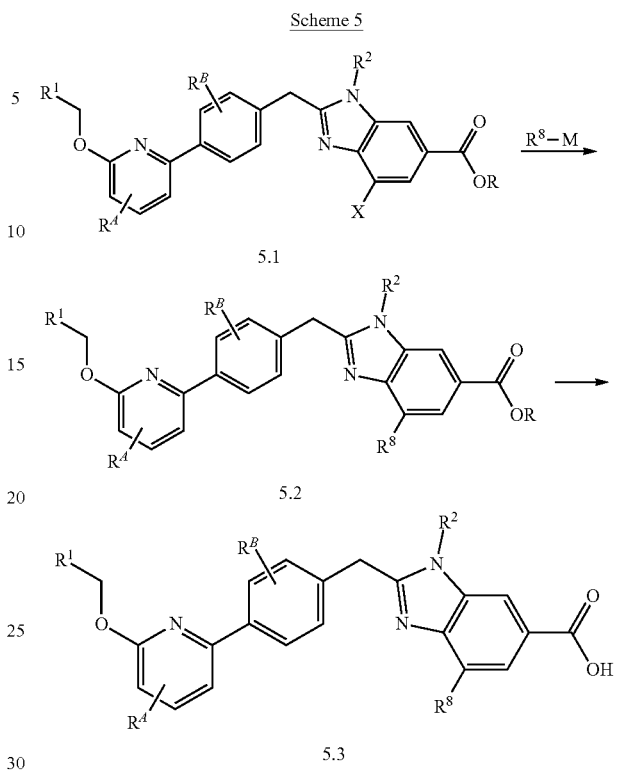

A compound of Formula (I-A-1) and/or Formula (I) having the structure of a compound of Formula 5.3 can be assembled via first coupling to the halogen —X (wherein X is Cl, Br, or I) of Intermediate 5.1 using a suitable coupling partner and palladium catalyst to deliver Intermediate 5.2 which can be converted to a compound of Formula 5.3 using standard ester hydrolysis conditions, e.g. LiOH, LiI and pyridine, etc. (Scheme 5).

Scheme 6

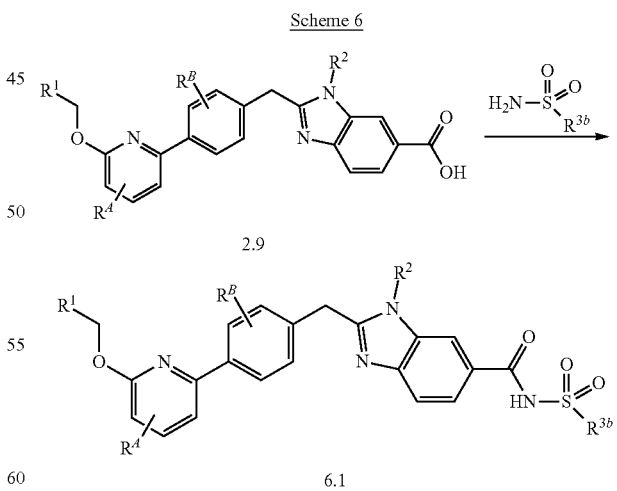

A compound of Formula (I) having the structure of a compound of Formula 6.1 can be obtained through the reaction of Intermediate 2.9 with a sulfonamide under suitable coupling conditions (e.g. EDCI and DMAP, etc.) (Scheme 6).

Scheme 7

7.1

7.2

7.3

A compound of Formula (I) having the structure of a compound of Formula 7.3 can be assembled via first coupling to the halogen —X of Intermediate 7.1 using a suitable coupling partner and palladium catalyst to deliver Intermediate 7.2, which can be converted to a compound of Formula 7.3 using standard ester hydrolysis conditions (e.g. LiOH, LiI and pyridine, etc.) (Scheme 7).

Scheme 8

3.4

8.1

2.8

2.9

A compound of Formula (I) having the structure of a compound of Formula 2.9 can be assembled through first cross-coupling of an Intermediate 3.4 with Intermediate 2.1 using a suitable transition metal catalyst (e.g. palladium, etc.) (Scheme 8). This can then be coupled with a heteroatom containing Intermediate 2.2 (where Y=O, N or S) using either a suitable base (e.g. DIPEA, KOtBu, etc.) or through metal mediated cross-coupling using a suitable palladium catalyst to give Intermediate 2.8. Intermediate 2.8 can be converted to the compound of Formula (I) having the structure of a compound of Formula 2.9 using standard ester hydrolysis conditions (e.g. LiOH, LiI and pyridine, etc.).

Scheme 9

3.4

9.2

2.8

-continued

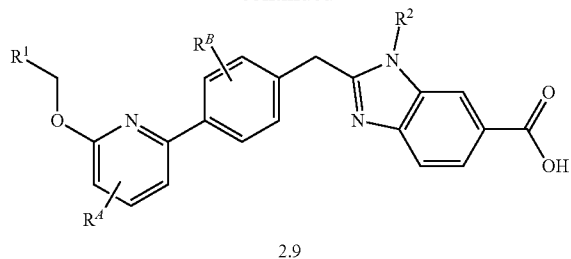

2.9

A compound of Formula (I) having the structure of a compound of Formula 2.9 can be assembled through first cross-coupling of an Intermediate 3.4 with Intermediate 9.1 using a suitable transition metal catalyst (e.g. palladium, etc.) (Scheme 9). The benzyl ether can then be removed through reduction using $H_2$ and a suitable catalyst (Pd/C, etc.) to yield intermediate 9.2. Intermediate 9.2 can then be alkylated using a suitable base ($K_2CO_3$, $Cs_2CO_3$, $Ag_2CO_3$, etc.) a suitable electrophile represented by intermediate 9.3 where $X^{91}$ can be —Cl, —Br, I, or —OTs. Intermediate 2.8 can be converted to the compound of Formula (I) having the structure of a compound of Formula 2.9 using standard ester hydrolysis conditions (e.g. LiOH, LiI and pyridine, etc.).

Scheme 10

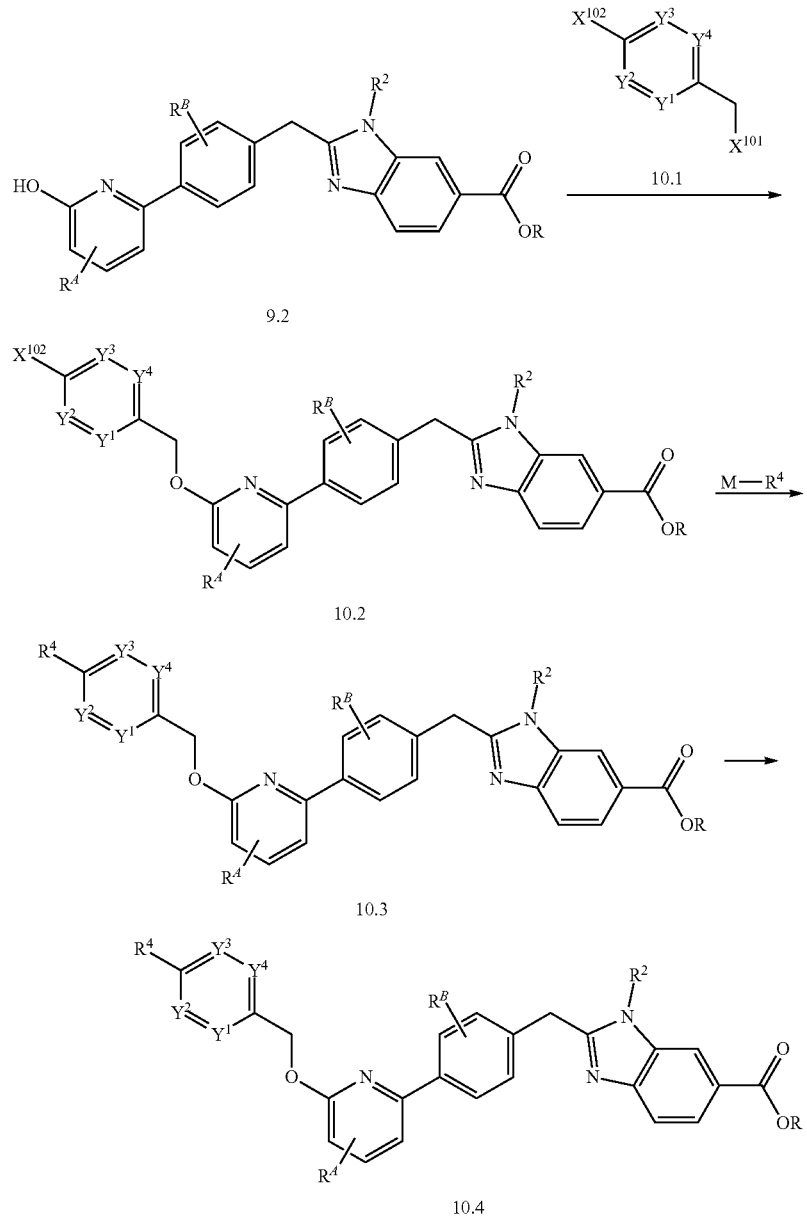

A compound of Formula (I) having the structure of a compound of Formula 10.4 can be assembled through first alkylation if intermediate 9.2 with an intermediate of the type 10.1 using a suitable base ($K_2CO_3$, $Cs_2CO_3$, $Ag_2CO_3$, etc.) where $X^{101}$ and $X^{102}$ are each independently —Cl, —Br, —I, —OTs, or —OTf and $Y^1$, $Y^2$, $Y^3$, and $Y^4$ are each independently —CH═ or —N═. Intermediate 10.2 is then converted to intermediate 10.3 using a suitable transition metal catalyst (e.g. palladium, etc.). Intermediate 10.3 can be converted to the compound of Formula (I) having the structure of a compound of Formula 10.4 using standard ester hydrolysis conditions (e.g. LiOH, LiI and pyridine, etc.).

IV. Pharmaceutical Formulations

In some embodiments, the present disclosure provides a pharmaceutical composition comprising a compound of the present disclosure (e.g. a compound of Formula (I)), or a pharmaceutically acceptable salt thereof, and a pharmaceutically acceptable carrier or excipient.

In some embodiments of the disclosure, the pharmaceutical composition comprises a compound of Formula (I), or a pharmaceutically acceptable salt thereof, and one or more additional therapeutic agents, as more fully set forth below.

Pharmaceutical compositions comprising the compounds disclosed herein, or pharmaceutically acceptable salts thereof, may be prepared with one or more pharmaceutically acceptable excipients which may be selected in accord with ordinary practice. Tablets may contain excipients including glidants, fillers, binders and the like. Aqueous compositions may be prepared in sterile form, and when intended for delivery by other than oral administration generally may be isotonic. In some embodiments, compositions may contain excipients such as those set forth in the Rowe et al, Handbook of Pharmaceutical Excipients, 6th edition, American Pharmacists Association, 2009. Excipients can include ascorbic acid and other antioxidants, chelating agents such as EDTA, carbohydrates such as dextrin, hydroxyalkyl cellulose, hydroxyalkylmethyl cellulose, stearic acid and the like. In some embodiments, the composition is provided as a solid dosage form, including a solid oral dosage form.

The compositions include those suitable for various administration routes, including oral administration. The compositions may be presented in unit dosage form and may be prepared by any of the methods well known in the art of pharmacy. Such methods include the step of bringing into association the active ingredient (e.g., a compound of the present disclosure or a pharmaceutical salt thereof) with one or more pharmaceutically acceptable excipients. The compositions may be prepared by uniformly and intimately bringing into association the active ingredient with liquid excipients or finely divided solid excipients or both, and then, if desired, shaping the product. Techniques and formulations generally are found in Remington: The Science and Practice of Pharmacy, 21st Edition, Lippincott Williams and Wilkins, Philadelphia, Pa., 2006.

Compositions described herein that are suitable for oral administration may be presented as discrete units (a unit dosage form) including but not limited to capsules, sachets or tablets each containing a predetermined amount of the active ingredient. In one embodiment, the pharmaceutical composition of the disclosure is a tablet.

Pharmaceutical compositions disclosed herein comprise one or more compounds disclosed herein, or a pharmaceutically acceptable salt thereof, together with a pharmaceutically acceptable excipient and optionally other therapeutic agents. Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more excipients including sweetening agents, flavoring agents, coloring agents and preserving agents, in order to provide a palatable preparation. Tablets containing the active ingredient in admixture with non-toxic pharmaceutically acceptable excipients which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

The amount of active ingredient that may be combined with the inactive ingredients to produce a dosage form may vary depending upon the intended treatment subject and the mode of administration. For example, in some embodiments, a dosage form for oral administration to humans may contain approximately 1 to 1000 mg of active material formulated with an appropriate and convenient amount of a pharmaceutically acceptable excipient. In some embodiments, the pharmaceutically acceptable excipient varies from about 5 to about 95% of the total compositions (weight:weight).

In some embodiments, a composition comprising a compound of the present disclosure, or a pharmaceutically acceptable salt thereof in one variation does not contain an agent that affects the rate at which the active ingredient is metabolized. Thus, it is understood that compositions comprising a compound of the present disclosure in one aspect do not comprise an agent that would affect (e.g., slow, hinder or retard) the metabolism of a compound of the present disclosure or any other active ingredient administered separately, sequentially or simultaneously with a compound of the present disclosure. It is also understood that any of the methods, kits, articles of manufacture and the like detailed herein in one aspect do not comprise an agent that would affect (e.g., slow, hinder or retard) the metabolism of a compound of the present disclosure or any other active ingredient administered separately, sequentially or simultaneously with a compound of the present disclosure.

In some embodiments, the pharmaceutical compositions described above are for use in a human or an animal.

The disclosure further includes a compound of the present disclosure for administration as a single active ingredient of a pharmaceutically acceptable composition which can be prepared by conventional methods known in the art, for example by binding the active ingredient to a pharmaceutically acceptable, therapeutically inert organic and/or inorganic carrier or excipient, or by mixing therewith.

In one aspect, provided herein is the use of a compound of the present disclosure as a second or other active ingredient having a synergistic effect with other active ingredients in known drugs, or administration of the compound of the present disclosure together with such drugs.

The compound of the present disclosure may also be used in the form of a prodrug or other suitably modified form which releases the active ingredient in vivo.

V. Routes of Administration

The compounds of the present disclosure (also referred to herein as the active ingredients), can be administered by any route appropriate to the condition to be treated. Suitable routes include oral, rectal, nasal, topical (including buccal and sublingual), transdermal, vaginal and parenteral (including subcutaneous, intramuscular, intravenous, intradermal, intratumoral, intrathecal and epidural), and the like. It will be appreciated that the preferred route may vary with for example the condition of the recipient. An advantage of certain compounds disclosed herein is that they are orally bioavailable and can be dosed orally.

A compound of the present disclosure may be administered to an individual in accordance with an effective dosing regimen for a desired period of time or duration, such as at least about one month, at least about 2 months, at least about 3 months, at least about 6 months, or at least about 12 months or longer. In one variation, the compound is administered on a daily or intermittent schedule for the duration of the individual's life.

The dosage or dosing frequency of a compound of the present disclosure may be adjusted over the course of the treatment, based on the judgment of the administering physician.

The compound may be administered to an individual (e.g., a human) in an effective amount. In some embodiments, the compound is administered once daily.

The compound can be administered by any useful route and means, such as by oral or parenteral (e.g., intravenous) administration. Therapeutically effective amounts of the compound may include from about 0.00001 mg/kg body weight per day to about 10 mg/kg body weight per day, such as from about 0.0001 mg/kg body weight per day to about 10 mg/kg body weight per day, or such as from about 0.001 mg/kg body weight per day to about 1 mg/kg body weight per day, or such as from about 0.01 mg/kg body weight per day to about 1 mg/kg body weight per day, or such as from about 0.05 mg/kg body weight per day to about 0.5 mg/kg body weight per day, or such as from about 0.3 mg to about 30 mg per day, or such as from about 30 mg to about 300 mg per day.

A compound of the present disclosure may be combined with one or more additional therapeutic agents in any dosage amount of the compound of the present disclosure (e.g., from 1 mg to 1000 mg of compound). Therapeutically effective amounts may include from about 1 mg per dose to about 1000 mg per dose, such as from about 50 mg per dose to about 500 mg per dose, or such as from about 100 mg per dose to about 400 mg per dose, or such as from about 150 mg per dose to about 350 mg per dose, or such as from about 200 mg per dose to about 300 mg per dose. Other therapeutically effective amounts of the compound of the present disclosure are about 100, 125, 150, 175, 200, 225, 250, 275, 300, 325, 350, 375, 400, 425, 450, 475, or about 500 mg per dose. Other therapeutically effective amounts of the compound of the present disclosure are about 100 mg per dose, or about 125, 150, 175, 200, 225, 250, 275, 300, 350, 400, 450, or about 500 mg per dose. A single dose can be administered hourly, daily, or weekly. For example, a single dose can be administered once every 1 hour, 2, 3, 4, 6, 8, 12, 16 or once every 24 hours. A single dose can also be administered once every 1 day, 2, 3, 4, 5, 6, or once every 7 days. A single dose can also be administered once every 1 week, 2, 3, or once every 4 weeks. In some embodiments, a single dose can be administered once every week. A single dose can also be administered once every month.

Kits that comprise a compound of the present disclosure, or an enantiomer, or pharmaceutically acceptable salt thereof, or a pharmaceutical composition containing any of the above, are also included in the present disclosure. In one embodiment, a kit further includes instructions for use. In one aspect, a kit includes a compound of the disclosure, or a pharmaceutically acceptable salt, tautomer, stereoisomer, mixture of stereoisomers, prodrug, or deuterated analog thereof, and a label and/or instructions for use of the compounds in the treatment of the indications, such as the diseases or conditions, described herein. In one embodiment, kits comprising a compound of the present disclosure, or a pharmaceutically acceptable salt thereof, in combination with one or more (e.g., one, two, three, four, one or two, or one to three, or one to four) additional therapeutic agents are provided.

Provided herein are also articles of manufacture that include a compound of the present disclosure or a pharmaceutically acceptable salt, tautomer, stereoisomer, mixture of stereoisomers, prodrug, or deuterated analog thereof in a suitable container. The container may be a vial, jar, ampoule, preloaded syringe, and intravenous bag.

VI. Combination Therapy

In some embodiments, a compound of the present disclosure, or a pharmaceutically acceptable salt thereof, can be combined with a therapeutically effective amount of one or more (e.g., one, two, three, four, one or two, one to three, or one to four) additional therapeutic agents. In some embodiments, the additional therapeutic agent comprises an apoptotic signal-regulating kinase (ASK-1) inhibitor, a farnesoid X receptor (FXR) agonist, a peroxisome proliferator-activated receptor alpha (PPARα) agonist, fish oil, an acetyl-coA carboxylase (ACC) inhibitor, a TGFβ antagonist, a LPAR antagonist, a SGLT2 inhibitor, a Tpl2 inhibitor, or a GLP-1 agonist combination thereof.

The benefit of combination may be increased efficacy and/or reduced side effects for a component as the dose of that component may be adjusted down to reduce its side effects while benefiting from its efficacy augmented by the efficacy of the compound of the present disclosure.

In some embodiments, the therapeutic agent, or combination of therapeutic agents, are a(n) ACE inhibitor, 2-Acylglycerol O-acyltransferase 2 (DGAT2) inhibitor, Acetaldehyde dehydrogenase inhibitor, Acetyl CoA carboxylase inhibitor, Adrenergic receptor agonist, Alstrom syndrome protein 1 (ALMS1)/PKC alpha protein interaction inhibitor, Apelin receptor agonist, Diacylglycerol O acyltransferase 2 inhibitor, Adenosine A3 receptor agonist, Adenosine A3 receptor antagonist, Adiponectin receptor agonist, Aldehyde dehydrogenase 2 stimulator, AKT protein kinase inhibitor, AMP-activated protein kinases (AMPK), AMP kinase activator, ATP citrate lyase inhibitor, AMP activated protein kinase stimulator, Endothelial nitric oxide synthase stimulator, NAD-dependent deacetylase sirtuin-1 stimulator, Adrenergic receptor antagonist, Androgen receptor agonist, Amylin receptor agonist, Angiotensin II AT-1 receptor antagonist, Apical sodium-dependent bile acid transport inhibitor, Autophagy protein modulator, Autotaxin inhibitors, Axl tyrosine kinase receptor inhibitor, Bax protein stimulator, Beta-catenin inhibitor, Bioactive lipid, Calcitonin agonist, Cannabinoid receptor modulator, Caspase inhibitor, Caspase-3 stimulator, Cathepsin inhibitor, Caveolin 1 inhibitor, CCK receptor antagonist, CCL26 gene inhibitor, CCR2 chemokine antagonist, CCR2 chemokine antagonist, Angiotensin II AT-1 receptor antagonist, CCR3 chemokine antagonist, CCR5 chemokine antagonist, CD3 antagonist, CDGSH iron sulfur domain protein modulator, chitinase inhibitor, Chloride channel stimulator, Chitotriosidase 1 inhibitor, CNR1 inhibitor, Connective tissue growth factor ligand inhibitor, COT protein kinase inhibitor, Cyclin D1 inhibitor, Cytochrome P450 7A1 inhibitor, Cytochrome P450 reductase inhibitors, DGAT1/2 inhibitor, Diacylglycerol O acyltransferase 1 inhibitor (DGAT1), Cytochrome P450 2E1 inhibitor (CYP2E1), CXCR3 chemokine antagonist, CXCR4 chemokine antagonist, Dihydroceramide delta 4 desaturase inhibitor, Dihydroorotate dehydrogenase inhibitor, Dipeptidyl peptidase IV inhibitor, Endosialin modulator, Eotaxin ligand inhibitor, Extracellular matrix protein modulator, Farnesoid X receptor agonist, Fatty acid synthase inhibitors, FGF1 receptor agonist, Fibroblast growth factor (FGF-15, FGF-19, FGF-21) ligands, fibroblast activation protein inhibitor, Free fatty acid receptor 1 agonist, Galectin-3 inhibitor, GDNF family receptor alpha like agonist, Glucagon receptor agonist, Glucagon-like peptide 1 agonist, Glucocorticoid receptor antagonist, Glucose 6-phosphate 1-dehydrogenase inhibitor, G-protein coupled bile acid receptor 1 agonist, G-protein coupled receptor-119 agonist, G-protein coupled receptor 84 antagonist, Hedgehog (Hh) modulator, Hepatitis C virus NS3 protease inhibitor, Hepatocyte nuclear factor 4 alpha modulator (HNF4A), Hepatocyte growth factor modulator, Histone deacetylase inhibitor, STAT-3 modulator, HMG CoA reductase inhibitor, HSD17B13 gene inhibitor, 5-HT 2a receptor antagonist, Hydrolase inhibitor, Hypoxia inducible factor-2 alpha inhibitor, IL-10 agonist, IL-17 antagonist, IL-22 agonist, Ileal sodium bile acid cotransporter inhibitor, Insulin sensitizer, Insulin ligand agonist, Insulin receptor agonist, integrin modulator, Integrin Antagonist, Integrin alpha-V/beta-1 antagonist, Integrin alpha-V/beta-6 antagonist, intereukin-1 receptor-associated kinase 4 (IRAK4) inhibitor, IL-6 receptor agonist, interleukin 17 ligand inhibitor, Jak2 tyrosine kinase inhibitor, Jun N terminal kinase-1 inhibitor, Kelch like ECH associated protein 1 modulator, Ketohexokinase (KHK) inhibitor, Klotho beta stimulator, Leukotriene A4 hydrolase inhibitor, 5-Lipoxygenase inhibitor, Lipoprotein lipase inhibitor, Liver X receptor, LPL gene stimulator, Lysophosphatidate-1 receptor antagonist, Lysyl oxidase homolog 2 inhibitor, LXR inverse agonists, Macrophage mannose receptor 1 modulator, Matrix metalloproteinases (MMPs) inhibitor, MEKK-5 protein kinase inhibitor, MCH receptor-1 antagonist, Membrane copper amine oxidase (VAP-1) inhibitor, Methionine aminopeptidase-2 inhibitor, Methyl CpG binding protein 2 modulator, MicroRNA-132 (miR-132) antagonist, MicroRNA-21 (miR-21) inhibitor, Mitochondrial uncoupler, Mixed lineage kinase-3 inhibitor, Motile sperm domain protein 2 inhibitor, Myelin basic protein stimulator, NACHT LRR PYD domain protein 3 (NLRP3) inhibitor, NAD-dependent deacetylase sirtuin stimulator, NADPH oxidase inhibitor (NOX), NFE2L2 gene inhibitor, Nicotinic acid receptor 1 agonist, Opioid receptor mu antagonist, P2Y13 purinoceptor stimulator, Nuclear erythroid 2-related factor 2 stimulator, Nuclear receptor modulators, Nuclear transport of transcription factor modulator, P2X7 purinoceptor modulator, PACAP type I receptor agonist, PDE 3 inhibitor, PDE 4 inhibitor, PDE 5 inhibitor, PDGF receptor beta modulator, Phenylalanine hydroxylase stimulator, Phospholipase C inhibitor, Phosphoric diester hydrolase inhibitor, PPAR alpha agonist, PPAR delta agonist, PPAR gamma agonist, Peptidyl-prolyl cis-trans isomerase A inhibitor, PNPLA3 gene inhibitor, PPAR gamma modulator, Protease-activated receptor-2 antagonist, Protein kinase modulator, Protein NOV homolog modulator, PTGS2 gene inhibitor, renin inhibitor, Resistin/CAP1 (adenylyl cyclase associated protein 1) interaction inhibitor, Rho associated protein kinase inhibitor, RNA polymerase inhibitors, S-nitrosoglutathione reductase (GSNOR) enzyme inhibitor, Sodium glucose transporter-2 inhibitor, Sphingolipid delta 4 desaturase DES1 inhibitor, SREBP transcription factor inhibitor, STAT-1 inhibitor, Stearoyl CoA desaturase-1 inhibitor, STK25 inhibitor, Suppressor of cytokine signalling-1 stimulator, Suppressor of cytokine signalling-3 stimulator, Taste receptor type 2 agonist, Telomerase stimulator, TERT gene modulator, TGF beta (TGFB1) ligand inhibitor, TNF antagonist, Transforming growth factor β (TGF-β), Transforming growth factor β activated Kinase 1 (TAK1), Thyroid hormone receptor beta agonist, TLR-4 antagonist, Transglutaminase inhibitor, Tyrosine kinase receptor modulator, GPCR modulator, nuclear hormone receptor modulator, TLR-9 antagonist, VDR agonist, Vitamin D3 receptor modulators, WNT modulators, YAP/TAZ modulator or a Zonulin inhibitor, and combinations thereof.

Non-limiting examples of the one or more additional therapeutic agents include:

ACE inhibitors, such as enalapril;

Acetaldehyde dehydrogenase inhibitors, such as ADX-629;

Acetyl CoA carboxylase (ACC) inhibitors, such as NDI-010976 (firsocostat), DRM-01, gemcabene, GS-834356, PF-05175157, QLT-091382, PF-05221304;

Acetyl CoA carboxylase/Diacylglycerol O acyltransferase 2 inhibitors, such as PF-07055341;

Adenosine receptor agonists, such as CF-102 (namodenoson), CF-101 (piclidenoson), CF-502, CGS21680;

Adenosine A3 receptor antagonist, such as FM-101;

Adiponectin receptor agonists, such as ADP-355, ADP-399, ALY668-SR;

Adrenergic receptor antagonist, such as bromocriptine, phentermine, VI-0521;

Aldehyde dehydrogenase 2 stimulators, such as FP-045;

Amylin/calcitonin receptor agonists, such as KBP-042, KBP-089;

AMP activated protein kinase stimulators, such as C-455, PXL-770, O-304;

AMP kinase activators/ATP citrate lyase inhibitors, such as bempedoic acid (ETC-1002, ESP-55016);

AMP activated protein kinase/Endothelial nitric oxide synthase/NAD-dependent deacetylase sirtuin-1 stimulators, such as NS-0200 (leucine+metformin+sildenafil);

Androgen receptor agonists, such as LPCN-1144, LPCN-1148, testosterone prodrug;

Angiotensin II AT-1 receptor antagonists, such as irbesartan; Angiopoietin-related protein-3 inhibitors, such as vupanorsen (IONIS-ANGPTL3-LRx);

Apelin receptor agonist, such as CB-5064, MBT-2;

Apical sodium-dependent bile acid transport inhibitors, such as A-3907;

Autophagy protein modulators, such as A-2906, GM-90194;

Autotaxin (ectonucleotide pyrophosphatase/phosphodiesterase 2 (NPP2 or ENPP2)) inhibitors, such as FP10.47, PAT-505, PAT-048, GLPG-1690, X-165, PF-8380, TJC-0265, TJC-0316, AM-063, BBT-877;

Axl tyrosine kinase receptor inhibitors, such as bemcentinib (BGB-324, R-428);

Bax protein stimulators, such as CBL-514;

Bioactive lipids, such as DS-102;

Cannabinoid receptor modulators, such as namacizumab (nimacimab), GWP-42004, REV-200, CRB-4001, INV-101, SCN-002;

Caspase inhibitors, such as emricasan;

Pan cathepsin B inhibitors, such as VBY-376;

Pan cathepsin inhibitors, such as VBY-825;

CCK receptor antagonist, such as proglumide;

CCL26 gene inhibitor, such as mosedipimod, KDDF-201410-10;

CCR2/CCR5 chemokine antagonists, such as BMS-687681, cenicriviroc, maraviroc, CCX-872, leronlimab, WXSH-0213;

CCR2/CCR5 chemokine antagonists and FXR agonists, such as LJC-242 (tropifexor+cenivriviroc);

CCR2 chemokine antagonists, such as propagermanium;

CCR2 chemokine/Angiotensin II AT-1 receptor antagonists, such as DMX-200, DMX-250;

CCR3 chemokine antagonists, such as bertilimumab;

CD3 antagonists, such as NI-0401 (foralumab);

CDGSH iron sulfur domain protein modulators, such as EYP-002;

Chitinase inhibitor, such as OATD-01;

Chitotriosidase 1 inhibitors, such as OAT-2068;

Chloride channel stimulators, such as cobiprostone, and lubiprostone;

Casein kinase-1 (CK1) delta/epsilon inhibitors, such as PF-05006739;

Connective tissue growth factor ligand inhibitor, such as PBI-4050;

COT protein kinase inhibitors, such as GS-4875, GS-5290;

CXCR4 chemokine antagonists, such as AD-214;

Cytochrome P450 reductase inhibitors, such as SNP-630;

Diglyceride acyltransferase 2 (DGAT2) inhibitors, such as IONIS-DGAT2Rx, PF-06865571;

Diglyceride acyltransferase 1 (DGAT1) inhibitors, such as GSK-3008356;

Diacylglycerol O acyltransferase 1 (DGAT1)/Cytochrome P450 2E1 inhibitors (CYP2E1), such as SNP-610;

Dihydroorotate dehydrogenase inhibitor, such as vidofludimus;

Dipeptidyl peptidase IV inhibitors, such as linagliptin, evogliptin;

Eotaxin ligand inhibitors, such as bertilimumab, CM-101;

Extracellular matrix protein modulators, such as CNX-024;

Farnesoid X receptor (FXR) agonists, such as AGN-242266, AGN-242256, ASC-42, EDP-297 (EP-024297), RDX-023, BWL-200, AKN-083, EDP-305, GNF-5120, cilofexor tromethamine (GS-9674), HPG-1860, IOT-022, LMB-763, obeticholic acid, Px-102, Px-103, M790, M780, M450, M-480, MET-409, MET-642, PX20606, SYHA-1805, vonafexor (EYP-001), TERN-101, TC-100, INT-2228, TQA-3526, ZG-5266, HPD-001, alendronate;

Farnesoid X receptor (FXR)/G-protein coupled bile acid receptor 1 (TGR5) agonists, such as INT-767;

Fatty acid synthase inhibitors, such as TVB-2640, FT-8225;

Fibroblast growth factor 19 (rhFGF19)/cytochrome P450 (CYP) 7A1 inhibitors, such as aldafermin (NGM-282);

Fibroblast growth factor 21 (FGF-21) ligand modulators, such as AP-025, BMS-986171, B-1654, BIO89-100, BOS-580, Pegbelfermin (BMS-986036), B-1344, NN-9499;

Fibroblast growth factor 21 (FGF-21)/glucagon like peptide 1 (GLP-1) agonists, such as YH-25723 (YH-25724; YH-22241), efruxifermin (AKR-001);

FGF receptor agonists/Klotho beta stimulators, such as BFKB-8488A (RG-7992);

Free fatty acid receptor 1 agonist, such as SCO-267;

Galectin-3 inhibitors, such as belapectin (GR-MD-02), GB-1107 (Gal-300), GB-1211 (Gal-400), IMT-001;

GDNF family receptor alpha like agonist, such as NGM-395;

Glucagon-like peptide 1 (GLP1R) agonists, such as ALT-801, AC-3174, liraglutide, cotadutide (MEDI-0382), SAR-425899, LY-3305677, HM-15211, YH-25723, YH-GLP1, RPC-8844, PB-718, PF-06882961, semaglutide;

Glucagon-like peptide 1 receptor agonist; Oxyntomodulin ligand; Glucagon receptor agonist, such as efinopegdutide;

Gastric inhibitory polypeptide/Glucagon-like peptide-1 (GIP/GLP-1) receptor co-agonist, such as tirzepatide (LY-3298176);

PEGylated long-acting glucagon-like peptide-1/glucagon (GLP-1R/GCGR) receptor dual agonist, such as DD-01;

Glucagon/GLP1-receptor agonist, such as BI-456906, NN-6177;

Glucocorticoid receptor antagonists, such as CORT-118335 (miricorilant);

Glucose 6-phosphate 1-dehydrogenase inhibitors, such as ST001;

Glucokinase stimulator, such as dorzagliatin, sinogliatin (RO-5305552);

G-protein coupled bile acid receptor 1 (TGR5) agonists, such as RDX-009, INT-777, HY-209;

G-protein coupled receptor 84 antagonist, such as PBI-4547;

G-protein coupled receptor-119 agonist, such as DA-1241;

Heat shock protein 47 (HSP47) inhibitors, such as ND-L02-s0201;

Hedgehog protein TGF beta ligand inhibitors, such as Oxy-210;

Histone deacetylase inhibitors/STAT-3 modulators, such as SFX-01;

HMG CoA reductase inhibitors, such as atorvastatin, fluvastatin, pitavastatin, pravastatin, rosuvastatin, simvastatin;

HSD17B13 gene inhibitor, such as ALN-HSD, ARO-HSD;

Hydrolase inhibitor, such as ABD-X;

Hypoxia inducible factor-2 alpha inhibitors, such as PT-2567;

IL-10 agonists, such as peg-ilodecakin;

Ileal sodium bile acid cotransporter inhibitors, such as odevixibat (A-4250), volixibat potassium ethanolate hydrate (SHP-262), GSK2330672, CJ-14199, elobixibat (A-3309);

Insulin sensitizers, such as, KBP-042, azemiglitazone potassium (MSDC-0602K), ION-224, MSDC-5514, Px-102, RG-125 (AZD4076), Tolimidone, VVP-100X, CB-4211, ETI-101;

Insulin ligand/dsInsulin receptor agonists, such as ORMD-0801;
Integrin antagonists, such as IDL-2965;
IL-6 receptor agonists, such as KM-2702;
Integrin alpha-V/beta-6 and alpha-V/beta-1 dual inhibitor; such as PLN-74809;
Interleukin 17 ligand inhibitor, such as netakimab;
Jak1/2 tyrosine kinase inhibitor, such as baricitinib;
Jun N terminal kinase-1 inhibitor, such as CC-90001;
Kelch like ECH associated protein 1 modulator, such as alpha-cyclodextrin-stabilized sulforaphane;
Ketohexokinase (KHK) inhibitors, such as PF-06835919, LY-3478045, LY-3522348;
beta Klotho (KLB)-FGF1c agonists, such as MK-3655 (NGM-313);
Leukotriene A4 hydrolase inhibitor, such as LYS-006;
5-Lipoxygenase inhibitors, such as tipelukast (MN-001), epeleuton (DS-102, AF-102);
Lipoprotein lipase inhibitors, such as CAT-2003;
LPL gene stimulators, such as alipogene tiparvovec;
Liver X receptor (LXR) inhibitors, such as PX-665, PX-L603, PX-L493, BMS-852927, T-0901317, GW-3965, SR-9238;
Lysophosphatidate-1 receptor antagonists, such as BMT-053011, UD-009 (CP-2090), AR-479, ITMN-10534, BMS-986020, KI-16198;
Lysyl oxidase homolog 2 inhibitors, such as simtuzumab, PXS-5382A (PXS-5338);
Macrophage mannose receptor 1 modulators, such as tilmanocept-Cy3 (technetium Tc 99m tilmanocept);
Matrix metalloprotease inhibitors, such as ALS-L1023;
Membrane copper amine oxidase (VAP-1) inhibitors, such as TERN-201, TT-01025;
MEKK-5 protein kinase (ASK-1) inhibitors, such as CJ-16871, CS-17919, selonsertib (GS-4997), SRT-015, GS-444217, GST-HG-151, TERN-301;
MCH receptor-1 antagonists, such as CSTI-100 (ALB-127158);
Semicarbazide-Sensitive Amine Oxidase/Vascular Adhesion Protein-1 (SSAO/VAP-1) Inhibitors, such as PXS-4728A (BI-1467335);
Methionine aminopeptidase-2 inhibitors, such as ZGN-1061, ZGN-839, ZN-1345;
Methyl CpG binding protein 2 modulators, such as mercaptamine;
Mineralocorticoid receptor antagonists (MCRA), such as MT-3995 (apararenone);
Mitochondrial uncouplers, such as 2,4-dinitrophenol, HU6, Mito-99-0053;
Mixed lineage kinase-3 inhibitors, such as URMC-099-C;
Motile sperm domain protein 2 inhibitors, such as VB-601;
Myelin basic protein stimulators, such as olesoxime;
Myeloperoxidase inhibitors, such as PF-06667272, AZM-198;
NADPH oxidase inhibitors, such as GKT-831, GenKyoTex, APX-311, setanaxib;
Nicotinic acid receptor 1 agonists, such as ARI-3037MO;
NACHT LRR PYD domain protein 3 (NLRP3) inhibitors, such as KDDF-201406-03, NBC-6, IFM-514, JT-194 (JT-349);
NFE2L2 gene inhibitor, such as GeRP-amiR-144;
Nuclear transport of transcription factor modulators, such as AMTX-100;
Nuclear receptor modulators, such as DUR-928 (DV-928);
Opioid receptor mu antagonists, such as methylnaltrexone;
P2X7 purinoceptor modulators, such as SGM-1019;
P2Y13 purinoceptor stimulators, such as CER-209;
PDE 3/4 inhibitors, such as tipelukast (MN-001);
PDE 5 inhibitors, such as sildenafil, MSTM-102;
PDGF receptor beta modulators, such as BOT-191, BOT-509;
Peptidyl-prolyl cis-trans isomerase inhibitors, such as CRV-431 (CPI-432-32), NVP-018, NV-556 (NVP-025);
Phenylalanine hydroxylase stimulators, such as HepaStem;
Phosphoric diester hydrolase inhibitor, such as ZSP-1601;
PNPLA3 gene inhibitor, such as AZD-2693;
PPAR agonists, such as Chiglitazar, elafibranor (GFT-505), seladelpar lysine (MBX-8025), deuterated pioglitazone R-enantiomer, pioglitazone, PXL-065 (DRX-065), saroglitazar, lanifibranor (IVA-337), CHS-131, pemafibrate (K-877), ZG-0588, ZSP-0678; ZSYM-008;
Protease-activated receptor-2 antagonists, such as PZ-235;
Protein kinase modulators, such as CNX-014;
Protein NOV homolog modulators, such as BLR-200;
PTGS2 gene inhibitors, such as STP-705, STP-707;
Renin inhibitors, such as PRO-20;
Resistin/CAP1 (adenylyl cyclase associated protein 1) interaction inhibitors, such as DWJ-211;
Rev protein modulator, such as ABX-464;
Rho associated protein kinase (ROCK) inhibitors, such as REDX-10178 (REDX-10325), KD-025, RXC-007, TDI-01;
RNA polymerase inhibitors, such as rifaximin;
Snitrosoglutathione reductase (GSNOR) enzyme inhibitors, such as SL-891;
Sodium glucose transporter-2 (SGLT2) inhibitors, such as ipragliflozin, remogliflozin etabonate, ertugliflozin, dapagliflozin, tofogliflozin, sotagliflozin;
Sodium glucose transporter-1/2 (SGLT 1/2) inhibitors, such as licogliflozin bis(prolinate) (LIK-066);
SREBP transcription factor inhibitors, such as CAT-2003, HPN-01, MDV-4463;
Stearoyl CoA desaturase-1 inhibitors, such as aramchol;
Taste receptor type 2 agonists, such as ARD-101;
Thyroid hormone receptor beta agonists, such as ALG-009, ASC-41, CNPT-101101; CNPT-101207, CS-27186, KY-41111, resmetirom (MGL-3196), MGL-3745, TERN-501, VK-2809, HP-515;
TLR-2/TLR-4 antagonists, such as VB-201 (CI-201);
TLR-4 antagonists, such as JKB-121, JKB-122, naltrexone;
Tyrosine kinase receptor modulators, such as CNX-025, GFE-2137 (repurposed nitazoxanide);
TLR-9 antagonist, such as GNKS-356, AVO-101;
TNF antagonist, such as ALF-421;
GPCR modulators, such as CNX-023;
Nuclear hormone receptor modulators, such as Px-102;
VDR agonist, such as CK-15;
Xanthine oxidase inhibitors, such as ACQT-1127;
Xanthine oxidase/Urate anion exchanger 1 (URAT1) inhibitors, such as RLBN-1001, RLBN-1127; or
Zonulin Inhibitors, such as larazotide acetate (INN-202).
In certain specific embodiments, the one or more additional therapeutic agents are selected from A-4250, AC-3174, acetylsalicylic acid, AK-20, alipogene tiparvovec, AMX-342, AN-3015, anti-CXCR3 antibodies, anti-TAGE antibody, aramchol, ARI-3037MO, ASP-8232, AXA-1125, bertilimumab, Betaine anhydrous, BI-1467335, BMS-986036, BMS-986171, BMT-053011, BOT-191, BTT-1023, budesonide, BX-003, CAT-2003, cenicriviroc, CBW-511, CER-209, CF-102, CGS21680, CNX-014, CNX-023, CNX-024, CNX-025, cobiprostone, colesevelam, dabigatran etexilate mesylate, dapagliflozin, DCR-LIV1, deuterated pioglitazone R-enantiomer, 2,4-dinitrophenol, DRX-065, DS-102, DUR-928, edaravone (TTYP-01), EDP-305, elafibranor (GFT-505), emricasan, enalapril, ertugliflozin, evogliptin, F-351, fluasterone (ST-002), FT-4101, GDD-3898, GH-509, GKT-831, GNF-5120, GRI-0621, GR-MD-02, GS-300, GS-4997, GS-9674, GS-4875, GS-5290, HEC-96719, HTD-1801, HS-10356, HSG-4112, HST-202, HST-201, HU-6, hydrochlorothiazide, icosabutate (PRC-4016), icosapent ethyl ester, IMM-124-E, INT-767, INV-240, ION-455, IONIS-DGAT2Rx, ipragliflozin, Irbesarta, propagermanium, IVA-337, J2H-1702, JKB-121, KB-GE-001, KBLP-004, KBLP-009, KBP-042, KD-025, M790, M780, M450, metformin, sildenafil, LB-700, LC-280126, linagliptin, liraglutide, (LJN-452) tropifexor, LM-011, LM-002 (CVI-LM-002), LMB-763, LYN-100, MB-N-008, MBX-8025, MDV-4463, mercaptamine, MGL-3196, MGL-3745, MP-301, MSDC-0602K, namacizumab, NC-101, NDI-010976, ND-L02-s0201 (BMS-986263), NGM-282, NGM-313, NGM-386, NGM-395, NP-011, NP-135, NP-160, norursodeoxycholic acid, NV-422, NVP-022, 0-304, obeticholic acid (OCA), 25HC3S, olesoxime, PAT-505, PAT-048, peg-ilodecakin, pioglitazone, pirfenidone, PRI-724, PX20606, Px-102, PX-L603, PX-L493, PXS-4728A, PZ-235, PZH-2109, RCYM-001, RDX-009, remogliflozin etabonate, RG-125 (AZD4076), RP-005, RPI-500, S-723595, saroglitazar, SBP-301, semaglutide, SH-2442, SHC-028, SHC-023, simtuzumab, solithromycin, sotagliflozin, statins (atorvastatin, fluvastatin, pitavastatin, pravastatin, rosuvastatin, simvastatin), TCM-606F, TEV-45478, TQA-3526, TQA-3563, tipelukast (MN-001), TLY-012, TRX-318, TVB-2640, TXR-611, TXR-612, TS-20004, UD-009, UN-03, ursodeoxycholic acid, VBY-376, VBY-825, VK-2809, vismodegib, volixibat potassium ethanolate hydrate (SHP-626), VVP-100X, WAV-301, WNT-974, WXSH-0038, WXSH-0078, XEN-103, XRx-117, XTYW-003, XW-003, XW-004, XZP-5610, ZGN-839, ZG-5216, ZSYM-008, or ZYSM-007.

In some embodiments, the compound of the present disclosure is combined with one or more therapeutic agents selected from an anti-obesity agent including but not limited to peptide YY or an analogue thereof, a neuropeptide Y receptor type 2 (NPYR2) agonist, a NPYR1 agonist, an NPYR5 antagonist, a cannabinoid receptor type 1 (CB1 R) antagonist, a lipase inhibitor (e.g., orlistat), a human proislet peptide (HIP), a melanocortin receptor 4 agonist (e.g., setmelanotide), a melanin concentrating hormone receptor 1 antagonist, a farnesoid X receptor (FXR) agonist (e.g. obeticholic acid), apoptotic signal-regulating kinase (ASK-1) inhibitor, zonisamide, phentermine (alone or in combination with topiramate), a norepinephrine/dopamine reuptake inhibitor (e.g., buproprion), an opioid receptor antagonist (e.g., naltrexone), a combination of norepinephrine/dopamine reuptake inhibitor and opioid receptor antagonist (e.g., a combination of bupropion and naltrexone), a GDF-15 analog, sibutramine, a cholecystokinin agonist, amylin and analogues thereof (e.g., pramlintide), leptin and analogues thereof (e.g., metroleptin), a serotonergic agent (e.g., lorcaserin), a methionine aminopeptidase 2 (MetAP2) inhibitor (e.g., beloranib or ZGN-1061), phendimetrazine, diethylpropion, benzphetamine, an SGLT2 inhibitor (e.g., empagliflozin, canagliflozin, dapagliflozin, ipragliflozin, tofogliflozin, sergliflozin etabonate, remogliflozin etabonate, or ertugliflozin), an SGLTL1 inhibitor, a dual SGLT2/SGLT1 inhibitor, a fibroblast growth factor receptor (FGFR) modulator, an AMP-activated protein kinase (AMPK) activator, biotin, a MAS receptor modulator, or a glucagon receptor agonist (alone or in combination with another GLP-1 R agonist, e.g., liraglutide, exenatide, dulaglutide, albiglutide, lixisenatide, or semaglutide), an insulin sensitizer such as thiazolidinediones (TZDs), a peroxisome proliferator-activated receptor alpha (PPARα) agonist, fish oil, an acetyl-coA carboxylase (ACC) inhibitor, a transforming growth factor beta (TGFβ) antagonist, a GDNF family receptor alpha like (GFRAL) agonist, a melanocortin-4 receptor (MC4R) agonist, including the pharmaceutically acceptable salts of the specifically named agents and the pharmaceutically acceptable solvates of said agents and salts.

VII. Methods of Treatment

In some embodiments, compounds of Formula (I), or pharmaceutically acceptable salt thereof, are useful in a method of treating and/or preventing a GLP-1R mediated disease or condition. In some embodiments, a method for treating and/or preventing a GLP-1R mediated disease or condition includes administering to a subject in need thereof a pharmaceutically effective amount of a compound of the present disclosure or pharmaceutically acceptable salt thereof. In some embodiments, compounds of the present disclosure have desirable properties, including for example advantageous pharmacokinetic properties, physicochemical properties such as hepatic uptake properties, and/or bile salt export pump (BSEP) inhibition characteristics. In one embodiment, compounds of the present disclosure have desirable pharmacokinetic properties, such as prolonged exposures and/or higher oral bioavailability. In one embodiment, compounds of the present disclosure have desirable hepatic uptake properties, such as reduced transporter-mediated hepatic uptake. In one embodiment, compounds of the present disclosure demonstrate desirable BSEP inhibition.

In some embodiments, the disease or condition comprises a liver disease or related diseases or conditions, e.g., liver fibrosis, non-alcoholic fatty liver disease (NAFLD), non-alcoholic steatohepatitis (NASH), liver cirrhosis, compensated liver fibrosis, decompensated liver fibrosis, hepatocellular carcinoma, Primary Biliary Cirrhosis (PBC), or Primary Sclerosing Cholangitis (PSC). In some embodiments, the disease or condition comprises a metabolic disease or related diseases or conditions, such as diabetes mellitus, obesity, or cardiometabolic diseases.

GLP-1R agonists are currently being investigated in connection with certain disorders and conditions, including for example diabetes. GLP-1 analogs that are DPP4 resistant and have longer half-lives than endogenous GLP-1 have been reported to be associated with weight loss and improved insulin action. Liraglutide, a peptide GLP-1R agonist approved in connection with treatment of diabetes, has been reported to show favorable improvements in outcomes in NASH subjects.

In some embodiments, the present disclosure relates to the use of compounds of Formula (I), or a pharmaceutically acceptable salt thereof in the preparation of a medicament for the prevention and/or treatment of a disease or condition mediated by GLP-1R, such as a liver disease or metabolic disease. In some embodiments, the present disclosure relates to the use of compounds of Formula (I), or a pharmaceutically acceptable salt thereof in the preparation of a medicament for the prevention and/or treatment of a disease or condition mediated by GLP-1R, such as a liver disease or metabolic disease. For example, some embodiments provide a compound of Formula (I), or a pharmaceutically acceptable salt thereof, or a use thereof, for treatment and/or prevention of chronic intrahepaatic or some forms of extrahepatic cholestatic conditions, of liver fibrosis, of acute intrahepatic cholestatic conditions, of obstructive or chronic inflammatory disorders that arise out of improper bile composition, of gastrointestinal conditions with a reduced uptake of dietary fat and fat-soluble dietary vitamins, of inflammatory bowel diseases, of lipid and lipoprotein disorders, of type II diabetes and clinical complications of type I and type II diabetes, of conditions and diseases which result from chronic fatty and fibrotic degeneration of organs due to enforced lipid and specifically triglyceride accumulation and subsequent activation of profibrotic pathways, of obesity and metabolic syndrome (combined conditions of dyslipidemia, diabetes and abnormally high body-mass index), of acute myocardial infarction, of acute stroke, of thrombosis which occurs as an endpoint of chronic obstructive atherosclerosis, of persistent infections by intracellular bacteria or parasitic protozoae, of non-malignant hyperproliferative disorders, of malignant hyperproliferative disorders, of colon adenocarcinoma and hepatocellular carcinoma for instance, of liver steatosis and associated syndromes, of liver failure or liver malfunction as an outcome of chronic liver diseases or of surgical liver resection, of Hepatitis B infection, of Hepatitis C infection and/or of cholestatic and fibrotic effects that are associated with alcohol-induced cirrhosis or with viral-borne forms of hepatitis, of type I diabetes, pre-diabetes, idiopathic type 1 diabetes, latent autoimmune diabetes, maturity onset diabetes of the young, early onset diabetes, malnutrition-related diabetes, gestational diabetes, hyperglycemia, insulin resistance, hepatic insulin resistance, impaired glucose tolerance, diabetic neuropathy, diabetic nephropathy, kidney disease, diabetic retinopathy, adipocyte dysfunction, visceral adipose deposition, obesity, eating disorders, sleep apnea, weight gain, sugar craving, dyslipidemia, hyperinsulinemia, congestive heart failure, myocardial infarction, stroke, hemorrhagic stroke, ischemic stroke, traumatic brain injury, pulmonary hypertension, restenosis after angioplasty, intermittent claudication, post-prandial lipemia, metabolic acidosis, ketosis, arthritis, left ventricular hypertrophy, Parkinson's Disease, peripheral arterial disease, macular degeneration, cataract, glomerulosclerosis, chronic renal failure, metabolic syndrome, angina pectoris, premenstrual syndrome, thrombosis, atherosclerosis, impaired glucose metabolism, or vascular restenosis.

In some embodiments, a method of treating and/or preventing a non-alcoholic fatty liver disease (NAFLD), comprises administering to a subject in need thereof a compound of the present disclosure or a pharmaceutically acceptable salt thereof.

The disclosure also relates to a compound according to Formula (I) or a pharmaceutical composition comprising said compound for preventive and posttraumatic treatment of a cardiovascular disorder, such as acute myocardial infarction, acute stroke, or thrombosis which occur as an endpoint of chronic obstructive atherosclerosis. In some embodiments, a method for treating and/or preventing cardiovascular disorder comprises administering a compounds of Formula (I) to a subject in need thereof.

The disclosure further relates to a compound or pharmaceutical composition for the treatment and/or prevention of obesity and associated disorders such as metabolic syndrome (combined conditions of dyslipidemias, diabetes and abnormally high body-mass index) which can be overcome by GLP-1R-mediated lowering of serum triglycerides, blood glucose and increased insulin sensitivity and GLP-1R-mediated weight loss. In some embodiments, a method for treating and/or preventing a metabolic disease comprises administering a compounds of Formula (I) to a subject in need thereof. In some embodiments, a method for treating and/or preventing a metabolic disease comprises administering a compounds of Formula (I), to a subject in need thereof.

In a further embodiment, the compounds or pharmaceutical composition of the present disclosure are useful in preventing and/or treating clinical complications of Type I and Type II Diabetes. Examples of such complications include diabetic nephropathy, diabetic retinopathy, diabetic neuropathies, or Peripheral Arterial Occlusive Disease (PAOD). Other clinical complications of diabetes are also encompassed by the present disclosure. In some embodiments, a method for treating and/or preventing complications of Type I and Type II Diabetes comprises administering a compounds of Formula (I) to a subject in need thereof. In some embodiments, a method for treating and/or preventing complications of Type I and Type II Diabetes comprises administering a compounds of Formula (I) to a subject in need thereof.

Furthermore, conditions and diseases which result from chronic fatty and fibrotic degeneration of organs due to enforced lipid and/or triglyceride accumulation and subsequent activation of profibrotic pathways may also be prevented and/or treated by administering the compounds or pharmaceutical composition of the present disclosure. Such conditions and diseases can include NASH and chronic cholestatic conditions in the liver, Glomerulosclerosis and Diabetic Nephropathy in the kidney, Macular Degeneration and Diabetic Retinopathy in the eye and neurodegenerative diseases, such as Alzheimer's Disease in the brain, or Diabetic Neuropathies in the peripheral nervous system. In some embodiments, a method for treating and/or preventing conditions and diseases which result from chronic fatty and fibrotic degeneration of organs due to enforced lipid and/or triglyceride accumulation and subsequent activation of profibrotic pathways comprises administering a compounds of Formula (I) to a subject in need thereof. In some embodiments, a method for treating and/or preventing conditions and diseases which result from chronic fatty and fibrotic degeneration of organs due to enforced lipid and/or triglyceride accumulation and subsequent activation of profibrotic pathways comprises administering a compounds of Formula (I) to a subject in need thereof. In some embodiments, a method for treating and/or preventing NASH comprises administering a compounds of Formula (I) to a subject in need thereof. In some embodiments, a method for treating and/or preventing NASH comprises administering a compounds of Formula (I) to a subject in need thereof.

Further provided herein is a pharmaceutical composition for use in treating a GLP-1R mediated disease or condition described herein, comprising a compound of the present disclosure or a pharmaceutically acceptable salt thereof.

The present disclosure also describes a use for the manufacture of a medicament in treating a GLP-1R mediated disease or condition comprising a compound of the present disclosure or a pharmaceutically acceptable salt thereof. Medicaments as referred to herein may be prepared by conventional processes, including the combination of a compound according to the present disclosure and a pharmaceutically acceptable carrier.

Also disclosed is a compound of the present disclosure or a pharmaceutically acceptable salt thereof for the treatment of a GLP-1R mediated disease or condition. Also disclosed is a compound of the present disclosure or a pharmaceutically acceptable salt thereof for the prevention of a GLP-1R mediated disease or condition.

VIII. Examples

Many general references providing commonly known chemical synthetic schemes and conditions useful for synthesizing the disclosed compounds are available (see, e.g., Smith, March's Advanced Organic Chemistry: Reactions, Mechanisms, and Structure, $7^{th}$ edition, Wiley-Interscience, 2013).

Compounds as described herein can be purified by any of the means known in the art, including chromatographic means, such as high-performance liquid chromatography (HPLC), preparative thin layer chromatography, flash column chromatography and ion exchange chromatography. Any suitable stationary phase can be used, including normal and reversed phases as well as ionic resins. For example, the disclosed compounds can be purified via silica gel and/or alumina chromatography. See, e.g., Introduction to Modern Liquid Chromatography, 2nd ed., ed. L. R. Snyder and J. J. Kirkland, John Wiley and Sons, 1979; and Thin Layer Chromatography, E. Stahl (ed.), Springer-Verlag, New York, 1969.

During any of the processes for preparation of the subject compounds, it may be desirable to protect sensitive or reactive groups on any of the molecules concerned. This may be achieved by means of conventional protecting groups as described in standard works, such as T. W. Greene and P. G. M. Wuts, "Protective Groups in Organic Synthesis," 4th ed., Wiley, New York 2006. The protecting groups may be removed at a convenient subsequent stage using methods known from the art.

Exemplary chemical entities useful in methods of the embodiments will now be described by reference to illustrative synthetic schemes for their general preparation herein and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the pendant groups. Each of the reactions depicted in the general schemes can be run at a temperature from about 0° C. to the reflux temperature of the organic solvent used.

The Examples provided herein describe the synthesis of compounds disclosed herein as well as intermediates used to prepare the compounds. It is to be understood that individual steps described herein may be combined. It is also to be understood that separate batches of a compound may be combined and then carried forth in the next synthetic step.

In the following description of the Examples, specific embodiments are described. These embodiments are described in sufficient detail to enable those skilled in the art to practice certain embodiments of the present disclosure. Other embodiments may be utilized, and logical and other changes may be made without departing from the scope of the disclosure. The embodiments are also directed to processes and intermediates useful for preparing the subject compounds or pharmaceutically acceptable salts thereof. The following description is, therefore, not intended to limit the scope of the present disclosure.

In some embodiments, the present disclosure generally provides a specific enantiomer or diastereomer as the desired product, although the stereochemistry of the enantiomer or diastereomer was not determined in all cases. When the stereochemistry of the specific stereocenter in the enantiomer or diastereomer is not determined, the compound is drawn without showing any stereochemistry at that specific stereocenter even though the compound can be substantially enantiomerically or diastereomerically pure.

Representative syntheses of compounds of the present disclosure are described in schemes below, and the examples that follow.

The compounds detailed in the Examples were synthesized according to the general synthetic methods described below. Compounds were named using ChemDraw version 18. 1. 0. 535 (PerkinElmer Informatics, Inc.) unless otherwise indicated.

Abbreviations

Certain abbreviations and acronyms are used in describing the experimental details. Although most of these would be understood by one skilled in the art, Table 1 contains a list of many of these abbreviations and acronyms.

TABLE 1

| List of Abbreviations and Acronyms | |
|---|---|
| Abbreviation | Meaning |
| Ac | acetate |
| AcOH | Acetic acid |
| ACN or MeCN | acetonitrile |
| AmPhos | di-tert-butyl(4-dimethylaminophenyl)phosphine |
| Aq. | aqueous |
| AUC | Area under the curve |
| Bn | benzyl |
| Bpin | (pinacolato)boron |
| $B_2Pin_2$ | bis(pinacolato)diboron |
| Bu | butyl |
| Bz | benzoyl |
| BSA | bovine serum albumin |
| BzCl | benzoyl chloride |
| cAMP | Cyclic adenosine monophosphate |
| cataCXium ® A Pd G3 | Mesylate[(di(1-adamantyl)-n-butylphosphine)-2-(2'-amino-1,1'-biphenyl)]palladium(II) |
| CAN | Cerium Ammonium Nitrate |
| CDI | 1,1'-carbonyldiimidazole |
| CHO | Chinese hamster ovary |
| DBA | dibenzalacetone |
| DBU | 1,8-Diazabicyclo[5. 4. 0]undec-7-ene |
| DCM | dichloromethane |
| DCE | dichlorethane |
| DEA | diethylamine |
| Deoxofluor | Bis(2-methoxyethyl)aminosulfur trifluoride |
| DIPEA | diisopropylethylamine |
| DMAP | 4-dimethylaminopyridine |
| DME | dimethoxyethane |
| DMEM | Dulbecco's Modified Eagle Medium |
| DMF | dimethylformamide |
| DMSO | dimethylsulfoxide |
| DPBS | Dulbecco's phosphate buffered saline |
| dppf | 1,1'-Ferrocenediyl-bis(diphenylphosphine) |
| EDCI | N-(3-dimethylaminopropyl)-N'-ethylcarbodiimide hydrochloride |

TABLE 1-continued

List of Abbreviations and Acronyms

| Abbreviation | Meaning |
| --- | --- |
| ES/MS | electron spray mass spectrometry |
| Et | ethyl |
| EtOAc | Ethyl acetate |
| FBS | fetal bovine serum |
| HATU | 1-[Bis(dimethylamino)methylene]-1H-1,2,3-triazolo[4,5-b]pyridinium 3-oxide hexafluorophosphate |
| HBSS | Hank's balanced salt solution |
| HEPES | (4-(2-hydroxyethyl)-1-piperazineethanesulfonic acid) |
| Hex or hex | hexane |
| HPLC | High performance liquid chromatography |
| IPA | isopropanol |
| JohnPhos | (2-Biphenyl)di-tert-butylphosphine |
| KOtBu | potassium tert-butoxide |
| LC | liquid chromatography |
| LCMS | liquid chromatography/mass spectrometry |
| MCPBA | meta-chloroperbenzoic acid |
| Me | methyl |
| m/z | mass to charge ratio |
| MS or ms | mass spectrum |
| NMP | N-methyl-2-pyrrolidone |
| NMR | nuclear magnetic resonance |
| NOE | nuclear Overhauser effect |
| NOESY | nuclear Overhauser effect spectroscopy |
| OTs | Tosylate, p-toluenesulfonate |
| OTf | Tritiate, trifluoromethanesulfonate |
| Pd Rockphos G3 | [(2-Di-tert-butylphosphino-3-methoxy-6-methyl-2',4',6'-triisopropyl-1,1'-biphenyl)-2-(2-aminobiphenyl)]palladium(II) methanesulfonate |
| PEG300 | Polyethylene glycol 300 |
| Ph | phenyl |
| Ph$_3$P | triphenylphosphine |
| pin | pinacol |
| PO | By mouth/orally |
| POCl$_3$ | Phosphorus oxychloride |
| Pyr | pyridine |
| RBF | round bottom flask |
| RP-HPLC or RP HPLC | reverse phase high performance liquid chromatography |
| RT/rt | room temperature |
| SFC | supercritical fluid chromatography |
| tBu | tert-butyl |
| tBuXPhos Pd G3 | [(2-Di-tert-butylphosphino-2',4',6'-triisopropyl-1,1'-biphenyl)-2-(2'-amino-1,1'-biphenyl)] palladium(II) methanesulfonate |
| TCFH | N,N,N'N'-tetramethylchloroformamidinium hexafluorophosphate |
| TEA | triethylamine |
| TFA | trifluoroacetic acid |
| Tf$_2$O | Trifluoromethanesulfonic anhydride |
| THF | tetrahydrofuran |
| TLC | Thin layer chromatography |
| TPPO | Triphenylphosphine oxide |
| Ts | 4-toluenesulfonyl |
| XPhos Pd G2 | Chloro(2-dicyclohexylphosphino-2',4',6'-triisopropyl-1,1'-biphenyl)[2-(2'-amino-1,1'-biphenyl)]palladium(II) |
| XPhos Pd G3 | (2-Dicyclohexylphosphino-2',4',6'-triisopropyl-1,1'-biphenyl)[2-(2'-amino-1,1'-biphenyl)]palladium(II) methanesulfonate |
| δ | parts per million referenced to residual solvent peak |

A. Synthesis of Intermediates

Preparation of Intermediate I-1

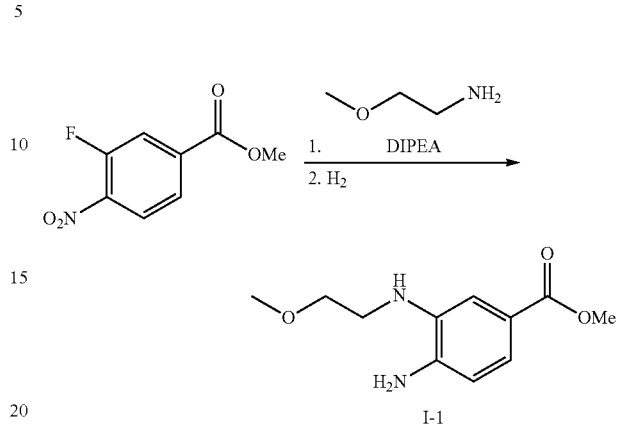

Methyl 4-amino-3-(2-methoxyethylamino)benzoate (I-1): To a solution of methyl 3-fluoro-4-nitro-benzoate (50.0 g, 251 mmol) in THF (400 mL) was added diisopropylethylamine (70.0 mL, 402 mmol) and 2-Methoxyethylamine (34.9 mL, 402 mmol). The resulting solution was heated to 55° C. for 6 hrs. Upon completion the solvent was removed, and the resulting residue taken up in EtOAc (150 mL), washed with brine (30 mL), concentrated and carried forward without further purification. Methyl 3-(2-methoxyethylamino)-4-nitro-benzoate (20.0 g, 78.7 mmol) was then dissolved in EtOAc:EtOH (1:1, 140 mL) after which 10% palladium on carbon (5.02 g, 4.72 mmol) was then added. The resulting suspension was stirred under a hydrogen balloon at room temperature for 16 hrs. The mixture was filtered through Celite washing with EtOAc (100 mL) and concentrated to give the desired compound without further purification: ES/MS: 225.2 (M+H$^+$).

Preparation of Intermediate I-2

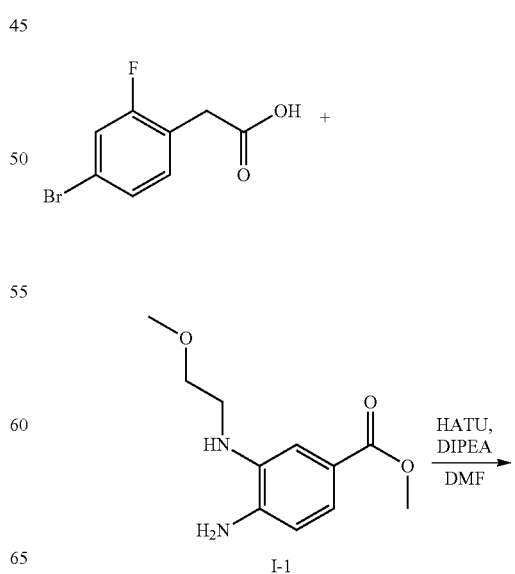

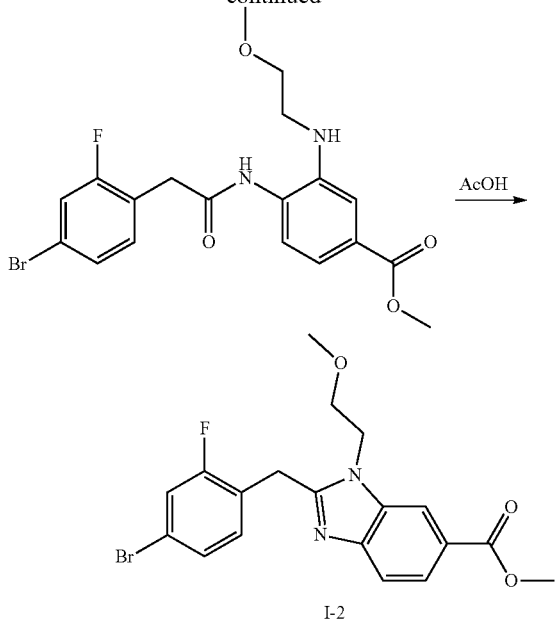

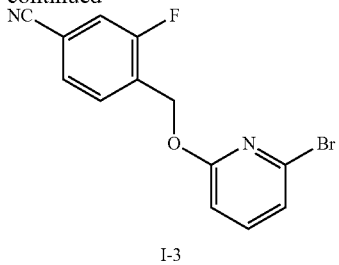

I-3

4-[(6-bromo-2-pyridyl)oxymethyl]-3-fluoro-benzonitrile (I-3): To a dried 100 mL RBF was added 3-fluoro-4-(hydroxymethyl)benzonitrile (2 g, 13.2 mmol). The material was dissolved in dry THF (20 mL) under a nitrogen atmosphere at 0° C. Sodium hydride (60% dispersion in mineral oil, 0.507 g, 13.2 mmol) was added in one portion, and the mixture was stirred for 30 mins at 0° C. under $N_2$. Subsequently, 2,6-dibromopyridine (3.13 g, 13.2 mmol) was added, and the mixture was stirred room temperature overnight. The mixture was diluted with EtOAc (100 mL) and water (20 mL). The layers were separated, and the aqueous layer was extracted with ethyl acetate (2×30 mL). The combined organic layers were dried over $MgSO_4$, filtered, and concentrated under reduced pressure. The crude material was purified by silica gel column chromatography (eluent: EtOAc/hexanes) to afford the Intermediate I-6: ES/MS: 307.058 (M+H$^+$); $^1$H NMR (400 MHz, Chloroform-d) δ 7.72-7.63 (m, 1H), 7.52-7.46 (m, 2H), 7.41 (dd, J=9.2, 1.5 Hz, 1H), 7.14 (dd, J=7.5, 0.7 Hz, 1H), 6.79 (dd, J=8.2, 0.7 Hz, 1H), 5.50 (t, J=0.9 Hz, 2H).

Methyl 4-{[2-(4-bromo-2-fluoro-phenyl)acetyl]amino}-3-(2-methoxyethylamino)benzoate: To a solution of 2-(4-bromo-2-fluoro-phenyl)acetic acid (1.00 g, 4.29 mmol) in DMF (20.0 mL) was added methyl 4-amino-3-(2-methoxyethylamino)benzoate (1.18 g, 5.28 mmol) and O-(7-Azabenzotriazol-1-yl)-N,N,N',N'-tetramethyluronium hexafluorophosphate (1.96 g, 5.15 mmol) followed by N,N-diisopropylethylamine (3.74 mL, 21.5 mmol) and the mixture was stirred for 2 hr. at room temperature. The mixture was concentrated in vacuo, the residue was taken up in EtOAc and washed with water (1×) and brine (1×). The organic layer was dried over sodium sulfate, filtered and concentrated in vacuo. The crude residue was taken forward without further purification, assuming full conversion: ES/MS m/z: 441.2 (M+H$^+$).

Methyl 2-[(4-bromo-2-fluoro-phenyl)methyl]-3-(2-methoxyethyl)benzimidazole-5-carboxylate (I-2): The crude product from the previous step, methyl 4-{[2-(4-bromo-2-fluoro-phenyl)acetyl]amino}-3-(2-methoxyethylamino)benzoate (1.89 g, 4.29 mmol) was dissolved in AcOH (40.0 mL) and the mixture was heated to 60° C. for 2 hr. The mixture was concentrated in vacuo and the crude residue was taken up in DCM and washed with saturated aqueous sodium bicarbonate. The layers were separated, and the aqueous layer was extracted with DCM (2×). The combined organic extracts were dried over sodium sulfate, filtered and the filtrate was concentrated in vacuo. The crude residue was purified by column chromatography (0-100% EtOAc in hexane) to give the title compound: ES/MS m/z: 421.9 (M+H$^+$).

Preparation of Intermediate I-3

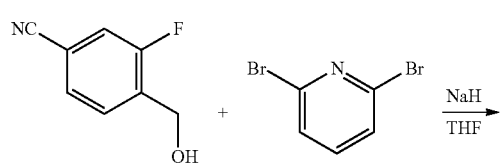

Preparation of Intermediate I-4

I-4

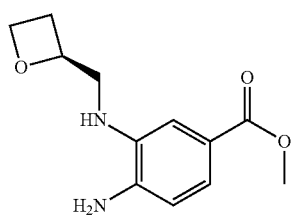

Methyl (S)-4-amino-3-((oxetan-2-ylmethyl)amino)benzoate (I-4): Methyl (S)-4-amino-3-((oxetan-2-ylmethyl)amino)benzoate was prepared following procedure Intermediate I-1 substituting (S)-oxetan-2-ylmethanamine for 2-methoxyethylamine. ES/MS: 237.2 (M+H$^+$).

Intermediate I-5

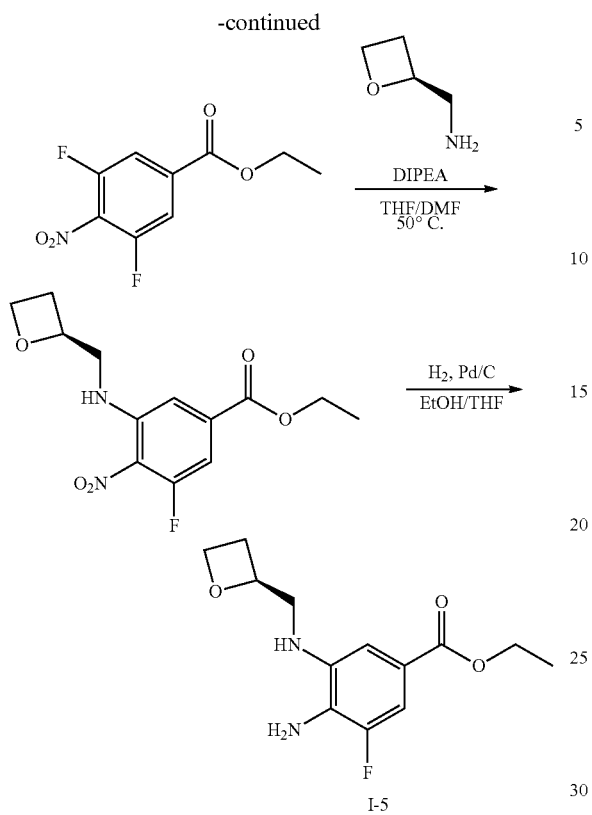

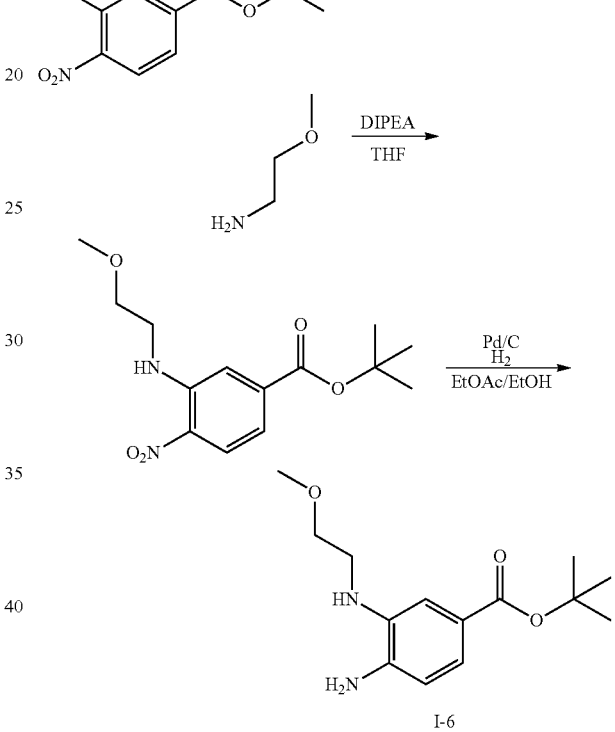

Ethyl 3,5-difluoro-4-nitrobenzoate: Ethyl 4-amino-3,5-difluorobenzoate (5.00 g, 24.9 mmol) was taken up in acetic acid (50.0 mL) and sulfuric acid (12.1 M, 2.05 mL, 24.9 mmol) and hydrogen peroxide (30% aqueous solution, 46.7 mL, 74.6 mmol) were added sequentially. The mixture was heated to 100° C. for 1 hour. The mixture was then cooled to room temperature and then slowly poured into 300 mL of ice water while swirling. The mixture was then diluted with EtOAc (200 mL), transferred to a separatory funnel, and the organic phase collected. The aqueous phase was extracted with EtOAc (2×100 mL) and the combined organics were dried over MgSO$_4$ and concentrated in vacuo. The residue was purified by column chromatography (eluent: EtOAc/Hexanes gradient) to afford the product.

Ethyl (S)-3-fluoro-4-nitro-5-((oxetan-2-ylmethyl)amino) benzoate: Ethyl 3,5-difluoro-4-nitro-benzoate (2.50 g, 10.8 mmol) and (S)-oxetan-2-ylmethanamine (989 mg, 11.4 mol) were taken up in tetrahydrofuran (12.0 mL) and N,N-dimethylformamide (6.0 mL), and N,N-diisopropylethylamine (9.42 mL, 54.1 mmol) was added. The mixture was heated to 50° C. for 16 hours. Following this time, the mixture was concentrated in vacuo and the residue purified by column chromatography (eluent: 0-25% EtOAc/Hexanes) to afford the product. ES/MS: 299.2 (M+H$^+$).

Ethyl (S)-4-amino-3-fluoro-5-((oxetan-2-ylmethyl) amino)benzoate (I-5): Ethyl (S)-3-fluoro-4-nitro-5-((oxetan-2-ylmethyl)amino)benzoate (2.20 g, 7.38 mmol) was taken up in ethanol (10 mL) and tetrahydrofuran (5 mL) and the mixture sparged with nitrogen for 5 minutes. Palladium on carbon (10 wt. % loading, 785 mg, 0.74 mmol) was then added and sparging continued for 5 minutes. Hydrogen was then bubbled through the solution for one minute and then the mixture was set up under balloon hydrogen atmosphere for 21 hours. Following this time, the reaction was stopped, and the mixture was filtered through Celite. The filter was washed with EtOAc (2×20 mL) and methanol (2×10 mL) and the filtrate concentrated in vacuo to afford ethyl (S)-4-amino-3-fluoro-5-((oxetan-2-ylmethyl)amino)benzoate (I-5). ES/MS: 269.2 (M+H$^+$); $^1$H NMR (400 MHz, chloroform) δ 7.44-7.30 (m, 2H), 5.13 (qd, J=7.1, 3.4 Hz, 1H), 4.72 (ddd, J=8.7, 7.4, 6.0 Hz, 1H), 4.62 (dt, J=9.1, 6.1 Hz, 1H), 4.33 (q, J=7.1 Hz, 2H), 3.58-3.30 (m, 2H), 2.76 (dtd, J=11.4, 8.0, 6.1 Hz, 1H), 2.56 (ddt, J=11.3, 9.0, 7.1 Hz, 1H), 1.37 (t, J=7.1 Hz, 3H).

Preparation of Intermediate I-6

Tert-butyl 3-((2-methoxyethyl)amino)-4-nitrobenzoate: To a 500 mL RBF was added tert-butyl 3-fluoro-4-nitrobenzoate (10 g, 41.5 mmol). The material was dissolved in THF (150 mL), and 2-methoxyethanamine (7.2 mL, 82.9 mmol) and N,N-diisopropylethylamine (21.7 mL, 124 mmol) were added. The mixture was stirred at 50° C. overnight. Afterward, the mixture was concentrated to remove most of the THF, and the crude material was dissolved in EtOAc (400 mL). The organics were washed with 50% NH$_4$Cl (2×100 mL) and with brine (1×50 mL). The organics were subsequently dried over MgSO$_4$, filtered, and concentrated under reduced pressure. The crude material was carried forward without further purification: ES/MS: 297.1 (M+H$^+$); $^1$H NMR (400 MHz, Chloroform-d) δ 8.21 (d, J=8.9 Hz, 1H), 7.55 (d, J=1.7 Hz, 1H), 7.20 (dd, J=8.9, 1.7 Hz, 1H), 3.72 (dd, J=5.8, 4.8 Hz, 2H), 3.57 (q, J=5.2 Hz, 2H), 3.46 (s, 3H), 1.62 (s, 9H).

Tert-butyl 4-amino-3-((2-methoxyethyl)amino)benzoate (I-6): To a 1 L RBF was added tert-butyl 3-((2-methoxyethyl)amino)-4-nitrobenzoate (13 g, 43.9 mmol), ethanol (100 mL), and EtOAc (50 mL). The mixture was stirred and sonicated until all material was dissolved. Nitrogen was bubbled through the mixture for 5 minutes, and then palladium on carbon (10% wt, 2.33 g, 2.19 mmol) was added. Hydrogen was bubbled through the mixture for 5 minutes, and the mixture was stirred overnight under a hydrogen balloon. Nitrogen was subsequently bubbled through the flask for 10 minutes, and then the mixture was filtered through Celite to remove the catalyst. The filtrate was concentrated under reduced pressure and was used without further purification: ES/MS: 267.2 (M+H$^+$).

Preparation of Intermediate I-7

(6-((4-cyano-2-fluorobenzyl)oxy)pyridin-2-yl)-2,5-difluorophenyl)acetate (12.5 g, 30.3 mmol) and lithium hydroxide (0.2 M, 19.7 mL, 39.4 mmol) in CH$_3$CN (50 mL) was heated at 50° C. for 2 hours. The mixture was acidified with 1 N of hydrochloride to pH=6-7. The material crashed out and was filtered by filter funnel. The solid was washed with water and dried overnight to yield the product: ES/MS: 399.2 (M+H$^+$); $^1$H NMR (400 MHz, Methanol-d4) δ 7.83-7.77 (m, 1H), 7.78-7.65 (m, 2H), 7.64-7.59 (m, 2H), 7.58-7.51 (m, 1H), 7.26-7.14 (m, 1H), 6.91 (d, J=8.2 Hz, 1H), 5.63 (s, 2H), 3.73 (d, J=1.2 Hz, 2H).

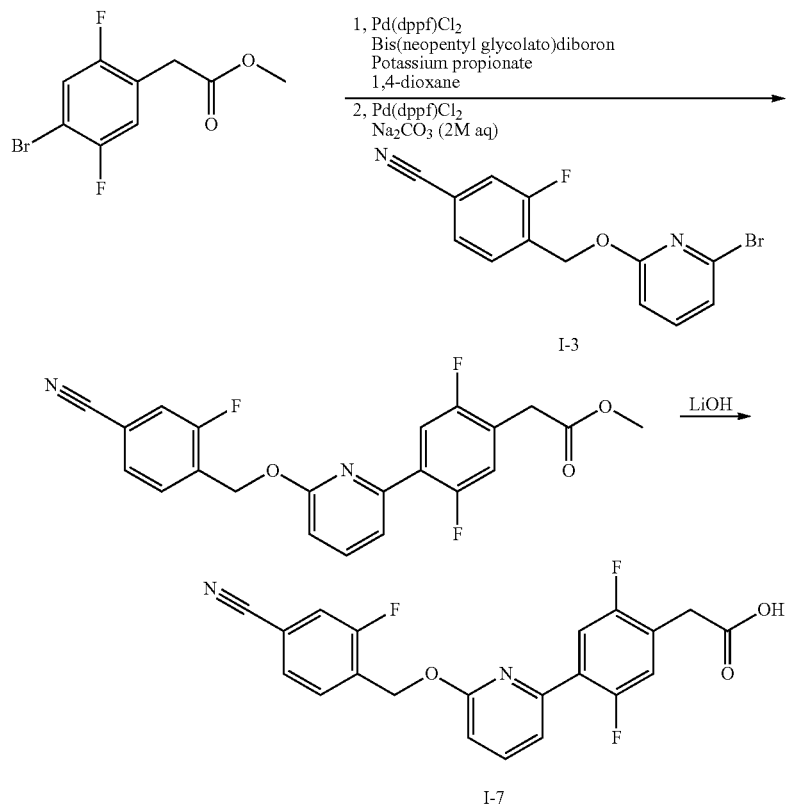

Methyl 2-(4-(6-((4-cyano-2-fluorobenzyl)oxy)pyridin-2-yl)-2,5-difluorophenyl)acetate: A suspension of methyl 2-(4-bromo-2,5-difluorophenyl)acetate (10.5 g, 39.6 mmol), Bis(neopentyl glycolato)diboron (17.9 g, 79.2 mmol), [1,1'-Bis(diphenylphosphino)ferrocene] dichloropalladium(II); PdCl$_2$(dppf) (2.94 g, 3.96 mmol), and potassium propionate (15.6 g, 139 mmol) in dioxane (50 mL) was degassed with Ar for 20 min. The mixture was sealed and heated at 100° C. for 2 hours. Sodium carbonate (2.0 M, 39.6 mL, 79.2 mmol) was added and the mixture was stirred at RT for 10 min. [1,1'-Bis(diphenylphosphino)ferrocene] dichloropalladium(II); PdCl$_2$(dppf) (1.47 g, 1.98 mmol) and I-3 (14 g, 45.6 mmol) were added, the mixture was degassed for 10 min with Ar, then sealed and heated at 100° C. for 1 hour. The mixture was diluted with EtOAc and washed with brine. The organic extract was dried over sodium sulfate and chromatographed (eluent: EtOAc/hexanes) to give the title product: ES/MS: 413.2 (M+H$^+$).

2-(4-(6-((4-cyano-2-fluorobenzyl)oxy)pyridin-2-yl)-2,5-difluorophenyl)acetic acid (I-7). A solution of methyl 2-(4-

Preparation of Intermediate I-8

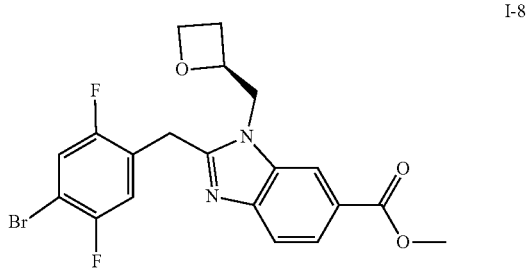 [SMILES: COC(=O)c1ccc2nc(Cc3cc(F)c(Br)cc3F)n(C[C@@H]3CCO3)c2c1]

Methyl (S)-2-(4-bromo-2,5-difluorobenzyl)-1-(oxetan-2-ylmethyl)-1H-benzo[d]imidazole-6-carboxylate (I-8): Methyl (S)-2-(4-bromo-2,5-difluorobenzyl)-1-(oxetan-2-ylmethyl)-1H-benzo[d]imidazole-6-carboxylate was prepared following procedure Intermediate I-2 substituting I-4 for I-1 and 2-(4-bromo-2,5-difluorophenyl)acetic acid for 2-(4-bromo-2-fluoro-phenyl)acetic acid. ES/MS: 451.0, 453.0 (M+H+).

Preparation of Intermediate I-9

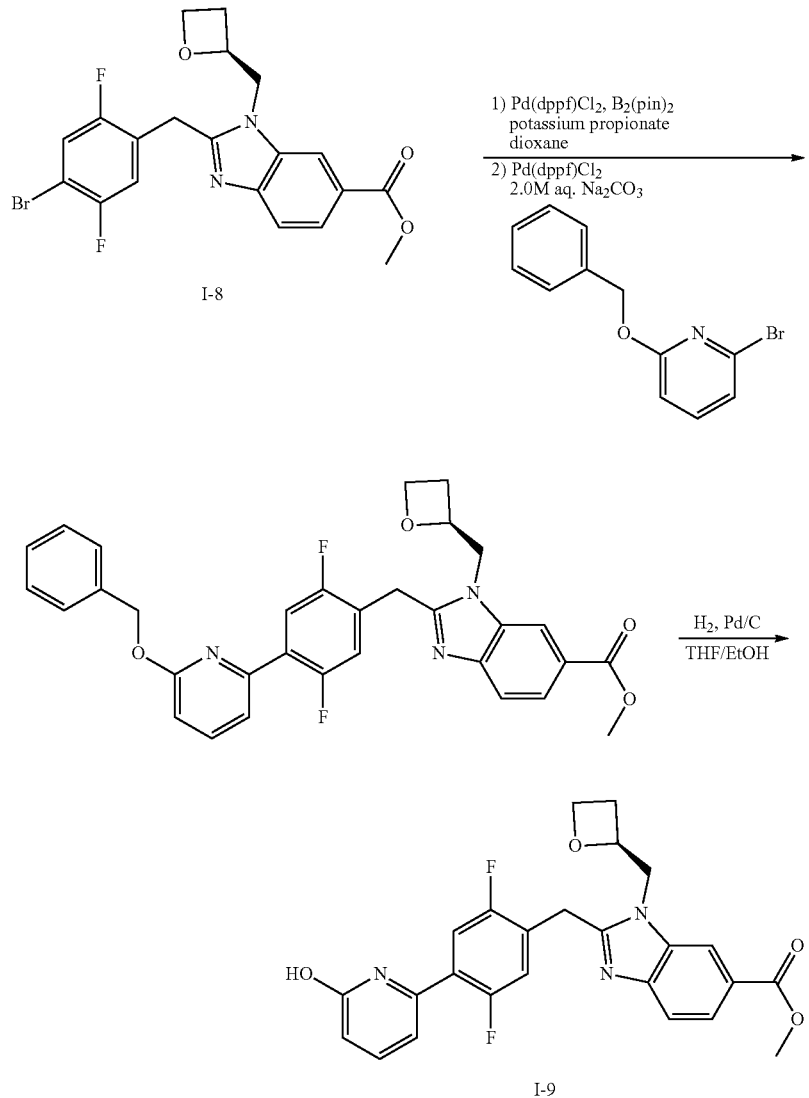

Methyl (S)-2-(4-(6-(benzyloxy)pyridin-2-yl)-2,5-difluorobenzyl)-1-(oxetan-2-ylmethyl)-1H-benzo[d]imidazole-6-carboxylate: Methyl (S)-2-(4-bromo-2,5-difluorobenzyl)-1-(oxetan-2-ylmethyl)-1H-benzo[d]imidazole-6-carboxylate (I-8) (450 mg, 0.997 mmol), Pd(dppf)Cl$_2$ (74.0 mg, 0.100 mmol), potassium propionate (336 mg, 2.99 mmol), and bis(pinacolato)diboron (304 mg, 2.99 mmol) were taken up in 1,4-dioxane (4.00 mL) and the mixture sparged with argon for 5 minutes. The mixture was then heated to 110° C. for one hour. Following this time, complete conversion to the intermediate boronate ester was observed. The mixture was cooled to rt. and aqueous sodium carbonate (2.0 M, 0.997 mL, 1.99 mmol) was added. The mixture was stirred for 5 minutes, then 2-(benzyloxy)-6-bromopyridine (290 mg, 1.10 mmol) and Pd(dppf)Cl$_2$ (37.0 mg, 0.050 mmol) were added and the mixture heated to 90° C. for 1 hour. The mixture was then loaded directly onto SiO$_2$ for purification with normal phase column chromatography (eluent: EtOAc/CH$_2$Cl$_2$ gradient) which afforded the desired product. ES/MS: 556.2 (M+H+)

Methyl (S)-2-(2,5-difluoro-4-(6-hydroxypyridin-2-yl)benzyl)-1-(oxetan-2-ylmethyl)-1H-benzo[d]imidazole-6-carboxylate (I-9): Methyl (S)-2-(4-(6-(benzyloxy)pyridin-2-yl)-2,5-difluorobenzyl)-1-(oxetan-2-ylmethyl)-1H-benzo[d]imidazole-6-carboxylate (426.0 mg, 0.767 mmol) was taken up in ethanol (6.0 mL) and tetrahydrofuran (3.0 mL) and the solution sparged with nitrogen for 5 minutes. Pd/C (408 mg, 0.383 mmol) was added and nitrogen bubbled through the suspension for an additional 5 minutes. Hydrogen was then bubbled through the solution for 5 minutes before the mixture was set up under balloon hydrogen atmosphere. The mixture was stirred at RT for 30 minutes. Following this time, the suspension was filtered through celite, washed with EtOAc (3×10 mL). The filtrate was concentrated in vacuo to afford the methyl (S)-2-(2,5-difluoro-4-(6-hydroxypyridin-2-yl)benzyl)-1-(oxetan-2-ylmethyl)-1H-benzo[d]imidazole-6-carboxylate (I-9). ES/MS: 466.2 (M+H+)

Preparation of Intermediate I-10

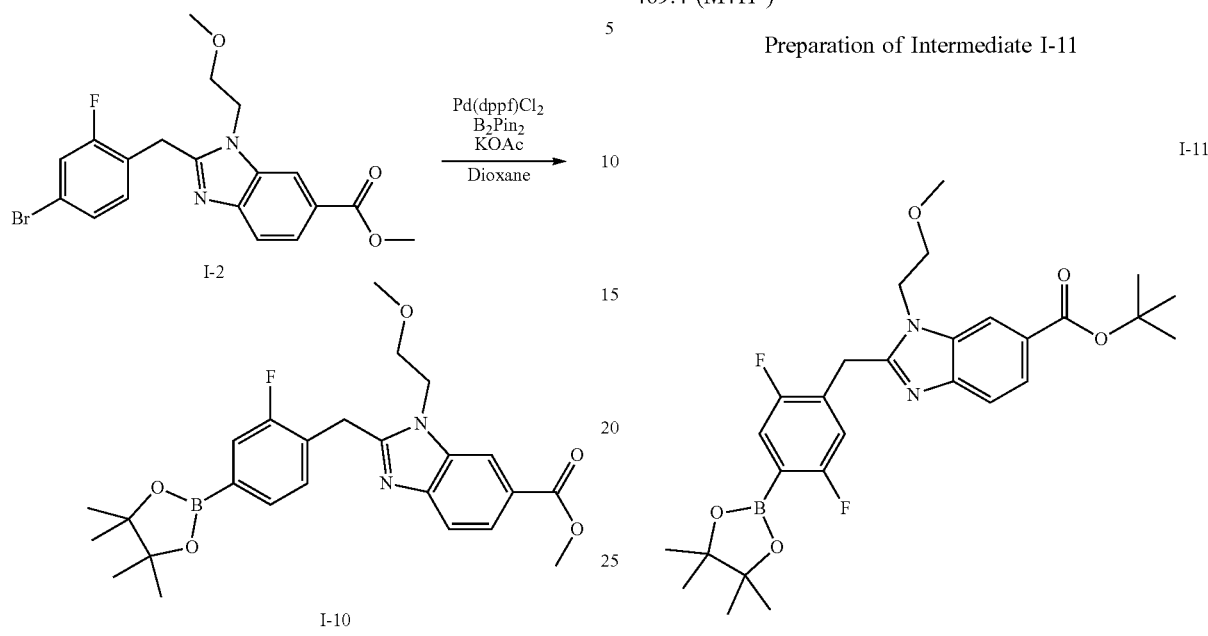

Methyl 2-[[2-fluoro-4-(4,4,5,5-tetramethyl-1,3,2-dioxaborolan-2-yl)phenyl]methyl]-3-(2-methoxyethyl)benzimidazole-5-carboxylate (I-10): To a vial, methyl 2-[(4-bromo-2-fluoro-phenyl)methyl]-3-(2-methoxyethyl)benzimidazole-5-carboxylate (I-2) (200 mg, 0.475 mmol), 4,4,5,5-tetramethyl-2-(4,4,5,5-tetramethyl-1,3,2-dioxaborolan-2-yl)-1,3,2-dioxaborolane (145 mg, 0.570 mmol), (1,1'-bis(diphenylphosphino)ferrocene)-dichloropalladium(II) (33.6 mg, 0.0475 mmol) and potassium acetate (0.140 g, 1.42 mmol) was added. Next, 1,4-dioxane (4.80 mL) was added and the mixture was heated to 100° C. for 24 hr. The mixture was filtered through celite, eluting with DCM and the filtrate was concentrated in vacuo. The crude residue was purified by column chromatography (0-100% EtOAc in hexane) to give methyl 2-[[2-fluoro-4-(4,4,5,5-tetramethyl-1,3,2-dioxaborolan-2-yl)phenyl]methyl]-3-(2-methoxyethyl)benzimidazole-5-carboxylate (I-10). ES/MS m/z: 469.4 (M+H$^+$)

Preparation of Intermediate I-11

Tert-butyl 2-(2,5-difluoro-4-(4,4,5,5-tetramethyl-1,3,2-dioxaborolan-2-yl)benzyl)-1-(2-methoxyethyl)-1H-benzo[d]imidazole-6-carboxylate (I-11): tert-butyl 2-(2,5-difluoro-4-(4,4,5,5-tetramethyl-1,3,2-dioxaborolan-2-yl)benzyl)-1-(2-methoxyethyl)-1H-benzo[d]imidazole-6-carboxylate was prepared in a manner as described for Intermediate I-10 substituting 2-(4-bromo-2,5-difluorophenyl)acetic acid for 2-(4-bromo-2-fluorophenyl)acetic acid and tert-butyl 4-amino-3-((2-methoxyethyl)amino)benzoate (I-6) for methyl 4-amino-3-(2-methoxyethylamino)benzoate. ES/MS: 529.3 (M+H$^+$); $^1$H NMR (400 MHz, DMSO-d$^6$) δ 8.13 (s, 1H), 7.74 (dd, J=8.4, 1.6 Hz, 1H), 7.56 (d, J=8.4 Hz, 1H), 7.33 (dd, J=9.3, 4.6 Hz, 1H), 7.17 (dd, J=9.1, 5.5 Hz, 1H), 4.54 (t, J=5.1 Hz, 2H), 4.39 (s, 2H), 3.65 (t, J=5.1 Hz, 2H), 3.20 (s, 3H), 1.57 (s, 9H), 1.31 (s, 12H).

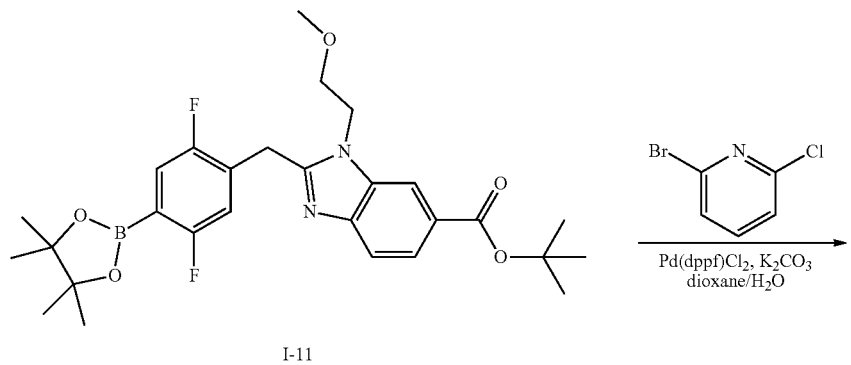

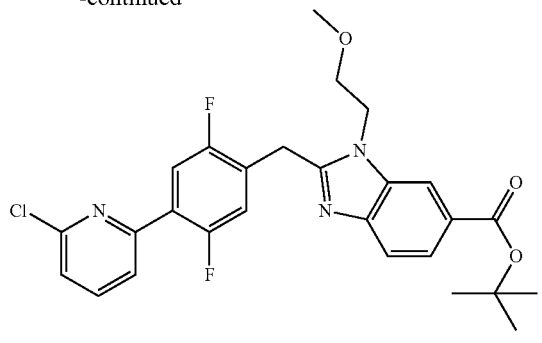

I-12

Preparation of Intermediate I-12

Tert-butyl 2-[[4-(6-chloropyridin-2-yl)-2,5-difluorophenyl]methyl]-3-(2-methoxyethyl)-1,3-benzodiazole-5-carboxylate (I-12): tert-butyl 2-[[2,5-difluoro-4-(4,4,5,5-tetramethyl-1,3,2-dioxaborolan-2-yl)phenyl]methyl]-3-(2-methoxyethyl)-1,3-benzodiazole-5-carboxylate (I-11) (30.0 g, 56.7 mmol, 1.00 equivalent) and 2-bromo-6-chloropyridine (14.2 g, 73.8 mmol, 1.30 equivalent) were dissolved in 1,4-dioxane (600 mL) and H₂O (60 mL). To the solution Pd(dppf)Cl₂ (4.15 g, 5.68 mmol, 0.1 equivalent) and K₂CO₃ (15.7 g, 114 mmol, 2.0 equivalent) were added. The resulting solution was heated to 90° C. overnight under nitrogen atmosphere. The resulting mixture was concentrated under reduced pressure. The residue was purified by silica gel column chromatography, eluted with petroleum ether/EtOAc (2/1) to afford tert-butyl 2-[[4-(6-chloropyridin-2-yl)-2,5-difluorophenyl]methyl]-3-(2-methoxyethyl)-1,3-benzodiazole-5-carboxylate (1-12). ES/MS: 513.8 (M+H⁺); ¹H NMR (400 MHz, DMSO-d⁶) δ 8.14 (s, 1H), 8.02 (t, J=7.9 Hz, 1H), 7.87 (d, J=7.7 Hz, 1H), 7.78-7.69 (m, 2H), 7.59 (d, J=8.2 Hz, 2H), 7.41 (dd, J=11.4, 6.0 Hz, 1H), 4.58 (t, J=5.1 Hz, 2H), 4.44 (s, 2H), 3.68 (t, J=5.1 Hz, 2H), 3.22 (s, 3H), 1.58 (s, 9H).

Preparation of Intermediate I-13

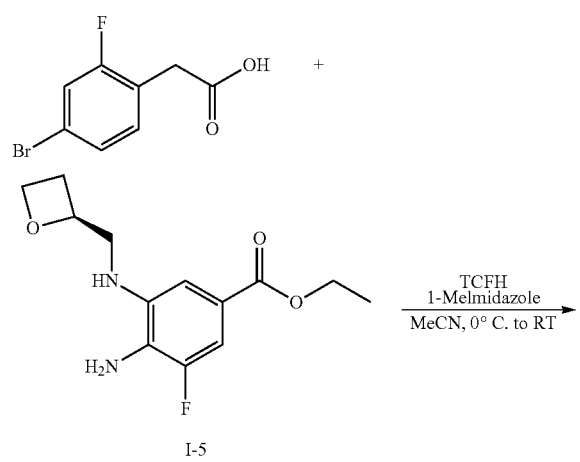

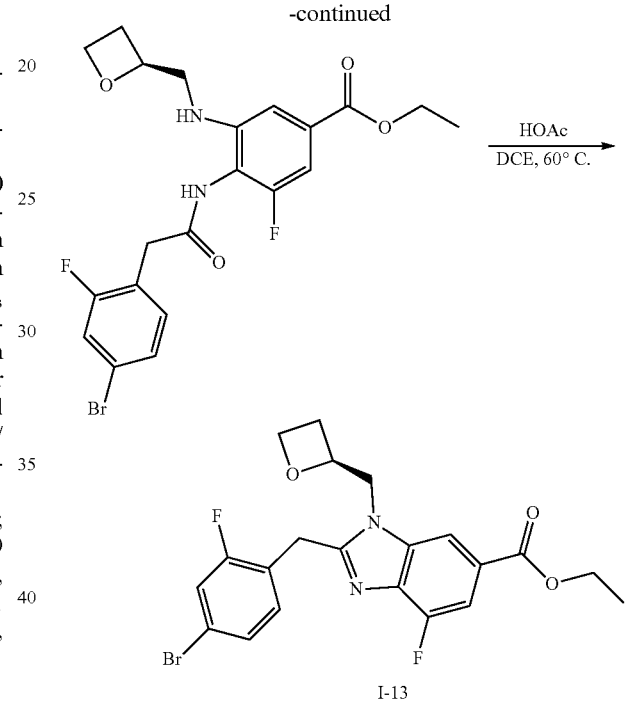

I-13

Ethyl (S)-4-(2-(4-bromo-2-fluorophenyl)acetamido)-3-fluoro-5-((oxetan-2-ylmethyl)amino)benzoate: A solution of 1-5 (500 mg, 1.86 mmol) and 2-(4-bromo-2-fluorophenyl)acetic acid (521 mg, 2.24 mmol) in MeCN (9.0 mL) was cooled to 0° C. and 1-methylimidazole (765 mg, 0.74 mL, 9.32 mmol) was added followed by N,N,N',N'-Tetramethylchloroformamidinium Hexafluorophosphate (732 mg, 2.61 mmol). The mixture was warmed to RT and stirred for 30 minutes. The crude mixture was concentrated in vacuo, then partitioned between water and EtOAc. The organic layer was isolated and washed with an additional portion of water and then brine. The isolated organic layer was dried over sodium sulfate, isolated by vacuum filtration, concentrated in vacuo, and purified by silica gel column chromatography (eluent: EtOAc/hexanes) to provide ethyl (S)-4-(2-(4-bromo-2-fluorophenyl)acetamido)-3-fluoro-5-((oxetan-2-ylmethyl)amino)benzoate. ES/MS: 483.0, 485.0 [M+H]⁺.

Ethyl (S)-2-(4-bromo-2-fluorobenzyl)-4-fluoro-1-(oxetan-2-ylmethyl)-1H-benzo[d]imidazole-6-carboxylate (I-13): To a solution of ethyl (S)-4-(2-(4-bromo-2-fluorophenyl)acetamido)-3-fluoro-5-((oxetan-2-ylmethyl)amino)

benzoate (530 mg, 1.10 mmol) in DCE (12.0 mL) was added acetic acid (1.88 mL, 32.9 mmol). The mixture was heated to 60° C. for 12 hours. The mixture was concentrated and partitioned between EtOAc and saturated aqueous sodium bicarbonate. The organic layer was isolated and dried over sodium sulfate, isolated by vacuum filtration, concentrated in vacuo, and purified by silica gel column chromatography (eluent: EtOAc/hexanes) to provide ethyl (S)-2-(4-bromo-2-fluorobenzyl)-4-fluoro-1-(oxetan-2-ylmethyl)-1H-benzo[d]imidazole-6-carboxylate (I-13). ES/MS: 465.0, 467.0 [M+H]$^+$.

Preparation of Intermediate I-14

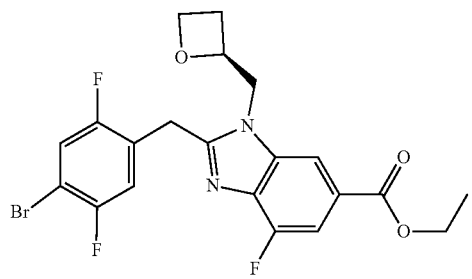

I-14

Ethyl (S)-2-(4-bromo-2,5-difluorobenzyl)-4-fluoro-1-(oxetan-2-ylmethyl)-1H-benzo[d]imidazole-6-carboxylate (I-14): Ethyl (S)-2-(4-bromo-2,5-difluorobenzyl)-4-fluoro-1-(oxetan-2-ylmethyl)-1H-benzo[d]imidazole-6-carboxylate was prepared in a manner as described for Intermediate I-13 substituting 2-(4-bromo-2,5-difluorophenyl)acetic acid for 2-(4-bromo-2-fluorophenyl)acetic acid. ES/MS: 483.0, 485.0 (M+H$^+$).

Preparation of Intermediate I-15

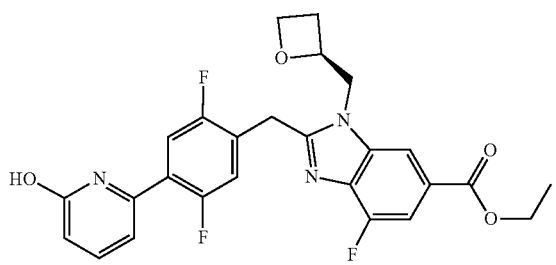

I-15

Ethyl (S)-2-(2,5-difluoro-4-(6-hydroxypyridin-2-yl)benzyl)-4-fluoro-1-(oxetan-2-ylmethyl)-1H-benzo[d]imidazole-6-carboxylate (I-15): Ethyl (S)-2-(2,5-difluoro-4-(6-hydroxypyridin-2-yl)benzyl)-4-fluoro-1-(oxetan-2-ylmethyl)-1H-benzo[d]imidazole-6-carboxylate was prepared in a manner as described for Intermediate I-9 substituting 1-14 for 1-8. ES/MS: 498.2 (M+H$^+$).

Preparation of Intermediate I-16

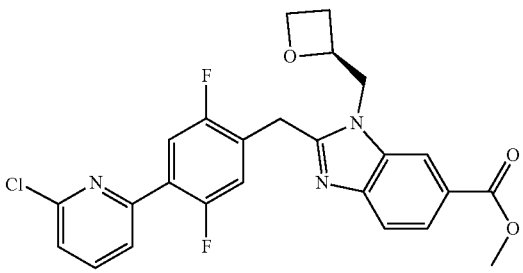

I-16

Methyl (S)-2-(4-(6-chloropyridin-2-yl)-2,5-difluorobenzyl)-1-(oxetan-2-ylmethyl)-1H-benzo[d]imidazole-6-carboxylate (I-16): Methyl (S)-2-(4-(6-chloropyridin-2-yl)-2,5-difluorobenzyl)-1-(oxetan-2-ylmethyl)-1H-benzo[d]imidazole-6-carboxylate was prepared in a manner a described for Intermediate I-12 substituting 1-4 for 1-6. ES/MS: 484.0 (M+H$^+$).

Preparation of Intermediate 17

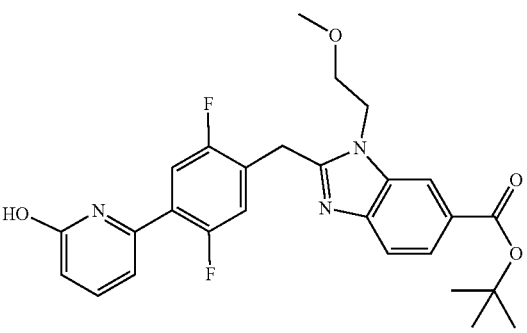

I-17

Tert-butyl 2-(2,5-difluoro-4-(6-hydroxypyridin-2-yl)benzyl)-1-(2-methoxyethyl)-1H-benzo[d]imidazole-6-carboxylate (I-17): Tert-butyl 2-(2,5-difluoro-4-(6-hydroxypyridin-2-yl)benzyl)-1-(2-methoxyethyl)-1H-benzo[d]imidazole-6-carboxylate was prepared in a manner as described for Intermediate I-9 substituting tert-butyl 2-(4-bromo-2,5-difluorobenzyl)-1-(2-methoxyethyl)-1H-benzo[d]imidazole-6-carboxylate (prepared in a manner as described for intermediate 1-2 substituting 2-(4-bromo-2,5-difluorophenyl)acetic acid for 2-(4-bromo-2-fluorophenyl)acetic acid) and 1-6 for I-1. ES/MS: 496.9 (M+H$^+$).

Preparation of Intermediate I-18

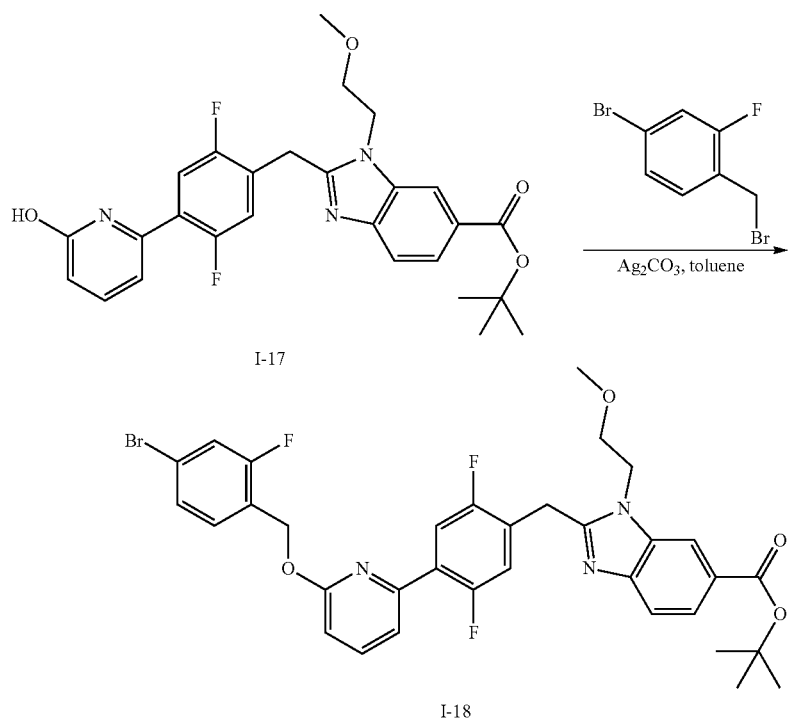

Tert-butyl 2-(4-(6-((4-bromo-2-fluorobenzyl)oxy)pyridin-2-yl)-2,5-difluorobenzyl)-1-(2-methoxyethyl)-1H-benzo[d]imidazole-6-carboxylate (I-18): To a solution of tert-butyl 2-[[2,5-difluoro-4-(6-hydroxy-2-pyridyl)phenyl]methyl]-3-(2-methoxyethyl)benzimidazole-5-carboxylate (I-17) (500 mg, 1.0 mmol) in toluene (5 ml), 4-bromo-1-(bromomethyl)-2-fluoro-benzene (406 mg, 1.5 mmol) and Silver carbonate (835 mg, 3 mmol) were added. The solution was stirred at 70° C. for 8 hr., cooled and filtered. The solution was concentrated and purified by silica gel column chromatography (eluent: EtOAc/hexanes) to provide tert-butyl 2-(4-(6-((4-bromo-2-fluorobenzyl)oxy)pyridin-2-yl)-2,5-difluorobenzyl)-1-(2-methoxyethyl)-1H-benzo[d]imidazole-6-carboxylate (I-18): ES/MS: 683.2, 684.1 (M+H⁺).

Preparation of Intermediate I-19

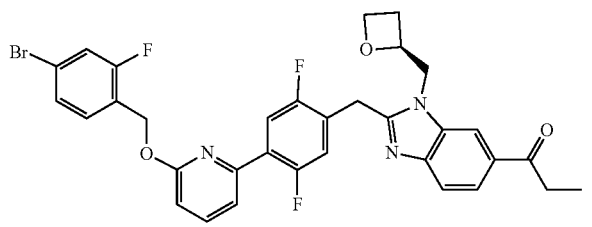

Methyl (S)-2-(4-(6-((4-bromo-2-fluorobenzyl)oxy)pyridin-2-yl)-2,5-difluorobenzyl)-1-(oxetan-2-ylmethyl)-1H-benzo[d]imidazole-6-carboxylate (I-19): Methyl (S)-2-(4-(6-((4-bromo-2-fluorobenzyl)oxy)pyridin-2-yl)-2,5-difluorobenzyl)-1-(oxetan-2-ylmethyl)-1H-benzo[d]imidazole-6-carboxylate was prepared in a manner as described for Intermediate I-18 substituting 1-9 for 1-17. ES/MS: 652.3 (M+H⁺).

Preparation of Intermediate I-20

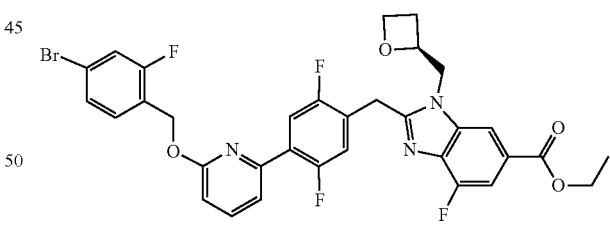

Ethyl (S)-2-(4-(6-((4-bromo-2-fluorobenzyl)oxy)pyridin-2-yl)-2,5-difluorobenzyl)-4-fluoro-1-(oxetan-2-ylmethyl)-1H-benzo[d]imidazole-6-carboxylate (I-20): Ethyl (S)-2-(4-(6-((4-bromo-2-fluorobenzyl)oxy)pyridin-2-yl)-2,5-difluorobenzyl)-4-fluoro-1-(oxetan-2-ylmethyl)-1H-benzo[d]imidazole-6-carboxylate was prepared in a manner as described for Intermediate I-18 substituting 1-15 for 1-17. ES/MS: 684.2 (M+H⁺).

Preparation of Intermediate I-21

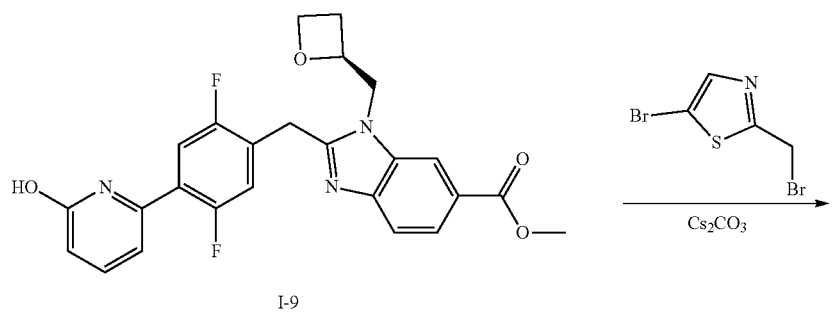

I-9

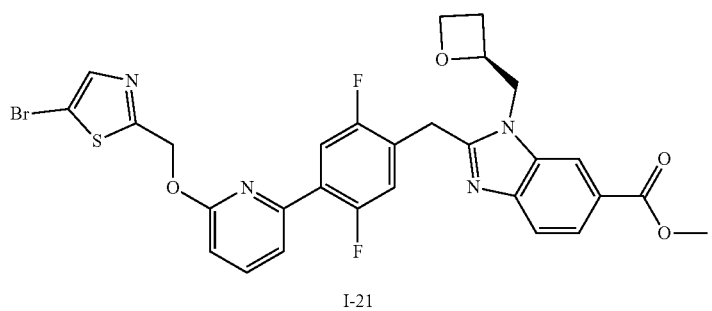

I-21

Methyl (S)-2-(4-(6-((5-bromothiazol-2-yl)methoxy)pyridin-2-yl)-2,5-difluorobenzyl)-1-(oxetan-2-ylmethyl)-1H-benzo[d]imidazole-6-carboxylate (I-21): To a solution of methyl (S)-2-(2,5-difluoro-4-(6-hydroxypyridin-2-yl)benzyl)-1-(oxetan-2-ylmethyl)-1H-benzo[d]imidazole-6-carboxylate (I-9) (500 mg, 1.07 mmol) in acetonitrile (15 mL) was added cesium carbonate (560 mg, 1.72 mmol) and 5-bromo-2-(bromomethyl)thiazole (290 mg, 1.13 mmol) and the resulting mixture stirred for 1 hr. at 50° C. Upon completion the crude mixture was filtered through celite, rinsing with DCM. The filtrate was concentrated, and the crude residue purified by silica gel column chromatography (eluent: EtOAc/hexanes) to provide methyl (S)-2-(4-(6-((5-bromothiazol-2-yl)methoxy)pyridin-2-yl)-2,5-difluorobenzyl)-1-(oxetan-2-ylmethyl)-1H-benzo[d]imidazole-6-carboxylate (I-21). ES/MS: 643.0 (M+H$^+$).

Preparation of Intermediate I-22

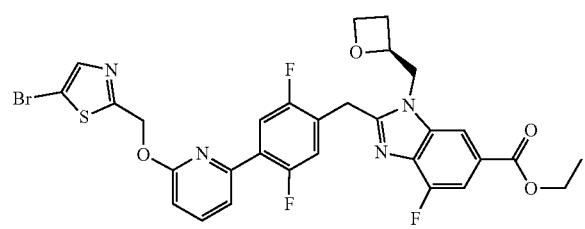

I-22

Ethyl (S)-2-(4-(6-((5-bromothiazol-2-yl)methoxy)pyridin-2-yl)-2,5-difluorobenzyl)-4-fluoro-1-(oxetan-2-ylmethyl)-1H-benzo[d]imidazole-6-carboxylate (I-22): Ethyl (S)-2-(4-(6-((5-bromothiazol-2-yl)methoxy)pyridin-2-yl)-2,5-difluorobenzyl)-4-fluoro-1-(oxetan-2-ylmethyl)-1H-benzo[d]imidazole-6-carboxylate was prepared in a manner as described for Intermediate I-21 substituting I-15 for I-17. ES/MS: 673.0 (M+H$^+$).

Preparation of Intermediate I-23

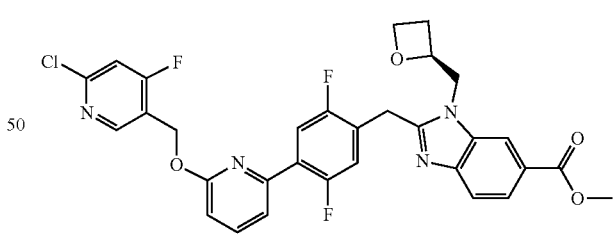

I-23

Methyl (S)-2-(4-(6-((6-chloro-4-fluoropyridin-3-yl)methoxy)pyridin-2-yl)-2,5-difluorobenzyl)-1-(oxetan-2-ylmethyl)-1H-benzo[d]imidazole-6-carboxylate (I-23): Methyl (S)-2-(4-(6-((6-chloro-4-fluoropyridin-3-yl)methoxy)pyridin-2-yl)-2,5-difluorobenzyl)-1-(oxetan-2-ylmethyl)-1H-benzo[d]imidazole-6-carboxylate was prepared in a manner as described for Intermediate I-19 substituting 5-(bromomethyl)-2-chloro-4-fluoropyridine for 4-bromo-1-(bromomethyl)-2-fluoro-benzene ES/MS: 609.2 (M+H$^+$).

Preparation of Intermediate I-24

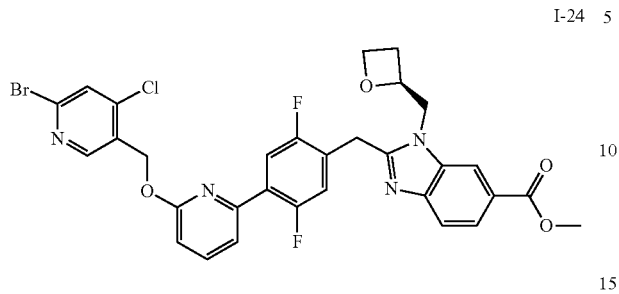

Methyl (S)-2-(4-(6-((6-bromo-4-chloropyridin-3-yl)methoxy)pyridin-2-yl)-2,5-difluorobenzyl)-1-(oxetan-2-ylmethyl)-1H-benzo[d]imidazole-6-carboxylate (I-24): Methyl (S)-2-(4-(6-((6-bromo-4-chloropyridin-3-yl)methoxy)pyridin-2-yl)-2,5-difluorobenzyl)-1-(oxetan-2-ylmethyl)-1H-benzo[d]imidazole-6-carboxylate was prepared in a manner as described for Intermediate I-19 substituting 2-bromo-5-(bromomethyl)-4-chloropyridine for 4-bromo-1-(bromomethyl)-2-fluoro-benzene ES/MS: 654.0, 656.0 (M+H$^+$).

Preparation of Intermediate I-25

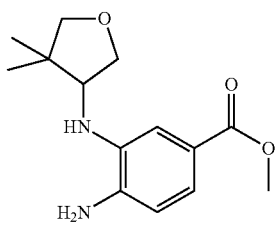

Methyl 4-amino-3-((4,4-dimethyltetrahydrofuran-3-yl)amino)benzoate (I-25): Methyl 4-amino-3-((4,4-dimethyltetrahydrofuran-3-yl)amino)benzoate was prepared in a manner as described for Intermediate I-1 substituting (±)-4,4-dimethyltetrahydrofuran-3-amine for 2-methoxyethylamine, as follows: to a solution of methyl 3-fluoro-4-nitrobenzoate (3.94 g, 19.8 mmol) and 4,4-dimethyltetrahydrofuran-3-amine hydrochloride (3.00 g, 19.8 mmol) in 2-methyltetrahydrofuran (40 mL) under argon was added DIPEA (17.2 mL, 98.9 mmol). The resulting solution was refluxed at 80° C. for 3 days. The mixture was concentrated in vacuo and partitioned between EtOAc and water. The aqueous phase was extracted with additional EtOAc. The combined organic phase was washed with brine, dried over MgSO$_4$, filtered and concentrated in vacuo. The resulting residue was redissolved in EtOH (52 ml) and tetrahydrofuran (26 mL) under argon, then 10% palladium on carbon (2.1 g, 1.98 mmol). The mixture was cycled between argon and vacuum, then placed under hydrogen atmosphere and stirred at rt for 18 hrs. The mixture was filtered through Celite and concentrated in vacuo. The crude was purified by silica gel flash column chromatography (EtOAc/hexane gradient) to yield methyl 4-amino-3-((4,4-dimethyltetrahydrofuran-3-yl)amino)benzoate (Intermediate I-25). ES/MS: 265.2 (M+H$^+$).

Preparation of Intermediate I-26

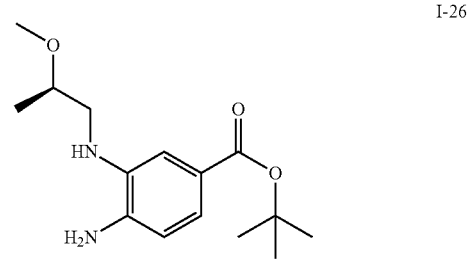 [SMILES: CO[C@H](C)CNc1cc(C(=O)OC(C)(C)C)ccc1N]

Tert-butyl (R)-4-amino-3-((2-methoxypropyl)amino)benzoate (I-26): Tert-butyl (R)-4-amino-3-((2-methoxypropyl)amino)benzoate was prepared in a manner as described for Intermediate I-6 substituting (R)-2-methoxypropan-1-amine for 2-methoxyethylamine. ES/MS: 281.1 (M+H$^+$).

Preparation of Intermediate I-27

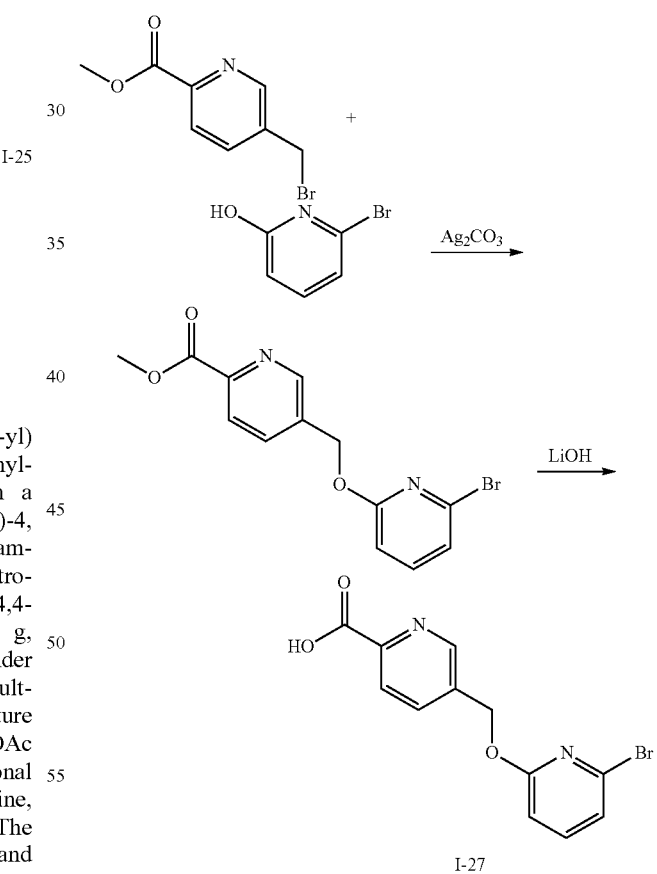

Methyl 5-(((6-bromopyridin-2-yl)oxy)methyl)picolinate: To a solution of 6-bromopyridin-2-ol (3.00 g, 17 mmol) in acetonitrile (100 mL) was added silver carbonate (10.2 g, 37 mmol) and methyl 5-(bromomethyl)pyridine-2-carboxylate (5.00 g, 22 mmol) and the resultant mixture heated to 60° C. for 3 hours. Upon completion the mixture was filtered through celite, concentrated and purified by silica gel column chromatography (eluent: EtOAc/hexanes) to provide the desired product. ES/MS: 325.2 (M+H⁺).

5-(((6-bromopyridin-2-yl)oxy)methyl)picolinic acid (I-27): To a solution of methyl 5-(((6-bromopyridin-2-yl)oxy)methyl)picolinate (5.57 g, 17 mmol) in acetonitrile (75 mL) was added lithium hydroxide (2.17 g, 51.7 mmol) as an solution in water (25 mL) and mixture stirred at RT temperature for 1 hr. pH was adjusted to ~6 with 1N HCl, after which the mixture was diluted with EtOAc (200 mL) and the layers separated. The organic layer was washed with brine, dried over MgSO₄, filtered and concentrated to give 5-(((6-bromopyridin-2-yl)oxy)methyl)picolinic acid (I-27) without further purification. ES/MS: 309.1 (M+H⁺).

Preparation of Intermediate I-28

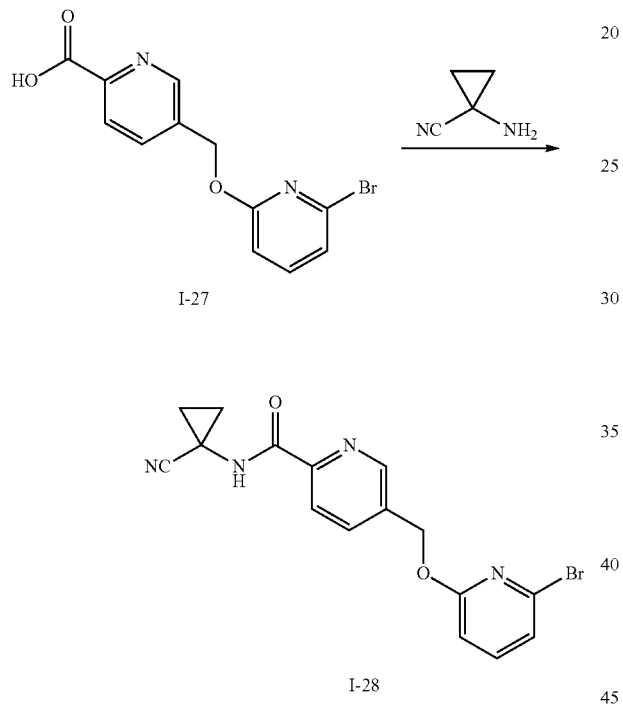

5-(((6-bromopyridin-2-yl)oxy)methyl)-N-(1-cyanocyclopropyl)picolinamide (I-28): To a solution of 5-(((6-bromopyridin-2-yl)oxy)methyl)picolinic acid (I-27) (5.32 g, 17 mmol) in DMF (80 mL), 1-aminocyclopropanecarbonitrile hydrochloride (3.14 g, 26 mmol), HATU (9.62 g, 25 mmol), and diisopropylethylamine (12 mL, 69 mmol) was added sequentially. The resultant solution was stirred at RT temperature for 30 minutes. Upon completion the mixture was diluted with EtOAc (250 mL, wash with water (2×50 mL), brine (1×40 mL), dried over MgSO₄, filtered and concentrated to give 5-(((6-bromopyridin-2-yl)oxy)methyl)-N-(1-cyanocyclopropyl)picolinamide (I-28) without further purification. ES/MS: 375.1 (M+H⁺).

The following intermediates were synthesized in an analogous manner as described for Intermediate I-28

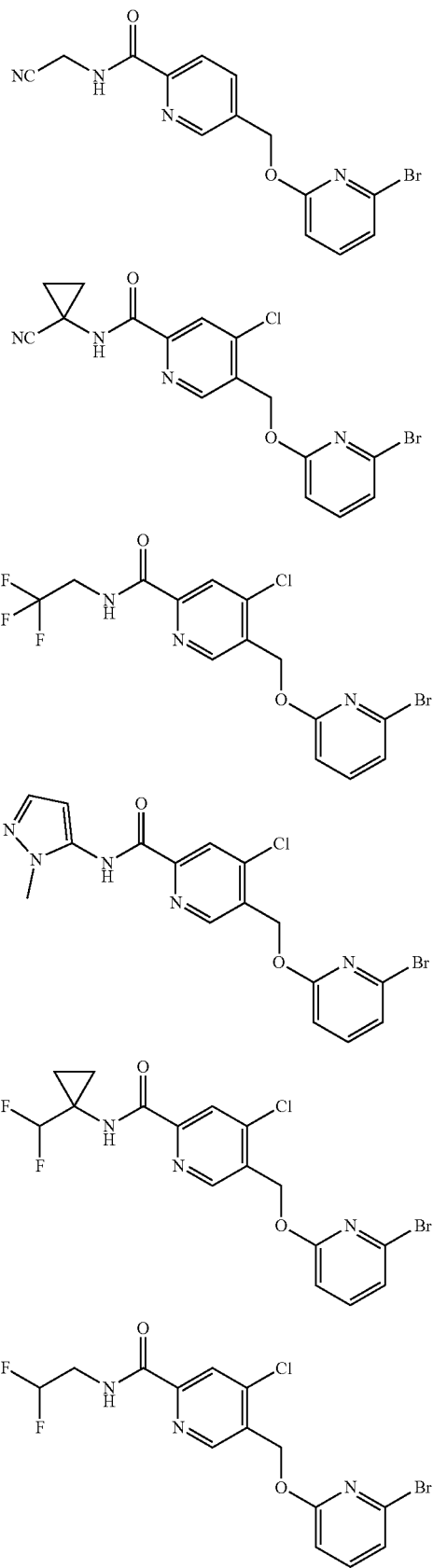

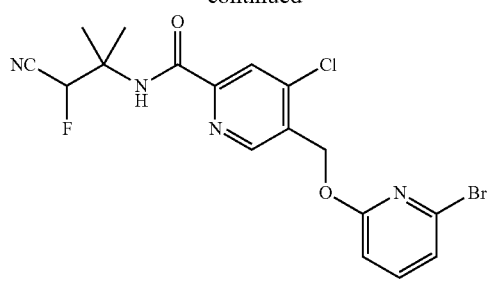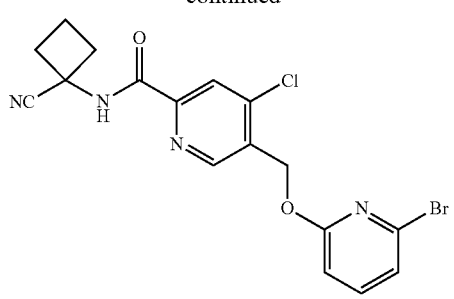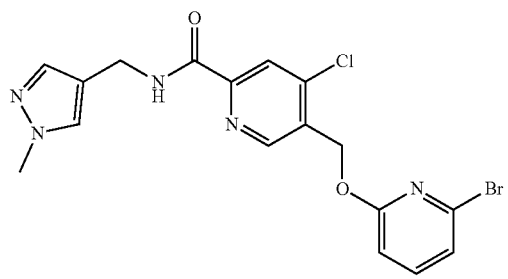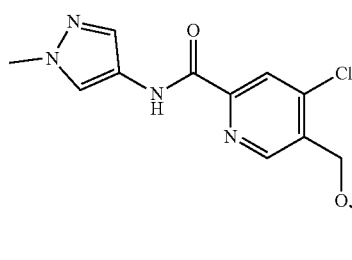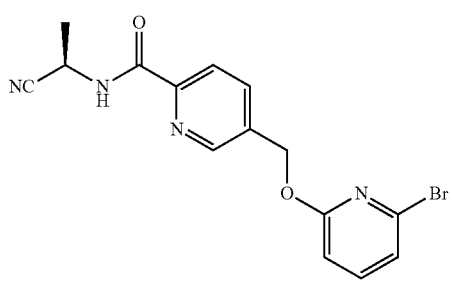
Preparation of Intermediates I-29 and I-30
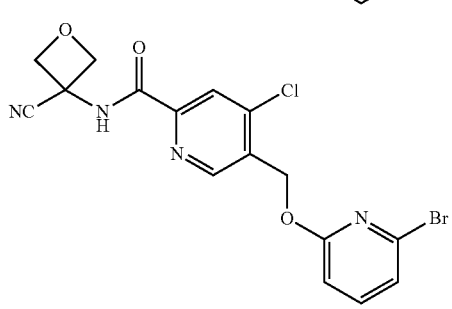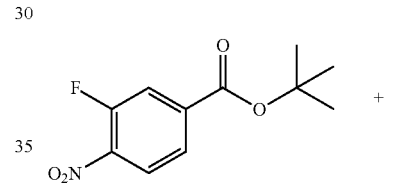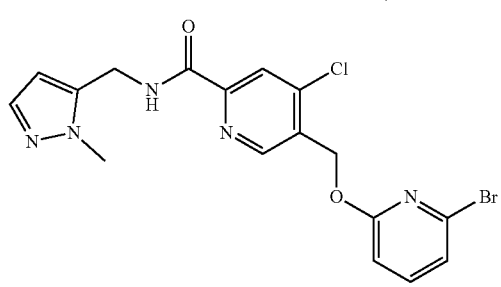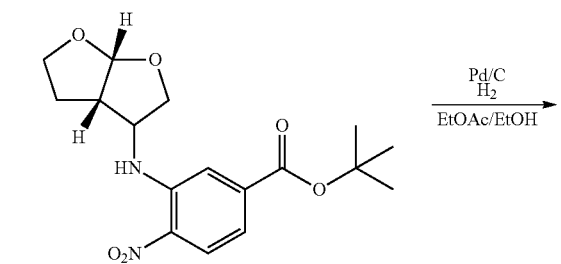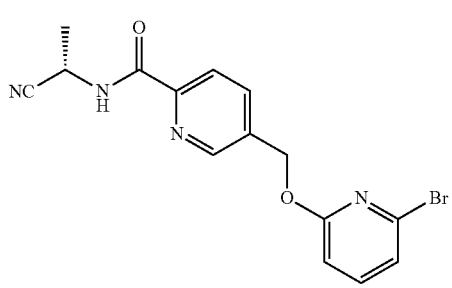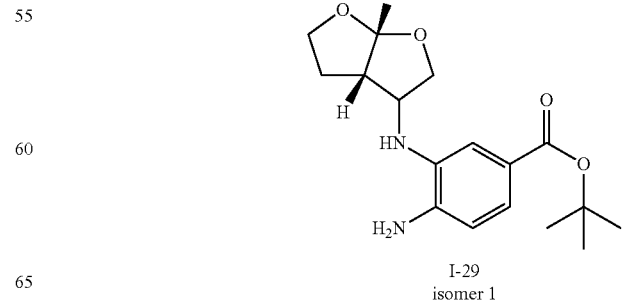
I-29
isomer 1

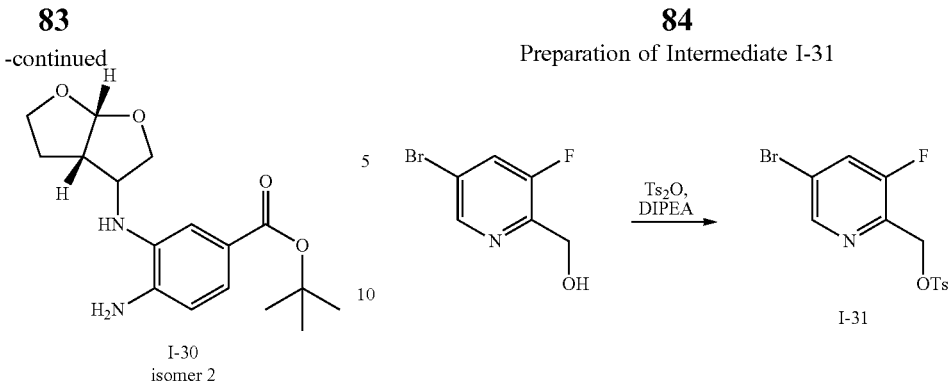

I-30
isomer 2

Preparation of Intermediate I-31

Tert-butyl 4-amino-3-(((3aS,6aR)-hexahydrofuro[2,3-b]furan-3-yl)amino)benzoate (I-29 and I-30):

Tert-butyl 3-(((3aS,6aR)-hexahydrofuro[2,3-b]furan-3-yl)amino)-4-nitrobenzoate: A solution of tert-butyl 3-fluoro-4-nitro-benzoate (0.150 g, 0.622 mmol), (3aS,6aR)-2,3,3a,4,5,6a-hexahydrofuro[2,3-b]furan-4-amine (0.0984 g, 0.762 mmol), and N-ethyl-N-isopropyl-propan-2-amine (0.325 mL, 1.87 mmol) in NMP (4 mL) was heated at 90 C overnight. The mixture was diluted with EtOAc and washed with 5% LiCl and brine. The organic extract was dried over sodium sulfate and purified by flash chromatography (eluent: EtOAc/hexanes) to give tert-butyl 3-(((3aS,6aR)-hexahydrofuro[2,3-b]furan-3-yl)amino)-4-nitrobenzoate as an unseparable mixture of two compounds. ES/MS: 351.0 (M+H$^+$).

Tert-butyl 4-amino-3-(((3aS,6aR)-hexahydrofuro[2,3-b]furan-3-yl)amino)benzoate (I-29 and I-30): A solution of tert-butyl 3-[[(3aS,6aR)-2,3,3a,4,5,6a-hexahydrofuro[2,3-b]furan-4-yl]amino]-4-nitro-benzoate (156 mg, 0.445 mmol) in EtOH (15 mL) was degassed by cycling the mixture between argon and vacuum 3×. Pd/C (10.0%, 47.4 mg, 0.0445 mmol) was added to the solution and then the solution was degassed 1× by cycling the mixture between argon and vacuum and stirred at RT with a balloon of hydrogen overnight. The mixture was filtered over a Celite plug and rinsed with EtOAc. Concentrated and purified by flash chromatography (eluent: 30 to 40% EtOAc/hexanes) to give two distinct isomers of tert-butyl 4-amino-3-(((3aS,6aR)-hexahydrofuro[2,3-b]furan-3-yl)amino)benzoate (I-29 and I-

Isomer 1 (Less Polar, Eluted First), I-29

ES/MS: 321.0 (M+H$^+$). 1H NMR (400 MHz, Chloroform-d) δ 7.45 (dd, J=8.1, 1.8 Hz, 1H), 7.37 (d, J=1.8 Hz, 1H), 6.74 (d, J=8.1 Hz, 1H), 5.87 (d, J=5.1 Hz, 1H), 4.32-4.06 (m, 2H), 4.05-3.81 (m, 2H), 3.66 (t, J=8.7 Hz, 1H), 3.24 (tt, J=8.7, 4.2 Hz, 1H), 2.03-1.90 (m, 1H), 1.90-1.79 (m, 1H), 1.60 (s, 9H).

Isomer 2 (More Polar, Eluted Second), I-30

ES/MS: 321.0 (M+H$^+$). 1H NMR (400 MHz, Chloroform-d) δ 7.45 (dd, J=8.1, 1.8 Hz, 1H), 7.38 (d, J=1.8 Hz, 1H), 6.75 (d, J=8.0 Hz, 1H), 5.87 (d, J=5.1 Hz, 1H), 4.34-4.05 (m, 2H), 4.02-3.82 (m, 2H), 3.67 (t, J=8.6 Hz, 1H), 3.24 (tt, J=8.6, 4.2 Hz, 1H), 2.02-1.81 (m, 2H), 1.60 (s, 9H).

(5-bromo-3-fluoropyridin-2-yl)methyl 4-methylbenzenesulfonate (I-31): (5-bromo-3-fluoro-2-pyridyl)methanol (200 mg, 0.97 mmol), p-Toluenesulfonic anhydride (350 mg, 1.1 mmol), diisopropylethylamine (0.34 mL, 1.9 mmol), and DCM (10 mL were combined and stirred at ambient temperature for 16 hours. Upon completion the mixture was washed with saturated aqueous NaHCO$_3$ (5 mL) and brine (5 mL), dried over MgSO$_4$, filtered and concentrated to give (5-bromo-3-fluoropyridin-2-yl)methyl 4-methylbenzenesulfonate (I-31), which was used without further purification. ES/MS The following intermediate was prepared in a manner as described for Intermediate I-31

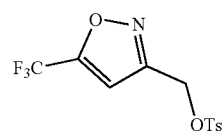

Preparation of Intermediate I-32

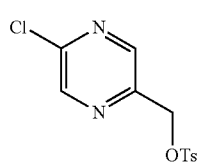

I-32

(5-chloropyrazin-2-yl)methyl 4-methylbenzenesulfonate (I-32): (5-chloropyrazin-2-yl)methyl 4-methylbenzenesulfonate was prepared in a manner as described for Intermediate I-31 substituting (5-chloropyrazin-2-yl)methanol for (5-bromo-3-fluoro-2-pyridyl)methanol.

Preparation of Intermediate I-33

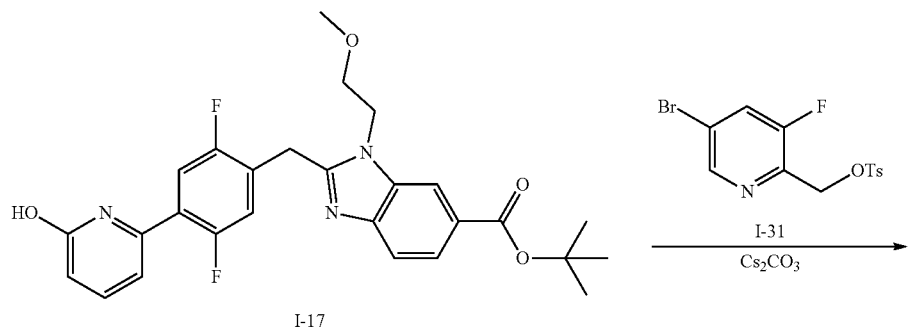

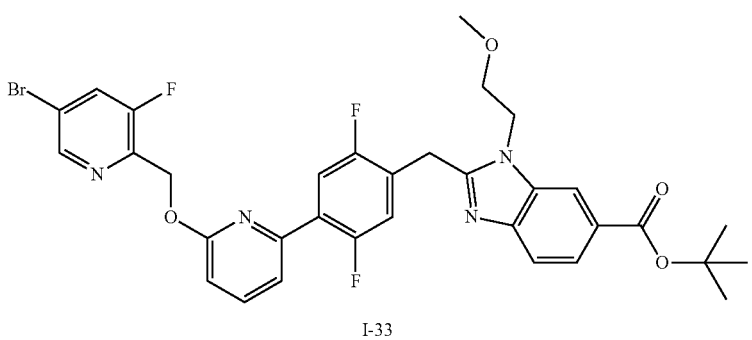

Tert-butyl 2-[[4-[6-[(5-bromo-3-fluoro-2-pyridyl)methoxy]-2-pyridyl]-2,5-difluoro-phenyl]methyl]-3-(2-methoxyethyl)benzimidazole-5-carboxylate (I-33): To a solution of tert-butyl 2-[[2,5-difluoro-4-(6-hydroxy-2-pyridyl)phenyl]methyl]-3-(2-methoxyethyl)benzimidazole-5-carboxylate (I-17) (400 mg, 0.80 mmol) and (5-bromo-3-fluoro-2-pyridyl)methyl 4-methylbenzenesulfonate (I-31) (350 mg, 0.97 mmol) in 15 mL of acetonitrile was added Cs$_2$CO$_3$ (400 mg, 1.20 mmol). The solution was then heated to 50° C. for 30 minutes. The solution was cooled to RT, filtered, and then concentrated. The crude material was purified by silica gel column chromatography (eluent: EtOAc/hexanes) to provide tert-butyl 2-[[4-[6-[(5-bromo-3-fluoro-2-pyridyl)methoxy]-2-pyridyl]-2,5-difluoro-phenyl]methyl]-3-(2-methoxyethyl)benzimidazole-5-carboxylate (I-33): product. ES/MS: 686.0 (M+H$^+$).

Preparation of Intermediate I-34

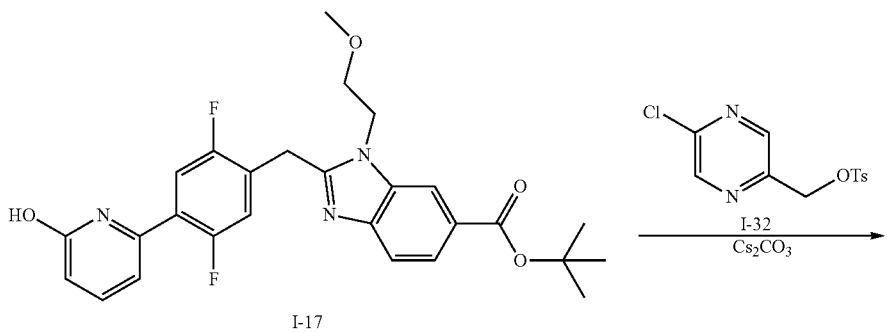

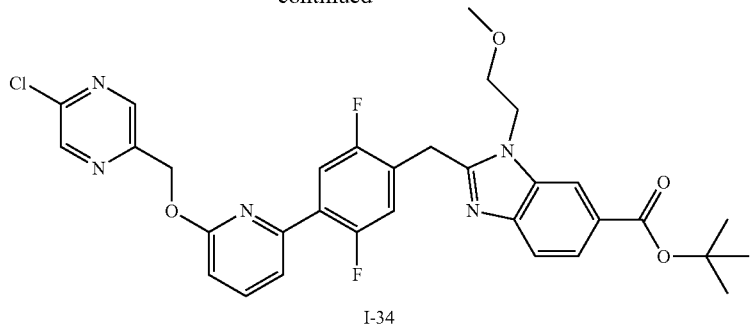

I-34

Tert-butyl 2-[[4-[6-[(5-chloropyrazin-2-yl)methoxy]-2-pyridyl]-2,5-difluoro-phenyl]methyl]-3-(2-methoxyethyl)benzimidazole-5-carboxylate (I-34): tert-butyl 2-[[4-[6-[(5-chloropyrazin-2-yl)methoxy]-2-pyridyl]-2,5-difluoro-phenyl]methyl]-3-(2-methoxyethyl)benzimidazole-5-carboxylate was prepared in a manner as described for Intermediate I-33 substituting I-31 for I-32. ES/MS: 566.0 (M+H+).

Preparation of Intermediate I-35

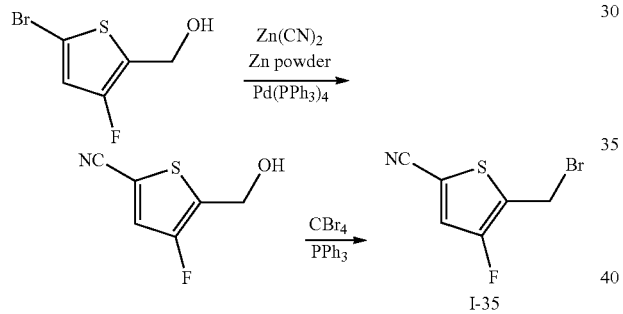

I-35

4-fluoro-5-(hydroxymethyl)thiophene-2-carbonitrile: (5-bromo-3-fluoro-2-thienyl)methanol (220 mg, 1.04 mmol), zinc cyanide (182 mg, 1.55 mmol), zinc powder (3 mg, 0.05 mmol), and Pd(PPh$_3$)$_4$ (300 mg, 0.26 mmol) in DMF (10 mL) was degassed by bubbling argon for 1 minute, sealed and heated to 100° C. for 20 hours. Upon completion, the mixture was poured into H$_2$O (10 mL) and extracted with EtOAc (2×20 mL). The organic layers were combined, washed with brine (5 mL), dried over MgSO$_4$, filtered, concentrated, and purified by flash chromatography (Eluent: EtOAc/hexane) to give 4-fluoro-5-(hydroxymethyl)thiophene-2-carbonitrile. ES/MS: 158.2 (M+1).

5-(bromomethyl)-4-fluoro-thiophene-2-carbonitrile (I-35): Carbon tetrabromide (111 mg, 0.34 mmol was added to a solution comprising 4-fluoro-5-(hydroxymethyl)thiophene-2-carbonitrile (48 mg, 0.31 mmol), triphenylphosphine (88 mg, 0.34 mmol) in DCM (3 mL) at RT. The mixture was stirred for 30 min at RT. Upon completion the mixture was concentrated and purified by flash chromatography (Eluent: EtOAc/hexane) to give 5-(bromomethyl)-4-fluoro-thiophene-2-carbonitrile (I-35). ES/MS: 221.2 (M+1).

Preparation of Intermediate I-36

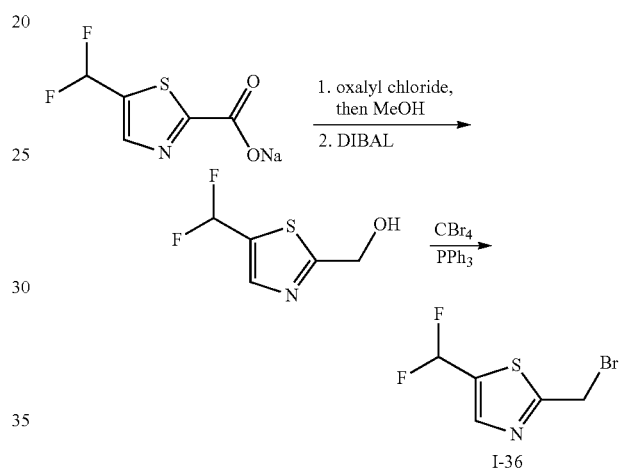

I-36

[5-(difluoromethyl)thiazol-2-yl]methanol: To a solution of [5-(difluoromethyl)thiazole-2-carbonyl]oxysodium (200 mg, 1.08 mmol) in DCM (5 mL), at RT, was added oxalyl chloride (2.0 M in DCM, 0.65 mL, 1.3 mmol). After stirring for 1 hour at RT, MeOH (1 mL) was added and the mixture was stirred for additional 30 minutes before pouring into H$_2$O (10 mL) and extracted with EtOAc (2×20 mL). The organic layers were combined, washed with brine (5 mL), dried over MgSO$_4$, filtered, and concentrated. The residue was re-dissolved in THF (5 mL) and cooled to 0° C. Diisobutylaluminium hydride (1.0 M in DCM, 3.3 mL, 3.3 mmol) was added, and the mixture was warmed to RT and stirred for 1 hour. Upon completion, the reaction was quenched with 2M NaOH (0.4 mL), H$_2$O (0.4 mL), and diluted with EtOAc (10 mL). The mixture was then filtered through a plug of Celite. The organic layers were combined, washed with brine (5 mL), dried over MgSO$_4$, filtered, concentrated, and purified by flash chromatography (Eluent: EtOAc/hexane) to give the desired product. ES/MS: 166.2 (M+1).

2-(bromomethyl)-5-(difluoromethyl)thiazole (I-36): [5-(difluoromethyl)thiazol-2-yl]methanol (88 mg, 0.53 mmol), triphenylphosphine (150 mg, 0.56 mmol) in DCM (3 mL) was added carbon tetrabromide (190 mg, 0.56 mmol) at rt. The mixture was stirred at rt for 30 min. Upon completion, the mixture was concentrated and purified by flash chromatography (Eluent: EtOAc/hexane) to give I-36. ES/MS: 229.2 (M+1).

Preparation of Intermediate I-37

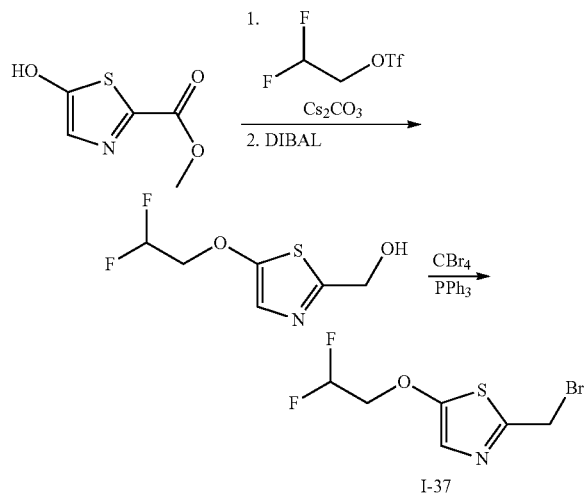

[5-(2,2-difluoroethoxy)thiazol-2-yl]methanol: A suspension of methyl 5-hydroxythiazole-2-carboxylate (200 mg, 1.3 mmol), 2,2-difluoroethyl trifluoromethanesulfonate (300 mg, 1.4 mmol), and cesium carbonate (610 mg, 1.9 mmol) in MeCN (5 mL) was stirred at RT for 16 h. Upon completion, the mixture was filtered through a plug of Celite and concentrated. The residue was re-dissolved in THF (5 mL) and cooled to 0° C. Diisobutylaluminium hydride (1.0 M in DCM, 2.8 mL, 2.8 mmol) was added, and the mixture was warmed to RT and stirred for 1 hour. Upon completion, the reaction was quenched with 2M NaOH (0.4 mL), H$_2$O (0.4 mL) and diluted with EtOAc (10 mL). The mixture was then filtered through a plug of Celite. The organic layers were combined, washed with brine (5 mL), dried over MgSO$_4$, filtered, concentrated, and purified by flash chromatography (Eluent: EtOAc/hexane) to give the desired product.

2-(bromomethyl)-5-(2,2-difluoroethoxy)thiazole (I-37): [5-(2,2-difluoroethoxy)thiazol-2-yl]methanol (91 mg, 0.47 mmol), triphenylphosphine (125 mg, 0.48 mmol) in DCM (5 mL) was added carbon tetrabromide (160 mg, 0.48 mmol) at RT. The mixture was stirred for 30 min at RT. Upon completion the mixture was concentrated and purified by flash chromatography (Eluent: EtOAc/hexane) to give I-37. ES/MS: 258.2 (M+1).

Preparation of Intermediate I-38

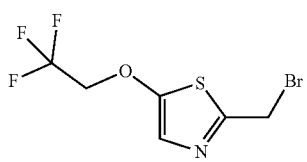

2-(bromomethyl)-5-(2,2,2-trifluoroethoxy)thiazole (I-38): 2-(bromomethyl)-5-(2,2,2-trifluoroethoxy)thiazole was prepared in a manner as described for Intermediate I-37 substituting 2,2-difluoroethyl trifluoromethanesulfonate for 2,2,2-trifluoroethyl trifluoromethanesulfonate. ES/MS: 277.2 (M+1).

Preparation of Intermediate I-39

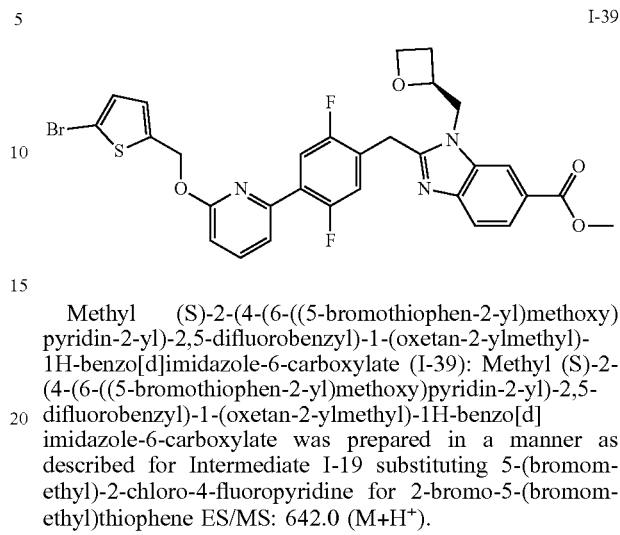

Methyl (S)-2-(4-(6-((5-bromothiophen-2-yl)methoxy)pyridin-2-yl)-2,5-difluorobenzyl)-1-(oxetan-2-ylmethyl)-1H-benzo[d]imidazole-6-carboxylate (I-39): Methyl (S)-2-(4-(6-((5-bromothiophen-2-yl)methoxy)pyridin-2-yl)-2,5-difluorobenzyl)-1-(oxetan-2-ylmethyl)-1H-benzo[d]imidazole-6-carboxylate was prepared in a manner as described for Intermediate I-19 substituting 5-(bromomethyl)-2-chloro-4-fluoropyridine for 2-bromo-5-(bromomethyl)thiophene ES/MS: 642.0 (M+H$^+$).

Preparation of Intermediate I-40

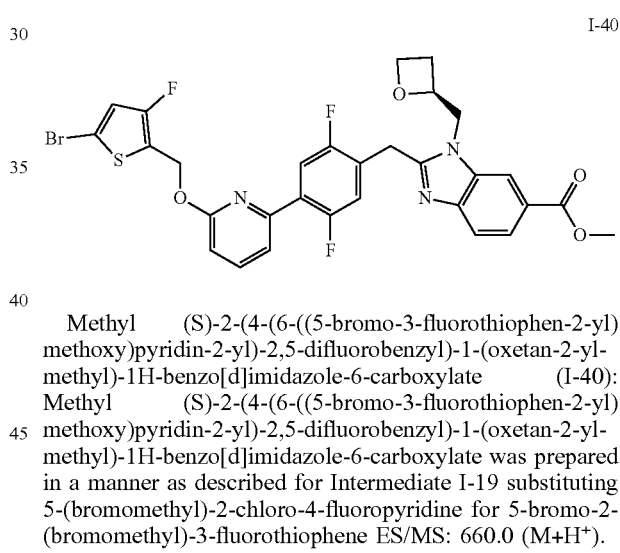

Methyl (S)-2-(4-(6-((5-bromo-3-fluorothiophen-2-yl)methoxy)pyridin-2-yl)-2,5-difluorobenzyl)-1-(oxetan-2-ylmethyl)-1H-benzo[d]imidazole-6-carboxylate (I-40): Methyl (S)-2-(4-(6-((5-bromo-3-fluorothiophen-2-yl)methoxy)pyridin-2-yl)-2,5-difluorobenzyl)-1-(oxetan-2-ylmethyl)-1H-benzo[d]imidazole-6-carboxylate was prepared in a manner as described for Intermediate I-19 substituting 5-(bromomethyl)-2-chloro-4-fluoropyridine for 5-bromo-2-(bromomethyl)-3-fluorothiophene ES/MS: 660.0 (M+H$^+$).

Preparation of Intermediate I-41

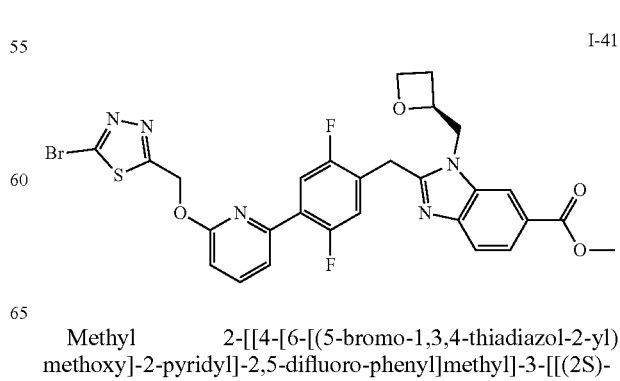

Methyl 2-[[4-[6-[(5-bromo-1,3,4-thiadiazol-2-yl)methoxy]-2-pyridyl]-2,5-difluoro-phenyl]methyl]-3-[[(2S)- oxetan-2-yl]methyl]benzimidazole-5-carboxylate (I-41): methyl 2-[[4-[6-[(5-bromo-1,3,4-thiadiazol-2-yl)methoxy]-2-pyridyl]-2,5-difluoro-phenyl]methyl]-3-[[(2S)-oxetan-2-yl]methyl]benzimidazole-5-carboxylate was prepared in a manner as described for Intermediate I-19 substituting 5-(bromomethyl)-2-chloro-4-fluoropyridine for 2-bromo-5-(bromomethyl)-1,3,4-thiadiazole ES/MS: 660.0 (M+H$^+$).

Preparation of Intermediate I-42

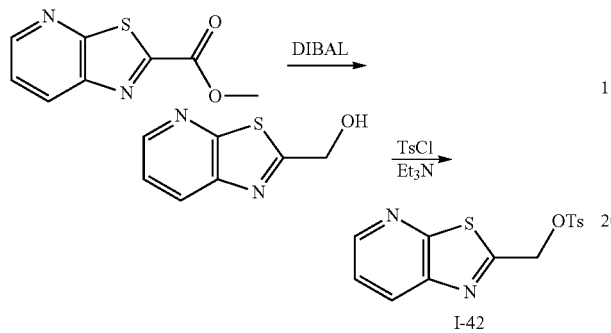

Thiazolo[5,4-b]pyridin-2-ylmethanol: methyl thiazolo[5,4-b]pyridine-2-carboxylate (100 mg, 0.52 mmol) in THF (5 mL) was cooled to 0° C. Diisobutylaluminium hydride (1.0 M in DCM, 1.5 mL, 1.5 mmol) was added, and the mixture was warmed to rt and stirred for 1 hour. Upon completion, the reaction was quenched with 2M NaOH (0.4 mL), H$_2$O (0.4 mL), and diluted with EtOAc (10 mL). The mixture was then filtered through a plug of Celite. The organic layers were combined, washed with brine (5 mL), dried over MgSO$_4$, filtered, concentrated, and purified by flash chromatography (Eluent: EtOAc/hexane) to give the titled product. ES/MS: 167.2 (M+1).

Thiazolo[5,4-b]pyridin-2-ylmethyl 4-methylbenzenesulfonate (I-42): To a solution of thiazolo[5,4-b]pyridin-2-ylmethanol (40 mg, 0.24 mmol), triethylamine (0.07 mL, 0.5 mmol) in DCM (5 mL) was added toluene-4-sulfonyl chloride (46 mg, 0.24 mmol) at rt. The mixture was stirred at rt for 20 hours. Upon completion the mixture was concentrated and purified by flash chromatography (Eluent: EtOAc/hexane) to give the title product. ES/MS: 321.2 (M+1).

Preparation of Intermediate I-43

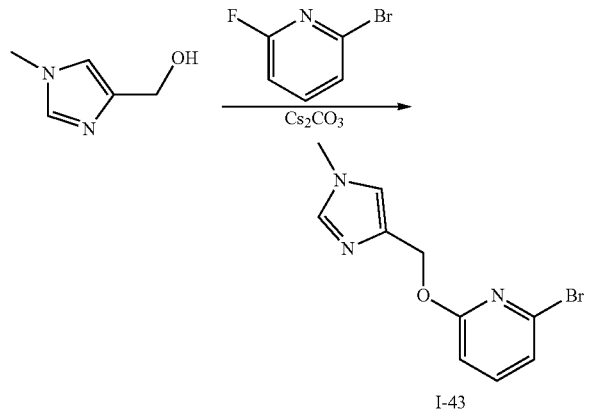

2-bromo-6-[(1-methylimidazol-4-yl)methoxy]pyridine (I-43): To a solution of 2-bromo-6-fluoro-pyridine (90.7 mg, 0.52 mmol) and (1-methylimidazol-4-yl)methanol (75.1 mg, 0.67 mmol) in 2.0 mL of acetonitrile was added Cs$_2$CO$_3$ (338 mg, 1.04 mmol). The solution was then heated to 50° C. for 30 minutes. The solution was cooled to rt, filtered, then concentrated. The crude material was purified by normal phase chromatography 1-12% DCM/MeOH. The product containing fractions were combined and concentrated to give the title product. ES/MS m/z: 268.0, 270.2 (M+H$^+$).

The following intermediates were synthesized in a manner as described for intermediate I-43

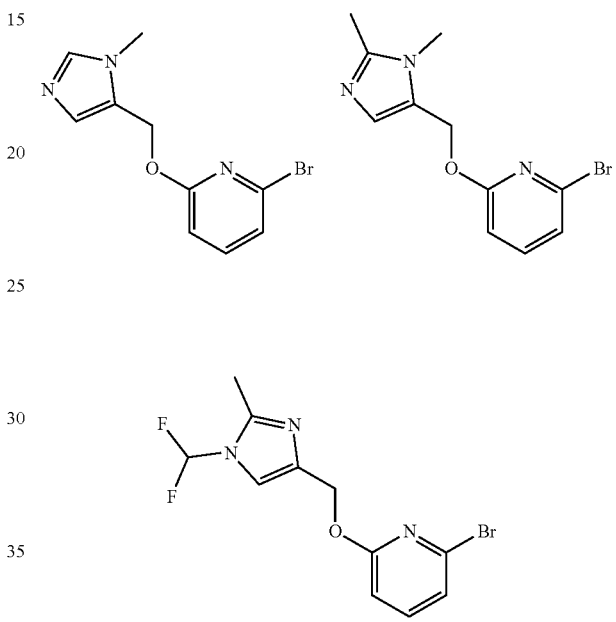

Preparation of Intermediate I-44

2-bromo-6-[[1-(difluoromethyl)-2-methyl-imidazol-4-yl]methoxy]pyridine (I-44): This intermediate was prepared in a manner as described for Intermediate I-43 substituting [1-(difluoromethyl)-2-methyl-imidazol-4-yl]methanol for (1-methylimidazol-4-yl)methanol. ES/MS m/z: 318.2 (M+H$^+$).

Preparation of Intermediate I-45

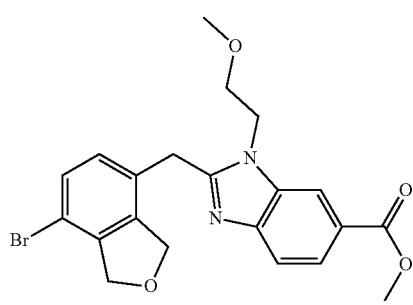

I-45

Methyl 2-[(7-bromo-1,3-dihydroisobenzofuran-4-yl)methyl]-3-(2-methoxyethyl)benzimidazole-5-carboxylate (I-45): This intermediate was prepared in a manner as described for Intermediate I-13 substituting 2-(7-bromo-1,3-dihydroisobenzofuran-4-yl)acetic acid for (2-(4-bromo-2-fluorophenyl)acetic acid. ES/MS m/z: 447.1 (M+H+).

Preparation of Intermediate I-46

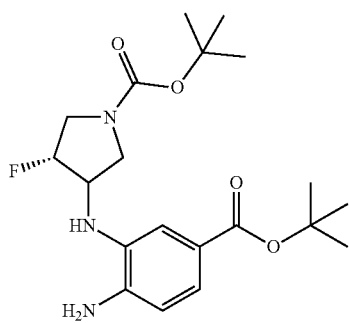

I-46

Tert-butyl (3R,4R)-3-(2-amino-5-methoxycarbonyl-anilino)-4-fluoro-pyrrolidine-1-carboxylate (I-46): This intermediate was prepared in a manner as described for Intermediate I-6 substituting tert-butyl (3R,4R)-3-amino-4-fluoro-pyrrolidine-1-carboxylate for 2-methoxyethanamine. ES/MS m/z: 418.4 (M+Na+).

Preparation of Intermediate I-47

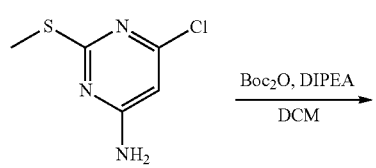

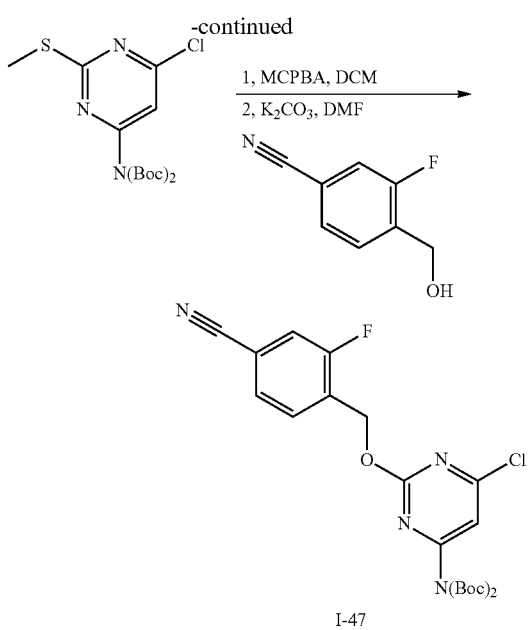

I-47

Tert-butyl N-tert-butoxycarbonyl-N-(6-chloro-2-methylsulfanyl-pyrimidin-4-yl)carbamate: A solution of methylsulfanyl-pyrimidin-4-amine (1 g, 5.7 mmol), tert-butoxycarbonyl tert-butyl carbonate (2.61 g, 12 mmol), ethyldiisopropylamine (3 mL, 17.1 mmol) and 4-dimethylaminopyridine (140 mg, 1.14 mmol) in 20 mL of DCM, was stirred overnight. The mixture was washed with H₂O and brine. The combined organic extracts were dried over sodium sulfate, filtered and the filtrate was concentrated in vacuo. The crude residue was purified by column chromatography (0-50% EtOAc in hexane) to give the title compound: ES/MS m/z: 375.2 (M+H+).

Tert-butyl N-tert-butoxycarbonyl-N-[6-chloro-2-[(4-cyano-2-fluoro-phenyl)methoxy]pyrimidin-4-yl]carbamate (I-47): A solution of tert-butyl N-tert-butoxycarbonyl-N-(6-chloro-2-methylsulfanyl-pyrimidin-4-yl)carbamate (0.5 g, 1.33 mmol) and 3-chloroperoxybenzoic acid (0.6 g, 2.7 mmol, 77%) in 5 mL of DCM, was stirred for overnight. The mixture was washed with H₂O and brine. The solvent was removed, and the resulting residue was dried in vacuo. The crude product was dissolved in 3 mL of DMF; to this solution 3-fluoro-4-(hydroxymethyl)benzonitrile (220 mg, 1.46 mmol) and potassium carbonate (366 mg, 2.65 mmol) was added and let sit at rt for 2 hr. After the 2 hours, the resulting solution was diluted with EtOAc (50 mL) and washed with H₂O. The combined organic extracts were dried over sodium sulfate, filtered and the filtrate was concentrated in vacuo. The crude residue was purified by column chromatography (0-50% EtOAc in hexane) to give the title compound: ES/MS m/z: 479.1 (M+H+).

Preparation of Intermediate I-48

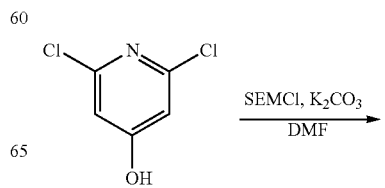

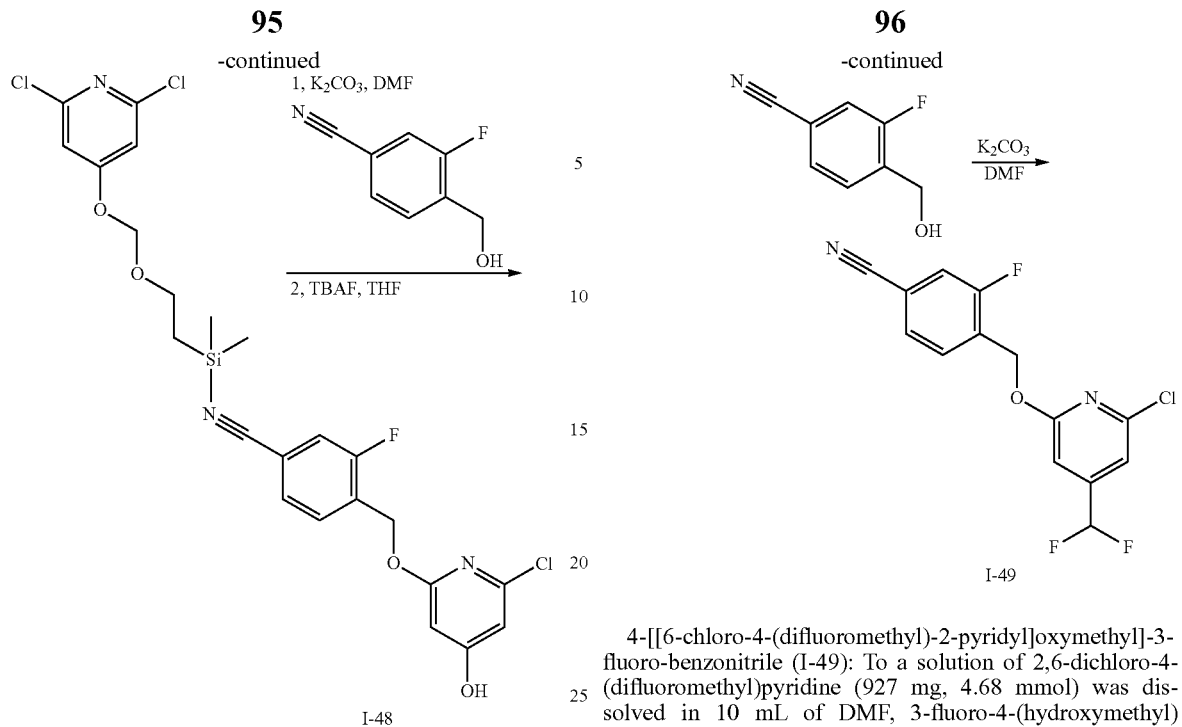

2-[(2,6-dichloro-4-pyridyl)oxymethoxy]ethyl-trimethylsilane: A solution of 2,6-dichloropyridin-4-ol (1 g, 6.1 mmol) and 2-(chloromethoxy)ethyl-trimethyl-silane (1.07 g, 6.4 mmol) in 10 mL of THF, lithium bis(trimethylsilyl)amide (6.4 mL, 6.4 mmol) was stirred overnight. The solution was washed with H₂O and brine. The combined organic extracts were dried over sodium sulfate, filtered and the filtrate was concentrated in vacuo. The crude residue was purified by column chromatography (0-50% EtOAc in hexane) to give the title compound: ES/MS m/z: 294.1 (M+H+).

4-[(6-chloro-4-hydroxy-2-pyridyl)oxymethyl]-3-fluoro-benzonitrile (I-48): To a solution of 2-[(2,6-dichloro-4-pyridyl)oxymethoxy]ethyl-trimethyl-silane (1.0 g, 3.4 mmol) was dissolved in 5 mL of DMF, 3-fluoro-4-(hydroxymethyl)benzonitrile (0.77 g, 5.1 mmol) and potassium carbonate (0.94 g, 6.8 mmol) was added. The solution was heated to 120° C. for 6 hours. Upon completion, the solution was diluted with EtOAc (50 mL) and washed with H₂O. The combined organic extracts were dried over sodium sulfate, filtered and the filtrate was concentrated in vacuo. The crude product was dissolved in 2 mL of THF. To the resulting solution tetrabutylammonium fluoride (4.0 mL, 4 mmol) was added. The mixture was stirred for 3 hr. The solvent was removed, and the resulting residue was purified by column chromatography (0-80% EtOAc in hexane) to give the title compound: ES/MS m/z: 279.2 (M+H+).

Preparation of Intermediate I-49

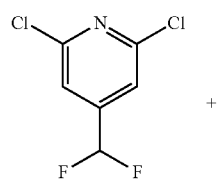

4-[[6-chloro-4-(difluoromethyl)-2-pyridyl]oxymethyl]-3-fluoro-benzonitrile (I-49): To a solution of 2,6-dichloro-4-(difluoromethyl)pyridine (927 mg, 4.68 mmol) was dissolved in 10 mL of DMF, 3-fluoro-4-(hydroxymethyl)benzonitrile (708 mg, 4.68 mmol) and potassium carbonate (971 mg, 7 mmol) was added to the solution. It was heated to 60° C. overnight and diluted with EtOAc (50 mL) and washed with water. The combined organic extracts were dried over sodium sulfate, filtered and the filtrate was concentrated in vacuo. The solvent was removed, and the resulting residue was purified by column chromatography (0-60% EtOAc in hexane) to give the title compound: ES/MS m/z: 313.1 (M+H+).

Preparation of Intermediate I-50

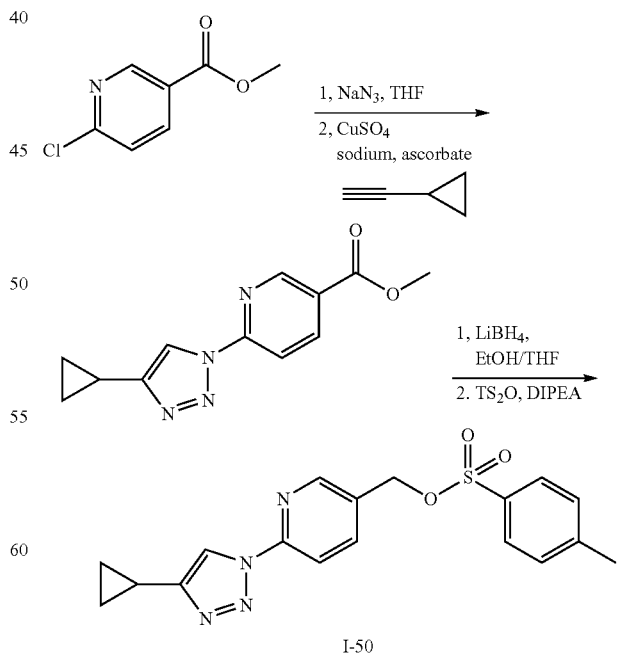

Methyl 6-(4-cyclopropyltriazol-1-yl)pyridine-3-carboxylate: A suspension of methyl 6-chloropyridine-3-carboxylate (300 mg, 1.75 mmol) and sodium azide (227 mg, 3.5 mmol) in THF, was heated to 60° C. for 5 hours. Upon completion, the mixture was diluted with EtOAc and washed with saturated solution of sodium bicarbonate (20 mL) and brine. The combined organic extracts were dried over sodium sulfate, filtered and the filtrate was concentrated in vacuo. To the crude residue, ethynylcyclopropane (145 mg, 2.2 mmol) in tert-butanol (5 mL) was added. To the resulting mixtures, solutions of sodium ascorbate (0.19 mmol, 38 mg) in water (2.5 mL) and copper sulfate pentahydrate (0.19 mmol, 48 mg) in H$_2$O (2.5 mL) were sequentially added. The mixture was stirred at rt conditions for 18 hr. Upon completion the mixture was diluted with 5 mL 1M aq. NH$_4$OH and extracted with EtOAc (2×30 mL). The combined organic extracts were washed with brine, dried over Na$_2$SO$_4$ and concentrated under reduced pressure. Crude product was purified by flash chromatography on silica gel (0-100% EtOAc in hexane) to give the title compound: ES/MS m/z: 245.2 (M+H+).

[6-(4-cyclopropyltriazol-1-yl)-3-pyridyl]methyl 4-methylbenzenesulfonate (I-50): To a solution of methyl 6-(4-cyclopropyltriazol-1-yl)pyridine-3-carboxylate (300 mg, 1.23 mmol) in 2 mL of THF, 0.92 mL of 2 N of lithium borohydride in THF was added. The resulting solution was stirred for 8 hours and then diluted with 50 mL of EtOAc and washed with H$_2$O and brine. The combined organic extracts were washed with brine, dried over Na$_2$SO$_4$ and concentrated under reduced pressure. The resulting crude product was dissolved in 5 mL of DCM. Next, p-tolylsulfonyl 4-methylbenzenesulfonate (365 mg, 1.12 mmol) and ethyldiisopropylamine (0.37 mL, 2.13 mmol) was added to the solution. The mixture was stirred for overnight. Upon completion the resulting solution was diluted with 20 mL of DCM and washed with H$_2$O and brine. The organic layer was dried over Na$_2$SO$_4$ and concentrated under reduced pressure. The crude product was purified by flash chromatography on silica gel (0-100% EtOAc in hexane) to give the title compound: ES/MS m/z: 371.2 (M+H+).

Methyl 6-(3-cyclopropyl-1,2,4-triazol-1-yl)pyridine-3-carboxylate: A suspension of methyl 6-chloropyridine-3-carboxylate (300 mg, 1.75 mmol), 3-cyclopropyl-1H-1,2,4-triazole (191 mg, 1.75 mmol) and potassium carbonate (483 mg, 3.5 mmol) in THF, was heated to reflux for 8 hours. Following this time, the solution was diluted with EtOAc and washed with saturated solution of sodium bicarbonate (20 mL) and brine. The combined organic extracts were dried over sodium sulfate, filtered and the filtrate was concentrated in vacuo. The crude residue was purified by flash chromatography on silica gel (0-100% EtOAc in hexane) to give the title compound: ES/MS m/z: 245.2 (M+H+).

[6-(3-cyclopropyl-1,2,4-triazol-1-yl)-3-pyridyl]methyl 4-methylbenzenesulfonate (I-51): To a solution of methyl 6-(3-cyclopropyl-1,2,4-triazol-1-yl)pyridine-3-carboxylate (300 mg, 1.23 mmol) in 2 mL of THF, 0.92 mL of 2 N of lithium borohydride in THF was added. The solution was stirred overnight and diluted with 50 mL of EtOAc and washed with water and brine. The combined organic extracts were washed with brine, dried over Na$_2$SO$_4$ and concentrated under reduced pressure. The crude product was dissolved in 5 mL of DCM, 4-methylbenzenesulfonyl chloride (241 mg, 1.26 mmol) and triethylamine (0.34 mL, 2.4 mmol) was added to the solution. The mixture was stirred for overnight and diluted with 20 mL of DCM and then washed with water and brine. The organic layer was dried over sodium sulfate, filtered and the filtrate was concentrated in vacuo. The crude residue was purified by flash chromatography on silica gel (0-100% EtOAc in hexane) to give I-51: ES/MS m/z: 371.1 (M+H+).

Preparation of Intermediate I-52

Preparation of Intermediate I-51

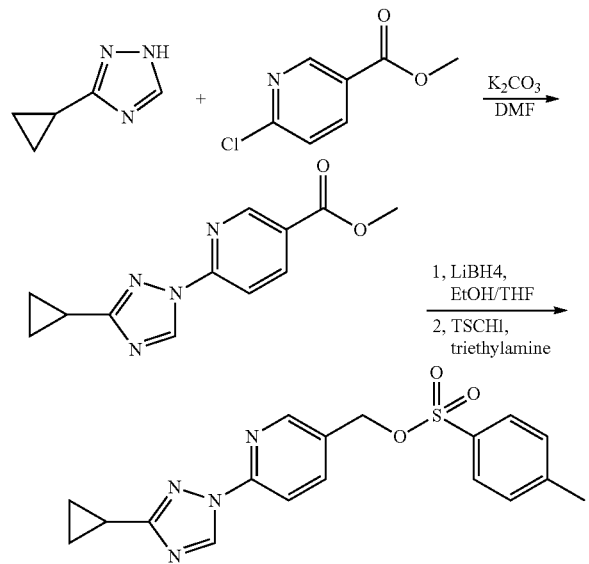

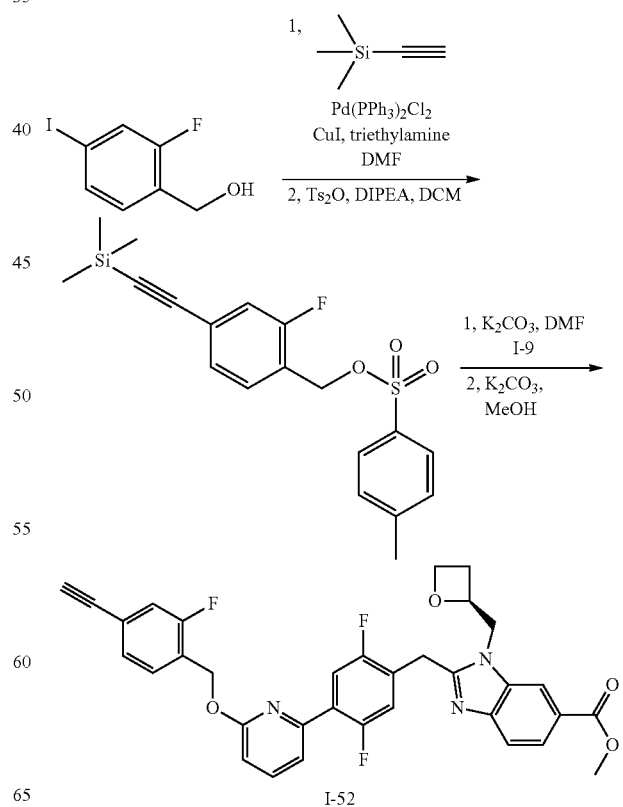

[2-fluoro-4-(2-trimethylsilylethynyl)phenyl]methyl 4-methylbenzenesulfonate: (2-fluoro-4-iodo-phenyl)methanol (2 g, 7.94 mmol), ethynyl(trimethyl)silane (1.17 g, 11.9 mmol), copper iodide (75.6 mg, 0.4 mmol), bis(triphenylphosphine)palladium chloride (280 mg, 0.4 mmole) and triethylamine (3.3 mL, 23.8 mmol) was suspended in THF (15 mL). The mixture was degassed with nitrogen and stirred for 16 hours at rt. Following this, the mixture was filtered with celite and washed with 20 mL of DCM three times. The solvent was removed, and the resulting crude product was dried in vacuo. Next, the crude product was dissolved in 20 mL of DCM, followed by the addition of p-tolylsulfonyl 4-methylbenzenesulfonate (2.58 g, 7.92 mmol) and ethyldiisopropylamine (2.76 mL, 15.8 mmol) to the solution. The mixture was stirred for 5 hours and checked via LC/MS. Then the mixture was then diluted with 20 mL of DCM and washed with water and brine. The organic layer was dried over sodium sulfate, filtered and the filtrate was concentrated in vacuo. The crude residue was purified by flash chromatography on silica gel (0-50% EtOAc in hexane) to give the title compound: ES/MS m/z: 377.1 (M+H+).

Methyl 2-[[4-[6-[(4-ethynyl-2-fluoro-phenyl)methoxy]-2-pyridyl]-2,5-difluoro-phenyl]methyl]-3-[[(2S)-oxetan-2-yl]methyl]benzimidazole-5-carboxylate (I-52): Potassium carbonate (742 mg, 5.37 mmol) was added to a solution of methyl 2-[[2,5-difluoro-4-(6-hydroxy-2-pyridyl)phenyl]methyl]-3-[[(2S)-oxetan-2-yl]methyl]benzimidazole-5-carboxylate (500 mg, 1.07 mmol) and [2-fluoro-4-(2-trimethylsilylethynyl)phenyl]methyl 4-methylbenzenesulfonate (420 mg, 1.12 mmol) in 5 mL of DMF, and stirred for 3 hours. Following this time, 50 mL of water was added to the solution and the aqueous phase was extracted 2×EtOAc. The combined organic phase was dried over sodium sulfate, filtered and the filtrate was concentrated in vacuo. The crude product was dissolved in MeOH (20 mL) and potassium carbonate (51.6 mg, 0.37 mmol) was added to the solution. After 2 hours, the solution was filtered, and the filtrate was concentrated in vacuo. The crude residue was purified by flash chromatography on silica gel (0-80% EtOAc in hexane) to give I-52. ES/MS m/z: 598.2 (M+H+).

Preparation of Intermediate I-53

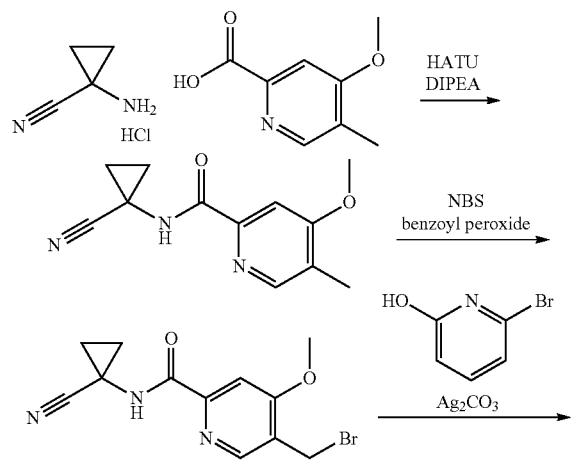

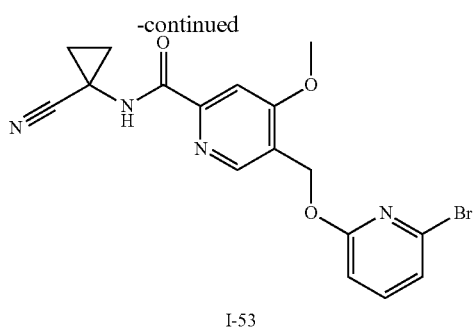

I-53

N-(1-cyanocyclopropyl)-4-methoxy-5-methyl-pyridine-2-carboxamide: N,N-Diisopropylethylamine (2.14 mL, 12.3 mmol) was added to a solution of 4-methoxy-5-methyl-pyridine-2-carboxylic acid; hydrochloride (500 mg, 2.46 mmol), 1-aminocyclopropanecarbonitrile; hydrochloride (349 mg, 2.95 mmol), and o-(7-Azabenzotriazol-1-yl)-N,N,N',N'-tetramethyluronium hexafluorophosphate (1373 mg, 3.61 mmol) in DMF (10 mL). The mixture was stirred at rt overnight. Following this time, the mixture was diluted with EtOAc and washed with 5% LiCl, saturated NaHCO3, and brine. The organic extract was dried over sodium sulfate and purified by flash chromatography (eluent: EtOAc/hexanes) to give the title compound.

5-(bromomethyl)-N-(1-cyanocyclopropyl)-4-methoxy-pyridine-2-carboxamide: To a suspension of N-(1-cyanocyclopropyl)-4-methoxy-5-methyl-pyridine-2-carboxamide (400 mg, 1.73 mmol) in CCl4 (10 mL), was added N-Bromosuccinimide (403 mg, 2.26 mmol) followed by benzoyl peroxide (45.1 mg, 0.186 mmol). The resulting solution was heated at 90° C. for 1 hr. Upon completion the mixture was cooled to rt, diluted with 5 mL hexanes and the suspension was filtered. The filtrate was concentrated and purified by flash chromatography (eluent: EtOAc/hexanes) to give the title compound. ES/MS: 310, 312 (M+H+).

5-[(6-bromo-2-pyridyl)oxymethyl]-N-(1-cyanocyclopropyl)-4-methoxy-pyridine-2-carboxamide (Intermediate I-53): A suspension of 5-(bromomethyl)-N-(1-cyanocyclopropyl)-4-methoxy-pyridine-2-carboxamide (112 mg, 0.36 mmol), 6-bromopyridin-2-ol (50 mg, 0.29 mmol), and silver carbonate (169 mg, 0.61 mmol) in CH3CN (5 mL) was heated at 50° C. overnight. Upon completion, the mixture was diluted with EtOAc and brine-filtered over Celite frit. The mixture was partitioned, and the organic phase was washed one more time with brine. The crude produced was dried over sodium sulfate, concentrated, and purified by flash chromatography (eluent: EtOAc/hexanes) to give I-53. ES/MS: 403, 405 (M+H+).

Preparation of Intermediate I-54

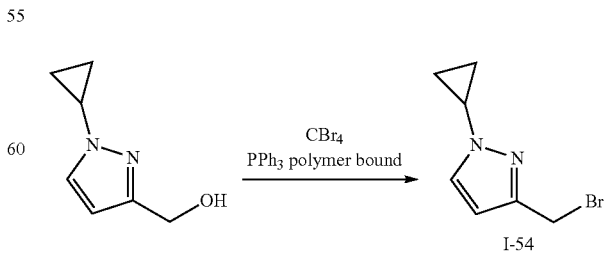

3-(bromomethyl)-1-cyclopropyl-pyrazole (I-54): Carbon tetrabromide (0.541 g, 0.00163 mol) was added to a solution of (1-cyclopropylpyrazol-3-yl)methanol (0.188 g, 1.36 mmol) and (4-diphenylphosphanylphenyl polymer bound) (78.7%, 0.542 g, 0.00163 mol) in DCM (10 mL) at 0° C. The mixture was gradually warmed to rt and stirred overnight. The resulting suspension was filtered, and the filtrate was diluted with DCM and washed with brine. The organic extract was dried over sodium sulfate, concentrated, and purified by flash chromatography (eluent: EtOAc/hexanes) to give I-54. ES/MS: 201.2, 203.2 (M+H$^+$).

The following intermediates were prepared in a manner as described for intermediate I-54

0.707 mmol) and (4-diphenylphosphanylphenyl polymer bound) (78.7%, 0.282 g, 0.000848 mol) in DCM (10 mL) at 0° C. The mixture was gradually warmed to rt and stirred overnight. The resulting suspension was filtered, and the filtrate was diluted with DCM and washed with brine. The organic extract was dried over sodium sulfate, concentrated, and purified by flash chromatography (eluent: Et$_2$O/hexanes) to give I-55. ES/MS: 217.2, 219.2 (M+H$^+$).

Preparation of Intermediate I-56

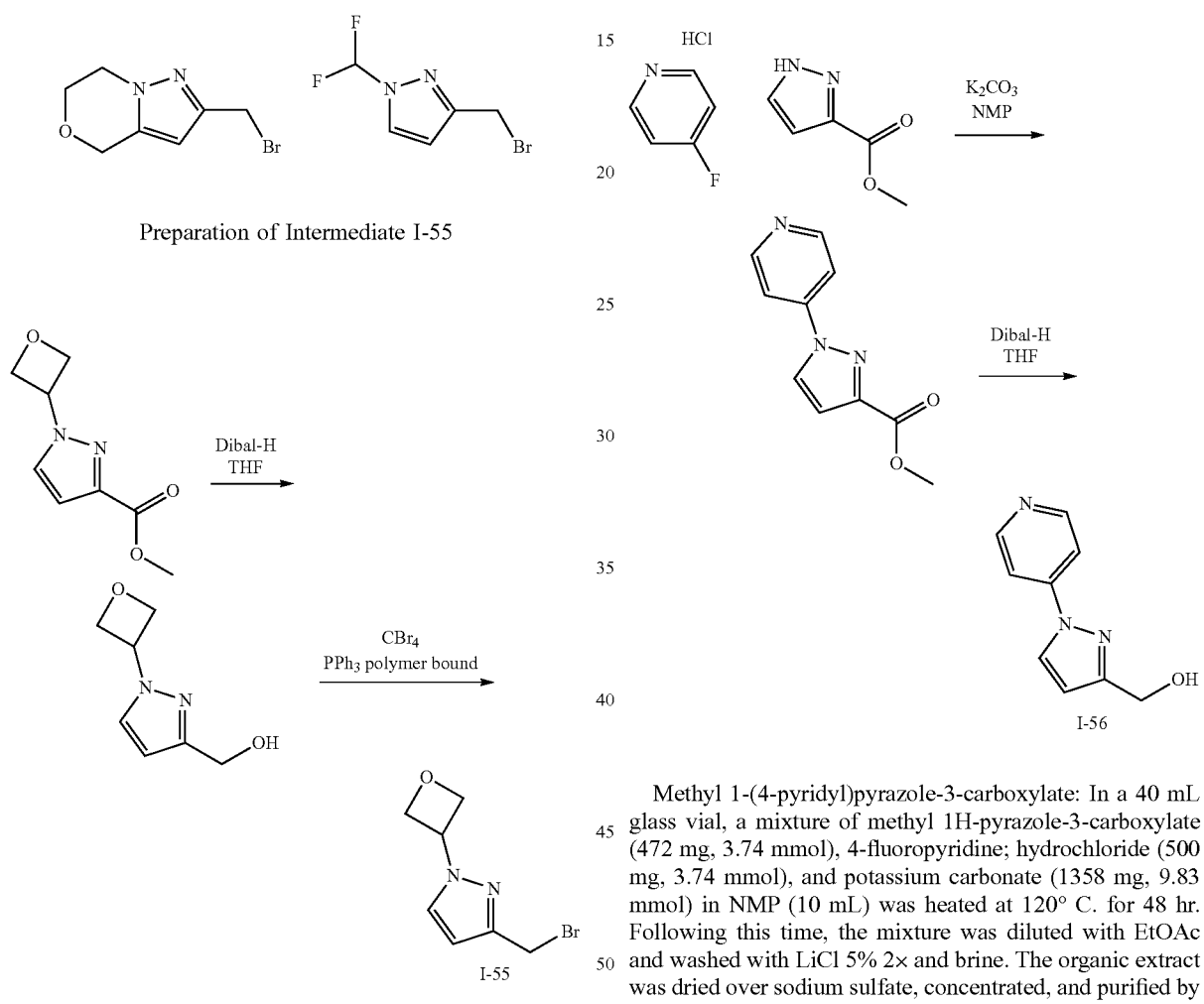

Preparation of Intermediate I-55

[1-(oxetan-3-yl)pyrazol-3-yl]methanol: Diisobutylaluminium hydride (1000 mmol/L in DCM, 2.40 mL, 2.40 mmol) was added to a solution of methyl 1-(oxetan-3-yl) pyrazole-3-carboxylate (175 mg, 0.961 mmol) in THF (5 mL) at 0° C. and stirred for 1 hr. Following this time, the mixture was diluted with 5 mL Et$_2$O and cooled to 0° C. Then, 0.100 mL water, 0.100 mL 15% NaOH, and 0.240 mL water was added. The solution was warmed to rt and stirred for 15 min. Following this time, MgSO$_4$ was added and the solution was stirred for an additional 15 min, then filtered to give titled product that was carried onto the next step without further purification. ES/MS: 155.2 (M+H$^+$).

3-(bromomethyl)-1-(oxetan-3-yl)pyrazole (I-55): Carbon tetrabromide (0.281 g, 0.000848 mol) was added to a solution of [1-(oxetan-3-yl)pyrazol-3-yl]methanol (0.109 g, Methyl 1-(4-pyridyl)pyrazole-3-carboxylate: In a 40 mL glass vial, a mixture of methyl 1H-pyrazole-3-carboxylate (472 mg, 3.74 mmol), 4-fluoropyridine; hydrochloride (500 mg, 3.74 mmol), and potassium carbonate (1358 mg, 9.83 mmol) in NMP (10 mL) was heated at 120° C. for 48 hr. Following this time, the mixture was diluted with EtOAc and washed with LiCl 5% 2× and brine. The organic extract was dried over sodium sulfate, concentrated, and purified by flash chromatography (eluent: EtOAc/hexanes) to give the title compound. ES/MS: 204.2 (M+H$^+$).

[1-(4-pyridyl)pyrazol-3-yl]methanol (I-56): To a solution of methyl 1-(4-pyridyl)pyrazole-3-carboxylate (106 mg, 0.520 mmol) in THF (5 mL) at 0° C., was added diisobutylaluminium hydride (1.0 M in DCM, 1.30 mL, 1.30 mmol). The solution was stirred for 1 hr. Following this time, the mixture was diluted with 5 mL Et$_2$O and cooled to 0° C. Upon completion of the cooling, 0.05 mL water, 0.05 mL 15% NaOH, and 0.130 mL water was added to the solution. The solution was then warmed to rt and stirred for 15 min, followed by the addition of MgSO$_4$. The solution was stirred and additional 15 min, and then filtered. The crude product was purified by flash chromatography (eluent: EtOAc/hexanes) to give I-56. ES/MS: 176.2 (M+H$^+$).

Preparation of Intermediate I-57

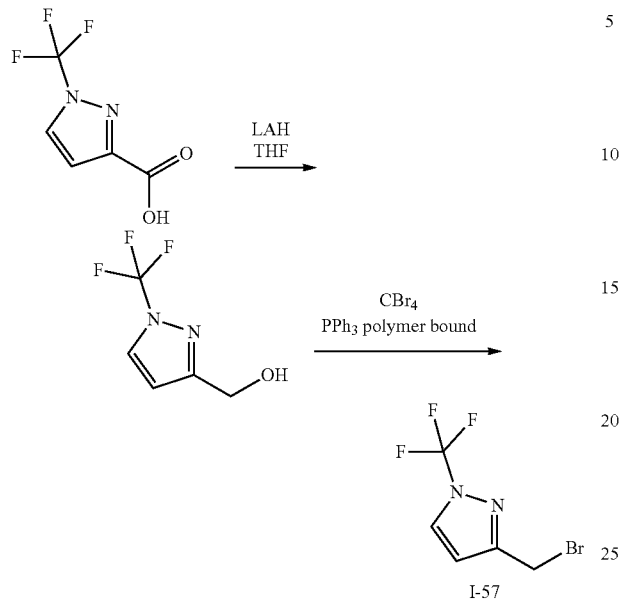

[1-(trifluoromethyl)pyrazol-3-yl]methanol: To a solution of 1-(trifluoromethyl)pyrazole-3-carboxylic acid (321 mg, 1.78 mmol) in THF (10 mL) at 0° C., was added lithium aluminum hydride (2.0M in THF) (2.00 mmol/L, 980 mL, 1.96 mmol). The solution was gradually warmed to rt and stirred for 1 hr. Following this time, the solution was diluted with Et$_2$O, and cooled to 0° C. Upon completion of the cooling, 0.075 mL water, 0.075 mL 15% aqueous NaOH, and 0.225 mL water was added to the solution, which was then warmed to rt and stirred for an additional 15 min. Following the additional 15 min. MgSO$_4$, was added and the solution was stirred another 15 min, then filtered to give title product that was carried onto the next step without further purification. ES/MS: 167.2 (M+H$^+$).

3-(bromomethyl)-1-(trifluoromethyl)pyrazole (I-57): Carbon tetrabromide (0.465 g, 0.00140 mol) was added to a solution of [1-(trifluoromethyl)pyrazol-3-yl]methanol (0.194 g, 1.17 mmol) and (4-diphenylphosphanylphenyl polymer bound) (78.7%, 0.465 g, 0.00140 mol) in DCM (10 mL) at 0° C. The mixture was gradually warmed to rt and stirred overnight. The resulting suspension was filtered, and the filtrate was diluted with DCM and washed with brine. The organic extract was dried over sodium sulfate, concentrated, and purified by flash chromatography (eluent: Et2O/hexanes) to give I-57. ES/MS: 230.2 (M+H$^+$).

Preparation of Intermediate I-58

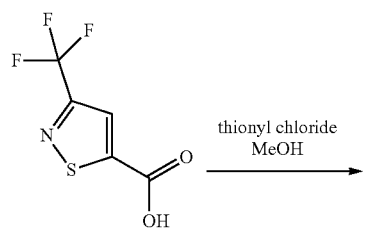

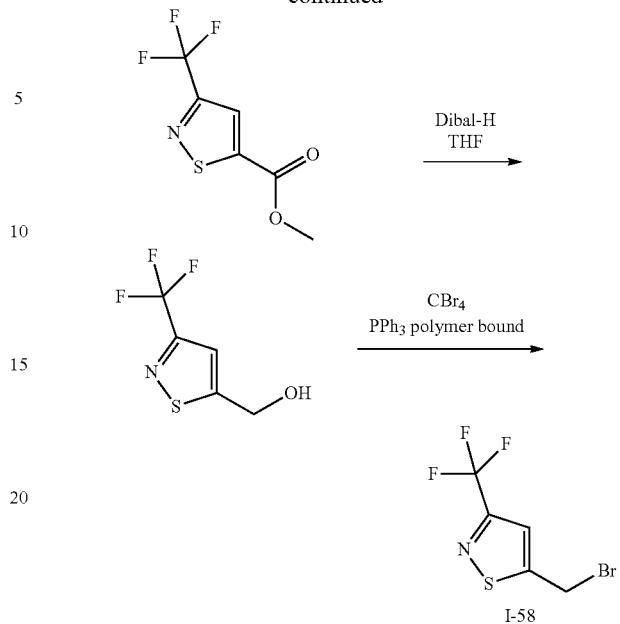

Methyl 3-(trifluoromethyl)isothiazole-5-carboxylate: To a solution of 3-(trifluoromethyl)isothiazole-5-carboxylic acid (303 mg, 1.54 mmol) in MeOH (3 mL) at 0° C., thionyl chloride (0.125 mL, 1.69 mmol) was added. The resulting solution was gradually warmed to rt and stirred overnight. Following this time, more thionyl chloride (0.125 mL, 1.69 mmol) was added and stirred for 9 hr. Upon completion of this time, the mixture was concentrated and purified by flash chromatography (eluent: EtOAc/hexanes) to give the title compound. 1H NMR (400 MHz, Chloroform-d) δ 8.01 (s, 1H), 4.01 (s, 3H).

[3-(trifluoromethyl)isothiazol-5-yl]methanol: To a solution of methyl 3-(trifluoromethyl)isothiazole-5-carboxylate (136 mg, 0.644 mmol) in THF (5 mL) at 0° C., was added diisobutylaluminium hydride (1.0 M in DCM, 1.61 mL, 1.61 mmol). The resulting solution was stirred for 3 hr. Upon completion of this time the mixture was diluted with 5 mL Et$_2$O and cooled to 0° C. Once the mixture was cooled, 0.064 mL water, 0.064 mL 15% NaOH, and 0.161 mL water, was added and the solution was warmed to rt and stirred for 15 min. Following this time, MgSO$_4$ was added and the solution was stirred an additional 15 min, then filtered. The crude product was purified by flash chromatography (eluent: EtOAc/hexanes) to give the title compound. ES/MS: 184.2 (M+H$^+$).

5-(bromomethyl)-3-(trifluoromethyl)isothiazole (I-58): To a solution of [3-(trifluoromethyl)isothiazol-5-yl]methanol (85 mg, 0.464 mmol) and (4-diphenylphosphanylphenyl polymer bound) (78.7%, 185 mg, 0.557 mol) in DCM (10 mL) at 0° C., was added carbon tetrabromide (185 mg, 0.557 mmol). The mixture was gradually warmed to rt and stirred overnight. The resulting suspension was filtered, and the filtrate was diluted with DCM and washed with brine. The organic extract was dried over sodium sulfate, concentrated, and purified by flash chromatography (eluent: Et$_2$O/hexanes) to give I-58. 1H NMR (400 MHz, Chloroform-d) δ 7.49 (d, J=0.8 Hz, 1H), 4.72 (d, J=0.8 Hz, 2H).

Preparation of Intermediate I-59

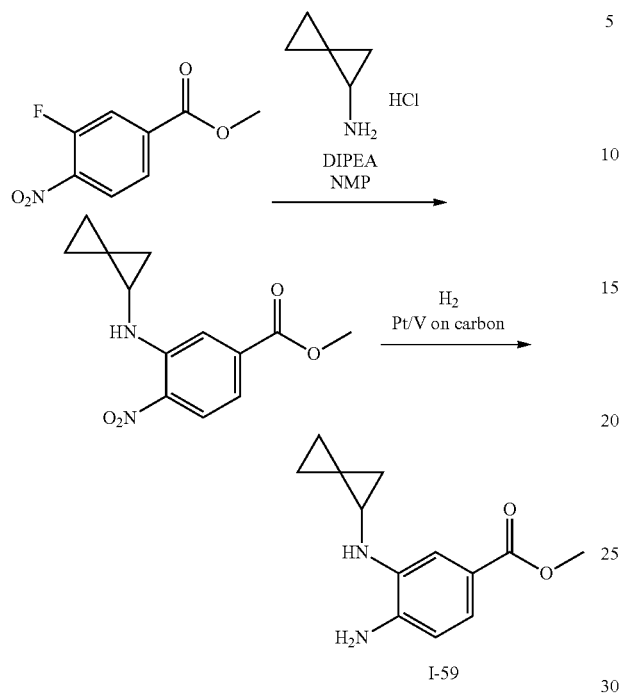

Methyl 4-nitro-3-(spiro[2.2]pentan-2-ylamino)benzoate: A solution of methyl 3-fluoro-4-nitro-benzoate (0.205 g, 1.03 mmol), spiro[2.2]pentan-2-amine; hydrochloride (0.151 g, 1.26 mmol) and N,N-Diisopropylethylamine (0.538 mL, 3.09 mmol) in NMP (3 mL) was heated at 90° C. for 12 hr. Following this time, the mixture was diluted with EtOAc, washed with 5% LiCl, brine and water. The organic extract was dried over sodium sulfate, concentrated, and purified by flash chromatography (eluent: EtOAc/hexanes) to give the title compound. ES/MS: 263.2 (M+H+); 1H NMR (400 MHz, Chloroform-d) δ 8.22 (d, J=8.8 Hz, 1H), 8.06 (s, 1H), 7.79 (d, J=1.8 Hz, 1H), 7.29 (dd, J=8.9, 1.8 Hz, 1H), 3.98 (s, 3H), 3.01 (dd, J=6.3, 3.1 Hz, 1H), 1.54-1.42 (m, 1H), 1.14 (ddd, J=9.0, 5.5, 4.1 Hz, 1H), 1.06-0.98 (m, 2H), 0.95 (td, J=8.5, 4.7 Hz, 2H).

Methyl 4-amino-3-(spiro[2.2]pentan-2-ylamino)benzoate (I-59): A solution of methyl 4-nitro-3-(spiro[2.2]pentan-2-ylamino)benzoate (101 mg, 0.4385 mmol) in EtOAc (8 mL) was degassed by cycling the mixture between argon and vacuum 3×. To the mixture was added platinum (1%), vanadium (2%) on carbon (50-70% wetted) and I-59 was carried onto the next step without further purification. ES/MS: 233.2 (M+H+);

Preparation of Intermediates I-60 and I-61

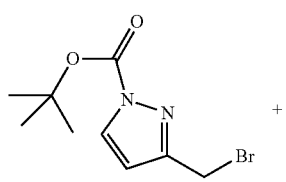

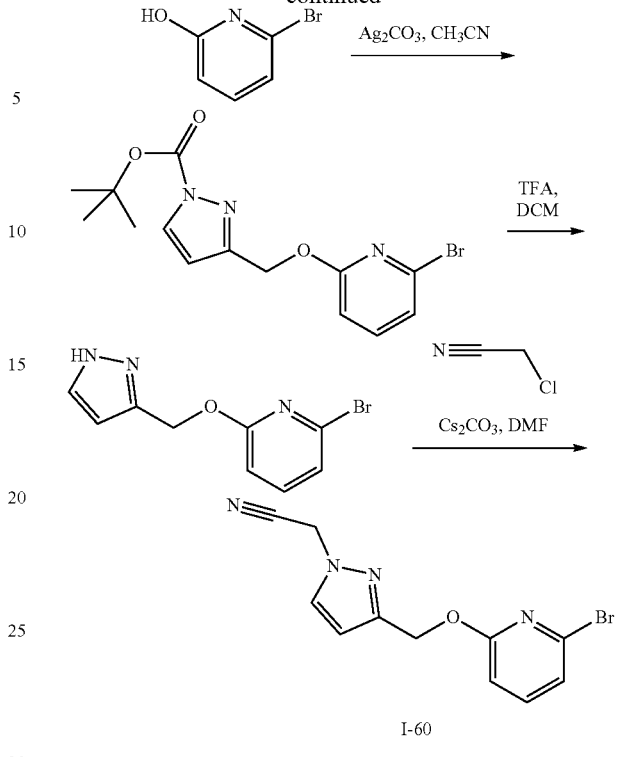

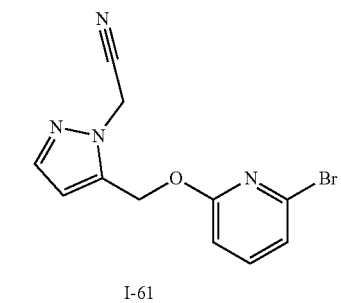

Tert-butyl 3-[(6-bromo-2-pyridyl)oxymethyl]pyrazole-1-carboxylate: A suspension of tert-butyl 3-(bromomethyl)pyrazole-1-carboxylate (946 mg, 3.6 mmol), 6-bromopyridin-2-ol (500 mg, 2.9 mmol), and silver carbonate (1694 mg, 6.1 mmol) in CH₃CN (15 mL) was heated at 50° C. for 15 hr. Following this time, 335 mg of 6-bromopyridin-2-ol and 5 mL CH₃CN were added and the solution was heated at 50° C. for 5 hr. Upon completion of time, 500 mg of 6-bromopyridin-2-ol was added and heating was resumed for 2 hr. Following this time, the mixture was diluted with EtOAc and brine. The mixture was filtered over a plug of Celite. The mixture was partitioned, and the organic phase was washed with brine. The organic extract was dried over sodium sulfate, concentrated, and purified by flash chromatography (eluent: EtOAc/hexanes) to give the title compound. ES/MS: 298, 300 (M+H+).

2-bromo-6-(1H-pyrazol-3-ylmethoxy)pyridine: A solution of tert-butyl 3-[(6-bromo-2-pyridyl)oxymethyl]pyrazole-1-carboxylate (456 mg, 1.3 mmol) and TFA (0.49 mL, 6.4 mmol) in DCM (5 mL) was stirred at rt overnight. Following this time, the solution was diluted with DCM and washed with saturated sodium bicarbonate solution, dried over sodium sulfate, concentrated, and carried onto the next step without further purification. ES/MS: 254, 256 (M+H+).

2-[3-[(6-bromo-2-pyridyl)oxymethyl]pyrazol-1-yl]acetonitrile (I-60) and 2-[5-[(6-bromo-2-pyridyl)oxymethyl]pyrazol-1-yl]acetonitrile (I-61): To a suspension of 2-bromo-6-(1H-pyrazol-3-ylmethoxy)pyridine (0.115 g, 0.453 mmol) and cesium carbonate (0.177 g, 0.543 mmol) in DMF (3 mL), was added 2-chloroacetonitrile (0.0314 mL, 0.498 mmol). The solution was stirred at rt overnight. Following this time, the solution was then warmed to 40° C. for 2 hr., then diluted with EtOAc and washed with 5% LiCl 2× and brine. The organic extract was dried over sodium sulfate, concentrated, and purified by flash chromatography (eluent: EtOAc/hexanes) to give the I-60 and I-61.

2-[3-[(6-bromo-2-pyridyl)oxymethyl]pyrazol-1-yl]acetonitrile (I-60): ES/MS: 293.2, 295.1 (M+H⁺); 1H NMR (400 MHz, Chloroform-d) δ 7.55 (d, J=2.4 Hz, 1H), 7.45 (dd, J=8.2, 7.5 Hz, 1H), 7.11 (dd, J=7.5, 0.7 Hz, 1H), 6.76 (dd, J=8.2, 0.7 Hz, 1H), 6.52 (d, J=2.4 Hz, 1H), 5.39 (s, 2H), 5.10 (s, 2H).

2-[5-[(6-bromo-2-pyridyl)oxymethyl]pyrazol-1-yl]acetonitrile (I-61): ES/MS: 293.2, 295.0 (M+H⁺); 1H NMR (400 MHz, Chloroform-d) δ 7.57 (d, J=1.9 Hz, 1H), 7.50 (dd, J=8.2, 7.5 Hz, 1H), 7.15 (d, J=7.4 Hz, 1H), 6.80 (d, J=8.1 Hz, 1H), 6.48 (d, J=1.9 Hz, 1H), 5.47 (s, 2H), 5.35 (s, 2H).

Preparation of Intermediate I-62

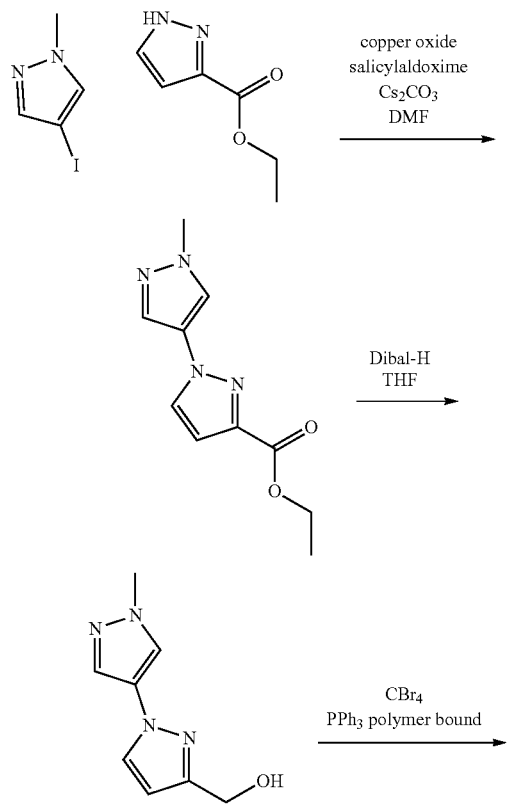

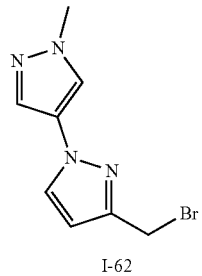

I-62

Ethyl 1-(1-methylpyrazol-4-yl)pyrazole-3-carboxylate: In a 40 mL glass vial, a mixture of ethyl 1H-pyrazole-3-carboxylate (1000 mg, 7.14 mmol), 4-iodo-1-methyl-pyrazole (1484 mg, 7.14 mmol), cesium carbonate (5812 mg, 17.8 mmol), copper(I) oxide (60.0 mg, 0.419 mmol), and salicylaldoxime (120 mg, 0.875 mmol) in DMF (20 mL) was heated at 110° C. for 48 hr. Following this time, the mixture was diluted with EtOAc and washed with 5% LiCl, saturated sodium bicarbonate, and brine. The organic extract was dried over sodium sulfate and purified by flash chromatography (eluent: EtOAc/hexanes) to give the title compound. ES/MS: 221.2 (M+H⁺).

[1-(1-methylpyrazol-4-yl)pyrazol-3-yl]methanol: To a solution of ethyl 1-(1-methylpyrazol-4-yl)pyrazole-3-carboxylate (287 mg, 1.30 mmol) in THF (6 mL) at 0° C., diisobutylaluminium hydride (1.0 M in DCM, 3.26 mL, 3.26 mmol) was added. The resulting solution was stirred for 1 hr. while gradually warming to rt. Following this time, the solution was diluted with Et₂O and cooled to 0° C. Upon completion of the cooling, 0.130 mL water, 0.130 mL 15% aqueous NaOH, and 0.326 mL water were added to the solution and then the resulting solution was warmed to rt. Following the warming, the solution was stirred for 15 min, then MgSO₄ was added and the solution was stirred for an additional 15 min, then filtered. The filtrate was concentrated and purified by flash chromatography (eluent: EtOAc/hexanes) to give the title compound. ES/MS: 179.2 (M+H⁺).

3-(bromomethyl)-1-(1-methylpyrazol-4-yl)pyrazole (I-62): To a solution of [1-(1-methylpyrazol-4-yl)pyrazol-3-yl]methanol (136 mg, 0.762 mmol) and (4-diphenylphosphanylphenyl polymer bound) (78.7%, 303 mg, 0.914 mmol) in DCM (10 mL) at 0° C., was added carbon tetrabromide (303 mg, 0.914 mmol). The mixture was gradually warmed to rt and stirred overnight. The resulting suspension was filtered, and the filtrate was diluted with DCM and washed with brine. The organic extract was dried over sodium sulfate, concentrated, and purified by flash chromatography (eluent: Et2O/hexanes) to give I-62. ES/MS: 241.2, 243.2 (M+H⁺); 1H NMR (400 MHz, Chloroform-d) δ 7.71 (s, 1H), 7.69 (d, J=0.8 Hz, 1H), 7.61 (d, J=2.4 Hz, 1H), 6.47 (d, J=2.4 Hz, 1H), 4.56 (s, 2H), 3.96 (s, 3H).

The following intermediate was prepared in a manner as described for intermediate I-62

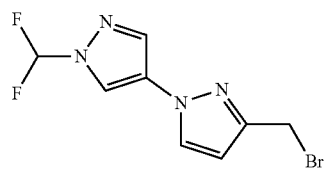 [SMILES: FC(F)n1cc(-n2ccc(CBr)n2)cn1]

Preparation of Intermediate I-63

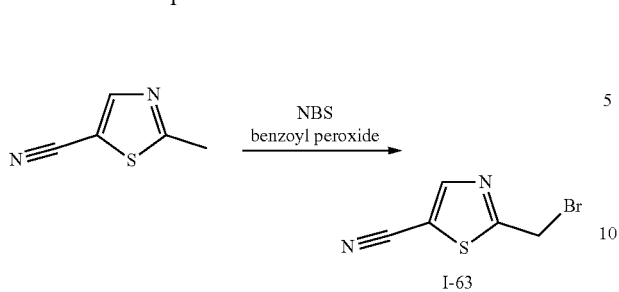

2-(bromomethyl)thiazole-5-carbonitrile (I-63): To a solution of 2-methylthiazole-5-carbonitrile (200 mg, 1.61 mmol) in CCl$_4$ (8 mL), was added N-Bromosuccinimide (375 mg, 2.11 mmol), followed by benzoyl peroxide (42.0 mg, 0.173 mmol). The solution was heated at 90° C. for 9 hrs. Following this time, the mixture was cooled to rt and 5 mL hexanes was added. The suspension was filtered, and the filtrate was concentrated, and purified by flash chromatography (eluent: EtOAc/hexanes) to give I-63. ES/MS: 203.0, 205.2 (M+H$^+$); 1H NMR (400 MHz, Chloroform-d) δ 8.23 (s, 1H), 4.74 (s, 2H).

The following intermediates were prepared in a manner as described for intermediate I-63

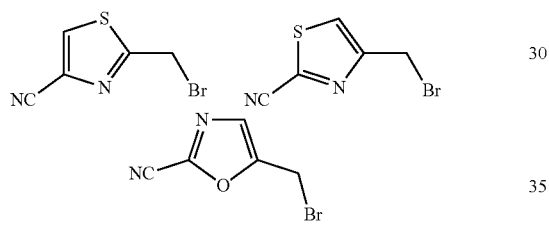

Preparation of Intermediate I-64

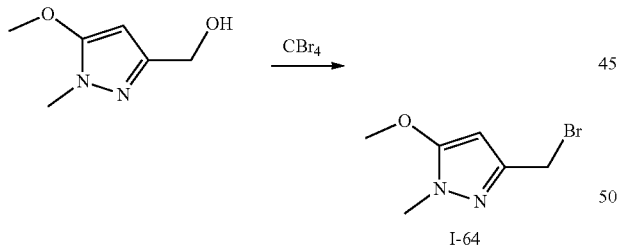

3-(bromomethyl)-5-methoxy-1-methyl-1H-pyrazole (I-64): To a stirring solution of (5-methoxy-1-methyl-1H-pyrazol-3-yl)methanol (1.42 g, 10 mmol, 1.0 eq) in DCM (15 mL), was added at rt, CBr4 (7.2 g, 21 mmol, 2.0 eq) and triphenylphosphine (5.7 g, 21 mmol, 2.0 eq). The mixture was stirred for an additional 16 h. Upon completion, the mixture was diluted with water (150 mL), extracted with DCM (3×150 mL), washed with brine (50 mL), dried over Na$_2$SO$_4$ and concentrated to get the crude product which was purified by column chromatography (0 to 2% MeOH-DCM) to afford 3-(bromomethyl)-5-methoxy-1-methyl-1H-pyrazole (I-64).

The following intermediates were prepared in a manner as describe for intermediate I-64

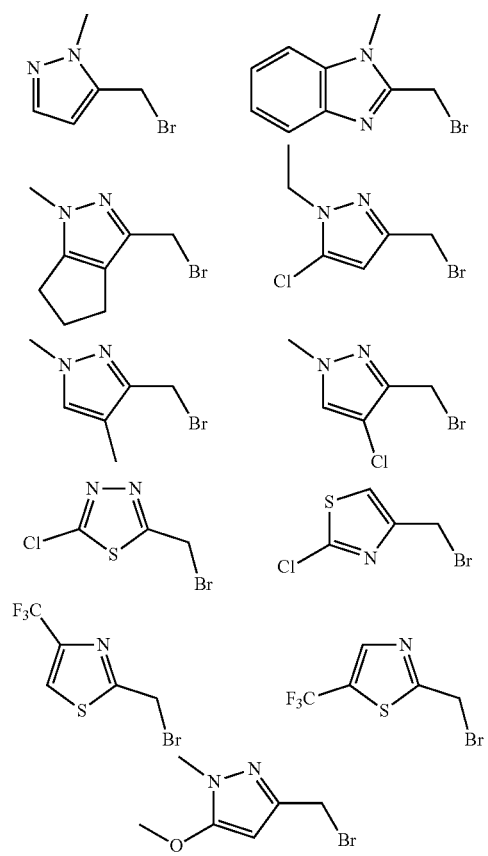

Preparation of Intermediate I-65

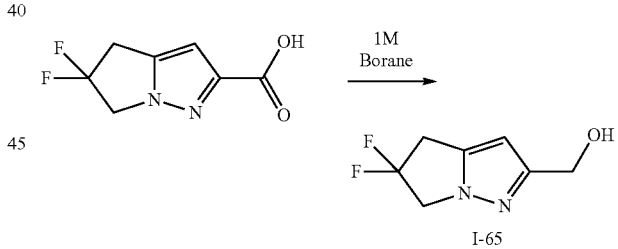

(5,5-difluoro-5,6-dihydro-4H-pyrrolo[1,2-b]pyrazol-2-yl)methanol (I-65): 5,5-difluoro-5,6-dihydro-4H-pyrrolo[1,2-b]pyrazole-2-carboxylic acid (105 mg, 0.56 mmol) was dissolved in THF (3 mL) and stirred at 0° C. for 5 min. Next, 1M Borane (3.4 mL) solution was added dropwise to the mixture at 0° C. over a period of 30 min. The ice bath was removed and stirring continued at rt for 7 hours. Following this time, the mixture was cooled in an ice bath and treated with 3M HCl (5 mL). The solution was heated for 1 h at 50° C. Upon completion of the time, the solution was washed with EtOAc (2×) and the aqueous layer was cooled in an ice bath and neutralized with 3M NaOH. The solution was extracted with EtOAc (3×), the combined organic layers were washed with brine, dried (Na$_2$SO$_4$) and concentrated in vacuo to obtain (5,5-difluoro-5,6-dihydro-4H-pyrrolo[1,2-b]pyrazol-2-yl)methanol (I-65).

Preparation of Intermediate I-66

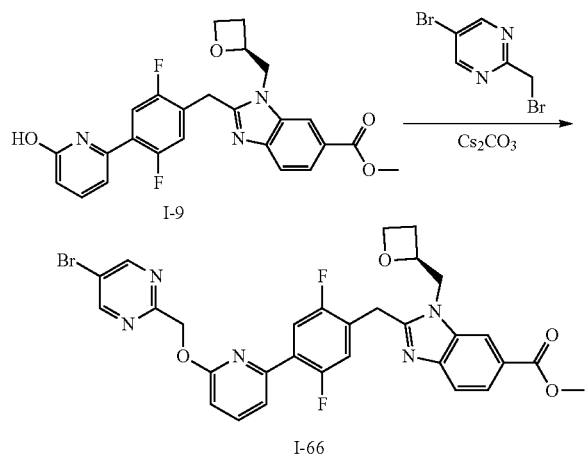

Methyl 2-[[4-[6-[(5-bromopyrimidin-2-yl)methoxy]-2-pyridyl]-2,5-difluoro-phenyl]methyl]-3-[[(2S)-oxetan-2-yl]methyl]benzimidazole-5-carboxylate (I-66): Methyl 2-[[4-[6-[(5-bromopyrimidin-2-yl)methoxy]-2-pyridyl]-2,5-difluoro-phenyl]methyl]-3-[[(2S)-oxetan-2-yl]methyl]benzimidazole-5-carboxylate was prepared in a manner as described for Intermediate I-21 to provide I-66. ES/MS: 637.4 (M+H+).

Preparation of Intermediate I-67

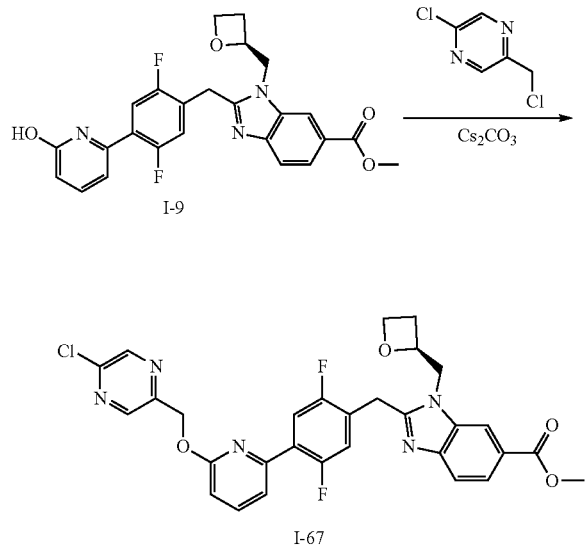

Methyl 2-[[4-[6-[(5-chloropyrazin-2-yl)methoxy]-2-pyridyl]-2,5-difluoro-phenyl]methyl]-3-[[(2S)-oxetan-2-yl]methyl]benzimidazole-5-carboxylate (I-67): Methyl 2-[[4-[6-[(5-chloropyrazin-2-yl)methoxy]-2-pyridyl]-2,5-difluoro-phenyl]methyl]-3-[[(2S)-oxetan-2-yl]methyl]benzimidazole-5-carboxylate was prepared in a manner as described for Intermediate I-21 to provide I-67. ES/MS: 593 (M+H+).

Preparation of Intermediate I-68

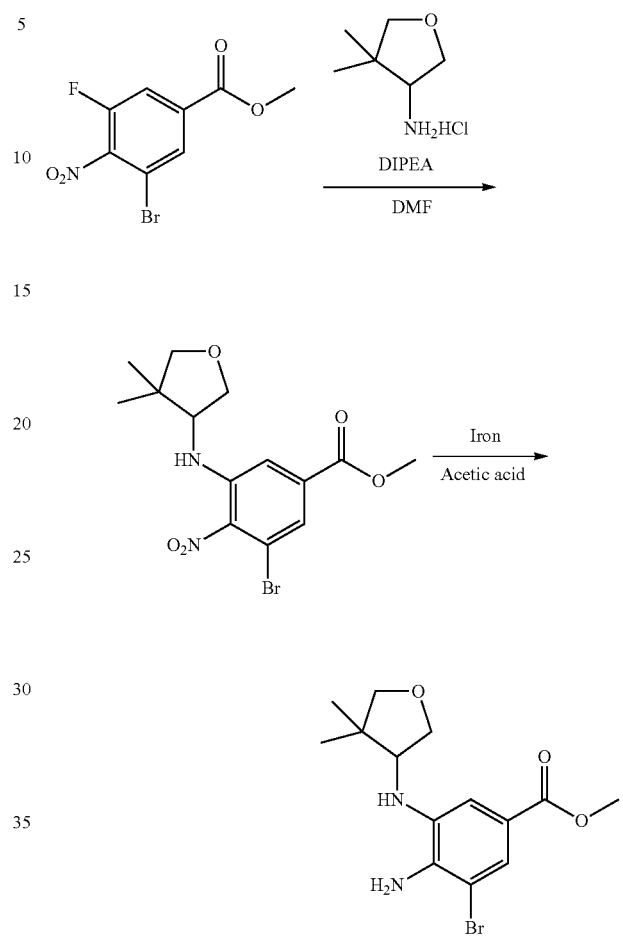

Methyl 3-bromo-5-((4,4-dimethyltetrahydrofuran-3-yl)amino-4-nitrobenzoate: Methyl 3-bromo-5-fluoro-4-nitrobenzoate (0.5 g, 1.8 mmol) was dissolved in a 100 mL round bottom flask containing DMF (10 mL). Next, 4,4-dimethyltetrahydrofuran-3-amine hydrochloride (0.46 g, 3 mmol) and N,N-diisopropylethylamine (0.63 mL, 3.6 mmol) were added to the solution. The mixture was stirred at 50° C. overnight. Afterward, the mixture was concentrated to remove most of the THF, and the crude material was dissolved in EtOAc (40 mL). The organics were washed with 50% NH$_4$Cl (2×10 mL) and with brine (1×50 mL). The organics were subsequently dried over MgSO$_4$, filtered, and concentrated under reduced pressure. The crude material was carried forward without further purification: ES/MS: 374.2 (M+H+)

Methyl 4-amino-3-bromo-5-[(4,4-dimethyltetrahydrofuran-3-yl)amino]benzoate (I-68): To a 100 mL round bottom flask, methyl 3-bromo-5-((4,4-dimethyltetrahydrofuran-3-yl) amino-4-nitrobenzoate (0.58 g, 1.6 mmol), Iron (0.43 g, 7.8 mmol), and Acetic acid (10 mL) were added. The mixture was stirred and heated at 100° C. for 1 h. Following this time, the mixture was filtered through Celite to remove the catalyst. The filtrate was concentrated under reduced pressure to give I-68 which was used without further purification: ES/MS: 344.2 (M+H+).

Preparation of Intermediate I-69

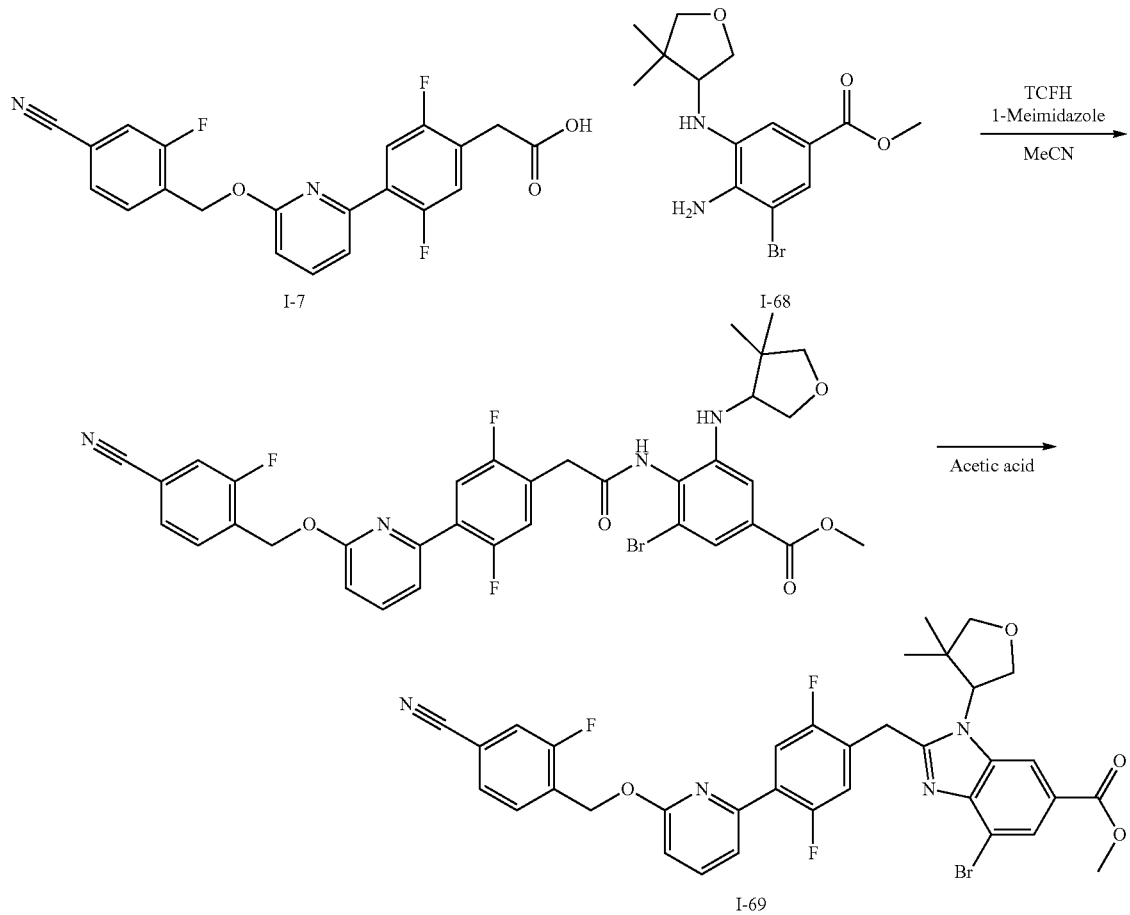

Methyl 3-bromo-4-[[2-[4-[6-[(4-cyano-2-fluoro-phenyl)methoxy]-2-pyridyl]-2,5-difluoro-phenyl]acetyl]amino]-5-[(4,4-dimethyltetrahydrofuran-3-yl)amino]benzoate: To a solution of I-68 (200 mg, 0.58 mmol) and I-7 (180 mg, 0.45 mmol) in MeCN (5 mL) and cooled to 0° C. was added 1-methylimidazole (239 mg, 0.23 mL, 2.9 mmol) followed by N,N,N',N'-Tetramethylchloroformamidinium Hexafluorophosphate (204 mg, 0.73 mmol). The mixture was warmed to rt and stirred for 30 min. Upon completion of the 30 min, the crude mixture was concentrated in vacuo, then partitioned between water and EtOAc. The organic layer was isolated and washed with an additional portion of water and then brine. The isolated organic layer was dried over sodium sulfate, isolated by vacuum filtration, concentrated in vacuo, and purified by silica gel column chromatography (eluent: EtOAc/hexanes) to provide the desired product. ES/MS: 724.4 [M+H]+.

Methyl 7-bromo-2-[[4-[6-[(4-cyano-2-fluoro-phenyl)methoxy]-2-pyridyl]-2,5-difluoro-phenyl]methyl]-3-(4,4-dimethyltetrahydrofuran-3-yl)benzimidazole-5-carboxylate (I-69): A solution of methyl 3-bromo-4-[[2-[4-[6-[(4-cyano-2-fluoro-phenyl)methoxy]-2-pyridyl]-2,5-difluoro-phenyl]acetyl]amino]-5-[(4,4-dimethyltetrahydrofuran-3-yl)amino]benzoate (100 mg, 0.14 mmol) in acetic acid (2 mL) was heated to 80° C. for 5 days. The mixture was concentrated and partitioned between EtOAc and saturated aqueous sodium bicarbonate. The organic layer was isolated and dried over sodium sulfate, isolated by vacuum filtration, concentrated in vacuo, and purified by silica gel column chromatography (eluent: EtOAc/hexanes) to provide I-69. ES/MS: 706.5 [M+H]+.

Preparation of Intermediate I-70

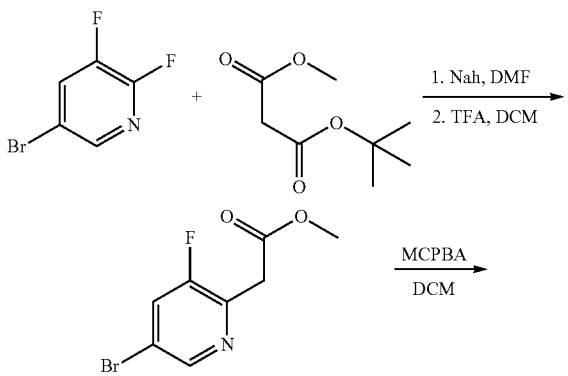

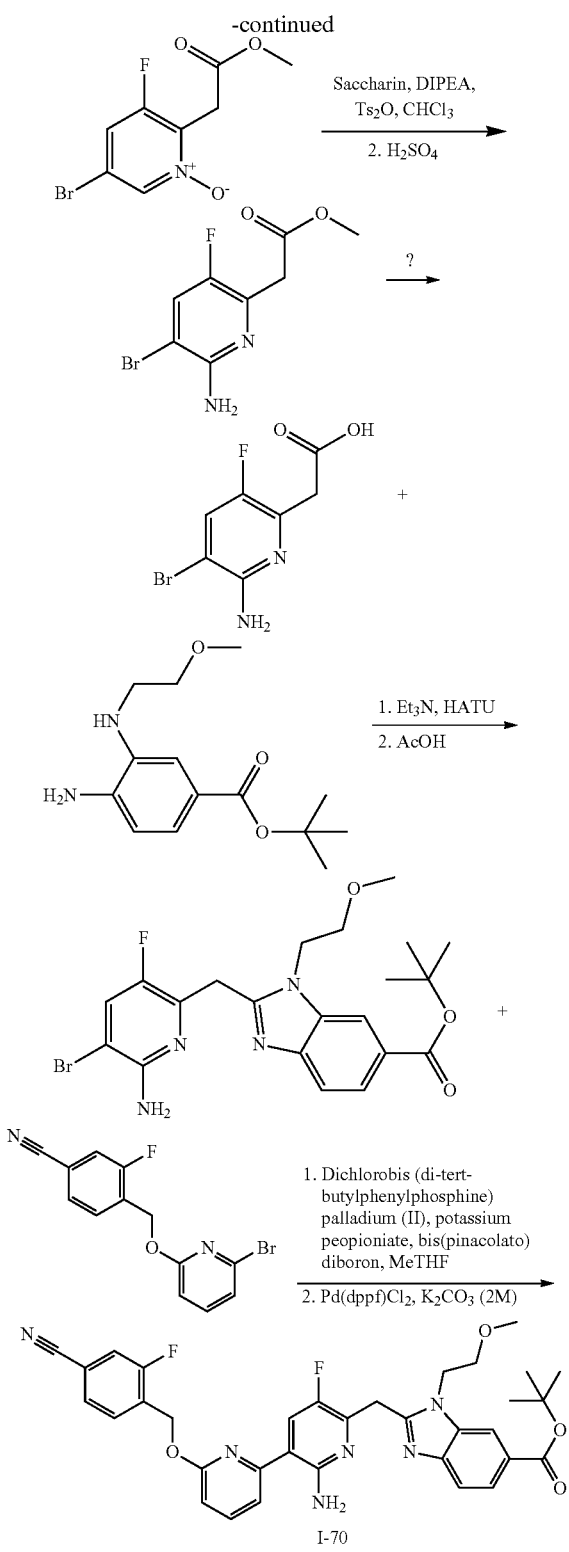

Methyl 2-(5-bromo-3-fluoropyridin-2-yl)acetate: Tert-butyl methyl malonate was added dropwise to a suspension of NaH (60% in mineral oil, 1.3 g, 34 mmol) in DMF (20 mL) at 5° C., and the suspension was stirred for 5 min. Next, 5-bromo-2,3-difluoropyridine was added dropwise, and the resulting suspension was warmed to 60° C. and stirred at that temperature overnight. Following this time, NH$_4$Cl was added, and the mixture was extracted with ether. The organic phase was rinsed with brine, and concentrated. The residue was redissolved in DCM (10 mL). Next, TFA (10 mL) was added, and the resulting solution was warmed to 40° C. and stirred for 5 hours. Upon completion of time, the mixture was concentrated and purified by flash chromatography (EtOAc/hexanes) to give title product: ES/MS: 248.2 (M+H$^+$).

5-bromo-3-fluoro-2-(2-methoxy-2-oxoethyl)pyridine 1-oxide: MCPBA (3.51 g, 16 mmol) was added to a solution of methyl 2-(5-bromo-3-fluoropyridin-2-yl)acetate (2.68 g, 11 mmol) in DCM (30 mL) at 0° C., and the resulting solution was allowed to warm to rt and stirred overnight. Next, the mixture was diluted with hexanes (20 mL) and filtered. The filtrate was concentrated and purified by flash chromatography (EtOAc/hexanes) to give title product: ES/MS: 265.2 (M+H$^+$).

Methyl 2-(6-amino-5-bromo-3-fluoropyridin-2-yl)acetate: P-toluenesulfonic anhydride (1.5 g) was added over the course of 1.5 hours to a solution of 5-bromo-3-fluoro-2-(2-methoxy-2-oxoethyl)pyridine 1-oxide (1.24 g, 4.7 mmol), saccharin (6.3 g, 34 mmol), and DIPEA (6.5 mL, 38 mmol) in chloroform (5 mL). The resulting solution was stirred at rt for 2 hours. Following this time, an additional amount of p-toluenesulfonic anhydride (1.3 g) was added and stirred for 1 hr. After the one hour, a further additional amount of p-toluenesulfonic anhydride (2.0 g) was added and stirred over the weekend. The reaction was quenched with Na$_2$CO$_3$ and filtered. The phases were separated, and the aqueous phase was extracted with DCM. The combined organics were washed with 10% citric acid, dried, filtered, concentrated, and purified by flash chromatography (EtOAc/hexanes). The resulting product was suspended in 2M H$_2$SO$_4$ (4 mL), and stirred at 90° C. for 18 hours, warmed to reflux, and stirred for 24 hours. The mixture was filtered, and filtrate washed with CHCl$_3$. The aqueous phase was basified with NaOH to pH~ 7 and filtered. Filtrate was acidified to pH~5 and extracted with CHCl$_3$ (3×). Organics were dried and concentrated to give title product: ES/MS: 249.0 (M+H$^+$). $^1$H NMR (400 MHz, Chloroform-d) δ 7.59 (d, J=7.7 Hz, 1H), 5.05 (s, 2H), 3.80 (d, J=2.2 Hz, 2H). $^{19}$F NMR (376 MHz, Chloroform-d) 6-137.76 (d, J=7.5 Hz).

2-(6-amino-5-bromo-3-fluoropyridin-2-yl)acetic acid: The title intermediate was prepared in a manner as described for intermediate I-7 (step 2) substituting methyl 2-(6-amino-5-bromo-3-fluoropyridin-2-yl)acetate for methyl 2-(4-(6-((4-cyano-2-fluorobenzyl)oxy)pyridin-2-yl)-2,5-difluorophenyl)acetate.

Tert-butyl 2-((6-amino-5-bromo-3-fluoropyridin-2-yl)methyl)-1-(2-methoxyethyl)-1H-benzo[d]imidazole-6-carboxylate: The title compound was prepared in a manner as described for Intermediate I-2, using 2-(6-amino-5-bromo-3-fluoropyridin-2-yl)acetic acid in place of 2-(4-bromo-2-fluoro-phenyl)acetic acid, and tert-butyl 4-amino-3-((2-methoxyethyl)amino)benzoate in place of methyl 4-amino-3-(2-methoxyethylamino)benzoate. ES/MS: 481.1 (M+H$^+$). $^1$H NMR (400 MHz, Chloroform-d) δ 8.07 (d, J=1.5 Hz, 1H), 7.94 (d, J=8.6 Hz, 1H), 7.78 (d, J=8.5 Hz, 1H), 7.51 (d, J=7.8 Hz, 1H), 4.79 (s, 2H), 4.57-4.39 (m, 4H), 3.70 (t, J=5.3 Hz, 2H), 3.30 (s, 3H), 1.65 (s, 9H).

Tert-butyl 2-((2'-amino-6-((4-cyano-2-fluorobenzyl)oxy)-5'-fluoro-[2,3'-bipyridin]-6'-yl)methyl)-1-(2-methoxyethyl)-1H-benzo[d]imidazole-6-carboxylate (I-70): I-70 was prepared in a manner as described for Intermediate I-7, using dichlorobis(di-tert-butylphenylphosphine)palladium(II) in place of Pd(dppf)Cl2 in step 1, and tert-butyl 2-((6-amino-5-bromo-3-fluoropyridin-2-yl)methyl)-1-(2-methoxyethyl)-

1H-benzo[d]imidazole-6-carboxylate in place of methyl 2-(4-bromo-2,5-difluorophenyl)acetate. ES/MS: 627.5 (M+H⁺).

Preparation of Intermediate I-71

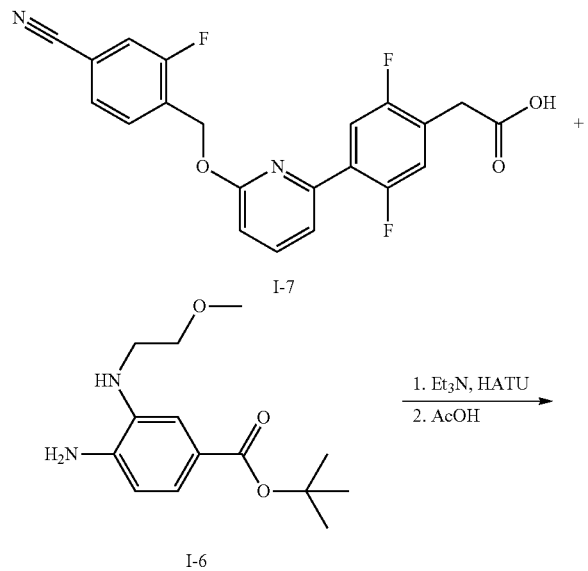

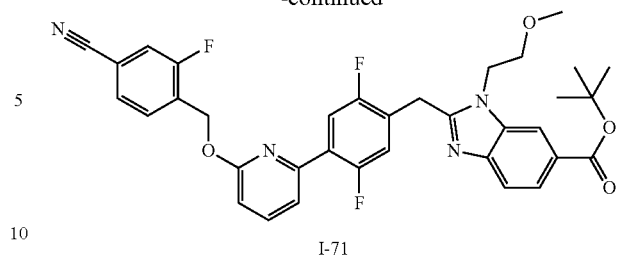

Tert-butyl 2-(4-(6-((4-cyano-2-fluorobenzyl)oxy)pyridin-2-yl)-2,5-difluorobenzyl)-1-(2-methoxyethyl)-1H-benzo[d]imidazole-6-carboxylate (I-71): The title compound was prepared in a manner as described for Intermediate I-2, using Intermediate I-6 and Intermediate I-7. ES/MS: 629.5 (M+H⁺).

Preparation of Intermediate I-72

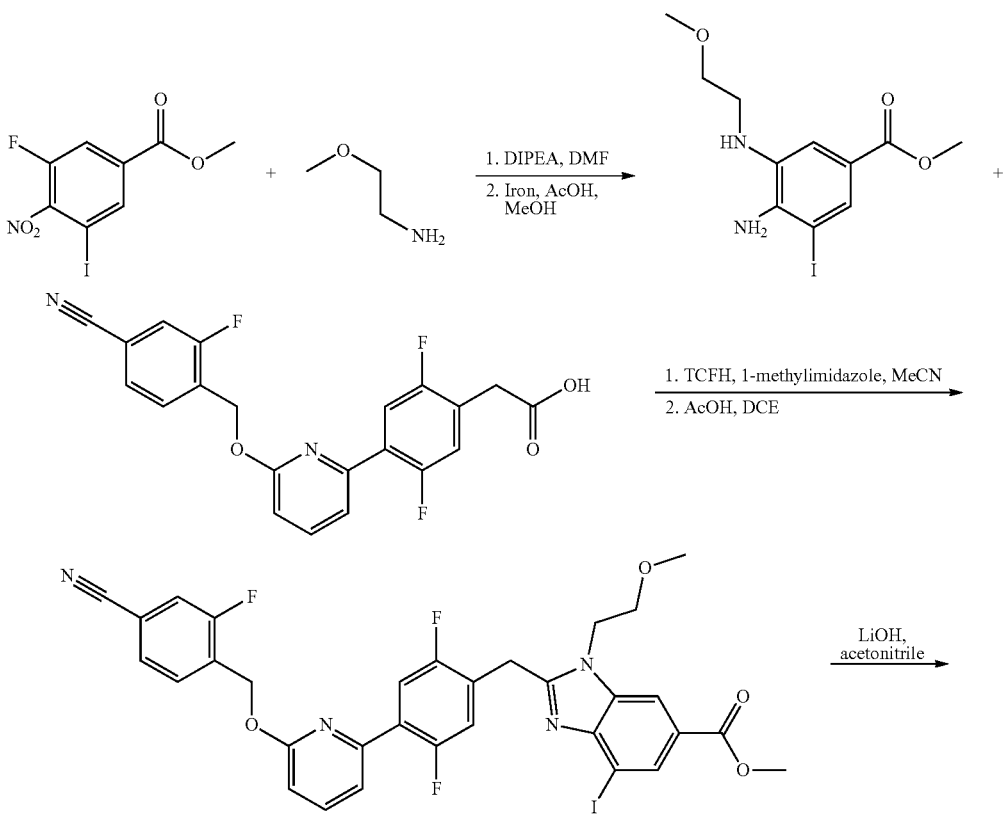

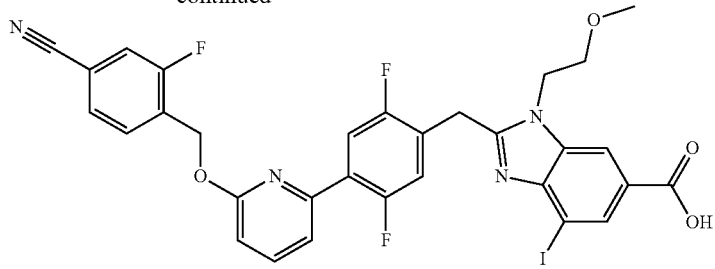

I-72

Methyl 4-amino-3-iodo-5-((2-methoxyethyl)amino)benzoate: The title compound was prepared in a manner as described for intermediate I-1. Reduction was executed by stirring Iron (603 mg, 10.8 mmol), acetic acid (12.0 mL, 1.8 mmol), and crude methyl 3-iodo-5-(2-methoxyethylamino)-4-nitro-benzoate (821 mg, 2.16 mmol) in methanol (5.0 mL) at reflux for 1 hour. The mixture was diluted with DCM, filtered, and organics were dried, filtered, concentrated, and carried on crude.

Methyl 2-(4-(6-((4-cyano-2-fluorobenzyl)oxy)pyridin-2-yl)-2,5-difluorobenzyl)-4-iodo-1-(2-methoxyethyl)-1H-benzo[d]imidazole-6-carboxylate: The title compound was prepared in a manner as described for Intermediate I-13, using methyl 4-amino-3-iodo-5-((2-methoxyethyl)amino) benzoate and Intermediate I-7.

2-[[4-[6-[(4-cyano-2-fluoro-phenyl)methoxy]-2-pyridyl]-2,5-difluoro-phenyl]methyl]-7-iodo-3-(2-methoxyethyl)benzimidazole-5-carboxylic acid (I-72): In an 8 mL glass vial, a solution of methyl 2-[[4-[6-[(4-cyano-2-fluoro-phenyl)methoxy]-2-pyridyl]-2,5-difluoro-phenyl]methyl]-7-iodo-3-(2-methoxyethyl)benzimidazole-5-carboxylate (105 mg, 0.15 mmol) and lithium hydroxide, monohydrate (25 mg, 0.59 mmol) in THF/water (2:1, 3 mL) was heated at 70° C. until completion (15 min). Following completion of the mixture, trifluoroacetic anhydride (0.3 mL) was added and the solution purified directly by RP-HPLC (eluent: MeCN/H₂O) to give I-72. ES/MS: 699.1

Preparation of Intermediate I-73

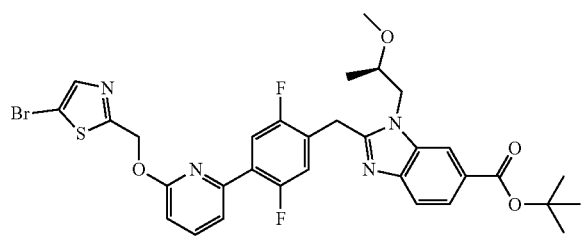

I-73

Tert-butyl (R)-2-(4-(6-((5-bromothiazol-2-yl)methoxy)pyridin-2-yl)-2,5-difluorobenzyl)-1-(2-methoxypropyl)-1H-benzo[d]imidazole-6-carboxylate (I-73): tert-butyl (R)-2-(4-(6-((5-bromothiazol-2-yl)methoxy)pyridin-2-yl)-2,5-difluorobenzyl)-1-(2-methoxypropyl)-1H-benzo[d]imidazole-6-carboxylate was prepared in a manner as described for Intermediate I-21 substituting I-26 for I-4. ES/MS: 686.8 (M+H⁺).

Preparation of Intermediate I-74

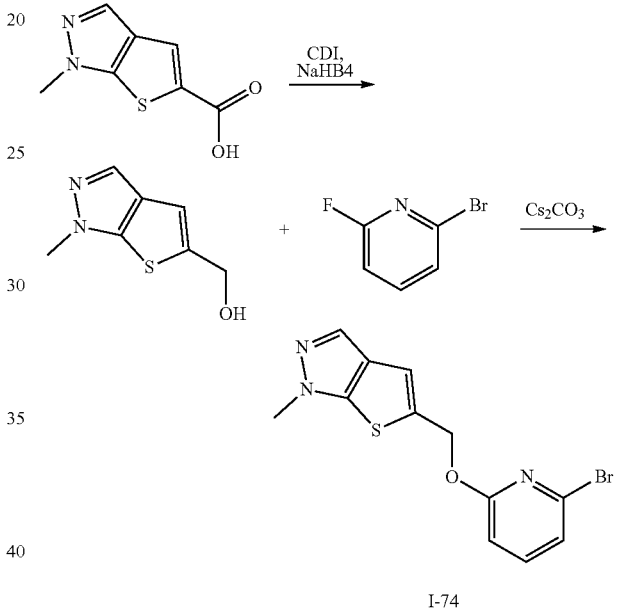

I-74

(1-methylthieno[2,3-c]pyrazol-5-yl)methanol: To a solution of 1-methylthieno[2,3-c]pyrazole-5-carboxylic acid (140 mg, 0.77 mmol) in THF (6 mL) was added CDI (249 mg, 1.54 mmol) and the resultant slurry stirred for 2 hours at ambient temperature. Following this time, NaBH₄ (145 mg, 3.84 mmol) was added portion wise and the mixture stirred overnight. Upon completion MeOH was added (2 mL) and the crude mixture concentrated directly. The crude residue purified by silica gel column chromatography (eluent: EtOAc/hexanes) to provide desired product. ES/MS: 169.1 (M+H⁺).

5-[(6-bromo-2-pyridyl)oxymethyl]-1-methyl-thieno[2,3-c]pyrazole (I-74): To a solution of 2-bromo-6-fluoro-pyridine (122 mg, 0.69 mmol) in acetonitrile (2 mL) was added (1-methylthieno[2,3-c]pyrazol-5-yl)methanol (106 mg, 0.63 mmol) and cesium carbonate (411 mg, 1.26 mmol) and the resultant mixture stirred for 2 hours at 80° C. Upon completion the mixture was diluted with EtOAc (25 mL), washed with water (5 mL) and brine (5 mL). The organic layer was dried over MgSO₄, filtered, concentrated and purified by silica gel column chromatography (eluent: EtOAc/hexanes) to provide I-74. ES/MS: 326.1 (M+H⁺).

Preparation of Intermediate I-75

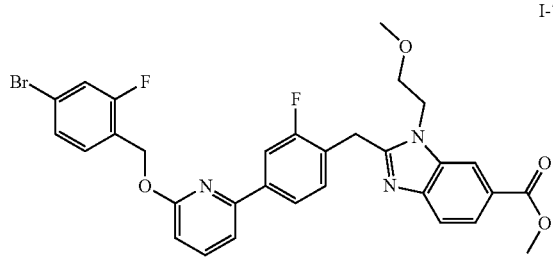

Methyl 2-(4-(6-((4-bromo-2-fluorobenzyl)oxy)pyridin-2-yl)-2-fluorobenzyl)-1-(2-methoxyethyl)-1H-benzo[d]imidazole-6-carboxylate (I-75): Methyl 2-(4-(6-((4-bromo-2-fluorobenzyl)oxy)pyridin-2-yl)-2-fluorobenzyl)-1-(2-methoxyethyl)-1H-benzo[d]imidazole-6-carboxylate was prepared in a manner as described for Intermediate I-19 substituting I-2 for I-96. ES/MS: 623.3 (M+H$^+$).

Preparation of Intermediate I-76

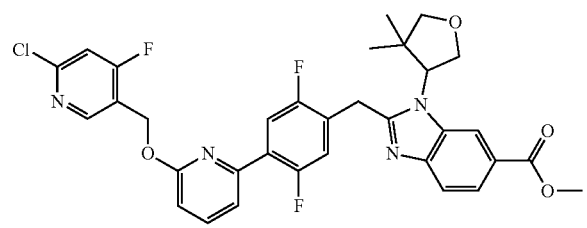

Methyl 2-(4-(6-((6-chloro-4-fluoropyridin-3-yl)methoxy)pyridin-2-yl)-2,5-difluorobenzyl)-1-(4,4-dimethyltetrahydrofuran-3-yl)-1H-benzo[d]imidazole-6-carboxylate (I-76): Methyl 2-(4-(6-((6-chloro-4-fluoropyridin-3-yl)methoxy)pyridin-2-yl)-2,5-difluorobenzyl)-1-(4,4-dimethyltetrahydrofuran-3-yl)-1H-benzo[d]imidazole-6-carboxylate was prepared in a manner as described for Intermediate I-23 substituting I-25 for I-4. ES/MS: 638.0 (M+H$^+$).

Preparation of Intermediate I-77

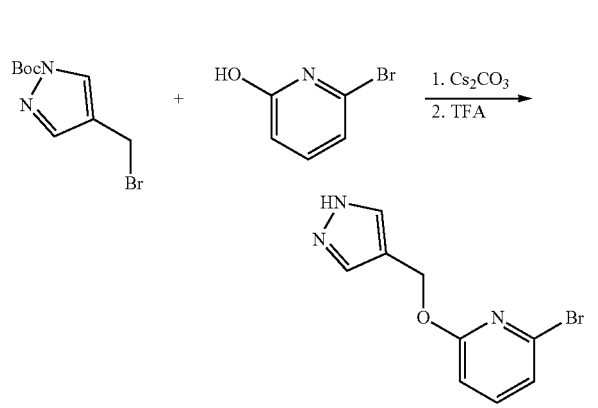

2-bromo-6-(1H-pyrazol-3-ylmethoxy)pyridine (I-77): To a solution of 6-bromopyridin-2-ol (180 mg, 1.0 mmol) in acetonitrile (4 mL) was added cesium carbonate (482 mg, 1.5 mmol) and tert-butyl 3-(bromomethyl)pyrazole-1-carboxylate (378 mg, 1.4 mmol) after which the mixture was heated to 65° C. for 30 minutes. Upon completion the mixture was filtered through celite, concentrated and purified by silica gel column chromatography (eluent: EtOAc/hexanes) to provide desired product. The so obtained tert-butyl 3-[(6-bromo-2-pyridyl)oxymethyl]pyrazole-1-carboxylate (343 mg, 0.97 mmol) was dissolved in DCM (4.4 mL) and TFA (1.1 mL) and stirred at ambient temperature for 2 hours. Upon completion, the mixture was diluted with EtOAc (25 mL) washed with saturated aqueous NaHCO$_3$ until gas evolution ceased, dried over MgSO$_4$, filtered and concentrated to give I-77 which was used without further purification. ES/MS: 254.2, 256.2 (M+H$^+$).

Preparation of Intermediate I-78

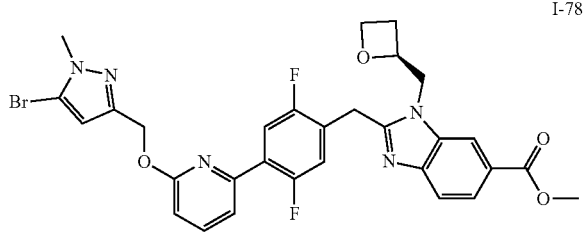 [SMILES: COC(=O)c1ccc2nc(Cc3cc(F)c(-c4cccc(OCc5cc(Br)n(C)n5)n4)cc3F)n(C[C@@H]3CCO3)c2c1]

Methyl (S)-2-(4-(6-((5-bromo-1-methyl-1H-pyrazol-3-yl)methoxy)pyridin-2-yl)-2,5-difluorobenzyl)-1-(oxetan-2-ylmethyl)-1H-benzo[d]imidazole-6-carboxylate (I-78): Methyl (S)-2-(4-(6-((5-bromo-1-methyl-1H-pyrazol-3-yl)methoxy)pyridin-2-yl)-2,5-difluorobenzyl)-1-(oxetan-2-ylmethyl)-1H-benzo[d]imidazole-6-carboxylate was prepared in a manner as described for Intermediate I-21 substituting 5-bromo-3-(bromomethyl)-1-methyl-1H-pyrazole for 5-bromo-2-(bromomethyl)thiazole. ES/MS: 638.0, 640.0 (M+H$^+$).

Preparation of Intermediate I-79

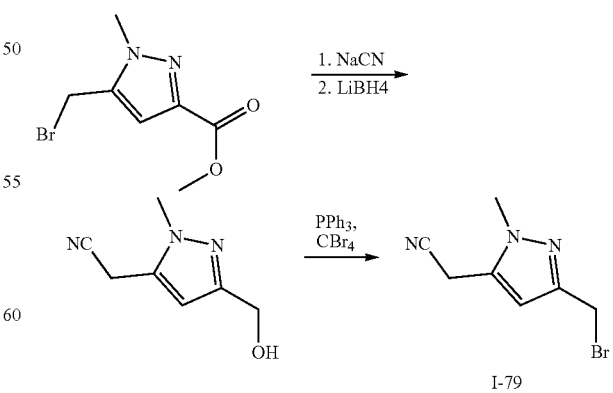

2-[5-(hydroxymethyl)-2-methyl-pyrazol-3-yl]acetonitrile: To a solution of methyl 5-(bromomethyl)-1-methyl-pyrazole-3-carboxylate (750 mg, 3.22 mmol) in DMF (9.5 mL) and water (1.2 mL), was added sodium cyanide (241 mg, 4.83 mmol) and the resultant mixture stirred at rt for 3.5 hours. Upon completion the mixture was diluted with EtOAc (50 mL), washed with water (10 mL) and brine (10 mL). The organic layer was dried over MgSO$_4$, filtered, concentrated and purified by silica gel column chromatography (eluent: EtOAc/hexanes) to provide desired product. The so obtained methyl 5-(cyanomethyl)-1-methyl-pyrazole-3-carboxylate (328 mg, 1.83 mmol), was dissolved in THF (10 mL) and lithium borohydride (2.0M in THF, 1.83 mL, 3.66 mmol) was added at 0° C. The mixture was allowed to warm to rt and stir for 6 hr. at which point additional lithium borohydride (2.0M in THF, 1.83 mL, 3.66 mmol) was added and the mixture stirred for 2 hr. Upon completion the reaction was quenched by the addition of water (5 mL), diluted with EtOAc (50 mL) and the layers separated. The organic layer was dried over MgSO$_4$, filtered, concentrated and purified by silica gel column chromatography (eluent: EtOAc/hexanes) to provide desired product.

2-[5-(bromomethyl)-2-methyl-pyrazol-3-yl]acetonitrile (I-79): 2-[5-(Hydroxymethyl)-2-methyl-pyrazol-3-yl]acetonitrile (100 mg, 0.662 mmol) was taken up in dichloromethane (2.65 mL) and triphenylphosphine (0.208 g, 0.794 mmol) was added followed by the addition of carbontetrabromide (0.263 g, 0.794 mmol). The mixture was left to stir at rt for 5 minutes at which point the reaction was quenched by the addition of water (5 mL), diluted with EtOAc (25 mL) and the layers separated. The organic layer was dried over MgSO$_4$, filtered, concentrated and purified by silica gel column chromatography (eluent: EtOAc/hexanes) to provide I-79. ES/MS: 214.0, 216.0 (M+H$^+$).

Preparation of Intermediates I-80 and I-81 (Method 1)

Methyl 4-amino-3-((4,4-dimethyltetrahydrofuran-3-yl)amino)benzoate (I-80, 1-81): Methyl 4-amino-3-((4,4-dimethyltetrahydrofuran-3-yl)amino)benzoate as a mixture of 2 stereoisomers were separated by chiral SFC (SFC IB column with EtOH cosolvent) to give two distinct stereoisomers.

Methyl (S)-4-amino-3-((4,4-dimethyltetrahydrofuran-3-yl)amino)benzoate, isomer 1 (I-80): Isolated as the earlier eluting of two isomers by chiral SFC (4.6×100 mm 5 μm IB column, 10% EtOH in CO$_2$). ES/MS: 265.2 (M+H$^+$).

Methyl (R)-4-amino-3-((4,4-dimethyltetrahydrofuran-3-yl)amino)benzoate, isomer 2 (I-81): Isolated as the later-eluting of two isomers by chiral SFC (4.6×100 mm 5 μm IB column, 10% EtOH in CO$_2$). ES/MS: 265.2 (M+H$^+$).

Preparation of Intermediate I-80 (Method 2)

Methyl 4-amino-3-[[(3S)-4,4-dimethyltetrahydrofuran-3-yl]amino]benzoate isomer 2 (I-80): A solution of methyl 3-[[(3S)-4,4-dimethyltetrahydrofuran-3-yl]amino]-4-nitrobenzoate (Intermediate I-100, 17.8 g, 60.5 mmol) in EtOAc (380 mL) was degassed with argon then vacuum 3×. Palladium on carbon (10.0%, 6.07 g, 5.70 mmol) was added. The mixture was degassed with argon then vacuum 3 times and stirred at rt under an atmosphere of hydrogen until completion. The suspension was filtered over a Celite plug and rinsed with EtOAc. The mixture was concentrated to yield methyl 4-amino-3-[[(3S)-4,4-dimethyltetrahydrofuran-3-yl]amino]benzoate, which was carried forward to subsequent steps without further purification. ES/MS: 265.0 (M+H$^+$). 1H NMR (400 MHz, Chloroform-d) δ 7.49 (dd, J=8.0, 1.8 Hz, 1H), 7.35 (d, J=1.8 Hz, 1H), 6.73 (d, J=8.1 Hz, 1H), 4.36 (dd, J=9.1, 6.4 Hz, 1H), 3.89 (s, 3H), 3.76 (t, J=5.9 Hz, 1H), 3.72-3.63 (m, 2H), 3.63-3.59 (m, 1H), 1.22 (s, 3H), 1.15 (s, 3H).

Preparation of Intermediates I-82 and I-83 (Method 1)

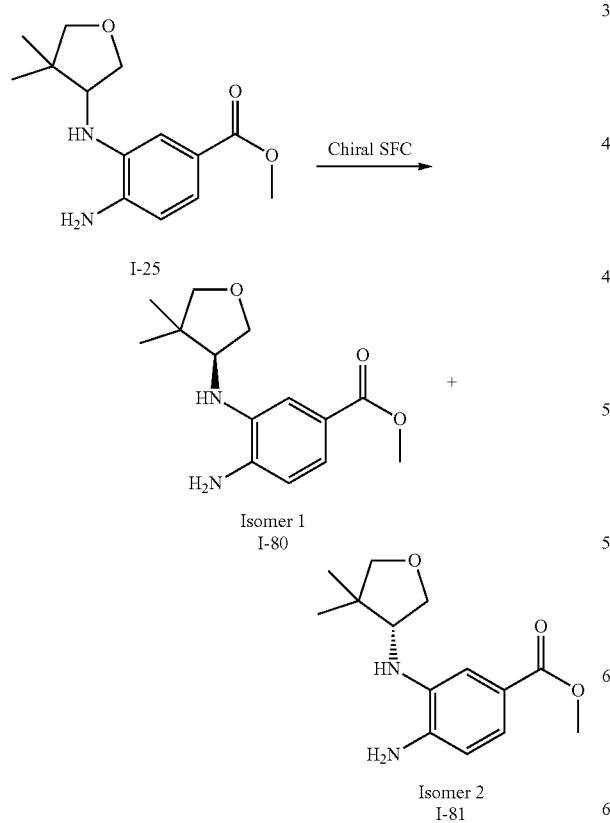

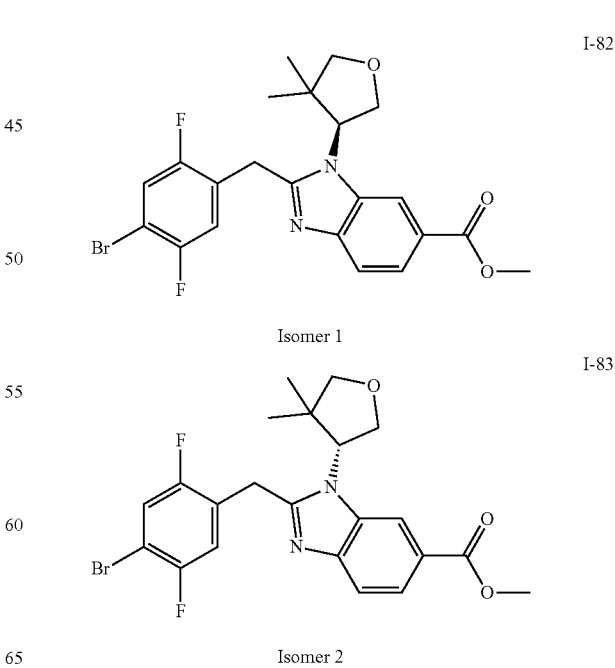

Methyl 2-(4-bromo-2,5-difluorobenzyl)-1-(4,4-dimethyltetrahydrofuran-3-yl)-1H-benzo[d]imidazole-6-carboxylate (I-82, I-83): I-82 and I-83 were prepared separately in a manner as described for Intermediate I-8 substituting I-80 (for Intermediate I-82) and I-81 (for Intermediate I-83) for I-4.

Methyl (S)-2-(4-bromo-2,5-difluorobenzyl)-1-(4,4-dimethyltetrahydrofuran-3-yl)-1H-benzo[d]imidazole-6-carboxylate isomer 1 (Intermediate I-82): ES/MS: 479.0, 481.0 (M+H$^+$).

Methyl (R)-2-(4-bromo-2,5-difluorobenzyl)-1-(4,4-dimethyltetrahydrofuran-3-yl)-1H-benzo[d]imidazole-6-carboxylate isomer 2 (Intermediate I-83): ES/MS: 479.0, 481.0 (M+H$^+$).

Preparation of Intermediate I-82 (Method 2)

Methyl 2-[[(4-bromo-2,5-difluoro-phenyl)methyl]-3-[(3S)-4,4-dimethyltetrahydrofuran-3-yl]benzimidazole-5-carboxylate (Intermediate I-82): To a solution of 2-(4-bromo-2,5-difluorophenyl)acetic acid (3301 mg, 13.2 mmol), methyl 4-amino-3-[[(3S)-4,4-dimethyltetrahydrofuran-3-yl]amino]benzoate (Intermediate I-80, 3.16 g, 12.0 mmol), and o-(7-Azabenzotriazol-1-yl)-N,N,N',N'-tetramethyluronium hexafluorophosphate (6360 mg, 16.7 mmol) in DMF (20 mL) and CH3CN (20 mL), was added N,N-Diisopropylethylamine (10.2 mL, 58.4 mmol). The solution was stirred at rt overnight. Then to the mixture was added 0.2 eq of 2-(4-bromo-2,5-difluoro-phenyl)acetic acid (600 mg, 2.39 mmol) and o-(7-Azabenzotriazol-1-yl)-N,N,N',N'-tetramethyluronium hexafluorophosphate (930 mg, 2.39 mmol) and continued stirring until complete conversion to product. The crude mixture was diluted with 200 mL EtOAc and washed with saturated NH$_4$Cl (200 mL), 5% LiCl (100 mL), saturated NaHCO$_3$ (100 mL), and brine (100 mL). The organic extract was dried over sodium sulfate to give methyl 4-[[2-(4-bromo-2,5-difluoro-phenyl)acetyl]amino]-3-[[(3S)-4,4-dimethyltetrahydrofuran-3-yl]amino]benzoate.

A solution of methyl 4-[[2-(4-bromo-2,5-difluoro-phenyl)acetyl]amino]-3-[[(3S)-4,4-dimethyltetrahydrofuran-3-yl]amino]benzoate (5.96 g, 12.0 mmol) in AcOH (60 mL) was heated to 180° C. for 90 min in a microwave reactor. The mixture was concentrated, then diluted with EtOAc and washed with saturated NaHCO$_3$, and brine. The mixture was dried over sodium sulfate and purified by silica gel column chromatography (eluent: EtOAc/hexanes) to afford methyl 2-[(4-bromo-2,5-difluoro-phenyl)methyl]-3-[(3S)-4,4-dimethyltetrahydrofuran-3-yl]benzimidazole-5-carboxylate (Intermediate I-82). ES/MS: 478.6, 480.6 (M+H$^+$). 1H NMR (400 MHz, Chloroform-d) δ 8.55 (s, 1H), 8.02 (dd, J=8.5, 1.5 Hz, 1H), 7.78 (d, J=8.5 Hz, 1H), 7.37 (dd, J=8.7, 5.6 Hz, 1H), 7.12 (dd, J=8.4, 6.3 Hz, 1H), 4.59 (d, J=10.5 Hz, 2H), 4.40 (dd, J=11.1, 7.3 Hz, 1H), 4.31 (s, 2H), 3.97 (s, 4H), 3.80 (d, J=8.8 Hz, 1H), 1.35 (s, 3H), 0.67 (s, 3H).

Preparation of Intermediate I-84

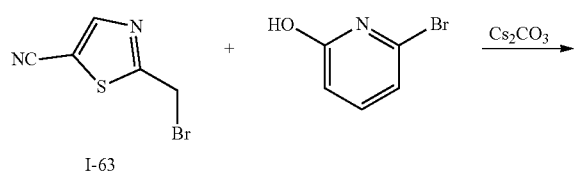

I-63

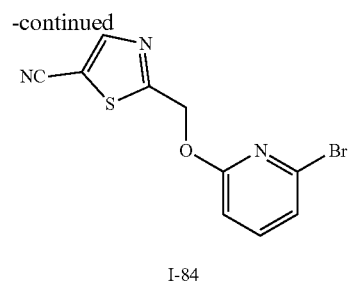

I-84

2-[(6-bromo-2-pyridyl)oxymethyl]thiazole-5-carbonitrile (I-84): To a solution of 6-bromopyridin-2-ol (500 mg, 2.9 mmol) in acetonitrile (10 mL) was added 2-(bromomethyl)thiazole-5-carbonitrile (I-63) (584 mg, 2.9 mmol) and cesium carbonate (1.34 g, 4.1 mmol) and the resultant mixture stirred at 65° C. for 1 hour. Upon completion the mixture was filtered through celite, concentrated and purified by silica gel column chromatography (eluent: EtOAc/hexanes) to provide I-84. ES/MS: 296.0, 298.0 (M+H$^+$).

Preparation of Intermediate I-85

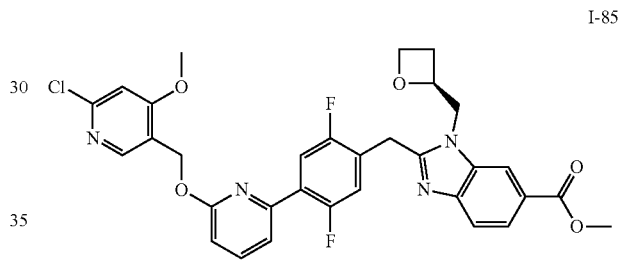

I-85

Methyl 2-[[4-[6-[(6-chloro-4-methoxy-3-pyridyl)methoxy]-2-pyridyl]-2,5-difluoro-phenyl]methyl]-3-[[(2S)-oxetan-2-yl]methyl]benzimidazole-5-carboxylate (I-85): Methyl 2-[[4-[6-[(6-chloro-4-methoxy-3-pyridyl)methoxy]-2-pyridyl]-2,5-difluoro-phenyl]methyl]-3-[[(2S)-oxetan-2-yl]methyl]benzimidazole-5-carboxylate was prepared in a manner as described for Intermediate I-23 substituting 5-(bromomethyl)-2-chloro-4-methoxypyridine for 5-(bromomethyl)-2-chloro-4-fluoropyridine. ES/MS: 621.2 (M+H$^+$).

Preparation of Intermediate I-86

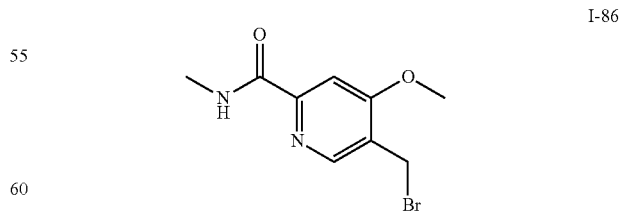

I-86

5-(bromomethyl)-4-methoxy-N-methylpicolinamide (I-86): 5-(bromomethyl)-4-methoxy-N-methylpicolinamide was prepared in a manner as described for Intermediate I-53 substituting methylamine HCl for 1-aminocyclopropane-1-carbonitrile. ES/MS: 259.2, 261.2 (M+H$^+$).

Preparation of Intermediate I-87

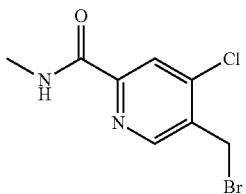

I-87

5-(bromomethyl)-4-chloro-N-methylpicolinamide (I-87): 5-(bromomethyl)-4-chloro-N-methylpicolinamide was prepared in a manner as described for Intermediate I-53 substituting methylamine HCl for 1-aminocyclopropane-1-carbonitrile and 4-chloro-5-methylpicolinic acid for 4-methoxy-5-methylpicolinic acid. ES/MS: 263.0, 265.0 (M+H$^+$).

Preparation of Intermediate I-88

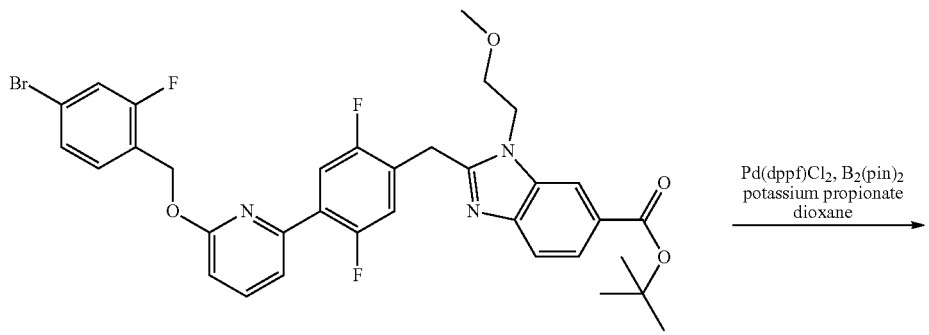

reactor. Upon completion the mixture was concentrated directly and purified by silica gel column chromatography (eluent: EtOAc/hexanes) to provide I-88. ES/MS: 730.8 (M+H$^+$).

Preparation of Intermediate I-89

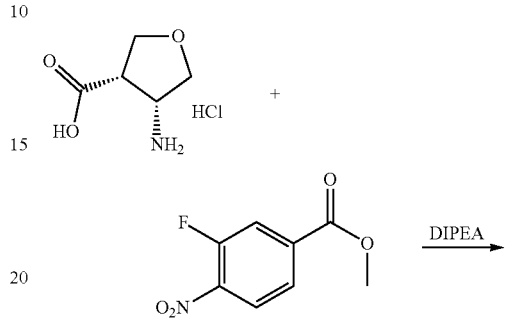

Tert-butyl 2-[[2,5-difluoro-4-[6-[[2-fluoro-4-(4,4,5,5-tetramethyl-1,3,2-dioxaborolan-2-yl)phenyl]methoxy]-2-pyridyl]phenyl]methyl]-3-(2-methoxyethyl)benzimidazole-5-carboxylate (I-88): To a solution of tert-butyl 2-[[4-[6-[(4-bromo-2-fluoro-phenyl)methoxy]-2-pyridyl]-2,5-difluoro-phenyl]methyl]-3-(2-methoxyethyl)benzimidazole-5-carboxylate (300 mg, 0.44 mmol) in 1,4-dioxane (20 mL) was added Bis(pinacolato)diboron (179 mg, 0.70 mmol), Pd(dppf)Cl$_2$ (33 mg, 0.044 mmol), and potassium propionate (148 mg, 1.3 mmol). Argon was bubbled through the mixture for 1 minute after which the reaction vessel was sealed and heated to 110° C. for 45 minutes in a microwave -continued

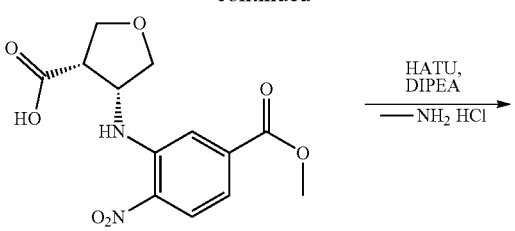

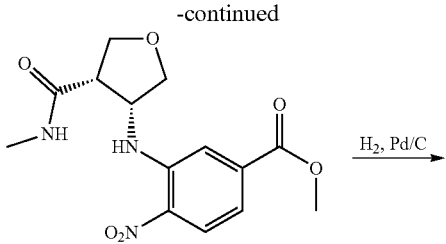

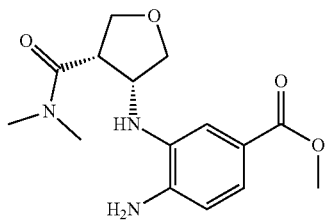

Preparation of Intermediate I-90

Methyl 4-amino-3-(((3R,4S)-4-(dimethylcarbamoyl)tetrahydrofuran-3-yl)amino)benzoate (I-90): Methyl 4-amino-3-(((3R,4S)-4-(dimethylcarbamoyl)tetrahydrofuran-3-yl)amino)benzoate was prepared in a manner as described for Intermediate I-89 substituting dimethylamine for methylamine. ES/MS: 308.2 (M+H$^+$).

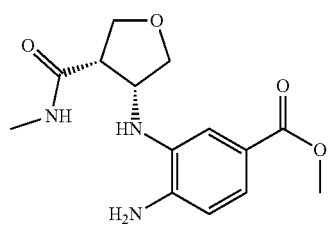

I-89

Preparation of Intermediate I-91

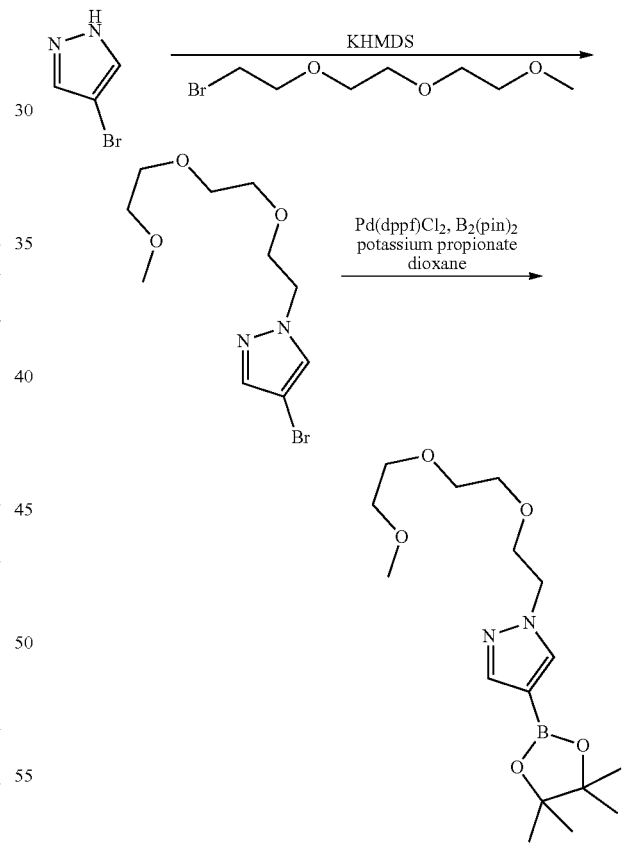

I-91

(3S,4R)-4-(5-methoxycarbonyl-2-nitro-anilino)tetrahydrofuran-3-carboxylic acid: To a solution of methyl 3-fluoro-4-nitro-benzoate (700 mg, 3.52 mmol) and (3S,4R)-4-aminotetrahydrofuran-3-carboxylic acid; hydrochloride (648 mg, 17.6 mmol) in DMF (2.5 mL) and THF (5 mL) was added diisopropylethylamine (3.1 mL, 17.6 mmol) and the resultant solution heated to 70° C. for 3 days. Upon completion, the mixture was diluted with EtOAc (50 mL), washed with water (10 mL), brine (10 mL), dried over MgSO$_4$, filtered, concentrated to give the desired product which was used without further purification. ES/MS: 311.2 (M+H$^+$).

Methyl 3-[[(3R,4S)-4-(methylcarbamoyl)tetrahydrofuran-3-yl]amino]-4-nitro-benzoate: (3S,4R)-4-(5-methoxycarbonyl-2-nitro-anilino)tetrahydrofuran-3-carboxylic acid (370 mg, 0.00119 mol), 1-hydroxybenzotriazole hydrate (0.192 g, 0.00125 mol), and methylamine (2000 mmol/L in THF, 1.19 mL, 0.00239 mol) were taken up in tetrahydrofuran (8.00 mL) and triethylamine (0.151 g, 0.00149 mol) was added followed by 1-(3-dimethylaminopropyl)-3-ethyl-carbodiimide hydrochloride (0.251 g, 0.00131 mol). The mixture was stirred at rt overnight. Upon completion the mixture was diluted with EtOAc (50 mL), washed with water (10 mL), brine (10 mL), dried over MgSO$_4$, filtered, and concentrated to give the desired product which was used without further purification. ES/MS: 324.2 (M+H$^+$).

Methyl 4-amino-3-[[(3R,4S)-4-(methylcarbamoyl)tetrahydrofuran-3-yl]amino]benzoate (I-89): To a solution of methyl 3-[[(3R,4S)-4-(methylcarbamoyl)tetrahydrofuran-3-yl]amino]-4-nitro-benzoate (168 mg, 0.52 mmol) in EtOH (2 mL) and THF (1 mL) was added palladium on carbon (10%, 111 mg, 0.10 mmol). The mixture was then purged with H$_2$ gas and stirred under 1 atm of H$_2$ for 1 hr. Upon completion the mixture was filtered through celite, concentrated and the crude residue, I-89, was used without further purification. ES/MS: 294.2 (M+H$^+$).

4-bromo-1-[2-[2-(2-methoxyethoxy)ethoxy]ethyl]pyrazole: To a solution of 4-bromo-1H-pyrazole (100 mg, 0.68 mmol) in 2-Me tetrahydrofuran (2 mL) was added Potassium Bis(trimethylsilyl)amide (204 mg, 1.0 mmol) and 1-[2-(2-bromoethoxy)ethoxy]-2-methoxy-ethane (309 mg, 1.4 mmol) and heated to 50° C. for 2 hours. Upon completion, the mixture was diluted with EtOAc (25 mL), washed with water (5 mL), brine (5 mL), dried over MgSO$_4$, filtered and concentrated to give the desired product which was used without further purification. ES/MS: 293.3 (M+H$^+$).

1-[2-[2-(2-methoxyethoxy)ethoxy]ethyl]-4-(4,4,5,5-tetramethyl-1,3,2-dioxaborolan-2-yl)pyrazole (I-91): 4-bromo-1-[2-[2-(2-methoxyethoxy)ethoxy]ethyl]pyrazole was converted to 1-[2-[2-(2-methoxyethoxy)ethoxy]ethyl]-4-(4,4,5,5-tetramethyl-1,3,2-dioxaborolan-2-yl)pyrazole (I-91) in a manner as described for intermediate I-88. ES/MS: 341.1 (M+H$^+$).

Preparation of Intermediate I-92

I-92

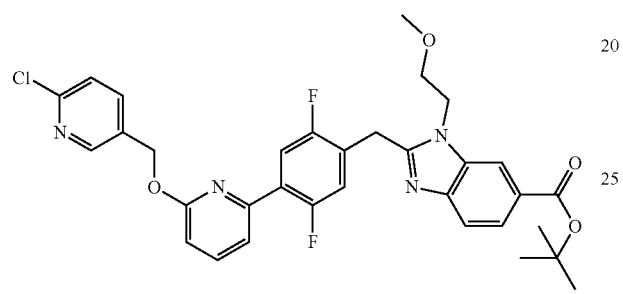

Tert-butyl 2-(4-(6-(((6-chloropyridin-3-yl)methoxy)pyridin-2-yl)-2,5-difluorobenzyl)-1-(2-methoxyethyl)-1H-benzo[d]imidazole-6-(I-92): Tert-butyl 2-(4-(6-(((6-chloropyridin-3-yl)methoxy)pyridin-2-yl)-2,5-difluorobenzyl)-1-(2-methoxyethyl)-1H-benzo[d]imidazole-6- was prepared in manner as described for Intermediate I-18 substituting 5-(bromomethyl)-2-chloropyridine for 4-bromo-1-(bromomethyl)-2-fluoro-benzene. ES/MS: 621.2 (M+H$^+$).

Preparation of Intermediate I-93

I-93

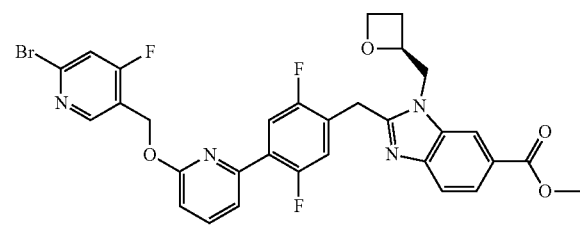

Methyl (S)-2-(4-(6-(((6-bromo-4-fluoropyridin-3-yl)methoxy)pyridin-2-yl)-2,5-difluorobenzyl)-1-(oxetan-2-ylmethyl)-1H-benzo[d]imidazole-6-carboxylate (I-93): Methyl (S)-2-(4-(6-(((6-bromo-4-fluoropyridin-3-yl)methoxy)pyridin-2-yl)-2,5-difluorobenzyl)-1-(oxetan-2-ylmethyl)-1H-benzo[d]imidazole-6-carboxylate was prepared in manner as described for Intermediate I-19 substituting 2-bromo-5-(bromomethyl)-4-fluoropyridine for 4-bromo-1-(bromomethyl)-2-fluoro-benzene ES/MS: 654.0, 656.0 (M+H$^+$).

Preparation of Intermediate I-94

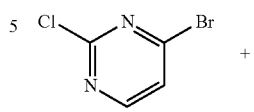

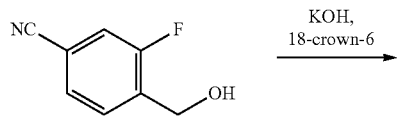

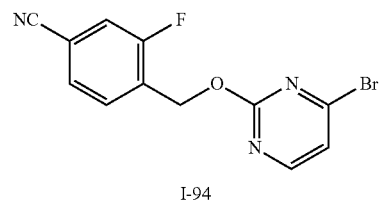

I-94

4-[(4-bromopyrimidin-2-yl)oxymethyl]-3-fluoro-benzonitrile (I-94): 4-bromo-2-chloro-pyrimidine (1.7 g, 8.8 mmol), 3-fluoro-4-(hydroxymethyl)benzonitrile (1.46 g, 9.7 mmol), potassium hydroxide (542 mg, 9.7 mmol), 18-crown-6 (116 mg, 0.44 mmol), and toluene (20 mL) were combined and heated to 110° C. for 2 hours. Upon completion the mixture was diluted with EtOAc (100 mL) washed with water (25 mL), washed with brine (25 mL), dried over MgSO$_4$, filtered, concentrated and purified by silica gel chromatography (eluent: EtOAc/hexanes) to give I-94. ES/MS: 309.2 (M+H$^+$).

Preparation of Intermediate I-95

I-95

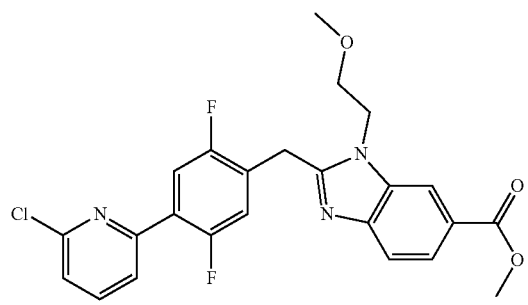

Methyl 2-(4-(6-chloropyridin-2-yl)-2,5-difluorobenzyl)-1-(2-methoxyethyl)-1H-benzo[d]imidazole-6-carboxylate (I-95): Methyl (S)-2-(4-(6-chloropyridin-2-yl)-2,5-difluorobenzyl)-1-(oxetan-2-ylmethyl)-1H-benzo[d]imidazole-6-carboxylate was prepared in a manner as described for Intermediate I-12 substituting I-1 for I-6. ES/MS: 472.8 (M+H$^+$).

Preparation of Intermediate I-96

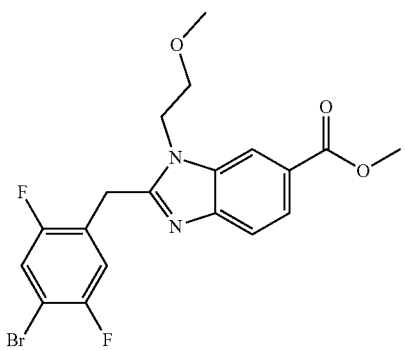

Methyl 2-(4-bromo-2,5-difluorobenzyl)-1-(2-methoxyethyl)-1H-benzo[d]imidazole-6-carboxylate (I-96). Methyl 2-(2,5-difluoro-4-(4,4,5,5-tetramethyl-1,3,2-dioxaborolan-2-yl)benzyl)-1-(2-methoxyethyl)-1H-benzo[d]imidazole-6-carboxylate was prepared in a manner as described for Intermediate I-2 substituting 2-(4-bromo-2,5-difluorophenyl)acetic acid for 2-(4-bromo-2-fluorophenyl)acetic acid. ES/MS: 439.8 (M+H$^+$).

Preparation of Intermediate I-97

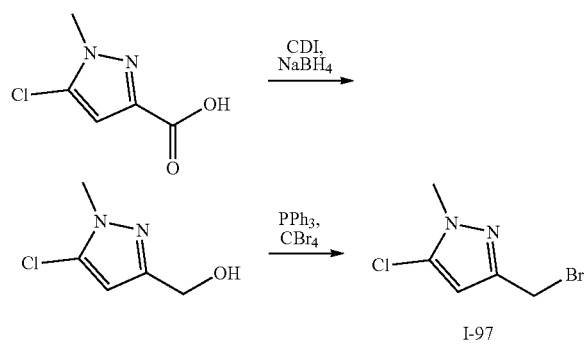

(5-chloro-1-methyl-pyrazol-3-yl)methanol: 5-chloro-1-methyl-pyrazole-3-carboxylic acid (700 mg, 4.36 mmol) was taken up in THF (20.0 mL) and 1,1'-Carbonyldiimidazole (1.41 g, 8.72 mmol) was added. The mixture was stirred at rt for 2 hours. Upon completion, the mixture was cooled to 0° C. and a solution of sodium borohydride (0.825 g, 21.8 mmol) in water (3.30 mL) was added slowly, after which the mixture was allowed to warm to rt over 40 minutes. Upon completion methanol (5 mL) was added, the mixture was concentrated directly and purified by flash chromatography (Eluent: EtOAc/hexane) to give the desired product.

3-(bromomethyl)-5-chloro-1-methyl-pyrazole (I-97): (5-chloro-1-methyl-pyrazol-3-yl)methanol (550 mg, 3.75 mmol) was taken up in DCM (25.0 mL) and (4-diphenylphosphanylphenyl) polymer bound (78.7%, 1.50 g, 0.00450 mol) was added. The mixture was cooled to 0° C. and carbon tetrabromide (1.49 g, 0.00450 mol) was added as a single portion. The mixture was stirred for 16 hr. at rt. Upon completion, the mixture was filtered, concentrated, and purified by flash chromatography (Eluent: EtOAc/hexane) to give I-97. ES/MS: 209.0, 211.0 (M+H$^+$).

The following intermediates were prepared in a manner as described for intermediate I-97

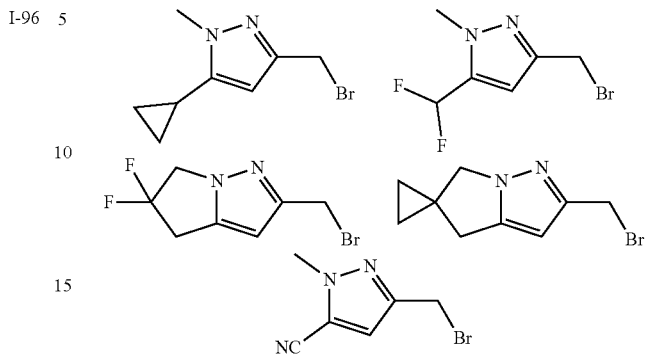

Preparation of Intermediate I-98

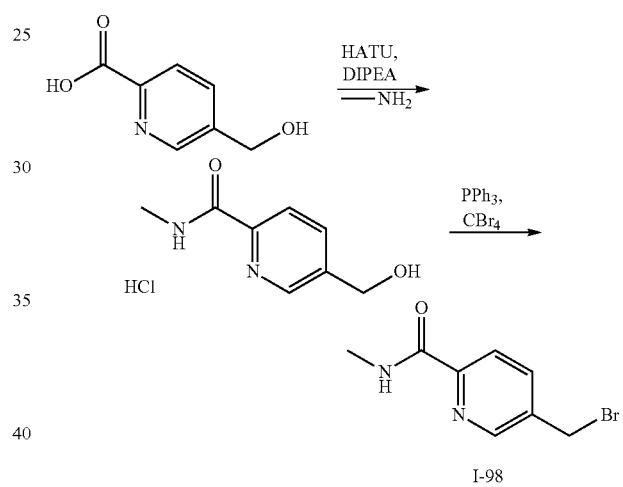

5-(hydroxymethyl)-N-methyl-pyridine-2-carboxamide: 5-(hydroxymethyl)pyridine-2-carboxylic acid (400 mg, 2.61 mmol), methanamine hydrochloride (194 mg, 2.87 mmol), and o-(7-Azabenzotriazol-1-yl)-N,N,N',N'-tetramethyluronium hexafluorophosphate (1192 mg, 3.14 mmol) were taken up in DMF (5.00 mL). N,N-Diisopropylethylamine (2.27 mL, 13.1 mmol) was added after which the mixture was stirred for 30 min. Upon completion the mixture was diluted with EtOAc (50 mL) washed with water (10 mL), washed with brine (10 mL), dried over MgSO$_4$, filtered, concentrated and purified by silica gel chromatography (eluent: MeOH/EtOAc/hexanes) to give desired product. ES/MS: 167.2 (M+H$^+$).

5-(bromomethyl)-N-methyl-pyridine-2-carboxamide (I-98): 5-(hydroxymethyl)-N-methyl-pyridine-2-carboxamide (106 mg, 0.638 mmol) and triphenylphosphine (0.167 g, 0.638 mmol) were taken up in dichloromethane (2.60 mL) and carbon tetrabromide (0.212 g, 0.638 mmol), was added. The mixture was stirred for 15 min. Upon completion the mixture was filtered, concentrated, and purified by flash chromatography (Eluent: EtOAc/hexane) to give I-98. ES/MS: 229.0 (M+H$^+$).

The following intermediate was prepared in a manner as described for intermediate I-98

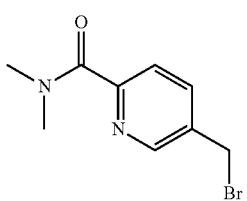

Preparation of Intermediate I-99

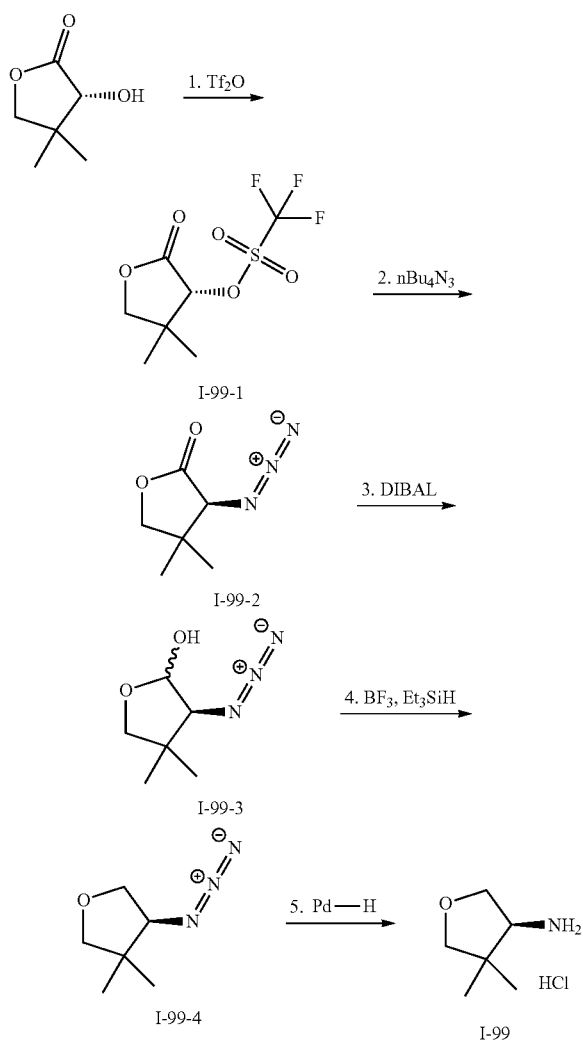

(R)-4,4-dimethyl-2-oxotetrahydrofuran-3-yl trifluoromethanesulfonate (I-99-1): A round-bottom flask was charged with (D)-(−)-pantolactone (4.20 g, 32.3 mmol, 1.0 equivalent). Anhydrous dichloromethane (20 mL) and pyridine (3.39 mL, 42.0 mmol, 1.30 equivalent) were added, and the resulting solution was cooled to −78° C. A solution of trifluoromethanesulfonic anhydride (5.96 mL, 35.4 mmol, 1.10 equivalent) in dichloromethane (100 mL) was added slowly to the mixture via an addition funnel while stirring at −78° C. Following the addition, the mixture was maintained with stirring at −78° C. for 30 min before the cooling bath was removed. The mixture was maintained with stirring at rt for an additional 3 hrs. The solvent was removed in vacuo, and the residue was dissolved in ethyl ether (200 mL) and washed with 10% aqueous sodium bicarbonate (100 mL), and brine (100 mL). The organic layer was dried over anhydrous sodium sulfate, filtered, and concentrated in vacuo to afford (R)-4,4-dimethyl-2-oxotetrahydrofuran-3-yl trifluoromethanesulfonate. 1H NMR (500 MHz, CDCl3) δ=5.10 (s, 1H), 4.13 (d, J=9.5 Hz, 1H), 4.07 (d, J=9.5 Hz, 1H), 1.28 (s, 3H), 1.18 (s, 3H).

(S)-3-azido-4,4-dimethyldihydrofuran-2(3H)-one (I-99-2): A round-bottom flask was charged with tetrabutylammonium azide (10.5 g, 36.8 mmol, 1.15 equivalent). Anhydrous toluene (50 mL) was added, and the resulting solution was cooled to 0° C. A solution of (R)-4,4-dimethyl-2-oxotetrahydrofuran-3-yl trifluoromethanesulfonate prepared as above (8.40 g, 32 mmol, 1.0 equivalent) in toluene (50 mL) was added slowly via an addition funnel at 0° C. The mixture was maintained at 0° C. for 30 min before the cooling bath was removed and the mixture was stirred at rt for 4 hrs. The mixture was diluted with ethyl ether (200 mL) and washed with 10% aqueous sodium bicarbonate (200 mL), and brine (100 mL). The organic layer was dried over anhydrous sodium sulfate, filtered, and concentrated in vacuo to afford 3-azido-4,4-dimethyldihydrofuran-2(3H)-one. The crude material was carried forward immediately to the next step without purification.

3-azido-4,4-dimethyltetrahydrofuran-2-ol (I-99-3): 3-azido-4,4-dimethyldihydrofuran-2(3H)-one (4.16 g, 26.8 mmol) was taken in dichloromethane (40 mL), cooled to −78° C. then diisobutylaluminum hydride (1.0 M in toluene) (32.2 mL, 32.2 mmol, 1.2 equivalent) was added slowly followed at same temperature. The mixture was stirred at −78° C. for 2 hrs until no starting material remained. The reaction was quenched by adding saturated solution of potassium sodium tartarate (100 mL). The mixture was extracted with dichloromethane (3×50 mL). The organic extract was dried with anhydrous $Na_2SO_4$ and concentrated under reduced pressure. The crude compound was purified by column chromatography (silica gel) to yield 3-azido-4,4-dimethyltetrahydrofuran-2-ol 1H NMR (400 MHz, $CDCl_3$) δ=5.58-5.29 (m, 1H), 3.93-3.76 (m, 2H), 3.66-3.50 (m, 2H), 1.19-1.08 (m, 6H)

4-azido-3,3-dimethyltetrahydrofuran (I-99-4): 3-azido-4,4-dimethyltetrahydrofuran-2-ol was taken in dichloromethane (80 mL), cooled to −78° C. then $BF_3·Et_2O$ (3.6 mL, 28.7 mmol, 1.5 equivalent) was added slowly followed by addition of triethylsilane (6.1 mL, 2.0 mmol) at same temperature. The mixture was stirred at 0° C. for 4 hrs until no starting material remained. Then water (100 mL) was added to the mixture. The resulting phases were separated, then the aqueous phase was extracted with dichloromethane (2×50 mL). The organic extract was dried with anhydrous $Na_2SO_4$ and concentrated under reduced pressure. The crude compound was purified by column chromatography (silica gel) to yield (S)-4-azido-3,3-dimethyltetrahydrofuran. 1H NMR (400 MHz, CDCl3)=4.17 (dd, J=6.1, 9.8 Hz, 1H), 3.77 (dd, J=3.9, 9.8 Hz, 1H), 3.65 (dd, J=3.9, 6.1 Hz, 1H), 3.58-3.50 (m, 2H), 1.13 (d, J=6.1 Hz, 6H).

4,4-dimethyltetrahydrofuran-3-amine (I-99): 4-azido-3,3-dimethyltetrahydrofuran (1.89 g, 13.4 mmol) dissolved in ethyl acetate (50 mL) was added 10% palladium on carbon (2.14 g, 2.0 mmol, 0.15 equivalent). The mixture was stirred at rt for 16 hrs. under 1 atm of hydrogen before filtering through a plug of celite. The solution was acidified 4 M HCl in methanol (5.0 mL) before concentrating in vacuo to afford 4,4-dimethyltetrahydrofuran-3-amine as the hydrochloride salt. 1H NMR (400 MHz, CDCl3)=4.09-4.05 (m, 1H), 3.72-3.68 (m, 1H), 3.59-3.56 (m, 1H), 3.44-3.42 (m, 1H), 3.35 (m, 1H), 1.07 (s, 6H).

Preparation of Intermediate I-100

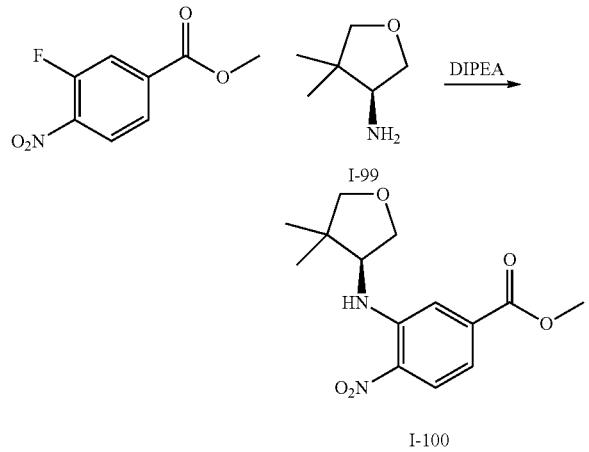

Methyl 3-[[(S)-4,4-dimethyltetrahydrofuran-3-yl]amino]-4-nitrobenzoate (I-100): To a suspension of methyl 3-fluoro-4-nitrobenzoate (15.0 g, 75.3 mmol) and 4,4-dimethyltetrahydrofuran-3-amine hydrochloride (Intermediate I-99, 12.6 g, 82.9 mmol) in THF (100 mL) and DMF (50 mL), was added N,N-diisopropylethylamine (65.6 mL, 377 mmol). The resulting solution was heated at 80° C. overnight. The crude mixture was diluted with EtOAc (300 mL), washed with 5% LiCl (250 mL) and brine (250 mL). The organic extract was dried over sodium sulfate and purified by silica gel column chromatography (eluent: EtOAc/hexanes) to afford methyl 3-[[(3S)-4,4-dimethyltetrahydrofuran-3-yl]amino]-4-nitrobenzoate, the structure of which was confirmed by X-ray crystallography. 1H NMR (400 MHz, Chloroform-d) δ 8.24 (d, J=8.8 Hz, 2H), 7.57 (d, J=1.6 Hz, 1H), 7.27 (dd, J=8.9, 1.7 Hz, 1H), 4.41 (dd, J=9.2, 6.8 Hz, 1H), 4.02 (s, 1H), 3.97 (s, 3H), 3.76-3.64 (m, 3H), 1.26 (s, 3H), 1.18 (s, 3H). ES/MS: 295.0 (M+H+).

I-101

Methyl 2-[[4-[6-[(4-cyano-2-fluoro-phenyl)methoxy]-2-pyridyl]-2,5-difluoro-phenyl]methyl]-3-[(3S)-4,4-dimethyl-tetrahydrofuran-3-yl]benzimidazole-5-carboxylate (Intermediate I-101): In a 200 mL flask, a suspension of methyl 2-[(4-bromo-2,5-difluoro-phenyl)methyl]-3-[(3S)-4,4-dimethyltetrahydrofuran-3-yl]benzimidazole-5-carboxylate (Intermediate I-82, 2329 mg, 4.86 mmol), Bis(pinacolato) diboron (1506 mg, 5.93 mmol), [1,1'-Bis(diphenylphosphino)ferrocene] dichloropalladium(II) (541 mg, 0.729 mmol), and potassium propionate (1635 mg, 14.6 mmol) in dioxane (24 mL) was degassed with Argon for 5 min, then heated for 50 min at 110° C. The mixture was cooled to rt. To the mixture was added sodium carbonate (2000 mmol/L, 5.48 mL, 11.0 mmol). The mixture was stirred at rt for 5 min. To the mixture was added [1,1'-Bis(diphenylphosphino)ferrocene] dichloropalladium(II) (358 mg, 0.483 mmol) and 4-[(6-bromo-2-pyridyl)oxymethyl]-3-fluorobenzonitrile (Intermediate I-3, 2238 mg, 7.29 mmol). The mixture was degassed for 5 min with Argon, then heated thermally at 90° C. for 1 hr. 15 min. The mixture was diluted with EtOAc and filtered over Celite. The filtrate was washed with brine, dried over sodium sulfate, and purified by silica gel column chromatography (eluent: EtOAc/hexanes) to afford methyl 2-[[4-[6-[(4-cyano-2-fluoro-phenyl)methoxy]-2-pyridyl]-2,5-difluoro-phenyl]methyl]-3-[(3S)-4,4-dimethyltetrahydrofuran-3-yl]benzimidazole-5-carboxylate (Intermediate I-101), the structure of which was confirmed by X-ray crystallography. ES/MS: 626.6 (M+H+). 1H NMR (400 MHz, Chloroform-d) δ 8.56 (s, 1H), 8.02 (dd, J=8.5, 1.5 Hz, 1H), 7.79 (dd, J=9.7, 5.6 Hz, 2H), 7.70 (dt, J=14.3, 7.6 Hz, 2H), 7.53 (dt, J=7.3, 1.1 Hz, 1H), 7.49 (dd, J=7.9, 1.5 Hz, 1H), 7.43 (dd, J=9.3, 1.5 Hz, 1H), 7.09 (dd, J=11.3, 6.0 Hz, 1H), 6.86 (d, J=8.1 Hz, 1H), 5.61 (s, 2H), 4.73-4.56 (m, 2H), 4.46-4.32 (m, 34H), 3.96 (d, J=6.8 Hz, 4H), 3.81 (d, J=8.7 Hz, 1H), 1.36 (s, 3H), 0.69 (s, 3H).

Preparation of Intermediate I-101 (Method 2)

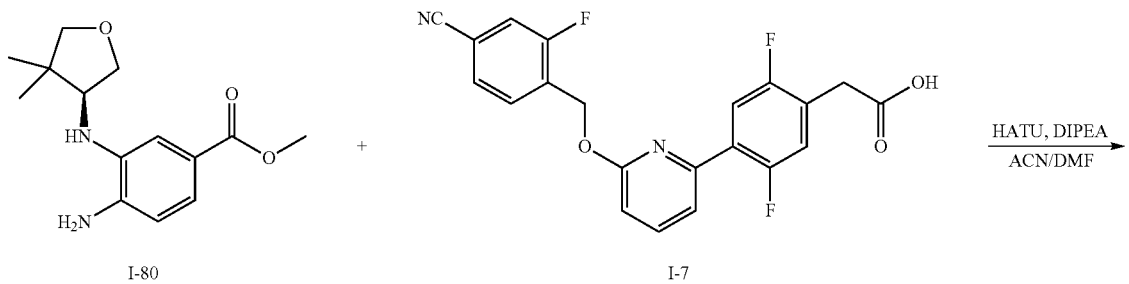

-continued

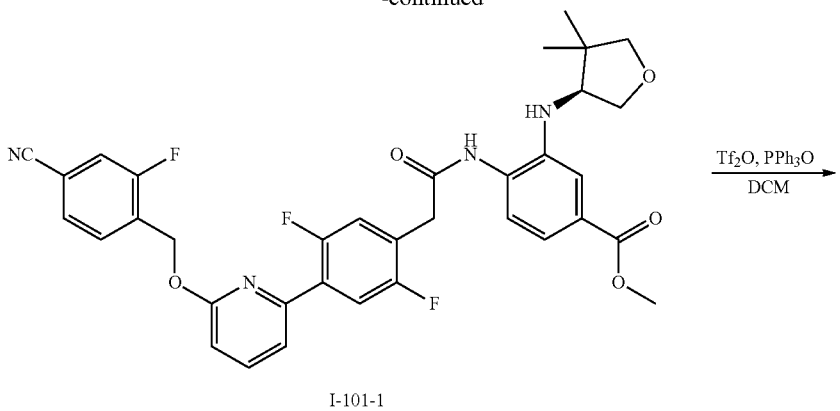

I-101-1

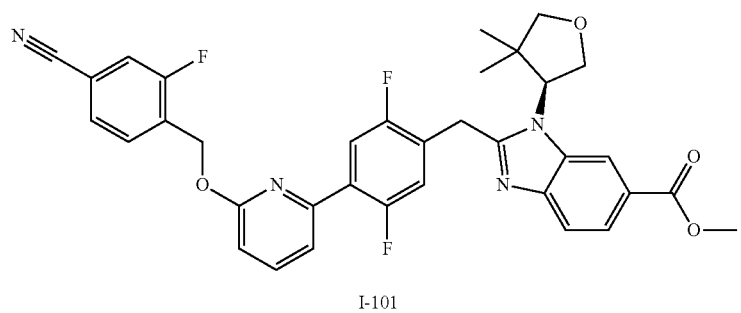

I-101

Methyl (S)-4-(2-(4-(6-((4-cyano-2-fluorobenzyl)oxy)pyridin-2-yl)-2,5-difluorophenyl)acetamido)-3-((4,4-dimethyltetrahydrofuran-3-yl)amino)benzoate (I-101-1): HATU (12.2 g, 32.3 mmol) followed by N,N-Diisopropylethylamine (19.6 mL, 112 mmol) was added to a solution of 2-(4-(6-((4-cyano-2-fluorobenzyl)oxy)pyridin-2-yl)-2,5-difluorophenyl)acetic acid (Intermediate I-7, 10.1 g, 25.3 mmol) and methyl (S)-4-amino-3-((4,4-dimethyltetrahydrofuran-3-yl)amino)benzoate (Intermediate I-80, 6.07 g, 23.0 mmol) in DMF (36 mL) and MeCN (36 mL), and the resulting solution was stirred at rt overnight. Next, the mixture was diluted with EtOAc and washed sequentially with sat. NH₄Cl, 10% LiCl, sat. NaHCO₃ (×2), 1N NaOH, and brine. The organic phase was dried over MgSO₄, filtered, and concentrated to give methyl (S)-4-(2-(4-(6-((4-cyano-2-fluorobenzyl)oxy)pyridin-2-yl)-2,5-difluorophenyl)acetamido)-3-((4,4-dimethyltetrahydrofuran-3-yl)amino)benzoate (Intermediate I-101-1), which was taken forward assuming 100% yield. ES/MS: 645.2 (M+1).

Methyl (S)-2-(4-(6-((4-cyano-2-fluorobenzyl)oxy)pyridin-2-yl)-2,5-difluorobenzyl)-1-(4,4-dimethyltetrahydrofuran-3-yl)-1H-benzo[d]imidazole-6-carboxylate (Intermediate I-101): Trifluoromethanesulfonic anhydride (5.79 mL, 34.4 mmol) was added dropwise to a solution of methyl (S)-4-(2-(4-(6-((4-cyano-2-fluorobenzyl)oxy)pyridin-2-yl)-2,5-difluorophenyl)acetamido)-3-((4,4-dimethyltetrahydrofuran-3-yl)amino)benzoate (I-101-1, 14.8 g, 23.0 mmol) and triphenylphosphine oxide (9.59 g, 34.4 mmol) in DCM under argon at 0° C. for 10 min. The mixture was stirred for 15 min, brought to rt, and stirred for 25 min. The reaction was quenched with sat. NaHCO₃, and phases were separated. The aqueous layer was extracted with DCM. Combined organic layers were dried over MgSO₄, filtered, concentrated, and purified by silica gel flash column chromatography (EtOAc/Hex gradient) to give methyl (S)-2-(4-(6-((4-cyano-2-fluorobenzyl)oxy)pyridin-2-yl)-2,5-difluorobenzyl)-1-(4,4-dimethyltetrahydrofuran-3-yl)-1H-benzo[d]imidazole-6-carboxylate (Intermediate I-101).

Preparation of Intermediate I-102

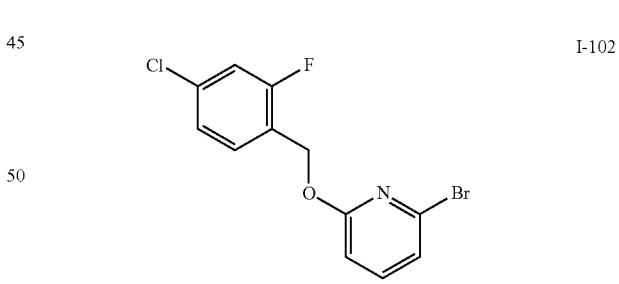

I-102

2-bromo-6-[(4-chloro-2-fluoro-phenyl)methoxy]pyridine (Intermediate I-102): A round-bottom flask was charged with (4-chloro-2-fluoro-phenyl)methanol (800 mg, 5.0 mmol, 1.1 equivalent), 2-bromo-6-fluoropyridine (800 mg, 4.6 mol, 1.0 equivalent), and cesium carbonate (2.3 g, 6.8 mmol, 1.5 equivalent). Anhydrous acetonitrile (15 mL) was added, and the resulting mixture was heated to reflux and stirred for 12 hrs. After cooling to rt, the mixture was filtered through a plug of Celite and then concentrated in vacuo. The residue was purified by column chromatography (silica gel, EtOAc/hexane gradient) to yield the title compound. ES/MS m/z: 317.8 (M+H)+.

Preparation of Intermediate I-103

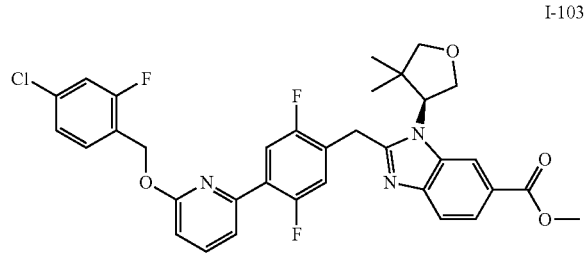 [SMILES: COC(=O)c1ccc2nc(Cc3cc(F)c(-c4cccc(OCc5ccc(Cl)cc5F)n4)cc3F)n([C@@H]3COCC3(C)C)c2c1]

Methyl 2-[[4-[6-[(4-chloro-2-fluoro-phenyl)methoxy]-2-pyridyl]-2,5-difluoro-phenyl]methyl]-3-[(3S)-4,4-dimethyl-tetrahydrofuran-3-yl]benzimidazole-5-carboxylate (Intermediate I-103). To a 25-mL microwave vial was charged with methyl 2-[(4-bromo-2,5-difluoro-phenyl)methyl]-3-[(3S)-4,4-dimethyltetrahydrofuran-3-yl]benzimidazole-5-carboxylate (Intermediate I-82, 800 mg, 1.67 mmol, 1.0 equivalent), $PdCl_2(dppf)2$ (186 mg, 0.25 mmol, 0.15 equivalent), potassium propionate (560 mg, 5.01 mmol, 3.0 equivalent), and $B_2Pin_2$ (510 mg, 2.00 mol, 1.2 equivalent). Anhydrous 1,4-dioxane (10 mL) was added and the resulting mixture was purged with argon for 2 min. The mixture was sealed and heated to 120° C. by microwave and stirred for 1 h. After cooling down to rt, 2-bromo-6-[(4-chloro-2-fluoro-phenyl)methoxy]pyridine (Intermediate I-102, 580 mg, 1.84 mmol, 1.1 equivalent), $PdCl_2(dppf)2$ (62 mg, 0.0834 mmol, 0.05 equivalent), 2 M aqueous $Na_2CO_3$ (2.0 mL, 4.17 mmol, 2.5 equivalent) were added, respectively. The resulting mixture was heated to 100° C. under argon and stirred for 3 hrs. before cooling to rt and filtered through a plug of Celite and $MgSO_4$. The filtrate was concentrated and purified by column chromatography (silica gel, EtOAc/hexane gradient) to yield the title compound. ES/MS m/z: 635.6 $(M+H)^+$.

Preparation of Intermediate I-104

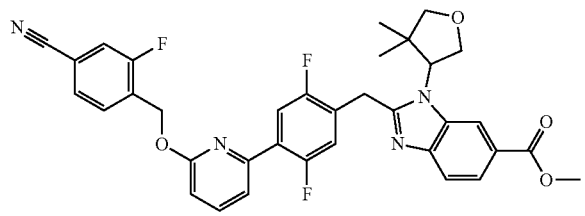

Methyl 2-(4-(6-((4-cyano-2-fluorobenzyl)oxy)pyridin-2-yl)-2,5-difluorobenzyl)-1-(4,4-dimethyltetrahydrofuran-3-yl)-1H-benzo[d]imidazole-6-carboxylate (Intermediate I-104). 2-[4-[6-[(4-Cyano-2-fluoro-phenyl)methoxy]-2-pyridyl]-2,5-difluoro-phenyl]acetic acid (Intermediate I-7, 500 mg, 1.26 mmol), methyl 4-amino-3-[(4,4-dimethyltetrahydrofuran-3-yl)amino]benzoate (Intermediate I-25, 365 mg, 1.38 mmol), and o-(7-Azabenzotriazol-1-yl)-N,N,N',N'-tetramethyluronium hexafluorophosphate (573 mg, 1.51 mmol) were combined in DMF (5.00 mL) and N,N-Diisopropylethylamine (1.09 mL, 6.28 mmol) was added. The mixture was stirred at r.t. for 3 hrs. The mixture was partitioned between EtOAc and sat. $NH_4C_1$. The organic phase was dried, filtered and concentrated in vacuo. The crude was taken up in acetic acid (2 mL) and heated to 100° C. for 72 hrs. The resulting mixture was then concentrated in vacuo and partitioned between EtOAc and sat. $NaHCO_3$. The organic phase was dried, filtered and concentrated in vacuo. Silica gel flash chromatography (EtOAc/hexane) yielded the title compound. ES/MS m/z 627.2 $(M+H)^+$.

Preparation of Intermediate I-105

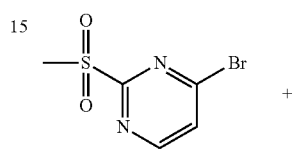

+

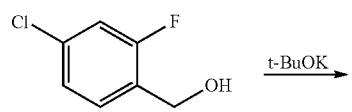

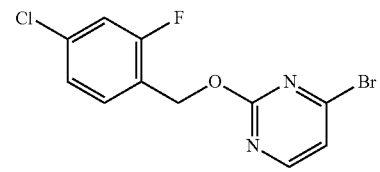

Intermediate I-105

4-bromo-2-[(4-chloro-2-fluoro-phenyl)methoxy]pyrimidine (Intermediate I-105): To a 50 mL RBF was added (4-chloro-2-fluoro-phenyl)methanol (186 mg, 1.16 mmol) to THF (6 mL) and the flask was placed under nitrogen, and cooled to 0° C. Potassium tert-butoxide (1.05 mL, 0.362 mmol, 1 M THF) was added dropwise, and the solution was stirred 15 min at 0° C. To a separate 50 mL RBF was added 4-bromo-2-methylsulfonyl-pyrimidine (250 mg, 1.05 mmol) in THF (6 mL) and the mixture was cooled to −78° C. The first solution (deprotonated alcohol) was taken up in a syringe, and added dropwise to the second solution at −78° C. The solution was stirred for 1 h at −78° C., then 1 mL water was added dropwise, and the solution allowed to warm to rt. The solution was diluted with EtOAc and water, and 2 mL saturated aqueous $NH_4Cl$ was added to acidify the solution. Then the layers were separated, and the aqueous layer was extracted once with EtOAc. The combined organic layers were dried over $MgSO_4$, filtered, concentrated, and purified by silica gel flash column chromatography (EtOAc/Hex gradient) to yield 4-bromo-2-[(4-chloro-2-fluoro-phenyl)methoxy]pyrimidine (Intermediate I-105). ES/MS m/z: 318.9 (M+H)+.

Preparation of Intermediate I-106

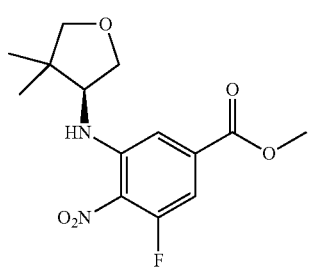

Methyl (S)-3-((4,4-dimethyltetrahydrofuran-3-yl)amino)-5-fluoro-4-nitrobenzoate (Intermediate I-106): To a solution of methyl 3,5-difluoro-4-nitro-benzoate (2.21 g, 10.2 mmol) and (S)-4,4-dimethyltetrahydrofuran-3-amine hydrochloride (Intermediate I-99, 1.70 g, 11.2 mmol) in tetrahydrofuran (12.5 mL) and N,N-dimethylformamide (6.0 mL) was added N,N-diisopropylethylamine (8.86 mL, 50.9 mmol). The mixture was stirred at 70° C. overnight before being cooled to rt. The mixture was diluted with water, extracted with EtOAc, washed with brine, dried over sodium sulfate, filtered, and concentrated to yield the title compound, which was carried forward to subsequent steps without further purification.

Preparation of Intermediate I-107

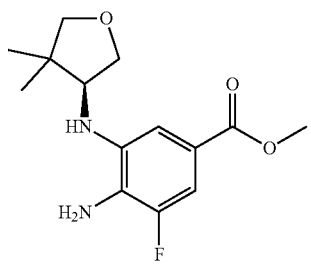

Methyl (S)-4-amino-3-((4,4-dimethyltetrahydrofuran-3-yl)amino)-5-fluorobenzoate (Intermediate I-107): Methyl (S)-3-((4,4-dimethyltetrahydrofuran-3-yl)amino)-5-fluoro-4-nitrobenzoate (Intermediate I-106, 2.88 g, 10.2 mmol) was dissolved in EtOAc, and put under argon. To this mixture was added 10% palladium on carbon (1.08 g, 1.02 mmol), and then the mixture was placed under hydrogen gas. The mixture was stirred overnight, then the mixture filtered through celite, and concentrated in vacuo. Purification by silica gel flash column chromatography (EtOAc/Hexane gradient) yielded methyl (S)-4-amino-3-((4,4-dimethyltetrahydrofuran-3-yl)amino)-5-fluorobenzoate (Intermediate I-107). ES/MS m/z: 283.2 (M+H)$^+$.

Preparation of Intermediate I-108

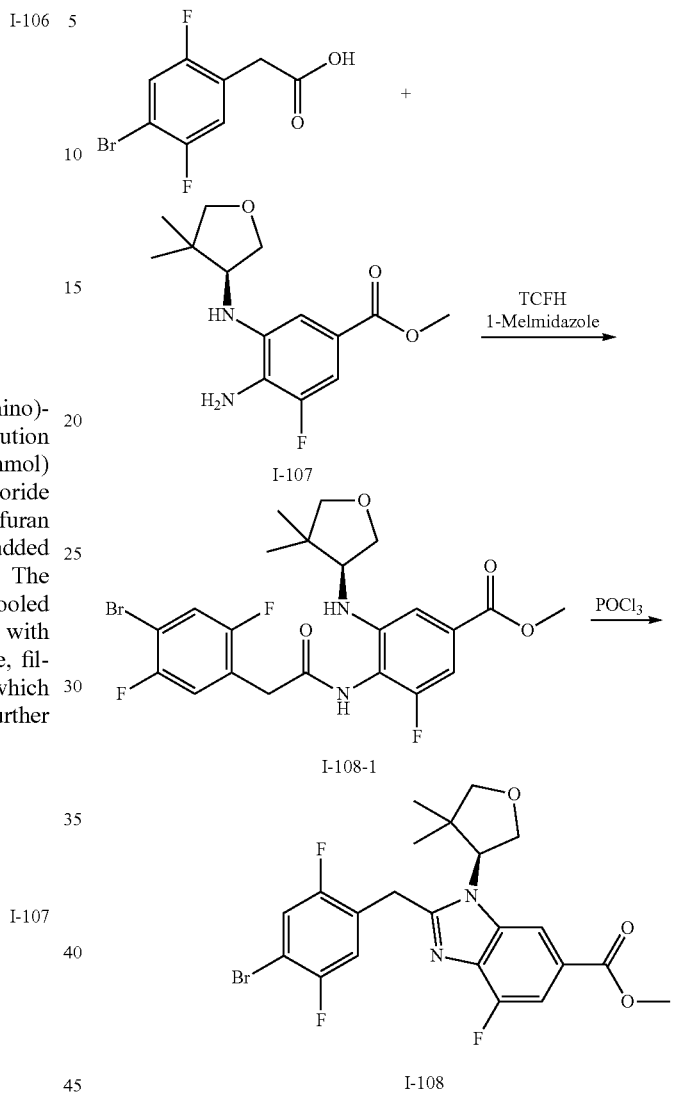

Methyl (S)-4-(2-(4-bromo-2,5-difluorophenyl)acetamido)-3-((4,4-dimethyltetrahydrofuran-3-yl)amino)-5-fluorobenzoate (I-108-1): To a solution of methyl (S)-4-amino-3-((4,4-dimethyltetrahydrofuran-3-yl)amino)-5-fluorobenzoate (Intermediate I-107, 2000 mg, 7.08 mmol) and 2-(4-bromo-2,5-difluoro-phenyl)acetic acid (1867 mg, 7.44 mmol) in MeCN (10.0 mL) and cooled to 0° C. was added 1-methylimidazole (2.91 g, 2.82 mL, 35.4 mmol) followed by N,N,N',N'-Tetramethylchloroformamidinium Hexafluorophosphate (2.39 g, 8.50 mmol). The mixture was warmed to rt and stirred for 30 min. The mixture was concentrated in vacuo to yield methyl (S)-4-(2-(4-bromo-2,5-difluorophenyl)acetamido)-3-((4,4-dimethyltetrahydrofuran-3-yl)amino)-5-fluorobenzoate (I-108-1), which was carried forward to the next step without further purification.

Methyl 2-[(4-bromo-2,5-difluoro-phenyl)methyl]-3-[(3S)-4,4-dimethyltetrahydrofuran-3-yl]-7-fluorobenzimidazole-5-carboxylate (Intermediate I-108): To methyl (S)-4-(2-(4-bromo-2,5-difluorophenyl)acetamido)-3-((4,4-dimethyltetrahydrofuran-3-yl)amino)-5-fluorobenzoate (I-108-1, 2.2 g, 4.3 mmol) in 21 mL of 1,2-dichloroethane was added phosphoryl trichloride (2.6 g, 17 mmol, 1.6 mL). The solution was heated to 80° C. for 24 hrs., then cooled to rt. An aliquot of 20 mL of water was added and stirring for 1 h, then aqueous sodium hydroxide (26 mL, 51 mmol, 2 M) was added. The mixture was diluted with DCM, layers separated, and the organic phase washed with brine, dried with MgSO₄, filtered, and concentrated. Purification by silica chromatography (EtOAc/hexane gradient) yielded methyl 2-[(4-bromo-2,5-difluoro-phenyl)methyl]-3-[(3S)-4,4-dimethyltetrahydrofuran-3-yl]-7-fluorobenzimidazole-5-carboxylate (Intermediate I-108). ES/MS m/z: 497.0 (M+H)⁺.

Preparation of Intermediate I-109

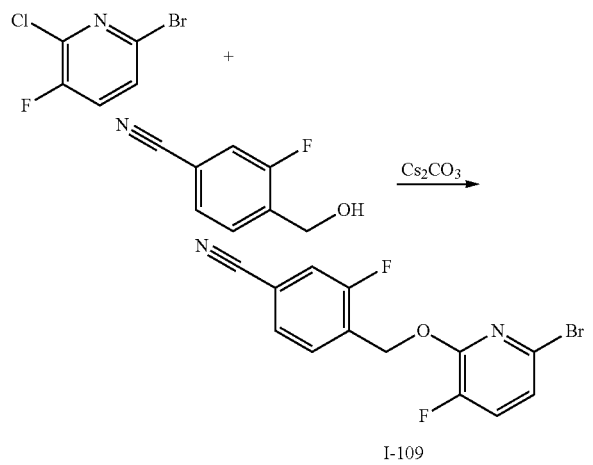

I-109

4-[(6-bromo-3-fluoro-2-pyridyl)oxymethyl]-3-fluoro-benzonitrile (Intermediate I-109): To a solution of 6-bromo-2-chloro-3-fluoro-pyridine (4.90 g, 23.3 mmol) and 3-fluoro-4-(hydroxymethyl)benzonitrile (3.87 g, 25.6 mmol) in acetonitrile (40 mL) was added cesium carbonate (15.2 g, 25.6 mmol). The mixture was stirred at 60° C. overnight before being cooled to rt. The mixture was diluted with water, extracted three times with EtOAc, washed with brine, dried over sodium sulfate, filtered, and concentrated. Purification by silica gel flash column chromatography (EtOAc in Hexane gradient) yielded 4-[(6-bromo-3-fluoro-2-pyridyl)oxymethyl]-3-fluoro-benzonitrile (Intermediate I-109). ES/MS m/z: 326.1 (M+H)⁺.

Preparation of Intermediate I-110

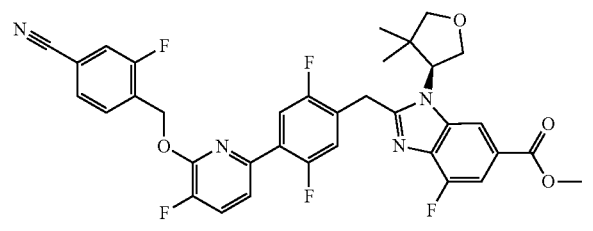

I-110

Methyl 2-[[4-[6-[(4-cyano-2-fluoro-phenyl)methoxy]-5-fluoro-2-pyridyl]-2,5-difluoro-phenyl]methyl]-3-[(3S)-4,4-dimethyltetrahydrofuran-3-yl]-7-fluoro-benzimidazole-5-carboxylate (Intermediate I-110): A 2 mL microwave vial was charged with methyl 2-[(4-bromo-2,5-difluorophenyl)methyl]-3-[(3S)-4,4-dimethyltetrahydrofuran-3-yl]-7-fluorobenzimidazole-5-carboxylate (Intermediate I-108, 400 mg, 0.69 mmol), 4,4,5,5-tetramethyl-2-(4,4,5,5-tetramethyl-1,3,2-dioxaborolan-2-yl)-1,3,2-dioxaborolane (184 mg, 0.73 mmol), [1,1'-Bis(diphenylphosphino)ferrocene] dichloropalladium(II) (77.7 mg, 0.1 mmol), potassium propionate (233 mg, 2.08 mmol), and 2.5 mL of 1,4-dioxane. This mixture had argon bubbled through for 5 min before being heated in a microwave for 1 h at 120° C. Then sodium carbonate (0.72 mL, 1.44 mmol, 2M) was added followed by 4-[(6-bromo-3-fluoro-2-pyridyl)oxymethyl]-3-fluorobenzonitrile (Intermediate I-109, 247 mg, 0.76 mmol). The mixture was heated to 110° C. for 1 h, then filtered, concentrated, and purified by silica gel chromatography (EtOAc/hexane gradient) to yield methyl 2-[[4-[6-[(4-cyano-2-fluoro-phenyl)methoxy]-5-fluoro-2-pyridyl]-2,5-difluorophenyl]methyl]-3-[(3S)-4,4-dimethyltetrahydrofuran-3-yl]-7-fluorobenzimidazole-5-carboxylate (Intermediate I-110). ES/MS m/z: 663.6 (M+H)⁺.

Preparation of Intermediate I-111

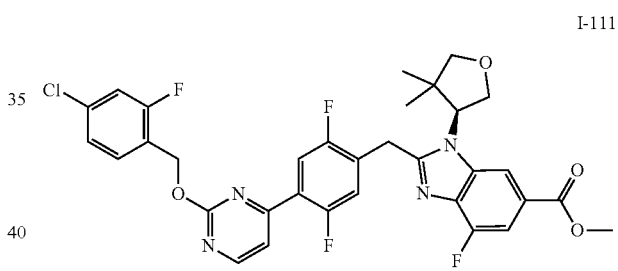

I-111

Methyl (S)-2-(4-(2-((4-chloro-2-fluorobenzyl)oxy)pyrimidin-4-yl)-2,5-difluorobenzyl)-1-(4,4-dimethyltetrahydrofuran-3-yl)-4-fluoro-1H-benzo[d]imidazole-6-carboxylate (Intermediate I-111): A 2 mL microwave vial was charged with methyl 2-[(4-bromo-2,5-difluorophenyl)methyl]-3-[(3S)-4,4-dimethyltetrahydrofuran-3-yl]-7-fluorobenzimidazole-5-carboxylate (Intermediate I-108, 45 mg, 0.09 mmol), 4,4,5,5-tetramethyl-2-(4,4,5,5-tetramethyl-1,3,2-dioxaborolan-2-yl)-1,3,2-dioxaborolane (24 mg, 0.09 mmol), [1,1'-Bis(diphenylphosphino)ferrocene] dichloropalladium(II) (10.2 mg, 0.01 mmol), potassium propionate (30.4 mg, 0.27 mmol), and 2.5 mL of 1,4-dioxane. This mixture had argon bubbled through for 5 min before being heated in a microwave for 1 h at 120° C. Then sodium carbonate (0.09 mL, 0.188 mmol, 2M) was added followed by 4-bromo-2-[(4-chloro-2-fluoro-phenyl)methoxy]pyrimidine (Intermediate I-105, 46.0 mg, 0.14 mmol). The mixture was heated to 110° C. for 1 h, then filtered, concentrated, and purified by silica gel chromatography (EtOAc/hexane gradient) to yield methyl (S)-2-(4-(2-((4-chloro-2-fluorobenzyl)oxy)pyrimidin-4-yl)-2,5-difluorobenzyl)-1-(4,4-dimethyltetrahydrofuran-3-yl)-4-fluoro-1H-benzo[d]imidazole-6-carboxylate (Intermediate I-111). ES/MS m/z: 656.1 (M+H)⁺.

Preparation of Intermediate I-112

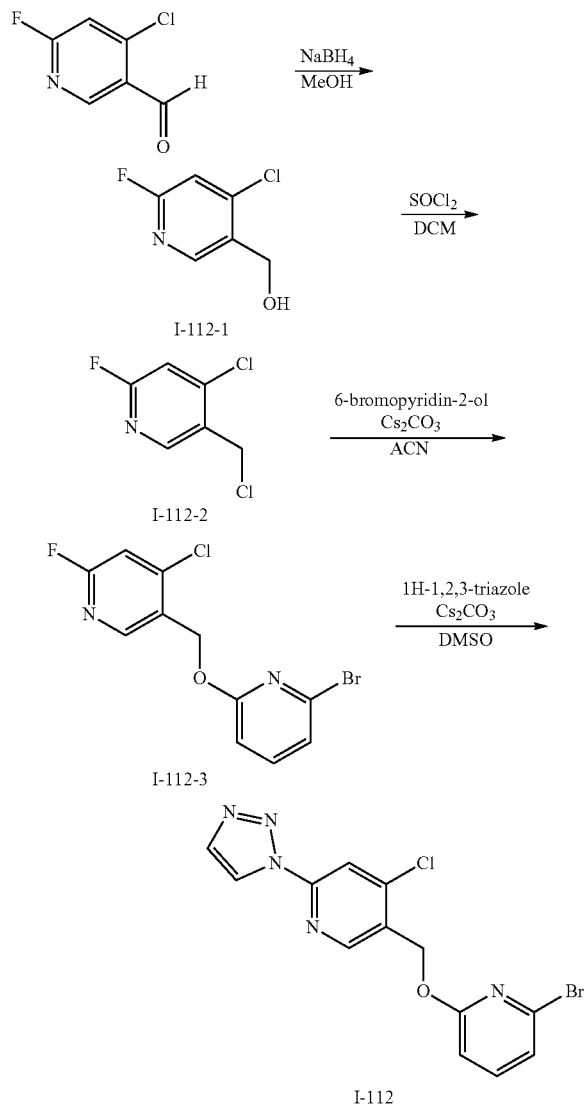

min. The reaction was quenched with saturated NH₄Cl and concentrated. It was dissolved in EtOAc, washed with water then brine, dried over MgSO₄, filtered, and concentrated to give (4-chloro-6-fluoropyridin-3-yl)methanol (I-112-1). ES/MS: 161.9 (M+H)⁺.

4-chloro-5-(chloromethyl)-2-fluoropyridine (I-112-2): Thionyl chloride (0.53 mL, 7.4 mmol) was added to a solution of (4-chloro-6-fluoropyridin-3-yl)methanol (I-112-1, 476 mg, 2.95 mmol) in DCM (25 mL), and the resulting solution was stirred for 1 hr. More thionyl chloride (0.53 mL, 7.4 mmol) was added, and the resulting solution was stirred for 1 hr. More thionyl chloride (0.21 mL, 2.9 mmol) was added, and the resulting solution was stirred for 30 min. The mixture was concentrated, redissolved in DCM, and saturated NaHCO₃ was added dropwise slowly. Phases were separated, and the organic phase was dried over MgSO₄, filtered, and concentrated to give 4-chloro-5-(chloromethyl)-2-fluoropyridine (I-112-2). 1H NMR (400 MHz, Chloroform-d) δ 8.30 (s, 1H), 7.05 (d, J=2.7 Hz, 1H), 4.67 (s, 2H).

5-(((6-bromopyridin-2-yl)oxy)methyl)-4-chloro-2-fluoropyridine (I-112-3): A slurry of 6-bromopyridin-2-ol (557 mg, 3.2 mmol), 4-chloro-5-(chloromethyl)-2-fluoropyridine (I-112-2, 480 mg, 2.7 mmol), and Cs₂CO₃ (2.17 g, 6.7 mmol) in CAN (9 mL) was heated at 70° C. for 30 min. The mixture was filtered through celite, concentrated, and purified by silica gel flash column chromatography (EtOAc in Hex gradient) to give 5-(((6-bromopyridin-2-yl)oxy)methyl)-4-chloro-2-fluoropyridine (I-112-3). ES/MS: 317.0 (M+H)⁺.

5-(((6-bromopyridin-2-yl)oxy)methyl)-4-chloro-2-(1H-1,2,3-triazol-1-yl)pyridine (Intermediate I-112): A slurry of 5-(((6-bromopyridin-2-yl)oxy)methyl)-4-chloro-2-fluoropyridine (I-112-3, 110 mg, 0.31 mmol), 1H-1,2,3-triazole (0.018 mL, 0.31 mmol), and K₂CO₃ (87 mg, 0.63 mmol) in DMSO (1.4 mL) was heated at 70° C. for 4 hrs. The mixture was diluted with brine and extracted 2× with EtOAc. The combined organic phase was dried over MgSO₄, filtered, concentrated, and purified by silica gel flash column chromatography (EtOAc in Hex gradient) to give 5-(((6-bromopyridin-2-yl)oxy)methyl)-4-chloro-2-(1H-1,2,3-triazol-1-yl)pyridine (Intermediate I-112) as the earlier eluting of two isomeric compounds. 1H NMR (400 MHz, Chloroform-d) δ 8.66 (s, 1H), 8.58 (s, 1H), 8.31 (s, 1H), 7.84 (d, J=1.2 Hz, 1H), 7.48 (t, J=7.8 Hz, 1H), 7.13 (d, J=7.5 Hz, 1H), 6.79 (d, J=8.2 Hz, 1H), 5.54 (s, 2H).

Preparation of Intermediate I-113

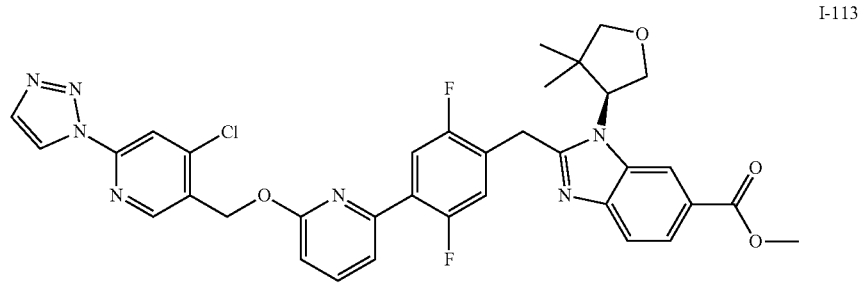 [SMILES: COC(=O)c1ccc2nc(Cc3cc(F)c(-c4cccc(OCc5cnc(-n6ccnn6)cc5Cl)n4)cc3F)n([C@@H]3COCC3(C)C)c2c1]

(4-chloro-6-fluoropyridin-3-yl)methanol (I-112-1): NaBH₄ (117 mg, 3.09 mmol) was added to a solution of 4-chloro-6-fluoronicotinaldehyde (470 mg, 2.95 mmol) in MeOH (12 mL) at 0° C., and the solution was stirred for 5

Methyl (S)-2-(4-(6-((4-chloro-6-(1H-1,2,3-triazol-1-yl)pyridin-3-yl)methoxy)pyridin-2-yl)-2,5-difluorobenzyl)-1-(4,4-dimethyltetrahydrofuran-3-yl)-1H-benzo[d]imidazole-6-carboxylate (Intermediate I-113): A slurry of methyl (S)-

2-(4-bromo-2,5-difluorobenzyl)-1-(4,4-dimethyltetrahydrofuran-3-yl)-1H-benzo[d]imidazole-6-carboxylate (Intermediate I-82, 20 mg, 0.04 mmol), bis(pinacolato)diboron (13.8 mg, 0.05 mmol), potassium propionate (14 mg, 0.125 mmol), and bis(diphenylphosphino)ferrocene] dichloropalladium (II) (4.6 mg, 0.006 mmol) in dioxane (1 mL) was sparged with argon for 5 min, sealed, and heated at 110° C. for 1 hr. The mixture was cooled to rt, sodium carbonate (2M, 0.05 mL, 0.1 mmol) was added, and the mixture was stirred at rt for 5 min. Bis(diphenylphosphino)ferrocene] dichloropalladium(II) (3.1 mg, 0.004 mmol) and a solution of 5-(((6-bromopyridin-2-yl)oxy)methyl)-4-chloro-2-(1H-1,2,3-triazol-1-yl)pyridine (Intermediate I-112) in dioxane (1 mL) were added, and the mixture was degassed for 5 min with Ar, then heated at 90° C. for 2 hrs. The mixture was diluted with EtOAc, washed with brine (2×), dried over MgSO$_4$, filtered, concentrated, and purified by silica gel flash chromatography (EtOAc in Hexane gradient) to give methyl (S)-2-(4-(6-((4-chloro-6-(1H-1,2,3-triazol-1-yl)pyridin-3-yl)methoxy)pyridin-2-yl)-2,5-difluorobenzyl)-1-(4,4-dimethyltetrahydrofuran-3-yl)-1H-benzo[d]imidazole-6-carboxylate (Intermediate I-113). ES/MS m/z: 686.1 (M+H)$^+$.

Preparation of Intermediate I-114

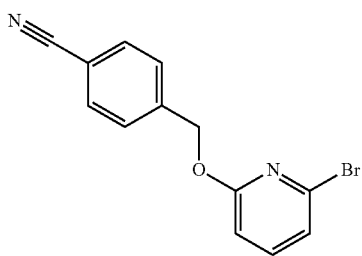

I-114

4-[(6-bromo-2-pyridyl)oxymethyl]benzonitrile (Intermediate I-114): A mixture of 4-(bromomethyl)benzonitrile (200 mg, 1.0 mmol), 6-bromopyridin-2-ol (180 mg, 1.0 mmol), and cesium carbonate (400 mg, 1.2 mmol) was stirred in acetonitrile (5 mL) at rt for 3 hrs. The mixture was filtered through Celite and concentrated in vacuo to yield 4-[(6-bromo-2-pyridyl)oxymethyl]benzonitrile (Intermediate I-114). ES/MS m/z: 289.2 (M+H)$^+$.

Preparation of Intermediate I-115

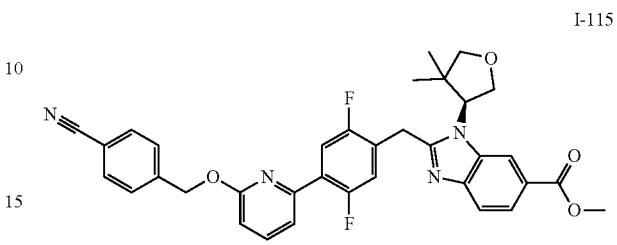

I-115

Methyl 2-[[4-[6-[(4-cyanophenyl)methoxy]-2-pyridyl]-2,5-difluoro-phenyl]methyl]-3-[(3S)-4,4-dimethyltetrahydrofuran-3-yl]benzimidazole-5-carboxylate (Intermediate I-115): To methyl 2-[(4-bromo-3-fluoro-phenyl)methyl]-3-[[(2S)-oxetan-2-yl]methyl]benzimidazole-5-carboxylate (Intermediate I-82, 30 mg, 0.0626 mmol) was added bis(pinacolato)diboron (23 mg, 0.090 mmol), potassium propionate (23 mg, 0.208 mmol), Pd(dppf)C$_{12}$ (7.7 mg, 0.0104 mmol, and dioxane (1.5 mL). The mixture was degassed 30 sec under argon, and heated for 16 hrs. at 100° C. Then sodium carbonate (2M in water, 0.070 mL, 0.14 mmol) was added and the mixture stirred for 1 min at rt. Then more Pd(dppf)Cl$_2$ (3.9 mg, 0.0052 mmol) was added, followed by 4-[(6-bromo-2-pyridyl)oxymethyl]benzonitrile (Intermediate I-114, 20 mg, 0.0692 mmol). The mixture was sealed under argon and heated for 3 hrs. at 90° C. The organic layer was purified directly by silica gel flash chromatography (EtOAc in Hex gradient) to yield methyl 2-[[4-[6-[(4-cyanophenyl)methoxy]-2-pyridyl]-2,5-difluoro-phenyl]methyl]-3-[(3S)-4,4-dimethyltetrahydrofuran-3-yl]benzimidazole-5-carboxylate (Intermediate I-115). ES/MS m/z: 609.5 [M+H]$^+$.

Preparation of Intermediate I-116

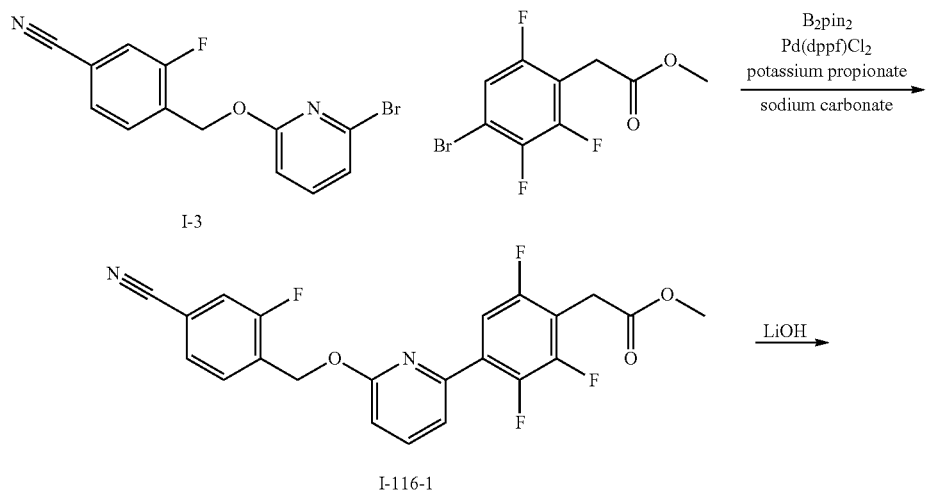

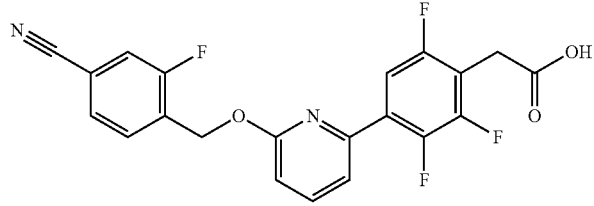

I-116

Methyl 2-(4-(6-((4-cyano-2-fluorobenzyl)oxy)pyridin-2-yl)-2,3,6-trifluorophenyl)acetate (I-116-1): A mixture of methyl (4-bromo-2,3,6-trifluorophenyl)acetate (26.0 g, 91.9 mmol, 1.0 eq), Bis(pinacolato)diboron (30.3 g, 119.4 mmol, 1.3 eq), Pd(dppf)Cl$_2$ (3.36 g, 4.6 mmol, 0.05 eq), and potassium propionate (36.1 g, 321.7 mmol, 3.5 eq) in dioxane (400 mL) was degassed with Argon. The mixture was stirred at 100° C. overnight. The mixture was cooled to room temperature, followed by added aq. Na$_2$CO$_3$ (2.0 M, 92 mL, 183.8 mmol, 2.0 eq), Pd(dppf)Cl$_2$ (3.36 g, 4.6 mmol, 0.05 eq) and 4-(((6-bromopyridin-2-yl)oxy)methyl)-3-fluorobenzonitrile (Intermediate I-3, 28.2 g, 91.9 mmol, 1.0 eq). The mixture was degassed with Argon gas, then the mixture was stirred at 100° C. for 2 hrs. The mixture was diluted with EtOAc (1000 mL) and washed with brine (500 mL×2). The organic layer was dried over Na$_2$SO$_4$, filtered and concentrated. The residue was purified by silica gel flash chromatography (petroleum ether/EtOAc gradient) to give methyl 2-(4-(6-((4-cyano-2-fluorobenzyl)oxy)pyridin-2-yl)-2,3,6-trifluorophenyl)acetate (I-116-1). 1H NMR (400 MHz, DMSO-d6): δ 7.93-7.90 (m, 2H), 7.78-7.72 (m, 2H), 7.65-7.60 (m, 1H), 7.56-7.54 (m, 1H), 7.04 (d, J=8.4 Hz, 1H), 5.59 (s, 2H), 3.88 (s, 2H), 3.68 (s, 3H). ES/MS m/z: 431.0 [M+H]$^+$.

2-(4-(6-((4-cyano-2-fluorobenzyl)oxy)pyridin-2-yl)-2,3,6-trifluorophenyl)acetic acid (Intermediate I-116): A solution of methyl 2-(4-(6-((4-cyano-2-fluorobenzyl)oxy)pyridin-2-yl)-2,3,6-trifluorophenyl)acetate (I-116-1, 12.0 g, 27.9 mmol, 1.0 eq) and aq. LiOH (2 M, 16.8 mL, 33.5 mmol, 1.3 eq) in CH$_3$CN (130 mL) was stirred at room temperature for 5 hrs. The mixture was acidified with 1N HCl to pH=6. The precipitated solid was collected by filtration and washed with water (10 mL×2), then dried to afford 2-(4-(6-((4-cyano-2-fluorobenzyl)oxy)pyridin-2-yl)-2,3,6-trifluorophenyl)acetic acid (Intermediate I-116). 1H NMR (400 MHz, DMSO-d6): δ 7.93-7.90 (m, 2H), 7.89-7.86 (m, 2H), 7.50-7.42 (m, 2H), 6.98 (d, J=8.4 Hz, 1H), 5.58 (s, 2H), 3.28 (s, 2H). ES/MS m/z: 417.0 [M+H]$^+$.

Preparation of Intermediate I-117

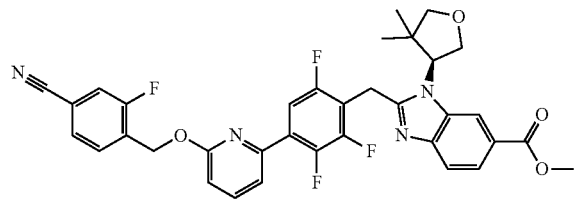

I-117

Methyl (S)-2-(4-(6-((4-cyano-2-fluorobenzyl)oxy)pyridin-2-yl)-2,3,6-trifluorobenzyl)-1-(4,4-dimethyltetrahydrofuran-3-yl)-1H-benzo[d]imidazole-6-carboxylate (Intermediate 117): To a solution of 2-(4-(6-((4-cyano-2-fluorobenzyl)oxy)pyridin-2-yl)-2,3,6-trifluorophenyl)acetic acid (Intermediate I-116, 320 mg, 0.77 mmol) in DMF (20 mL) was added methyl 4-amino-3-[[(3S)-4,4-dimethyltetrahydrofuran-3-yl]amino]benzoate (Intermediate I-80, 203 mg, 0.77 mmol), o-(7-Azabenzotriazol-1-yl)-N,N,N',N'-tetramethyluronium hexafluorophosphate (292 mg, 0.77 mmol), and DIPEA (0.4 mL, 2.31 mmol). The resulting solution was stirred at room temperature for 2 hrs. after which the mixture was poured into 100 mL of saturated sodium bicarbonate solution and extracted with EtOAc (2×50 mL). The combined organic extracts were washed with 20 mL of brine, dried over MgSO$_4$. The organic layer was filtered and concentrated. The resulting residue was dissolved in 5.0 mL of acetic acid and stirred at 100° C. for 16 hrs. The mixture was cooled down and the solvent removed in vacuo. The mixture was diluted with 50 mL of EtOAc and washed with 50 mL of saturated aqueous NaHCO$_3$. The organic layer was dried over sodium sulfate. The organic layer was filtered and concentrated. It was purified by silica gel chromatography (eluent: EtOAc/hexanes) to give methyl (S)-2-(4-(6-((4-cyano-2-fluorobenzyl)oxy)pyridin-2-yl)-2,3,6-trifluorobenzyl)-1-(4,4-dimethyltetrahydrofuran-3-yl)-1H-benzo[d]imidazole-6-carboxylate (Intermediate 117). ES/MS: 645.7 (M+H)$^+$.

Preparation of Intermediate I-118

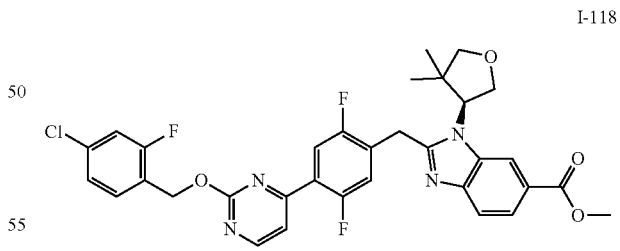

I-118

Methyl (S)-2-(4-(2-((4-chloro-2-fluorobenzyl)oxy)pyrimidin-4-yl)-2,5-difluorobenzyl)-1-(4,4-dimethyltetrahydrofuran-3-yl)-1H-benzo[d]imidazole-6-carboxylate (Intermediate I-118): To a vial was added methyl (S)-2-(4-bromo-2,5-difluorobenzyl)-1-(4,4-dimethyltetrahydrofuran-3-yl)-1H-benzo[d]imidazole-6-carboxylate (Intermediate I-82, 100 mg, 0.21 mmol), [1,1'-Bis(diphenylphosphino)ferrocene] dichloropalladium(II) (15.5 mg, 0.021 mmol), Bis(pinacolato)diboron (80 mg, 0.3 mmol) and potassium propionate (70 mg, 0.63 mmol) followed by 1,4-Dioxane (1.0 mL). Argon was bubbled through the solution for 3 min then the mixture was heated to 110° C. for 70 min. To the mixture was added aqueous sodium carbonate (2.00 M, 0.21 mL, 0.42 mmol), [1,1'-Bis(diphenylphosphino)ferrocene]dichloropalladium(II) (6.6 mg, 0.009 mmol), and 4-bromo-2-[(4-chloro-2-fluoro-phenyl)methoxy]pyrimidine (Intermediate I-105, 99.3 mg, 0.3 mmol). Argon was bubbled through the solution for 3 min then the mixture was heated to 100° C. for 45 min. The mixture was filtered through celite, washing with DCM and concentrated in vacuo. The crude residue was purified by silica gel flash column chromatography (0-100% EtOAc in hexane) to give Methyl (S)-2-(4-(2-((4-chloro-2-fluorobenzyl)oxy)pyrimidin-4-yl)-2,5-difluorobenzyl)-1-(4,4-dimethyltetrahydrofuran-3-yl)-1H-benzo[d]imidazole-6-carboxylate (Intermediate I-118). ES/MS m/z: 637.8 (M+H$^+$).

Preparation of Intermediate I-119

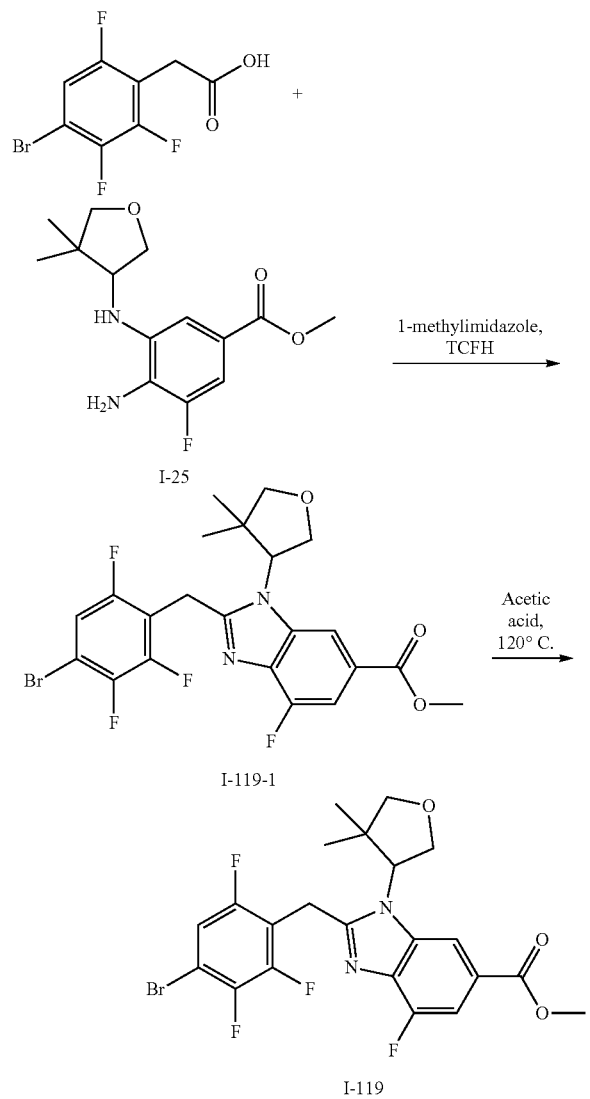

Methyl 2-(4-bromo-2,3,6-trifluorobenzyl)-1-(4,4-dimethyltetrahydrofuran-3-yl)-4-fluoro-1H-benzo[d]imidazole-6-carboxylate (Intermediate I-119): To a solution of 2-(4-bromo-2,3,6-trifluorophenyl)acetic acid (1.2 g, 4.46 mmol) in ACN (50 mL) was added methyl 4-amino-3-((4,4-dimethyltetrahydrofuran-3-yl)amino)-5-fluorobenzoate (Intermediate I-25, 1.26 g, 4.46 mmol), Chloro-N,N,N',N'-tetramethylformamidinium hexafluorophosphate (1.5 g, 5.35 mmol), and 1-methylimidazole (1.83 mL, 22.3 mmol). The resulting solution was stirred at room temperature for 16 hrs. after which the mixture was poured into 100 mL of saturated sodium bicarbonate solution and extracted with EtOAc (2×50 mL). The combined organic extracts were washed with 50 mL of brine, dried over MgSO$_4$. The organic layer was filtered and concentrated. The mixture was purified by silica gel chromatography (eluent: EtOAc/hexanes) to yield Intermediate I-119-1, which was dissolved in 50.0 mL of acetic acid. It was stirred at 120° C. for 40 hrs. The mixture was cooled down and removed the solvent. The mixture was diluted with 100 mL of EtOAc and washed with 100 mL of saturated aqueous NaHCO$_3$. The organic layer was dried over sodium sulfate. The organic layer was filtered and concentrated. It was purified by silica gel flash column chromatography (eluent: EtOAc/hexanes) to give methyl 2-(4-bromo-2,3,6-trifluorobenzyl)-1-(4,4-dimethyltetrahydrofuran-3-yl)-4-fluoro-1H-benzo[d]imidazole-6-carboxylate (Intermediate I-119). ES/MS: 515.6 (M+H)$^+$.

Preparation of Intermediate I-120

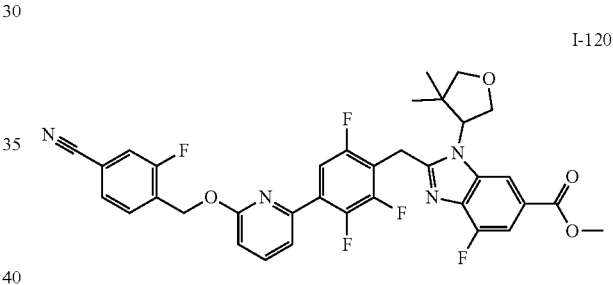

I-120

Methyl 2-(4-(6-((4-cyano-2-fluorobenzyl)oxy)pyridin-2-yl)-2,3,6-trifluorobenzyl)-1-(4,4-dimethyltetrahydrofuran-3-yl)-4-fluoro-1H-benzo[d]imidazole-6-carboxylate (Intermediate I-120): To methyl 2-(4-bromo-2,3,6-trifluorobenzyl)-1-(4,4-dimethyltetrahydrofuran-3-yl)-4-fluoro-1H-benzo[d]imidazole-6-carboxylate (Intermediate I-119, 300 mg, 0.58 mmol) was added [1,1'-Bis(diphenylphosphino)ferrocene]dichloropalladium(II) (43.2 mg, 0.058 mmol), Bis(pinacolato)diboron (222 mg, 0.87 mmol) and potassium propionate (196 mg, 1.75 mmol) followed by 1,4-Dioxane (3.0 mL). Argon was bubbled through the solution for 3 min then the mixture was heated to 110° C. for 90 min. To the mixture was added aqueous sodium carbonate (2.00 M, 0.58 mL, 1.16 mmol), [1,1'-Bis(diphenylphosphino)ferrocene] dichloropalladium(II) (18.1 mg, 0.024 mmol) and 4-[(6-bromo-2-pyridyl)oxymethyl]-3-fluorobenzonitrile (Intermediate I-3, 268 mg, 0.87 mmol). Argon was bubbled through the solution for 3 min then the mixture was heated to 100° C. for 60 min. The mixture was filtered through celite, eluted with DCM, and the filtrate was concentrated in vacuo. The crude residue was purified by silica gel flash column chromatography (EtOAc/Hex gradient) to give methyl 2-(4-(6-((4-cyano-2-fluorobenzyl)oxy)pyridin-2-yl)-2,3,6-trifluorobenzyl)-1-(4,4-dimethyltetrahydrofuran-3-yl)-4-fluoro-1H-benzo[d]imidazole-6-carboxylate (Intermediate I-120). ES/MS m/z: 663.5 (M+H$^+$).

Preparation of Intermediate I-121

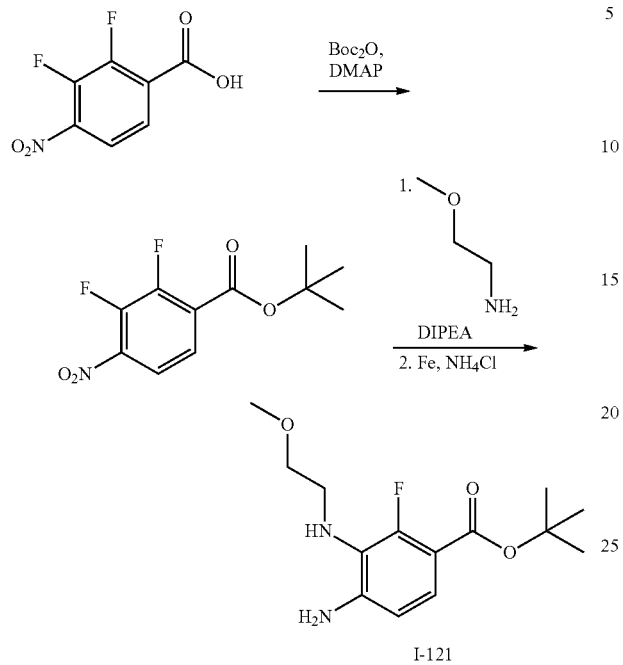

Preparation of Intermediate I-122

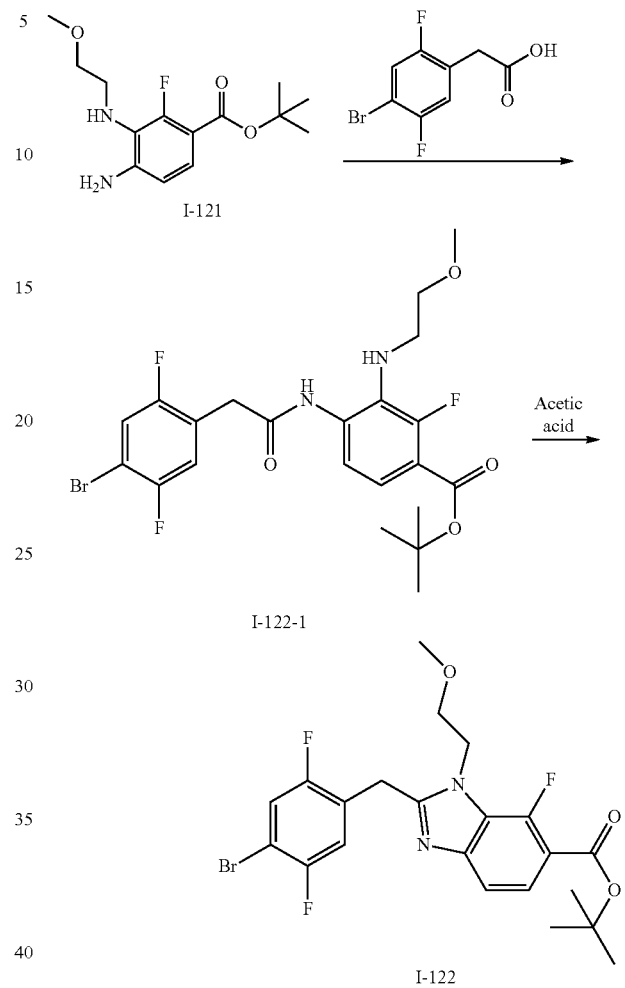

Tert-butyl 2,3-difluoro-4-nitrobenzoate: 2,3-difluoro-4-nitrobenzoic acid (1.00 g, 4.92 mmol) in THF (15 mL) at ambient temperature was treated with di-tert-butyl decarbonate (2.15 g, 9.9 mmol) followed by 4-dimethylaminopyridine (180 mg, 1.5 mmol) and the resulting mixture was heated to 40° C. for 3 hrs. Upon completion, the mixture was poured into water (20 mL) and extracted with EtOAc (3×30 mL). The combined organic extracts were washed with brine (15 mL), dried over MgSO$_4$, and purified by silica gel chromatography (eluent: EtOAc/hexanes) to yield tert-butyl 2,3-difluoro-4-nitrobenzoate.

Tert-butyl 4-amino-2-fluoro-3-((2-methoxyethyl)amino) benzoate (Intermediate I-121): tert-butyl 2,3-difluoro-4-nitrobenzoate (200 mg, 0.77 mmol) was dissolved in THF (2 mL) after which 2-methoxyethanamine (0.080 mL, 0.93 mmol) and diisopropylethylamine (0.40 mL, 2.3 mmol) were added and the resulting mixture heated to 60° C. for 16 hrs. Upon completion the mixture was concentrated directly, the crude residue then taken up in EtOAc (25 mL) and washed with saturated aq. NH$_4$Cl (2×5 mL). The combined organic extracts were washed with brine (5 mL), dried over MgSO$_4$, concentrated and carried forward without purification. Crude tert-butyl 2-fluoro-3-((2-methoxyethyl)amino)-4-nitrobenzoate was dissolved in EtOH (5 mL) after which iron (216 mg, 3.9 mmol) and saturated aq. NH$_4$Cl (2 mL) were added. The resulting mixture was heated to 60° C. for 3 hrs. Upon completion the solids were removed by filtration washing with EtOAc (20 mL) and MeOH (20 mL). The filtrate was then concentrated, taken up in EtOAc (25 mL), and washed with water (5 mL) and brine (5 mL). The organic layer was then dried over MgSO$_4$ and purified by silica gel chromatography (eluent: EtOAc/hexanes) to give tert-butyl 4-amino-2-fluoro-3-((2-methoxyethyl)amino)benzoate (Intermediate I-121). ES/MS: 284.9 (M+H$^+$).

Tert-butyl 2-(4-bromo-2,5-difluorobenzyl)-7-fluoro-1-(2-methoxyethyl)-1H-benzo[d]imidazole-6-carboxylate (Intermediate I-122): To a solution of 2-(4-bromo-2,5-difluorophenyl)acetic acid (318 mg, 1.27 mmol) and tert-butyl 4-amino-2-fluoro-3-(2-methoxyethylamino)benzoate (Intermediate I-121, 250 mg, 0.9 mmol) in MeCN (8 mL) was added 1-methylimidazole (0.35 mL, 4.4 mmol) and N,N,N', N'-tetramethylchloroformamidinium hexafluorophosphate (TCFH, 300 mg, 1.1 mmol). The solution was stirred at room temperature for 2 hrs., diluted with EtOAc and washed with HCl (1 M, aqueous). The organic layer was concentrated to provide tert-butyl 4-[[2-(4-bromo-2,5-difluoro-phenyl) acetyl] amino]-2-fluoro-3-(2-methoxyethylamino)benzoate (I-122-1), which was dissolved in 5 mL of DCE and 0.38 mL of acetic acid. The mixture was stirred at 60° C. for 4 hrs. The reaction was quenched with NaHCO$_3$ and extracted 2× with DCM. The organic phase was washed with brine, dried, filtered, concentrated, and purified by silica gel flash chromatography (EtOAc in Hexane gradient) to give tert-butyl 2-(4-bromo-2,5-difluorobenzyl)-7-fluoro-1-(2-methoxyethyl)-1H-benzo[d]imidazole-6-carboxylate (Intermediate I-122). 1H NMR (400 MHz, Chloroform-d) δ 7.86 (dd, J=8.6, 6.7 Hz, 1H), 7.65 (d, J=8.6 Hz, 1H), 7.35 (dd, J=8.7, 5.6 Hz, 1H), 7.13 (dd, J=8.3, 6.4 Hz, 1H), 4.62-4.40 (m, 4H), 3.78 (t, J=5.1 Hz, 2H), 3.29 (s, 3H), 1.64 (s, 9H).

Preparation of Intermediate I-123

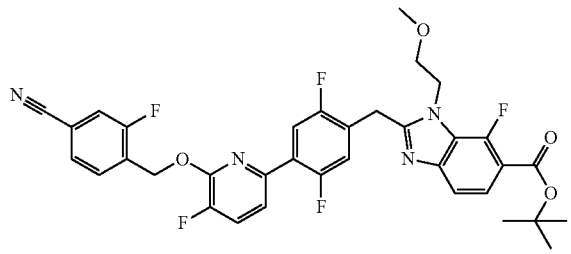

I-123

Tert-butyl 2-(4-(6-((4-cyanobenzyl)oxy)pyridin-2-yl)-2,5-difluorobenzyl)-7-fluoro-1-(2-methoxyethyl)-1H-benzo[d]imidazole-6-carboxylate (Intermediate I-123). A suspension of tert-butyl 2-(4-bromo-2,5-difluorobenzyl)-7-fluoro-1-(2-methoxyethyl)-1H-benzo[d]imidazole-6-carboxylate (Intermediate I-122, 50 mg, 0.1 mmol), Bis(pinacolato)diboron (34 mg, 0.135 mmol), [1,1'-Bis(diphenylphosphino)ferrocene]dichloropalladium(II) (11.5 mg, 0.016 mmol), and potassium propionate (35 mg, 0.3 mmol) in dioxane (2 mL) was degassed with Ar for 20 min. The mixture was sealed and heated at 100° C. for 2 hrs. Sodium carbonate (2.0 M, 0.1 mL, 0.2 mmol) was added and the mixture was stirred at rt for 10 min. [1,1'-Bis(diphenylphosphino)ferrocene]dichloropalladium(II) (6 mg, 0.008 mmol) and 4-[(6-bromo-3-fluoro-2-pyridyl)oxymethyl]-3-fluoro-benzonitrile (Intermediate I-109, 34 mg, 0.1 mmol) were added, the mixture was degassed for 10 min with Ar$_2$, then sealed and heated at 90° C. for 3 hrs. The mixture was diluted with EtOAc and washed with brine. The organic extract was dried over sodium sulfate and chromatographed (eluent: EtOAc/hexanes) to give tert-butyl 2-(4-(6-((4-cyanobenzyl)oxy)pyridin-2-yl)-2,5-difluorobenzyl)-7-fluoro-1-(2-methoxyethyl)-1H-benzo[d]imidazole-6-carboxylate (Intermediate I-123). ES/MS m/z: 665.2 (M+H$^+$).

Preparation of Intermediate I-1001

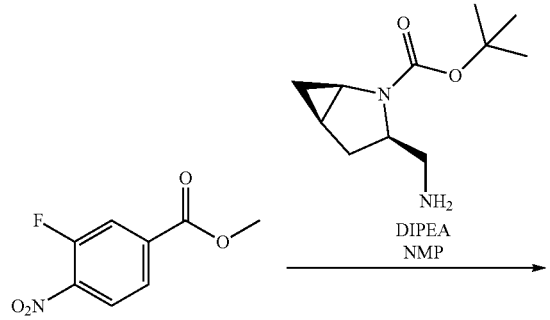

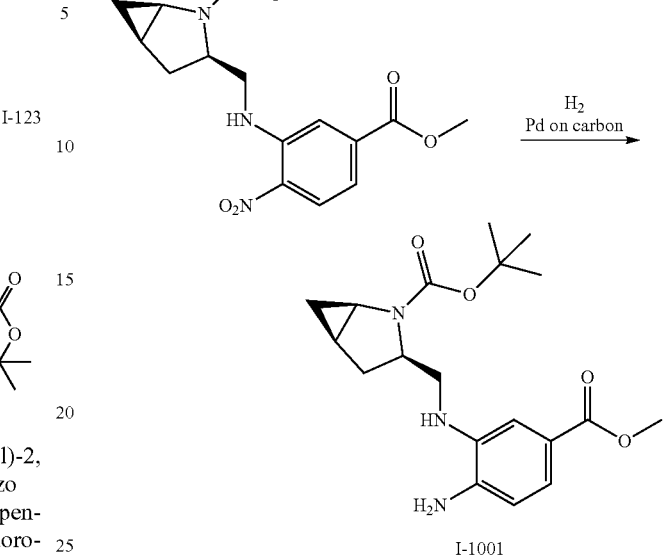

I-1001

Tert-Butyl (1R,3R,5R)-3-[(2-amino-5-methoxycarbonyl-anilino)methyl]-2-azabicyclo[3.1.0]hexane-2-carboxylate (Intermediate I-1001): Tert-Butyl (1R,3R,5R)-3-[(2-amino-5-methoxycarbonyl-anilino)methyl]-2-azabicyclo[3.1.0]hexane-2-carboxylate was prepared in a manner as described for Intermediate I-1 substituting tert-butyl (1R,3R,5R)-3-(aminomethyl)-2-azabicyclo[3.1.0]hexane-2-carboxylate for 2-methoxyethylamine. ES/MS: 362.2 (M+H+). 1H NMR (400 MHz, Chloroform-d) δ 7.39 (d, J=8.1 Hz, 1H), 7.15 (s, 1H), 6.63 (d, J=8.1 Hz, 1H), 4.58 (t, J=11.0 Hz, 1H), 3.87 (s, 3H), 3.64 (d, J=7.3 Hz, 1H), 3.27-3.09 (m, 1H), 3.00 (t, J=11.0 Hz, 1H), 2.56 (q, J=11.7 Hz, 1H), 1.95-1.70 (m, 1H), 1.53 (s, 10H), 0.81 (q, J=7.1 Hz, 1H), 0.57 (d, J=5.7 Hz, 1H).

Preparation of Intermediate I-1002

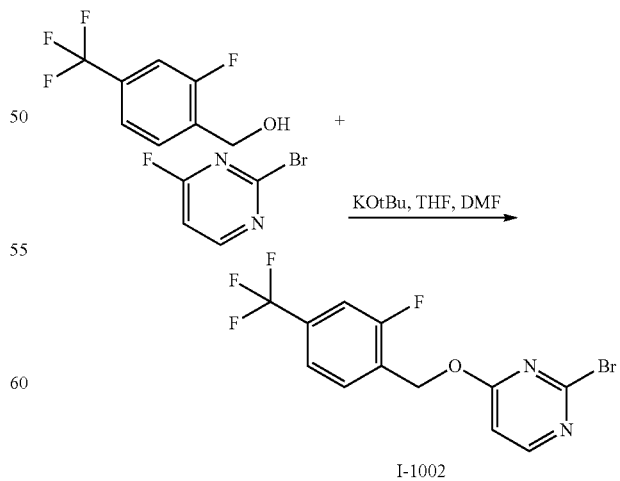

I-1002

2-bromo-4-[[2-fluoro-4-(trifluoromethyl)phenyl]methoxy]pyrimidine (I-1002): To a solution of [2-fluoro-4-

(trifluoromethyl)phenyl]methanol (1.1 g, 5.65 mmol) in tetrahydrofuran (3 mL) was added potassium tert-butoxide (0.333 g, 2.97 mmol). The solution was then stirred for 5 min at room temperature. Next, 2-bromo-4-fluoro-pyrimidine (0.500 g, 2.83 mmol) in N,N-dimethylformamide (5 mL) were added and the mixture was cooled to −78° C. Next, the mixture was removed from the dry-ice bath and stirred at rt over weekend. Following this, the mixture was diluted with EtOAc and washed with 5% LiCl (2×) and brine. The organic extract was dried over sodium sulfate, filtered and concentrated. The crude residue was purified by flash chromatography (eluent: EtOAc/hexanes) to yield desired product. ES/MS: 351.0, 353.0 (M+H$^+$). 1H NMR (400 MHz, Chloroform-d) δ 8.31 (d, J=5.7 Hz, 1H), 7.66 (t, J=7.5 Hz, 1H), 7.48 (dd, J=8.0, 1.5 Hz, 1H), 7.41 (dd, J=9.7, 1.7 Hz, 1H), 6.79 (d, J=5.7 Hz, 1H), 5.56 (s, 2H). 19F NMR (376 MHz, Chloroform-d) δ −63.43, −115.50 (d, J=7.5 Hz).

Preparation of Intermediate I-1003

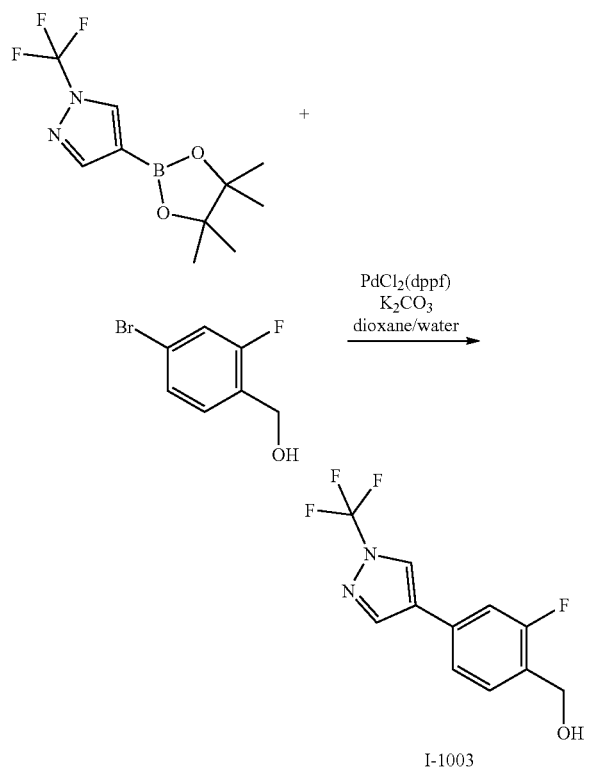

[2-fluoro-4-[1-(trifluoromethyl)pyrazol-4-yl]phenyl] methanol (I-1003): A suspension of (4-bromo-2-fluoro-phenyl)methanol (100 mg, 0.49 mmol), 4-(4,4,5,5-tetramethyl-1,3,2-dioxaborolan-2-yl)-1-(trifluoromethyl)pyrazole (153 mg, 0.59 mmol), 1,1′-Bis(di-isopropylphosphino)ferrocene palladium dichloride (29 mg, 0.049 mmol), and potassium carbonate (200 mg, 1.4 mmol) in 1,4-Dioxane anhydrous, 99.8% (2 mL) and Water (1 mL) was degassed with argon for 5 min, then heated thermally at 100° C. for 1 hr. Upon completion, the mixture was diluted with EtOAc and washed with brine. The organic extract was dried over sodium sulfate, filtered and concentrated. The crude residue was purified by flash chromatography (eluent: EtOAc/hexanes) to yield desired product. ES/MS: 261.2 (M+H$^+$). 1H NMR (400 MHz, Chloroform-d) δ 8.06 (s, 1H), 8.04 (t, J=0.9 Hz, 1H), 7.51 (t, J=7.8 Hz, 1H), 7.33 (dd, J=7.8, 1.7 Hz, 1H), 7.22 (dd, J=10.8, 1.7 Hz, 1H), 4.82 (s, 2H). 19F NMR (376 MHz, Chloroform-d) δ −61.00, −119.32.

Preparation of Intermediate I-1004

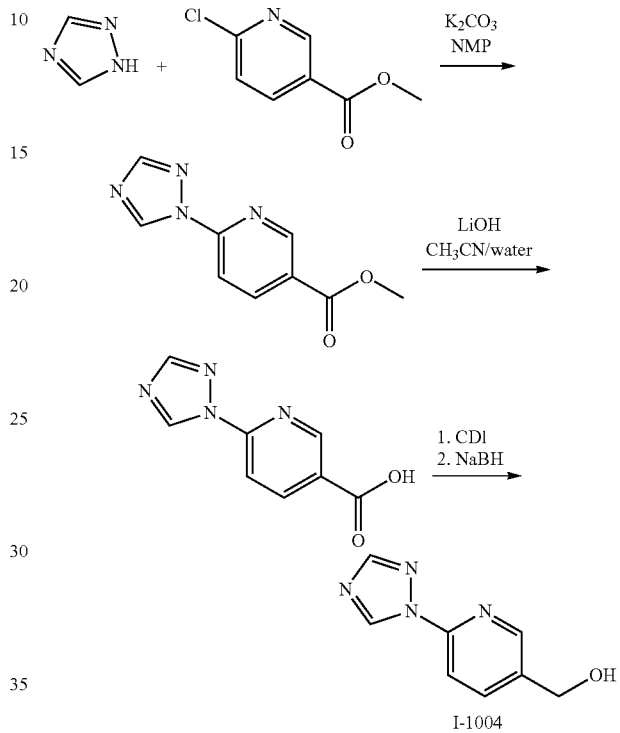

Methyl 6-(1,2,4-triazol-1yl)pyridine-3-carboxylate: A suspension of methyl 6-chloropyridine-3-carboxylate (500 mg, 2.91 mmol), 1H-1,2,4-triazole (282 mg, 4.08 mmol), and Potassium carbonate (564 mg, 4.08 mmol) in NMP (10 mL) was heated at 80° C. overnight. Upon completion, the mixture was diluted with EtOAc and washed with 5% LiCl (2×) and brine. The organic extract was dried over sodium sulfate, filtered and concentrated. The crude residue was purified by flash chromatography (eluent: EtOAc/hexanes) to yield desired product. ES/MS: 205.2 (M+H$^+$). 1H NMR (400 MHz, Chloroform-d) δ 9.27 (s, 1H), 9.10 (dd, J=2.2, 0.8 Hz, 1H), 8.51 (dd, J=8.6, 2.2 Hz, 1H), 8.15 (s, 1H), 8.01 (dd, J=8.5, 0.8 Hz, 1H), 4.01 (s, 3H).

6-(1,2,4-triazol-1-yl)pyridine-3-carboxylic acid: A solution of methyl 6-(1,2,4-triazol-1-yl)pyridine-3-carboxylate (200 mg, 0.980 mmol) and Lithium hydroxide, monohydrate (215 mg, 5.12 mmol) in CH$_3$CN (9 mL) and water (3 mL) was stirred at rt overnight. Next, the mixture was diluted with EtOAc. Adjusted to pH-6 with 1N HCl (2.8 mL) and then filtered and air-dried to give desired product, which was used in the next step without further purification. ES/MS: 191.2 (M+H$^+$). 1H NMR (400 MHz, DMSO-d6) δ 9.48 (s, 1H), 9.01 (d, J=2.2 Hz, 1H), 8.52 (dd, J=8.5, 2.2 Hz, 1H), 8.38 (s, 1H), 7.99 (d, J=8.6 Hz, 1H).

[6-(1,2,4-triazol-1-yl)-3-pyridyl]methanol (I-1004): 1,1′-carbonyldiimidazole (261 mg, 1.61 mmol) was added to a solution of 6-(1,2,4-triazol-1-yl)pyridine-3-carboxylic acid (153 mg, 0.805 mmol) in THF (6 mL) was added. The solution was stirred for 2 hr. Upon completion, the mixture was cooled to 0° C. and then a solution of NaBH₄ (152 mg, 4.02 mmol) in 1 mL water was added. Next, the mixture was stirred for 30 min at rt. Upon completion, 1 mL conc HCL slowly added, then the mixture concentrated to remove the THF. Upon removal of the THF, the mixture was neutralized with saturated NaHCO₃ and extracted with EtOAc 3×. The organic extract was washed with brine and dried over sodium sulfate. The crude residue was purified by chromatography (eluent: EtOAc/hexanes) to give desired product. ES/MS: 177.2 (M+H⁺). 1H NMR (400 MHz, Chloroform-d) δ 9.21 (s, 1H), 8.48 (s, 1H), 8.13 (s, 1H), 7.94 (t, J=1.6 Hz, 2H), 4.83 (s, 2H)

Preparation of Intermediate I-1005

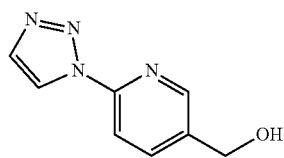

I-1005

[6-(triazol-1-yl)-3-pyridyl]methanol (I-1005): [6-(triazol-1-yl)-3-pyridyl]methanol was prepared in a manner as described for Intermediate I-1004 substituting 1H-triazole for 1H-1,2,4-triazole. ES/MS: 177.2 (M+H⁺). 1H NMR (400 MHz, Chloroform-d) δ 8.62 (d, J=1.2 Hz, 1H), 8.56-8.45 (m, 1H), 8.23 (d, J=8.2 Hz, 1H), 7.98 (dd, J=8.4, 2.3 Hz, 1H), 7.86 (d, J=1.2 Hz, 1H), 4.85 (s, 2H).

Preparation of Intermediate I-1006

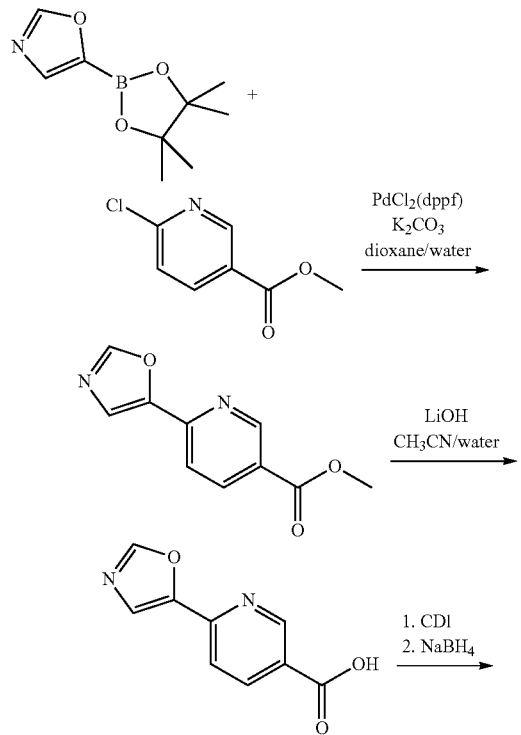

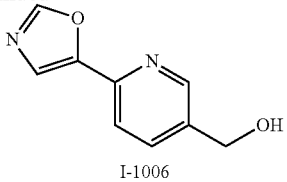

I-1006

Methyl 6-oxazol-5-ylpyridine-3-carboxylate: A suspension of methyl 6-chloropyridine-3-carboxylate (200 mg, 1.2 mmol), 5-(4,4,5,5-tetramethyl-1,3,2-dioxaborolan-2-yl)oxazole (273 mg, 1.4 mmol), 1,1'-Bis(di-isopropylphosphino)ferrocene palladium dichloride (69 mg, 0.12 mmol), and potassium carbonate (477 mg, 3.5 mmol) in 1,4-Dioxane (4 mL) and water (2 mL) was degassed with argon for 5 min. The mixture was then heated thermally at 100° C. for 1 hr. Upon completion, the mixture was diluted with EtOAc and washed with brine. The organic extract was dried over sodium sulfate, filtered and concentrated. The crude residue was purified by flash chromatography (eluent: EtOAc/hexanes) to yield desired product. ES/MS: 205.2 (M+H⁺) 0.1H NMR (400 MHz, Chloroform-d) δ 9.25 (dd, J=2.1, 0.9 Hz, 1H), 8.40 (dd, J=8.3, 2.1 Hz, 1H), 8.05 (s, 1H), 7.86 (s, 1H), 7.77 (dd, J=8.3, 0.9 Hz, 1H), 4.00 (s, 3H).

6-oxazol-5-ylpyridine-3-carboxylic acid: A solution of methyl 6-oxazol-5-ylpyridine-3-carboxylate (117 mg, 0.573 mmol) and lithium hydroxide, monohydrate (68.0 mg, 1.62 mmol), in CH₃CN (3 mL) and water (1 mL) was stirred at rt overnight. The mixture was diluted with EtOAc. Next the mixture was adjusted to pH-6 with 1N HCl (1.6 mL) and then filtered and air-dried to give desired product, which was used in the next step without further purification. ES/MS: 191.2 (M+H⁺) 0.1H NMR (400 MHz, Chloroform-d) δ 8.31 (d, J=5.7 Hz, 1H), 7.66 (t, J=7.5 Hz, 1H), 7.48 (dd, J=8.0, 1.5 Hz, 1H), 7.41 (dd, J=9.7, 1.7 Hz, 1H), 6.79 (d, J=5.7 Hz, 1H), 5.56 (s, 2H). 19F NMR (376 MHz, Chloroform-d) δ −63.43, −115.50 (d, J=7.5 Hz).

(6-oxazol-5-yl-3-pyridyl)methanol (I-1006): 1,1'-carbonyldiimidazole (141 mg, 0.872 mmol) was added to a suspension of 6-oxazol-5-ylpyridine-3-carboxylic acid (82.9 mg, 0.436 mmol) in THE (6 mL). The mixture was stirred for 2 hr. Upon completion, the mixture was cooled to 0° C.° C. then a solution of NaBH₄ (152 mg, 4.02 mmol) in 1 mL water was added. The mixture was stirred for 30 min at rt. Upon completion 1 mL of concentrated HCL was slowly added and then concentrated to remove THF. The mixture was then neutralized with saturated NaHCO₃ and extracted with EtOAc 3×. The organic extract was washed with brine and dried over sodium sulfate. The crude residue was purified by chromatography (eluent: EtOAc/hexanes) to give desired product. ES/MS: 177.2 (M+H+). 1H NMR (400 MHz, Chloroform-d) δ 8.65 (dd, J=2.0, 0.9 Hz, 1H), 8.00 (s, 1H), 7.85 (dd, J=8.1, 2.2 Hz, 1H), 7.75-7.67 (m, 2H), 4.81 (s, 2H).

Preparation of Intermediate I-1007

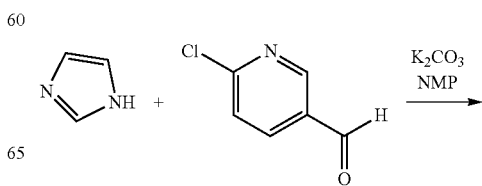

Preparation of Intermediate I-1009

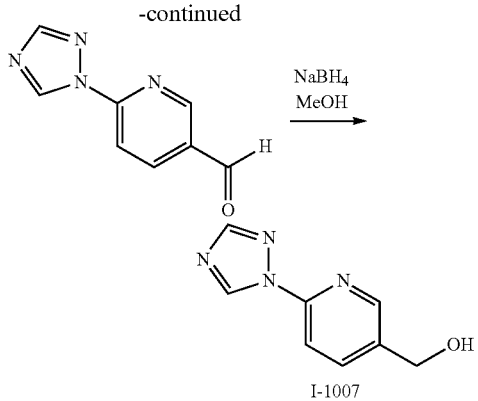

I-1007

2-imidazol-1-ylpyrimidine-5-carbaldehyde: A suspension of 2-chloropyrimidine-5-carbaldehyde (250 mg, 1.75 mmol), imidazole (150 mg, 2.21 mmol), and potassium carbonate (339 mg, 2.46 mmol) in DMF (10 mL) was heated at 50° C. overnight. The next day the mixture was diluted with EtOAc and washed with 5% LiCl (2×) and brine. The organic extract was dried over sodium sulfate, filtered and concentrated. The crude residue was purified by flash chromatography (eluent: EtOAc/hexanes) to yield desired product. ES/MS: 175.2 (M+H$^+$). 1H NMR (400 MHz, Methanol-d4) δ 8.86 (s, 2H), 8.70 (t, J=1.1 Hz, 1H), 8.03 (t, J=1.4 Hz, 1H), 7.16 (t, J=1.3 Hz, 1H).

(2-imidazol-1-ylpyrimidin-5-yl)methanol (I-1007): sodium borohydride (23.3 mg, 0.616 mmol) was added to a solution of 2-imidazol-1-ylpyrimidine-5-carbaldehyde (107 mg, 0.616 mmol) in MeOH (5 mL) at 0° C. The mixture was gradually warmed to rt and stirred for 4 hr. Upon completion of time, the mixture was quenched with 1 mL water, diluted with EtOAc and concentrated to dryness to remove all MeOH. Then the mixture was diluted with EtOAc and washed with brine. Aqueous layer was extracted once more with EtOAc. The combined organic extracts were dried over sodium sulfate to give desired product. ES/MS: 177.2 (M+H$^+$). 1H NMR (400 MHz, Chloroform-d) δ 8.77 (s, 1H), 8.75 (s, 2H), 7.97 (s, 1H), 7.26 (s, 1H), 4.84 (s, 2H).

Preparation of Intermediate I-1008

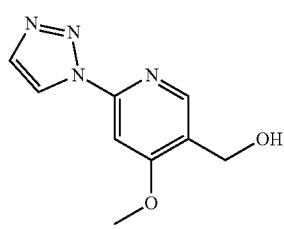

I-1008

[4-methoxy-6-(triazol-1-yl)-3-pyridyl]methanol (I-1008): [4-methoxy-6-(triazol-1-yl)-3-pyridyl]methanol was prepared in a manner as described for Intermediate I-1004 substituting 1H-triazole for 1H-1,2,4-triazole and substituting methyl 6-chloro-4-methoxy-pyridine-3-carboxylate for methyl 6-chloropyridine-3-carboxylate. ES/MS: 207.2 (M+H+). 1H NMR (400 MHz, Chloroform-d) δ 8.62 (d, J=1.2 Hz, 1H), 8.33 (s, 1H), 7.86 (d, J=1.1 Hz, 1H), 7.79 (s, 1H), 4.77 (s, 2H), 4.08 (s, 3H).

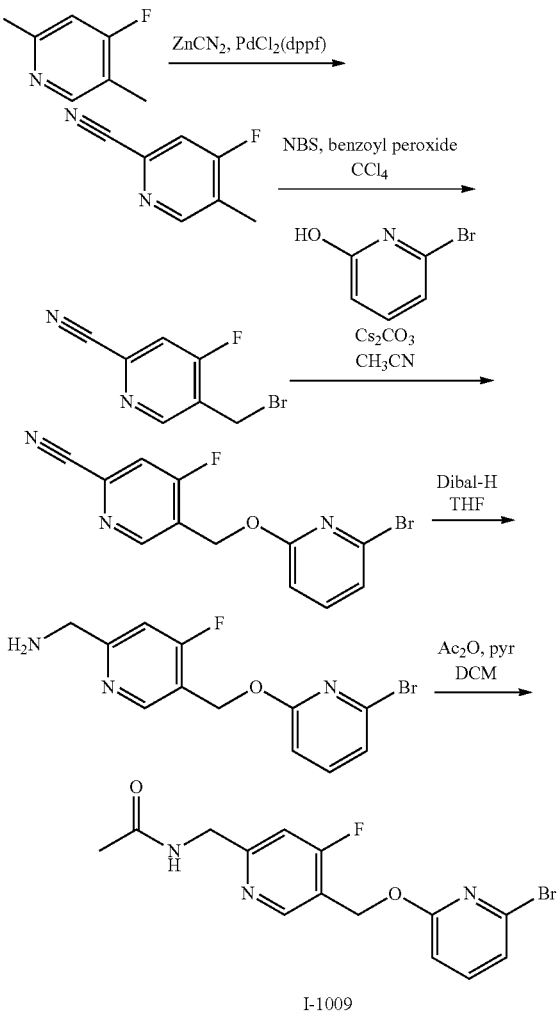

I-1009

4-fluoro-5-methyl-pyridine-2-carbonitrile: 2-chloro-4-fluoro-5-methyl-pyridine (3.0 g, 21 mmol), zinc cyanide (1452 mg, 12 mmol), zinc (135 mg, 2.1 mmol), and 1,1'-Bis(diphenylphosphino)ferrocene-palladium(II)dichloride dichloromethane complex (852 mg, 1.0 mmol) were taken up in DMF (20 mL). The resulting mixture was sparged with argon for 5 minutes then heated to 100° C. in a sealed 20 mL MW vial for 3 hr. The reaction was purified by chromatography (eluent: EtOAc/hexanes) to give desired product.

5-(bromomethyl)-4-fluoro-pyridine-2-carbonitrile: 4-fluoro-5-methyl-pyridine-2-carbonitrile (2.16 g, 15.9 mmol) was taken up in carbon tetrachloride (30.0 mL) and N-Bromosuccinimide (3389 mg, 19.0 mmol) was added followed by Benzoyl peroxide (231 mg, 0.952 mmol). The mixture was heated to 90° C. for 5 hr. Upon completion of time the mixture was filtered to remove succinimide (washed with DCM) and conc. in vacuo. The crude residue was purified by chromatography (eluent: EtOAc/hexanes) to give desired product. ES/MS: 215, 217 (M+H+).

5-[(6-bromo-2-pyridyl)oxymethyl]-4-fluoro-pyridine-2-carbonitrile: 6-bromopyridin-2-ol (1.3 g, 7.5 mmol) was taken up in acetonitrile (15 mL) and 5-(bromomethyl)-4-fluoro-pyridine-2-carbonitrile (1767 mg, 8.2 mmol) and cesium carbonate (3478 mg, 11 mmol) were added. The mixture was heated to 65° C. for 45 min. Next, the mixture was filtered through Celite and the filtrate was concentrated to dryness. The crude residue was purified by chromatography (eluent: EtOAc/hexanes) to give desired product. ES/MS: 308, 310 (M+H+).

[5-[(6-bromo-2-pyridyl)oxymethyl]-4-fluoro-2-pyridyl]methanamine: To a solution of 5-[(6-bromo-2-pyridyl)oxymethyl]-4-fluoro-pyridine-2-carbonitrile (102 mg, 0.331 mmol) in THF (3 mL) at 0° C. was added diisobutylaluminium hydride (1000 mmol/L, 0.993 mL, 0.993 mmol). The resulting mixture was gradually warmed to rt. Additional aliquots of Dibal-H were added until the mixture no longer progressed (2×0.5 mL added). The mixture was then cooled to 0° C. and diluted with Et₂O. Next, a solution of 100 uL of water, 100 uL 15% aqueous NaOH, and 250 uL water was slowly added to the mixture. The resulting mixture was warmed to rt and stirred for 15 min. Upon completion of time MgSO₄ was added the resulting mixture was stirred for 15 min, then filtered and concentrated to give desired product, which was carried onto the next step without purification. ES/MS: 312, 314 (M+H+).

N-[[5-[(6-bromo-2-pyridyl)oxymethyl]-4-fluoro-2-pyridyl]methyl]acetamide (I-1009): To a suspension of [5-[(6-bromo-2-pyridyl)oxymethyl]-4-fluoro-2-pyridyl]methanamine (56.0 mg, 0.179 mmol) and pyridine (0.0217 mL, 0.269 mmol) in DCM (5 mL) at 0° C., acetic anhydride (0.0200 mL, 0.212 mmol) was added. The mixture was gradually warmed to rt and stirred overnight. Next, the organic extract was washed with brine and dried over sodium sulfate. The crude residue was purified by chromatography (eluent: EtOAc/hexanes) to give desired product. ES/MS: 354, 356 (M+H+). 1H NMR (400 MHz, Chloroform-d) δ 8.70 (d, J=9.6 Hz, 1H), 7.53-7.36 (m, 1H), 7.12 (d, J=7.5 Hz, 1H), 7.06 (d, J=9.8 Hz, 1H), 6.75 (d, J=8.1 Hz, 1H), 6.65 (s, 1H), 5.45 (s, 2H), 4.57 (d, J=5.1 Hz, 2H), 2.10 (s, 3H).

Preparation of Intermediate I-1010

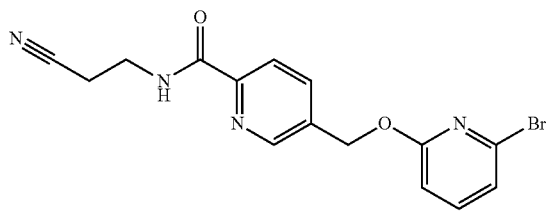

I-1010

5-[(6-bromo-2-pyridyl)oxymethyl]-N-(2-cyanoethyl)pyridine-2-carboxamide (I-1010): 5-[(6-bromo-2-pyridyl)oxymethyl]-N-(2-cyanoethyl)pyridine-2-carboxamide was prepared in a manner as described for Intermediate I-28 substituting 3-aminopropanenitrile for 1-aminocyclopropanecarbonitrile hydrochloride. ES/MS: 361.0, 363.0 (M+H+). 1H NMR (400 MHz, Chloroform-d) δ 8.68 (d, J=2.0 Hz, 1H), 8.46 (d, J=6.7 Hz, 1H), 8.20 (d, J=8.0 Hz, 1H), 7.98 (dd, J=8.0, 2.1 Hz, 1H), 7.48 (t, J=7.8 Hz, 1H), 7.13 (d, J=7.5 Hz, 1H), 6.79 (d, J=8.1 Hz, 1H), 5.48 (s, 2H), 3.78 (q, J=6.5 Hz, 2H), 2.77 (t, J=6.5 Hz, 2H).

Preparation of Intermediate I-1011

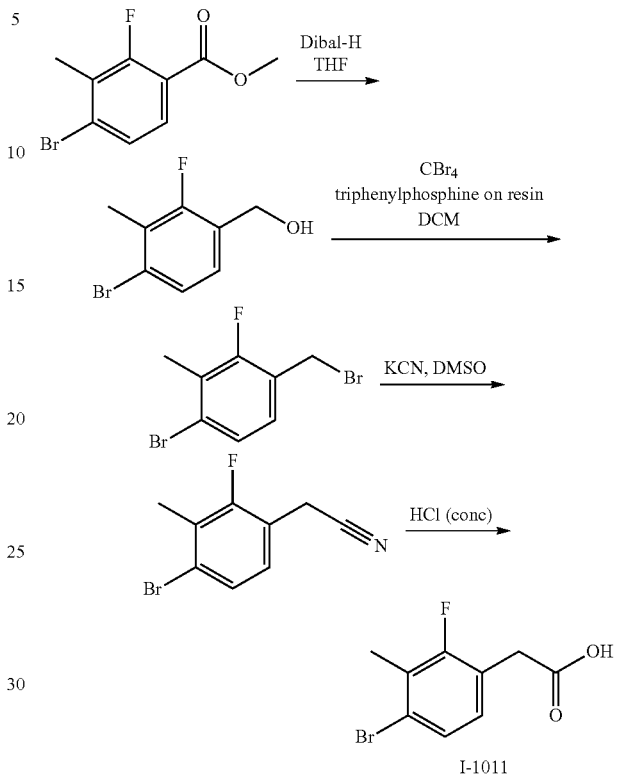

I-1011

(4-bromo-2-fluoro-3-methyl-phenyl)methanol: To a solution of methyl 4-bromo-2-fluoro-3-methyl-benzoate (500 mg, 2.02 mmol) in THF (10 mL) at 0° C., diisobutylaluminum hydride (1000 mmol/L, 5.06 mL, 5.06 mmol) was added. The mixture was stirred for 1 hr. Next, the mixture was diluted with 25 mL Et₂O and cooled to 0° C. Then 0.200 mL water, 0.200 mL 15% NaOH added and then an additional 0.500 mL water was added. The resulting mixture was warmed to rt and stirred for 15 min. Upon completion, MgSO₄ was added and the mixture was stirred for 15 min, then filtered and rinsed with Et₂O to give crude residue which was purified by chromatography (eluent: EtOAc/hexanes) to give desired product. 1H NMR (400 MHz, Chloroform-d) δ 7.37 (dd, J=8.2, 1.3 Hz, 1H), 7.16 (t, J=7.9 Hz, 1H), 4.73 (s, 2H), 2.36 (d, J=2.5 Hz, 3H).

1-bromo-4-(bromomethyl)-3-fluoro-2-methyl-benzene: To a solution of (4-bromo-2-fluoro-3-methyl-phenyl)methanol (358 mg, 1.63 mmol) and (4-diphenylphosphanylphenyl) polymer bound (78.7%, 651 mg, 1.966 mmol), in DCM (10 mL) at 0° C., carbon tetrabromide (650 mg, 1.96 mmol) was added. The mixture was then gradually warmed to rt overnight. The suspension was filtered, diluted with DCM and washed with brine. The organic extract was dried over sodium sulfate, concentrated and purified by chromatography (eluent: EtOAc/hexanes) to give desired product. 1H NMR (400 MHz, Chloroform-d) δ 7.35 (dd, J=8.3, 1.3 Hz, 1H), 7.12 (t, J=8.0 Hz, 1H), 4.49 (d, J=1.2 Hz, 2H), 2.37 (d, J=2.5 Hz, 3H).

2-(4-bromo-2-fluoro-3-methyl-phenyl)acetonitrile: To a solution of 1-bromo-4-(bromomethyl)-3-fluoro-2-methyl-benzene (299 mg, 1.06 mmol) in DMSO (6 ml) at rt, potassium cyanide (138 mg, 2.12 mmol) was added. The mixture was then stirred at rt overnight. Next, the mixture was diluted with EtOAc and washed with 10% Na₂CO₃. The organic extract was washed once more with brine. Next, organic extract was dried over sodium sulfate to give desired product. 1H NMR (400 MHz, Chloroform-d) δ 7.41 (dd, J=8.3, 1.4 Hz, 1H), 7.17 (t, J=8.0 Hz, 1H), 3.73 (d, J=1.0 Hz, 2H), 2.37 (d, J=2.6 Hz, 3H).

2-(4-bromo-2-fluoro-3-methyl-phenyl)acetic acid (I-1011): A solution of 2-(4-bromo-2-fluoro-3-methyl-phenyl)acetonitrile (164 mg, 0.717 mmol) in concentrated HCl (2 mL) was heated at 100° C. overnight. Next, the mixture was cooled to rt, diluted with EtOAc and neutralized carefully with 6 NaOH (4 mL). The organic extract was dried organic extract over sodium sulfate, filtered and concentrated to give desired product. 1H NMR (400 MHz, Methanol-d4) δ 7.35 (dd, J=8.3, 1.3 Hz, 1H), 7.08 (t, J=8.0 Hz, 1H), 3.64 (d, J=1.8 Hz, 2H), 2.35 (d, J=2.5 Hz, 3H).

Preparation of Intermediate I-1012

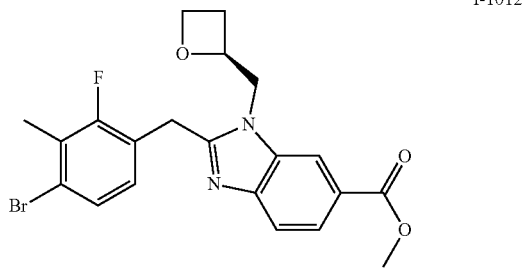

I-1012

Methyl 2-[(4-bromo-2-fluoro-3-methyl-phenyl)methyl]-3-[[(2S)-oxetan-2-yl]methyl]benzimidazole-5-carboxylate (I-1012): Methyl 2-[(4-bromo-2-fluoro-3-methyl-phenyl)methyl]-3-[[(2S)-oxetan-2-yl]methyl]benzimidazole-5-carboxylate was prepared in a manner as described for Intermediate I-2 substituting I-4 for I-1 and 2-(4-bromo-2-fluoro-3-methyl-phenyl)acetic acid (I-1011) for 2-(4-bromo-2-fluoro-phenyl)acetic acid. ES/MS: 447.0, 449.0 (M+H+). 1H NMR (400 MHz, Chloroform-d) δ 8.11 (d, J=1.7 Hz, 1H), 7.98 (dd, J=8.5, 1.6 Hz, 1H), 7.75 (d, J=8.5 Hz, 1H), 7.29 (dd, J=8.3, 1.3 Hz, 1H), 6.99 (t, J=8.0 Hz, 1H), 5.14 (qd, J=6.8, 2.9 Hz, 1H), 4.72-4.51 (m, 1H), 4.51-4.27 (m, 5H), 3.96 (s, 3H), 2.73 (dtd, J=11.4, 8.1, 6.1 Hz, 1H), 2.51-2.38 (m, 1H), 2.35 (d, J=2.6 Hz, 3H).

Preparation of Intermediate I-1013

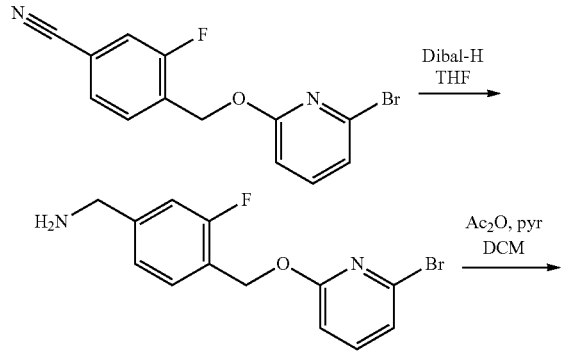

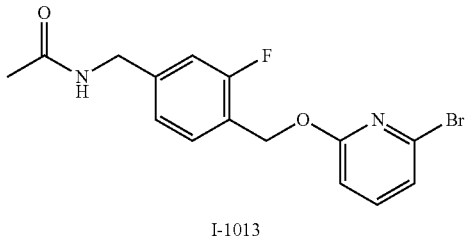

I-1013

[4-[(6-bromo-2-pyridyl)oxymethyl]-3-fluoro-phenyl]methanamine: To a solution of 4-[(6-bromo-2-pyridyl)oxymethyl]-3-fluoro-benzonitrile (257 mg, 0.837 mmol) in THF (12 mL) at 0° C., diisobutylaluminium hydride (1000 mmol/L, 6.28 mL, 6.28 mmol) was added. The mixture was then gradually warmed to rt and stirred overnight. Next, the mixture was cooled to 0° C. and diluted with Et₂O. Next, 250 uL of water was slowly added, followed by the addition of 250 uL 15% aq. NaOH, followed by an additional 625 uL water. The resulting mixture was warmed to rt and stirred for 15 min. Upon completion of time MgSO₄ was added and the mixture was stirred 15 min, then filtered and concentrated to give desired product, which was carried onto the next step without purification. ES/MS: 312.1, 314.1 (M+H+).

N-[[4-[(6-bromo-2-pyridyl)oxymethyl]-3-fluoro-phenyl]methyl]acetamide (I-1013): To a suspension of [4-[(6-bromo-2-pyridyl)oxymethyl]-3-fluoro-phenyl]methanamine (194 mg, 0.623 mmol) and Pyridine (0.0753 mL, 0.935 mmol) in DCM (5 mL) at 0° C., acetic anhydride (0.0695 mL, 0.736 mmol) was added. The resulting mixture was gradually warmed to rt and stirred overnight. The organic extract was washed with brine and dried over sodium sulfate. The crude residue was purified by chromatography (eluent: EtOAc/hexanes) to give desired product. ES/MS: 353.1, 355.1 (M+H+). 1H NMR (400 MHz, Chloroform-d) δ 7.50 (t, J=7.6 Hz, 1H), 7.47-7.41 (m, 1H), 7.10 (dd, J=7.7, 3.9 Hz, 2H), 7.05 (d, J=10.6 Hz, 1H), 6.74 (d, J=8.1 Hz, 1H), 5.77 (s, 1H), 5.42 (s, 2H), 4.46 (d, J=5.8 Hz, 2H), 2.07 (d, J=1.0 Hz, 3H).

Preparation of Intermediate I-1014

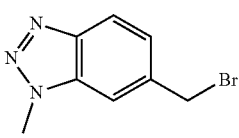

I-1014

6-(bromomethyl)-1-methyl-benzotriazole (I-1014): 6-(bromomethyl)-1-methyl-benzotriazole was prepared in a manner as described for Intermediate I-36 substituting 3-methylbenzotriazole-5-carboxylic acid for [5-(difluoromethyl)thiazole-2-carbonyl]oxysodium. ES/MS: 226.2, 228.2 (M+H+). 1H NMR (400 MHz, Chloroform-d) δ 8.05 (dd, J=8.6, 0.8 Hz, 1H), 7.58 (dd, J=1.5, 0.8 Hz, 1H), 7.43 (dd, J=8.6, 1.5 Hz, 1H), 4.69 (s, 2H), 4.33 (s, 3H).

Preparation of Intermediate I-1015

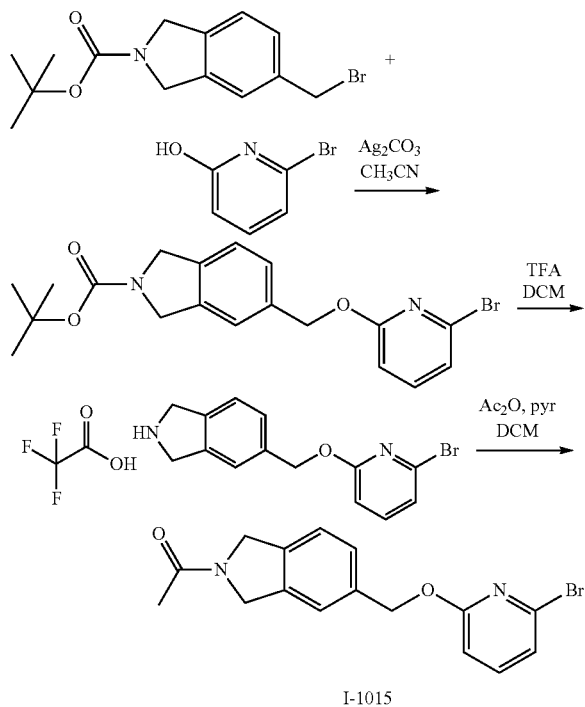

I-1015

Tert-butyl 5-[(6-bromo-2-pyridyl)oxymethyl]isoindoline-2-carboxylate: A suspension of tert-butyl 5-(bromomethyl) isoindoline-2-carboxylate (510 mg, 1.6 mmol), 6-bromopyridin-2-ol (280 mg, 1.6 mmol), and silver carbonate (949 mg, 3.4 mmol) in $CH_3CN$ (10 mL) was heated at 50° C. overnight. The mixture was diluted with EtOAc and brine. Then the mixture was filtered over Celite frit, partitioned. The organic extract was next washed with brine once more. The organic extract was then dried over sodium sulfate, concentrated, and purified by chromatography (eluent: EtOAc/hexanes) to give desired product. ES/MS: 349, 351 (M+H+). 1H NMR (400 MHz, Chloroform-d) δ 7.53-7.42 (m, 1H), 7.39 (d, J=8.1 Hz, 1H), 7.28 (s, 1H), 7.10 (d, J=7.4 Hz, 1H), 6.75 (d, J=8.1 Hz, 1H), 5.38 (s, 2H), 4.70 (d, J=12.8 Hz, 4H), 1.54 (s, 9H).

5-[(6-bromo-2-pyridyl)oxymethyl]isoindoline; 2,2,2-trifluoroacetic acid: A solution of tert-butyl 5-[(6-bromo-2-pyridyl)oxymethyl]isoindoline-2-carboxylate (399 mg, 0.98 mmol) and TFA (0.38 mL, 4.9 mmol) in DCM (5 mL) was stirred at rt overnight. The mixture was then concentrated to dryness and carried onto the next step without purification. ES/MS: 305, 307 (M+H+).

1-[5-[(6-bromo-2-pyridyl)oxymethyl]isoindolin-2-yl] ethenone (I-1015): To a solution of 5-[(6-bromo-2-pyridyl) oxymethyl]isoindoline; 2,2,2-trifluoroacetic acid (206 mg, 0.491 mmol) and Pyridine (0.0792 mL, 0.983 mmol)) in DCM (5 mL) at 0° C., acetic anhydride (0.0548 mL, 0.580 mmol) was added. The mixture was gradually warmed to rt and stirred overnight. Next, the mixture was diluted with EtOAc, washed with brine, dried over sodium sulfate, concentrated, and purified by chromatography (eluent: EtOAc/hexanes) to give desired product. ES/MS: 347, 349 (M+H+). 1H NMR (400 MHz, Chloroform-d) δ 7.49-7.37 (m, 3H), 7.31 (dd, J=17.0, 7.8 Hz, 1H), 7.10 (d, J=7.5 Hz, 1H), 6.76 (dd, J=8.2, 3.4 Hz, 1H), 5.38 (s, 2H), 4.88-4.71 (m, 4H), 2.19 (s, 3H).

Preparation of Intermediate I-1016

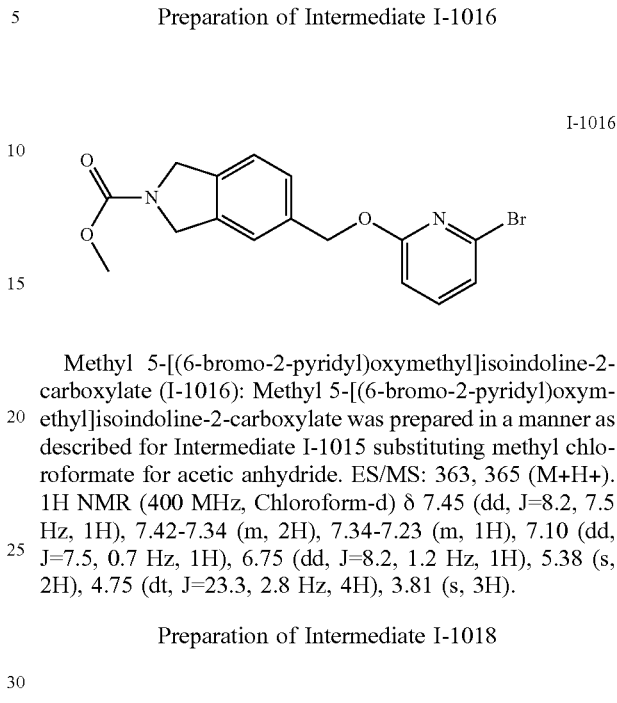

I-1016

Methyl 5-[(6-bromo-2-pyridyl)oxymethyl]isoindoline-2-carboxylate (I-1016): Methyl 5-[(6-bromo-2-pyridyl)oxymethyl]isoindoline-2-carboxylate was prepared in a manner as described for Intermediate I-1015 substituting methyl chloroformate for acetic anhydride. ES/MS: 363, 365 (M+H+). 1H NMR (400 MHz, Chloroform-d) δ 7.45 (dd, J=8.2, 7.5 Hz, 1H), 7.42-7.34 (m, 2H), 7.34-7.23 (m, 1H), 7.10 (dd, J=7.5, 0.7 Hz, 1H), 6.75 (dd, J=8.2, 1.2 Hz, 1H), 5.38 (s, 2H), 4.75 (dt, J=23.3, 2.8 Hz, 4H), 3.81 (s, 3H).

Preparation of Intermediate I-1018

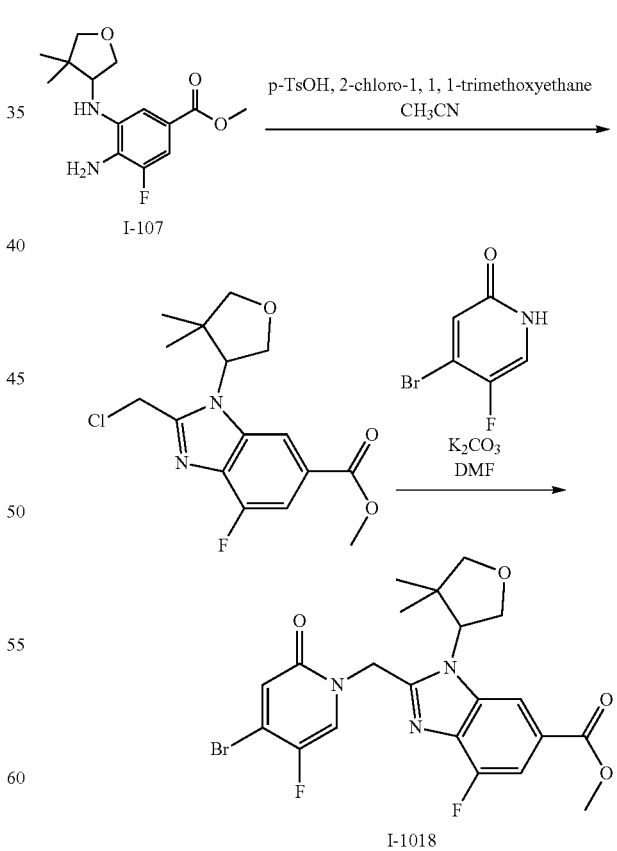

I-1018

Methyl 2-(chloromethyl)-3-(4,4-dimethyltetrahydrofuran-3-yl)-7-fluoro-benzimidazole-5-carboxylate: To a solution of methyl 4-amino-3-[(4,4-dimethyltetrahydrofuran-3-yl)amino]-5-fluoro-benzoate 1-107 (1.13 g, 4.00 mmol) in CH₃CN (20 mL), p-Toluenesulfonic Acid, monohydrate (0.0345 g, 0.200 mmol), and 2-Chloro-1,1,1-trimethoxyethane (0.547 mL, 5.20 mmol) were added. The mixture was heated at 60° C. overnight. Upon completion, more 2-Chloro-1,1,1-trimethoxyethane (0.547 mL, 5.20 mmol) and p-Toluenesulfonic Acid, monohydrate (0.0345 g, 0.200 mmol) were added and then the mixture was heated at 60° C. for 3 hr. Upon completion, the mixture was diluted with EtOAc washed with brine, dried over sodium sulfate, concentrated, and purified by chromatography (eluent: EtOAc/hexanes) to give desired product. ES/MS: 341.2 (M+H+). 1H NMR (400 MHz, Chloroform-d) δ 8.41 (s, 1H), 7.71 (dd, J=10.6, 1.4 Hz, 1H), 4.96 (d, J=12.6 Hz, 1H), 4.90-4.76 (m, 2H), 4.61 (dd, J=11.2, 1.9 Hz, 1H), 4.50 (dd, J=11.2, 7.0 Hz, 1H), 3.97 (d, J=1.2 Hz, 4H), 3.83 (d, J=9.3 Hz, 1H), 1.43 (s, 3H), 0.73 (s, 3H).

Methyl 2-[(4-bromo-5-fluoro-2-oxo-1-pyridyl)methyl]-3-(4,4-dimethyltetrahydrofuran-3-yl)-7-fluoro-benzimidazole-5-carboxylate (I-1018): A suspension of 4-bromo-5-fluoro-1H-pyridin-2-one (115 mg, 0.599 mmol) methyl 2-(chloromethyl)-3-(4,4-dimethyltetrahydrofuran-3-yl)-7-fluoro-benzimidazole-5-carboxylate (205 mg, 0.602 mmol), and potassium carbonate (414 mg, 3.00 mmol) in DMF (3 mL) was heated at 60° C. for 24 hr. Next, the mixture was cooled to rt, diluted with EtOAc, filtered, and concentrated. The mixture was diluted with EtOAc and washed with 5% LiCl and brine. the mixture was dried over sodium sulfate, concentrated, and purified by chromatography (eluent: EtOAc/hexanes) to give desired product. Submitted for chiral-SFC separation (SFC IG column with EtOH cosolvent) gave 2 distinct stereoisomers. ES/MS: 497, 499 (M+H+). 1H NMR (400 MHz, Chloroform-d) δ 8.45 (s, 1H), 7.82 (d, J=3.9 Hz, 1H), 7.72 (dd, J=10.8, 1.2 Hz, 1H), 6.93 (d, J=6.4 Hz, 1H), 5.73 (d, J=14.8 Hz, 1H), 5.28 (d, J=6.6 Hz, 1H), 5.11 (d, J=14.8 Hz, 1H), 4.69-4.36 (m, 2H), 3.97 (s, 3H), 3.90-3.72 (m, 2H), 1.43 (s, 3H), 0.61 (s, 3H).

Preparation of Intermediate I-1019 and I-1020

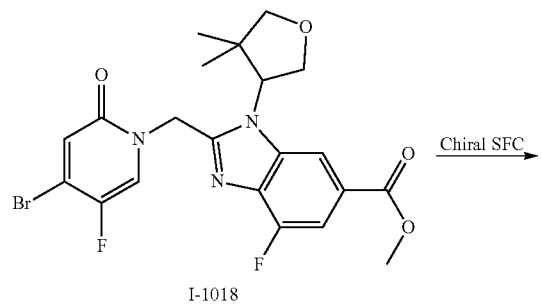

I-1018

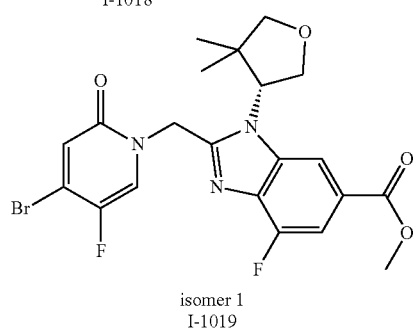

isomer 1
I-1019

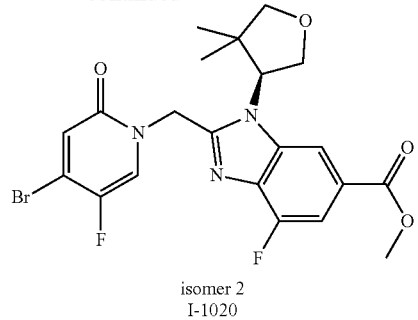

isomer 2
I-1020

Methyl 2-[(4-bromo-5-fluoro-2-oxo-1-pyridyl)methyl]-3-(4,4-dimethyltetrahydrofuran-3-yl)-7-fluoro-benzimidazole-5-carboxylate: Methyl 2-[(4-bromo-5-fluoro-2-oxo-1-pyridyl)methyl]-3-(4,4-dimethyltetrahydrofuran-3-yl)-7-fluoro-benzimidazole-5-carboxylate was submitted for chiral-SFC separation (SFC IG column with EtOH cosolvent) gave 2 distinct stereoisomers.

Methyl 2-[(4-bromo-5-fluoro-2-oxo-1-pyridyl)methyl]-3-(4,4-dimethyltetrahydrofuran-3-yl)-7-fluoro-benzimidazole-5-carboxylate (I-1019 isomer 1): RT 2.46 min. ES/MS: 496, 498 (M+H+). 1H NMR (400 MHz, Chloroform-d) δ 8.46 (s, 1H), 7.82 (d, J=3.9 Hz, 1H), 7.73 (dd, J=10.8, 1.2 Hz, 1H), 6.94 (d, J=6.4 Hz, 1H), 5.74 (d, J=14.8 Hz, 1H), 5.29 (d, J=6.5 Hz, 1H), 5.10 (d, J=14.8 Hz, 1H), 4.68-4.45 (m, 2H), 3.97 (s, 3H), 3.93-3.77 (m, 2H), 1.44 (s, 3H), 0.62 (s, 3H).

Methyl 2-[(4-bromo-5-fluoro-2-oxo-1-pyridyl)methyl]-3-(4,4-dimethyltetrahydrofuran-3-yl)-7-fluoro-benzimidazole-5-carboxylate (I-1020 isomer 2): RT 5.88 min. ES/MS: 496, 498 (M+H+). 1H NMR (400 MHz, Chloroform-d) δ 8.46 (s, 1H), 7.82 (d, J=3.9 Hz, 1H), 7.73 (dd, J=10.8, 1.2 Hz, 1H), 6.94 (d, J=6.4 Hz, 1H), 5.74 (d, J=14.8 Hz, 1H), 5.29 (d, J=6.5 Hz, 1H), 5.10 (d, J=14.8 Hz, 1H), 4.68-4.45 (m, 2H), 3.97 (s, 3H), 3.93-3.77 (m, 2H), 1.44 (s, 3H), 0.62 (s, 3H).

Preparation of Intermediate I-1021

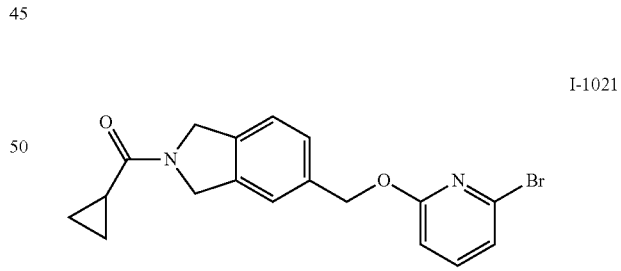

I-1021

[5-[(6-bromo-2-pyridyl)oxymethyl]isoindolin-2-yl]-cyclopropyl-methanone (I-1021): [5-[(6-bromo-2-pyridyl)oxymethyl]isoindolin-2-yl]-cyclopropyl-methanone was prepared in a manner as described for Intermediate I-1015 substituting cyclopropane carboxylic acid chloride for acetic anhydride. ES/MS: 373, 375 (M+H+). 1H NMR (400 MHz, Chloroform-d) δ 7.49-7.37 (m, 3H), 7.32 (t, J=8.7 Hz, 1H), 7.11 (d, J=7.5 Hz, 1H), 6.76 (d, J=8.1 Hz, 1H), 5.39 (s, 2H), 5.10-4.91 (m, 2H), 4.84 (d, J=5.8 Hz, 2H), 1.75 (dq, J=8.2, 4.6, 4.1 Hz, 1H), 1.09 (dt, J=4.8, 3.3 Hz, 2H), 0.87 (dt, J=7.9, 3.4 Hz, 2H).

Preparation of Intermediate I-1022

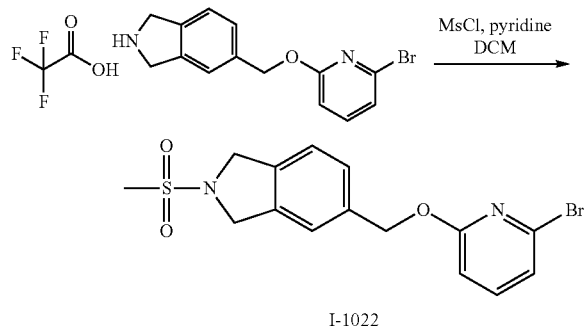

I-1022

5-[(6-bromo-2-pyridyl)oxymethyl]-2-methylsulfonyl-isoindoline (I-1022): A suspension of 5-[(6-bromo-2-pyridyl)oxymethyl]isoindoline; 2,2,2-trifluoroacetic acid (206 mg, 0.491 mmol) was washed with saturated NaHCO$_3$. The mixture was then dried with sodium sulfate to give free amine, which was then dissolved in DCM (5 mL). The solution was cooled to 0° C. Next, pyridine (0.0292 mL, 0.363 mmol) was added, followed by a solution of methanesulfonyl chloride (1.00 mmol/L, 174 mL, 0.174 mmol). The resulting mixture was gradually warmed to rt and stirred overnight. Next, the mixture was diluted with EtOAc and washed with brine. The mixture was then dried over sodium sulfate, concentrated, and purified by chromatography (eluent: EtOAc/hexanes) to give desired product. ES/MS: 383, 385 (M+H+). 1H NMR (400 MHz, Chloroform-d) δ 7.49-7.37 (m, 3H), 7.29 (d, J=7.6 Hz, 1H), 7.11 (dd, J=7.5, 0.7 Hz, 1H), 6.76 (dd, J=8.1, 0.7 Hz, 1H), 5.39 (s, 2H), 4.74 (t, J=2.5 Hz, 4H), 2.90 (s, 3H).

Preparation of Intermediate I-1023

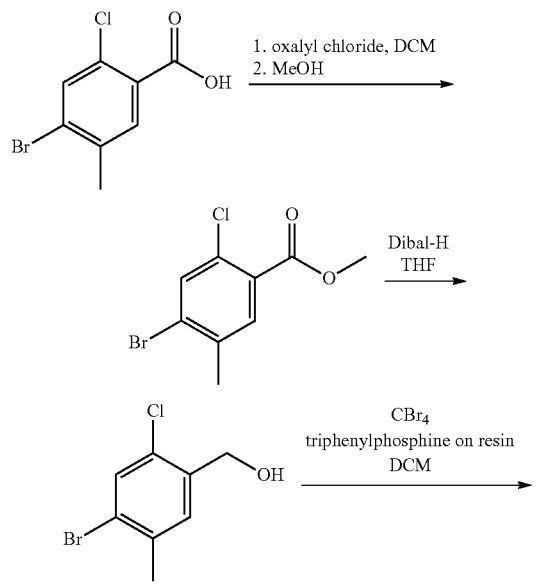

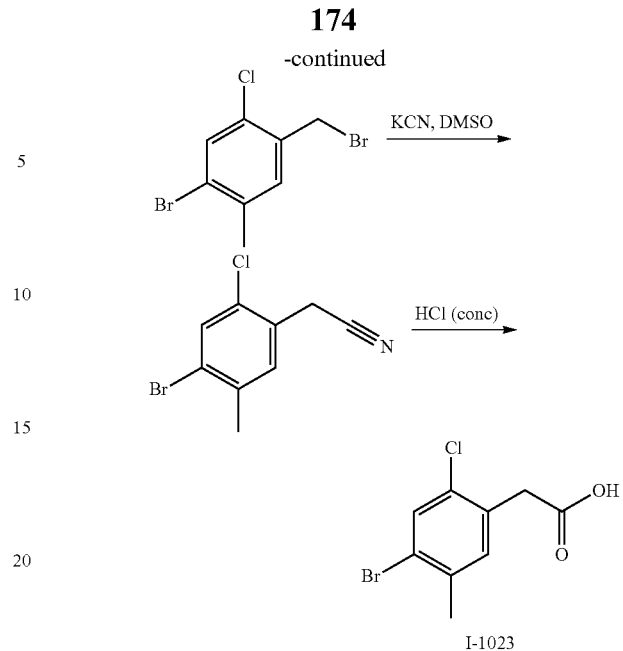

I-1023

2-(4-bromo-2-chloro-5-methyl-phenyl)acetic acid (I-1023): To a solution of 4-bromo-2-chloro-5-methyl-benzoic acid (996 mg, 3.99 mmol) in DCM (10 mL) at 0° C., oxalyl dichloride (2000 mmol/L, 2.40 mL, 4.79 mmol) and 5 drops of DMF were added. The resulting mixture was stirred for 1 hr., then 10 mL MeOH was added and the resulting mixture was stirred overnight at rt. Next, the mixture was diluted with DCM, washed with saturated NaHCO$_3$, dried over sodium sulfate, concentrated, and purified by chromatography (eluent: EtOAc/hexanes) to give desired product. 1H NMR (400 MHz, Chloroform-d) δ 7.74 (s, 1H), 7.68 (d, J=1.1 Hz, 1H), 3.94 (d, J=1.2 Hz, 3H), 2.42 (s, 3H).

(4-bromo-2-chloro-5-methyl-phenyl)methanol: To a solution of methyl 4-bromo-2-chloro-5-methyl-benzoate (931 mg, 3.53 mmol) in THF (15 mL) at 0° C., diisobutylaluminium hydride (1000 mmol/L, 8.83 mL, 8.83 mmol) was added. The mixture was then stirred for 1 hr. Next, the mixture was diluted with 25 mL Et$_2$O and cooled to 0° C. Next, 0.350 mL water, and 0.350 mL 15% NaOH were added, then an additional 0.900 mL water was added. The mixture was then warmed to rt and stirred for 15 min. Next, MgSO$_4$ was added and the resulting mixture was stirred 15 min, filtered and rinsed with Et$_2$O to give crude residue which was purified by chromatography (eluent: EtOAc/hexanes) to give desired product. 1H MR (400 MHz, Chloroform-d) δ 7.56 (d, J=1.4 Hz, 1H), 7.38 (s, 1H), 4.73 (s, 2H), 2.41 (d, J=1.3 Hz, 4H).

1-bromo-4-(bromomethyl)-5-chloro-2-methyl-benzene: To a solution of (4-bromo-2-chloro-5-methyl-phenyl)methanol (639 mg, 2.71 mmol) and (4-diphenylphosphanylphenyl) polymer bound (78.7%, 1081 mg, 3.26 mmol), in DCM (10 mL) at 0° C., carbon tetrabromide (1080 mg, 3.26 mmol) was added. The mixture was then gradually warmed to rt overnight. Next, the mixture was filtered, diluted with DCM and washed with brine. The organic extract was dried over sodium sulfate, concentrated and purified by chromatography (eluent: EtOAc/hexanes) to give desired product. 1H NMR (400 MHz, Chloroform-d) δ 7.60 (s, 1H), 7.32 (s, 1H), 4.53 (s, 2H), 2.39 (s, 3H).

2-(4-bromo-2-chloro-5-methyl-phenyl)acetonitrile: To a solution of 1-bromo-4-(bromomethyl)-5-chloro-2-methylbenzene (721 mg, 2.42 mmol) in DMSO (12 ml) at rt, potassium cyanide (315 mg, 4.83 mmol) was added. The mixture was then stirred at rt overnight. The mixture was diluted with EtOAc and washed with 10% Na₂CO₃. The organic extract was washed once more with brine, then dried over sodium sulfate to give desired product. 1H NMR (400 MHz, Chloroform-d) δ 7.62 (s, 1H), 7.52-7.33 (m, 1H), 3.78 (s, 2H), 2.42 (s, 3H).

2-(4-bromo-2-chloro-5-methyl-phenyl)acetic acid (I-1023): A solution of 2-(4-bromo-2-chloro-5-methyl-phenyl)acetonitrile (179 mg, 0.732 mmol) in concentrated HCl (5 mL) was heated at 100° C. overnight. The mixture was then cooled to rt, and diluted with EtOAc, and neutralized carefully with 6 N NaOH (10 mL). Next the organic extract was dried over sodium sulfate to give desired product. 1H NMR (400 MHz, Methanol-d4) δ 7.59 (s, 1H), 7.29 (s, 1H), 3.71 (s, 2H), 2.37 (s, 3H).

Preparation of Intermediate I-1024

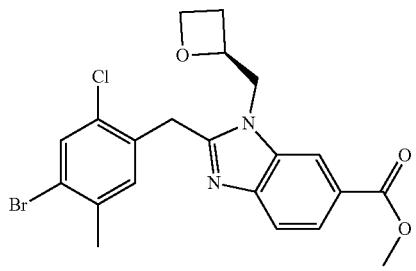

I-1024

Methyl 2-[(4-bromo-2-chloro-5-methyl-phenyl)methyl]-3-[[(2S)-oxetan-2-yl]methyl]benzimidazole-5-carboxylate (I-1024): methyl 2-[(4-bromo-2-chloro-5-methyl-phenyl)methyl]-3-[[(2S)-oxetan-2-yl]methyl]benzimidazole-5-carboxylate was prepared in a manner as described for Intermediate I-2 substituting I-4 for I-1 and 2-(4-bromo-2-chloro-5-methyl-phenyl)acetic acid (I-1023) for 2-(4-bromo-2-fluoro-phenyl)acetic acid. ES/MS: 463, 465 (M+H+). 1H NMR (400 MHz, Chloroform-d) δ 8.12 (d, J=1.6 Hz, 1H), 8.00 (dd, J=8.5, 1.4 Hz, 1H), 7.78 (d, J=8.5 Hz, 1H), 7.62 (s, 1H), 7.13 (s, 1H), 5.13 (dd, J=7.1, 2.9 Hz, 1H), 4.77-4.59 (m, 1H), 4.59-4.23 (m, 5H), 3.97 (d, J=1.0 Hz, 3H), 2.74 (ddt, J=14.1, 11.7, 6.6 Hz, 1H), 2.52-2.35 (m, 1H), 2.29 (s, 3H).

Preparation of Intermediate I-1025

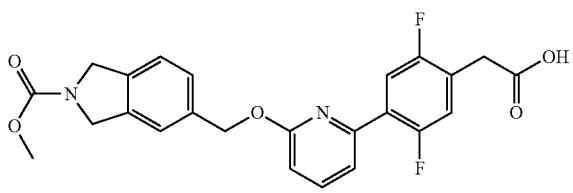

I-1025

2-[2,5-difluoro-4-[6-[(2-methoxycarbonylisoindolin-5-yl)methoxy]-2-pyridyl]phenyl]acetic acid (I-1025): 2-[2,5-difluoro-4-[6-[(2-methoxycarbonylisoindolin-5-yl)methoxy]-2-pyridyl]phenyl]acetic acid was prepared in a manner as described for Intermediate I-7 substituting methyl 5-[(6-bromo-2-pyridyl)oxymethyl]isoindoline-2-carboxylate (I-1016) for I-3. ES/MS: 455.1 (M+H+). 1H NMR (400 MHz, Methanol-d4) δ 7.82-7.65 (m, 2H), 7.53-7.45 (m, 2H), 7.44 (d, J=7.3 Hz, 2H), 7.32 (dd, J=10.9, 8.0 Hz, 1H), 7.23-7.09 (m, 1H), 6.85 (d, J=8.2 Hz, 1H), 5.48 (s, 2H), 4.71 (d, J=4.2 Hz, 4H), 3.78 (s, 3H), 3.73 (d, J=1.3 Hz, 2H).

Preparation of Intermediate I-1026

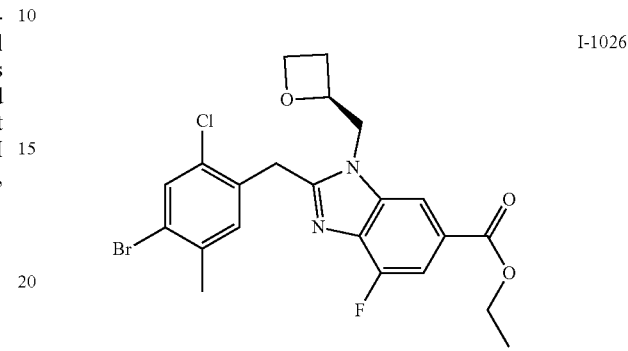

I-1026

Ethyl 4-[[2-(4-bromo-2-chloro-5-methyl-phenyl)acetyl]amino]-3-fluoro-5-[[(2S)-oxetan-2-yl]methylamino]benzoate: To a solution of 2-(4-bromo-2-chloro-5-methyl-phenyl)acetic acid (501 mg, 1.90 mmol) and ethyl 4-amino-3-fluoro-5-[[(2S)-oxetan-2-yl]methylamino]benzoate (510 mg, 1.90 mmol) in CH₃CN (19 mL) at 0° C., 1-Methylimidazole (0.758 mL, 9.50 mmol) was added, followed by the addition of TCFH (640 mg, 2.28 mmol). The mixture was stirred at rt overnight. Next, the mixture was diluted with EtOAc, washed with saturated NH₄C₁, 1N NaOH, and brine, and then subsequently dried over sodium sulfate, concentrated, and carried onto next step below. ES/MS: 513, 515 (M+H+).

Ethyl 2-[(4-bromo-2-chloro-5-methyl-phenyl)methyl]-7-fluoro-3-[[(2S)-oxetan-2-yl]methyl]benzimidazole-5-carboxylate (I-1026): A solution of ethyl 4-[[2-(4-bromo-2-chloro-5-methyl-phenyl)acetyl]amino]-3-fluoro-5-[[(2S)-oxetan-2-yl]methylamino]benzoate (977 mg, 1.90 mmol) and acetic acid (3426 mg, 57.0 mmol) in DCE (15 mL) was heated at 60° C. overnight. The mixture was cooled to rt, diluted with EtOAc and carefully neutralized with NaHCO₃ (4.78 g). The organic layer was washed with brine and dried over sodium sulfate and concentrated. Purification by chromatography (eluent: EtOAc/hexanes) gave desired product. ES/MS: 495, 497 (M+H+). 1H NMR (400 MHz, Chloroform-d) δ 7.94 (d, J=1.3 Hz, 1H), 7.69 (dd, J=11.0, 1.3 Hz, 1H), 7.62 (s, 1H), 7.12 (s, 1H), 5.08 (qd, J=6.9, 2.8 Hz, 1H), 4.74-4.59 (m, 1H), 4.59-4.24 (m, 8H), 2.73 (dtd, J=11.4, 8.1, 6.1 Hz, 1H), 2.39 (ddt, J=11.5, 9.0, 7.2 Hz, 1H), 2.29 (s, 3H), 1.44 (t, J=7.2 Hz, 3H).

Preparation of Intermediate I-1027

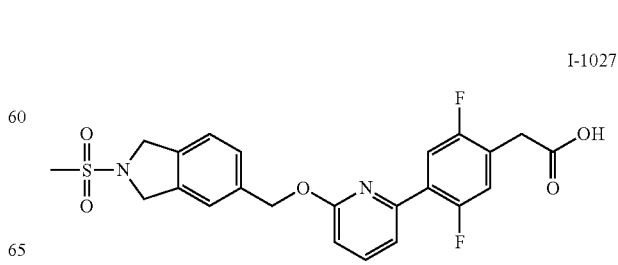

I-1027

2-[2,5-difluoro-4-[6-[(2-methylsulfonylisoindolin-5-yl)methoxy]-2-pyridyl]phenyl]acetic acid (I-1027): 2-[2,5-difluoro-4-[6-[(2-methylsulfonylisoindolin-5-yl)methoxy]-2-pyridyl]phenyl]acetic acid was prepared in a manner as described for Intermediate I-7 substituting 5-[(6-bromo-2-pyridyl)oxymethyl]-2-methylsulfonyl-isoindoline (I-1022) for I-3. ES/MS: 475.0 (M+H+). 1H NMR (400 MHz, Methanol-d4) δ 7.75 (t, J=7.8 Hz, 1H), 7.67 (dd, J=10.7, 6.5 Hz, 1H), 7.53-7.43 (m, 3H), 7.33 (d, J=7.8 Hz, 1H), 7.19 (dd, J=11.9, 6.2 Hz, 1H), 6.83 (d, J=8.2 Hz, 1H), 5.51 (s, 2H), 4.71 (d, J=4.7 Hz, 5H), 3.56 (s, 2H), 2.92 (s, 3H).

Preparation of Intermediate I-1028

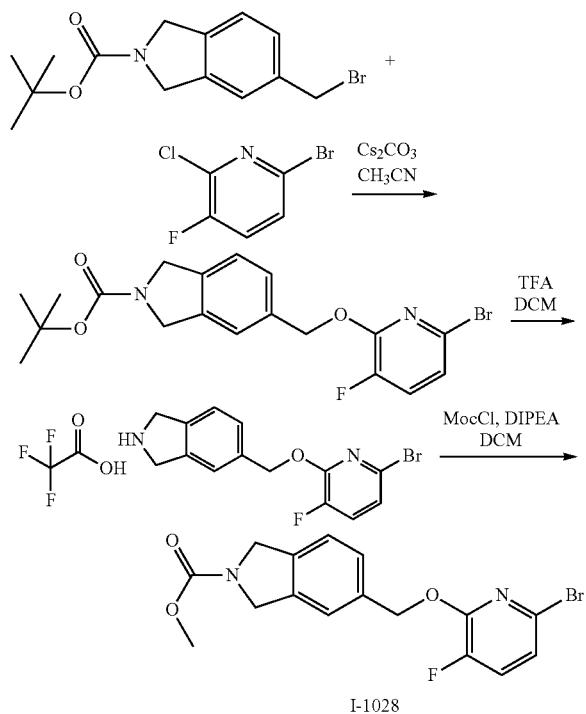

Tert-butyl 5-[(6-bromo-3-fluoro-2-pyridyl)oxymethyl]isoindoline-2-carboxylate: A suspension of 6-bromo-2-chloro-3-fluoro-pyridine (1000 mg, 4.75 mmol), tert-butyl 5-(hydroxymethyl)isoindoline-2-carboxylate (1.18 g, 4.75 mmol), and cesium carbonate (3.10 g, 9.50 mmol) in CH₃CN (20 mL) was heated at 60° C. for 30 hr. Upon completion the solid was filtered off, the filtrate was diluted with EtOAc and washed with brine. Next, the filtrate was dried over sodium sulfate, concentrated, and purified by chromatography (eluent: EtOAc/hexanes) to give desired product. ES/MS: 366.8, 368.8 (M+H+). 1H NMR (400 MHz, Chloroform-d) δ 7.41 (q, J=7.9, 6.4 Hz, 2H), 7.33-7.18 (m, 2H), 7.04 (dd, J=8.1, 2.7 Hz, 1H), 5.45 (s, 2H), 4.78-4.63 (m, 4H), 1.54 (s, 9H).

5-[(6-bromo-3-fluoro-2-pyridyl)oxymethyl]isoindoline; 2,2,2-trifluoroacetic acid: A solution of tert-butyl 5-[(6-bromo-3-fluoro-2-pyridyl)oxymethyl]isoindoline-2-carboxylate (449 mg, 1.1 mmol) and TFA (0.81 mL, 11 mmol) in DCM (5 mL) was stirred at rt overnight. The mixture was concentrated to dryness and carried onto the next step without purification. ES/MS: 323.2, 325.2 (M+H+).

Methyl 5-[(6-bromo-3-fluoro-2-pyridyl)oxymethyl]isoindoline-2-carboxylate (I-1028): To a solution of 5-[(6-bromo-3-fluoro-2-pyridyl)oxymethyl]isoindoline; 2,2,2-trifluoroacetic acid (464 mg, 1.06 mmol) and N,N-diisopropylethylamine (0.370 mL, 2.12 mmol) in DCM (10 mL) at 0° C., methyl chloroformate (0.107 mL, 1.38 mmol) was added. The resulting mixture was gradually warmed to rt and stirred overnight. Next, the mixture was diluted with EtOAc and washed with brine. Dried over sodium sulfate, concentrated, and purified by chromatography (eluent: EtOAc/hexanes) to give desired product. ES/MS: 381, 383 (M+H+). 1H NMR (400 MHz, Chloroform-d) δ 7.48-7.37 (m, 2H), 7.31 (d, J=7.8 Hz, 1H), 7.25 (dd, J=9.3, 8.1 Hz, 1H), 7.05 (dd, J=8.1, 2.7 Hz, 1H), 5.46 (s, 2H), 4.83-4.66 (m, 4H), 3.81 (s, 3H).

Preparation of Intermediate I-1029

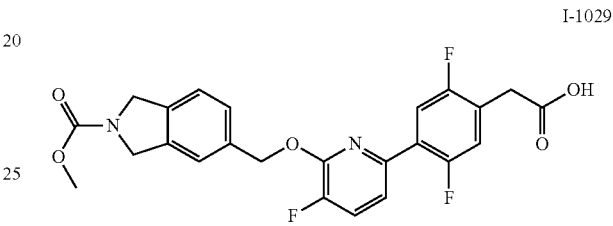

2-[2,5-difluoro-4-[5-fluoro-6-[(2-methoxycarbonylisoindolin-5-yl)methoxy]-2-pyridyl]phenyl]acetic acid (I-1029): 2-[2,5-difluoro-4-[5-fluoro-6-[(2-methoxycarbonylisoindolin-5-yl)methoxy]-2-pyridyl]phenyl]acetic acid was prepared in a manner as described for Intermediate I-7 substituting methyl 5-[(6-bromo-3-fluoro-2-pyridyl)oxymethyl]isoindoline-2-carboxylate (I-1028) for I-3. ES/MS: 473.0 (M+H+). 1H NMR (400 MHz, Methanol-d4) δ 7.68 (dd, J=10.7, 6.4 Hz, 1H), 7.57 (dd, J=9.9, 8.2 Hz, 1H), 7.53-7.41 (m, 3H), 7.40-7.29 (m, 1H), 7.22 (dd, J=11.6, 6.1 Hz, 1H), 5.56 (s, 2H), 4.71 (d, J=5.2 Hz, 4H), 3.78 (s, 3H), 3.73 (s, 2H).

Preparation of Intermediate I-1030

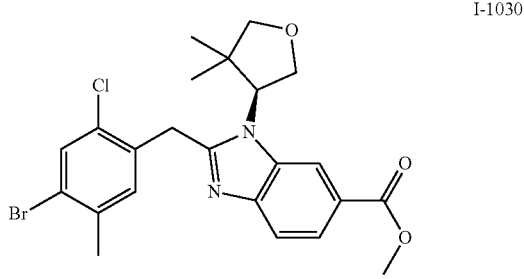 [SMILES: COC(=O)c1ccc2nc(Cc3cc(C)c(Br)cc3Cl)n([C@@H]3COCC3(C)C)c2c1]

Methyl 2-[(4-bromo-2-chloro-5-methyl-phenyl)methyl]-3-[(3S)-4,4-dimethyltetrahydrofuran-3-yl]benzimidazole-5-carboxylate (I-1030): Methyl 2-[(4-bromo-2-chloro-5-methyl-phenyl)methyl]-3-[(3S)-4,4-dimethyltetrahydrofuran-3-yl]benzimidazole-5-carboxylate was prepared in a manner as described for Intermediate I-2 substituting 1-80 for I-1 and 2-(4-bromo-2-chloro-5-methyl-phenyl)acetic acid (I-1023) for 2-(4-bromo-2-fluoro-phenyl)acetic acid. ES/MS: 490.6, 492.6 (M+H+). 1H NMR (400 MHz, Chloroform-d) δ 8.56 (s, 1H), 8.02 (dd, J=8.5, 1.4 Hz, 1H), 7.80 (d, J=8.5 Hz, 1H), 7.64 (s, 1H), 7.06 (s, 1H), 4.60-4.47 (m, 2H), 4.45-4.26 (m, 3H), 3.95 (d, J=10.4 Hz, 5H), 3.78 (d, J=8.8 Hz, 1H), 2.28 (s, 3H), 2.07 (s, 1H), 1.31 (s, 3H), 0.67 (s, 3H).

Preparation of Intermediate I-1031

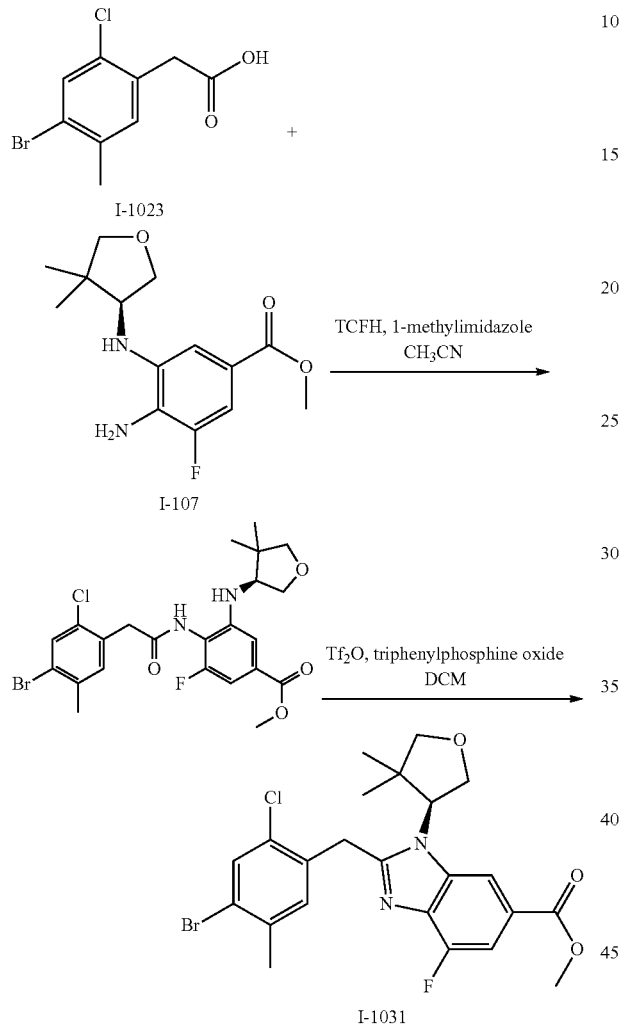

Methyl 4-[[2-(4-bromo-2-chloro-5-methyl-phenyl)acetyl]amino]-3-[[(3S)-4,4-dimethyltetrahydrofuran-3-yl]amino]-5-fluoro-benzoate: To a solution of 2-(4-bromo-2-chloro-5-methyl-phenyl)acetic acid (399 mg, 1.51 mmol) and methyl 4-amino-3-[[(3S)-4,4-dimethyltetrahydrofuran-3-yl]amino]-5-fluoro-benzoate (427 mg, 1.51 mmol) in CH$_3$CN (7 mL) at 0° C., 1-Methylimidazole (0.603 mL, 7.56 mmol) was added, followed by the addition of TCFH (509 mg, 1.82 mmol). The resulting mixture was stirred at rt overnight. Next, the mixture was diluted with EtOAc and washed with saturated NH$_4$C$_1$, 1N NaOH, and brine. Next, the mixture was dried over sodium sulfate, concentrated and carried onto next step below without purification. ES/MS: 527, 529 (M+H+).

Methyl 2-[(4-bromo-2-chloro-5-methyl-phenyl)methyl]-3-[(3S)-4,4-dimethyltetrahydrofuran-3-yl]-7-fluoro-benzimidazole-5-carboxylate (I-1031): To a solution of methyl 4-[[2-(4-bromo-2-chloro-5-methyl-phenyl)acetyl]amino]-3-[[(3S)-4,4-dimethyltetrahydrofuran-3-yl]amino]-5-fluoro-benzoate (798 mg, 1.51 mmol) and Triphenylphosphine oxide (1262 mg, 4.54 mmol) in DCM (15 mL) at 0° C., Triflic anhydride (1000 mmol/L, 2.27 mL, 2.27 mmol) was added. The resulting mixture was gradually warmed to rt and stirred for 1 hr. Next, the mixture was diluted with DCM and washed with saturated NaHCO$_3$ solution and brine. The mixture was then dried over sodium sulfate, concentrated and purified by chromatography (eluent: EtOAc/hexanes) to give desired product. ES/MS: 508.6, 510.6 (M+H+). 1H NMR (400 MHz, Chloroform-d) δ 8.38 (s, 1H), 7.71 (dd, J=10.8, 1.2 Hz, 1H), 7.64 (s, 1H), 7.06 (s, 1H), 4.55-4.42 (m, 2H), 4.41 (d, J=2.8 Hz, 2H), 4.32 (dd, J=11.0, 7.0 Hz, 1H), 3.97 (s, 3H), 3.92 (d, J=8.8 Hz, 1H), 3.77 (d, J=8.8 Hz, 1H), 2.27 (s, 3H), 1.29 (s, 3H), 0.64 (s, 3H).

Preparation of Intermediate I-1032

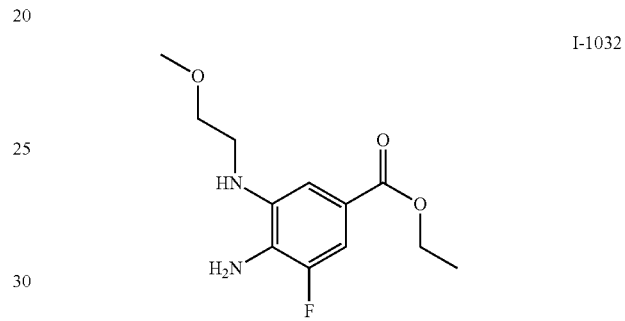

Ethyl (S)-4-amino-3-fluoro-5-((oxetan-2-ylmethyl)amino)benzoate (I-1032): Ethyl (S)-4-amino-3-fluoro-5-((oxetan-2-ylmethyl)amino)benzoate was prepared in a manner as described for Intermediate I-1 substituting ethyl 3,5-difluoro-4-nitrobenzoate for methyl 3-fluoro-4-nitrobenzoate. ES/MS: 257.2 (M+H+); $^1$H NMR (400 MHz, CDCl3) δ 7.32 (dd, J=10.8, 1.7 Hz, 1H), 7.20 (t, J=1.4 Hz, 1H), 4.35 (q, J=7.1 Hz, 2H), 3.78 (s, 3H), 3.68 (dd, J=5.6, 4.5 Hz, 2H), 3.43 (s, 3H), 3.35 (dd, J=5.6, 4.5 Hz, 2H), 1.39 (t, J=7.1 Hz, 3H).

Preparation of Intermediate I-1033

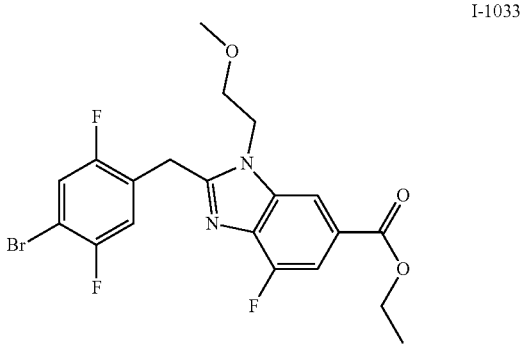 [SMILES: CCOC(=O)c1cc(F)c2nc(Cc3cc(F)c(Br)cc3F)n(CCOC)c2c1]

Ethyl 2-(4-bromo-2,5-difluorobenzyl)-4-fluoro-1-(2-methoxyethyl)-1H-benzo[d]imidazole-6-carboxylate (I-1033): Ethyl 2-(4-bromo-2,5-difluorobenzyl)-4-fluoro-1-(2-methoxyethyl)-1H-benzo[d]imidazole-6-carboxylate was prepared in a manner as described for Intermediate I-2 substituting ethyl 4-amino-3-fluoro-5-((2-methoxyethyl) amino)benzoate (I-1032) for I-1 and 2-(4-bromo-2,5-difluorophenyl)acetic acid for 2-(4-bromo-2-fluoro-phenyl)acetic acid. ES/MS: 471.0, 473.0 (M+H+). 1H NMR (400 MHz, CDCl3) δ 7.91 (d, J=1.3 Hz, 1H), 7.70 (dd, J=10.8, 1.3 Hz, 1H), 7.34 (dd, J=8.7, 5.5 Hz, 1H), 7.12 (dd, J=8.6, 6.3 Hz, 1H), 4.44 (q, J=7.1 Hz, 2H), 4.39 (s, 2H), 4.37-4.29 (m, 2H), 3.66 (t, J=5.1 Hz, 2H), 3.25 (s, 3H), 1.45 (t, J=7.1 Hz, 3H).

Preparation of Intermediate I-1034

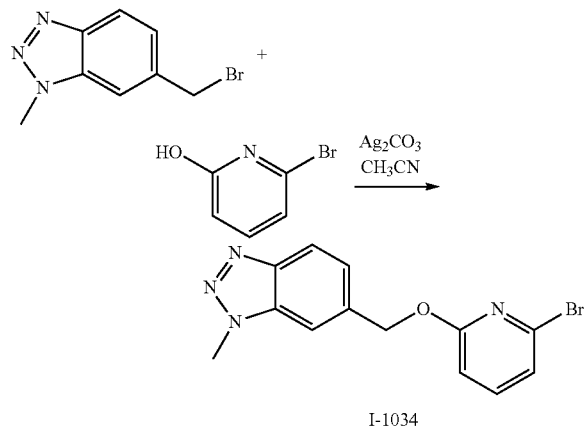

q6-[(6-bromo-2-pyridyl)oxymethyl]-1-methyl-benzotriazole (I-1034): A suspension of 6-(bromomethyl)-1-methyl-benzotriazole (62 mg, 0.28 mmol), 6-bromopyridin-2-ol (60 mg, 0.34 mmol), and silver carbonate (203 mg, 0.74 mmol) in CH$_3$CN (5 mL) was heated at 50° C. overnight. Next, the mixture was diluted with EtOAc and brine. The mixture was then filtered over Celite frit and partitioned. The partitioned layers were washed and separated. The organic layer was washed once more with brine, then dried over sodium sulfate, concentrated, and purified by chromatography (eluent: EtOAc/hexanes) to give desired product. ES/MS: 318.8, 320.8 (M+H+). 1H NMR (400 MHz, Chloroform-d) δ 8.08 (d, J=8.6 Hz, 1H), 7.71 (s, 1H), 7.48 (dd, J=8.4, 7.1 Hz, 2H), 7.13 (d, J=7.4 Hz, 1H), 6.80 (d, J=8.1 Hz, 1H), 5.57 (s, 2H), 4.35 (s, 3H).

Preparation of Intermediate I-1035

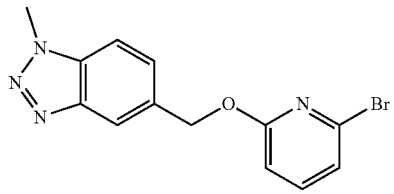

5-[(6-bromo-2-pyridyl)oxymethyl]-1-methyl-benzotriazole (I-1035): 5-[(6-bromo-2-pyridyl)oxymethyl]-1-methyl-benzotriazole was prepared in a manner as described for Intermediate I-1034 substituting 5-(bromomethyl)-1-methyl-benzotriazole for 6-(bromomethyl)-1-methyl-benzotriazole. ES/MS: 318.8, 320.8 (M+H+). 1H NMR (400 MHz, Chloroform-d) δ 8.18 (t, J=1.1 Hz, 1H), 7.65 (dd, J=8.5, 1.4 Hz, 1H), 7.55 (dd, J=8.5, 0.9 Hz, 1H), 7.47 (dd, J=8.1, 7.5 Hz, 1H), 7.11 (d, J=7.5 Hz, 1H), 6.78 (d, J=8.2 Hz, 1H), 5.55 (s, 2H), 4.34 (s, 3H).

Preparation of Intermediate I-1036

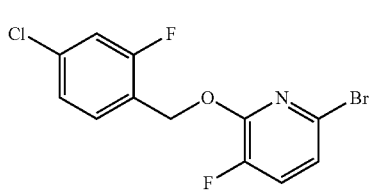

6-bromo-2-[(4-chloro-2-fluoro-phenyl)methoxy]-3-fluoro-pyridine (I-1036): 6-bromo-2-[(4-chloro-2-fluorophenyl)methoxy]-3-fluoro-pyridine was prepared in a manner as described for Intermediate I-1034 substituting 1-(bromomethyl)-4-chloro-2-fluoro-benzene for 6-(bromomethyl)-1-methyl-benzotriazole and 6-bromo-3-fluoropyridin-2-ol for 6-bromopyridin-2-ol. 1H NMR (400 MHz, Chloroform-d) δ 7.51 (t, J=8.0 Hz, 1H), 7.30-7.22 (m, 1H), 7.21-7.11 (m, 2H), 7.07 (dd, J=8.1, 2.7 Hz, 1H), 5.48 (d, J=1.2 Hz, 2H).

Preparation of Intermediate I-1037

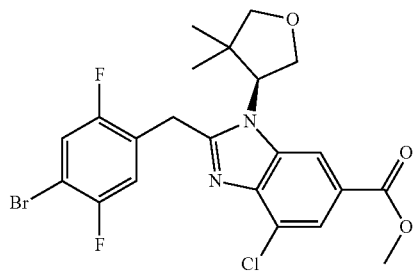

Methyl 2-[(4-bromo-2,5-difluoro-phenyl)methyl]-7-chloro-3-[(3S)-4,4-dimethyltetrahydrofuran-3-yl]benzimidazole-5-carboxylate (I-1037): Methyl 2-[(4-bromo-2,5-difluoro-phenyl)methyl]-7-chloro-3-[(3S)-4,4-dimethyltetrahydrofuran-3-yl]benzimidazole-5-carboxylate was prepared in a manner as described for Intermediate I-1031 substituting 2-(4-bromo-2,5-difluoro-phenyl)acetic acid for 2-(4-bromo-2-chloro-5-methyl-phenyl)acetic acid and methyl 4-amino-3-chloro-5-[[(3S)-4,4-dimethyltetrahydrofuran-3-yl]amino]benzoate I-1038 for methyl 4-amino-3-[[(3S)-4,4-dimethyltetrahydrofuran-3-yl]amino]-5-fluoro-benzoate. ES/MS: 513.0, 514.9 (M+H+). 1H NMR (400 MHz, Chloroform-d) δ 8.50 (s, 1H), 8.07 (d, J=1.3 Hz, 1H), 7.38 (dd, J=8.7, 5.6 Hz, 1H), 7.23-7.07 (m, 1H), 4.61-4.40 (m, 3H), 4.40-4.29 (m, 2H), 3.97 (s, 3H), 3.92 (d, J=8.9 Hz, 1H), 3.78 (d, J=8.9 Hz, 1H), 1.32 (s, 3H), 0.63 (s, 3H).

Preparation of Intermediate I-1038

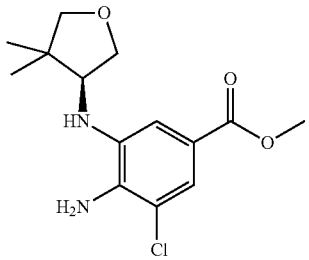

Methyl 4-amino-3-chloro-5-[[(3S)-4,4-dimethyltetrahydrofuran-3-yl]amino]benzoate (I-1038): Methyl 4-amino-3-chloro-5-[[(3S)-4,4-dimethyltetrahydrofuran-3-yl]amino]benzoate was prepared in a manner as described for Intermediate I-68 substituting methyl 3-chloro-5-fluoro-4-nitro-benzoate for methyl 3-bromo-5-fluoro-4-nitro-benzoate. ES/MS: 299.2 (M+).

Preparation of Intermediate I-1041

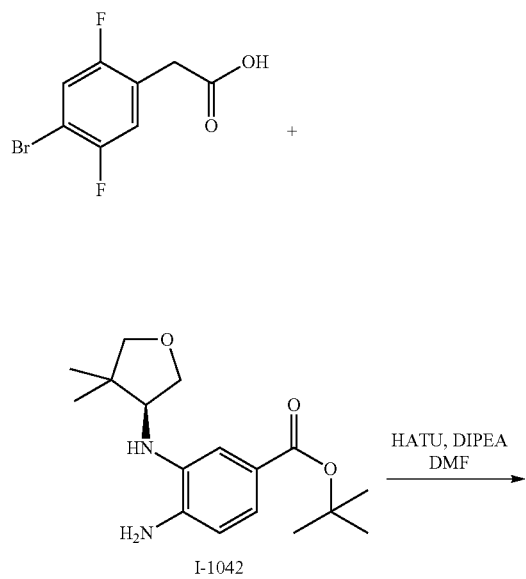

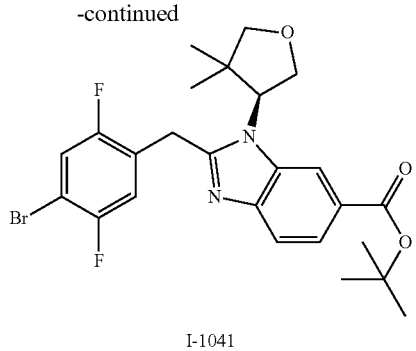

Tert-butyl 4-[[2-(4-bromo-2,5-difluoro-phenyl)acetyl]amino]-3-[[(3S)-4,4-dimethyltetrahydrofuran-3-yl]amino]benzoate: To a solution of 2-(4-bromo-2,5-difluoro-phenyl)acetic acid (575 mg, 2.29 mmol), tert-butyl 4-amino-3-[[(3S)-4,4-dimethyltetrahydrofuran-3-yl]amino]benzoate (696 mg, 2.27 mmol), and o-(7-Azabenzotriazol-1-yl)-N,N,N',N'-tetramethyluronium hexafluorophosphate (1292 mg, 3.40 mmol) in DMF (10 mL), N,N-diisopropylethylamine (1.22 mL, 6.98 mmol was added). The mixture was stirred at rt overnight. Next the mixture was diluted with EtOAc and washed with 5% LiCl, saturated NaHCO₃, and brine. Dried over sodium sulfate, concentrated and carried onto next step below without purification. ES/MS: 539, 541 (M+H+).

Tert-butyl 2-[(4-bromo-2,5-difluoro-phenyl)methyl]-3-[(3S)-4,4-dimethyltetrahydrofuran-3-yl]benzimidazole-5-carboxylate (I-1041): To a solution of tert-butyl 4-[[2-(4-bromo-2,5-difluoro-phenyl)acetyl]amino]-3-[[(3S)-4,4-dimethyltetrahydrofuran-3-yl]amino]-5-fluoro-benzoate (1236 mg, 2.22 mmol) and triphenylphosphine oxide, 99% (1851 mg, 6.65 mmol) in DCM (20 mL) at 0° C., triflic anhydride (0.559 mL, 3.33 mmol) was added. The mixture was gradually warmed to rt and stirred for 1 hr. Next, the mixture was diluted with DCM and washed with saturated NaHCO₃ solution and brine. Next, the mixture was dried over sodium sulfate, concentrated and purified by chromatography (eluent: EtOAc/hexanes) to give desired product. ES/MS: 521, 523 (M+H+). 1H NMR (400 MHz, Chloroform-d) δ 8.55 (s, 1H), 7.97 (dd, J=8.5, 1.5 Hz, 1H), 7.77 (d, J=8.5 Hz, 1H), 7.37 (dd, J=8.7, 5.5 Hz, 1H), 7.15 (t, J=7.4 Hz, 1H), 4.59 (t, J=8.9 Hz, 2H), 4.47-4.25 (m, 3H), 3.96 (d, J=8.8 Hz, 1H), 3.81 (d, J=8.8 Hz, 1H), 1.34 (s, 3H), 0.66 (s, 3H).

Preparation of Intermediate I-1042

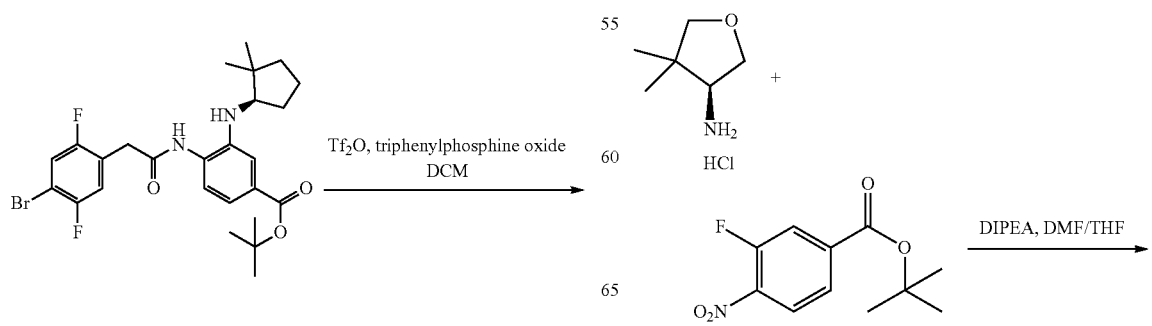

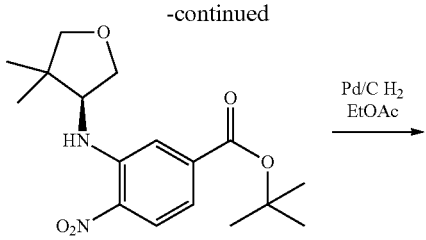

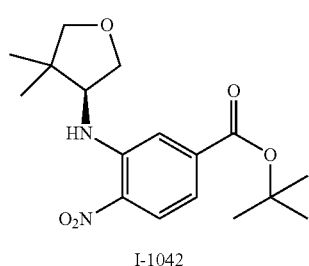

I-1042

Tert-butyl 3-[[(3S)-4,4-dimethyltetrahydrofuran-3-yl]amino]-4-nitro-benzoate: To a suspension of tert-butyl 3-fluoro-4-nitro-benzoate (3.50 g, 14.5 mmol), (3S)-4,4-dimethyltetrahydrofuran-3-amine; hydrochloride (2.50 g, 16.5 mmol) and (3S)-4,4-dimethyltetrahydrofuran-3-amine; hydrochloride (2.50 g, 16.5 mmol) in THF (30 mL) and DMF (15 mL), N,N-diisopropylethylamine (12.6 mL, 72.5 mmol) was added. The resulting mixture was heated at 80° C. for 18 hr. Upon completion, the mixture was diluted with EtOAc (300 mL), washed with 5% LiCl (250 mL) and brine (250 mL). The organic extract was dried over sodium sulfate and purified by silica gel column chromatography (eluent: EtOAc/hexanes) to afford desired product. ES/MS: 337.2 (M+H$^+$); 1H NMR (400 MHz, Chloroform-d) δ 8.21 (t, J=7.8 Hz, 2H), 7.54 (d, J=1.6 Hz, 1H), 7.22 (dd, J=8.9, 1.7 Hz, 1H), 4.41 (dd, J=9.2, 6.8 Hz, 1H), 4.00 (q, J=7.0 Hz, 1H), 3.81-3.59 (m, 3H), 1.63 (s, 9H), 1.26 (s, 3H), 1.18 (s, 3H).

Tert-butyl 4-amino-3-[[(3S)-4,4-dimethyltetrahydrofuran-3-yl]amino]benzoate (I-1042): A solution of tert-butyl 3-[[(3S)-4,4-dimethyltetrahydrofuran-3-yl]amino]-4-nitro-benzoate (4.35 g, 12.9 mmol) in EtOAc (86 mL) was degassed by cycling the mixture between argon and vacuum 3×. Next, palladium on carbon (10.0%, 1.38 g, 1.29 mmol) was added followed by degassing by cycling the mixture between argon and vacuum. Next, the mixture was stirred at rt with a balloon of hydrogen for 24 hr. Upon completion, the mixture was filtered through Celite and concentrated in vacuo to give desired product. ES/MS m/z: 307.2 (M+H)$^+$. 1H NMR (400 MHz, Chloroform-d) δ 7.40 (d, J=16.5 Hz, 2H), 6.81 (s, 1H), 4.33 (d, J=8.6 Hz, 1H), 3.82-3.54 (m, 4H), 1.60 (s, 9H), 1.23 (s, 3H), 1.17 (s, 2H).

Preparation of Intermediate I-1043

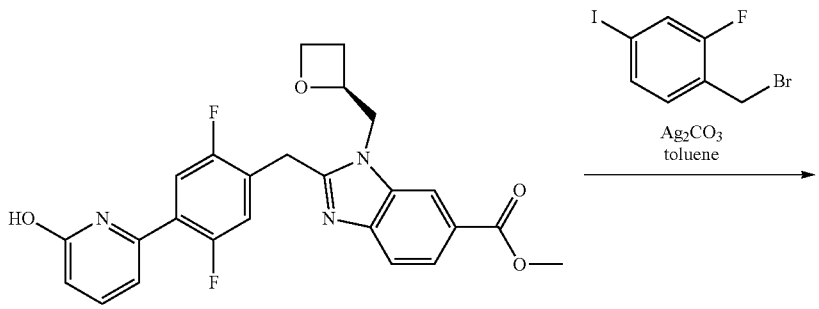

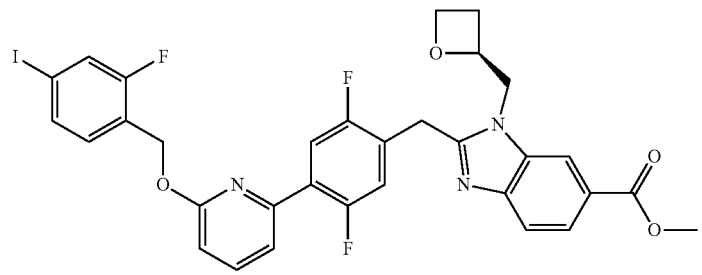

I-1043

Methyl (S)-2-(2,5-difluoro-4-(6-((2-fluoro-4-iodobenzyl)oxy)pyridin-2-yl)benzyl)-1-(oxetan-2-ylmethyl)-1H-benzo[d]imidazole-6-carboxylate (Intermediate I-1043): A slurry of methyl (S)-2-(2,5-difluoro-4-(6-hydroxypyridin-2-yl)benzyl)-1-(oxetan-2-ylmethyl)-1H-benzo[d]imidazole-6-carboxylate (250 mg, 0.54 mmol), 1-(bromomethyl)-2-fluoro-4-iodobenzene (203 mg, 0.65 mmol), and silver carbonate (370 mg, 1.3 mmol) in toluene (5 mL) was heated at 70° C. for 1 hr. The mixture was filtered through celite, washing with EtOAc, concentrated, and purified (24 g GOLD, 0-100% EtOAc in Hex). ES/MS: 700.1 (M+H⁺).

Preparation of Intermediate I-1044

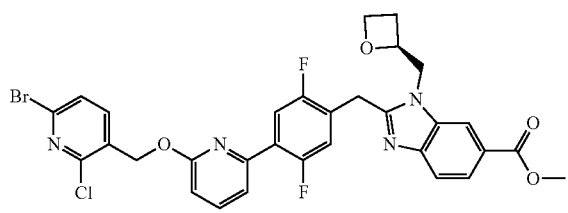

I-1044

Methyl (S)-2-(4-(6-((6-bromo-2-chloropyridin-3-yl)methoxy)pyridin-2-yl)-2,5-difluorobenzyl)-1-(oxetan-2-ylmethyl)-1H-benzo[d]imidazole-6-carboxylate (I-1044): Methyl (S)-2-(4-(6-((6-bromo-2-chloropyridin-3-yl)methoxy)pyridin-2-yl)-2,5-difluorobenzyl)-1-(oxetan-2-ylmethyl)-1H-benzo[d]imidazole-6-carboxylate was prepared in a manner as described for Intermediate I-18 substituting 6-bromo-3-(bromomethyl)-2-chloropyridine for 4-bromo-1-(bromomethyl)-2-fluorobenzene and methyl (S)-2-(2,5-difluoro-4-(6-hydroxypyridin-2-yl)benzyl)-1-(oxetan-2-ylmethyl)-1H-benzo[d]imidazole-6-carboxylate (I-9) for tert-butyl 2-[[2,5-difluoro-4-(6-hydroxy-2-pyridyl)phenyl]methyl]-3-(2-methoxyethyl)benzimidazole-5-carboxylate (I-17). ES/MS: 671.1 (M+H⁺).

Preparation of Intermediate I-1045

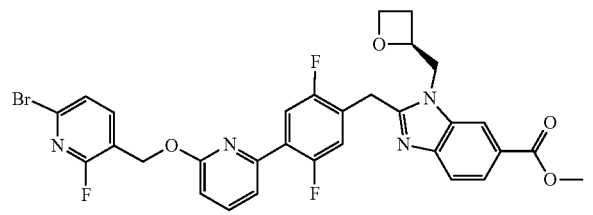

I-1045

Methyl (S)-2-(4-(6-((6-bromo-2-fluoropyridin-3-yl)methoxy)pyridin-2-yl)-2,5-difluorobenzyl)-1-(oxetan-2-ylmethyl)-1H-benzo[d]imidazole-6-carboxylate (I-1045): Methyl (S)-2-(4-(6-((6-bromo-2-fluoropyridin-3-yl)methoxy)pyridin-2-yl)-2,5-difluorobenzyl)-1-(oxetan-2-ylmethyl)-1H-benzo[d]imidazole-6-carboxylate was prepared in a manner as described for Intermediate I-18 substituting 6-bromo-3-(bromomethyl)-2-fluoropyridine for 4-bromo-1-(bromomethyl)-2-fluorobenzene and methyl (S)-2-(2,5-difluoro-4-(6-hydroxypyridin-2-yl)benzyl)-1-(oxetan-2-ylmethyl)-1H-benzo[d]imidazole-6-carboxylate (I-9) for tert-butyl 2-[[2,5-difluoro-4-(6-hydroxy-2-pyridyl)phenyl]methyl]-3-(2-methoxyethyl)benzimidazole-5-carboxylate (I-17). ES/MS: 653.2 (M+H⁺).

Preparation of Intermediate I-1046

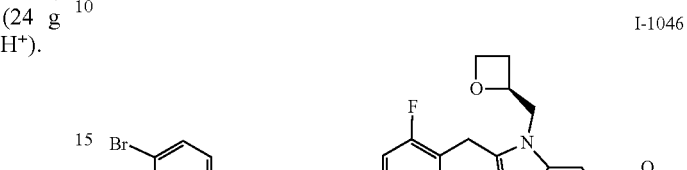

I-1046

Methyl (S)-2-(4-(6-((6-bromo-2-methoxypyridin-3-yl)methoxy)pyridin-2-yl)-2,5-difluorobenzyl)-1-(oxetan-2-ylmethyl)-1H-benzo[d]imidazole-6-carboxylate (I-1046): Methyl (S)-2-(4-(6-((6-bromo-2-methoxypyridin-3-yl)methoxy)pyridin-2-yl)-2,5-difluorobenzyl)-1-(oxetan-2-ylmethyl)-1H-benzo[d]imidazole-6-carboxylate was prepared in a manner as described for Intermediate I-18 substituting 6-bromo-3-(chloromethyl)-2-methoxypyridine for 4-bromo-1-(bromomethyl)-2-fluorobenzene and methyl (S)-2-(2,5-difluoro-4-(6-hydroxypyridin-2-yl)benzyl)-1-(oxetan-2-ylmethyl)-1H-benzo[d]imidazole-6-carboxylate (I-9) for tert-butyl 2-[[2,5-difluoro-4-(6-hydroxy-2-pyridyl)phenyl]methyl]-3-(2-methoxyethyl)benzimidazole-5-carboxylate (I-17). ES/MS: 665.2 (M+H⁺).

Preparation of Intermediate I-1047

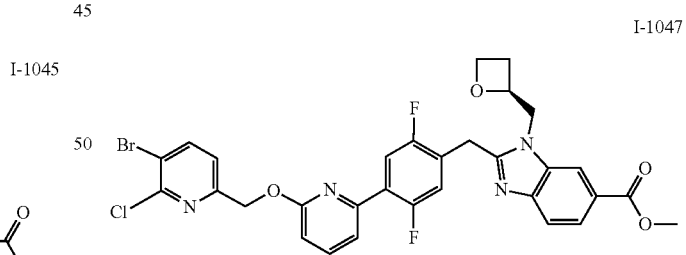

I-1047

Methyl (S)-2-(4-(6-((5-bromo-6-chloropyridin-2-yl)methoxy)pyridin-2-yl)-2,5-difluorobenzyl)-1-(oxetan-2-ylmethyl)-1H-benzo[d]imidazole-6-carboxylate (I-1047): Methyl (S)-2-(4-(6-((6-bromo-2-methoxypyridin-3-yl)methoxy)pyridin-2-yl)-2,5-difluorobenzyl)-1-(oxetan-2-ylmethyl)-1H-benzo[d]imidazole-6-carboxylate was prepared in a manner as described for Intermediate I-21 substituting 3-bromo-2-chloro-6-(chloromethyl)pyridine for 5-bromo-2-(bromomethyl)thiazole. ES/MS: 671.1 (M+H⁺).

Preparation of Intermediate I-1048

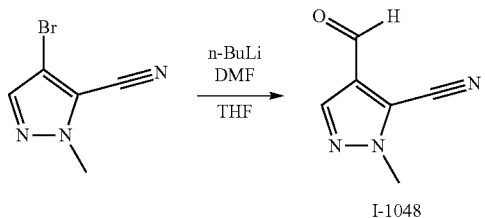

I-1048

4-formyl-1-methyl-1H-pyrazole-5-carbonitrile (I-1048): n-BuLi (2.5M, 0.645 mL, 1.61 mmol) was added dropwise to a solution of 4-bromo-2-methyl-pyrazole-3-carbonitrile (250 mg, 1.34 mmol) in THF (12 mL) at −78° C., and the solution was stirred for 15 min. DMF (0.21 mL, 2.69 mmol) was added dropwise and the solution was stirred for 20 min. Reaction was quenched with saturated NH₄Cl and water, and warmed to rt. It was extracted with EtOAc (2×) and organic was washed with brine, dried over MgSO₄, filtered, concentrated, and purified (ISCO 12 g, 0-80% EtOAc in Hex).

Preparation of Intermediate I-1049

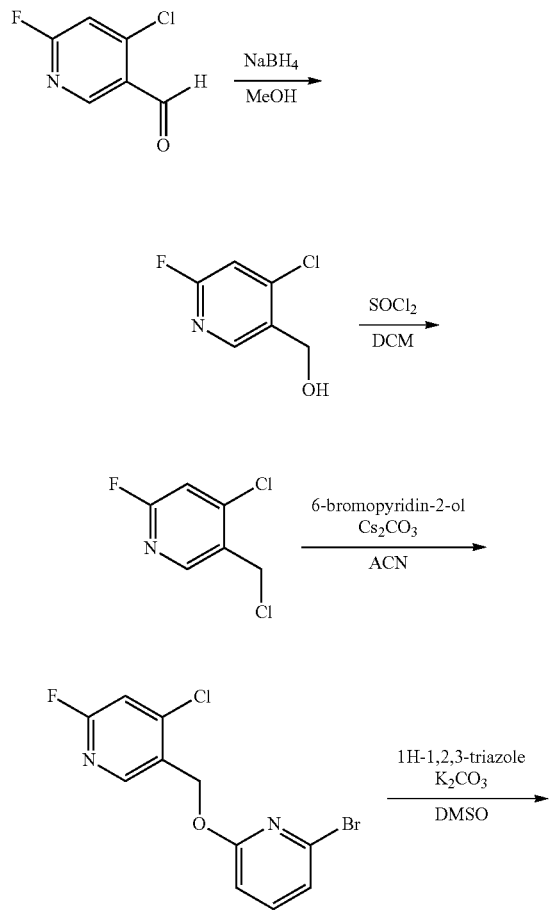

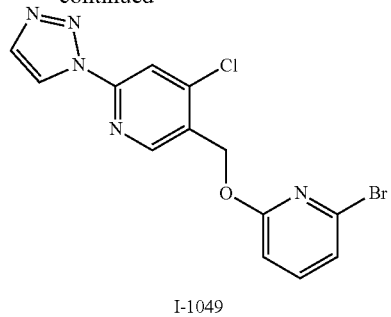

I-1049

(4-chloro-6-fluoropyridin-3-yl)methanol: NaBH₄ (117 mg, 3.09 mmol) was added to a solution of 4-chloro-6-fluoronicotinaldehyde (470 mg, 2.95 mmol) in MeOH (12 mL) at 0° C., and the solution was stirred for 5 min. The mixture was quenched with saturated NH₄Cl and concentrated. The concentrate was dissolved in EtOAc, washed with water then brine, dried over MgSO₄, filtered, and concentrated to give (4-chloro-6-fluoropyridin-3-yl)methanol (1), which was taken forward crude. ES/MS: 161.9 (M+1).

4-chloro-5-(chloromethyl)-2-fluoropyridine: Thionyl chloride (0.53 mL, 7.4 mmol) was added to a solution of (4-chloro-6-fluoropyridin-3-yl)methanol (476 mg, 2.95 mmol) in DCM (25 mL), and the resulting solution was stirred for 1 hour. Thionyl chloride (0.53 mL, 7.4 mmol) was added, and the resulting solution was stirred for 1 hour. Thionyl chloride (0.21 mL, 2.9 mmol) was added, and the resulting solution was stirred for 30 min. The mixture was concentrated, redissolved in DCM, and saturated NaHCO₃ was added dropwise carefully. Next, the phases were separated, and organic was dried over MgSO₄, filtered, and concentrated to give 4-chloro-5-(chloromethyl)-2-fluoropyridine (2), which was taken forward crude. $^1$H NMR (400 MHz, Chloroform-d) δ 8.30 (s, 1H), 7.05 (d, J=2.7 Hz, 1H), 4.67 (s, 2H).

5-(((6-bromopyridin-2-yl)oxy)methyl)-4-chloro-2-fluoropyridine: A slurry of 6-bromopyridin-2-ol (557 mg, 3.2 mmol), 4-chloro-5-(chloromethyl)-2-fluoropyridine (480 mg, 2.7 mmol), and Cs₂CO₃ (2.17 g, 6.7 mmol) in CAN (9 mL) was heated at 70° C. for 30 min. The mixture was filtered through celite, concentrated, and purified (ISCO 12 g GOLD, 0-100% EtOAc in Hex) to give 5-(((6-bromopyridin-2-yl)oxy)methyl)-4-chloro-2-fluoropyridine (3). ES/MS: 317.0 (M+1).

5-(((6-bromopyridin-2-yl)oxy)methyl)-4-chloro-2-(1H-1,2,3-triazol-1-yl)pyridine (I-1049): A slurry of 5-(((6-bromopyridin-2-yl)oxy)methyl)-4-chloro-2-fluoropyridine (110 mg, 0.31 mmol), 1H-1,2,3-triazole (0.018 mL, 0.31 mmol), and K₂CO₃ (87 mg, 0.63 mmol) in DMSO (1.4 mL) was heated at 70° C. under an atmosphere of air for 4 hours. The mixture was diluted with brine and extracted 2× with EtOAc. Organic was dried over MgSO₄, filtered, concentrated, and purified (ISCO 12 g GOLD, 0-100% EtOAc in Hex, product eluted at ~80% EtOAc) to give 5-(((6-bromopyridin-2-yl)oxy)methyl)-4-chloro-2-(1H-1,2,3-triazol-1-yl)pyridine (4) as the first eluting of two peaks. 1H NMR (400 MHz, Chloroform-d) δ 8.66 (s, 1H), 8.58 (s, 1H), 8.31 (s, 1H), 7.84 (d, J=1.2 Hz, 1H), 7.48 (t, J=7.8 Hz, 1H), 7.13 (d, J=7.5 Hz, 1H), 6.79 (d, J=8.2 Hz, 1H), 5.54 (s, 2H).

Preparation of Intermediate I-1050

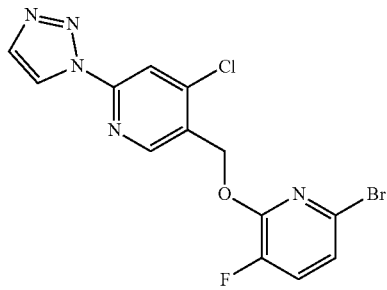

6-bromo-2-((4-chloro-6-(1H-1,2,3-triazol-1-yl)pyridin-3-yl)methoxy)-3-fluoropyridine: 6-bromo-2-((4-chloro-6-(1H-1,2,3-triazol-1-yl)pyridin-3-yl)methoxy)-3-fluoropyridine (I-1050) was prepared in a manner as described for Intermediate I-1049 substituting 6-bromo-3-fluoropyridin-2-ol for 6-bromopyridin-2-ol 1H NMR (400 MHz, Chloroform-d) δ 8.68 (s, 1H), 8.58 (d, J=1.2 Hz, 1H), 8.32 (s, 1H), 7.84 (d, J=1.2 Hz, 1H), 7.27 (dd, J=9.3, 8.1 Hz, 1H), 7.09 (dd, J=8.1, 2.7 Hz, 1H), 5.60 (s, 2H).

Preparation of Intermediate I-1051

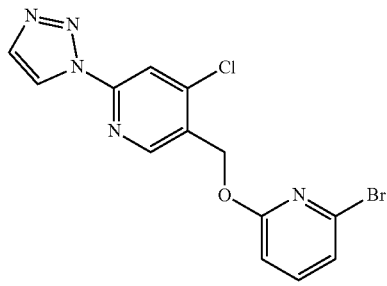

5-(((6-bromopyridin-2-yl)oxy)methyl)-4-chloro-2-(1H-imidazol-1-yl)pyridine: 5-(((6-bromopyridin-2-yl)oxy)methyl)-4-chloro-2-(1H-imidazol-1-yl)pyridine (I-1051) was prepared in a manner as described for Intermediate I-1049 substituting 1H-imidazole for 1H-1,2,3-triazole. ¹H NMR (400 MHz, Chloroform-d) δ 8.65 (s, 1H), 8.58 (d, J=1.2 Hz, 1H), 8.31 (s, 1H), 7.84 (d, J=1.2 Hz, 1H), 7.47 (t, J=7.8 Hz, 1H), 7.13 (d, J=7.5 Hz, 1H), 6.78 (d, J=8.2 Hz, 1H), 5.54 (s, 2H).

Preparation of Intermediate I-1052

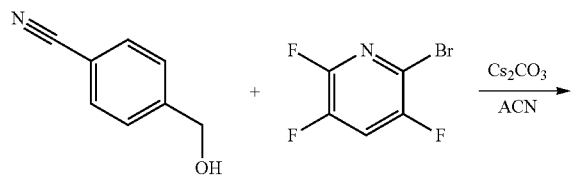

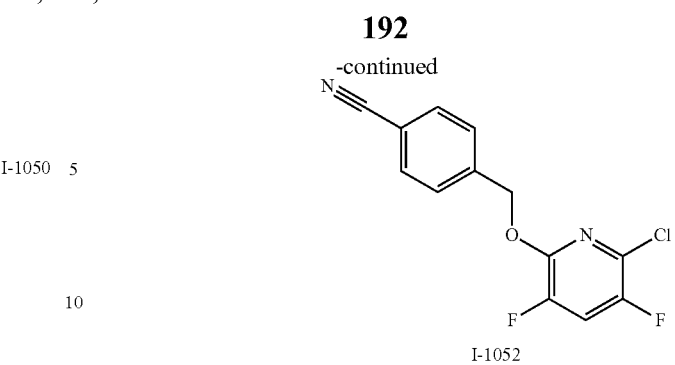

4-(((6-bromo-3,5-difluoropyridin-2-yl)oxy)methyl)benzonitrile (I-1052): A suspension of 4-(hydroxymethyl)benzonitrile (377 mg, 2.8 mmol), 2-bromo-3,5,6-trifluoropyridine (600 mg, 2.8 mmol), and cesium carbonate (1.8 g, 5.7 mmol) in ACN (9.5 mL) was stirred at rt overnight. The mixture was diluted with EtOAc, filtered through celite, concentrated, and purified (0-100% EtOAc in Hex). 1H NMR (400 MHz, Chloroform-d) δ 7.69 (d, J=8.2 Hz, 2H), 7.58 (d, J=8.0 Hz, 2H), 7.30 (dd, J=8.5, 6.5 Hz, 1H), 5.48 (s, 2H).

Preparation of Intermediate I-1053

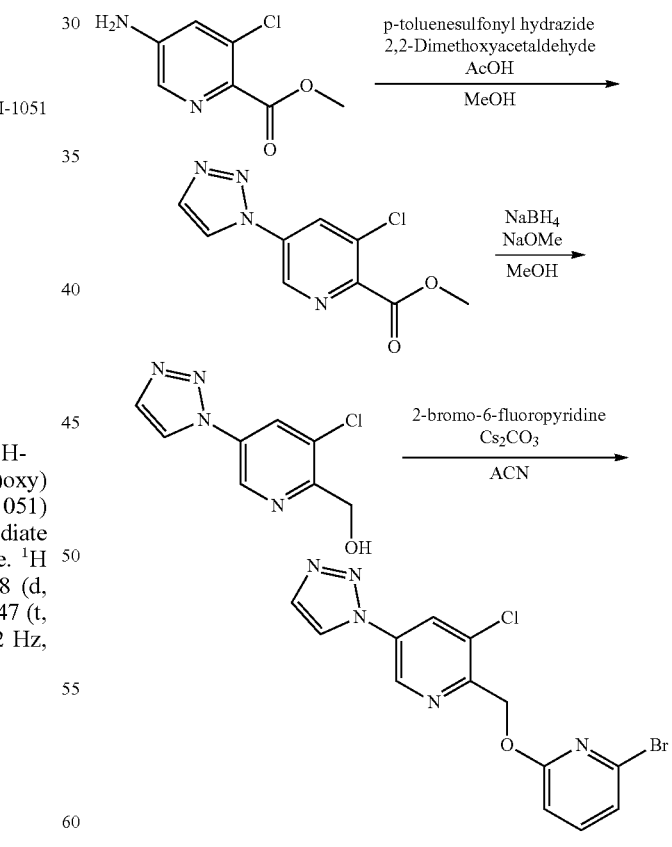

Methyl 3-chloro-5-(1H-1,2,3-triazol-1-yl)picolinate: Glyoxal dimethyl acetal (60% in H₂O, 0.17 mL, 1.13 mmol) was added to a solution of tosyl hydrazide (200 mg, 1.07 mmol) in MeOH (2.7 mL) in a microwave vial. The mixture was stirred for 2 hours at rt, and methyl 5-amino-3-chloro-pyridine-2-carboxylate (220 mg, 1.18 mmol) followed by the addition of AcOH (0.06 mL, 1.07 mmol). The reaction was sealed and heated to 75° C. overnight. Next, the mixture was neutralized with DIPEA, concentrated, and purified (0-100% EtOAc in Hex). 1H NMR (400 MHz, Chloroform-d) δ 9.00 (d, J=2.2 Hz, 1H), 8.36 (d, J=2.2 Hz, 1H), 8.12 (d, J=1.3 Hz, 1H), 7.95 (d, J=1.3 Hz, 1H), 4.06 (s, 3H).

(3-chloro-5-(1H-1,2,3-triazol-1-yl)pyridin-2-yl)metha-nol: NaBH₄ (57 mg, 1.5 mmol) was added to a solution of methyl 3-chloro-5-(1H-1,2,3-triazol-1-yl)picolinate (180 mg, 0.75 mmol) and sodium methoxide (0.5M in MeOH, 0.075 mL, 0.038 mmol) in MeOH (0.7 mL), and the resulting suspension was stirred at rt for 2 hr. The mixture was quenched with saturated NH₄Cl and partitioned between EtOAc and water. The organic was washed with brine, dried over MgSO₄, filtered, concentrated, and taken forward crude. ES/MS: 210.9 (M+H⁺).

2-(((6-bromopyridin-2-yl)oxy)methyl)-3-chloro-5-(1H-1,2,3-triazol-1-yl)pyridine (I-1053): A suspension of (3-chloro-5-(1H-1,2,3-triazol-1-yl)pyridin-2-yl)methanol (50 mg, 0.24 mmol), 2-bromo-6-fluoropyridine (50 mg, 0.29 mmol), and cesium carbonate (155 mg, 0.48 mmol) in ACN (1 mL) was stirred at 70° C. overnight. The mixture was diluted with EtOAc, filtered through celite, concentrated, and purified (0-100% EtOAc in Hex). ES/MS: 367.8 (M+H⁺).

Preparation of Intermediate I-1054

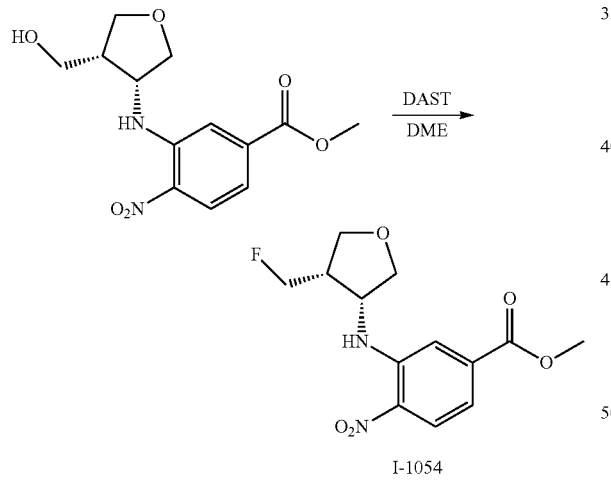

I-1054

Methyl 3-((cis-4-(fluoromethyl)tetrahydrofuran-3-yl)amino)-4-nitrobenzoate: To a solution of methyl 3-((cis-4-(hydroxymethyl)tetrahydrofuran-3-yl)amino)-4-nitrobenzoate (100 mg, 0.338 mmol) in 1,2-dimethoxyethane (4 mL) at −50° C. was added a solution of DAST (0.054 mL, 0.41 mmol) in 1,2-dimethoxyethane (2 mL). The reaction was stirred for 10 min at −50° C., warmed up to rt and stirred for 4 hr. To the mixture was added cold saturated NaHCO₃ (20 mL). The product was extracted with EtOAc (3×). The combined organic layers were washed with brine, dried over MgSO₄, filtered, concentrated, redissolved in DMSO, and purified (RP HPLC, 0-100% ACN in H₂O). ES/MS: 299.0 (M+H⁺).

Preparation of Intermediate I-1055

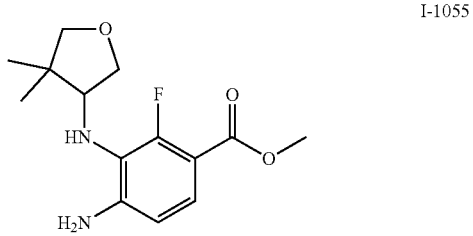

I-1055

Methyl 4-amino-3-((4,4-dimethyltetrahydrofuran-3-yl)amino)-2-fluorobenzoate: Methyl 4-amino-3-((4,4-dimethyltetrahydrofuran-3-yl)amino)-2-fluorobenzoate (I-1055) was prepared in a manner as described for Intermediate I-1 substituting methyl 2,3-difluoro-4-nitrobenzoate for methyl 3-fluoro-4-nitro-benzoate and 4,4-dimethyltetrahydrofuran-3-amine hydrochloride for 2-methoxyethylamine. ES/MS: 283.0 (M+H⁺).

Preparation of Intermediate I-1056 (Peak 1) and I-1057 (Peak 2)

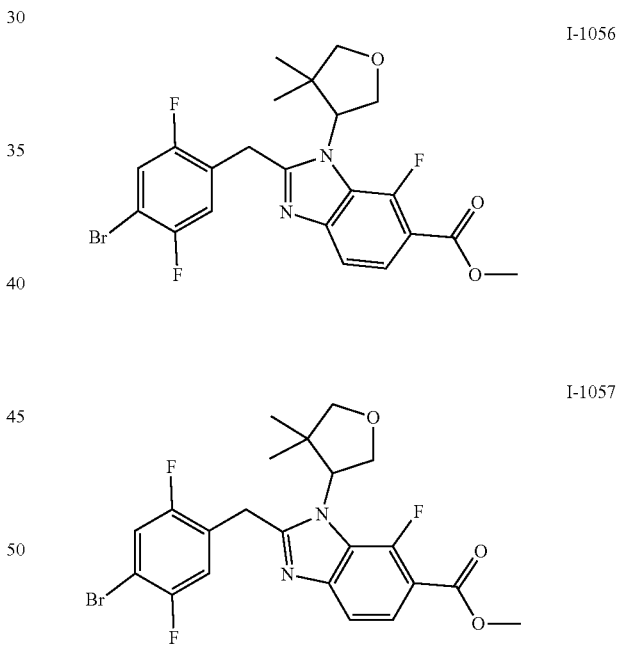

I-1056

I-1057

Methyl 2-(4-bromo-2,5-difluorobenzyl)-1-(4,4-dimethyl-tetrahydrofuran-3-yl)-7-fluoro-1H-benzo[d]imidazole-6-carboxylate: Methyl 2-(4-bromo-2,5-difluorobenzyl)-1-(4,4-dimethyltetrahydrofuran-3-yl)-7-fluoro-1H-benzo[d]imidazole-6-carboxylate was prepared in a manner as described for Intermediate I-13 substituting methyl 4-amino-3-((4,4-dimethyltetrahydrofuran-3-yl)amino)-2-fluorobenzoate for ethyl (S)-4-amino-3-fluoro-5-((oxetan-2-ylmethyl)amino)benzoate and 2-(4-bromo-2,5-difluoro-phenyl)acetic acid for 2-(4-bromo-2-fluorophenyl)acetic acid, separating the two enantiomers (Peak 1, I-1056) and (Peak 2, I-1057) by chiral SFC. ES/MS: 497.0 (M+H⁺).

Preparation of Intermediate I-1058

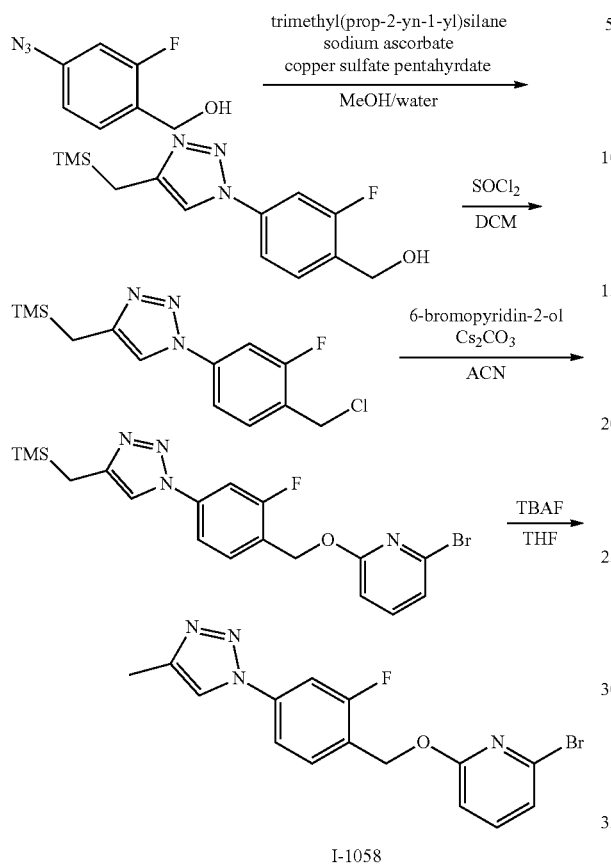

I-1058

(2-fluoro-4-(4-((trimethylsilyl)methyl)-1H-1,2,3-triazol-1-yl)phenyl)methanol: A suspension of trimethyl(prop-2-yn-1-yl)silane (0.21 mL, 1.44 mmol), (4-azido-2-fluoro-phenyl)methanol (200 mg, 1.2 mmol), sodium ascorbate (84 mg, 0.48 mmol), copper(II) sulfate pentahydrate (60 mg, 0.24 mmol) was stirred at rt overnight. The mixture was then diluted with 2M NH₄OH and extracted with EtOAc (2×). The organic layer was washed with water then brine, dried over MgSO₄, filtered, concentrated, and purified (12 g, 0-100% EtOAc in Hex). ES/MS: 280.1 (M+H⁺).

1-(4-(chloromethyl)-3-fluorophenyl)-4-((trimethylsilyl)methyl)-1H-1,2,3-triazole: Thionyl chloride (0.18 mL, 2.4 mmol) was added to a solution of (2-fluoro-4-(4-((trimethylsilyl)methyl)-1H-1,2,3-triazol-1-yl)phenyl)methanol (270 mg, 0.97 mmol) in DCM (9 mL), and the resulting solution was stirred for 1 hour. The mixture was concentrated, redissolved in DCM, and saturated NaHCO₃ was added dropwise. The phases were separated, and the organic extract was dried over MgSO₄, filtered, concentrated, and taken forward crude. ES/MS: 298.0 (M+H⁺).

2-bromo-6-((2-fluoro-4-(4-((trimethylsilyl)methyl)-1H-1,2,3-triazol-1-yl)benzyl)oxy)pyridine: A suspension of 1-(4-(chloromethyl)-3-fluorophenyl)-4-((trimethylsilyl)methyl)-1H-1,2,3-triazole (80 mg, 0.27 mmol), 6-bromopyridin-2-ol (51 mg, 0.30 mmol), and cesium carbonate (219 mg, 0.67 mmol) in were heated at 70° C. for 30 min. The mixture was diluted with EtOAc, washed with water then brine, dried over MgSO₄, filtered, concentrated, and taken forward crude. ES/MS: 435.1 (M+H⁺).

2-bromo-6-((2-fluoro-4-(4-methyl-1H-1,2,3-triazol-1-yl)benzyl)oxy)pyridine (I-1058): TBAF (1M in THF, 0.54 mL, 0.54 mmol) was added dropwise to a solution of 2-bromo-6-((2-fluoro-4-(4-((trimethylsilyl)methyl)-1H-1,2,3-triazol-1-yl)benzyl)oxy)pyridine (117 mg, 0.27 mmol) in THF at 0° C. The resulting solution was stirred at 0° C. for 1 hr. Next, the mixture was partitioned between EtOAc and sat. NH₄Cl. The organic layer was washed with sat. NH₄Cl, and brine, dried over MgSO₄, filtered, concentrated, and purified (0-100% EtOAc in Hex). ES/MS: 363.1 (M+H⁺).

Preparation of Intermediate I-1059

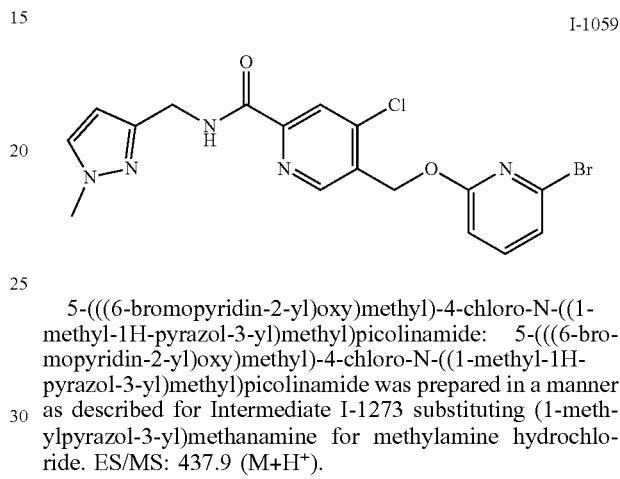

I-1059

5-(((6-bromopyridin-2-yl)oxy)methyl)-4-chloro-N-((1-methyl-1H-pyrazol-3-yl)methyl)picolinamide: 5-(((6-bromopyridin-2-yl)oxy)methyl)-4-chloro-N-((1-methyl-1H-pyrazol-3-yl)methyl)picolinamide was prepared in a manner as described for Intermediate I-1273 substituting (1-methylpyrazol-3-yl)methanamine for methylamine hydrochloride. ES/MS: 437.9 (M+H⁺).

Intermediate I-1059

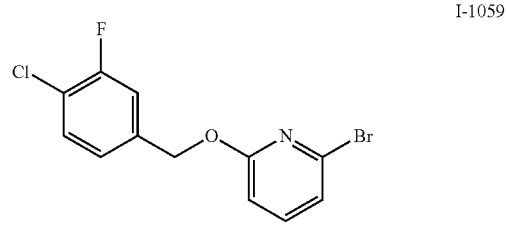 [SMILES: Fc1cc(COc2cccc(Br)n2)ccc1Cl]

I-1059

2-bromo-6-((4-chloro-3-fluorobenzyl)oxy)pyridine (I-1059a): 2-bromo-6-((4-chloro-3-fluorobenzyl)oxy)pyridine was prepared in a manner as described for Intermediate I-84 substituting 4-(bromomethyl)-1-chloro-2-fluorobenzene for 2-(bromomethyl)thiazole-5-carbonitrile.

Preparation of Intermediate I-1060

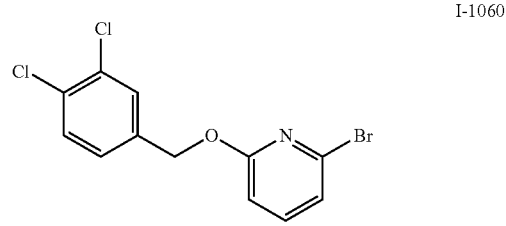 [SMILES: Clc1ccc(COc2cccc(Br)n2)cc1Cl]

I-1060

2-bromo-6-((3,4-dichlorobenzyl)oxy)pyridine (I-1060): 2-bromo-6-((3,4-dichlorobenzyl)oxy)pyridine was prepared in a manner as described for Intermediate I-84 substituting 4-(bromomethyl)-1,2-dichlorobenzene for 2-(bromomethyl)thiazole-5-carbonitrile.

Preparation of Intermediate I-1061

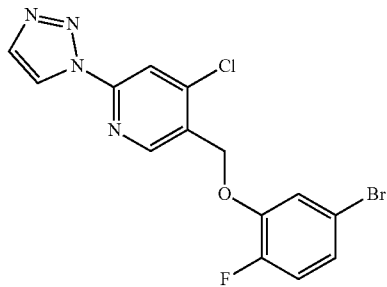

I-1061

5-((5-bromo-2-fluorophenoxy)methyl)-4-chloro-2-(1H-1,2,3-triazol-1-yl)pyridine (I-1061): 5-((5-bromo-2-fluorophenoxy)methyl)-4-chloro-2-(1H-1,2,3-triazol-1-yl)pyridine was prepared in a manner as described for Intermediate I-1049 substituting 5-bromo-2-fluorophenol for 6-bromopyridin-2-ol. $^1$H NMR (400 MHz, Chloroform-d) δ 8.67 (s, 1H), 8.59 (d, J=1.1 Hz, 1H), 8.34 (s, 1H), 7.86 (d, J=1.2 Hz, 1H), 7.23 (dd, J=7.4, 2.3 Hz, 1H), 7.13 (ddd, J=8.6, 4.0, 2.2 Hz, 1H), 7.02 (dd, J=10.7, 8.7 Hz, 1H), 5.27 (s, 2H).

Preparation of Intermediate I-1062

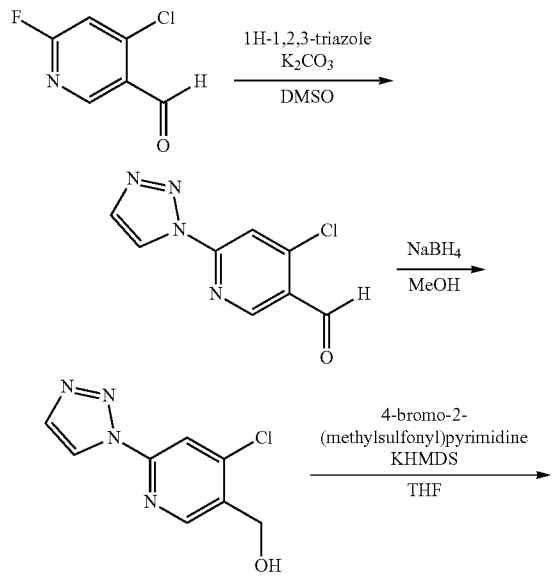

-continued

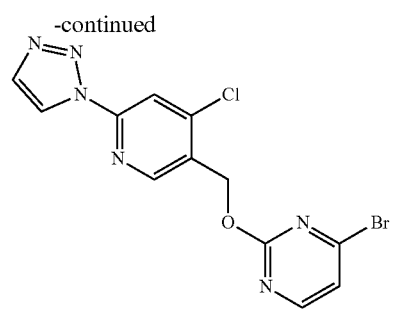

I-1062

4-chloro-6-(1H-1,2,3-triazol-1-yl)nicotinaldehyde: Potassium carbonate (1.7 g, 13 mmol) was added to a solution of 4-chloro-6-fluoro-pyridine-3-carbaldehyde (1.0 g, 6.3 mmol) and 1H-1,2,3-triazole (0.36 mL, 6.3 mmol) in DMSO (28 mL). The solution was stirred at rt for 2 hours. Next, the solution was partitioned between brine and EtOAc. The phases were separated and the aqueous phase. was extracted with EtOAc. The combined organic phases were dried over MgSO$_4$, filtered, concentrated, and purified (0-100% EtOAc in Hex) to give 4-chloro-6-(1H-1,2,3-triazol-1-yl)nicotinaldehyde.

(4-chloro-6-(1H-1,2,3-triazol-1-yl)pyridin-3-yl)methanol: NaBH$_4$ (103 mg, 2.72 mmol) was added to a solution of 4-chloro-6-(triazol-1-yl)pyridine-3-carbaldehyde (540 mg, 2.59 mmol) in MeOH (10 mL) at 0° C. The mixture was stirred for 5 min. Next, the mixture was quenched with saturated NH$_4$Cl and concentrated. The concentrate was dissolved in EtOAc, washed with water then brine, dried over MgSO$_4$, filtered, concentrated, and taken forward crude. ES/MS: 211.0 (M+1).

4-bromo-2-((4-chloro-6-(1H-1,2,3-triazol-1-yl)pyridin-3-yl)methoxy)pyrimidine (I-1062): KHMDS (1M in THF, 0.70 mL, 0.70 mmol) was added dropwise to a solution of [4-chloro-6-(triazol-1-yl)-3-pyridyl]methanol (140 mg, 0.67 mmol) and 4-bromo-2-(methylsulfonyl)pyrimidine (158 mg, 0.67 mmol) in THE at −30° C. The mixture was stirred at −30° C. for 30 min. Next, the mixture was quenched with water dropwise then brine, and extracted 2× with EtOAc. The organic extract was dried over MgSO$_4$, filtered, concentrated, and purified (30% EtOAc in Hex for 5 min then 30-70% for 5 min) to give dp. $^1$H NMR (400 MHz, Chloroform-d) δ 8.68 (s, 1H), 8.58 (d, J=1.2 Hz, 1H), 8.34-8.30 (m, 2H), 7.84 (d, J=1.2 Hz, 1H), 7.23 (d, J=5.1 Hz, 1H), 5.61 (s, 2H). ES/MS: 367.0 (M+1).

Preparation of Intermediate I-1063

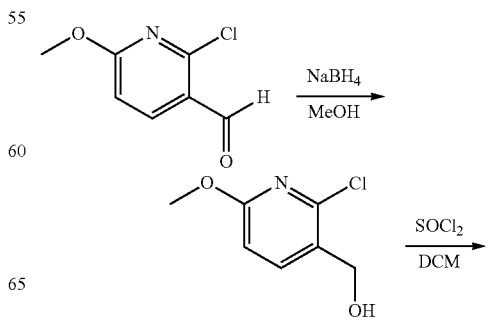

-continued

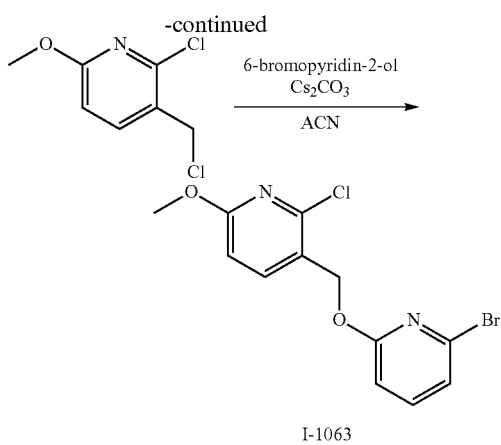

I-1063

(2-chloro-6-methoxypyridin-3-yl)methanol: NaBH₄ (116 mg, 3.06 mmol) was added to a solution of 2-chloro-6-methoxynicotinaldehyde (500 mg, 2.91 mmol) in MeOH (12 mL) at 0° C., and the solution was stirred for 5 min. The mixture was quenched with saturated NH₄Cl and concentrated. The concentrate was dissolved in EtOAc, washed with water then brine. Next, the concentrates were dried over MgSO₄, filtered, and concentrated to give (2-chloro-6-methoxypyridin-3-yl)methanol, which was taken forward crude. ES/MS: 173.9 (M+1).

2-chloro-3-(chloromethyl)-6-methoxypyridine: Thionyl chloride (0.30 mL, 4.09 mmol) was added to a solution of (2-chloro-6-methoxypyridin-3-yl)methanol (284 mg, 1.64 mmol) in DCM (13 mL), and the resulting solution was stirred for 1 hour. The mixture was concentrated, then redissolved in DCM. Next, saturated NaHCO₃ was added dropwise carefully. The phases were separated, and organic phase was dried over MgSO₄, filtered, and concentrated to give 2-chloro-3-(chloromethyl)-6-methoxypyridine which was taken forward crude.

3-(((6-bromopyridin-2-yl)oxy)methyl)-2-chloro-6-methoxypyridine (I-1063): A slurry of 6-bromopyridin-2-ol (67 mg, 0.38 mmol), 2-chloro-3-(chloromethyl)-6-methoxypyridine (82 mg, 0.43 mmol), and Cs₂CO₃ (348 mg, 1.1 mmol) in ACN (2 mL) was heated at 70° C. for 30 min. The mixture was filtered through celite, concentrated, and purified (ISCO 12 g GOLD, 0-100% EtOAc in Hex) to give 3-(((6-bromopyridin-2-yl)oxy)methyl)-2-chloro-6-methoxypyridine. ES/MS: 330.8 (M+1). ¹H NMR (400 MHz, Chloroform-d) δ 7.70 (d, J=7.6 Hz, 1H), 7.44 (dd, J=8.2, 7.5 Hz, 1H), 7.08 (dd, J=7.5, 0.6 Hz, 1H), 6.92 (d, J=7.6 Hz, 1H), 6.74 (dd, J=8.1, 0.7 Hz, 1H), 5.32 (s, 2H), 4.00 (s, 3H).

Preparation of Intermediate I-1064

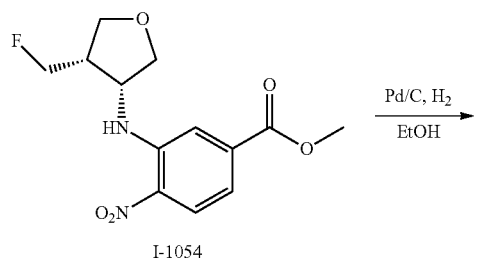

I-1054

-continued

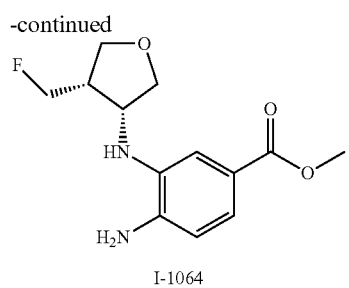

I-1064

Methyl 4-amino-3-((cis-4-(fluoromethyl)tetrahydrofuran-3-yl)amino)benzoate (I-1340): A mixture of methyl 3-[[(3R,4S)-4-(fluoromethyl)tetrahydrofuran-3-yl]amino]-4-nitrobenzoate (I-1054, 31 mg, 0.1 mmol) and Pd/C (10%, 11.1 mg, 0.01 mmol) in EtOH (4 mL) was degassed and backfilled with argon 3× then with H₂ 3×. The mixture was stirred at rt under H₂ for 20 min. The mixture was diluted with EtOAc, filtered through celite, concentrated to give the title compound. ES/MS: 269.1 (M+H⁺).

Preparation of Intermediate I-1065

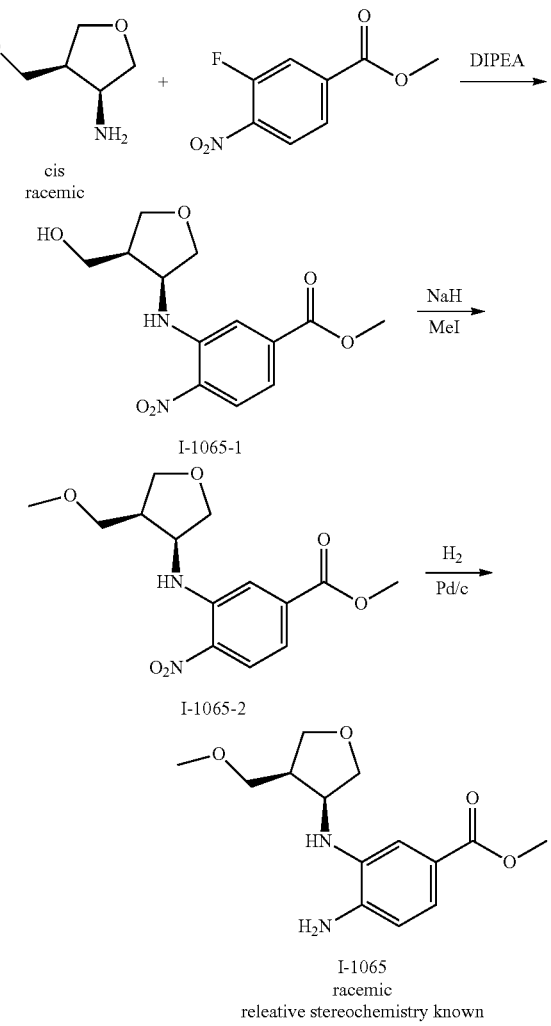

I-1065
racemic
releative stereochemistry known

Methyl 4-amino-3-(((1-(fluoromethyl)cyclopropyl)methyl)amino)benzoate (I-1065-1-1): N,N-diisopropylethylamine (0.525 mL, 3.01 mmol was added to a suspension of methyl 3-fluoro-4-nitro-benzoate (120 mg, 0.603 mmol), racemic cis 4-aminotetrahydrofuran-3-yl]methanol (77.7 mg, 0.66 mmol) in THF (4 mL) and DMF (2 mL). The mixture was heated at 80 deg. for 18 hr. The crude mixture was diluted with EtOAc, washed with 5% LiCi and brine. The organic extract was dried over sodium sulfate and purified by silica gel column chromatography (eluent: EtOAc/hexanes) to afford the title compound. ES/MS: 297.2 (M+H$^+$).

Methyl 3-[[-4-(methoxymethyl)tetrahydrofuran-3-yl]amino]-4-nitro-benzoate (I-1065-2): NaH (24.2 mg, 0.633 mmol, 60% dispersion) was added to a solution of methyl 3-[[4-(hydroxymethyl)tetrahydrofuran-3-yl]amino]-4-nitro-benzoate (75 mg, 0.253 mmol) in DMF (4 mL) at 0 deg. To this solution was added methyl iodide (35.9 mg, 0.253 mmol) and the solution stirred for 1 hour at rt. The solution was then split between saturated aqueous ammonium chloride and EtOAc, the aqueous layer was extracted with EtOAc five times, washed with brine. The organic extract was dried over sodium sulfate and purified by silica gel column chromatography (eluent: EtOAc/hexanes) to afford desired product. ES/MS: 311.2 (M+H$^+$).

Methyl 4-amino-3-[[-4-(methoxymethyl)tetrahydrofuran-3-yl]amino]benzoate (I-1065, racemic, relative stereochemistry known): A solution of methyl 3-[[-4-(methoxymethyl)tetrahydrofuran-3-yl]amino]-4-nitro-benzoate (80 mg, 0.258 mmol) in EtOAc (5 mL) was degassed by cycling between argon and vacuum 3×. Then palladium on carbon (10.0%, 27.4 mg, 0.258 mmol) was added and then the mixture was degassed by cycling between argon and vacuum and stirred at rt with a balloon of hydrogen for 24 hr. The mixture was filtered through Celite and concentrated in vacuo to give the title compound. ES/MS: 281.2 (M+H$^+$)

Preparation of Intermediate I-1066

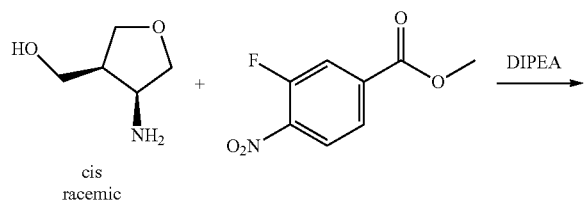

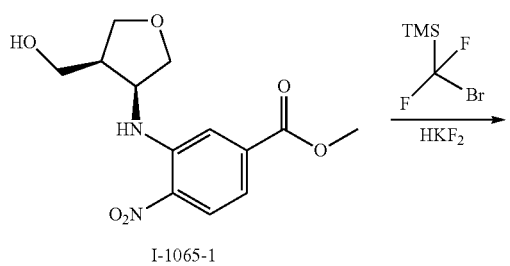

I-1065-1

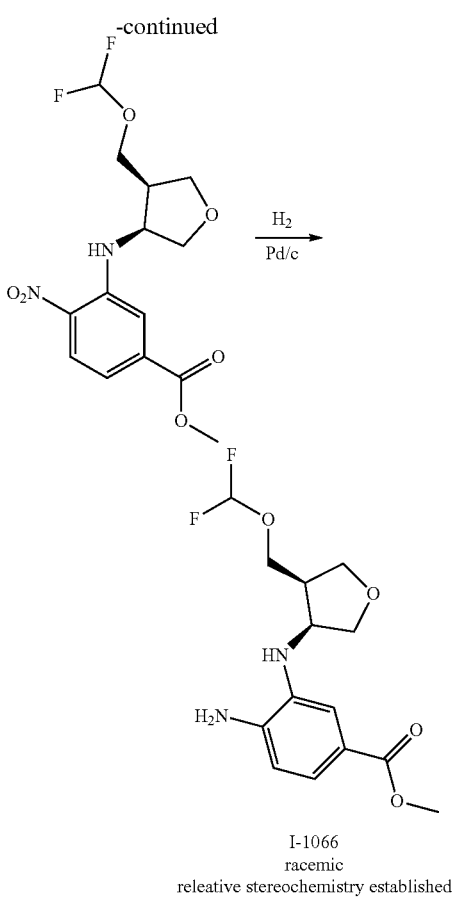

I-1066
racemic
releative stereochemistry established

Methyl 4-amino-3-(((1-(fluoromethyl)cyclopropyl)methyl)amino)benzoate (cis, relative stereochemistry known): Methyl 4-amino-3-(((1-(fluoromethyl)cyclopropyl)methyl)amino)benzoate was added N,N-diisopropylethylamine (0.525 mL, 3.01 mmol) was added to a suspension of methyl 3-fluoro-4-nitro-benzoate (120 mg, 0.603 mmol), 4-aminotetrahydrofuran-3-yl]methanol (77.7 mg, 0.66 mmol) in THE (4 mL) and DMF (2 mL). The mixture was heated at 80° C. for 18 hr. The crude mixture was diluted with EtOAc, washed with 5% LiCl and brine. The organic extract was dried over sodium sulfate and purified by silica gel column chromatography (eluent: EtOAc/hexanes) to afford desired product. ES/MS: 297.2 (M+H$^+$)

Methyl 3-[[-4-(difluoromethoxymethyl)tetrahydrofuran-3-yl]amino]-4-nitro-benzoate: Trimethyl(bromodifluoromethyl)silane (308 mg, 1.52 mmol, 0.237 mL) and potassium hydrogen fluoride (356, 4.56 mmol) were added to a solution of methyl 3-[[-4-(hydroxymethyl)tetrahydrofuran-3-yl]amino]-4-nitro-benzoate (75 mg, 0.253 mmol) in DCM (2 mL) and water (2 mL). The solution was stirred vigorously overnight at rt. The solution was then split between water and DCM, washed with brine, and dried over sodium sulfate and purified by silica gel column chromatography (eluent: EtOAc/hexanes) to afford desired product. ES/MS: 347.6 (M+H$^+$)

Methyl 4-amino-3-[[-4-(difluoromethoxymethyl)tetrahydrofuran-3-yl]amino]benzoate (I-1066): A solution of methyl 3-[[-4-(difluoromethoxymethyl)tetrahydrofuran-3-yl]amino]-4-nitro-benzoate (88 mg, 0.254 mmol) in EtOAc (5 mL) was degassed by cycling the mixture between argon and vacuum 3×. Next, palladium on carbon (10.0%, 27.0 mg, 0.254 mmol) was added and then the mixture was degassed by cycling the mixture between argon and vacuum and stirred at rt with a balloon of hydrogen for 24 hr. The mixture was filtered through Celite and concentrated in vacuo to give desired product. ES/MS: 317.2 (M+H⁺)

Preparation of Intermediate I-1067

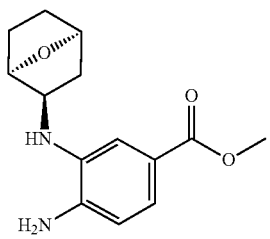

I-1067

Methyl 4-amino-3-[[(1R,2R,4S)-7-oxabicyclo[2.2.1]heptan-2-yl]amino]benzoate (I-1067): Methyl 4-amino-3-[[(1R,2R,4S)-7-oxabicyclo[2.2.1]heptan-2-yl]amino]benzoate (I-1067) was prepared in a manner as described for I-1 substituting (1R,2R,4S)-7-oxabicyclo[2.2.1]heptan-2-amine for 2-methoxyethylamine. ES/MS: 263.5 (M+H⁺).

Preparation of Intermediate I-1068

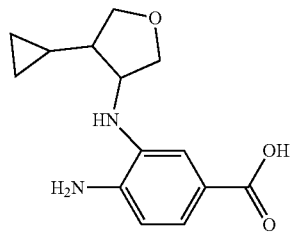

I-1068

2-[[4-[6-[(4-cyano-2-fluoro-phenyl)methoxy]-2-pyridyl]-2,5-difluoro-phenyl]methyl]-3-(4-cyclopropyltetrahydrofuran-3-yl)benzimidazole-5-carboxylic acid (I-1068): Methyl 4-amino-3-[(4-cyclopropyltetrahydrofuran-3-yl)amino]benzoate (I-1068) as a mixture of four different stereoisomers was prepared in a manner as described for I-72 substituting 4-cyclopropyltetrahydrofuran-3-amine hydrochloride for 2-methoxyethylamine and methyl 3-fluoro-4-nitro-benzoate for methyl 3-fluoro-5-iodo-4-nitrobenzoate. ES/MS: 624.6 (M+H⁺).

Preparation of Intermediate I-1069

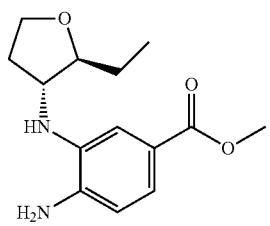

I-1069

Methyl 4-amino-3-[[(2S,3R)-2-ethyltetrahydrofuran-3-yl]amino]benzoate (I-1069): Methyl 4-amino-3-[[(2S,3R)-2-ethyltetrahydrofuran-3-yl]amino]benzoate (I-1069) was prepared in a manner as described for I-1 substituting (2S,3R)-2-ethyltetrahydrofuran-3-amine for 2-methoxyethylamine. ES/MS: 265.2 (M+H⁺).

Preparation of Intermediate I-1070

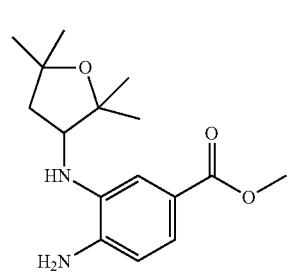

I-1070

Methyl 4-amino-3-[(2,2,5,5-tetramethyltetrahydrofuran-3-yl)amino]benzoate (I-1070): Methyl 4-amino-3-[(2,2,5,5-tetramethyltetrahydrofuran-3-yl)amino]benzoate (I-1070) was prepared in a manner as described for I-1 substituting 2,2,5,5-tetramethyltetrahydrofuran-3-amine for 2-methoxyethylamine. ES/MS: 293.2 (M+H⁺).

Preparation of Intermediate I-1071

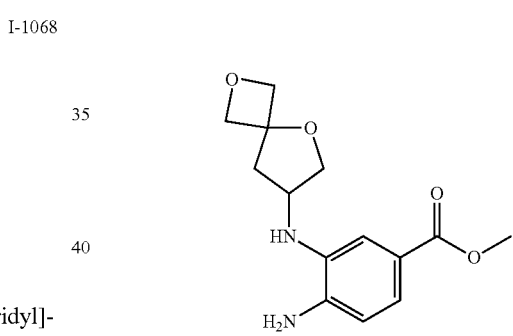

I-1071

Methyl 4-amino-3-(2,5-dioxaspiro[3.4]octan-7-ylamino)benzoate (I-1071): Methyl 4-amino-3-(2,5-dioxaspiro[3.4]octan-7-ylamino)benzoate (I-1071) was prepared in a manner as described for I-1 substituting 2,5-dioxaspiro[3.4]octan-7-amine for 2-methoxyethylamine. ES/MS: 279.2 (M+H⁺).

Preparation of Intermediate I-1072

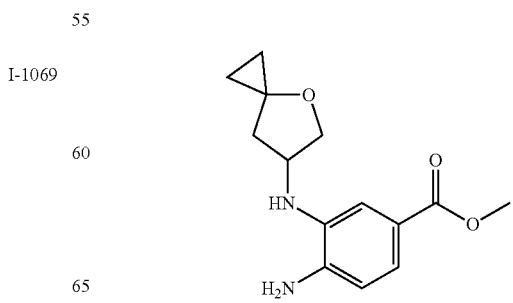

I-1072

Methyl 4-amino-3-(4-oxaspiro[2.4]heptan-6-ylamino) benzoate (I-1072): methyl 4-amino-3-(4-oxaspiro[2.4]heptan-6-ylamino)benzoate (I-1072) was prepared in a manner as described for Intermediate I-1 substituting 4-oxaspiro[2.4]heptan-6-amine for 2-methoxyethylamine. ES/MS: 263.2 (M+H$^+$).

Preparation of Intermediate I-1073

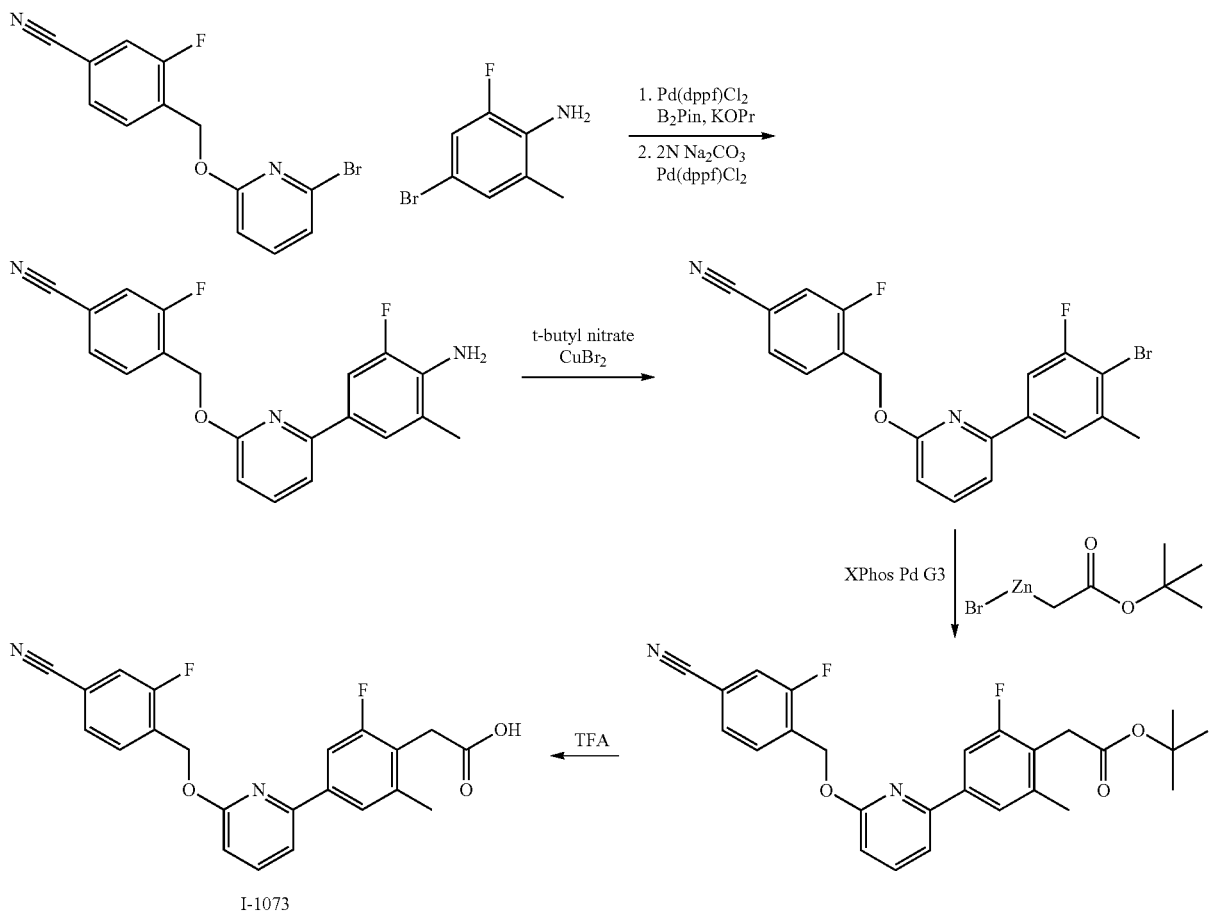

4-[[6-(4-amino-3-fluoro-5-methyl-phenyl)-2-pyridyl]oxymethyl]-3-fluoro-benzonitrile: A suspension of 4-bromo-2-fluoro-6-methyl-aniline (160 mg, 0.78 mmol), [1,1'-Bis(diphenylphosphino)ferrocene] dichloropalladium(II); PdCl$_2$(dppf) (88 mg, 0.12 mmol), potassium propionate (264 mg, 2.35 mmol), and Bis(pinacolato)diboron (209 mg, 0.823 mmol) was degassed, then heated at 120° C. for 1 hr. Next, sodium carbonate (2000 mmol/L, 0.81 mL, 1.63 mmol), 4-[(6-bromo-2-pyridyl)oxymethyl]-3-fluoro-benzonitrile (289 mg, 0.94 mmol) was added, and then the mixture was heated at 110° C. for 1 hr. The mixture was diluted with EtOAc and water. The organic extract was dried over magnesium sulfate, filtered and concentrated. The crude residue was purified by flash chromatography (eluent: EtOAc/hexanes) to yield desired product. ES/MS: 352.2 (M+H+)

4-[[6-(4-bromo-3-fluoro-5-methyl-phenyl)-2-pyridyl]oxymethyl]-3-fluoro-benzonitrile: To CuBr$_2$ (110 mg, 0.617 mmol) and tert-butyl nitrite (0.07 mL, 0.617 mmol) in MeCN, preheated to 60 deg. Next, 4-[[6-(4-amino-3-fluoro-5-methyl-phenyl)-2-pyridyl]oxymethyl]-3-fluoro-benzonitrile (145 mg, 0.411 mmol) as a solution in MeCN (2 mL) was added dropwise. The mixture was then warmed to 80° C. and stirred 1 h. Next, the mixture was left to cool to rt, then diluted with DCM, poured over 0.5 N HCl, extracted with DCM, dried (MgSO$_4$), concentrated, and purified by column chromatography to yield the product. ES/MS: 415.0 (M+)

Tert-butyl 2-[4-[6-[(4-cyano-2-fluoro-phenyl)methoxy]-2-pyridyl]-2-fluoro-6-methyl-phenyl]acetate: A suspension of 4-[[6-(4-bromo-3-fluoro-5-methyl-phenyl)-2-pyridyl]oxymethyl]-3-fluoro-benzonitrile (103 mg, 0.248 mmol), XPhos Pd G3 (18.7 mg, 0.025 mmol), and bromo-(2-tert-butoxy-2-oxo-ethyl)zinc (1.49 mL, 0.744 mmol, 0.5 M) was added to a dry vial under argon, then heated at 65° C. for 12 h. The mixture was diluted with EtOAc and water. The organic extract was dried over magnesium sulfate, filtered and concentrated. The crude residue was purified by flash chromatography (eluent: EtOAc/hexanes) to yield desired product. ES/MS: 451.2 (M+H+)

2-[4-[6-[(4-cyano-2-fluoro-phenyl)methoxy]-2-pyridyl]-2-fluoro-6-methyl-phenyl]acetic acid (I-1073): A solution of tert-butyl 2-[4-[6-[(4-cyano-2-fluoro-phenyl)methoxy]-2-pyridyl]-2-fluoro-6-methyl-phenyl]acetate (32 mg, 0.071 mmol) in DCM had added 2,2,2-trifluoroacetic acid (0.54 mL, 7.1 mmol) added and the solution was stirred at rt for 3 h. The solution was concentrated to give 2-[4-[6-[(4-cyano-2-fluoro-phenyl)methoxy]-2-pyridyl]-2-fluoro-6-methyl-phenyl]acetic acid (I-1073) which was carried forward without further purification. ES/MS: 395.2 (M+H+)

Preparation of Intermediate I-1074

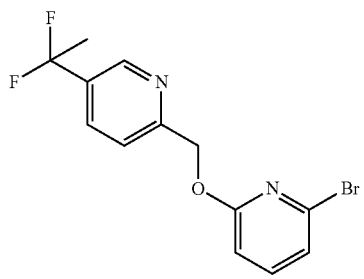

I-1074

2-bromo-6-[[5-(1,1-difluoroethyl)-2-pyridyl]methoxy] pyridine (I-1074): 2-bromo-6-[[5-(1,1-difluoroethyl)-2-pyridyl]methoxy]pyridine (I-1074) was prepared in a manner as described for Intermediate I-1034 substituting 2-(bromomethyl)-5-(1,1-difluoroethyl)pyridine for 6-(bromomethyl)-1-methyl-benzotriazole. ES/MS: 330.2 (M+H+).

Preparation of Intermediate I-1075

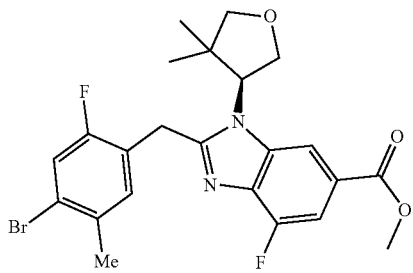

I-1075

Methyl 2-[(4-bromo-2-fluoro-5-methyl-phenyl)methyl]-3-[(3S)-4,4-dimethyltetrahydrofuran-3-yl]-7-fluoro-benzimidazole-5-carboxylate (I-1075): This compound was made analogous to 1-1031 replacing 2-(4-bromo-2-chloro-5-methyl-phenyl)acetic acid for 2-(4-bromo-2-fluoro-5-methyl-phenyl)acetic acid. ES/MS: 493.1, 495.0 (M+H+).

Preparation of Intermediate I-1076

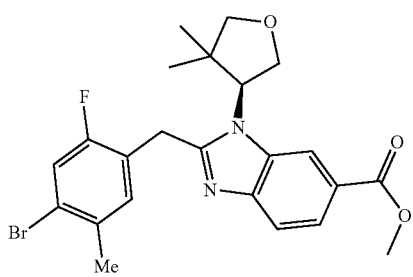

I-1076

Methyl 2-[(4-bromo-2-fluoro-5-methyl-phenyl)methyl]-3-[(3S)-4,4-dimethyltetrahydrofuran-3-yl]benzimidazole-5-carboxylate (I-1076): This compound was made analogous to 1-2 replacing 2-(4-bromo-2-fluoro-phenyl)acetic acid with 2-(4-bromo-2-fluoro-5-methyl-phenyl)acetic acid and I-1 with 1-80. ES/MS: 492.6, 494.6 (M+H+).

Preparation of Intermediate I-1077

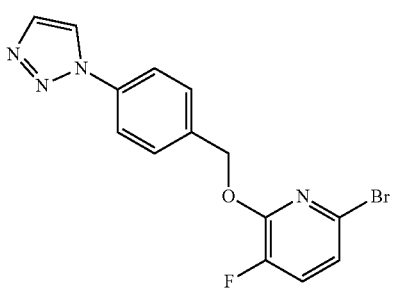

I-1077

6-bromo-3-fluoro-2-[[4-(triazol-1-yl)phenyl]methoxy] pyridine (I-1077): 6-bromo-3-fluoro-2-[[4-(triazol-1-yl)phenyl]methoxy]pyridine (I-1077) was prepared in a manner as described for intermediate 1-1034 substituting 1-(4-(bromomethyl)phenyl)-1H-1,2,3-triazole for 6-(bromomethyl)-1-methyl-benzotriazole and 6-bromo-3-fluoro-pyridin-2-ol for 6-bromopyridin-2-ol ES/MS: 348.2, 350.2 (M+H+).

Preparation of Intermediate I-1086

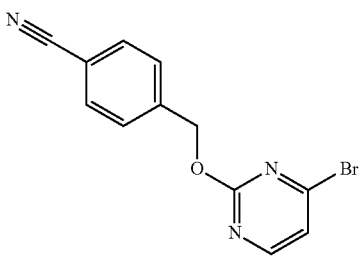

I-1086

4-[(4-bromopyrimidin-2-yl)oxymethyl]benzonitrile (I-1086): 4-[(4-bromopyrimidin-2-yl)oxymethyl]benzonitrile (I-1086) was made analogous to I-94 replacing 3-fluoro-4-(hydroxymethyl)benzonitrile with 4-(hydroxymethyl)benzonitrile. ES/MS: 475.0, 477.0 (M+H+).

Preparation of Intermediate I-1087

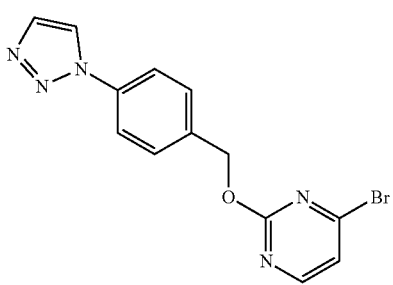

I-1087

4-bromo-2-[[4-(triazol-1-yl)phenyl]methoxy]pyrimidine (I-1087): 4-bromo-2-[[4-(triazol-1-yl)phenyl]methoxy]pyrimidine (I-1087) was made analogous to I-94 replacing 3-fluoro-4-(hydroxymethyl)benzonitrile with [4-(triazol-1-yl)phenyl]methanol. ES/MS: 332.0, 334.0 (M+H+).

Preparation for Intermediate I-1088

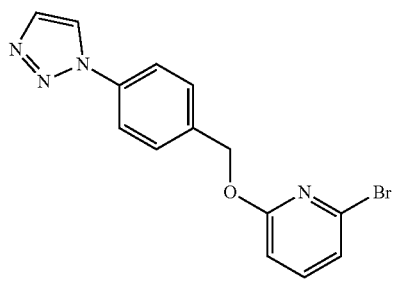

2-bromo-6-[[4-(triazol-1-yl)phenyl]methoxy]pyridine (I-1088): 2-bromo-6-[[4-(triazol-1-yl)phenyl]methoxy]pyridine (I-1088) was prepared in a manner as described for intermediate 1-1034 substituting 1-(4-(bromomethyl)phenyl)-1H-1,2,3-triazole for 6-(bromomethyl)-1-methyl-benzotriazole. ES/MS: 331.2, 333.2 (M+H+).

Preparation of Intermediate I-1091

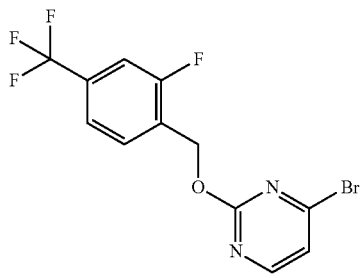

4-bromo-2-((2-fluoro-4-(trifluoromethyl)benzyl)oxy)pyrimidine (I-1091): 4-bromo-2-((2-fluoro-4-(trifluoromethyl)benzyl)oxy)pyrimidine (I-1091) was made analogous to I-94 replacing 3-fluoro-4-(hydroxymethyl)benzonitrile with (2-fluoro-4-(trifluoromethyl)phenyl)methanol. ES/MS: 351.0, 353.0 (M+H+).

Preparation of Intermediate I-1098

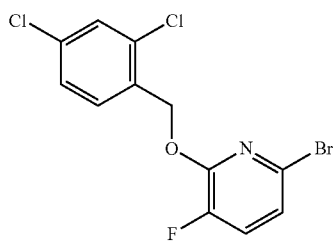

6-bromo-2-((2,4-dichlorobenzyl)oxy)-3-fluoropyridine (I-1098): 6-bromo-2-((2,4-dichlorobenzyl)oxy)-3-fluoropyridine (I-1098) was prepared in a manner as described for intermediate I-1034 substituting 1-(bromomethyl)-2,4-dichlorobenzene for 6-(bromomethyl)-1-methyl-benzotriazol and 6-bromo-3-fluoro-pyridin-2-ol for 6-bromopyridin-2-ol. ES/MS: 351.2 (M+H+).

Preparation of Intermediate I-1099

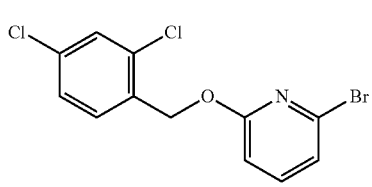

2-bromo-6-[(2,4-dichlorophenyl)methoxy]pyridine (I-1099): 2-bromo-6-[(2,4-dichlorophenyl)methoxy]pyridine (I-1099) was prepared in a manner as described for intermediate I-1040 substituting (2,4-dichlorophenyl)methanol for 6-(bromomethyl)-1-methyl-benzotriazole and 2-bromo-6-fluoro-pyridine for 4-bromo-2-fluoro-pyrimidine. ES/MS: 334.0, 336.0 (M+H+).

Preparation of Intermediate I-1100

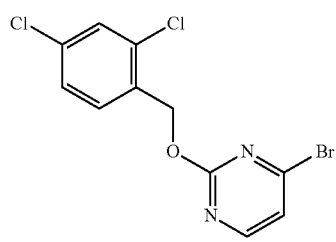

4-bromo-2-[(2,4-dichlorophenyl)methoxy]pyrimidine (I-1100): 4-bromo-2-[(2,4-dichlorophenyl)methoxy]pyrimidine (I-1100) was made analogous to I-94 replacing 3-fluoro-4-(hydroxymethyl)benzonitrile with (2,4-dichlorophenyl)methanol. ES/MS: 334.0, 336.0 (M+H+).

Preparation of Intermediate I-1101

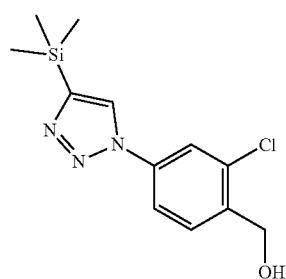

(2-chloro-4-(4-(trimethylsilyl)-11H-1,2,3-triazol-1-yl)phenyl)methanol (I-1101): (2-chloro-4-(4-(trimethylsilyl)-

1H-1,2,3-triazol-1-yl)phenyl)methanol (I-1101) was made analogous to 1-50 replacing methyl 6-chloropyridine-3-carboxylate with methyl 2-chloro-4-fluoro-benzoate and ethynylcyclopropane with ethynyl(trimethyl)silane. ES/MS: 282.0 (M+H+).

Preparation of Intermediate I-1102

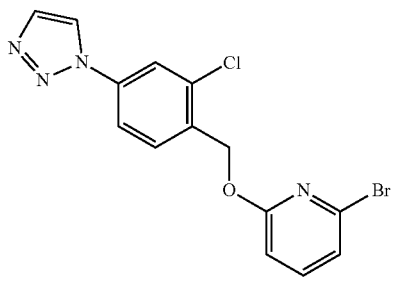

I-1102

2-bromo-6-[[2-chloro-4-(triazol-1-yl)phenyl]methoxy]pyridine (I-1102): 2-bromo-6-[[2-chloro-4-(triazol-1-yl)phenyl]methoxy]pyridine (I-1102) was made analogous to 1-1040 substituting [2-chloro-4-(4-trimethylsilyltriazol-1-yl)phenyl]methanol for 6-(bromomethyl)-1-methyl-benzotriazole and 2-bromo-6-fluoro-pyridine for 4-bromo-2-fluoro-pyrimidine. ES/MS: 366.0, 368.0 (M+H+).

Preparation of Intermediate I-1103

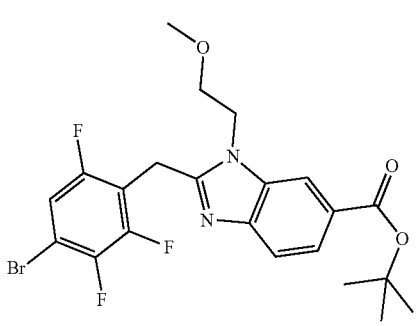

I-1103

Tert-butyl 2-[(4-bromo-2,3,6-trifluoro-phenyl)methyl]-3-(2-methoxyethyl)benzimidazole-5-carboxylate (I-1103): tert-butyl 2-[(4-bromo-2,3,6-trifluoro-phenyl)methyl]-3-(2-methoxyethyl)benzimidazole-5-carboxylate (I-1103) was made analogous to I-2 replacing 2-(4-bromo-2-fluoro-phenyl)acetic acid with 2-(4-bromo-2,3,6-trifluorophenyl)acetic acid and I-1 with 1-6. ES/MS: 500.0, 502.0 (M+H+).

Preparation of Intermediate I-1104

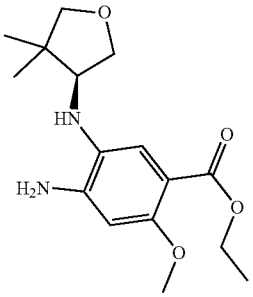

I-1104

Ethyl 4-amino-5-[[(3S)-4,4-dimethyltetrahydrofuran-3-yl]amino]-2-methoxy-benzoate (I-1104): ethyl 4-amino-5-[[(3S)-4,4-dimethyltetrahydrofuran-3-yl]amino]-2-methoxy-benzoate (I-1104) was made analogous to I-1 replacing methyl 3-fluoro-4-nitro-benzoate with methyl 5-fluoro-2-methoxy-4-nitro-benzoate and 2-Methoxyethylamine with (3S)-4,4-dimethyltetrahydrofuran-3-amine; hydrochloride. ES/MS: 309.0 (M+H+).

Preparation of Intermediate I-1105

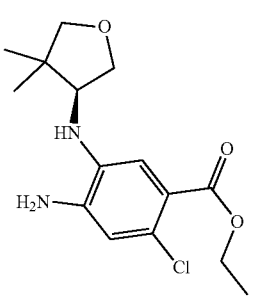

I-1105

Ethyl 4-amino-2-chloro-5-[[(3S)-4,4-dimethyltetrahydrofuran-3-yl]amino]benzoate (I-1105): ethyl 4-amino-2-chloro-5-[[(3S)-4,4-dimethyltetrahydrofuran-3-yl]amino]benzoate (I-1105) was made analogous to I-1 replacing methyl 3-fluoro-4-nitro-benzoate with ethyl 2-chloro-5-fluoro-4-nitro-benzoate and 2-Methoxyethylamine with (3S)-4,4-dimethyltetrahydrofuran-3-amine; hydrochloride. ES/MS: 313.0 (M+H+).

Preparation of Intermediate I-1106

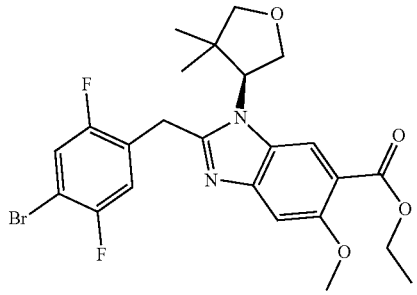

I-1106

Methyl 2-[(4-bromo-2,5-difluoro-phenyl)methyl]-3-[(3S)-4,4-dimethyltetrahydrofuran-3-yl]-6-methoxy-benzimidazole-5-carboxylate (I-1106): methyl 2-[(4-bromo-2,5-difluoro-phenyl)methyl]-3-[(3S)-4,4-dimethyltetrahydrofuran-3-yl]-6-methoxy-benzimidazole-5-carboxylate (I-1106) was made analogous to I-2 replacing 2-(4-bromo-2-fluoro-phenyl)acetic acid with 2-(4-bromo-2,5-difluoro-phenyl)acetic acid and I-1 with I-1104. ES/MS: 510.0 (M+H+).

Preparation of Intermediate I-1107

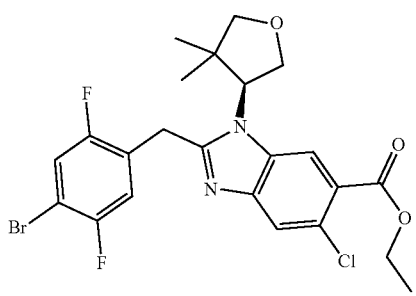

I-1107

Ethyl 2-[(4-bromo-2,5-difluoro-phenyl)methyl]-6-chloro-3-[(3S)-4,4-dimethyltetrahydrofuran-3-yl]benzimidazole-5-carboxylate (I-1107): ethyl 2-[(4-bromo-2,5-difluoro-phenyl)methyl]-6-chloro-3-[(3S)-4,4-dimethyltetrahydrofuran-3-yl]benzimidazole-5-carboxylate (I-1107) was made prepared in a manner as described for I-2 replacing 2-(4-bromo-2-fluoro-phenyl)acetic acid with 2-(4-bromo-2,5-difluoro-phenyl)acetic acid and I-1 with I-1105. ES/MS: 528.0 (M+H+).

Preparation of Intermediate I-1110

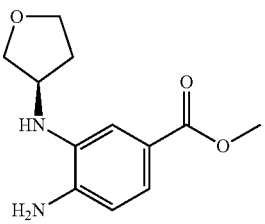

I-1110

Methyl (R)-4-amino-3-((tetrahydrofuran-3-yl)amino)benzoate (I-1110): methyl (R)-4-amino-3-((tetrahydrofuran-3-yl)amino)benzoate (I-1110) was prepared in a manner as described for Intermediate I-1 substituting 4-methylbenzenesulfonic acid; (3R)-tetrahydrofuran-3-amine for 2-methoxyethylamine. ES/MS: 237.2 (M+H+).

Preparation of Intermediate I-1111

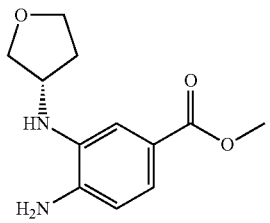

I-1111

Methyl (S)-4-amino-3-((tetrahydrofuran-3-yl)amino)benzoate (I-1111): methyl (S)-4-amino-3-((tetrahydrofuran-3-yl)amino)benzoate (I-1111) was prepared in a manner as described for Intermediate I-1 substituting 4-methylbenzenesulfonic acid; (3S)-tetrahydrofuran-3-amine for 2-methoxyethylamine. ES/MS: 237.1 (M+H+).

Preparation of Intermediate I-1112

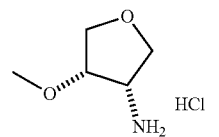

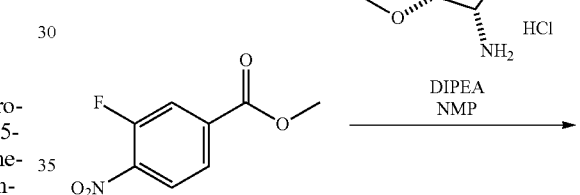

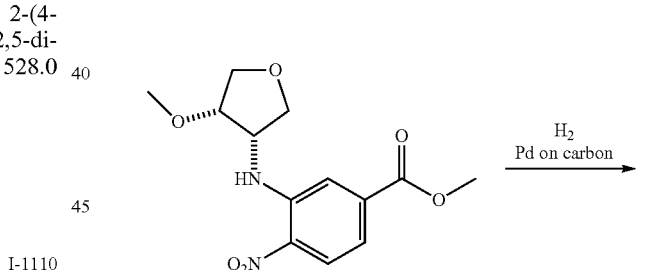

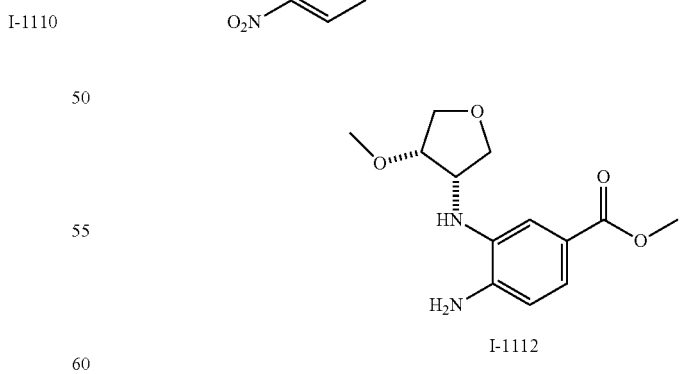

I-1112

Methyl 4-amino-3-((cis-4-methoxytetrahydrofuran-3-yl)amino)benzoate (I-1112): methyl 4-amino-3-((cis-4-methoxytetrahydrofuran-3-yl)amino)benzoate was prepared in a manner as described for Intermediate I-1 substituting cis-4-methoxytetrahydrofuran-3-amine hydrochloride for 2-methoxyethylamine. ES/MS: 367.2 (M+H+)

Preparation of Intermediate I-1113

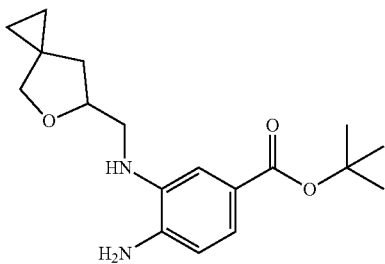

I-1113

Tert-butyl 3-(((5-oxaspiro[2.4]heptan-6-yl)methyl)amino)-4-aminobenzoate (I-1113): tert-butyl 3-(((5-oxaspiro[2.4]heptan-6-yl)methyl)amino)-4-aminobenzoate was prepared in a manner as described for Intermediate I-6 substituting (5-oxaspiro[2.4]heptan-6-yl)methanamine hydrochloride for 2-methoxyethylamine. ES/MS: 319.0 (M+H+)

Preparation of Intermediate I-1114

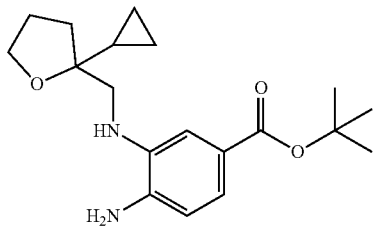

I-1114

Tert-butyl 4-amino-3-(((2-cyclopropyltetrahydrofuran-2-yl)methyl)amino)benzoate (I-1114): tert-butyl 3-(((5-oxaspiro[2.4]heptan-6-yl)methyl)amino)-4-aminobenzoate was prepared in a manner as described for Intermediate I-6 substituting (2-cyclopropyltetrahydrofuran-2-yl)methanamine for 2-methoxyethylamine. ES/MS: 333.3 (M+H+)

Preparation of Intermediate I-1115

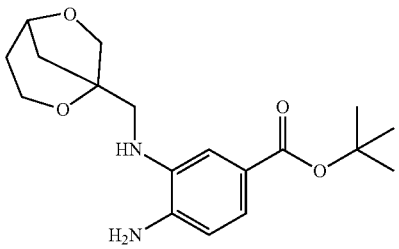

I-1115

Tert-butyl 3-(((2,6-dioxabicyclo[3.2.1]octan-1-yl)methyl)amino)-4-aminobenzoate (I-1115): tert-butyl 3-(((2,6-dioxabicyclo[3.2.1]octan-1-yl)methyl)amino)-4-aminobenzoate was prepared in a manner as described for Intermediate I-6 substituting 2,6-dioxabicyclo[3.2.1]octan-1-ylmethanamine hydrochloride for 2-methoxyethylamine. ES/MS: 335.2 (M+H+)

Preparation of Intermediate I-1116

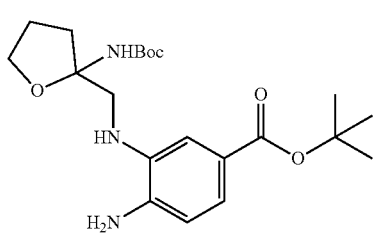

I-1116

Methyl 4-amino-3-(((2-((tert-butoxycarbonyl)amino)tetrahydrofuran-2-yl)methyl)amino)benzoate (I-1116): methyl 4-amino-3-(((2-((tert-butoxycarbonyl)amino)tetrahydrofuran-2-yl)methyl)amino)benzoate was prepared in a manner as described for Intermediate I-1 substituting tert-butyl (2-(aminomethyl)tetrahydrofuran-2-yl)carbamate hydrochloride for 2-methoxyethylamine. ES/MS: 333.3 (M+H+)

Preparation of Intermediate I-1117

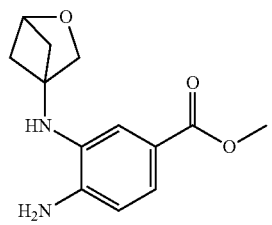

I-1117

Methyl 4-amino-3-(2-oxabicyclo[2.1.1]hexan-4-ylamino)benzoate (I-1117): methyl 4-amino-3-(2-oxabicyclo[2.1.1]hexan-4-ylamino)benzoate was prepared in a manner as described for Intermediate I-1 substituting 2-oxabicyclo[2.1.1]hexan-4-amine hydrochloride for 2-methoxyethylamine. ES/MS: 249.2 (M+H+)

Preparation of Intermediate I-1118

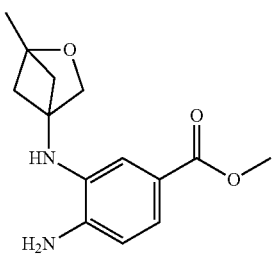

I-1118

Methyl 4-amino-3-[(1-methyl-2-oxabicyclo[2.1.1]hexan-4-yl)amino]benzoate (I-1118): methyl 4-amino-3-[(1-methyl-2-oxabicyclo[2.1.1]hexan-4-yl)amino]benzoate was prepared in a manner as described for Intermediate I-1 substituting 1-methyl-2-oxabicyclo[2.1.1]hexan-4-amine hydrochloride for 2-methoxyethylamine. ES/MS: 249.2 (M+H+)

Preparation of Intermediate I-1119

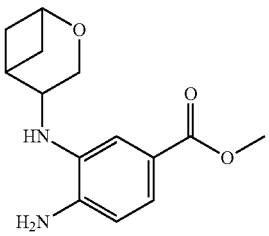

I-1119

Methyl 4-amino-3-(2-oxabicyclo[3.1.1]heptan-4-ylamino)benzoate (I-1119): methyl 4-amino-3-(2-oxabicyclo[3.1.1]heptan-4-ylamino)benzoate was prepared in a manner as described for Intermediate I-1 substituting 2-oxabicyclo[3.1.1]heptan-4-amine for 2-methoxyethylamine. ES/MS: 263.2 (M+H+)

Preparation of Intermediate I-1120

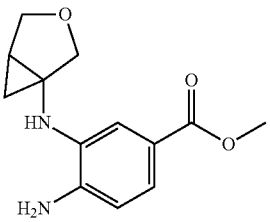

I-1120

Methyl 4-amino-3-(3-oxabicyclo[3.1.0]hexan-1-ylamino)benzoate (I-1120): methyl 4-amino-3-(3-oxabicyclo[3.1.0]hexan-1-ylamino)benzoate was prepared in a manner as described for Intermediate I-1 substituting 3-oxabicyclo[3.1.0]hexan-1-amine hydrochloride for 2-methoxyethylamine. ES/MS: 249.2 (M+H+)

Preparation of Intermediate I-1121

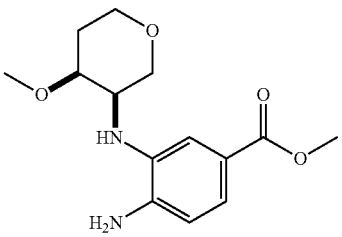

I-1121

Methyl 4-amino-3-[[cis-4-methoxytetrahydropyran-3-yl]amino]benzoate (I-1121): methyl 4-amino-3-[[cis-4-methoxytetrahydropyran-3-yl]amino]benzoate was prepared in a manner as described for Intermediate I-1 substituting cis-4-methoxytetrahydropyran-3-amine hydrochloride for 2-methoxyethylamine. ES/MS: 281.1 (M+H+)

Preparation of Intermediate I-1122

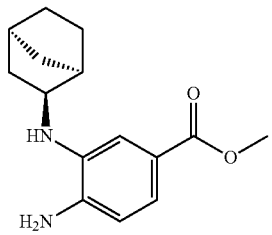

I-1122

Methyl 4-amino-3-[[(1r,4r,6s)-2-oxabicyclo[2.2.1]heptan-6-yl]amino]benzoate (I-1122): methyl 4-amino-3-[[(1r,4r,6s)-2-oxabicyclo[2.2.1]heptan-6-yl]amino]benzoate was prepared in a manner as described for Intermediate I-1 substituting (1r,4r,6s)-2-oxabicyclo[2.2.1]heptan-6-amine hydrochloride for 2-methoxyethylamine. ES/MS: 263.2 (M+H+)

Preparation of Intermediate I-1123

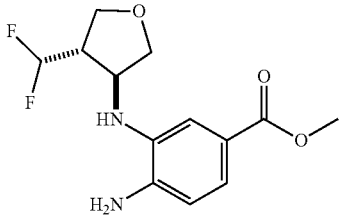

I-1123

Methyl 4-amino-3-[[trans-4-(difluoromethyl)tetrahydrofuran-3-yl]amino]benzoate (I-1123): methyl 4-amino-3-[[trans-4-(difluoromethyl)tetrahydrofuran-3-yl]amino]benzoate was prepared in a manner as described for Intermediate I-1 substituting trans-4-(difluoromethyl)tetrahydrofuran-3-amine hydrochloride for 2-methoxyethylamine. ES/MS: 287.2 (M+H+)

Preparation of Intermediate I-1124

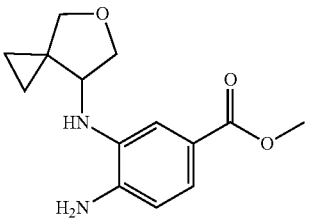

I-1124

Methyl 4-amino-3-(5-oxaspiro[2.4]heptan-7-ylamino)benzoate (I-1124): methyl 4-amino-3-(5-oxaspiro[2.4]heptan-7-ylamino)benzoate was prepared in a manner as described for Intermediate I-69 substituting 5-oxaspiro[2.4]heptan-7-amine hydrochloride for 4,4-dimethyltetrahydrofuran-3-amine hydrochloride. ES/MS: 263.2 (M+H+)

Preparation of Intermediate I-1125

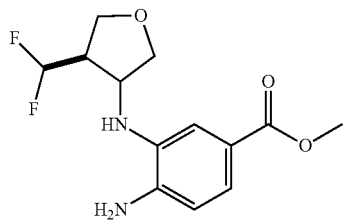

I-1125

Methyl 4-amino-3-[[cis-4-(difluoromethyl)tetrahydrofuran-3-yl]amino]benzoate (I-1125): methyl 4-amino-3-[[trans-4-(difluoromethyl)tetrahydrofuran-3-yl]amino]benzoate was prepared in a manner as described for Intermediate I-1 substituting cis-4-(difluoromethyl)tetrahydrofuran-3-amine hydrochloride for 2-methoxyethylamine. ES/MS: 287.2 (M+H+)

Preparation of Intermediate I-1126

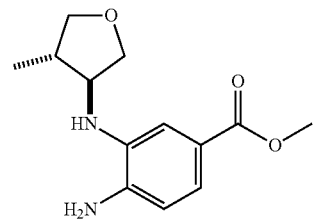

I-1126

Methyl 4-amino-3-[[trans-4-methyltetrahydrofuran-3-yl]amino]benzoate (I-1126): methyl 4-amino-3-[[trans-4-methyltetrahydrofuran-3-yl]amino]benzoate was prepared in a manner as described for Intermediate I-1 substituting trans-4-methyltetrahydrofuran-3-amine hydrochloride for 2-methoxyethylamine. ES/MS: 251.2 (M+H+)

Preparation of Intermediate I-1129

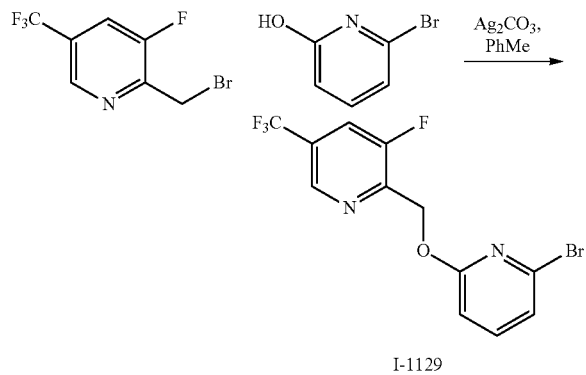

I-1129

2-[(6-bromo-2-pyridyl)oxymethyl]-3-fluoro-5-(trifluoromethyl)pyridine (I-1129): 2-(bromomethyl)-3-fluoro-5-(trifluoromethyl)pyridine (107 mg, 0.41 mmol), 6-bromopyridin-2-ol (60 mg, 0.35 mmol), and silver carbonate (190 mg, 0.69 mmol) in toluene (5 mL) was stirred at 90° C. for 1 h. The mixture was cooled to rt and filtered through a Celite plug. The resulting solution was concentrated and purified by flash chromatography (eluent: EtOAc/hexanes) to yield the desired product. ES/MS: 351.0 (M+H+)

Preparation of Intermediate I-1131

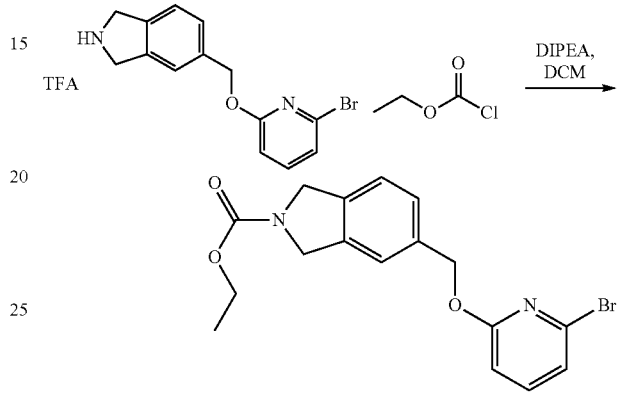

I-1131

Ethyl 5-[(6-bromo-2-pyridyl)oxymethyl]isoindoline-2-carboxylate (I-1131): DIPEA (0.075 mL, 0.43 mmol) and ethyl chloroformate (0.016 mL, 0.17 mmol) were added to a solution of 5-[(6-bromo-2-pyridyl)oxymethyl]isoindoline; 2,2,2-trifluoroacetic acid (60 mg, 0.14 mmol) in DCM at rt. The mixture was stirred at rt for 2 hr. before concentrating in vacuo. Purification by flash chromatography (eluent: EtOAc/hexanes) yielded the desired product. ES/MS: 379.0 (M+H+)

Preparation of Intermediate I-1132

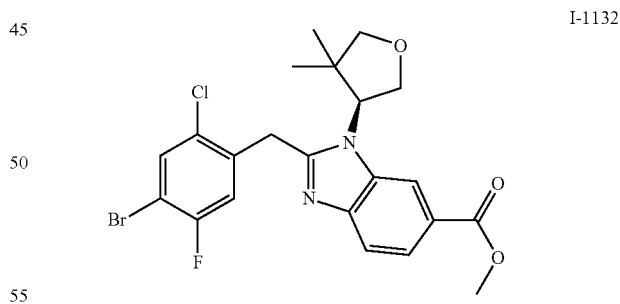

I-1132

Methyl 2-[(4-bromo-2-chloro-5-fluoro-phenyl)methyl]-3-[(3S)-4,4-dimethyltetrahydrofuran-3-yl]benzimidazole-5-carboxylate (I-1132): Methyl 2-[(4-bromo-2-chloro-5-fluoro-phenyl)methyl]-3-[(3S)-4,4-dimethyltetrahydrofuran-3-yl]benzimidazole-5-carboxylate was prepared in a manner as described for Intermediate I-2 substituting methyl 4-amino-3-((4,4-dimethyltetrahydrofuran-3-yl)amino)benzoate 1-80 for methyl 4-amino-3-(2-methoxyethylamino)benzoate I-1 and 2-(4-bromo-2-chloro-5-fluoro-phenyl)acetic acid for 2-(4-bromo-2-fluoro-phenyl)acetic acid. ES/MS: 497.3 (M+H+).

Preparation of Intermediate I-1133

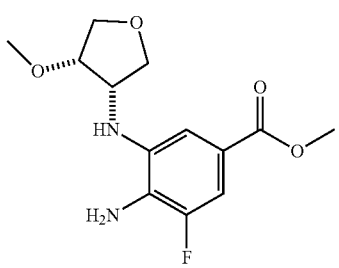

I-1133

Methyl 4-amino-3-fluoro-5-((cis-4-methoxytetrahydrofuran-3-yl)amino)benzoate (I-1133): methyl 4-amino-3-fluoro-5-((cis-4-methoxytetrahydrofuran-3-yl)amino)benzoate was prepared in a manner as described for Intermediate I-1 substituting trans-4-methoxytetrahydrofuran-3-amine hydrochloride for 2-methoxyethylamine and methyl 3,5-difluoro-4-nitro-benzoate for methyl 3-fluoro-4-nitro-benzoate. ES/MS: 285.2 (M+H+)

Preparation of Intermediate I-1134

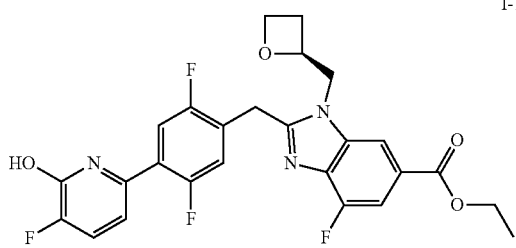

I-1134

Ethyl 2-[[2,5-difluoro-4-(5-fluoro-6-hydroxy-2-pyridyl)phenyl]methyl]-7-fluoro-3-[[(2S)-oxetan-2-yl]methyl]benzimidazole-5-carboxylate (I-1134): ethyl 2-[[2,5-difluoro-4-(5-fluoro-6-hydroxy-2-pyridyl)phenyl]methyl]-7-fluoro-3-[[(2S)-oxetan-2-yl]methyl]benzimidazole-5-carboxylate was prepared in a manner as described for Intermediate 1-9 substituting 1-14 for 1-8 and 2-benzyloxy-6-bromo-3-fluoro-pyridine for 2-benzyloxy-6-bromopyridine. ES/MS: 516.1 (M+H+).

Preparation of Intermediate I-1135

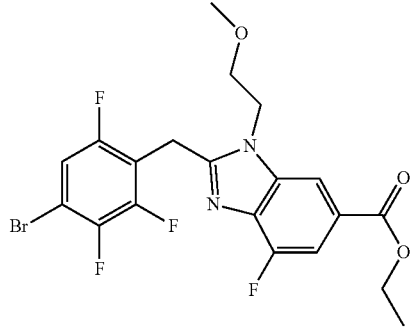

I-1135

Ethyl 2-(4-bromo-2,3,6-trifluorobenzyl)-4-fluoro-1-(2-methoxyethyl)-1H-benzo[d]imidazole-6-carboxylate (I-1135): ethyl 2-(4-bromo-2,3,6-trifluorobenzyl)-4-fluoro-1-(2-methoxyethyl)-1H-benzo[d]imidazole-6-carboxylate was prepared in a manner as described for I-2 substituting ethyl 4-amino-3-fluoro-5-((2-methoxyethyl)amino)benzoate I-1032 for methyl 4-amino-3-(2 methoxyethylamino)benzoate I-1 and 2-(4-bromo-2,5,6-trifluorophenyl)acetic acid for 2-(4-bromo-2,5-difluorophenyl)acetic acid. ES/MS: 490.2 (M+H+).

Preparation of Intermediate I-1136

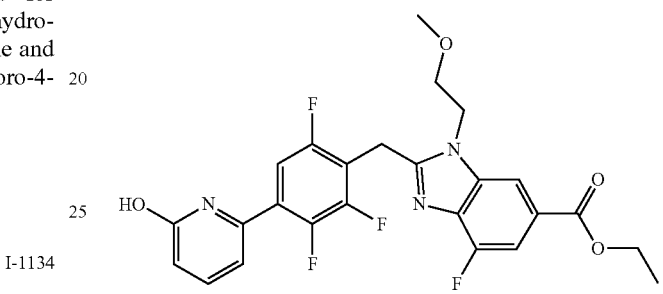

I-1136

Ethyl 7-fluoro-3-(2-methoxyethyl)-2-[[2,3,6-trifluoro-4-(6-hydroxy-2-pyridyl)phenyl]methyl]benzimidazole-5-carboxylate (I-1136): ethyl 7-fluoro-3-(2-methoxyethyl)-2-[[2,3,6-trifluoro-4-(6-hydroxy-2-pyridyl)phenyl]methyl]benzimidazole-5-carboxylate was prepared in a manner as described for Intermediate I-9 substituting ethyl 2-(4-bromo-2,3,6-trifluorobenzyl)-4-fluoro-1-(2-methoxyethyl)-1H-benzo[d]imidazole-6-carboxylate I-1135 for I-8. ES/MS: 504.1 (M+H+).

Preparation of Intermediate I-1140

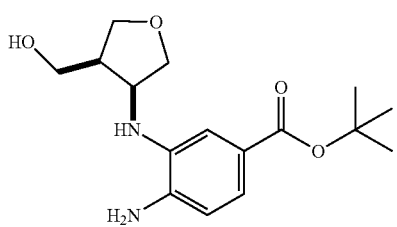

I-1140

Tert-butyl 4-amino-3-((cis-4-(hydroxymethyl)tetrahydrofuran-3-yl)amino)benzoate (I-1140): tert-butyl 4-amino-3-((cis-4-(hydroxymethyl)tetrahydrofuran-3-yl)amino)benzoate was prepared in a manner as described for Intermediate I-6 substituting (cis-4-aminotetrahydrofuran-3-yl)methanol for 2-methoxyethylamine. ES/MS: 339.2 (M+H+)

Preparation of Intermediate I-1141

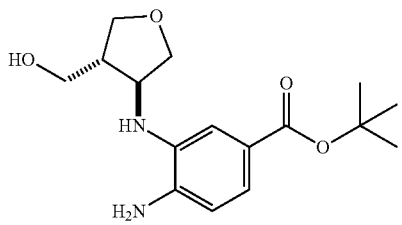

Tert-butyl 4-amino-3-((trans-4-(hydroxymethyl)tetrahydrofuran-3-yl)amino)benzoate (I-1141): tert-butyl 4-amino-3-((trans-4-(hydroxymethyl)tetrahydrofuran-3-yl)amino)benzoate was prepared in a manner as described for Intermediate I-6 substituting (trans-4-aminotetrahydrofuran-3-yl)methanol for 2-methoxyethylamine. ES/MS: 339.2 (M+H+)

Preparation of Intermediate I-1142

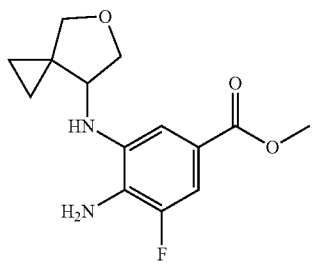

Methyl 3-((5-oxaspiro[2.4]heptan-7-yl)amino)-4-amino-5-fluorobenzoate (I-1142): methyl 3-((5-oxaspiro[2.4]heptan-7-yl)amino)-4-amino-5-fluorobenzoate was prepared in a manner as described for Intermediate I-1 substituting 5-oxaspiro[2.4]heptan-7-amine hydrochloride for 2-methoxyethylamine and methyl 3,5-difluoro-4-nitro-benzoate for methyl 3-fluoro-4-nitro-benzoate. ES/MS: 281.2 (M+H+)

Preparation of Intermediate I-1143

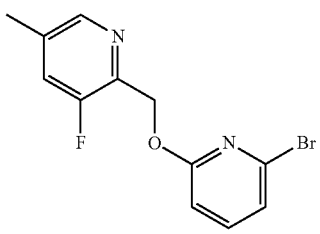

2-[(6-bromo-2-pyridyl)oxymethyl]-3-fluoro-5-methyl-pyridine (I-1143): 2-[(6-bromo-2-pyridyl)oxymethyl]-3-fluoro-5-methyl-pyridine was prepared in a manner as described for Intermediate I-43 substituting (3-fluoro-5-methyl-2-pyridyl)methanol for (1-methylimidazol-4-yl)methanol. ES/MS: 298.8 (M+H+)

Preparation of Intermediate I-1144

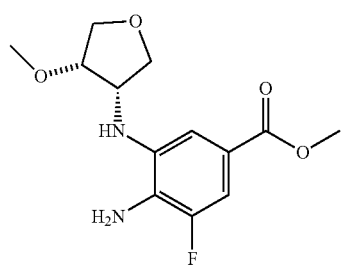

Methyl 4-amino-3-fluoro-5-((cis-4-methoxytetrahydrofuran-3-yl)amino)benzoate (I-1144): methyl 4-amino-3-fluoro-5-((cis-4-methoxytetrahydrofuran-3-yl)amino)benzoate was prepared in a manner as described for Intermediate I-1 substituting 5-oxaspiro[2.4]heptan-7-amine hydrochloride for 2-methoxyethylamine and methyl 3,5-difluoro-4-nitro-benzoate for methyl 3-fluoro-4-nitro-benzoate. ES/MS: 281.2 (M+H+)

Preparation of Intermediate I-1149

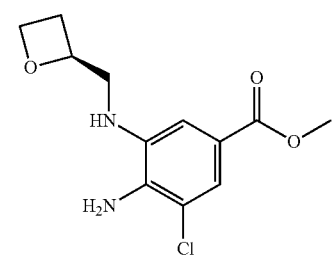

Methyl (S)-4-amino-3-chloro-5-((oxetan-2-ylmethyl)amino)benzoate (I-1149): methyl (S)-4-amino-3-chloro-5-((oxetan-2-ylmethyl)amino)benzoate was prepared in a manner as described for Intermediate I-68 substituting (S)-oxetan-2-ylmethanamine for 2-methoxyethylamine and methyl 3-chloro-5-fluoro-4-nitrobenzoate for methyl 3-fluoro-4-nitro-benzoate. ES/MS: 271.0 (M+H+).

Preparation of Intermediate I-1150

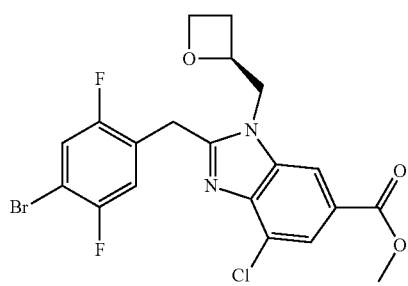

Methyl (S)-2-(4-bromo-2,5-difluorobenzyl)-4-chloro-1-(oxetan-2-ylmethyl)-1H-benzo[d]imidazole-6-carboxylate (I-1150): methyl (S)-2-(4-bromo-2,5-difluorobenzyl)-4-chloro-1-(oxetan-2-ylmethyl)-1H-benzo[d]imidazole-6-carboxylate was prepared in a manner as described for Intermediate I-2 substituting methyl (S)-4-amino-3-chloro-5-((oxetan-2-ylmethyl)amino)benzoate 1-1149 for methyl 4-amino-3-(2-methoxyethylamino)benzoate I-1 and 2-(4-bromo-2,5-difluoro-phenyl)acetic acid for 2-(4-bromo-2-fluoro-phenyl)acetic acid. ES/MS: 504.9 (M+H+).

Preparation of Intermediate I-1152

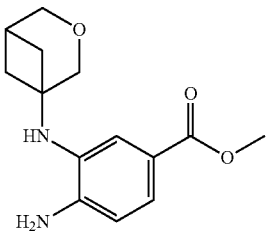

I-1152

Methyl 4-nitro-3-(3-oxabicyclo[3.1.1]heptan-1-ylamino)benzoate (I-1152): methyl 4-nitro-3-(3-oxabicyclo[3.1.1]heptan-1-ylamino)benzoate was prepared in a manner as described for Intermediate I-1 substituting 3-oxabicyclo[3.1.1]heptan-1-amine hydrochloride for 2-methoxyethylamine. ES/MS: 293.0 (M+H+).

Preparation of Intermediate I-1153

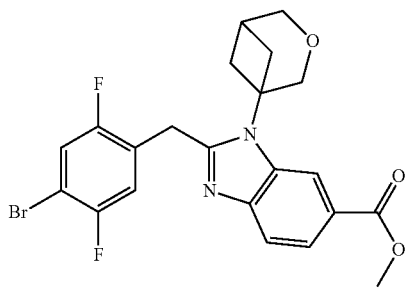

I-1153

Methyl 2-[(4-bromo-2,5-difluoro-phenyl)methyl]-3-(3-oxabicyclo[3.1.1]heptan-1-yl)benzimidazole-5-carboxylate (I-1153): Methyl 2-[(4-bromo-2,5-difluoro-phenyl)methyl]-3-(3-oxabicyclo[3.1.1]heptan-1-yl)benzimidazole-5-carboxylate was prepared in a manner as described for Intermediate I-2 substituting methyl 4-nitro-3-(3-oxabicyclo[3.1.1]heptan-1-ylamino)benzoate 1-1152 for methyl 4-amino-3-(2-methoxyethylamino)benzoate I-1 and 2-(4-bromo-2,5-difluoro-phenyl)acetic acid for 2-(4-bromo-2-fluoro-phenyl)acetic acid. ES/MS: 477.0 (M+H+).

Preparation of Intermediate I-1154

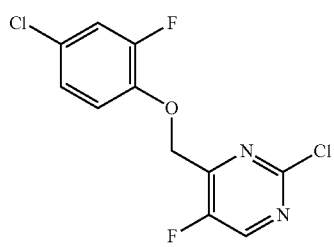

I-1154

2-chloro-4-[(4-chloro-2-fluoro-phenyl)methoxy]-5-fluoro-pyrimidine (I-1154): 2-chloro-4-[(4-chloro-2-fluoro-phenyl)methoxy]-5-fluoro-pyrimidine was prepared in a manner as described for Intermediate I-1129 substituting 1-(bromomethyl)-4-chloro-2-fluoro-benzene for 2-(bromomethyl)-3-fluoro-5-(trifluoromethyl)pyridine and 2-chloro-5-fluoro-pyrimidin-4-ol for 6-bromopyridin-2-ol. ES/MS: 291.0 (M+H+)

Preparation of Intermediate I-1155

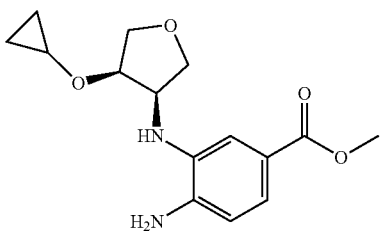

I-1155

Methyl 4-amino-3-[[cis-4-(cyclopropoxy)tetrahydrofuran-3-yl]amino]benzoate (I-1155): Methyl 4-amino-3-[[cis-4-(cyclopropoxy)tetrahydrofuran-3-yl]amino]benzoate was prepared in a manner as described for Intermediate I-68 substituting cis-4-(cyclopropoxy)tetrahydrofuran-3-amine hydrochloride for 2-methoxyethylamine. ES/MS: 293.0 (M+H+)

Preparation of Intermediate I-1156

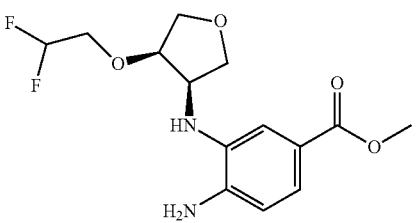

I-1156

Methyl 3-[[cis-4-(2,2-difluoroethoxy)tetrahydrofuran-3-yl]amino]-4-nitro-benzoate (I-1156): Methyl 3-[[cis-4-(2,2-difluoroethoxy)tetrahydrofuran-3-yl]amino]-4-nitro-benzoate was prepared in a manner as described for Intermediate I-1 substituting cis-4-(2,2-difluoroethoxy)tetrahydrofuran-3-amine hydrochloride for 2-methoxyethylamine. ES/MS: 317.2 (M+H+).

Preparation of Intermediate I-1157

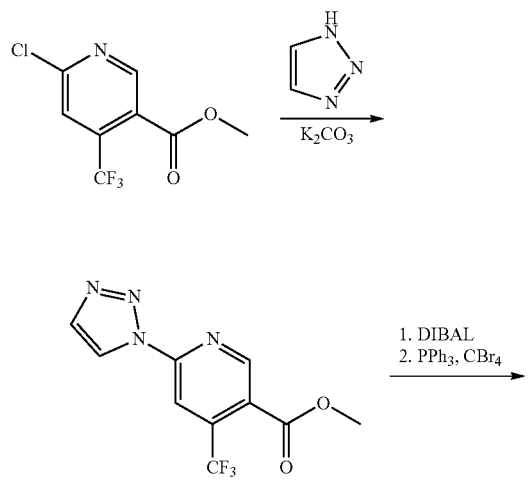

I-1157

Methyl 6-(triazol-1-yl)-4-(trifluoromethyl)pyridine-3-carboxylate: 2H-triazole (170 mg, 2.5 mmol), methyl 6-chloro-4-(trifluoromethyl)pyridine-3-carboxylate (500 mg, 2.0 mmol), and K$_2$CO$_3$ (580 mg, 4.2 mmol) in DMF (15 mL) was stirred at 80° C. for 10 h. The mixture was diluted with EtOAc and water, and the layers were separated. The combined organic extracts were washed with brine, dried over MgSO$_4$, filtered, and concentrated. Purification by flash chromatography (eluent: EtOAc/hexanes) yielded the desired product. ES/MS: 273.1 (M+H+)

5-(bromomethyl)-2-(triazol-1-yl)-4-(trifluoromethyl) pyridine (I-1157): Methyl 6-(triazol-1-yl)-4-(trifluoromethyl)pyridine-3-carboxylate (140 mg, 0.51 mmol) in THF (10 mL) was cooled to 0° C. DIABL (1M in THF, 2.0 mL, 2.0 mmol) was added dropwise and the mixture was slowly warmed to rt for 5 h. The mixture was next quenched with saturated aqueous NH$_4$Cl and diluted with EtOAc, and the layers were separated. The combined organic extracts were washed with brine, dried over MgSO$_4$, filtered, and concentrated. The residue was dissolved in DCM and cooled to 0° C. Triphenylphosphine (100 mg, 0.37 mmol) and CBr$_4$ (120 mg, 0.37 mmol) were added, respectively. The mixture was warmed to rt and stirred for 2 h before concentrating in vacuo. Purification by flash chromatography (eluent: EtOAc/hexanes) yielded the desired product. ES/MS: 308.0 (M+H+)

Preparation of Intermediate I-1158

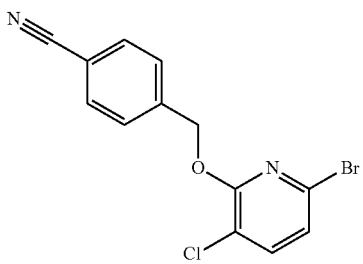

I-1158

4-[(6-bromo-3-chloro-2-pyridyl)oxymethyl]benzonitrile (I-1158): 4-[(6-bromo-3-chloro-2-pyridyl)oxymethyl]benzonitrile was prepared in a manner as described for Intermediate I-1129 substituting 4-(bromomethyl)benzonitrile for 2-(bromomethyl)-3-fluoro-5-(trifluoromethyl)pyridine and 6-bromo-3-chloro-pyridin-2-ol for 6-bromopyridin-2-ol. ES/MS: 324.0 (M+H+)

Preparation of Intermediate I-1159

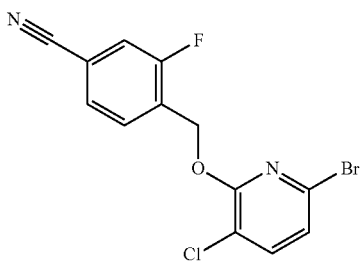

I-1159

4-[(6-bromo-3-chloro-2-pyridyl)oxymethyl]-3-fluoro-benzonitrile (I-1159): 4-[(6-bromo-3-chloro-2-pyridyl)oxymethyl]-3-fluoro-benzonitrile was prepared in a manner as described for Intermediate I-1129 substituting 4-(bromomethyl)-3-fluorobenzonitrile for 2-(bromomethyl)-3-fluoro-5-(trifluoromethyl)pyridine and 6-bromo-3-chloro-pyridin-2-ol for 6-bromopyridin-2-ol. ES/MS: 342.0 (M+H+)

Preparation of Intermediate I-1160

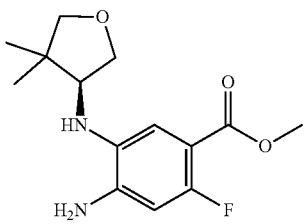

I-1160

Methyl (S)-4-amino-5-((4,4-dimethyltetrahydrofuran-3-yl)amino)-2-fluorobenzoate (I-1160): Methyl (S)-4-amino-5-((4,4-dimethyltetrahydrofuran-3-yl)amino)-2-fluorobenzoate was prepared in a manner as described for Intermediate I-1 substituting (S)-4,4-dimethyltetrahydrofuran-3-amine hydrochloride for 2-methoxyethylamine and methyl 2,5-difluoro-4-nitrobenzoate for methyl 3-fluoro-4-nitrobenzoate. ES/MS: 283.2 (M+H+)

Preparation of Intermediate I-1161

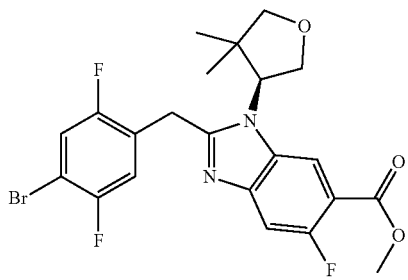

I-1161

Methyl 2-[(4-bromo-2,5-difluoro-phenyl)methyl]-3-[(3S)-4,4-dimethyltetrahydrofuran-3-yl]-6-fluoro-benzimidazole-5-carboxylate (I-1161): Methyl 2-[(4-bromo-2,5-difluoro-phenyl)methyl]-3-[(3S)-4,4-dimethyltetrahydrofuran-3-yl]-6-fluoro-benzimidazole-5-carboxylate was prepared in a manner as described for Intermediate I-2 substituting methyl (S)-4-amino-5-((4,4-dimethyltetrahydrofuran-3-yl)amino)-2-fluorobenzoate 1-1160 for methyl 4-amino-3-(2-methoxyethylamino)benzoate I-1 and 2-(4-bromo-2,5-difluoro-phenyl)acetic acid for 2-(4-bromo-2-fluoro-phenyl)acetic acid. ES/MS: 498.0 (M+H+).

Preparation of Intermediate I-1162

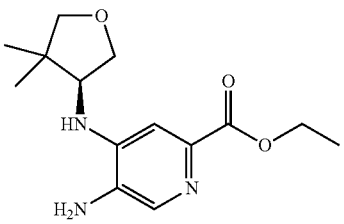

I-1162

Ethyl (S)-5-amino-4-((4,4-dimethyltetrahydrofuran-3-yl)amino)picolinate (I-1162): ethyl (S)-5-amino-4-((4,4-dimethyltetrahydrofuran-3-yl)amino)picolinate was prepared in a manner as described for Intermediate I-1 substituting (S)-4,4-dimethyltetrahydrofuran-3-amine hydrochloride for 2-methoxyethylamine and ethyl 4-chloro-5-nitropicolinate for methyl 3-fluoro-4-nitrobenzoate. ES/MS: 280.0 (M+H+)

Preparation of Intermediate I-1163

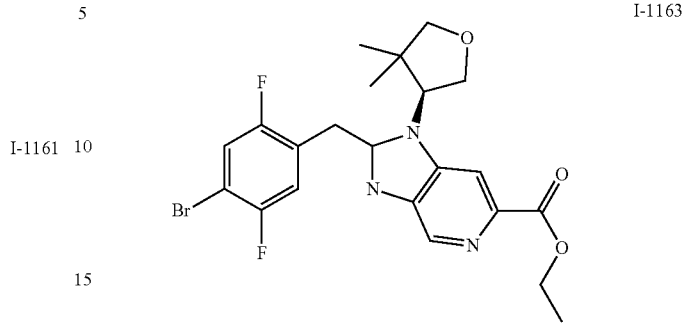

I-1163

Ethyl 2-[(4-bromo-2,5-difluoro-phenyl)methyl]-1-[(3S)-4,4-dimethyltetrahydrofuran-3-yl]imidazo[4,5-c]pyridine-6-carboxylate (I-1163): Ethyl 2-[(4-bromo-2,5-difluorophenyl)methyl]-1-[(3S)-4,4-dimethyltetrahydrofuran-3-yl]imidazo[4,5-c]pyridine-6-carboxylate was prepared in a manner as described for Intermediate I-2 substituting ethyl (S)-5-amino-4-((4,4-dimethyltetrahydrofuran-3-yl)amino)picolinate 1-1162 for methyl 4-amino-3-(2-methoxyethylamino)benzoate I-1 and 2-(4-bromo-2,5-difluoro-phenyl)acetic acid for 2-(4-bromo-2-fluoro-phenyl)acetic acid. ES/MS: 495.0 (M+H+).

Preparation of Intermediate I-1164

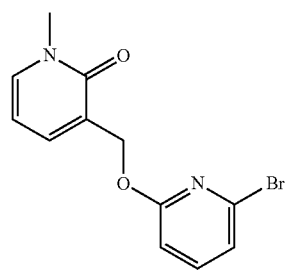

I-1164

3-[(6-bromo-2-pyridyl)oxymethyl]-1-methyl-pyridin-2-one (I-1164): 3-[(6-bromo-2-pyridyl)oxymethyl]-1-methyl-pyridin-2-one was prepared in a manner as described for Intermediate I-43 substituting [3-(hydroxymethyl)-1-methyl-pyridin-2-one for (1-methylimidazol-4-yl)methanol. ES/MS: 295.0 (M+H+)

Preparation of Intermediate I-1165

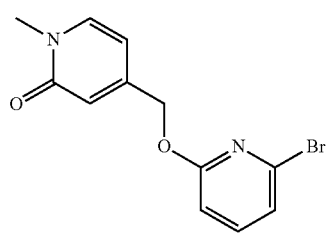

I-1165

4-[(6-bromo-2-pyridyl)oxymethyl]-1-methyl-pyridin-2-one (I-1165): 3-[(6-bromo-2-pyridyl)oxymethyl]-1-methyl-pyridin-2-one was prepared in a manner as described for Intermediate I-43 substituting [4-(hydroxymethyl)-1-methyl-pyridin-2-one for (1-methylimidazol-4-yl)methanol. ES/MS: 295.0 (M+H+)

Preparation of Intermediate I-1166

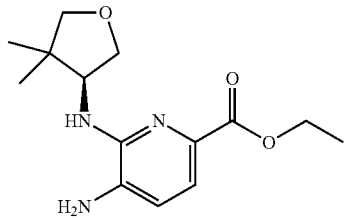

I-1166

Ethyl (S)-5-amino-6-((4,4-dimethyltetrahydrofuran-3-yl)amino)picolinate (I-1166): ethyl (S)-5-amino-6-((4,4-dimethyltetrahydrofuran-3-yl)amino)picolinate was prepared in a manner as described for Intermediate I-1 substituting (S)-4,4-dimethyltetrahydrofuran-3-amine hydrochloride for 2-methoxyethylamine and ethyl 6-chloro-5-nitropicolinate for methyl 3-fluoro-4-nitrobenzoate. ES/MS: 280.0 (M+H+)

Preparation of Intermediate I-1167

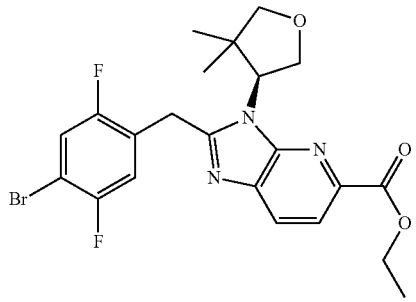

I-1167

Ethyl 2-[(4-bromo-2,5-difluoro-phenyl)methyl]-3-[(3S)-4,4-dimethyltetrahydrofuran-3-yl]imidazo[4,5-b]pyridine-5-carboxylate (I-1167): Ethyl 2-[(4-bromo-2,5-difluoro-phenyl)methyl]-3-[(3S)-4,4-dimethyltetrahydrofuran-3-yl]imidazo[4,5-b]pyridine-5-carboxylate was prepared in a manner as described for Intermediate I-2 substituting ethyl (S)-5-amino-6-((4,4-dimethyltetrahydrofuran-3-yl)amino)picolinate I-1166 for methyl 4-amino-3-(2-methoxyethylamino)benzoate I-1 and 2-(4-bromo-2,5-difluoro-phenyl)acetic acid for 2-(4-bromo-2-fluoro-phenyl)acetic acid. ES/MS: 495.0 (M+H+).

Preparation of Intermediate I-1168

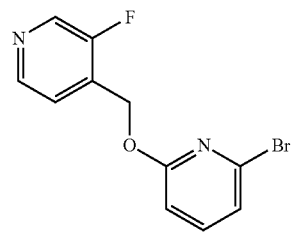

I-1168

2-bromo-6-[(3-fluoro-4-pyridyl)methoxy]pyridine (I-1168): 2-bromo-6-[(3-fluoro-4-pyridyl)methoxy]pyridine was prepared in a manner as described for Intermediate I-43 substituting (3-fluoro-4-pyridyl)methanol for (1-methylimidazol-4-yl)methanol. ES/MS: 283.0 (M+H+)

Preparation of Intermediate I-1169

I-1169

2-bromo-6-[(3-methoxy-4-pyridyl)methoxy]pyridine (I-1169): 2-bromo-6-[(3-methoxy-4-pyridyl)methoxy]pyridine was prepared in a manner as described for Intermediate I-43 substituting (3-methoxy-4-pyridyl)methanol for (1-methylimidazol-4-yl)methanol. ES/MS: 295.0 (M+H+)

Preparation of Intermediate I-1170

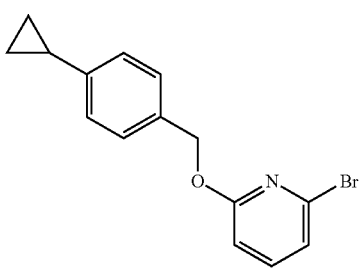

I-1170

2-bromo-6-[(4-cyclopropylphenyl)methoxy]pyridine (I-1170): 2-bromo-6-[(4-cyclopropylphenyl)methoxy]pyridine was prepared in a manner as described for Intermediate I-43 substituting (4-cyclopropylphenyl)methanol for (1-methylimidazol-4-yl)methanol. ES/MS: 305.2 (M+H+)

Preparation of Intermediate I-1172

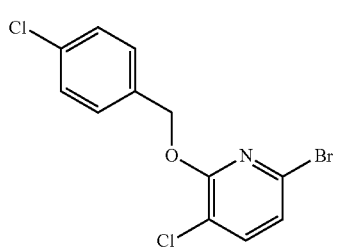

6-bromo-3-chloro-2-[(4-chlorophenyl)methoxy]pyridine (I-1172): 6-bromo-3-chloro-2-[(4-chlorophenyl)methoxy]pyridine was prepared in a manner as described for Intermediate I-1129 substituting 1-(bromomethyl)-4-chloro-benzene for 2-(bromomethyl)-3-fluoro-5-(trifluoromethyl)pyridine and 6-bromo-3-chloro-pyridin-2-ol for 6-bromopyridin-2-ol. ES/MS: 352.2 (M+H+)

Preparation of Intermediate I-1173

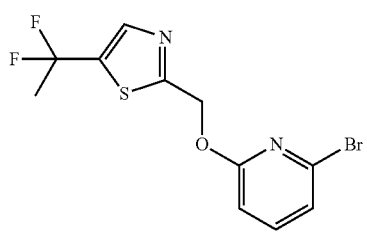

2-(((6-bromopyridin-2-yl)oxy)methyl)-5-(1,1-difluoroethyl)thiazole (I-1173): 2-(((6-bromopyridin-2-yl)oxy)methyl)-5-(1,1-difluoroethyl)thiazole was prepared in a manner as described for Intermediate I-1129 substituting 2-(bromomethyl)-5-(1,1-difluoroethyl)thiazole for 2-(bromomethyl)-3-fluoro-5-(trifluoromethyl)pyridine. ES/MS: 335.0 (M+H+)

Preparation of Intermediate I-1174

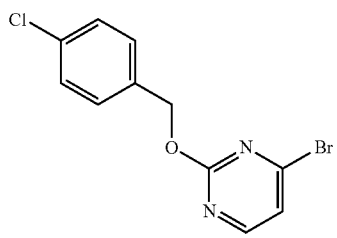

4-bromo-2-((4-chlorobenzyl)oxy)pyrimidine (I-1174): 4-bromo-2-((4-chlorobenzyl)oxy)pyrimidine was prepared in a manner as described for Intermediate I-43 substituting (4-chlorophenyl)methanol for (1-methylimidazol-4-yl)methanol and 4-bromo-2-fluoropyrimidine for 2-bromo-6-fluoropyridine. ES/MS: 299.2 (M+H+)

Preparation of Intermediate I-1175

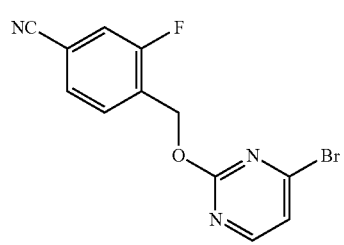

4-(((4-bromopyrimidin-2-yl)oxy)methyl)-3-fluorobenzonitrile (I-1175): 4-(((4-bromopyrimidin-2-yl)oxy)methyl)-3-fluorobenzonitrile was prepared in a manner as described for Intermediate I-43 substituting 3-fluoro-4-(hydroxymethyl)benzonitrile for (1-methylimidazol-4-yl)methanol and 4-bromo-2-fluoropyrimidine for 2-bromo-6-fluoropyridine. ES/MS: 308.0 (M+H+)

Preparation of Intermediate I-1177

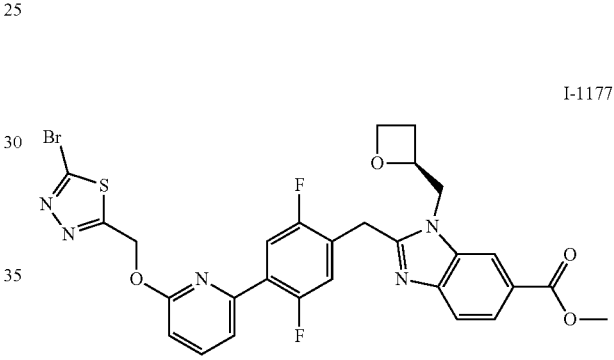

Methyl (S)-2-(4-(6-((5-bromo-1,3,4-thiadiazol-2-yl)methoxy)pyridin-2-yl)-2,5-difluorobenzyl)-1-(oxetan-2-ylmethyl)-1H-benzo[d]imidazole-6-carboxylate (I-1177): Methyl (S)-2-(4-(6-((5-bromo-1,3,4-thiadiazol-2-yl)methoxy)pyridin-2-yl)-2,5-difluorobenzyl)-1-(oxetan-2-ylmethyl)-1H-benzo[d]imidazole-6-carboxylate was prepared in a manner as described for Intermediate I-1096 substituting 2-bromo-5-(chloromethyl)-1,3,4-thiadiazole for 2-bromo-5-(bromomethyl)thiazole. ES/MS: 642.1 (M+H+)

Preparation of Intermediate I-1178

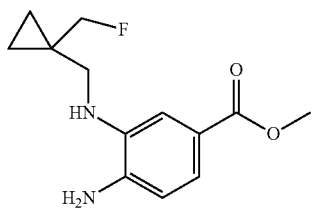

Methyl 4-amino-3-(((1-(fluoromethyl)cyclopropyl)methyl)amino)benzoate (I-1178): Methyl 4-amino-3-(((1-(fluoromethyl)cyclopropyl)methyl)amino)benzoate was prepared in a manner as described for Intermediate I-1 substituting (1-(fluoromethyl)cyclopropyl)methanamine for 2-methoxyethylamine. ES/MS: 253.2 (M+H+).

Preparation of Intermediate I-1179

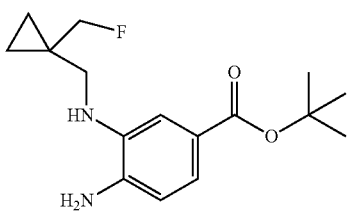

I-1179

Tert-butyl 4-amino-3-(((1-(fluoromethyl)cyclopropyl)methyl)amino)benzoate (I-1179): Tert-butyl 4-amino-3-(((1-(fluoromethyl)cyclopropyl)methyl)amino)benzoate was prepared in a manner as described for Intermediate I-6 substituting (1-(fluoromethyl)cyclopropyl)methanamine for 2-methoxyethylamine. ES/MS: 295.2 (M+H+).

Preparation of Intermediate I-1180

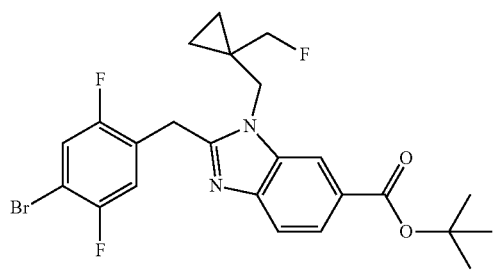

I-1180

Tert-butyl 2-[(4-bromo-2,5-difluoro-phenyl)methyl]-3-[[1-(fluoromethyl)cyclopropyl]methyl]benzimidazole-5-carboxylate (I-1180): Tert-butyl 2-[(4-bromo-2,5-difluoro-phenyl)methyl]-3-[[1-(fluoromethyl)cyclopropyl]methyl]benzimidazole-5-carboxylate was prepared in a manner as described for Intermediate I-2 substituting I-1179 for I-1 and 2-(4-bromo-2,5-difluorophenyl)acetic acid for 2-(4-bromo-2-fluoro-phenyl)acetic acid. ES/MS: 509, 511 (M+H+).

Preparation of Intermediate I-1076

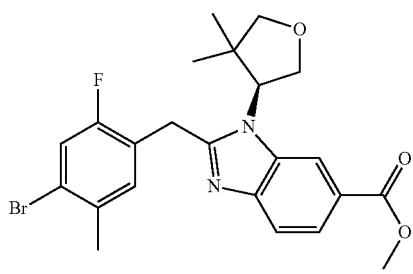

I-1076

Methyl 2-[(4-bromo-2-fluoro-5-methyl-phenyl)methyl]-3-[(3S)-4,4-dimethyltetrahydrofuran-3-yl]benzimidazole-5-carboxylate (I-1076): Methyl 2-[(4-bromo-2-fluoro-5-methyl-phenyl)methyl]-3-[(3S)-4,4-dimethyltetrahydrofuran-3-yl]benzimidazole-5-carboxylate was prepared in a manner as described for Intermediate I-2 substituting I-80 for I-1 and 2-(4-bromo-2-fluoro-5-methyl-phenyl)acetic acid I-1277 for 2-(4-bromo-2-fluoro-phenyl)acetic acid. ES/MS: 475, 477 (M+H+).

Preparation of Intermediate I-1182

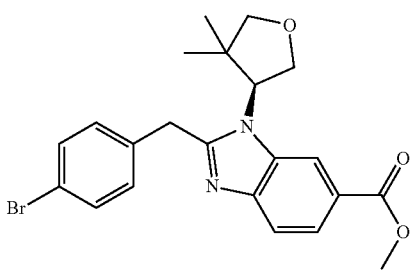

I-1182

Methyl 2-[(4-bromophenyl)methyl]-3-[(3S)-4,4-dimethyltetrahydrofuran-3-yl]benzimidazole-5-carboxylate (I-1182): Methyl 2-[(4-bromophenyl)methyl]-3-[(3S)-4,4-dimethyltetrahydrofuran-3-yl]benzimidazole-5-carboxylate was prepared in a manner as described for Intermediate I-2 substituting I-80 for I-1 and 2-(4-bromophenyl)acetic acid for 2-(4-bromo-2-fluoro-phenyl)acetic acid. ES/MS: 443, 445 (M+H+).

Preparation of Intermediate I-1184

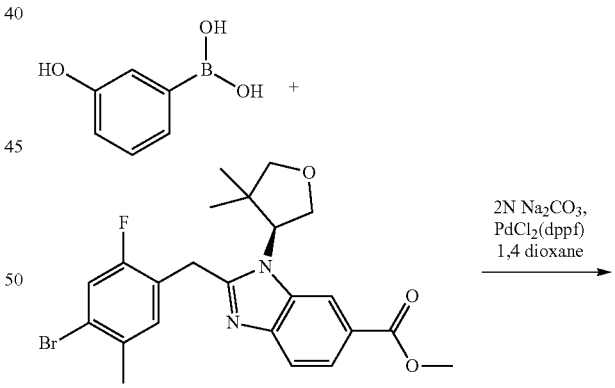

I-1184

237

Methyl 3-[(3S)-4,4-dimethyltetrahydrofuran-3-yl]-2-[[2-fluoro-4-(3-hydroxyphenyl)-5-methyl-phenyl]methyl]benzimidazole-5-carboxylate (I-1184): A suspension of methyl 2-[(4-bromo-2-fluoro-5-methyl-phenyl)methyl]-3-[(3S)-4,4-dimethyltetrahydrofuran-3-yl]benzimidazole-5-carboxylate (130 mg, 0.273 mmol) (I-1076), (3-hydroxyphenyl) boronic acid (75.4 mg, 0.547 mmol), [1,1'-Bis(diphenylphosphino)ferrocene]dichloropalladium(II); PdCl$_2$(dppf) (20.3 mg, 0.0273 mmol, sodium carbonate (2000 mmol/L, 0.273 mL, 0.547 mmol) was degassed. The mixture was heated at 100° C. for 1 hr. Next, the mixture was diluted with EtOAc and water. The organic extract was dried over magnesium sulfate, filtered and concentrated. The crude residue was purified by flash chromatography (eluent: EtOAc/hexanes) to yield desired product. ES/MS: 489.1 (M+H+)

Preparation of Intermediate I-1185

I-1185

Methyl 2-(4-bromo-2,3,6-trifluorobenzyl)-1-(4,4-dimethyltetrahydrofuran-3-yl)-1H-benzo[d]imidazole-6-carboxylate (I-1185): Methyl 2-(4-bromo-2,3,6-trifluorobenzyl)-1-(4,4-dimethyltetrahydrofuran-3-yl)-1H-benzo[d]imidazole-6-carboxylate was prepared in a manner as described for Intermediate I-2 substituting 1-25 for I-1 and 2-(4-bromo-2,3,6-trifluorophenyl)acetic acid for 2-(4-bromo-2-fluoro-phenyl)acetic acid. ES/MS: 497, 499 (M+H+).

Preparation of Intermediate I-1186

I-1186

Tert-butyl 2-(4-bromo-2,3,6-trifluorobenzyl)-1-(2-methoxyethyl)-1H-benzo[d]imidazole-6-carboxylate (I-1186): Tert-butyl 2-(4-bromo-2,3,6-trifluorobenzyl)-1-(2-methoxyethyl)-1H-benzo[d]imidazole-6-carboxylate was prepared in a manner as described for Intermediate I-2 substituting I-6 for I-1 and 2-(4-bromo-2,3,6-trifluorophenyl)acetic acid for 2-(4-bromo-2-fluoro-phenyl)acetic acid. ES/MS: 499, 501 (M+H+).

238

Preparation of Intermediate I-1187

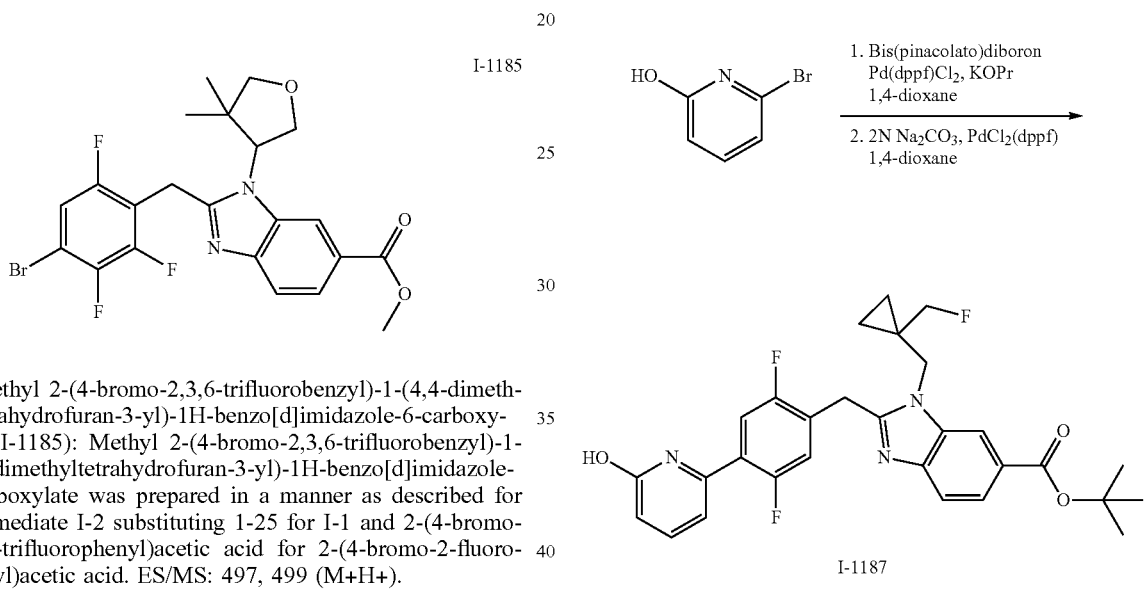

Tert-butyl 2-(2,5-difluoro-4-(6-hydroxypyridin-2-yl)benzyl)-1-((1-(fluoromethyl)cyclopropyl)methyl)-1H-benzo[d]imidazole-6-carboxylate (I-1187): A suspension of tert-butyl 2-[(4-bromo-2,5-difluoro-phenyl)methyl]-3-[[1-(fluoromethyl)cyclopropyl]methyl]benzimidazole-5-carboxylate (500 mg, 0.98 mmol), [1,1'-Bis(diphenylphosphino)ferrocene] dichloropalladium(II), PdCl$_2$(dppf) (72.8 mg, 0.098 mmol), potassium propionate (330 mg, 2.94 mmol), and Bis(pinacolato)diboron (324 mg, 1.28 mmol) was degassed, then heated at 110° C. for 2 hr. Next, sodium carbonate (2000 mmol/L, 0.98 mL, 1.96 mmol), 6-bromopyridin-2-ol 256 mg, 1.47 mmol), and [1,1'-Bis(diphenylphosphino)ferrocene] dichloropalladium(II); PdCl$_2$(dppf) (30.4 mg, 0.04 mmol) was added and then the resulting mixture was degassed. The mixture was then heated at 100° C. for 1 hr. Upon completion the mixture was diluted with EtOAc and water. The organic extract was dried over magnesium sulfate, filtered and concentrated. The crude residue was purified by flash chromatography (eluent: EtOAc/hexanes) to yield desired product. ES/MS: 523.7 (M+H+)

Preparation of Intermediate I-1188

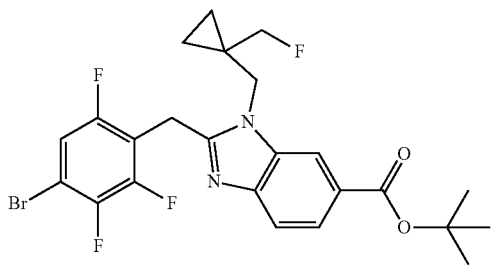

Tert-butyl 2-[(4-bromo-2,3,6-trifluoro-phenyl)methyl]-3-[[1-(fluoromethyl)cyclopropyl]methyl]benzimidazole-5-carboxylate (I-1188): Tert-butyl 2-[(4-bromo-2,3,6-trifluoro-phenyl)methyl]-3-[[1-(fluoromethyl)cyclopropyl]methyl]benzimidazole-5-carboxylate was prepared in a manner as described for Intermediate I-2 substituting I-1179 for I-1 and 2-(4-bromo-2,3,6-trifluorophenyl)acetic acid for 2-(4-bromo-2-fluoro-phenyl)acetic acid. ES/MS: 527, 529 (M+H+).

Preparation of Intermediate I-1189

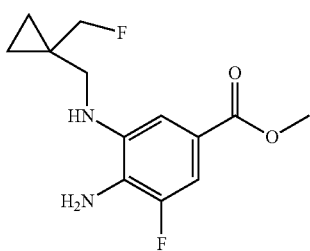

Methyl 4-amino-3-fluoro-5-[[1-(fluoromethyl)cyclopropyl]methylamino]benzoate (I-1189): Methyl 4-amino-3-fluoro-5-[[1-(fluoromethyl)cyclopropyl]methylamino]benzoate was prepared in a manner as described for Intermediate I-1 substituting (1-(fluoromethyl)cyclopropyl)methanamine for 2-methoxyethylamine and methyl 3,5-difluoro-4-nitrobenzoate for methyl 3-fluoro-4-nitrobenzoate. ES/MS: 270.2 (M+H+).

Preparation of Intermediate I-1190

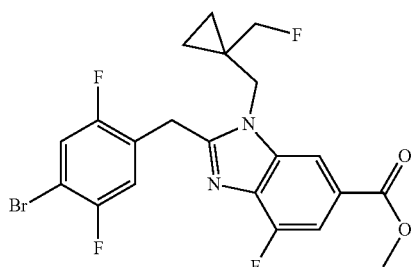

Methyl 2-[(4-bromo-2,5-difluoro-phenyl)methyl]-7-fluoro-3-[[1-(fluoromethyl)cyclopropyl]methyl]benzimidazole-5-carboxylate (I-1190): Methyl 2-[(4-bromo-2,5-difluoro-phenyl)methyl]-7-fluoro-3-[[1-(fluoromethyl)cyclopropyl]methyl]benzimidazole-5-carboxylate was prepared in a manner as described for Intermediate I-13 substituting 1-1189 for 1-5 and 2-(4-bromo-2,5-difluorophenyl)acetic acid for 2-(4-bromo-2-fluoro-phenyl)acetic acid. ES/MS: 485, 487 (M+H+).

Preparation of Intermediate I-1191

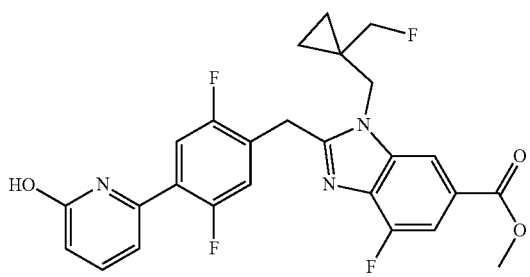

Methyl 2-[[2,5-difluoro-4-(6-hydroxy-2-pyridyl)phenyl]methyl]-7-fluoro-3-[[1-(fluoromethyl)cyclopropyl]methyl]benzimidazole-5-carboxylate (I-1191): Methyl 2-[[2,5-difluoro-4-(6-hydroxy-2-pyridyl)phenyl]methyl]-7-fluoro-3-[[1-(fluoromethyl)cyclopropyl]methyl]benzimidazole-5-carboxylate was prepared in a manner as described for Intermediate I-1187 substituting 1-1190 for 1-1180. ES/MS: 499, 501 (M+H+).

Preparation of Intermediate I-1192

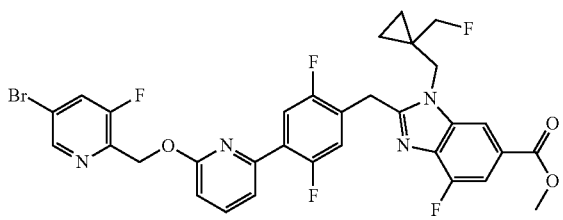

Methyl 2-[[4-[6-[(5-bromo-3-fluoro-2-pyridyl)methoxy]-2-pyridyl]-2,5-difluoro-phenyl]methyl]-7-fluoro-3-[[1-(fluoromethyl)cyclopropyl]methyl]benzimidazole-5-carboxylate (I-1192): Methyl 2-[[4-[6-[(5-bromo-3-fluoro-2-pyridyl)methoxy]-2-pyridyl]-2,5-difluoro-phenyl]methyl]-7-fluoro-3-[[1-(fluoromethyl)cyclopropyl]methyl]benzimidazole-5-carboxylate was prepared in a manner as described for Intermediate I-21 substituting 1-1191 for 1-9 and 5-bromo-2-(chloromethyl)-3-fluoro-pyridine for 5-bromo-2-(bromomethyl)thiazole. ES/MS: 687, 689 (M+H+).

241

Preparation of Intermediate I-1193

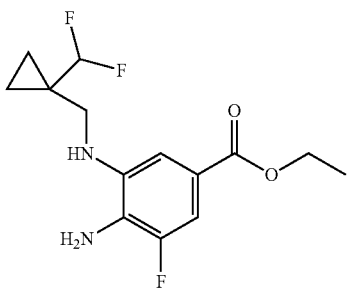

I-1193

Ethyl 3-[[1-(difluoromethyl)cyclopropyl]methylamino]-5-fluoro-4-nitro-benzoate (I-1193): Ethyl 3-[[1-(difluoromethyl)cyclopropyl]methylamino]-5-fluoro-4-nitro-benzoate was prepared in a manner as described for Intermediate I-1 substituting [1-(difluoromethyl)cyclopropyl]methanamine for 2-methoxyethylamine and ethyl 3,5-difluoro-4-nitrobenzoate for methyl 3-fluoro-4-nitrobenzoate. ES/MS: 302.2 (M+H+).

Preparation of Intermediate I-1194

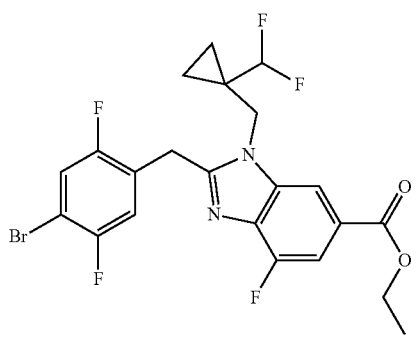

I-1194

Ethyl 2-[(4-bromo-2,5-difluoro-phenyl)methyl]-3-[[1-(difluoromethyl)cyclopropyl]methyl]-7-fluoro-benzimidazole-5-carboxylate (I-1194): Ethyl 2-[(4-bromo-2,5-difluoro-phenyl)methyl]-3-[[1-(difluoromethyl)cyclopropyl]methyl]-7-fluoro-benzimidazole-5-carboxylate was prepared in a manner as described for Intermediate I-13 substituting I-1193 for I-5 and 2-(4-bromo-2,5-difluorophenyl)acetic acid for 2-(4-bromo-2-fluoro-phenyl)acetic acid. ES/MS: 517.1, 519 (M+H+).

Preparation of Intermediate I-1195

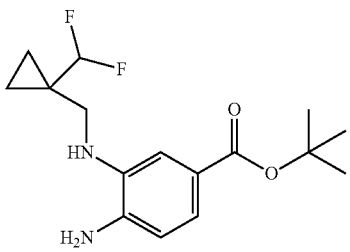

I-1195

242

Tert-butyl 4-amino-3-(((1-(difluoromethyl)cyclopropyl)methyl)amino)benzoate (I-1195): Tert-butyl 4-amino-3-(((1-(difluoromethyl)cyclopropyl)methyl)amino)benzoate was prepared in a manner as described for Intermediate I-6 substituting (1-(difluoromethyl)cyclopropyl)methanamine for 2-methoxyethylamine. ES/MS: 295.2 (M+H+).

Preparation of Intermediate I-1196

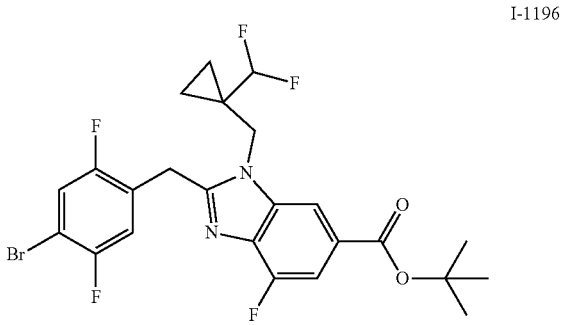 [SMILES: CC(C)(C)OC(=O)c1cc(F)c2nc(Cc3cc(F)c(Br)cc3F)n(CC3(C(F)F)CC3)c2c1]

I-1196

Tert-butyl 2-[(4-bromo-2,5-difluoro-phenyl)methyl]-3-[[1-(difluoromethyl)cyclopropyl]methyl]benzimidazole-5-carboxylate (I-1196): Tert-butyl 2-[(4-bromo-2,5-difluoro-phenyl)methyl]-3-[[1-(difluoromethyl)cyclopropyl]methyl]benzimidazole-5-carboxylate was prepared in a manner as described for Intermediate I-2 substituting I-1195 for I-1 and 2-(4-bromo-2,5-difluorophenyl)acetic acid for 2-(4-bromo-2-fluoro-phenyl)acetic acid. ES/MS: 527, 529 (M+H+).

Preparation of Intermediate I-1197

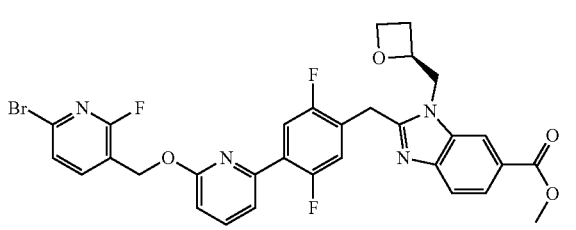

I-1197

Methyl 2-[[4-[6-[(6-bromo-2-fluoro-3-pyridyl)methoxy]-2-pyridyl]-2,5-difluoro-phenyl]methyl]-3-[[(2S)-oxetan-2-yl]methyl]benzimidazole-5-carboxylate (I-1197): Methyl 2-[[4-[6-[(6-bromo-2-fluoro-3-pyridyl)methoxy]-2-pyridyl]-2,5-difluoro-phenyl]methyl]-3-[[(2S)-oxetan-2-yl]methyl]benzimidazole-5-carboxylate was prepared in a manner as described for Intermediate I-21 substituting 6-bromo-3-(bromomethyl)-2-fluoropyridine for 5-bromo-2-(bromomethyl)thiazole. ES/MS: 653, 655 (M+H+).

Preparation of Intermediate I-1198

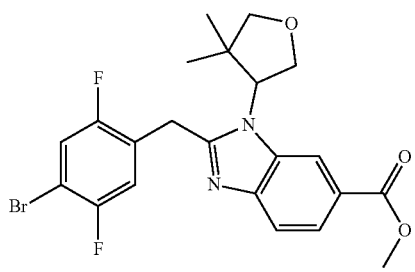

Methyl 2-[(4-bromo-2,5-difluoro-phenyl)methyl]-3-(4,4-dimethyltetrahydrofuran-3-yl)benzimidazole-5-carboxylate (I-1198): Methyl 2-[(4-bromo-2,5-difluoro-phenyl)methyl]-3-(4,4-dimethyltetrahydrofuran-3-yl)benzimidazole-5-carboxylate was prepared in a manner as described for Intermediate I-2 substituting I-25 for I-1 and 2-(4-bromo-2,5-difluorophenyl)acetic acid for 2-(4-bromo-2-fluoro-phenyl)acetic acid. ES/MS: 479, 481 (M+H+).

Preparation of Intermediate I-1199

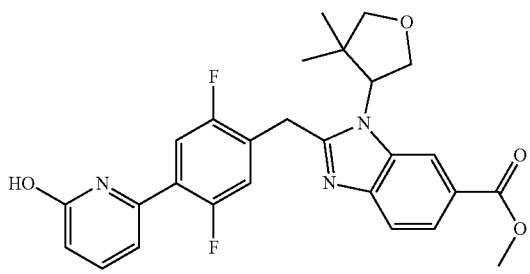

Methyl 2-[[2,5-difluoro-4-(6-hydroxy-2-pyridyl)phenyl]methyl]-3-(4,4-dimethyltetrahydrofuran-3-yl)benzimidazole-5-carboxylate (I-1199): Methyl 2-[[2,5-difluoro-4-(6-hydroxy-2-pyridyl)phenyl]methyl]-3-(4,4-dimethyltetrahydrofuran-3-yl)benzimidazole-5-carboxylate was prepared in a manner as described for Intermediate I-1187 substituting I-1198 for I-1180. ES/MS: 493, 495 (M+H+).

Preparation of Intermediate I-1200

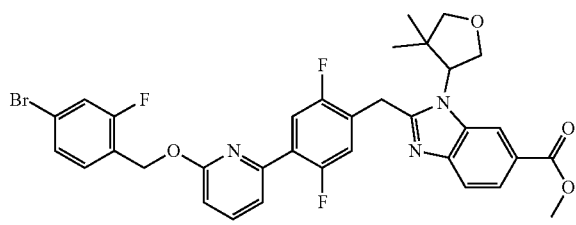

Methyl 2-[[4-[6-[(4-bromo-2-fluoro-phenyl)methoxy]-2-pyridyl]-2,5-difluoro-phenyl]methyl]-3-(4,4-dimethyltetrahydrofuran-3-yl)benzimidazole-5-carboxylate (I-1200): Methyl 2-[[4-[6-[(4-bromo-2-fluoro-phenyl)methoxy]-2-pyridyl]-2,5-difluoro-phenyl]methyl]-3-(4,4-dimethyltetrahydrofuran-3-yl)benzimidazole-5-carboxylate was prepared in a manner as described for Intermediate I-21 substituting I-1199 for I-9 and 4-bromo-1-(bromomethyl)-2-fluoro-benzene for 5-bromo-2-(bromomethyl)thiazole. ES/MS: 680, 682 (M+H+).

Preparation of Intermediate I-1201

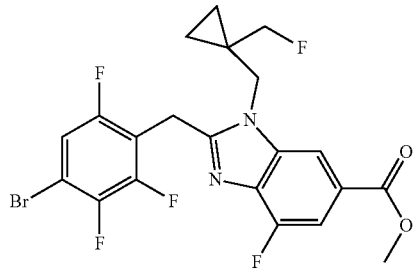

Methyl 2-(4-bromo-2,3,6-trifluorobenzyl)-4-fluoro-1-((1-(fluoromethyl)cyclopropyl)methyl)-1H-benzo[d]imidazole-6-carboxylate (I-1201): Methyl 2-(4-bromo-2,3,6-trifluorobenzyl)-4-fluoro-1-((1-(fluoromethyl)cyclopropyl)methyl)-1H-benzo[d]imidazole-6-carboxylate was prepared in a manner as described for Intermediate I-13 substituting 1-1189 for 1-5 and 2-(4-bromo-2,3,6-trifluorophenyl)acetic acid for 2-(4-bromo-2-fluoro-phenyl)acetic acid. ES/MS: 485, 487 (M+H+).

Preparation of Intermediate I-1202

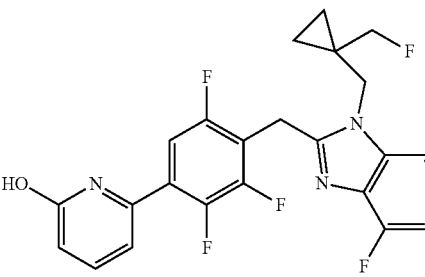

Methyl 7-fluoro-3-[[1-(fluoromethyl)cyclopropyl]methyl]-2-[[2,3,6-trifluoro-4-(6-hydroxy-2-pyridyl)phenyl]methyl]benzimidazole-5-carboxylate (I-1202): Methyl 7-fluoro-3-[[1-(fluoromethyl)cyclopropyl]methyl]-2-[[2,3,6-trifluoro-4-(6-hydroxy-2-pyridyl)phenyl]methyl]benzimidazole-5-carboxylate was prepared in a manner as described for Intermediate I-1187 substituting 1-1201 for 1-1180. ES/MS: 517, 519 (M+H+).

Preparation of Intermediate I-1203

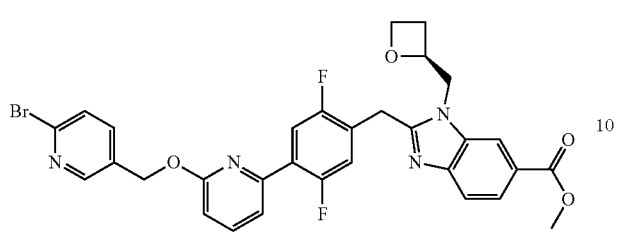

I-1203

Methyl 2-[[4-[6-[(6-bromo-3-pyridyl)methoxy]-2-pyridyl]-2,5-difluoro-phenyl]methyl]-3-[[(2S)-oxetan-2-yl]methyl]benzimidazole-5-carboxylate (I-1203): Methyl 2-[[4-[6-[(6-bromo-3-pyridyl)methoxy]-2-pyridyl]-2,5-difluoro-phenyl]methyl]-3-[[(2S)-oxetan-2-yl]methyl]benzimidazole-5-carboxylate was prepared in a manner as described for Intermediate I-21 substituting 2-bromo-5-(bromomethyl)pyridine for 5-bromo-2-(bromomethyl)thiazole. ES/MS: 635, 637 (M+H+).

Preparation of Intermediate I-1204

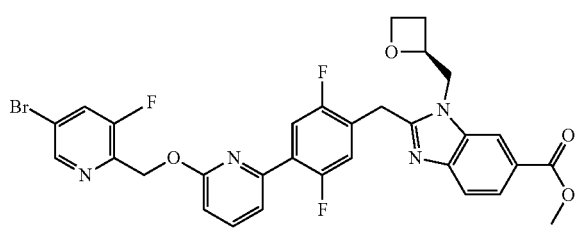

I-1204

Methyl 2-[[4-[6-[(6-bromo-3-pyridyl)methoxy]-2-pyridyl]-2,5-difluoro-phenyl]methyl]-3-[[(2S)-oxetan-2-yl]methyl]benzimidazole-5-carboxylate (I-1204): Methyl 2-[[4-[6-[(6-bromo-3-pyridyl)methoxy]-2-pyridyl]-2,5-difluoro-phenyl]methyl]-3-[[(2S)-oxetan-2-yl]methyl]benzimidazole-5-carboxylate was prepared in a manner as described for Intermediate I-21 substituting I-31 for 5-bromo-2-(bromomethyl)thiazole. ES/MS: 653, 655 (M+H+).

Preparation of Intermediate I-1205

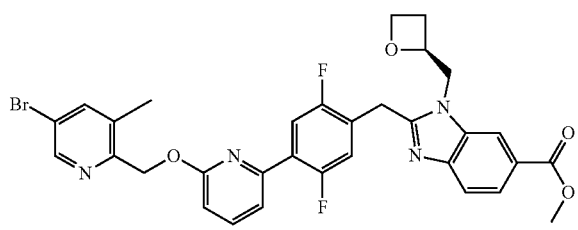

Methyl 2-[[4-[6-[(5-bromo-3-methyl-2-pyridyl)methoxy]-2-pyridyl]-2,5-difluoro-phenyl]methyl]-3-[[(2S)-oxetan-2-yl]methyl]benzimidazole-5-carboxylate (I-1205): Methyl 2-[[4-[6-[(5-bromo-3-methyl-2-pyridyl)methoxy]-2-pyridyl]-2,5-difluoro-phenyl]methyl]-3-[[(2S)-oxetan-2-yl]methyl]benzimidazole-5-carboxylate was prepared in a manner as described for Intermediate I-21 substituting 5-bromo-2-(chloromethyl)-3-methyl-pyridine for 5-bromo-2-(bromomethyl)thiazole. ES/MS: 649, 651 (M+H+).

Preparation of Intermediate I-1206

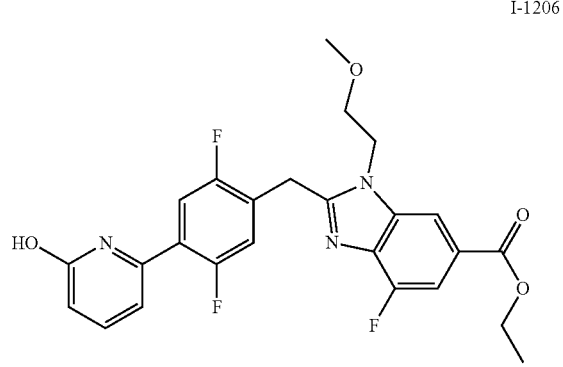 [SMILES: CCOC(=O)c1cc(F)c2nc(Cc3cc(F)c(-c4cccc(O)n4)cc3F)n(CCOC)c2c1]

I-1206

Ethyl 2-[[2,5-difluoro-4-(6-hydroxy-2-pyridyl)phenyl]methyl]-7-fluoro-3-(2-methoxyethyl)benzimidazole-5-carboxylate (I-1206): Ethyl 2-[[2,5-difluoro-4-(6-hydroxy-2-pyridyl)phenyl]methyl]-7-fluoro-3-(2-methoxyethyl)benzimidazole-5-carboxylate was prepared in a manner as described for Intermediate I-1187 substituting I-1033 for I-1180. ES/MS: 485, 487 (M+H+).

Preparation of Intermediate I-1208

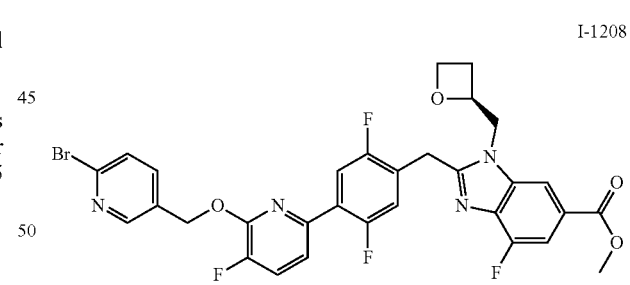

I-1208

Ethyl 2-[[4-[6-[(6-bromo-3-pyridyl)methoxy]-5-fluoro-2-pyridyl]-2,5-difluoro-phenyl]methyl]-7-fluoro-3-[[(2S)-oxetan-2-yl]methyl]benzimidazole-5-carboxylate (I-1208): Ethyl 2-[[4-[6-[(6-bromo-3-pyridyl)methoxy]-5-fluoro-2-pyridyl]-2,5-difluoro-phenyl]methyl]-7-fluoro-3-[[(2S)-oxetan-2-yl]methyl]benzimidazole-5-carboxylate was prepared in a manner as described for Intermediate I-21 substituting ethyl 2-[[2,5-difluoro-4-(5-fluoro-6-hydroxy-2-pyridyl)phenyl]methyl]-7-fluoro-3-[[(2S)-oxetan-2-yl]methyl]benzimidazole-5-carboxylate for I-9 and 2-bromo-5-(bromomethyl)pyridine for 5-bromo-2-(bromomethyl)thiazole. ES/MS: 686, 687 (M+H+).

Preparation of Intermediate I-1209

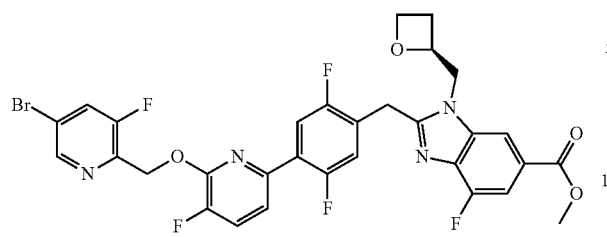

I-1209

Ethyl 2-[[4-[6-[(5-bromo-3-fluoro-2-pyridyl)methoxy]-5-fluoro-2-pyridyl]-2,5-difluoro-phenyl]methyl]-7-fluoro-3-[[(2S)-oxetan-2-yl]methyl]benzimidazole-5-carboxylate (I-1209): Ethyl 2-[[4-[6-[(5-bromo-3-fluoro-2-pyridyl)methoxy]-5-fluoro-2-pyridyl]-2,5-difluoro-phenyl]methyl]-7-fluoro-3-[[(2S)-oxetan-2-yl]methyl]benzimidazole-5-carboxylate was prepared in a manner as described for Intermediate I-21 substituting ethyl 2-[[2,5-difluoro-4-(5-fluoro-6-hydroxy-2-pyridyl)phenyl]methyl]-7-fluoro-3-[[(2S)-oxetan-2-yl]methyl]benzimidazole-5-carboxylate for I-9 and 5-bromo-2-(chloromethyl)-3-fluoro-pyridine for 5-bromo-2-(bromomethyl)thiazole. ES/MS: 703, 705 (M+H+).

Preparation of Intermediate I-1210

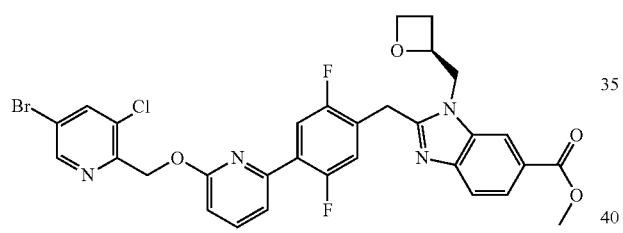

I-1210

Methyl 2-[[4-[6-[(5-bromo-3-chloro-2-pyridyl)methoxy]-2-pyridyl]-2,5-difluoro-phenyl]methyl]-3-[[(2S)-oxetan-2-yl]methyl]benzimidazole-5-carboxylate (I-1210): Methyl 2-[[4-[6-[(5-bromo-3-chloro-2-pyridyl)methoxy]-2-pyridyl]-2,5-difluoro-phenyl]methyl]-3-[[(2S)-oxetan-2-yl]methyl]benzimidazole-5-carboxylate was prepared in a manner as described for Intermediate I-21 substituting 5-bromo-3-chloro-2-(chloromethyl)pyridine for 5-bromo-2-(bromomethyl)thiazole. ES/MS: 670, 672 (M+H+).

Preparation of Intermediate I-1211

I-1211

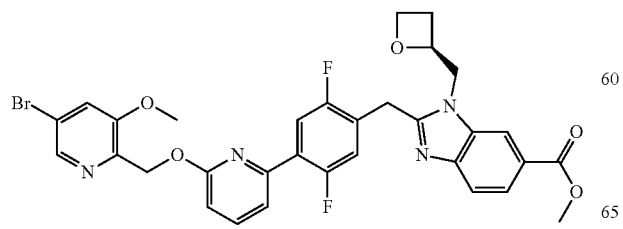

Methyl 2-[[4-[6-[(4-bromo-2-methoxy-phenyl)methoxy]-2-pyridyl]-2,5-difluoro-phenyl]methyl]-3-[[(2S)-oxetan-2-yl]methyl]benzimidazole-5-carboxylate (I-1211): Methyl 2-[[4-[6-[(4-bromo-2-methoxy-phenyl)methoxy]-2-pyridyl]-2,5-difluoro-phenyl]methyl]-3-[[(2S)-oxetan-2-yl]methyl]benzimidazole-5-carboxylate was prepared in a manner as described for Intermediate I-21 substituting 4-bromo-1-(bromomethyl)-2-methoxy-benzene for 5-bromo-2-(bromomethyl)thiazole. ES/MS: 664, 666 (M+H+).

Preparation of Intermediate I-1212

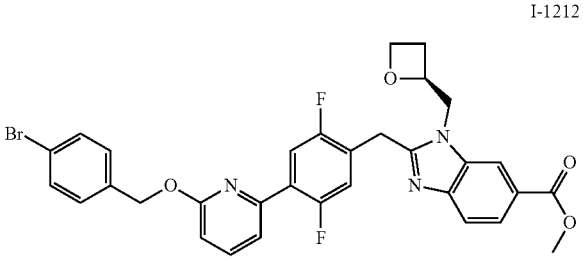 [SMILES: COC(=O)c1ccc2nc(Cc3cc(F)c(-c4cccc(OCc5ccc(Br)cc5)n4)cc3F)n(C[C@@H]3CCO3)c2c1]

I-1212

Methyl 2-[[4-[6-[(4-bromophenyl)methoxy]-2-pyridyl]-2,5-difluoro-phenyl]methyl]-3-[[(2S)-oxetan-2-yl]methyl]benzimidazole-5-carboxylate (I-1212): Methyl 2-[[4-[6-[(4-bromophenyl)methoxy]-2-pyridyl]-2,5-difluoro-phenyl]methyl]-3-[[(2S)-oxetan-2-yl]methyl]benzimidazole-5-carboxylate was prepared in a manner as described for Intermediate I-21 substituting 1-bromo-4-(bromomethyl)benzene for 5-bromo-2-(bromomethyl)thiazole. ES/MS: 634, 636 (M+H+).

Preparation of Intermediate I-1217

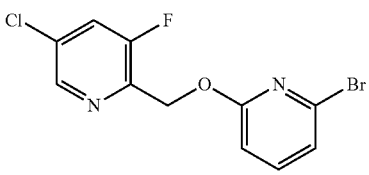

I-1217

2-(((6-bromopyridin-2-yl)oxy)methyl)-5-chloro-3-fluoropyridine (I-1217): 2-(((6-bromopyridin-2-yl)oxy)methyl)-5-chloro-3-fluoropyridine was prepared in a manner as described for Intermediate I-84 substituting 2-(chloromethyl)-3-fluoro-pyridine for 2-(bromomethyl)thiazole-5-carbonitrile. ES/MS: 317, 319 (M+H+).

Preparation of Intermediate I-1218

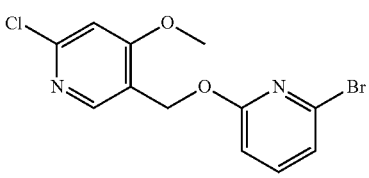

I-1218

5-[(6-bromo-2-pyridyl)oxymethyl]-2-chloro-4-methoxy-pyridine (I-1218): 5-[(6-bromo-2-pyridyl)oxymethyl]-2-chloro-4-methoxy-pyridine was prepared in a manner as described for Intermediate I-84 substituting 5-(bromomethyl)-2-chloro-4-methoxy-pyridine for 2-(bromomethyl)thiazole-5-carbonitrile. ES/MS: 329, 331 (M+H+).

Preparation of Intermediate I-1219

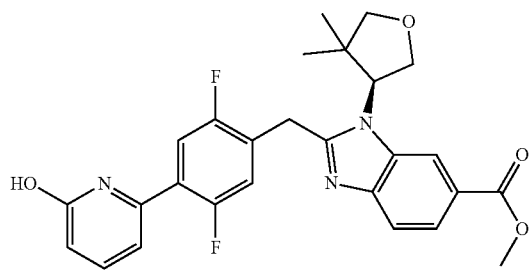

Methyl (S)-2-(2,5-difluoro-4-(6-hydroxypyridin-2-yl)benzyl)-1-(4,4-dimethyltetrahydrofuran-3-yl)-1H-benzo[d]imidazole-6-carboxylate (I-1219): Methyl (S)-2-(2,5-difluoro-4-(6-hydroxypyridin-2-yl)benzyl)-1-(4,4-dimethyltetrahydrofuran-3-yl)-1H-benzo[d]imidazole-6-carboxylate was prepared in a manner as described for Intermediate I-1187 substituting I-82 for I-1180. ES/MS: 493, 495 (M+H+).

Preparation of Intermediate I-1220

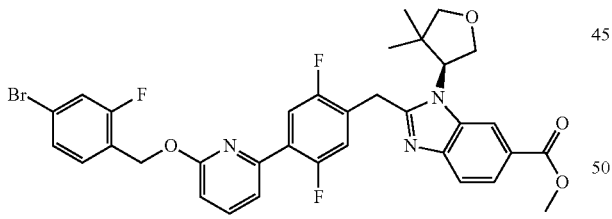

Methyl (S)-2-(4-(6-((4-bromo-2-fluorobenzyl)oxy)pyridin-2-yl)-2,5-difluorobenzyl)-1-(4,4-dimethyltetrahydrofuran-3-yl)-1H-benzo[d]imidazole-6-carboxylate (I-1220): Methyl (S)-2-(4-(6-((4-bromo-2-fluorobenzyl)oxy)pyridin-2-yl)-2,5-difluorobenzyl)-1-(4,4-dimethyltetrahydrofuran-3-yl)-1H-benzo[d]imidazole-6-carboxylate was prepared in a manner as described for Intermediate I-21 substituting I-1219 for I-9 and 4-bromo-1-(bromomethyl)-2-fluoro-benzene for 5-bromo-2-(bromomethyl)thiazole. ES/MS: 680, 682 (M+H+).

Preparation of Intermediate I-1222

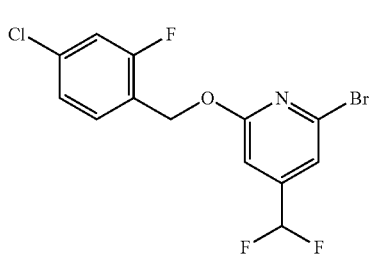

2-bromo-6-[(4-chloro-2-fluoro-phenyl)methoxy]-4-(difluoromethyl)pyridine (I-1222): 2-bromo-6-[(4-chloro-2-fluoro-phenyl)methoxy]-4-(difluoromethyl)pyridine was prepared in a manner as described for Intermediate I-49 substituting (4-chloro-2-fluoro-phenyl)methanol for 3-fluoro-4-(hydroxymethyl)benzonitrile and 2,6-dibromo-4-(difluoromethyl)pyridine for 2,6-dichloro-4-(difluoromethyl)pyridine. ES/MS: 366, 368 (M+H+).

Preparation of Intermediate I-1226

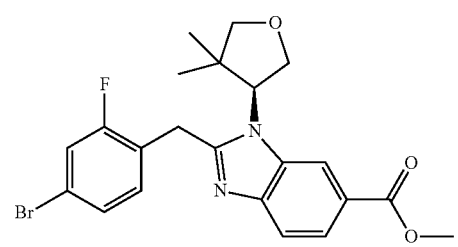

Methyl (S)-4-amino-3-((4,4-dimethyltetrahydrofuran-3-yl)amino)-5-fluorobenzoate: Methyl (S)-4-amino-3-((4,4-dimethyltetrahydrofuran-3-yl)amino)-5-fluorobenzoate was prepared the following the procedure for 1-5 substituting (3S)-4,4'-dimethyltetrahydrofuran-3-amine hydrochloride for (S)-oxetan-2-ylmethanamine. ES/MS: 338.5 (M+Na+):

Preparation of Intermediate I-1229

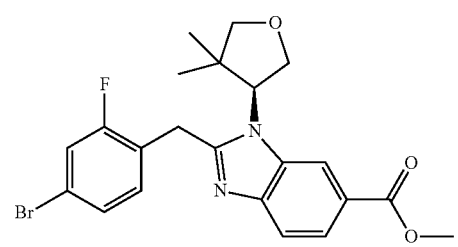

Methyl (S)-2-(4-bromo-2-fluorobenzyl)-1-(4,4-dimethyltetrahydrofuran-3-yl)-1H-benzo[d]imidazole-6-carboxylate (I-1229): Methyl (S)-2-(4-bromo-2-fluorobenzyl)-1-(4,4-dimethyltetrahydrofuran-3-yl)-1H-benzo[d]imidazole-6-carboxylate was prepared following the procedure for I-1041 substituting INTERMEDIATE I-80 for I-1042 and 2-(4-bromo-2-fluoro-phenyl)acetic acid for 2-(4-bromo-2,5-difluoro-phenyl)acetic acid. ES/MS: 469.8 (M+H$^+$).

Preparation of Intermediate I-1230

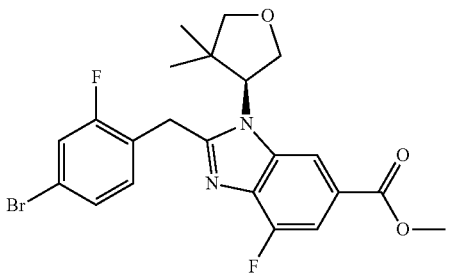

I-1230

Methyl (S)-2-(4-bromo-2-fluorobenzyl)-1-(4,4-dimethyltetrahydrofuran-3-yl)-4-fluoro-1H-benzo[d]imidazole-6-carboxylate (I-1230): Methyl (S)-2-(4-bromo-2-fluorobenzyl)-1-(4,4-dimethyltetrahydrofuran-3-yl)-4-fluoro-1H-benzo[d]imidazole-6-carboxylate was prepared following the procedure for 1-2 substituting Intermediate I-1226 for I-1042 and 2-(4-bromo-2-fluoro-phenyl)acetic acid for 2-(4-bromo-2,5-di-fluoro-phenyl)acetic acid. ES/MS: 479.6 (M+H$^+$);

Preparation of Intermediate I-1231

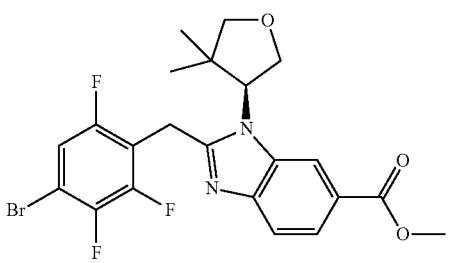

I-1231

Methyl (S)-2-(4-bromo-2,3,6-trifluorobenzyl)-1-(4,4-dimethyltetrahydrofuran-3-yl)-1H-benzo[d]imidazole-6-carboxylate: Methyl (S)-2-(4-bromo-2,3,6-trifluorobenzyl)-1-(4,4-dimethyltetrahydrofuran-3-yl)-1H-benzo[d]imidazole-6-carboxylate was prepared following the procedure for 1-1041 substituting Intermediate I-80 for 1-1042 and 2-(4-bromo-2,3,6-trifluorophenyl)acetic acid for 2-(4-bromo-2,5-difluorophenyl)acetic acid. ES/MS: 498.0 (M+H$^+$);

Preparation of Intermediate I-1232

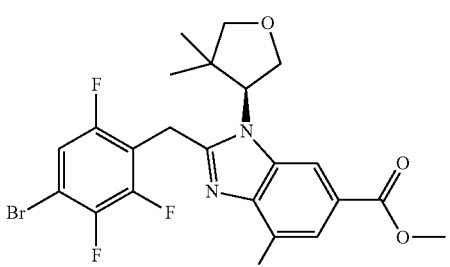

I-1232

Methyl (S)-2-(4-bromo-2,3,6-trifluorobenzyl)-1-(4,4-dimethyltetrahydrofuran-3-yl)-4-fluoro-1H-benzo[d]imidazole-6-carboxylate: Methyl (S)-2-(4-bromo-2,3,6-trifluorobenzyl)-1-(4,4-dimethyltetrahydrofuran-3-yl)-4-fluoro-1H-benzo[d]imidazole-6-carboxylate was prepared following the procedure for 1-2 substituting Intermediate I-1226 for I-1042 and 2-(4-bromo-2,3,6-trifluorophenyl)acetic acid for 2-(4-bromo-2,5-difluorophenyl)acetic acid. ES/MS: 515.7 (M+H$^+$);

Preparation of Intermediate I-1233

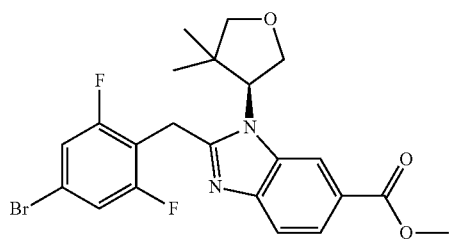

I-1233

Methyl (S)-2-(4-bromo-2,6-difluorobenzyl)-1-(4,4-dimethyltetrahydrofuran-3-yl)-1H-benzo[d]imidazole-6-carboxylate: Methyl (S)-2-(4-bromo-2,6-difluorobenzyl)-1-(4,4-dimethyltetrahydrofuran-3-yl)-1H-benzo[d]imidazole-6-carboxylate was prepared following the procedure for 1-1041 substituting Intermediate I-80 for 1-1042 and 2-(4-bromo-2,6-difluorophenyl)acetic acid for 2-(4-bromo-2,5-difluorophenyl)acetic acid. ES/MS: 479.9 (M+H$^+$);

Preparation of Intermediate I-1234

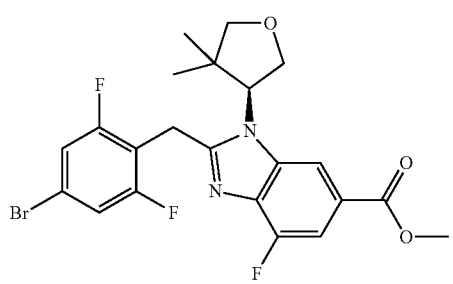

I-1234

Methyl (S)-2-(4-bromo-2,6-difluorobenzyl)-1-(4,4-dimethyltetrahydrofuran-3-yl)-4-fluoro-1H-benzo[d]imidazole-6-carboxylate: Methyl (S)-2-(4-bromo-2,6-difluorobenzyl)-1-(4,4-dimethyltetrahydrofuran-3-yl)-4-fluoro-1H-benzo[d]imidazole-6-carboxylate was prepared following the procedure for 1-2 substituting Intermediate I-1226 for 1-1042 and 2-(4-bromo-2,6-trifluorophenyl)acetic acid for 2-(4-bromo-2,6-difluorophenyl)acetic acid. ES/MS: 497.6 (M+H$^+$);

Preparation of Intermediate I-1235

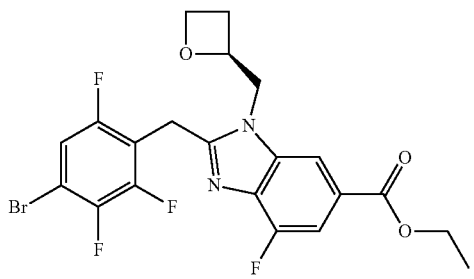

I-1235

Ethyl (S)-2-(4-bromo-2,3,6-trifluorobenzyl)-4-fluoro-1-(oxetan-2-ylmethyl)-1H-benzo[d]imidazole-6-carboxylate: Ethyl (S)-2-(4-bromo-2,3,6-trifluorobenzyl)-4-fluoro-1-(oxetan-2-ylmethyl)-1H-benzo[d]imidazole-6-carboxylate was prepared following the procedure for I-2 substituting I-5 for I-1 and 2-(4-bromo-2,3,6-trifluorophenyl)acetic acid for 2-(4-bromo-2-fluoro-phenyl)acetic acid. ES/MS: 501.3 (M+H$^+$);

Preparation of Intermediate I-1237

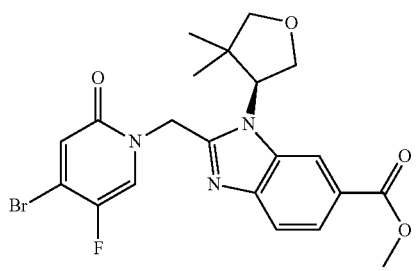

I-1237

Methyl (S)-2-((4-bromo-5-fluoro-2-oxopyridin-1(2H)-yl)methyl)-1-(4,4-dimethyltetrahydrofuran-3-yl)-1H-benzo[d]imidazole-6-carboxylate: Methyl (S)-2-((4-bromo-5-fluoro-2-oxopyridin-1(2H)-yl)methyl)-1-(4,4-dimethyltetrahydrofuran-3-yl)-1H-benzo[d]imidazole-6-carboxylate was prepared following the procedure for 1-1018 substituting Intermediate I-80 for 1-107. ES/MS: 322.5 (M+H+).

Preparation of Intermediate I-1238

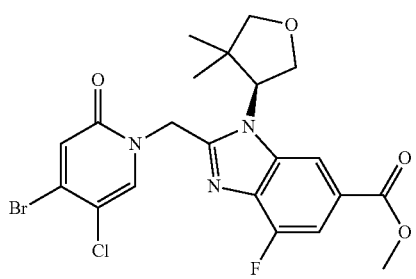

I-1238

Methyl (S)-2-((4-bromo-5-chloro-2-oxopyridin-1(2H)-yl)methyl)-1-(4,4-dimethyltetrahydrofuran-3-yl)-4-fluoro-1H-benzo[d]imidazole-6-carboxylate: Methyl (S)-2-((4-bromo-5-chloro-2-oxopyridin-1(2H)-yl)methyl)-1-(4,4-dimethyltetrahydrofuran-3-yl)-4-fluoro-1H-benzo[d]imidazole-6-carboxylate was prepared following the procedure for I-1018 substituting Intermediate I-1226 for 1-107 and 4-chloro-5-fluoro-1H-pyridin-2-one for 4-bromo-5-fluoro-1H-pyridin-2-one. ES/MS: 514.4 (M+H+).

Preparation of Intermediate I-1239

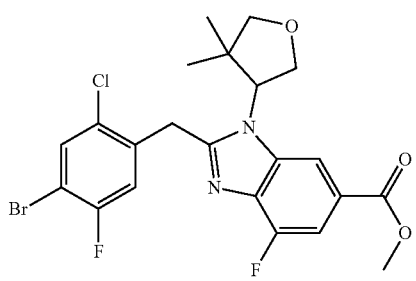

I-1239

Methyl 2-(4-bromo-2-chloro-5-fluorobenzyl)-1-(4,4-dimethyltetrahydrofuran-3-yl)-4-fluoro-1H-benzo[d]imidazole-6-carboxylate: Methyl 2-(4-bromo-2-chloro-5-fluorobenzyl)-1-(4,4-dimethyltetrahydrofuran-3-yl)-4-fluoro-1H-benzo[d]imidazole-6-carboxylate was prepared in a manner as described for 1-1031 substituting methyl 4-amino-3-[(4,4-dimethyltetrahydrofuran-3-yl)amino]-5-fluoro-benzoate 1-107 for ethyl 4-amino-3-fluoro-5-[[(2S)-oxetan-2-yl]methylamino]benzoate and 2-(4-bromo-2-chloro-5-fluoro-phenyl)acetic acid. For 2-(4-bromo-2-chloro-5-methyl-phenyl)acetic acid. ES/MS: 513.8 (M+H+).

Preparation of Intermediate I-1240

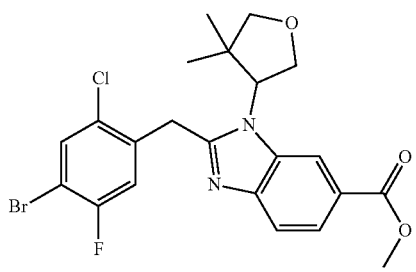

I-1240

Methyl 2-(4-bromo-2-chloro-5-fluorobenzyl)-1-(4,4-dimethyltetrahydrofuran-3-yl)-1H-benzo[d]imidazole-6-carboxylate: Methyl 2-(4-bromo-2-chloro-5-fluorobenzyl)-1-(4,4-dimethyltetrahydrofuran-3-yl)-1H-benzo[d]imidazole-6-carboxylate was prepared in a manner as described for 1-1031 substituting methyl 4-amino-3-[(4,4-dimethyltetrahydrofuran-3-yl)amino]-benzoate 1-107 for ethyl 4-amino-3-fluoro-5-[[(2S)-oxetan-2-yl]methylamino]benzoate and 2-(4-bromo-2-chloro-5-fluoro-phenyl)acetic acid. For 2-(4-bromo-2-chloro-5-methyl-phenyl)acetic acid. ES/MS: 494.6 (M+H+).

Preparation of Intermediate I-1242

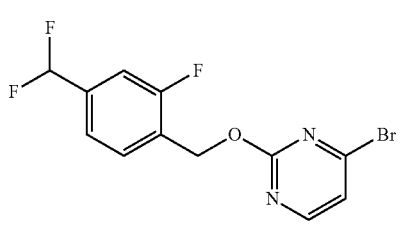

I-1242

4-bromo-2-((4-(difluoromethyl)-2-fluorobenzyl)oxy)pyrimidine: 4-bromo-2-((4-(difluoromethyl)-2-fluorobenzyl)oxy)pyrimidine was prepared in a manner as described for Intermediate I-1034 substituting 1-(bromomethyl)-4-difluoromethyl-2-fluoro-benzene for 6-(bromomethyl)-1-methyl-benzotriazole and 6-bromo-pyrimidin-3-ol for 6-bromopyridin-2-ol. ES/MS: 289.7 (M+H+).

Preparation of Intermediate I-1243

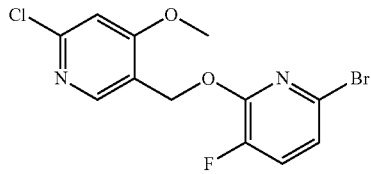

I-1243

6-bromo-2-((6-chloro-4-methoxypyridin-3-yl)methoxy)-3-fluoropyridine: 6-bromo-2-((6-chloro-4-methoxypyridin-3-yl)methoxy)-3-fluoropyridine was prepared in a manner as described for Intermediate I-1034 substituting 5-(bromomethyl)-2-chloro-4-methoxypyridine for 6-(bromomethyl)-1-methyl-benzotriazole and 6-bromo-3-fluoro-pyridin-2-ol for 6-bromopyridin-2-ol. ES/MS: 348.8 (M+H+).

Preparation of Intermediate I-1246

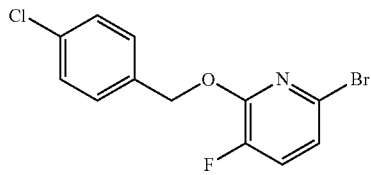

I-1246

6-bromo-2-[(4-chloro-phenyl)methoxy]-3-fluoro-pyridine: 6-bromo-2-[(4-chloro-phenyl)methoxy]-3-fluoro-pyridine was prepared in a manner as described for Intermediate I-1034 substituting 1-(bromomethyl)-4-chloro-benzene for 6-(bromomethyl)-1-methyl-benzotriazole and 6-bromo-3-fluoro-pyridin-2-ol for 6-bromopyridin-2-ol. ES/MS: 317.6 (M+H+).

Preparation of Intermediate I-1247

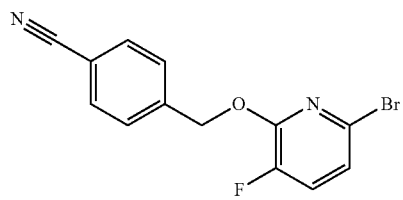

I-1247

4-(((6-bromo-3-fluoropyridin-2-yl)oxy)methyl)benzonitrile: 4-(((6-bromo-3-fluoropyridin-2-yl)oxy)methyl)benzonitrile was prepared in a manner as described for Intermediate I-1034 substituting 1-(bromomethyl)-4-benzonitrile for 6-(bromomethyl)-1-methyl-benzotriazole and 6-bromo-3-fluoro-pyridin-2-ol for 6-bromopyridin-2-ol. ES/MS: 308.3 (M+H+).

Preparation of Intermediate I-1248

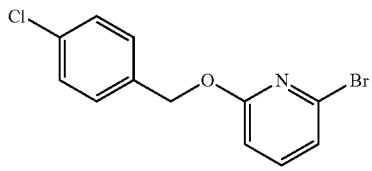

I-1248

2-bromo-6-((4-chlorobenzyl)oxy)pyridine: 2-bromo-6-((4-chlorobenzyl)oxy)pyridine was prepared in a manner as described for Intermediate I-1034 substituting 1-(bromomethyl)-4-chloro-benzene for 6-(bromomethyl)-1-methyl-benzotriazole. ES/MS: 298.6 (M+H+).

Preparation of Intermediate I-1249

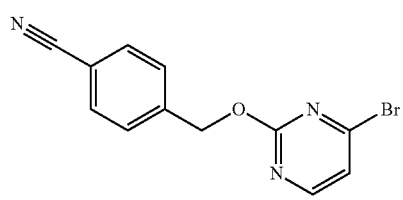

I-1249

4-(((4-bromopyrimidin-2-yl)oxy)methyl)benzonitrile: 4-(((4-bromopyrimidin-2-yl)oxy)methyl)benzonitrile was prepared in a manner as described for Intermediate I-1034 substituting 1-(bromomethyl)-4-benzonitrile for 6-(bromomethyl)-1-methyl-benzotriazole and 6-bromo-3-fluoro-pyrimidin-2-ol for 6-bromopyridin-2-ol. ES/MS: 290.1 (M+H+).

Preparation of Intermediate I-1253 cis-isomer 1 and I-1253 trans-isomer 2

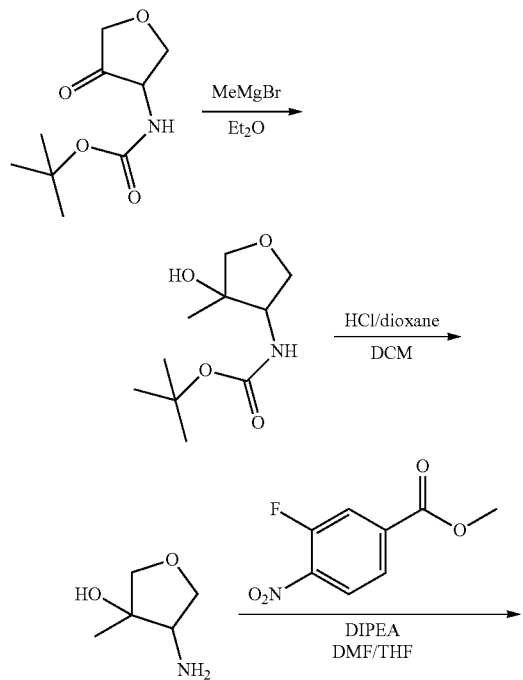

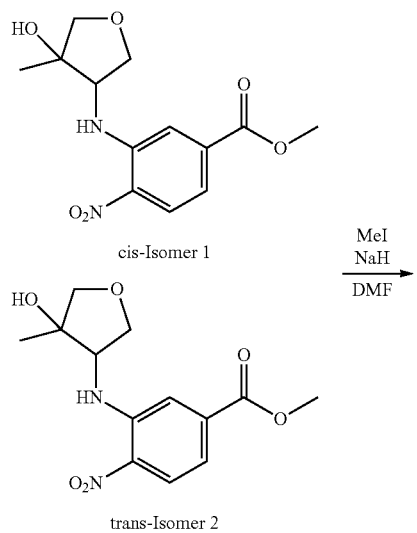

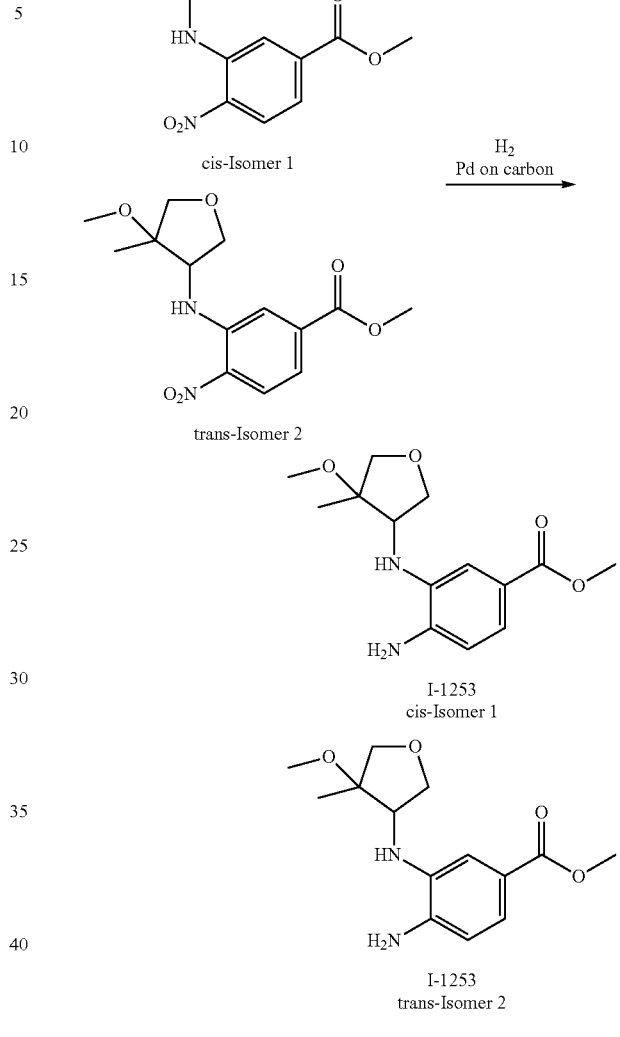

Tert-butyl (4-hydroxy-4-methyltetrahydrofuran-3-yl)carbamate: A suspension of tert-butyl (4-oxotetrahydrofuran-3-yl)carbamate (500 mg, 2.5 mmol) in diethyl ether (212.5 mL) was cooled to 0° C. Next, methylmagnesium bromide (2.48 mL, 3.0 Min diethyl ether, 7.45 mmol) was added slowly. The mixture was allowed to warm to 25° C. and then stirred for 16 h. Then the mixture was diluted with diethyl ether and washed with brine. Then the mixture was dried over sodium sulfate, concentrated, and used without further purification. 1H NMR (400 MHz, CDCl3) δ 5.02 (s, 1H), 4.68 (d, J=8.1 Hz, 1H), 4.32-4.24 (m, 1H), 4.21-4.13 (m, 1H), 4.06-3.91 (m, 1H), 3.85-3.72 (m, 2H), 3.62-3.46 (m, 1H), 1.47 (d, J=3.5 Hz, 12H), 1.38 (s, 2H).

4-amino-3-methyltetrahydrofuran-3-ol: A suspension of tert-butyl (4-hydroxy-4-methyltetrahydrofuran-3-yl)carbamate (491 mg, 2.26 mmol) and hydrochloric acid (1.25 mL, 4.0M in dioxane, 5.00 mmol) in DCM (5.00 mL) was stirred overnight. The mixture was diluted in EtOAc and washed with brine, dried over sodium sulfate, concentrated and used without further purification. 1H NMR (400 MHz, CDCl3) δ 3.95 (ddt, J=7.8, 3.8, 2.0 Hz, 1H), 3.77 (tq, J=7.2, 5.3, 3.7 Hz, 2H), 3.72-3.60 (m, 2H), 3.55 (dd, J=9.4, 2.0 Hz, 2H), 3.52-3.41 (m, 2H), 3.38 (t, J=1.8 Hz, 0H), 3.33-3.23

(m, 2H), 3.09 (t, J=6.2 Hz, 2H), 1.20 (t, J=1.8 Hz, 5H), 1.17 (d, J=2.0 Hz, 4H), 1.02-0.92 (m, 6H).

Methyl 3-((4-hydroxy-4-methyltetrahydrofuran-3-yl)amino)-4-nitrobenzoate: A suspension of 4-amino-3-methyltetrahydrofuran-3-ol (424 mg, 2.76 mmol), methyl 3-fluoro-4-nitro-benzoate (500 mg, 2.51 mmol) and N,N-Diisopropylethylamine (2.19 mL, 1.26 mmol) in THF (4 mL) and DMF (2 mL) was stirred at 82° C. for 16 h. The mixture was diluted in EtOAc and washed with brine, dried over sodium sulfate, concentrated, and purified by chromatography (eluent: EtOAc/hexanes) to give desired product. ES/MZ: 297.1 (M+H+).

Isomer 1: 1H NMR (400 MHz, CDCl3) δ 3.95 (ddt, J=7.8, 3.8, 2.0 Hz, 1H), 3.77 (tq, J=7.2, 5.3, 3.7 Hz, 2H), 3.72-3.60 (m, 2H), 3.55 (dd, J=9.4, 2.0 Hz, 2H), 3.52-3.41 (m, 2H), 3.38 (t, J=1.8 Hz, 0H), 3.33-3.23 (m, 2H), 3.09 (t, J=6.2 Hz, 2H), 1.20 (t, J=1.8 Hz, 5H), 1.17 (d, J=2.0 Hz, 4H), 1.02-0.92 (m, 6H). Isomer 2

Methyl 3-((4-methoxy-4-methyltetrahydrofuran-3-yl)amino)-4-nitrobenzoate: A suspension of methyl 3-((4-hydroxy-4-methyltetrahydrofuran-3-yl)amino)-4-nitrobenzoate (144 mg, 0.49 mmol), sodium hydride (20.5 mg, 0.54 mmol) and iodomethane (33 uL, 0.54 mmol) in DMF (1.00 mL) was stirred at 0° C. for 15 min. Next, the mixture was warmed to 25° C. and stirred for 16 h. The mixture was diluted in EtOAc and washed with brine, dried over sodium sulfate, concentrated, and purified by chromatography (eluent: EtOAc/hexanes) to give desired product EZ/MS: 311.3 (M+H+).

Methyl 4-amino-3-((4-methoxy-4-methyltetrahydrofuran-3-yl)amino)benzoate: A suspension of methyl 3-((4-methoxy-4-methyltetrahydrofuran-3-yl)amino)-4-nitrobenzoate (133 mg, 0.43 mmol), and Palladium on carbon (10% loading, 45.5 mg, 0.43 mmol) in ethanol (5.0 mL) and placed under hydrogen at 25° C. for 5 h. The mixture was diluted in EtOAc and washed with brine, dried over sodium sulfate, concentrated and used without further purification. EZ/MS: 281.1 (M+H+)

Preparation of Intermediate I-1255

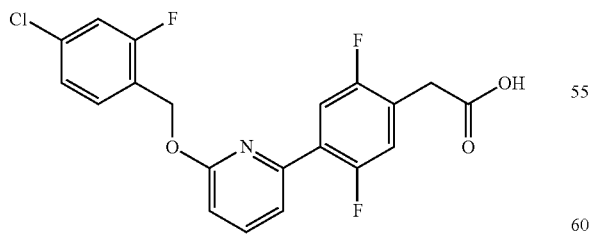

I-1255

2-(4-(6-((4-chloro-2-fluorobenzyl)oxy)pyridin-2-yl)-2,5-difluorophenyl)acetic acid: 2-(4-(6-((4-chloro-2-fluorobenzyl)oxy)pyridin-2-yl)-2,5-difluorophenyl)acetic acid: was prepared in a manner as described for the Intermediate I-7 substituting I-102 for I-3. ES/MZ: 316.6 (M+H+).

Preparation of Intermediate I-1256

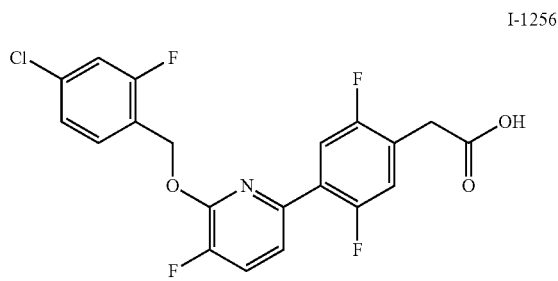 [SMILES: O=C(O)Cc1cc(F)c(-c2ccc(F)c(OCc3ccc(Cl)cc3F)n2)cc1F]

I-1256

2-(4-(6-((4-chloro-2-fluorobenzyl)oxy)-5-fluoropyridin-2-yl)-2,5-difluorophenyl)acetic acid: 2-(4-(6-((4-chloro-2-fluorobenzyl)oxy)-5-fluoropyridin-2-yl)-2,5-difluorophenyl)acetic acid: was prepared in a manner as described for the Intermediate I-7 substituting I-1036 for I-3. ES/MZ: 425.1 (M+H+).

Preparation of Intermediate I-1257 cis-isomer 1

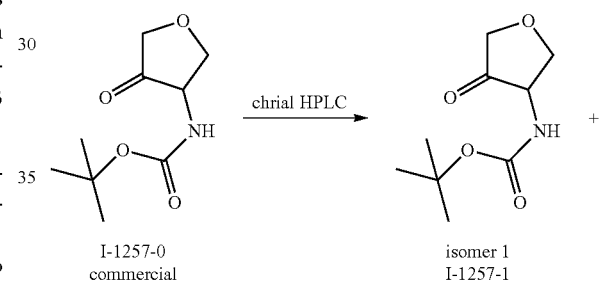

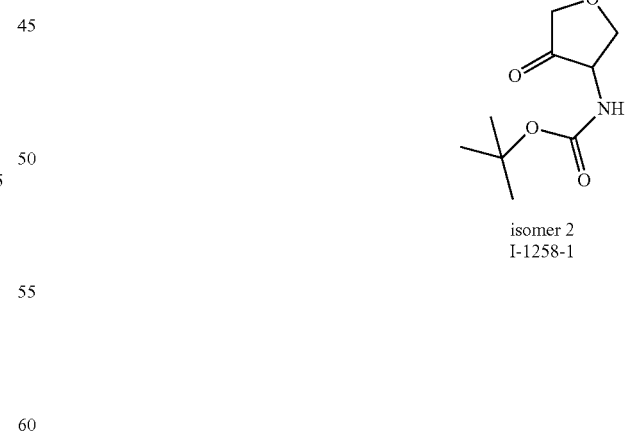

tert-butyl (4-hydroxy-4-methyltetrahydrofuran-3-yl)carbamate) (Isomer 1 I-1257, Isomer 2 I-1258-1): was obtained via preparative chiral HPLC (Chiralpak IH column, Hexanes/iPrOH eluent) on racemic I-1257-0, giving two distinct stereoisomers (I-1257-1 as the earlier eluting isomer, I-1258-1 as the later eluting isomer).

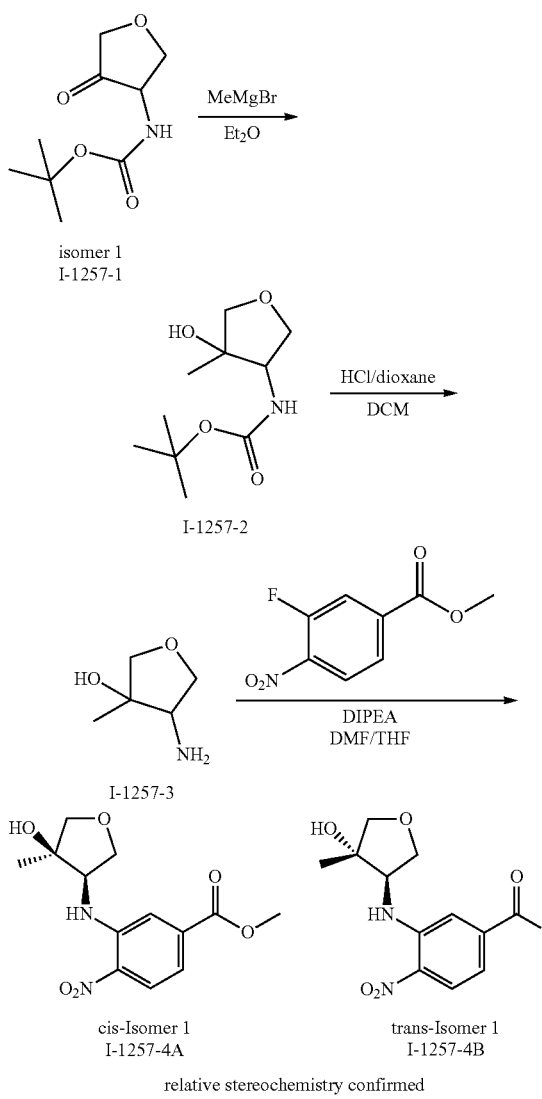

2.0 Hz, 2H), 3.52-3.41 (m, 2H), 3.38 (t, J=1.8 Hz, 0H), 3.33-3.23 (m, 2H), 3.09 (t, J=6.2 Hz, 2H), 1.20 (t, J=1.8 Hz, 5H), 1.17 (d, J=2.0 Hz, 4H), 1.02-0.92 (m, 6H).

methyl 3-((4-hydroxy-4-methyltetrahydrofuran-3-yl)amino)-4-nitrobenzoate (cis-isomer Peak 1, I-1257-4A, relative stereochemistry established): A suspension of 4-amino-3-methyltetrahydrofuran-3-ol (424 mg, 2.76 mmol) (I-1257-3), methyl 3-fluoro-4-nitro-benzoate (500 mg, 2.51 mmol) and N,N-Diisopropylethylamine (2.19 mL, 1.26 mmol) in THF (4 mL) and DMF (2 mL) was stirred at 82° C. for 16 h. Purification by silica gel flash column chromatography (EtOAc/hexane) provided both cis (I-1257-4A, Isomer 1, the earlier eluting of two diastereomers) and trans (I-1257-4B, Isomer 2, the later eluting of two diastereomers) isomers. ES/MZ: 297.1 (M+H+). Isomer 1, I-1257-4A: 1H NMR (400 MHz, CDCl3) δ 3.95 (ddt, J=7.8, 3.8, 2.0 Hz, 1H), 3.77 (tq, J=7.2, 5.3, 3.7 Hz, 2H), 3.72-3.60 (m, 2H), 3.55 (dd, J=9.4, 2.0 Hz, 2H), 3.52-3.41 (m, 2H), 3.38 (t, J=1.8 Hz, 0H), 3.33-3.23 (m, 2H), 3.09 (t, J=6.2 Hz, 2H), 1.20 (t, J=1.8 Hz, 5H), 1.17 (d, J=2.0 Hz, 4H), 1.02-0.92 (m, 6H). Two dimensional NOESY NMR identified a O17-OH to N11-NH NOE correlation and a C12-CH to C21-CH3 NOE correlation to confirm relative stereochemistry of I-1257-4A as the cis diastereomer. Isomer 2, I-1257-4B: 1H NMR (400 MHz, CDCl3) δ 8.27 (d, J=8.9 Hz, 1H), 8.11 (d, J=7.7 Hz, 1H), 7.75 (d, J=1.7 Hz, 1H), 7.33 (dd, J=8.9, 1.7 Hz, 1H), 4.53 (dd, J=9.6, 6.3 Hz, 1H), 4.24 (q, J=7.0, 6.4 Hz, 1H), 3.98 (s, 3H), 3.91 (d, J=9.8 Hz, 1H), 3.80 (d, J=9.8 Hz, 1H), 3.73 (dd, J=9.6, 4.6 Hz, 1H), 1.42 (s, 3H).

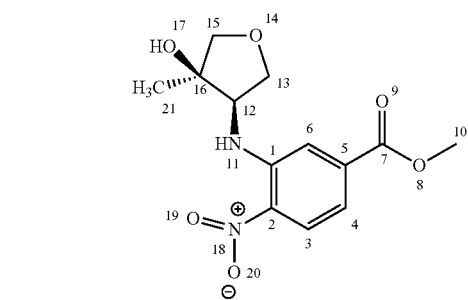

tert-butyl (4-hydroxy-4-methyltetrahydrofuran-3-yl)carbamate (I-1257-2): A mixture of tert-butyl (4-oxotetrahydrofuran-3-yl)carbamate (500 mg, 2.5 mmol) (Peak 1 I-1257-1) in diethyl ether (212.5 mL) was cooled to 0° C., then methylmagnesium bromide (2.48 mL, 3.0 M in diethyl ether, 7.45 mmol) was added slowly. The mixture was allowed to warm to 25° C. and allowed to stirred for 16 h. Then the mixture was diluted with diethyl ether and washed with brine. Then the mixture was dried over sodium sulfate and concentrated to yield the title compound. 1H NMR (400 MHz, CDCl3) δ 5.02 (s, 1H), 4.68 (d, J=8.1 Hz, 1H), 4.32-4.24 (m, 1H), 4.21-4.13 (m, 1H), 4.06-3.91 (m, 1H), 3.85-3.72 (m, 2H), 3.62-3.46 (m, 1H), 1.47 (d, J=3.5 Hz, 12H), 1.38 (s, 2H).

4-amino-3-methyltetrahydrofuran-3-ol (I-1257-3): A suspension of tert-butyl (4-hydroxy-4-methyltetrahydrofuran-3-yl)carbamate (491 mg, 2.26 mmol) (I-1257-2) and hydrochloric acid (1.25 mL, 4.0M in dioxane, 5.00 mmol) in DCM (5.00 mL) was stirred overnight. The mixture was diluted in EtOAc and washed with brine, dried over sodium sulfate, and concentrated to yield the title compound. 1H NMR (400 MHz, CDCl3) δ 3.95 (ddt, J=7.8, 3.8, 2.0 Hz, 1H), 3.77 (tq, J=7.2, 5.3, 3.7 Hz, 2H), 3.72-3.60 (m, 2H), 3.55 (dd, J=9.4,

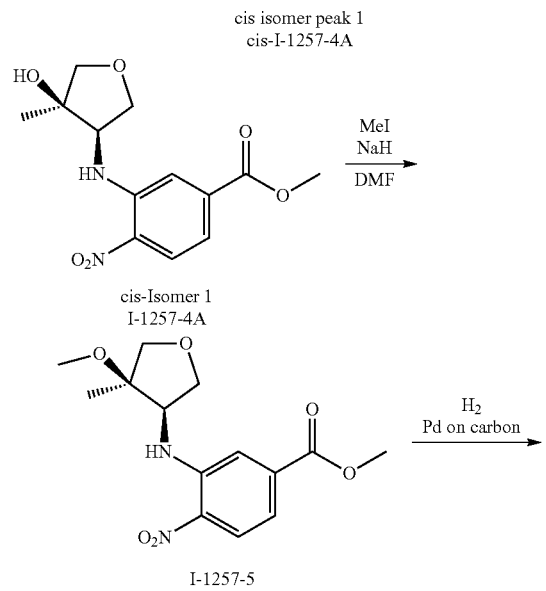

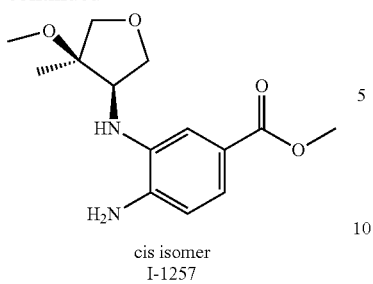

cis isomer
I-1257

Methyl 3-((cis-4-methoxy-4-methyltetrahydrofuran-3-yl) amino)-4-nitrobenzoate (cis-isomer peak 1, I-1257-5, relative stereochemistry established): A mixture of methyl 3-((4-hydroxy-4-methyltetrahydrofuran-3-yl)amino)-4-nitrobenzoate (144 mg, 0.49 mmol) (cis-isomer peak 1, I-1257-4A), sodium hydride (20.5 mg, 0.54 mmol) and iodomethane (33 uL, 0.54 mmol) in DMF (1.00 mL) was stirred at 0° C. for 15 min then warmed to 25° C. and stirred for 16 h. The mixture was diluted in EtOAc and washed with brine, then dried over sodium sulfate, concentrated, and purified by silica gel flash column chromatography (eluent: EtOAc/hexanes) to give the title compound. ES/MS: 311.3 (M+H+).

Methyl 4-amino-3-((4-methoxy-4-methyltetrahydrofuran-3-yl)amino)benzoate (cis-isomer peak 1, I-1257, relative stereochemistry established): A mixture of methyl 3-((4-methoxy-4-methyltetrahydrofuran-3-yl)amino)-4-nitrobenzoate (133 mg, 0.43 mmol) (cis-isomer peak 1, I-1257-5), and 10% palladium on carbon (45.5 mg, 0.043 mmol) in ethanol (5.0 mL) and placed under hydrogen at 25° C. for 5 h. The mixture was diluted in EtOAc and washed with brine, dried over sodium sulfate, and concentrated to yield the title compound. ES/MS: 281.1 (M+H+)

Preparation of Intermediate I-1258 cis-isomer 2

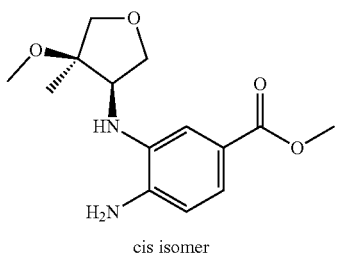

I-1258 cis isomer

Methyl 4-amino-3-((4-methoxy-4-methyltetrahydrofuran-3-yl)amino)benzoate (cis-isomer 2, I-1258, relative stereochemistry established): methyl 4-amino-3-((4-methoxy-4-methyltetrahydrofuran-3-yl)amino)benzoate (cis-isomer 2, I-1258, relative stereochemistry established) was prepared as described for cis-isomer peak 1 I-1257, using Intermediate isomer 2 I-1258-1 in place of isomer 1 I-1257-1.

Preparation of Intermediate I-1260

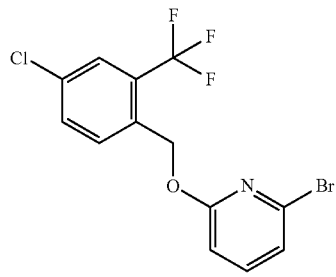

I-1260

2-bromo-6-((4-chloro-2-(trifluoromethyl)benzyl)oxy) pyridine: 2-bromo-6-((4-chloro-2-(trifluoromethyl)benzyl) oxy)pyridine benzonitrile was prepared in a manner as described for the Intermediate I-1034 substituting 1-(bromomethyl)-4-chloro-2-(trifluoromethyl)benzene for 6-(bromomethyl)-1-methyl-benzotriazole. ES/MZ: 366.6 (M+H+).

Preparation of Intermediate I-1261

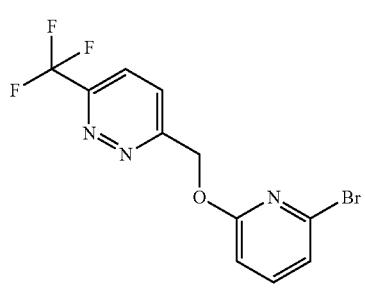

I-1261

6-bromo-2-((2,6-difluorobenzyl)oxy)-3-fluoropyridine: 6-bromo-2-((2,6-difluorobenzyl)oxy)-3-fluoropyridine was prepared in a manner as described for the Intermediate I-1034 substituting 3-(((6-bromopyridin-2-yl)oxy)methyl)-6-(trifluoromethyl)pyridazine for 6-(bromomethyl)-1-methyl-benzotriazole ES/MZ: 334.1 (M+H+).

Preparation of Intermediate I-1262

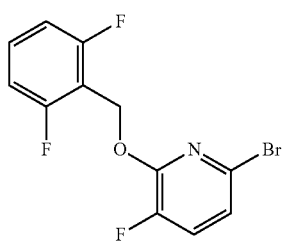

i-1262

6-bromo-2-((2,6-difluorobenzyl)oxy)-3-fluoropyridine: 6-bromo-2-((2,6-difluorobenzyl)oxy)-3-fluoropyridine was prepared in a manner as described for the Intermediate I-1034 substituting 2-(bromomethyl)-1,3-difluorobenzene for 6-(bromomethyl)-1-methyl-benzotriazole and 6-bromopyridin-2-ol for 6-bromo-3-fluoropyridin-2-ol. ES/MZ: 318.1 (M+H+).

Preparation of Intermediate I-1263

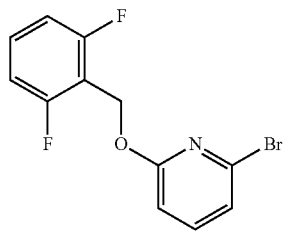
I-1263

2-bromo-6-((2,6-difluorobenzyl)oxy)pyridine: 2-bromo-6-((2,6-difluorobenzyl)oxy)pyridine was prepared in a manner as described for the intermediate I-1034 substituting 2-(bromomethyl)-1,3-difluorobenzene for 6-(bromomethyl)-1-methyl-benzotriazole. ES/MZ: 300.1 (M+H+).

Preparation of Intermediate I-1264

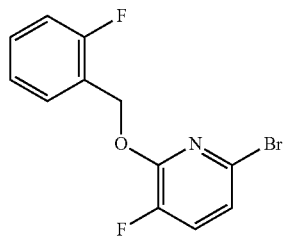
I-1264

6-bromo-3-fluoro-2-((2-fluorobenzyl)oxy)pyridine: 6-bromo-3-fluoro-2-((2-fluorobenzyl)oxy)pyridine was prepared in a manner as described for the Intermediate I-1034 substituting 1-(bromomethyl)-2-fluorobenzene for 6-(bromomethyl)-1-methyl-benzotriazole and 6-bromopyridin-2-ol for 6-bromo-3-fluoropyridin-2-ol. ES/MZ: 300.1 (M+H+).

Preparation of Intermediate I-1265

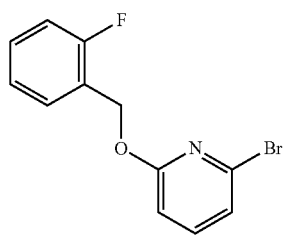
I-1265

2-bromo-6-((2-fluorobenzyl)oxy)pyridine: 2-bromo-6-((2-fluorobenzyl)oxy)pyridine was prepared in a manner as described for the Intermediate I-1034 substituting 1-(bromomethyl)-2-fluorobenzene for 6-(bromomethyl)-1-methyl-benzotriazole. ES/MZ: 282.1 (M+H+).

Preparation of Intermediate I-1266

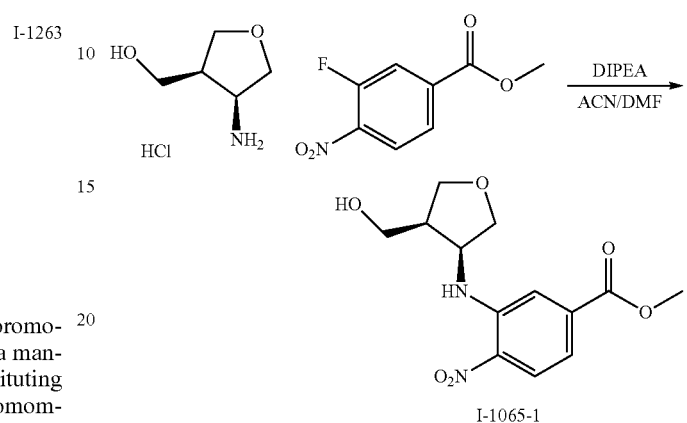
I-1065-1

Methyl rac-cis-4-amino-3-(((1-(fluoromethyl)cyclopropyl)methyl)amino)benzoate (I-1065-1): To a mixture of methyl 3-fluoro-4-nitro-benzoate (120 mg, 0.603 mmol), racemic cis-4-aminotetrahydrofuran-3-yl]methanol (77.7 mg, 0.66 mmol) in THF (4 mL) and DMF (2 mL), was added N,N-diisopropylethylamine (0.525 mL, 3.01 mmol). The mixture was heated at 80° C. for 18 hr. The crude mixture was diluted with EtOAc, washed with 5% LiCl and brine. The organic extract was dried over sodium sulfate and purified by silica gel column chromatography (eluent: EtOAc/hexanes) to afford the title compound. ES/MS: 297.2 (M+H$^+$).

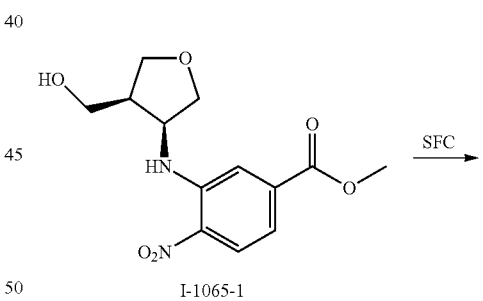
I-1065-1

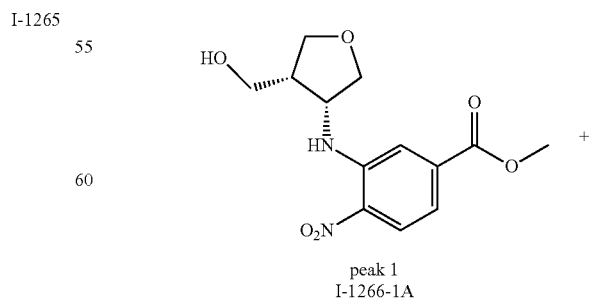
peak 1
I-1266-1A

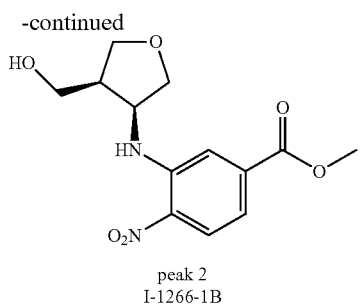

peak 2
I-1266-1B

Methyl 3-((cis-4-(hydroxymethyl)tetrahydrofuran-3-yl)amino)-4-nitrobenzoate (Peak 1-I-1266-1A, Peak 2-I-1266-1B, relative stereochemistry established): was obtained via preparative chiral SFC (Daicel Chiralpak AD-H column with EtOH/CO$_2$ eluent) on I-1065-1, which gave 2 distinct stereoisomers.

Methyl 3-(((3R,4R)-4-(hydroxymethyl)tetrahydrofuran-3-yl)amino)-4-nitrobenzoate (Peak 1, I-1266-1A): the earlier eluting of the two stereoisomers.

Methyl 3-(((3S,4S)-4-(hydroxymethyl)tetrahydrofuran-3-yl)amino)-4-nitrobenzoate (Peak 2, I-1266-1B): the later eluting of the two stereoisomers.

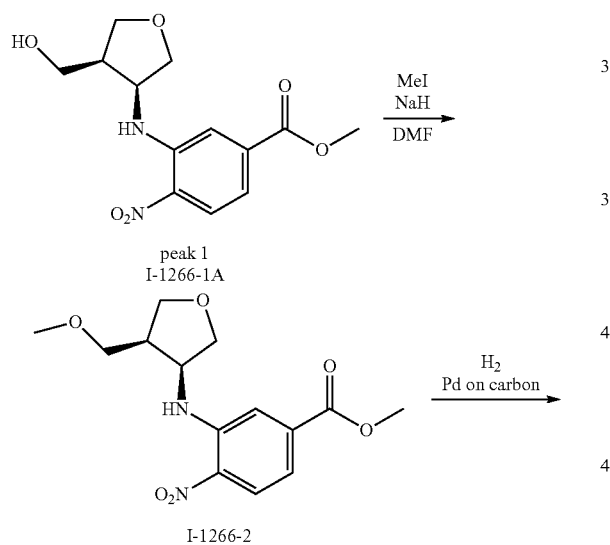

Methyl 3-(((3S,4S)-4-(methoxymethyl)tetrahydrofuran-3-yl)amino)-4-nitrobenzoate (I-1266-2): To a mixture of methyl 3-(((3S,4S)-4-(hydroxymethyl)tetrahydrofuran-3-yl)amino)-4-nitrobenzoate (I-1266-1A) (75 mg, 0.253 mmol) in DMF (4 mL) was added NaH (24.2 mg, 0.633 mmol, 60% dispersion) at 0° C. To this mixture was added methyl iodide (35.9 mg, 0.253 mmol) and the mixture stirred for 1 hour at rt. The mixture was then split between saturated aqueous ammonium chloride and EtOAc, the aqueous layer was extracted with EtOAc five times, washed with brine. The organic extract was dried over sodium sulfate and purified by silica gel column chromatography (eluent: EtOAc/hexanes) to afford the title compound. ES/MS: 311.2 (M+H$^+$)

Methyl 4-amino-3-(((3S,4S)-4-(methoxymethyl)tetrahydrofuran-3-yl)amino)benzoate (I-1266, relative stereochemistry established): A mixture of methyl 3-(((3S,4S)-4-(methoxymethyl)tetrahydrofuran-3-yl)amino)-4-nitrobenzoate (I-1266-2) (80 mg, 0.258 mmol) in EtOAc (5 mL) was degassed with cycles of argon then vacuum 3×. Added Palladium on carbon (10.0%, 27.4 mg, 0.258 mmol). The mixture was degassed with cycles of argon then vacuum and Preparation of Intermediate I-1267

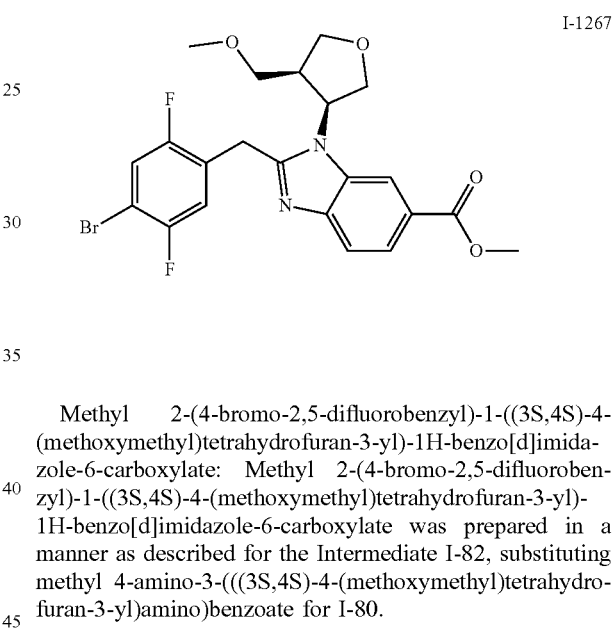

Methyl 2-(4-bromo-2,5-difluorobenzyl)-1-((3S,4S)-4-(methoxymethyl)tetrahydrofuran-3-yl)-1H-benzo[d]imidazole-6-carboxylate: Methyl 2-(4-bromo-2,5-difluorobenzyl)-1-((3S,4S)-4-(methoxymethyl)tetrahydrofuran-3-yl)-1H-benzo[d]imidazole-6-carboxylate was prepared in a manner as described for the Intermediate I-82, substituting methyl 4-amino-3-(((3S,4S)-4-(methoxymethyl)tetrahydrofuran-3-yl)amino)benzoate for I-80.

Preparation of Intermediate I-1268

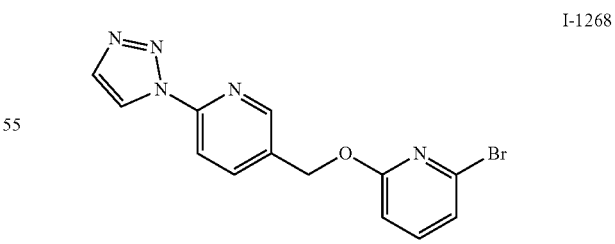

2-bromo-6-[[6-(triazol-1-yl)-3-pyridyl]methoxy]pyridine (I-1268): 2-bromo-6-[[6-(triazol-1-yl)-3-pyridyl]methoxy]pyridine was prepared in a manner as described for Intermediate I-84 substituting 5-(bromomethyl)-2-(triazol-1-yl)pyridine for 2-(bromomethyl)thiazole-5-carbonitrile. ES/MS: 332, 334 (M+H+).

Preparation of Intermediate I-1269

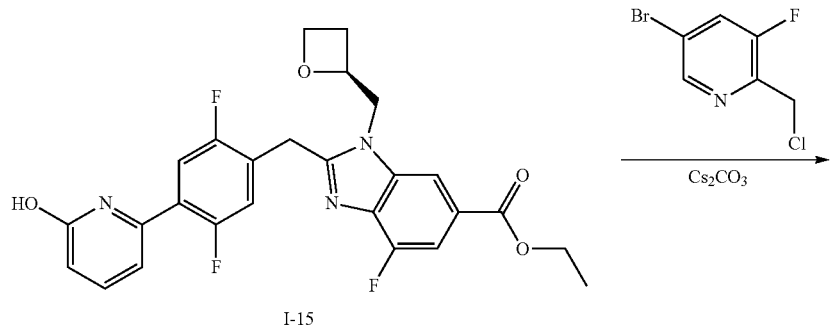

I-15

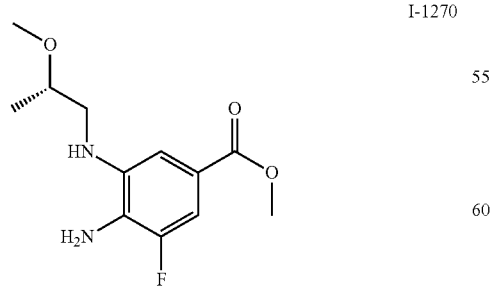

I-1043

Ethyl 2-[[4-[6-[(5-bromo-3-fluoro-2-pyridyl)methoxy]-2-pyridyl]-2,5-difluoro-phenyl]methyl]-7-fluoro-3-[[(2S)-oxetan-2-yl]methyl]benzimidazole-5-carboxylate (I-1269): A suspension of ethyl 2-[[2,5-difluoro-4-(6-hydroxy-2-pyridyl)phenyl]methyl]-7-fluoro-3-[[(2S)-oxetan-2-yl]methyl]benzimidazole-5-carboxylate (300 mg, 0.603 mmol), 5-bromo-2-(chloromethyl)-3-fluoro-pyridine (162 mg, 0.724 mmol), and cesium carbonate (491 mg, 1.51 mmol) in $CH_3CN$ was heated at 70° C. for 1 hr. The mixture was filtered, concentrated, and purified by silica gel column chromatography (eluent: EtOAc/hexanes) to give desired product. ES/MS: 686.0 (M+H$^+$).

Preparation of Intermediate I-1270

I-1270

Methyl 4-amino-3-fluoro-5-[[(2S)-2-methoxypropyl]amino]benzoate (I-1270): Methyl 4-amino-3-fluoro-5-[[(2S)-2-methoxypropyl]amino]benzoate was prepared in a manner as described for Intermediate I-5 substituting (S)-2-methoxypropan-1-amine for (S)-oxetan-2-ylmethanamine and methyl 3,5-difluoro-4-nitrobenzoate for Ethyl 3,5-difluoro-4-nitrobenzoate. ES/MS: 257.1 (M+H$^+$).

Preparation of Intermediate I-1271

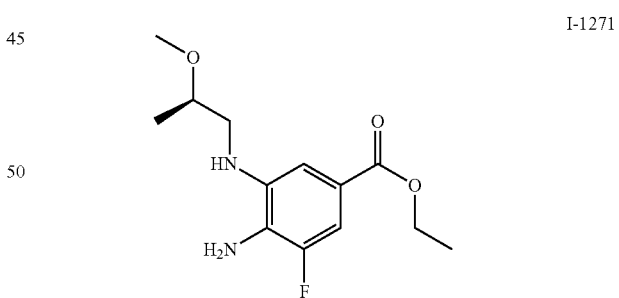

Ethyl 4-amino-3-fluoro-5-[[(2R)-2-methoxypropyl]amino]benzoate (I-1271) Ethyl 4-amino-3-fluoro-5-[[(2R)-2-methoxypropyl]amino]benzoate was prepared in a manner as described for Intermediate I-5 substituting (R)-2-methoxypropan-1-amine for (S)-oxetan-2-ylmethanamine. ES/MS: 271.2 (M+H$^+$).

Preparation of Intermediate I-1272

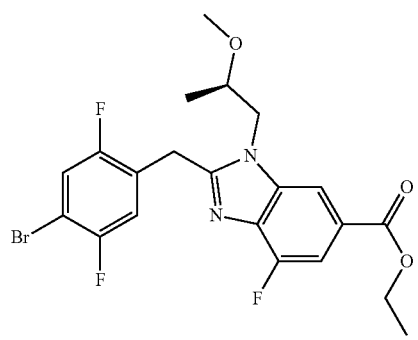

I-1272

Ethyl 2-[(4-bromo-2,5-difluoro-phenyl)methyl]-7-fluoro-3-[(2R)-2-methoxypropyl]benzimidazole-5-carboxylate (I-1272): Ethyl 2-[(4-bromo-2,5-difluoro-phenyl)methyl]-7-fluoro-3-[(2R)-2-methoxypropyl]benzimidazole-5-carboxylate was prepared in a manner as described for Intermediate I-2 substituting Ethyl 4-amino-3-fluoro-5-[[(2R)-2-methoxypropyl]amino] (I-1271) for I-1 and 2-(4-bromo-2,5-difluorophenyl)acetic acid for 2-(4-bromo-2-fluoro-phenyl)acetic acid. ES/MS: 485, 487 (M+H+).

Preparation of Intermediate I-1273

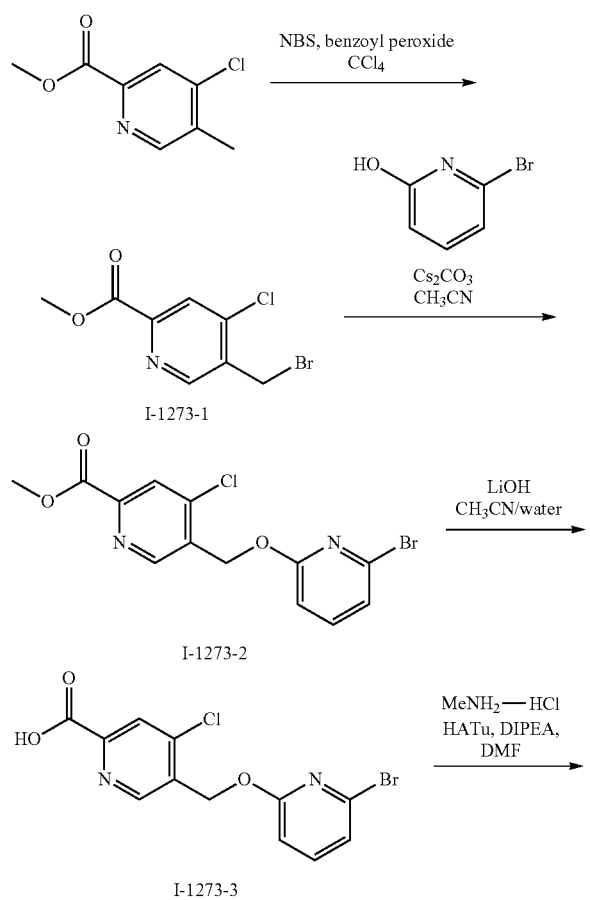

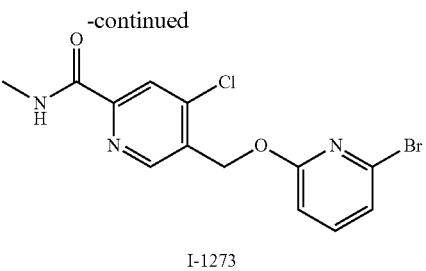

I-1273

Methyl 5-(bromomethyl)-4-chloro-pyridine-2-carboxylate (I-1273-1): Methyl 4-chloro-5-methyl-pyridine-2-carboxylate (1.00 g, 5.39 mmol) was taken up in carbon tetrachloride (10.0 mL) and N-Bromosuccinimide (1255 mg, 7.05 mmol) was added followed by Benzoyl peroxide (140 mg, 0.580 mmol). The mixture was heated to 90° C. for 45 min. The mixture was concentrated. in vacuo. The crude residue was purified by chromatography (eluent: EtOAc/hexanes) to give desired product. ES/MS: 264, 266 (M+H+).

Methyl 5-[(6-bromo-2-pyridyl)oxymethyl]-4-chloro-pyridine-2-carboxylate (I-1273-2): 6-Bromopyridin-2-ol (600 mg, 3.4 mmol), methyl 5-(bromomethyl)-4-chloro-pyridine-2-carboxylate (1003 mg, 3.8 mmol), and cesium carbonate (1685 mg, 5.2 mmol) were taken up in Acetonitrile (12 mL) and the mixture was heated to 65° C. for 1 hr. The mixture was filtered through Celite and concentrated in vacuo. The crude residue was purified by chromatography (eluent: EtOAc/hexanes) to give desired product. ES/MS: 357, 359 (M+H+).

5-[(6-bromo-2-pyridyl)oxymethyl]-4-chloro-pyridine-2-carboxylic acid (I-1273-3): Methyl 5-[(6-bromo-2-pyridyl)oxymethyl]-4-chloro-pyridine-2-carboxylate (1.17 g, 3.27 mmol) was taken up in CH3CN (15.0 mL) and water (5.00 mL) and then lithium hydroxide, monohydrate (408 mg, 9.72 mmol) was added. The mixture was stirred at rt for 1 hr. The mixture was diluted with EtOAc then acidified to pH-6 with 1N HCl. A precipitate formed. The precipitate was collected and washed with H2O and Et2O. Remaining material extracted into EtOAc (dried over MgSO4 and conc. in vacuo). The combined solids were used in subsequent reactions without purification. ES/MS: 343, 345 (M+H+).

5-[(6-bromo-2-pyridyl)oxymethyl]-4-chloro-N-methyl-pyridine-2-carboxamide (I-1273): N,N-Diisopropylethylamine (1.22 mL, 6.99 mmol) was added to a solution of 5-[(6-bromo-2-pyridyl)oxymethyl]-4-chloro-pyridine-2-carboxylic acid (600 mg, 1.75 mmol), methanamine; hydrochloride (236 mg, 3.49 mmol), and o-(7-Azabenzotriazol-1-yl)-N,N,N',N'-tetramethyluronium hexafluorophosphate (976 mg, 2.57 mmol) in DMF (10 mL). The mixture was stirred at rt for 10 min. The mixture was partitioned with EtOAc and water. The organic extract was dried over MgSO4, filtered, and concentrated to give desired product. ES/MS: 356, 358 (M+H+).

Preparation of Intermediate I-1274

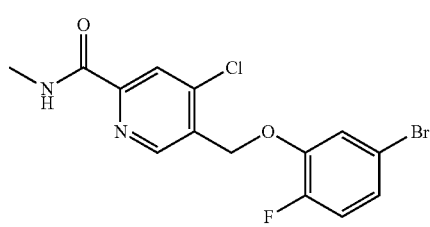

I-1274

Methyl 5-[(5-bromo-2-fluoro-phenoxy)methyl]-4-chloro-pyridine-2-carboxylate (I-1274): Methyl 5-[(5-bromo-2-fluoro-phenoxy)methyl]-4-chloro-pyridine-2-carboxylate was prepared in a similar manner as described for Intermediate I-1273 substituting 5-bromo-2-fluoro-phenol for 6-bromopyridin-2-ol in step 2. ES/MS: 374, 376 (M+H+).

Preparation of Intermediate I-1275

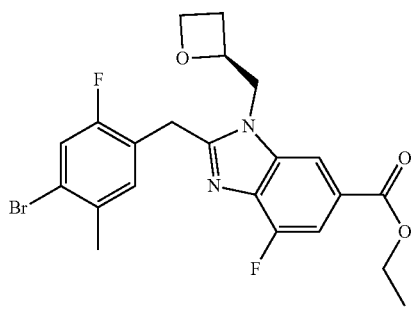

I-1275

Ethyl 2-[(4-bromo-2-fluoro-5-methyl-phenyl)methyl]-7-fluoro-3-[[(2S)-oxetan-2-yl]methyl]benzimidazole-5-carboxylate (I-1275): ethyl 2-[(4-bromo-2-fluoro-5-methyl-phenyl)methyl]-7-fluoro-3-[[(2S)-oxetan-2-yl]methyl]benzimidazole-5-carboxylate was prepared in a manner as described for Intermediate I-2 substituting I-5 for I-1 and 2-(4-bromo-2-fluoro-5-methyl-phenyl)acetic acid I-1277 for 2-(4-bromo-2-fluoro-phenyl)acetic acid. ES/MS: 479, 481 (M+H+).

Preparation of Intermediate I-1276

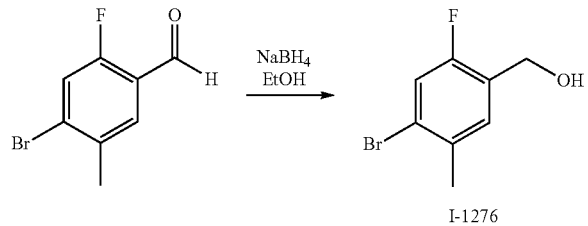

I-1276

(4-bromo-2-fluoro-5-methyl-phenyl)methanol (I-1276): Sodium borohydride (436 mg, 11.5 mmol) was added in one portion to a solution of 4-bromo-2-fluoro-5-methyl-benzaldehyde (5.0 g, 23.0 mmol) in EtOH (115 mL) at 0° C. The mixture was placed under an inert atmosphere of argon and allowed to warm to room temperature and stirred for 2 h. The mixture was then quenched with saturated sodium NaHCO₃ (2×30 ml), extracted with EtOAc (2×30 ml) and dried over magnesium sulfate. The mixture was then filtered and concentrated in vacuo. The crude residue was purified by chromatography (eluent: EtOAc/hexanes) to give desired product. ¹HNMR (400 MHz, CDCl3) δ 7.29 (d, J=7.8 Hz, 1H), 7.25 (d, J=9.3 Hz, 1H), 4.68 (s, 2H), 2.36 (s, 3H). ¹⁹F NMR (376 MHz, Chloroform-d) δ -122.82.

Preparation of Intermediate I-1277

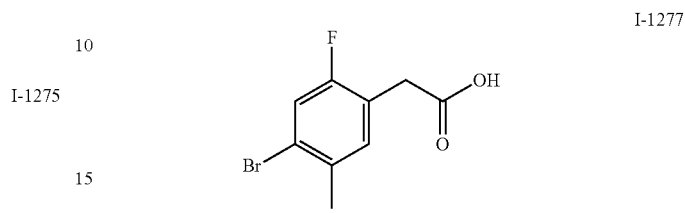

I-1277

2-(4-bromo-2-fluoro-5-methyl-phenyl)acetic acid (I-1277): 2-(4-bromo-2-fluoro-5-methyl-phenyl)acetic acid was prepared in a manner as described for Intermediate I-1023 substituting (4-bromo-2-fluoro-5-methyl-phenyl)methanol 1-1276 for (4-bromo-2-chloro-5-methyl-phenyl)methanol in step 3. ¹H NMR (400 MHz, CDCl3) δ 7.28 (d, J=9.0 Hz, 1H), 7.12 (d, J=7.8 Hz, 1H), 3.64 (s, 2H), 2.34 (s, 3H). ¹⁹F NMR (376 MHz, CDCl3) δ -119.92.

Preparation of Intermediate I-1278

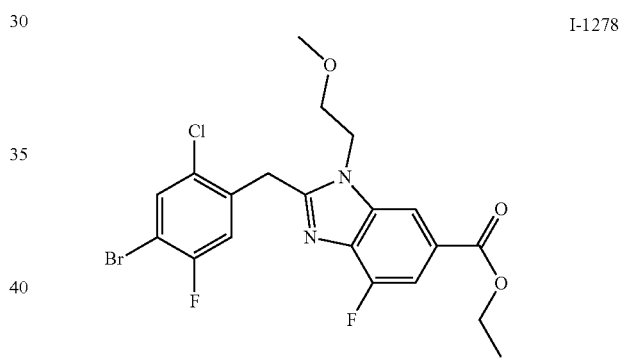

I-1278

Ethyl 2-[(4-bromo-2-chloro-5-fluoro-phenyl)methyl]-7-fluoro-3-(2-methoxyethyl)benzimidazole-5-carboxylate (I-1278): Ethyl 2-[(4-bromo-2-chloro-5-fluoro-phenyl)methyl]-7-fluoro-3-(2-methoxyethyl)benzimidazole-5-carboxylate was prepared in a manner as described for Intermediate I-26 substituting ethyl 4-amino-3-fluoro-5-((2-methoxyethyl)amino)benzoate 1-1032 for ethyl 4-amino-3-fluoro-5-[[(2S)-oxetan-2-yl]methylamino]benzoate and 2-(4-bromo-2-chloro-5-fluoro-phenyl)acetic acid for 2-(4-bromo-2-chloro-5-methyl-phenyl)acetic acid. ES/MS: 488, 489 (M+H+).

Preparation of Intermediate I-1279

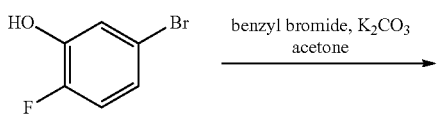

benzyl bromide, K₂CO₃
acetone

-continued

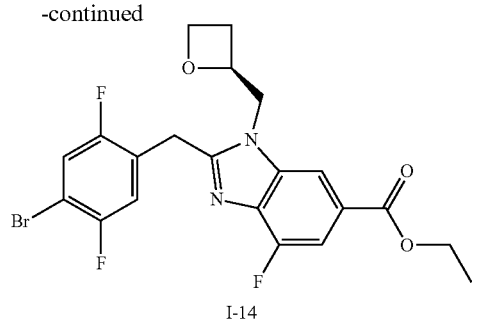

I-14

1. Bis(pinacolato)diboron
   Pd(dppf)Cl₂, KOPr
   1,4-dioxane
2. 2N Na₂CO₃, PdCl₂(dppf)
   1,4-dioxane

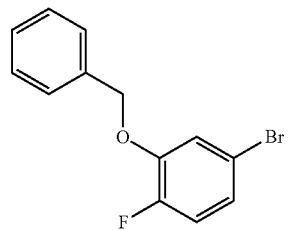

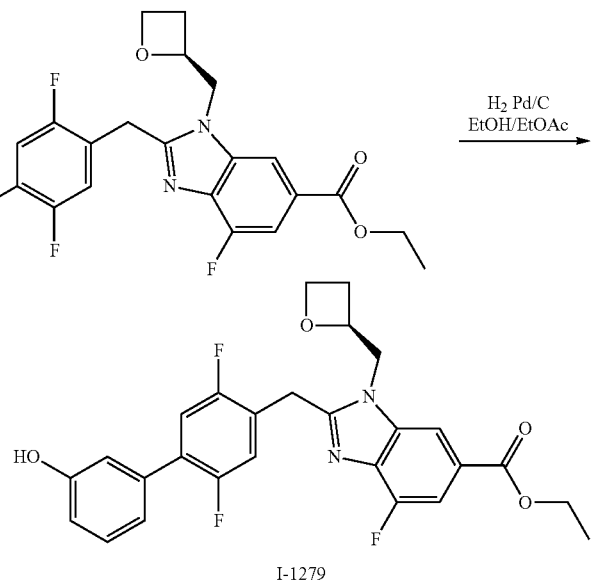

I-1279

2-benzyloxy-4-bromo-1-fluoro-benzene: A suspension of 5-bromo-2-fluoro-phenol (5.00 g, 0.0262 mol), Benzyl bromide, reagent grade, 98% (3.74 mL, 0.0314 mol), and potassium carbonate (7.96 g, 0.0576 mol) in acetone (30 mL) was heated at 70° C. for 1 hr. The mixture was partitioned with EtOAc and water. The organic extract was dried over MgSO₄, concentrated and purified by chromatography (eluent: EtOAc/hexanes) to give desired product.

Ethyl 2-[[4-(3-benzyloxy-4-fluoro-phenyl)-2,5-difluoro-phenyl]methyl]-7-fluoro-3-[[(2S)-oxetan-2-yl]methyl]benzimidazole-5-carboxylate: A suspension of ethyl 2-[(4-bromo-2,5-difluoro-phenyl)methyl]-7-fluoro-3-[[(2S)-oxetan-2-yl]methyl]benzimidazole-5-carboxylate (500 mg, 1.03 mmol) (I-14), [1,1'-Bis(diphenylphosphino)ferrocene] dichloropalladium(II); PdCl₂(dppf) (76.7 mg, 0.103 mmol), potassium propionate (348 mg, 3.10 mmol), and Bis(pinacolato)diboron (394 mg, 1.55 mmol) was degassed, then heated at 110° C. for 2 hr. Next, sodium carbonate (2000 mmol/L, 1.03 mL, 2.07 mmol), 2-benzyloxy-4-bromo-1-fluoro-benzene (320 mg, 1.14 mmol), and [1,1'-Bis(diphenylphosphino)ferrocene] dichloropalladium(II); PdCl₂(dppf) (38.4 mg, 0.0517 mmol) were added and followed by degassing. The reaction was heated at 100° C. for 1 hr. The mixture was diluted with EtOAc and water. The organic extract was dried over magnesium sulfate, filtered and concentrated. The crude residue was purified by flash chromatography (eluent: EtOAc/hexanes) to yield desired product. ES/MS: 606.1 (M+H+).

Ethyl 2-[[2,5-difluoro-4-(4-fluoro-3-hydroxy-phenyl)phenyl]methyl]-7-fluoro-3-[[(2S)-oxetan-2-yl]methyl]benzimidazole-5-carboxylate (I-1279): A suspension of ethyl 2-[[4-(3-benzyloxy-4-fluoro-phenyl)-2,5-difluoro-phenyl]methyl]-7-fluoro-3-[[(2S)-oxetan-2-yl]methyl]benzimidazole-5-carboxylate (626 mg, 1.04 mmol) and Palladium on carbon 10 wt. % (5.00%, 2204 mg, 1.04 mmol) was degassed by cycling the mixture between argon and vacuum 3×. Next, the mixture was stirred at rt with a balloon of hydrogen for 2 hr. The mixture was then filtered through Celite and concentrated in vacuo to give desired product. ES/MS: 515.6 (M+H+)

Preparation of Intermediate I-1281

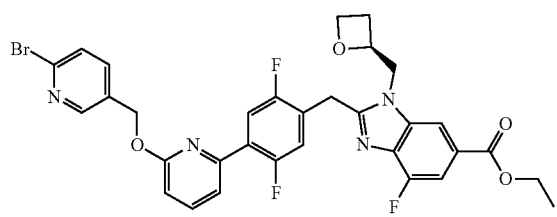

I-1281

Ethyl 2-[[4-[6-[(6-bromo-3-pyridyl)methoxy]-2-pyridyl]-2,5-difluoro-phenyl]methyl]-7-fluoro-3-[[(2S)-oxetan-2-yl]methyl]benzimidazole-5-carboxylate (I-1281): Ethyl 2-[[4-[6-[(6-bromo-3-pyridyl)methoxy]-2-pyridyl]-2,5-difluoro-phenyl]methyl]-7-fluoro-3-[[(2S)-oxetan-2-yl]methyl] benzimidazole-5-carboxylate was prepared in a manner as described for Intermediate I-1269 substituting 2-bromo-5-(bromomethyl)pyridine for 5-bromo-2-(chloromethyl)-3-fluoro-pyridine. ES/MS: 667, 669 (M+H$^+$).

Preparation of Intermediate I-1282

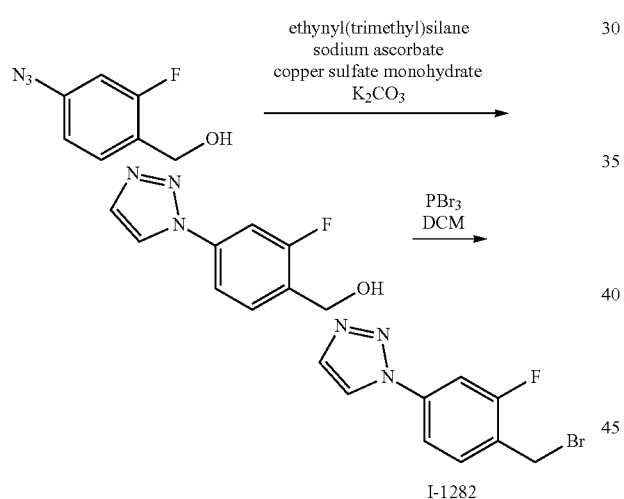

I-1282

[2-fluoro-4-(triazol-1-yl)phenyl]methanol: A suspension of ethynyl(trimethyl)silane (0.372 mL, 0.00269 mol), (4-azido-2-fluoro-phenyl)methanol (300 mg, 0.00179 mol), sodium ascorbate (0.126 g, 0.000718 mol), copper sulfate monohydrate (0.0638 g, 0.000359 mol), and potassium carbonate (0.298 g, 0.00215 mol) was stirred at rt overnight. The mixture was partitioned with EtOAc and water. The organic extract was dried over magnesium sulfate, filtered and concentrated. The crude residue was purified by flash chromatography (eluent: EtOAc/hexanes) to yield desired product. ES/MS: 194.1 (M+H$^+$).

1-[4-(bromomethyl)-3-fluoro-phenyl]triazole (I-1282): A solution of [2-fluoro-4-(triazol-1-yl)phenyl]methanol (245 mg, 0.00127 mol) and phosphorus tribromide (0.149 mL, 0.00159 mol) in DCM (2 mL) was stirred at rt for 3 hr. The mixture was carefully quenched with saturated NaHCO$_3$ solution and partitioned with EtOAc and water. The organic extract was dried over magnesium sulfate and concentrated to give desired product, which was used without further purification. ES/MS: 256, 258 (M+H$^+$).

Preparation of Intermediate I-1283

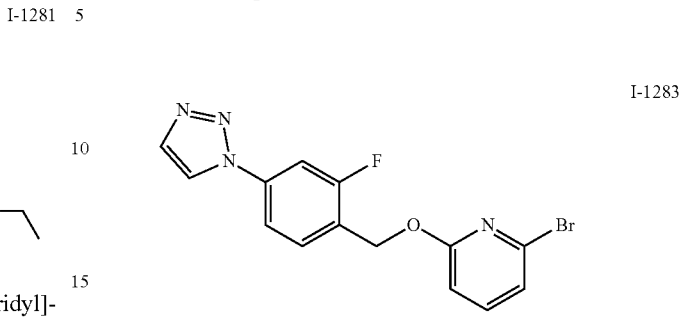

I-1283

2-bromo-6-[[2-fluoro-4-(triazol-1-yl)phenyl]methoxy]pyridine (I-1283): 2-bromo-6-[[2-fluoro-4-(triazol-1-yl)phenyl]methoxy]pyridine was prepared in a manner as described for Intermediate I-84 substituting 1-[4-(bromomethyl)-3-fluoro-phenyl]triazole 1-1282 for 2-(bromomethyl)thiazole-5-carbonitrile. ES/MS: 349, 351 (M+H+).

Preparation of Intermediate I-1284

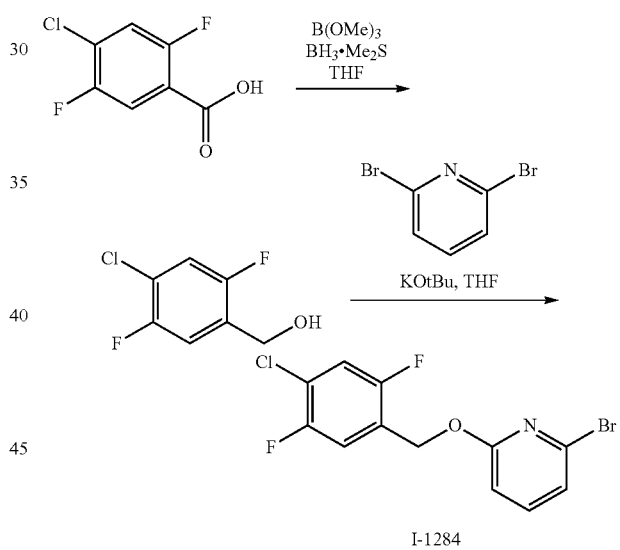

I-1284

(4-chloro-2,5-difluorophenyl)methanol: To a solution of 4-chloro-2,5-difluorobenzoic acid (10.0 g, 51.9 mmol) and B(OMe)$_3$ (15.6 g, 150 mmol, 17.0 mL) in THF (50.0 mL) at 0° C. was added BH$_3$-Me$_2$S (10 M, 7.79 mL). The mixture was stirred at 20° C. for 16 h. The reaction was poured into 1N NaOH (100 mL) and extracted with EtOAc (30 mL×3). The combined organic layers were washed with brine (50 mL), dried over sodium sulfate, and concentrated to dryness. The crude residue was recrystallized from petroleum ether to give desired product. 1H NMR (CDCl$_3$ 400 MHz): δ 7.19-7.23 (m, 1H), 7.05 (dd, J=8.99, 5.93 Hz, 1H), 4.66 (d, J=5.62 Hz, 2H), 1.76 (t, J=5.93 Hz, 1H).

2-bromo-6-[(4-chloro-2,5-difluoro-phenyl)methoxy]pyridine (I-1284): To a solution of (4-chloro-2,5-difluorophenyl)methanol (6.0 g, 33.6 mmol) in THF (60 mL) at 0° C. was slowly added KOtBu (1.0 M, 50.4 mL, 50.4 mmol). The mixture was stirred at 20° C. for 1 hr, then cooled to 0° C.

and added a solution of 2,6-dibromopyridine (7.16 g, 30.2 mmol) in THF (20 mL). The reaction was stirred at 20° C. for 1 hr, then poured into saturated NH₄Cl solution and extracted 3× with EtOAc. The organic extracts were washed with brine, dried over magnesium sulfate and concentrated. The crude residue was triturated with petroleum ether, and the resulting suspension was filtered to give desired product. ES/MS: 332.9 (M+H⁺). ¹H NMR (CDCl₃ 400 MHz): δ 7.48 (t, J=7.82 Hz, 1H), 7.35 (dd, J=8.93, 6.24 Hz, 1H), 7.19 (dd, J=8.80, 5.87 Hz, 1H), 7.13 (d, J=7.46 Hz, 1H), 6.78 (d, J=8.19 Hz, 1H), 5.40 (s, 2H). ¹⁹F NMR (CDCl₃ 374 MHz): δ −120.89−−120.98 (m, 1F), −121.30−−121.40 (m, 1F).

Preparation of Intermediate I-1285

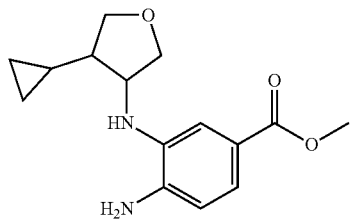

I-1285

Methyl 4-amino-3-((4-cyclopropyltetrahydrofuran-3-yl)amino)benzoate (I-1285): methyl 4-amino-3-((4-cyclopropyltetrahydrofuran-3-yl)amino)benzoate was prepared in a manner as described for Intermediate I-68 substituting 4-cyclopropyltetrahydrofuran-3-amine hydrochloride for 2-methoxyethylamine. ES/MS: 277.2 (M+H+).

Preparation of Intermediate I-1286

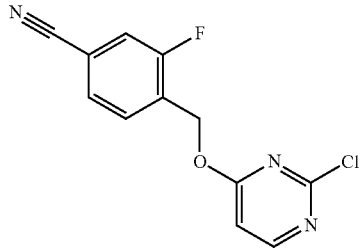

I-1286

4-(((2-chloropyrimidin-4-yl)oxy)methyl)-3-fluorobenzonitrile (I-1286): 4-(((2-chloropyrimidin-4-yl)oxy)methyl)-3-fluorobenzonitrile was prepared in a manner as described for Intermediate I-1129 substituting 4-(bromomethyl)-3-fluorobenzonitrile for 2-(bromomethyl)-3-fluoro-5-(trifluoromethyl)pyridine and 2-chloropyrimidin-4-ol for 6-bromopyridin-2-ol. ES/MS: 264.0 (M+H+).

Preparation of Intermediate I-1287

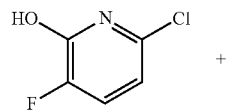

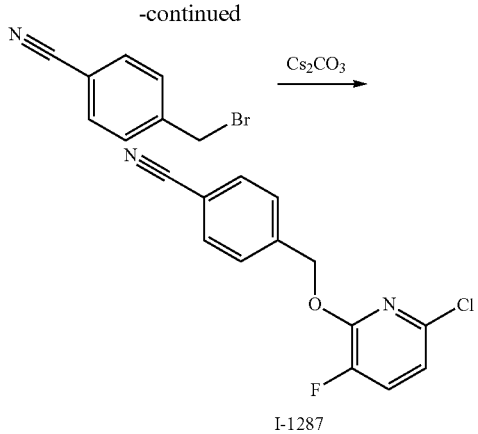

I-1287

4-[(6-chloro-3-fluoro-2-pyridyl)oxymethyl]benzonitrile (I-1287): A mixture of 6-chloro-3-fluoro-pyridin-2-ol (265 mg, 1.0 equivalent), 4-(bromomethyl)benzonitrile (370 mg, 1.05 equivalent), cesium carbonate (0.878 g, 1.5 equivalent) in acetonitrile (9 mL) was stirred at in metal heating block at 90° C. until all starting material was consumed as determined by LCMS. The mixture was filtered, concentrated in vacuo, and purified by silica gel flash column chromatography to yield the title compound. 1H NMR (400 MHz, Chloroform-d) δ 7.68 (dd, J=8.2, 1.2 Hz, 2H), 7.59 (d, J=7.9 Hz, 2H), 7.39-7.30 (m, 1H), 6.90 (ddd, J=8.1, 2.7, 1.1 Hz, 1H), 5.49 (s, 2H).

Preparation of Intermediate I-1288

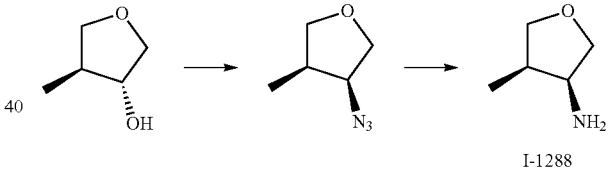

I-1288

Racemic (3S,4R)-4-methyltetrahydrofuran-3-amine (I-1288): Diisopropyl azodicarboxylate (0.74 mL, 1.2 equivalent) was added to a mixture of racemic (3R,4S)-4-methyltetrahydrofuran-3-ol (320 mg, 1.0 equivalent), triphenylphosphine (985 mg, 1.2 equivalent), diisopropylethylamine (0.56 mL, 1.02 equivalent) in THF (15 mL) precooled to 0° C. equivalent. The mixture was stirred at 0° C. for 15 min, then diphenylphosphoryl azide (0.81 mL, 1.2 equivalent) was added. The mixture was allowed to warm to 20° C. with stirring for 3 hr., then cooled back to 0° C. Additional triphenylphosphine (1.06 g, 1.3 equivalent) as a solution in THF (6 mL) was added to the mixture, and the mixture was allowed to stir at 20° C. for 2.5 hr. Upon completion of time, water (1.5 mL) was added, and the mixture was stirred at 65° C. for 18 hr. (OPERATIONAL NOTE: significant gas evolution was observed). The mixture was cooled and partitioned between ethyl acetate and a mixture of 1 N aqueous NaOH, saturated aqueous NaHCO₃ and brine; extracted aqueous phase twice more with EtOAc. The combined organic phases were dried over MgSO₄, filtered, and concentrated in vacuo to yield the title compound, which was carried forward crude without further purification. ES/MS m/z: 101.9 (M+H⁺).

Preparation of Intermediate I-1289

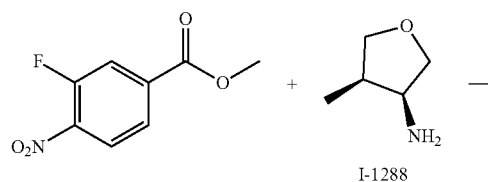

I-1288

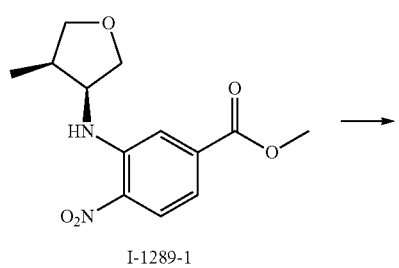

I-1289-1

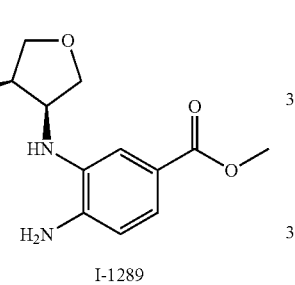

I-1289

Racemic methyl 3-[[(3R,4S)-4-methyltetrahydrofuran-3-yl]amino]-4-nitrobenzoate (I-1289-1): Methyl 3-fluoro-4-nitrobenzoate (687 mg, 1.1 equivalent), THF (8.8 mL), DMF (4.4 mL), and diisopropylethylamine (2.73 mL, 5.0 equivalent) were added to a crude racemic (3R,4S)-4-methyltetrahydrofuran-3-amine (I-1288, 317 mg, 1.0 equivalent) equivalent. The mixture was stirred at 80° C. for 16 hr., or until completion as determined by LCMS. The mixture was then diluted with ethyl acetate and washed with saturated aqueous NH₄Cl, then brine, then dried over magnesium sulfate, filtered and concentrated in vacuo to yield the title compound.

Racemic methyl 4-amino-3-[[(3R,4S)-4-methyltetrahydrofuran-3-yl]amino]benzoate (I-1289): A mixture of crude racemic methyl 3-[[(3R,4S)-4-methyltetrahydrofuran-3-yl]amino]-4-nitrobenzoate (I-1289-1, 878 mg, 1.0 equivalent), 10% palladium on carbon (333 mg, 0.10 equivalent) and ethanol (60 mL) was stirred under an atmosphere of hydrogen for 6 hr., or until completion as determined by LCMS. The mixture was filtered, concentrated in vacuo and purified by silica gel flash column chromatography (hexane/EtOAc) to yield the title compound. 1H NMR (400 MHz, Chloroform-d) δ 7.45 (dd, J=8.1, 1.8 Hz, 1H), 7.34 (d, J=1.9 Hz, 1H), 6.69 (d, J=8.1 Hz, 1H), 4.09-4.02 (m, 3H), 3.85 (s, 3H), 3.68 (h, J=3.8 Hz, 1H), 3.57 (dd, J=8.5, 7.2 Hz, 1H), 2.66-2.54 (m, 1H), 1.01 (d, J=7.0 Hz, 3H). ES/MS m/z: 251.0 (M+H⁺).

Preparation of Intermediate I-1290, I-1291

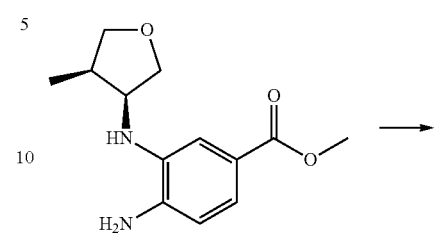

I-1289 racemic

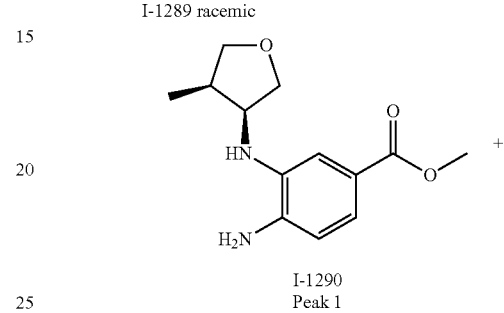

I-1290
Peak 1

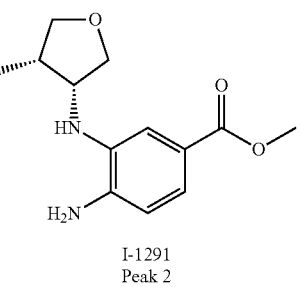

I-1291
Peak 2

Methyl 4-amino-3-[[(3S,4R)-4-methyltetrahydrofuran-3-yl]amino]benzoate (I-1290), Methyl 4-amino-3-[[(3R,4S)-4-methyltetrahydrofuran-3-yl]amino]benzoate (I-1291): Racemic I-1289 was purified by preparative chiral SFC (IG, 20% MeOH) to yield methyl 4-amino-3-[[(3S,4R)-4-methyltetrahydrofuran-3-yl]amino]benzoate (I-1290) as the earlier eluting isomer (Peak 1) and methyl 4-amino-3-[[(3R,4S)-4-methyltetrahydrofuran-3-yl]amino]benzoate (I-1291) as the later-eluting isomer (Peak 2).

Methyl 4-amino-3-[[(3S,4R)-4-methyltetrahydrofuran-3-yl]amino]benzoate (I-1290): ES/MS m/z: 251.0 (M+H⁺).

Methyl 4-amino-3-[[(3R,4S)-4-methyltetrahydrofuran-3-yl]amino]benzoate (I-1291): ES/MS m/z: 251.0 (M+H⁺).

Preparation of Intermediate I-1292

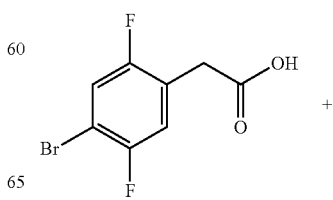

Preparation of Intermediate I-1293

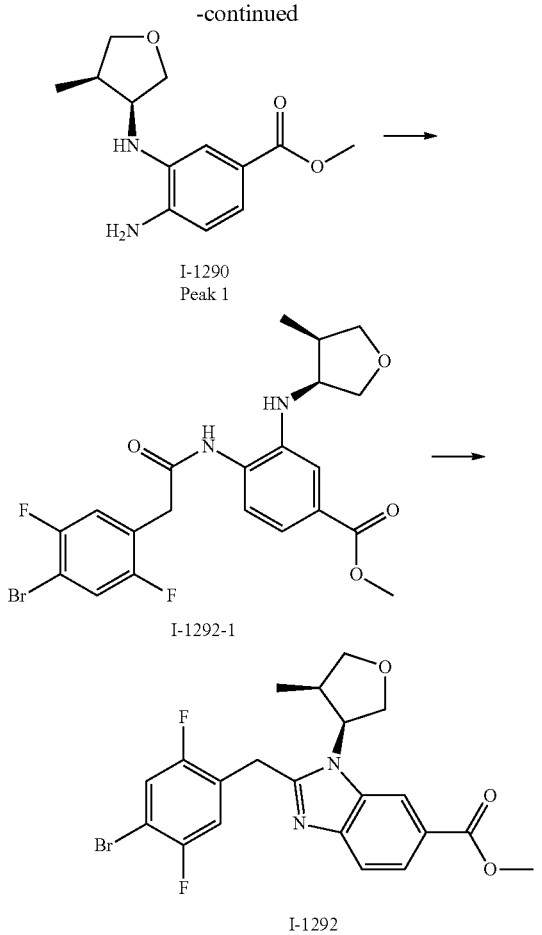

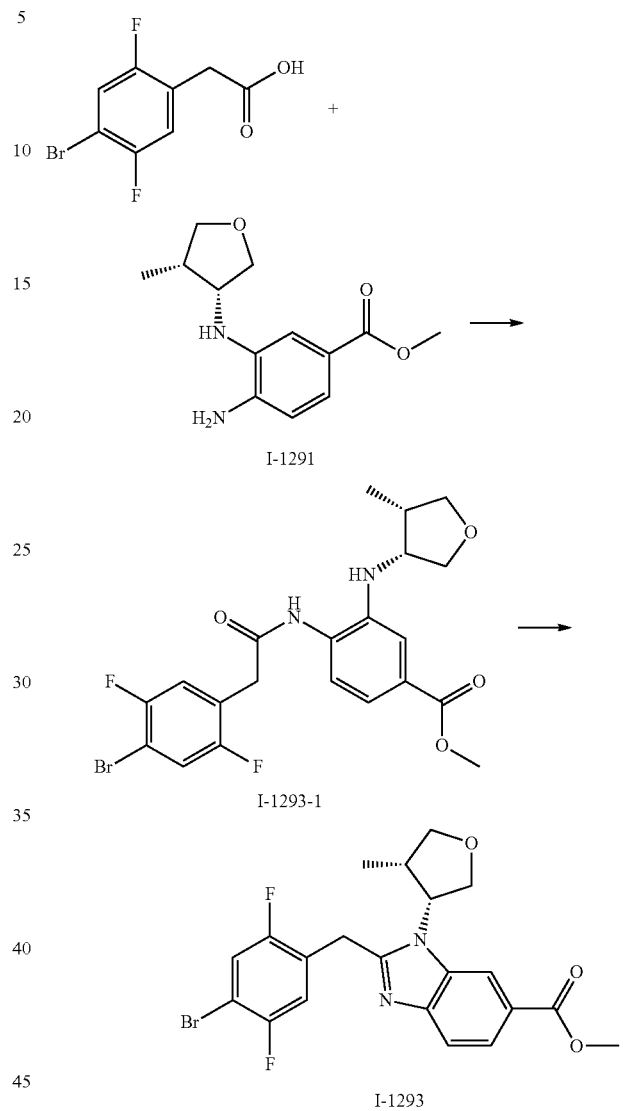

Methyl 4-[[2-(4-bromo-2,5-difluoro-phenyl)acetyl]amino]-3-[[(3S,4R)-4-methyltetrahydrofuran-3-yl]amino]benzoate (I-1292-1): A mixture of methyl 4-amino-3-[[(3S,4R)-4-methyltetrahydrofuran-3-yl]amino]benzoate (I-1290, 57 mg, 1.0 equivalent), 2-(4-bromo-2,5-difluorophenyl)acetic acid (63 mg, 1.1 equivalent), chloro-N,N,N',N'-tetramethylformamidinium hexafluorophosphate (77 mg, 1.2 equivalent), 1-methylimidazole (94 mg, 5.0 equivalent) and acetonitrile (2.3 mL) was stirred at 20° C. for 1 hr. The mixture was then diluted with EtOAc, washed with saturated aqueous NH$_4$Cl. Next, the mixture was saturated aqueous NaHCO$_3$, then brine. The organic phase was dried over MgSO$_4$, filtered, and concentrated in vacuo to yield the title compound, which was carried forward without further purification. ES/MS m/z: 483.2 (M+H$^+$).

Methyl 2-[(4-bromo-2,5-difluoro-phenyl)methyl]-3-[(3S,4R)-4-methyltetrahydrofuran-3-yl]benzimidazole-5-carboxylate (I-1292): A mixture of methyl 4-[[2-(4-bromo-2,5-difluoro-phenyl)acetyl]amino]-3-[[(3S,4R)-4-methyltetrahydrofuran-3-yl]amino]benzoate (I-1292-1, 110 mg, 1.0 equivalent), glacial acetic acid (0.91 mL) and 1,2-dichloroethane (4.6 mL) was stirred at 80-95° C. for 48 hr., or until completion as determined by LCMS. The mixture was diluted with EtOAc, quenched with saturated aqueous NaHCO$_3$ and batchwise addition of solid NaHCO$_3$. The organic phase was washed with brine, dried over MgSO$_4$, filtered, and concentrated in vacuo to yield the title compound. ES/MS m/z: 465.2 (M+H$^+$).

Methyl 2-[(4-bromo-2,5-difluoro-phenyl)methyl]-3-[(3R,4S)-4-methyltetrahydrofuran-3-yl]benzimidazole-5-carboxylate (I-1293): The title compound was prepared in a similar manner as described for Intermediate I-1292, substituting Intermediate I-1291 in place of Intermediate I-1290. ES/MS m/z: 465.2 (M+H$^+$).

Preparation of Intermediate I-1294

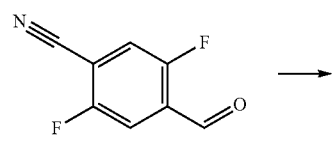

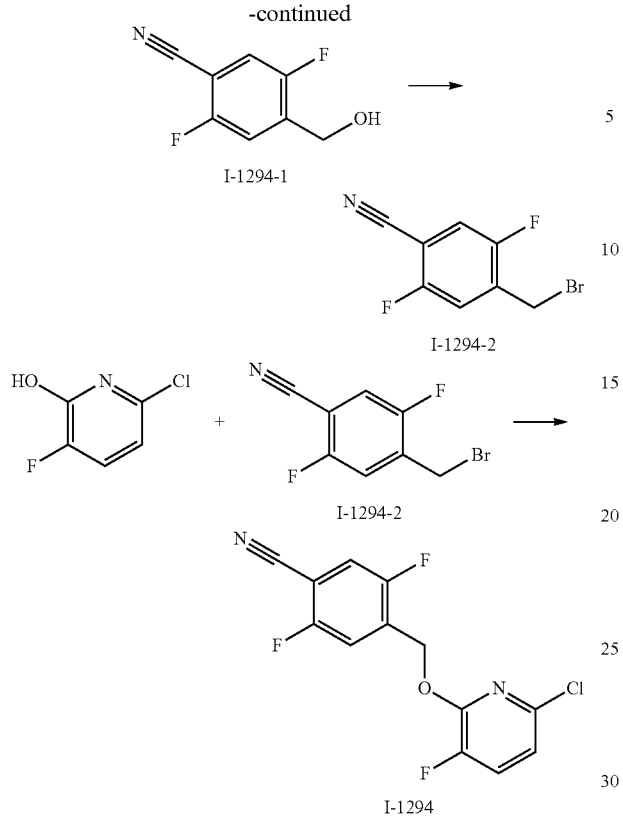

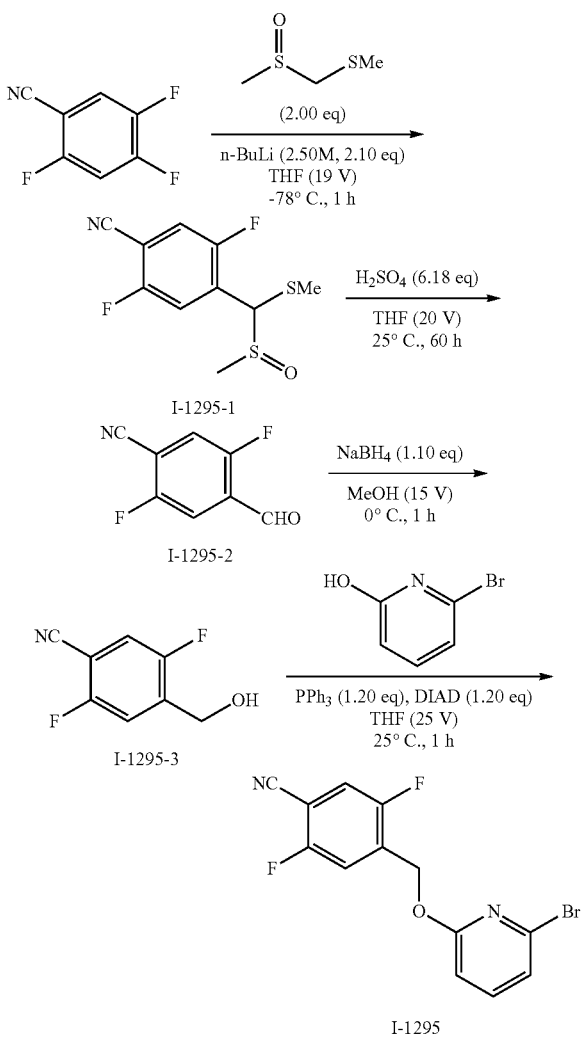

Preparation of Intermediate I-1295

2,5-difluoro-4-(hydroxymethyl)benzonitrile (I-1294-1): Sodium borohydride (1.35 g, 1.05 equivalent) was added to a mixture of 2,5-difluoro-4-formylbenzonitrile (5.66 g, 1.0 equivalent) in methanol (100 mL). equivalent. The mixture was stirred at 20° C. for 2 hr., then concentrated in vacuo. The crude material was quenched with slow addition of saturated aqueous ammonium chloride, then extracted with ethyl acetate. The organic phases were washed with brine, dried over sodium sulfate, filtered, and concentrated in vacuo to yield the title compound, which was carried forward without further purification. 1H NMR (400 MHz, CDCl3) δ 7.43 (dd, J=8.9, 5.6 Hz, 1H), 7.28 (dd, J=8.5, 4.9 Hz, 1H), 4.84 (d, J=4.8 Hz, 2H), 1.96 (t, J=5.7 Hz, 1H). ES/MS m/z: 170.2 (M+H+).

4-(bromomethyl)-2,5-difluorobenzonitrile (I-1294-2): Carbon tetrabromide (412 mg, 1.05 equivalent) was added to a mixture of 2,5-difluoro-4-(hydroxymethyl)benzonitrile (I-1294-1, 200 mg, 1.0 equivalent), triphenylphosphine (326 mg, 1.05 equivalent) and DCM (11 mL) precooled to 0° C. equivalent. The mixture was allowed to warm to 20° C. with stirring for 15 min, then the mixture was purified directly by silica gel flash column chromatography (EtOAc/hexane) to yield the title compound. 1H NMR (400 MHz, Chloroform-d) δ 7.40-7.28 (m, 2H), 4.45 (s, 2H).

4-[(6-chloro-3-fluoro-2-pyridyl)oxymethyl]-2,5-difluorobenzonitrile (I-1294): A mixture of 4-(bromomethyl)-2,5-difluorobenzonitrile (I-1294-2, 182 mg, 1.05 equivalent), 6-chloro-3-fluoropyridin-2-ol (110 mg, 1.0 equivalent), cesium carbonate (364 mg, 1.5 equivalent) and acetonitrile (3.8 mL) was stirred at 90° C. for 1 hr. The mixture was then diluted with ethyl acetate, filtered, and concentrated in vacuo. Silica gel flash column chromatography (EtOAc/hexane) yielded the title compound. 1H NMR (400 MHz, Chloroform-d) δ 7.47 (dd, J=8.7, 5.5 Hz, 1H), 7.43-7.35 (m, 2H), 6.97 (dd, J=8.2, 2.6 Hz, 1H), 5.55 (s, 2H).

2,5-difluoro-4-((methylsulfinyl)(methylthio)methyl)benzonitrile (I-1295-1): n-BuLi (2.50 M in hexane, 134 mL, 2.1 equivalent) was added to a mixture of methyl methylthiomethyl sulfoxide (39.5 g, 1.0 equivalent) in THE (380 mL) at −80° C. equivalent The mixture was stirred at −80° C. for 30 min, then a solution of 2,4,5-trifluorobenzonitrile (25.0 g, 1.00 equivalent) in THF (380 mL) was added. The mixture was stirred at −80° C. for 30 min, with monitoring by TLC. The mixture was then quenched with water and extracted with ethyl acetate. The organic phase was washed with brine, then concentrated in vacuo. Silica gel flash column chromatography (EtOAc/petroleum ether) yielded the title compound. 1H NMR (CDCl₃ 400 MHz) δ=7.47-7.32 (m, 2H), 4.98-4.84 (m, 1H), 2.56-2.50 (m, 3H), 2.42-2.34 (m, 3H).

2,5-difluoro-4-formylbenzonitrile (I-1295-2): A mixture of 2,5-difluoro-4-((methylsulfinyl)(methylthio)methyl)benzonitrile (I-1295-1, 34.0 g, 1.00 equivalent) and concentrated sulfuric acid (42.9 mL, 6.18 equivalent) was stirred at 25° C. for 60 hr. The mixture was then partitioned between water and ethyl acetate. The organic phase was washed with brine, then concentrated in vacuo to yield the title compound. 1H NMR (CDCl$_3$ 400 MHz) δ=10.34 (d, J=2.6 Hz, 1H), 7.70 (dd, J=5.3, 7.9 Hz, 1H), 7.53 (dd, J=4.6, 8.6 Hz, 1H).

2,5-difluoro-4-(hydroxymethyl)benzonitrile (I-1295-3): Sodium borohydride (4.98 g, 1.1 equivalent) was added To a mixture of 2,5-difluoro-4-formylbenzonitrile (I-1295-2, 20.0 g, 1.0 equivalent) in methanol (300 mL) pre-cooled to 0° C. The mixture was stirred for 1 hr., with monitoring by TLC. The mixture was quenched with 1N HCl, then the mixture was concentrated in vacuo. The resulting mixture was partitioned between water and ethyl acetate. The organic phase was washed with brine, then concentrated in vacuo. Silica gel flash column chromatography (EtOAc/petroleum ether) yielded the title compound. $^1$H NMR (CDCl$_3$ 400 MHz) δ=7.89 (dd, J=5.2, 9.2 Hz, 1H), 7.51 (dd, J=5.6, 9.6 Hz, 1H), 5.65 (t, J=5.7 Hz, 1H), 4.59 (td, J=1.2, 5.7 Hz, 2H).

4-(((6-bromopyridin-2-yl)oxy)methyl)-2,5-difluorobenzonitrile (I-1295): Triphenylphosphine (9.31 g, 1.2 equivalent), then diisopropyl azodicarboxylate (7.17 g, 1.2 equivalent) were added to a mixture of 2,5-difluoro-4-(hydroxymethyl)benzonitrile (I-1295-3, 5.00 g, 1.00 equivalent) and 6-bromo-2-pyridinol (5.14 g, 1.00 equivalent) in THF (125 mL)equivalent. The mixture was stirred at 25° C. for 1 hr., with monitoring by TLC. The mixture was partitioned between water and ethyl acetate. The organic phase was washed with brine, then concentrated in vacuo. Silica gel flash column chromatography (EtOAc/petroleum ether) yielded the title compound. $^1$H NMR (CDCl$_3$ 400 MHz) δ=7.49 (t, J=7.8 Hz, 1H), 7.42 (dd, J=5.5, 8.6 Hz, 1H), 7.34 (dd, J=5.0, 8.3 Hz, 1H), 7.14 (d, J=7.5 Hz, 1H), 6.80 (d, J=8.2 Hz, 1H), 5.46 (s, 2H). ES/MS m/z: 324.0 (M+H$^+$).

Preparation of Intermediate I-1296

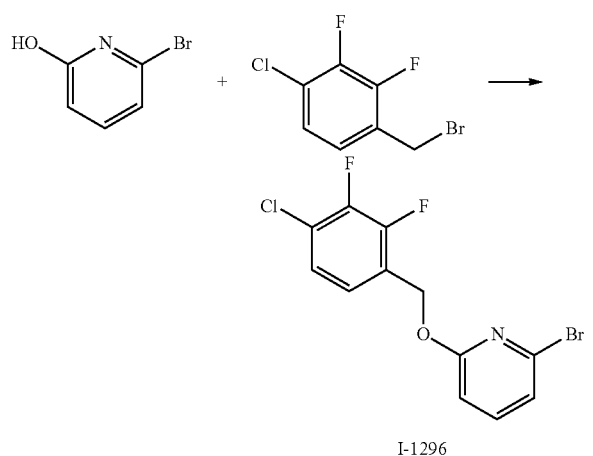

2-bromo-6-((4-chloro-2,3-difluorobenzyl)oxy)pyridine (I-1296): A mixture of 1-(bromomethyl)-4-chloro-2,3-difluorobenzene (729 mg, 1.05 equivalent), 6-bromo-2-pyridinol (500 mg, 1.00 equivalent), cesium carbonate (1.40 g, 1.5 equivalent) and acetonitrile (14 mL) was stirred at 80° C. for 3 hr. The mixture was then diluted with ethyl acetate, filtered, and concentrated in vacuo. Silica gel flash column chromatography (EtOAc/hexane) yielded the title compound. 1H NMR (400 MHz, Chloroform-d) δ 7.45 (dd, J=8.2, 7.5 Hz, 1H), 7.25-7.21 (m, 1H), 7.18 (ddd, J=8.4, 6.1, 1.7 Hz, 1H), 7.10 (dd, J=7.5, 0.7 Hz, 1H), 6.73 (dd, J=8.2, 0.7 Hz, 1H), 5.41 (d, J=1.4 Hz, 2H). ES/MS m/z: 333.9 (M+H$^+$).

Preparation of Intermediate I-1297

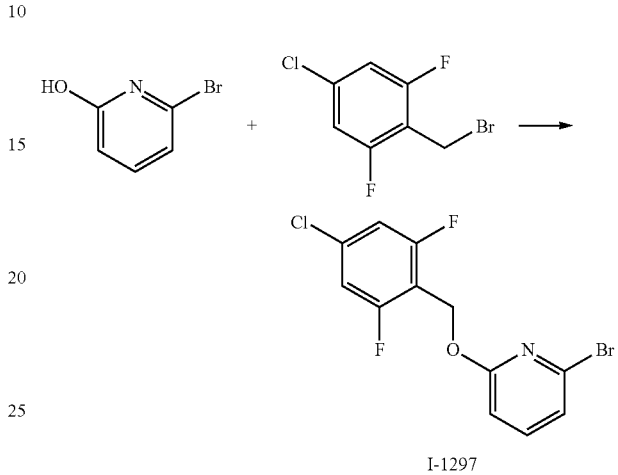

2-bromo-6-((4-chloro-2,6-difluorobenzyl)oxy)pyridine (I-1297): A mixture of 1-(bromomethyl)-4-chloro-2,6-difluorobenzene (305 mg, 1.1 equivalent), 6-bromo-2-pyridinol (200 mg, 1.00 equivalent), cesium carbonate (600 mg, 1.5 equivalent) and acetonitrile (5.5 mL) was stirred at 80° C. for 6 hr. The mixture was then diluted with ethyl acetate, filtered, and concentrated in vacuo. Silica gel flash column chromatography (EtOAc/hexane) yielded the title compound. 1H NMR (400 MHz, Chloroform-d) δ 7.43 (dd, J=8.2, 7.5 Hz, 1H), 7.10 (dd, J=7.5, 0.6 Hz, 1H), 7.03-6.93 (m, 2H), 6.69 (dd, J=8.2, 0.6 Hz, 1H), 5.38 (s, 2H). ES/MS m/z: 335.8 (M+H$^+$).

Preparation of Intermediate I-1298

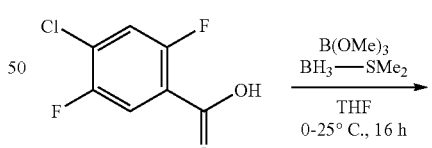

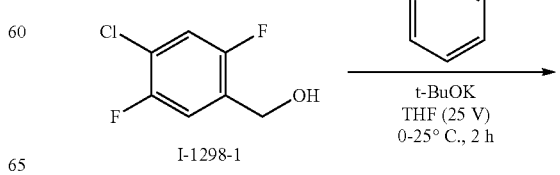

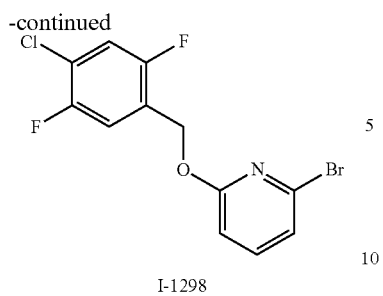

I-1298

(4-chloro-2,5-difluorophenyl)methanol (I-1298-1): BH$_3$-Me$_2$S (7.79 mL, 1.5 equivalent) was added to a mixture of 4-chloro-2,5-difluorobenzoic acid (10.0 g, 1.00 equivalent) and B(OMe)$_3$ (15.6 g, 2.9 equivalent) in THF (50 mL) pre-cooled to 0° C. The mixture was allowed to warm to 20° C. and stirred for 16 hr., with monitoring by TLC. The mixture was then poured into 1 N aqueous sodium hydroxide and extracted with ethyl acetate. The organic phase was washed with brine, dried over sodium sulfate, filtered, and concentrated in vacuo. Next, recrystallization from petroleum ether yielded the title compound. $^1$H NMR (CDCl$_3$ 400 MHz): δ 7.19-7.23 (m, 1H), 7.05 (dd, J=8.99, 5.93 Hz, 1H), 4.66 (d, J=5.62 Hz, 2H), 1.76 (t, J=5.93 Hz, 1H).

4-(((6-bromopyridin-2-yl)oxy)methyl)-2,5-difluorobenzonitrile (I-1298): Potassium tert butoxide (1 M in THF, 50.4 mL, 1.5 equivalent) was slowly added to a mixture of (4-chloro-2,5-difluorophenyl)methanol (I-1298-1, 6.0 g, 1.00 equivalent) in THF (60 mL) pre-cooled to 0° C. equivalent. The mixture was stirred at 20° C. for 1 hr., then it was cooled back to 0° C. 2,6-dibromopyridine (7.16 g, 0.90 equivalent) was a solution in THE (20 mL) was then added and the mixture was again stirred at 20° C. for 1 hr., with monitoring by TLC. The mixture was poured into saturated aqueous ammonium chloride and extracted with ethyl acetate. The organic phase was washed with brine, dried over sodium sulfate, filtered, and concentrated in vacuo. Titration with petroleum ether yielded the title compound. $^1$H NMR (CDCl$_3$ 400 MHz): δ 7.48 (t, J=7.82 Hz, 1H), 7.35 (dd, J=8.93, 6.24 Hz, 1H), 7.19 (dd, J=8.80, 5.87 Hz, 1H), 7.13 (d, J=7.46 Hz, 1H), 6.78 (d, J=8.19 Hz, 1H), 5.40 (s, 2H). ES/MS m/z: 324.0 (M+H$^+$).

Preparation of Intermediate I-1300

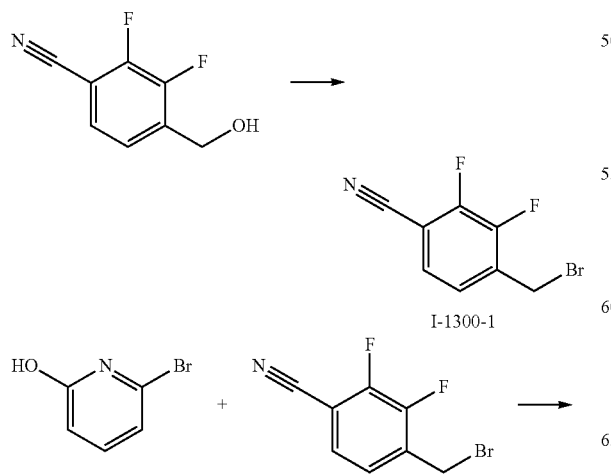

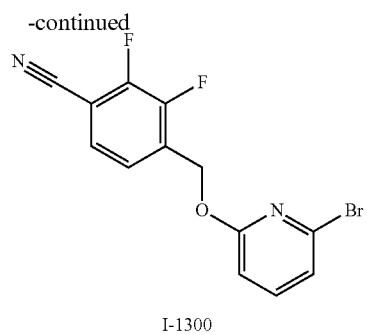

I-1300

4-(bromomethyl)-2,3-difluorobenzonitrile (I-1300-1): Carbon tetrabromide (165 mg, 1.05 equivalent) was added to a mixture of 2,3-difluoro-4-(hydroxymethyl)benzonitrile (80 mg, 1.0 equivalent), triphenylphosphine (130 mg, 1.05 equivalent) and DCM (4.7 mL) precooled to 0° C. equivalent. The mixture was allowed to warm to 20° C. with stirring for 15 min, then the mixture was purified directly by silica gel flash column chromatography (EtOAc/hexane) to yield the title compound. 1H NMR (400 MHz, Chloroform-d) δ 7.40 (ddd, J=7.5, 5.4, 1.9 Hz, 1H), 7.30 (td, J=6.3, 3.1 Hz, 1H), 4.49 (d, J=1.4 Hz, 2H).

4-[(6-bromo-2-pyridyl)oxymethyl]-2,3-difluorobenzonitrile (I-1300): A mixture of 4-(bromomethyl)-2,3-difluorobenzonitrile (I-1300-1, 18 mg, 1.0 equivalent), 6-bromo-2-pyridinol (27 mg, 2.00 equivalent), cesium carbonate (51 mg, 2.0 equivalent) and acetonitrile (0.8 mL) was stirred at 90° C. for 3 hr. The mixture was then diluted with ethyl acetate, filtered, and concentrated in vacuo. Silica gel flash column chromatography (EtOAc/hexane) yielded the title compound. 1H NMR (400 MHz, Chloroform-d) δ 7.48 (t, J=7.9 Hz, 1H), 7.46-7.36 (m, 2H), 7.13 (d, J=7.5 Hz, 1H), 6.77 (d, J=8.1 Hz, 1H), 5.50 (d, J=1.3 Hz, 2H). ES/MS m/z: 325.0 (M+H$^+$).

Preparation of Intermediate I-1301

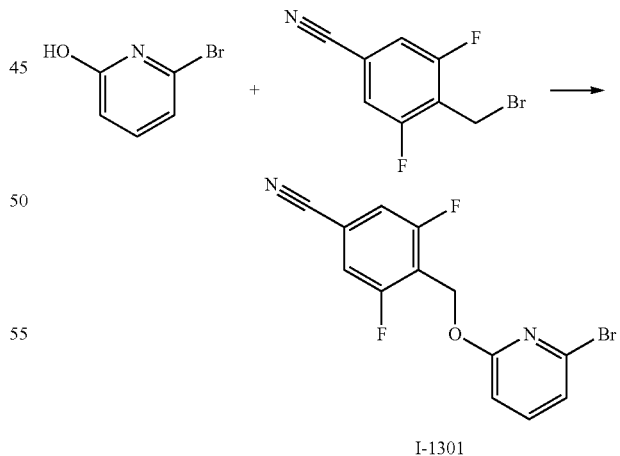

I-1301

4-[(6-bromo-2-pyridyl)oxymethyl]-3,5-difluorobenzonitrile (I-1301): A mixture of 4-(bromomethyl)-3,5-difluorobenzonitrile (90 mg, 1.0 equivalent), 6-bromo-2-pyridinol (74 mg, 1.1 equivalent), cesium carbonate (253 mg, 2.0 equivalent) and acetonitrile (3.9 mL) was stirred at 90° C. for 30 min. The mixture was then diluted with ethyl acetate, filtered, and concentrated in vacuo. Silica gel flash column chromatography (EtOAc/hexane) yielded the title compound. ES/MS m/z: 325.0 (M+H$^+$).

Preparation of Intermediate I-1302

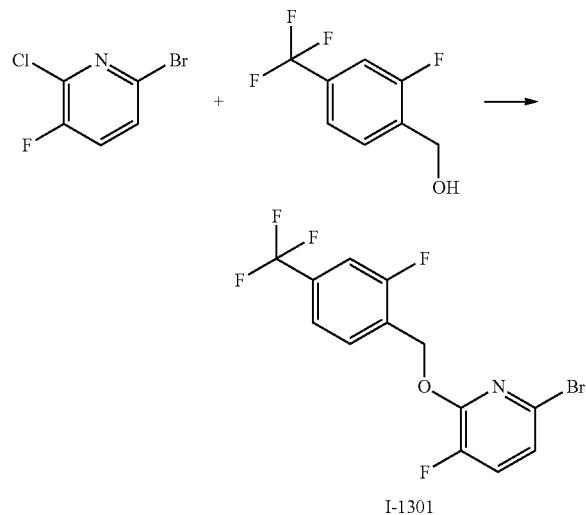

I-1301

6-bromo-3-fluoro-2-[[2-fluoro-4-(trifluoromethyl)phenyl]methoxy]pyridine (I-1301): A mixture of [2-fluoro-4-(trifluoromethyl)phenyl]methanol (923 mg, 1.0 equivalent), 6-bromo-2-chloro-3-fluoropyridine (1000 mg, 1.0 equivalent), cesium carbonate (3100 mg, 2.0 equivalent) and acetonitrile (9.5 mL) was stirred at 60° C. for 16 hr. The mixture was then diluted with ethyl acetate, filtered, and concentrated in vacuo. Silica gel flash column chromatography (EtOAc/hexane) yielded the title compound as the earlier eluting of two isomers. 1H NMR (400 MHz, Chloroform-d) δ 7.72 (t, J=7.5 Hz, 1H), 7.52-7.42 (m, 1H), 7.39 (dd, J=9.7, 1.7 Hz, 1H), 7.32-7.21 (m, 2H), 7.09 (dd, J=8.1, 2.7 Hz, 1H), 5.57 (s, 2H).

Preparation of Intermediate I-1303

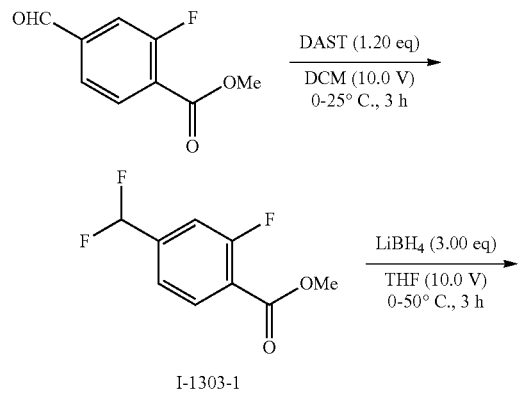

I-1303-1

-continued

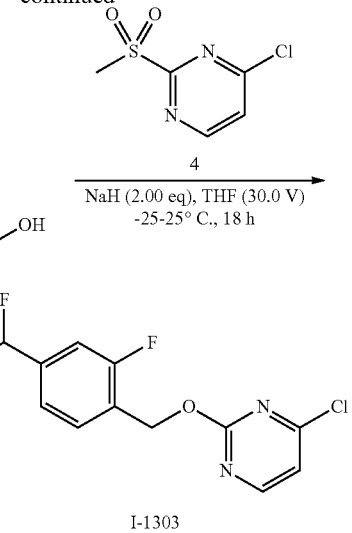

I-1303

Methyl 4-(difluoromethyl)-2-fluorobenzoate (I-1303-1): Diethylaminosulfur trifluoride (72.8 g, 1.20 equivalent) was added to a mixture of methyl 2-fluoro-4-formylbenzoate (50.0 g, 1.00 equivalent) in dichloromethane (500 mL) pre-cooled to 0° C. equivalent. The mixture was allowed to warm to 25° C. with stirring for 3 hr., with monitoring by silica gel TLC. The mixture was slowly poured into a mixture of ice and water, and the pH adjusted to pH 7-8 with aqueous sodium bicarbonate. The mixture was extracted with EtOAc. The organic phase was washed with brine, dried over sodium sulfate, filtered, and concentrated in vacuo. Purification by silica gel flash column chromatography (EtOAc/petroleum ether) yielded the title compound. $^1$H NMR (DMSO-d$_6$ 400 MHz): δ 7.97-8.10 (m, 1H) 7.51-7.65 (m, 2H) 6.95-7.32 (m, 1H) 3.82-3.95 (m, 3H).

(4-(difluoromethyl)-2-fluorophenyl)methanol (I-1303-2): LiBH$_4$ (14.4 g, 3.0 equivalent) was added to a mixture of methyl 4-(difluoromethyl)-2-fluorobenzoate (I-1303-1, 45.0 g, 1.00 equivalent) in THF (450 mL) pre-cooled to 0° C. The mixture was stirred at 50° C. for 3 hr., with monitoring by silica gel TLC. The mixture was diluted with water, acidified to pH 7 with aqueous HCl, and stirred at 20° C. for 1 hr. The mixture was filtered and extracted with ethyl acetate. The organic phase was washed with brine, dried over sodium sulfate, filtered, and concentrated in vacuo to yield the title compound. $^1$H NMR (CDCl$_3$ 400 MHz): δ 7.29-7.52 (m, 1H) 7.07-7.24 (m, 2H) 6.36-6.72 (m, 1H) 4.64-5.03 (m, 2H).

4-chloro-2-((4-(difluoromethyl)-2-fluorobenzyl)oxy)pyrimidine (I-1303): NaH (60% in mineral oil, 4.54 g, 2.00 equivalent) was added to a mixture of (4-(difluoromethyl)-2-fluorophenyl)methanol (I-1303-2, 10.0 g, 1.00 equivalent) in THE (80 mL)equivalent. The mixture was cooled to −25° C., then 4-chloro-2-(methylsulfonyl)pyrimidine (14.2 g, 1.30 equivalent) was added as a mixture in THE (100 mL). The mixture was stirred at 25° C. for 6 hr, with monitoring by silica gel TLC. The mixture was diluted with water and extracted with ethyl acetate. The organic phase was washed with brine, dried over sodium sulfate, filtered, and concentrated in vacuo. Purification by silica gel flash column chromatography (EtOAc/petroleum ether) yielded the title compound. $^1$H NMR (CDCl$_3$ 400 MHz): δ 8.34-8.49 (m, 1H) 7.68 (t, J=7.60 Hz, 1H) 7.23-7.37 (m, 3H) 7.00-7.10 (m, 1H) 6.46-6.84 (m, 1H) 5.51-5.63 (m, 2H). ES/MS m/z: 288.0 (M+H$^+$).

Preparation of Intermediate I-1304

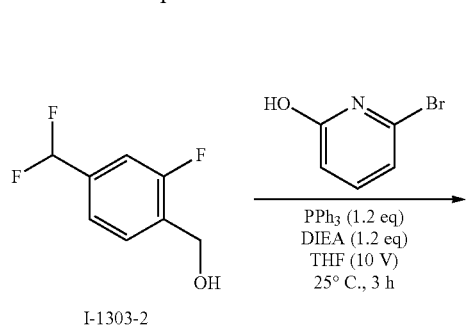

2-bromo-6-((4-(difluoromethyl)-2-fluorobenzyl)oxy) pyridine (I-1304): triphenylphosphine (35.7 g, 1.2 equivalent), then diisopropyl azodicarboxylate (27.6 g, 1.2 equivalent) were added to a mixture of (4-(difluoromethyl)-2-fluorophenyl)methanol (I-1303-2, 20.0 g, 1.00 equivalent) in THF (200 mL)equivalent. The mixture was stirred at 25° C. for 1 hr., or with monitoring by TLC. The mixture was partitioned between water and ethyl acetate. The organic phase was washed with brine, then concentrated in vacuo. Silica gel flash column chromatography (EtOAc/petroleum ether) yielded the title compound. $^1$H NMR (CDCl$_3$ 400 MHz): δ=7.60 (t, J=7.6 Hz, 1H), 7.43 (dd, J=7.5, 8.1 Hz, 1H), 7.31-7.25 (m, 2H), 7.23 (s, 1H), 7.08 (dd, J=0.7, 7.5 Hz, 1H), 6.77-6.46 (m, 2H), 5.44 (s, 2H). ES/MS m/z: 331.0 (M+H$^+$).

Preparation of Intermediate I-1305

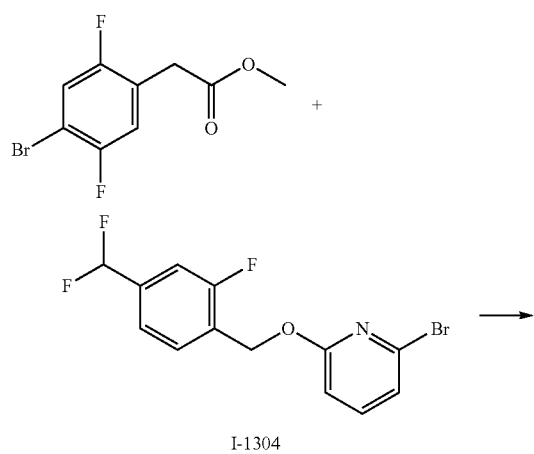

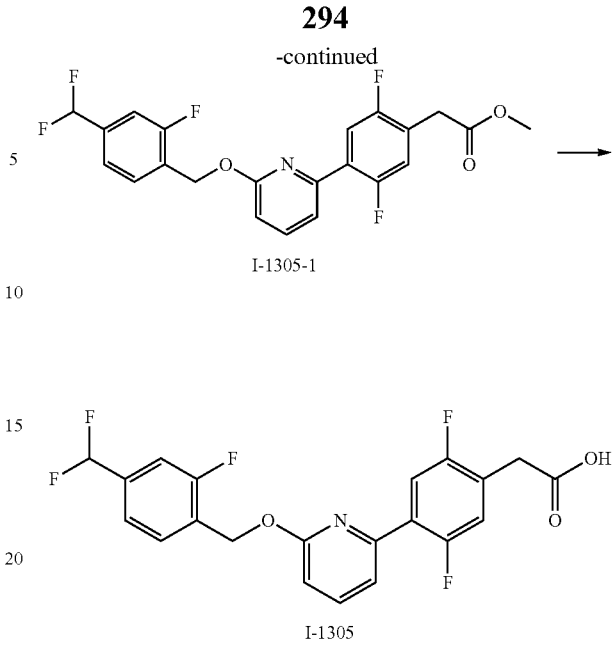

Methyl 2-(4-(6-((4-(difluoromethyl)-2-fluorobenzyl)oxy) pyridin-2-yl)-2,5-difluorophenyl)acetate (I-1305-1): A mixture of methyl 2-(4-bromo-2,5-difluoro-phenyl)acetate (500 mg, 1.0 equivalent), PdCl$_2$(dppf) (140 mg, 0.10 equivalent), potassium propionate (635 mg, 3.0 equivalent), and bis (pinacolato)diboron (623 mg, 1.3 equivalent) in 1,4-dioxane (9.4 mL) was purged with argon for 1 min. The mixture was sealed and heated to 90° C. for 2 h. After cooling down to room temperature, 2-bromo-6-[[4-(difluoromethyl)-2-fluoro-phenyl]methoxy]pyridine (Intermediate I-1304, 580 mg, 1.84 mmol, 1.1 equivalent), PdCl$_2$(dppf) (66 mg, 0.05 equivalent), 2 M aqueous Na2CO3 (1.89 mL, 2.0 equivalent) were added, respectively. The resulting mixture was heated to 100° C. under argon and stirred for 2 hr., with monitoring by LCMS. The mixture was cooled to rt and partitioned between water and ethyl acetate. The organic phase was washed with brine, dried over magnesium sulfate, filtered and concentrated in vacuo. Next, purification by silica gel flash column chromatography (EtOAc/hexane gradient) yielded the title compound. 1H NMR (400 MHz, Chloroform-d) δ 7.77 (dd, J=10.5, 6.4 Hz, 1H), 7.65 (dt, J=22.8, 7.7 Hz, 2H), 7.51 (dd, J=7.7, 1.6 Hz, 1H), 7.30 (d, J=8.1 Hz, 2H), 7.09 (dd, J=11.2, 6.0 Hz, 1H), 6.81 (d, J=8.2 Hz, 1H), 6.63 (s, 1H), 5.56 (s, 2H), 3.75 (s, 3H), 3.70 (s, 2H). ES/MS m/z: 438.0 (M+H)$^+$.

2-(4-(6-((4-(difluoromethyl)-2-fluorobenzyl)oxy)pyridin-2-yl)-2,5-difluorophenyl)acetic acid (I-1305): A mixture of methyl 2-(4-(6-((4-(difluoromethyl)-2-fluorobenzyl)oxy) pyridin-2-yl)-2,5-difluorophenyl)acetate (I-1305-1, 535 mg, 1.0 equivalent), lithium hydroxide (2.0 M in H$_2$O, 1.22 mL, 2.0 equivalent) and acetonitrile (4.3 mL) was stirred at 50-60° C. for 4 hr., with monitoring by LCMS. The mixture was quenched with aqueous HCl until pH<2, then extracted with ethyl acetate. The organic phase was washed with brine, dried over MgSO$_4$, filtered and concentrated in vacuo to yield the title compound. 1H NMR (400 MHz, Methanol-d4) δ 7.82-7.68 (m, 2H), 7.66 (t, J=7.5 Hz, 1H), 7.57-7.41 (m, 1H), 7.41-7.26 (m, 2H), 7.20 (dd, J=11.5, 6.0 Hz, 1H), 6.96-6.56 (m, 2H), 5.58 (s, 2H), 3.84-3.61 (m, 2H). ES/MS m/z: 424.0 (M+H)$^+$.

Preparation of Intermediate I-1306

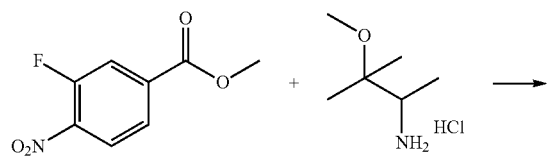

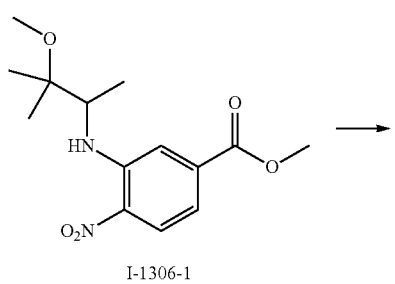

I-1306-1

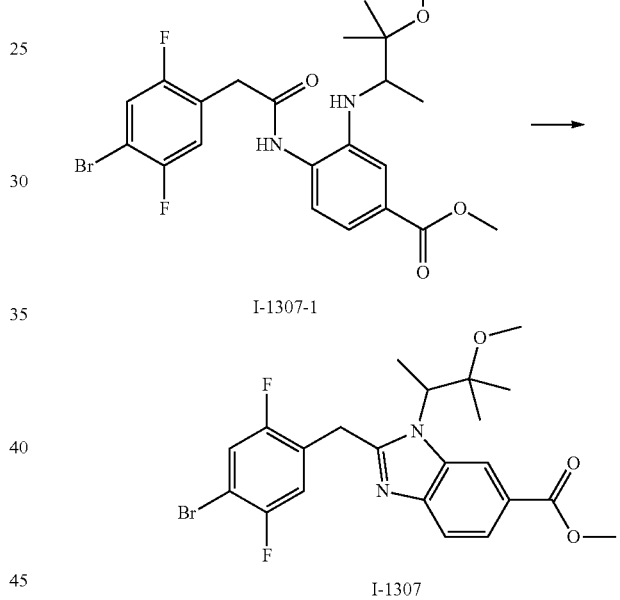

I-1306

Racemic methyl 3-[(2-methoxy-1,2-dimethyl-propyl)amino]-4-nitrobenzoate (I-1306-1): Methyl 3-fluoro-4-nitrobenzoate (310 mg, 1.0 equivalent), THF (2.0 mL), DMF (1.0 mL), and diisopropylethylamine (1.36 mL, 5.0 equivalent) were added to racemic 3-methoxy-3-methylbutan-2-amine hydrochloride (251 mg, 1.05 equivalent)equivalent. The mixture was stirred at 80° C. for 20 hr., with monitoring by LCMS. The mixture was diluted with ethyl acetate and washed with saturated aqueous NH$_4$Cl, then brine, then dried over magnesium sulfate, filtered and concentrated in vacuo to yield the title compound. ES/MS m/z: 296.9 (M+H)$^+$.

Racemic methyl 4-amino-3-((3-methoxy-3-methylbutan-2-yl)amino)benzoate (I-1306): A mixture of crude racemic methyl 3-[(2-methoxy-1,2-dimethyl-propyl)amino]-4-nitrobenzoate (I-1306-1, 461 mg, 1.0 equivalent), 10% palladium on carbon (83 mg, 0.10 equivalent) and ethanol (16 mL) was stirred under an atmosphere of hydrogen for 16 hr., with monitoring by LCMS. The mixture was filtered, concentrated in vacuo and purified by silica gel flash column chromatography (hexane/EtOAc) to yield the title compound. 1H NMR (400 MHz, Methanol-d4) δ 7.34-7.26 (m, 2H), 6.68 (d, J=8.0 Hz, 1H), 3.82 (s, 3H), 3.47 (q, J=6.5 Hz, 1H), 3.25 (s, 3H), 1.27 (s, 6H), 1.16 (d, J=6.5 Hz, 3H). ES/MS m/z: 266.9 (M+H)$^+$.

Preparation of Intermediate I-1307

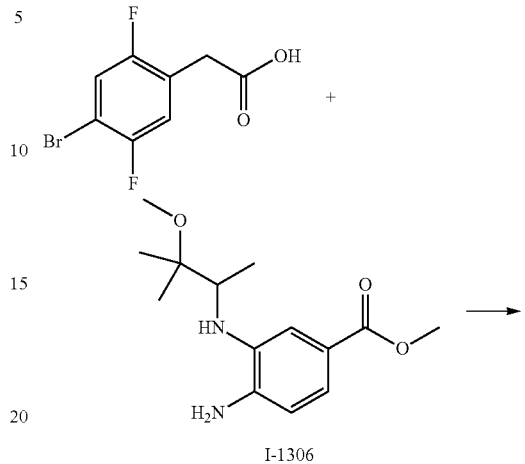

I-1306

I-1307-1

I-1307

Racemic methyl 4-[[2-(4-bromo-2,5-difluoro-phenyl)acetyl]amino]-3-[(2-methoxy-1,2-dimethyl-propyl)amino]benzoate (I-1307-1): A mixture of racemic methyl 4-amino-3-((3-methoxy-3-methylbutan-2-yl)amino)benzoate (I-1306, 440 mg, 1.00 equivalent), 2-(4-bromo-2,5-difluorophenyl)acetic acid (435 mg, 1.05 equivalent), chloro-N,N,N',N'-tetramethylformamidinium hexafluorophosphate (487 mg, 1.05 equivalent), 1-methylimidazole (678 mg, 5.0 equivalent) and acetonitrile (8.1 mL) was stirred at 20° C. for 1 hr., with monitoring by LCMS. The mixture was then diluted with EtOAc, washed with saturated aqueous NH$_4$Cl, then saturated aqueous NaHCO$_3$, then brine. The organic phase was dried over MgSO$_4$, filtered, and concentrated in vacuo to yield the title compound, which was carried forward without further purification. ES/MS m/z: 499.0 (M+H)$^+$.

Racemic methyl 2-(4-bromo-2,5-difluorobenzyl)-1-(3-methoxy-3-methylbutan-2-yl)-1H-benzo[d]imidazole-6-carboxylate (I-1307): A mixture of racemic methyl 4-[[2-(4-bromo-2,5-difluoro-phenyl)acetyl]amino]-3-[(2- methoxy-1,2-dimethyl-propyl)amino]benzoate (I-1307-1, 825 mg, 1.0 equivalent), glacial acetic acid (3.3 mL) and 1,2-dichloroethane (8.3 mL) was stirred at 80-95° C. for 96 hr., or until completion as determined by LCMS. The mixture was diluted with EtOAc, quenched with saturated aqueous NaHCO₃ and batchwise addition of solid NaHCO₃. The organic phase was washed with brine, dried over MgSO₄, filtered, and concentrated in vacuo to yield the title compound. 1H NMR (400 MHz, Chloroform-d) δ 8.56-8.50 (m, 1H), 7.91 (dd, J=8.5, 1.5 Hz, 1H), 7.69 (d, J=8.5 Hz, 1H), 7.29 (dd, J=8.6, 5.6 Hz, 1H), 7.03 (dd, J=8.6, 6.3 Hz, 1H), 4.39-4.22 (m, 3H), 3.90 (s, 3H), 3.15 (s, 3H), 1.56 (d, J=7.1 Hz, 3H), 1.26 (s, 3H), 0.98 (s, 3H). ES/MS m/z: 481.2 (M+H⁺).

Preparation of Intermediate I-1308

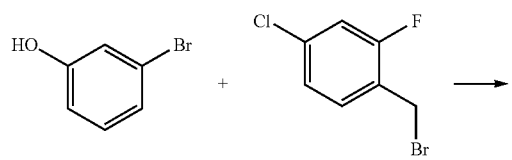

1-((3-bromophenoxy)methyl)-4-chloro-2-fluorobenzene (I-1308): A mixture of 1-(bromomethyl)-4-chloro-2-fluorobenzene (581 mg, 1.0 equivalent), 3-bromophenol (450 mg, 1.0 equivalent), cesium carbonate (2.54 g, 3.0 equivalent) and acetone (13 mL) was stirred at 70° C. for 2 hr. The mixture was then diluted with ethyl acetate, filtered, and concentrated in vacuo. Silica gel flash column chromatography (EtOAc/hexane) yielded the title compound. 1H NMR (400 MHz, Chloroform-d) δ 7.42 (t, J=8.0 Hz, 1H), 7.21-7.07 (m, 5H), 6.89 (ddd, J=7.8, 2.5, 1.4 Hz, 1H), 5.07 (s, 2H).

Preparation of Intermediate I-1309

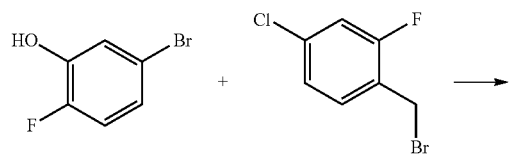

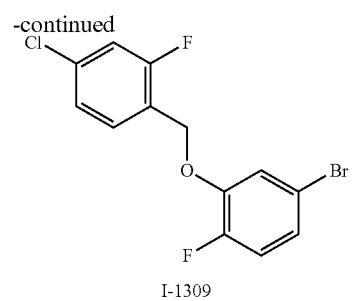

1-[(5-bromo-2-fluoro-phenoxy)methyl]-4-chloro-2-fluorobenzene (I-1309): A mixture of 1-(bromomethyl)-4-chloro-2-fluorobenzene (585 mg, 1.0 equivalent), 5-bromo-2-fluorophenol (500 mg, 1.0 equivalent), cesium carbonate (2.56 g, 3.0 equivalent) and acetone (13 mL) was stirred at 70° C. for 2 hr. The mixture was then diluted with ethyl acetate, filtered, and concentrated in vacuo. Silica gel flash column chromatography (EtOAc/hexane) yielded the title compound. 1H NMR (400 MHz, Chloroform-d) δ 7.46 (t, J=8.0 Hz, 1H), 7.23-7.12 (m, 3H), 7.06 (dd, J=4.0, 2.3 Hz, 1H), 6.98 (dd, J=10.7, 8.6 Hz, 1H), 5.12 (s, 2H).

Preparation of Intermediate I-1310

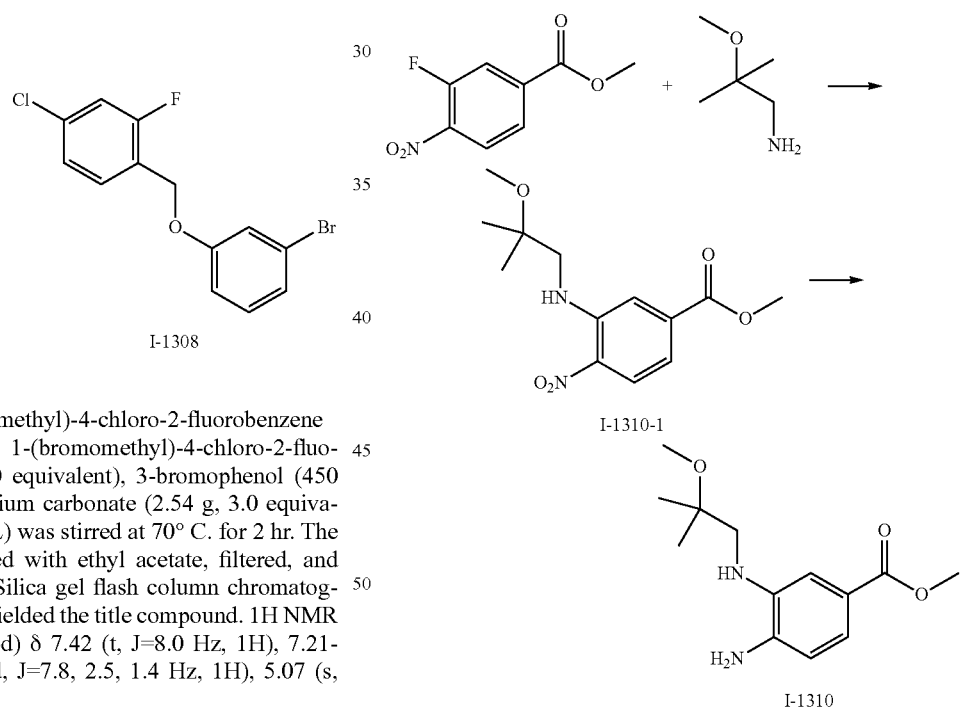

Methyl 3-[(2-methoxy-2-methyl-propyl)amino]-4-nitrobenzoate (I-1310-1): Methyl 3-fluoro-4-nitrobenzoate (500 mg, 1.0 equivalent), 2-methyltetrahydrofuran (3.4 mL), DMF (1.7 mL), and diisopropylethylamine (2.2 mL, 5.0 equivalent) were added To 2-methoxy-2-methyl-propan-1-amine (285 mg, 1.1 equivalent)equivalent. The mixture was stirred at 80° C. for 16 hr., with monitoring by LCMS. The mixture was diluted with ethyl acetate and washed with saturated aqueous NH₄Cl, then brine, then dried over magnesium sulfate, filtered and concentrated in vacuo to yield the title compound. ES/MS m/z: 282.8 (M+H)⁺.

Methyl 4-amino-3-[(2-methoxy-2-methylpropyl)amino]benzoate (I-1310): A mixture of crude methyl 3-[(2-methoxy-2-methyl-propyl)amino]-4-nitrobenzoate (I-13010-1, 555 mg, 1.0 equivalent), 10% palladium on carbon (105 mg, 0.10 equivalent) and ethanol (20 mL) was stirred under an atmosphere of hydrogen for 16 hr., with monitoring by LCMS. The mixture was filtered, concentrated in vacuo and purified by silica gel flash column chromatography (hexane/EtOAc) to yield the title compound. 1H NMR (400 MHz, Methanol-d4) δ 7.32 (d, J=8.0 Hz, 1H), 7.24 (d, J=1.8 Hz, 1H), 6.68 (d, J=8.1 Hz, 1H), 3.82 (s, 3H), 3.25 (s, 3H), 3.11 (s, 2H), 1.31 (s, 6H). ES/MS m/z: 252.9 (M+H)$^+$.

Preparation of Intermediate I-1311

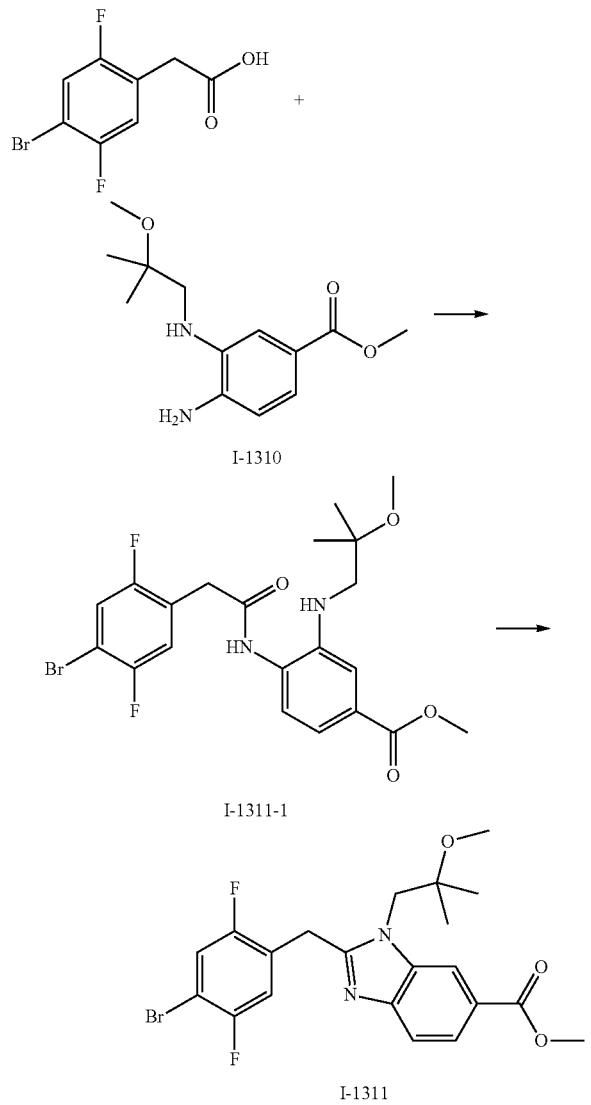

Methyl 4-[[2-(4-bromo-2,5-difluorophenyl)acetyl]amino]-3-[(2-methoxy-2-methylpropyl)amino]benzoate (I-1311-1): A mixture of methyl 4-amino-3-[(2-methoxy-2-methylpropyl)amino]benzoate (I-1310, 655 mg, 1.00 equivalent), 2-(4-bromo-2,5-difluorophenyl)acetic acid (684 mg, 1.05 equivalent), chloro-N,N,N',N'-tetramethylformamidinium hexafluorophosphate (765 mg, 1.05 equivalent), 1-methylimidazole (1066 mg, 5.0 equivalent) and acetonitrile (13 mL) was stirred at 20° C. for 2.5 hr., with monitoring by LCMS. The mixture was then diluted with EtOAc, washed with saturated aqueous NH$_4$Cl, then saturated aqueous NaHCO$_3$, then brine. The organic phase was dried over MgSO$_4$, filtered, and concentrated in vacuo to yield the title compound, which was carried forward without further purification. ES/MS m/z: 485.0 (M+H$^+$).

Methyl 2-(4-bromo-2,5-difluorobenzyl)-1-(2-methoxy-2-methylpropyl)-1H-benzo[d]imidazole-6-carboxylate (I-1311): A mixture of methyl 4-[[2-(4-bromo-2,5-difluorophenyl)acetyl]amino]-3-[(2-methoxy-2-methylpropyl)amino]benzoate (I-1311-1, 1260 mg, 1.0 equivalent), glacial acetic acid (5.3 mL) and 1,2-dichloroethane (13 mL) was stirred at 80° C. for 16 hr., with monitoring by LCMS. The mixture was diluted with EtOAc, quenched with saturated aqueous NaHCO$_3$ and batchwise addition of solid NaHCO$_3$. The organic phase was washed with brine, dried over MgSO$_4$, filtered, and concentrated in vacuo to yield the title compound. 1H NMR (400 MHz, Chloroform-d) δ 8.16 (s, 1H), 8.05 (d, J=8.6 Hz, 1H), 7.86 (d, J=8.4 Hz, 1H), 7.35 (s, 1H), 7.30 (dd, J=8.7, 5.5 Hz, 1H), 4.62 (s, 2H), 4.20 (s, 2H), 3.96 (s, 3H), 3.14 (s, 3H), 1.23 (s, 6H). ES/MS m/z: 467.2 (M+H$^+$).

Preparation of Intermediate I-1312

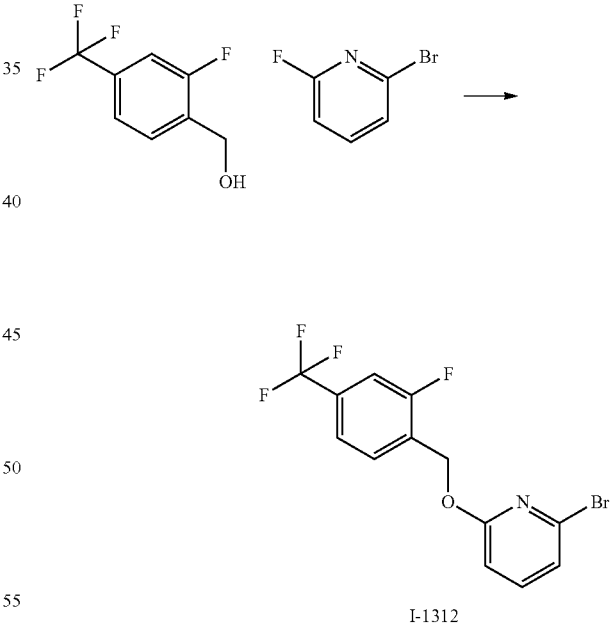

2-bromo-6-((2-fluoro-4-(trifluoromethyl)benzyl)oxy)pyridine (I-1312): A mixture of [2-fluoro-4-(trifluoromethyl)phenyl]methanol (1213 mg, 1.1 equivalent), 2-bromo-6-fluoropyridine (1000 mg, 1.0 equivalent), cesium carbonate (3.71 g, 2.0 equivalent) and acetonitrile (8.0 mL) was stirred at 25° C. for 16 hr. with monitoring by LCMS. The mixture was then filtered and concentrated in vacuo. Silica gel flash column chromatography (EtOAc/hexane) yielded the title compound. ES/MS m/z: 351.8 (M+H$^+$).

Preparation of Intermediate I-1313

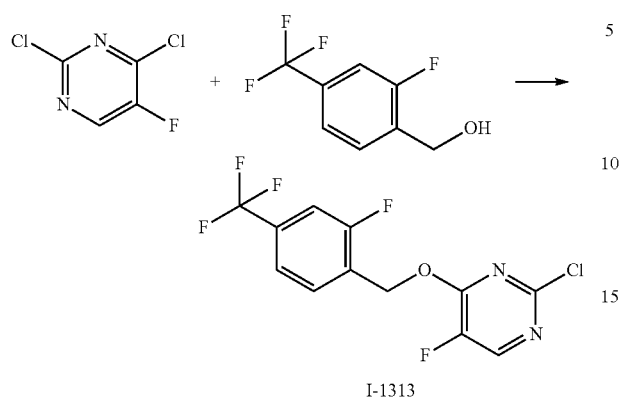

4-chloro-5-fluoro-2-[[2-fluoro-4-(trifluoromethyl)phenyl]methoxy]pyrimidine (I-1313): Sodium hydride (46 mg, 60% in mineral oil, 1.20 equivalent), then [2-fluoro-4-(trifluoromethyl)phenyl]methanol (326 mg, 1.00 equivalent) were added to mixture of 2,4-dichloro-5-fluoro-pyrimidine (280 mg, 1.0 equivalent) and THF (3.2 mL)equivalent. The mixture was stirred at 20° C. for 16 hr. The mixture was partitioned between ethyl acetate and brine. The organic phase was dried over MgSO$_4$, filtered and concentrated in vacuo. Silica gel flash column chromatography (EtOAc/hexane) yielded the title compound. 1H NMR (400 MHz, Chloroform-d) δ 8.25 (d, J=2.2 Hz, 1H), 7.67 (t, J=7.5 Hz, 1H), 7.48 (dd, J=7.8, 1.6 Hz, 1H), 7.40 (dd, J=9.6, 1.7 Hz, 1H), 5.61 (s, 2H). ES/MS m/z: 324.9 (M+H$^+$).

Preparation of Intermediate I-1319

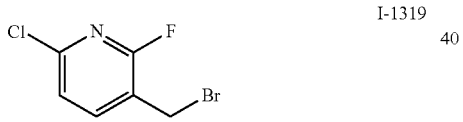

3-(bromomethyl)-6-chloro-2-fluoro-pyridine (I-1319): Carbon tetrabromide (431 mg, 1.05 equivalent) was added to a mixture of (6-chloro-2-fluoro-3-pyridyl)methanol (200 mg, 1.0 equivalent), triphenylphosphine (357 mg, 1.10 equivalent) and DCM (5.0 mL) precooled to 0° C. equivalent The mixture stirred at 0° C. for 1 hr., then the mixture was concentrated in vacuo. Purification by silica gel flash column chromatography (EtOAc/hexane) yielded the title compound.

Preparation of Intermediate I-1322

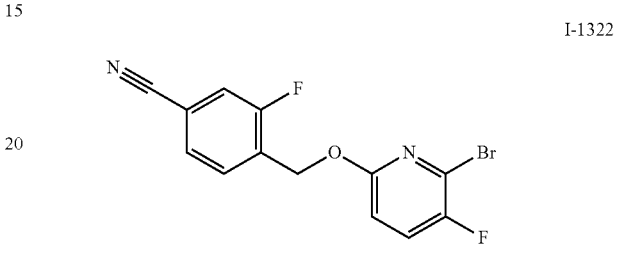

4-(((6-bromo-5-fluoropyridin-2-yl)oxy)methyl)-3-fluorobenzonitrile (I-1322): A mixture of 3-Fluoro-4-(hydroxymethyl)benzonitrile (160 mg, 1.06 mmol), cesium carbonate (332 mg, 1.02 mmol), and 2-bromo-3,6-difluoropyridine (98.0 mg, 0.505 mmol) in MeCN (2 mL) was stirred for 4 days at 20 C. The mixture was diluted with ethyl acetate, filtered, and concentrated in vacuo. Silica gel flash column chromatography (EtOAc/hexane) yielded the title compound. 1H NMR (400 MHz, CDCl3) δ 7.67 (t, J=7.5 Hz, 1H), 7.50 (dd, J=8.0, 1.5 Hz, 1H), 7.42 (ddd, J=8.7, 4.0, 2.4 Hz, 2H), 6.78 (dd, J=8.8, 2.8 Hz, 1H), 5.47 (s, 2H). ES/MS m/z: 327.1 (M+H$^+$).

Preparation of Intermediate I-1324

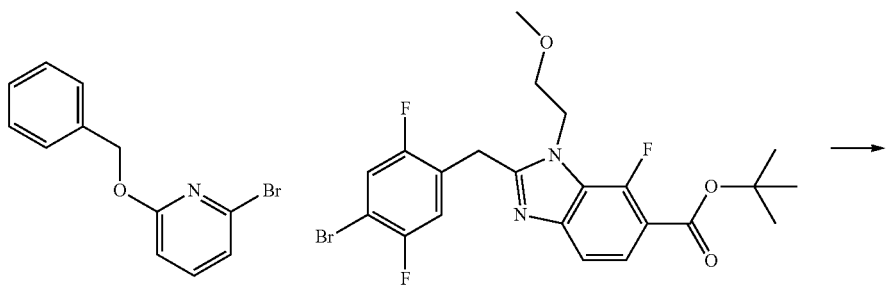

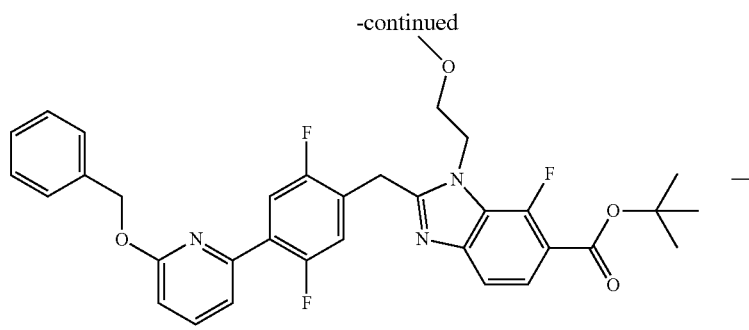

I-1324-1

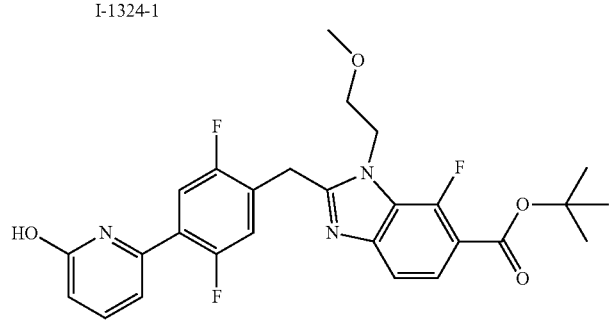

I-1324

Tert-butyl 2-(4-(6-(benzyloxy)pyridin-2-yl)-2,5-difluorobenzyl)-7-fluoro-1-(2-methoxyethyl)-1H-benzo[d]imidazole-6-carboxylate (I-1324-1): A mixture of tert-butyl 2-(4-bromo-2,5-difluorobenzyl)-7-fluoro-1-(2-methoxyethyl)-1H-benzo[d]imidazole-6-carboxylate (49 mg, 0.965 equivalent), PdCl$_2$(dppf) (11.4 mg, 0.15 equivalent), potassium propionate (34 mg, 3.0 equivalent), and bis(pinacolato)diboron (34 mg, 1.3 equivalent) in 1,4-dioxane (2.0 mL) was purged with argon for 1 min. The mixture was sealed and heated to 100° C. for 2 h. After cooling down to room temperature, 2-(benzyloxy)-6-bromopyridine (27 mg, 1.1 equivalent), PdCl$_2$(dppf) (5.7 mg, 0.075 equivalent), 2 M aqueous Na$_2$CO$_3$ (0.10 mL, 2.0 equivalent) were added, respectively. The resulting mixture was heated to 90° C. under argon and stirred for 2 hr., with monitoring LCMS. The mixture was filtered and concentrated in vacuo. Purification by silica gel flash column chromatography (EtOAc/hexane gradient) yielded the title compound.

Tert-butyl 2-(2,5-difluoro-4-(6-hydroxypyridin-2-yl)benzyl)-7-fluoro-1-(2-methoxyethyl)-1H-benzo[d]imidazole-6-carboxylate (I-1324): A mixture of tert-butyl 2-(4-(6-(benzyloxy)pyridin-2-yl)-2,5-difluorobenzyl)-7-fluoro-1-(2-methoxyethyl)-1H-benzo[d]imidazole-6-carboxylate (I-1324-1, 40 mg, 1.0 equivalent), 10% palladium on carbon (10 mg, 0.14 equivalent), and ethanol (3.0 mL) was stirred under an atmosphere of hydrogen for 3 hr. The mixture was filtered and concentrated in vacuo to yield the title compound. ES/MS m/z: 514.7 (M+H$^+$).

Preparation of Intermediate I-1325

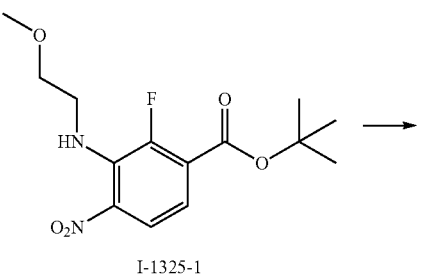

I-1325-1

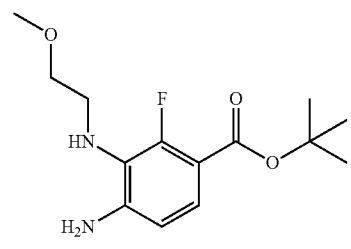

I-1325-2

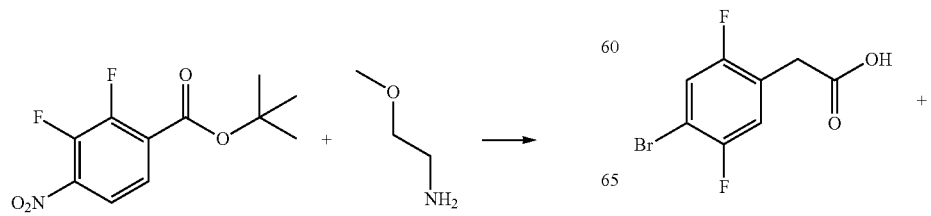

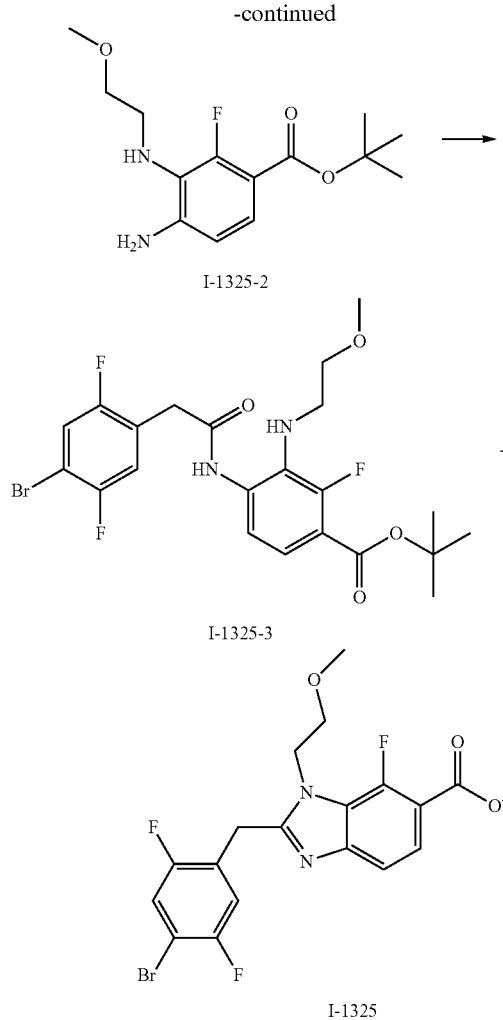

I-1325-2

I-1325-3

I-1325

Tert-butyl 2-fluoro-3-((2-methoxyethyl)amino)-4-nitrobenzoate (I-1325-1): Tert-butyl 2,3-difluoro-4-nitrobenzoate (600 mg, 1.0 equivalent), THF (10 mL), and diisopropylethylamine (2.0 mL, 5.0 equivalent) were added to 2-methoxyethanamine (191 mg, 1.1 equivalent)equivalent. The mixture was stirred at 60° C. for 16 hr., with monitoring by LCMS. The mixture was diluted with ethyl acetate and washed with saturated aqueous NH₄Cl, then brine, then dried over magnesium sulfate, filtered and concentrated in vacuo to yield the title compound, which was carried forward without further purification.

Tert-butyl 4-amino-2-fluoro-3-((2-methoxyethyl)amino)benzoate (I-1325-2): A mixture of crude tert-butyl 2-fluoro-3-((2-methoxyethyl)amino)-4-nitrobenzoate (I-1325-1, 560 mg, 1.0 equivalent), 10% palladium on carbon (190 mg, 0.10 equivalent) and ethanol (15 mL) was stirred under an atmosphere of hydrogen for 4 hr., with monitoring by LCMS. The mixture was filtered, concentrated in vacuo and purified by silica gel flash column chromatography (hexane/EtOAc) to yield the title compound.

Tert-butyl 4-(2-(4-bromo-2,5-difluorophenyl)acetamido)-2-fluoro-3-((2-methoxyethyl)amino)benzoate (I-1325-3): A mixture of tert-butyl 4-amino-2-fluoro-3-((2-methoxyethyl)amino)benzoate (I-1325-2, 250 mg, 1.00 equivalent), 2-(4-bromo-2,5-difluorophenyl)acetic acid (318 mg, 1.44 equivalent), chloro-N,N,N',N'-tetramethylformamidinium hexafluorophosphate (300 mg, 1.22 equivalent), 1-methylimidazole (360 mg, 5.0 equivalent) and acetonitrile (8 mL) was stirred at 20° C. for 2 hr., with monitoring by LCMS. The mixture was then diluted with EtOAc, then washed with 1 N HCl. The organic phase was dried over MgSO₄, filtered, and concentrated in vacuo to yield the title compound, which was carried forward without further purification.

Tert-butyl 2-(4-bromo-2,5-difluorobenzyl)-7-fluoro-1-(2-methoxyethyl)-1H-benzo[d]imidazole-6-carboxylate (I-1325): A mixture of tert-butyl 4-(2-(4-bromo-2,5-difluorophenyl)acetamido)-2-fluoro-3-((2-methoxyethyl)amino)benzoate (I-1325-3, 331 mg, 1.0 equivalent), glacial acetic acid (0.38 mL) and 1,2-dichloroethane (5 mL) was stirred at 60° C. for 4 hr., with monitoring by LCMS. The mixture was diluted with EtOAc, quenched with saturated aqueous NaHCO₃. The organic phase was washed with brine, dried over MgSO₄, filtered, and concentrated in vacuo to yield the title compound. 1H NMR (400 MHz, Chloroform-d) δ 7.86 (dd, J=8.6, 6.7 Hz, 1H), 7.65 (d, J=8.6 Hz, 1H), 7.35 (dd, J=8.7, 5.6 Hz, 1H), 7.13 (dd, J=8.3, 6.4 Hz, 1H), 4.62-4.40 (m, 4H), 3.78 (t, J=5.1 Hz, 2H), 3.29 (s, 3H), 1.64 (s, 9H).

Preparation of Intermediate I-1326

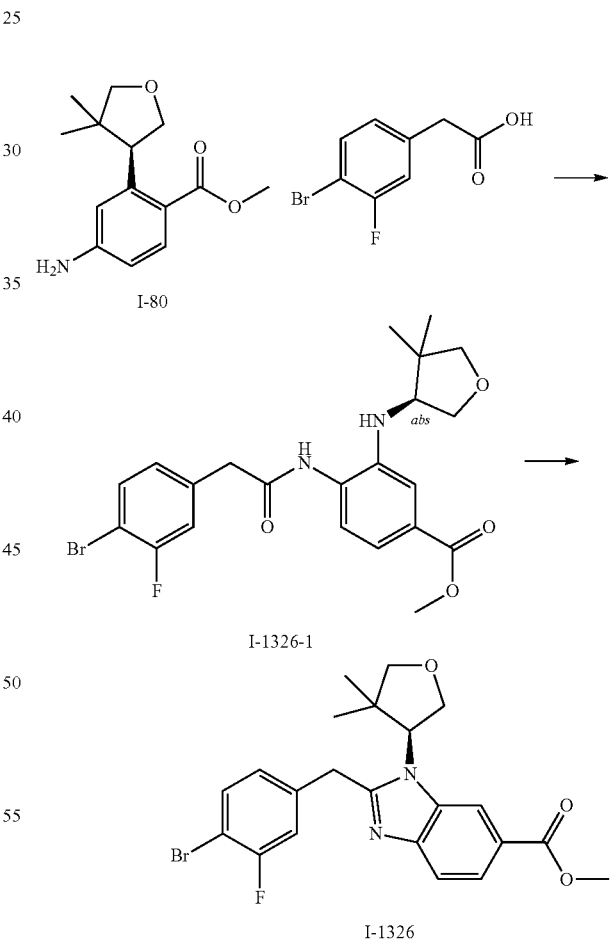

I-80

I-1326-1

I-1326

Methyl (S)-4-(2-(4-bromo-3-fluorophenyl)acetamido)-3-((4,4-dimethyltetrahydrofuran-3-yl)amino)benzoate (I-1326-1): A mixture of methyl (S)-4-amino-3-((4,4-dimethyltetrahydrofuran-3-yl)amino)benzoate (I-80, 200 mg, 1.0 equivalent), 2-(4-bromo-3-fluorophenyl)acetic acid (83 mg, 1.1 equivalent), chloro-N,N,N',N'-tetramethylformamidinium hexafluorophosphate (265 mg, 1.25 equivalent), 1-methylimidazole (311 mg, 5.0 equivalent) and acetonitrile (3.0 mL) was stirred at 20° C. for 2 hr., with monitoring by LCMS. The mixture was then diluted with EtOAc, then washed with 1 N HCl. The organic phase was dried over MgSO₄, filtered, and concentrated in vacuo to yield the title compound, which was carried forward without further purification.

Methyl (S)-2-(4-bromo-3-fluorobenzyl)-1-(4,4-dimethyl-tetrahydrofuran-3-yl)-1H-benzo[d]imidazole-6-carboxylate (I-1326): A mixture of methyl (S)-4-(2-(4-bromo-3-fluoro-phenyl)acetamido)-3-((4,4-dimethyltetrahydrofuran-3-yl) amino)benzoate (I-1326-1, 250 mg, 1.0 equivalent) and glacial acetic acid (0.2 mL) was stirred at 180° C. for 2 hr., with monitoring by LCMS. The mixture was diluted with EtOAc, quenched with saturated aqueous NaHCO₃ and batchwise addition of solid NaHCO₃. The organic phase was washed with brine, dried over MgSO₄, filtered, and concentrated in vacuo to yield the title compound. ES/MS m/z: 462.9 (M+H⁺).

Preparation of Intermediate I-1327

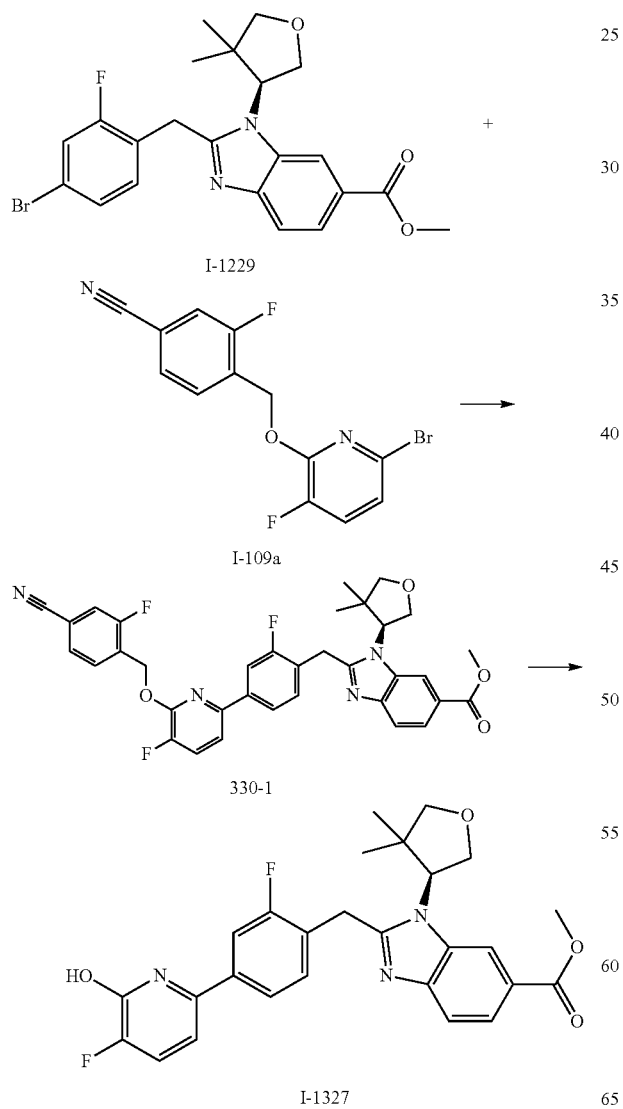

Methyl (S)-2-(4-(6-((4-cyano-2-fluorobenzyl)oxy)-5-fluoropyridin-2-yl)-2-fluorobenzyl)-1-(4,4-dimethyltetrahydrofuran-3-yl)-1H-benzo[d]imidazole-6-carboxylate (330-1): A mixture of methyl (S)-2-(4-bromo-2-fluorobenzyl)-1-(4,4-dimethyltetrahydrofuran-3-yl)-1H-benzo[d]imidazole-6-carboxylate (Intermediate I-1229, 800 mg, 1.67 mmol, 1.0 equivalent), PdCl₂(dppf) (186 mg, 0.25 mmol, 0.15 equivalent), potassium propionate (560 mg, 5.01 mmol, 3.0 equivalent), and bis(pinacolato)diboron (510 mg, 2.00 mol, 1.2 equivalent) was mixed with 1,4-dioxane (10 mL) and the resulting mixture was purged with argon for 2 min. The mixture was sealed and heated to 120° C. by microwave. The mixture was then stirred for 1 h. After cooling down to room temperature, 4-[(6-bromo-3-fluoro-2-pyridyl)oxymethyl]-3-fluoro-benzonitrile (Intermediate I-109a, 580 mg, 1.84 mmol, 1.1 equivalent), PdCl₂(dppf) (62 mg, 0.0834 mmol, 0.05 equivalent), 2 M aqueous Na₂CO₃ (2.0 mL, 4.17 mmol, 2.5 equivalent) were added, respectively. The resulting mixture was heated to 100° C. under argon and stirred for 3 hrs. before cooling to rt. Once cooled the mixture was filtered through a plug of Celite and MgSO₄. The filtrate was concentrated and purified by column chromatography (silica gel, EtOAc/hexane gradient) to yield the title compound. ES/MS m/z: 627.7 (M+H⁺).

Methyl (S)-1-(4,4-dimethyltetrahydrofuran-3-yl)-2-(2-fluoro-4-(5-fluoro-6-hydroxypyridin-2-yl)benzyl)-1H-benzo[d]imidazole-6-carboxylate (I-1327): A mixture of methyl (S)-2-(4-(6-((4-cyano-2-fluorobenzyl)oxy)-5-fluoropyridin-2-yl)-2-fluorobenzyl)-1-(4,4-dimethyltetrahydrofuran-3-yl)-1H-benzo[d]imidazole-6-carboxylate (Intermediate 330-1, 200 mg, 1.0 equivalent) in 4M HCl solution in dioxane (8.0 mL, 10 equivalent) was heated at 80° C. overnight. The mixture was diluted with EtOAc and washed with brine, saturated aqueous NaHCO₃ and water. The organic phase was dried, concentrated in vacuo, and purified by preparative reverse-phase HPLC (CH3CN/water, 0.1% TFA) to yield the title compound. ES/MS m/z: 494.7 (M+H⁺).

Preparation of Intermediate I-1328

Methyl (S)-1-(4,4-dimethyltetrahydrofuran-3-yl)-2-(2-fluoro-4-(6-hydroxypyridin-2-yl)benzyl)-1H-benzo[d]imidazole-6-carboxylate (Intermediate I-1328): Methyl (S)-1-(4,4-dimethyltetrahydrofuran-3-yl)-2-(2-fluoro-4-(6-hydroxypyridin-2-yl)benzyl)-1H-benzo[d]imidazole-6-carboxylate was prepared in a manner similar to Intermediate I-1327. ES/MS m/z: 476.6 (M+H⁺).

Preparation of Intermediate I-1329

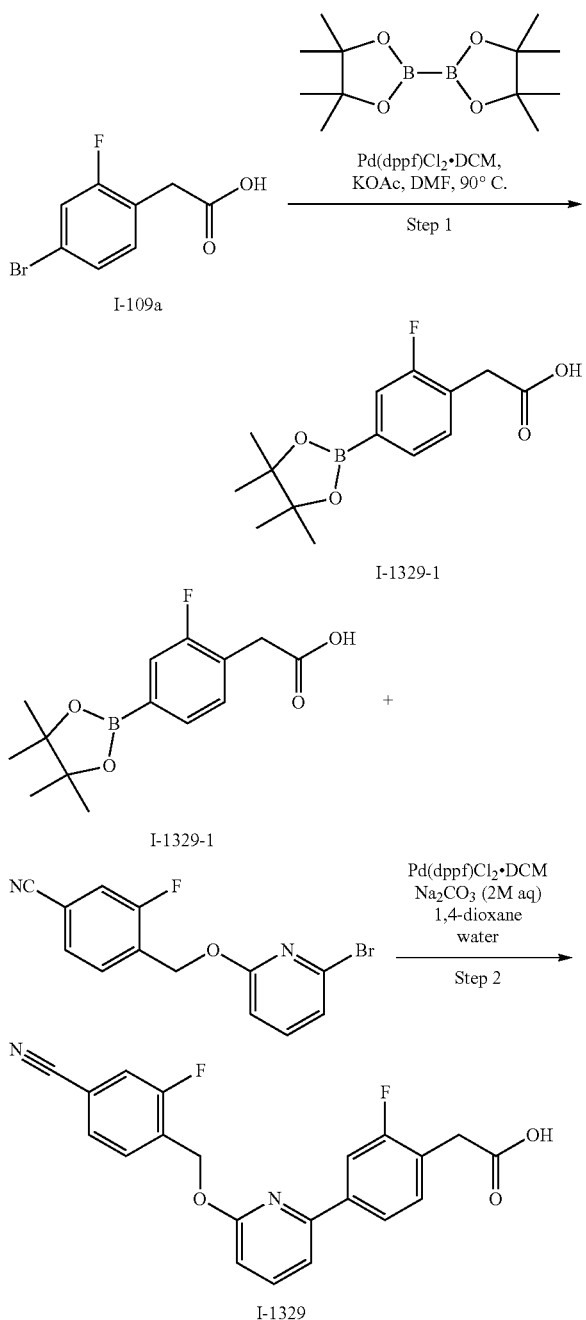

2-(2-fluoro-4-(4,4,5,5-tetramethyl-1,3,2-dioxaborolan-2-yl)phenyl)acetic acid (I-1329-1). Pd(dppf)Cl$_2$·DCM (7.75 g, 9.5 mmol, 0.05 eq) was added to a solution of 2-(4-bromo-2-fluorophenyl)acetic acid (45.0 g, 0.19 mol, 1.0 eq), 4,4,4',4', 5,5,5', 5'-octamethyl-2, 2'-bi(1, 3,2-dioxaborolane) (58.8 g, 0.23 mol, 1.2 eq) and potassium acetate (74.6 g, 0.76 mol, 4.0 eq) in DMF (450 mL). The mixture was flushed thoroughly with nitrogen for 5-10 mins. The mixture was then purged with nitrogen for three times. The mixture was heated at 90° C. for overnight. HPLC and LCMS showed completion. After cooling to room temperature, the mixture was then filtered through a pad of Celite and washed with EtOAc (500 mL). The filtrate was concentrated. Next, water (1200 mL) was added and the pH was adjusted to ~ 3 with 3 N HCl. The resulting mixture was extracted with EtOAc (600 mL×3). The combined organic layers were washed with brine, dried over MgSO$_4$, concentrated under reduced pressure. The residue was purified by silica gel flash column chromatography, eluting with 0-20% EtOAc in hexanes to give the title compound. $^1$HNMR (400 MHz, DMSO-d$_6$) δ 12.50 (br s, 1H), 7.45-7.35 (m, 1H), 7.35-7.31 (m, 2H), 3.65 (s, 2H), 1.23 (s, 12H).

2-(4-(6-((4-cyano-2-fluorobenzyl)oxy)pyridin-2-yl)-2-fluorophenyl)acetic acid (I-1329): 2-(2-fluoro-4-(4,4,5,5-tetramethyl-1,3,2-dioxaborolan-2-yl)phenyl)acetic acid (I-1329-1, 13.7 g, 48.9 mmol, 1.0 eq) and 4-(((6-bromopyridin-2-yl)oxy)methyl)-3-fluorobenzonitrile (I-3, 15.0 g, 48.9 mmol, 1.0 eq) were taken up in 1,4-dioxane (240 mL) and aqueous sodium carbonate (2.0 M, 67.5 mL, 135.0 mmol, 2.8 eq) and the mixture sparged with nitrogen for 5 minutes. Pd(dppf)Cl$_2$·DCM (566 mg, 0.49 mmol) was then added and the system was purged with nitrogen for three times. The mixture was heated to 90° C. and stirred for 3 h. HPLC and LCMS showed completion. Upon completion the mixture was cooled to room temperature. After cooling the mixture was filtered and washed with EtOAc (100 mL×3). The filtrate was concentrated. Next, water (500 mL) was added, filtered and the filter cake was triturated with EtOAc (100 mL×3) for three times. The solid obtained by filtration and then water (800 mL) was added, the pH was adjusted to ~ 6 with 1 N HCl. The resulting mixture was extracted with EtOAc (600 mL×3). The combined organic layers were washed with brine, dried over MgSO$_4$, concentrated under reduced pressure to give the title compound. $^1$HNMR (400 MHz, DMSO-d$_6$) δ 12.53 (br s, 1H), 7.94-7.91 (m, 1H), 7.87-7.81 (m, 3H), 7.78-7.71 (m, 2H), 7.64 (d, J=7.6 Hz, 1H), 7.44 (t, J=8.0 Hz, 1H), 6.92 (d, J=8.0 Hz, 1H), 5.62 (s, 2H), 3.69 (s, 2H). ES/MS m/z: 381.1 (M+H)$^+$.

Preparation of Intermediate I-1330

Tert-butyl 2-(4-bromo-2-fluorobenzyl)-1-((1-(fluoromethyl)cyclopropyl)methyl)-1H-benzo[d]imidazole-6-carboxylate (Intermediate I-1330): Tert-butyl 2-(4-bromo-2-fluorobenzyl)-1-((1-(fluoromethyl)cyclopropyl)methyl)-1H-benzo[d]imidazole-6-carboxylate was prepared in a manner described for Intermediate I-2 using Intermediate I-1196 and 2-(4-bromo-2-fluorophenyl)acetic acid. ES/MS m/z: 509.7 (M+H)$^+$.

Preparation of Intermediate I-1332

Preparation of Intermediate I-1335

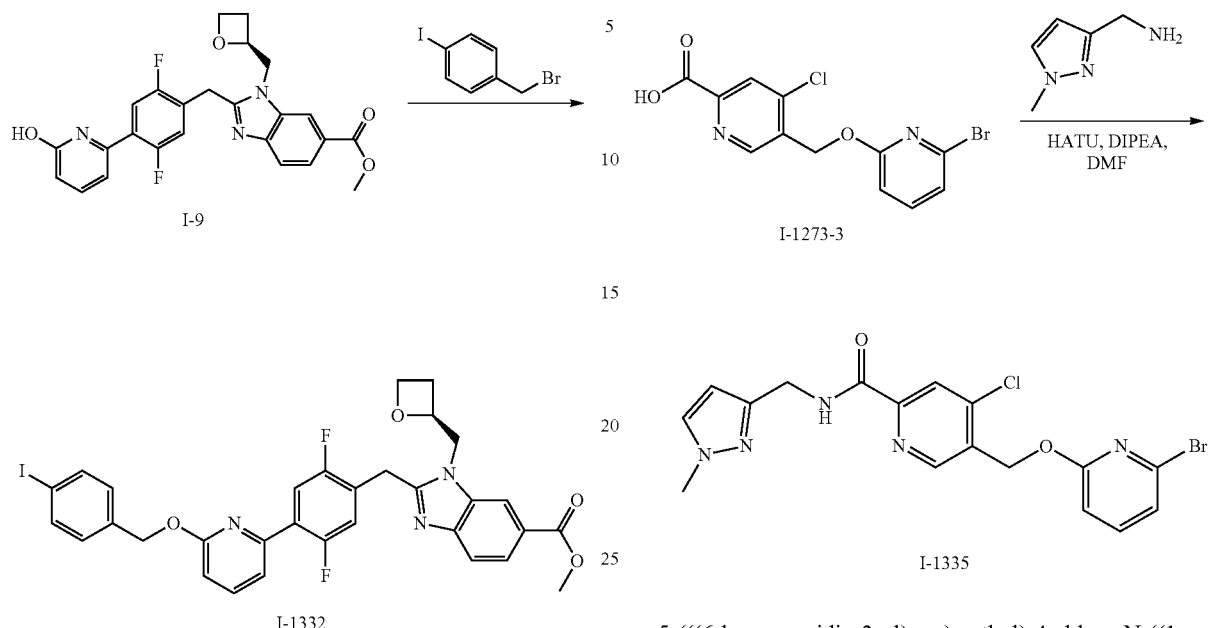

I-1332

Methyl (S)-2-(2,5-difluoro-4-(6-((4-iodobenzyl)oxy)pyridin-2-yl)benzyl)-1-(oxetan-2-ylmethyl)-1H-benzo[d]imidazole-6-carboxylate (I-1332): A mixture of methyl (S)-2-(2,5-difluoro-4-(6-hydroxypyridin-2-yl)benzyl)-1-(oxetan-2-ylmethyl)-1H-benzo[d]imidazole-6-carboxylate (I-9, 157 mg, 1.0 equivalent), 1-(bromomethyl)-4-iodobenzene (100 mg, 1.0 equivalent), cesium carbonate (150 mg, 1.4 equivalent) and acetonitrile (3.0 mL) was stirred at 50° C. for 1.5 hr, with monitoring by LCMS. The mixture was then filtered and concentrated in vacuo. Silica gel flash column chromatography (EtOAc/hexane) yielded the title compound. ES/MS m/z: 683.2 (M+H+).

Preparation of Intermediate I-1333

I-1333

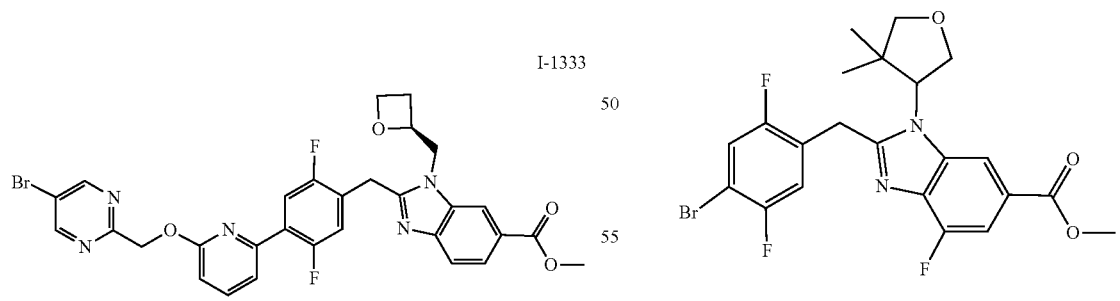

Methyl (S)-2-(4-(6-((5-bromopyrimidin-2-yl)methoxy)pyridin-2-yl)-2,5-difluorobenzyl)-1-(oxetan-2-ylmethyl)-1H-benzo[d]imidazole-6-carboxylate (I-1333): Methyl (S)-2-(4-(6-((5-bromopyrimidin-2-yl)methoxy)pyridin-2-yl)-2,5-difluorobenzyl)-1-(oxetan-2-ylmethyl)-1H-benzo[d]imidazole-6-carboxylate was prepared in a manner described for preparation of Intermediate I-1332, using Intermediate I-9. ES/MS m/z: 638 (M+H+).

I-1335

5-(((6-bromopyridin-2-yl)oxy)methyl)-4-chloro-N-((1-methyl-1H-pyrazol-3-yl)methyl)picolinamide (I-1335): A mixture of Intermediate I-1273-3 (from Intermediate I-1273, 50 mg, 1.0 equivalent), (1-methylpyrazol-3-yl)methanamine (24 mg, 1.5 equivalent), HATU (83 mg, 1.5 equivalent), diisopropylethylamine (60 μL, 2.5 equivalent) in DMF (2 mL) was stirred at room temperature for 2 hr. The mixture was diluted with EtOAc, washed with 10% LiCl. Next, a mixture of saturated aqueous NaHCO3 and brine, then brine, dried over MgSO4, filtered, and concentrated in vacuo. Silica gel flash column chromatography (EtOAc/hexane) yielded the title compound. ES/MS m/z: 435.9 (M+H+).

Preparation of Intermediate I-1336

I-1336

Methyl 2-(4-bromo-2,5-difluorobenzyl)-1-(4,4-dimethyltetrahydrofuran-3-yl)-4-fluoro-1H-benzo[d]imidazole-6-carboxylate (I-1336): Methyl 2-(4-bromo-2,5-difluorobenzyl)-1-(4,4-dimethyltetrahydrofuran-3-yl)-4-fluoro-1H-benzo[d]imidazole-6-carboxylate was prepared in a manner described for Intermediate I-108 substituting with 4,4-dimethyltetrahydrofuran-3-amine hydrochloride for (S)-4,4-dimethyltetrahydrofuran-3-amine hydrochloride. ES/MS: 338.5 (M+Na+).

Preparation of Intermediate I-1337

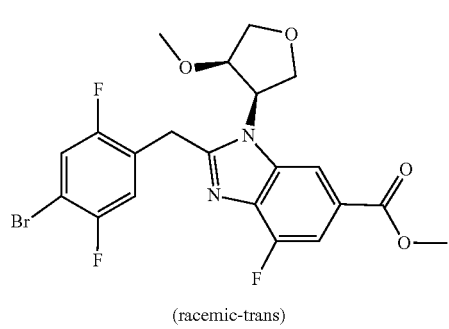

JH-I-67

(racemic-trans)

Racemic methyl 2-(4-bromo-2,5-difluorobenzyl)-4-fluoro-1-((3R,4R)-4-methoxytetrahydrofuran-3-yl)-1H-benzo[d]imidazole-6-carboxylate (Intermediate I-1337): Racemic methyl 2-(4-bromo-2,5-difluorobenzyl)-4-fluoro-1-((3R,4R)-4-methoxytetrahydrofuran-3-yl)-1H-benzo[d]imidazole-6-carboxylate was prepared in a manner described for preparation of Intermediate I-1326, using Intermediate I-1133. ES/MS: 499.0 (M+H$^+$).

Preparation of Intermediate I-1338

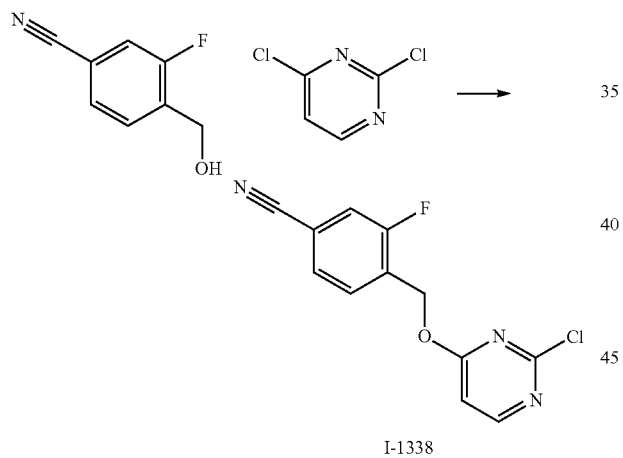

I-1338

4-[(2-chloropyrimidin-4-yl)oxymethyl]-3-fluoro-benzonitrile (I-1338): Potassium tert-butoxide (0.237 g, 2.11 mmol) was added to a mixture of 3-fluoro-4-(hydroxymethyl)benzonitrile (0.609 g, 4.03 mmol) in tetrahydrofuran (1.00 mL) and the resulting mixture was stirred for 5 min at room temperature. This solution was then added to a mixture of 2,4-dichloropyrimidine (300 mg, 2.01 mmol) in N,N-dimethylformamide (1.50 mL) pre-cooled to −78° C. and the mixture was warmed slowly to room temperature and stirred for 1 h, or until LCMS showed complete conversion to desired product. The mixture was poured into 50 mL of water and stirred for 5 min, then the precipitate was filtered off to give the title compound. 1H NMR (400 MHz, Chloroform-d) δ 8.39 (d, J=5.7 Hz, 1H), 7.66 (t, J=7.4 Hz, 1H), 7.53 (dd, J=8.0, 1.5 Hz, 1H), 7.44 (dd, J=9.2, 1.5 Hz, 1H), 6.78 (d, J=5.7 Hz, 1H), 5.57 (s, 2H). ES/MS m/z: 264.1 (M+H$^+$).

Preparation of Intermediate I-1339

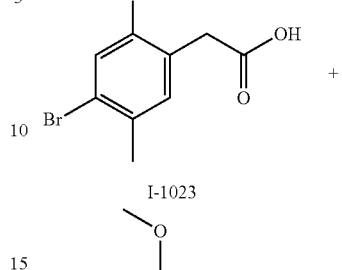

I-1023

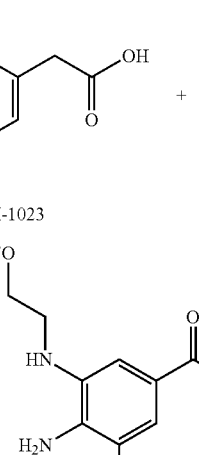

I-1032

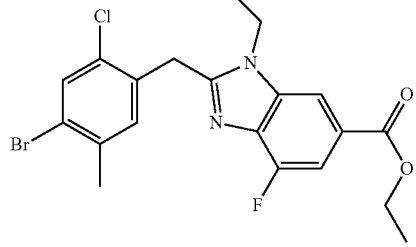

I-1339-1

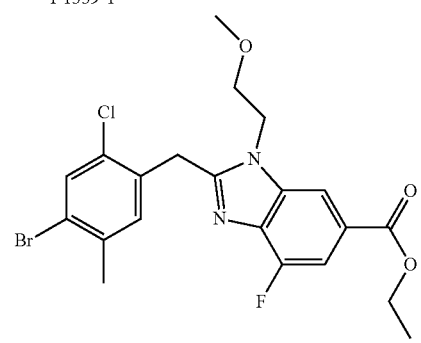

I-1339

Ethyl 2-(4-bromo-2-chloro-5-methylbenzyl)-4-fluoro-1-(2-methoxyethyl)-1H-benzo[d]imidazole-6-carboxylate (I-1339-1): A mixture of ethyl 4-amino-3-fluoro-5-(2-methoxyethylamino)benzoate (I-1032, 73 mg, 1.0 equivalent), 2-(4-bromo-2-chloro-5-methyl-phenyl)acetic acid (I-1023, 90 mg, 1.2 equivalent), chloro-N,N,N',N'-tetramethylformamidinium hexafluorophosphate (100 mg, 1.25 equivalent), 1-methylimidazole (70 mg, 3.0 equivalent) and DMF (5.0 mL) was stirred at 20° C. for 5 hr., with monitoring by LCMS. The mixture was then diluted with EtOAc, then washed with water, then brine. The organic phase was dried over MgSO$_4$, filtered, and concentrated in vacuo to yield the title compound, which was carried forward without further purification.

Ethyl 2-[(4-bromo-2-chloro-5-methyl-phenyl)methyl]-7-fluoro-3-(2-methoxyethyl)benzimidazole-5-carboxylate (I-1339): A mixture of crude ethyl 2-(4-bromo-2-chloro-5-methylbenzyl)-4-fluoro-1-(2-methoxyethyl)-1H-benzo[d]imidazole-6-carboxylate (I-1339-1, 143 mg, 1.0 equivalent) and glacial acetic acid (5.0 mL) was stirred at reflux for 20 hr., with monitoring by LCMS. The mixture was concentrated in vacuo and purified by silica gel flash column chromatography (EtOAc/hexane) to yield the title compound. ES/MS m/z: 483.3 (M+H⁺).

Preparation of Intermediate I-1340

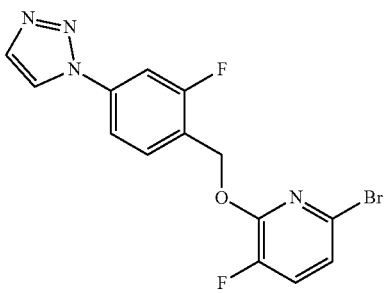

6-bromo-3-fluoro-2-((2-fluoro-4-(1H-1,2,3-triazol-1-yl)benzyl)oxy)pyridine (I-1340): 6-bromo-3-fluoro-2-((2-fluoro-4-(1H-1,2,3-triazol-1-yl)benzyl)oxy)pyridine was prepared in a similar manner to 5-(((6-bromopyridin-2-yl)oxy)methyl)-4-chloro-2-fluoropyridine (Intermediate I-1049) using (2-fluoro-4-(1H-1,2,3-triazol-1-yl)phenyl)methanol (from preparation of Intermediate I-1282) and 6-bromo-3-fluoropyridin-2-ol. ES/MS: 367.1 (M+1).

Preparation of Intermediate I-1341

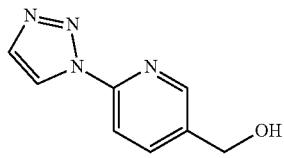

(6-(1H-1,2,3-triazol-1-yl)pyridin-3-yl)methanol (I-1341): To a mixture of I-1005 (120 mg, 1.0 equivalent), triphenylphosphine 197 mg, 1.10 equivalent) in DCM (5 mL) pre-cooled to 0° C. was added carbon tetrabromide (260 mg, 1.15 equivalent). The mixture was stirred at 0° C., then allowed to warm to 20° C., concentrated in vacuo, and purified by silica gel flash column chromatography (EtOAc/hexane) to yield the title compound. ES/MS m/z: 177.2 (M+H+).

Preparation of Intermediate I-1347

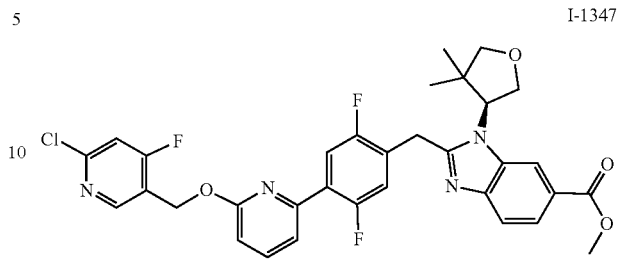

Methyl 2-[[4-[6-[(6-chloro-4-fluoro-3-pyridyl)methoxy]-2-pyridyl]-2,5-difluoro-phenyl]methyl]-3-[(3S)-4,4-dimethyltetrahydrofuran-3-yl]benzimidazole-5-carboxylate (I-1347): Methyl 2-[[4-[6-[(6-chloro-4-fluoro-3-pyridyl)methoxy]-2-pyridyl]-2,5-difluoro-phenyl]methyl]-3-[(3S)-4,4-dimethyltetrahydrofuran-3-yl]benzimidazole-5-carboxylate was prepared in a manner as described for Intermediate I-21 substituting 1-1219 for 1-9 and 5-(bromomethyl)-2-chloro-4-fluoro-pyridine for 5-bromo-2-(bromomethyl)thiazole. ES/MS: 637.3 (M+H+).

Preparation of Intermediate I-1348

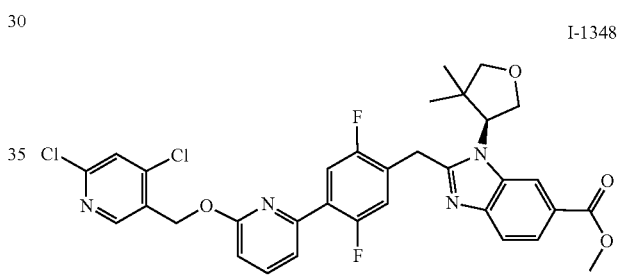

Methyl 2-[[4-[6-[(4,6-dichloro-3-pyridyl)methoxy]-2-pyridyl]-2,5-difluoro-phenyl]methyl]-3-[(3S)-4,4-dimethyltetrahydrofuran-3-yl]benzimidazole-5-carboxylate (I-1348): Methyl 2-[[4-[6-[(4,6-dichloro-3-pyridyl)methoxy]-2-pyridyl]-2,5-difluoro-phenyl]methyl]-3-[(3S)-4,4-dimethyltetrahydrofuran-3-yl]benzimidazole-5-carboxylate was prepared in a manner as described for Intermediate I-21 substituting 1-1219 for 1-9 and 2,4-dichloro-5-(chloromethyl)pyridine for 5-bromo-2-(bromomethyl)thiazole. ES/MS: 653.3 (M+H+).

Preparation of Intermediate I-1349

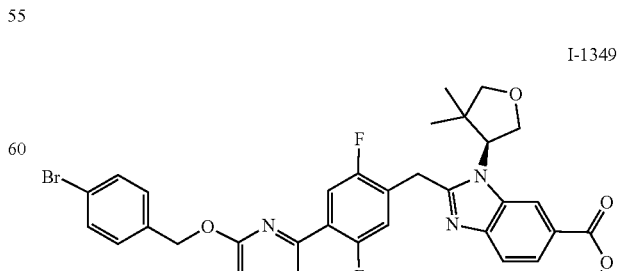

317

Methyl 2-[[4-[6-[(4-bromophenyl)methoxy]-2-pyridyl]-2,5-difluoro-phenyl]methyl]-3-[(3S)-4,4-dimethyltetrahydrofuran-3-yl]benzimidazole-5-carboxylate (I-1349): Methyl 2-[[4-[6-[(4-bromophenyl)methoxy]-2-pyridyl]-2,5-difluoro-phenyl]methyl]-3-[(3S)-4,4-dimethyltetrahydrofuran-3-yl]benzimidazole-5-carboxylate was prepared in a manner as described for Intermediate I-21 substituting 1-1219 for 1-9 and 1-bromo-4-(bromomethyl)benzene for 5-bromo-2-(bromomethyl)thiazole. ES/MS: 662, 664 (M+H+).

Preparation of Intermediate I-1350

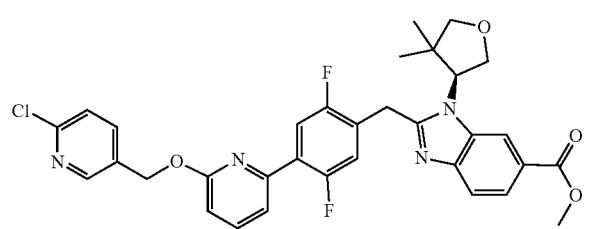

I-1350

Methyl 2-[[4-[6-[(6-chloro-3-pyridyl)methoxy]-2-pyridyl]-2,5-difluoro-phenyl]methyl]-3-[(3S)-4,4-dimethyltetrahydrofuran-3-yl]benzimidazole-5-carboxylate (I-1350): Methyl 2-[[4-[6-[(6-chloro-3-pyridyl)methoxy]-2-pyridyl]-2,5-difluoro-phenyl]methyl]-3-[(3S)-4,4-dimethyltetrahydrofuran-3-yl]benzimidazole-5-carboxylate was prepared in a manner as described for Intermediate I-21 substituting 1-1219 for 1-9 and 5-(bromomethyl)-2-chloro-pyridine for 5-bromo-2-(bromomethyl)thiazole. ES/MS: 619.2 (M+H+).

Preparation of Intermediate I-1351

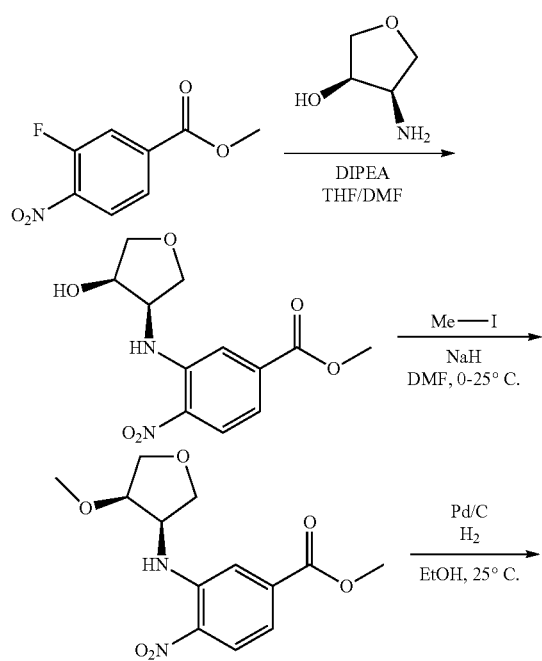

318

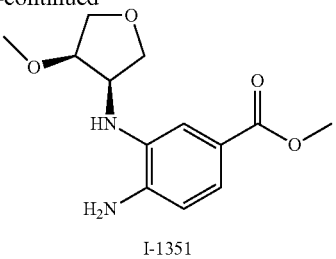

I-1351

Methyl 3-(((3R,4R)-4-hydroxytetrahydrofuran-3-yl)amino)-4-nitrobenzoate: Methyl 3-(((3R,4R)-4-hydroxytetrahydrofuran-3-yl)amino)-4-nitrobenzoate was prepared in a manner described for Intermediate I-103 substituting (3R,4R)-4-aminotetrahydrofuran-3-ol for (S)-4,4-dimethyltetrahydrofuran-3-amine and methyl 3-fluoro-4-nitrobenzoate for methyl 3,5-difluoro-4-nitrobenzoate. ES/MS m/z: 283.0 (M+H$^+$).

Methyl 3-(((3R,4R)-4-methoxytetrahydrofuran-3-yl)amino)-4-nitrobenzoate: A mixture of methyl 3-(((3R,4R)-4-hydroxytetrahydrofuran-3-yl)amino)-4-nitrobenzoate (200 mg, 0.71 mmol), sodium hydride (19.5 mg, 0.85 mmol) and iodomethane (71 uL, 0.85 mmol) in DMF (4.00 mL) was stirred at 0° C. for 15 min. Upon completion the mixture was then warmed to 25° C. and stirred for 16 h. The mixture was neutralized with 1M hydrochloride acid diluted in EtOAc and washed with brine. Next the mixture was dried over sodium sulfate, concentrated, and purified by chromatography (EtOAc/hexane) to give desired product ES/MS m/z: 297.2 (M+H$^+$).

Methyl 4-amino-3-(((3R,4R)-4-methoxytetrahydrofuran-3-yl)amino)benzoate: A mixture of methyl 3-(((3R,4R)-4-methoxytetrahydrofuran-3-yl)amino)-4-nitrobenzoate (210 mg, 0.68 mmol), and Palladium on carbon (10% loading, 72.2 mg, 0.71 mmol) in ethanol (5.0 mL) and placed under hydrogen at 25° C. for 1 h. The mixture was diluted in EtOAc and washed with brine. Next, the mixture was dried over sodium sulfate, concentrated and used without further purification. ES/MS m/z: 267.1 (M+H$^+$).

Preparation of Intermediate I-1352

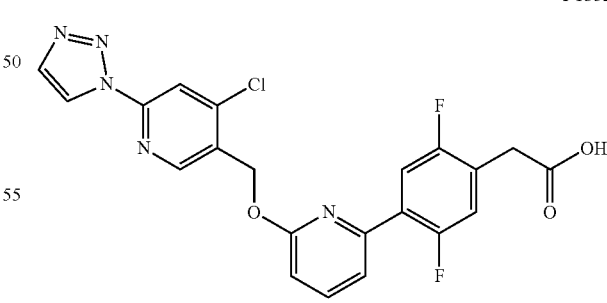

I-1352

2-(4-(6-((4-chloro-6-(1H-1,2,3-triazol-1-yl)pyridin-3-yl)methoxy)pyridin-2-yl)-2,5-difluorophenyl)acetic acid (I-1352): 2-(4-(6-((4-chloro-6-(1H-1,2,3-triazol-1-yl)pyridin-3-yl)methoxy)pyridin-2-yl)-2,5-difluorophenyl)acetic acid was prepared in a manner as described for 2-(4-(6-((4-cyano-2-fluorobenzyl)oxy)pyridin-2-yl)-2,5-difluorophenyl)acetic acid (Intermediate I-7) using 5-((((6-bromopyridin-2-yl)oxy)methyl)-4-chloro-2-(1H-1,2,3-triazol-1-yl) pyridine (I-1049) in place of 4-[(6-bromo-2-pyridyl) oxymethyl]-3-fluoro-benzonitrile (I-3). ES/MS: 457.9 (M+H+).

Preparation of Intermediate I-1353 and I-1354

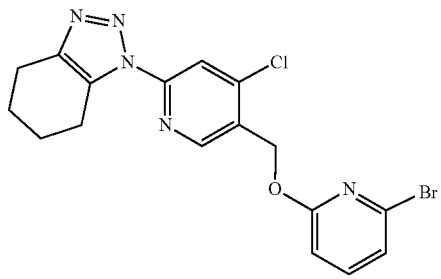

I-1353

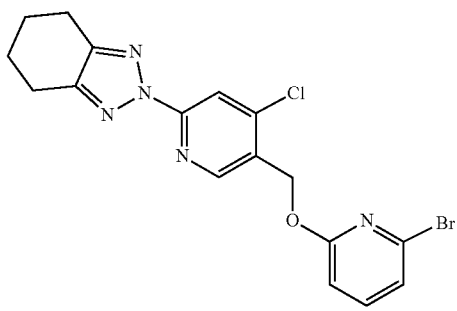

I-1354

1-(5-(((6-bromopyridin-2-yl)oxy)methyl)-4-chloropyridin-2-yl)-4,5,6,7-tetrahydro-1H-benzo[d][1,2,3]triazole (I-1353) and 2-(5-(((6-bromopyridin-2-yl)oxy)methyl)-4-chloropyridin-2-yl)-4,5,6,7-tetrahydro-2H-benzo[d][1,2,3] triazole (I-1354): 1-(5-(((6-bromopyridin-2-yl)oxy)methyl)-4-chloropyridin-2-yl)-4,5,6,7-tetrahydro-1H-benzo[d][1,2,3]triazole (I-1353) and 2-(5-(((6-bromopyridin-2-yl)oxy)methyl)-4-chloropyridin-2-yl)-4,5,6,7-tetrahydro-2H-benzo[d][1,2,3]triazole (I-1354) were prepared in a manner as described for 5-(((6-bromopyridin-2-yl)oxy)methyl)-4-chloro-2-(1H-1,2,3-triazol-1-yl)pyridine (Intermediate I-1049) using 4,5,6,7-tetrahydro-1H-benzo[d][1,2,3]triazole in place of 1H-1,2,3-triazole and running the final step at room temperature overnight.

1-(5-(((6-bromopyridin-2-yl)oxy)methyl)-4-chloropyridin-2-yl)-4,5,6,7-tetrahydro-1H-benzo[d][1,2,3]triazole (I-1353): $^1$H NMR (400 MHz, Chloroform-d) δ 8.62 (s, 1H), 8.24 (s, 1H), 7.47 (dd, J=8.1, 7.5 Hz, 1H), 7.13 (dd, J=7.5, 0.7 Hz, 1H), 6.78 (dd, J=8.2, 0.7 Hz, 1H), 5.53 (s, 2H), 3.13 (s, 2H), 2.83 (s, 2H), 1.87 (d, J=3.7 Hz, 4H).

2-(5-(((6-bromopyridin-2-yl)oxy)methyl)-4-chloropyridin-2-yl)-4,5,6,7-tetrahydro-2H-benzo[d][1,2,3]triazole (I-1354): $^1$H NMR (400 MHz, Chloroform-d) δ 8.67 (s, 1H), 8.06 (s, 1H), 7.45 (t, J=7.8 Hz, 1H), 7.11 (d, J=7.5 Hz, 1H), 6.77 (d, J=8.2 Hz, 1H), 5.50 (s, 2H), 2.84 (t, J=3.4 Hz, 4H), 1.91 (p, J=3.3 Hz, 4H).

Preparation of Intermediate I-1355

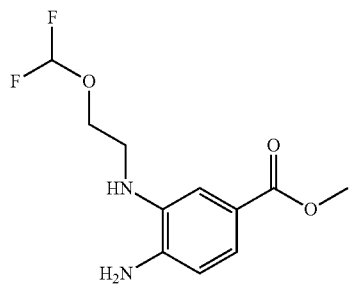

I-1355

Methyl 4-amino-3-((2-(difluoromethoxy)ethyl)amino) benzoate (I-1355): Methyl 4-amino-3-((2-(difluoromethoxy)ethyl)amino)benzoate (I-1355) was prepared in a similar manner to tert-butyl 4-amino-3-((2-methoxyethyl) amino)benzoate (Intermediate I-6) using 2-(difluoromethoxy)ethan-1-amine in place of 2-methoxyethanamine, and methyl 3-fluoro-4-nitrobenzoate in place of tert-butyl 3-fluoro-4-nitrobenzoate. ES/MS: 261.0 (M+1).

Preparation of Intermediate I-1356

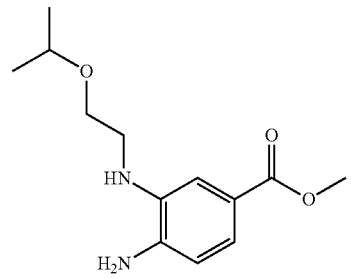

I-1356

Methyl 4-amino-3-((2-isopropoxyethyl)amino)benzoate (I-1356): Methyl 4-amino-3-((2-isopropoxyethyl)amino) benzoate (Intermediate I-1356) was prepared in a similar manner to tert-butyl 4-amino-3-((2-methoxyethyl)amino) benzoate (Intermediate I-6) using 2-isopropoxyethan-1-amine in place of 2-methoxyethanamine, and methyl 3-fluoro-4-nitrobenzoate in place of tert-butyl 3-fluoro-4-nitrobenzoate. ES/MS: 253.0 (M+1).

Preparation of Intermediate I-1357

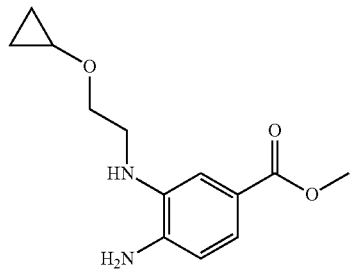

I-1357

Methyl 4-amino-3-((2-cyclopropoxyethyl)amino)benzoate (I-1357): Methyl 4-amino-3-((2-cyclopropoxyethyl)amino)benzoate was prepared in a similar manner to tert-butyl 4-amino-3-((2-methoxyethyl)amino)benzoate (Intermediate I-6) using 2-cyclopropoxyethan-1-amine in place of 2-methoxyethanamine, and methyl 3-fluoro-4-nitrobenzoate in place of tert-butyl 3-fluoro-4-nitrobenzoate. ES/MS: 251.0 (M+1).

Preparation of Intermediate I-1358

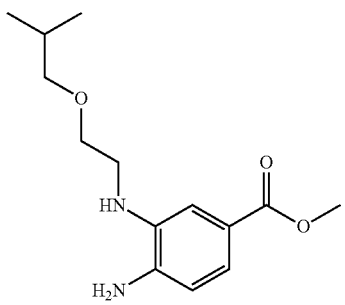

I-1358

Methyl 4-amino-3-((2-isobutoxyethyl)amino)benzoate (I-1358): Methyl 4-amino-3-((2-isobutoxyethyl)amino)benzoate was prepared in a similar manner to tert-butyl 4-amino-3-((2-methoxyethyl)amino)benzoate (Intermediate I-6) using 2-isobutoxyethan-1-amine in place of 2-methoxyethanamine, and methyl 3-fluoro-4-nitrobenzoate in place of tert-butyl 3-fluoro-4-nitrobenzoate. ES/MS: 267.0 (M+1).

Preparation of Intermediate I-1359

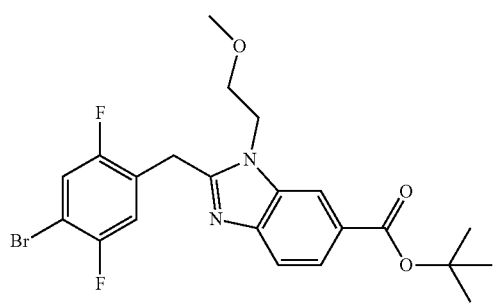

I-1359

Tert-butyl 2-(4-bromo-2,5-difluorobenzyl)-1-(2-methoxyethyl)-1H-benzo[d]imidazole-6-carboxylate (I-1359): tert-butyl 2-(4-bromo-2,5-difluorobenzyl)-1-(2-methoxyethyl)-1H-benzo[d]imidazole-6-carboxylate was prepared in a similar manner to Intermediate I-11. ES/MS: 481.05 (M+1). $^1$H NMR (400 MHz, DMSO-$d_6$) δ 8.12 (s, 1H), 7.77-7.71 (m, 2H), 7.59-7.55 (m, 1H), 7.44 (dd, J=9.1, 6.3 Hz, 1H), 4.55 (t, J=5.2 Hz, 2H), 4.36 (s, 2H), 3.66 (t, J=5.0 Hz, 2H), 3.20 (s, 3H), 1.57 (s, 9H).

Preparation of Intermediate I-1360

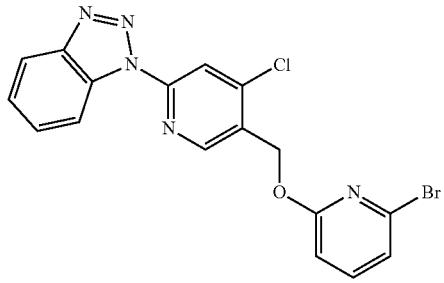

I-1360

1-(5-(((6-bromopyridin-2-yl)oxy)methyl)-4-chloropyridin-2-yl)-1H-benzo[d][1,2,3]triazole (I-1360): 1-(5-(((6-bromopyridin-2-yl)oxy)methyl)-4-chloropyridin-2-yl)-1H-benzo[d][1,2,3]triazole was prepared in a manner as described for 5-(((6-bromopyridin-2-yl)oxy)methyl)-4-chloro-2-(1H-1,2,3-triazol-1-yl)pyridine (Intermediate I-1049) using 1H-benzo[d][1,2,3]triazole in place of 1H-1,2,3-triazole. $^1$H NMR (400 MHz, Chloroform-d) δ 8.76 (s, 1H), 8.64 (dt, J=8.5, 1.0 Hz, 1H), 8.43 (s, 1H), 8.14 (dt, J=8.3, 1.0 Hz, 1H), 7.63 (ddd, J=8.3, 7.0, 1.1 Hz, 1H), 7.48 (ddd, J=8.5, 7.2, 1.3 Hz, 2H), 7.14 (dd, J=7.6, 0.6 Hz, 1H), 6.80 (dd, J=8.2, 0.6 Hz, 1H), 5.57 (s, 2H).

Preparation of Intermediate I-1361

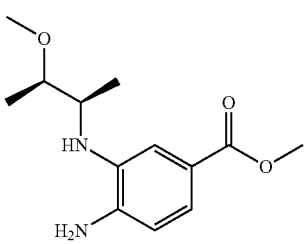

I-1361

Methyl 4-amino-3-[[(1R,2R)-2-methoxy-1-methyl-propyl]amino]benzoate (I-1361) was prepared in a manner as described for Intermediate I-1, using (2R,3R)-3-methoxybutan-2-amine hydrochloride. ES/MS m/z: 253.0 (M+H$^+$).

Preparation of Intermediate I-1362

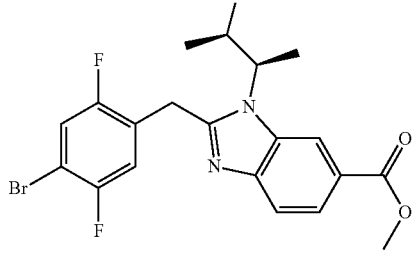

I-1362

Methyl 2-[(4-bromo-2,5-difluoro-phenyl)methyl]-3-[(1R,2R)-2-methoxy-1-methyl-propyl]benzimidazole-5-carboxylate (I-1362) was prepared in a manner as described for Intermediate I-2, using 2-(4-bromo-2,5-difluoro-phenyl)acetic acid and Intermediate I-1361. ES/MS m/z: 467.1 (M+H⁺).

Preparation of Intermediate I-1363

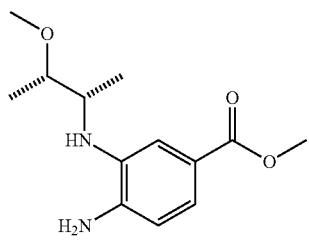

Methyl 4-amino-3-[[(1S,2S)-2-methoxy-1-methyl-propyl]amino]benzoate (I-1363) was prepared in a manner as described for Intermediate I-1, using (2S,3S)-3-methoxybutan-2-amine hydrochloride. ES/MS m/z: 253.0 (M+H⁺).

Preparation of Intermediate I-1364

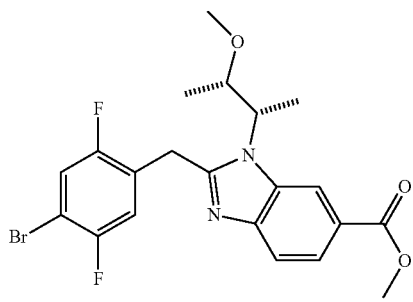

Methyl 2-[(4-bromo-2,5-difluoro-phenyl)methyl]-3-[(1S,2S)-2-methoxy-1-methyl-propyl]benzimidazole-5-carboxylate (I-1364) was prepared in a manner as described for Intermediate I-2 using 2-(4-bromo-2,5-difluoro-phenyl)acetic acid and Intermediate I-1363. ES/MS m/z: 467.1 (M+H⁺).

Preparation of Intermediate I-1365

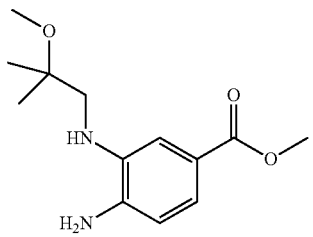

Methyl 4-amino-3-[(2-methoxy-2-methyl-propyl)amino]benzoate (I-1361): methyl 4-amino-3-[(2-methoxy-2-methyl-propyl)amino]benzoate was prepared in a manner as described for Intermediate I-1, using 2-methoxy-2-methyl-propan-1-amine. ES/MS m/z: 252.9 (M+H⁺).

Preparation of Intermediate I-1366

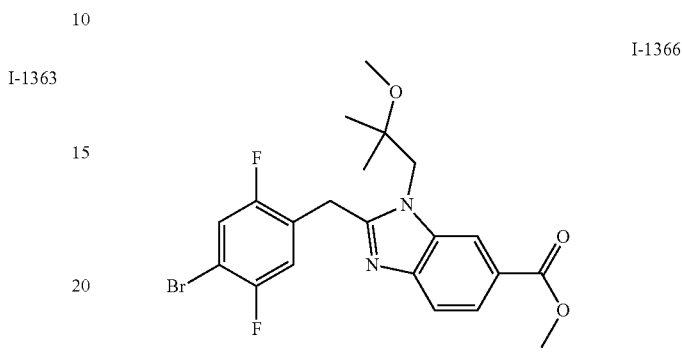

Methyl 2-[(4-bromo-2,5-difluoro-phenyl)methyl]-3-(2-methoxy-2-methyl-propyl)benzimidazole-5-carboxylate (I-1366) was prepared in a manner as described for Intermediate I-2 using 2-(4-bromo-2,5-difluoro-phenyl)acetic acid and Intermediate I-1365. ES/MS m/z: 467.2 (M+H⁺).

Preparation of Intermediate I-1367

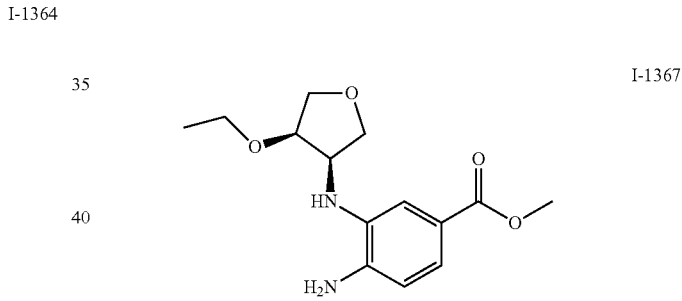

Methyl 4-amino-3-(((3R,4R)-4-ethoxytetrahydrofuran-3-yl)amino)benzoate (I-1367): methyl 4-amino-3-(((3R,4R)-4-ethoxytetrahydrofuran-3-yl)amino)benzoate was prepared in a manner described for Intermediate I-1351 substituting iodoethane for iodomethane. ES/MS m/z: 281.3 (M+H⁺).

Preparation of Intermediate I-1368

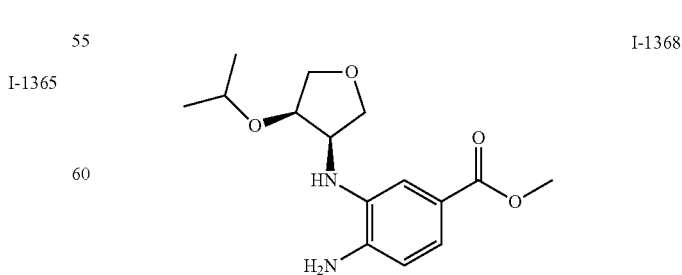

Methyl 4-amino-3-(((3R,4R)-4-isopropoxytetrahydrofuran-3-yl)amino)benzoate (I-1368): methyl 4-amino-3-

(((3R,4R)-4-isopropoxytetrahydrofuran-3-yl)amino)benzoate was prepared in a manner described for Intermediate I-1351 substituting 2-bromopropane for iodomethane. ES/MS m/z: 295.5 (M+H⁺).

Preparation of Intermediates 1-1369, 1-1370, 1-1371, 1-1372

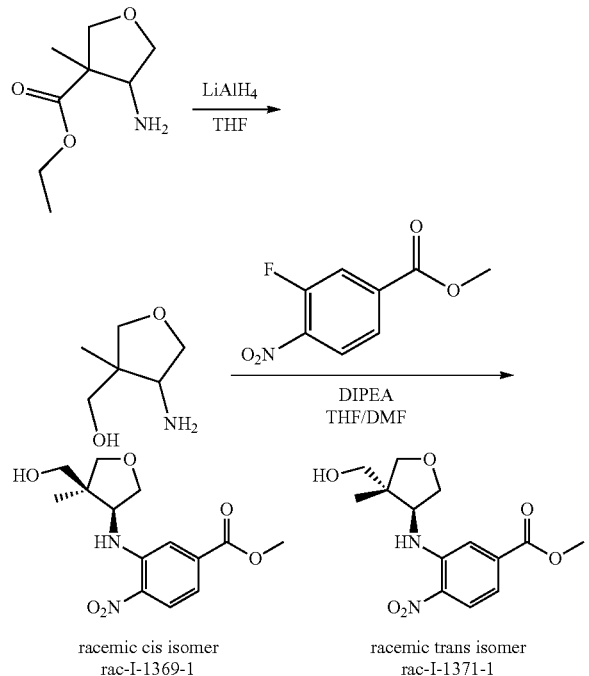

racemic cis isomer
rac-I-1369-1 racemic trans isomer
rac-I-1371-1

(4-amino-3-methyl-tetrahydrofuran-3-yl)methanol: Lithium aluminum hydride (2.0M in THF, 5.77 mL, 5.77 mmol) at 0° C. was added to a solution of ethyl 4-amino-3-methyl-tetrahydrofuran-3-carboxylate (500 mg, 2.89 mmol) in THF (1.0 M, 5.0 mL). The mixture was stirred at 0° C. The mixture was then warmed to 25° C. and stirred for 2 h. the mixture was then quenched with water (2 mL) and NaOH (2 m, 2.0 mL) diluted in EtOAc, dried over magnesium sulfate, filtered and concentrated in vaccuo. ¹H NMR (400 MHz, CDCl3) δ 4.14-4.04 (m, 1H), 3.81 (d, J=8.8 Hz, 1H), 3.72 (dd, J=18.4, 9.9 Hz, 1H), 3.60-3.50 (m, 2H), 3.48 (d, J=8.7 Hz, 1H), 3.39 (d, J=5.0 Hz, 1H), 3.28 (t, J=5.7 Hz, 1H), 1.10 (s, 2H).

Methyl 3-((4-(hydroxymethyl)-4-methyltetrahydrofuran-3-yl)amino)-4-nitrobenzoate: methyl 3-((4-(hydroxymethyl)-4-methyltetrahydrofuran-3-yl)amino)-4-nitrobenzoate was prepared in a manner described for Intermediate I-103 substituting (4-amino-3-methyl-tetrahydrofuran-3-yl) methanol for (S)-4,4-dimethyltetrahydrofuran-3-amine and methyl 3-fluoro-4-nitrobenzoate for methyl 3,5-difluoro-4-nitrobenzoate. The mixture was purified by silica gel flash column chromatography (EtOAc/hexane) provided both cis and trans diastereomers. ES/MS m/z: 311.0 (M+H⁺).

Methyl-rac-cis-3-((4-(hydroxymethyl)-4-methyltetrahydrofuran-3-yl)amino)-4-nitrobenzoate (rac-I-1369-1): The title compound was the earlier of two stereoisomers to elute during silica gel flash column chromatography. 1H NMR (400 MHz, CDCl3) δ 8.25 (d, J=8.9 Hz, 1H), 7.60 (d, J=1.6 Hz, 1H), 7.27 (s, 1H), 4.39 (dd, J=9.0, 6.9 Hz, 1H), 4.15 (d, J=7.1 Hz, 1H), 4.04 (d, J=9.1 Hz, 1H), 3.98 (s, 3H), 3.92-3.84 (m, 2H), 3.82-3.67 (m, 4H), 1.27 (s, 3H). Two-dimensional NOESY NMR identified no H17 correlation of C17-CH₃ to N11-NH and a strong C12 C—H correlation with C17-CH₃ to confirm relative stereochemistry as cis diastereomer.

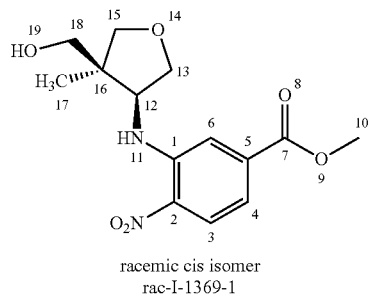 [SMILES: COC(=O)c1ccc([N+](=O)[O-])c(N[C@@H]2COC[C@]2(C)CO)c1]

racemic cis isomer
rac-I-1369-1

Methyl-rac-trans-3-((4-(hydroxymethyl)-4-methyltetrahydrofuran-3-yl)amino)-4-nitrobenzoate (rac-I-1371-1): The title compound was the later of two stereoisomers to elute during silica gel flash column chromatography. 1H NMR (400 MHz, CDCl3) δ 8.25 (d, J=8.9 Hz, 1H), 7.83 (d, J=1.7 Hz, 1H), 7.30 (d, J=1.6 Hz, 1H), 4.49-4.36 (m, 2H), 3.95 (d, J=15.9 Hz, 5H), 3.74-3.59 (m, 4H), 1.16 (s, 3H). Two-dimensional NOESY NMR identified a C17-CH₃ to N11-NH correlation and a very weak C12 C—H correlation with C17-CH₃ correlation to confirm relative stereochemistry as the trans diastereomer.

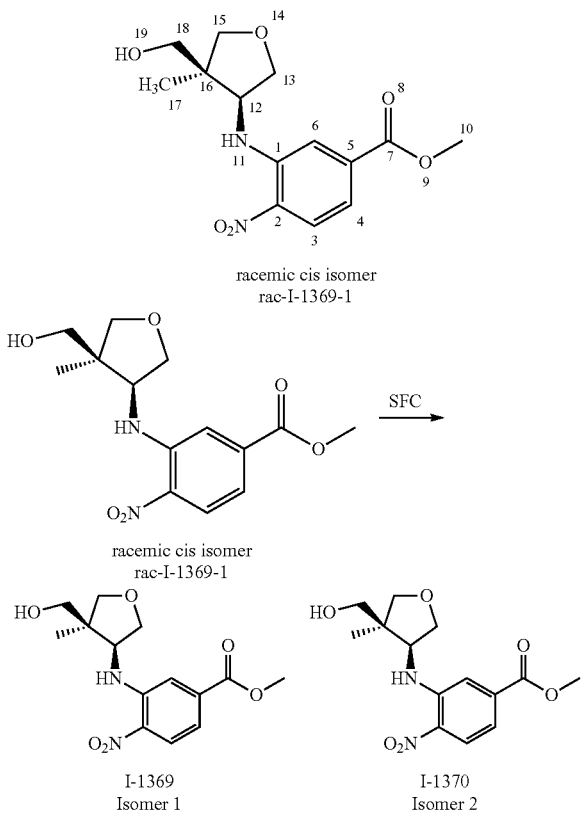

racemic cis isomer
rac-I-1369-1

I-1369
Isomer 1

I-1370
Isomer 2

Methyl 3-(((3S,4S)-4-(hydroxymethyl)-4-methyltetrahydrofuran-3-yl)amino)-4-nitrobenzoate (I-1369, I-1370, relative stereochemistry established): was obtained via preparative chiral SFC (Daicel Chiralpak AD-H column with EtOH/CO₂ eluent) which gave 2 distinct stereoisomers.

Methyl 3-(((3S,4S)-4-(hydroxymethyl)-4-methyltetrahydrofuran-3-yl)amino)-4-nitrobenzoate (I-1369, Isomer 1, relative stereochemistry established): The earlier-eluting of two stereoisomers.

Methyl 3-(((3S,4S)-4-(hydroxymethyl)-4-methyltetrahydrofuran-3-yl)amino)-4-nitrobenzoate (I-1370, Isomer 2, relative stereochemistry established): The later-eluting of two stereoisomers.

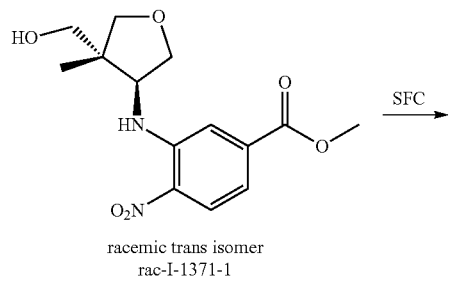

racemic trans isomer
rac-I-1371-1

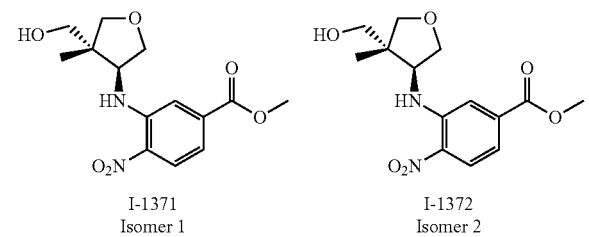

I-1371
Isomer 1

I-1372
Isomer 2

Methyl 3-(((3S,4R)-4-(hydroxymethyl)-4-methyltetrahydrofuran-3-yl)amino)-4-nitrobenzoate (I-1371, I-1372, relative stereochemistry established): was obtained via preparative chiral SFC (Daicel Chiralpak IC column with MeOH/CO₂ eluent) which gave 2 distinct stereoisomers.

Methyl 3-(((3S,4R)-4-(hydroxymethyl)-4-methyltetrahydrofuran-3-yl)amino)-4-nitrobenzoate (I-1371, Isomer 1, relative stereochemistry established): The earlier-eluting of two stereoisomers.

Methyl 3-(((3S,4R)-4-(hydroxymethyl)-4-methyltetrahydrofuran-3-yl)amino)-4-nitrobenzoate (I-1372, Isomer 2, relative stereochemistry established): The later-eluting of two stereoisomers.

Preparation of Intermediate I-1373 (Isomer 1):

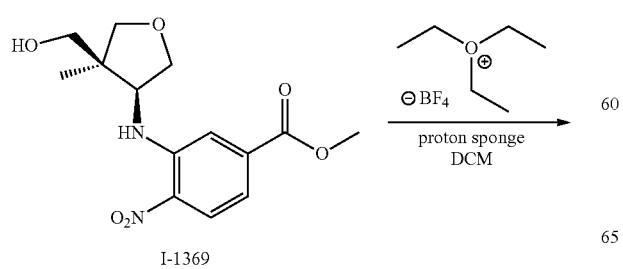

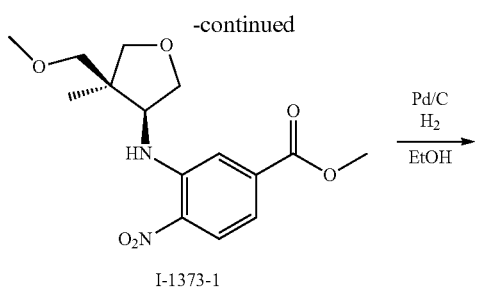

I-1373-1

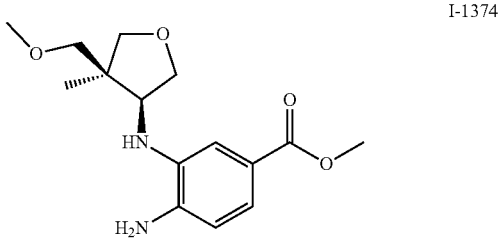

I-1373

Methyl 3-(((3S,4S)-4-(methoxymethyl)-4-methyltetrahydrofuran-3-yl)amino)-4-nitrobenzoate (I-1373-1, relative stereochemistry established): N1,N1,N8,N8-tetramethylnaphthalene-1,8-diamine (66.3 mg, 0.31 mmol) followed by Trimethyloxonium Tetrafluoroborate (43.9 mg, 0.34 mmol) were added to a solution of methyl 3-((4-(hydroxymethyl)-4-methyltetrahydrofuran-3-yl)amino)-4-nitrobenzoate (I-1369) (96 mg, 0.31 mmol) in DCM (3.0 mL, 2.0 M) at 0° C. The mixture was stirred at 25° C. for 16 h, then diluted with DCM, filtered and purified by column chromatography. ES/MS m/z: 325.1 (M+H⁺).

Methyl 4-amino-3-(((3S,4S)-4-(methoxymethyl)-4-methyltetrahydrofuran-3-yl)amino)benzoate (I-1373, Isomer 1, relative stereochemistry established): methyl 4-amino-3-(((3S,4S)-4-(methoxymethyl)-4-methyltetrahydrofuran-3-yl)amino)benzoate (relative stereochemistry established) was prepared in a manner as described for Intermediate I-107 using I-1373-1. ES/MS m/z: 295.2 (M+H⁺).

Preparation of Intermediate I-1374 (Isomer 2)

I-1374

Methyl 4-amino-3-(((3S,4S)-4-(methoxymethyl)-4-methyltetrahydrofuran-3-yl)amino)benzoate (I-1374, Isomer 2, relative stereochemistry established): The title compound was prepared in a manner as described for Intermediate I-1373, using Intermediate I-1370.

Preparation of Intermediate I-1375 (Isomer 1)

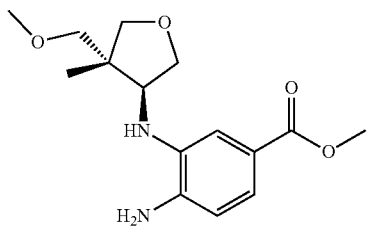

I-1375

Methyl 4-amino-3-(((3S,4R)-4-(methoxymethyl)-4-methyltetrahydrofuran-3-yl)amino)benzoate (I-1375, Isomer 1, relative stereochemistry established): The title compound was prepared in a manner as described for Intermediate I-1373, using Intermediate I-1371.

Preparation of Intermediate I-1376 (Isomer 2)

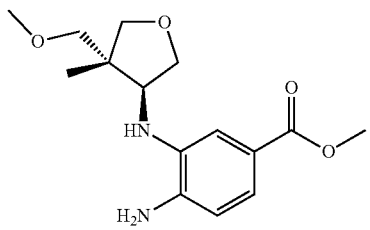

I-1376

Methyl 4-amino-3-(((3S,4R)-4-(methoxymethyl)-4-methyltetrahydrofuran-3-yl)amino)benzoate (I-1376, Isomer 2, relative stereochemistry established): The title compound was prepared in a manner as described for Intermediate I-1373, using Intermediate I-1372.

Preparation of Intermediate I-1377 (Isomer 1)

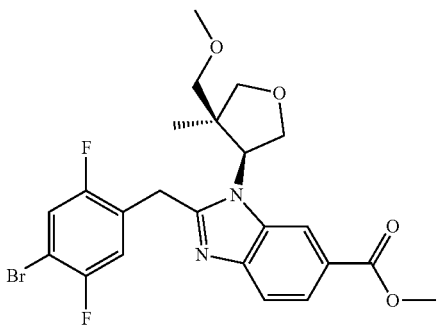

I-1377

Methyl 2-(4-bromo-2,5-difluorobenzyl)-1-((3S,4S)-4-(methoxymethyl)-4-methyltetrahydrofuran-3-yl)-1H-benzo[d]imidazole-6-carboxylate (Intermediate I-1377, Isomer 1, relative stereochemistry established): Methyl 2-(4-bromo-2,5-difluorobenzyl)-1-(4-(methoxymethyl)-4-methyltetrahydrofuran-3-yl)-1H-benzo[d]imidazole-6-carboxylate (I-1377) was prepared in a manner as described for Intermediate I-2 using 2-(4-bromo-2,5-difluoro-phenyl)acetic acid and Intermediate I-1373. ES/MS m/z: 509.2 (M+H$^+$).

Preparation of Intermediate I-1378 (Isomer 2)

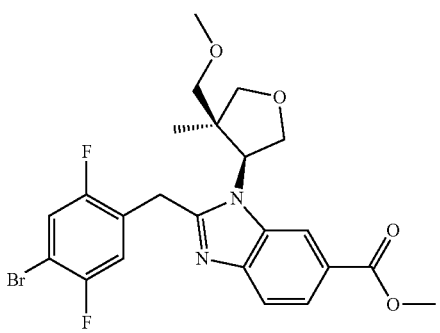

I-1378

Methyl 2-(4-bromo-2,5-difluorobenzyl)-1-((3S,4S)-4-(methoxymethyl)-4-methyltetrahydrofuran-3-yl)-1H-benzo[d]imidazole-6-carboxylate (Intermediate I-1378, Isomer 2, relative stereochemistry established): Methyl 2-(4-bromo-2,5-difluorobenzyl)-1-(4-(methoxymethyl)-4-methyltetrahydrofuran-3-yl)-1H-benzo[d]imidazole-6-carboxylate (I-1378) Intermediate I-2 using 2-(4-bromo-2,5-difluorophenyl)acetic acid and Intermediate I-1374. ES/MS: 509.0 (M+H$^+$).

Preparation of Intermediate I-1379 (prophetic, Isomer 1)

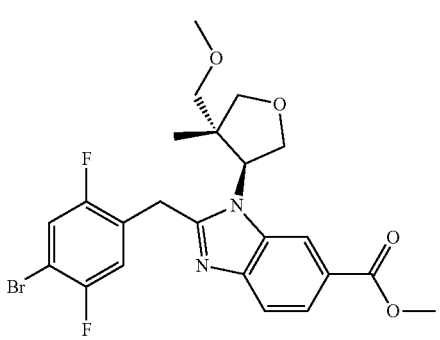

I-1379

Methyl 2-(4-bromo-2,5-difluorobenzyl)-1-((3S,4R)-4-(methoxymethyl)-4-methyltetrahydrofuran-3-yl)-1H-benzo[d]imidazole-6-carboxylate (Intermediate I-1379, Isomer 1, relative stereochemistry established): methyl 2-(4-bromo-2,5-difluorobenzyl)-1-(4-(methoxymethyl)-4-methyltetrahydrofuran-3-yl)-1H-benzo[d]imidazole-6-carboxylate (I-1379) can be prepared in a manner as described for Intermediate I-2 using 2-(4-bromo-2,5-difluoro-phenyl)acetic acid and Intermediate I-1375.

Preparation of Intermediate I-1380 (Isomer 2)

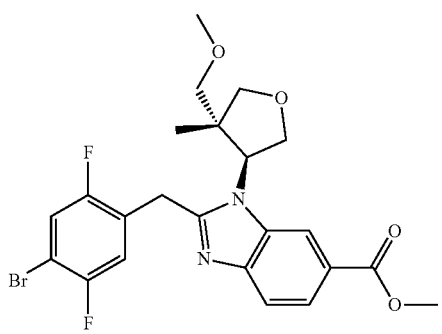

I-1380

Methyl 2-(4-bromo-2,5-difluorobenzyl)-1-((3S,4R)-4-(methoxymethyl)-4-methyltetrahydrofuran-3-yl)-1H-benzo[d]imidazole-6-carboxylate (Intermediate I-1380, Isomer 2, relative stereochemistry established): Methyl 2-(4-bromo-2,5-difluorobenzyl)-1-(4-(methoxymethyl)-4-methyltetrahydrofuran-3-yl)-1H-benzo[d]imidazole-6-carboxylate (I-1380) was prepared in a manner as described for Intermediate I-2 using 2-(4-bromo-2,5-difluoro-phenyl)acetic acid and Intermediate I-1376. ES/MS: 509.1 (M+H$^+$).

Preparation of Intermediate I-1381

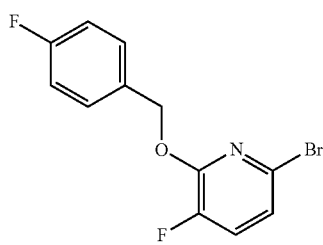

I-1381

6-bromo-3-fluoro-2-[(4-fluorophenyl)methoxy]pyridine (I-1381): 6-bromo-3-fluoro-2-[(4-fluorophenyl)methoxy]pyridine was prepared in a manner as described for Intermediate I-1129 substituting 1-(bromomethyl)-4-fluoro-benzene for 2-(bromomethyl)-3-fluoro-5-(trifluoromethyl)pyridine and 6-bromo-3-fluoro-pyridin-2-ol for 6-bromopyridin-2-ol. ES/MS: 301.2 (M+H$^+$).

Preparation of Intermediate I-1382

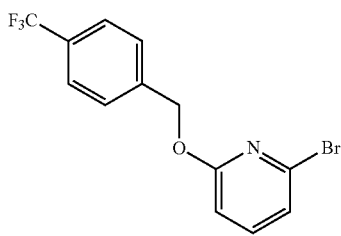

I-1382

2-bromo-6-[[4-(trifluoromethyl)phenyl]methoxy]pyridine (I-1382): 2-bromo-6-[[4-(trifluoromethyl)phenyl]methoxy]pyridine was prepared in a manner as described for Intermediate I-43 substituting (4-(trifluoromethyl)phenyl)methanol for (1-methylimidazol-4-yl)methanol. ES/MS: 334.0 (M+H$^+$).

Preparation of Intermediate I-1383

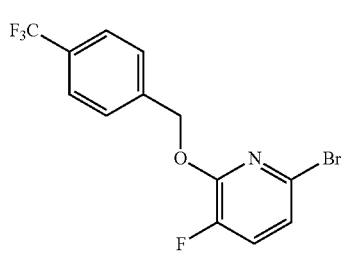

I-1383

6-bromo-3-fluoro-2-[[4-(trifluoromethyl)phenyl]methoxy]pyridine (I-1383): 6-bromo-3-fluoro-2-[[4-(trifluoromethyl)phenyl]methoxy]pyridine was prepared in a manner as described for Intermediate I-1129 substituting 1-(bromomethyl)-4-(trifluoromethyl)benzene for 2-(bromomethyl)-3-fluoro-5-(trifluoromethyl)pyridine and 6-bromo-3-fluoro-pyridin-2-ol for 6-bromopyridin-2-ol. ES/MS: 350.0 (M+H$^+$).

Preparation of Intermediate I-1384

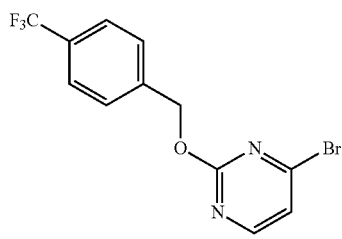

I-1384

4-bromo-2-[[4-(trifluoromethyl)phenyl]methoxy]pyrimidine (I-1384): 4-bromo-2-[[4-(trifluoromethyl)phenyl]methoxy]pyrimidine was prepared in a manner as described for Intermediate I-43 substituting (4-(trifluoromethyl)phenyl)methanol for (1-methylimidazol-4-yl)methanol and 4-bromo-2-fluoropyrimidine for 4-bromo-2-fluoropyridine. ES/MS: 334.0 (M+H$^+$).

Preparation of Intermediate I-1385

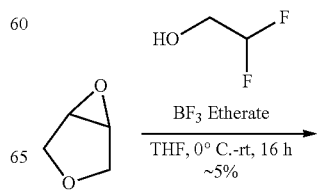

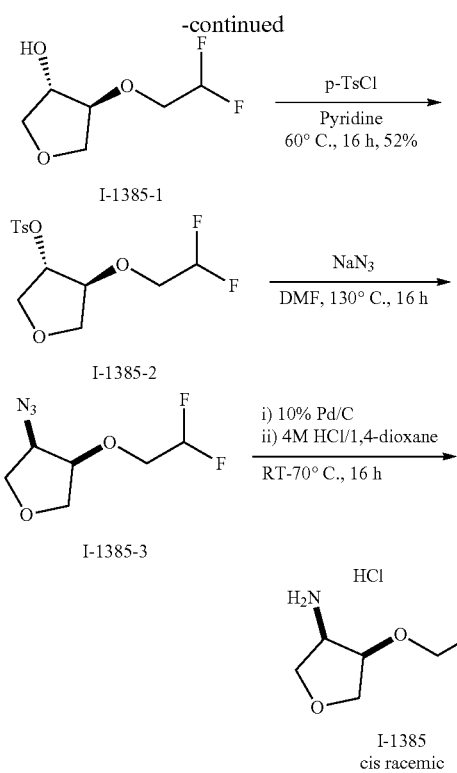

Racemic (3S,4S)-4-(2,2-difluoroethoxy)tetrahydrofuran-3-ol (I-1385-1): To a mixture of 3,6-dioxabicyclo[3.1.0]hexane (20.0 g, 1.0 equivalent) in DCM (200 mL) at 0° C. under argon atmosphere was added BF3-etherate (6.58 g, 0.2 equivalent). The resulting mixture was stirred at 0° C. for 20 min. Then 2,2-difluoroethan-1-ol (27.9 g, 1.2 equivalent) was added to the mixture at 0° C. The mixture was stirred for 16 h at RT, with monitoring by silica gel TLC (EtOAc/petroleum ether). The mixture was quenched with aqueous NaHCO3 solution and extracted with DCM twice. The combined organic layer was washed with brine solution, dried over Na2SO4 and evaporated under vacuum. Purification by silica gel flash column chromatography (ethyl acetate: petroleum ether) yielded the title compound. 1H NMR (400 MHz, CDCl3) δ 5.99-5.71 (m, 1H), 4.33-4.31 (m, 1H), 4.11-4.06 (m, 1H), 4.00-3.95 (m, 2H), 3.80-3.53 (m, 4H).

Racemic (3S,4S)-4-(2,2-difluoroethoxy)tetrahydrofuran-3-yl 4-methylbenzenesulfonate (I-1385-2): To a mixture of racemic (3S,4S)-4-(2,2-difluoroethoxy)tetrahydrofuran-3-ol (I-1385-1, 1.3 g, 1.0 equivalent) and pyridine (7.8 mL) was added p-TsCl (1.59 g, 1.2 equivalent) at 0° C. and then the resulting solution was stirred at 60° C. for 16 h, with monitoring by TLC (EtOAc/petroleum ether). The mixture was cooled to RT, evaporated under reduced pressure. Then the mixture was purified by silica gel flash column chromatography (ethyl acetate: petroleum ether) yielded the title compound. 1H NMR (400 MHz, CDCl3) δ 7.86 (d, 2H), 7.51 (d, 2H), 6.21-6.05 (m, 1H), 4.95-4.93 (m, 1H), 4.18-4.16 (m, 1H), 3.93-3.89 (m, 1H), 3.84-3.80 (m, 1H), 3.67-3.55 (m, 4H), 2.43 (s, 3H).

Racemic (3R,4R)-3-azido-4-(2,2-difluoroethoxy)tetrahydrofuran (I-1385-3): To a mixture of racemic (3S,4S)-4-(2,2-difluoroethoxy)tetrahydrofuran-3-yl 4-methylbenzenesulfonate (I-1385-2, 1.3 g, 1.0 equivalent) in DMF (9.1 mL) was added sodium azide (1.24 g, 5.0 equivalent) at RT. The resulting mixture was stirred at 130° C. for 16 hr., with monitoring by TLC (EtOAc/petroleum ether). The mixture was cooled to RT, quenched with ice cold water. The organic layer was extracted with diethyl ether twice. The combined organic layer was washed with brine solution, dried over Na2SO4. To the organic layer was added methanol (4V) and the resulting mixture was concentrated under vacuum (30° C., 350 mmHg) to remove most of diethyl ether to yield the title compound, which was used directly in the next step. 1H NMR (400 MHz, CDCl3) δ 6.31-6.02 (m, 1H), 4.40-4.36 (m, 1H), 4.16-4.12 (m, 1H), 3.89-3.80 (m, 4H), 3.71-3.61 (m, 2H).

Racemic (3R,4R)-4-(2,2-difluoroethoxy)tetrahydrofuran-3-amine (I-1385): To a mixture of racemic (3R,4R)-3-azido-4-(2,2-difluoroethoxy)tetrahydrofuran (I-1385-3, 1.22 g, 1.0 equivalent) in MeOH (20.4 mL) was added 10% Pd/C (0.2 g) The mixture was stirred under an atmosphere of hydrogen in a Parr apparatus (60) psi at RT for 16 hr, with monitoring by TLC (5% MeOH in DCM). The mixture was passed through a plug of celite and concentrated under reduced pressure. The mixture was diluted with DCM, then 4M HCl in 1,4-dioxane was added at 0° C. and stirred at RT for 1 h. The mixture was concentrated under reduced pressure and triturated with diethyl ether to yield the title compound. 1H NMR (400 MHz, DMSO-d6) δ 6.34-6.04 (m, 1H), 4.32-4.29 (m, 1H), 3.91-3.78 (m, 6H), 3.72-3.68 (m, 1H). ES/MS m/z 168.1 (M+H+).

Preparation of Intermediate I-1386

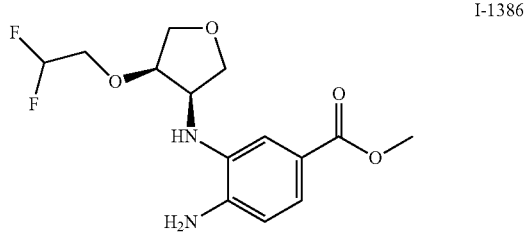 [SMILES: COC(=O)c1ccc(N)c(N[C@@H]2COC[C@@H]2OCC(F)F)c1]

Racemic methyl 4-amino-3-(((3R,4R)-4-(2,2-difluoroethoxy)tetrahydrofuran-3-yl)amino)benzoate (I-1386): racemic methyl 4-amino-3-(((3R,4R)-4-(2,2-difluoroethoxy)tetrahydrofuran-3-yl)amino)benzoate (relative stereochemistry known) was prepared in a manner as described for Intermediate I-1, using Intermediate I-1385. ES/MS m/z: 317.2 (M+H+).

Preparation of Intermediate I-1387

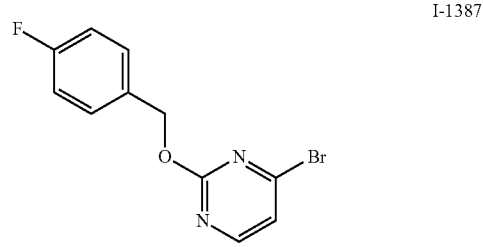 [SMILES: Fc1ccc(COc2nccc(Br)n2)cc1]

4-bromo-2-((4-fluorobenzyl)oxy)pyrimidine (I-1387): 4-bromo-2-((4-fluorobenzyl)oxy)pyrimidine was prepared in a manner as described for Intermediate I-43 substituting (4-fluorophenyl)methanol for (1-methylimidazol-4-yl)methanol and 4-bromo-2-fluoropyrimidine for 4-bromo-2-fluoropyridine. ES/MS: 283.0 (M+H⁺).

Preparation of Intermediate I-1395

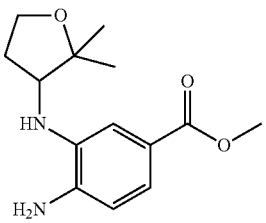

I-1395

Methyl 4-amino-3-((2,2-dimethyltetrahydrofuran-3-yl)amino)benzoate (I-1395): methyl 4-amino-3-((2,2-dimethyltetrahydrofuran-3-yl)amino)benzoate was prepared in a manner as described for Intermediate I-1, using 2,2-dimethyltetrahydrofuran-3-amine.

B. Compound Examples

Procedure 1: Example 1

Tert-butyl (S)-2-(4-(6-((4-cyano-2-fluorobenzyl)oxy)pyridin-2-yl)-2,5-difluorobenzyl)-1-(tetrahydrofuran-3-yl)-1H-indole-6-carboxylate: Tert-butyl (S)-4-amino-3-((tetrahydrofuran-3-yl)amino)benzoate (25 mg, 0.091 mmol), o-(7-Azabenzotriazol-1-yl)-N,N,N',N'-tetramethyluronium hexafluorophosphate (47 mg, 0.12 mmol), and DIPEA (0.04 mL, 0.25 mmol were added to a solution of 2-(4-(6-((4-cyano-2-fluorobenzyl)oxy)pyridin-2-yl)-2,5-difluorophenyl)acetic acid (33 mg, 0.083 mmol) in DMF (1 mL). The resulting solution was stirred at rt for 2 hrs. The mixture was then poured into H₂O (5 mL) and extracted with EtOAc (2×15 mL). The combined organic extracts were washed with brine (5 mL), dried over MgSO₄, and purified by silica gel chromatography (eluent: EtOAc/hexanes) to give desired product. The crude intermediate was then dissolved in acetic acid (1 mL) and heated to 60° C. for 3 hrs. The mixture was concentrated directly and purified by silica gel chromatography (eluent: EtOAc/hexanes): ES/MS: 641.6 (M+H⁺).

(S)-2-(4-(6-((4-cyano-2-fluorobenzyl)oxy)pyridin-2-yl)-2,5-difluorobenzyl)-1-(tetrahydrofuran-3-yl)-1H-benzo[d]imidazole-6-carboxylic acid (Example 1): 0.25 mL TFA was added to a solution of tert-butyl (S)-2-(4-(6-((4-cyano-2-fluorobenzyl)oxy)pyridin-2-yl)-2,5-difluorobenzyl)-1-(tetrahydrofuran-3-yl)-1H-indole-6-carboxylate (76 mg, 0.057 mmol) in DCM (2 mL). The solution was stirred at 40° C. for 1 hour. The mixture was further diluted with EtOAc (30 mL), washed with water (3×5 mL), concentrated and purified by RP-HPLC (eluent: water/MeCN 0.1% TFA). The combined fractions were then frozen and placed on a lyophilizer to provide Example 1. ES/MS: 585.3 (M+H⁺). 1H NMR (400 MHz, DMSO-d6) δ 8.43 (d, J=1.4 Hz, 1H), 7.97-7.85 (m, 3H), 7.83-7.71 (m, 3H), 7.68 (d, J=8.5 Hz,

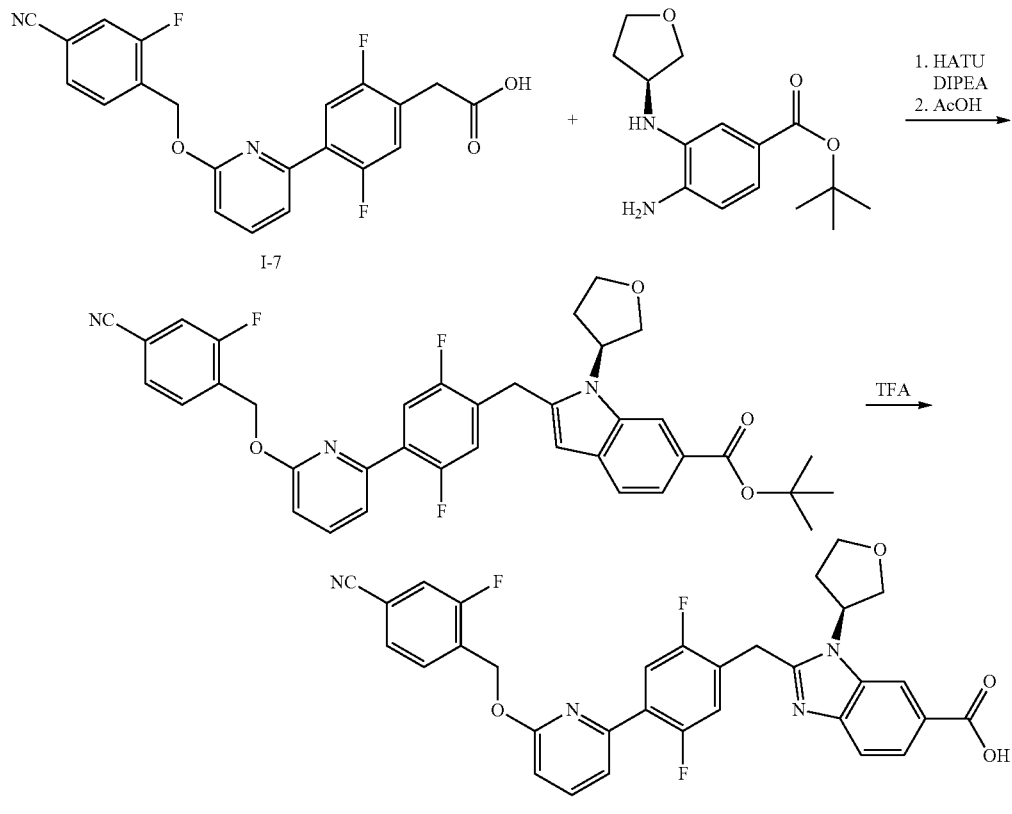

Example 1

1H), 7.53 (dd, J=7.5, 1.7 Hz, 1H), 7.40 (dd, J=11.5, 6.1 Hz, 1H), 7.00 (d, J=8.2 Hz, 1H), 5.60 (s, 2H), 5.58-5.49 (m, 1H), 4.58 (s, 2H), 4.31 (td, J=8.7, 2.8 Hz, 1H), 4.22 (dd, J=10.4, 2.8 Hz, 1H), 3.97 (dd, J=10.5, 7.7 Hz, 1H), 3.72 (td, J=9.3, 7.0 Hz, 1H), 2.23-2.06 (m, 1H).

Example 2: (S)-2-(4-(6-((4-cyano-2-fluorobenzyl) oxy)pyridin-2-yl)-2,5-difluorobenzyl)-1-(5-oxopyrrolidin-3-yl)-1H-benzo[d]imidazole-6-carboxylic acid (S)-2-(4-(6-((4-cyano-2-fluorobenzyl)oxy)pyridin-2-yl)-2,5-difluorobenzyl)-1-(5-oxopyrrolidin-3-yl)-1H-benzo[d]imidazole-6-carboxylic acid was prepared in a manner as described in Procedure 1. 1H NMR (400 MHz, DMSO) δ 8.22 (s, 1H), 8.09 (d, J=1.4 Hz, 1H), 7.97-7.82 (m, 3H), 7.81-7.71 (m, 3H), 7.68 (d, J=8.4 Hz, 1H), 7.54 (dd, J=7.5, 1.7 Hz, 1H), 7.38 (dd, J=11.5, 6.1 Hz, 1H), 7.00 (d, J=8.3 Hz, 1H), 5.68 (tt, J=10.0, 5.2 Hz, 1H), 5.60 (s, 2H), 4.51 (s, 2H), 3.89 (t, J=10.1 Hz, 1H), 3.62 (dd, J=10.9, 4.6 Hz, 1H), 2.86 (dd, J=17.9, 10.4 Hz, 1H), 2.62 (dd, J=17.8, 5.7 Hz, 1H).

Example 3: (R)-2-(4-(6-((4-cyano-2-fluorobenzyl) oxy)pyridin-2-yl)-2,5-difluorobenzyl)-1-(5-oxopyrrolidin-3-yl)-1H-benzo[d]imidazole-6-carboxylic acid (R)-2-(4-(6-((4-cyano-2-fluorobenzyl)oxy)pyridin-2-yl)-2,5-difluorobenzyl)-1-(5-oxopyrrolidin-3-yl)-1H-benzo[d]imidazole-6-carboxylic acid was prepared in a manner as described in Procedure 1. 1H NMR (400 MHz, DMSO) δ 8.22 (s, 1H), 8.09 (d, J=1.5 Hz, 1H), 7.96-7.82 (m, 3H), 7.81-7.71 (m, 3H), 7.68 (d, J=8.5 Hz, 1H), 7.54 (dd, J=7.6, 1.7 Hz, 1H), 7.38 (dd, J=11.4, 6.1 Hz, 1H), 7.00 (d, J=8.2 Hz, 1H), 5.68 (tt, J=10.1, 5.2 Hz, 1H), 5.60 (s, 2H), 4.51 (s, 2H), 3.89 (t, J=10.1 Hz, 1H), 3.61 (dd, J=11.0, 4.6 Hz, 1H), 2.86 (dd, J=17.9, 10.4 Hz, 1H), 2.62 (dd, J=17.9, 5.7 Hz, 1H).

Example 4: 2-(4-(6-((4-cyano-2-fluorobenzyl)oxy) pyridin-2-yl)-2,5-difluorobenzyl)-1-((1R,2S)-2-(difluoromethyl)cyclopropyl)-1H-benzo[d]imidazole-6-carboxylic acid 2-(4-(6-((4-cyano-2-fluorobenzyl)oxy)pyridin-2-yl)-2,5-difluorobenzyl)-1-((1R,2S)-2-(difluoromethyl)cyclopropyl)-1H-benzo[d]imidazole-6-carboxylic acid was prepared in a manner as described in Procedure 1. 1H NMR (400 MHz, Methanol-d4) δ 8.64-8.45 (m, 1H), 8.15 (td, J=9.0, 1.5 Hz, 1H), 7.91-7.78 (m, 2H), 7.78-7.66 (m, 2H), 7.66-7.48 (m, 3H), 7.33 (ddd, J=17.3, 11.2, 6.1 Hz, 1H), 7.09-6.83 (m, 1H), 6.16 (td, J=56.2, 4.3 Hz, 1H), 5.67-5.59 (m, 2H), 4.72 (d, J=3.1 Hz, 2H), 3.91 (q, J=5.4, 4.0 Hz, 1H), 2.36 (d, J=57.4 Hz, 1H), 1.94 (d, J=9.4 Hz, 1H), 1.86-1.75 (m, 1H).

Example 5: (R)-2-(4-(6-((4-cyano-2-fluorobenzyl) oxy)pyridin-2-yl)-2,5-difluorobenzyl)-1-(tetrahydrofuran-3-yl)-1H-benzo[d]imidazole-6-carboxylic acid (R)-2-(4-(6-((4-cyano-2-fluorobenzyl)oxy)pyridin-2-yl)-2,5-difluorobenzyl)-1-(tetrahydrofuran-3-yl)-1H-benzo[d]imidazole-6-carboxylic acid was prepared in a manner as described in Procedure 1. 1H NMR (400 MHz, DMSO-d6) δ 8.43 (d, J=1.4 Hz, 1H), 7.97-7.85 (m, 3H), 7.83-7.71 (m, 3H), 7.68 (d, J=8.5 Hz, 1H), 7.53 (dd, J=7.5, 1.7 Hz, 1H), 7.40 (dd, J=11.5, 6.1 Hz, 1H), 7.00 (d, J=8.2 Hz, 1H), 5.60 (s, 2H), 5.58-5.49 (m, 1H), 4.58 (s, 2H), 4.31 (td, J=8.7, 2.8 Hz, 1H), 4.22 (dd, J=10.4, 2.8 Hz, 1H), 3.97 (dd, J=10.5, 7.7 Hz, 1H), 3.72 (td, J=9.3, 7.0 Hz, 1H), 2.23-2.06 (m, 1H).

Example 6: 2-(4-(6-((4-cyano-2-fluorobenzyl)oxy) pyridin-2-yl)-2,5-difluorobenzyl)-1-cyclopentyl-1H-benzo[d]imidazole-6-carboxylic acid 2-(4-(6-((4-cyano-2-fluorobenzyl)oxy)pyridin-2-yl)-2,5-difluorobenzyl)-1-cyclopentyl-1H-benzo[d]imidazole-6-carboxylic acid was prepared in a manner as described in Procedure 1. 1H NMR (400 MHz, DMSO-d6) δ 8.18 (d, J=1.4 Hz, 1H), 7.97-7.85 (m, 3H), 7.83-7.68 (m, 4H), 7.53 (dd, J=7.5, 1.7 Hz, 1H), 7.41 (dd, J=11.5, 6.1 Hz, 1H), 7.00 (d, J=8.2 Hz, 1H), 5.60 (s, 2H), 5.16 (p, J=8.8 Hz, 1H), 4.58 (s, 2H), 2.22-2.08 (m, 4H), 2.06-1.94 (m, 2H), 1.89-1.69 (m, 2H).

Procedure 2: Example 7

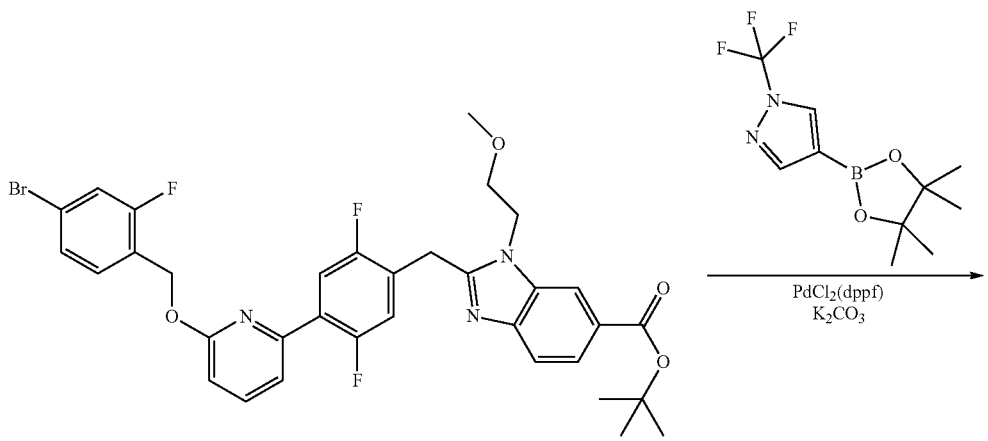

I-18

-continued

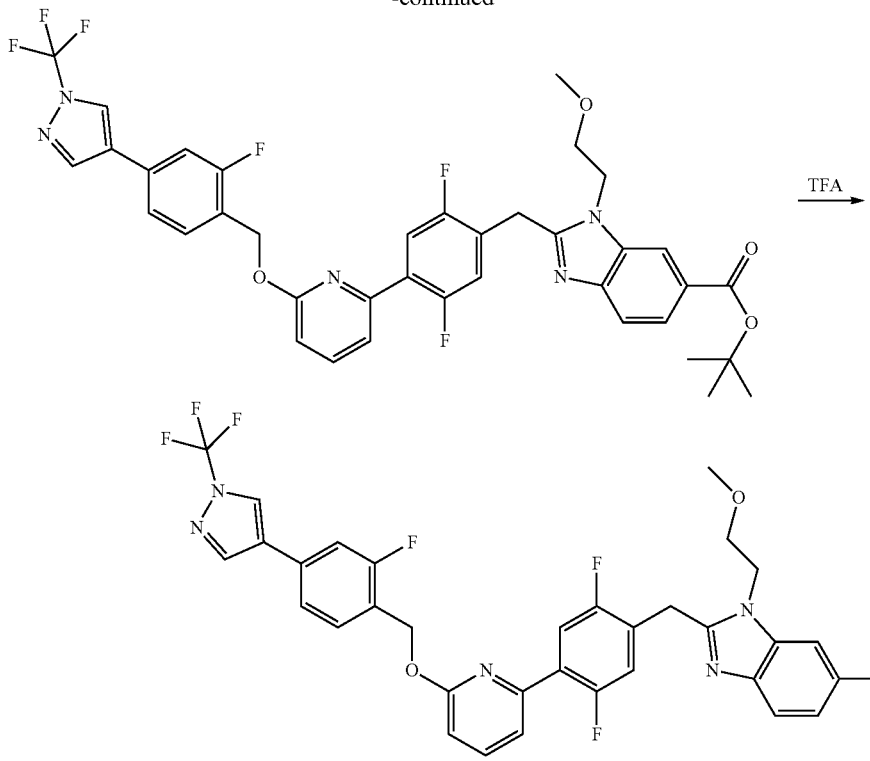

Example 7

Tert-butyl 2-(2,5-difluoro-4-(6-((2-fluoro-4-(1-(trifluoromethyl)-1H-pyrazol-4-yl)benzyl)oxy)pyridin-2-yl)benzyl)-1-(2-methoxyethyl)-1H-benzo[d]imidazole-6-carboxylate: A suspension of tert-butyl 2-[[4-[6-[(4-bromo-2-fluorophenyl)methoxy]-2-pyridyl]-2,5-difluoro-phenyl]methyl]-3-(2-methoxyethyl)benzimidazole-5-carboxylate (25 mg, 0.037 mmol), 4-(4,4,5,5-tetramethyl-1,3,2-dioxaborolan-2-yl)-1-(trifluoromethyl)pyrazole (15 mg, 0.058 mmol), 1,1'-Bis(di-phenylphosphino)ferrocene palladium dichloride (4.0 mg, 0.0054 mmol), and potassium carbonate (15 mg, 0.11 mmol) in 1,4-Dioxane anhydrous, 99.8% (1.0 mL) and $H_2O$ (0.50 mL) was degassed with argon for 5 min. The mixture was then heated at 100° C. for 30 min. Following this time, the mixture was diluted with EtOAc, and washed with brine. The organic extract was dried over sodium sulfate and purified by flash chromatography (eluent: EtOAc/hexanes) to give the title compound. 1H NMR (400 MHz, Chloroform-d) δ 8.09-7.99 (m, 3H), 7.96 (dd, J=8.5, 1.5 Hz, 1H), 7.87 (dd, J=10.7, 6.3 Hz, 1H), 7.77 (d, J=8.5 Hz, 1H), 7.68 (t, J=7.8 Hz, 1H), 7.59 (t, J=7.7 Hz, 1H), 7.50 (dd, J=7.4, 1.5 Hz, 1H), 7.37-7.20 (m, 2H), 7.08 (dd, J=11.3, 6.0 Hz, 1H), 6.82 (d, J=8.2 Hz, 1H), 5.57 (s, 2H), 4.46 (s, 2H), 4.38 (t, J=5.2 Hz, 2H), 3.69 (t, J=5.2 Hz, 2H), 3.28 (s, 3H), 1.65 (s, 9H).

2-(2,5-difluoro-4-(6-((2-fluoro-4-(1-(trifluoromethyl)-1H-pyrazol-4-yl)benzyl)oxy)pyridin-2-yl)benzyl)-1-(2-methoxyethyl)-1H-benzo[d]imidazole-6-carboxylic acid: To a solution of tert-butyl 2-[[2,5-difluoro-4-[6-[[2-fluoro-4-[1-(trifluoromethyl)pyrazol-4-yl]phenyl]methoxy]-2-pyridyl]phenyl]methyl]-3-(2-methoxyethyl)benzimidazole-5-carboxylate (22.7 mg, 0.0308 mmol) in DCM (3 mL), was added 2,2,2-trifluoroacetic acid (0.103 mL, 1.35 mmol). The mixture was stirred at 40° C. for 1 hr. After 1 hr. more TFA (100 uL) was added and the mixture was heated until completion (3 hr.). The crude residue was concentrated to dryness and purified by RP-HPLC (eluent: MeCN/$H_2O$). The resulting product fractions were diluted with EtOAc and neutralized with sodium bicarbonate solution. The organic extract was dried over sodium sulfate, filtered and concentrated to yield Example 7. ES/MS: 682.2 (M+H$^+$); 1H NMR (400 MHz, DMSO-d6) δ 9.08 (s, 1H), 8.54 (s, 1H), 8.20 (s, 1H), 7.91-7.82 (m, 2H), 7.79 (dd, J=8.4, 1.6 Hz, 1H), 7.73 (d, J=11.5 Hz, 1H), 7.67-7.54 (m, 3H), 7.52 (d, J=7.3 Hz, 1H), 7.38 (dd, J=11.7, 6.1 Hz, 1H), 6.96 (d, J=8.2 Hz, 1H), 6.53 (s, 1H), 5.53 (s, 2H), 4.59 (t, J=5.1 Hz, 2H), 4.44 (s, 2H), 3.68 (t, J=5.1 Hz, 2H), 3.21 (s, 3H).

Procedure 3: Example 8

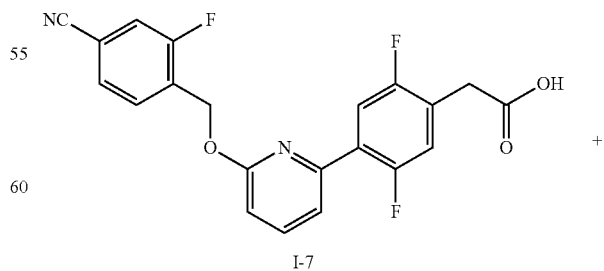

I-7

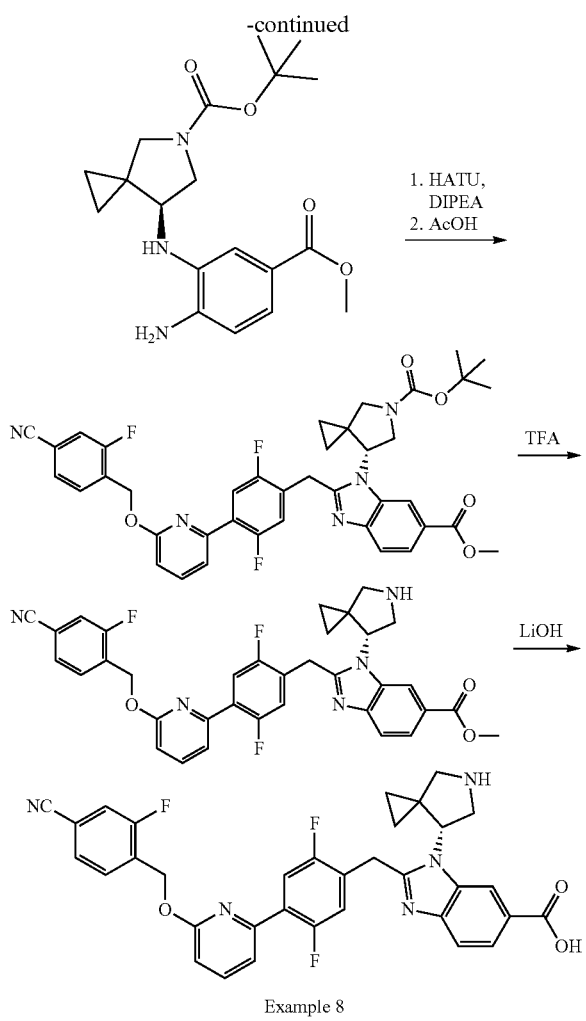

Example 8

Methyl (R)-1-(5-(tert-butoxycarbonyl)-5-azaspiro[2.4]heptan-7-yl)-2-(4-(6-((4-cyano-2-fluorobenzyl)pyridin-2-yl)-2,5-difluorobenzyl)-1H-indole-6-carboxylate: N,N-Diisopropylethylamine (0.173 mL, 0.995 mmol) was added to a solution of 2-[4-[6-[(4-cyano-2-fluoro-phenyl)methoxy]-2-pyridyl]-2,5-difluoro-phenyl]acetic acid (130 mg, 0.326 mmol), tert-butyl (7R)-7-(2-amino-5-methoxycarbonyl-anilino)-5-azaspiro[2.4]heptane-5-carboxylate (122 mg, 0.338 mmol), and o-(7-Azabenzotriazol-1-yl)-N,',N',N'-tetramethyluronium hexafluorophosphate (184 mg, 0.484 mmol) in DMF (3 mL). The solution was stirred overnight at rt. Following this time, the solution was diluted with EtOAc and washed with 5% LiCl, saturated NaHCO₃, and brine. The organic extract was dried over sodium sulfate. The crude product was diluted with DCE (5 mL) and added acetic acid (1.26 mL, 22.0 mmol). The mixture was heated at 60° C. overnight. The next day the mixture was stirred at 80° C. until completion (8 hr.). The mixture was diluted with DCM and neutralized carefully with NaHCO₃. The organic extract was dried over sodium sulfate. The crude residue was purified by flash chromatography (eluent: EtOAc/hexanes) to yield desired product. 19F NMR (376 MHz, Chloroform-d) δ −115.41 (t, J=8.2 Hz), −119.67, −124.02.

Methyl (R)-2-(4-(6-((4-cyano-2-fluorobenzyl)oxy)pyridin-2-yl)-2,5-difluorobenzyl)-1-(5-azaspiro[2.4]heptan-7-yl)-1H-indole-6-carboxylate: A solution of methyl 3-[(7R)-5-tert-butoxycarbonyl-5-azaspiro[2.4]heptan-7-yl]-2-[[4-[6-[(4-cyano-2-fluoro-phenyl)methoxy]-2-pyridyl]-2,5-difluoro-phenyl]methyl]benzimidazole-5-carboxylate (60.5 mg, 0.0836 mmol) and 2,2,2-trifluoroacetic acid (0.318 mL, 4.18 mmol) in DCM (5 mL) was stirred at rt for 4 hr. Following this time, the mixture was diluted with EtOAc and neutralized carefully with NaHCO₃. The organic extract was dried over sodium sulfate. The extract was then concentrated and carried onto the next step without purification. ES/MS: 624.2 (M+H⁺);

(R)-2-(4-(6-((4-cyano-2-fluorobenzyl)oxy)pyridin-2-yl)-2,5-difluorobenzyl)-1-(5-azaspiro[2.4]heptan-7-yl)-1H-indole-6-carboxylic acid: A solution of methyl 3-[(7R)-5-azaspiro[2.4]heptan-7-yl]-2-[[4-[6-[(4-cyano-2-fluoro-phenyl)methoxy]-2-pyridyl]-2,5-difluoro-phenyl]methyl]benzimidazole-5-carboxylate (16.0 mg, 0.0257 mmol) and Lithium hydroxide, monohydrate (300 mmol/L, 0.257 mL, 0.0770 mmol) in CH₃CN (3 mL) in a 40 mL glass vial was heated at 100° C. until completion (2 h). The mixture was diluted with EtOAc and brine. Next, 0.110 mL 1M citric acid was added to the mixture. The organic extract was dried over sodium sulfate, filtered and concentrated. Purified by RP-HPLC (eluent: MeCN/H₂O). The resulting product fractions were diluted with EtOAc and neutralized with sodium bicarbonate solution. The organic extract was dried over sodium sulfate, filtered and concentrated to give Example 8. ES/MS: 610.2 (M+H⁺); 1H NMR (400 MHz, DMSO-d6) δ 8.42 (s, 1H), 7.97-7.85 (m, 2H), 7.82-7.67 (m, 4H), 7.63 (d, J=8.4 Hz, 1H), 7.53 (dd, J=7.7, 1.6 Hz, 1H), 7.31 (dd, J=11.5, 6.2 Hz, 1H), 7.00 (d, J=8.3 Hz, 1H), 5.60 (s, 2H), 5.07 (s, 1H), 4.41 (s, 2H), 3.68 (t, J=10.4 Hz, 2H), 3.14 (d, J=11.0 Hz, 2H), 0.83 (d, J=23.4 Hz, 2H), 0.58 (m, 2H).

Example 9: (S)-2-(4-(6-((4-cyano-2-fluorobenzyl)oxy)pyridin-2-yl)-2,5-difluorobenzyl)-1-(5-azaspiro[2.4]heptan-7-yl)-1H-benzo[d]imidazole-6-carboxylic acid (S)-2-(4-(6-((4-cyano-2-fluorobenzyl)oxy)pyridin-2-yl)-2,5-difluorobenzyl)-1-(5-azaspiro[2.4]heptan-7-yl)-1H-benzo[d]imidazole-6-carboxylic acid was prepared in a manner as described in Procedure 3. 1H NMR (400 MHz, DMSO-d6) δ 8.48 (s, 1H), 7.98-7.81 (m, 2H), 7.77 (ddd, J=16.8, 8.1, 1.5 Hz, 5H), 7.62 (d, J=8.5 Hz, 1H), 7.57-7.45 (m, 1H), 7.30 (d, J=10.5 Hz, 1H), 6.99 (d, J=8.3 Hz, 1H), 6.54 (s, OH), 5.60 (s, 2H), 5.40 (s, OH), 5.01 (s, 1H), 4.40 (s, 2H), 3.60 (s, 1H), 3.11-2.99 (m, 1H), 0.76 (d, J=8.8 Hz, 1H), 0.58 (s, 3H), −0.06 (s, 1H).

Example 10: 2-(4-(6-((4-cyano-2-fluorobenzyl)oxy)pyridin-2-yl)-2,5-difluorobenzyl)-1-((3S,4S)-4-methoxypyrrolidin-3-yl)-1H-benzo[d]imidazole-6-carboxylic acid 2-(4-(6-((4-cyano-2-fluorobenzyl)oxy)pyridin-2-yl)-2,5-difluorobenzyl)-1-((3 S,4S)-4-methoxypyrrolidin-3-yl)-1H-benzo[d]imidazole-6-carboxylic acid was prepared in a manner as described in Procedure 3. 1H NMR (400 MHz, DMSO-d6) δ 9.34 (s, 2H), 8.27 (d, J=1.4 Hz, 1H), 7.99-7.84 (m, 4H), 7.83-7.67 (m, 5H), 7.53 (dd, J=7.5, 1.7 Hz, 1H), 7.01 (d, J=8.3 Hz, 1H), 5.60 (s, 2H), 5.28 (td, J=10.2, 7.9 Hz, 1H), 4.68 (q, J=7.0 Hz, 1H), 4.56-4.34 (m, 2H), 3.34 (d, J=11.4 Hz, 1H), 3.15 (s, 3H).

Example 11: (R)-2-(4-(6-((4-cyano-2-fluorobenzyl)oxy)pyridin-2-yl)-2,5-difluorobenzyl)-1-(4,4-dimethyltetrahydrofuran-3-yl)-4-fluoro-1H-benzo[d]imidazole-6-carboxylic acid (S)-2-(4-(6-((4-cyano-2-fluorobenzyl)oxy)pyridin-2-yl)-2,5-difluorobenzyl)-1-(4,4-dimethyltetrahydrofuran-3-yl)-

4-fluoro-1H-benzo[d]imidazole-6-carboxylic acid was prepared in a manner as described in Procedure 3. 1H NMR (400 MHz, DMSO) δ 13.09 (s, 1H), 8.35 (s, 1H), 7.96-7.86 (m, 2H), 7.83-7.70 (m, 3H), 7.59-7.42 (m, 3H), 7.00 (d, J=8.2 Hz, 1H), 5.61 (s, 2H), 5.03 (d, J=6.6 Hz, 1H), 4.59-4.49 (m, 2H), 4.48-4.35 (m, 2H), 3.75 (q, J=8.7 Hz, 2H), 1.34 (s, 3H), 0.61 (s, 3H).

Example 12: (S)-2-(4-(6-((4-cyano-2-fluorobenzyl)oxy)pyridin-2-yl)-2,5-difluorobenzyl)-1-(4,4-dimethyltetrahydrofuran-3-yl)-4-fluoro-1H-benzo[d]imidazole-6-carboxylic acid (R)-2-(4-(6-((4-cyano-2-fluorobenzyl)oxy)pyridin-2-yl)-2,5-difluorobenzyl)-1-(4,4-dimethyltetrahydrofuran-3-yl)-4-fluoro-1H-benzo[d]imidazole-6-carboxylic acid was prepared in a manner as described in Procedure 3. 1H NMR (400 MHz, DMSO) δ 13.10 (s, 1H), 8.35 (s, 1H), 7.96-7.86 (m, 2H), 7.83-7.70 (m, 3H), 7.59-7.48 (m, 2H), 7.46 (dd, J=11.4, 6.1 Hz, 1H), 7.00 (d, J=8.2 Hz, 1H), 5.61 (s, 2H), 5.03 (d, J=6.5 Hz, 1H), 4.59-4.49 (m, 2H), 4.48-4.35 (m, 2H), 3.75 (q, J=8.7 Hz, 2H), 1.33 (s, 3H), 0.61 (s, 3H).

Example 13: 4-bromo-2-(4-(6-((4-cyano-2-fluorobenzyl)oxy)pyridin-2-yl)-2,5-difluorobenzyl)-1-(4,4-dimethyltetrahydrofuran-3-yl)-1H-benzo[d]imidazole-6-carboxylic acid 4-bromo-2-(4-(6-((4-cyano-2-fluorobenzyl)oxy)pyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 3. 1H NMR (400 MHz, Methanol-d4) δ 8.71 (s, 1H), 8.17 (d, J=1.2 Hz, 1H), 7.90-7.67 (m, 3H), 7.66-7.47 (m, 3H), 7.19 (dd, J=11.5, 6.0 Hz, 1H), 6.92 (d, J=8.2 Hz, 1H), 5.63 (s, 2H), 4.55 (dd, J=11.4, 1.9 Hz, 3H), 4.44 (dd, J=11.3, 6.8 Hz, 1H), 3.93 (d, J=8.9 Hz, 1H), 3.78 (d, J=8.8 Hz, 1H), 3.37-3.34 (m, 2H), 1.30 (s, 3H), 0.61 (s, 3H).

Procedure 4: Example 14

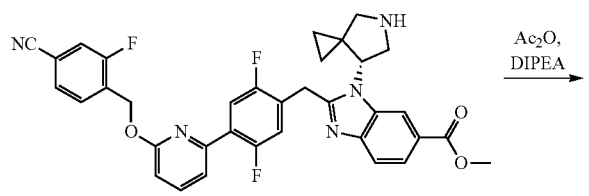

Ac₂O, DIPEA

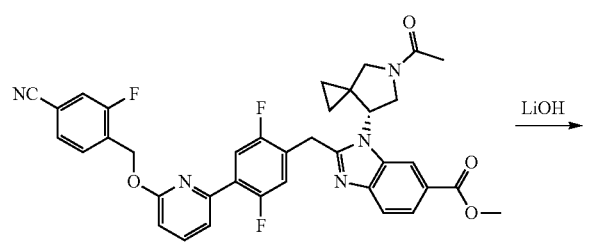

LiOH

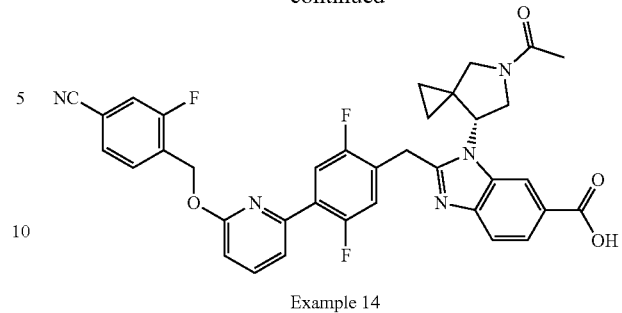

Example 14

Methyl (R)-1-(5-acetyl-5-azaspiro[2.4]heptan-7-yl)-2-(4-(6-((4-cyano-2-fluorobenzyl)oxy)pyridin-2-yl)-2,5-difluorobenzyl)-1H-indole-6-carboxylate: Acetic anhydride (1000 mmol/L in DCM, 0.0696 mL, 0.0696 mmol) was added to a solution of methyl 3-[(7R)-5-azaspiro[2.4]heptan-7-yl]-2-[[4-[6-[(4-cyano-2-fluoro-phenyl)methoxy]-2-pyridyl]-2,5-difluoro-phenyl]methyl]benzimidazole-5-carboxylate, see Procedure 3, (34.7 mg, 0.0556 mmol) and N,N-Diisopropylethylamine (0.0291 mL, 0.167 mmol) in DCM (3 mL). The mixture was stirred overnight at rt. Following this time, the mixture was diluted with brine and EtOAc. The organic extract was dried over sodium sulfate. The crude residue was purified by flash chromatography (eluent: EtOAc/hexanes) to yield desired product. ES/MS: 666.2 (M+H⁺).

(R)-1-(5-acetyl-5-azaspiro[2.4]heptan-7-yl)-2-(4-(6-((4-cyano-2-fluorobenzyl)oxy)pyridin-2-yl)-2,5-difluorobenzyl)-1H-indole-6-carboxylic acid (Example 14): In a 40 mL glass vial a solution of methyl 3-[(7R)-5-acetyl-5-azaspiro[2.4]heptan-7-yl]-2-[[4-[6-[(4-cyano-2-fluoro-phenyl)methoxy]-2-pyridyl]-2,5-difluoro-phenyl]methyl]benzimidazole-5-carboxylate (23.7 mg, 0.0356 mmol) and lithium hydroxide, monohydrate (300 mmol/L, 0.356 mL, 0.107 mmol) in CH₃CN (3 mL) was heated at 100° C. until completion (20 min). Upon completion, the solution was diluted with EtOAc and brine, followed by the addition of 0.110 mL 1M citric acid. The organic extract was dried over sodium sulfate, filtered and concentrated. Purified by RP-HPLC (eluent: MeCN/H₂O). The resulting product fractions were diluted with EtOAc and neutralized with sodium bicarbonate solution. The organic extract was dried over sodium sulfate, filtered and concentrated to yield Example 14. ES/MS: 652.2 (M+H⁺); 1H NMR (400 MHz, DMSO-d6) δ 8.06 (s, 1H), 7.96-7.86 (m, 2H), 7.83-7.67 (m, 4H), 7.64-7.55 (m, 1H), 7.54 (dd, J=7.5, 1.6 Hz, 1H), 7.40 (dd, J=11.5, 6.1 Hz, 1H), 7.00 (d, J=8.3 Hz, 1H), 5.34 (s, 1H), 5.19 (d, J=8.0 Hz, 1H), 4.35 (dt, J=28.0, 16.9 Hz, 3H), 4.23-4.07 (m, 1H), 4.07-3.82 (m, 2H), 3.82-3.53 (m, 1H), 2.10 (s, 2H), 2.03 (s, 1H), 1.07-0.78 (m, 2H), 0.78-0.53 (m, 1H), 0.29-0.04 (m, 1H).

Example 15: (S)-1-(5-acetyl-5-azaspiro[2.4]heptan-7-yl)-2-(4-(6-((4-cyano-2-fluorobenzyl)oxy)pyridin-2-yl)-2,5-difluorobenzyl)-1H-benzo[d]imidazole-6-carboxylic acid (S)-1-(5-acetyl-5-azaspiro[2.4]heptan-7-yl)-2-(4-(6-((4-cyano-2-fluorobenzyl)oxy)pyridin-2-yl)-2,5-difluorobenzyl)-1H-benzo[d]imidazole-6-carboxylic acid was prepared in a manner described in Procedure 4. 1H NMR (400 MHz, DMSO-d6) δ 12.79 (s, 1H), 8.12 (s, OH), 8.06 (d, J=1.4 Hz, 1H), 7.96-7.84 (m, 2H), 7.83-7.66 (m, 4H), 7.63 (dd, J=8.5, 3.3 Hz, 1H), 7.54 (dd, J=7.5, 1.6 Hz, 1H), 7.40 (dd, J=11.5, 6.1 Hz, 1H), 7.00 (d, J=8.2 Hz, 1H), 5.60 (s, 2H), 5.34 (s, OH), 5.19 (d, J=8.0 Hz, 1H), 4.63-4.22 (m, 3H), 4.19-4.05 (m, 1H), 3.99 (dd, J=13.5, 3.3 Hz, 1H), 3.92 (d, J=10.7 Hz, 1H), 3.82-3.46 (m, 2H), 2.10 (s, 2H), 2.03 (s, 1H), 1.08-0.75 (m, 2H), 0.71 (dd, J=10.2, 5.3 Hz, 1H), 0.17 (ddt, J=16.4, 11.2, 5.8 Hz, 1H).

Example 16: 1-((3S,4S)-1-acetyl-4-methoxypyrrolidin-3-yl)-2-(4-(6-((4-cyano-2-fluorobenzyl)oxy)pyridin-2-yl)-2,5-difluorobenzyl)-1H-benzo[d]imidazole-6-carboxylic acid 1-((3S,4S)-1-acetyl-4-methoxypyrrolidin-3-yl)-2-(4-(6-((4-cyano-2-fluorobenzyl)oxy)pyridin-2-yl)-2,5-difluorobenzyl)-1H-benzo[d]imidazole-6-carboxylic acid was prepared in a manner described in Procedure 4. 1H NMR (400 MHz, DMSO-d6) δ 8.12 (dd, J=37.9, 1.4 Hz, 1H), 7.96-7.81 (m, 3H), 7.79-7.71 (m, 3H), 7.68 (d, J=8.5 Hz, 1H), 7.56-7.51 (m, 1H), 7.43-7.33 (m, 1H), 7.00 (d, J=8.3 Hz, 1H), 5.60 (s, 2H), 5.33 (dq, J=27.6, 8.0 Hz, 1H), 4.55 (dd, J=13.1, 6.1 Hz, 2H), 4.43 (dd, J=16.8, 5.7 Hz, 1H), 4.24-4.07 (m, 1H), 4.07-3.93 (m, 1H), 3.41 (ddd, J=84.8, 11.4, 6.6 Hz, 1H), 3.17 (d, J=5.9 Hz, 3H), 2.05 (d, J=24.1 Hz, 3H).

Example 17: 1-((3R,4S)-4-acetamidotetrahydrofuran-3-yl)-2-(4-(6-((4-cyano-2-fluorobenzyl)oxy)pyridin-2-yl)-2,5-difluorobenzyl)-1H-benzo[d]imidazole-6-carboxylic acid 1-((3R,4S)-4-acetamidotetrahydrofuran-3-yl)-2-(4-(6-((4-cyano-2-fluorobenzyl)oxy)pyridin-2-yl)-2,5-difluorobenzyl)-1H-benzo[d]imidazole-6-carboxylic acid was prepared in a manner as described in Procedure 4. Obtained as a mixture of enantiomers. 1H NMR (400 MHz, DMSO-d6) δ 8.25 (s, 1H), 8.00 (s, 1H), 7.97-7.86 (m, 4H), 7.76 (m, 3H), 7.54 (d, J=8.4 Hz, 2H), 6.99 (d, J=8.2 Hz, 2H), 5.64 (s, 2H), 4.64 (d, J=17.2 Hz, 5H), 4.53 (d, J=16.0 Hz, 3H).

Example 18: 1-((3S,3aR,6aS)-5-acetylhexahydro-2H-furo[2,3-c]pyrrol-3-yl)-2-(4-(6-((4-cyano-2-fluorobenzyl)oxy)pyridin-2-yl)-2,5-difluorobenzyl)-1H-benzo[d]imidazole-6-carboxylic acid 1-((3S,3aR,6aS)-5-acetylhexahydro-2H-furo[2,3-c]pyrrol-3-yl)-2-(4-(6-((4-cyano-2-fluorobenzyl)oxy)pyridin-2-yl)-2,5-difluorobenzyl)-1H-benzo[d]imidazole-6-carboxylic acid was prepared in a manner described in Procedure 4. 1H NMR (400 MHz, DMSO-d6) δ 8.57 (dd, J=15.4, 1.4 Hz, 1H), 7.95-7.85 (m, 2H), 7.84-7.68 (m, 4H), 7.63 (dd, J=8.5, 7.0 Hz, 1H), 7.54 (dt, J=7.5, 1.9 Hz, 1H), 7.44 (dt, J=11.3, 5.4 Hz, 1H), 7.00 (dd, J=8.3, 1.9 Hz, 1H), 5.66-5.52 (m, 3H), 4.76-4.57 (m, 2H), 4.57-4.45 (m, 3H), 4.13-4.05 (m, 2H), 4.00 (d, J=13.2 Hz, 0H), 3.89 (d, J=12.4 Hz, 1H), 3.55 (dd, J=12.5, 4.6 Hz, 1H), 3.40 (d, J=9.1 Hz, 0H), 3.28 (t, J=9.9 Hz, 0H), 3.21-3.06 (m, 1H), 2.76 (dd, J=12.9, 9.8 Hz, 1H), 2.70-2.57 (m, 1H), 2.42-2.31 (m, 1H), 1.74 (s, 3H), 0.89 (s, 1H).

Procedure 5: Example 19

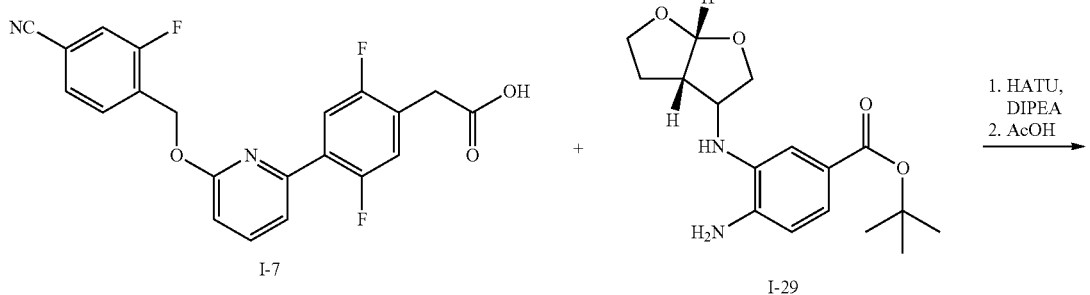

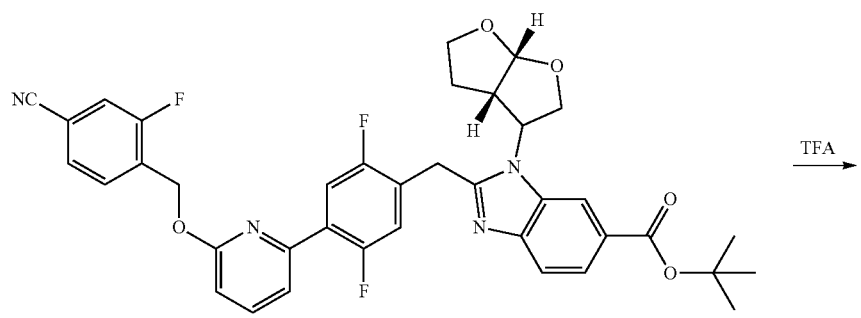

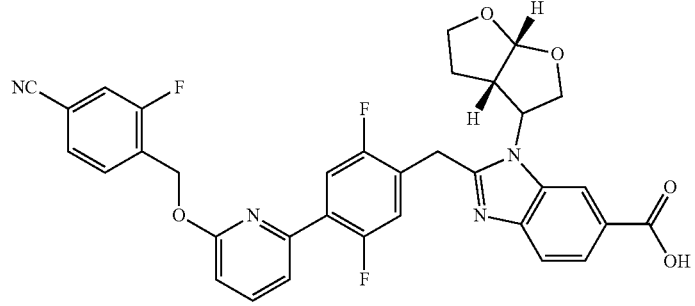

Example 19

Tert-butyl 2-(4-(6-((4-cyano-2-fluorobenzyl)oxy)pyridin-2-yl)-2,5-difluorobenzyl)-1-((3aS,6aR)-hexahydrofuro[2,3-b]furan-3-yl)-1H-indole-6-carboxylate: To a solution of 2-[4-[6-[(4-cyano-2-fluoro-phenyl)methoxy]-2-pyridyl]-2,5-difluoro-phenyl]acetic acid (120 mg, 0.301 mmol), tert-butyl 3-[[(3aS,4S,6aR)-2,3,3a,4,5,6a-hexahydrofuro[2,3-b]furan-4-yl]amino]-4-amino-benzoate (102 mg, 0.318 mmol), and o-(7-Azabenzotriazol-1-yl)-N,N,N',N'-tetramethyluronium hexafluorophosphate (170 mg, 0.447 mmol) in DMF (3 mL), was added N,N-Diisopropylethylamine purified by redistillation, 99.5% (0.160 mL, 0.919 mmol). Next, the solution was stirred overnight at rt. Following this time, the solution was diluted with EtOAc and washed with 5% LiCl, saturated NaHCO₃, and brine. The organic extract was dried over sodium sulfate. The crude product was diluted with DCE (5 mL) and acetic acid was added (1.26 mL, 22.0 mmol). The mixture was heated at 60° C. overnight. Following this time, the mixture was increased to 80° C. until completion (8 hr.). The mixture was diluted with DCM and neutralized carefully with NaHCO₃. The organic extract was dried over sodium sulfate. The crude residue was purified by flash chromatography (eluent: EtOAc/hexanes) to yield desired product. ES/MS: 683.2 (M+H⁺).

2-(4-(6-((4-cyano-2-fluorobenzyl)oxy)pyridin-2-yl)-2,5-difluorobenzyl)-1-((3aS,6aR)-hexahydrofuro[2,3-b]furan-3-yl)-1H-indole-6-carboxylic acid: To a solution of tert-butyl 3-[(3aS,4S,6aR)-2,3,3a,4,5,6a-hexahydrofuro[2,3-b]furan-4-yl]-2-[[4-[6-[(4-cyano-2-fluoro-phenyl)methoxy]-2-pyridyl]-2,5-difluoro-phenyl]methyl]benzimidazole-5-carboxylate (77.0 mg, 0.113 mmol) in DCM (3 mL), was added 2,2,2-trifluoroacetic acid (0.376 mL, 4.95 mmol). The solution was stirred at 40° C. for 75 min. Following this time, the crude residue was concentrated to dryness and purified by RP-HPLC (eluent: MeCN/H₂O). The resulting product fractions were diluted with EtOAc and neutralized with sodium bicarbonate solution. The organic extract was dried over sodium sulfate, filtered and concentrated to give Example 19. ES/MS: 627.2 (M+H⁺); 1H NMR (400 MHz, DMSO-d6) δ 12.78 (s, 1H), 8.51 (d, J=1.4 Hz, 1H), 7.97-7.85 (m, 2H), 7.84-7.68 (m, 5H), 7.64 (d, J=8.5 Hz, 1H), 7.54 (dd, J=7.3, 1.6 Hz, 1H), 7.41 (dd, J=11.4, 6.1 Hz, 1H), 7.00 (d, J=8.2 Hz, 1H), 5.80 (d, J=5.3 Hz, 1H), 5.60 (s, 2H), 5.48-5.30 (m, 1H), 4.71 (dd, J=11.1, 2.5 Hz, 1H), 4.65-4.30 (m, 2H), 4.16 (dd, J=11.1, 7.0 Hz, 1H), 3.82-3.62 (m, 1H), 3.57-3.45 (m, 1H), 3.30 (s, 1H), 1.73-1.56 (m, 1H).

Example 20: 2-(4-(6-((4-cyano-2-fluorobenzyl)oxy)pyridin-2-yl)-2,5-difluorobenzyl)-1-((3R,3aS,6aR)-hexahydrofuro[2,3-b]furan-3-yl)-1H-benzo[d]imidazole-6-carboxylic acid 2-(4-(6-((4-cyano-2-fluorobenzyl)oxy)pyridin-2-yl)-2,5-difluorobenzyl)-1-((3R,3aS,6aR)-hexahydrofuro[2,3-b]furan-3-yl)-1H-benzo[d]imidazole-6-carboxylic acid was prepared in a manner described in Procedure 5. 1H NMR (400 MHz, DMSO-d6) δ 12.78 (s, 1H), 8.51 (d, J=1.4 Hz, 1H), 7.98-7.84 (m, 2H), 7.84-7.68 (m, 4H), 7.64 (d, J=8.4 Hz, 1H), 7.54 (dd, J=7.5, 1.6 Hz, 1H), 7.41 (dd, J=11.4, 6.1 Hz, 1H), 7.00 (d, J=8.3 Hz, 1H), 5.80 (d, J=5.3 Hz, 1H), 5.60 (s, 2H), 5.40 (ddd, J=9.5, 7.0, 2.6 Hz, 1H), 4.72 (dd, J=11.0, 2.6 Hz, 1H), 4.58-4.27 (m, 2H), 4.16 (dd, J=11.1, 6.9 Hz, 1H), 3.72 (td, J=8.6, 2.2 Hz, 1H), 3.62-3.42 (m, 1H), 1.61 (dtd, J=13.2, 10.7, 8.7 Hz, 1H), 0.77 (dd, J=13.3, 6.3 Hz, 1H).

Example: 21: 2-(4-(6-((4-(difluoromethyl)-2-fluorobenzyl)oxy)pyridin-2-yl)-2,5-difluorobenzyl)-1-(4,4-dimethyltetrahydrofuran-3-yl)-1H-benzo[d]imidazole-6-carboxylic acid 2-(4-(6-((4-(difluoromethyl)-2-fluorobenzyl)oxy)pyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 5. 1H NMR (400 MHz, Methanol-d4) δ 8.85 (s, 1H), 8.13 (dd, J=8.6, 1.4 Hz, 1H), 8.00-7.81 (m, 2H), 7.81-7.73 (m, 1H), 7.68 (t, J=7.5 Hz, 1H), 7.58 (dd, J=7.4, 1.6 Hz, 1H), 7.46-7.30 (m, 3H), 7.01-6.85 (m, 1H), 6.79 (s, 1H), 5.61 (s, 2H), 5.09 (d, J=6.6 Hz, 1H), 4.70-4.61 (m, 3H), 4.52 (dd, J=11.5, 6.7 Hz, 1H), 3.99 (d, J=8.9 Hz, 1H), 3.84 (d, J=8.9 Hz, 1H), 1.40 (s, 3H), 0.74 (s, 3H).

Example 22: 2-(4-(6-((4-cyano-2-fluorobenzyl)oxy)pyridin-2-yl)-2,5-difluorobenzyl)-1-(2-(difluoromethoxy)propyl)-1H-benzo[d]imidazole-6-carboxylic acid 2-(4-(6-((4-cyano-2-fluorobenzyl)oxy)pyridin-2-yl)-2,5-difluorobenzyl)-1-(2-(difluoromethoxy)propyl)-1H-benzo[d]imidazole-6-carboxylic acid was prepared in a manner as described in Procedure 5. 1H NMR (400 MHz, Methanol-d4) δ 8.53 (t, J=0.9 Hz, 1H), 8.19 (dd, J=8.6, 1.4 Hz, 1H), 7.90-7.79 (m, 2H), 7.79-7.67 (m, 2H), 7.60 (ddt, J=9.3, 8.0, 1.5 Hz, 3H), 7.37 (dd, J=11.2, 6.0 Hz, 1H), 6.96 (d, J=8.2 Hz, 1H), 6.26 (t, J=74.2 Hz, 1H), 5.64 (s, 2H), 4.82-4.62 (m, 5H), 1.54 (d, J=5.1 Hz, 3H).

Procedure 6: Example 23

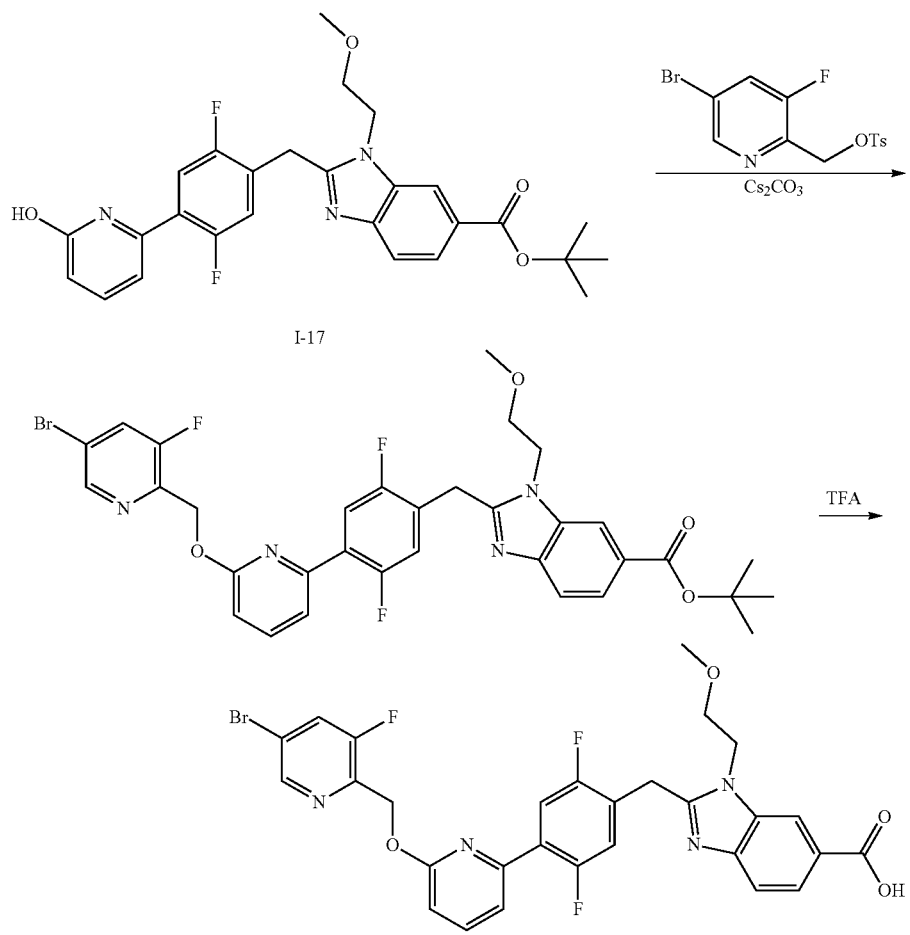

Example 23

Tert-butyl 2-[[4-[6-[(5-bromo-3-fluoro-2-pyridyl)methoxy]-2-pyridyl]-2,5-difluoro-phenyl]methyl]-3-(2-methoxyethyl)benzimidazole-5-carboxylate: Cs$_2$CO$_3$ (400 mg, 1.20 mmol) was added to solution of tert-butyl 2-[[2,5-difluoro-4-(6-hydroxy-2-pyridyl)phenyl]methyl]-3-(2-methoxyethyl)benzimidazole-5-carboxylate (400 mg, 0.80 mmol) and (5-bromo-3-fluoro-2-pyridyl)methyl 4-methyl-benzenesulfonate (350 mg, 0.97 mmol) in 15 mL of acetonitrile. The resulting mixture was heated to 50° C. for 30 minutes. Following this time, the solution was cooled to rt, filtered, then concentrated. The crude material was purified by silica gel column chromatography (eluent: EtOAc/hexanes) to provide desired product. ES/MS: 686.0 (M+H$^+$).

2-[[4-[6-[(5-bromo-3-fluoro-2-pyridyl)methoxy]-2-pyridyl]-2,5-difluoro-phenyl]methyl]-3-(2-methoxyethyl)benzimidazole-5-carboxylic acid: 0.5 mL TFA was added to a solution of tert-butyl 2-[[4-[6-[(5-bromo-3-fluoro-2-pyridyl)methoxy]-2-pyridyl]-2,5-difluoro-phenyl]methyl]-3-(2-methoxyethyl)benzimidazole-5-carboxylate (64 mg, 0.094 mmol) in DCM (2.5 mL). The resulting solution stirred at rt for 1 hour. Upon completion the mixture was diluted with EtOAc (30 mL), washed with water (3×5 mL), concentrated and purified by RP-HPLC (eluent: water/MeCN 0.1% TFA). The combined fractions were then frozen and placed on a lyophilizer to provide the final compound Example 23. ES/MS: 628.0 (M+H$^+$). 1H NMR (400 MHz, DMSO-d6) δ 8.59 (t, J=1.3 Hz, 1H), 8.30 (d, J=1.5 Hz, 1H), 8.25 (dd, J=9.5, 1.9 Hz, 1H), 7.94-7.84 (m, 2H), 7.74 (dd, J=10.6, 6.4 Hz, 1H), 7.66 (d, J=8.5 Hz, 1H), 7.52 (dd, J=7.5, 1.6 Hz, 1H), 7.41 (dd, J=11.5, 6.1 Hz, 1H), 6.96 (d, J=8.2 Hz, 1H), 5.58 (d, J=1.8 Hz, 2H), 4.66 (t, J=5.1 Hz, 2H), 4.52 (s, 2H), 3.72-3.68 (m, 2H), 3.21 (s, 3H).

Example 24: 2-(4-(6-(((5-chloropyrazin-2-yl)methoxy)pyridin-2-yl)-2,5-difluorobenzyl)-1-(2-methoxyethyl)-1H-benzo[d]imidazole-6-carboxylic acid 2-(4-(6-((5-chloropyrazin-2-yl)methoxy)pyridin-2-yl)-2,5-difluorobenzyl)-1-(2-methoxyethyl)-1H-benzo[d]imidazole-6-carboxylic acid was prepared in a manner described in Procedure 6. 1H NMR (400 MHz, DMSO-d6) δ 8.82 (d, J=1.3 Hz, 1H), 8.68 (d, J=1.3 Hz, 1H), 8.27 (d, J=1.5 Hz, 1H), 7.91 (t, J=7.9 Hz, 1H), 7.85 (dd, J=8.5, 1.5 Hz, 1H), 7.71 (dd, J=10.5, 6.4 Hz, 1H), 7.64 (d, J=8.4 Hz, 1H), 7.53 (dd, J=7.5, 1.6 Hz, 1H), 7.39 (dd, J=11.5, 6.1 Hz, 1H), 7.03 (d, J=8.3 Hz, 1H), 5.63 (s, 2H), 4.63 (t, J=5.1 Hz, 2H), 4.49 (s, 2H), 3.69 (t, J=5.0 Hz, 2H), 3.21 (s, 3H).

Example 25: 2-(4-(6-((2,6-dimethylpyridin-3-yl)methoxy)pyridin-2-yl)-2,5-difluorobenzyl)-1-(2-methoxyethyl)-1H-benzo[d]imidazole-6-carboxylic acid 2-(4-(6-((2,6-dimethylpyridin-3-yl)methoxy)pyridin-2-yl)-2,5-difluorobenzyl)-1-(2-methoxyethyl)-1H-benzo[d]imidazole-6-carboxylic acid was prepared in a manner as described in Procedure 6. 1H NMR (400 MHz, Methanol-d4) δ 8.56-8.44 (m, 2H), 8.17 (dt, J=8.6, 1.4 Hz, 1H), 7.91-7.80 (m, 2H), 7.73 (dd, J=14.4, 8.3 Hz, 2H), 7.56 (dd, J=7.5, 1.6 Hz, 1H), 7.33 (dd, J=11.2, 6.1 Hz, 1H), 6.96 (d, J=8.2 Hz, 1H), 5.65 (s, 2H), 4.76 (t, J=5.0 Hz, 2H), 4.71 (s, 2H), 3.81 (t, J=4.9 Hz, 2H), 3.30 (s, 3H), 2.83 (s, 3H), 2.74 (s, 3H).

Example 26: 2-(4-(6-((2,5-difluorobenzyl)oxy)pyridin-2-yl)-2,5-difluorobenzyl)-1-(2-methoxyethyl)-1H-benzo[d]imidazole-6-carboxylic acid 2-(4-(6-((2,5-difluorobenzyl)oxy)pyridin-2-yl)-2,5-difluorobenzyl)-1-(2-methoxyethyl)-1H-benzo[d]imidazole-6-carboxylic acid was prepared in a manner as described in Procedure 6. 1H NMR (400 MHz, Methanol-d4) δ 8.32 (dd, J=1.5, 0.7 Hz, 1H), 8.12 (dd, J=8.6, 1.5 Hz, 1H), 7.83 (dd, J=10.7, 6.3 Hz, 1H), 7.78-7.69 (m, 2H), 7.56-7.47 (m, 1H), 7.22 (ddd, J=8.7, 5.6, 3.2 Hz, 1H), 7.18-7.13 (m, 1H), 7.13-7.04 (m, 1H), 7.04-6.94 (m, 1H), 6.86 (dd, J=8.3, 0.7 Hz, 1H), 5.50 (d, J=1.2 Hz, 2H), 4.63-4.55 (m, 4H), 3.76 (t, J=5.0 Hz, 2H), 3.29 (s, 3H).

Example 27: 2-(2,5-difluoro-4-(6-((2,4,5-trifluorobenzyl)oxy)pyridin-2-yl)benzyl)-1-(2-methoxyethyl)-1H-benzo[d]imidazole-6-carboxylic acid 2-(2,5-difluoro-4-(6-((2,4,5-trifluorobenzyl)oxy)pyridin-2-yl)benzyl)-1-(2-methoxyethyl)-1H-benzo[d]imidazole-6-carboxylic acid was prepared in a manner as described in Procedure 6. 1H NMR (400 MHz, Methanol-d4) δ 8.46 (d, J=1.3 Hz, 1H), 8.15 (dd, J=8.6, 1.5 Hz, 1H), 7.89 (dd, J=10.8, 6.3 Hz, 1H), 7.81 (t, J=7.9 Hz, 1H), 7.74 (d, J=8.5 Hz, 1H), 7.56 (dd, J=7.4, 1.6 Hz, 1H), 7.48 (ddd, J=10.8, 8.9, 6.6 Hz, 1H), 7.30 (dd, J=11.3, 6.0 Hz, 1H), 7.22 (td, J=10.0, 6.5 Hz, 1H), 6.91 (d, J=8.2 Hz, 1H), 5.50 (s, 2H), 4.74 (t, J=5.0 Hz, 2H), 4.68 (s, 2H), 3.81 (t, J=4.9 Hz, 2H), 3.30 (s, 3H).

Example 28: 2-(4-(6-((2,5-difluoro-4-methylbenzyl)oxy)pyridin-2-yl)-2,5-difluorobenzyl)-1-(2-methoxyethyl)-1H-benzo[d]imidazole-6-carboxylic acid 2-(4-(6-((2,5-difluoro-4-methylbenzyl)oxy)pyridin-2-yl)-2,5-difluorobenzyl)-1-(2-methoxyethyl)-1H-benzo[d]imidazole-6-carboxylic acid was prepared in a manner as described in Procedure 6. 1H NMR (400 MHz, Methanol-d4) δ 8.37 (d, J=1.4 Hz, 1H), 8.14 (dd, J=8.6, 1.5 Hz, 1H), 7.87 (dd, J=10.8, 6.3 Hz, 1H), 7.78-7.71 (m, 2H), 7.52 (dd, J=7.3, 1.6 Hz, 1H), 7.27-7.10 (m, 2H), 6.96 (dd, J=10.0, 6.1 Hz, 1H), 6.86 (d, J=8.1 Hz, 1H), 5.46 (s, 2H), 4.65 (t, J=5.0 Hz, 2H), 4.62 (s, 2H), 3.84-3.70 (m, 2H), 3.30 (s, 3H), 2.25 (d, J=2.0 Hz, 3H).

Example 29: 2-(2,5-difluoro-4-(6-((5-methylpyrazin-2-yl)methoxy)pyridin-2-yl)benzyl)-1-(2-methoxyethyl)-1H-benzo[d]imidazole-6-carboxylic acid 2-(2,5-difluoro-4-(6-((5-methylpyrazin-2-yl)methoxy)pyridin-2-yl)benzyl)-1-(2-methoxyethyl)-1H-benzo[d]imidazole-6-carboxylic acid was prepared in a manner as described in Procedure 6. 1H NMR (400 MHz, Methanol-d4) δ 8.65 (d, J=1.4 Hz, 1H), 8.58 (t, J=1.0 Hz, 1H), 8.53 (d, J=1.4 Hz, 1H), 8.25 (dd, J=8.6, 1.4 Hz, 1H), 7.85 (d, J=7.7 Hz, 1H), 7.82 (t, J=3.2 Hz, 1H), 7.79 (d, J=8.6 Hz, 1H), 7.58 (dd, J=7.5, 1.6 Hz, 1H), 7.37 (dd, J=11.2, 6.1 Hz, 1H), 6.98 (d, J=8.1 Hz, 1H), 5.61 (s, 2H), 4.84 (d, J=5.0 Hz, 2H), 4.78 (s, 2H), 3.91-3.79 (m, 2H), 3.32 (s, 3H), 2.56 (s, 3H).

Example 30: 2-(2,5-difluoro-4-(6-(imidazo[1,2-a]pyridin-6-ylmethoxy)pyridin-2-yl)benzyl)-1-(2-methoxyethyl)-1H-benzo[d]imidazole-6-carboxylic acid 2-(2,5-difluoro-4-(6-(imidazo[1,2-a]pyridin-6-ylmethoxy)pyridin-2-yl)benzyl)-1-(2-methoxyethyl)-1H-benzo[d]imidazole-6-carboxylic acid was prepared in a manner as described in Procedure 6. 1H NMR (400 MHz, Methanol-d4) δ 8.99 (t, J=1.3 Hz, 1H), 8.49 (d, J=1.5 Hz, 1H), 8.29-8.22 (m, 1H), 8.15 (td, J=8.6, 1.5 Hz, 2H), 8.06 (d, J=2.2 Hz, 1H), 8.00-7.83 (m, 3H), 7.75 (d, J=8.5 Hz, 1H), 7.60 (dd, J=7.4, 1.6 Hz, 1H), 7.34 (dd, J=11.3, 6.0 Hz, 1H), 6.99 (d, J=8.2 Hz, 1H), 5.69 (d, J=1.1 Hz, 2H), 4.76 (t, J=5.0 Hz, 2H), 4.70 (s, 2H), 3.88-3.73 (m, 2H), 3.31 (s, 3H).

Example 31: 2-(4-(6-((3,5-difluoropyridin-2-yl)methoxy)pyridin-2-yl)-2,5-difluorobenzyl)-1-(2-methoxyethyl)-1H-benzo[d]imidazole-6-carboxylic acid 2-(4-(6-((3,5-difluoropyridin-2-yl)methoxy)pyridin-2-yl)-2,5-difluorobenzyl)-1-(2-methoxyethyl)-1H-benzo[d]imidazole-6-carboxylic acid was prepared in a manner as described in Procedure 6. 1H NMR (400 MHz, Methanol-d4) δ 8.56 (t, J=1.0 Hz, 1H), 8.39 (d, J=2.4 Hz, 1H), 8.23 (dd, J=8.6, 1.4 Hz, 1H), 7.94 (dd, J=10.9, 6.3 Hz, 1H), 7.88-7.74 (m, 2H), 7.66 (ddd, J=9.7, 8.5, 2.4 Hz, 1H), 7.58 (dd, J=7.3, 1.6 Hz, 1H), 7.36 (dd, J=11.2, 6.1 Hz, 1H), 6.91 (dd, J=8.3, 0.6 Hz, 1H), 5.62 (d, J=2.0 Hz, 2H), 4.83 (t, J=5.0 Hz, 2H), 4.77 (s, 2H), 3.85 (dd, J=5.4, 4.4 Hz, 2H), 3.33 (s, 3H).

Example 32: 2-(2,5-difluoro-4-(6-((4-(trifluoromethoxy)benzyl)oxy)pyridin-2-yl)benzyl)-1-(2-methoxyethyl)-1H-benzo[d]imidazole-6-carboxylic acid 2-(2,5-difluoro-4-(6-((4-(trifluoromethoxy)benzyl)oxy)pyridin-2-yl)benzyl)-1-(2-methoxyethyl)-1H-benzo[d]imidazole-6-carboxylic acid was prepared in a manner as described in Procedure 6. 1H NMR (400 MHz, Methanol-d4) δ 8.50 (d, J=1.4 Hz, 1H), 8.18 (dd, J=8.5, 1.5 Hz, 1H), 7.92-7.68 (m, 3H), 7.66-7.46 (m, 3H), 7.40-7.20 (m, 3H), 6.92 (d, J=8.3 Hz, 1H), 5.52 (s, 2H), 4.77 (t, J=5.0 Hz, 2H), 4.71 (s, 2H), 3.82 (t, J=4.9 Hz, 2H), 3.31 (s, 3H).

Example 33: 2-(2,5-difluoro-4-(6-((2-methyl-6-(trifluoromethyl)pyridin-3-yl)methoxy)pyridin-2-yl)benzyl)-1-(2-methoxyethyl)-1H-benzo[d]imidazole-6-carboxylic acid 2-(2,5-difluoro-4-(6-((2-methyl-6-(trifluoromethyl)pyridin-3-yl)methoxy)pyridin-2-yl)benzyl)-1-(2-methoxyethyl)-1H-benzo[d]imidazole-6-carboxylic acid was prepared in a manner as described in Procedure 6. 1H NMR (400 MHz, Methanol-d4) δ 8.53 (d, J=1.3 Hz, 1H), 8.20 (dd, J=8.6, 1.4 Hz, 1H), 8.05 (d, J=7.9 Hz, 1H), 7.91-7.70 (m, 3H), 7.64 (d, J=7.9 Hz, 1H), 7.57 (dd, J=7.4, 1.6 Hz, 1H), 7.35 (dd, J=11.2, 6.1 Hz, 1H), 6.98 (d, J=8.2 Hz, 1H), 5.62 (s, 2H), 4.83-4.64 (m, 4H), 3.88-3.78 (m, 2H), 3.32 (s, 3H), 2.69 (s, 3H).

Example 34: 2-(4-(6-((2-chloro-6-(trifluoromethyl) pyridin-3-yl)methoxy)pyridin-2-yl)-2,5-difluorobenzyl)-1-(2-methoxyethyl)-1H-benzo[d]imidazole-6-carboxylic acid 2-(4-(6-((2-chloro-6-(trifluoromethyl)pyridin-3-yl) methoxy)pyridin-2-yl)-2,5-difluorobenzyl)-1-(2-methoxyethyl)-1H-benzo[d]imidazole-6-carboxylic acid was prepared in a manner as described in Procedure 6. 1H NMR (400 MHz, Chloroform-d) δ 8.24 (t, J=0.9 Hz, 1H), 8.13 (dd, J=8.6, 1.4 Hz, 1H), 8.10-8.03 (m, 1H), 7.99 (d, J=8.6 Hz, 1H), 7.82-7.69 (m, 2H), 7.65 (d, J=7.8 Hz, 1H), 7.56 (dd, J=7.5, 1.3 Hz, 1H), 7.35-7.32 (m, 1H), 6.92 (dd, J=8.2, 0.7 Hz, 1H), 5.63 (s, 2H), 4.74 (s, 2H), 4.57 (t, J=4.9 Hz, 2H), 3.78 (t, J=4.8 Hz, 2H), 3.32 (s, 3H).

Example 35: 2-(2,5-difluoro-4-(6-((6-(2,2,2-trifluoroethoxy)pyridin-3-yl)methoxy)pyridin-2-yl)benzyl)-1-(2-methoxyethyl)-1H-benzo[d]imidazole-6-carboxylic acid 2-(2,5-difluoro-4-(6-((6-(2,2,2-trifluoroethoxy)pyridin-3-yl)methoxy)pyridin-2-yl)benzyl)-1-(2-methoxyethyl)-1H-benzo[d]imidazole-6-carboxylic acid was prepared in a manner as described in Procedure 6. 1H NMR (400 MHz, Chloroform-d) δ 8.24 (d, J=19.5 Hz, 2H), 8.09 (d, J=8.5 Hz, 1H), 7.96 (d, J=8.4 Hz, 1H), 7.91-7.73 (m, 2H), 7.68 (t, J=8.0 Hz, 1H), 7.50 (d, J=7.5 Hz, 1H), 6.90 (d, J=8.4 Hz, 1H), 6.79 (d, J=8.2 Hz, 1H), 5.42 (s, 2H), 4.78 (dd, J=16.8, 8.5 Hz, 4H), 4.56 (s, 2H), 3.78 (d, J=5.2 Hz, 2H), 3.33 (s, 3H).

Procedure 7: Example 36

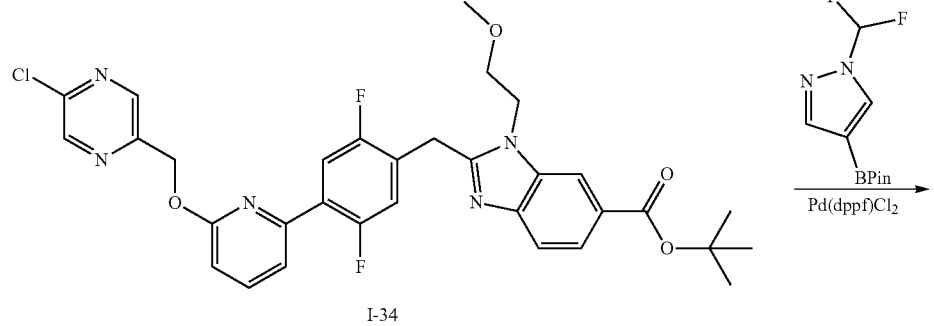

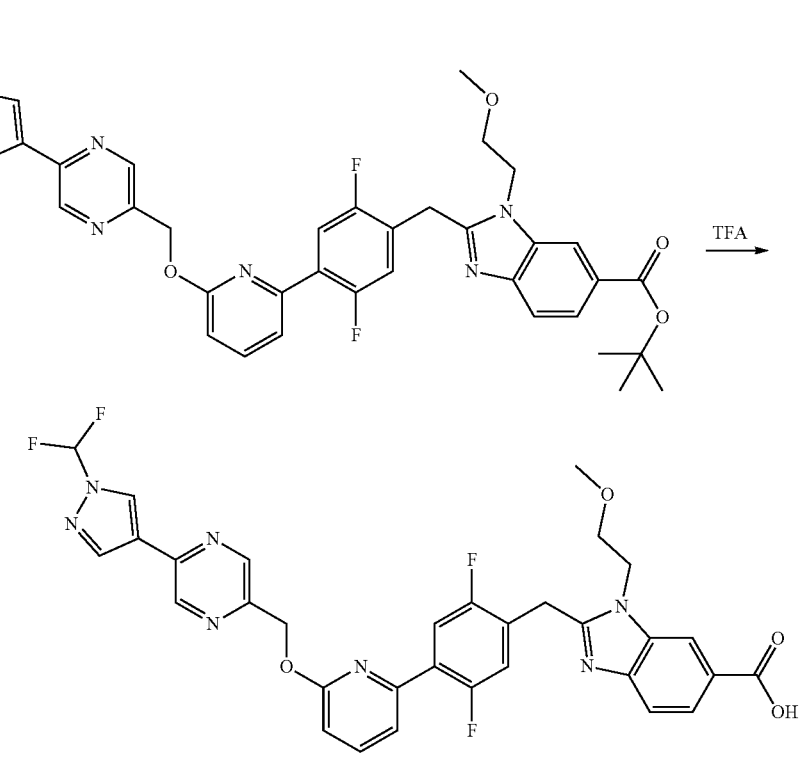

Example 36

Tert-butyl 2-[[4-[6-[[5-[1-(difluoromethyl)pyrazol-4-yl]pyrazin-2-yl]methoxy]-2-pyridyl]-2,5-difluoro-phenyl]methyl]-3-(2-methoxyethyl)benzimidazole-5-carboxylate:
Aqueous sodium carbonate solution (0.13 mL, 0.2 mmol) was added to a solution of tert-butyl 2-[[4-[6-[(5-chloropyrazin-2-yl)methoxy]-2-pyridyl]-2,5-difluoro-phenyl]methyl]-3-(2-methoxyethyl)benzimidazole-5-carboxylate (I-34) (60 mg, 0.097 mmol), 1-(difluoromethyl)-4-(4,4,5,5-tetramethyl-1,3,2-dioxaborolan-2-yl)pyrazole (30 mg, 0.12 mmol), and bis(diphenylphosphino)ferrocene] dichloropalladium(II) (14 mg, 0.0020 mmol) in 1,4-dioxane (1.5 mL)ed. The resulting solution was degassed by bubbling argon for 1 minute, sealed and heated to 100° C. for 2 hr. Upon completion the mixture was poured into water (5 mL) and extracted with EtOAc (2×5 mL). The organic layers were combined, washed with brine (5 mL), dried over MgSO$_4$, filtered, concentrated, and purified by flash chromatography (Eluent: EtOAc/hexane) to give the desired product. ES/MS: 704.2 (M+1).

2-[[4-[6-[[5-[1-(difluoromethyl)pyrazol-4-yl]pyrazin-2-yl]methoxy]-2-pyridyl]-2,5-difluoro-phenyl]methyl]-3-(2-methoxyethyl)benzimidazole-5-carboxylic acid; 2,2,2-trifluoroacetic acid (Example 36): 0.5 mL TFA was added to a solution of tert-butyl 2-[[4-[6-[[5-[1-(difluoromethyl)pyrazol-4-yl]pyrazin-2-yl]methoxy]-2-pyridyl]-2,5-difluorophenyl]methyl]-3-(2-methoxyethyl)benzimidazole-5-carboxylate (37 mg, 0.053 mmol) in DCM (2.5 mL). The resulting solution stirred at rt for 3 hours. Following this time, the mixture was diluted with EtOAc (30 mL), washed with water (3×5 mL), concentrated and purified by RP-HPLC (eluent: water/MeCN 0.1% TFA). The combined fractions were then frozen and placed on a lyophilizer to provide the final compound Example 36. ES/MS: 648.2 (M+H$^+$). 1H NMR (400 MHz, DMSO-d6) δ 9.13 (d, J=1.5 Hz, 1H), 8.98 (s, 1H), 8.78 (d, J=1.4 Hz, 1H), 8.45 (s, 1H), 8.26 (d, J=1.5 Hz, 1H), 8.09-7.71 (m, 4H), 7.63 (d, J=8.4 Hz, 1H), 7.53 (dd, J=7.6, 1.7 Hz, 1H), 7.39 (dd, J=11.5, 6.1 Hz, 1H), 7.03 (d, J=8.3 Hz, 1H), 5.62 (s, 2H), 4.63 (t, J=5.1 Hz, 2H), 4.48 (s, 2H), 3.69 (t, J=5.1 Hz, 2H), 3.20 (s, 3H).

Example 37: 2-(2,5-difluoro-4-(6-((5-(1-methyl-1H-1,2,3-triazol-4-yl)pyrazin-2-yl)methoxy)pyridin-2-yl)benzyl)-1-(2-methoxyethyl)-1H-benzo[d]imidazole-6-carboxylic acid 2-(2,5-difluoro-4-(6-((5-(1-methyl-1H-1,2,3-triazol-4-yl)pyrazin-2-yl)methoxy)pyridin-2-yl)benzyl)-1-(2-methoxyethyl)-1H-benzo[d]imidazole-6-carboxylic acid was prepared in a manner as described in Procedure 7. 1H NMR (400 MHz, DMSO-d6) δ 9.19 (d, J=1.5 Hz, 1H), 8.94 (d, J=1.4 Hz, 1H), 8.45 (s, 1H), 8.28 (d, J=1.5 Hz, 1H), 7.92 (t, J=7.9 Hz, 1H), 7.86 (dd, J=8.4, 1.5 Hz, 1H), 7.72 (dd, J=10.5, 6.4 Hz, 1H), 7.64 (d, J=8.5 Hz, 1H), 7.54 (dd, J=7.5, 1.7 Hz, 1H), 7.40 (dd, J=11.5, 6.1 Hz, 1H), 7.05 (d, J=8.3 Hz, 1H), 5.69 (s, 2H), 4.64 (t, J=5.1 Hz, 2H), 4.49 (s, 2H), 4.31 (s, 3H), 3.69 (t, J=5.0 Hz, 2H), 3.20 (s, 3H).

Example 38: 2-(2,5-difluoro-4-(6-((5-(1-methyl-1H-pyrazol-4-yl)pyrazin-2-yl)methoxy)pyridin-2-yl)benzyl)-1-(2-methoxyethyl)-1H-benzo[d]imidazole-6-carboxylic acid 2-(2,5-difluoro-4-(6-((5-(1-methyl-1H-pyrazol-4-yl)pyrazin-2-yl)methoxy)pyridin-2-yl)benzyl)-1-(2-methoxyethyl)-1H-benzo[d]imidazole-6-carboxylic acid was prepared in a manner as described in Procedure 7. 1H NMR (400 MHz, DMSO-d6) δ 8.97 (d, J=1.5 Hz, 1H), 8.70 (d, J=1.4 Hz, 1H), 8.41 (s, 1H), 8.28 (d, J=1.5 Hz, 1H), 8.10 (s, 1H), 7.90 (t, J=7.9 Hz, 1H), 7.86 (dd, J=8.4, 1.5 Hz, 1H), 7.78 (dd, J=10.5, 6.4 Hz, 1H), 7.65 (d, J=8.4 Hz, 1H), 7.53 (dd, J=7.5, 1.7 Hz, 1H), 7.40 (dd, J=11.5, 6.1 Hz, 1H), 7.01 (d, J=8.2 Hz, 1H), 5.58 (s, 2H), 4.65 (t, J=5.2 Hz, 2H), 4.51 (s, 2H), 3.90 (s, 3H), 3.69 (t, J=5.0 Hz, 2H), 3.21 (s, 3H).

Procedure 8: Example 39

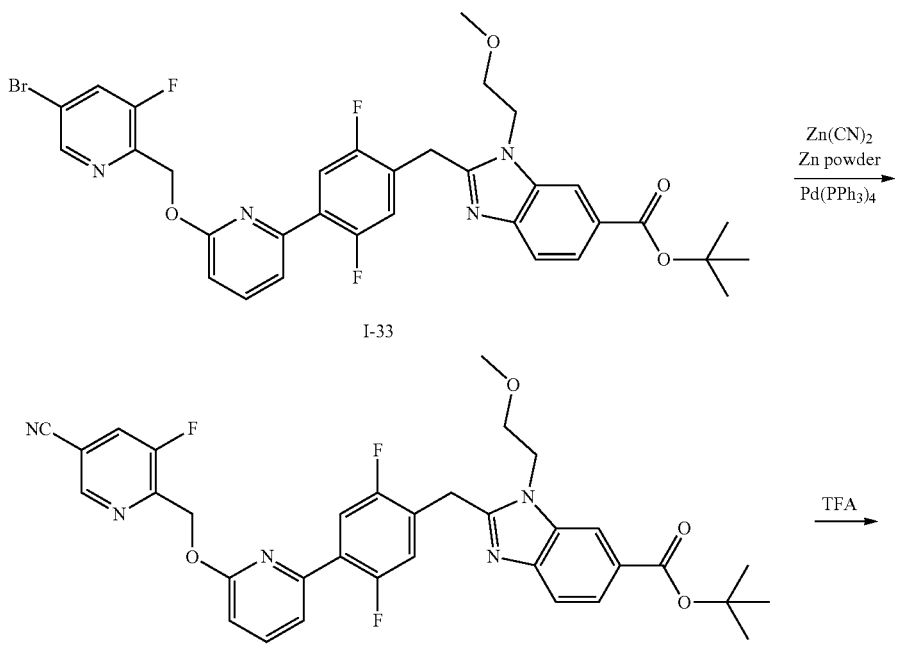

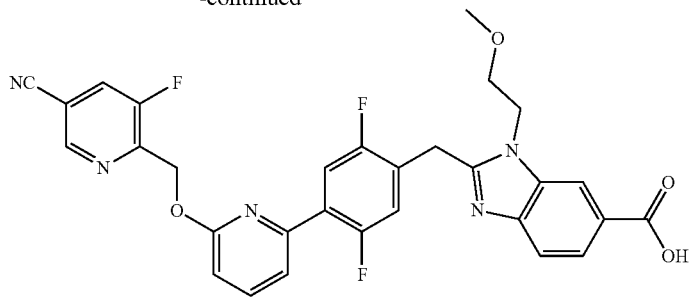

Example 39 tert-butyl 2-[[4-[6-[(5-cyano-3-fluoro-2-pyridyl)methoxy]-2-pyridyl]-2,5-difluoro-phenyl]methyl]-3-(2-methoxyethyl)benzimidazole-5-carboxylate: A solution of tert-butyl 2-[[4-[6-[(5-bromo-3-fluoro-2-pyridyl)methoxy]-2-pyridyl]-2,5-difluoro-phenyl]methyl]-3-(2-methoxyethyl)benzimidazole-5-carboxylate (I-33) (70 mg, 0.10 mmol), zinc cyanide (14 mg, 0.12 mmol), zinc powder (0.3 mg, 0.005 mmol), and Pd(PPh$_3$)$_4$ (60 mg, 0.050 mmol) in DMF (1.5 mL) was degassed by bubbling argon for 1 minute. The solution was then sealed and heated to 100° C. for 20 hrs. Upon completion the mixture was poured into water (5 mL) and extracted with EtOAc (2×5 mL). The organic layers were combined, washed with brine (5 mL), dried over MgSO$_4$, filtered, concentrated, and purified by flash chromatography (Eluent: EtOAc/hexane) to give the desired product. ES/MS: 630.2 (M+1).

2-[[4-[6-[(5-cyano-3-fluoro-2-pyridyl)methoxy]-2-pyridyl]-2,5-difluoro-phenyl]methyl]-3-(2-methoxyethyl)benzimidazole-5-carboxylic acid; 2,2,2-trifluoroacetic acid: 0.5 mL TFA was added to a solution of tert-butyl 2-[[4-[6-[(5-cyano-3-fluoro-2-pyridyl)methoxy]-2-pyridyl]-2,5-difluoro-phenyl]methyl]-3-(2-methoxyethyl)benzimidazole-5-carboxylate (51 mg, 0.081 mmol) in DCM (2.5 mL). The resulting solution stirred at rt for 3 hours. Upon completion the mixture was diluted with EtOAc (30 mL), washed with water (3×5 mL), concentrated and purified by RP-HPLC (eluent: water/MeCN 0.1% TFA). The combined fractions were then frozen and placed on a lyophilizer to provide the final compound Example 39. ES/MS: 574.2 (M+H⁺). 1H NMR (400 MHz, DMSO-d6) δ 8.89 (t, J=1.2 Hz, 1H), 8.48 (dd, J=9.9, 1.7 Hz, 1H), 8.29 (d, J=1.5 Hz, 1H), 7.93-7.82 (m, 2H), 7.66 (d, J=8.5 Hz, 1H), 7.61 (dd, J=10.6, 6.4 Hz, 1H), 7.51 (dd, J=7.5, 1.6 Hz, 1H), 7.39 (dd, J=11.6, 6.1 Hz, 1H), 6.99 (d, J=8.3 Hz, 1H), 5.69 (d, J=1.7 Hz, 2H), 4.65 (t, J=5.1 Hz, 2H), 4.51 (s, 2H), 3.69 (t, J=5.0 Hz, 2H), 3.21 (s, 3H).

Procedure 9: Example 40

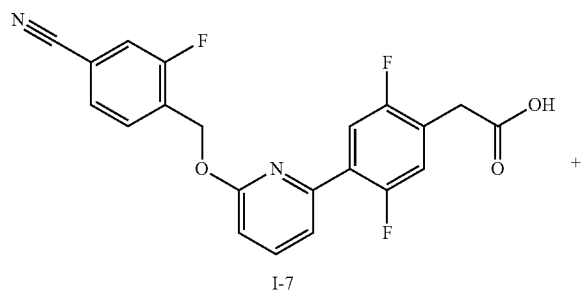

I-7

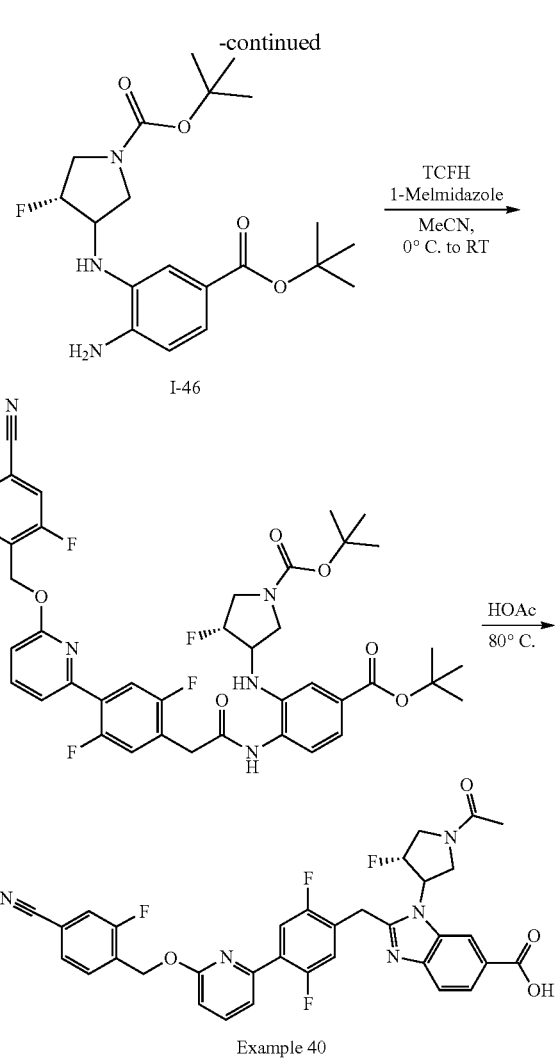

Example 40

3-[(3R,4R)-1-acetyl-4-fluoro-pyrrolidin-3-yl]-2-[[4-[6-[(4-cyano-2-fluoro-phenyl)methoxy]-2-pyridyl]-2,5-difluoro-phenyl]methyl]benzimidazole-5-carboxylic acid (Example 40): 1-methylimidazole (82.4 mg, 0.08 mL, 1.00 mmol) followed by N,N,N',N'-Tetramethylchloroformamidinium Hexafluorophosphate (60.0 mg, 0.214 mmol) were added to a solution of I-46 (82.0 mg, 0.21 mmol) and I-7 (70.0 mg, 0.176 mmol) in MeCN (2.50 mL) and cooled to 0° C. Next, the mixture was warmed to rt and stirred for 30 min. The crude mixture was concentrated in vacuo, then partitioned between 1M HCl and EtOAc. The organic layer was isolated and back extracted with an additional portion of EtOAc. The isolated organic layer was dried over magnesium sulfate, isolated by vacuum filtration, and concentrated in vacuo. The resulting crude material was dissolved in 1.5 mL of AcOH and the solution stirred for 3 days at 80° C. Upon completion the solution was concentrated, and the crude taken up into 1 mL of DMF and purified by reverse phase chromatography 10-70% MeCN/H$_2$O with 0.1% TFA. Product containing fractions were combined and concentrated to give 3-[(3R,4R)-1-acetyl-4-fluoro-pyrrolidin-3-yl]-2-[[4-[6-[(4-cyano-2-fluoro-phenyl)methoxy]-2-pyridyl]-2, 5-difluoro-phenyl]methyl]benzimidazole-5-carboxylic acid. Example 40. ES/MS m/z: 644.4 (M+H$^+$); $^1$H NMR (400 MHz, DMSO) δ 8.06 (dd, J=43.2, 1.5 Hz, 1H), 7.95-7.87 (m, 2H), 7.84 (dt, J=8.4, 1.9 Hz, 1H), 7.81-7.71 (m, 4H), 7.68 (d, J=8.5 Hz, 1H), 7.54 (dd, J=7.5, 1.7 Hz, 1H), 7.45-7.36 (m, 1H), 7.00 (d, J=8.3 Hz, 1H), 5.83-5.62 (m, 1H), 5.62 (s, 2H), 4.63-4.39 (m, 2H), 4.32-4.06 (m, 2H), 4.02-3.86 (m, 1H), 2.09 (d, J=13.4 Hz, 3H).

Procedure 10: Example 41

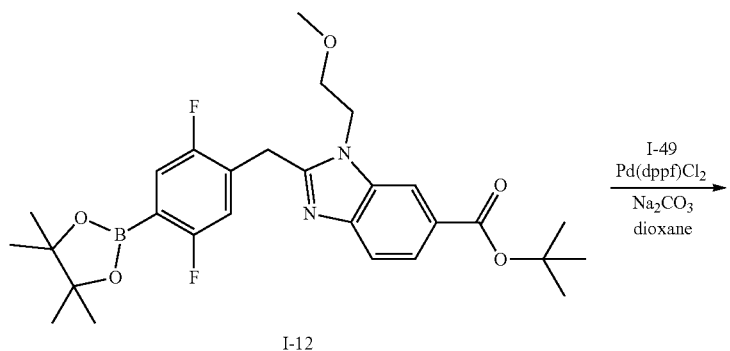

I-12

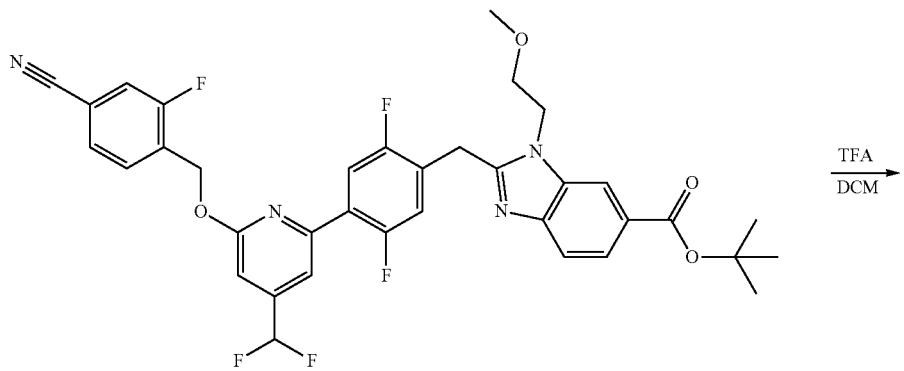

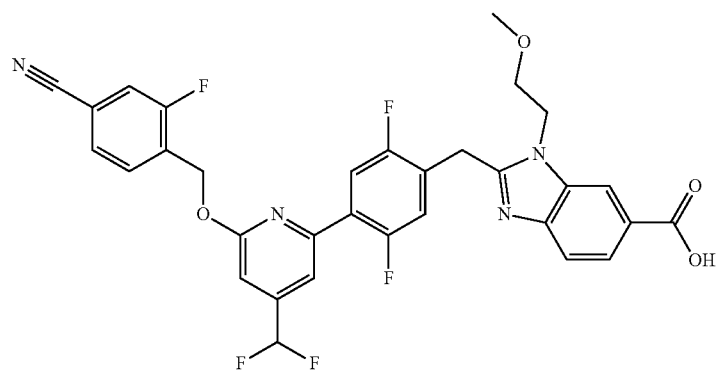

Example 41

Tert-butyl 2-[[4-[6-[(4-cyano-2-fluoro-phenyl)methoxy]-4-(difluoromethyl)-2-pyridyl]-2,5-difluoro-phenyl]methyl]-3-(2-methoxyethyl)benzimidazole-5-carboxylate: Tert-butyl 2-[[2,5-difluoro-4-(4,4,5,5-tetramethyl-1,3,2-dioxaborolan-2-yl)phenyl]methyl]-3-(2-methoxyethyl)benzimidazole-5-carboxylate (50 mg, 0.09 mmol), 4-[[6-chloro-4-(difluoromethyl)-2-pyridyl]oxymethyl]-3-fluoro-benzonitrile (32.5 mg, 0.1 mmol), 2 N of sodium carbonate (0.1 mL, 0.2 mmol) and (1,1'-bis(diphenylphosphino)ferrocene)-dichloropalladium (II) (10.5 mg, 0.014 mmole) were suspended in dioxane (0.5 mL). The mixture was degassed by nitrogen. After which, the mixture was heated to 120° C. in the microwave reactor for 30 minutes. Upon completion the solvent was removed the solvent and crude product was dissolved in 1 mL of DMF. The mixture was filtered and purified by RP-HPLC (eluent: water/MeCN 0.1% TFA) to give the desired product. ES/MS: 679.3 (M+H$^+$).

2-[[4-[6-[(4-cyano-2-fluoro-phenyl)methoxy]-4-(difluoromethyl)-2-pyridyl]-2,5-difluoro-phenyl]methyl]-3-(2-methoxyethyl)benzimidazole-5-carboxylic acid (Example 41): Tert-butyl 2-[[4-[6-[(4-cyano-2-fluoro-phenyl)methoxy]-4-(difluoromethyl)-2-pyridyl]-2,5-difluoro-phenyl]methyl]-3-(2-methoxyethyl)benzimidazole-5-carboxylate (35 mg, 0.052 mmol) was added to 1 mL of DCM and 0.4 mL of TFA stirred for 2 hrs. Upon completion the solvent was removed, and the crude residue was dissolved in 1 mL of DMF. The mixture was filtered and purified by RP-HPLC (eluent: water/MeCN 0.1% TFA) to give Example 41. ES/MS: 623.2 (M+H$^+$).

Example 42: 2-(4-(4-chloro-6-((4-cyano-2-fluorobenzyl)oxy)pyridin-2-yl)-2,5-difluorobenzyl)-1-(2-methoxyethyl)-1H-benzo[d]imidazole-6-carboxylic acid 2-(4-(4-chloro-6-((4-cyano-2-fluorobenzyl)oxy)pyridin-2-yl)-2,5-difluorobenzyl)-1-(2-methoxyethyl)-1H-benzo[d]imidazole-6-carboxylic acid was prepared in a manner as described in Procedure 10. 1H NMR (400 MHz, Methanol-d4) δ 8.33 (d, J=1.4 Hz, 1H), 8.12 (dd, J=8.6, 1.5 Hz, 1H), 7.80-7.65 (m, 3H), 7.58-7.48 (m, 3H), 7.19 (dd, J=11.3, 6.0 Hz, 1H), 6.94 (d, J=1.4 Hz, 1H), 5.60 (s, 2H), 4.64-4.56 (m, 4H), 3.77 (t, J=5.0 Hz, 2H), 3.29 (s, 3H).

Example 43: 2-(4-(6-((4-cyano-2-fluorobenzyl)oxy)-4-methoxypyridin-2-yl)-2,5-difluorobenzyl)-1-(2-methoxyethyl)-1H-benzo[d]imidazole-6-carboxylic acid 2-(4-(6-((4-cyano-2-fluorobenzyl)oxy)-4-methoxypyridin-2-yl)-2,5-difluorobenzyl)-1-(2-methoxyethyl)-1H-benzo[d]imidazole-6-carboxylic acid was prepared in a manner as described in Procedure 10. 1H NMR (400 MHz, DMSO-d6) δ 8.29 (d, J=1.5 Hz, 1H), 7.97-7.89 (m, 1H), 7.86 (dd, J=8.4, 1.5 Hz, 1H), 7.81-7.70 (m, 3H), 7.65 (d, J=8.4 Hz, 1H), 7.40 (dd, J=11.5, 6.1 Hz, 1H), 7.08 (t, J=1.5 Hz, 1H), 6.57 (d, J=1.9 Hz, 1H), 5.58 (s, 2H), 4.65 (t, J=5.1 Hz, 2H), 4.51 (s, 2H), 3.87 (s, 3H), 3.70 (t, J=5.0 Hz, 2H), 3.21 (s, 3H).

Example 44: 2-(4-(6-((4-cyano-2-fluorobenzyl)oxy)-4-hydroxypyridin-2-yl)-2,5-difluorobenzyl)-1-(2-methoxyethyl)-1H-benzo[d]imidazole-6-carboxylic acid 2-(4-(6-((4-cyano-2-fluorobenzyl)oxy)-4-hydroxypyridin-2-yl)-2,5-difluorobenzyl)-1-(2-methoxyethyl)-1H-benzo[d]imidazole-6-carboxylic acid was prepared in a manner as described in Procedure 10. 1H NMR (400 MHz, Methanol-d4) δ 8.52 (d, J=1.2 Hz, 1H), 8.19 (dd, J=8.6, 1.5 Hz, 1H), 7.83-7.74 (m, 2H), 7.68 (dt, J=12.8, 6.7 Hz, 1H), 7.63-7.52 (m, 2H), 7.30 (dd, J=11.3, 6.1 Hz, 1H), 7.07 (t, J=1.6 Hz, 1H), 6.29 (d, J=1.8 Hz, 1H), 5.58 (s, 2H), 4.78 (t, J=5.0 Hz, 2H), 4.71 (s, 2H), 3.82 (t, J=4.9 Hz, 2H).

Example 45: 2-(4-(6-amino-2-((4-cyano-2-fluorobenzyl)oxy)pyrimidin-4-yl)-2,5-difluorobenzyl)-1-(2-methoxyethyl)-1H-benzo[d]imidazole-6-carboxylic acid 2-(4-(6-amino-2-((4-cyano-2-fluorobenzyl)oxy)pyrimidin-4-yl)-2,5-difluorobenzyl)-1-(2-methoxyethyl)-1H-benzo[d]imidazole-6-carboxylic acid was prepared in a manner as described in Procedure 10. 1H NMR (400 MHz, DMSO-d6) δ 8.25 (s, 1H), 7.92 (d, J=10.0 Hz, 1H), 7.87-7.78 (m, 2H), 7.74 (s, 2H), 7.62 (d, J=8.5 Hz, 1H), 7.38 (dd, J=11.7, 6.0 Hz, 1H), 7.26 (s, 2H), 6.71 (d, J=1.4 Hz, 1H), 5.50 (s, 2H), 4.61 (t, J=5.1 Hz, 2H), 4.47 (s, 2H), 3.68 (t, J=5.1 Hz, 2H), 3.20 (s, 3H).

Procedure 11: Example 46

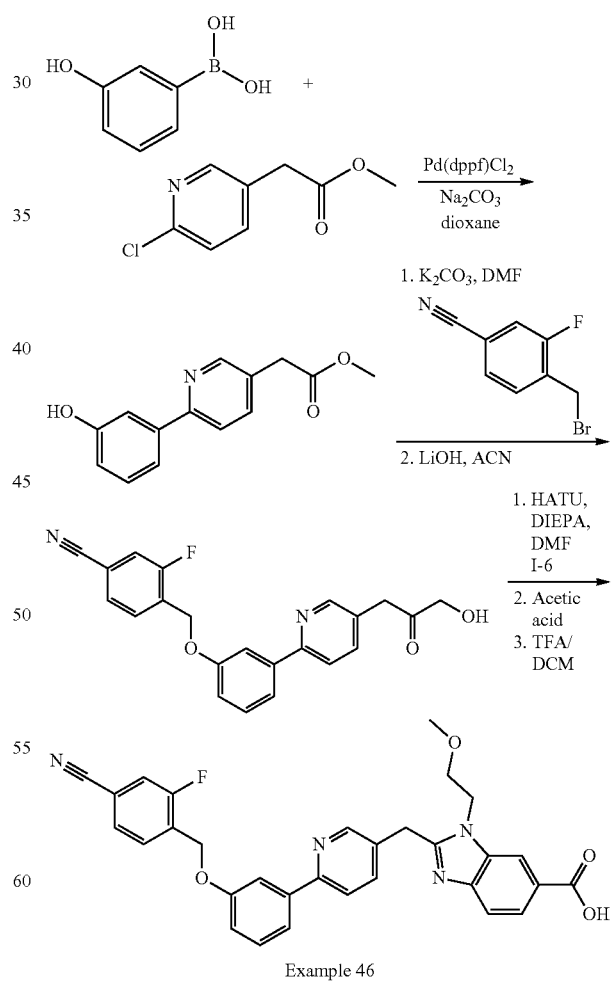

Example 46

Methyl 2-[6-(3-hydroxyphenyl)-3-pyridyl]acetate: Methyl 2-(6-chloro-3-pyridyl)acetate (300 mg, 1.62 mmol), (3-hydroxyphenyl)boronic acid (223 mg, 1.62 mmol), 2 N of sodium carbonate (1.62 mL, 3.23 mmol) and (1,1'-bis(diphenylphosphino)ferrocene)-dichloropalladium(II) (57 mg, 0.08 mmole) was suspended in dioxane (5 mL). The mixture was degassed by nitrogen. After which, the mixture was heated to 100° C. in the microwave reactor for 45 minutes. Following this time, the solvent was removed, and the crude product was dissolved in 1 mL of DCM. The crude residue was purified by column chromatography (0-50% EtOAc in hexane) to give the title compound: ES/MS m/z: 244.1 (M+H$^+$).

2-[6-[3-[(4-cyano-2-fluoro-phenyl)methoxy]phenyl]-3-pyridyl]acetic acid: A solution of methyl 2-[6-(3-hydroxyphenyl)-3-pyridyl]acetate (200.0 mg, 0.82 mmol), 4-(bromomethyl)-3-fluoro-benzonitrile (194 mg, 0.9 mmol) and potassium carbonate (227 mg, 1.64 mmol) in 5 mL of DMF, was stirred for 2 hrs. Next, 30 mL of water was added to the mixture and the compound was crashed out, filtered and washed with water. To the solid was added 3 mL of ACN and 1 mL of 1 N lithium hydroxide. The mixture was heated to 80° C. for 30 minutes. Upon completion the mixture was neutralized with 1 N hydrochloride in water and the organics were extracted with EtOAc (30 mL twice). The combined organic extracts were dried over sodium sulfate, filtered and the filtrate was concentrated in vacuo. The crude residue was purified by column chromatography (0-100% EtOAc in hexane) to give the title compound: ES/MS m/z: 363.2 (M+H$^+$).

2-[[6-[3-[(4-cyano-2-fluoro-phenyl)methoxy]phenyl]-3-pyridyl]methyl]-3-(2-methoxyethyl)benzimidazole-5-carboxylic acid: Tert-butyl 4-amino-3-(2-methoxyethylamino)benzoate (73.5 mg, 0.27 mmol) and O-(7-Azabenzotriazol-1-yl)-N,N,N',N'-tetramethyluronium hexafluorophosphate (126 mg, 0.33 mmol) followed by N,N-diisopropylethylamine (0.24 mL, 1.38 mmol) were added to a solution of 2-[6-[3-[(4-cyano-2-fluoro-phenyl)methoxy]phenyl]-3-pyridyl]acetic acid (100 mg, 0.27 mmol) in DMF (1.0 mL). the resulting mixture was stirred for 2 hrs. at rt. Upon completion the mixture was diluted in 20 mL of EtOAc and washed with water (1x) and brine (1x). The organic layer was dried over sodium sulfate, filtered and concentrated in vacuo. The crude residue was taken forward without further purification, assuming full conversion. The mixture was dissolved in AcOH (2.0 mL) and the mixture was heated to 60° C. for 2 hrs. The mixture was concentrated in vacuo and the crude residue was taken up in DCM and washed with saturated aqueous sodium bicarbonate. The layers were separated, and the aqueous layer was extracted with DCM (2x). The combined organic extracts were dried over sodium sulfate, filtered and the filtrate was concentrated in vacuo. The crude residue was added 1 mL of DCM and 0.4 mL of TFA stirred for 4 hours. Removed the solvent. The crude residue was dissolved in 2 mL of DMF. The mixture was filtered and purified by RP-HPLC (eluent: water/MeCN 0.1% TFA) to give Example 46. ES/MS: 537.4 (M+H+). 1H NMR (400 MHz, Methanol-d4) δ 8.74 (t, J=1.5 Hz, 1H), 8.52 (t, J=1.0 Hz, 1H), 8.19 (dd, J=8.6, 1.5 Hz, 1H), 8.12-8.00 (m, 2H), 7.80 (t, J=7.7 Hz, 1H), 7.75 (dd, J=8.6, 0.7 Hz, 1H), 7.70 (t, J=2.1 Hz, 1H), 7.67-7.60 (m, 3H), 7.50 (t, J=8.0 Hz, 1H), 7.21 (ddd, J=8.3, 2.6, 0.9 Hz, 1H), 5.35 (s, 2H), 4.81 (t, J=4.9 Hz, 2H), 4.77 (s, 2H), 3.84 (t, J=4.9 Hz, 2H), 3.32 (s, 3H).

Procedure 12: Example 47

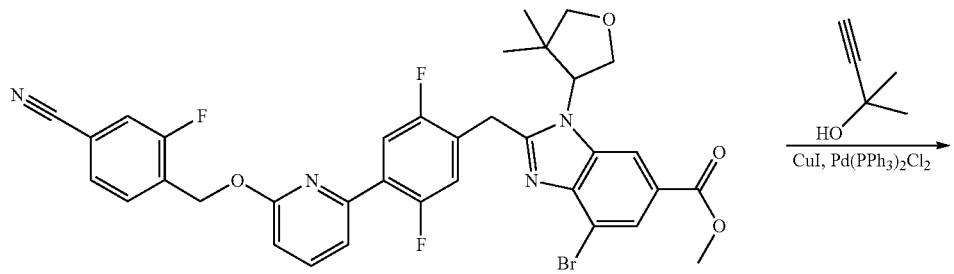

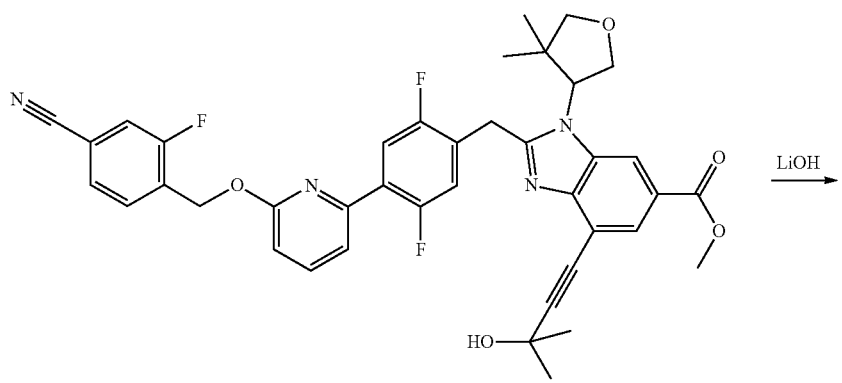

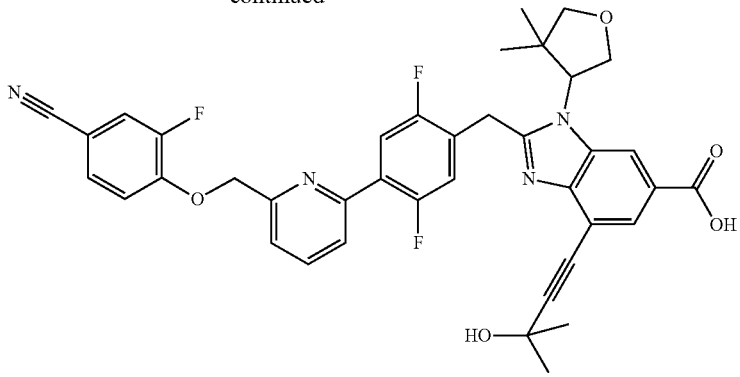

Example 47

Methyl 2-[[4-[6-[(4-cyano-2-fluoro-phenyl)methoxy]-2-pyridyl]-2,5-difluoro-phenyl]methyl]-3-(4,4-dimethyltetrahydrofuran-3-yl)-7-(3-hydroxy-3-methyl-but-1-ynyl)benzimidazole-5-carboxylate: Methyl 7-bromo-2-[[4-[6-[(4-cyano-2-fluoro-phenyl)methoxy]-2-pyridyl]-2,5-difluoro-phenyl]methyl]-3-(4,4-dimethyltetrahydrofuran-3-yl) benzimidazole-5-carboxylate (I-69) (20 mg, 0.028 mmol), 2-methylbut-3-yn-2-ol (11 mg, 0.13 mmol), copper iodide (3 mg, 0.16 mmol), bis(triphenylphosphine)palladium Chloride (4 mg, 0.006 mmole) and diisopropylamine (0.04 mL) was suspended in DMF (1 mL). The mixture was degassed by nitrogen. After which, the mixture was heated to 90° C. for 2 hrs. Next, the solvent was removed, and the crude product was dissolved in 1 mL of DMF. The mixture was filtered and purified by RP-HPLC (eluent: water/MeCN 0.1% TFA) to give the desired product. ES/MS: 709.6 (M+H+).

(S) 2-[[4-[6-[(4-cyano-2-fluoro-phenyl)methoxy]-2-pyridyl]-2,5-difluoro-phenyl]methyl]-3-(4,4-dimethyltetrahydrofuran-3-yl)-7-(3-hydroxy-3-methyl-but-1-ynyl)benzimidazole-5-carboxylic acid: 1 mL of ACN and 0.4 mL of 1 N lithium hydroxide was added to a vial of Methyl 2-[[4-[6-[(4-cyano-2-fluoro-phenyl)methoxy]-2-pyridyl]-2,5-difluoro-phenyl]methyl]-3-(4,4-dimethyltetrahydrofuran-3-yl)-7-(3-hydroxy-3-methyl-but-1-ynyl)benzimidazole-5-carboxylate (10 mg, 0.014 mmol). The mixture was heated to 80° C. for 30 min. Upon completion the filtrate was purified by RP-HPLC (eluent: water/MeCN*0.1% TFA) to give Example 47. ES/MS: 695.3 (M+H+). 1H NMR (400 MHz, Methanol-d4) δ 8.69 (s, 1H), 8.04 (d, J=1.4 Hz, 1H), 7.93-7.67 (m, 3H), 7.67-7.48 (m, 3H), 7.15 (dd, J=11.0, 6.7 Hz, 1H), 7.00-6.85 (m, 1H), 5.63 (s, 2H), 5.00-4.92 (m, 1H), 4.64-4.39 (m, 4H), 3.93 (d, J=8.9 Hz, 1H), 3.78 (d, J=8.9 Hz, 1H), 2.00 (d, J=39.2 Hz, 1H), 1.64 (s, 6H), 1.30 (s, 3H), 0.61 (s, 3H).

Example 48: 2-(4-(6-((4-cyano-2-fluorobenzyl)oxy)pyridin-2-yl)-2,5-difluorobenzyl)-4-(cyclopropylethynyl)-1-(4,4-dimethyltetrahydrofuran-3-yl)-1H-benzo[d]imidazole-6-carboxylic acid 2-(4-(6-((4-cyano-2-fluorobenzyl)oxy)pyridin-2-yl)-2,5-difluorobenzyl)-4-(cyclopropylethynyl)-1-(4,4-dimethyltetrahydrofuran-3-yl)-1H-benzo[d]imidazole-6-carboxylic acid was prepared in a manner as described in Procedure 12. 1H NMR (400 MHz, Methanol-d4) δ 8.67 (s, 1H), 8.01 (d, J=1.4 Hz, 1H), 7.90-7.69 (m, 3H), 7.69-7.47 (m, 3H), 7.19 (dd, J=11.3, 6.0 Hz, 1H), 6.93 (d, J=8.2 Hz, 1H), 5.63 (s, 2H), 5.00-4.90 (m, 2H), 4.56 (dd, J=19.4, 8.0 Hz, 3H), 4.43 (dd, J=11.4, 6.8 Hz, 1H), 3.94 (d, J=8.9 Hz, 1H), 3.78 (d, J=8.9 Hz, 1H), 1.61 (ddd, J=12.8, 8.3, 5.1 Hz, 1H), 1.28 (s, 3H), 1.02-0.84 (m, 4H), 0.61 (s, 3H).

Procedure 13: Example 49

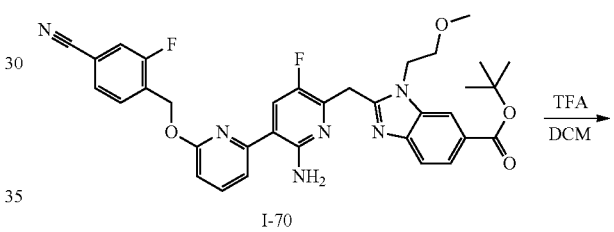

I-70

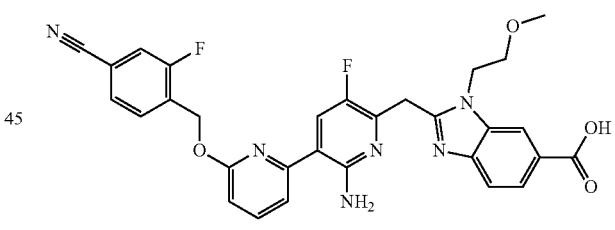

Example 49

2-((2'-amino-6-((4-cyano-2-fluorobenzyl)oxy)-5'-fluoro-[2,3'-bipyridin]-6'-yl)methyl)-1-(2-methoxyethyl)-1H-benzo[d]imidazole-6-carboxylic acid (Example 49): 0.7 mL TFA was added to a solution of tert-butyl 2-((2'-amino-6-((4-cyano-2-fluorobenzyl)oxy)-5'-fluoro-[2,3'-bipyridin]-6'-yl)methyl)-1-(2-methoxyethyl)-1H-benzo[d]imidazole-6-carboxylate (I-70, 30 mg, 0.048 mmol) in DCM (2 mL). The resulting mixture was stirred at rt for 40 min. Upon completion the solution was heated at 35° C. for 1 hour. The mixture was concentrated and purified by RP-HPLC (eluent: water/MeCN 0.1% TFA) to give Example 49. ES/MS: 571.3 (M+H+). H NMR (400 MHz, Methanol-d₄) δ 8.60 (t, J=1.0 Hz, 1H), 8.28 (dd, J=8.6, 1.4 Hz, 1H), 7.91-7.81 (m, 3H), 7.70 (t, J=7.5 Hz, 1H), 7.63-7.55 (m, 2H), 7.48 (d, J=7.5 Hz, 1H), 6.95 (d, J=8.3 Hz, 1H), 5.56 (s, 2H), 4.87-4.82 (m, 4H), 3.96-3.71 (m, 2H), 3.30 (s, 3H).

Procedure 14: Example 50

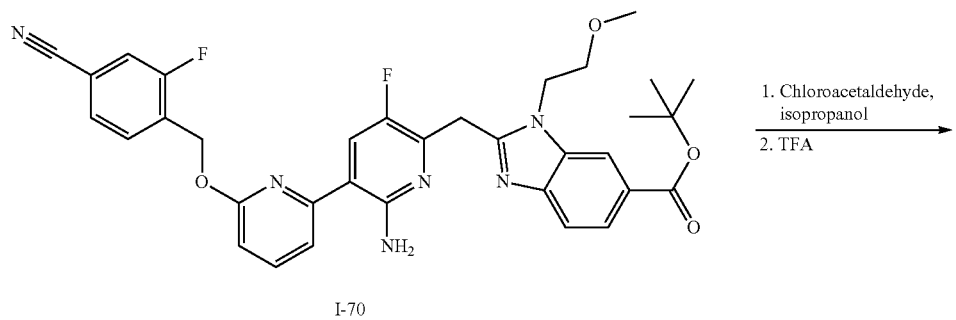

I-70

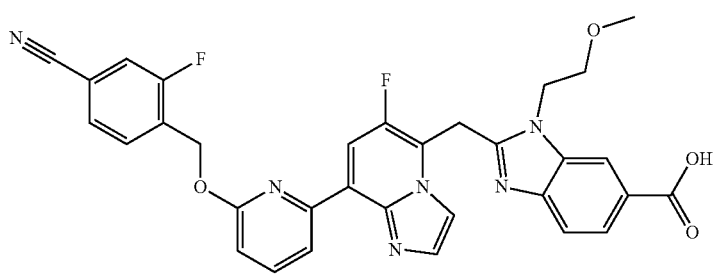

Example 50

2-((8-(6-((4-cyano-2-fluorobenzyl)oxy)pyridin-2-yl)-6-fluoroimidazo[1,2-a]pyridin-5-yl)methyl)-1-(2-methoxyethyl)-1H-benzo[d]imidazole-6-carboxylic acid (Example 50): A solution of tert-butyl 2-((2'-amino-6-((4-cyano-2-fluorobenzyl)oxy)-5'-fluoro-[2,3'-bipyridin]-6'-yl)methyl)-1-(2-methoxyethyl)-1H-benzo[d]imidazole-6-carboxylate (I-70, 41 mg, 0.065 mmol) and chloroacetaldehyde (50% in H$_2$O, 0.09 mL, 0.65 mmol) in isopropanol (2 mL) was heated at 90° C. for 40 min. Upon completion the mixture was cooled to rt, diluted with EtOAc (25 mL), washed with water (5 mL), brine (5 mL), dried over MgSO$_4$, filtered, concentrated and the crude residue purified by flash chromatography (EtOAc/hexanes). The residue was dissolved in TFA (0.5 mL) and stirred for 25 min. Following this time, the mixture was concentrated and purified by RP-HPLC (eluent: water/MeCN 0.1% TFA) to give Example 50: ES/MS: 595.3 (M+H$^+$). $^1$H NMR (400 MHz, Methanol-d$_4$) δ 8.57 (d, J=9.5 Hz, 1H), 8.35 (d, J=1.4 Hz, 1H), 8.18 (s, 2H), 8.07 (dd, J=8.4, 7.5 Hz, 1H), 7.96 (dd, J=8.5, 1.5 Hz, 1H), 7.85 (d, J=7.4 Hz, 1H), 7.79 (t, J=7.6 Hz, 1H), 7.66-7.55 (m, 2H), 7.50 (d, J=8.5 Hz, 1H), 7.19 (d, J=8.3 Hz, 1H), 5.73 (s, 2H), 5.22 (dd, J=6.9, 2.1 Hz, 1H), 4.78 (t, J=4.8 Hz, 2H), 3.96-3.83 (m, 2H), 3.41 (s, 3H).

Procedure 15: Example 51 and 52

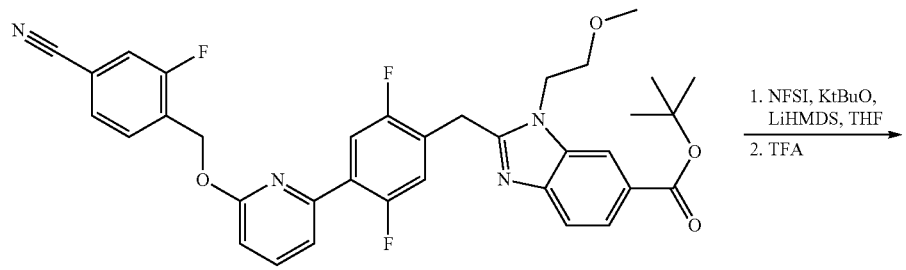

I-71

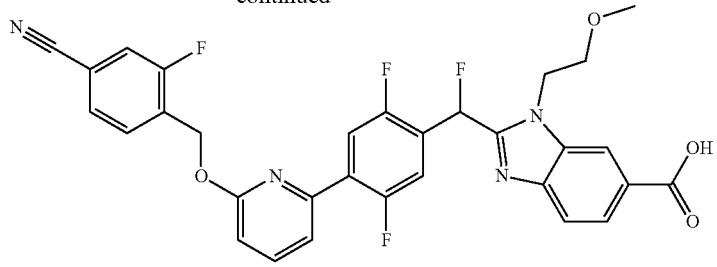

Example 51

+

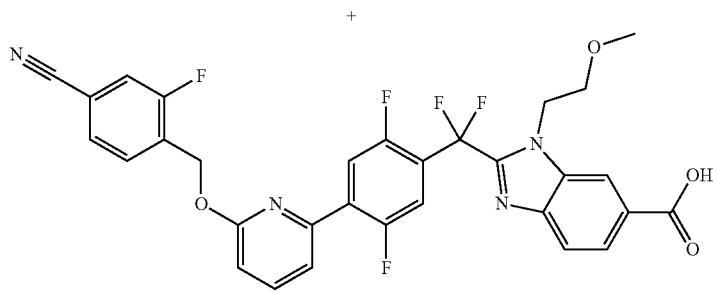

Example 52

2-((4-(6-((4-cyano-2-fluorobenzyl)oxy)pyridin-2-yl)-2,5-difluorophenyl)fluoromethyl)-1-(2-methoxyethyl)-1H-benzo[d]imidazole-6-carboxylic acid and 2-((4-(6-((4-cyano-2-fluorobenzyl)oxy)pyridin-2-yl)-2,5-difluorophenyl)difluoromethyl)-1-(2-methoxyethyl)-11H-benzo[d]imidazole-6-carboxylic acid: A suspension of tert-butyl 2-(4-(6-((4-cyano-2-fluorobenzyl)oxy)pyridin-2-yl)-2,5-difluorobenzyl)-1-(2-methoxyethyl)-1H-benzo[d]imidazole-6-carboxylate (I-71, 50 mg, 0.08 mmol), n-fluorobenzenesulfonimide (75 mg, 0.24 mmol), potassium tert-butoxide (18 mg, 0.16 mmol) in THF (1.0 mL) was stirred for 30 min at rt. Upon completion additional n-fluorobenzenesulfonimide (75 mg, 0.24 mmol) was added followed by the addition of LiHMDS (1M in THF, 0.16 mL, 0.16 mmol) and the mixture was stirred for 15 min. Following this the mixture was diluted with EtOAc (25 mL), washed with water (5 mL), brine (5 mL), dried over MgSO$_4$, filtered, concentrated and the crude residue, redissolved in TFA, and stirred for 10 min. Upon completion the mixture was concentrated and purified by RP-HPLC (eluent: water/MeCN 0.1% TFA) to give the title compounds.

2-((4-(6-((4-cyano-2-fluorobenzyl)oxy)pyridin-2-yl)-2,5-difluorophenyl)fluoromethyl)-1-(2-methoxyethyl)-1H-benzo[d]imidazole-6-carboxylic acid (Example 51): ES/MS: 591.2 (M+H$^+$); $^1$H NMR (400 MHz, Methanol-d$_4$) δ 8.38 (d, J=1.4 Hz, 1H), 8.02 (dd, J=8.6, 1.5 Hz, 1H), 7.88-7.63 (m, 4H), 7.63-7.48 (m, 4H), 7.41 (d, J=45.5 Hz, 1H), 6.93 (d, J=8.2 Hz, 1H), 5.60 (s, 2H), 4.79-4.62 (m, 2H), 3.89-3.67 (m, 2H), 3.25 (s, 3H). 19F NMR (376 MHz, Methanol-d4) δ −78.14, −117.82 (dd, J=9.6, 7.2 Hz), −121.92 (ddd, J=17.8, 11.2, 6.2 Hz), −124.47 (ddd, J=17.3, 11.0, 5.8 Hz), −179.57 (d, J=45.4 Hz).

2-((4-(6-((4-cyano-2-fluorobenzyl)oxy)pyridin-2-yl)-2,5-difluorophenyl)difluoromethyl)-1-(2-methoxyethyl)-11H-benzo[d]imidazole-6-carboxylic acid (Example 52): ES/MS: 609.3 (M+H$^+$); $^1$H NMR (400 MHz, Methanol-d$_4$) δ 8.47-8.20 (m, 1H), 8.16-7.83 (m, 1H), 7.83-7.71 (m, 2H), 7.71-7.33 (m, 6H), 6.99-6.80 (m, 1H), 5.60-5.35 (m, 2H), 4.71-4.56 (m, 2H), 3.86-3.66 (m, 2H), 3.22 (s, 3H). 19F NMR (376 MHz, Methanol-d4) δ −78.33 (d, J=11.0 Hz), −91.17 (t, J=11.0 Hz), −117.83 (d, J=9.4 Hz), −120.07, −121.85.

Procedure 16: Example 53

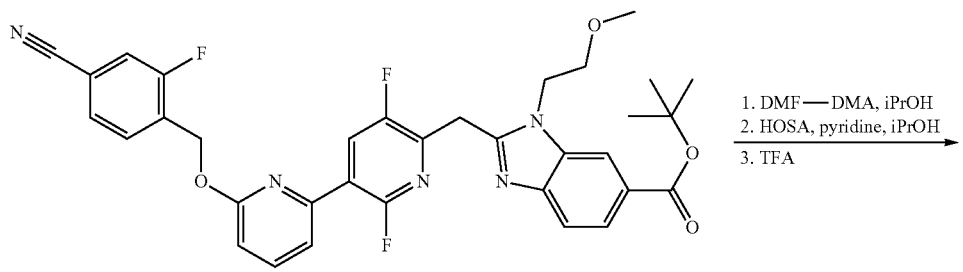

I-70

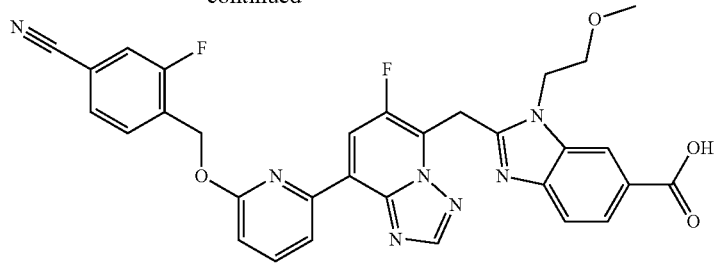

Example 53

2-((8-(6-((4-cyano-2-fluorobenzyl)oxy)pyridin-2-yl)-6-fluoro-[1,2,4]triazolo[1,5-a]pyridin-5-yl)methyl)-1-(2-methoxyethyl)-1H-benzo[d]imidazole-6-carboxylic acid (Example 53): A suspension of tert-butyl 2-(4-(6-((4-cyano-2-fluorobenzyl)oxy)pyridin-2-yl)-2,5-difluorobenzyl)-1-(2-methoxyethyl)-1H-benzo[d]imidazole-6-carboxylate (I-70, 30 mg, 0.048 mmol) and DMF-DMA (200 mg, 1.7 mmol) in isopropanol (0.7 mL) was heated at 60° C. for 20 min, followed by an additional heating at 90° C. for 3 hours. Upon completion the mixture was concentrated, redissolved in isopropanol (0.7 mL) and pyridine. Upon completion hydroxylamine-o-sulfonic acid was added to the solution and heated at 40° C. for 25 min. Following this time, the solution was concentrated, dissolved in TFA (0.5 mL) and stirred for 10 min. Upon completion the mixture was concentrated and purified by RP-HPLC (eluent: water/MeCN 0.1% TFA) to give Example 53. ES/MS: 596.7 (M+H+). H NMR (400 MHz, Methanol-d4) δ 8.78 (d, J=7.5 Hz, 1H), 8.59 (d, J=10.5 Hz, 1H), 8.53 (d, J=6.9 Hz, 1H), 8.48 (s, 1H), 8.22-8.08 (m, 1H), 7.94 (t, J=7.9 Hz, 1H), 7.78 (t, J=7.6 Hz, 1H), 7.74-7.55 (m, 3H), 7.05 (d, J=8.3 Hz, 1H), 5.72 (s, 2H), 5.37-5.25 (m, 2H), 4.92 (t, J=4.9 Hz, 2H), 3.89 (t, J=4.9 Hz, 2H), 3.28 (s, 3H).

Procedure 17: Example 54

2-(1-(4-(6-((4-cyano-2-fluorobenzyl)oxy)pyridin-2-yl)-2,5-difluorophenyl)-2-hydroxyethyl)-1-(2-methoxyethyl)-1H-benzo[d]imidazole-6-carboxylic acid (Example 54): LiHMDS (1M in THF, 0.12 mL, 0.12 mmol) was added to a solution of tert-butyl 2-((3'-((4-cyano-2-fluorobenzyl)oxy)-2,5-difluoro-[1,1'-biphenyl]-4-yl)methyl)-1-(2-methoxyethyl)-1H-benzo[d]imidazole-6-carboxylate (I-71, 46 mg, 0.073 mmol) and paraformaldehyde (8.8 mg, 0.29 mmol) in THF (1.0 mL) at 0° C., and stirred for 5 min. Upon completion the reaction was quenched with aqueous TFA and concentrated. The residue was redissolved in DCM (0.3 mL) and TFA (0.5 mL) was added and stirred for 2 hours. The mixture was concentrated and purified by RP-HPLC (eluent: water/MeCN 0.1% TFA) to give Example 54. ES/MS: 603.3 (M+H+); 1H NMR (400 MHz, Methanol-d4) δ 8.49 (t, J=1.0 Hz, 1H), 8.20 (dd, J=8.6, 1.4 Hz, 1H), 7.86 (d, J=8.6 Hz, 1H), 7.84-7.75 (m, 2H), 7.72 (t, J=7.5 Hz, 1H), 7.66-7.50 (m, 4H), 7.42 (dd, J=11.8, 6.0 Hz, 1H), 6.95 (d, J=8.2 Hz, 1H), 5.62 (s, 2H), 5.25 (t, J=6.1 Hz, 1H), 4.82-4.73 (m, 1H), 4.67 (ddd, J=15.3, 7.2, 3.5 Hz, 1H), 4.40 (dd, J=11.0, 6.5 Hz, 1H), 4.32 (dd, J=11.0, 5.7 Hz, 1H), 3.85-3.66 (m, 2H), 3.21 (s, 3H).

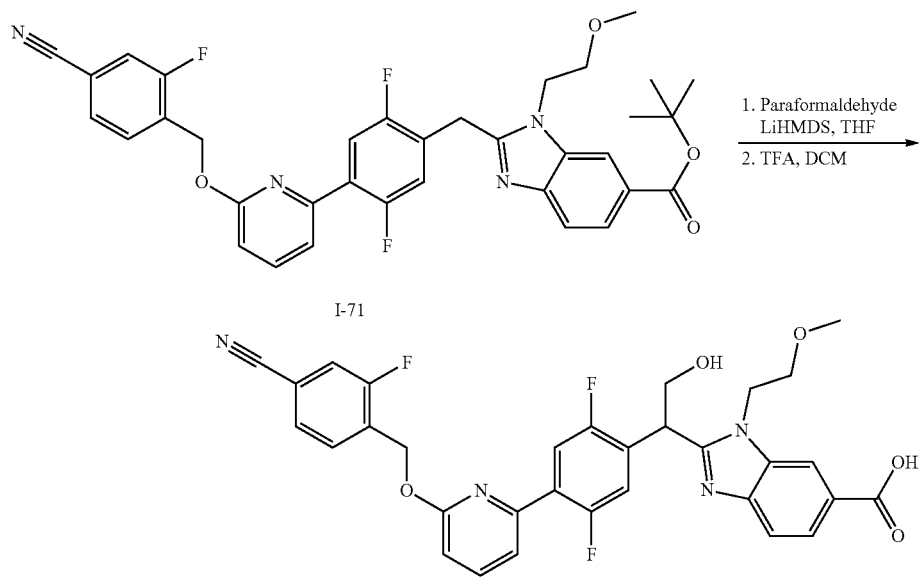

Example 54

Procedure 18: Example 55

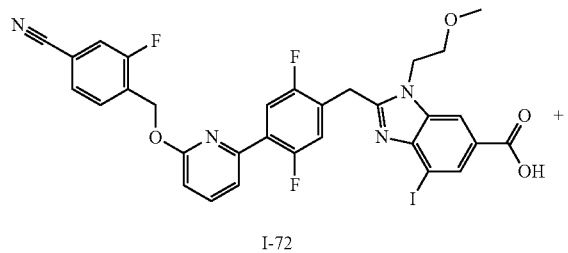

I-72

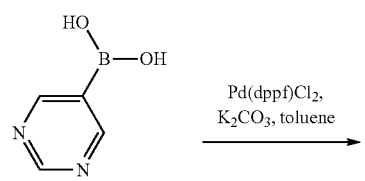

Pd(dppf)Cl₂, K₂CO₃, toluene →

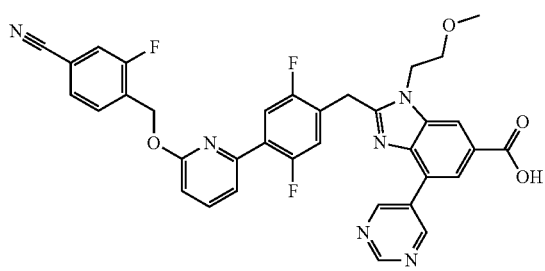

Example 55

2-(4-(6-((4-cyano-2-fluorobenzyl)oxy)pyridin-2-yl)-2,5-difluorobenzyl)-1-(2-methoxyethyl)-4-(pyrimidin-5-yl)-1H-benzo[d]imidazole-6-carboxylic acid (Example 55): A solution of methyl 2-(4-(6-((4-cyano-2-fluorobenzyl)oxy)pyridin-2-yl)-2,5-difluorobenzyl)-4-iodo-1-(2-methoxyethyl)-1H-benzo[d]imidazole-6-carboxylate (I-72, 7 mg, 0.01 mmol), pyrimidin-5-ylboronic acid (3.7 mg, 0.03 mmol), Pd(dppf)Cl₂ (0.7 mg, 0.001 mmol), and K₂CO₃ (5.5 mg, 0.04 mmol) in toluene (0.4 mL) was degassed with argon, and stirred for 30 min at 90° C. Upon completion the mixture was diluted with EtOAc (25 mL), washed with water (5 mL), brine (5 mL), dried over MgSO₄, filtered, concentrated and purified by RP-HPLC (eluent: water/MeCN 0.1% TFA) to give Example 55. ES/MS: 651.3 (M+H⁺); ¹H NMR (400 MHz, Acetonitrile-d₃) δ 8.32 (d, J=1.4 Hz, 1H), 8.21 (d, J=1.4 Hz, 1H), 7.99 (s, 2H), 7.88-7.77 (m, 2H), 7.73 (t, J=7.5 Hz, 1H), 7.64-7.51 (m, 3H), 7.21 (dd, J=11.7, 6.1 Hz, 1H), 6.92 (d, J=8.3 Hz, 1H), 5.63 (s, 2H), 4.56 (t, J=5.0 Hz, 2H), 4.49 (s, 2H), 3.74 (t, J=5.0 Hz, 2H), 3.25 (s, 3H).

Example 56: 2-(4-(6-((4-cyano-2-fluorobenzyl)oxy)pyridin-2-yl)-2,5-difluorobenzyl)-1-(2-methoxyethyl)-4-(1-(2-morpholinoethyl)-1H-pyrazol-4-yl)-1H-benzo[d]imidazole-6-carboxylic acid 2-(4-(6-((4-cyano-2-fluorobenzyl)oxy)pyridin-2-yl)-2,5-difluorobenzyl)-1-(2-methoxyethyl)-4-(1-(2-morpholinoethyl)-1H-pyrazol-4-yl)-1H-benzo[d]imidazole-6-carboxylic acid was prepared in a manner as described in Procedure 18. 1H NMR (400 MHz, Acetonitrile-d3) δ 8.53 (s, 1H), 8.33 (d, J=0.7 Hz, 1H), 8.16 (d, J=1.5 Hz, 1H), 8.12 (d, J=1.5 Hz, 1H), 7.88-7.76 (m, 2H), 7.73 (t, J=7.6 Hz, 1H), 7.64-7.50 (m, 3H), 7.24 (dd, J=11.7, 6.1 Hz, 1H), 6.92 (dd, J=8.3, 0.6 Hz, 1H), 5.63 (s, 2H), 4.61 (t, J=5.8 Hz, 2H), 4.55-4.43 (m, 4H), 3.88 (s, 8H), 3.72 (t, J=5.0 Hz, 2H), 3.63 (t, J=5.8 Hz, 2H), 3.23 (s, 3H).

Procedure 19: Example 57 & 58

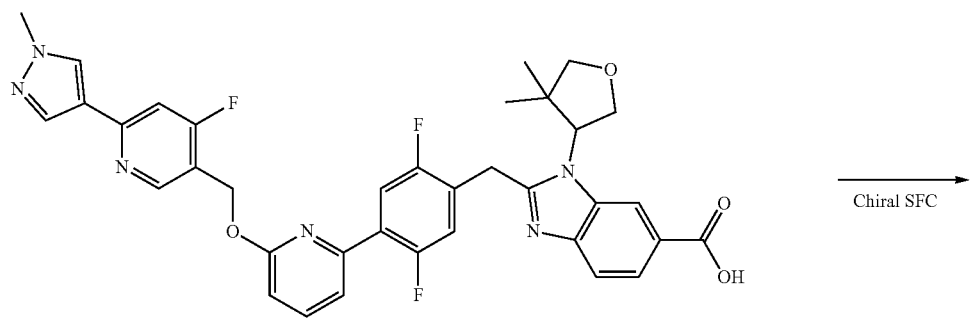

Example 90

Chiral SFC →

-continued

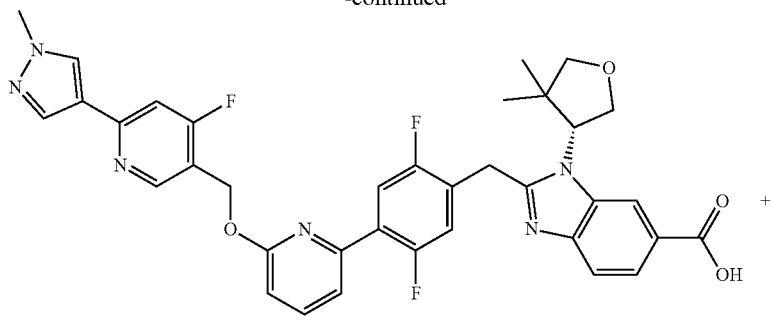

Isomer 1
Example 57

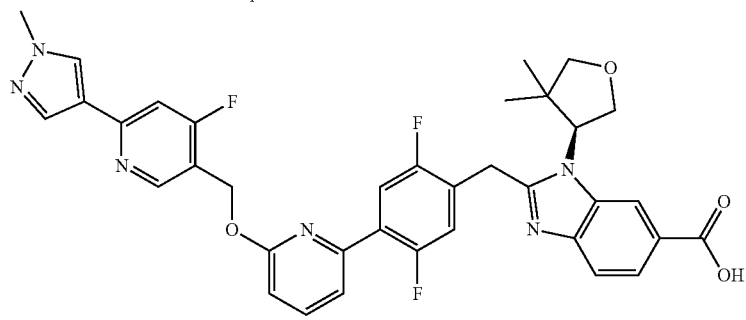

Isomer 2
Example 57

2-(2,5-difluoro-4-(6-((4-fluoro-6-(1-methyl-1H-pyrazol-4-yl)pyridin-3-yl)methoxy)pyridin-2-yl)benzyl)-1-(4,4-dimethyltetrahydrofuran-3-yl)-1H-benzo[d]imidazole-6-carboxylic acid as a mixture of 2 stereoisomers were separated by chiral SFC (SFC IA column with MeOH cosolvent) to give two distinct stereoisomers.

2-(2,5-difluoro-4-(6-((4-fluoro-6-(1-methyl-1H-pyrazol-4-yl)pyridin-3-yl)methoxy)pyridin-2-yl)benzyl)-1-(4,4-dimethyltetrahydrofuran-3-yl)-1H-benzo[d]imidazole-6-carboxylic acid (Isomer 1, Example 57): ES/MS: 669.6 (M+H$^+$). 1H NMR (400 MHz, DMSO-d6) δ 8.69 (d, J=10.4 Hz, 1H), 8.51 (s, 1H), 8.35 (s, 1H), 8.06 (s, 1H), 8.00-7.86 (m, 2H), 7.83 (dd, J=8.4, 1.5 Hz, 1H), 7.73-7.61 (m, 2H), 7.55 (dd, J=7.5, 1.6 Hz, 1H), 7.48 (dd, J=11.2, 6.3 Hz, 1H), 6.95 (d, J=8.3 Hz, 1H), 5.55 (s, 2H), 5.04 (d, J=6.6 Hz, 1H), 4.65-4.51 (m, 2H), 4.49-4.36 (m, 2H), 3.89 (s, 3H), 3.79 (d, J=8.7 Hz, 1H), 3.74 (d, J=8.6 Hz, 1H), 1.34 (s, 3H), 0.62 (s, 3H).

2-(2,5-difluoro-4-(6-((4-fluoro-6-(1-methyl-1H-pyrazol-4-yl)pyridin-3-yl)methoxy)pyridin-2-yl)benzyl)-1-(4,4-dimethyltetrahydrofuran-3-yl)-1H-benzo[d]imidazole-6-carboxylic acid (Isomer 2, Example 58): ES/MS: 669.6 (M+H$^+$). 1H NMR (400 MHz, DMSO-d6) δ 8.69 (d, J=10.4 Hz, 1H), 8.51 (s, 1H), 8.35 (s, 1H), 8.06 (s, 1H), 8.00-7.86 (m, 2H), 7.83 (dd, J=8.4, 1.5 Hz, 1H), 7.73-7.61 (m, 2H), 7.55 (dd, J=7.5, 1.6 Hz, 1H), 7.48 (dd, J=11.2, 6.3 Hz, 1H), 6.95 (d, J=8.3 Hz, 1H), 5.55 (s, 2H), 5.04 (d, J=6.6 Hz, 1H), 4.65-4.51 (m, 2H), 4.49-4.36 (m, 2H), 3.89 (s, 3H), 3.79 (d, J=8.7 Hz, 1H), 3.74 (d, J=8.6 Hz, 1H), 1.34 (s, 3H), 0.62 (s, 3H).

Procedure 20: Example 59, 60 (Method 1)

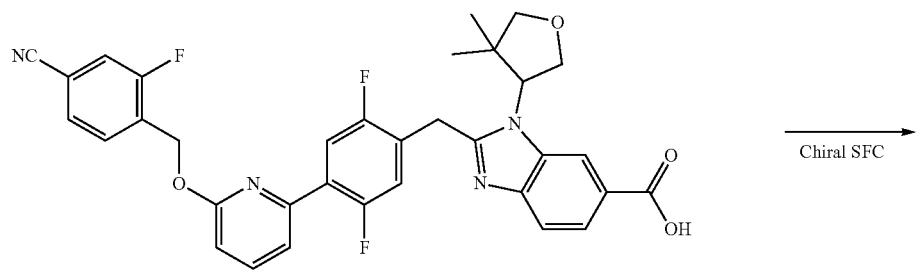

Example 78

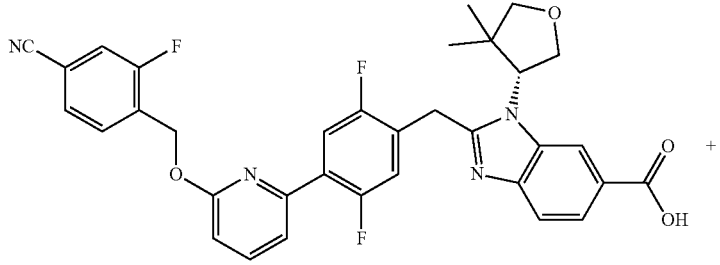

Isomer 1
Example 59

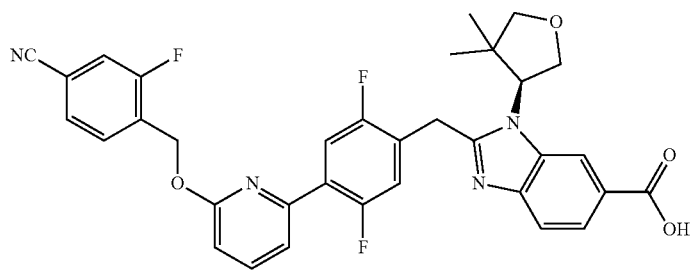

Isomer 2
Example 60

2-[[4-[6-[(4-cyano-2-fluoro-phenyl)methoxy]-2-pyridyl]-2,5-difluoro-phenyl]methyl]-3-(4,4-dimethyltetrahydrofuran-3-yl)benzimidazole-5-carboxylic acid (Example 78) as a mixture of 2 stereoisomers was separated by chiral SFC (SFC AD-H column with EtOH cosolvent) to give two distinct stereoisomers.

(R)-2-[[4-[6-[(4-cyano-2-fluoro-phenyl)methoxy]-2-pyridyl]-2,5-difluoro-phenyl]methyl]-3-(4,4-dimethyltetrahydrofuran-3-yl)benzimidazole-5-carboxylic acid (Isomer 1, Example 59). Earlier eluting of two isomers ES/MS: 613.2 (M+H⁺). 1H NMR (400 MHz, DMSO-d6) δ 12.77 (s, 1H), 8.48 (s, 1H), 7.96-7.86 (m, 2H), 7.83-7.70 (m, 4H), 7.61 (d, J=8.5 Hz, 1H), 7.55 (dd, J=7.5, 1.6 Hz, 1H), 7.45 (dd, J=11.3, 6.2 Hz, 1H), 7.00 (d, J=8.2 Hz, 1H), 5.61 (s, 2H), 5.01 (d, J=6.7 Hz, 1H), 4.58-4.47 (m, 2H), 4.44 (dd, J=11.1, 6.8 Hz, 1H), 4.36 (d, J=16.9 Hz, 1H), 3.82-3.70 (m, 2H), 1.33 (s, 3H), 1.24 (s, 1H), 0.60 (s, 3H).

(S)-2-[[4-[6-[(4-cyano-2-fluoro-phenyl)methoxy]-2-pyridyl]-2,5-difluoro-phenyl]methyl]-3-(4,4-dimethyltetrahydrofuran-3-yl)benzimidazole-5-carboxylic acid (Isomer 2, Example 60): Later eluting of two isomers. ES/MS: 613.2 (M+H⁺). 1H NMR (400 MHz, DMSO-d6) δ 8.49 (s, 1H), 7.96-7.85 (m, 2H), 7.85-7.68 (m, 4H), 7.63 (d, J=8.5 Hz, 1H), 7.55 (dd, J=7.5, 1.6 Hz, 1H), 7.46 (dd, J=11.3, 6.2 Hz, 1H), 7.00 (d, J=8.3 Hz, 1H), 5.02 (d, J=6.6 Hz, 1H), 4.58-4.49 (m, 2H), 4.49-4.34 (m, 2H), 3.82-3.70 (m, 2H), 1.33 (s, 3H), 0.61 (s, 3H).

2-[[4-[6-[(4-cyano-2-fluoro-phenyl)methoxy]-2-pyridyl]-2,5-difluorophenyl]methyl]-3-[(3S)-4,4-dimethyltetrahydrofuran-3-yl]benzimidazole-5-carboxylic acid (Example 60, Method 2): Example 60 was also prepared in a manner similar to Procedure 22, with the following modifications: A suspension of methyl 2-[[4-[6-[(4-cyano-2-fluorophenyl)methoxy]-2-pyridyl]-2,5-difluoro-phenyl]methyl]-3-[(3S)-4,4-dimethyltetrahydrofuran-3-yl]benzimidazole-5-carboxylate (Intermediate I-101, 2020 mg, 3.2 mmol) and lithium hydroxide, monohydrate (300 mmol/L, 24 mL, 7.2 mmol) in in CH3CN (24 mL) was heated at 90° C. for until complete conversion to product (~20 min). The mixture was cooled to rt and diluted with EtOAc and brine. Then 7.3 mL 1M citric acid was added. The organic extract was dried over sodium sulfate, concentrated and purified by reverse-phase preparative HPLC (water/MeCN gradient, with 0.1% TFA) to provide Example 60.

2-[[4-[6-[(4-cyano-2-fluoro-phenyl)methoxy]-2-pyridyl]-2,5-difluorophenyl]methyl]-3-[(3S)-4,4-dimethyltetrahydrofuran-3-yl]benzimidazole-5-carboxylic acid (Example 60, Method 3). Example 60 was also prepared in a manner similar to Procedure 22 with the following modifications: LiOH (2N in H₂O, 20.5 mL, 41.1 mmol) was added to a solution of methyl 2-[[4-[6-[(4-cyano-2-fluorophenyl)methoxy]-2-pyridyl]-2,5-difluorophenyl]methyl]-3-[(3S)-4,4-dimethyltetrahydrofuran-3-yl]benzimidazole-5-carboxylate (Intermediate I-101, 11.7 g, 18.7 mmol) in ACN (90 mL) and water (70 mL), and the resulting solution was heated to 95° C. for 40 min. The mixture was partitioned between EtOAc and brine acidified with 20.5 mL 1M citric acid. Phases were separated, and aqueous phase again extracted with EtOAc. Combined organic layers were dried over MgSO₄, filtered, concentrated, and purified by silica gel flash chromatography (EtOAc/Hexane gradient) to give Example 60.

Procedure 21: Example 61

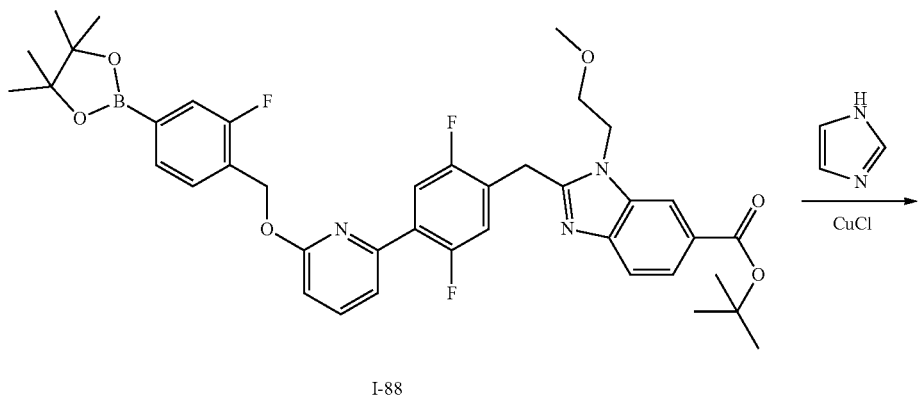

I-88

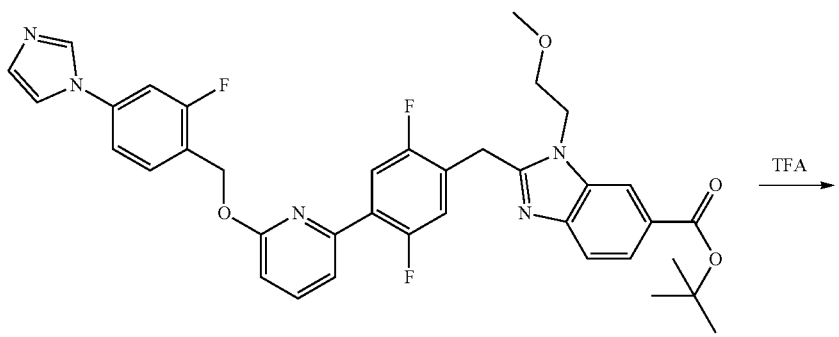

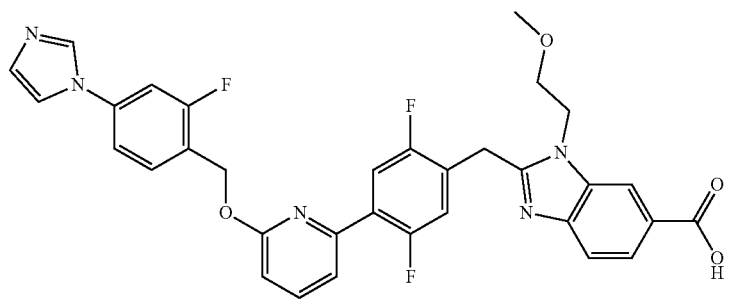

Example 61

Tert-butyl 2-[[2,5-difluoro-4-[6-[(2-fluoro-4-imidazol-1-yl-phenyl)methoxy]-2-pyridyl]phenyl]methyl]-3-(2-methoxyethyl)benzimidazole-5-carboxylate: Copper(I) chloride (0.6 mg, 0.006 mmol) and imidazole (6.5 mg, 0.096 mmol) were added to a solution of tert-butyl 2-[[2,5-difluoro-4-[[2-fluoro-4-(4,4,5,5-tetramethyl-1,3,2-dioxaborolan-2-yl)phenyl]methoxy]-2-pyridyl]phenyl]methyl]-3-(2-methoxyethyl)benzimidazole-5-carboxylate (I-88) (70 mg, 0.096 mmol) in MeOH (3 mL). The mixture was stirred at 60° C. for 3 hrs. Following this time, the mixture was concentrated directly, and the crude residue purified by RP-HPLC (eluent: water/MeCN 0.1% TFA) to give the desired product.

2-[[2,5-difluoro-4-[6-[(2-fluoro-4-imidazol-1-yl-phenyl)methoxy]-2-pyridyl]phenyl]methyl]-3-(2-methoxyethyl)benzimidazole-5-carboxylic acid (Example 61): 0.25 mL TFA was added to a solution of tert-butyl 2-[[2,5-difluoro-4-[6-[(2-fluoro-4-imidazol-1-yl-phenyl)methoxy]-2-pyridyl]phenyl]methyl]-3-(2-methoxyethyl)benzimidazole-5-carboxylate (15 mg, 0.022 mmol) in DCM (2 mL). The resulting solution stirred at 40° C. for 1 hour. Following this time mixture was concentrated directly and purified by RP-HPLC (eluent: water/MeCN 0.1% TFA). The combined fractions were then frozen and placed on a lyophilizer to provide Example 61. ES/MS: 614.1 (M+H$^+$). 1H NMR (400 MHz, DMSO-d6) δ 12.81 (s, 1H), 9.32 (s, 1H), 8.25-8.16 (m, 2H), 7.94-7.77 (m, 5H), 7.73-7.64 (m, 2H), 7.60 (d, 1H), 7.54 (dd, 1H), 7.40 (dd, 1H), 6.97 (d, 1H), 5.60 (s, 2H), 4.61 (t, 2H), 4.46 (s, 2H), 3.69 (t, 2H), 3.22 (s, 3H).

Procedure 22: Example 62

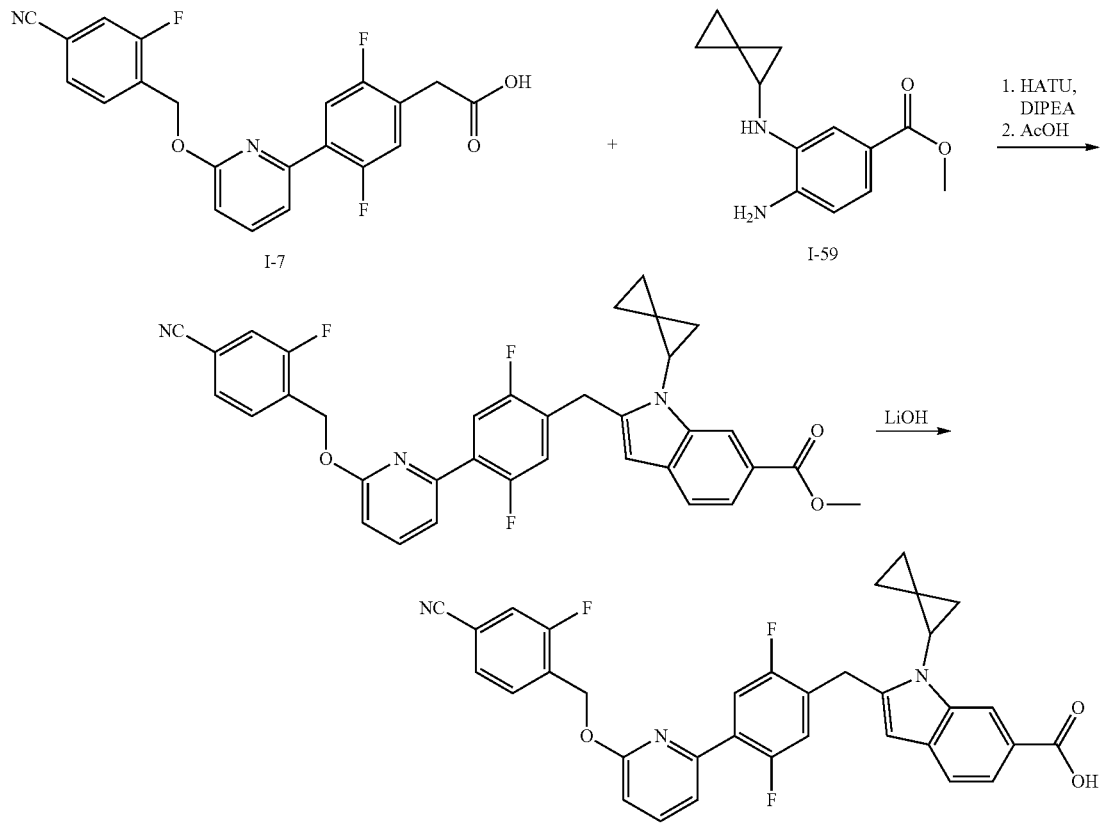

Example 62

Methyl 2-[[4-[6-[(4-cyano-2-fluoro-phenyl)methoxy]-2-pyridyl]-2,5-difluoro-phenyl]methyl]-3-spiro[2.2]pentan-2-yl-benzimidazole-5-carboxylate: N,N-Diisopropylethylamine (0.147 mL, 0.842 mmol) was added to a solution of 2-[4-[6-[(4-cyano-2-fluoro-phenyl)methoxy]-2-pyridyl]-2,5-difluoro-phenyl]acetic acid (110 mg, 0.276 mmol), methyl 4-amino-3-(spiro[2.2]pentan-2-ylamino)benzoate (60.0%, 89.5 mg, 0.231 mmol), and o-(7-Azabenzotriazol-1-yl)-N,N,N',N'-tetramethyluronium hexafluorophosphate (156 mg, 0.410 mmol) in DMF (5 mL)ed. The solution was stirred at rt overnight. Following this time, the solution was diluted with EtOAc and washed with 5% LiCl, saturated NaHCO$_3$, and brine. The organic extract was dried over sodium sulfate. The crude residue was purified by flash chromatography (eluent: EtOAc/hexanes). The resulting product was diluted with DCE (4 mL) and acetic acid (0.12 mL, 2.1 mmol) was added. The mixture was heated at 80° C. for 4 hr. Upon completion the mixture was diluted with DCM and neutralized carefully with NaHCO$_3$. The organic extract was dried over sodium sulfate. The crude residue was purified by flash chromatography (eluent: EtOAc/hexanes) to yield desired product. ES/MS: 595.2 (M+H$^+$).

2-[[4-[6-[(4-cyano-2-fluoro-phenyl)methoxy]-2-pyridyl]-2,5-difluoro-phenyl]methyl]-3-spiro[2.2]pentan-2-yl-benzimidazole-5-carboxylic acid (Example 62): Lithium hydroxide, monohydrate (0.3 M, 0.148 mmol, 1.86 mmol) in CH$_3$CN (3 mL) was added to a solution of methyl 2-[[4-[6-[(4-cyano-2-fluoro-phenyl)methoxy]-2-pyridyl]-2,5-difluoro-phenyl]methyl]-3-spiro[2.2]pentan-2-yl-benzimidazole-5-carboxylate (8.80 mg, 0.0148 mmol) in CH3CN (3 mL)d. The mixture was heated at 80° C. until completion (~2 hr.). Upon completion the mixture was diluted with EtOAc and brine and 0.120 mL 1M citric acid was added. The organic extract was dried over sodium sulfate, filtered and concentrated. Purified by RP-HPLC (eluent: MeCN/H$_2$O). The resulting product fractions were diluted with EtOAc and neutralized with sodium bicarbonate solution. The organic extract was dried over sodium sulfate, filtered and concentrated to give Example 62. ES/MS: 581.2 (M+H$^+$); 1H NMR (400 MHz, DMSO-d6) δ 7.94 (s, 1H), 7.92-7.87 (m, 2H), 7.80-7.65 (m, 4H), 7.61 (d, J=8.5 Hz, 1H), 7.53 (d, J=7.3 Hz, 1H), 7.44 (dd, J=11.5, 6.0 Hz, 1H), 6.99 (d, J=8.2 Hz, 1H), 5.60 (s, 2H), 4.34 (s, 2H), 3.91 (dd, J=7.2, 4.0 Hz, 1H), 1.94-1.77 (m, 2H), 1.36 (s, 1H), 1.08 (td, J=9.2, 4.6 Hz, 2H), 0.90 (m, 1H).

Example 63: 2-(4-(6-((4-cyano-2-fluorobenzyl)oxy)pyridin-2-yl)-2,5-difluorobenzyl)-1-(spiro[2.4]heptan-4-yl)-1H-benzo[d]imidazole-6-carboxylic acid 2-(4-(6-((4-cyano-2-fluorobenzyl)oxy)pyridin-2-yl)-2,5-difluorobenzyl)-1-(spiro[2.4]heptan-4-yl)-1H-benzo[d]imidazole-6-carboxylic acid was prepared in a manner as described in Procedure 22. 1H NMR (400 MHz, DMSO-d6) δ 8.24 (d, J=1.4 Hz, 1H), 8.00-7.82 (m, 2H), 7.82-7.67 (m, 4H), 7.62 (d, J=8.4 Hz, 1H), 7.53 (dd, J=7.5, 1.6 Hz, 1H), 7.31 (dd, J=11.4, 6.1 Hz, 1H), 6.99 (d, J=8.2 Hz, 1H), 5.60 (s, 2H), 4.97 (t, J=8.4 Hz, 1H), 4.38 (s, 2H), 2.26 (ddt, J=30.5, 18.5, 6.2 Hz, 3H), 2.04 (d, J=7.1 Hz, 1H), 1.87 (dq, J=11.9, 6.6, 5.8 Hz, 1H), 1.77-1.57 (m, 1H), 0.83-0.61 (m, 1H), 0.55 (dt, J=9.3, 5.1 Hz, 1H), 0.48 (dd, J=9.2, 3.2 Hz, 1H), −0.09 (dd, J=10.0, 4.9 Hz, 1H).

Example 64: 2-(4-(6-((4-cyano-2-fluorobenzyl)oxy)pyridin-2-yl)-2,5-difluorobenzyl)-1-(spiro[2.3]hexan-4-yl)-1H-benzo[d]imidazole-6-carboxylic acid 2-(4-(6-((4-cyano-2-fluorobenzyl)oxy)pyridin-2-yl)-2,5-difluorobenzyl)-1-(spiro[2.3]hexan-4-yl)-1H-benzo[d]imidazole-6-carboxylic acid was prepared in a manner as described in Procedure 22. 1H NMR (400 MHz, DMSO-d6) δ 12.84 (s, 1H), 8.50 (d, J=1.5 Hz, 1H), 7.99-7.84 (m, 2H), 7.82 (dd, J=8.4, 1.5 Hz, 1H), 7.78-7.70 (m, 3H), 7.64 (d, J=8.2 Hz, 1H), 7.51 (dd, J=7.5, 1.7 Hz, 1H), 7.22 (dd, J=11.5, 6.0 Hz, 1H), 6.99 (d, J=8.2 Hz, 1H), 5.60 (s, 2H), 5.37 (dd, J=9.1, 7.0 Hz, 1H), 4.40 (s, 2H), 2.99-2.78 (m, 1H), 2.76-2.52 (m, 1H), 2.45-2.15 (m, 2H), 0.59 (td, J=7.4, 6.7, 4.3 Hz, 2H), 0.44-0.22 (m, 1H), 0.22-0.05 (m, 1H).

Example 65: 2-(4-(6-((4-cyano-2-fluorobenzyl)oxy)pyridin-2-yl)-2,5-difluorobenzyl)-1-((1S,2R)-2-methoxycyclobutyl)-1H-benzo[d]imidazole-6-carboxylic acid 2-(4-(6-((4-cyano-2-fluorobenzyl)oxy)pyridin-2-yl)-2,5-difluorobenzyl)-1-((1S,2R)-2-methoxycyclobutyl)-1H-benzo[d]imidazole-6-carboxylic acid was prepared in a manner as described in Procedure 22. 1H NMR (400 MHz, DMSO-d6) δ 8.45 (d, J=1.4 Hz, 1H), 7.95-7.86 (m, 2H), 7.82 (dd, J=8.5, 1.5 Hz, 1H), 7.79-7.69 (m, 3H), 7.63 (d, J=8.5 Hz, 1H), 7.53 (dd, J=7.5, 1.7 Hz, 1H), 7.34 (dd, J=11.5, 6.1 Hz, 1H), 7.00 (d, J=8.2 Hz, 1H), 5.60 (s, 2H), 5.48-5.32 (m, 1H), 4.59-4.42 (m, 2H), 4.30 (dd, J=5.9, 3.2 Hz, 1H), 3.22-3.07 (m, 1H), 2.95 (s, 3H), 2.63 (pd, J=9.7, 8.8, 3.3 Hz, 1H), 2.24 (ddd, J=14.2, 9.1, 5.5 Hz, 1H), 2.12 (t, J=11.7 Hz, 1H).

Example 66: 1-(2-oxabicyclo[2.1.1]hexan-4-yl)-2-(4-(6-((4-cyano-2-fluorobenzyl)oxy)pyridin-2-yl)-2,5-difluorobenzyl)-1H-benzo[d]imidazole-6-carboxylic acid 1-(2-oxabicyclo[2.1.1]hexan-4-yl)-2-(4-(6-((4-cyano-2-fluorobenzyl)oxy)pyridin-2-yl)-2,5-difluorobenzyl)-1H-benzo[d]imidazole-6-carboxylic acid was prepared in a manner as described in Procedure 22. 1H NMR (400 MHz, DMSO-d6) δ 8.08 (d, J=1.4 Hz, 1H), 7.94-7.88 (m, 2H), 7.84-7.71 (m, 4H), 7.64 (d, J=8.4 Hz, 1H), 7.55 (dd, J=7.5, 1.6 Hz, 1H), 7.41 (dd, J=11.4, 6.1 Hz, 1H), 7.00 (d, J=8.2 Hz, 1H), 5.61 (s, 2H), 4.77 (s, 1H), 4.40 (s, 2H), 3.94 (s, 2H), 2.61 (t, J=1.7 Hz, 4H).

Example 67: 2-(4-(6-((4-cyano-2-fluorobenzyl)oxy)pyridin-2-yl)-2,5-difluorobenzyl)-1-(pyrrolidin-1-yl)-1H-benzo[d]imidazole-6-carboxylic acid 2-(4-(6-((4-cyano-2-fluorobenzyl)oxy)pyridin-2-yl)-2,5-difluorobenzyl)-1-(pyrrolidin-1-yl)-1H-benzo[d]imidazole-6-carboxylic acid was prepared in a manner as described in Procedure 22. 1H NMR (400 MHz, DMSO-d6) δ 8.10 (d, J=1.4 Hz, 1H), 7.94-7.86 (m, 2H), 7.84 (dd, J=8.5, 1.5 Hz, 1H), 7.78-7.71 (m, 3H), 7.69 (d, J=8.5 Hz, 1H), 7.52 (dd, J=7.6, 1.6 Hz, 1H), 7.38 (dd, J=11.6, 6.0 Hz, 1H), 6.99 (d, J=8.3 Hz, 1H), 5.59 (s, 2H), 4.39 (s, 2H), 3.38-3.25 (m, 4H), 2.13-1.94 (m, 4H).

Example 68: 1-(2-oxabicyclo[3.1.1]heptan-4-yl)-2-(4-(6-((4-cyano-2-fluorobenzyl)oxy)pyridin-2-yl)-2,5-difluorobenzyl)-1H-benzo[d]imidazole-6-carboxylic acid 1-(2-oxabicyclo[3.1.1]heptan-4-yl)-2-(4-(6-((4-cyano-2-fluorobenzyl)oxy)pyridin-2-yl)-2,5-difluorobenzyl)-1H-benzo[d]imidazole-6-carboxylic acid was prepared in a manner as described in Procedure 22. 1H NMR (400 MHz, DMSO-d6) δ 8.68 (d, J=1.4 Hz, 1H), 7.96-7.86 (m, 2H), 7.82 (dd, J=8.5, 1.5 Hz, 1H), 7.80-7.70 (m, 3H), 7.63 (d, J=8.5 Hz, 1H), 7.54 (dd, J=7.5, 1.6 Hz, 1H), 7.44 (dd, J=11.4, 6.1 Hz, 1H), 7.00 (d, J=8.3 Hz, 1H), 5.61 (s, 2H), 5.50-5.36 (m, 1H), 4.73-4.61 (m, 2H), 4.58-4.37 (m, 3H), 3.07 (p, J=5.6 Hz, 1H), 2.36 (ddd, J=9.6, 5.7, 3.5 Hz, 1H), 2.27 (t, J=10.0 Hz, 1H), 2.09 (q, J=5.3, 4.3 Hz, 1H), 2.04-1.96 (m, 1H).

Example 69: 1-(3-oxabicyclo[3.1.0]hexan-1-yl)-2-(4-(6-((4-cyano-2-fluorobenzyl)oxy)pyridin-2-yl)-2,5-difluorobenzyl)-1H-benzo[d]imidazole-6-carboxylic acid 1-(3-oxabicyclo[3.1.0]hexan-1-yl)-2-(4-(6-((4-cyano-2-fluorobenzyl)oxy)pyridin-2-yl)-2,5-difluorobenzyl)-1H-benzo[d]imidazole-6-carboxylic acid was prepared in a manner as described in Procedure 22. 1H NMR (400 MHz, DMSO-d6) δ 7.95-7.88 (m, 2H), 7.83 (dd, J=8.4, 1.5 Hz, 1H), 7.82-7.71 (m, 4H), 7.65 (d, J=8.6 Hz, 1H), 7.58-7.52 (m, 1H), 7.46 (s, 1H), 7.00 (d, J=8.3 Hz, 1H), 5.61 (s, 2H), 4.49 (d, J=7.5 Hz, 2H), 4.21 (dd, J=8.9, 2.8 Hz, 1H), 4.03-3.91 (m, 1H), 3.79-3.70 (m, 3H), 1.83-1.54 (m, 1H), 1.42 (s, 1H).

Example 70: 2-(4-(6-((4-cyano-2-fluorobenzyl)oxy)pyridin-2-yl)-2,5-difluorobenzyl)-1-((3R,4S)-4-methoxytetrahydro-2H-pyran-3-yl)-1H-benzo[d]imidazole-6-carboxylic acid 2-(4-(6-((4-cyano-2-fluorobenzyl)oxy)pyridin-2-yl)-2,5-difluorobenzyl)-1-((3R,4S)-4-methoxytetrahydro-2H-pyran-3-yl)-1H-benzo[d]imidazole-6-carboxylic acid was prepared in a manner as described in Procedure 22. 1H NMR (400 MHz, DMSO-d6) δ 8.54 (s, 1H), 7.91 (t, J=9.9 Hz, 2H), 7.85-7.68 (m, 4H), 7.61 (d, J=8.4 Hz, 1H), 7.54 (d, J=7.3 Hz, 1H), 7.40 (dd, J=11.4, 6.0 Hz, 1H), 7.00 (d, J=8.2 Hz, 1H), 5.61 (s, 2H), 4.87 (dd, J=9.0, 4.7 Hz, 1H), 4.63 (d, J=16.9 Hz, 1H), 4.59-4.46 (m, 2H), 3.90 (dd, J=10.7, 4.6 Hz, 1H), 3.84-3.77 (m, 2H), 3.14 (s, 3H), 1.99 (q, J=4.6, 4.0 Hz, 3H).

Example 71: 1-((1R,4R,6S)-2-oxabicyclo[2.2.1]heptan-6-yl)-2-(4-(6-((4-cyano-2-fluorobenzyl)oxy)pyridin-2-yl)-2,5-difluorobenzyl)-1H-benzo[d]imidazole-6-carboxylic acid 1-((1R,4R,6S)-2-oxabicyclo[2.2.1]heptan-6-yl)-2-(4-(6-((4-cyano-2-fluorobenzyl)oxy)pyridin-2-yl)-2,5-difluorobenzyl)-1H-benzo[d]imidazole-6-carboxylic acid was prepared in a manner as described in Procedure 22. 1H NMR (400 MHz, DMSO-d6) δ 8.49 (s, 1H), 7.96-7.87 (m, 2H), 7.83 (d, J=8.5 Hz, 1H), 7.81-7.70 (m, 3H), 7.63 (d, J=8.4 Hz, 1H), 7.59-7.48 (m, 1H), 7.41 (dd, J=11.5, 6.0 Hz, 1H), 7.00 (d, J=8.2 Hz, 1H), 5.61 (s, 2H), 5.07 (dd, J=11.5, 5.6 Hz, 1H), 4.54 (d, J=12.8 Hz, 3H), 4.06 (d, J=7.1 Hz, 1H), 3.95-3.83 (m, 1H), 2.81 (t, J=3.1 Hz, 1H), 2.40 (t, J=13.9 Hz, 1H), 2.18-1.95 (m, 2H), 1.83 (d, J=10.4 Hz, 1H).

Example 72: 1-((3R,4S)-4-((tert-butoxycarbonyl)amino)tetrahydrofuran-3-yl)-2-(4-(6-((4-cyano-2-fluorobenzyl)oxy)pyridin-2-yl)-2,5-difluorobenzyl)-1H-benzo[d]imidazole-6-carboxylic acid 1-((3R,4S)-4-((tert-butoxycarbonyl)amino)tetrahydrofuran-3-yl)-2-(4-(6-((4-cyano-2-fluorobenzyl)oxy)pyridin-2-yl)-2,5-difluorobenzyl)-1H-benzo[d]imidazole-6-carboxylic acid (as a racemic mixture of enantiomers) was prepared in a manner as described in Procedure 22. 1H NMR (400 MHz, DMSO-d6) δ 8.44 (s, 1H), 7.94-7.86 (m, 2H), 7.81-7.70 (m, 4H), 7.54 (dd, J=11.0, 7.7 Hz, 2H), 7.30 (dd, J=11.2, 6.4 Hz, 1H), 7.09 (s, 1H), 7.00 (d, J=8.3 Hz, 1H), 5.62 (s, 2H), 5.40 (s, 1H), 4.63-4.43 (m, 4H), 4.30 (d, J=17.0 Hz, 1H), 4.20 (dd, J=10.9, 7.0 Hz, 1H), 4.08-3.89 (m, 3H), 1.12 (s, 9H).

Example 73: 2-(4-(6-((4-cyano-2-fluorobenzyl)oxy)pyridin-2-yl)-2,5-difluorobenzyl)-1-((2R,3R)-2-methyltetrahydrofuran-3-yl)-1H-benzo[d]imidazole-6-carboxylic acid 2-(4-(6-((4-cyano-2-fluorobenzyl)oxy)pyridin-2-yl)-2,5-difluorobenzyl)-1-((2R,3R)-2-methyltetrahydrofuran-3-yl)-1H-benzo[d]imidazole-6-carboxylic acid (as a racemic mixture of enantiomers) was prepared in a manner as described in Procedure 22. 1H NMR (400 MHz, DMSO-d6) δ 8.32 (d, J=1.4 Hz, 1H), 7.94-7.87 (m, 2H), 7.83 (dd, J=8.5, 1.5 Hz, 1H), 7.80-7.71 (m, 3H), 7.65 (d, J=8.5 Hz, 1H), 7.54 (dd, J=7.5, 1.5 Hz, 1H), 7.43 (dd, J=11.4, 6.1 Hz, 1H), 7.00 (d, J=8.3 Hz, 1H), 4.54 (d, J=5.8 Hz, 4H), 4.38-4.32 (m, 2H), 4.00 (p, J=6.2 Hz, 1H), 3.73 (q, J=9.0 Hz, 1H), 0.80 (d, J=6.3 Hz, 3H).

Example 74: 2-(4-(6-((4-cyano-2-fluorobenzyl)oxy)pyridin-2-yl)-2,5-difluorobenzyl)-1-(2,2-dimethyltetrahydrofuran-3-yl)-1H-benzo[d]imidazole-6-carboxylic acid 2-(4-(6-((4-cyano-2-fluorobenzyl)oxy)pyridin-2-yl)-2,5-difluorobenzyl)-1-(2,2-dimethyltetrahydrofuran-3-yl)-1H-benzo[d]imidazole-6-carboxylic acid was prepared in a manner as described in Procedure 22. 1H NMR (400 MHz, DMSO-d6) δ 8.25 (d, J=1.5 Hz, 1H), 7.96-7.87 (m, 2H), 7.82-7.69 (m, 4H), 7.63 (d, J=8.4 Hz, 1H), 7.54 (d, J=6.7 Hz, 1H), 7.43 (dd, J=11.4, 6.4 Hz, 2H), 7.00 (d, J=8.2 Hz, 1H), 5.60 (s, 2H), 5.01 (s, 2H), 4.48 (t, J=14.0 Hz, 3H), 4.29 (d, J=3.5 Hz, 2H), 3.99 (d, J=8.4 Hz, 2H), 1.29 (s, 3H), 0.77 (s, 3H).

Example 75: 2-(4-(6-((4-cyano-2-fluorobenzyl)oxy)pyridin-2-yl)-2,5-difluorobenzyl)-1-((3R,4S)-4-(methylcarbamoyl)tetrahydrofuran-3-yl)-1H-benzo[d]imidazole-6-carboxylic acid 2-(4-(6-((4-cyano-2-fluorobenzyl)oxy)pyridin-2-yl)-2,5-difluorobenzyl)-1-((3R,4S)-4-(methylcarbamoyl)tetrahydrofuran-3-yl)-1H-benzo[d]imidazole-6-carboxylic acid (as a racemic mixture of enantiomers) was prepared in a manner as described in Procedure 22. 1H NMR (400 MHz, DMSO-d6) δ 8.37 (d, J=1.4 Hz, 1H), 7.99 (q, J=4.6 Hz, 1H), 7.96-7.82 (m, 3H), 7.82-7.71 (m, 3H), 7.68 (d, J=8.4 Hz, 1H), 7.52 (dd, J=7.6, 1.7 Hz, 1H), 7.23 (dd, J=11.5, 6.0 Hz, 1H), 7.00 (d, J=8.2 Hz, 1H), 5.71 (td, J=7.1, 3.3 Hz, 1H), 5.60 (s, 2H), 4.59-4.48 (m, 2H), 4.48-4.42 (m, 1H), 4.27 (dd, J=10.3, 3.4 Hz, 1H), 4.13 (dd, J=10.5, 8.3 Hz, 1H), 3.65 (t, J=9.4 Hz, 1H), 3.45 (ddd, J=9.9, 8.0, 6.2 Hz, 1H), 2.50 (s, 3H).

Example 76: 2-(4-(6-((4-cyano-2-fluorobenzyl)oxy)pyridin-2-yl)-2,5-difluorobenzyl)-1-((3R,4S)-4-(dimethylcarbamoyl)tetrahydrofuran-3-yl)-1H-benzo[d]imidazole-6-carboxylic acid 2-(4-(6-((4-cyano-2-fluorobenzyl)oxy)pyridin-2-yl)-2,5-difluorobenzyl)-1-((3R,4S)-4-(dimethylcarbamoyl)tetrahydrofuran-3-yl)-1H-benzo[d]imidazole-6-carboxylic acid (as a racemic mixture of enantiomers) was prepared in a manner as described in Procedure 22. 1H NMR (400 MHz, DMSO-d6) δ 8.53 (d, J=1.5 Hz, 0H), 8.46 (d, J=1.5 Hz, 1H), 7.97-7.83 (m, 5H), 7.83-7.63 (m, 7H), 7.61-7.46 (m, 2H), 7.37 (dd, J=11.5, 6.1 Hz, 0H), 7.21 (dd, J=11.6, 6.1 Hz, 1H), 7.00 (dd, J=8.3, 2.0 Hz, 2H), 5.87 (d, J=8.6 Hz, 0H), 5.82 (s, 1H), 5.61 (d, J=2.3 Hz, 3H), 4.69 (t, J=8.6 Hz, 1H), 4.61-4.42 (m, 3H), 4.40-4.31 (m, 2H), 4.31-4.20 (m, 1H), 4.20-4.05 (m, 2H), 3.77 (td, J=8.8, 5.6 Hz, 1H), 3.57 (t, J=9.1 Hz, 1H), 3.02 (s, 1H), 2.78 (s, 3H), 2.72 (s, 3H).

Example 77: 2-(4-(6-((4-cyano-2-fluorobenzyl)oxy)pyridin-2-yl)-2,5-difluorobenzyl)-1-((3R,4S)-4-fluorotetrahydrofuran-3-yl)-1H-benzo[d]imidazole-6-carboxylic acid 2-(4-(6-((4-cyano-2-fluorobenzyl)oxy)pyridin-2-yl)-2,5-difluorobenzyl)-1-((3R,4S)-4-fluorotetrahydrofuran-3-yl)-1H-benzo[d]imidazole-6-carboxylic acid (as a racemic mixture of enantiomers) was prepared in a manner as described in Procedure 22. 1H NMR (400 MHz, DMSO-d6) δ 8.29 (d, J=1.4 Hz, 1H), 7.96-7.89 (m, 2H), 7.89-7.82 (m, 1H), 7.82-7.71 (m, 3H), 7.68 (d, J=8.5 Hz, 1H), 7.53 (dd, J=7.5, 1.7 Hz, 1H), 7.41 (dd, J=11.5, 6.1 Hz, 1H), 7.00 (d, J=8.2 Hz, 1H), 5.66 (dq, J=5.0, 2.3 Hz, 1H), 5.60 (s, 2H), 5.54 (q, J=5.3, 3.7 Hz, 1H), 4.55 (q, J=16.8 Hz, 2H), 4.46-4.24 (m, 3H), 4.08 (ddd, J=24.6, 11.4, 3.1 Hz, 1H).

Example 78: 2-(4-(6-((4-cyano-2-fluorobenzyl)oxy)pyridin-2-yl)-2,5-difluorobenzyl)-1-(4,4-dimethyltetrahydrofuran-3-yl)-1H-benzo[d]imidazole-6-carboxylic acid Example 78 was prepared in a manner similar to Procedure 22, with the following modifications: Methyl 2-[[4-[6-[(4-cyano-2-fluoro-phenyl)methoxy]-2-pyridyl]-2,5-difluoro-phenyl]methyl]-3-(4,4-dimethyltetrahydrofuran-3-yl)benzimidazole-5-carboxylate (Intermediate I-104, 468 mg, 0.000746 mol) was taken up in Acetonitrile (3.80 mL) and lithium hydroxide (300 mmol/L, 3.73 mL, 0.00112 mol) was added. The mixture was heated to 100° C. After 10 min the mixture was removed from heat, then diluted with water and acidified to pH~5 with 5% aqueous citric acid. The aqueous phase was extracted 3× with EtOAc. Combined organics were dried over MgSO$_4$, filtered and concentrated in vacuo. Purification by preparative HPLC, MeCN/H$_2$O gradient with 0.1% TFA yielded 2-(4-(6-((4-cyano-2-fluorobenzyl)oxy)pyridin-2-yl)-2,5-difluorobenzyl)-1-(4,4-dimethyltetrahydrofuran-3-yl)-1H-benzo[d]imidazole-6-carboxylic acid (Example 78). 1H NMR (400 MHz, DMSO-d6) δ 8.50 (s, 1H), 7.96-7.87 (m, 2H), 7.86-7.71 (m, 5H), 7.63 (d, J=8.5 Hz, 1H), 7.55 (dd, J=7.5, 1.6 Hz, 1H), 7.46 (dd, J=11.3, 6.2 Hz, 1H), 7.00 (d, J=8.3 Hz, 1H), 5.61 (s, 2H), 5.03 (d, J=6.6

Hz, 1H), 4.60-4.49 (m, 2H), 4.49-4.33 (m, 2H), 3.83-3.68 (m, 2H), 1.33 (s, 3H), 0.61 (s, 3H).

Example 79: 2-(4-(6-((4-cyano-2-fluorobenzyl)oxy) pyridin-2-yl)-2,5-difluorobenzyl)-1-((3S,3aR,6aR)-hexahydrofuro[3,4-b]furan-3-yl)-1H-benzo[d]imidazole-6-carboxylic acid 2-(4-(6-((4-cyano-2-fluorobenzyl)oxy)pyridin-2-yl)-2,5-difluorobenzyl)-1-((3S,3aR,6aR)-hexahydrofuro[3,4-b]furan-3-yl)-1H-benzo[d]imidazole-6-carboxylic acid was prepared in a manner as described in Procedure 22. 1H NMR (400 MHz, DMSO-d6) δ 8.47 (d, J=1.4 Hz, 1H), 7.96-7.85 (m, 3H), 7.85-7.65 (m, 5H), 7.53 (dd, J=7.5, 1.6 Hz, 1H), 7.40 (dd, J=11.5, 6.1 Hz, 1H), 7.00 (d, J=8.3 Hz, 1H), 5.60 (s, 2H), 5.25 (td, J=5.2, 2.6 Hz, 1H), 5.09 (dd, J=7.0, 4.1 Hz, 1H), 4.60 (s, 2H), 4.23 (d, J=5.1 Hz, 2H), 3.96 (dd, J=12.2, 9.2 Hz, 2H), 3.58-3.48 (m, 2H), 3.18 (ddt, J=6.9, 4.5, 2.3 Hz, 1H).

Example 80: 2-(4-(6-((4-cyano-2-fluorobenzyl)oxy) pyridin-2-yl)-2,5-difluorobenzyl)-1-((3S,3aR,6aS)-hexahydro-2H-furo[2,3-c]pyrrol-3-yl)-1H-benzo[d]imidazole-6-carboxylic acid 2-(4-(6-((4-cyano-2-fluorobenzyl)oxy)pyridin-2-yl)-2,5-difluorobenzyl)-1-((3S,3aR,6aS)-hexahydro-2H-furo[2,3-c]pyrrol-3-yl)-1H-benzo[d]imidazole-6-carboxylic acid was prepared in a manner as described in Procedure 22. 1H NMR (400 MHz, DMSO-d6) δ 8.50 (d, J=1.4 Hz, 1H), 7.98-7.87 (m, 2H), 7.84 (dd, J=8.4, 1.5 Hz, 1H), 7.81-7.70 (m, 3H), 7.66 (d, J=8.5 Hz, 1H), 7.55 (dd, J=7.5, 1.6 Hz, 1H), 7.43 (dd, J=11.5, 6.1 Hz, 1H), 7.01 (d, J=8.3 Hz, 1H), 5.61 (s, 3H), 4.86 (dd, J=11.1, 2.3 Hz, 1H), 4.76 (td, J=6.0, 2.5 Hz, 1H), 4.55-4.36 (m, 2H), 4.23 (dd, J=11.1, 7.3 Hz, 1H), 3.71-3.48 (m, 2H), 3.46-3.29 (m, 1H), 3.04 (s, 1H), 2.46-2.29 (m, 2H).

Example 81: 2-(4-(6-((4-cyano-2-fluorobenzyl)oxy) pyridin-2-yl)-2,5-difluorobenzyl)-1-(1,1-dioxidotetrahydrothiophen-3-yl)-1H-benzo[d]imidazole-6-carboxylic acid 2-(4-(6-((4-cyano-2-fluorobenzyl)oxy)pyridin-2-yl)-2,5-difluorobenzyl)-1-(1,1-dioxidotetrahydrothiophen-3-yl)-1H-benzo[d]imidazole-6-carboxylic acid was prepared in a manner as described in Procedure 22. 1H NMR (400 MHz, DMSO-d6) δ 8.41 (d, J=1.3 Hz, 1H), 7.94-7.88 (m, 2H), 7.86 (dd, J=8.5, 1.4 Hz, 1H), 7.81-7.71 (m, 3H), 7.68 (d, J=8.4 Hz, 1H), 7.54 (dd, J=7.4, 1.6 Hz, 1H), 7.38 (dd, J=11.4, 6.1 Hz, 1H), 7.00 (d, J=8.2 Hz, 1H), 5.73 (ddd, J=18.8, 10.9, 7.8 Hz, 1H), 5.61 (s, 2H), 4.53 (s, 2H), 3.78 (dd, J=14.3, 10.6 Hz, 1H), 3.70-3.53 (m, 2H), 3.32 (td, J=13.1, 6.8 Hz, 1H), 2.86-2.60 (m, 2H).

Example 82: 2-(4-(6-((4-cyano-2-fluorobenzyl)oxy) pyridin-2-yl)-2,5-difluorobenzyl)-1-(5-oxaspiro[2.5] octan-8-yl)-1H-benzo[d]imidazole-6-carboxylic acid 2-(4-(6-((4-cyano-2-fluorobenzyl)oxy)pyridin-2-yl)-2,5-difluorobenzyl)-1-(5-oxaspiro[2.5]octan-8-yl)-1H-benzo[d]imidazole-6-carboxylic acid was prepared in a manner as described in Procedure 22. 1H NMR (400 MHz, DMSO-d6) δ 8.28 (d, J=1.4 Hz, 1H), 7.96-7.86 (m, 2H), 7.81-7.70 (m, 4H), 7.61 (d, J=8.4 Hz, 1H), 7.54 (dd, J=7.6, 1.7 Hz, 1H), 7.48 (dd, J=11.4, 6.0 Hz, 1H), 7.00 (d, J=8.3 Hz, 1H), 5.61 (s, 2H), 5.27-5.19 (m, 1H), 4.55 (d, J=16.8 Hz, 1H), 4.37 (d, J=16.8 Hz, 1H), 4.22 (d, J=11.5 Hz, 1H), 4.00 (dd, J=11.8, 2.1 Hz, 1H), 3.79-3.68 (m, 1H), 3.19 (d, J=11.7 Hz, 1H), 2.89 (td, J=12.5, 11.5, 4.5 Hz, 1H), 2.05 (d, J=11.6 Hz, 1H), 0.61 (dt, J=10.1, 5.2 Hz, 1H), 0.40 (s, 1H), 0.22 (dt, J=10.2, 5.3 Hz, 1H).

Example 83: 2-(4-(6-((4-cyano-2-fluorobenzyl)oxy) pyridin-2-yl)-2,5-difluorobenzyl)-1-(3,3-dimethyltetrahydro-2H-pyran-4-yl)-1H-benzo[d]imidazole-6-carboxylic acid 2-(4-(6-((4-cyano-2-fluorobenzyl)oxy)pyridin-2-yl)-2,5-difluorobenzyl)-1-(3,3-dimethyltetrahydro-2H-pyran-4-yl)-1H-benzo[d]imidazole-6-carboxylic acid was prepared in a manner as described in Procedure 22. 1H NMR (400 MHz, DMSO-d6) δ 8.30 (s, 1H), 7.96-7.86 (m, 2H), 7.86-7.70 (m, 5H), 7.61 (d, J=8.4 Hz, 1H), 7.55 (dd, J=7.5, 1.7 Hz, 1H), 7.46 (dd, J=11.5, 6.1 Hz, 1H), 7.00 (d, J=8.3 Hz, 1H), 5.61 (s, 2H), 4.75 (dd, J=12.6, 3.9 Hz, 1H), 4.63 (d, J=16.9 Hz, 1H), 4.42 (d, J=16.9 Hz, 1H), 4.19-4.11 (m, 1H), 3.63-3.53 (m, 2H), 3.47 (d, J=11.4 Hz, 1H), 2.91 (dt, J=12.7, 5.8 Hz, 1H), 1.75 (d, J=10.8 Hz, 1H), 1.20 (s, 3H), 0.91 (s, 3H).

Procedure 23: Example 84

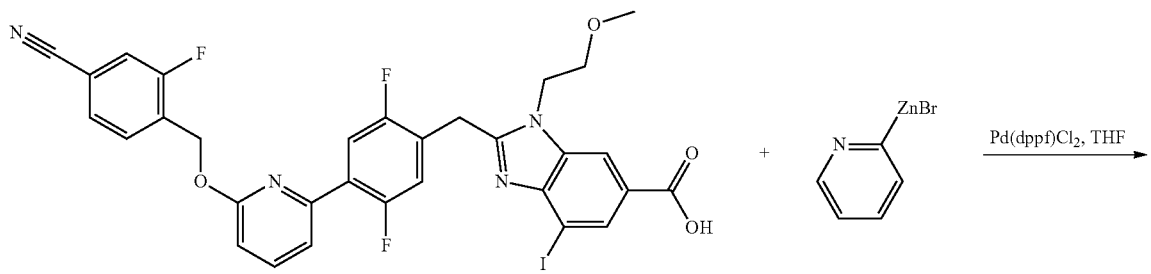

I-72

-continued

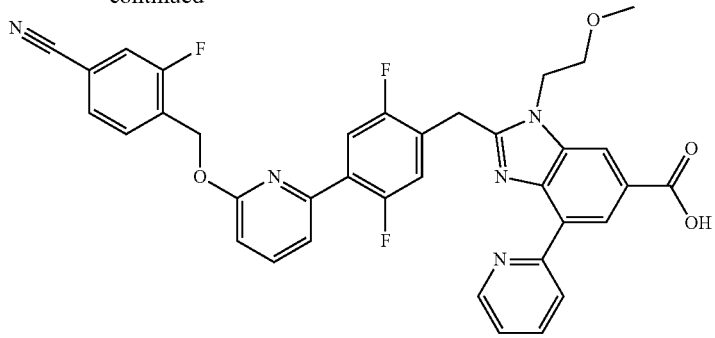

Example 84

2-[[4-[6-[(4-cyano-2-fluoro-phenyl)methoxy]-2-pyridyl]-2,5-difluoro-phenyl]methyl]-3-(2-methoxyethyl)-7-(2-pyridyl)benzimidazole-5-carboxylic acid (Example 84): A solution of methyl 2-(4-(6-((4-cyano-2-fluorobenzyl)oxy)pyridin-2-yl)-2,5-difluorobenzyl)-4-iodo-1-(2-methoxyethyl)-1H-benzo[d]imidazole-6-carboxylate (I-72, 7 mg, 0.01 mmol), bromo(2-pyridyl)zinc (11.2 mg, 0.05 mmol), and Pd(dppf)Cl$_2$ (0.7 mg, 0.001 mmol) in THF (0.4 mL) was degassed with argon, and stirred for 30 min at 90° C. Following this time, the mixture was purified directly by RP-HPLC (eluent: water/MeCN 0.1% TFA) to give Example 84. ES/MS: 650.3 (M+H$^+$); 1H NMR (400 MHz, Acetonitrile-d$_3$) δ 8.83 (s, 1H), 8.75 (d, J=6.4 Hz, 2H), 8.54 (s, 1H), 8.43 (s, 1H), 7.90-7.75 (m, 3H), 7.72 (t, J=7.4 Hz, 1H), 7.57 (t, J=8.1 Hz, 3H), 7.26 (dd, J=11.6, 6.0 Hz, 1H), 6.94 (d, J=8.3 Hz, 1H), 5.63 (s, 2H), 4.77-4.41 (m, 4H), 3.75 (t, J=5.0 Hz, 2H), 3.23 (s, 3H).

Procedure 24: Example 85

Example 85

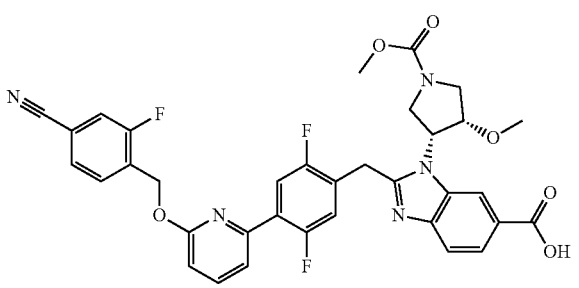

2-[[4-[6-[(4-cyano-2-fluoro-phenyl)methoxy]-2-pyridyl]-2,5-difluoro-phenyl]methyl]-3-[(3R,4S)-4-methoxy-1-methoxycarbonyl-pyrrolidin-3-yl]benzimidazole-5-carboxylic acid (Example 85): The title compound was prepared according to procedure 4 substituting methyl chloroformate for acetic anhydride. ES/MS: 672.2 (M+H$^+$); $^1$H NMR (400 MHz, DMSO-d$_6$) δ 8.26 (d, J=5.2 Hz, 1H), 7.99-7.87 (m, 2H), 7.83-7.71 (m, 4H), 7.60 (d, J=8.4 Hz, 1H), 7.54 (d, J=7.3 Hz, 1H), 7.34 (dd, J=11.5, 6.0 Hz, 1H), 7.00 (d, J=8.3 Hz, 1H), 5.61 (s, 2H), 5.49 (d, J=5.7 Hz, 1H), 4.62-4.43 (m, 2H), 4.15 (d, J=8.8 Hz, 2H), 3.88 (t, J=9.9 Hz, 1H), 3.69 (d, J=4.8 Hz, 3H), 3.10 (s, 3H) (note: 3 protons hidden by solvent).

Example 86: 2-(4-(6-((4-cyano-2-fluorobenzyl)oxy)pyridin-2-yl)-2,5-difluorobenzyl)-1-((3R,4R)-4-methoxy-1-(methoxycarbonyl)pyrrolidin-3-yl)-1H-benzo[d]imidazole-6-carboxylic acid 2-(4-(6-((4-cyano-2-fluorobenzyl)oxy)pyridin-2-yl)-2,5-difluorobenzyl)-1-((3R,4R)-4-methoxy-1-(methoxycarbonyl)pyrrolidin-3-yl)-1H-benzo[d]imidazole-6-carboxylic acid was prepared in a manner as described in Procedure 24. 1H NMR (400 MHz, DMSO-d6) δ 8.12 (s, 1H), 7.99-7.87 (m, 2H), 7.84 (dd, J=8.4, 1.4 Hz, 1H), 7.79-7.72 (m, 3H), 7.67 (d, J=8.4 Hz, 1H), 7.53 (dd, J=7.5, 1.7 Hz, 1H), 7.38 (dd, J=11.5, 6.1 Hz, 1H), 7.00 (d, J=8.3 Hz, 1H), 5.60 (s, 2H), 5.33 (s, 1H), 4.63-4.37 (m, 3H), 3.68 (s, 4H), 3.36 (d, J=9.4 Hz, 1H), 3.17 (s, 3H).

Example 87: 2-(4-(6-((4-cyano-2-fluorobenzyl)oxy)pyridin-2-yl)-2,5-difluorobenzyl)-1-((3S,4R)-4-methoxy-1-(methoxycarbonyl)pyrrolidin-3-yl)-1H-benzo[d]imidazole-6-carboxylic acid 2-(4-(6-((4-cyano-2-fluorobenzyl)oxy)pyridin-2-yl)-2,5-difluorobenzyl)-1-((3S,4R)-4-methoxy-1-(methoxycarbonyl)pyrrolidin-3-yl)-1H-benzo[d]imidazole-6-carboxylic acid was prepared in a manner as described in Procedure 24. 1H NMR (400 MHz, DMSO-d6) δ 8.27 (d, J=5.9 Hz, 1H), 7.97-7.87 (m, 2H), 7.84-7.58 (m, 4H), 7.54 (dd, J=7.6, 1.7 Hz, 1H), 7.35 (dd, J=11.5, 6.1 Hz, 1H), 7.00 (d, J=8.3 Hz, 1H), 5.61 (s, 2H), 5.55-5.42 (m, 1H), 4.62-4.43 (m, 2H), 4.16 (d, J=9.1 Hz, 2H), 3.88 (t, J=9.9 Hz, 1H), 3.10 (s, 3H).

Procedure 25: Example 88

Example 88

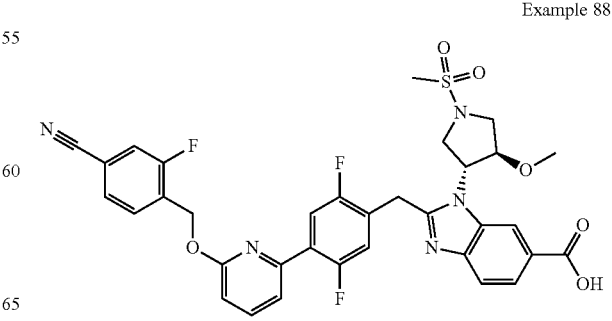

2-[[4-[6-[(4-cyano-2-fluoro-phenyl)methoxy]-2-pyridyl]-2,5-difluoro-phenyl]methyl]-3-[(3R,4R)-4-methoxy-1-methylsulfonyl-pyrrolidin-3-yl]benzimidazole-5-carboxylic acid (Example 88): The title compound was prepared in a manner as described in Procedure 24 substituting methane sulfonyl chloride for methyl chloroformate. ES/MS: 692.2 (M+H$^+$); $^1$H NMR (400 MHz, DMSO-d$_6$) δ 8.27 (d, J=1.5 Hz, 1H), 7.96-7.83 (m, 3H), 7.80-7.73 (m, 3H), 7.68 (d, J=8.4 Hz, 1H), 7.53 (dd, J=7.4, 1.7 Hz, 1H), 7.38 (dd, J=11.5, 6.1 Hz, 1H), 7.00 (d, J=8.3 Hz, 1H), 5.60 (s, 2H), 5.34 (dt, J=9.6, 6.6 Hz, 1H), 4.61-4.38 (m, 3H), 4.06-3.92 (m, 2H), 3.30 (dd, J=10.1, 6.9 Hz, 1H), 3.18 (s, 3H), 3.13 (s, 3H).

Example 89: 2-(4-(6-((4-cyano-2-fluorobenzyl)oxy)pyridin-2-yl)-2,5-difluorobenzyl)-1-((3S,4R)-4-methoxy-1-(methylsulfonyl)pyrrolidin-3-yl)-1H-benzo[d]imidazole-6-carboxylic acid 2-(4-(6-((4-cyano-2-fluorobenzyl)oxy)pyridin-2-yl)-2,5-difluorobenzyl)-1-((3S,4R)-4-methoxy-1-(methylsulfonyl)pyrrolidin-3-yl)-1H-benzo[d]imidazole-6-carboxylic acid was prepared in a manner as described in procedure 25. 1H NMR (400 MHz, DMSO-d6) δ 8.41 (s, 1H), 7.97-7.87 (m, 2H), 7.82-7.71 (m, 4H), 7.60 (d, J=8.4 Hz, 1H), 7.56-7.52 (m, 1H), 7.34 (dd, J=11.4, 6.1 Hz, 1H), 7.00 (d, J=8.3 Hz, 1H), 5.61 (s, 2H), 5.53 (td, J=8.6, 5.1 Hz, 1H), 4.62-4.46 (m, 2H), 4.19 (q, J=4.6, 3.7 Hz, 1H), 4.05 (dd, J=10.3, 8.2 Hz, 1H), 3.84 (t, J=9.7 Hz, 1H), 3.10 (s, 3H), 3.08 (s, 3H).

Procedure 26: Example 90

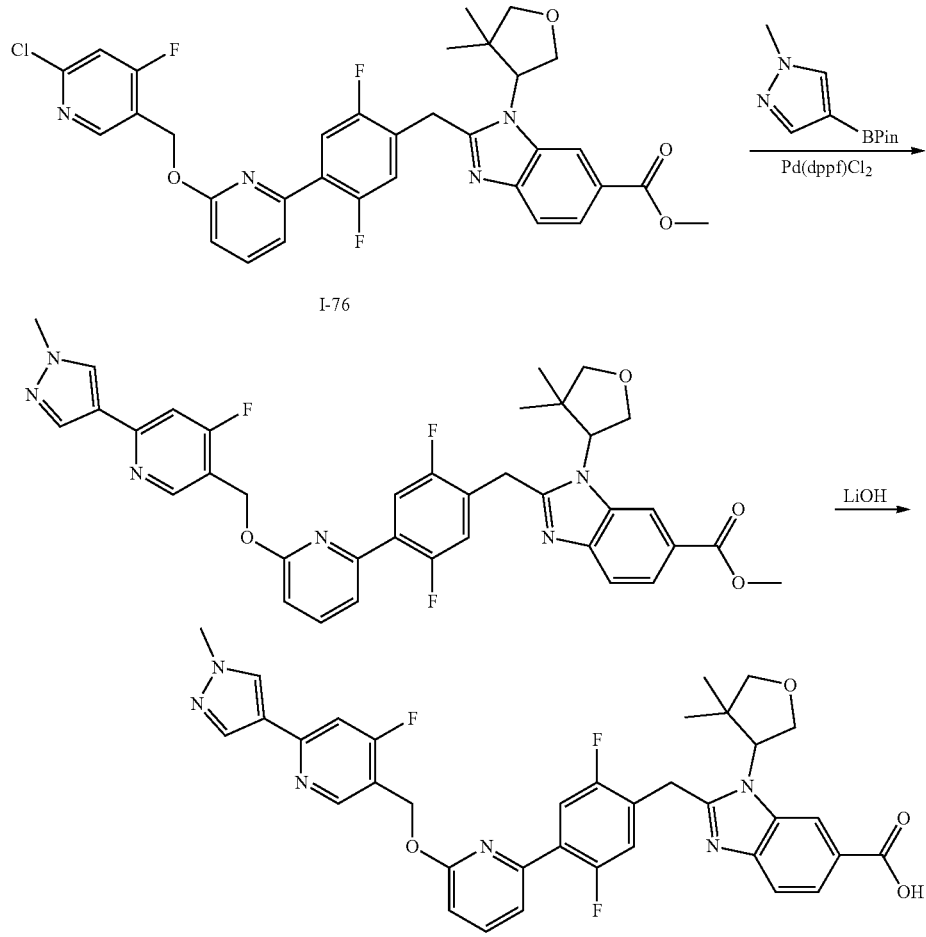

Methyl 2-[[2,5-difluoro-4-[6-[[4-fluoro-6-(1-methylpyrazol-4-yl)-3-pyridyl]methoxy]-2-pyridyl]phenyl]methyl]-3-(4,4-dimethyltetrahydrofuran-3-yl)benzimidazole-5-carboxylate: Methyl 2-[[4-[6-[(6-chloro-4-fluoro-3-pyridyl)methoxy]-2-pyridyl]-2,5-difluoro-phenyl]methyl]-3-(4,4-dimethyltetrahydrofuran-3-yl)benzimidazole-5-carboxylate (I-76) (120 mg, 0.19 mmol), 1-methyl-4-(4,4,5,5-tetramethyl-1,3,2-dioxaborolan-2-yl)pyrazole (78 mg, 0.38 mmol), 2 N of sodium carbonate (0.19 mL, 0.38 mmol) and (1,1'-bis(diphenylphosphino)ferrocene)-dichloropalladium(II) (14 mg, 0.019 mmol) was suspended in dioxane (1 mL). The mixture was degassed by bubbling argon after which, the mixture was heated to 120° C. in the microwave reactor for 30 minutes. Upon completion the mixture was poured into water (5 mL) and extracted with EtOAc (2×15 mL). The organic layers were combined, washed with brine (5 mL), dried over MgSO$_4$, filtered, concentrated, and purified by flash chromatography (Eluent: EtOAc/hexane) to give the desired product. ES/MS: 683.7 (M+H$^+$).

2-[[2,5-difluoro-4-[6-[[4-fluoro-6-(1-methylpyrazol-4-yl)-3-pyridyl]methoxy]-2-pyridyl]phenyl]methyl]-3-(4,4-dimethyltetrahydrofuran-3-yl)benzimidazole-5-carboxylic acid (Example 90): 1 mL of ACN and 0.3 mL of 1 N lithium hydroxide were added to a vial of methyl 2-[[2,5-difluoro-4-[6-[[4-fluoro-6-(1-methylpyrazol-4-yl)-3-pyridyl]methoxy]-2-pyridyl]phenyl]methyl]-3-(4,4-dimethyltetrahydrofuran-3-yl)benzimidazole-5-carboxylate (81 mg, 0.12 mmol). The mixture was heated to 100° C. for 10 minutes. Upon completion a 5% citric acid solution in water was added (2 mL), the resulting mixture diluted with EtOAc (25 mL), washed with brine (5 mL), dried over MgSO$_4$, filtered, concentrated, and purified by RP-HPLC (eluent: water/MeCN*0.1% TFA) to give Example 90. ES/MS: 669.6 (M+H+). 1H NMR (400 MHz, DMSO-d6) δ 8.69 (d, J=10.4 Hz, 1H), 8.51 (s, 1H), 8.35 (s, 1H), 8.06 (s, 1H), 8.00-7.86 (m, 2H), 7.83 (dd, J=8.4, 1.5 Hz, 1H), 7.73-7.61 (m, 2H), 7.55 (dd, J=7.5, 1.6 Hz, 1H), 7.48 (dd, J=11.2, 6.3 Hz, 1H), 6.95 (d, J=8.3 Hz, 1H), 5.55 (s, 2H), 5.04 (d, J=6.6 Hz, 1H), 4.65-4.51 (m, 2H), 4.49-4.36 (m, 2H), 3.89 (s, 3H), 3.79 (d, J=8.7 Hz, 1H), 3.74 (d, J=8.6 Hz, 1H), 1.34 (s, 3H), 0.62 (s, 3H).

Example 91: (R)-2-(2,5-difluoro-4-(6-((4-methoxy-6-(1-methyl-1H-pyrazol-4-yl)pyridin-3-yl)methoxy)pyridin-2-yl)benzyl)-1-(2-methoxypropyl)-1H-benzo[d]imidazole-6-carboxylic acid (R)-2-(2,5-difluoro-4-(6-((4-methoxy-6-(1-methyl-1H-pyrazol-4-yl)pyridin-3-yl)methoxy)pyridin-2-yl)benzyl)-1-(2-methoxypropyl)-1H-benzo[d]imidazole-6-carboxylic acid was prepared in a manner as described in Procedure 26. 1H NMR (400 MHz, DMSO-d6) δ 8.65 (s, 1H), 8.60 (s, 1H), 8.32 (s, 1H), 8.27 (d, J=1.5 Hz, 1H), 7.96-7.79 (m, 3H), 7.75 (s, 1H), 7.62 (d, J=8.4 Hz, 1H), 7.55 (dd, J=7.5, 1.6 Hz, 1H), 7.42 (dd, J=11.5, 6.1 Hz, 1H), 6.97 (d, J=8.3 Hz, 1H), 5.50 (s, 2H), 4.54 (dd, J=15.2, 3.2 Hz, 1H), 4.49 (s, 2H), 4.38 (dd, J=15.2, 8.8 Hz, 1H), 4.16 (s, 3H), 3.97 (s, 3H), 3.71 (ddd, J=9.3, 6.2, 3.2 Hz, 1H), 3.09 (s, 3H), 1.24 (d, J=6.1 Hz, 3H).

Procedure 27: Example 92

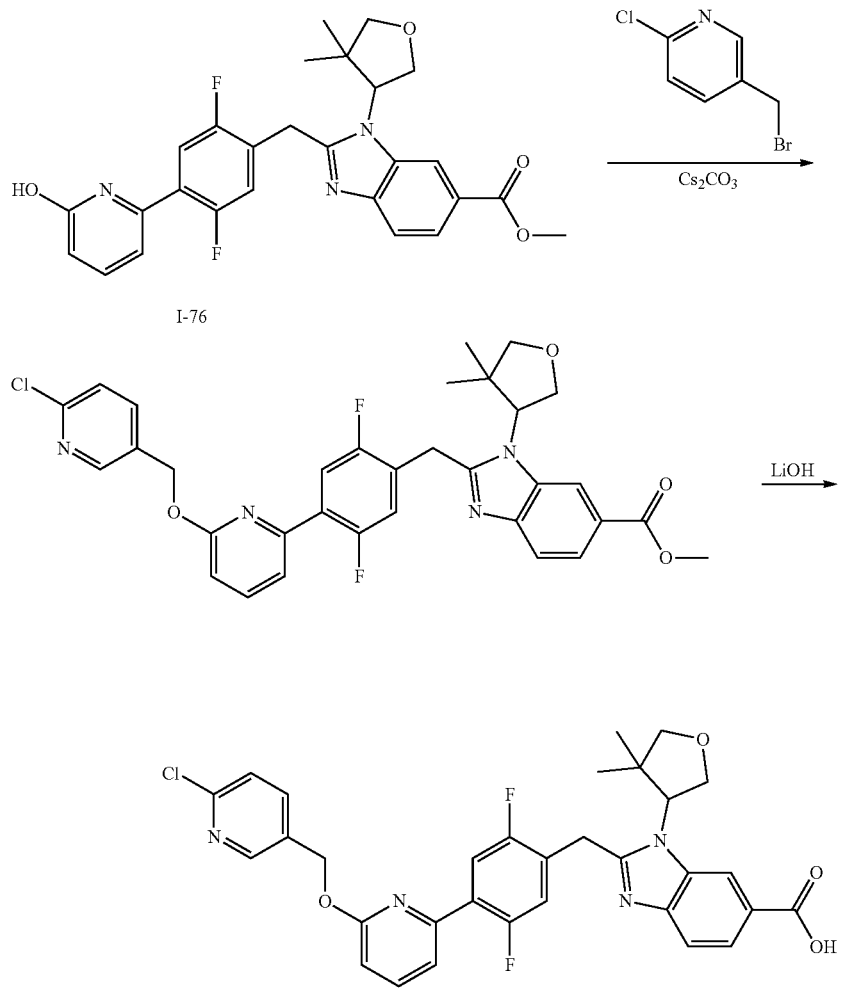

Example 92

Methyl 2-[[4-[6-[(6-chloro-3-pyridyl)methoxy]-2-pyridyl]-2,5-difluoro-phenyl]methyl]-3-(4,4-dimethyltetrahydrofuran-3-yl)benzimidazole-5-carboxylate: To a solution of methyl 2-[[2,5-difluoro-4-(6-hydroxy-2-pyridyl)phenyl]methyl]-3-(4,4-dimethyltetrahydrofuran-3-yl)benzimidazole-5-carboxylate (30.0 mg, 0.061 mmol) and 5-(bromomethyl)-2-chloro-pyridine (13 mg, 0.061 mmol) in 11 mL of acetonitrile was added Cs$_2$CO$_3$ (40 mg, 0.12 mmol). The solution was then heated to 50° C. for 30 minutes. Upon completion the solution was cooled to rt, filtered, then concentrated. The crude material was purified by normal phase chromatography (eluent: EtOAc/hexanes).

2-[[4-[6-[(6-chloro-3-pyridyl)methoxy]-2-pyridyl]-2,5-difluoro-phenyl]methyl]-3-(4,4-dimethyltetrahydrofuran-3-yl)benzimidazole-5-carboxylic acid (Example 92): To a methyl 2-[[4-[6-[(6-chloro-3-pyridyl)methoxy]-2-pyridyl]-2,5-difluoro-phenyl]methyl]-3-(4,4-dimethyltetrahydrofuran-3-yl)benzimidazole-5-carboxylate (20.0 mg, 0.032 mmol) in 3 mL of acetonitrile and 1 mL of water was added aqueous LiOH (0.02 mL, 0.04 mmol, 2 M). The solution was then stirred at 80° C. for 1 hour. Upon completion the solution was cooled to rt, filtered through celite and concentrated. The crude material was purified by reverse phase chromatography (eluent ACN/water with 0.1% TFA added) to give Example 92. ES/MS m/z: 605.9 (M+H$^+$); 1H NMR (400 MHz, Methanol-d4) δ 8.89 (s, 1H), 8.51 (d, J=2.4 Hz, 1H), 8.17 (dd, J=8.6, 1.3 Hz, 1H), 8.05-7.88 (m, 2H), 7.88-7.72 (m, 2H), 7.58 (dd, J=7.5, 1.6 Hz, 1H), 7.48 (d, J=8.2 Hz, 1H), 7.40 (dd, J=11.1, 6.1 Hz, 1H), 6.94 (d, J=8.3 Hz, 1H), 5.55 (s, 2H), 5.14 (d, J=6.6 Hz, 1H), 4.78-4.61 (m, 3H), 4.52 (dd, J=11.6, 6.7 Hz, 1H), 4.00 (d, J=8.9 Hz, 1H), 3.84 (d, J=8.9 Hz, 1H), 1.41 (s, 3H), 0.76 (s, 3H).

Example 93: 2-(4-(6-((5-chloropyrazin-2-yl)methoxy)pyridin-2-yl)-2,5-difluorobenzyl)-1-(4,4-dimethyltetrahydrofuran-3-yl)-1H-benzo[d]imidazole-6-carboxylic acid 2-(4-(6-((5-chloropyrazin-2-yl)methoxy)pyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 27. 1H NMR (400 MHz, Methanol-d4) δ 8.92 (s, 1H), 8.66 (d, J=1.4 Hz, 1H), 8.59 (d, J=1.3 Hz, 1H), 8.20 (d, J=8.6 Hz, 1H), 7.94-7.72 (m, 3H), 7.60 (dd, J=7.5, 1.6 Hz, 1H), 7.41 (dd, J=11.2, 6.0 Hz, 1H), 7.01 (d, J=8.3 Hz, 1H), 5.64 (s, 2H), 5.15 (d, J=6.6 Hz, 1H), 4.79-4.59 (m, 3H), 4.53 (dd, J=11.7, 6.7 Hz, 1H), 4.00 (d, J=8.9 Hz, 1H), 3.85 (d, J=8.9 Hz, 1H), 1.41 (s, 3H), 0.76 (s, 3H).

Procedure 28: Example 94

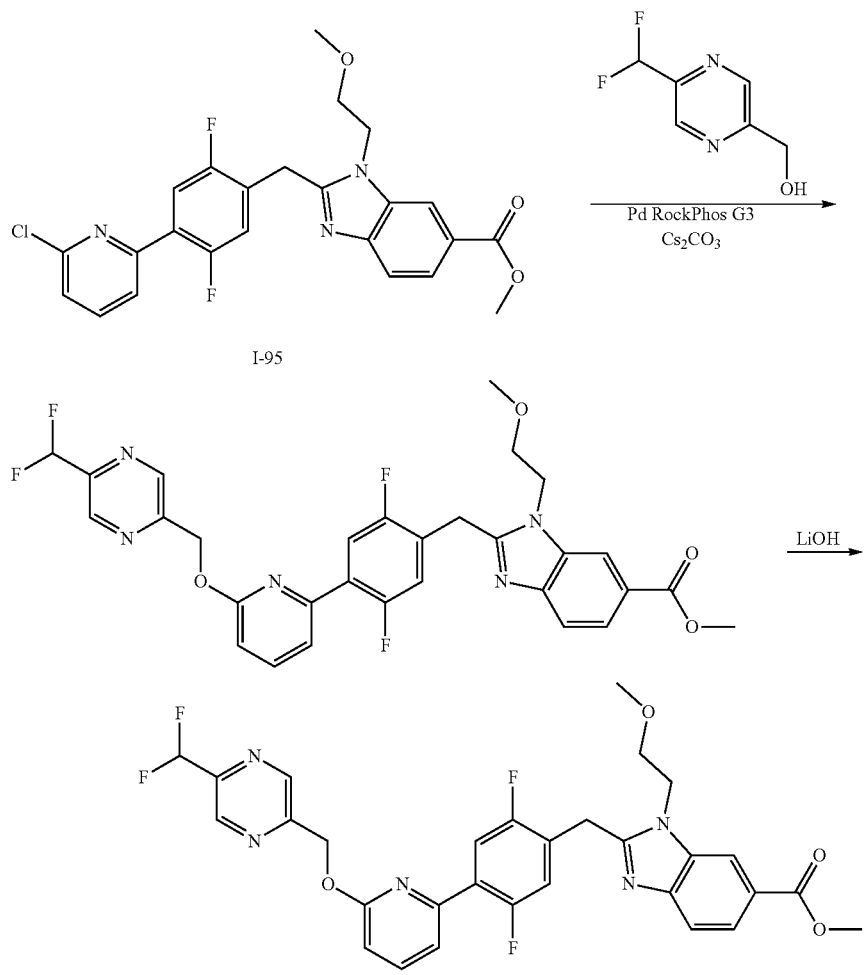

Example 94

Methyl 2-[[4-[6-[[5-(difluoromethyl)pyrazin-2-yl]methoxy]-2-pyridyl]-2,5-difluoro-phenyl]methyl]-3-(2-methoxyethyl)benzimidazole-5-carboxylate: A suspension of methyl 2-[[4-(6-chloro-2-pyridyl)-2,5-difluoro-phenyl]methyl]-3-(2-methoxyethyl)benzimidazole-5-carboxylate (40.0 mg, 0.085 mmol), [5-(difluoromethyl)pyrazin-2-yl]methanol (17 mg, 0.11 mmol), Pd RockPhos G3 (11 mg, 0.013 mmol), and cesium carbonate (83 mg, 0.25 mmol) in toluene (1.5 mL) was degassed with Ar for 5 min, then heated at 100° C. overnight. Upon completion the mixture was diluted with EtOAc and washed with brine. The organic extract was dried over sodium sulfate and purified by flash chromatography (eluent: EtOAc/hexanes) to give the title compound. ES/MS: 596.2 (M+H⁺).

2-[[4-[6-[[5-(difluoromethyl)pyrazin-2-yl]methoxy]-2-pyridyl]-2,5-difluoro-phenyl]methyl]-3-(2-methoxyethyl)benzimidazole-5-carboxylic acid (Example 94): A suspension of methyl 2-[[4-[6-[[5-(difluoromethyl)pyrazin-2-yl]methoxy]-2-pyridyl]-2,5-difluoro-phenyl]methyl]-3-(2-methoxyethyl)benzimidazole-5-carboxylate (30.0 mg, 0.0209 mmol) and lithium hydroxide, monohydrate (300 mmol/L, 0.50 mL, 0.15 mmol) in CH₃CN (0.5 mL) was heated at 105° C. for 6 min. Upon completion the reaction was quenched with 5% aqueous citric acid (1 mL) diluted with EtOAc (25 mL) and washed with brine (5 mL). The organic extract was dried over sodium sulfate, filtered and concentrated. The crude residue was purified by RP-HPLC (eluent: MeCN/H₂O) to give Example 94. ES/MS: 582.2 (M+H⁺); 1H NMR (400 MHz, DMSO-d6) δ 8.97 (s, 1H), 8.93 (d, J=1.4 Hz, 1H), 8.25 (d, J=1.5 Hz, 1H), 7.92 (t, J=7.9 Hz, 1H), 7.84 (dd, J=8.4, 1.5 Hz, 1H), 7.68-7.59 (m, 2H), 7.53 (dd, J=7.6, 1.6 Hz, 1H), 7.38 (dd, J=11.5, 6.1 Hz, 1H), 7.29-6.93 (m, 2H), 5.71 (s, 2H), 4.62 (t, J=5.1 Hz, 2H), 4.47 (s, 2H), 3.69 (t, J=5.1 Hz, 2H), 3.21 (s, 3H).

Example 95: 2-(4-(6-((6-(1H-imidazol-1-yl)pyridin-3-yl)methoxy)pyridin-2-yl)-2,5-difluorobenzyl)-1-(2-methoxyethyl)-1H-benzo[d]imidazole-6-carboxylic acid 2-(4-(6-((6-(1H-imidazol-1-yl)pyridin-3-yl)methoxy)pyridin-2-yl)-2,5-difluorobenzyl)-1-(2-methoxyethyl)-1H-benzo[d]imidazole-6-carboxylic acid was prepared in a manner as described in Procedure 28. 1H NMR (400 MHz, DMSO-d6) δ 8.65 (d, J=2.2 Hz, 1H), 8.55 (s, 1H), 8.20 (d, J=1.4 Hz, 1H), 8.14 (dd, J=8.4, 2.3 Hz, 1H), 7.97 (s, 1H), 7.92-7.83 (m, 3H), 7.79 (dd, J=8.4, 1.5 Hz, 1H), 7.60 (d, J=8.5 Hz, 1H), 7.53 (d, J=7.1 Hz, 1H), 7.39 (dd, J=11.5, 6.1 Hz, 1H), 7.13 (s, 1H), 6.97 (d, J=8.3 Hz, 1H), 5.56 (s, 2H), 5.40 (s, 1H), 4.59 (d, J=5.6 Hz, 2H), 4.44 (s, 2H), 3.69 (t, J=5.0 Hz, 2H), 3.22 (s, 3H).

Example 96: 2-(4-(6-((4-(1,1-difluoroethyl)benzyl)oxy)pyridin-2-yl)-2,5-difluorobenzyl)-1-(2-methoxyethyl)-1H-benzo[d]imidazole-6-carboxylic acid 2-(4-(6-((4-(1,1-difluoroethyl)benzyl)oxy)pyridin-2-yl)-2,5-difluorobenzyl)-1-(2-methoxyethyl)-1H-benzo[d]imidazole-6-carboxylic acid was prepared a manner as described in Procedure 28. 1H NMR (400 MHz, DMSO-d6) δ 12.84 (s, 1H), 8.32 (d, 1H), 7.93-7.84 (m, 2H), 7.79 (dd, 1H), 7.70-7.59 (m, 1H), 7.59 (d, 4H), 7.51 (dd, 1H), 7.43 (dd, 1H), 6.97 (dd, 1H), 5.53 (s, 2H), 4.67 (t, 2H), 3.70 (t, 2H), 3.21 (s, 3H), 2.49 (s, OH), 1.96 (t, 3H).

Procedure 29: Example 97

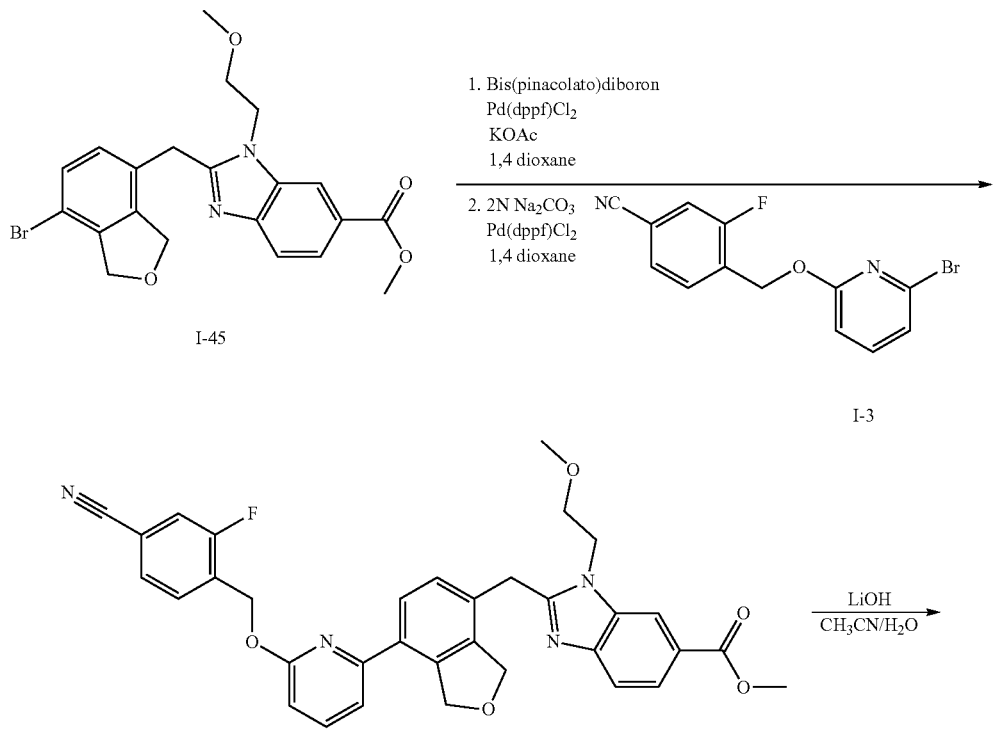

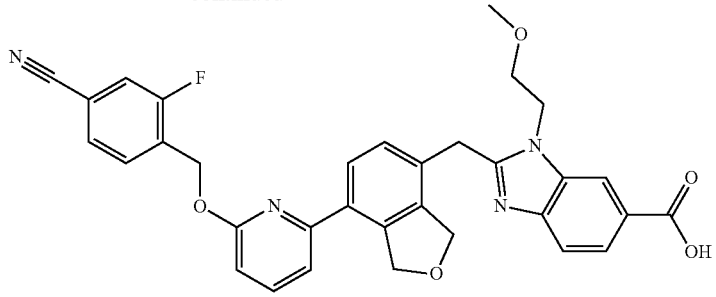

Example 97

Methyl 2-((7-(6-((4-cyano-2-fluorobenzyl)oxy)pyridin-2-yl)-1,3-dihydroisobenzofuran-4-yl)methyl)-1-(2-methoxyethyl)-1H-benzo[d]imidazole-6-carboxylate: In a 8 mL glass vial, a suspension of methyl 2-[(7-bromo-1,3-dihydroisobenzofuran-4-yl)methyl]-3-(2-methoxyethyl)benzimidazole-5-carboxylate (I-45) (80.0 mg, 0.177 mmol), bis(pinacolato)diboron (48 mg, 0.19 mmol), [1,1'-bis(diphenylphosphino)ferrocene] dichloropalladium(II); PdCl$_2$(dppf) (10 mg, 0.014 mmol), and potassium acetate (38 mg, 0.39 mmol) in dioxane (1.5 mL) was degassed with Ar for 5 min. Upon completion the mixture was heated at 120° C. for 30 min in a microwave reactor. Following this time, the mixture was cooled to rt. Sodium carbonate (2.00 M, 0.18 mL, 0.36 mmol) was added and the mixture was stirred at rt for 5 min. Upon completion 4-[(6-bromo-2-pyridyl)oxymethyl]-3-fluoro-benzonitrile (I-3) (64 mg, 0.21 mmol) was added to the mixture followed by degassing the mixture for 5 min with argon and then heated at 120° C. for 20 min in a microwave reactor. Following this time, the mixture was diluted with EtOAc filtered through celite, concentrated and purified by flash chromatography (eluent: EtOAc/hexanes) to yield desired product. ES/MS: 593.3.

2-((7-(6-((4-cyano-2-fluorobenzyl)oxy)pyridin-2-yl)-1,3-dihydroisobenzofuran-4-yl)methyl)-1-(2-methoxyethyl)-1H-benzo[d]imidazole-6-carboxylic acid (Example 97): A suspension of methyl 2-((7-(6-((4-cyano-2-fluorobenzyl)oxy)pyridin-2-yl)-1,3-dihydroisobenzofuran-4-yl)methyl)-1-(2-methoxyethyl)-1H-benzo[d]imidazole-6-carboxylate (41 mg, 0.069 mmol) and lithium hydroxide, monohydrate (1M, 0.2 mL, 0.2 mmol) in CH$_3$CN (1.25 mL) in a 4 mL glass vial was heated at 100° C. for 5 min. Upon completion the mixture was diluted with acetonitrile/DMF (1:1, 1 mL). 2 drops of TFA was added and the mixture was then purified directly by RP-HPLC (eluent: MeCN/H$_2$O) to obtain Example 97. ES/MS: 579.2; 1H NMR (400 MHz, DMSO) δ 8.26 (s, 1H), 7.98-7.92 (m, 1H), 7.91-7.81 (m, 3H), 7.78-7.68 (m, 2H), 7.65 (d, J=8.4 Hz, 1H), 7.59 (d, J=7.6 Hz, 1H), 7.27 (d, J=8.0 Hz, 1H), 6.93 (d, J=8.2 Hz, 1H), 5.58 (s, 2H), 5.36 (s, 2H), 4.99 (s, 2H), 4.58 (t, J=5.3 Hz, 2H), 4.42 (s, 2H), 3.63 (t, J=5.1 Hz, 2H), 3.20 (s, 3H).

Procedure 30: Example 98

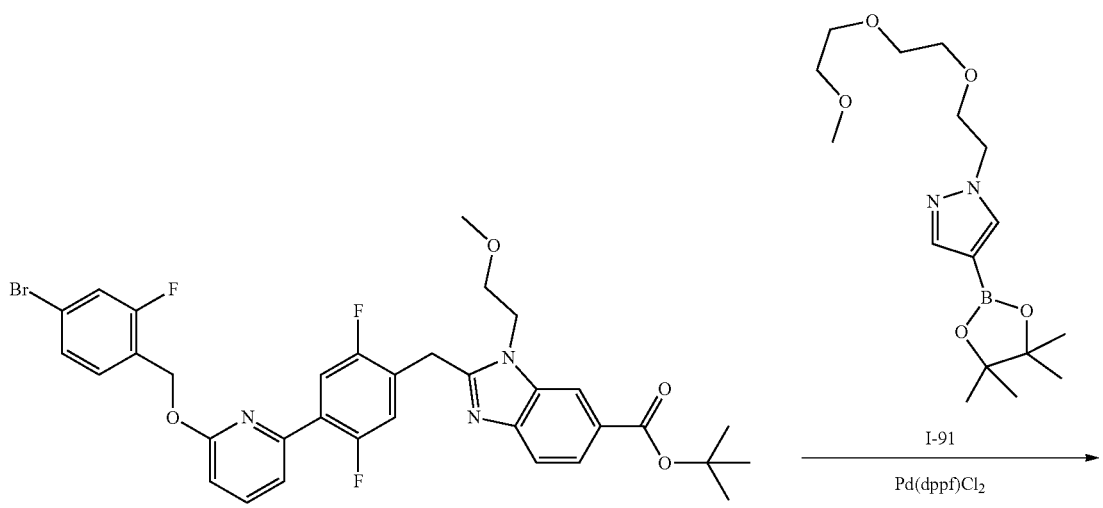

-continued

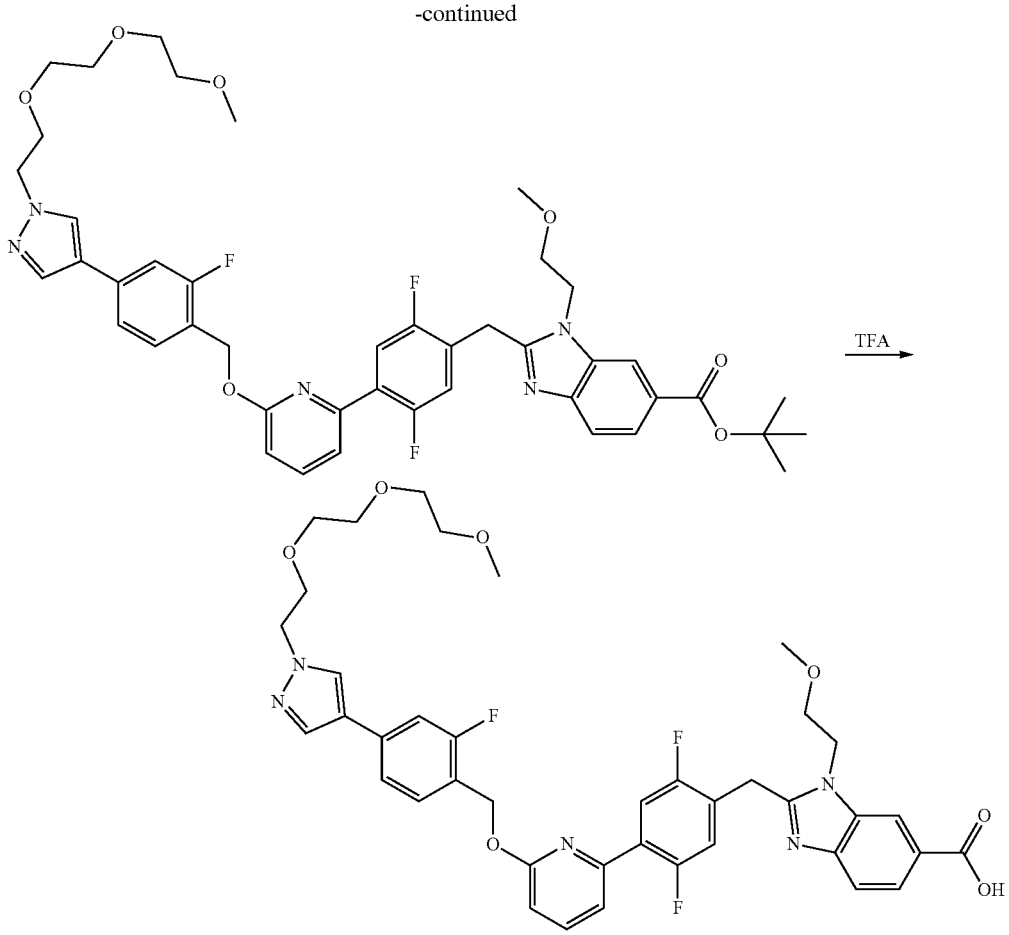

Example 98

Tert-butyl 2-[[2,5-difluoro-4-[6-[[2-fluoro-4-[1-[2-[2-(2-methoxyethoxy)ethoxy]ethyl]pyrazol-4-yl]phenyl]methoxy]-2-pyridyl]phenyl]methyl]-3-(2-methoxyethyl)benzimidazole-5-carboxylate: 1-[2-[2-(2-methoxyethoxy)ethoxy]ethyl]-4-(4,4,5,5-tetramethyl-1,3,2-dioxaborolan-2-yl)pyrazole (36 mg, 0.18 mmol), Pd(dppf)Cl$_2$ (12 mg, 0.037 mmol) and aqueous potassium carbonate (2.0M, 36 uL, 0.073 mmol) were added to a solution of tert-butyl 2-[[4-[6-[(4-bromo-2-fluoro-phenyl)methoxy]-2-pyridyl]-2,5-difluoro-phenyl]methyl]-3-(2-methoxyethyl)benzimidazole-5-carboxylate (I-18) (25 mg, 0.037 mmol) in 1,4-dioxane (2 mL). The mixture was bubbled with argon for 1 minute, then the reaction vessel sealed and heated to 100° C. for 10 minutes. Upon completion the mixture was concentrated directly, diluted with acetonitrile/water (9:1, 10 mL), passed through a C18 SPE column, concentrated and purified by RP-HPLC (eluent: MeCN/H$_2$O) to obtain the desired product. ES/MS: 816.4 (M+H$^+$).

2-[[2,5-difluoro-4-[6-[[2-fluoro-4-[1-[2-[2-(2-methoxyethoxy)ethoxy]ethyl]pyrazol-4-yl]phenyl]methoxy]-2-pyridyl]phenyl]methyl]-3-(2-methoxyethyl)benzimidazole-5-carboxylic acid (Example 98): 1 mL TFA 1 mL TFA was added to a solution of tert-butyl 2-[[2,5-difluoro-4-[6-[[2-fluoro-4-[1-[2-[2-(2-methoxyethoxy)ethoxy]ethyl]pyrazol-4-yl]phenyl]methoxy]-2-pyridyl]phenyl]methyl]-3-(2-methoxyethyl)benzimidazole-5-carboxylate (15 mg, 0.018 mmol) in DCM (2 mL). The resulting solution was stirred at rt for 1 hr. Upon completion the mixture was concentrated directly and purified by RP-HPLC (eluent: water/MeCN 0.1% TFA). The combined fractions were then frozen and placed on a lyophilizer to give Example 98. ES/MS: 760.4 (M+H$^+$). 1H NMR (400 MHz, DMSO-d6) δ 8.25 (d, 1H), 7.96 (s, 1H), 7.93-7.79 (m, 2H), 7.63 (d, 1H), 7.59-7.35 (m, 4H), 6.94 (d, 1H), 5.50 (s, 1H), 4.63 (d, OH), 4.62 (s, 1H), 4.48 (s, 1H), 4.26 (d, 1H), 3.79 (s, 1H), 3.48 (dt, 5H), 3.36 (q, 2H), 3.19 (dd, 4H) (note: multiple protons hidden under water peak).

Example 99: 2-(2,5-difluoro-4-(6-((2-fluoro-4-(1-methyl-1H-1,2,3-triazol-4-yl)benzyl)oxy)pyridin-2-yl)benzyl)-1-(2-methoxyethyl)-1H-benzo[d]imidazole-6-carboxylic acid 2-(2,5-difluoro-4-(6-((2-fluoro-4-(1-methyl-1H-1,2,3-triazol-4-yl)benzyl)oxy)pyridin-2-yl)benzyl)-1-(2-methoxyethyl)-1H-benzo[d]imidazole-6-carboxylic acid was prepared in a manner as described in Procedure 30. $^1$H NMR (400 MHz, DMSO-d$_6$) δ 8.29 (d, 1H), 7.99 (s, 1H), 7.92-7.82 (m, 3H), 7.73 (t, 1H), 7.65 (d, 1H), 7.62 (dd, 1H), 7.53 (dd, 1H), 7.50 (dd, 1H), 7.42 (dd, 1H), 6.98 (dd, 1H), 5.59 (s, 2H), 4.65 (t, 2H), 4.52 (s, 2H), 4.11 (s, 3H), 3.70 (t, 2H), 3.22 (s, 3H).

Example 100: 2-(4-(6-((4-(1-(difluoromethyl)-1H-pyrazol-4-yl)-2-fluorobenzyl)oxy)pyridin-2-yl)-2,5-difluorobenzyl)-1-(2-methoxyethyl)-1H-benzo[d]imidazole-6-carboxylic acid 2-(4-(6-((4-(1-(difluoromethyl)-1H-pyrazol-4-yl)-2-fluorobenzyl)oxy)pyridin-2-yl)-2,5-difluorobenzyl)-1-(2-methoxyethyl)-1H-benzo[d]imidazole-6-carboxylic acid was prepared in a manner as described in Procedure 30. $^1$H NMR (400 MHz, DMSO-d$_6$) δ 12.87 (s, 1H), 8.82 (s, 1H), 8.35 (s, 1H), 8.29 (d, 1H), 7.95-7.82 (m, 4H), 7.72-7.54 (m, 5H), 7.52 (dd, 1H), 7.42 (dd, 1H), 6.96 (d, 1H), 5.52 (s, 2H), 4.65 (t, 2H), 4.52 (s, 2H), 3.70 (t, 2H), 3.22 (s, 3H).

Example 101: 2-(2,5-difluoro-4-(6-((2-fluoro-4-(1-methyl-1H-pyrazol-5-yl)benzyl)oxy)pyridin-2-yl)benzyl)-1-(2-methoxyethyl)-1H-benzo[d]imidazole-6-carboxylic acid 2-(2,5-difluoro-4-(6-((2-fluoro-4-(1-methyl-1H-pyrazol-5-yl)benzyl)oxy)pyridin-2-yl)benzyl)-1-(2-methoxyethyl)-1H-benzo[d]imidazole-6-carboxylic acid was prepared in a manner as described in Procedure 30. $^1$H NMR (400 MHz, DMSO-d$_6$) δ 12.86 (s, 1H), 8.29 (d, 1H), 7.94-7.81 (m, 3H), 7.73-7.62 (m, 2H), 7.57-7.45 (m, 3H), 7.47-7.38 (m, 2H), 6.98 (d, 1H), 6.49 (d, 1H), 5.58 (s, 2H), 4.66 (t, 2H), 4.52 (s, 2H), 3.88 (s, 3H), 3.70 (t, 2H), 3.22 (s, 3H).

Example 102: 2-(2,5-difluoro-4-(6-((2-fluoro-4-(1-methyl-3-(trifluoromethyl)-1H-pyrazol-5-yl)benzyl)oxy)pyridin-2-yl)benzyl)-1-(2-methoxyethyl)-1H-benzo[d]imidazole-6-carboxylic acid 2-(2,5-difluoro-4-(6-((2-fluoro-4-(1-methyl-3-(trifluoromethyl)-1H-pyrazol-5-yl)benzyl)oxy)pyridin-2-yl)benzyl)-1-(2-methoxyethyl)-1H-benzo[d]imidazole-6-carboxylic acid was prepared in a manner as described in Procedure 30. $^1$H NMR (400 MHz, DMSO-d$_6$) δ 8.27 (d, 1H), 7.94-7.80 (m, 3H), 7.73 (t, 1H), 7.67-7.37 (m, 5H), 7.03-6.95 (m, 2H), 5.59 (s, 2H), 4.64 (t, 2H), 4.50 (s, 2H), 3.70 (t, 2H), 3.21 (s, 3H).

Example 103: 2-(2,5-difluoro-4-(6-((2-fluoro-4-(pyridin-3-yl)benzyl)oxy)pyridin-2-yl)benzyl)-1-(2-methoxyethyl)-1H-benzo[d]imidazole-6-carboxylic acid 2-(2,5-difluoro-4-(6-((2-fluoro-4-(pyridin-3-yl)benzyl)oxy)pyridin-2-yl)benzyl)-1-(2-methoxyethyl)-1H-benzo[d]imidazole-6-carboxylic acid was prepared in a manner as described in Procedure 30. $^1$H NMR (400 MHz, DMSO-d$_6$) δ 9.05 (d, 1H), 8.69 (dd, 1H), 8.35 (dt, 1H), 8.27 (d, 1H), 7.94-7.80 (m, 3H), 7.80-7.60 (m, 5H), 7.53 (dd, 1H), 7.42 (dd, 1H), 6.98 (d, 1H), 5.59 (s, 2H), 4.64 (t, 2H), 4.50 (s, 2H), 3.70 (t, 2H), 3.21 (s, 3H).

Example 104: 2-(2,5-difluoro-4-(6-((2-fluoro-4-(2-methylpyridin-3-yl)benzyl)oxy)pyridin-2-yl)benzyl)-1-(2-methoxyethyl)-1H-benzo[d]imidazole-6-carboxylic acid 2-(2,5-difluoro-4-(6-((2-fluoro-4-(2-methylpyridin-3-yl)benzyl)oxy)pyridin-2-yl)benzyl)-1-(2-methoxyethyl)-1H-benzo[d]imidazole-6-carboxylic acid was prepared in a manner as described on Procedure 30. $^1$H NMR (400 MHz, DMSO-d$_6$) δ 8.74 (dd, 1H), 8.27 (d, 1H), 8.20 (d, 1H), 7.95-7.80 (m, 3H), 7.75 (dt, 2H), 7.63 (d, 1H), 7.57-7.32 (m, 4H), 6.99 (d, 1H), 5.60 (s, 2H), 4.64 (t, 2H), 4.50 (s, 2H), 3.70 (t, 2H), 3.22 (s, 3H), 2.59 (s, 3H).

Example 105: 2-(2,5-difluoro-4-(6-((2-fluoro-4-(6-methylpyridin-3-yl)benzyl)oxy)pyridin-2-yl)benzyl)-1-(2-methoxyethyl)-1H-benzo[d]imidazole-6-carboxylic acid 2-(2,5-difluoro-4-(6-((2-fluoro-4-(6-methylpyridin-3-yl)benzyl)oxy)pyridin-2-yl)benzyl)-1-(2-methoxyethyl)-1H-benzo[d]imidazole-6-carboxylic acid was prepared in a manner as described in Procedure 30. $^1$H NMR (400 MHz, DMSO-d$_6$) δ 12.88 (s, 1H), 9.03 (d, 1H), 8.51 (dd, 1H), 8.27 (d, 1H), 7.94-7.65 (m, 7H), 7.63 (d, 1H), 7.53 (dd, 1H), 7.42 (dd, 1H), 6.97 (d, 1H), 5.59 (s, 2H), 4.64 (t, 2H), 3.70 (t, 2H), 3.21 (s, 3H), 2.66 (s, 3H).

Example 106: 2-(2,5-difluoro-4-(6-((2-fluoro-4-(1-(2-methoxyethyl)-1H-pyrazol-4-yl)benzyl)oxy)pyridin-2-yl)benzyl)-1-(2-methoxyethyl)-1H-benzo[d]imidazole-6-carboxylic acid 2-(2,5-difluoro-4-(6-((2-fluoro-4-(1-(2-methoxyethyl)-1H-pyrazol-4-yl)benzyl)oxy)pyridin-2-yl)benzyl)-1-(2-methoxyethyl)-1H-benzo[d]imidazole-6-carboxylic acid was prepared in a manner as described in Procedure 30. $^1$H NMR (400 MHz, DMSO-d$_6$) δ 8.28-8.21 (m, 4H), 7.96 (s, 2H), 7.92-7.79 (m, 6H), 7.63 (d, 2H), 7.57-7.47 (m, 7H), 7.45 (d, 1H), 7.43 (s, 1H), 6.94 (d, 2H), 5.49 (s, 4H), 4.63 (t, 4H), 4.49 (s, 4H), 4.27 (t, 4H), 3.70 (dt, 9H), 3.24 (s, 6H), 3.22 (s, 6H).

Example 107: 2-(2,5-difluoro-4-(6-(((6-(1-methyl-11H-1,2,3-triazol-4-yl)pyridin-3-yl)methoxy)pyridin-2-yl)benzyl)-1-(2-methoxyethyl)-1H-benzo[d]imidazole-6-carboxylic acid 2-(2,5-difluoro-4-(6-(((6-(1-methyl-1H-1,2,3-triazol-4-yl)pyridin-3-yl)methoxy)pyridin-2-yl)benzyl)-1-(2-methoxyethyl)-1H-benzo[d]imidazole-6-carboxylic acid was prepared in a manner as described in Procedure 30. $^1$H NMR (400 MHz, Acetonitrile-d$_3$) δ 8.85 (d, 1H), 8.34 (s, 1H), 8.09-7.98 (m, 3H), 7.93-7.70 (m, 4H), 7.56 (dd, 1H), 7.27 (dd, 1H), 6.96-6.89 (m, 1H), 5.60 (s, 2H), 4.57 (dd, 4H), 4.35 (s, 3H), 3.75 (t, 2H), 3.26 (s, 3H).

Example 108: 2-(2,5-difluoro-4-(6-(((6-(1-methyl-1H-pyrazol-4-yl)pyridin-3-yl)methoxy)pyridin-2-yl)benzyl)-1-(2-methoxyethyl)-1H-benzo[d]imidazole-6-carboxylic acid 2-(2,5-difluoro-4-(6-(((6-(1-methyl-1H-pyrazol-4-yl)pyridin-3-yl)methoxy)pyridin-2-yl)benzyl)-1-(2-methoxyethyl)-1H-benzo[d]imidazole-6-carboxylic acid was prepared in a manner as described in Procedure 30. $^1$H NMR (400 MHz, Acetonitrile-d$_3$) δ 8.80 (d, 1H), 8.43-8.30 (m, 3H), 8.16 (d, 1H), 8.08 (dd, 1H), 7.98-7.77 (m, 3H), 7.76 (d, 1H), 7.54 (dd, 1H), 7.29 (dd, 1H), 6.92 (d, 1H), 5.60 (s, 2H), 4.65 (d, 1H), 4.63 (s, 3H), 3.95 (s, 3H), 3.78 (t, 2H), 3.28 (s, 3H).

Example 109: 2-(4-(6-(((6-(1-(difluoromethyl)-1H-pyrazol-4-yl)pyridin-3-yl)methoxy)pyridin-2-yl)-2,5-difluorobenzyl)-1-(2-methoxyethyl)-1H-benzo[d]imidazole-6-carboxylic acid 2-(4-(6-((6-(1-(difluoromethyl)-1H-pyrazol-4-yl)pyridin-3-yl)methoxy)pyridin-2-yl)-2,5-difluorobenzyl)-1-(2- methoxyethyl)-1H-benzo[d]imidazole-6-carboxylic acid was prepared in a manner as described in Procedure 30. $^1$H NMR (400 MHz, Acetonitrile-d$_3$) δ 8.79 (d, 1H), 8.63 (s, 1H), 8.45-8.40 (m, 1H), 8.31 (s, 1H), 8.11 (ddd, 2H), 7.97-7.87 (m, 1H), 7.87-7.76 (m, 3H), 7.62-7.52 (m, 1H), 7.45 (s, OH), 7.35-7.26 (m, 1H), 6.92 (d, 1H), 5.59 (s, 2H), 4.65 (t, 2H), 3.78 (t, 2H), 3.27 (s, 3H), 1.97-1.86 (m, 1H).

Example 110: 2-(2,5-difluoro-4-(6-((6-(1-methyl-1H-pyrazol-5-yl)pyridin-3-yl)methoxy)pyridin-2-yl)benzyl)-1-(2-methoxyethyl)-1H-benzo[d]imidazole-6-carboxylic acid 2-(2,5-difluoro-4-(6-((6-(1-methyl-1H-pyrazol-5-yl)pyridin-3-yl)methoxy)pyridin-2-yl)benzyl)-1-(2-methoxyethyl)-1H-benzo[d]imidazole-6-carboxylic acid was prepared in a manner as described in Procedure 30. $^1$H NMR (400 MHz, Acetonitrile-d$_3$) δ 8.81 (d, 1H), 8.39 (s, 1H), 8.08 (dd, 1H), 7.97 (dd, 1H), 7.91 (dd, 1H), 7.85-7.75 (m, 2H), 7.72 (d, 1H), 7.56 (dd, 1H), 7.47 (d, 1H), 7.30 (dd, 1H), 6.93 (d, 1H), 6.69 (d, 1H), 5.58 (s, 2H), 4.62 (s, 3H), 4.62 (d, 1H), 4.16 (s, 3H), 3.76 (t, 2H), 3.26 (s, 3H).

Tert-butyl 2-[[4-[6-[(4-ethynyl-2-fluoro-phenyl)methoxy]-2-pyridyl]-2,5-difluoro-phenyl]methyl]-3-(2-methoxyethyl)benzimidazole-5-carboxylate: Cuprous iodide (4 mg, 0.021 mmol), trans-Dichlorobis(triphenylphosphine)palladium (7.7 mg, 0.011 mmol), trimethylsilyl acetylene (11 uL, 0.22 mmol) and diisopropylethylamine (0.15 mL, 0.88 mmol) were added to a solution of tert-butyl 2-[[4-[6-[(4-bromo-2-fluoro-phenyl)methoxy]-2-pyridyl]-2,5-difluoro-phenyl]methyl]-3-(2-methoxyethyl)benzimidazole-5-carboxylate (I-18) (30 mg, 0.044 mmol) in DMF (2 mL). The resulting solution was degassed by bubbling argon for 1 min, sealed and heated to 100° C. for 3 hours. Upon completion the mixture was poured into water (5 mL) and extracted with EtOAc (2×15 mL). The organic layers were combined, washed with brine (5 mL), dried over MgSO$_4$, filtered, concentrated, and the crude residue was dissolved in THF (2 mL) and TBAF (1.0M in THF, 0.35 mL, 0.35 mmol) was added. After stirring at rt for 10 min the mixture was diluted with EtOAc (25 mL), washed with water (5 mL) and brine (5 mL). The organic layer was dried over MgSO$_4$, filtered, concentrated and purified by flash chromatography (Eluent: EtOAc/hexane) to give the desired product. ES/MS: 628.3 (M+H+).

2-[[4-[6-[(4-ethynyl-2-fluoro-phenyl)methoxy]-2-pyridyl]-2,5-difluoro-phenyl]methyl]-3-(2-methoxyethyl)

Procedure 31: Example 111

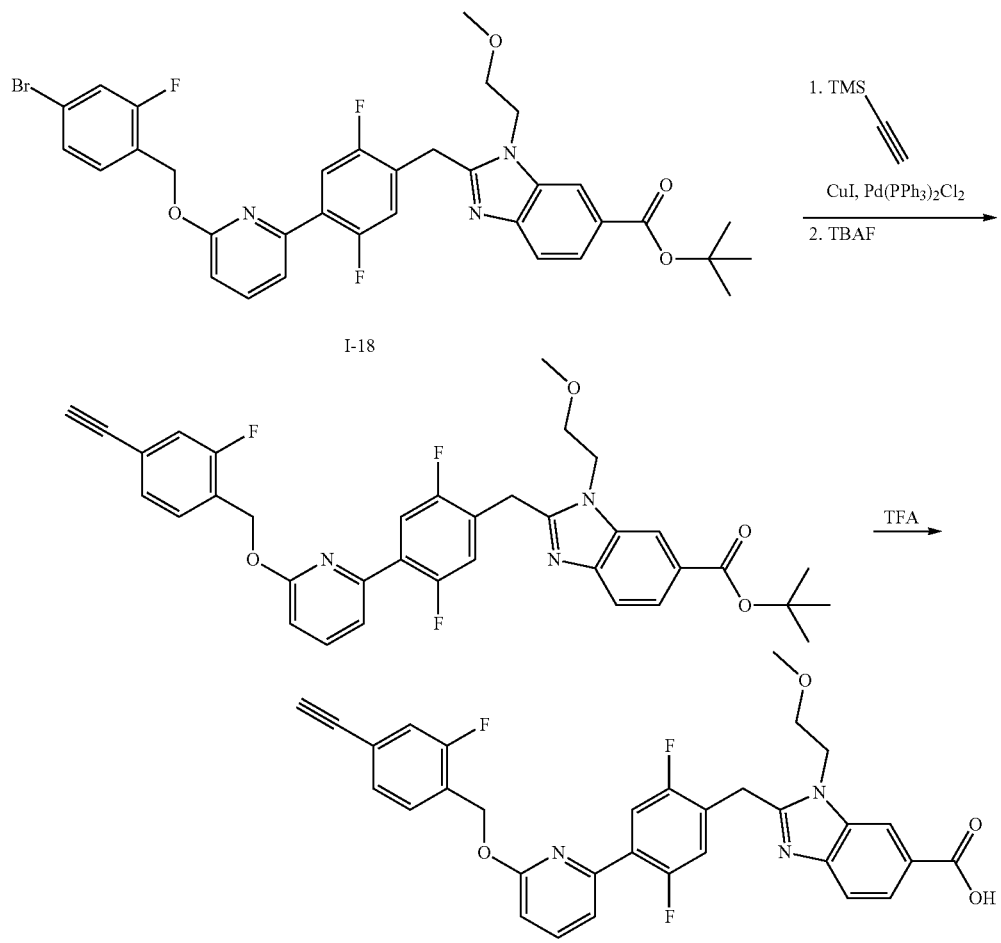

Example 111 benzimidazole-5-carboxylic acid (Example 111): 1 mL TFA was added to a solution of tert-butyl 2-[[4-[6-[(4-ethynyl-2-fluoro-phenyl)methoxy]-2-pyridyl]-2,5-difluoro-phenyl]methyl]-3-(2-methoxyethyl)benzimidazole-5-carboxylate (27 mg, 0.043 mmol) in DCM (2 mL). The resulting solution stirred at rt for 1 hr. Upon completion the mixture was concentrated directly and purified by RP-HPLC (eluent: water/MeCN 0.1% TFA). The combined fractions were then frozen and placed on a lyophilizer to provide Example 111. ES/MS: 572.4 (M+H⁺). 1H NMR (400 MHz, DMSO-d6) δ 8.28 (d, J=1.4 Hz, 1H), 7.93-7.84 (m, 2H), 7.81 (dd, J=10.5, 6.5 Hz, 1H), 7.65 (d, J=8.4 Hz, 1H), 7.57 (t, J=7.8 Hz, 1H), 7.52 (dd, J=7.5, 1.7 Hz, 1H), 7.41 (ddd, J=11.4, 4.4, 2.8 Hz, 2H), 7.35 (d, J=7.8, 1.6 Hz, 1H), 6.96 (d, J=8.3 Hz, 1H), 5.53 (s, 2H), 4.65 (t, J=5.1 Hz, 2H), 4.51 (s, 2H), 4.34 (s, 1H), 3.70 (t, J=5.0 Hz, 2H), 3.22 (s, 3H).

Procedure 32: Example 112 bromo-2-fluoro-phenyl)methoxy]-2-pyridyl]-2,5-difluoro-phenyl]methyl]-3-(2-methoxyethyl)benzimidazole-5-carboxylate (I-18) (140 mg, 0.21 mmol), Bis(pinacolato)diboron (68 mg, 0.27 mmol), [1,1'-Bis(diphenylphosphino)ferrocene] dichloropalladium(II); PdCl₂(dppf) (23 mg, 0.031 mmol), and potassium propionate (69 mg, 0.62 mmol) in dioxane (1.5 mL) was degassed with Ar for 1 min. Upon completion the mixture was heated at 110° C. for 45 min. Following this time, the mixture was cooled to rt, followed by the addition of sodium carbonate (2.00 M, 0.21 mL, 0.41 mmol) and stirred at rt for 5 min. Upon completion 5-bromo-1-methyl-1,2,4-triazole (50 mg, 0.31 mmol) was added to the mixture and then the mixture was degassed for 5 min with argon, followed by heating at 90° C. for 45 min. Following this time, the mixture was diluted with EtOAc filtered through celite, concentrated and purified by flash chromatography (eluent: EtOAc/hexanes) to yield desired product.

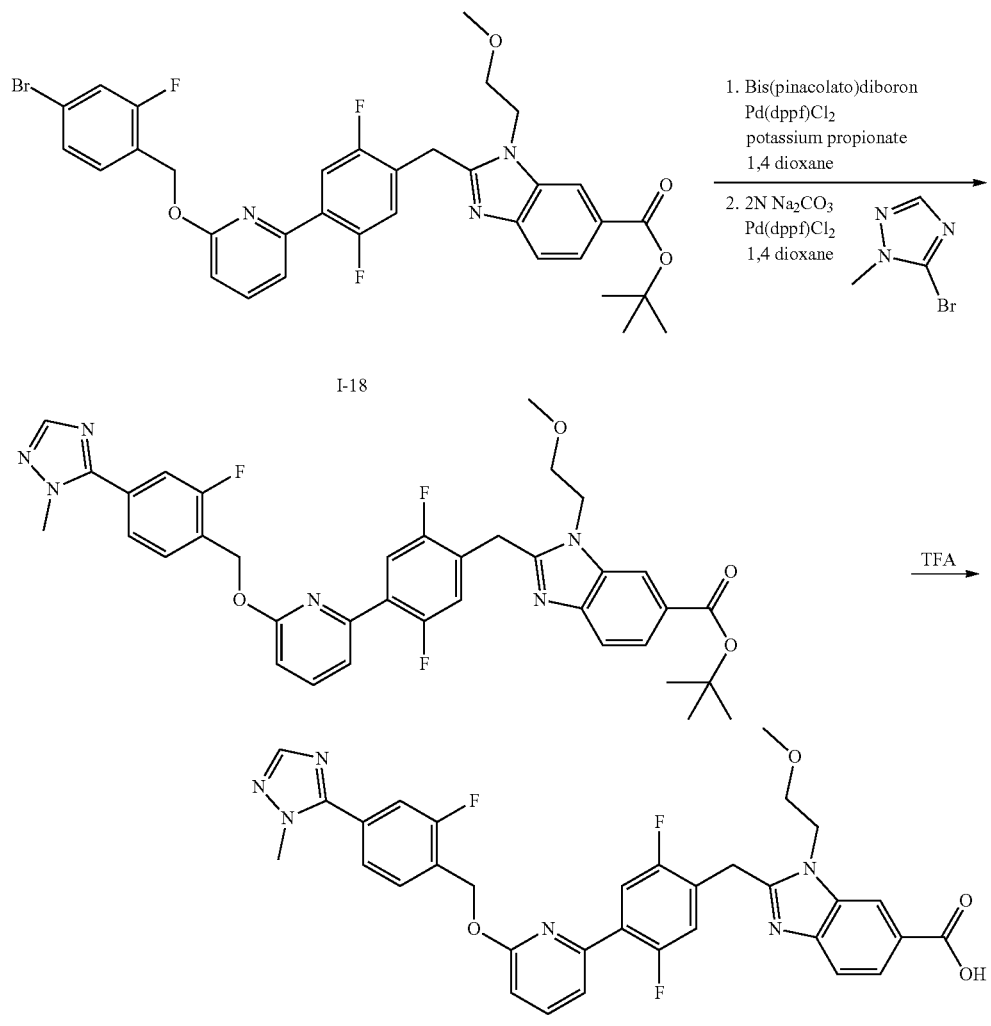

Example 112

Tert-butyl 2-[[2,5-difluoro-4-[6-[[2-fluoro-4-(2-methyl-1,2,4-triazol-3-yl)phenyl]methoxy]-2-pyridyl]phenyl]methyl]-3-(2-methoxyethyl)benzimidazole-5-carboxylate: In a 8 mL glass vial, a suspension of tert-butyl 2-[[4-[6-[(4-

2-[[2,5-difluoro-4-[6-[[2-fluoro-4-(2-methyl-1,2,4-triazol-3-yl)phenyl]methoxy]-2-pyridyl]phenyl]methyl]-3-(2-methoxyethyl)benzimidazole-5-carboxylic acid (Example 112): 1.6 mL TFA was added to a solution of tert-butyl 2-[[2,5-difluoro-4-[6-[[2-fluoro-4-(2-methyl-1,2,4-triazol-3-yl)phenyl]methoxy]-2-pyridyl]phenyl]methyl]-3-(2-methoxyethyl)benzimidazole-5-carboxylate (112 mg, 0.16 mmol) in DCE (4 mL). The resulting solution stirred at 60° C. for 1 hr. Upon completion the mixture was concentrated directly and purified by RP-HPLC (eluent: water/MeCN 0.1% TFA). The combined fractions were then frozen and placed on a lyophilizer to provide Example 112. ES/MS: 629.2 (M+H$^+$). 1H NMR (400 MHz, DMSO-d6) δ 8.31 (d, J=1.4 Hz, 1H), 8.03 (s, 1H), 7.92-7.82 (m, 3H), 7.79-7.61 (m, 4H), 7.54 (dd, J=7.6, 1.7 Hz, 1H), 7.43 (dd, J=11.5, 6.1 Hz, 1H), 6.99 (d, J=8.2 Hz, 1H), 5.61 (s, 2H), 4.67 (t, J=5.1 Hz, 2H), 4.54 (s, 2H), 4.00 (s, 3H), 3.70 (d, J=5.0 Hz, 2H), 3.21 (s, 3H).

Procedure 33: Example 113

(I-18) (90 mg, 0.13 mmol), tributyl-(3-methylimidazol-4-yl) stannane (73 mg, 0.20), tetrakis(triphenylphosphine) palladium (23 mg, 0.020 mmol), and lithium chloride (17 mg, 0.40 mmol) in dioxane (2 mL) was degassed with Ar for 1 min. Following the degassing the mixture was heated at 100° C. for 16 hrs. Upon completion the mixture was cooled to rt, concentrated directly and the crude residue purified by flash chromatography (eluent: EtOAc/hexanes) to yield desired product. ES/MS: 684.2 (M+H$^+$).

2-[[2,5-difluoro-4-[6-[[2-fluoro-4-(3-methylimidazol-4-yl)phenyl]methoxy]-2-pyridyl]phenyl]methyl]-3-(2-methoxyethyl)benzimidazole-5-carboxylic acid (Example 113): 1.6 mL TFA was added to a solution of tert-butyl 2-[[2,5-difluoro-4-[6-[[2-fluoro-4-(3-methylimidazol-4-yl)phenyl]methoxy]-2-pyridyl]phenyl]methyl]-3-(2-methoxyethyl)benzimidazole-5-carboxylate (112 mg, 0.16 mmol) in DCE (4 mL). The resulting solution stirred at 60° C. for 1 hr.

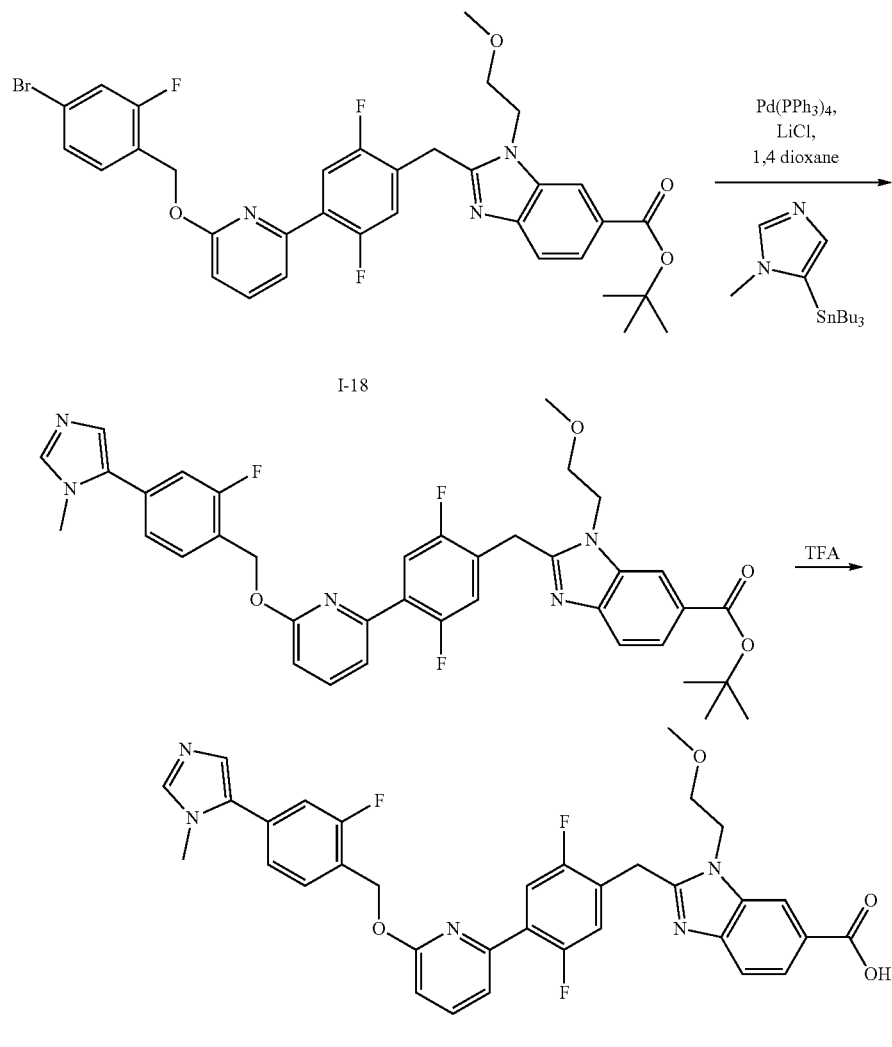

Tert-butyl 2-[[2,5-difluoro-4-[6-[[2-fluoro-4-(3-methylimidazol-4-yl)phenyl]methoxy]-2-pyridyl]phenyl]methyl]-3-(2-methoxyethyl)benzimidazole-5-carboxylate: In a 8 mL glass vial, a suspension of tert-butyl 2-[[4-[6-[(4-bromo-2-fluoro-phenyl)methoxy]-2-pyridyl]-2,5-difluoro-phenyl]methyl]-3-(2-methoxyethyl)benzimidazole-5-carboxylate Upon completion the mixture was concentrated directly and purified by RP-HPLC (eluent: water/MeCN 0.1% TFA). The combined fractions were then frozen and placed on a lyophilizer to provide Example 113. ES/MS: 628.2 (M+H$^+$). 1H NMR (400 MHz, DMSO-d6) δ 9.18 (d, J=1.4 Hz, 1H), 8.25 (d, J=1.4 Hz, 1H), 7.97-7.80 (m, 4H), 7.76 (t, J=7.8 Hz, 1H), 7.65-7.57 (m, 2H), 7.52 (ddd, J=15.7, 7.7, 1.7 Hz, 2H), 7.41 (dd, J=11.5, 6.0 Hz, 1H), 6.98 (d, J=8.2 Hz, 1H), 5.61 (s, 2H), 4.63 (t, J=5.1 Hz, 2H), 4.48 (s, 2H), 3.88 (s, 3H), 3.70 (s, 2H), 3.22 (s, 3H).

Procedure 34: Example 114

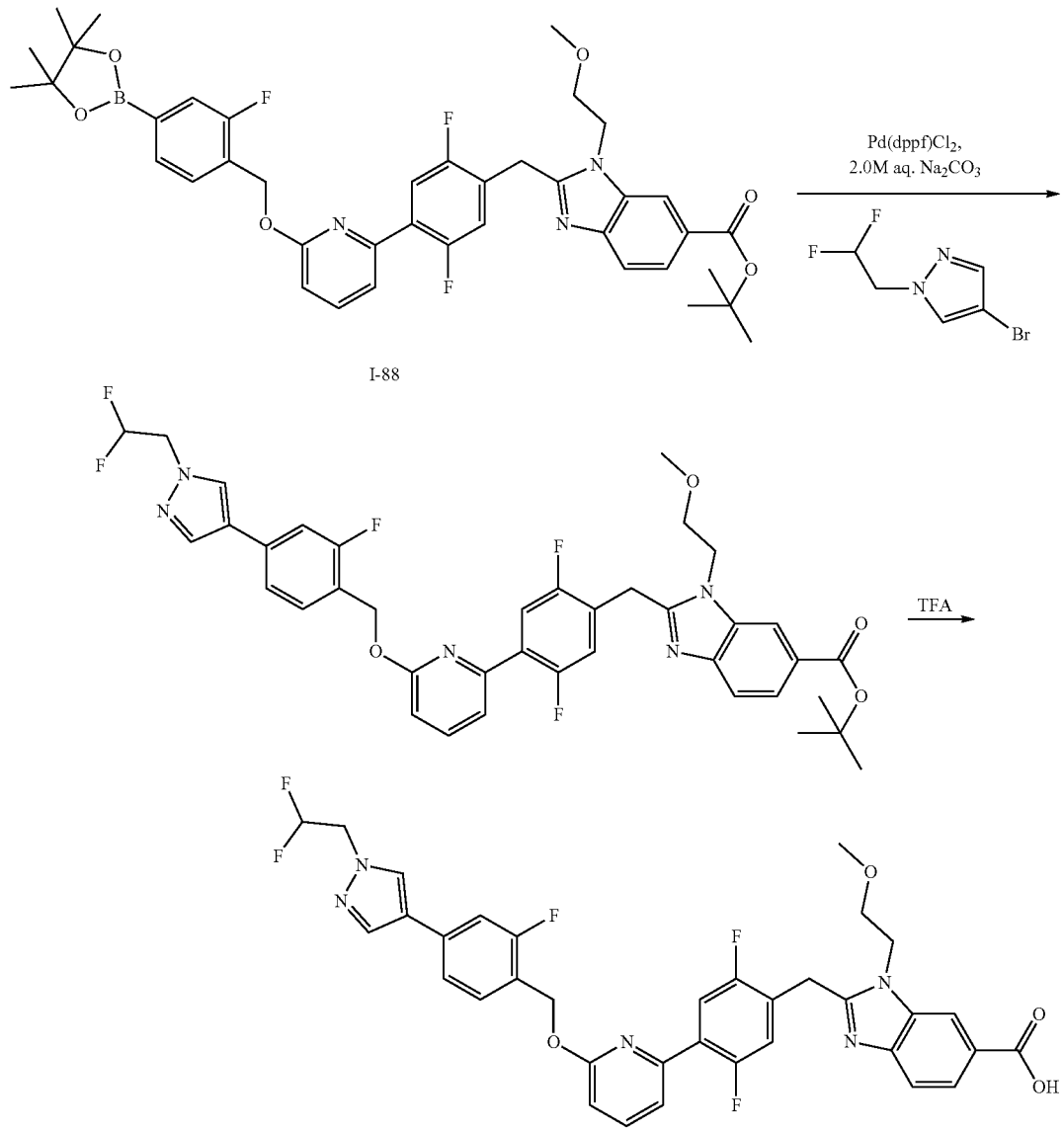

water (0.5 mL) were combined in a glass vial, degassed via bubbling argon for 1 min, and then the mixture heated to 100° C. for 10 min in a microwave reactor. Upon completion the mixture was concentrated directly, diluted with 9:1 acetonitrile:water, passed through a C18 SPE column, concentrated and carried forward without further purification.

Tert-butyl 2-[[4-[6-[[4-[1-(2,2-difluoroethyl)pyrazol-4-yl]-2-fluoro-phenyl]methoxy]-2-pyridyl]-2,5-difluoro-phenyl]methyl]-3-(2-methoxyethyl)benzimidazole-5-carboxylate: Tert-butyl 2-[[2,5-difluoro-4-[6-[[2-fluoro-4-(4,4,5,5-tetramethyl-1,3,2-dioxaborolan-2-yl)phenyl]methoxy]-2-pyridyl]phenyl]methyl]-3-(2-methoxyethyl)benzimidazole-5-carboxylate (I-88) (23 mg, 0.032 mmol), 4-bromo-1-(2,2-difluoroethyl)pyrazole (6.7 mg, 0.032 mmol), 1,1'-Bis(diphenylphosphino)ferrocene-palladium(II)dichloride dichloromethane complex (2.6 mg, 0.0032 mmol), sodium carbonate (6.7 mg, 0.063 mmol) 1,4-dioxane (1 mL), and 2-[[4-[6-[[4-[1-(2,2-difluoroethyl)pyrazol-4-yl]-2-fluoro-phenyl]methoxy]-2-pyridyl]-2,5-difluoro-phenyl]methyl]-3-(2-methoxyethyl)benzimidazole-5-carboxylic acid (Example 114): 0.25 mL TFA was added to a solution of tert-butyl 2-[[4-[6-[[4-[1-(2,2-difluoroethyl)pyrazol-4-yl]-2-fluoro-phenyl]methoxy]-2-pyridyl]-2,5-difluoro-phenyl]methyl]-3-(2-methoxyethyl)benzimidazole-5-carboxylate (23 mg, 0.031 mmol) in DCM (2 mL). The resulting solution stirred at 40° C. for 1 hr. The mixture was concentrated directly and purified by RP-HPLC (eluent: water/MeCN 0.1% TFA). The combined fractions were then frozen and placed on a lyophilizer to provide Example 114. ES/MS: 678.2 (M+H⁺). 1H NMR (400 MHz, Acetonitrile-d₃) δ 8.28 (s, 1H), 8.00 (s, 1H), 7.96 (s, 1H), 7.93-7.88 (m, 2H), 7.80 (t, 1H), 7.69 (d, 1H), 7.56 (t, 3H), 7.42-7.35 (m, 2H), 7.23 (dd, 1H), 6.87 (d, 1H), 6.24 (tt, 1H), 5.56 (s, 2H), 4.55-4.51 (m, 2H), 4.49 (s, 2H), 3.73 (t, 2H), 3.25 (s, 3H).

Procedure 35: Example 115 filtrate was concentrated and purified by column chromatography (silica gel, EtOAc/hexane gradient) to yield the title compound. ES/MS m/z: 635.6 (M+H)⁺.

2-[[4-[6-[(4-chloro-2-fluoro-phenyl)methoxy]-2-pyridyl]-2,5-difluoro-phenyl]methyl]-3-[(3S)-4,4-dimethyl-tetrahydrofuran-3-yl]benzimidazole-5-carboxylic acid (Example 115): 2-[[4-[6-[(4-chloro-2-fluoro-phenyl)methoxy]-2-pyridyl]-2,5-difluoro-phenyl]methyl]-3-[(3S)-4,4-dimethyltetrahydrofuran-3-yl]benzimidazole-5-carboxylic

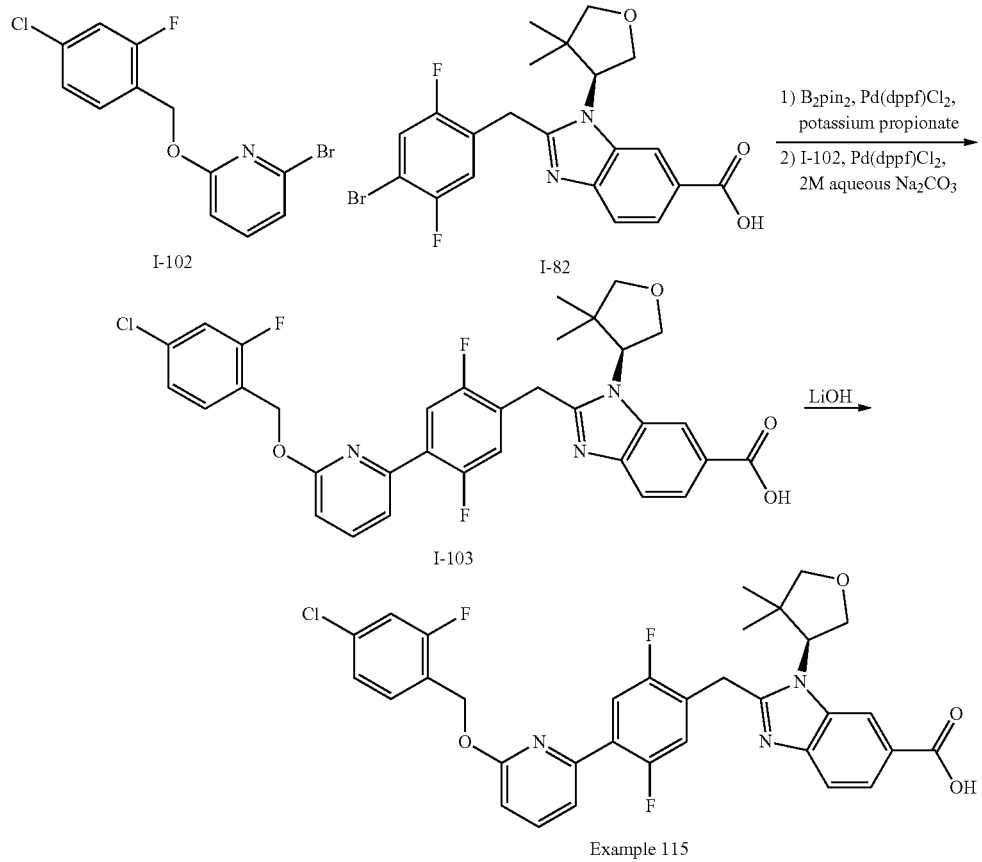

Methyl 2-[[4-[6-[(4-chloro-2-fluoro-phenyl)methoxy]-2-pyridyl]-2,5-difluoro-phenyl]methyl]-3-[(3S)-4,4-dimethyl-tetrahydrofuran-3-yl]benzimidazole-5-carboxylate (Intermediate I-103). A mixture of methyl 2-[(4-bromo-2,5-difluoro-phenyl)methyl]-3-[(3S)-4,4-dimethyltetrahydrofuran-3-yl]benzimidazole-5-carboxylate (Intermediate I-82, 800 mg, 1.67 mmol, 1.0 equivalent), PdCl₂(dppf) (186 mg, 0.25 mmol, 0.15 equivalent), potassium propionate (560 mg, 5.01 mmol, 3.0 equivalent), and bis(pinacolato)diboron (510 mg, 2.00 mol, 1.2 equivalent) was mixed with 1,4-dioxane (10 mL) and the resulting mixture was purged with argon for 2 min. The mixture was sealed and heated to 120° C. by microwave followed by stirring for 1 hr. After cooling down to room temperature, 2-bromo-6-[(4-chloro-2-fluoro-phenyl)methoxy]pyridine (Intermediate I-102, 580 mg, 1.84 mmol, 1.1 equivalent), PdCl₂(dppf) (62 mg, 0.0834 mmol, 0.05 equivalent), 2 M aqueous Na₂CO₃ (2.0 mL, 4.17 mmol, 2.5 equivalent) were added, respectively. The resulting mixture was heated to 100° C. under argon and stirred for 3 hrs. before cooling to rt and filtered through a plug of Celite and MgSO₄. The acid was prepared in a manner similar to Procedure 22, with the following modifications: LiOH (1.0 M in H₂O, 3.5 mL, 3.5 mmol) was added to a solution of methyl 2-[[4-[6-[(4-chloro-2-fluoro-phenyl)methoxy]-2-pyridyl]-2,5-difluoro-phenyl]methyl]-3-[(3S)-4,4-dimethyltetrahydrofuran-3-yl]benzimidazole-5-carboxylate (Intermediate I-103, 550 mg, 0.865 mmol) in acetonitrile (10 mL), and the resulting solution was heated to reflux for 8 min. The reaction was quenched with 1 mL acetic acid and diluted with EtOAc (100 mL). The organic extracts were washed with water (4×50 mL), dried over MgSO₄, filtered, concentrated in vacuo. The crude material was purified by reverse phase chromatography (MeCN/water gradient with 0.1% TFA added). The product containing fractions were combined and concentrated to give Example 115. 1H NMR (400 MHz, DMSO-d6) δ 8.50 (s, 1H), 7.94-7.76 (m, 3H), 7.62 (dd, J=12.6, 8.3 Hz, 2H), 7.57-7.42 (m, 3H), 7.33 (dd, J=8.2, 2.0 Hz, 1H), 6.96 (d, J=8.2 Hz, 1H), 5.51 (s, 2H), 5.02 (d, J=6.6 Hz, 1H), 4.54 (dd, J=14.1, 2.9 Hz, 2H), 4.49-4.33 (m, 2H), 3.82-3.72 (m, 2H), 1.34 (s, 3H), 0.61 (s, 3H). ES/MS m/z: 622.2 (M+H)⁺.

Example 116: 2-[[4-[6-[(4-cyano-2-fluoro-phenyl)methoxy]-5-fluoro-2-pyridyl]-2,5-difluoro-phenyl]methyl]-3-[(3S)-4,4-dimethyltetrahydrofuran-3-yl]-7-fluorobenzimidazole-5-carboxylic acid 2-[[4-[6-[(4-cyano-2-fluoro-phenyl)methoxy]-5-fluoro-2-pyridyl]-2,5-difluoro-phenyl]methyl]-3-[(3S)-4,4-dimethyltetrahydrofuran-3-yl]-7-fluorobenzimidazole-5-carboxylic acid was prepared in a manner similar to Procedure 22, with the following modifications: To a solution of methyl 2-[[4-[6-[(4-cyano-2-fluoro-phenyl)methoxy]-5-fluoro-2-pyridyl]-2,5-difluorophenyl]methyl]-3-[(3S)-4,4-dimethyltetrahydrofuran-3-yl]-7-fluorobenzimidazole-5-carboxylate (Intermediate I-110, 437 mg, 0.66 mmol) in 15 mL of acetonitrile and 5 mL of water was added aqueous LiOH (2.0 mL, 2.0 mmol, 2 M). The solution was then stirred at rt overnight. The following day, trifluoroacetic acid (0.15 mL, 2.0 mmol) was added, then concentrated into 1 mL of DMF. The crude material was purified by reverse phase preparative HPLC (ACN/water gradient with 0.1% TFA added) to give Example 116. ES/MS m/z: 648.6 (M+H$^+$); 1H NMR (400 MHz, DMSO) δ 13.12 (s, 1H), 8.79 (d, J=5.2 Hz, 1H), 8.36 (s, 1H), 7.96 (dd, J=10.2, 6.2 Hz, 1H), 7.68-7.60 (m, 2H), 7.60-7.51 (m, 2H), 7.51 (d, J=2.1 Hz, 1H), 7.35 (dd, J=8.2, 2.0 Hz, 1H), 5.54 (s, 2H), 5.04 (d, J=6.6 Hz, 1H), 4.58 (d, J=17.0 Hz, 1H), 4.53 (d, J=11.8 Hz, 1H), 4.48-4.38 (m, 2H), 3.76 (d, J=16.5 Hz, 2H), 1.34 (s, 3H), 0.62 (s, 3H).

Example 117: (S)-2-(4-(2-((4-chloro-2-fluorobenzyl)oxy)pyrimidin-4-yl)-2,5-difluorobenzyl)-1-(4,4-dimethyltetrahydrofuran-3-yl)-4-fluoro-1H-benzo[d]imidazole-6-carboxylic acid (S)-2-(4-(2-((4-chloro-2-fluorobenzyl)oxy)pyrimidin-4-yl)-2,5-difluorobenzyl)-1-(4,4-dimethyltetrahydrofuran-3-yl)-4-fluoro-1H-benzo[d]imidazole-6-carboxylic acid was prepared in a manner similar to Procedure 22, with the following modifications: To a solution of methyl (S)-2-(4-(2-((4-chloro-2-fluorobenzyl)oxy)pyrimidin-4-yl)-2,5-difluorobenzyl)-1-(4,4-dimethyltetrahydrofuran-3-yl)-4-fluoro-1H-benzo[d]imidazole-6-carboxylate (Intermediate I-111, 37 mg, 0.06 mmol) in 3 mL of acetonitrile and 1 mL of water was added aqueous LiOH (0.04 mL, 0.08 mmol, 2 M). The solution was then stirred at rt overnight. The following day, a drop of trifluoroacetic acid was added, then concentrated into 1 mL of DMF. The crude material was purified by reverse-phase preparative HPLC (ACN/water gradient with 0.1% TFA added) to yield Example 117. ES/MS m/z: 642.0 (M+H$^+$); $^1$H NMR (400 MHz, DMSO) δ 8.79 (d, J=5.2 Hz, 1H), 8.36 (s, 1H), 7.96 (dd, J=10.2, 6.2 Hz, 1H), 7.68-7.48 (m, 5H), 7.35 (dd, J=8.3, 2.1 Hz, 1H), 5.54 (s, 2H), 5.04 (d, J=6.5 Hz, 1H), 4.59 (d, J=17.0 Hz, 1H), 4.53 (d, J=11.8 Hz, 1H), 4.48-4.38 (m, 2H), 3.75 (q, J=8.7 Hz, 2H), 1.34 (s, 3H), 0.62 (s, 3H).

Example 118: (S)-2-(4-(6-((4-chloro-6-(1H-1,2,3-triazol-1-yl)pyridin-3-yl)methoxy)pyridin-2-yl)-2,5-difluorobenzyl)-1-(4,4-dimethyltetrahydrofuran-3-yl)-1H-benzo[d]imidazole-6-carboxylic acid (S)-2-(4-(6-((4-chloro-6-(1H-1,2,3-triazol-1-yl)pyridin-3-yl)methoxy)pyridin-2-yl)-2,5-difluorobenzyl)-1-(4,4-dimethyltetrahydrofuran-3-yl)-1H-benzo[d]imidazole-6-carboxylic acid was prepared in a manner similar to Procedure 22 with the following modifications: A solution of methyl (S)-2-(4-(6-((4-chloro-6-(1H-1,2,3-triazol-1-yl)pyridin-3-yl)methoxy)pyridin-2-yl)-2,5-difluorobenzyl)-1-(4,4-dimethyltetrahydrofuran-3-yl)-1H-benzo[d]imidazole-6-carboxylate (Intermediate I-113) and LiOH (2N, 0.1 mL, 0.2 mmol) in ACN (0.5 mL) and H$_2$O (0.4 mL) was heated at 100° C. for 6 min. The mixture was neutralized with acetic acid (0.01 mL, 0.2 mmol), diluted with DMSO, filtered, and purified (RP HPLC, 0-100% ACN in H2O, 0.1% TFA) to give Example 118. 1H NMR (400 MHz, DMSO-d6) δ 8.89 (d, J=1.3 Hz, 1H), 8.82 (s, 1H), 8.47 (s, 1H), 8.30 (s, 1H), 8.02 (d, J=1.3 Hz, 1H), 7.97-7.84 (m, 2H), 7.79 (dd, J=8.5, 1.5 Hz, 1H), 7.61 (d, J=8.5 Hz, 1H), 7.56 (d, J=7.2 Hz, 1H), 7.46 (dd, J=11.1, 6.4 Hz, 1H), 7.01 (d, J=8.3 Hz, 1H), 5.67 (s, 2H), 5.01 (d, J=6.7 Hz, 1H), 4.57-4.48 (m, 2H), 4.46-4.33 (m, 2H), 3.79-3.70 (m, 2H), 1.33 (s, 3H), 0.60 (s, 3H). ES/MS m/z: 672.1 (M+H)$^+$.

Example 119: (S)-2-(4-(6-((4-cyanobenzyl)oxy)pyridin-2-yl)-2,5-difluorobenzyl)-1-(4,4-dimethyltetrahydrofuran-3-yl)-benzimidazole-6-carboxylic acid (S)-2-(4-(6-((4-cyanobenzyl)oxy)pyridin-2-yl)-2,5-difluorobenzyl)-1-(4,4-dimethyltetrahydrofuran-3-yl)-benzimidazole-6-carboxylic acid was prepared in a manner similar to Procedure 22, with the following modifications: To methyl 2-[[4-[6-[(4-cyanophenyl)methoxy]-2-pyridyl]-2,5-difluoro-phenyl]methyl]-3-[(3S)-4,4-dimethyltetrahydrofuran-3-yl]benzimidazole-5-carboxylate (Intermediate I-115, 52 mg, 0.0854 mmol) dissolved in acetonitrile (0.8 mL) was added lithium hydroxide monohydrate (4.3 mg, 0.103 mmol), and water (0.4 mL). The resulting mixture was stirred for 1 h at 90° C. The mixture was diluted with EtOAc and washed with brine, dried, filtered and concentrated in vacuo. Purification by reverse-phase preparative HPLC (CH3CN/water gradient, with 0.1% TFA) yielded Example 119. 1H NMR (400 MHz, Methanol-d4) δ 8.87 (s, 1H), 8.16 (dd, J=8.6, 1.4 Hz, 1H), 7.91-7.72 (m, 5H), 7.66 (d, J=8.4 Hz, 2H), 7.58 (dd, J=7.5, 1.6 Hz, 1H), 7.37 (dd, J=11.2, 6.1 Hz, 1H), 6.97 (d, J=8.2 Hz, 1H), 5.59 (s, 2H), 5.12 (d, J=6.6 Hz, 1H), 4.76-4.60 (m, 3H), 4.52 (dd, J=11.6, 6.7 Hz, 1H), 3.99 (d, J=8.9 Hz, 1H), 3.84 (d, J=8.9 Hz, 1H), 1.40 (s, 3H), 0.75 (s, 3H). ES/MS m/z: 595.6 (M+H)$^+$.

Example 120: (S)-2-(4-(6-((4-cyano-2-fluorobenzyl)oxy)pyridin-2-yl)-2,3,6-trifluorobenzyl)-1-(4,4-dimethyltetrahydrofuran-3-yl)-benzimidazole-6-carboxylic acid (S)-2-(4-(6-((4-cyano-2-fluorobenzyl)oxy)pyridin-2-yl)-2,3,6-trifluorobenzyl)-1-(4,4-dimethyltetrahydrofuran-3-yl)-benzimidazole-6-carboxylic acid was prepared in a manner similar to Procedure 22, with the following modifications: Methyl (S)-2-(4-(6-((4-cyano-2-fluorobenzyl)oxy)pyridin-2-yl)-2,3,6-trifluorobenzyl)-1-(4,4-dimethyltetrahydrofuran-3-yl)-1H-benzo[d]imidazole-6-carboxylate (Intermediate I-117, 400 mg, 0.62 mmol) was dissolved in acetonitrile (3 mL), after which 1.0 mL of 2 N LiOH was added and the resulting mixture stirred at 80° C. for 40 min. To the mixture was added 0.5 mL acetic acid. The solvent was removed in vacuo, and the crude product dissolved in 4 mL of DMF and purified by reverse-phase preparative HPLC (eluent: water/MeCN 0.1% TFA) to yield Example 120. ES/MS m/z: 631.2 (M+H$^+$). 1H NMR (400 MHz, Methanol-d4) δ 8.85 (s, 1H), 8.11 (dd, J=8.6, 1.4 Hz, 1H), 7.89 (t, J=7.9 Hz, 1H), 7.81-7.66 (m, 3H), 7.66-7.55 (m, 3H), 7.01 (d, J=8.3 Hz, 1H), 5.65 (s, 2H), 5.17 (d, J=6.6 Hz, 1H), 4.84-4.68 (m, 2H), 4.68-4.49 (m, 2H), 4.00 (d, J=8.8 Hz, 1H), 3.87 (d, J=8.8 Hz, 1H), 1.48 (s, 3H), 0.82 (s, 3H).

Example 121: (S)-2-(4-(2-((4-chloro-2-fluorobenzyl)oxy)pyrimidin-4-yl)-2,5-difluorobenzyl)-1-(4,4-dimethyltetrahydrofuran-3-yl)-1H-benzo[d]imidazole-6-carboxylic acid (S)-2-(4-(2-((4-chloro-2-fluorobenzyl)oxy)pyrimidin-4-yl)-2,5-difluorobenzyl)-1-(4,4-dimethyltetrahydrofuran-3-yl)-1H-benzo[d]imidazole-6-carboxylic acid (Example 121) was prepared in a manner similar to Procedure 22, with the following modifications: To a mixture of methyl (S)-2-(4-(2-((4-chloro-2-fluorobenzyl)oxy)pyrimidin-4-yl)-2,5-difluorobenzyl)-1-(4,4-dimethyltetrahydrofuran-3-yl)-1H-benzo[d]imidazole-6-carboxylate (Intermediate I-118, 50.0 mg, 0.079 mmol) in acetonitrile (1.00 mL) and 0.3 mL of 2 N lithium hydroxide was added and the resulting mixture stirred at 80° C. for 35 min. To the mixture was added 0.3 mL of acetic acid. The solvent was removed in vacuo and the residue was dissolved in 1 mL of DMF and purified by reverse-phase preparative HPLC (eluent: water/MeCN 0.1% TFA) to yield Example 121. ES/MS m/z: 623.5 (M+H$^+$). 1H NMR (400 MHz, Methanol-d4) δ 8.86 (s, 1H), 8.72 (d, J=5.2 Hz, 1H), 8.14 (dd, J=8.6, 1.4 Hz, 1H), 8.06 (dd, J=10.4, 6.1 Hz, 1H), 7.75 (d, J=8.6 Hz, 1H), 7.68 (dd, J=5.2, 1.6 Hz, 1H), 7.60 (t, J=8.1 Hz, 1H), 7.46 (dd, J=11.2, 5.9 Hz, 1H), 7.32-7.22 (m, 2H), 5.61 (s, 2H), 5.12 (d, J=6.6 Hz, 1H), 4.81-4.58 (m, 3H), 4.53 (dd, J=11.5, 6.8 Hz, 1H), 3.99 (d, J=8.9 Hz, 1H), 3.84 (d, J=8.9 Hz, 1H), 1.42 (s, 3H), 0.76 (s, 3H).

Example 122: 2-(4-(6-((4-cyano-2-fluorobenzyl)oxy)pyridin-2-yl)-2,3,6-trifluorobenzyl)-1-(4,4-dimethyltetrahydrofuran-3-yl)-4-fluoro-1H-benzo[d]imidazole-6-carboxylic acid 2-(4-(6-((4-cyano-2-fluorobenzyl)oxy)pyridin-2-yl)-2,3,6-trifluorobenzyl)-1-(4,4-dimethyltetrahydrofuran-3-yl)-4-fluoro-1H-benzo[d]imidazole-6-carboxylic acid was prepared in a manner similar to Procedure 22, with the following modifications: To a mixture of methyl 2-(4-(6-((4-cyano-2-fluorobenzyl)oxy)pyridin-2-yl)-2,3,6-trifluorobenzyl)-1-(4,4-dimethyltetrahydrofuran-3-yl)-4-fluoro-1H-benzo[d]imidazole-6-carboxylate (Intermediate I-120, 167.0 mg, 0.25 mmol) in acetonitrile (3.00 mL) and 1 mL of 2 N lithium hydroxide was added and the resulting mixture stirred at 80° C. for 35 min. To the mixture was added 0.5 mL of acetic acid. Solvent was removed in vacuo and the resulting residue was dissolved in 1 mL of DMF and purified by reverse-phase preparative HPLC (eluent: water/MeCN 0.1% TFA) to yield Example 122. ES/MS m/z: 649.7 (M+H$^+$). 1H NMR (400 MHz, Methanol-d4) δ 8.57 (s, 1H), 7.86 (t, J=7.9 Hz, 1H), 7.74 (t, J=7.5 Hz, 1H), 7.69-7.50 (m, 5H), 6.98 (d, J=8.2 Hz, 1H), 5.64 (s, 2H), 5.10 (d, J=6.6 Hz, 1H), 4.75-4.61 (m, 2H), 4.55 (dd, J=11.4, 6.8 Hz, 1H), 4.45 (d, J=17.2 Hz, 1H), 3.95 (d, J=8.8 Hz, 1H), 3.84 (d, J=8.8 Hz, 1H), 1.46 (s, 3H), 0.78 (s, 3H).

Examples 123 and 124: 2-(4-(6-((4-cyano-2-fluorobenzyl)oxy)pyridin-2-yl)-2,3,6-trifluorobenzyl)-1-(4,4-dimethyltetrahydrofuran-3-yl)-4-fluoro-1H-benzo[d]imidazole-6-carboxylic acid

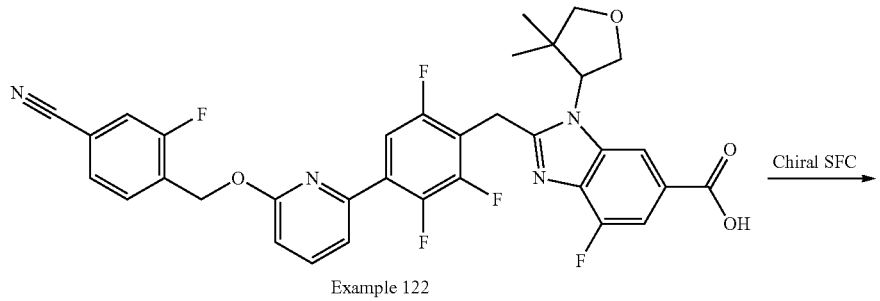

Example 122

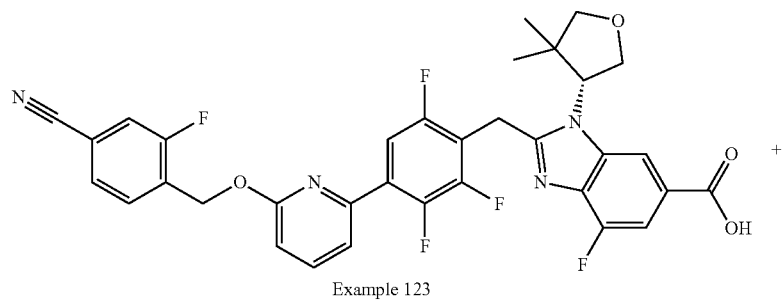

Example 123

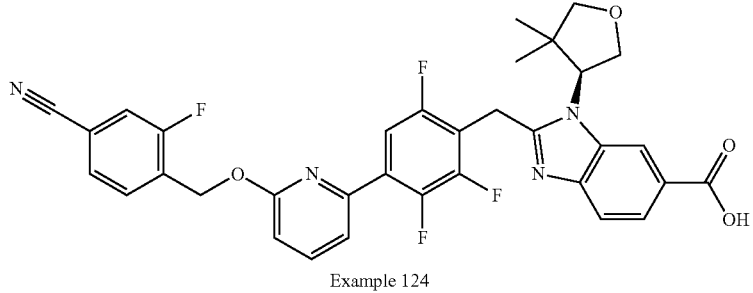

Example 124

2-(4-(6-((4-cyano-2-fluorobenzyl)oxy)pyridin-2-yl)-2,3,6-trifluorobenzyl)-1-(4,4-dimethyltetrahydrofuran-3-yl)-4-fluoro-1H-benzo[d]imidazole-6-carboxylic acid was prepared in a manner similar to Procedure 20, with the following modifications: 2-(4-(6-((4-cyano-2-fluorobenzyl)oxy)pyridin-2-yl)-2,3,6-trifluorobenzyl)-1-(4,4-dimethyltetrahydrofuran-3-yl)-4-fluoro-1H-benzo[d]imidazole-6-carboxylic acid (Example 122) as a mixture of 2 stereoisomers was separated by preparative chiral SFC (AD-H column with MeOH cosolvent) to give two distinct stereoisomers.

(R)-2-(4-(6-((4-cyano-2-fluorobenzyl)oxy)pyridin-2-yl)-2,3,6-trifluorobenzyl)-1-(4,4-dimethyltetrahydrofuran-3-yl)-4-fluoro-1H-benzo[d]imidazole-6-carboxylic acid (Example 123): Earlier eluting isomer was validated with X-ray Crystallography). ES/MS m/z: 649.6 (M+H$^+$). 1H NMR (400 MHz, Methanol-d4) δ 8.56 (s, 1H), 7.87 (t, J=7.9 Hz, 1H), 7.75 (t, J=7.5 Hz, 1H), 7.69-7.53 (m, 5H), 6.98 (d, J=8.3 Hz, 1H), 5.64 (s, 2H), 5.10 (d, J=6.6 Hz, 1H), 4.78-4.60 (m, 2H), 4.55 (dd, J=11.3, 6.8 Hz, 1H), 4.44 (d, J=17.1 Hz, 1H), 3.95 (d, J=8.8 Hz, 1H), 3.84 (d, J=8.8 Hz, 1H), 1.46 (s, 3H), 0.78 (s, 3H).

(S)-2-(4-(6-((4-cyano-2-fluorobenzyl)oxy)pyridin-2-yl)-2,3,6-trifluorobenzyl)-1-(4,4-dimethyltetrahydrofuran-3-yl)-4-fluoro-1H-benzo[d]imidazole-6-carboxylic acid (Example 124): Later eluting isomer ES/MS m/z: 649.5 (M+H$^+$). 1H NMR (400 MHz, Methanol-d4) δ 8.56 (s, 1H), 7.87 (t, J=7.9 Hz, 1H), 7.75 (t, J=7.5 Hz, 1H), 7.69-7.53 (m, 5H), 6.98 (d, J=8.3 Hz, 1H), 5.64 (s, 2H), 5.10 (d, J=6.6 Hz, 1H), 4.78-4.60 (m, 2H), 4.55 (dd, J=11.3, 6.8 Hz, 1H), 4.44 (d, J=17.1 Hz, 1H), 3.95 (d, J=8.8 Hz, 1H), 3.84 (d, J=8.8 Hz, 1H), 1.46 (s, 3H), 0.78 (s, 3H).

Example 125: 2-(4-(6-((4-cyano-2-fluorobenzyl)oxy)-5-fluoropyridin-2-yl)-2,5-difluorobenzyl)-7-fluoro-1-(2-methoxyethyl)-1H-benzo[d]imidazole-6-carboxylic acid 2-(4-(6-((4-cyano-2-fluorobenzyl)oxy)-5-fluoropyridin-2-yl)-2,5-difluorobenzyl)-7-fluoro-1-(2-methoxyethyl)-1H-benzo[d]imidazole-6-carboxylic acid was prepared in a manner similar to Procedure 1 (step 2), with the following modifications: To a solution of tert-butyl 2-(4-(6-((4-cyanobenzyl)oxy)pyridin-2-yl)-2,5-difluorobenzyl)-7-fluoro-1-(2-methoxyethyl)-1H-benzo[d]imidazole-6-carboxylate (Intermediate I-123, 37 mg, 0.0557 mmol) in dichloromethane (1 mL) was added trifluoroacetic acid (0.11 mL, 0.667 mmol). The mixture was stirred at rt for 3 hrs., then concentrated in vacuo. Purification by reverse-phase preparative HPLC (eluent: water/MeCN 0.1% TFA) gave Example 125. 1H NMR (400 MHz, Chloroform-d) δ 8.03 (dd, J=8.7, 6.6 Hz, 1H), 7.82-7.63 (m, 3H), 7.60-7.37 (m, 4H), 7.18 (dd, J=11.1, 6.0 Hz, 1H), 5.66 (s, 2H), 5.32 (s, 1H), 4.64 (d, J=6.9 Hz, 4H), 3.83 (t, J=4.8 Hz, 2H), 3.34 (s, 3H). ES/MS m/z: 609.5 (M+H$^+$).

Example 126: (S)-4-chloro-2-(4-(6-((4-chloro-2-fluorobenzyl)oxy)pyridin-2-yl)-2,5-difluorobenzyl)-1-(4,4-dimethyltetrahydrofuran-3-yl)-1H-benzo[d]imidazole-6-carboxylic acid (S)-4-chloro-2-(4-(6-((4-chloro-2-fluorobenzyl)oxy)pyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 35, starting with Intermediates I-102 and I-1037. 1H NMR (400 MHz, DMSO-d6) δ 8.47 (s, 1H), 7.95-7.83 (m, 2H), 7.81 (d, J=1.3 Hz, 1H), 7.61 (t, J=8.2 Hz, 1H), 7.54 (dd, J=7.6, 1.6 Hz, 1H), 7.47 (ddd, J=17.2, 10.7, 4.1 Hz, 2H), 7.33 (dd, J=8.2, 2.0 Hz, 1H), 6.95 (d, J=8.2 Hz, 1H), 5.51 (s, 2H), 5.03 (d, J=6.6 Hz, 1H), 4.69-4.25 (m, 4H), 3.88-3.67 (m, 2H), 1.32 (s, 3H), 0.60 (s, 3H). ES/MS m/z: 656.0 (M+H$^+$).

Example 127: (S)-4-chloro-2-(4-(6-((4-cyano-2-fluorobenzyl)oxy)-5-fluoropyridin-2-yl)-2,5-difluorobenzyl)-1-(4,4-dimethyltetrahydrofuran-3-yl)-1H-benzo[d]imidazole-6-carboxylic acid (S)-4-chloro-2-(4-(6-((4-cyano-2-fluorobenzyl)oxy)-5-fluoropyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 35, starting with Intermediates I-109 and I-1037. 1H NMR (400 MHz, DMSO-d6) δ 8.46 (s, 1H), 7.94 (dd, J=10.0, 1.4 Hz, 1H), 7.88 (dd, J=10.2, 8.2 Hz, 1H), 7.84-7.67 (m, 4H), 7.63-7.49 (m, 1H), 7.45 (dd, J=11.4, 6.2 Hz, 1H), 5.70 (s, 2H), 5.03 (d, J=6.6 Hz, 1H), 4.61-4.34 (m, 4H), 3.79-3.72 (m, 2H), 3.17 (s, 1H), 1.32 (s, 3H), 0.59 (s, 3H). ES/MS m/z: 665.0 (M+H$^+$).

Example 129: (S)-4-chloro-2-(4-(2-((4-cyano-2-fluorobenzyl)oxy)pyrimidin-4-yl)-2,5-difluorobenzyl)-1-(4,4-dimethyltetrahydrofuran-3-yl)-1H-benzo[d]imidazole-6-carboxylic acid (S)-4-chloro-2-(4-(2-((4-cyano-2-fluorobenzyl)oxy)pyrimidin-4-yl)-2,5-difluorobenzyl)-1-(4,4-dimethyltetrahydrofuran-3-yl)-1H-benzo[d]imidazole-6-carboxylic acid was prepared in a manner as described in Procedure 35, starting with Intermediates I-94 and I-1037. 1H NMR (400 MHz, DMSO-d6) δ 13.12 (s, 1H), 8.79 (d, J=5.2 Hz, 1H), 8.47 (s, 1H), 7.95 (dt, J=10.5, 3.2 Hz, 2H), 7.83-7.72 (m, 3H), 7.66 (dd, J=5.2, 1.7 Hz, 1H), 7.55 (dd, J=11.5, 5.9 Hz, 1H), 5.64 (s, 2H), 5.03 (d, J=6.6 Hz, 1H), 4.66-4.35 (m, 5H), 3.75 (q, J=8.7 Hz, 2H), 1.32 (s, 3H), 0.60 (s, 3H). ES/MS m/z: 648.0 (M+H$^+$).

Example 130: (S)-4-chloro-2-(4-(6-((4-cyano-2-fluorobenzyl)oxy)pyridin-2-yl)-2,5-difluorobenzyl)-1-(4,4-dimethyltetrahydrofuran-3-yl)-1H-benzo[d]imidazole-6-carboxylic acid S)-4-chloro-2-(4-(6-((4-cyano-2-fluorobenzyl)oxy)pyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 35, starting with Intermediates I-3 and I-1037. 1H NMR (400 MHz, DMSO-d6) δ 8.47 (s, 1H), 8.02-7.84 (m, 2H), 7.86-7.79 (m, 2H), 7.79-7.70 (m, 2H), 7.55 (dd, J=7.6, 1.6 Hz, 1H), 7.45 (dd, J=11.4, 6.1 Hz, 1H), 7.00 (d, J=8.3 Hz, 1H), 5.61 (s, 2H), 5.03 (d, J=6.6 Hz, 1H), 4.70-4.28 (m, 4H), 3.88-3.56 (m, 3H), 1.32 (s, 3H), 0.59 (s, 3H). ES/MS m/z: 647.0 (M+H$^+$).

Example 131: (S)-2-((6-((4-chloro-2-fluorobenzyl)oxy)-5,5'-difluoro-2'-oxo-[2,4'-bipyridin]-1'(2'H)-yl)methyl)-1-(4,4-dimethyltetrahydrofuran-3-yl)-4-fluoro-1H-benzo[d]imidazole-6-carboxylic acid (S)-2-((6-((4-chloro-2-fluorobenzyl)oxy)-5,5'-difluoro-2'-oxo-[2,4'-bipyridin]-1'(2'H)-yl)methyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1036 and I-1020. 1H NMR (400 MHz, DMSO-d6) δ 8.36 (s, 1H), 8.27 (d, J=7.0 Hz, 1H), 7.90 (dd, J=10.2, 8.2 Hz, 1H), 7.67-7.48 (m, 4H), 7.35 (dd, J=8.3, 2.0 Hz, 1H), 6.98 (d, J=7.6 Hz, 1H), 5.64-5.35 (m, 4H), 5.14 (d, J=6.5 Hz, 1H), 4.54 (d, J=11.3 Hz, 1H), 4.43 (dd, J=11.3, 6.7 Hz, 1H), 3.93-3.69 (m, 2H), 1.38 (s, 3H), 0.67 (s, 3H). ES/MS m/z: 657.0 (M+H$^+$).

Example 132: (S)-2-((6-((4-cyano-2-fluorobenzyl)oxy)-5,5'-difluoro-2'-oxo-[2,4'-bipyridin]-1'(2'H)-yl)methyl)-1-(4,4-dimethyltetrahydrofuran-3-yl)-4-fluoro-1H-benzo[d]imidazole-6-carboxylic acid (S)-2-((6-((4-cyano-2-fluorobenzyl)oxy)-5,5'-difluoro-2'-oxo-[2,4'-bipyridin]-1'(2'H)-yl)methyl)-1-(4,4-dimethyltetrahydrofuran-3-yl)-4-fluoro-1H-benzo[d]imidazole-6-carboxylic acid was prepared in a manner as described in Procedure 35, starting with Intermediates I-109 and I-1020. 1H NMR (400 MHz, DMSO-d6) δ 8.36 (s, 1H), 8.27 (d, J=7.0 Hz, 1H), 8.03-7.85 (m, 2H), 7.85-7.69 (m, 2H), 7.62-7.57 (m, 1H), 7.55 (d, J=11.2 Hz, 1H), 6.93 (d, J=7.6 Hz, 1H), 5.68 (s, 2H), 5.61-5.33 (m, 2H), 5.14 (d, J=6.6 Hz, 1H), 4.61-4.45 (m, 1H), 4.45-4.28 (m, 1H), 3.89-3.68 (m, 2H), 1.38 (s, 3H), 0.67 (s, 3H). ES/MS m/z: 648.0 (M+H$^+$).

Example 133: (S)-2-(2-chloro-4-(6-((4-cyanobenzyl)oxy)pyridin-2-yl)-5-methylbenzyl)-1-(4,4-dimethyltetrahydrofuran-3-yl)-4-fluoro-1H-benzo[d]imidazole-6-carboxylic acid (S)-2-(2-chloro-4-(6-((4-cyanobenzyl)oxy)pyridin-2-yl)-5-methylbenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-114 and I-1031. 1H NMR (400 MHz, DMSO-d6) δ 8.36 (s, 1H), 7.92-7.82 (m, 3H), 7.64 (d, J=8.0 Hz, 2H), 7.51 (d, J=11.2 Hz, 1H), 7.43 (s, 1H), 7.33 (s, 1H), 7.25 (d, J=7.3 Hz, 1H), 6.98 (d, J=8.3 Hz, 1H), 5.51 (s, 2H), 5.02 (d, J=6.6 Hz, 1H), 4.62-4.44 (m, 2H), 4.44-4.27 (m, 2H), 3.91-3.64 (m, 2H), 2.23 (s, 3H), 1.33 (s, 3H). ES/MS m/z: 625.3 (M+H$^+$).

Example 134: (S)-2-(2-chloro-4-(6-((4-cyanobenzyl)oxy)pyridin-2-yl)-5-methylbenzyl)-1-(4,4-dimethyltetrahydrofuran-3-yl)-1H-benzo[d]imidazole-6-carboxylic acid (S)-2-(2-chloro-4-(6-((4-cyanobenzyl)oxy)pyridin-2-yl)-5-methylbenzyl)-1-(4,4-dimethyltetrahydrofuran-3-yl)-1H-benzo[d]imidazole-6-carboxylic acid was prepared in a manner as described in Procedure 35, starting with Intermediates I-114 and I-1030. 1H NMR (400 MHz, DMSO-d6) δ 8.50 (s, 1H), 7.92-7.83 (m, 4H), 7.81 (dd, J=8.5, 1.5 Hz, 1H), 7.63 (t, J=8.2 Hz, 3H), 7.42 (s, 1H), 7.33 (s, 1H), 7.25 (d, J=7.3 Hz, 1H), 6.98 (d, J=8.2 Hz, 1H), 5.51 (s, 2H), 5.01 (d, J=6.7 Hz, 1H), 4.66-4.46 (m, 2H), 4.46-4.27 (m, 2H), 2.23 (s, 3H), 1.33 (s, 3H), 0.65 (s, 3H). ES/MS m/z: 607.5 (M+H$^+$).

Example 135: (S)-2-(2-chloro-4-(6-((4-cyanobenzyl)oxy)-5-fluoropyridin-2-yl)-5-methylbenzyl)-1-(4,4-dimethyltetrahydrofuran-3-yl)-1H-benzo[d]imidazole-6-carboxylic acid (S)-2-(2-chloro-4-(6-((4-cyanobenzyl)oxy)-5-fluoropyridin-2-yl)-5-methylbenzyl)-1-(4,4-dimethyltetrahydrofuran-3-yl)-1H-benzo[d]imidazole-6-carboxylic acid was prepared in a manner as described in Procedure 35, starting with Intermediates I-1247 and I-1030. 1H NMR (400 MHz, DMSO-d6) δ 8.49 (s, 1H), 8.01-7.83 (m, 2H), 7.83-7.73 (m, 1H), 7.66 (d, J=8.1 Hz, 2H), 7.61 (d, J=8.5 Hz, 1H), 7.43 (s, 1H), 7.34 (s, 1H), 7.29 (dd, J=8.1, 2.8 Hz, 1H), 5.59 (s, 2H), 5.00 (d, J=6.7 Hz, 1H), 4.61-4.48 (m, 2H), 4.48-4.27 (m, 2H), 3.80 (d, J=8.6 Hz, 1H), 3.73 (d, J=8.6 Hz, 1H), 2.23 (s, 2H), 1.33 (s, 3H), 0.65 (s, 3H). ES/MS m/z: 624.6 (M+H$^+$).

Example 136: (S)-2-(2-chloro-4-(6-((4-cyanobenzyl)oxy)-5-fluoropyridin-2-yl)-5-methylbenzyl)-1-(4,4-dimethyltetrahydrofuran-3-yl)-4-fluoro-1H-benzo[d]imidazole-6-carboxylic acid (S)-2-(2-chloro-4-(6-((4-cyanobenzyl)oxy)-5-fluoropyridin-2-yl)-5-methylbenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1247 and I-1031. 1H NMR (400 MHz, DMSO-d6) δ 8.36 (s, 1H), 7.95-7.78 (m, 3H), 7.66 (d, J=8.1 Hz, 2H), 7.51 (d, J=11.2 Hz, 1H), 7.43 (s, 1H), 7.34 (s, 1H), 7.29 (dd, J=8.1, 2.8 Hz, 1H), 5.59 (s, 2H), 5.02 (d, J=6.7 Hz, 1H), 4.64-4.45 (m, 2H), 4.45-4.26 (m, 2H), 3.88-3.69 (m, 2H), 2.23 (s, 3H), 1.33 (s, 4H), 0.65 (s, 3H). ES/MS m/z: 642.6 (M+H$^+$).

Example 137: (S)-2-((6-((4-chloro-2-fluorobenzyl)oxy)-5'-fluoro-2'-oxo-[2,4'-bipyridin]-1'(2'H)-yl)methyl)-1-(4,4-dimethyltetrahydrofuran-3-yl)-4-fluoro-1H-benzo[d]imidazole-6-carboxylic acid (S)-2-((6-((4-chloro-2-fluorobenzyl)oxy)-5'-fluoro-2'-oxo-[2,4'-bipyridin]-1'(2'H)-yl)methyl)-1-(4,4-dimethyltetrahydrofuran-3-yl)-4-fluoro-1H-benzo[d]imidazole-6-carboxylic acid was prepared in a manner as described in Procedure 35, starting with Intermediates I-102 and I-1020. 1H NMR (400 MHz, DMSO-d6) δ 8.36 (s, 1H), 8.26 (d, J=6.9 Hz, 1H), 7.99-7.88 (m, 1H), 7.61 (t, J=8.2 Hz, 1H), 7.57-7.51 (m, 2H), 7.49 (dd, J=10.0, 2.1 Hz, 1H), 7.33 (dd, J=8.2, 2.0 Hz, 1H), 7.05 (d, J=8.3 Hz, 1H), 7.00 (d, J=7.5 Hz, 1H), 5.64-5.40 (m, 4H), 5.14 (d, J=6.6 Hz, 1H), 4.54 (d, J=11.3 Hz, 1H), 4.43 (dd, J=11.3, 6.8 Hz, 1H), 3.79-3.67 (m, 2H), 1.38 (s, 3H), 0.67 (s, 3H). ES/MS m/z: 638.6 (M+H$^+$).

Example 138: (S)-2-(2-chloro-4-(6-((4-cyano-2-fluorobenzyl)oxy)-5-fluoropyridin-2-yl)-5-methylbenzyl)-1-(4,4-dimethyltetrahydrofuran-3-yl)-4-fluoro-1H-benzo[d]imidazole-6-carboxylic acid (S)-2-(2-chloro-4-(6-((4-cyano-2-fluorobenzyl)oxy)-5-fluoropyridin-2-yl)-5-methylbenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-109 and I-1031. 1H NMR (400 MHz, DMSO-d6) δ 8.36 (s, 1H), 7.97-7.89 (m, 1H), 7.85 (dd, J=10.5, 8.1 Hz, 1H), 7.74 (dd, J=3.6, 1.9 Hz, 2H), 7.51 (dd, J=11.3, 1.2 Hz, 1H), 7.45 (s, 1H), 7.38-7.29 (m, 2H), 5.62 (s, 2H), 5.01 (d, J=6.7 Hz, 1H), 4.63-4.45 (m, 2H), 4.45-4.34 (m, 2H), 3.79 (d, J=8.7 Hz, 1H), 3.72 (d, J=8.6 Hz, 1H), 2.27 (s, 3H), 1.33 (s, 3H), 0.65 (s, 3H). ES/MS m/z: 660.6 (M+H$^+$).

Example 139: (S)-2-(2-chloro-4-(6-((4-cyano-2-fluorobenzyl)oxy)pyridin-2-yl)-5-methylbenzyl)-1-(4,4-dimethyltetrahydrofuran-3-yl)-4-fluoro-1H-benzo[d]imidazole-6-carboxylic acid (S)-2-(2-chloro-4-(6-((4-cyano-2-fluorobenzyl)oxy)pyridin-2-yl)-5-methylbenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-3 and I-1031. 1H NMR (400 MHz, DMSO-d6) δ 8.36 (s, 1H), 7.96-7.82 (m, 2H), 7.72 (d, J=5.8 Hz, 2H), 7.53-7.48 (m, 1H), 7.44 (s, 1H), 7.34 (s, 1H), 7.28 (d, J=7.3 Hz, 1H), 6.97 (d, J=8.3 Hz, 1H), 5.53 (s, 2H), 5.01 (d, J=6.7 Hz, 1H), 4.62-4.48 (m, 2H), 4.44-4.33 (m, 2H), 3.79 (d, J=8.7 Hz, 1H), 3.72 (d, J=8.7 Hz, 1H), 2.27 (s, 3H), 1.32 (s, 3H), 0.65 (s, 3H). ES/MS m/z: 642.6 (M+H$^+$).

Example 140: (S)-2-(2-chloro-4-(6-((4-cyano-2-fluorobenzyl)oxy)-5-fluoropyridin-2-yl)-5-methylbenzyl)-1-(4,4-dimethyltetrahydrofuran-3-yl)-1H-benzo[d]imidazole-6-carboxylic acid (S)-2-(2-chloro-4-(6-((4-cyano-2-fluorobenzyl)oxy)-5-fluoropyridin-2-yl)-5-methylbenzyl)-1-(4,4-dimethyltetrahydrofuran-3-yl)-1H-benzo[d]imidazole-6-carboxylic acid was prepared in a manner as described in Procedure 35, starting with Intermediates I-109 and I-1030. 1H NMR (400 MHz, DMSO-d6) δ 8.50 (s, 1H), 7.96-7.90 (m, 1H), 7.90-7.79 (m, 2H), 7.74 (d, J=5.6 Hz, 2H), 7.63 (d, J=8.5 Hz, 1H), 7.45 (s, 1H), 7.35 (s, 1H), 7.31 (dd, J=8.1, 2.8 Hz, 1H), 5.61 (s, 2H), 5.01 (d, J=6.7 Hz, 1H), 4.64-4.46 (m, 2H), 4.46-4.26 (m, 2H), 3.74 (m, 2H), 2.26 (s, 3H), 1.33 (s, 3H), 0.65 (s, 3H). ES/MS m/z: 642.6 (M+H$^+$).

Example 141: (S)-2-(2-chloro-4-(6-((4-cyano-2-fluorobenzyl)oxy)pyridin-2-yl)-5-methylbenzyl)-1-(4,4-dimethyltetrahydrofuran-3-yl)-1H-benzo[d]imidazole-6-carboxylic acid (S)-2-(2-chloro-4-(6-((4-cyano-2-fluorobenzyl)oxy)pyridin-2-yl)-5-methylbenzyl)-1-(4,4-dimethyltetrahydrofuran-3-yl)-1H-benzo[d]imidazole-6-carboxylic acid was prepared in a manner as described in Procedure 35, starting with Intermediates I-3 and I-1030. 1H NMR (400 MHz, DMSO-d6) δ 8.50 (s, 1H), 7.96-7.85 (m, 2H), 7.81 (d, J=8.6 Hz, 1H), 7.78-7.66 (m, 2H), 7.63 (d, J=8.5 Hz, 1H), 7.44 (s, 1H), 7.35 (s, 1H), 7.27 (d, J=7.3 Hz, 1H), 6.98 (d, J=8.3 Hz, 1H), 5.53 (s, 2H), 5.01 (d, J=6.7 Hz, 1H), 4.63-4.47 (m, 2H), 4.47-4.31 (m, 2H), 3.74 (m, 2H), 2.26 (s, 3H), 1.32 (s, 3H), 0.65 (s, 3H). ES/MS m/z: 624.6 (M+H$^+$).

Example 142: (S)-2-(2-chloro-4-(6-((4-cyano-2-fluorobenzyl)oxy)-5-fluoropyridin-2-yl)-5-methylbenzyl)-4-fluoro-1-(oxetan-2-ylmethyl)-1H-benzo[d]imidazole-6-carboxylic acid (S)-2-(2-chloro-4-(6-((4-cyano-2-fluorobenzyl)oxy)-5-fluoropyridin-2-yl)-5-methylbenzyl)-4-fluoro-1-(oxetan-2-ylmethyl)-1H-benzo[d]imidazole-6-carboxylic acid was prepared in a manner as described in Procedure 35 starting with Intermediates I-109 and I-1026. 1H NMR (400 MHz, Methanol-d4) δ 8.17 (d, J=1.2 Hz, 1H), 7.73 (t, J=7.6 Hz, 1H), 7.68-7.54 (m, 4H), 7.43 (s, 1H), 7.16 (q, J=3.8, 3.3 Hz, 2H), 5.63 (s, 2H), 5.22-5.02 (m, 1H), 4.75-4.59 (m, 3H), 4.59-4.38 (m, 3H), 2.77 (q, J=8.5, 7.4 Hz, 1H), 2.49 (t, J=9.8 Hz, 1H), 2.25 (s, 3H). ES/MS m/z: 633.0 (M+H$^+$).

Example 143: (S)-2-(2-chloro-4-(6-((4-cyano-2-fluorobenzyl)oxy)pyridin-2-yl)-5-methylbenzyl)-4-fluoro-1-(oxetan-2-ylmethyl)-1H-benzo[d]imidazole-6-carboxylic acid (S)-2-(2-chloro-4-(6-((4-cyano-2-fluorobenzyl)oxy)pyridin-2-yl)-5-methylbenzyl)-4-fluoro-1-(oxetan-2-ylmethyl)-1H-benzo[d]imidazole-6-carboxylic acid was prepared in a manner as described in Procedure 35 starting with Intermediates I-3 and I-1026. 1H NMR (400 MHz, Methanol-d4) δ 8.16 (d, J=1.3 Hz, 1H), 7.81 (dd, J=8.3, 7.3 Hz, 1H), 7.72-7.60 (m, 2H), 7.60-7.49 (m, 2H), 7.41 (s, 1H), 7.19-7.10 (m, 2H), 6.91 (d, J=8.3 Hz, 1H), 5.54 (s, 2H), 5.12 (dd, J=7.4, 2.4 Hz, 1H), 4.76-4.59 (m, 3H), 4.59-4.35 (m, 3H), 2.77 (dtd, J=11.4, 8.2, 6.1 Hz, 1H), 2.48 (ddt, J=11.5, 9.1, 7.2 Hz, 1H), 2.24 (s, 3H). ES/MS m/z: 615.0 (M+H$^+$).

Example 144: (S)-2-(2-chloro-4-(6-((4-cyano-2-fluorobenzyl)oxy)-5-fluoropyridin-2-yl)-5-methylbenzyl)-1-(oxetan-2-ylmethyl)-1H-benzo[d]imidazole-6-carboxylic acid (S)-2-(2-chloro-4-(6-((4-cyano-2-fluorobenzyl)oxy)-5-fluoropyridin-2-yl)-5-methylbenzyl)-1-(oxetan-2-ylmethyl)-1H-benzo[d]imidazole-6-carboxylic acid was prepared in a manner as described in Procedure 35 starting with Intermediate I-1024 and I 8. 1H NMR (400 MHz, Methanol-d4) δ 8.31 (d, J=1.4 Hz, 1H), 7.98 (dd, J=8.5, 1.5 Hz, 1H), 7.72 (t, J=7.6 Hz, 1H), 7.68-7.64 (m, 1H), 7.64-7.55 (m, 3H), 7.42 (s, 1H), 7.19 (s, 1H), 7.15 (dd, J=8.1, 2.8 Hz, 1H), 5.63 (s, 2H), 5.17 (qd, J=7.1, 2.6 Hz, 1H), 4.76-4.39 (m, 6H), 2.95-2.66 (m, 1H), 2.50 (ddt, J=11.5, 9.1, 7.2 Hz, 1H), 2.25 (s, 3H). ES/MS m/z: 615.0 (M+H$^+$).

Example 145: (S)-2-((6-((4-cyano-2-fluorobenzyl)oxy)-5'-fluoro-2'-oxo-[2,4'-bipyridin]-1'(2'H)-yl)methyl)-1-(4,4-dimethyltetrahydrofuran-3-yl)-4-fluoro-1H-benzo[d]imidazole-6-carboxylic acid (S)-2-((6-((4-cyano-2-fluorobenzyl)oxy)-5'-fluoro-2'-oxo-[2,4'-bipyridin]-1'(2'H)-yl)methyl)-1-(4,4-dimethyltetrahydrofuran-3-yl)-4-fluoro-1H-benzo[d]imidazole-6-carboxylic acid was prepared in a manner as described in Procedure 35, starting with Intermediates I-3 and I-1020. 1H NMR (400 MHz, DMSO-d6) δ 13.14 (s, 1H), 8.36 (s, 1H), 8.26 (d, J=6.9 Hz, 1H), 7.92 (t, J=9.0 Hz, 2H), 7.80-7.67 (m, 2H), 7.62-7.48 (m, 2H), 7.10 (d, J=8.3 Hz, 1H), 6.95 (d, J=7.4 Hz, 1H), 5.69-5.30 (m, 4H), 5.14 (d, J=6.7 Hz, 1H), 4.54 (d, J=11.2 Hz, 1H), 4.43 (dd, J=11.3, 6.7 Hz, 1H), 3.92-3.61 (m, 2H), 1.38 (s, 3H), 0.67 (s, 3H). ES/MS m/z: 630.2 (M+H$^+$).

Example 146: (S)-2-(4-(6-((4-cyano-2-fluorobenzyl)oxy)pyridin-2-yl)-2-fluoro-3-methylbenzyl)-1-(oxetan-2-ylmethyl)-1H-benzo[d]imidazole-6-carboxylic acid (S)-2-(4-(6-((4-cyano-2-fluorobenzyl)oxy)pyridin-2-yl)-2-fluoro-3-methylbenzyl)-1-(oxetan-2-ylmethyl)-1H-benzo[d]imidazole-6-carboxylic acid was prepared in a manner as described in Procedure 35, starting with Intermediate I-1012 and I-8. 1H NMR (400 MHz, Methanol-d4) δ 8.31 (d, J=1.4 Hz, 1H), 7.98 (dd, J=8.5, 1.5 Hz, 1H), 7.81 (dd, J=8.3, 7.3 Hz, 1H), 7.73-7.63 (m, 2H), 7.63-7.51 (m, 2H), 7.21-7.09 (m, 3H), 6.91 (d, J=8.2 Hz, 1H), 5.56 (s, 2H), 5.15 (d, J=7.1, 2.5 Hz, 1H), 4.70 (dd, J=15.7, 7.0 Hz, 1H), 4.66-4.39 (m, 6H), 2.77 (dtd, J=11.4, 8.2, 6.1 Hz, 1H), 2.56-2.38 (m, 1H), 2.22 (d, J=2.6 Hz, 3H). ES/MS m/z: 581.2 (M+H$^+$).

Example 147: (S)-2-(4-(6-((6-(acetamidomethyl)-4-fluoropyridin-3-yl)methoxy)pyridin-2-yl)-2,5-difluorobenzyl)-1-(oxetan-2-ylmethyl)-1H-benzo[d]imidazole-6-carboxylic acid (S)-2-(4-(6-((6-(acetamidomethyl)-4-fluoropyridin-3-yl)methoxy)pyridin-2-yl)-2,5-difluorobenzyl)-1-(oxetan-2-ylmethyl)-1H-benzo[d]imidazole-6-carboxylic acid was prepared in a manner as described in Procedure 35, starting with Intermediate I-1009 and I-8. 1H NMR (400 MHz, Methanol-d4) δ 8.67 (d, J=9.6 Hz, 1H), 8.56 (s, OH), 8.32 (d, J=1.4 Hz, 1H), 7.99 (dd, J=8.5, 1.5 Hz, 1H), 7.88 (dd, J=10.7, 6.3 Hz, 1H), 7.79 (t, J=7.9 Hz, 1H), 7.68 (d, J=8.5 Hz, 1H), 7.54 (dd, J=7.6, 1.6 Hz, 1H), 7.20 (dd, J=11.2, 6.0 Hz, 2H), 6.87 (d, J=8.1 Hz, 1H), 5.61 (s, 2H), 5.21 (tt, J=7.3, 3.6 Hz, 1H), 4.80-4.35 (m, 9H), 2.89-2.65 (m, 1H), 2.61-2.35 (m, 1H), 2.04 (s, 3H). ES/MS m/z: 632.2 (M+H$^+$).

Example 148: (S)-2-(2,5-difluoro-4-(5-fluoro-4-((2-fluoro-4-(trifluoromethyl)benzyl)oxy)pyrimidin-2-yl)benzyl)-4-fluoro-1-(oxetan-2-ylmethyl)-1H-benzo[d]imidazole-6-carboxylic acid (S)-2-(2,5-difluoro-4-(5-fluoro-4-((2-fluoro-4-(trifluoromethyl)benzyl)oxy)pyrimidin-2-yl)benzyl)-4-fluoro-1-(oxetan-2-ylmethyl)-1H-benzo[d]imidazole-6-carboxylic acid was prepared in a manner as described in Procedure 35, starting with Intermediate I-1313 and I-14. 1H NMR (400 MHz, DMSO-d6) δ 8.84 (d, J=2.8 Hz, 1H), 8.14 (s, 1H), 7.86 (dd, J=9.6, 6.3 Hz, 2H), 7.81-7.73 (m, 1H), 7.72-7.63 (m, 1H), 7.50 (dd, J=11.4, 1.2 Hz, 1H), 7.42 (dd, J=11.1, 6.0 Hz, 1H), 5.77 (s, 2H), 5.18-4.94 (m, 1H), 4.78 (dd, J=15.5, 7.1 Hz, 1H), 4.69-4.40 (m, 4H), 4.35 (dt, J=8.9, 5.9 Hz, 1H), 2.70 (ddd, J=16.1, 6.3, 2.8 Hz, 1H), 2.43-2.26 (m, 1H). ES/MS m/z: 665.0 (M+H$^+$).

Example 149: (S)-2-(2,5-difluoro-4-(4-((2-fluoro-4-(trifluoromethyl)benzyl)oxy)pyrimidin-2-yl)benzyl)-4-fluoro-1-(oxetan-2-ylmethyl)-1H-benzo[d]imidazole-6-carboxylic acid (S)-2-(2,5-difluoro-4-(4-((2-fluoro-4-(trifluoromethyl)benzyl)oxy)pyrimidin-2-yl)benzyl)-4-fluoro-1-(oxetan-2-ylmethyl)-1H-benzo[d]imidazole-6-carboxylic acid was prepared in a manner as described in Procedure 35, starting with Intermediate I-1002 and I-14. 1H NMR (400 MHz, DMSO-d6) δ 8.73 (d, J=5.8 Hz, 1H), 8.12 (s, 1H), 7.88 (dd, J=10.2, 6.2 Hz, 1H), 7.83 (t, J=7.6 Hz, 1H), 7.77 (dd, J=9.9, 1.6 Hz, 1H), 7.65 (d, J=8.0 Hz, 1H), 7.50 (dd, J=11.5, 1.2 Hz, 1H), 7.41 (dd, J=11.1, 6.0 Hz, 1H), 7.07 (d, J=5.8 Hz, 1H), 5.68 (s, 2H), 5.07 (qd, J=6.9, 2.8 Hz, 1H), 4.78 (dd, J=15.6, 7.1 Hz, 1H), 4.70-4.42 (m, 4H), 4.35 (dt, J=9.1, 6.0 Hz, 1H), 2.86-2.64 (m, 1H), 2.44-2.25 (m, 1H). ES/MS m/z: 647.0 (M+H$^+$).

Example 150: 1-(((1R,3R,5R)-2-acetyl-2-azabicyclo[3.1.0]hexan-3-yl)methyl)-2-(4-(6-((4-cyano-2-fluorobenzyl)oxy)pyridin-2-yl)-2,5-difluorobenzyl)-1H-benzo[d]imidazole-6-carboxylic acid 1-(((1R,3R,5R)-2-acetyl-2-azabicyclo[3.1.0]hexan-3-yl)methyl)-2-(4-(6-((4-cyano-2-fluorobenzyl)oxy)pyridin-2-yl)-2,5-difluorobenzyl)-1H-benzo[d]imidazole-6-carboxylic acid was prepared in a manner as described in Procedure 4, starting with Intermediates I-1001 and I-7. 1H NMR (400 MHz, DMSO-d6) δ 8.37 (s, 1H), 7.98-7.85 (m, 2H), 7.83 (dd, J=8.4, 1.5 Hz, 1H), 7.75 (q, J=5.4 Hz, 3H), 7.62 (d, J=8.4 Hz, 1H), 7.53 (dd, J=7.5, 1.7 Hz, 1H), 7.46 (dd, J=11.5, 6.0 Hz, 1H), 7.00 (d, J=8.2 Hz, 1H), 5.60 (s, 2H), 4.69 (s, 1H), 4.62-4.44 (m, 4H), 4.31 (dd, J=14.4, 8.5 Hz, 1H), 2.26 (d, J=14.1 Hz, 1H), 2.11 (s, 2H), 1.80 (dd, J=15.7, 13.0 Hz, 1H), 1.65 (d, J=7.0 Hz, 1H), 0.96-0.80 (m, 2H). ES/MS m/z: 652.2 (M+H$^+$).

Example 151: (S)-2-(4-(6-((4-cyanobenzyl)oxy)-3,5-difluoropyridin-2-yl)-2,6-difluorobenzyl)-1-(4,4-dimethyltetrahydrofuran-3-yl)-1H-benzo[d]imidazole-6-carboxylic acid (S)-2-(4-(6-((4-cyanobenzyl)oxy)-3,5-difluoropyridin-2-yl)-2,6-difluorobenzyl)-1-(4,4-dimethyltetrahydrofuran-3-yl)-1H-benzo[d]imidazole-6-carboxylic acid was prepared in a manner as described in Procedure 35, starting with Intermediates I-1052 and I-1233. 1H NMR (400 MHz, DMSO-d6) δ 8.46 (s, 1H), 8.20 (t, J=9.9 Hz, 1H), 7.89 (d, J=8.2 Hz, 2H), 7.78-7.73 (m, 1H), 7.71 (d, J=8.1 Hz, 2H), 7.61 (d, J=8.4 Hz, 2H), 7.56 (d, J=8.5 Hz, 1H), 5.67 (s, 2H), 5.08 (d, J=6.6 Hz, 1H), 4.57 (d, J=17.7 Hz, 2H), 4.46 (dd, J=11.1, 6.6 Hz, 1H), 4.29 (d, J=16.8 Hz, 1H), 3.80-3.71 (m, 2H), 1.37 (s, 3H), 0.64 (s, 3H). ES/MS m/z: 631.2 (M+H$^+$).

Example 152: (S)-2-(4-(6-((4-cyanobenzyl)oxy)-3,5-difluoropyridin-2-yl)-2-fluorobenzyl)-1-(4,4-dimethyltetrahydrofuran-3-yl)-1H-benzo[d]imidazole-6-carboxylic acid (S)-2-(4-(6-((4-cyanobenzyl)oxy)-3,5-difluoropyridin-2-yl)-2-fluorobenzyl)-1-(4,4-dimethyltetrahydrofuran-3-yl)-1H-benzo[d]imidazole-6-carboxylic acid was prepared in a manner as described in Procedure 35, starting with Intermediates I-1052 and I-1229. 1H NMR (400 MHz, DMSO-d6) δ 8.49 (s, 1H), 8.15 (t, J=9.9 Hz, 1H), 7.88 (d, J=8.1 Hz, 2H), 7.81 (dd, J=8.5, 1.4 Hz, 1H), 7.75-7.65 (m, 4H), 7.62 (d, J=8.5 Hz, 1H), 7.53 (t, J=8.0 Hz, 1H), 5.65 (s, 2H), 5.00 (d, J=6.6 Hz, 1H), 4.57-4.48 (m, 2H), 4.48-4.36 (m, 2H), 3.78 (d, J=8.6 Hz, 1H), 3.72 (d, J=8.6 Hz, 1H), 1.30 (s, 3H), 0.58 (s, 3H). ES/MS m/z: 613.3 (M+H$^+$).

Example 153: (S)-2-(4-(6-((4-chloro-6-(1H-1,2,3-triazol-1-yl)pyridin-3-yl)methoxy)-5-fluoropyridin-2-yl)-2,5-difluorobenzyl)-1-(4,4-dimethyltetrahydrofuran-3-yl)-4-fluoro-1H-benzo[d]imidazole-6-carboxylic acid (S)-2-(4-(6-((4-chloro-6-(1H-1,2,3-triazol-1-yl)pyridin-3-yl)methoxy)-5-fluoropyridin-2-yl)-2,5-difluorobenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1050 and I-108. 1H NMR (400 MHz, DMSO-d6) δ 8.90 (d, J=1.3 Hz, 1H), 8.84 (s, 1H), 8.35 (s, 1H), 8.32 (s, 1H), 8.03 (d, J=1.3 Hz, 1H), 7.88 (ddd, J=11.3, 7.4, 4.3 Hz, 2H), 7.64-7.55 (m, 1H), 7.55-7.44 (m, 2H), 5.76 (s, 2H), 5.03 (d, J=6.5 Hz, 1H), 4.59-4.47 (m, 2H), 4.47-4.35 (m, 2H), 3.74 (q, J=8.7 Hz, 2H), 1.33 (s, 3H), 0.60 (s, 3H). ES/MS m/z: 708.0 (M+H$^+$).

Example 154: (S)-2-(4-(6-((4-chloro-6-(1H-1,2,3-triazol-1-yl)pyridin-3-yl)methoxy)-5-fluoropyridin-2-yl)-2-fluorobenzyl)-1-(4,4-dimethyltetrahydrofuran-3-yl)-4-fluoro-1H-benzo[d]imidazole-6-carboxylic acid (S)-2-(4-(6-((4-chloro-6-(1H-1,2,3-triazol-1-yl)pyridin-3-yl)methoxy)-5-fluoropyridin-2-yl)-2-fluorobenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1050 and I-1230. 1H NMR (400 MHz, DMSO-d6) δ 8.89 (d, J=1.3 Hz, 1H), 8.86 (s, 1H), 8.34 (s, 1H), 8.32 (s, 1H), 8.02 (d, J=1.3 Hz, 1H), 7.99-7.91 (m, 2H), 7.85 (dd, J=10.2, 8.2 Hz, 1H), 7.73 (dd, J=8.3, 2.8 Hz, 1H), 7.50 (dd, J=9.7, 6.9 Hz, 2H), 5.78 (s, 2H), 5.00 (d, J=6.7 Hz, 1H), 4.50 (dd, J=14.1, 8.4 Hz, 2H), 4.46-4.34 (m, 2H), 3.79-3.66 (m, 2H), 1.29 (s, 3H), 0.57 (s, 3H). ES/MS m/z: 690.0 (M+H$^+$).

Example 155: 2-(4-(6-((4-chloro-6-(1H-1,2,3-triazol-1-yl)pyridin-3-yl)methoxy)-5-fluoropyridin-2-yl)-2-fluorobenzyl)-1-(2-methoxyethyl)-1H-benzo[d]imidazole-6-carboxylic acid 2-(4-(6-((4-chloro-6-(1H-1,2,3-triazol-1-yl)pyridin-3-yl)methoxy)-5-fluoropyridin-2-yl)-2-fluorobenzyl)-1-(2-methoxyethyl)-1H-benzo[d]imidazole-6-carboxylic acid was prepared in a manner as described in Procedure 35, starting with Intermediates I-1050 and I-10. 1H NMR (400 MHz, DMSO-d6) δ 8.90 (d, J=1.3 Hz, 1H), 8.86 (s, 1H), 8.32 (s, 1H), 8.23 (s, 1H), 8.02 (d, J=1.3 Hz, 1H), 7.97-7.88 (m, 2H), 7.88-7.79 (m, 2H), 7.72 (dd, J=8.2, 2.7 Hz, 1H), 7.60 (d, J=8.4 Hz, 1H), 7.45 (t, J=8.0 Hz, 1H), 5.77 (s, 2H), 4.59 (s, 2H), 4.47 (s, 2H), 3.66 (t, J=5.0 Hz, 2H), 3.20 (s, 3H). ES/MS m/z: 632.2 (M+H$^+$).

Example 156: (S)-2-(2-chloro-4-(6-((4-chloro-6-(1H-1,2,3-triazol-1-yl)pyridin-3-yl)methoxy)pyridin-2-yl)-5-methylbenzyl)-1-(4,4-dimethyltetrahydrofuran-3-yl)-1H-benzo[d]imidazole-6-carboxylic acid (S)-2-(2-chloro-4-(6-((4-chloro-6-(1H-1,2,3-triazol-1-yl)pyridin-3-yl)methoxy)pyridin-2-yl)-5-methylbenzyl)-1-(4,4-dimethyltetrahydrofuran-3-yl)-1H-benzo[d]imidazole-6-carboxylic acid was prepared in a manner as described in Procedure 35, starting with Intermediates I-1049 and I-1030. 1H NMR (400 MHz, DMSO-d6) δ 8.89 (d, J=1.3 Hz, 1H), 8.76 (s, 1H), 8.49 (s, 1H), 8.29 (s, 1H), 8.03 (d, J=1.2 Hz, 1H), 7.89 (t, J=7.8 Hz, 1H), 7.80 (dd, J=8.5, 1.5 Hz, 1H), 7.62 (d, J=8.5 Hz, 1H), 7.52 (s, 1H), 7.36 (s, 1H), 7.29 (d, J=7.3 Hz, 1H), 6.98 (d, J=8.3 Hz, 1H), 5.58 (s, 2H), 5.00 (d, J=6.8 Hz, 1H), 4.61-4.48 (m, 2H), 4.46-4.33 (m, 2H), 3.84-3.69 (m, 2H), 2.33 (s, 3H), 1.32 (s, 3H), 0.64 (s, 3H). ES/MS m/z: 684.2 (M+H$^+$).

Example 157: (S)-2-(4-(6-((4-chloro-6-(1H-1,2,3-triazol-1-yl)pyridin-3-yl)methoxy)pyridin-2-yl)-2,3,6-trifluorobenzyl)-1-(4,4-dimethyltetrahydrofuran-3-yl)-1H-benzo[d]imidazole-6-carboxylic acid (S)-2-(4-(6-((4-chloro-6-(1H-1,2,3-triazol-1-yl)pyridin-3-yl)methoxy)pyridin-2-yl)-2,3,6-trifluorobenzyl)-1-(4,4-dimethyltetrahydrofuran-3-yl)-1H-benzo[d]imidazole-6-carboxylic acid was prepared in a manner as described in Procedure 35, starting with Intermediates I-1049 and I-1231. 1H NMR (400 MHz, DMSO-d6) δ 8.90 (s, 1H), 8.83 (s, 1H), 8.47 (s, 1H), 8.31 (s, 1H), 8.03 (d, J=1.3 Hz, 1H), 7.96 (t, J=7.9 Hz, 1H), 7.77 (d, J=8.2 Hz, 2H), 7.60 (dd, J=10.7, 7.7 Hz, 2H), 7.06 (d, J=8.3 Hz, 1H), 5.68 (s, 2H), 5.08 (d, J=6.5 Hz, 1H), 4.68-4.53 (m, 2H), 4.46 (dd, J=11.3, 6.9 Hz, 1H), 4.35 (d, J=17.2 Hz, 2H), 3.76 (d, J=2.8 Hz, 2H), 1.38 (s, 3H), 0.65 (s, 3H). ES/MS m/z: 690.1 (M+H$^+$).

Example 158: (S)-2-(4-(6-((4-chloro-6-(1H-1,2,3-triazol-1-yl)pyridin-3-yl)methoxy)pyridin-2-yl)-2-fluorobenzyl)-1-(4,4-dimethyltetrahydrofuran-3-yl)-1H-benzo[d]imidazole-6-carboxylic acid (S)-2-(4-(6-((4-chloro-6-(1H-1,2,3-triazol-1-yl)pyridin-3-yl)methoxy)pyridin-2-yl)-2-fluorobenzyl)-1-(4,4-dimethyltetrahydrofuran-3-yl)-1H-benzo[d]imidazole-6-carboxylic acid was prepared in a manner as described in Procedure 35, starting with Intermediates I-1049 and I-1229. 1H NMR (400 MHz, DMSO-d6) δ 8.89 (d, J=1.3 Hz, 1H), 8.83 (s, 1H), 8.47 (s, 1H), 8.30 (s, 1H), 8.02 (d, J=1.3 Hz, 1H), 8.00-7.93 (m, 2H), 7.88 (t, J=7.9 Hz, 1H), 7.80 (dd, J=8.4, 1.5 Hz, 1H), 7.70 (d, J=7.5 Hz, 1H), 7.61 (d, J=8.5 Hz, 1H), 7.50 (t, J=8.1 Hz, 1H), 6.95 (d, J=8.2 Hz, 1H), 5.69 (s, 2H), 4.98 (d, J=6.8 Hz, 1H), 4.54-4.47 (m, 2H), 4.47-4.35 (m, 2H), 3.81-3.68 (m, 2H), 1.29 (s, 3H), 0.57 (s, 3H). ES/MS m/z: 654.2 (M+H$^+$).

Example 159: (S)-2-(4-(6-((4-chloro-6-(1H-1,2,3-triazol-1-yl)pyridin-3-yl)methoxy)-5-fluoropyridin-2-yl)-2,3,6-trifluorobenzyl)-1-(4,4-dimethyltetrahydrofuran-3-yl)-1H-benzo[d]imidazole-6-carboxylic acid (S)-2-(4-(6-((4-chloro-6-(1H-1,2,3-triazol-1-yl)pyridin-3-yl)methoxy)-5-fluoropyridin-2-yl)-2,3,6-trifluorobenzyl)-1-(4,4-dimethyltetrahydrofuran-3-yl)-1H-benzo[d]imidazole-6-carboxylic acid was prepared in a manner as described in Procedure 35, starting with Intermediates I-1050 and I-1231. 1H NMR (400 MHz, DMSO-d6) δ 8.91 (d, J=1.3 Hz, 1H), 8.85 (s, 1H), 8.47 (s, 1H), 8.33 (s, 1H), 8.03 (d, J=1.2 Hz, 1H), 7.99-7.87 (m, 1H), 7.77 (d, J=8.6 Hz, 2H), 7.64 (d, J=8.4 Hz, 1H), 7.58 (d, J=8.4 Hz, 1H), 5.77 (s, 2H), 5.08 (d, J=6.7 Hz, 1H), 4.64 (d, J=17.5 Hz, 1H), 4.57 (d, J=11.3 Hz, 1H), 4.51-4.42 (m, 1H), 4.35 (d, J=17.6 Hz, 1H), 3.76 (d, J=2.5 Hz, 2H), 1.38 (s, 3H), 0.65 (s, 3H). ES/MS m/z: 708.1 (M+H$^+$).

Example 160: (S)-2-(4-(6-((4-chloro-6-(1H-1,2,3-triazol-1-yl)pyridin-3-yl)methoxy)-5-fluoropyridin-2-yl)-2,5-difluorobenzyl)-1-(4,4-dimethyltetrahydrofuran-3-yl)-1H-benzo[d]imidazole-6-carboxylic acid (S)-2-(4-(6-((4-chloro-6-(1H-1,2,3-triazol-1-yl)pyridin-3-yl)methoxy)-5-fluoropyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 35, starting with Intermediates I-1050 and I-82. 1H NMR (400 MHz, DMSO-d6) δ 8.90 (d, J=1.3 Hz, 1H), 8.84 (s, 1H), 8.47 (s, 1H), 8.32 (s, 1H), 8.03 (d, J=1.2 Hz, 1H), 7.87 (td, J=9.7, 9.1, 7.4 Hz, 2H), 7.82-7.75 (m, 1H), 7.60 (t, J=9.5 Hz, 2H), 7.47 (dd, J=11.6, 6.1 Hz, 1H), 5.76 (s, 2H), 5.01 (d, J=6.8 Hz, 1H), 4.58-4.47 (m, 2H), 4.48-4.32 (m, 2H), 3.80-3.68 (m, 2H), 1.33 (s, 3H), 0.60 (s, 3H). ES/MS m/z: 690.1 (M+H⁺).

Example 161: (S)-2-(4-(6-((4-chloro-6-(1H-1,2,3-triazol-1-yl)pyridin-3-yl)methoxy)-5-fluoropyridin-2-yl)-2-fluorobenzyl)-1-(4,4-dimethyltetrahydrofuran-3-yl)-1H-benzo[d]imidazole-6-carboxylic acid (S)-2-(4-(6-((4-chloro-6-(1H-1,2,3-triazol-1-yl)pyridin-3-yl)methoxy)-5-fluoropyridin-2-yl)-2-fluorobenzyl)-1-(4,4-dimethyltetrahydrofuran-3-yl)-1H-benzo[d]imidazole-6-carboxylic acid was prepared in a manner as described in Procedure 35, starting with Intermediates I-1050 and I-1229. 1H NMR (400 MHz, DMSO-d6) δ 8.90 (d, J=1.3 Hz, 1H), 8.86 (s, 1H), 8.48 (s, 1H), 8.32 (s, 1H), 8.02 (d, J=1.3 Hz, 1H), 7.94 (t, J=8.5 Hz, 2H), 7.85 (dd, J=10.2, 8.3 Hz, 1H), 7.82-7.77 (m, 1H), 7.73 (dd, J=8.3, 2.7 Hz, 1H), 7.61 (d, J=8.4 Hz, 1H), 7.50 (t, J=8.1 Hz, 1H), 5.78 (s, 2H), 4.99 (d, J=6.6 Hz, 1H), 4.54-4.47 (m, 2H), 4.46-4.35 (m, 2H), 3.81-3.69 (m, 2H), 1.29 (s, 3H), 0.57 (s, 3H). ES/MS m/z: 672.2 (M+H⁺).

Example 162: (S)-2-(4-(6-((3-chloro-5-(1H-1,2,3-triazol-1-yl)pyridin-2-yl)methoxy)pyridin-2-yl)-2,5-difluorobenzyl)-1-(4,4-dimethyltetrahydrofuran-3-yl)-1H-benzo[d]imidazole-6-carboxylic acid (S)-2-(4-(6-((3-chloro-5-(1H-1,2,3-triazol-1-yl)pyridin-2-yl)methoxy)pyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 35, starting with Intermediates I-1053 and I-82. 1H NMR (400 MHz, DMSO-d6) δ 9.12 (d, J=2.2 Hz, 1H), 8.95 (d, J=1.2 Hz, 1H), 8.62 (d, J=2.3 Hz, 1H), 8.47 (s, 1H), 8.04 (d, J=1.2 Hz, 1H), 7.89 (t, J=7.9 Hz, 1H), 7.79 (dd, J=8.5, 1.4 Hz, 1H), 7.73 (dd, J=10.6, 6.4 Hz, 1H), 7.60 (d, J=8.4 Hz, 1H), 7.53 (d, J=7.3 Hz, 1H), 7.42 (dd, J=11.5, 6.0 Hz, 1H), 7.01 (d, J=8.3 Hz, 1H), 5.73 (s, 2H), 5.02-4.95 (m, 1H), 4.56-4.45 (m, 2H), 4.46-4.30 (m, 2H), 3.82-3.67 (m, 2H), 1.30 (s, 3H), 0.58 (s, 3H). ES/MS m/z: 672.2 (M+H⁺).

Example 163: (S)-2-(2,5-difluoro-4-(5-fluoro-6-((2-fluoro-4-(1H-1,2,3-triazol-1-yl)benzyl)oxy)pyridin-2-yl)benzyl)-1-(4,4-dimethyltetrahydrofuran-3-yl)-1H-benzo[d]imidazole-6-carboxylic acid (S)-2-(2,5-difluoro-4-(5-fluoro-6-((2-fluoro-4-(1H-1,2,3-triazol-1-yl)benzyl)oxy)pyridin-2-yl)benzyl)-1-(4,4-dimethyltetrahydrofuran-3-yl)-1H-benzo[d]imidazole-6-carboxylic acid was prepared in a manner as described in Procedure 35, starting with Intermediates I-1340 and I-82. 1H NMR (400 MHz, DMSO-d6) δ 8.89 (d, J=1.2 Hz, 1H), 8.48 (s, 1H), 8.00 (d, J=1.1 Hz, 1H), 7.95 (dd, J=10.8, 2.0 Hz, 1H), 7.88-7.83 (m, 3H), 7.91-7.76 (m, 2H), 7.61 (d, J=8.5 Hz, 1H), 7.59-7.53 (m, 1H), 7.46 (dd, J=11.4, 6.1 Hz, 1H), 5.68 (s, 2H), 5.01 (d, J=6.8 Hz, 1H), 4.57-4.48 (m, 2H), 4.48-4.30 (m, 2H), 3.82-3.69 (m, 2H), 1.33 (s, 3H), 0.60 (s, 3H). ES/MS m/z: 673.2 (M+H⁺).

Example 164: (S)-2-(2,5-difluoro-4-(6-((2-fluoro-4-(4-methyl-1H-1,2,3-triazol-1-yl)benzyl)oxy)pyridin-2-yl)benzyl)-1-(4,4-dimethyltetrahydrofuran-3-yl)-1H-benzo[d]imidazole-6-carboxylic acid (S)-2-(2,5-difluoro-4-(6-((2-fluoro-4-(4-methyl-1H-1,2,3-triazol-1-yl)benzyl)oxy)pyridin-2-yl)benzyl)-1-(4,4-dimethyltetrahydrofuran-3-yl)-1H-benzo[d]imidazole-6-carboxylic acid was prepared in a manner as described in Procedure 35, starting with Intermediates I-1058 and I-82. 1H NMR (400 MHz, DMSO-d6) δ 8.60 (s, 1H), 8.48 (s, 1H), 7.92-7.81 (m, 3H), 7.81-7.75 (m, 3H), 7.61 (d, J=8.4 Hz, 1H), 7.57-7.51 (m, 1H), 7.45 (dd, J=11.3, 6.2 Hz, 1H), 6.98 (d, J=8.3 Hz, 1H), 5.58 (s, 2H), 5.01 (d, J=6.7 Hz, 1H), 4.59-4.48 (m, 2H), 4.50-4.34 (m, 2H), 3.83-3.70 (m, 2H), 2.33 (s, 3H), 1.33 (s, 3H), 0.60 (s, 3H). ES/MS m/z: 669.2 (M+H⁺).

Example 165: 2-(4-(6-((4-cyano-2-fluorobenzyl)oxy)pyridin-2-yl)-2,5-difluorobenzyl)-1-(4,4-dimethyltetrahydrofuran-3-yl)-7-fluoro-1H-benzo[d]imidazole-6-carboxylic acid 2-(4-(6-((4-cyano-2-fluorobenzyl)oxy)pyridin-2-yl)-2,5-difluorobenzyl)-1-(4,4-dimethyltetrahydrofuran-3-yl)-7-fluoro-1H-benzo[d]imidazole-6-carboxylic acid was prepared in a manner as described in Procedure 35, starting with Intermediates I-3 and I-1057. 1H NMR (400 MHz, DMSO-d6) δ 7.94-7.86 (m, 2H), 7.80-7.71 (m, 3H), 7.66 (d, J=7.7 Hz, 1H), 7.54 (d, J=7.4 Hz, 1H), 7.41 (p, J=11.0, 9.8 Hz, 2H), 6.99 (d, J=8.2 Hz, 1H), 5.60 (s, 2H), 5.22 (d, J=112.0 Hz, 1H), 4.54 (d, J=24.0 Hz, 2H), 4.47-4.14 (m, 2H), 3.94-3.58 (m, 2H), 1.29 (d, J=21.9 Hz, 3H), 0.72 (d, J=14.3 Hz, 3H). ES/MS m/z: 631.1 (M+H⁺).

Example 166: 2-(4-(6-((4-cyano-2-fluorobenzyl)oxy)pyridin-2-yl)-2,5-difluorobenzyl)-1-(4,4-dimethyltetrahydrofuran-3-yl)-7-fluoro-1H-benzo[d]imidazole-6-carboxylic acid 2-(4-(6-((4-cyano-2-fluorobenzyl)oxy)pyridin-2-yl)-2,5-difluorobenzyl)-1-(4,4-dimethyltetrahydrofuran-3-yl)-7-fluoro-1H-benzo[d]imidazole-6-carboxylic acid was prepared in a manner as described in Procedure 35, starting with Intermediates I-3 and I-1056. 1H NMR (400 MHz, DMSO-d6) δ 7.95-7.86 (m, 2H), 7.79-7.71 (m, 3H), 7.66 (t, J=7.6 Hz, 1H), 7.54 (d, J=7.3 Hz, 1H), 7.43 (q, J=10.6, 7.8 Hz, 2H), 6.99 (d, J=8.3 Hz, 1H), 5.60 (s, 2H), 5.22 (d, J=111.9 Hz, 1H), 4.54 (d, J=24.1 Hz, 2H), 4.37 (d, J=18.0 Hz, 1H), 3.92-3.67 (m, 1H), 1.29 (d, J=21.9 Hz, 3H), 0.72 (d, J=14.2 Hz, 3H). ES/MS m/z: 631.2 (M+H⁺).

Example 167: (S)-2-(2,5-difluoro-4-(6-((2-fluoro-4-(1H-1,2,3-triazol-1-yl)benzyl)oxy)pyridin-2-yl)benzyl)-1-(4,4-dimethyltetrahydrofuran-3-yl)-1H-benzo[d]imidazole-6-carboxylic acid (S)-2-(2,5-difluoro-4-(6-((2-fluoro-4-(1H-1,2,3-triazol-1-yl)benzyl)oxy)pyridin-2-yl)benzyl)-1-(4,4-dimethyltetrahydrofuran-3-yl)-1H-benzo[d]imidazole-6-carboxylic acid was prepared in a manner as described in Procedure 35, starting with Intermediates I-1283 and I-82. 1H NMR (400 MHz, DMSO-d6) δ 8.89 (s, 1H), 8.48 (s, 1H), 8.00 (s, 1H), 7.95-7.87 (m, 3H), 7.87-7.81 (m, 2H), 7.79 (dd, J=8.3, 1.7 Hz, 2H), 7.61 (d, J=8.5 Hz, 1H), 7.54 (d, J=7.3 Hz, 1H), 7.46 (dd, J=11.3, 6.1 Hz, 1H), 6.98 (d, J=8.3 Hz, 1H), 5.59 (s, 2H), 5.01 (d, J=6.7 Hz, 1H), 4.58-4.47 (m, 2H), 4.47-4.28 (m, 2H), 3.81-3.63 (m, 2H), 1.33 (s, 3H), 0.60 (s, 3H). ES/MS m/z: 655.2 (M+H+).

Example 168: (S)-2-(2,5-difluoro-4-(6-((2-fluoro-4-(trifluoromethyl)benzyl)oxy)pyridin-2-yl)benzyl)-1-(4,4-dimethyltetrahydrofuran-3-yl)-1H-benzo[d]imidazole-6-carboxylic acid (S)-2-(2,5-difluoro-4-(6-((2-fluoro-4-(trifluoromethyl)benzyl)oxy)pyridin-2-yl)benzyl)-1-(4,4-dimethyltetrahydrofuran-3-yl)-1H-benzo[d]imidazole-6-carboxylic acid was prepared in a manner as described in Procedure 35, starting with Intermediates I-1312 and I-82. 1H NMR (400 MHz, DMSO-d6) δ 8.47 (s, 1H), 7.90 (t, J=7.9 Hz, 1H), 7.83-7.70 (m, 4H), 7.62 (t, J=7.8 Hz, 2H), 7.54 (d, J=7.3 Hz, 1H), 7.44 (dd, J=11.3, 6.1 Hz, 1H), 6.99 (d, J=8.3 Hz, 1H), 5.61 (s, 2H), 5.00 (d, J=6.6 Hz, 1H), 4.57-4.47 (m, 2H), 4.43 (dd, J=11.1, 6.8 Hz, 1H), 4.36 (d, J=17.0 Hz, 1H), 3.83-3.69 (m, 2H), 1.32 (s, 3H), 0.59 (s, 3H). ES/MS m/z: 656.2 (M+H+).

Example 169: (S)-2-(2,5-difluoro-4-(6-((2-fluoro-4-(trifluoromethyl)benzyl)oxy)pyridin-2-yl)benzyl)-1-(4,4-dimethyltetrahydrofuran-3-yl)-4-fluoro-1H-benzo[d]imidazole-6-carboxylic acid (S)-2-(2,5-difluoro-4-(6-((2-fluoro-4-(trifluoromethyl)benzyl)oxy)pyridin-2-yl)benzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1312 and I-108. 1H NMR (400 MHz, DMSO-d6) δ 8.35 (s, 1H), 7.90 (t, J=7.8 Hz, 1H), 7.81-7.71 (m, 3H), 7.62 (d, J=8.0 Hz, 1H), 7.53 (dd, J=12.7, 9.2 Hz, 2H), 7.45 (dd, J=11.4, 6.1 Hz, 1H), 6.99 (d, J=8.3 Hz, 1H), 5.61 (s, 2H), 5.02 (d, J=6.6 Hz, 1H), 4.59-4.47 (m, 2H), 4.47-4.34 (m, 2H), 3.74 (q, J=8.7 Hz, 2H), 1.33 (s, 3H), 0.60 (s, 3H). ES/MS m/z: 674.1 (M+H+).

Example 170: 2-(4-(6-((6-chloro-2-methoxypyridin-3-yl)methoxy)pyridin-2-yl)-2,5-difluorobenzyl)-1-(4,4-dimethyltetrahydrofuran-3-yl)-4-fluoro-1H-benzo[d]imidazole-6-carboxylic acid 2-(4-(6-((6-chloro-2-methoxypyridin-3-yl)methoxy)pyridin-2-yl)-2,5-difluorobenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1063 and I-1336. 1H NMR (400 MHz, DMSO-d6) δ 8.35 (s, 1H), 7.92-7.81 (m, 2H), 7.79 (dd, J=10.3, 6.5 Hz, 1H), 7.56-7.49 (m, 2H), 7.46 (dd, J=11.3, 6.2 Hz, 1H), 7.12 (d, J=7.7 Hz, 1H), 6.96 (d, J=8.2 Hz, 1H), 5.41 (s, 2H), 5.02 (d, J=6.6 Hz, 1H), 4.60-4.47 (m, 2H), 4.47-4.33 (m, 2H), 3.93 (s, 3H), 3.74 (q, J=8.7 Hz, 2H), 3.10 (qd, J=7.3, 4.8 Hz, 1H), 1.33 (s, 3H), 0.60 (s, 3H). ES/MS m/z: 653.2 (M+H+).

Example 171: (S)-2-(4-(6-((4-chloro-6-(1H-1,2,3-triazol-1-yl)pyridin-3-yl)methoxy)pyridin-2-yl)-2,5-difluorobenzyl)-1-(4,4-dimethyltetrahydrofuran-3-yl)-4-fluoro-1H-benzo[d]imidazole-6-carboxylic acid (S)-2-(4-(6-((4-chloro-6-(1H-1,2,3-triazol-1-yl)pyridin-3-yl)methoxy)pyridin-2-yl)-2,5-difluorobenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1049 and I-108. 1H NMR (400 MHz, DMSO-d6) δ 8.89 (d, J=1.4 Hz, 1H), 8.82 (s, 1H), 8.35 (s, 1H), 8.30 (s, 1H), 8.02 (d, J=1.4 Hz, 1H), 7.92 (d, J=7.7 Hz, 1H), 7.90-7.86 (m, 1H), 7.57 (dd, J=7.6, 1.5 Hz, 1H), 7.51 (d, J=11.4 Hz, 1H), 7.47 (dd, J=11.4, 6.4 Hz, 1H), 7.00 (d, J=8.2 Hz, 1H), 5.67 (s, 2H), 5.03 (d, J=6.6 Hz, 1H), 4.58-4.47 (m, 2H), 4.47-4.31 (m, 2H), 3.74 (q, J=8.7 Hz, 2H), 1.33 (s, 3H), 0.60 (s, 3H). ES/MS m/z: 690.1 (M+H+).

Procedure 36: Example 172

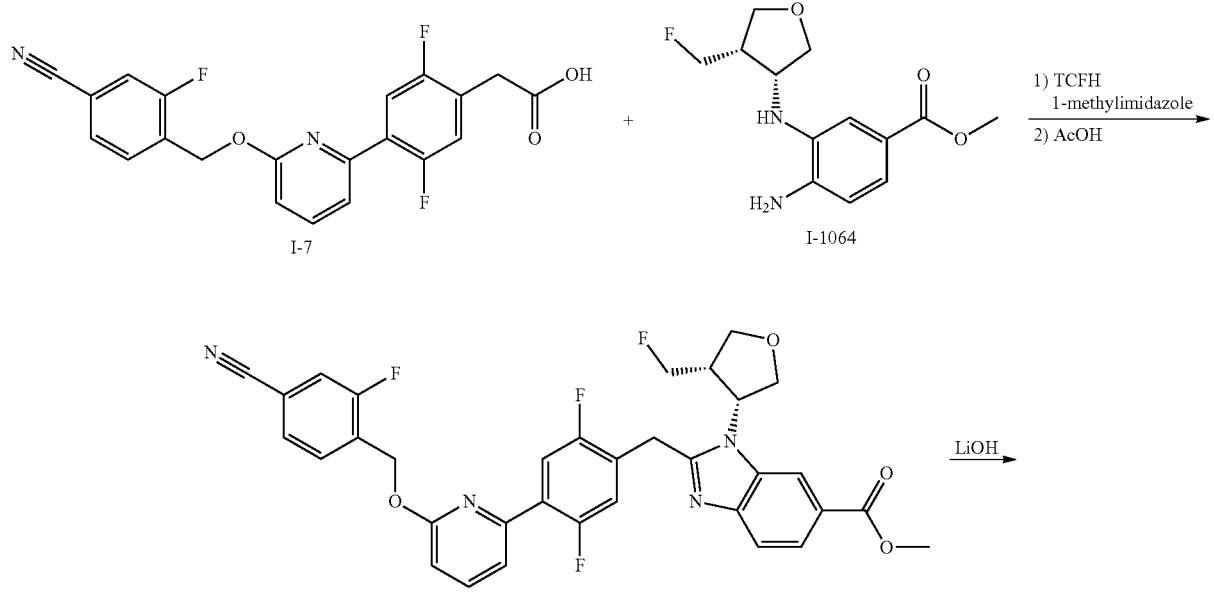

-continued

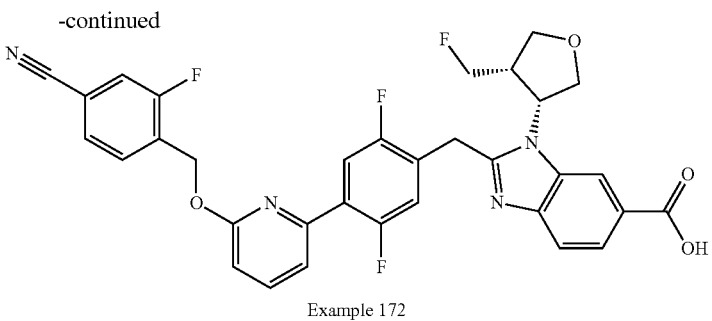

Example 172

Methyl 2-(4-(6-((4-cyano-2-fluorobenzyl)oxy)pyridin-2-yl)-2,5-difluorobenzyl)-1-((3R,4S)-4-(fluoromethyl)tetrahydrofuran-3-yl)-1H-benzo[d]imidazole-6-carboxylate. Chloro-N,N,N',N'-tetramethylformamidinium hexafluorophosphate (35 mg, 1.2 equivalent) followed by 1-methylimidazole (42 µL, 5.0 equivalent) were added to a mixture of 2-[4-[6-[(4-cyano-2-fluoro-phenyl)methoxy]-2-pyridyl]-3-fluoro-phenyl]acetic acid (I-7, 42 mg, 1.0 equivalent) and methyl 4-amino-3-[[(3R,4S)-4-(fluoromethyl)tetrahydrofuran-3-yl]amino]benzoate (I-1064, 28 mg, 1 equivalent) in MeCN (1 mL), and the mixture was stirred for 2 hours. An additional I-7 (10 mg, 0.25 equivalent) and chloro-N,N,N',N'-tetramethylformamidinium hexafluorophosphate (7 mg, 0.25 equivalent) were added, and the mixture was stirred overnight. The mixture was diluted with EtOAc and washed sequentially with saturated aqueous NH₄Cl, saturated aqueous NaHCO₃, and brine, dried over MgSO₄, filtered, and concentrated in vacuo. The crude was mixed with acetic acid (0.42 mL) and 1,2-dichloroethane (1.6 mL), and the mixture was heated in a sealed vial overnight at 95° C. The mixture was then heated at 180° C. in the microwave for 1 hour. The mixture was quenched by dropwise addition of saturated NaHCO₃ and diluted with EtOAc. Phases were separated, and organic layer was washed with saturated NaHCO₃ then brine, dried over MgSO₄, filtered, concentrated, and purified (0-100% EtOAc in Hex) to give methyl 2-(4-(6-((4-cyano-2-fluorobenzyl)oxy)pyridin-2-yl)-2,5-difluorobenzyl)-1-((3R,4S)-4-(fluoromethyl)tetrahydrofuran-3-yl)-1H-benzo[d]imidazole-6-carboxylate.

2-(4-(6-((4-cyano-2-fluorobenzyl)oxy)pyridin-2-yl)-2,5-difluorobenzyl)-1-((3R,4S)-4-(fluoromethyl)tetrahydrofuran-3-yl)-1H-benzo[d]imidazole-6-carboxylic acid (Example 172): Methyl 2-(4-(6-((4-cyano-2-fluorobenzyl)oxy)pyridin-2-yl)-2,5-difluorobenzyl)-1-((3R,4S)-4-(fluoromethyl)tetrahydrofuran-3-yl)-1H-benzo[d]imidazole-6-carboxylate (35 mg, 1.0 equivalent) was mixed with lithium hydroxide monohydrate (2 M in water, 83 µL, 3 equivalent) and acetonitrile (0.8 mL). All components were heated at 100° C. for 6 min. The mixture was neutralized with AcOH, diluted with DMSO, and purified (0-100% ACN in H₂O, 0.1% TFA) to give the title compound. 1H NMR (400 MHz, DMSO-d6) δ 8.53 (s, 1H), 7.94-7.90 (m, 1H), 7.89 (d, J=8.0 Hz, 1H), 7.81 (dd, J=8.4, 1.5 Hz, 1H), 7.79-7.70 (m, 3H), 7.62 (d, J=8.4 Hz, 1H), 7.53 (dd, J=7.5, 1.7 Hz, 1H), 7.39 (dd, J=11.4, 6.1 Hz, 1H), 6.99 (d, J=8.3 Hz, 1H), 5.61 (d, J=9.4 Hz, 3H), 4.56 (d, J=6.1 Hz, 1H), 4.52 (s, 1H), 4.42 (d, J=17.0 Hz, 1H), 4.34-4.10 (m, 2H), 4.06 (td, J=9.0, 1.7 Hz, 1H), 3.97-3.77 (m, 2H), 3.31 (dq, J=15.6, 7.6 Hz, 1H). ES/MS m/z: 617.3 (M+H⁺).

Example 173: 2-(4-(6-((4-chloro-6-(1H-1,2,3-triazol-1-yl)pyridin-3-yl)methoxy)pyridin-2-yl)-2,5-difluorobenzyl)-1-(4,4-dimethyltetrahydrofuran-3-yl)-4-fluoro-1H-benzo[d]imidazole-6-carboxylic acid 2-(4-(6-((4-chloro-6-(1H-1,2,3-triazol-1-yl)pyridin-3-yl)methoxy)pyridin-2-yl)-2,5-difluorobenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1049 and I-1336. 1H NMR (400 MHz, DMSO-d6) δ 8.89 (d, J=1.3 Hz, 1H), 8.82 (s, 1H), 8.35 (s, 1H), 8.30 (s, 1H), 8.02 (d, J=1.2 Hz, 1H), 7.94-7.91 (m, 1H), 7.90-7.87 (m, 1H), 7.57 (dd, J=7.6, 1.6 Hz, 1H), 7.52 (dd, J=11.2, 1.2 Hz, 1H), 7.47 (dd, J=11.4, 6.5 Hz, 1H), 7.01 (d, J=8.3 Hz, 1H), 5.67 (s, 2H), 5.03 (d, J=6.6 Hz, 1H), 4.53 (dd, J=14.2, 11.9 Hz, 2H), 4.47-4.35 (m, 2H), 3.74 (q, J=8.7 Hz, 2H), 1.33 (s, 3H), 0.60 (s, 3H). ES/MS m/z: 690.0 (M+H⁺).

Example 174: 2-(4-(6-((4-chloro-6-(1H-imidazol-1-yl)pyridin-3-yl)methoxy)pyridin-2-yl)-2,5-difluorobenzyl)-1-(4,4-dimethyltetrahydrofuran-3-yl)-4-fluoro-1H-benzo[d]imidazole-6-carboxylic acid 2-(4-(6-((4-chloro-6-(1H-imidazol-1-yl)pyridin-3-yl)methoxy)pyridin-2-yl)-2,5-difluorobenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1051 and I-1336. 1H NMR (400 MHz, DMSO-d6) δ 9.33 (s, 1H), 8.78 (s, 1H), 8.35 (s, 1H), 8.30 (s, 1H), 8.27 (t, J=1.6 Hz, 1H), 7.92 (d, J=7.9 Hz, 1H), 7.89 (t, J=3.3 Hz, 1H), 7.57 (dt, J=4.4, 1.7 Hz, 2H), 7.52 (dd, J=11.2, 1.2 Hz, 1H), 7.49-7.43 (m, 1H), 6.99 (d, J=8.3 Hz, 1H), 5.66 (s, 2H), 5.03 (d, J=6.5 Hz, 1H), 4.59-4.49 (m, 2H), 4.47-4.35 (m, 2H), 3.74 (q, J=8.7 Hz, 2H), 1.33 (s, 3H), 0.61 (s, 3H). ES/MS m/z: 689.4 (M+H⁺).

Example 175: 2-(2,5-difluoro-4-(6-((2-fluoro-4-(trifluoromethyl)benzyl)oxy)pyridin-2-yl)benzyl)-1-(4,4-dimethyltetrahydrofuran-3-yl)-4-fluoro-1H-benzo[d]imidazole-6-carboxylic acid 2-(2,5-difluoro-4-(6-((2-fluoro-4-(trifluoromethyl)benzyl)oxy)pyridin-2-yl)benzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1312 and I-1336. 1H NMR (400 MHz, DMSO-d6) δ 8.35 (s, 1H), 7.90 (t, J=7.9 Hz, 1H), 7.83-7.77 (m, 2H), 7.74 (dd, J=10.4, 1.9 Hz, 1H), 7.64-7.60 (m, 1H), 7.57-7.49 (m, 2H), 7.46 (dd, J=11.4, 6.1 Hz, 1H), 6.99 (d, J=8.2 Hz, 1H), 5.61 (s, 2H), 5.02 (d, J=6.6 Hz, 1H), 4.61-4.47 (m, 2H), 4.47-4.34 (m, 2H), 3.74 (q, J=8.7 Hz, 2H), 1.33 (s, 3H), 0.60 (s, 3H). ES/MS m/z: 674.1 (M+H$^+$).

Example 176A: 2-(4-(6-((4-cyano-2-fluorobenzyl) oxy)pyridin-2-yl)-2,5-difluorobenzyl)-1-((3S,4S)-4-(methoxymethyl)tetrahydrofuran-3-yl)-1H-benzo[d] imidazole-6-carboxylic acid 2-(4-(6-((4-cyano-2-fluorobenzyl)oxy)pyridin-2-yl)-2,5-difluorobenzyl)-1-((3S,4S)-4-(methoxymethyl)tetrahydrofuran-3-yl)-1H-benzo[d]imidazole-6-carboxylic acid was prepared from racemic Example 184 by preparative chiral SFC (Daicel Chiralcel AD-H column, 45% MeOH in CO$_2$) as the later eluting of two isomers. 1H NMR (400 MHz, DMSO) δ 8.45 (s, 1H), 7.96-7.86 (m, 2H), 7.80-7.71 (m, 4H), 7.53 (d, J=8.2 Hz, 2H), 7.35 (dd, J=11.0, 5.7 Hz, 1H), 7.00 (d, J=8.3 Hz, 1H), 5.61 (s, 2H), 5.48 (s, 1H), 4.49 (d, J=11.9 Hz, 2H), 4.42 (d, J=17.2 Hz, 1H), 4.21 (dd, J=10.8, 6.8 Hz, 1H), 4.16-4.03 (m, 1H), 3.78 (s, 1H), 3.09 (s, 2H), 3.07-2.99 (m, 1H), 2.92 (s, 3H), 2.59 (s, 1H).

Example 176B: 2-(4-(6-((4-cyano-2-fluorobenzyl) oxy)pyridin-2-yl)-2,5-difluorobenzyl)-1-((3R,4R)-4-(methoxymethyl)tetrahydrofuran-3-yl)-1H-benzo[d] imidazole-6-carboxylic acid 2-(4-(6-((4-cyano-2-fluorobenzyl)oxy)pyridin-2-yl)-2,5-difluorobenzyl)-1-((3R,4R)-4-(methoxymethyl)tetrahydrofuran-3-yl)-1H-benzo[d]imidazole-6-carboxylic acid was prepared from racemic Example 184 by preparative chiral SFC (Daicel Chiralcel AD-H column, 45% MeOH in CO$_2$) as the earlier eluting of two isomers. 1H NMR (400 MHz, DMSO) δ 8.51 (s, 1H), 7.96-7.86 (m, 2H), 7.82-7.71 (m, 4H), 7.62-7.51 (m, 2H), 7.36 (dd, J=11.4, 6.1 Hz, 1H), 7.00 (d, J=8.3 Hz, 1H), 5.61 (s, 2H), 5.50 (s, 1H), 4.56-4.47 (m, 2H), 4.43 (d, J=16.8 Hz, 1H), 4.21 (dd, J=10.9, 6.6 Hz, 1H), 4.08 (t, J=8.7 Hz, 1H), 3.77 (t, J=8.2 Hz, 1H), 3.14-3.00 (m, 2H), 2.92 (s, 3H), 2.63-2.52 (m, 1H), 1.24 (s, 1H). ES/MS m/z: 629.0 (M+H$^+$).

Example 177: (S)-2-(4-(6-((4-(1H-1,2,3-triazol-1-yl) benzyl)oxy)-5-fluoropyridin-2-yl)-2,5-difluorobenzyl)-1-(4,4-dimethyltetrahydrofuran-3-yl)-4-fluoro-1H-benzo[d]imidazole-6-carboxylic acid (S)-2-(4-(6-((4-(1H-1,2,3-triazol-1-yl)benzyl)oxy)-5-fluoropyridin-2-yl)-2,5-difluorobenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1077 and I-108. 1H NMR (400 MHz, DMSO) δ 13.05 (s, 1H), 8.84 (d, J=1.1 Hz, 1H), 8.35 (s, 1H), 8.01-7.93 (m, 3H), 7.85 (ddd, J=13.3, 10.3, 7.4 Hz, 2H), 7.75 (d, J=8.3 Hz, 2H), 7.60-7.43 (m, 3H), 5.66 (s, 2H), 5.03 (d, J=6.5 Hz, 1H), 4.59-4.49 (m, 2H), 4.47-4.34 (m, 2H), 3.75 (q, J=8.7 Hz, 2H), 1.34 (s, 3H), 0.61 (s, 3H). ES/MS m/z: x (M+H$^+$).

Example 178: (S)-2-(4-(2-((4-cyanobenzyl)oxy) pyrimidin-4-yl)-2-fluoro-5-methylbenzyl)-1-(4,4-dimethyltetrahydrofuran-3-yl)-1H-benzo[d]imidazole-6-carboxylic acid (S)-2-(4-(2-((4-cyanobenzyl)oxy)pyrimidin-4-yl)-2-fluoro-5-methylbenzyl)-1-(4,4-dimethyltetrahydrofuran-3-yl)-1H-benzo[d]imidazole-6-carboxylic acid was prepared in a manner as described in Procedure 35, starting with Intermediates I-1076 and I-1086. 1H NMR (400 MHz, DMSO) δ 8.74 (d, 1H), 8.49 (s, 1H) 7.80-7.90 (m, 3H), 7.70-7.60 (m, 3H), 7.46-7.36 (m, 3H), 5.56 (s, 2H), 5.02 (d, 1H), 4.53-4.43 (m, 4H), 3.82-3.72 (m, 2H), 2.33 (s, 3H), 1.32 (s, 3H), 0.60 (s, 3H). ES/MS m/z: 592.0 (M+H$^+$).

Example 179: (S)-2-(4-(6-((4-cyanobenzyl)oxy) pyridin-2-yl)-2-fluoro-5-methylbenzyl)-1-(4,4-dimethyltetrahydrofuran-3-yl)-1H-benzo[d]imidazole-6-carboxylic acid (S)-2-(4-(6-((4-cyanobenzyl)oxy)pyridin-2-yl)-2-fluoro-5-methylbenzyl)-1-(4,4-dimethyltetrahydrofuran-3-yl)-1H-benzo[d]imidazole-6-carboxylic acid was prepared in a manner as described in Procedure 35, starting with Intermediates I-1076 and I-7. 1H NMR (400 MHz, DMSO) δ 8.49 (s, 1H), 7.92-7.78 (m, 4H), 7.63 (dd, J=8.3, 4.5 Hz, 3H), 7.33-7.20 (m, 3H), 5.51 (s, 2H), 4.56-4.38 (m, 3H), 3.82-3.70 (m, 2H), 3.74 (s, 21H), 2.22 (s, 3H), 1.31 (s, 3H), 0.60 (s, 3H). ES/MS m/z: 591.2 (M+H$^+$).

Example 180: (S)-2-(4-(6-((4-cyanobenzyl)oxy)-5-fluoropyridin-2-yl)-2-fluoro-5-methylbenzyl)-1-(4,4-dimethyltetrahydrofuran-3-yl)-1H-benzo[d]imidazole-6-carboxylic acid (S)-2-(4-(6-((4-cyanobenzyl)oxy)-5-fluoropyridin-2-yl)-2-fluoro-5-methylbenzyl)-1-(4,4-dimethyltetrahydrofuran-3-yl)-1H-benzo[d]imidazole-6-carboxylic acid was prepared in a manner as described in Procedure 35, starting with Intermediates I-1247 and I-7. 1H NMR (400 MHz, DMSO) δ 8.49 (s, 1H), 7.90-7.78 (m, 4H), 7.64 (dd, J=12.6, 8.3 Hz, 3H), 7.33-7.21 (m, 3H), 5.59 (s, 2H), 5.02 (d, J=6.6 Hz, 1H), 4.56-4.38 (m, 3H), 4.33 (d, J=16.9 Hz, 1H), 3.79 (d, J=8.6 Hz, 1H), 3.73 (d, J=8.6 Hz, 1H), 2.22 (s, 3H), 1.31 (s, 3H), 0.60 (s, 3H). ES/MS m/z: 610.6 (M+H$^+$).

Example 181: (S)-2-(4-(6-((4-(1H-1,2,3-triazol-1-yl) benzyl)oxy)-5-fluoropyridin-2-yl)-2,5-difluorobenzyl)-1-(4,4-dimethyltetrahydrofuran-3-yl)-1H-benzo [d]imidazole-6-carboxylic acid (S)-2-(4-(6-((4-(1H-1,2,3-triazol-1-yl)benzyl)oxy)-5-fluoropyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 35, starting with Intermediates I-1077 and I-82. 1H NMR (400 MHz, DMSO) δ 8.84 (d, J=1.2 Hz, 1H), 8.51 (s, 1H), 8.01-7.93 (m, 3H), 7.91-7.83 (m, 1H), 7.87-7.79 (m, 2H), 7.78-7.71 (m, 2H), 7.64 (d, J=8.4 Hz, 1H), 7.60-7.52 (m, 1H), 7.48 (dd, J=11.4, 6.1 Hz, 1H), 5.66 (s, 2H), 5.04 (d, J=6.6 Hz, 1H), 4.60-4.51 (m, 2H), 4.48-4.37 (m, 2H), 3.79 (d, J=8.6 Hz, 1H), 3.73 (d, J=8.6 Hz, 1H), 1.33 (s, 3H), 0.61 (s, 3H). ES/MS m/z: 655.2 (M+H$^+$).

Example 182: (S)-2-(4-(2-((4-(1H-1,2,3-triazol-1-yl) benzyl)oxy)pyrimidin-4-yl)-2,5-difluorobenzyl)-1-(4,4-dimethyltetrahydrofuran-3-yl)-1H-benzo[d] imidazole-6-carboxylic acid (S)-2-(4-(2-((4-(1H-1,2,3-triazol-1-yl)benzyl)oxy)pyrimidin-4-yl)-2,5-difluorobenzyl)-1-(4,4-dimethyltetrahydrofuran-3-yl)-1H-benzo[d]imidazole-6-carboxylic acid was prepared in a manner as described in Procedure 35, starting with Intermediates I-1087 and I-82. 1H NMR (400 MHz, DMSO) δ 8.87-8.77 (m, 2H), 8.50 (s, 1H), 8.01-7.92 (m, 4H), 7.82 (dd, J=8.5, 1.5 Hz, 1H), 7.74 (d, J=8.4 Hz, 2H), 7.67-7.60 (m, 2H), 7.56 (dd, J=11.4, 5.9 Hz, 1H), 5.60

(s, 2H), 5.21 (s, 15H), 5.03 (d, J=6.6 Hz, 1H), 4.59 (d, J=17.1 Hz, 1H), 4.55 (d, J=11.7 Hz, 1H), 4.48-4.38 (m, 2H), 3.78 (d, J=8.6 Hz, 1H), 3.73 (d, J=8.6 Hz, 1H), 1.34 (s, 3H), 0.62 (s, 3H). ES/MS m/z: 638.3 (M+H$^+$).

Example 183: (S)-2-(4-(6-((4-(1H-1,2,3-triazol-1-yl)benzyl)oxy)pyridin-2-yl)-2,5-difluorobenzyl)-1-(4,4-dimethyltetrahydrofuran-3-yl)-1H-benzo[d]imidazole-6-carboxylic acid (S)-2-(4-(6-((4-(1H-1,2,3-triazol-1-yl)benzyl)oxy)pyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 35, starting with Intermediates I-1088 and I-82. 1H NMR (400 MHz, DMSO) δ 8.83 (d, J=1.2 Hz, 1H), 8.50 (s, 1H), 7.98 (d, J=1.2 Hz, 1H), 7.98-7.91 (m, 2H), 7.90 (t, J=7.8 Hz, 1H), 7.86 (dd, J=10.3, 6.6 Hz, 1H), 7.82 (dd, J=8.4, 1.5 Hz, 1H), 7.76-7.69 (m, 2H), 7.63 (d, J=8.4 Hz, 1H), 7.54 (dd, J=7.6, 1.6 Hz, 1H), 7.47 (dd, J=11.2, 6.3 Hz, 1H), 7.00 (d, J=8.2 Hz, 1H), 5.57 (s, 2H), 5.03 (d, J=6.6 Hz, 1H), 4.59-4.54 (m, 1H), 4.53 (s, 1H), 4.48-4.35 (m, 2H), 4.03 (s, 21H), 3.78 (d, J=8.7 Hz, 1H), 3.73 (d, J=8.6 Hz, 1H), 1.33 (s, 3H), 0.61 (s, 3H). ES/MS m/z: 636.6 (M+H$^+$).

Example 184: 2-(4-(6-((4-cyano-2-fluorobenzyl)oxy)pyridin-2-yl)-2,5-difluorobenzyl)-1-((3S,4S)-4-(methoxymethyl)tetrahydrofuran-3-yl)-1H-benzo[d]imidazole-6-carboxylic acid 2-(4-(6-((4-cyano-2-fluorobenzyl)oxy)pyridin-2-yl)-2,5-difluorobenzyl)-1-((3S,4S)-4-(methoxymethyl)tetrahydrofuran-3-yl)-1H-benzo[d]imidazole-6-carboxylic acid was prepared in a manner as described in Procedure 22, starting with Intermediates I-7 and I-1065. 1H NMR (400 MHz, DMSO) δ 12.76 (s, 1H), 8.55 (s, 1H), 7.96-7.86 (m, 2H), 7.81 (dd, J=8.3, 1.5 Hz, 1H), 7.81-7.68 (m, 3H), 7.62 (d, J=8.5 Hz, 1H), 7.54 (d, J=7.6, 1.7 Hz, 1H), 7.38 (dd, J=11.4, 6.1 Hz, 1H), 7.00 (d, J=8.3 Hz, 1H), 5.61 (s, 2H), 5.52 (s, 1H), 4.58-4.41 (m, 3H), 4.21 (dd, J=10.8, 6.5 Hz, 1H), 4.08 (t, J=8.7 Hz, 1H), 3.77 (t, J=8.1 Hz, 1H), 3.17-3.01 (m, 2H), 2.91 (s, 3H), 2.60 (t, J=8.7 Hz, 1H). ES/MS m/z: 628.2 (M+H$^+$).

Example 185: 2-(4-(6-((4-cyano-2-fluorobenzyl)oxy)pyridin-2-yl)-2,5-difluorobenzyl)-1-((3S,4R)-4-((difluoromethoxy)methyl)tetrahydrofuran-3-yl)-1H-benzo[d]imidazole-6-carboxylic acid 2-(4-(6-((4-cyano-2-fluorobenzyl)oxy)pyridin-2-yl)-2,5-difluorobenzyl)-1-((3S,4R)-4-((difluoromethoxy)methyl)tetrahydrofuran-3-yl)-1H-benzo[d]imidazole-6-carboxylic acid was prepared in a manner as described in Procedure 22, starting with Intermediates 1-7 and 1-1066. 1H NMR (400 MHz, DMSO) δ 8.53 (s, 1H), 7.96-7.86 (m, 2H), 7.81 (dd, J=8.4, 1.5 Hz, 1H), 7.81-7.70 (m, 3H), 7.66-7.50 (m, 2H), 7.38 (dd, J=11.4, 6.1 Hz, 1H), 7.00 (d, J=8.2 Hz, 1H), 6.6-6.25 (m, 1H), 5.61 (s, 2H), 4.56 (d, J=16.9 Hz, 1H), 4.50 (d, J=10.9 Hz, 1H), 4.42 (d, J=17.0 Hz, 1H), 4.19 (dd, J=10.9, 6.7 Hz, 1H), 4.09 (t, J=8.6 Hz, 1H), 3.93-3.86 (m, 1H), 3.61-3.51 (m, 1H). ES/MS m/z: 664.6 (M+H$^+$).

Example 186: (S)-2-(4-(6-((4-(1H-1,2,3-triazol-1-yl)benzyl)oxy)pyridin-2-yl)-2,5-difluorobenzyl)-1-(4,4-dimethyltetrahydrofuran-3-yl)-4-fluoro-1H-benzo[d]imidazole-6-carboxylic acid (S)-2-(4-(6-((4-(1H-1,2,3-triazol-1-yl)benzyl)oxy)pyridin-2-yl)-2,5-difluorobenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1088 and I-108. 1H NMR (400 MHz, DMSO) δ 13.14 (s, 1H), 8.83 (d, J=1.2 Hz, 1H), 8.36 (s, 1H), 8.00-7.82 (m, 5H), 7.73 (d, J=8.2 Hz, 2H), 7.58-7.49 (m, 2H), 7.47 (dd, J=11.2, 6.2 Hz, 1H), 7.00 (d, J=8.2 Hz, 1H), 5.58 (s, 2H), 5.04 (d, J=6.5 Hz, 1H), 4.59-4.49 (m, 2H), 4.48-4.35 (m, 2H), 4.26 (s, 13H), 3.75 (q, J=8.7 Hz, 2H), 2.55 (s, 1H), 1.34 (s, 3H), 0.61 (s, 3H). ES/MS m/z: 654.6 (M+H$^+$).

Example 187: 1-((1R,2R,4S)-7-oxabicyclo[2.2.1]heptan-2-yl)-2-(4-(6-((4-cyano-2-fluorobenzyl)oxy)pyridin-2-yl)-2,5-difluorobenzyl)-1H-benzo[d]imidazole-6-carboxylic acid 1-((1R,2R,4S)-7-oxabicyclo[2.2.1]heptan-2-yl)-2-(4-(6-((4-cyano-2-fluorobenzyl)oxy)pyridin-2-yl)-2,5-difluorobenzyl)-1H-benzo[d]imidazole-6-carboxylic acid was prepared in a manner as described in Procedure 36, starting with Intermediates I-7 and I-1067. 1H NMR (400 MHz, DMSO) δ 12.98 (s, 1H), 8.31 (d, J=1.5 Hz, 1H), 7.96-7.86 (m, 2H), 7.82 (dd, J=8.5, 1.3 Hz, 1H), 7.82-7.70 (m, 3H), 7.66 (d, J=8.4 Hz, 1H), 7.55 (d, J=7.5, 1.7 Hz, 1H), 7.41 (dd, J=11.3, 6.1 Hz, 1H), 7.00 (d, J=8.2 Hz, 1H), 5.61 (s, 2H), 5.02 (dt, J=11.1, 5.0 Hz, 1H), 4.85 (dt, J=12.8, 4.2 Hz, 2H), 4.58 (d, J=17.0 Hz, 1H), 4.47 (d, J=17.0 Hz, 1H), 2.37 (d, J=10.9 Hz, 1H), 2.10-1.96 (m, 1H), 1.90 (d, J=10.3 Hz, 1H), 1.68 (q, J=5.3 Hz, 2H). ES/MS m/z: 610.6 (M+H$^+$).

Example 188: (S)-2-(4-(6-((4-cyanobenzyl)oxy)-5-fluoropyridin-2-yl)-2,5-difluorobenzyl)-1-(4,4-dimethyltetrahydrofuran-3-yl)-1H-benzo[d]imidazole-6-carboxylic acid (S)-2-(4-(6-((4-cyanobenzyl)oxy)-5-fluoropyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 35, starting with Intermediates I-1247 and I-82. 1H NMR (400 MHz, DMSO) δ 8.49 (s, 1H), 7.92-7.77 (m, 4H), 7.72 (t, J=8.8 Hz, 3H), 7.62 (d, J=8.5 Hz, 1H), 7.59-7.52 (m, 1H), 7.46 (dd, J=11.4, 6.1 Hz, 1H), 5.67 (s, 2H), 5.02 (d, J=6.7 Hz, 1H), 4.58-4.49 (m, 2H), 4.44 (dd, J=11.2, 6.8 Hz, 1H), 4.38 (d, J=16.9 Hz, 1H), 3.82-3.70 (m, 2H), 1.34 (s, 3H), 0.61 (s, 3H). ES/MS m/z: 612.6 (M+H$^+$).

Example 189: 2-(4-(6-((4-cyano-2-fluorobenzyl)oxy)pyridin-2-yl)-2,5-difluorobenzyl)-1-((3R,4R)-4-cyclopropyltetrahydrofuran-3-yl)-1H-benzo[d]imidazole-6-carboxylic acid Example 190: 2-(4-(6-((4-cyano-2-fluorobenzyl)oxy)pyridin-2-yl)-2,5-difluorobenzyl)-1-((3S,4S)-4-cyclopropyltetrahydrofuran-3-yl)-1H-benzo[d]imidazole-6-carboxylic acid Example 191: 2-(4-(6-((4-cyano-2-fluorobenzyl)oxy)pyridin-2-yl)-2,5-difluorobenzyl)-1-((3S,4R)-4-cyclopropyltetrahydrofuran-3-yl)-1H-benzo[d]imidazole-6-carboxylic acid Example 192: 2-(4-(6-((4-cyano-2-fluorobenzyl)oxy)pyridin-2-yl)-2,5-difluorobenzyl)-1-((3R,4S)-4-cyclopropyltetrahydrofuran-3-yl)-1H-benzo[d]imidazole-6-carboxylic acid Examples 189, 190, 191 and 192 were prepared in a manner as described in Procedure 36, starting with Intermediates I-7 and I-1068. This yielded a mixture of four different stereoisomers which were purified by preparative chiral SFC (Daicel Chiralpak IG column, 35% EtOH in $CO_2$) to yield the title compounds.

Example 189: 2-(4-(6-((4-cyano-2-fluorobenzyl)oxy)pyridin-2-yl)-2,5-difluorobenzyl)-1-((3R,4R)-4-cyclopropyltetrahydrofuran-3-yl)-1H-benzo[d]imidazole-6-carboxylic acid was the fourth of four stereoisomers to elute under the conditions described above. 1H NMR (400 MHz, DMSO) δ 8.56 (s, 1H), 8.22 (s, 1H), 7.96-7.87 (m, 2H), 7.82-7.70 (m, 4H), 7.60 (d, J=8.4 Hz, 1H), 7.55 (dd, J=7.5, 1.7 Hz, 1H), 7.41 (dd, J=11.4, 6.1 Hz, 1H), 7.04-6.95 (m, 1H), 5.61 (s, 2H), 5.48 (t, J=7.2 Hz, 1H), 4.63-4.53 (m, 2H), 4.47 (d, J=17.0 Hz, 1H), 4.23 (dd, J=10.9, 6.6 Hz, 1H), 4.12 (t, J=8.5 Hz, 1H), 3.82 (t, J=8.4 Hz, 1H), 3.02-2.87 (m, 1H), 2.18 (p, J=8.4 Hz, 1H), 1.24 (s, 1H), 1.16 (t, J=7.3 Hz, 2H), 0.24 (s, 2H), 0.11 (d, J=7.1 Hz, 2H), −0.12 (s, 1H). ES/MS m/z: 624.6 (M+H$^+$).

Example 190: 2-(4-(6-((4-cyano-2-fluorobenzyl)oxy)pyridin-2-yl)-2,5-difluorobenzyl)-1-((3S,4S)-4-cyclopropyltetrahydrofuran-3-yl)-1H-benzo[d]imidazole-6-carboxylic acid was the third of four stereoisomers to elute under the conditions described above. 1H NMR (400 MHz, DMSO) δ 12.74 (s, 1H), 8.55 (s, 1H), 7.96-7.87 (m, 2H), 7.81-7.70 (m, 4H), 7.63-7.51 (m, 2H), 7.41 (dd, J=11.3, 6.1 Hz, 1H), 7.00 (d, J=8.2 Hz, 1H), 5.61 (s, 2H), 5.47 (t, J=7.2 Hz, 1H), 4.62-4.52 (m, 2H), 4.46 (d, J=16.9 Hz, 1H), 4.23 (dd, J=10.8, 6.7 Hz, 1H), 4.12 (t, J=8.5 Hz, 1H), 3.81 (t, J=8.4 Hz, 1H), 2.17 (p, J=8.5 Hz, 1H), 1.24 (s, 1H), 0.23 (s, 2H), 0.11 (s, 1H), −0.13 (s, 1H). ES/MS m/z: 624.6 (M+H$^+$).

Example 191: 2-(4-(6-((4-cyano-2-fluorobenzyl)oxy)pyridin-2-yl)-2,5-difluorobenzyl)-1-((3S,4R)-4-cyclopropyltetrahydrofuran-3-yl)-1H-benzo[d]imidazole-6-carboxylic acid was the second of four stereoisomers to elute under the conditions described above. 1H NMR (400 MHz, DMSO) δ 8.28 (s, 1H), 7.96-7.86 (m, 2H), 7.84-7.72 (m, 4H), 7.62 (d, J=8.4 Hz, 1H), 7.54 (d, J=7.4 Hz, 1H), 7.41 (dd, J=11.4, 6.0 Hz, 1H), 7.00 (d, J=8.3 Hz, 1H), 5.61 (s, 2H), 5.31 (s, 1H), 4.76-4.42 (m, 2H), 4.35 (t, J=8.2 Hz, 1H), 4.31-4.12 (m, 2H), 3.58 (t, J=9.6 Hz, 1H), 2.89 (d, J=7.4 Hz, 1H), 2.68 (s, 1H), 2.34 (s, 1H), 1.92 (s, OH), 1.24 (s, 2H), 1.14 (t, J=7.2 Hz, 2H), 1.04-0.78 (m, 2H), 0.38 (d, J=9.7 Hz, 2H), 0.11 (s, 1H), −0.38 (d, J=5.2 Hz, 1H). ES/MS m/z: 624.6 (M+H$^+$).

Example 192: 2-(4-(6-((4-cyano-2-fluorobenzyl)oxy)pyridin-2-yl)-2,5-difluorobenzyl)-1-((3R,4S)-4-cyclopropyltetrahydrofuran-3-yl)-1H-benzo[d]imidazole-6-carboxylic acid was the first of four stereoisomers to elute under the conditions described above. 1H NMR (400 MHz, DMSO) δ 12.79 (s, 1H), 8.28 (s, 1H), 8.00-7.84 (m, 2H), 7.77 (dd, J=15.6, 7.3 Hz, 3H), 7.63 (d, J=8.5 Hz, 1H), 7.54 (d, J=7.3 Hz, 1H), 7.41 (dd, J=11.5, 6.0 Hz, 1H), 7.00 (d, J=8.3 Hz, 1H), 5.61 (s, 2H), 5.32 (s, 1H), 4.62-4.42 (m, 2H), 4.40-4.09 (m, 2H), 3.58 (t, J=9.6 Hz, 1H), 1.92 (d, J=8.1 Hz, 0H), 1.02-0.82 (m, 1H), 0.37 (d, J=13.0 Hz, 1H), 0.10 (d, J=5.4 Hz, 1H), −0.37 (d, J=4.9 Hz, 1H). ES/MS m/z: 624.6 (M+H$^+$).

Example 193: (S)-2-(4-(2-((4-cyanobenzyl)oxy)pyrimidin-4-yl)-2,5-difluorobenzyl)-1-(4,4-dimethyltetrahydrofuran-3-yl)-1H-benzo[d]imidazole-6-carboxylic acid (S)-2-(4-(2-((4-cyanobenzyl)oxy)pyrimidin-4-yl)-2,5-difluorobenzyl)-1-(4,4-dimethyltetrahydrofuran-3-yl)-1H-benzo[d]imidazole-6-carboxylic acid was prepared in a manner as described in Procedure 35, starting with Intermediates I-1086 and I-82. 1H NMR (400 MHz, DMSO) δ 8.79 (d, J=5.2 Hz, 1H), 8.36 (s, 1H), 7.91 (dd, J=17.7, 7.2 Hz, 3H), 7.70 (d, J=8.2 Hz, 2H), 7.65 (dd, J=5.2, 1.8 Hz, 1H), 7.60-7.48 (m, 2H), 5.62 (s, 2H), 5.04 (d, J=6.6 Hz, 1H), 4.58 (d, J=17.1 Hz, 1H), 4.53 (d, J=11.8 Hz, 1H), 4.48-4.37 (m, 2H), 3.75 (q, J=8.7 Hz, 2H), 1.34 (s, 3H), 0.62 (s, 3H). ES/MS m/z: 595.6 (M+H$^+$).

Example 194: (S)-2-(4-(2-((4-cyanobenzyl)oxy)pyrimidin-4-yl)-2,5-difluorobenzyl)-1-(4,4-dimethyltetrahydrofuran-3-yl)-4-fluoro-1H-benzo[d]imidazole-6-carboxylic acid (S)-2-(4-(2-((4-cyanobenzyl)oxy)pyrimidin-4-yl)-2,5-difluorobenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1086 and I-108. 1H NMR (400 MHz, DMSO) δ 8.79 (d, J=5.2 Hz, 1H), 8.36 (s, 1H), 7.91 (dd, J=17.7, 7.2 Hz, 3H), 7.70 (d, J=8.2 Hz, 2H), 7.65 (dd, J=5.2, 1.8 Hz, 1H), 7.60-7.48 (m, 2H), 5.62 (s, 2H), 5.04 (d, J=6.6 Hz, 1H), 4.58 (d, J=17.1 Hz, 1H), 4.53 (d, J=11.8 Hz, 1H), 4.48-4.37 (m, 2H), 3.75 (q, J=8.7 Hz, 2H), 1.34 (s, 3H), 0.62 (s, 3H). ES/MS m/z: 613.6 (M+H$^+$).

Example 195: (S)-2-(4-(6-((5-(1,1-difluoroethyl)pyridin-2-yl)methoxy)pyridin-2-yl)-2,5-difluorobenzyl)-1-(4,4-dimethyltetrahydrofuran-3-yl)-1H-benzo[d]imidazole-6-carboxylic acid (S)-2-(4-(6-((5-(1,1-difluoroethyl)pyridin-2-yl)methoxy)pyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 35, starting with Intermediates I-1074 and I-82. 1H NMR (400 MHz, DMSO) δ 13.08 (s, 1H), 8.49 (d, J=1.3 Hz, 1H), 8.35 (s, 1H), 7.93 (dd, J=10.2, 8.3 Hz, 1H), 7.82 (dd, J=10.2, 6.7 Hz, 1H), 7.66-7.59 (m, 1H), 7.56-7.43 (m, 2H), 5.98 (s, 2H), 5.03 (d, J=6.6 Hz, 1H), 4.59-4.48 (m, 2H), 4.47-4.35 (m, 2H), 3.84 (s, 14H), 3.74 (q, J=8.7 Hz, 2H), 1.33 (s, 3H), 0.60 (s, 3H). ES/MS m/z: 634.6 (M+H$^+$).

Example 196: (S)-2-(4-(2-((4-chloro-2-fluorobenzyl)oxy)pyrimidin-4-yl)-2,3,6-trifluorobenzyl)-1-(4,4-dimethyltetrahydrofuran-3-yl)-4-fluoro-1H-benzo[d]imidazole-6-carboxylic acid (S)-2-(4-(2-((4-chloro-2-fluorobenzyl)oxy)pyrimidin-4-yl)-2,3,6-trifluorobenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1232 and I-105. 1H NMR (400 MHz, DMSO) δ 13.08 (s, 1H), 8.49 (d, J=1.3 Hz, 1H), 8.35 (s, 1H), 7.93 (dd, J=10.2, 8.3 Hz, 1H), 7.82 (dd, J=10.2, 6.7 Hz, 1H), 7.66-7.59 (m, 1H), 7.56-7.43 (m, 2H), 5.98 (s, 2H), 5.03 (d, J=6.6 Hz, 1H), 4.59-4.48 (m, 2H), 4.47-4.35 (m, 2H), 3.84 (s, 14H), 3.74 (q, J=8.7 Hz, 2H), 1.33 (s, 3H), 0.60 (s, 3H). ES/MS m/z: 658.6 (M+H$^+$).

Example 197: 2-(4-(6-((4-cyano-2-fluorobenzyl)oxy)pyridin-2-yl)-2,5-difluorobenzyl)-1-((2S,3R)-2-ethyltetrahydrofuran-3-yl)-1H-benzo[d]imidazole-6-carboxylic acid 2-(4-(6-((4-cyano-2-fluorobenzyl)oxy)pyridin-2-yl)-2,5-difluorobenzyl)-1-((2S,3R)-2-ethyltetrahydrofuran-3-yl)-1H-benzo[d]imidazole-6-carboxylic acid was prepared in a manner as described in Procedure 36, starting with Intermediates I-7 and I-1069. 1H NMR (400 MHz, DMSO) δ 8.32 (d, J=1.5 Hz, 1H), 7.96-7.64 (m, 7H), 7.53 (dd, J=7.5, 1.7 Hz, 1H), 7.42 (dd, J=11.5, 6.1 Hz, 1H), 7.00 (d, J=8.3 Hz, 1H), 5.60 (s, 2H), 5.09-4.99 (m, 1H), 4.60-4.44 (m, 2H), 4.23 (ddt, J=13.1, 8.7, 3.6 Hz, 2H), 4.00 (q, J=8.0 Hz, 1H), 2.39-2.26 (m, 1H), 1.66-1.47 (m, 2H), 0.86 (t, J=7.4 Hz, 3H). ES/MS m/z: 612.6 (M+H$^+$).

Example 198: (S)-2-(4-(2-((4-cyano-2-fluorobenzyl)oxy)pyrimidin-4-yl)-2,5-difluorobenzyl)-1-(4,4-dimethyltetrahydrofuran-3-yl)-1H-benzo[d]imidazole-6-carboxylic acid (S)-2-(4-(2-((4-cyano-2-fluorobenzyl)oxy)pyrimidin-4-yl)-2,5-difluorobenzyl)-1-(4,4-dimethyltetrahydrofuran-3-yl)-1H-benzo[d]imidazole-6-carboxylic acid was prepared in a manner as described in Procedure 35, starting with Intermediates I-1175 and I-82. 1H NMR (400 MHz, DMSO) δ 8.79 (d, J=5.2 Hz, 1H), 8.49 (s, 1H), 7.98-7.88 (m, 2H), 7.84-7.72 (m, 3H), 7.69-7.59 (m, 2H), 7.55 (dd, J=11.4, 5.9 Hz, 1H), 5.64 (s, 2H), 5.02 (d, J=6.6 Hz, 1H), 4.62-4.50 (m, 2H), 4.48-4.37 (m, 2H), 3.82-3.70 (m, 2H), 1.34 (s, 3H), 0.61 (s, 3H). ES/MS m/z: 614.5 (M+H$^+$).

Example 199: 2-(4-(6-((4-cyano-2-fluorobenzyl)oxy)pyridin-2-yl)-2,5-difluorobenzyl)-1-(2,2,5,5-tetramethyltetrahydrofuran-3-yl)-1H-benzo[d]imidazole-6-carboxylic acid 2-(4-(6-((4-cyano-2-fluorobenzyl)oxy)pyridin-2-yl)-2,5-difluorobenzyl)-1-(2,2,5,5-tetramethyltetrahydrofuran-3-yl)-1H-benzo[d]imidazole-6-carboxylic acid was prepared in a manner as described in Procedure 36, starting with Intermediates I-7 and I-1070. 1H NMR (400 MHz, DMSO) δ 8.37 (d, J=1.5 Hz, 1H), 7.95-7.63 (m, 7H), 7.54 (dd, J=7.5, 1.7 Hz, 1H), 7.44 (dd, J=11.5, 6.0 Hz, 1H), 7.00 (d, J=8.3 Hz, 1H), 5.60 (s, 2H), 5.23 (dd, J=10.7, 8.3 Hz, 1H), 4.67 (d, J=17.0 Hz, 1H), 4.44 (d, J=16.9 Hz, 1H), 3.00-2.90 (m, 1H), 2.39 (dd, J=12.7, 8.2 Hz, 1H), 1.50 (s, 3H), 1.39 (d, J=17.9 Hz, 6H), 1.07 (s, 3H). ES/MS m/z: 641.2 (M+H$^+$).

Example 200: 2-(2,5-difluoro-4-(2-((2-fluoro-4-(trifluoromethyl)benzyl)oxy)pyrimidin-4-yl)benzyl)-1-(4,4-dimethyltetrahydrofuran-3-yl)-4-fluoro-1H-benzo[d]imidazole-6-carboxylic acid 2-(2,5-difluoro-4-(2-((2-fluoro-4-(trifluoromethyl)benzyl)oxy)pyrimidin-4-yl)benzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1091 and I-108. 1H NMR (400 MHz, DMSO) δ 13.09 (s, 1H), 8.80 (d, J=5.1 Hz, 1H), 8.36 (s, 1H), 7.93 (dd, J=10.2, 6.2 Hz, 1H), 7.87-7.73 (m, 2H), 7.66 (dt, J=5.2, 2.6 Hz, 2H), 7.60-7.48 (m, 2H), 5.65 (s, 2H), 5.04 (d, J=6.6 Hz, 1H), 4.58 (d, J=17.1 Hz, 1H), 4.53 (d, J=11.9 Hz, 1H), 4.48-4.38 (m, 2H), 4.11 (s, 7H), 3.75 (q, J=8.7 Hz, 2H), 1.34 (s, 3H), 0.62 (s, 3H). ES/MS m/z: 675.0 (M+H$^+$).

Example 201: (S)-2-(4-(6-((4-chloro-2-fluorobenzyl)oxy)pyridin-2-yl)-2,5-difluorobenzyl)-1-(4,4-dimethyltetrahydrofuran-3-yl)-4-fluoro-1H-benzo[d]imidazole-6-carboxylic acid (S)-2-(4-(6-((4-chloro-2-fluorobenzyl)oxy)pyridin-2-yl)-2,5-difluorobenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-102 and I-108. 1H NMR (400 MHz, DMSO) δ 13.07 (s, 1H), 8.36 (s, 1H), 7.93-7.81 (m, 2H), 7.65-7.42 (m, 5H), 7.33 (dd, J=8.2, 2.1 Hz, 1H), 6.95 (d, J=8.3 Hz, 1H), 5.51 (s, 2H), 5.04 (d, J=6.5 Hz, 1H), 4.59-4.49 (m, 2H), 4.48-4.35 (m, 2H), 3.75 (q, J=8.6 Hz, 2H), 1.34 (s, 3H), 0.61 (s, 3H). ES/MS m/z: 640.2 (M+H$^+$).

Example 202: 2-(4-(6-((4-cyano-2-fluorobenzyl)oxy)pyridin-2-yl)-2,5-difluorobenzyl)-1-(2,5-dioxaspiro[3.4]octan-7-yl)-1H-benzo[d]imidazole-6-carboxylic acid 2-(4-(6-((4-cyano-2-fluorobenzyl)oxy)pyridin-2-yl)-2,5-difluorobenzyl)-1-(2,5-dioxaspiro[3.4]octan-7-yl)-1H-benzo[d]imidazole-6-carboxylic acid was prepared in a manner as described in Procedure 22, starting with Intermediates I-7 and I-1071. 1H NMR (400 MHz, DMSO) δ 8.20 (s, 1H), 7.96-7.86 (m, 2H), 7.83-7.70 (m, 4H), 7.61 (d, J=8.4 Hz, 1H), 7.53 (d, J=7.0 Hz, 1H), 7.34 (dd, J=11.5, 6.1 Hz, 1H), 7.00 (d, J=8.2 Hz, 1H), 5.60 (s, 2H), 5.53 (s, 1H), 4.89 (d, J=7.0 Hz, 1H), 4.75 (d, J=7.1 Hz, 1H), 4.63 (q, J=6.8 Hz, 2H), 4.47 (s, 2H), 4.25 (dd, J=10.4, 3.4 Hz, 1H), 4.16 (dd, J=10.4, 7.6 Hz, 1H), 3.31 (s, 1H), 2.93 (dd, J=14.0, 9.1 Hz, 1H), 2.51-2.39 (m, 1H), 1.24 (s, 1H). ES/MS m/z: 627.2 (M+H$^+$).

Example 203: 2-(4-(6-((4-cyano-2-fluorobenzyl)oxy)pyridin-2-yl)-2,5-difluorobenzyl)-1-(4-oxaspiro[2.4]heptan-6-yl)-1H-benzo[d]imidazole-6-carboxylic acid 2-(4-(6-((4-cyano-2-fluorobenzyl)oxy)pyridin-2-yl)-2,5-difluorobenzyl)-1-(4-oxaspiro[2.4]heptan-6-yl)-1H-benzo[d]imidazole-6-carboxylic acid was prepared in a manner as described in Procedure 22, starting with Intermediates I-7 and I-1072. 1H NMR (400 MHz, DMSO) δ 12.95 (s, 1H), 8.60 (d, J=1.5 Hz, 1H), 7.96-7.86 (m, 3H), 7.82-7.66 (m, 4H), 7.53 (dd, J=7.5, 1.7 Hz, 1H), 7.42 (dd, J=11.5, 6.1 Hz, 1H), 7.00 (d, J=8.2 Hz, 1H), 5.73 (qd, J=7.6, 3.6 Hz, 1H), 5.60 (s, 2H), 4.61 (s, 2H), 4.17 (qd, J=10.2, 5.5 Hz, 2H), 2.51-2.40 (m, 2H), 1.20-1.09 (m, 1H), 0.82 (td, J=10.4, 6.0 Hz, 2H), 0.65-0.54 (m, 1H). ES/MS m/z: 611.2 (M+H$^+$).

Example 204: (S)-2-(4-(6-((4-cyano-2,5-difluorobenzyl)oxy)pyridin-2-yl)-2,5-difluorobenzyl)-1-(4,4-dimethyltetrahydrofuran-3-yl)-4-fluoro-1H-benzo[d]imidazole-6-carboxylic acid (S)-2-(4-(6-((4-cyano-2,5-difluorobenzyl)oxy)pyridin-2-yl)-2,5-difluorobenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1295 and I-108. 1H NMR (400 MHz, DMSO) δ 8.36 (s, 1H), 8.05 (dd, J=9.2, 5.2 Hz, 1H), 7.92 (t, J=7.9 Hz, 1H), 7.77 (ddd, J=12.5, 9.8, 6.1 Hz, 2H), 7.60-7.42 (m, 3H), 7.02 (d, J=8.3 Hz, 1H), 5.60 (s, 2H), 5.04 (d, J=6.6 Hz, 1H), 4.59-4.49 (m, 2H), 4.48-4.35 (m, 2H), 3.75 (q, J=8.7 Hz, 3H), 1.34 (s, 3H), 0.61 (s, 3H). ES/MS m/z: 649.2 (M+H$^+$).

Example 205: (S)-2-(4-(2-((4-cyano-2-fluorobenzyl)oxy)pyrimidin-4-yl)-2,5-difluorobenzyl)-1-(4,4-dimethyltetrahydrofuran-3-yl)-4-fluoro-1H-benzo[d]imidazole-6-carboxylic acid (S)-2-(4-(2-((4-cyano-2-fluorobenzyl)oxy)pyrimidin-4-yl)-2,5-difluorobenzyl)-1-(4,4-dimethyltetrahydrofuran-3- yl)-4-fluoro-1H-benzo[d]imidazole-6-carboxylic acid was prepared in a manner as described in Procedure 35, starting with Intermediates I-1175 and I-108. 1H NMR (400 MHz, DMSO) δ 8.79 (d, J=5.1 Hz, 1H), 8.36 (s, 1H), 7.98-7.89 (m, 2H), 7.83-7.72 (m, 2H), 7.65-7.67 (m, 1H), 7.60-7.48 (m, 2H), 5.64 (s, 2H), 5.04-5.02 (m, 1H), 4.63-4.49 (m, 2H), 4.48-4.37 (m, 2H), 3.75 (q, J=8.7 Hz, 2H), 1.34 (s, 3H), 0.62 (s, 3H). ES/MS m/z: 632.2 (M+H$^+$).

Example 206: (S)-2-(4-(4-((4-cyano-2-fluorobenzyl)oxy)pyrimidin-2-yl)-2,5-difluorobenzyl)-1-(4,4-dimethyltetrahydrofuran-3-yl)-4-fluoro-1H-benzo[d]imidazole-6-carboxylic acid (S)-2-(4-(4-((4-cyano-2-fluorobenzyl)oxy)pyrimidin-2-yl)-2,5-difluorobenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1338 and I-108. 1H NMR (400 MHz, DMSO) δ 8.82-8.71 (m, 1H), 8.36 (s, 1H), 7.98-7.85 (m, 2H), 7.83-7.72 (m, 2H), 7.60-7.43 (m, 2H), 7.08 (d, J=5.8 Hz, 1H), 5.66 (d, J=13.7 Hz, 2H), 5.03 (d, J=6.6 Hz, 1H), 4.63-4.49 (m, 2H), 4.48-4.37 (m, 2H), 3.75 (q, J=8.7 Hz, 2H), 1.34 (d, J=2.8 Hz, 3H), 0.62 (d, J=2.7 Hz, 3H). ES/MS m/z: 632.2 (M+H$^+$).

Example 207: (S)-2-(4-(6-((4-cyano-2-fluorobenzyl)oxy)-5-fluoropyridin-2-yl)-2-fluoro-5-methylbenzyl)-1-(4,4-dimethyltetrahydrofuran-3-yl)-4-fluoro-1H-benzo[d]imidazole-6-carboxylic acid (S)-2-(4-(6-((4-cyano-2-fluorobenzyl)oxy)-5-fluoropyridin-2-yl)-2-fluoro-5-methylbenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-109 and I-1075. 1H NMR (400 MHz, DMSO) δ 13.06 (s, 1H), 8.35 (s, 1H), 7.96-7.89 (m, 1H), 7.85 (dd, J=10.5, 8.1 Hz, 1H), 7.74 (dd, J=3.5, 1.6 Hz, 2H), 7.52 (dd, J=11.2, 1.2 Hz, 1H), 7.34-7.24 (m, 3H), 5.61 (s, 2H), 5.02 (d, J=6.6 Hz, 1H), 4.55-4.38 (m, 3H), 4.34 (d, J=16.8 Hz, 1H), 3.80-3.69 (m, 2H), 2.26 (s, 3H), 1.31 (s, 3H), 0.60 (s, 3H). ES/MS m/z: 645.2 (M+H$^+$).

Example 208: (S)-2-(4-(6-((4-cyano-2-fluorobenzyl)oxy)pyridin-2-yl)-2-fluoro-5-methylbenzyl)-1-(4,4-dimethyltetrahydrofuran-3-yl)-4-fluoro-1H-benzo[d]imidazole-6-carboxylic acid (S)-2-(4-(6-((4-cyano-2-fluorobenzyl)oxy)pyridin-2-yl)-2-fluoro-5-methylbenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-3 and I-1075. 1H NMR (400 MHz, DMSO) δ 8.35 (s, 1H), 7.94-7.86 (m, 2H), 7.75-7.70 (m, 2H), 7.52 (d, 1H), 7.34-7.22 (m, 3H), 6.96 (d, 1H), 5.53 (s, 2H), 5.02 (d, 1H), 4.53-4.41 (m, 3H), 4.34 (d, 1H), 3.77-3.69 (dd, 2H), 2.26 (s, 3H), 1.31 (s, 3H), 0.59 (s, 3H). ES/MS m/z: 627.2 (M+H$^+$).

Example 209: (R)-2-(4-(6-((4-cyano-2-fluorobenzyl)oxy)pyridin-2-yl)-2-fluorobenzyl)-1-(tetrahydrofuran-3-yl)-1H-benzo[d]imidazole-6-carboxylic acid (R)-2-(4-(6-((4-cyano-2-fluorobenzyl)oxy)pyridin-2-yl)-2-fluorobenzyl)-1-(tetrahydrofuran-3-yl)-1H-benzo[d]imidazole-6-carboxylic acid was prepared in a manner as described in Procedure 22, starting with Intermediates I-1110 and I-1329. 1H NMR (400 MHz, MeOD) δ 8.81 (d, J=1.4 Hz, 1H), 8.22 (dd, J=8.6, 1.4 Hz, 1H), 7.97-7.86 (m, 2H), 7.86-7.79 (m, 2H), 7.73 (t, J=7.6 Hz, 1H), 7.61 (dd, J=9.7, 1.5 Hz, 1H), 7.57 (dd, J=7.7, 1.7 Hz, 2H), 7.50 (t, J=7.9 Hz, 1H), 6.92 (d, J=8.3 Hz, 1H), 5.65 (s, 2H), 4.78 (d, J=2.6 Hz, 2H), 4.48 (t, J=8.8 Hz, 1H), 4.40-4.32 (m, 1H), 4.04 (dd, J=11.0, 7.5 Hz, 1H), 3.80 (td, J=9.7, 6.9 Hz, 1H), 2.54 (dt, J=14.3, 7.3 Hz, 1H), 2.35-2.20 (m, 1H). ES/MS m/z: 567.4 (M+H$^+$).

Example 210: (S)-2-(4-(6-((4-cyano-2-fluorobenzyl)oxy)pyridin-2-yl)-2-fluorobenzyl)-1-(tetrahydrofuran-3-yl)-1H-benzo[d]imidazole-6-carboxylic acid (S)-2-(4-(6-((4-cyano-2-fluorobenzyl)oxy)pyridin-2-yl)-2-fluorobenzyl)-1-(tetrahydrofuran-3-yl)-1H-benzo[d]imidazole-6-carboxylic acid was prepared in a manner as described in Procedure 22, starting with Intermediates I-1111 and I-1329. 1H NMR (400 MHz, MeOD) δ 8.84 (d, J=4.2 Hz, 1H), 8.25 (dd, J=8.5, 4.2 Hz, 1H), 8.01-7.87 (m, 2H), 7.82 (t, J=7.7 Hz, 2H), 7.73 (t, J=7.6 Hz, 1H), 7.64-7.49 (m, 4H), 6.93 (d, J=8.2 Hz, 1H), 5.65 (s, 2H), 4.81 (s, 2H), 4.53-4.45 (m, 1H), 4.38 (d, J=11.1 Hz, 1H), 4.06 (dd, J=11.1, 7.5 Hz, 1H), 3.81 (td, J=9.7, 6.7 Hz, 1H), 2.56 (q, J=12.0, 10.2 Hz, 1H), 2.29 (d, J=13.8 Hz, 1H). ES/MS m/z: 567.3 (M+H$^+$).

Example 211: (S)-2-(4-(2-((4-chlorobenzyl)oxy)pyrimidin-4-yl)-2-fluoro-5-methylbenzyl)-1-(4,4-dimethyltetrahydrofuran-3-yl)-4-fluoro-1H-benzo[d]imidazole-6-carboxylic acid (S)-2-(4-(2-((4-chlorobenzyl)oxy)pyrimidin-4-yl)-2-fluoro-5-methylbenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1174 and I-1075. 1H NMR (400 MHz, DMSO-d6) δ 8.73 (d, J=5.0 Hz, 1H), 8.35 (s, 1H), 7.56-7.39 (m, 7H), 7.38 (d, J=7.5 Hz, 1H), 5.46 (s, 2H), 5.03 (d, J=6.6 Hz, 1H), 4.57-4.31 (m, 4H), 3.75 (q, J=8.7 Hz, 2H), 2.36 (s, 3H), 1.32 (s, 3H), 0.61 (s, 3H). ES/MS m/z: 619.3 (M+H$^+$).

Example 212: (S)-2-(2-chloro-4-(2-((4-chlorobenzyl)oxy)pyrimidin-4-yl)-5-methylbenzyl)-1-(4,4-dimethyltetrahydrofuran-3-yl)-4-fluoro-1H-benzo[d]imidazole-6-carboxylic acid (S)-2-(2-chloro-4-(2-((4-chlorobenzyl)oxy)pyrimidin-4-yl)-5-methylbenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1174 and I-1031. 1H NMR (400 MHz, DMSO-d6) δ 8.74 (d, J=5.1 Hz, 1H), 8.36 (s, 1H), 7.63 (s, 1H), 7.55-7.43 (m, 6H), 7.41 (s, 1H), 5.46 (s, 2H), 5.02 (d, J=6.7 Hz, 1H), 4.59 (d, J=17.1 Hz, 1H), 4.52 (d, J=11.1 Hz, 1H), 4.47-4.36 (m, 2H), 3.85-3.68 (m, 2H), 2.37 (s, 3H), 1.34 (s, 3H), 0.66 (s, 3H). ES/MS m/z: 635.0 (M+H$^+$).

Example 213: 2-(4-(6-((4-chloro-6-(1H-1,2,3-triazol-1-yl)pyridin-3-yl)methoxy)-5-fluoropyridin-2-yl)-2,3,6-trifluorobenzyl)-4-fluoro-1-(2-methoxyethyl)-1H-benzo[d]imidazole-6-carboxylic acid 2-(4-(6-((4-chloro-6-(1H-1,2,3-triazol-1-yl)pyridin-3-yl)methoxy)-5-fluoropyridin-2-yl)-2,3,6-trifluorobenzyl)-4-fluoro-1-(2-methoxyethyl)-1H-benzo[d]imidazole-6-carboxylic acid was prepared in a manner as described in Procedure 35, starting with Intermediates I-1050 and I-1135. 1H NMR (400 MHz, DMSO-d6) δ 8.92 (d, J=1.3 Hz, 1H), 8.86 (s, 1H), 8.33 (s, 1H), 8.11 (d, J=1.3 Hz, 1H), 8.04 (d, J=1.2 Hz, 1H), 7.94 (dd, J=10.2, 8.2 Hz, 1H), 7.77 (dd, J=10.4, 5.7 Hz, 1H), 7.69-7.60 (m, 1H), 7.54-7.46 (m, 1H), 5.77 (s, 2H), 4.68 (t, J=5.1 Hz, 2H), 4.55 (s, 2H), 3.73 (t, J=4.9 Hz, 2H), 3.25 (s, 3H). ES/MS m/z: 686.0 (M+H$^+$).

Example 214: 2-(4-(6-((4-chloro-6-(1H-1,2,3-triazol-1-yl)pyridin-3-yl)methoxy)pyridin-2-yl)-2,5-difluorobenzyl)-1-(2-methoxyethyl)-1H-benzo[d]imidazole-6-carboxylic acid 2-(4-(6-((4-chloro-6-(1H-1,2,3-triazol-1-yl)pyridin-3-yl)methoxy)pyridin-2-yl)-2,5-difluorobenzyl)-1-(2-methoxyethyl)-1H-benzo[d]imidazole-6-carboxylic acid was prepared in a manner as described in Procedure 38, starting with Intermediates I-1049 and I-11. 1H NMR (400 MHz, DMSO-d6) δ 8.91 (s, 1H), 8.83 (s, 1H), 8.31 (s, 1H), 8.22 (s, 1H), 8.03 (s, 1H), 7.95-7.84 (m, 2H), 7.80 (d, J=8.7 Hz, 1H), 7.62 (s, 1H), 7.55 (d, J=7.7 Hz, 1H), 7.40 (dd, J=11.6, 6.2 Hz, 1H), 7.01 (d, J=8.4 Hz, 1H), 5.67 (s, 2H), 4.60 (s, 2H), 4.46 (s, 2H), 3.69 (t, J=5.0 Hz, 2H), 3.21 (s, 3H). ES/MS m/z: 632.0 (M+H$^+$).

Example 215: 2-(4-(6-((4-chloro-6-(1H-1,2,3-triazol-1-yl)pyridin-3-yl)methoxy)-5-fluoropyridin-2-yl)-2,5-difluorobenzyl)-1-(2-methoxyethyl)-1H-benzo[d]imidazole-6-carboxylic acid 2-(4-(6-((4-chloro-6-(1H-1,2,3-triazol-1-yl)pyridin-3-yl)methoxy)-5-fluoropyridin-2-yl)-2,5-difluorobenzyl)-1-(2-methoxyethyl)-1H-benzo[d]imidazole-6-carboxylic acid was prepared in a manner as described in Procedure 35, starting with Intermediates I-1050 and I-11. 1H NMR (400 MHz, DMSO-d6) δ 8.91 (d, J=1.3 Hz, 1H), 8.85 (s, 1H), 8.33 (s, 1H), 8.22 (s, 1H), 8.04 (d, J=1.3 Hz, 1H), 7.93-7.83 (m, 2H), 7.83-7.78 (m, 1H), 7.61 (d, J=8.4 Hz, 1H), 7.57 (d, J=8.9 Hz, 1H), 7.41 (dd, J=10.9, 6.5 Hz, 1H), 5.76 (s, 2H), 4.60 (d, J=5.7 Hz, 2H), 4.46 (s, 2H), 3.69 (t, J=5.0 Hz, 2H), 3.21 (s, 3H). ES/MS m/z: 650.0 (M+H$^+$).

Example 216: racemic 2-(4-(6-((4-cyano-2-fluorobenzyl)oxy)pyridin-2-yl)-2,5-difluorobenzyl)-1-((3S,4S)-4-(hydroxymethyl)tetrahydrofuran-3-yl)-1H-benzo[d]imidazole-6-carboxylic acid Racemic 2-(4-(6-((4-cyano-2-fluorobenzyl)oxy)pyridin-2-yl)-2,5-difluorobenzyl)-1-((3S,4S)-4-(hydroxymethyl)tetrahydrofuran-3-yl)-1H-benzo[d]imidazole-6-carboxylic acid was prepared in a manner as described in Procedure 5, starting with Intermediates I-7 and I-1140. 1H NMR (400 MHz, DMSO-d6) δ 8.55 (s, 1H), 7.98-7.85 (m, 2H), 7.85-7.70 (m, 4H), 7.61 (d, J=8.4 Hz, 1H), 7.54 (d, J=7.3 Hz, 1H), 7.37 (dd, J=11.5, 6.0 Hz, 1H), 7.00 (d, J=8.3 Hz, 1H), 5.61 (s, 2H), 5.53 (d, J=7.6 Hz, 1H), 4.55 (s, 2H), 4.50 (d, J=10.8 Hz, 1H), 4.21 (dd, J=10.9, 6.5 Hz, 1H), 4.06 (t, J=8.7 Hz, 1H), 3.80 (t, J=8.3 Hz, 1H), 3.18-3.09 (m, 1H), 3.00 (q, J=7.8 Hz, 1H), 2.75 (t, J=9.5 Hz, 1H). ES/MS m/z: 615.0 (M+H$^+$).

Example 217: racemic 2-(4-(6-((4-cyano-2-fluorobenzyl)oxy)pyridin-2-yl)-2,5-difluorobenzyl)-1-((3S,4R)-4-(hydroxymethyl)tetrahydrofuran-3-yl)-1H-benzo[d]imidazole-6-carboxylic acid Racemic 2-(4-(6-((4-cyano-2-fluorobenzyl)oxy)pyridin-2-yl)-2,5-difluorobenzyl)-1-((3S,4R)-4-(hydroxymethyl)tetrahydrofuran-3-yl)-1H-benzo[d]imidazole-6-carboxylic acid was prepared in a manner as described in Procedure 5, starting with Intermediates I-7 and I-1141. 1H NMR (400 MHz, DMSO-d6) δ 8.42 (s, 1H), 7.96-7.86 (m, 2H), 7.84 (dd, J=8.5, 1.5 Hz, 1H), 7.77 (tt, J=8.8, 4.8 Hz, 3H), 7.65 (d, J=8.5 Hz, 1H), 7.54 (d, J=7.3 Hz, 1H), 7.39 (dd, J=11.5, 6.1 Hz, 1H), 7.00 (d, J=8.3 Hz, 1H), 5.61 (s, 2H), 5.26 (s, 1H), 4.65-4.46 (m, 2H), 4.37 (t, J=8.5 Hz, 1H), 4.21 (dd, J=10.5, 3.2 Hz, 1H), 4.08 (dd, J=10.4, 7.9 Hz, 1H), 3.62-3.46 (m, 3H), 2.76 (d, J=7.3 Hz, 1H). ES/MS m/z: 615.0 (M+H$^+$).

Example 218: (S)-2-(2-chloro-4-(2-((4-chlorobenzyl)oxy)pyrimidin-4-yl)-5-methylbenzyl)-1-(4,4-dimethyltetrahydrofuran-3-yl)-1H-benzo[d]imidazole-6-carboxylic acid (S)-2-(2-chloro-4-(2-((4-chlorobenzyl)oxy)pyrimidin-4-yl)-5-methylbenzyl)-1-(4,4-dimethyltetrahydrofuran-3-yl)-1H-benzo[d]imidazole-6-carboxylic acid was prepared in a manner as described in Procedure 35, starting with Intermediates I-1174 and I-1030. 1H NMR (400 MHz, DMSO-d6) δ 8.74 (d, J=5.0 Hz, 1H), 8.50 (s, 1H), 7.81 (dd, J=8.4, 1.5 Hz, 1H), 7.62 (t, J=4.2 Hz, 2H), 7.55-7.42 (m, 5H), 7.41 (s, 1H), 5.46 (s, 2H), 5.01 (d, J=6.7 Hz, 1H), 4.56 (dd, J=22.6, 14.0 Hz, 2H), 4.49-4.35 (m, 2H), 3.81 (d, J=8.7 Hz, 1H), 3.73 (d, J=8.6 Hz, 1H), 2.36 (s, 3H), 1.34 (s, 3H), 0.66 (s, 3H). ES/MS m/z: 618.0 (M+H$^+$).

Example 219: (S)-2-(4-(2-((4-chlorobenzyl)oxy)pyrimidin-4-yl)-2-fluoro-5-methylbenzyl)-1-(4,4-dimethyltetrahydrofuran-3-yl)-1H-benzo[d]imidazole-6-carboxylic acid (S)-2-(4-(2-((4-chlorobenzyl)oxy)pyrimidin-4-yl)-2-fluoro-5-methylbenzyl)-1-(4,4-dimethyltetrahydrofuran-3-yl)-1H-benzo[d]imidazole-6-carboxylic acid was prepared in a manner as described in Procedure 35, starting with Intermediates I-1174 and I-1076. 1H NMR (400 MHz, DMSO-d6) δ 8.73 (d, J=5.1 Hz, 1H), 8.49 (s, 1H), 7.81 (dd, J=8.5, 1.5 Hz, 1H), 7.62 (d, J=8.5 Hz, 1H), 7.54-7.45 (m, 4H), 7.44-7.33 (m, 3H), 5.45 (s, 2H), 5.01 (d, J=6.7 Hz, 1H), 4.58-4.29 (m, 4H), 3.82-3.67 (m, 2H), 2.36 (s, 3H), 1.32 (s, 3H), 0.60 (s, 3H). ES/MS m/z: 601.0 (M+H$^+$).

Example 220: 2-(4-(6-((4-chloro-2-fluorobenzyl)oxy)pyridin-2-yl)-2,5-difluorobenzyl)-4-fluoro-1-(5-oxaspiro[2.4]heptan-7-yl)-1H-benzo[d]imidazole-6-carboxylic acid 2-(4-(6-((4-chloro-2-fluorobenzyl)oxy)pyridin-2-yl)-2,5-difluorobenzyl)-4-fluoro-1-(5-oxaspiro[2.4]heptan-7-yl)-1H-benzo[d]imidazole-6-carboxylic acid was prepared in a manner as described in Procedure 35, starting with Intermediates I-102 and I-1142. 1H NMR (400 MHz, DMSO-d6) δ 8.39 (s, 1H), 7.92-7.79 (m, 2H), 7.61 (t, J=8.2 Hz, 1H), 7.57-7.45 (m, 3H), 7.43-7.26 (m, 2H), 6.95 (d, J=8.3 Hz, 1H), 5.51 (s, 2H), 5.24 (s, 1H), 4.42 (s, 2H), 4.35-4.23 (m, 2H), 4.03 (d, J=8.9 Hz, 1H), 3.90 (d, J=8.9 Hz, 1H), 1.00-0.44 (m, 3H), −0.11 (s, 1H). ES/MS m/z: 638.0 (M+H$^+$).

Example 221: 2-(4-(6-((6-(1H-1,2,3-triazol-1-yl)pyridin-3-yl)methoxy)pyridin-2-yl)-2,5-difluorobenzyl)-4-fluoro-1-(2-methoxyethyl)-1H-benzo[d]imidazole-6-carboxylic acid 2-(4-(6-((6-(1H-1,2,3-triazol-1-yl)pyridin-3-yl)methoxy)pyridin-2-yl)-2,5-difluorobenzyl)-4-fluoro-1-(2-methoxyethyl)-1H-benzo[d]imidazole-6-carboxylic acid was prepared in a manner as described in Procedure 35, starting with Intermediates I-1268 and I-1033. 1H NMR (400 MHz, DMSO-d6) δ 8.88 (d, J=1.2 Hz, 1H), 8.76 (d, J=2.1 Hz, 1H), 8.25 (dd, J=8.3, 2.2 Hz, 1H), 8.17 (d, J=8.4 Hz, 1H), 8.10 (d, J=1.3 Hz, 1H), 8.00 (d, J=1.2 Hz, 1H), 7.95-7.80 (m, 2H), 7.57-7.47 (m, 2H), 7.40 (dd, J=11.5, 6.1 Hz, 1H), 7.00 (d, J=8.2 Hz, 1H), 5.63 (s, 2H), 4.62 (t, J=5.1 Hz, 2H), 4.47 (s, 2H), 3.68 (t, J=5.0 Hz, 2H), 3.21 (s, 3H). ES/MS m/z: 616.0 (M+H$^+$).

Example 222: 2-(4-(6-((4-(1H-1,2,3-triazol-1-yl)benzyl)oxy)pyridin-2-yl)-2,3,6-trifluorobenzyl)-4-fluoro-1-(2-methoxyethyl)-1H-benzo[d]imidazole-6-carboxylic acid 2-(4-(6-((4-(1H-1,2,3-triazol-1-yl)benzyl)oxy)pyridin-2-yl)-2,3,6-trifluorobenzyl)-4-fluoro-1-(2-methoxyethyl)-1H-benzo[d]imidazole-6-carboxylic acid was prepared in a manner as described in Procedure 35, starting with Intermediates I-1088 and I-1135. 1H NMR (400 MHz, DMSO-d6) δ 8.84 (d, J=1.2 Hz, 1H), 8.11 (d, J=1.3 Hz, 1H), 8.04-7.89 (m, 4H), 7.73 (d, J=8.5 Hz, 3H), 7.63-7.55 (m, 1H), 7.53-7.44 (m, 1H), 7.05 (d, J=8.3 Hz, 1H), 5.58 (s, 2H), 4.68 (t, J=5.2 Hz, 2H), 4.55 (s, 2H), 3.73 (t, J=4.9 Hz, 2H), 3.24 (s, 3H). ES/MS m/z: 633.0 (M+H$^+$).

Example 223: 2-(4-(6-((4-(1H-1,2,3-triazol-1-yl)benzyl)oxy)-5-fluoropyridin-2-yl)-2,3,6-trifluorobenzyl)-4-fluoro-1-(2-methoxyethyl)-1H-benzo[d]imidazole-6-carboxylic acid 2-(4-(6-((4-(1H-1,2,3-triazol-1-yl)benzyl)oxy)-5-fluoropyridin-2-yl)-2,3,6-trifluorobenzyl)-4-fluoro-1-(2-methoxyethyl)-1H-benzo[d]imidazole-6-carboxylic acid was prepared in a manner as described in Procedure 35, starting with Intermediates I-1077 and I-1135. 1H NMR (400 MHz, DMSO-d6) δ 8.84 (d, J=1.2 Hz, 1H), 8.11 (d, J=1.3 Hz, 1H), 8.02-7.86 (m, 4H), 7.73 (dd, J=18.0, 8.6 Hz, 3H), 7.65-7.56 (m, 1H), 7.50 (dd, J=11.4, 1.3 Hz, 1H), 5.67 (s, 2H), 4.68 (t, J=5.0 Hz, 2H), 4.54 (s, 2H), 3.73 (t, J=5.0 Hz, 2H), 3.24 (s, 3H). ES/MS m/z: 651.0 (M+H$^+$).

Example 224: 2-(4-(6-((4-cyano-2-fluorobenzyl)oxy)-5-fluoropyridin-2-yl)-2,5-difluorobenzyl)-4-fluoro-1-(5-oxaspiro[2.4]heptan-7-yl)-1H-benzo[d]imidazole-6-carboxylic acid 2-(4-(6-((4-cyano-2-fluorobenzyl)oxy)-5-fluoropyridin-2-yl)-2,5-difluorobenzyl)-4-fluoro-1-(5-oxaspiro[2.4]heptan-7-yl)-1H-benzo[d]imidazole-6-carboxylic acid was prepared in a manner as described in Procedure 35, starting with Intermediates I-109 and I-1142. 1H NMR (400 MHz, DMSO-d6) δ 8.39 (s, 1H), 8.01-7.93 (m, 1H), 7.87 (dd, J=10.2, 8.2 Hz, 1H), 7.84-7.70 (m, 3H), 7.54 (dd, J=14.2, 10.3 Hz, 2H), 7.37 (dd, J=11.2, 6.3 Hz, 1H), 5.70 (s, 2H), 5.24 (s, 1H), 4.41 (s, 2H), 4.35-4.24 (m, 2H), 4.02 (d, J=8.9 Hz, 1H), 3.90 (d, J=8.9 Hz, 1H), 0.93-0.50 (m, 3H), −0.11 (s, 1H). ES/MS m/z: 647.0 (M+H$^+$).

Example 225: 2-(2-chloro-4-(6-((4-cyano-2-fluorobenzyl)oxy)-5-fluoropyridin-2-yl)-5-methylbenzyl)-4-fluoro-1-(2-methoxyethyl)-1H-benzo[d]imidazole-6-carboxylic acid 2-(2-chloro-4-(6-((4-cyano-2-fluorobenzyl)oxy)-5-fluoropyridin-2-yl)-5-methylbenzyl)-4-fluoro-1-(2-methoxy-ethyl)-1H-benzo[d]imidazole-6-carboxylic acid was prepared in a manner as described in Procedure 35, starting with Intermediates I-109 and I-1339. 1H NMR (400 MHz, DMSO-d6) δ 8.09 (d, J=1.2 Hz, 1H), 7.96-7.91 (m, 1H), 7.85 (dd, J=10.5, 8.1 Hz, 1H), 7.74 (d, J=4.7 Hz, 2H), 7.55-7.47 (m, 1H), 7.43 (s, 1H), 7.31 (d, J=9.4 Hz, 2H), 5.61 (s, 2H), 4.61 (t, J=5.1 Hz, 2H), 4.47 (s, 2H), 3.69 (t, J=5.0 Hz, 2H), 3.22 (s, 3H), 2.25 (s, 3H). ES/MS m/z: 621.0 (M+H$^+$).

Example 226: 2-(4-(6-((4-chloro-6-(1H-1,2,3-triazol-1-yl)pyridin-3-yl)methoxy)pyridin-2-yl)-2,3,6-trifluorobenzyl)-4-fluoro-1-(2-methoxyethyl)-1H-benzo[d]imidazole-6-carboxylic acid 2-(4-(6-((4-chloro-6-(1H-1,2,3-triazol-1-yl)pyridin-3-yl)methoxy)pyridin-2-yl)-2,3,6-trifluorobenzyl)-4-fluoro-1-(2-methoxyethyl)-1H-benzo[d]imidazole-6-carboxylic acid was prepared in a manner as described in Procedure 35, starting with Intermediates I-1049 and I-1135. 1H NMR (400 MHz, DMSO-d6) δ 8.91 (d, J=1.3 Hz, 1H), 8.84 (s, 1H), 8.31 (s, 1H), 8.11 (d, J=1.3 Hz, 1H), 8.03 (d, J=1.3 Hz, 1H), 7.96 (t, J=7.9 Hz, 1H), 7.84-7.74 (m, 1H), 7.61 (d, J=7.3 Hz, 1H), 7.50 (d, J=11.4 Hz, 1H), 7.06 (d, J=8.3 Hz, 1H), 5.68 (s, 2H), 4.68 (t, J=5.1 Hz, 2H), 4.56 (s, 2H), 3.73 (t, J=5.0 Hz, 2H), 3.25 (s, 3H). ES/MS m/z: 668.0 (M+H$^+$).

Example 227: 2-(2-chloro-4-(6-((4-cyano-2-fluorobenzyl)oxy)pyridin-2-yl)-5-methylbenzyl)-4-fluoro-1-(2-methoxyethyl)-1H-benzo[d]imidazole-6-carboxylic acid 2-(2-chloro-4-(6-((4-cyano-2-fluorobenzyl)oxy)pyridin-2-yl)-5-methylbenzyl)-4-fluoro-1-(2-methoxyethyl)-1H-benzo[d]imidazole-6-carboxylic acid was prepared in a manner as described in Procedure 35, starting with Intermediates I-3 and I-1339. 1H NMR (400 MHz, DMSO-d6) δ 8.09 (d, J=1.3 Hz, 1H), 7.95-7.84 (m, 2H), 7.72 (d, J=5.8 Hz, 2H), 7.50 (dd, J=11.4, 1.3 Hz, 1H), 7.43 (s, 1H), 7.29 (s, 1H), 7.27 (d, J=7.3 Hz, 1H), 6.96 (d, J=8.3 Hz, 1H), 5.52 (s, 2H), 4.60 (t, J=5.1 Hz, 2H), 4.47 (s, 2H), 3.68 (t, J=5.0 Hz, 2H), 3.22 (s, 3H), 2.25 (s, 3H). ES/MS m/z: 603.0 (M+H$^+$).

Example 228: (S)-2-(4-(6-((4-chlorobenzyl)oxy)-5-fluoropyridin-2-yl)-2,5-difluorobenzyl)-1-(4,4-dimethyltetrahydrofuran-3-yl)-4-fluoro-1H-benzo[d]imidazole-6-carboxylic acid (S)-2-(4-(6-((4-chlorobenzyl)oxy)-5-fluoropyridin-2-yl)-2,5-difluorobenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1246 and I-108. 1H NMR (400 MHz, DMSO-d6) δ 8.35 (s, 1H), 7.83 (ddd, J=20.6, 10.3, 7.3 Hz, 2H), 7.59-7.50 (m, 4H), 7.50-7.43 (m, 3H), 5.57 (s, 2H), 5.04 (d, J=6.8 Hz, 1H), 4.64-4.49 (m, 2H), 4.49-4.33 (m, 2H), 3.75 (q, J=8.7 Hz, 2H), 1.34 (s, 3H), 0.62 (s, 3H). ES/MS m/z: 640.1 (M+H$^+$).

Example 229: (S)-2-(4-(2-((4-chlorobenzyl)oxy)pyrimidin-4-yl)-2,3,6-trifluorobenzyl)-1-(4,4-dimethyltetrahydrofuran-3-yl)-4-fluoro-1H-benzo[d]imidazole-6-carboxylic acid (S)-2-(4-(2-((4-chlorobenzyl)oxy)pyrimidin-4-yl)-2,3,6-trifluorobenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1174 and I-1232. 1H NMR (400 MHz, DMSO-d6) δ 8.84 (d, J=5.1 Hz, 1H), 8.36 (s, 1H), 7.90-7.79 (m, 1H), 7.69 (dd, J=5.1, 1.7 Hz, 1H), 7.60-7.41 (m, 5H), 5.52 (s, 2H), 5.11 (d, J=6.5 Hz, 1H), 4.70 (d, J=17.4 Hz, 1H), 4.56 (d, J=11.5 Hz, 1H), 4.52-4.31 (m, 2H), 3.76 (s, 2H), 1.40 (s, 3H), 0.67 (s, 3H). ES/MS m/z: 641.6 (M+H$^+$).

Example 230: (S)-2-(4-(2-((4-chlorobenzyl)oxy) pyrimidin-4-yl)-2,5-difluorobenzyl)-1-(4,4-dimethyltetrahydrofuran-3-yl)-4-fluoro-1H-benzo[d]imidazole-6-carboxylic acid (S)-2-(4-(2-((4-chlorobenzyl)oxy)pyrimidin-4-yl)-2,5-difluorobenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1174 and I-108. 1H NMR (400 MHz, DMSO-d6) δ 8.78 (d, J=5.1 Hz, 1H), 8.36 (s, 1H), 7.95 (dd, J=10.2, 6.2 Hz, 1H), 7.63 (dd, J=5.3, 1.8 Hz, 1H), 7.59-7.49 (m, 4H), 7.47 (d, J=8.4 Hz, 2H), 5.51 (s, 2H), 5.04 (d, J=6.5 Hz, 1H), 4.56 (dd, J=22.4, 14.1 Hz, 2H), 4.49-4.35 (m, 2H), 3.75 (q, J=8.6 Hz, 2H), 1.34 (s, 3H), 0.62 (s, 3H). ES/MS m/z: 623.6 (M+H$^+$).

Example 231: (S)-2-(4-(2-((4-chlorobenzyl)oxy) pyrimidin-4-yl)-2,5-difluorobenzyl)-1-(4,4-dimethyltetrahydrofuran-3-yl)-1H-benzo[d]imidazole-6-carboxylic acid (S)-2-(4-(2-((4-chlorobenzyl)oxy)pyrimidin-4-yl)-2,5-difluorobenzyl)-1-(4,4-dimethyltetrahydrofuran-3-yl)-1H-benzo[d]imidazole-6-carboxylic acid was prepared in a manner as described in Procedure 35, starting with Intermediates I-1174 and I-82. 1H NMR (400 MHz, DMSO-d6) δ 8.78 (d, J=5.2 Hz, 1H), 8.48 (s, 1H), 7.93 (dd, J=10.2, 6.2 Hz, 1H), 7.79 (dd, J=8.5, 1.4 Hz, 1H), 7.65-7.59 (m, 2H), 7.59-7.51 (m, 3H), 7.47 (d, J=8.5 Hz, 2H), 5.51 (s, 2H), 5.01 (d, J=6.5 Hz, 1H), 4.61-4.49 (m, 2H), 4.49-4.34 (m, 2H), 3.76 (q, J=8.6 Hz, 2H), 1.34 (s, 3H), 0.61 (s, 3H). ES/MS m/z: 606.6 (M+H$^+$).

Example 232: 2-(4-(6-((4-cyano-2-fluorobenzyl) oxy)-5-fluoropyridin-2-yl)-2,3,6-trifluorobenzyl)-4-fluoro-1-(2-methoxyethyl)-1H-benzo[d]imidazole-6-carboxylic acid 2-(4-(6-((4-cyano-2-fluorobenzyl)oxy)-5-fluoropyridin-2-yl)-2,3,6-trifluorobenzyl)-4-fluoro-1-(2-methoxyethyl)-1H-benzo[d]imidazole-6-carboxylic acid was prepared in a manner as described in Procedure 35, starting with Intermediates I-109 and I-1135. 1H NMR (400 MHz, DMSO-d6) δ 8.11 (d, J=1.3 Hz, 1H), 7.97-7.86 (m, 2H), 7.83-7.74 (m, 2H), 7.64 (ddt, J=16.9, 8.4, 1.7 Hz, 2H), 7.50 (dd, J=11.4, 1.3 Hz, 1H), 5.70 (s, 2H), 4.68 (t, J=5.1 Hz, 2H), 4.54 (s, 2H), 3.73 (t, J=5.0 Hz, 2H), 3.24 (s, 3H). ES/MS m/z: 626.6 (M+H$^+$).

Example 233: 2-(4-(6-((4-cyano-2-fluorobenzyl) oxy)pyridin-2-yl)-2,5-difluorobenzyl)-1-((3S,4R)-4-(difluoromethyl)tetrahydrofuran-3-yl)-1H-benzo[d] imidazole-6-carboxylic acid 2-(4-(6-((4-cyano-2-fluorobenzyl)oxy)pyridin-2-yl)-2,5-difluorobenzyl)-1-((3S,4R)-4-(difluoromethyl)tetrahydrofuran-3-yl)-1H-benzo[d]imidazole-6-carboxylic acid was prepared via preparative chiral SFC (Daicel Chiralpak AD-H column, EtOH/CO$_2$) of Example 287, as the earlier-eluting of two stereoisomers. 1H NMR (400 MHz, DMSO-d6) δ 8.55 (s, 1H), 7.97-7.87 (m, 2H), 7.84-7.71 (m, 4H), 7.61 (d, J=8.5 Hz, 1H), 7.54 (dd, J=7.5, 1.7 Hz, 1H), 7.39 (dd, J=11.4, 6.1 Hz, 1H), 7.00 (d, J=8.3 Hz, 1H), 5.82-5.40 (m, 3H), 4.62-4.49 (m, 2H), 4.40 (d, J=17.0 Hz, 1H), 4.29-4.13 (m, 2H), 4.09 (t, J=9.1 Hz, 1H), 3.58-3.49 (m, 2H). ES/MS m/z: 634.6 (M+H$^+$).

Example 234: 2-(4-(6-((4-cyano-2-fluorobenzyl) oxy)pyridin-2-yl)-2,5-difluorobenzyl)-1-((3R,4S)-4-(difluoromethyl)tetrahydrofuran-3-yl)-1H-benzo[d] imidazole-6-carboxylic acid 2-(4-(6-((4-cyano-2-fluorobenzyl)oxy)pyridin-2-yl)-2,5-difluorobenzyl)-1-((3R,4S)-4-(difluoromethyl)tetrahydrofuran-3-yl)-1H-benzo[d]imidazole-6-carboxylic acid was prepared via preparative chiral SFC (Daicel Chiralpak AD-H column, EtOH/CO$_2$) of Example 287, as the later-eluting of two stereoisomers. 1H NMR (400 MHz, DMSO-d6) δ 8.55 (s, 1H), 7.97-7.87 (m, 2H), 7.84-7.71 (m, 4H), 7.61 (d, J=8.5 Hz, 1H), 7.54 (dd, J=7.5, 1.7 Hz, 1H), 7.39 (dd, J=11.4, 6.1 Hz, 1H), 7.00 (d, J=8.3 Hz, 1H), 5.82-5.40 (m, 3H), 4.62-4.49 (m, 2H), 4.40 (d, J=17.0 Hz, 1H), 4.29-4.13 (m, 2H), 4.09 (t, J=9.1 Hz, 1H), 3.58-3.49 (m, 2H). ES/MS m/z: 634.6 (M+H$^+$).

Example 235: (S)-1-(4,4-dimethyltetrahydrofuran-3-yl)-4-fluoro-2-(2-fluoro-4-(5-fluoro-6-((2-fluoro-4-(1H-1,2,3-triazol-1-yl)benzyl)oxy)pyridin-2-yl)benzyl)-1H-benzo[d]imidazole-6-carboxylic acid (S)-1-(4,4-dimethyltetrahydrofuran-3-yl)-4-fluoro-2-(2-fluoro-4-(5-fluoro-6-((2-fluoro-4-(1H-1,2,3-triazol-1-yl) benzyl)oxy)pyridin-2-yl)benzyl)-1H-benzo[d]imidazole-6-carboxylic acid was prepared in a manner as described in Procedure 35, starting with Intermediates I-1340 and I-1230. 1H NMR (400 MHz, DMSO-d6) δ 8.90 (d, J=1.2 Hz, 1H), 8.35 (s, 1H), 8.01 (d, J=1.2 Hz, 1H), 7.99-7.90 (m, 3H), 7.90-7.79 (m, 3H), 7.72 (dd, J=8.3, 2.8 Hz, 1H), 7.56-7.46 (m, 2H), 5.71 (s, 2H), 5.01 (d, J=6.5 Hz, 1H), 4.59-4.46 (m, 2H), 4.46-4.34 (m, 2H), 3.82-3.69 (m, 2H), 1.30 (s, 3H), 0.58 (s, 3H). ES/MS m/z: 673.3 (M+H$^+$).

Example 236: (S)-1-(4,4-dimethyltetrahydrofuran-3-yl)-2-(2-fluoro-4-(5-fluoro-6-((2-fluoro-4-(1H-1,2,3-triazol-1-yl)benzyl)oxy)pyridin-2-yl)benzyl)-1H-benzo[d]imidazole-6-carboxylic acid (S)-1-(4,4-dimethyltetrahydrofuran-3-yl)-2-(2-fluoro-4-(5-fluoro-6-((2-fluoro-4-(1H-1,2,3-triazol-1-yl)benzyl)oxy) pyridin-2-yl)benzyl)-1H-benzo[d]imidazole-6-carboxylic acid was prepared in a manner as described in Procedure 35, starting with Intermediates I-1340 and I-1229. 1H NMR (400 MHz, DMSO-d6) δ 8.90 (d, J=1.3 Hz, 1H), 8.50 (s, 1H), 8.01 (d, J=1.2 Hz, 1H), 7.99-7.90 (m, 3H), 7.90-7.81 (m, 4H), 7.72 (dd, J=8.2, 2.7 Hz, 1H), 7.63 (d, J=8.5 Hz, 1H), 7.51 (t, J=8.1 Hz, 1H), 5.71 (s, 2H), 5.01 (d, J=6.7 Hz, 1H), 4.63-4.49 (m, 2H), 4.49-4.37 (m, 2H), 3.83-3.67 (m, 2H), 1.30 (s, 3H), 0.58 (s, 3H). ES/MS m/z: 655.4 (M+H$^+$).

Example 237: (S)-2-(2,5-difluoro-4-(6-((3-fluoro-5-methylpyridin-2-yl)methoxy)pyridin-2-yl)benzyl)-1-(4,4-dimethyltetrahydrofuran-3-yl)-1H-benzo[d] imidazole-6-carboxylic acid (S)-2-(2,5-difluoro-4-(6-((3-fluoro-5-methylpyridin-2-yl) methoxy)pyridin-2-yl)benzyl)-1-(4,4-dimethyltetrahydrofuran-3-yl)-1H-benzo[d]imidazole-6-carboxylic acid was prepared in a manner as described in Procedure 35, starting with Intermediates I-1143 and I-82. 1H NMR (400 MHz, DMSO-d6) δ 8.51 (s, 1H), 8.29 (s, 1H), 7.93-7.79 (m, 3H), 7.63 (dd, J=11.7, 9.4 Hz, 2H), 7.53 (dd, J=7.5, 1.6 Hz, 1H), 7.46 (dd, J=11.5, 6.0 Hz, 1H), 6.94 (d, J=8.3 Hz, 1H), 5.56 (d, J=1.8 Hz, 2H), 5.04 (d, J=6.6 Hz, 1H), 4.61-4.50 (m, 2H), 4.49-4.36 (m, 2H), 3.86-3.57 (m, 2H), 2.34 (s, 3H), 1.33 (s, 3H), 0.61 (s, 3H). ES/MS m/z: 603.4 (M+H$^+$).

Example 238: 2-(4-(6-((4-cyano-2-fluorobenzyl)oxy)pyridin-2-yl)-2,5-difluorobenzyl)-4-fluoro-1-((3R,4R)-4-methoxytetrahydrofuran-3-yl)-1H-benzo[d]imidazole-6-carboxylic acid 2-(4-(6-((4-cyano-2-fluorobenzyl)oxy)pyridin-2-yl)-2,5-difluorobenzyl)-4-fluoro-1-((3R,4R)-4-methoxytetrahydrofuran-3-yl)-1H-benzo[d]imidazole-6-carboxylic acid was prepared was prepared via preparative chiral SFC (Daicel AD-H column, MeOH/CO$_2$) of Example 256, as the later-eluting of two stereoisomers. 1H NMR (400 MHz, DMSO-d6) δ 8.27 (d, J=1.3 Hz, 1H), 7.99-7.83 (m, 2H), 7.83-7.68 (m, 3H), 7.53 (dd, J=7.5, 1.7 Hz, 1H), 7.49 (dd, J=11.2, 1.3 Hz, 1H), 7.31 (dd, J=11.5, 6.1 Hz, 1H), 7.00 (d, J=8.2 Hz, 1H), 5.73-5.47 (m, 3H), 4.53 (s, 2H), 4.40 (dd, J=10.7, 3.4 Hz, 1H), 4.17-4.09 (m, 2H), 4.01 (dd, J=10.6, 8.2 Hz, 1H), 3.78 (dd, J=10.5, 4.6 Hz, 1H), 2.87 (s, 3H). ES/MS m/z: 633.0 (M+H$^+$).

Example 239: 2-(4-(6-((4-cyano-2-fluorobenzyl)oxy)pyridin-2-yl)-2,5-difluorobenzyl)-4-fluoro-1-((3S,4S)-4-methoxytetrahydrofuran-3-yl)-1H-benzo[d]imidazole-6-carboxylic acid 2-(4-(6-((4-cyano-2-fluorobenzyl)oxy)pyridin-2-yl)-2,5-difluorobenzyl)-4-fluoro-1-((3S,4S)-4-methoxytetrahydrofuran-3-yl)-1H-benzo[d]imidazole-6-carboxylic acid was prepared was prepared was prepared via preparative chiral SFC (Daicel AD-H column, MeOH/CO$_2$) of Example 256, as the earlier-eluting of two stereoisomers. 1H NMR (400 MHz, DMSO-d6) δ 8.27 (d, J=1.3 Hz, 1H), 7.99-7.83 (m, 2H), 7.83-7.68 (m, 3H), 7.53 (dd, J=7.5, 1.7 Hz, 1H), 7.49 (dd, J=11.2, 1.3 Hz, 1H), 7.31 (dd, J=11.5, 6.1 Hz, 1H), 7.00 (d, J=8.2 Hz, 1H), 5.73-5.47 (m, 3H), 4.53 (s, 2H), 4.40 (dd, J=10.7, 3.4 Hz, 1H), 4.17-4.09 (m, 2H), 4.01 (dd, J=10.6, 8.2 Hz, 1H), 3.78 (dd, J=10.5, 4.6 Hz, 1H), 2.87 (s, 3H). ES/MS m/z: 633.0 (M+H$^+$).

Example 240: (S)-2-(2,5-difluoro-4-(6-((2-(methylsulfonyl)isoindolin-5-yl)methoxy)pyridin-2-yl)benzyl)-1-(4,4-dimethyltetrahydrofuran-3-yl)-4-fluoro-1H-benzo[d]imidazole-6-carboxylic acid (S)-2-(2,5-difluoro-4-(6-((2-(methylsulfonyl)isoindolin-5-yl)methoxy)pyridin-2-yl)benzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1022 and I-108. 1H NMR (400 MHz, DMSO-d6) δ 8.36 (s, 1H), 7.94-7.78 (m, 2H), 7.55-7.42 (m, 5H), 7.35 (d, J=7.8 Hz, 1H), 6.94 (d, J=8.3 Hz, 1H), 5.49 (s, 2H), 5.04 (d, J=6.5 Hz, 1H), 4.64 (d, J=3.4 Hz, 4H), 4.60-4.34 (m, 4H), 3.75 (q, J=8.7 Hz, 2H), 2.96 (s, 3H), 1.34 (s, 3H), 0.62 (s, 3H). ES/MS m/z: 706.6 (M+H$^+$).

Example 241: (S)-1-(4,4-dimethyltetrahydrofuran-3-yl)-4-fluoro-2-(2,3,6-trifluoro-4-(6-((2-fluoro-4-(1H-1,2,3-triazol-1-yl)benzyl)oxy)pyridin-2-yl)benzyl)-1H-benzo[d]imidazole-6-carboxylic acid (S)-1-(4,4-dimethyltetrahydrofuran-3-yl)-4-fluoro-2-(2,3,6-trifluoro-4-(6-((2-fluoro-4-(1H-1,2,3-triazol-1-yl)benzyl)oxy)pyridin-2-yl)benzyl)-1H-benzo[d]imidazole-6-carboxylic acid was prepared in a manner as described in Procedure 35, starting with Intermediates I-1283 and I-1232. 1H NMR (400 MHz, DMSO-d6) δ 8.90 (d, J=1.2 Hz, 1H), 8.36 (s, 1H), 8.01 (d, J=1.2 Hz, 1H), 7.97-7.89 (m, 2H), 7.89-7.74 (m, 3H), 7.64-7.58 (m, 1H), 7.51 (dd, J=11.2, 1.2 Hz, 1H), 7.04 (d, J=8.3 Hz, 1H), 5.61 (s, 2H), 5.11 (d, J=6.4 Hz, 1H), 4.67 (d, J=17.4 Hz, 1H), 4.56 (d, J=11.3 Hz, 1H), 4.46 (dd, J=11.3, 6.6 Hz, 1H), 4.38 (d, J=17.5 Hz, 1H), 3.76 (s, 2H), 1.39 (s, 3H), 0.67 (s, 3H). ES/MS m/z: 690.6 (M+H$^+$).

Example 242: (S)-2-(4-(6-((4-chloro-2-fluorobenzyl)oxy)pyridin-2-yl)-2,3,6-trifluorobenzyl)-1-(4,4-dimethyltetrahydrofuran-3-yl)-4-fluoro-1H-benzo[d]imidazole-6-carboxylic acid (S)-2-(4-(6-((4-chloro-2-fluorobenzyl)oxy)pyridin-2-yl)-2,3,6-trifluorobenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-102 and I-1232. 1H NMR (400 MHz, DMSO-d6) δ 8.36 (s, 1H), 7.93 (t, J=7.9 Hz, 1H), 7.76 (ddd, J=10.4, 5.7, 2.0 Hz, 1H), 7.65-7.57 (m, 2H), 7.51 (ddd, J=10.0, 5.3, 1.6 Hz, 2H), 7.33 (dd, J=8.3, 2.0 Hz, 1H), 7.01 (d, J=8.3 Hz, 1H), 5.52 (s, 2H), 5.11 (d, J=6.4 Hz, 1H), 4.67 (d, J=17.4 Hz, 1H), 4.56 (d, J=11.3 Hz, 1H), 4.46 (dd, J=11.3, 6.7 Hz, 1H), 4.38 (d, J=17.4 Hz, 1H), 3.76 (s, 2H), 1.39 (s, 3H), 0.67 (s, 3H). ES/MS m/z: 659.5 (M+H$^+$).

Example 243: (S)-2-(4-(6-((4-chlorobenzyl)oxy)pyridin-2-yl)-2,3,6-trifluorobenzyl)-1-(4,4-dimethyltetrahydrofuran-3-yl)-4-fluoro-1H-benzo[d]imidazole-6-carboxylic acid (S)-2-(4-(6-((4-chlorobenzyl)oxy)pyridin-2-yl)-2,3,6-trifluorobenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1248 and I-1232. 1H NMR (400 MHz, DMSO-d6) δ 8.36 (s, 1H), 7.93 (t, J=7.9 Hz, 1H), 7.73 (ddd, J=10.7, 5.6, 1.9 Hz, 1H), 7.57 (dd, J=7.4, 1.7 Hz, 1H), 7.55-7.49 (m, 3H), 7.46 (d, J=8.5 Hz, 2H), 7.01 (d, J=8.3 Hz, 1H), 5.49 (s, 2H), 5.11 (d, J=6.5 Hz, 1H), 4.67 (d, J=17.4 Hz, 1H), 4.56 (d, J=11.2 Hz, 1H), 4.46 (dd, J=11.3, 6.6 Hz, 1H), 4.37 (d, J=17.4 Hz, 1H), 3.76 (s, 2H), 1.39 (s, 3H), 0.67 (s, 3H). ES/MS m/z: 641.6 (M+H$^+$).

Example 244: (S)-2-(4-(6-((4-cyanobenzyl)oxy)pyridin-2-yl)-2,3,6-trifluorobenzyl)-1-(4,4-dimethyltetrahydrofuran-3-yl)-4-fluoro-1H-benzo[d]imidazole-6-carboxylic acid (S)-2-(4-(6-((4-cyanobenzyl)oxy)pyridin-2-yl)-2,3,6-trifluorobenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-114 and I-1232. 1H NMR (400 MHz, DMSO-d6) δ 8.36 (s, 1H), 7.96 (d, J=7.7 Hz, 1H), 7.92-7.85 (m, 2H), 7.74-7.62 (m, 3H), 7.61-7.56 (m, 1H), 7.54-7.46 (m, 1H), 7.06 (d, J=8.3 Hz, 1H), 5.60 (s, 2H), 5.11 (d, J=6.5 Hz, 1H), 4.66 (d, J=17.4 Hz, 1H), 4.55 (d, J=11.2 Hz, 1H), 4.46 (dd, J=11.3, 6.6 Hz, 1H), 4.37 (d, J=17.4 Hz, 1H), 3.76 (s, 2H), 1.39 (s, 3H), 0.66 (s, 3H). ES/MS m/z: 630.6 (M+H$^+$).

Example 245: (S)-2-(4-(6-((4-cyanobenzyl)oxy)pyridin-2-yl)-2,3,6-trifluorobenzyl)-1-(4,4-dimethyltetrahydrofuran-3-yl)-1H-benzo[d]imidazole-6-carboxylic acid (S)-2-(4-(6-((4-cyanobenzyl)oxy)pyridin-2-yl)-2,3,6-trifluorobenzyl)-1-(4,4-dimethyltetrahydrofuran-3-yl)-1H- benzo[d]imidazole-6-carboxylic acid was prepared in a manner as described in Procedure 35, starting with Intermediates I-114 and I-1231. 1H NMR (400 MHz, DMSO-d6) δ 8.48 (s, 1H), 7.95 (t, J=7.9 Hz, 1H), 7.88 (d, J=8.2 Hz, 2H), 7.78 (dd, J=8.4, 1.4 Hz, 1H), 7.69 (d, J=8.0 Hz, 2H), 7.68-7.61 (m, 1H), 7.58 (dd, J=8.2, 2.9 Hz, 2H), 7.07 (d, J=8.3 Hz, 1H), 5.59 (s, 2H), 5.09 (d, J=6.6 Hz, 1H), 4.64 (d, J=17.4 Hz, 1H), 4.57 (d, J=11.1 Hz, 1H), 4.47 (dd, J=11.2, 6.8 Hz, 1H), 4.35 (d, J=17.3 Hz, 1H), 3.82-3.72 (m, 2H), 1.39 (s, 3H), 0.66 (s, 3H). ES/MS m/z: 612.6 (M+H+).

Example 246: (S)-2-(4-(6-((4-chlorobenzyl)oxy)pyridin-2-yl)-2,3,6-trifluorobenzyl)-1-(4,4-dimethyltetrahydrofuran-3-yl)-1H-benzo[d]imidazole-6-carboxylic acid (S)-2-(4-(6-((4-chlorobenzyl)oxy)pyridin-2-yl)-2,3,6-trifluorobenzyl)-1-(4,4-dimethyltetrahydrofuran-3-yl)-1H-benzo[d]imidazole-6-carboxylic acid was prepared in a manner as described in Procedure 35, starting with Intermediates I-1248 and I-1231. 1H NMR (400 MHz, DMSO-d6) δ 8.48 (s, 1H), 7.93 (t, J=7.9 Hz, 1H), 7.78 (dd, J=8.4, 1.5 Hz, 1H), 7.71 (ddd, J=10.4, 5.6, 2.0 Hz, 1H), 7.63-7.50 (m, 4H), 7.46 (d, J=8.4 Hz, 2H), 7.02 (d, J=8.3 Hz, 1H), 5.49 (s, 2H), 5.09 (d, J=6.6 Hz, 1H), 4.64 (d, J=17.3 Hz, 1H), 4.57 (d, J=11.1 Hz, 1H), 4.47 (dd, J=11.2, 6.7 Hz, 1H), 4.35 (d, J=17.3 Hz, 1H), 3.83-3.73 (m, 2H), 1.39 (s, 3H), 0.66 (s, 3H). ES/MS m/z: 623.6 (M+H+).

Example 247: (S)-2-(4-(6-((4-chloro-2-fluorobenzyl)oxy)pyridin-2-yl)-2,3,6-trifluorobenzyl)-1-(4,4-dimethyltetrahydrofuran-3-yl)-1H-benzo[d]imidazole-6-carboxylic acid (S)-2-(4-(6-((4-chloro-2-fluorobenzyl)oxy)pyridin-2-yl)-2,3,6-trifluorobenzyl)-1-(4,4-dimethyltetrahydrofuran-3-yl)-1H-benzo[d]imidazole-6-carboxylic acid was prepared in a manner as described in Procedure 35, starting with Intermediates I-102 and I-1231. 1H NMR (400 MHz, DMSO-d6) δ 8.49 (s, 1H), 7.93 (t, J=7.9 Hz, 1H), 7.79 (dd, J=8.5, 1.4 Hz, 1H), 7.77-7.71 (m, 1H), 7.65-7.56 (m, 3H), 7.50 (dd, J=10.0, 2.0 Hz, 1H), 7.34 (dd, J=8.3, 2.0 Hz, 1H), 7.01 (d, J=8.3 Hz, 1H), 5.52 (s, 2H), 5.10 (d, J=6.6 Hz, 1H), 4.66 (d, J=17.3 Hz, 1H), 4.58 (d, J=11.1 Hz, 1H), 4.47 (dd, J=11.2, 6.7 Hz, 1H), 4.37 (d, J=17.3 Hz, 1H), 3.84-3.69 (m, 2H), 1.39 (s, 3H), 0.66 (s, 3H). ES/MS m/z: 641.6 (M+H+).

Example 248: (S)-2-(2,5-difluoro-4-(6-((2-(methylsulfonyl)isoindolin-5-yl)methoxy)pyridin-2-yl)benzyl)-1-(4,4-dimethyltetrahydrofuran-3-yl)-1H-benzo[d]imidazole-6-carboxylic acid (S)-2-(2,5-difluoro-4-(6-((2-(methylsulfonyl)isoindolin-5-yl)methoxy)pyridin-2-yl)benzyl)-1-(4,4-dimethyltetrahydrofuran-3-yl)-1H-benzo[d]imidazole-6-carboxylic acid was prepared in a manner as described in Procedure 35, starting with Intermediates I-1022 and I-82. 1H NMR (400 MHz, DMSO-d6) δ 8.50 (s, 1H), 7.92-7.78 (m, 3H), 7.63 (d, J=8.5 Hz, 1H), 7.56-7.41 (m, 4H), 7.35 (d, J=7.8 Hz, 1H), 6.95 (d, J=8.3 Hz, 1H), 5.48 (s, 2H), 5.03 (d, J=6.7 Hz, 1H), 4.64 (q, J=2.5 Hz, 4H), 4.58-4.51 (m, 2H), 4.49-4.36 (m, 2H), 3.84-3.68 (m, 2H), 2.96 (s, 3H), 1.34 (s, 3H), 0.62 (s, 3H). ES/MS m/z: 688.6 (M+H+).

Example 249 (S)-2-(4-(6-((6-chloro-2-fluoropyridin-3-yl)methoxy)pyridin-2-yl)-2,5-difluorobenzyl)-1-(4,4-dimethyltetrahydrofuran-3-yl)-1H-benzo[d]imidazole-6-carboxylic acid

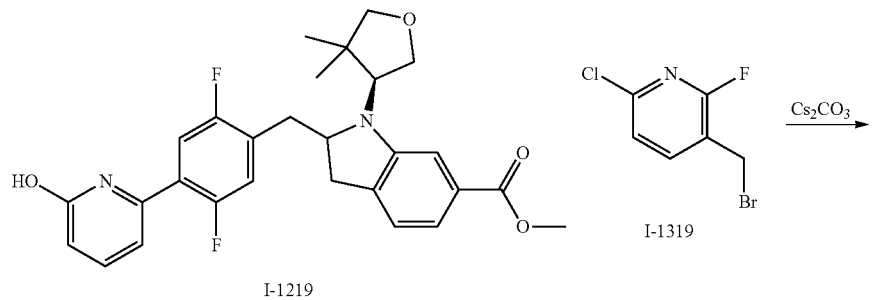

I-1219

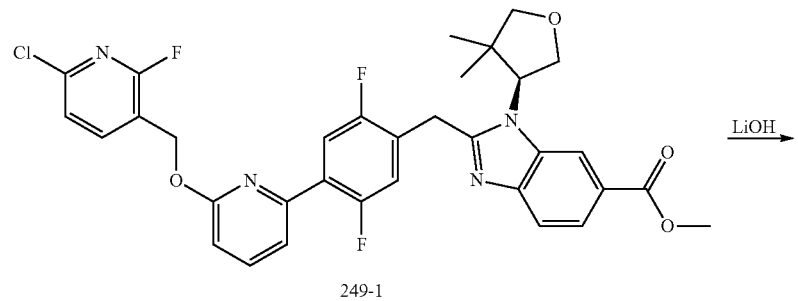

249-1

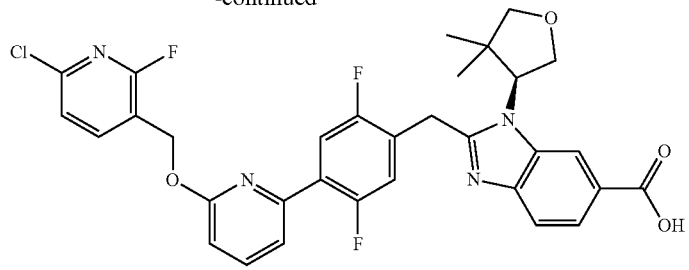

Example 249

(S)-2-(4-(6-((6-chloro-2-fluoropyridin-3-yl)methoxy)pyridin-2-yl)-2,5-difluorobenzyl)-1-(4,4-dimethyltetrahydrofuran-3-yl)-1H-benzo[d]imidazole-6-carboxylic acid (Example 249) was made in a manner similar to that described in Procedure 27, substituting intermediates I-1219 and I-1319.

Methyl (S)-2-(4-(6-((6-chloro-2-fluoropyridin-3-yl)methoxy)pyridin-2-yl)-2,5-difluorobenzyl)-1-(4,4-dimethyltetrahydrofuran-3-yl)-1H-benzo[d]imidazole-6-carboxylate (249-1): ES/MS m/z: 637.9 (M+H$^+$). A mixture of methyl (S)-2-(4-(6-((6-chloro-2-fluoropyridin-3-yl)methoxy)pyridin-2-yl)-2,5-difluorobenzyl)-1-(4,4-dimethyltetrahydrofuran-3-yl)-1H-benzo[d]imidazole-6-carboxylate (249-1, 38 mg, 1.0 equivalent), lithium hydroxide (0.3 M in water, 0.60 mL, 3.0 equivalent) and acetonitrile (0.8 mL) was heated at 105° C. for 4 min. The mixture was quenched with acetic acid and purified by preparative reverse-phase HPLC (acetonitrile/water, 0.1% TFA) to yield the title compound. 1H NMR (400 MHz, DMSO-d6) δ 8.50 (s, 1H), 8.18 (dd, J=9.6, 7.8 Hz, 1H), 7.90 (t, J=7.9 Hz, 1H), 7.87-7.78 (m, 2H), 7.63 (d, J=8.5 Hz, 1H), 7.55 (dd, J=7.8, 2.5 Hz, 2H), 7.47 (dd, J=11.2, 6.3 Hz, 1H), 6.98 (d, J=8.3 Hz, 1H), 5.53 (s, 2H), 5.02 (d, J=6.6 Hz, 1H), 4.59-4.50 (m, 2H), 4.49-4.35 (m, 2H), 3.83-3.70 (m, 2H), 1.34 (s, 3H), 0.61 (s, 3H). ES/MS m/z: 624.6 (M+H$^+$).

(S)-2-(4-(6-((6-chloro-2-fluoropyridin-3-yl)methoxy)pyridin-2-yl)-2,5-difluorobenzyl)-1-(4,4-dimethyltetrahydrofuran-3-yl)-1H-benzo[d]imidazole-6-carboxylic acid (Example 249): 1H NMR (400 MHz, DMSO-d6) δ 8.50 (s, 1H), 8.18 (dd, J=9.6, 7.8 Hz, 1H), 7.90 (t, J=7.9 Hz, 1H), 7.87-7.78 (m, 2H), 7.63 (d, J=8.5 Hz, 1H), 7.55 (dd, J=7.8, 2.5 Hz, 2H), 7.47 (dd, J=11.2, 6.3 Hz, 1H), 6.98 (d, J=8.3 Hz, 1H), 5.53 (s, 2H), 5.02 (d, J=6.6 Hz, 1H), 4.59-4.50 (m, 2H), 4.49-4.35 (m, 2H), 3.83-3.70 (m, 2H), 1.34 (s, 3H), 0.61 (s, 3H). ES/MS m/z: 624.6 (M+H$^+$).

Example 250: 4-fluoro-1-(2-methoxyethyl)-2-(2,3,6-trifluoro-4-(6-((2-fluoro-4-(1H-1,2,3-triazol-1-yl)benzyl)oxy)pyridin-2-yl)benzyl)-1H-benzo[d]imidazole-6-carboxylic acid 4-fluoro-1-(2-methoxyethyl)-2-(2,3,6-trifluoro-4-(6-((2-fluoro-4-(1H-1,2,3-triazol-1-yl)benzyl)oxy)pyridin-2-yl)benzyl)-1H-benzo[d]imidazole-6-carboxylic acid was prepared in a manner as described in Procedure 27, starting with Intermediates I-1282 and I-1136. 1H NMR (400 MHz, DMSO-d6) δ 8.90 (d, J=1.3 Hz, 1H), 8.11 (d, J=1.3 Hz, 1H), 8.03-7.90 (m, 3H), 7.89-7.73 (m, 3H), 7.59 (d, J=7.3 Hz, 1H), 7.50 (d, J=11.3 Hz, 1H), 7.03 (d, J=8.3 Hz, 1H), 5.60 (s, 2H), 4.68 (t, J=5.1 Hz, 2H), 4.55 (s, 2H), 3.73 (t, J=4.9 Hz, 2H), 3.24 (s, 3H). ES/MS m/z: 650.6 (M+H$^+$).

Example 251: 2-(4-(6-((4-chloro-2-fluorobenzyl)oxy)pyridin-2-yl)-2,3,6-trifluorobenzyl)-4-fluoro-1-(2-methoxyethyl)-1H-benzo[d]imidazole-6-carboxylic acid 2-(4-(6-((4-chloro-2-fluorobenzyl)oxy)pyridin-2-yl)-2,3,6-trifluorobenzyl)-4-fluoro-1-(2-methoxyethyl)-1H-benzo[d]imidazole-6-carboxylic acid was prepared in a manner as described in Procedure 27, starting with 4-chloro-2-fluorobenzyl bromide and Intermediate I-1136. 1H NMR (400 MHz, DMSO-d6) δ 8.11 (d, J=1.3 Hz, 1H), 7.93 (t, J=7.9 Hz, 1H), 7.77-7.69 (m, 1H), 7.64-7.56 (m, 2H), 7.54-7.46 (m, 2H), 7.33 (dd, J=8.2, 2.0 Hz, 1H), 7.00 (d, J=8.3 Hz, 1H), 5.52 (s, 2H), 4.68 (t, J=5.1 Hz, 2H), 4.55 (s, 2H), 3.73 (t, J=5.0 Hz, 2H), 3.24 (s, 3H). ES/MS m/z: 617.6 (M+H$^+$).

Procedure 37: Example 252

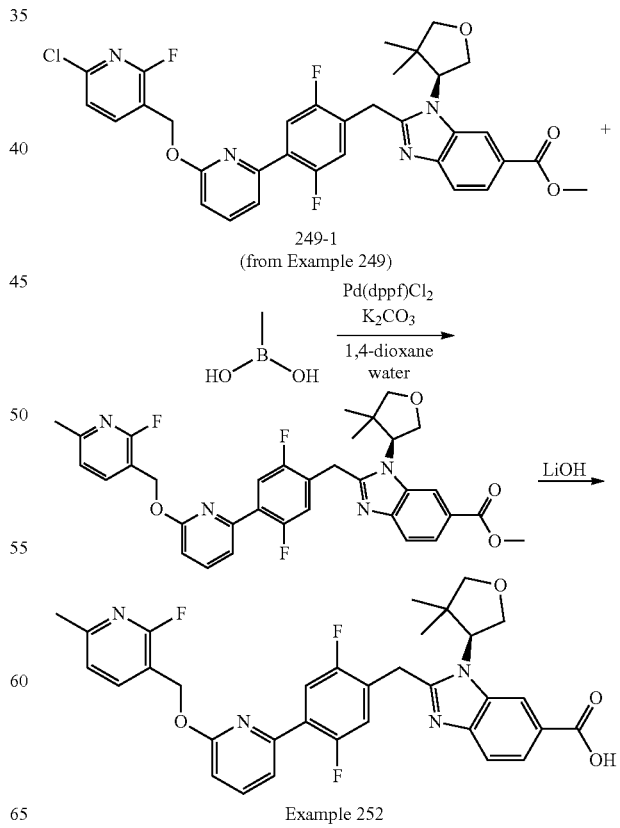

Example 252

Methyl (S)-2-(2,5-difluoro-4-(6-((2-fluoro-6-methylpyridin-3-yl)methoxy)pyridin-2-yl)benzyl)-1-(4,4-dimethyltetrahydrofuran-3-yl)-1H-benzo[d]imidazole-6-carboxylate. A mixture of methyl (S)-2-(4-(6-((6-chloro-2-fluoropyridin-3-yl)methoxy)pyridin-2-yl)-2,5-difluorobenzyl)-1-(4,4-dimethyltetrahydrofuran-3-yl)-1H-benzo[d]imidazole-6-carboxylate (249-1, from Example 249, 35 mg, 1.0 equivalent), methylboronic acid (32.9 mg, 10 equivalent), Pd(dppf)Cl$_2$ (6.1 mg, 0.15 equivalent), potassium carbonate (76 mg, 10 equivalent), and 1,4-dioxane (1.5 mL) was degassed by bubbling through argon for 2 min, then heated to 120° C. in a microwave reactor for 60 min. The mixture was filtered, concentrated in vacuo, and purified by silica gel flash column chromatography to yield methyl (S)-2-(2,5-difluoro-4-(6-((2-fluoro-6-methylpyridin-3-yl)methoxy)pyridin-2-yl)benzyl)-1-(4,4-dimethyltetrahydrofuran-3-yl)-1H-benzo[d]imidazole-6-carboxylate.

(S)-2-(2,5-difluoro-4-(6-((2-fluoro-6-methylpyridin-3-yl)methoxy)pyridin-2-yl)benzyl)-1-(4,4-dimethyltetrahydrofuran-3-yl)-1H-benzo[d]imidazole-6-carboxylic acid (Example 252): Methyl (S)-2-(2,5-difluoro-4-(6-((2-fluoro-6-methylpyridin-3-yl)methoxy)pyridin-2-yl)benzyl)-1-(4,4-dimethyltetrahydrofuran-3-yl)-1H-benzo[d]imidazole-6-carboxylate (31 mg, 1.0 equivalent) was mixed with lithium hydroxide monohydrate (0.3 M in water, 500 μL, 3 equivalent) and acetonitrile (0.8 mL). All components were heated at 105° C. for 4 min. The mixture was neutralized with AcOH, diluted with DMSO, and purified by preparative HPLC (0-100% ACN in H2O, 0.1% TFA) to give the title compound. 1H NMR (400 MHz, DMSO-d6) δ 8.50 (s, 1H), 7.99 (dd, J=10.1, 7.5 Hz, 1H), 7.94-7.78 (m, 3H), 7.64 (d, J=8.4 Hz, 1H), 7.54 (dd, J=7.5, 1.7 Hz, 1H), 7.47 (dd, J=11.3, 6.2 Hz, 1H), 7.24 (dd, J=7.6, 1.9 Hz, 1H), 6.96 (d, J=8.2 Hz, 1H), 5.48 (s, 2H), 5.03 (d, J=6.6 Hz, 1H), 4.62-4.51 (m, 2H), 4.51-4.35 (m, 2H), 3.81-3.69 (m, 2H), 2.43 (s, 3H), 1.34 (s, 3H), 0.61 (s, 3H). ES/MS m/z: 602.6 (M+H$^+$).

Example 253: 2-(4-(6-((6-(1H-1,2,3-triazol-1-yl)pyridin-3-yl)methoxy)pyridin-2-yl)-2,3,6-trifluorobenzyl)-4-fluoro-1-(2-methoxyethyl)-1H-benzo[d]imidazole-6-carboxylic acid 2-(4-(6-((6-(1H-1,2,3-triazol-1-yl)pyridin-3-yl)methoxy)pyridin-2-yl)-2,3,6-trifluorobenzyl)-4-fluoro-1-(2-methoxyethyl)-1H-benzo[d]imidazole-6-carboxylic acid was prepared in a manner as described in Procedure 27, starting with Intermediates I-1341 and I-1136. 1H NMR (400 MHz, DMSO-d6) δ 8.88 (d, J=1.3 Hz, 1H), 8.76 (d, J=2.2 Hz, 1H), 8.26 (dd, J=8.4, 2.2 Hz, 1H), 8.18 (d, J=8.4 Hz, 1H), 8.11 (d, J=1.3 Hz, 1H), 8.03-7.91 (m, 2H), 7.81-7.72 (m, 1H), 7.59 (dd, J=7.5, 1.8 Hz, 1H), 7.54-7.46 (m, 1H), 7.05 (d, J=8.3 Hz, 1H), 5.63 (s, 2H), 4.68 (t, J=5.1 Hz, 2H), 4.55 (s, 2H), 3.73 (t, J=5.0 Hz, 2H), 3.25 (s, 3H). ES/MS m/z: 633.6 (M+H$^+$).

Example 254: (S)-2-(4-(6-((6-(1H-1,2,3-triazol-1-yl)pyridin-3-yl)methoxy)pyridin-2-yl)-2,5-difluorobenzyl)-1-(4,4-dimethyltetrahydrofuran-3-yl)-1H-benzo[d]imidazole-6-carboxylic acid (S)-2-(4-(6-((6-(1H-1,2,3-triazol-1-yl)pyridin-3-yl)methoxy)pyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 35, starting with Intermediates I-1268 and I-82. 1H NMR (400 MHz, DMSO-d6) δ 8.88 (d, J=1.2 Hz, 1H), 8.76 (d, J=2.1 Hz, 1H), 8.49 (s, 1H), 8.26 (dd, J=8.4, 2.2 Hz, 1H), 8.17 (d, J=8.4 Hz, 1H), 8.00 (d, J=1.2 Hz, 1H), 7.96-7.85 (m, 2H), 7.81 (dd, J=8.4, 1.4 Hz, 1H), 7.62 (d, J=8.5 Hz, 1H), 7.55 (d, J=7.4 Hz, 1H), 7.47 (dd, J=10.4, 7.2 Hz, 1H), 7.01 (d, J=8.3 Hz, 1H), 5.63 (s, 2H), 5.02 (d, J=6.7 Hz, 1H), 4.59-4.49 (m, 2H), 4.49-4.30 (m, 2H), 3.78 (d, J=8.7 Hz, 1H), 3.73 (d, J=8.6 Hz, 1H), 1.34 (s, 3H), 0.61 (s, 3H). ES/MS m/z: 638.2 (M+H$^+$).

Example 255: 2-(2-chloro-4-(6-((4-chlorobenzyl)oxy)pyridin-2-yl)-5-fluorobenzyl)-4-fluoro-1-(2-methoxyethyl)-1H-benzo[d]imidazole-6-carboxylic acid 2-(2-chloro-4-(6-((4-chlorobenzyl)oxy)pyridin-2-yl)-5-fluorobenzyl)-4-fluoro-1-(2-methoxyethyl)-1H-benzo[d]imidazole-6-carboxylic acid was prepared in a manner as described in Procedure 35, starting with Intermediates I-1248 and I-1278. 1H NMR (400 MHz, DMSO-d6) δ 8.10 (d, J=1.3 Hz, 1H), 7.98 (d, J=7.2 Hz, 1H), 7.88 (t, J=7.9 Hz, 1H), 7.55-7.48 (m, 4H), 7.48-7.42 (m, 3H), 6.97 (d, J=8.2 Hz, 1H), 5.46 (s, 2H), 4.63 (t, J=5.1 Hz, 2H), 4.52 (s, 2H), 3.70 (t, J=5.0 Hz, 2H), 3.22 (s, 3H). ES/MS m/z: 598.0 (M+H$^+$).

Example 256: racemic 2-(4-(6-((4-cyano-2-fluorobenzyl)oxy)pyridin-2-yl)-2,5-difluorobenzyl)-4-fluoro-1-((4S)-4-methoxytetrahydrofuran-3-yl)-1H-benzo[d]imidazole-6-carboxylic acid Racemic 2-(4-(6-((4-cyano-2-fluorobenzyl)oxy)pyridin-2-yl)-2,5-difluorobenzyl)-4-fluoro-1-((4S)-4-methoxytetrahydrofuran-3-yl)-1H-benzo[d]imidazole-6-carboxylic acid was prepared in a manner as described in Procedure 35, starting with Intermediates I-3 and I-1337. 1H NMR (400 MHz, DMSO-d6) δ 8.27 (d, J=1.3 Hz, 1H), 7.95-7.86 (m, 2H), 7.75 (tdd, J=9.4, 7.2, 3.0 Hz, 3H), 7.53 (dd, J=7.5, 1.7 Hz, 1H), 7.48 (dd, J=11.2, 1.3 Hz, 1H), 7.31 (dd, J=11.5, 6.1 Hz, 1H), 6.99 (d, J=8.2 Hz, 1H), 5.64-5.51 (m, 3H), 4.53 (s, 2H), 4.40 (dd, J=10.6, 3.4 Hz, 1H), 4.13 (td, J=8.8, 7.6, 3.7 Hz, 2H), 4.00 (dd, J=10.6, 8.2 Hz, 1H), 3.78 (dd, J=10.4, 4.6 Hz, 1H), 2.87 (s, 3H). ES/MS m/z: 633.0 (M+H$^+$).

Example 257: (S)-2-(2-chloro-4-(6-((4-cyano-2-fluorobenzyl)oxy)pyridin-2-yl)-5-fluorobenzyl)-1-(4,4-dimethyltetrahydrofuran-3-yl)-1H-benzo[d]imidazole-6-carboxylic acid (S)-2-(2-chloro-4-(6-((4-cyano-2-fluorobenzyl)oxy)pyridin-2-yl)-5-fluorobenzyl)-1-(4,4-dimethyltetrahydrofuran-3-yl)-1H-benzo[d]imidazole-6-carboxylic acid was prepared in a manner as described in Procedure 35, starting with Intermediates I-3 and I-1132. 1H NMR (400 MHz, DMSO-d6) δ 8.51 (s, 1H), 7.97-7.87 (m, 3H), 7.82 (dd, J=8.5, 1.5 Hz, 1H), 7.78-7.70 (m, 2H), 7.63 (d, J=8.5 Hz, 1H), 7.58-7.45 (m, 2H), 7.02 (d, J=8.2 Hz, 1H), 5.60 (s, 2H), 5.02 (d, J=6.7 Hz, 1H), 4.63 (d, J=17.1 Hz, 1H), 4.55 (d, J=11.7 Hz, 1H), 4.49-4.36 (m, 2H), 3.81 (d, J=8.6 Hz, 1H), 3.73 (d, J=8.6 Hz, 1H), 1.35 (s, 3H), 0.66 (s, 3H). ES/MS m/z: 629.0 (M+H$^+$).

Example 258: 2-(2-chloro-5-fluoro-4-(6-((2-(methoxycarbonyl)isoindolin-5-yl)methoxy)pyridin-2-yl)benzyl)-4-fluoro-1-(2-methoxyethyl)-1H-benzo[d]imidazole-6-carboxylic acid 2-(2-chloro-5-fluoro-4-(6-((2-(methoxycarbonyl)isoindolin-5-yl)methoxy)pyridin-2-yl)benzyl)-4-fluoro-1-(2- methoxyethyl)-1H-benzo[d]imidazole-6-carboxylic acid was prepared in a manner as described in Procedure 35, starting with Intermediates I-1016 and I-1278. 1H NMR (400 MHz, DMSO-d6) δ 8.10 (s, 1H), 8.01 (d, J=7.1 Hz, 1H), 7.87 (t, J=7.9 Hz, 1H), 7.56-7.39 (m, 5H), 7.38-7.30 (m, 1H), 6.95 (d, J=8.3 Hz, 1H), 5.47 (s, 2H), 4.64 (t, J=7.8 Hz, 6H), 4.53 (s, 2H), 3.70 (t, J=5.1 Hz, 2H), 3.66 (d, J=2.4 Hz, 3H), 3.22 (s, 3H). ES/MS m/z: 663.0 (M+H$^+$).

Example 259: (R)-2-(4-(6-((4-cyano-2-fluorobenzyl) oxy)pyridin-2-yl)-2,5-difluorobenzyl)-1-(5-oxaspiro [2.4]heptan-7-yl)-1H-benzo[d]imidazole-6-carboxylic acid (R)-2-(4-(6-((4-cyano-2-fluorobenzyl)oxy)pyridin-2-yl)-2,5-difluorobenzyl)-1-(5-oxaspiro[2.4]heptan-7-yl)-1H-benzo[d]imidazole-6-carboxylic acid was prepared via preparative chiral SFC (Daicel AD-H column, MeOH/CO$_2$) of Example 268, as the later-eluting of two stereoisomers. 1H NMR (400 MHz, DMSO-d6) δ 8.57 (s, 1H), 7.98-7.83 (m, 3H), 7.81-7.71 (m, 3H), 7.67 (d, J=8.5 Hz, 1H), 7.53 (dd, J=7.5, 1.6 Hz, 1H), 7.40 (dd, J=11.4, 6.1 Hz, 1H), 7.00 (d, J=8.3 Hz, 1H), 5.60 (s, 2H), 5.27 (s, 1H), 4.47 (s, 2H), 4.37-4.23 (m, 2H), 4.05 (d, J=8.9 Hz, 1H), 3.91 (d, J=8.9 Hz, 1H), 0.75 (dd, J=24.6, 17.1 Hz, 3H), −0.07 (s, 1H). ES/MS m/z: 610.6 (M+H$^+$).

Example 260: (S)-2-(4-(6-((4-cyano-2-fluorobenzyl) oxy)pyridin-2-yl)-2,5-difluorobenzyl)-1-(5-oxaspiro [2.4]heptan-7-yl)-1H-benzo[d]imidazole-6-carboxylic acid (S)-2-(4-(6-((4-cyano-2-fluorobenzyl)oxy)pyridin-2-yl)-2,5-difluorobenzyl)-1-(5-oxaspiro[2.4]heptan-7-yl)-1H-benzo[d]imidazole-6-carboxylic acid was prepared via preparative chiral SFC (Daicel AD-H column, MeOH/CO$_2$) of Example 268, as the earlier-eluting of two stereoisomers. 1H NMR (400 MHz, DMSO-d6) δ 8.57 (s, 1H), 7.98-7.83 (m, 3H), 7.81-7.71 (m, 3H), 7.67 (d, J=8.5 Hz, 1H), 7.53 (dd, J=7.5, 1.6 Hz, 1H), 7.40 (dd, J=11.4, 6.1 Hz, 1H), 7.00 (d, J=8.3 Hz, 1H), 5.60 (s, 2H), 5.27 (s, 1H), 4.47 (s, 2H), 4.37-4.23 (m, 2H), 4.05 (d, J=8.9 Hz, 1H), 3.91 (d, J=8.9 Hz, 1H), 0.75 (dd, J=24.6, 17.1 Hz, 3H), −0.07 (s, 1H). ES/MS m/z: 610.6 (M+H$^+$).

Example 261: 2-(4-(6-((4-cyano-2-fluorobenzyl) oxy)pyridin-2-yl)-2,5-difluorobenzyl)-1-((3S,4S)-4-(difluoromethyl)tetrahydrofuran-3-yl)-1H-benzo[d] imidazole-6-carboxylic acid 2-(4-(6-((4-cyano-2-fluorobenzyl)oxy)pyridin-2-yl)-2,5-difluorobenzyl)-1-((3 S,4S)-4-(difluoromethyl)tetrahydrofuran-3-yl)-1H-benzo[d]imidazole-6-carboxylic acid was prepared via preparative chiral SFC (Daicel AD-H column, EtOH/CO$_2$) of Example 269, as the earlier-eluting of two stereoisomers. 1H NMR (400 MHz, DMSO-d6) δ 8.38 (d, J=1.4 Hz, 1H), 7.96-7.82 (m, 3H), 7.82-7.70 (m, 3H), 7.67 (d, J=8.5 Hz, 1H), 7.54 (dd, J=7.5, 1.6 Hz, 1H), 7.41 (dd, J=11.5, 6.0 Hz, 1H), 7.00 (d, J=8.3 Hz, 1H), 6.41 (td, J=55.8, 4.9 Hz, 1H), 5.65-5.50 (m, 3H), 4.59 (d, J=17.0 Hz, 1H), 4.49 (t, J=8.9 Hz, 1H), 4.41 (d, J=16.9 Hz, 1H), 4.28 (dd, J=10.5, 3.3 Hz, 1H), 4.15 (dd, J=10.5, 7.9 Hz, 1H), 3.81 (t, J=9.2 Hz, 1H), 3.25 (d, J=14.7 Hz, 1H). ES/MS m/z: 635.2 (M+H$^+$).

Example 262: 2-(4-(6-((4-cyano-2-fluorobenzyl) oxy)pyridin-2-yl)-2,5-difluorobenzyl)-1-((3R,4R)-4-(difluoromethyl)tetrahydrofuran-3-yl)-1H-benzo[d] imidazole-6-carboxylic acid 2-(4-(6-((4-cyano-2-fluorobenzyl)oxy)pyridin-2-yl)-2,5-difluorobenzyl)-1-((3R,4R)-4-(difluoromethyl)tetrahydrofuran-3-yl)-1H-benzo[d]imidazole-6-carboxylic acid was prepared via preparative chiral SFC (Daicel AD-H column, EtOH/CO$_2$) of Example 269, as the later-eluting of two stereoisomers. 1H NMR (400 MHz, DMSO-d6) δ 8.38 (d, J=1.4 Hz, 1H), 7.96-7.82 (m, 3H), 7.82-7.70 (m, 3H), 7.67 (d, J=8.5 Hz, 1H), 7.54 (dd, J=7.5, 1.6 Hz, 1H), 7.41 (dd, J=11.5, 6.0 Hz, 1H), 7.00 (d, J=8.3 Hz, 1H), 6.41 (td, J=55.8, 4.9 Hz, 1H), 5.65-5.50 (m, 3H), 4.59 (d, J=17.0 Hz, 1H), 4.49 (t, J=8.9 Hz, 1H), 4.41 (d, J=16.9 Hz, 1H), 4.28 (dd, J=10.5, 3.3 Hz, 1H), 4.15 (dd, J=10.5, 7.9 Hz, 1H), 3.81 (t, J=9.2 Hz, 1H), 3.25 (d, J=14.7 Hz, 1H). ES/MS m/z: 635.2 (M+H$^+$).

Example 263: (S)-2-(2,5-difluoro-4-(6-((2-(methoxycarbonyl)isoindolin-5-yl)methoxy)pyridin-2-yl)benzyl)-1-(4,4-dimethyltetrahydrofuran-3-yl)-4-fluoro-1H-benzo[d]imidazole-6-carboxylic acid (S)-2-(2,5-difluoro-4-(6-((2-(methoxycarbonyl)isoindolin-5-yl)methoxy)pyridin-2-yl)benzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1016 and I-108. 1H NMR (400 MHz, DMSO-d6) δ 8.36 (s, 1H), 7.92-7.76 (m, 2H), 7.57-7.40 (m, 5H), 7.34 (dd, J=10.8, 7.9 Hz, 1H), 6.94 (d, J=8.3 Hz, 1H), 5.48 (s, 2H), 5.04 (d, J=6.6 Hz, 1H), 4.69-4.60 (m, 4H), 4.59-4.49 (m, 2H), 4.48-4.35 (m, 2H), 3.75 (q, J=8.7 Hz, 2H), 3.66 (d, J=3.3 Hz, 3H), 1.34 (s, 3H), 0.62 (s, 3H). ES/MS m/z: 687.2 (M+H$^+$).

Example 264: 2-(2,5-difluoro-4-(6-((3-fluoro-5-(trifluoromethyl)pyridin-2-yl)methoxy)pyridin-2-yl) benzyl)-1-(4,4-dimethyltetrahydrofuran-3-yl)-4-fluoro-1H-benzo[d]imidazole-6-carboxylic acid 2-(2,5-difluoro-4-(6-((3-fluoro-5-(trifluoromethyl)pyridin-2-yl)methoxy)pyridin-2-yl)benzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1129 and I-1336. 1H NMR (400 MHz, DMSO-d6) δ 8.85 (s, 1H), 8.37 (d, J=11.1 Hz, 2H), 7.89 (t, J=7.9 Hz, 1H), 7.60 (dd, J=10.6, 6.4 Hz, 1H), 7.56-7.48 (m, 2H), 7.44 (dd, J=11.5, 6.0 Hz, 1H), 7.00 (d, J=8.2 Hz, 1H), 5.71 (s, 2H), 5.02 (d, J=6.6 Hz, 1H), 4.58-4.48 (m, 2H), 4.46-4.33 (m, 2H), 3.74 (q, J=8.7 Hz, 2H), 1.32 (s, 3H), 0.60 (s, 3H). ES/MS m/z: 675.2 (M+H$^+$).

Example 265: (S)-2-(4-(2-((4-cyano-2-fluorobenzyl) oxy)pyrimidin-4-yl)-2-fluoro-5-methylbenzyl)-1-(4, 4-dimethyltetrahydrofuran-3-yl)-4-fluoro-1H-benzo [d]imidazole-6-carboxylic acid (S)-2-(4-(2-((4-cyano-2-fluorobenzyl)oxy)pyrimidin-4-yl)-2-fluoro-5-methylbenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1175 and I-1075. 1H NMR (400 MHz, DMSO-d6) δ 8.75 (d, J=5.1 Hz, 1H), 8.35 (s, 1H), 7.94 (d, J=10.0 Hz, 1H), 7.80-7.70 (m, 2H), 7.52 (dd, J=11.3, 1.2 Hz, 1H), 7.48 (d, J=5.1 Hz, 1H), 7.42 (d, J=10.5 Hz, 1H), 7.38 (d, J=7.5 Hz, 1H), 5.59 (s, 2H), 5.02 (d, J=6.6 Hz, 1H), 4.56-4.46 (m, 2H), 4.42 (dd, J=11.3, 6.7 Hz, 1H), 4.36 (d, J=16.9 Hz, 1H), 3.77 (d, J=8.7 Hz, 1H), 3.72 (d, J=8.6 Hz, 1H), 2.36 (s, 3H), 1.32 (s, 3H), 0.61 (s, 3H). ES/MS m/z: 628.2 (M+H$^+$).

Example 266: racemic 2-(4-(6-((4-cyano-2-fluorobenzyl)oxy)pyridin-2-yl)-2,5-difluorobenzyl)-1-((3S,4S)-4-methyltetrahydrofuran-3-yl)-1H-benzo[d]imidazole-6-carboxylic acid Racemic 2-(4-(6-((4-cyano-2-fluorobenzyl)oxy)pyridin-2-yl)-2,5-difluorobenzyl)-1-((3S,4S)-4-methyltetrahydrofuran-3-yl)-1H-benzo[d]imidazole-6-carboxylic acid was prepared in a manner as described in Procedure 22, starting with Intermediates I-7 and I-1126. 1H NMR (400 MHz, DMSO-d6) δ 8.39 (d, J=1.5 Hz, 1H), 7.96-7.81 (m, 3H), 7.81-7.71 (m, 3H), 7.68 (d, J=8.5 Hz, 1H), 7.53 (dd, J=7.5, 1.6 Hz, 1H), 7.44 (dd, J=11.5, 6.1 Hz, 1H), 7.00 (d, J=8.2 Hz, 1H), 5.60 (s, 2H), 5.06 (td, J=7.6, 3.6 Hz, 1H), 4.56 (d, J=16.9 Hz, 1H), 4.48 (d, J=16.8 Hz, 1H), 4.37 (t, J=8.2 Hz, 1H), 4.22 (dd, J=10.5, 3.6 Hz, 1H), 4.13 (dd, J=10.5, 8.1 Hz, 1H), 3.38 (t, J=9.4 Hz, 1H), 2.68 (dq, J=9.7, 6.7 Hz, 1H), 1.06 (d, J=6.7 Hz, 3H). ES/MS m/z: 599.2 (M+H$^+$).

Example 267: racemic 2-(4-(6-((4-cyano-2-fluorobenzyl)oxy)pyridin-2-yl)-2,5-difluorobenzyl)-1-((4R)-4-(difluoromethyl)tetrahydrofuran-3-yl)-1H-benzo[d]imidazole-6-carboxylic acid Racemic 2-(4-(6-((4-cyano-2-fluorobenzyl)oxy)pyridin-2-yl)-2,5-difluorobenzyl)-1-((4R)-4-(difluoromethyl)tetrahydrofuran-3-yl)-1H-benzo[d]imidazole-6-carboxylic acid was prepared in a manner as described in Procedure 22, starting with Intermediates I-7 and I-1125. 1H NMR (400 MHz, DMSO-d6) δ 8.55 (s, 1H), 7.97-7.87 (m, 2H), 7.84-7.67 (m, 4H), 7.61 (d, J=8.4 Hz, 1H), 7.54 (dd, J=7.4, 1.7 Hz, 1H), 7.39 (dd, J=11.4, 6.1 Hz, 1H), 7.00 (d, J=8.3 Hz, 1H), 5.80-5.56 (m, 3H), 4.55 (d, J=12.6 Hz, 2H), 4.39 (d, J=17.0 Hz, 1H), 4.27-4.12 (m, 2H), 4.09 (t, J=9.2 Hz, 1H), 3.62-3.39 (m, 2H). ES/MS m/z: 635.2 (M+H$^+$).

Example 268: 2-(4-(6-((4-cyano-2-fluorobenzyl)oxy)pyridin-2-yl)-2,5-difluorobenzyl)-1-(5-oxaspiro[2.4]heptan-7-yl)-1H-benzo[d]imidazole-6-carboxylic acid 2-(4-(6-((4-cyano-2-fluorobenzyl)oxy)pyridin-2-yl)-2,5-difluorobenzyl)-1-(5-oxaspiro[2.4]heptan-7-yl)-1H-benzo[d]imidazole-6-carboxylic acid was prepared in a manner as described in Procedure 22, starting with Intermediates I-7 and I-1124. 1H NMR (400 MHz, DMSO-d6) δ 8.57 (s, 1H), 7.98-7.83 (m, 3H), 7.81-7.71 (m, 3H), 7.67 (d, J=8.5 Hz, 1H), 7.53 (dd, J=7.5, 1.6 Hz, 1H), 7.40 (dd, J=11.4, 6.1 Hz, 1H), 7.00 (d, J=8.3 Hz, 1H), 5.60 (s, 2H), 5.27 (s, 1H), 4.47 (s, 2H), 4.37-4.23 (m, 2H), 4.05 (d, J=8.9 Hz, 1H), 3.91 (d, J=8.9 Hz, 1H), 0.75 (dd, J=24.6, 17.1 Hz, 3H), −0.07 (s, 1H). ES/MS m/z: 611.2 (M+H$^+$).

Example 269: racemic 2-(4-(6-((4-cyano-2-fluorobenzyl)oxy)pyridin-2-yl)-2,5-difluorobenzyl)-1-((3S,4S)-4-(difluoromethyl)tetrahydrofuran-3-yl)-1H-benzo[d]imidazole-6-carboxylic acid Racemic 2-(4-(6-((4-cyano-2-fluorobenzyl)oxy)pyridin-2-yl)-2,5-difluorobenzyl)-1-((3S,4S)-4-(difluoromethyl)tetrahydrofuran-3-yl)-1H-benzo[d]imidazole-6-carboxylic acid was prepared in a manner as described in Procedure 22, starting with Intermediates I-7 and I-1123. 1H NMR (400 MHz, DMSO-d6) δ 8.38 (d, J=1.4 Hz, 1H), 7.96-7.82 (m, 3H), 7.82-7.70 (m, 3H), 7.67 (d, J=8.5 Hz, 1H), 7.54 (dd, J=7.5, 1.6 Hz, 1H), 7.41 (dd, J=11.5, 6.0 Hz, 1H), 7.00 (d, J=8.3 Hz, 1H), 6.41 (td, J=55.8, 4.9 Hz, 1H), 5.65-5.50 (m, 3H), 4.59 (d, J=17.0 Hz, 1H), 4.49 (t, J=8.9 Hz, 1H), 4.41 (d, J=16.9 Hz, 1H), 4.28 (dd, J=10.5, 3.3 Hz, 1H), 4.15 (dd, J=10.5, 7.9 Hz, 1H), 3.81 (t, J=9.2 Hz, 1H), 3.25 (d, J=14.7 Hz, 1H). ES/MS m/z. 635.2 (M+H$^+$).

Example 270: racemic 2-(4-(6-((4-cyano-2-fluorobenzyl)oxy)pyridin-2-yl)-2,5-difluorobenzyl)-1-((1s,4s)-1-methyl-2-oxabicyclo[2.1.1]hexan-4-yl)-1H-benzo[d]imidazole-6-carboxylic acid Racemic 2-(4-(6-((4-cyano-2-fluorobenzyl)oxy)pyridin-2-yl)-2,5-difluorobenzyl)-1-((1S,4S)-1-methyl-2-oxabicyclo[2.1.1]hexan-4-yl)-1H-benzo[d]imidazole-6-carboxylic acid was prepared in a manner as described in Procedure 22, starting with Intermediates I-7 and I-1118. 1H NMR (400 MHz, DMSO-d6) δ 8.09 (d, J=1.4 Hz, 1H), 7.95-7.87 (m, 2H), 7.84-7.74 (m, 4H), 7.64 (d, J=8.4 Hz, 1H), 7.54 (dd, J=7.5, 1.6 Hz, 1H), 7.38 (dd, J=11.5, 6.1 Hz, 1H), 7.00 (d, J=8.2 Hz, 1H), 5.61 (s, 2H), 4.39 (s, 2H), 3.99 (s, 2H), 2.63-2.55 (m, 2H), 1.51 (s, 3H). ES/MS m/z: 611.2 (M+H$^+$).

Example 271: 1-((3-aminotetrahydrofuran-3-yl)methyl)-2-(4-(6-((4-cyano-2-fluorobenzyl)oxy)pyridin-2-yl)-2,5-difluorobenzyl)-1H-benzo[d]imidazole-6-carboxylic acid 1-((3-aminotetrahydrofuran-3-yl)methyl)-2-(4-(6-((4-cyano-2-fluorobenzyl)oxy)pyridin-2-yl)-2,5-difluorobenzyl)-1H-benzo[d]imidazole-6-carboxylic acid was prepared in a manner as described in Procedure 3, starting with Intermediates I-7 and I-1116. 1H NMR (400 MHz, DMSO-d6) δ 8.40 (s, 3H), 8.37 (s, 1H), 7.96-7.88 (m, 2H), 7.84 (dd, J=8.5, 1.4 Hz, 1H), 7.79-7.71 (m, 3H), 7.66 (d, J=8.4 Hz, 1H), 7.56-7.50 (m, 1H), 7.46 (dd, J=11.6, 6.1 Hz, 1H), 7.01 (d, J=8.3 Hz, 1H), 5.60 (s, 2H), 4.80 (s, 2H), 4.41 (s, 2H), 4.00 (q, J=7.9 Hz, 1H), 3.97-3.88 (m, 1H), 3.88-3.79 (m, 2H), 2.37-2.12 (m, 2H).

Example 272: racemic 1-(((5S)-2,6-dioxabicyclo[3.2.1]octan-1-yl)methyl)-2-(4-(6-((4-cyano-2-fluorobenzyl)oxy)pyridin-2-yl)-2,5-difluorobenzyl)-1H-benzo[d]imidazole-6-carboxylic acid Racemic 1-(((5S)-2,6-dioxabicyclo[3.2.1]octan-1-yl)methyl)-2-(4-(6-((4-cyano-2-fluorobenzyl)oxy)pyridin-2-yl)-2,5-difluorobenzyl)-1H-benzo[d]imidazole-6-carboxylic acid was prepared in a manner as described in Procedure 5, starting with Intermediates I-7 and I-1115. 1H NMR (400 MHz, DMSO-d6) δ 8.38 (d, J=1.5 Hz, 1H), 7.94-7.88 (m, 2H), 7.84 (dd, J=8.5, 1.5 Hz, 1H), 7.80-7.70 (m, 3H), 7.63 (d, J=8.4 Hz, 1H), 7.53 (dd, J=7.6, 1.7 Hz, 1H), 7.39 (dd, J=11.5, 6.1 Hz, 1H), 7.00 (d, J=8.2 Hz, 1H), 5.60 (s, 2H), 4.86-4.65 (m, 2H), 4.52 (d, J=4.7 Hz, 3H), 3.98 (d, J=9.3 Hz, 1H), 3.91 (d, J=9.3 Hz, 1H), 2.13 (dd, J=11.0, 6.4 Hz, 1H), 1.64-1.38 (m, 4H). ES/MS m/z: 641.2 (M+H$^+$).

Example 273: 2-(4-(6-((4-cyano-2-fluorobenzyl)oxy)pyridin-2-yl)-2,5-difluorobenzyl)-1-((2-cyclopropyltetrahydrofuran-2-yl)methyl)-1H-benzo[d]imidazole-6-carboxylic acid 2-(4-(6-((4-cyano-2-fluorobenzyl)oxy)pyridin-2-yl)-2,5-difluorobenzyl)-1-((2-cyclopropyltetrahydrofuran-2-yl)methyl)-1H-benzo[d]imidazole-6-carboxylic acid was prepared in a manner as described in Procedure 5, starting with Intermediates I-7 and I-1114. 1H NMR (400 MHz, DMSO-d6) δ 8.43 (d, J=1.5 Hz, 1H), 7.95-7.83 (m, 3H), 7.80-7.71

(m, 3H), 7.64 (d, J=8.4 Hz, 1H), 7.53 (dd, J=7.5, 1.7 Hz, 1H), 7.43 (dd, J=11.5, 6.1 Hz, 1H), 7.00 (d, J=8.2 Hz, 1H), 5.60 (s, 2H), 4.62 (s, 2H), 4.57 (s, 2H), 3.75-3.58 (m, 2H), 1.99-1.86 (m, 2H), 1.86-1.72 (m, 1H), 1.66-1.51 (m, 1H), 1.12 (qd, J=8.1, 5.2 Hz, 1H), 0.31 (dq, J=9.1, 4.4, 3.9 Hz, 1H), 0.26-0.15 (m, 1H), 0.10--0.12 (m, 2H). ES/MS m/z: 639.2 (M+H$^+$).

8.32 (d, J=1.5 Hz, 1H), 7.95-7.83 (m, 3H), 7.80-7.71 (m, 3H), 7.65 (d, J=8.4 Hz, 1H), 7.53 (dd, J=7.5, 1.7 Hz, 1H), 7.43 (dd, J=11.5, 6.1 Hz, 1H), 7.00 (d, J=8.2 Hz, 1H), 5.60 (s, 2H), 4.67 (dd, J=15.2, 2.9 Hz, 1H), 4.62-4.46 (m, 3H), 4.40 (qd, J=7.1, 2.9 Hz, 1H), 3.67 (d, J=8.0 Hz, 1H), 3.51 (d, J=8.0 Hz, 1H), 2.03 (dd, J=12.4, 6.6 Hz, 1H), 1.78 (dd, J=12.3, 7.0 Hz, 1H), 0.70-0.45 (m, 4H). ES/MS m/z: 625.2 (M+H$^+$).

Example 274: 1-(5-oxaspiro[2.4]heptan-6-ylmethyl)-2-(4-(6-((4-cyano-2-fluorobenzyl)oxy)pyridin-2-yl)-2,5-difluorobenzyl)-1H-benzo[d]imidazole-6-carboxylic acid 1-(5-oxaspiro[2.4]heptan-6-ylmethyl)-2-(4-(6-((4-cyano-2-fluorobenzyl)oxy)pyridin-2-yl)-2,5-difluorobenzyl)-1H-benzo[d]imidazole-6-carboxylic acid was prepared in a manner as described in Procedure 5, starting with Intermediates I-7 and I-1113. 1H NMR (400 MHz, DMSO-d6) δ

Example 275: 2-(4-(6-((4-cyano-2-fluorobenzyl)oxy)pyridin-2-yl)-2,5-difluorobenzyl)-1-((3S,4S)-4-methoxytetrahydrofuran-3-yl)-1H-benzo[d]imidazole-6-carboxylic acid Example 276: 2-(4-(6-((4-cyano-2-fluorobenzyl)oxy)pyridin-2-yl)-2,5-difluorobenzyl)-1-((3R,4R)-4-methoxytetrahydrofuran-3-yl)-1H-benzo[d]imidazole-6-carboxylic acid

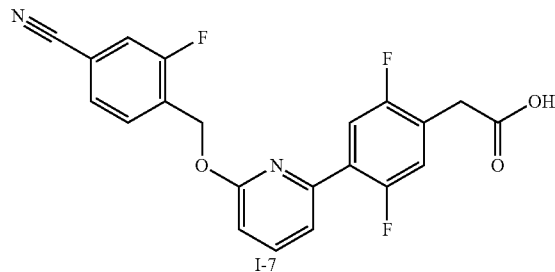
I-7

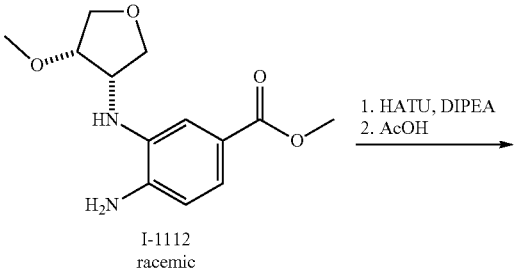
I-1112
racemic

1. HATU, DIPEA
2. AcOH

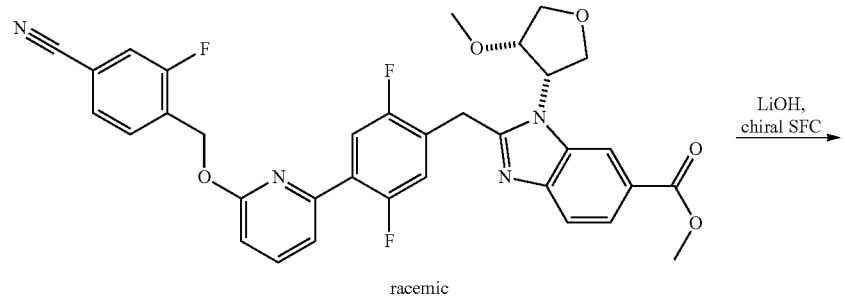
racemic

LiOH, chiral SFC

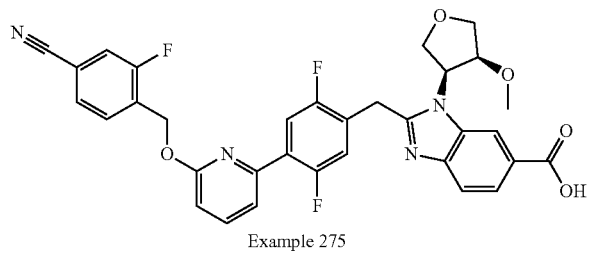
Example 275

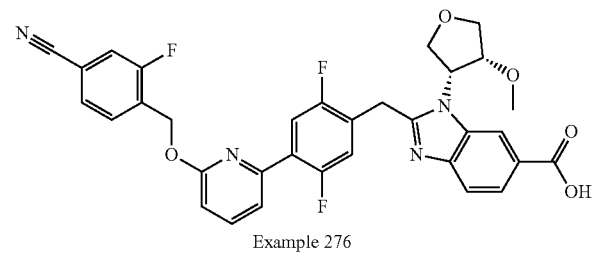
Example 276

Methyl 2-(4-(6-((4-cyano-2-fluorobenzyl)oxy)pyridin-2-yl)-2,5-difluorobenzyl)-1-(cis-4-methoxytetrahydrofuran-3-yl)-1H-benzo[d]imidazole-6-carboxylate: N,N-Diisopropylethylamine (1.2 mL, 6.90 mmol) was added to a solution of 2-[4-[6-[(4-cyano-2-fluoro-phenyl)methoxy]-2-pyridyl]-2,5-difluoro-phenyl]acetic acid (I-7, 550 mg, 1.38 mmol), methyl 4-amino-3-((cis-4-methoxytetrahydrofuran-3-yl)amino)benzoate (I-1112, 368 mg, 1.38 mmol), and o-(7-Azabenzotriazol-1-yl)-N,N,N',N'-tetramethyluronium hexafluorophosphate (630 mg, 1.66 mmol) in DMF (10 mL). The solution was stirred at rt overnight. Following this time, the solution was diluted with EtOAc and washed with 5% LiCl, saturated NaHCO$_3$, and brine. The organic extract was dried over sodium sulfate. The crude residue was purified by flash chromatography (eluent: EtOAc/hexanes). The resulting product was diluted with acetic acid (10 mL). The mixture was heated at 100° C. for 20 hr. Upon completion the mixture was concentrated and purified by flash chromatography (eluent: EtOAc/hexanes) to yield desired product. ES/MS: 629.2 (M+H+)

2-(4-(6-((4-cyano-2-fluorobenzyl)oxy)pyridin-2-yl)-2,5-difluorobenzyl)-1-(cis-4-methoxytetrahydrofuran-3-yl)-1H-benzo[d]imidazole-6-carboxylic acid (Isomer 1, GS-1157494) and 2-(4-(6-((4-cyano-2-fluorobenzyl)oxy)pyridin-2-yl)-2,5-difluorobenzyl)-1-(cis-4-methoxytetrahydrofuran-3-yl)-1H-benzo[d]imidazole-6-carboxylic acid (later-eluting of two stereoisomers, Example 275): Lithium hydroxide, monohydrate (2.0 M, 1.30 mL, 1.30 mmol) was added to a solution of methyl 2-(4-(6-((4-cyano-2-fluorobenzyl)oxy)pyridin-2-yl)-2,5-difluorobenzyl)-1-(cis-4-methoxytetrahydrofuran-3-yl)-1H-benzo[d]imidazole-6-carboxylate (400 mg, 0.636 mmol) in CH$_3$CN (4.0 mL). The mixture was heated at 100° C. until completion (~4 min). Next, the mixture was acidified with acetic acid and diluted with DMSO (2 mL). The mixture was purified by RP-HPLC (eluent: MeCN/H$_2$O 0.1% TFA). The resulting product fractions were combined and lyophilized, and subsequent separation using preparative chiral SFC (Chiralpak AD-H column with MeOH/CO$_2$) to give two distinct stereoisomers.

2-(4-(6-((4-cyano-2-fluorobenzyl)oxy)pyridin-2-yl)-2,5-difluorobenzyl)-1-(cis-4-methoxytetrahydrofuran-3-yl)-1H-benzo[d]imidazole-6-carboxylic acid (Isomer 1, Earlier eluting of two stereoisomers, Example 276):

1H NMR (400 MHz, DMSO-d6) δ 8.39 (d, J=1.5 Hz, 1H), 7.98-7.84 (m, 2H), 7.80-7.68 (m, 4H), 7.58 (d, J=8.4 Hz, 1H), 7.53 (d, J=6.8 Hz, 1H), 7.29 (dd, J=11.6, 6.0 Hz, 1H), 6.99 (d, J=8.3 Hz, 1H), 5.60 (s, 2H), 5.54 (t, J=9.6 Hz, 1H), 4.50 (s, 2H), 4.42 (dd, J=10.4, 3.7 Hz, 1H), 4.19-4.08 (m, 2H), 4.02 (t, J=9.4 Hz, 1H), 3.82 (dd, J=10.3, 4.5 Hz, 1H), 2.87 (s, 3H). ES/MS: 615.2 (M+H$^+$). 2-(4-(6-((4-cyano-2-fluorobenzyl)oxy)pyridin-2-yl)-2,5-difluorobenzyl)-1-(cis-4-methoxytetrahydrofuran-3-yl)-1H-benzo[d]imidazole-6-carboxylic acid (Isomer 2, later eluting of two stereoisomers, Example 275)

1H NMR (400 MHz, DMSO-d6) δ 8.38 (s, 1H), 7.97-7.86 (m, 2H), 7.75 (dt, J=6.5, 5.2 Hz, 4H), 7.60-7.43 (m, 2H), 7.29 (dd, J=11.4, 6.1 Hz, 1H), 6.99 (d, J=8.2 Hz, 1H), 5.60 (s, 2H), 5.53 (d, J=10.2 Hz, 1H), 4.49 (s, 2H), 4.42 (dd, J=10.3, 3.8 Hz, 1H), 4.17-4.06 (m, 2H), 4.02 (dd, J=10.3, 8.3 Hz, 1H), 3.82 (dd, J=10.1, 4.5 Hz, 1H), 2.87 (s, 3H). ES/MS: 615.2 (M+H$^+$).

Example 277: (S)-2-(4-(6-((4-cyano-2-fluorobenzyl)oxy)-5-fluoropyridin-2-yl)benzyl)-1-(4,4-dimethyltetrahydrofuran-3-yl)-1H-benzo[d]imidazole-6-carboxylic acid (S)-2-(4-(6-((4-cyano-2-fluorobenzyl)oxy)-5-fluoropyridin-2-yl)benzyl)-1-(4,4-dimethyltetrahydrofuran-3-yl)-1H-benzo[d]imidazole-6-carboxylic acid was prepared in a manner as described in Procedure 35, starting with Intermediates I-109 and I-1182. 1H NMR (400 MHz, Methanol-d4) δ 8.90 (s, 1H), 8.21 (dd, J=8.6, 1.4 Hz, 1H), 8.06 (d, J=8.2 Hz, 2H), 7.83 (d, J=8.6 Hz, 1H), 7.77 (t, J=7.5 Hz, 1H), 7.68-7.52 (m, 4H), 7.49 (d, J=8.1 Hz, 2H), 5.73 (s, 2H), 5.10 (d, J=6.2 Hz, 1H), 4.80-4.62 (m, 2H), 4.62-4.53 (m, 1H), 4.45 (dd, J=11.6, 6.7 Hz, 1H), 3.99 (d, J=9.0 Hz, 1H), 3.80 (d, J=8.9 Hz, 1H), 1.28 (s, 3H), 0.65 (s, 3H). ES/MS m/z: 595.2 (M+H$^+$).

Example 278: (S)-2-(4-(6-((4-cyano-2-fluorobenzyl)oxy)pyridin-2-yl)-2-fluoro-5-methylbenzyl)-1-(4,4-dimethyltetrahydrofuran-3-yl)-1H-benzo[d]imidazole-6-carboxylic acid (S)-2-(4-(6-((4-cyano-2-fluorobenzyl)oxy)pyridin-2-yl)-2-fluoro-5-methylbenzyl)-1-(4,4-dimethyltetrahydrofuran-3-yl)-1H-benzo[d]imidazole-6-carboxylic acid was prepared in a manner as described in Procedure 35, starting with Intermediates I-3 and I-1076. 1H NMR (400 MHz, Methanol-d4) δ 8.92 (s, 1H), 8.21 (dd, J=8.6, 1.4 Hz, 1H), 7.93-7.78 (m, 2H), 7.70 (t, J=7.6 Hz, 1H), 7.61-7.53 (m, 2H), 7.38 (d, J=7.6 Hz, 1H), 7.25 (d, J=10.8 Hz, 1H), 7.17 (d, J=7.4 Hz, 1H), 6.95 (d, J=8.3 Hz, 1H), 5.57 (s, 2H), 5.15 (d, J=6.5 Hz, 1H), 4.79-4.62 (m, 3H), 4.52 (dd, J=11.7, 6.6 Hz, 1H), 4.01 (d, J=8.9 Hz, 1H), 3.84 (d, J=8.9 Hz, 1H), 2.31 (s, 3H), 1.37 (s, 3H), 0.73 (s, 3H). ES/MS m/z: 609.3 (M+H$^+$).

Example 279: (S)-2-(4-(6-((4-cyano-2-fluorobenzyl)oxy)-5-fluoropyridin-2-yl)-2-fluoro-5-methylbenzyl)-1-(4,4-dimethyltetrahydrofuran-3-yl)-1H-benzo[d]imidazole-6-carboxylic acid (S)-2-(4-(6-((4-cyano-2-fluorobenzyl)oxy)-5-fluoropyridin-2-yl)-2-fluoro-5-methylbenzyl)-1-(4,4-dimethyltetrahydrofuran-3-yl)-1H-benzo[d]imidazole-6-carboxylic acid was prepared in a manner as described in Procedure 35, starting with Intermediates I-109 and I-1076. 1H NMR (400 MHz, Methanol-d4) δ 8.91 (s, 1H), 8.19 (dd, J=8.6, 1.4 Hz, 1H), 7.80 (d, J=8.6 Hz, 1H), 7.73 (t, J=7.6 Hz, 1H), 7.66 (dd, J=10.1, 8.1 Hz, 1H), 7.64-7.58 (m, 2H), 7.37 (d, J=7.6 Hz, 1H), 7.26 (d, J=10.8 Hz, 1H), 7.19 (dd, J=8.1, 2.8 Hz, 1H), 5.64 (s, 2H), 5.13 (d, J=6.4 Hz, 1H), 4.77-4.59 (m, 3H), 4.51 (dd, J=11.6, 6.7 Hz, 1H), 4.00 (d, J=9.0 Hz, 1H), 3.84 (d, J=8.9 Hz, 1H), 2.31 (s, 3H), 1.37 (s, 3H), 0.72 (s, 3H). ES/MS m/z: 627.3 (M+H$^+$).

Example 280: (S)-2-(4-(6-((4-chloro-2-fluorobenzyl)oxy)pyridin-2-yl)-2-fluoro-5-methylbenzyl)-1-(4,4-dimethyltetrahydrofuran-3-yl)-1H-benzo[d]imidazole-6-carboxylic acid (S)-2-(4-(6-((4-chloro-2-fluorobenzyl)oxy)pyridin-2-yl)-2-fluoro-5-methylbenzyl)-1-(4,4-dimethyltetrahydrofuran-3-yl)-1H-benzo[d]imidazole-6-carboxylic acid was prepared in a manner as described in Procedure 35, starting with Intermediates I-102 and I-1076. 1H NMR (400 MHz, Methanol-d4) δ 8.94 (s, 1H), 8.23 (dd, J=8.6, 1.4 Hz, 1H), 7.83 (t, J=8.0 Hz, 2H), 7.51 (t, J=8.3 Hz, 1H), 7.41 (d, J=7.6 Hz, 1H), 7.30 (d, J=10.8 Hz, 1H), 7.28-7.19 (m, 2H), 7.16 (d, J=7.3 Hz, 1H), 6.91 (d, J=8.3 Hz, 1H), 5.46 (s, 2H), 5.17 (d, J=7.0 Hz, 1H), 4.81-4.58 (m, 3H), 4.52 (dd, J=11.7, 6.7 Hz, 1H), 4.01 (d, J=8.9 Hz, 1H), 3.85 (d, J=9.0 Hz, 1H), 2.36 (s, 3H), 1.38 (s, 3H), 0.74 (s, 3H). ES/MS m/z: 618.25 (M+H$^+$).

Example 281: 2-(4-(6-((4-cyanobenzyl)oxy)pyridin-2-yl)-2,3,6-trifluorobenzyl)-1-(2-methoxyethyl)-1H-benzo[d]imidazole-6-carboxylic acid Procedure 38

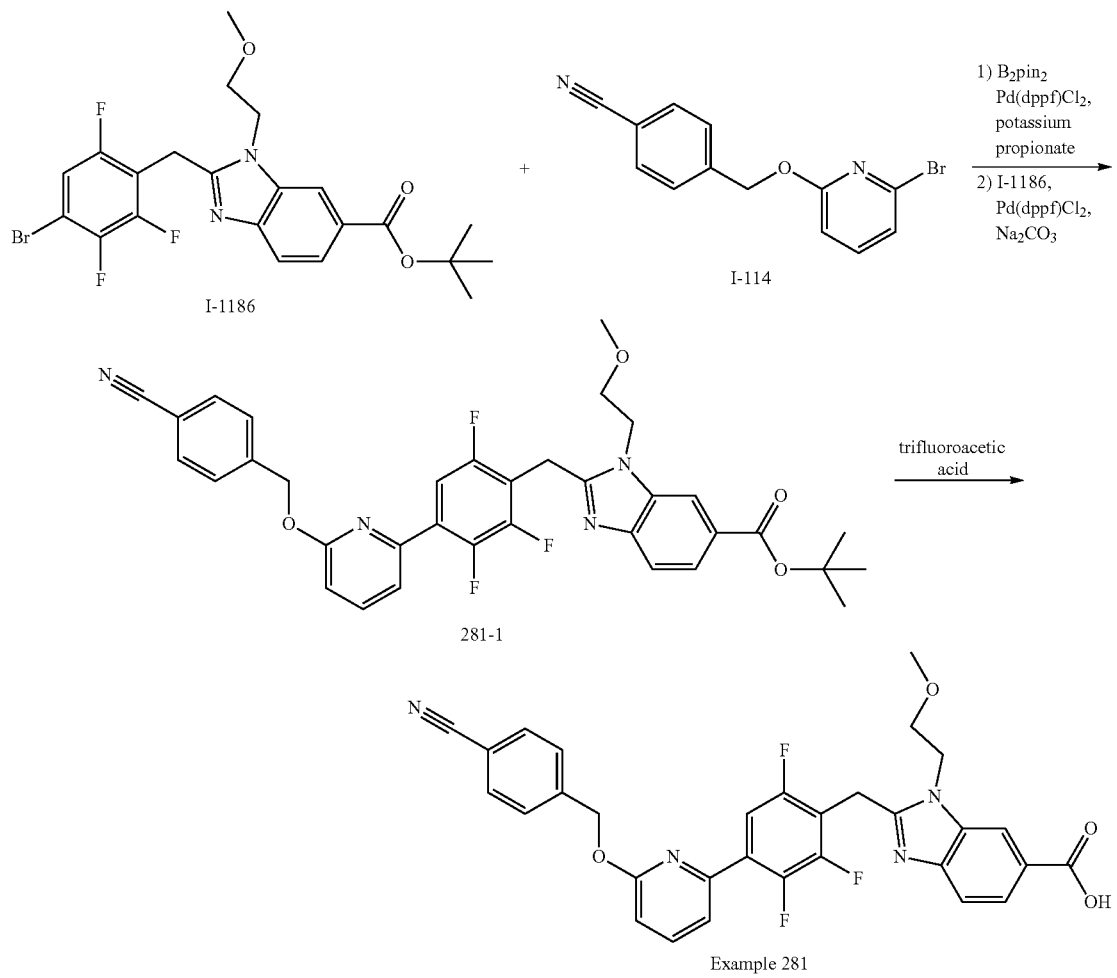

Example 281

Tert-butyl 2-(4-(6-((4-cyanobenzyl)oxy)pyridin-2-yl)-2,3,6-trifluorobenzyl)-1-(2-methoxyethyl)-1H-benzo[d]imidazole-6-carboxylate (281-1): A mixture of tert-butyl 2-[(4-bromo-2,3,6-trifluoro-phenyl)methyl]-3-(2-methoxyethyl)benzimidazole-5-carboxylate (160 mg, 1.0 equivalent), [1,1'-Bis(diphenylphosphino)ferrocene] dichloropalladium(II) (I-1186, 24 mg, 0.10 equivalent), potassium propionate (108 mg, 3.0 equivalent), and Bis(pinacolato)diboron (98 mg, 1.2 equivalent) in dioxane (3 mL) was degassed with Ar for 5 min. Upon completion the mixture was then heated at 110° C. for 1.5 h with a reflux condenser under Argon. Next, sodium carbonate (2 M in water, 0.32 mL, 2 equivalent) was added and the mixture stirred for 5 min. Upon completion 4-[(6-bromo-2-pyridyl)oxymethyl]benzonitrile (I-114, 139 mg, 1.5 equivalent) and [1,1'-Bis(diphenylphosphino)ferrocene] dichloropalladium(II) (12 mg, 0.05 equivalent) were added to the mixture. The resulting mixture was again degassed for 5 min with Argon, then heated at 80° C. for 2 hr. Upon completion, the mixture was filtered through Celite, concentrated in vacuo, and purified by silica gel flash column chromatography (ethyl acetate/hexane) to yield tert-butyl 2-(4-(6-((4-cyanobenzyl)oxy)pyridin-2-yl)-2,3,6-trifluorobenzyl)-1-(2-methoxyethyl)-1H-benzo[d]imidazole-6-carboxylate (281-1).

2-(4-(6-((4-cyanobenzyl)oxy)pyridin-2-yl)-2,3,6-trifluorobenzyl)-1-(2-methoxyethyl)-1H-benzo[d]imidazole-6-carboxylic acid (Example 281). Tert-butyl 2-(4-(6-((4-cyanobenzyl)oxy)pyridin-2-yl)-2,3,6-trifluorobenzyl)-1-(2-methoxyethyl)-1H-benzo[d]imidazole-6-carboxylate (281-1, 100 mg) in 1 mL of DCM and 0.4 mL of TFA was stirred for 4 hours at room temperature. The mixture was concentrated in vacuo and purified by preparative HPLC (MeCN in water, 0.1% TFA) to give the title compound. 1H NMR (400 MHz, Methanol-d4) δ 8.67 (s, 1H), 7.95 (dd, J=8.6, 1.5 Hz, 1H), 7.82-7.64 (m, 3H), 7.59 (d, J=8.5 Hz, 1H), 5.82 (s, 2H), 5.08 (d, J=6.8 Hz, 1H), 4.72 (d, J=11.0 Hz, 1H), 4.68-4.51 (m, 4H), 4.42 (d, J=17.1 Hz, 1H), 3.99 (d, J=8.7 Hz, 1H), 3.84 (d, J=8.7 Hz, 1H), 1.50-1.40 (m, 6H), 0.77 (s, 3H). ES/MS (m/z): 573.6 (M+H$^+$).

Example 282: (S)-2-(4-(6-((4-chlorobenzyl)oxy)-5-fluoropyridin-2-yl)-2,3,6-trifluorobenzyl)-1-(4,4-dimethyltetrahydrofuran-3-yl)-1H-benzo[d]imidazole-6-carboxylic acid (S)-2-(4-(6-((4-chlorobenzyl)oxy)-5-fluoropyridin-2-yl)-2,3,6-trifluorobenzyl)-1-(4,4-dimethyltetrahydrofuran-3-yl)-1H-benzo[d]imidazole-6-carboxylic acid was prepared in a manner as described in Procedure 35, starting with Intermediates I-1246 and I-1231. 1H NMR (400 MHz, Methanol-d4) δ 8.83 (s, 1H), 8.09 (dd, J=8.5, 1.4 Hz, 1H), 7.73-7.64 (m, 3H), 7.64-7.55 (m, 1H), 7.51 (d, J=8.4 Hz, 2H), 7.47-7.20 (m, 2H), 5.57 (s, 2H), 5.16 (d, J=6.6 Hz, 1H), 4.81-4.63 (m, 2H), 4.57 (dd, J=11.5, 6.7 Hz, 2H), 3.99 (d, J=8.8 Hz, 1H), 3.86 (d, J=8.8 Hz, 1H), 1.48 (s, 3H), 0.81 (s, 3H). ES/MS m/z: 640.5 (M+H$^+$).

Example 283: (S)-2-(4-(6-((4-cyanobenzyl)oxy)-5-fluoropyridin-2-yl)-2,3,6-trifluorobenzyl)-1-(4,4-dimethyltetrahydrofuran-3-yl)-1H-benzo[d]imidazole-6-carboxylic acid (S)-2-(4-(6-((4-cyanobenzyl)oxy)-5-fluoropyridin-2-yl)-2,3,6-trifluorobenzyl)-1-(4,4-dimethyltetrahydrofuran-3-yl)-1H-benzo[d]imidazole-6-carboxylic acid was prepared in a manner as described in Procedure 35, starting with Intermediates I-1247 and I-1231. 1H NMR (400 MHz, Methanol-d4) δ 8.83 (s, 1H), 8.09 (dd, J=8.6, 1.4 Hz, 1H), 7.84-7.74 (m, 2H), 7.74-7.66 (m, 4H), 7.66-7.51 (m, 2H), 5.68 (s, 2H), 5.16 (d, J=6.6 Hz, 1H), 4.80-4.66 (m, 2H), 4.57 (dd, J=11.6, 6.7 Hz, 2H), 3.99 (d, J=8.9 Hz, 1H), 3.86 (d, J=8.9 Hz, 1H), 1.48 (s, 3H), 0.81 (s, 3H). ES/MS m/z: 631.5 (M+H$^+$).

Example 284: (S)-2-(4-(2-((4-chloro-2-fluorobenzyl)oxy)pyrimidin-4-yl)-2-fluoro-5-methylbenzyl)-1-(4,4-dimethyltetrahydrofuran-3-yl)-1H-benzo[d]imidazole-6-carboxylic acid (S)-2-(4-(2-((4-chloro-2-fluorobenzyl)oxy)pyrimidin-4-yl)-2-fluoro-5-methylbenzyl)-1-(4,4-dimethyltetrahydrofuran-3-yl)-1H-benzo[d]imidazole-6-carboxylic acid was prepared in a manner as described in Procedure 35, starting with Intermediates I-105 and I-1076. 1H NMR (400 MHz, Methanol-d4) δ 8.91 (s, 1H), 8.71 (d, J=5.1 Hz, 1H), 8.19 (dd, J=8.6, 1.4 Hz, 1H), 7.79 (d, J=8.6 Hz, 1H), 7.58 (t, J=8.2 Hz, 1H), 7.44 (dd, J=14.0, 9.0 Hz, 2H), 7.34 (d, J=5.1 Hz, 1H), 7.31-7.20 (m, 2H), 5.57 (s, 2H), 5.15 (d, J=6.2 Hz, 1H), 4.79-4.58 (m, 3H), 4.52 (dd, J=11.6, 6.7 Hz, 1H), 4.00 (d, J=8.9 Hz, 1H), 3.84 (d, J=8.9 Hz, 1H), 2.43 (s, 3H), 1.39 (s, 3H), 0.75 (s, 3H). ES/MS m/z: 619.2 (M+H$^+$).

Example 285: (S)-2-(2,5-difluoro-4-(2-((2-fluoro-4-(trifluoromethyl)benzyl)oxy)pyrimidin-4-yl)benzyl)-1-(4,4-dimethyltetrahydrofuran-3-yl)-1H-benzo[d]imidazole-6-carboxylic acid (S)-2-(2,5-difluoro-4-(2-((2-fluoro-4-(trifluoromethyl)benzyl)oxy)pyrimidin-4-yl)benzyl)-1-(4,4-dimethyltetrahydrofuran-3-yl)-1H-benzo[d]imidazole-6-carboxylic acid was prepared in a manner as described in Procedure 35, starting with Intermediates I-1091 and I-82. 1H NMR (400 MHz, Methanol-d4) δ 8.85 (s, 1H), 8.73 (d, J=5.2 Hz, 1H), 8.13 (d, J=8.5, 1.4 Hz, 1H), 8.03 (dd, J=10.4, 6.1 Hz, 1H), 7.82 (t, J=7.5 Hz, 1H), 7.74 (d, J=8.6 Hz, 1H), 7.69 (dd, J=5.2, 1.7 Hz, 1H), 7.56 (d, J=7.9 Hz, 1H), 7.45 (dd, J=11.2, 5.9 Hz, 1H), 5.71 (s, 2H), 5.11 (d, J=6.6 Hz, 1H), 4.79-4.58 (m, 3H), 4.52 (dd, J=11.5, 6.8 Hz, 1H), 3.99 (d, J=8.9 Hz, 1H), 3.84 (d, J=8.9 Hz, 1H), 1.42 (s, 3H), 0.76 (s, 3H). ES/MS m/z: 657.3 (M+H$^+$).

Example 286: 2-(4-(6-((2-chloro-6-methylpyridin-3-yl)methoxy)pyridin-2-yl)-2,5-difluorobenzyl)-1-(4,4-dimethyltetrahydrofuran-3-yl)-1H-benzo[d]imidazole-6-carboxylic acid 2-(4-(6-((2-chloro-6-methylpyridin-3-yl)methoxy)pyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 27, starting with Intermediate I-1199. 1H NMR (400 MHz, Methanol-d4) δ 8.91 (s, 1H), 8.19 (dd, J=8.6, 1.4 Hz, 1H), 7.93-7.80 (m, 3H), 7.78 (d, J=8.6 Hz, 1H), 7.59 (dd, J=7.4, 1.6 Hz, 1H), 7.40 (dd, J=11.2, 6.0 Hz, 1H), 7.27 (d, J=7.8 Hz, 1H), 6.98 (d, J=8.2 Hz, 1H), 5.57 (s, 2H), 5.15 (d, J=6.4 Hz, 1H), 4.75 (d, J=17.3 Hz, 1H), 4.71-4.62 (m, 2H), 4.53 (dd, J=11.7, 6.7 Hz, 1H), 4.00 (d, J=8.9 Hz, 1H), 3.85 (d, J=8.9 Hz, 1H), 2.51 (s, 3H), 1.41 (s, 3H), 0.76 (s, 3H). ES/MS m/z: 619.4 (M+H$^+$).

Example 287: (S)-2-(4-(6-((5-chloro-3-fluoropyridin-2-yl)methoxy)pyridin-2-yl)-2,5-difluorobenzyl)-1-(4,4-dimethyltetrahydrofuran-3-yl)-4-fluoro-1H-benzo[d]imidazole-6-carboxylic acid (S)-2-(4-(6-((5-chloro-3-fluoropyridin-2-yl)methoxy)pyridin-2-yl)-2,5-difluorobenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1217 and I-108. 1H NMR (400 MHz, Methanol-d4) δ 8.56 (s, 1H), 8.43 (d, J=1.9 Hz, 1H), 7.93-7.74 (m, 3H), 7.68 (dd, J=11.1, 1.2 Hz, 1H), 7.60-7.50 (m, 1H), 7.21 (dd, J=11.5, 6.0 Hz, 1H), 6.89 (d, J=8.2 Hz, 1H), 5.63 (d, J=1.9 Hz, 2H), 4.95 (d, J=7.3 Hz, 1H), 4.62-4.44 (m, 4H), 3.94 (d, J=8.8 Hz, 1H), 3.80 (d, J=8.8 Hz, 1H), 1.35 (s, 3H), 0.66 (s, 3H). ES/MS m/z: 641.3 (M+H$^+$).

Example 288: (S)-2-(4-(6-((6-chloro-4-methoxypyridin-3-yl)methoxy)pyridin-2-yl)-2,5-difluorobenzyl)-1-(4,4-dimethyltetrahydrofuran-3-yl)-4-fluoro-1H-benzo[d]imidazole-6-carboxylic acid (S)-2-(4-(6-((6-chloro-4-methoxypyridin-3-yl)methoxy)pyridin-2-yl)-2,5-difluorobenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1218 and I-108. 1H NMR (400 MHz, Methanol-d4) δ 8.58 (s, 1H), 8.29 (s, 1H), 7.88 (dd, J=10.8, 6.3 Hz, 1H), 7.84-7.75 (m, 1H), 7.70 (dd, J=11.0, 1.2 Hz, 1H), 7.58-7.50 (m, 1H), 7.29-7.23 (m, 1H), 7.22 (d, J=11.4 Hz, 1H), 6.89 (dd, J=8.3, 0.7 Hz, 1H), 5.58-5.44 (m, 2H), 4.98 (d, J=6.7 Hz, 1H), 4.66-4.35 (m, 4H), 4.02 (s, 3H), 3.94 (d, J=8.8 Hz, 1H), 3.80 (d, J=8.8 Hz, 1H), 1.36 (s, 3H), 0.68 (s, 3H). ES/MS m/z: 653.5 (M+H$^+$).

Example 289A: (S)-2-(4-(6-((5-chloro-3-fluoropyridin-2-yl)methoxy)pyridin-2-yl)-2,5-difluorobenzyl)-1-(4,4-dimethyltetrahydrofuran-3-yl)-1H-benzo[d]imidazole-6-carboxylic acid

Example 289B: (R)-2-(4-(6-((5-chloro-3-fluoropyridin-2-yl)methoxy)pyridin-2-yl)-2,5-difluorobenzyl)-1-(4,4-dimethyltetrahydrofuran-3-yl)-1H-benzo[d]imidazole-6-carboxylic acid Examples 289A and 289B were prepared by preparative chiral SFC (Daicel Chiralpak AD-H column, EtOH/CO$_2$) of Example 296.

(S)-2-(4-(6-((5-chloro-3-fluoropyridin-2-yl)methoxy)pyridin-2-yl)-2,5-difluorobenzyl)-1-(4,4-dimethyltetrahydrofuran-3-yl)-1H-benzo[d]imidazole-6-carboxylic acid (Example 289A) was isolated as the later-eluting of two stereoisomers. 1H NMR (400 MHz, Methanol-d4) δ 8.81 (s, 1H), 8.43 (d, J=1.9 Hz, 1H), 8.09 (dd, J=8.6, 1.4 Hz, 1H), 7.95-7.78 (m, 3H), 7.74 (d, J=8.6 Hz, 1H), 7.58 (dd, J=7.6, 1.5 Hz, 1H), 7.31 (dd, J=11.4, 6.0 Hz, 1H), 6.91 (d, J=8.3 Hz, 1H), 5.63 (d, J=1.9 Hz, 2H), 5.06 (d, J=6.6 Hz, 1H), 4.74-4.43 (m, 4H), 3.98 (d, J=8.8 Hz, 1H), 3.83 (d, J=8.8 Hz, 1H), 1.40 (s, 3H), 0.72 (s, 3H). ES/MS m/z: 623.7 (M+H$^+$).

(R)-2-(4-(6-((5-chloro-3-fluoropyridin-2-yl)methoxy)pyridin-2-yl)-2,5-difluorobenzyl)-1-(4,4-dimethyltetrahydrofuran-3-yl)-1H-benzo[d]imidazole-6-carboxylic acid (Example 289B) was isolated as the earlier-eluting of two stereoisomers. 1H NMR (400 MHz, Methanol-d4) δ 8.90 (s, 1H), 8.43 (d, J=1.9 Hz, 1H), 8.18 (dd, J=8.6, 1.4 Hz, 1H), 7.91 (dd, J=10.9, 6.3 Hz, 1H), 7.88-7.74 (m, 3H), 7.59 (dd, J=7.4, 1.5 Hz, 1H), 7.38 (dd, J=11.2, 6.1 Hz, 1H), 6.92 (d, J=8.2 Hz, 1H), 5.63 (d, J=1.9 Hz, 2H), 5.14 (d, J=6.6 Hz, 1H), 4.80-4.61 (m, 3H), 4.53 (dd, J=11.6, 6.7 Hz, 1H), 4.00 (d, J=8.9 Hz, 1H), 3.85 (d, J=8.9 Hz, 1H), 1.41 (s, 3H), 0.76 (s, 3H). ES/MS m/z: 623.7 (M+H$^+$).

Example 290A: (S)-2-(4-(6-((6-chloro-4-methoxypyridin-3-yl)methoxy)pyridin-2-yl)-2,5-difluorobenzyl)-1-(4,4-dimethyltetrahydrofuran-3-yl)-1H-benzo[d]imidazole-6-carboxylic acid Example 290B: (R)-2-(4-(6-((6-chloro-4-methoxypyridin-3-yl)methoxy)pyridin-2-yl)-2,5-difluorobenzyl)-1-(4,4-dimethyltetrahydrofuran-3-yl)-1H-benzo[d]imidazole-6-carboxylic acid Examples 289A and 289B were prepared by preparative chiral SFC (Daicel Chiralpak AD-H column, EtOH/CO$_2$) of Example 296.

(S)-2-(4-(6-((6-chloro-4-methoxypyridin-3-yl)methoxy)pyridin-2-yl)-2,5-difluorobenzyl)-1-(4,4-dimethyltetrahydrofuran-3-yl)-1H-benzo[d]imidazole-6-carboxylic acid (Example 290A) was isolated as the later-eluting of two stereoisomers. 1H NMR (400 MHz, Methanol-d4) δ 8.88 (s, 1H), 8.28 (s, 1H), 8.16 (dd, J=8.6, 1.4 Hz, 1H), 7.93 (dd, J=10.8, 6.3 Hz, 1H), 7.85-7.72 (m, 2H), 7.58 (dd, J=7.4, 1.5 Hz, 1H), 7.39 (dd, J=11.2, 6.0 Hz, 1H), 7.18 (s, 1H), 6.91 (d, J=8.2 Hz, 1H), 5.51 (s, 2H), 5.13 (d, J=6.6 Hz, 1H), 4.76-4.58 (m, 3H), 4.53 (dd, J=11.6, 6.7 Hz, 1H), 4.00 (s, 4H), 3.84 (d, J=8.9 Hz, 1H), 1.42 (s, 3H), 0.76 (s, 3H). ES/MS m/z: 636.1 (M+H$^+$).

(R)-2-(4-(6-((6-chloro-4-methoxypyridin-3-yl)methoxy)pyridin-2-yl)-2,5-difluorobenzyl)-1-(4,4-dimethyltetrahydrofuran-3-yl)-1H-benzo[d]imidazole-6-carboxylic acid (Example 290B) was isolated as the earlier-eluting of two stereoisomers. 1H NMR (400 MHz, Methanol-d4) δ 8.88 (s, 1H), 8.28 (s, 1H), 8.16 (dd, J=8.6, 1.4 Hz, 1H), 7.93 (dd, J=10.8, 6.3 Hz, 1H), 7.85-7.72 (m, 2H), 7.58 (dd, J=7.4, 1.5 Hz, 1H), 7.39 (dd, J=11.2, 6.0 Hz, 1H), 7.18 (s, 1H), 6.91 (d, J=8.2 Hz, 1H), 5.51 (s, 2H), 5.13 (d, J=6.6 Hz, 1H), 4.76-4.58 (m, 3H), 4.53 (dd, J=11.6, 6.7 Hz, 1H), 4.00 (s, 4H), 3.84 (d, J=8.9 Hz, 1H), 1.42 (s, 3H), 0.76 (s, 3H). ES/MS m/z: 636.1 (M+H$^+$).

Example 291: 2-(4-(6-((6-chloro-4-methoxypyridin-3-yl)methoxy)pyridin-2-yl)-2,5-difluorobenzyl)-4-fluoro-1-(2-methoxyethyl)-1H-benzo[d]imidazole-6-carboxylic acid 2-(4-(6-((6-chloro-4-methoxypyridin-3-yl)methoxy)pyridin-2-yl)-2,5-difluorobenzyl)-4-fluoro-1-(2-methoxyethyl)-1H-benzo[d]imidazole-6-carboxylic acid was prepared in a manner as described in Procedure 27, starting with Intermediate I-1136. 1H NMR (400 MHz, Methanol-d4) δ 8.28 (s, 1H), 8.19 (d, J=1.2 Hz, 1H), 7.86 (dd, J=10.8, 6.3 Hz, 1H), 7.79 (t, J=7.9 Hz, 1H), 7.72 (dd, J=11.1, 1.2 Hz, 1H), 7.54 (dd, J=7.5, 1.6 Hz, 1H), 7.20 (q, J=6.2 Hz, 2H), 6.88 (d, J=8.2 Hz, 1H), 5.50 (s, 2H), 4.63 (t, J=5.0 Hz, 2H), 4.57 (s, 2H), 4.01 (s, 3H), 3.75 (t, J=4.9 Hz, 2H), 3.28 (s, 3H). ES/MS m/z: 613.4 (M+H$^+$).

Example 292: 2-(4-(6-((4-cyano-2-fluorobenzyl)oxy)pyridin-2-yl)-2,3,6-trifluorobenzyl)-4-fluoro-1-(2-methoxyethyl)-1H-benzo[d]imidazole-6-carboxylic acid 2-(4-(6-((4-cyano-2-fluorobenzyl)oxy)pyridin-2-yl)-2,3,6-trifluorobenzyl)-4-fluoro-1-(2-methoxyethyl)-1H-benzo[d]imidazole-6-carboxylic acid was prepared in a manner as described in Procedure 22, starting with Intermediates I-116 and I-1032. 1H NMR (400 MHz, Methanol-d4) δ 8.15 (d, J=1.3 Hz, 1H), 7.86 (t, J=7.9 Hz, 1H), 7.75 (t, J=7.5 Hz, 1H), 7.70-7.56 (m, 5H), 6.97 (d, J=8.3 Hz, 1H), 5.64 (s, 2H), 4.67 (t, J=5.0 Hz, 2H), 4.60 (s, 2H), 3.81 (t, J=4.9 Hz, 2H). ES/MS m/z: 609.3 (M+H$^+$).

Example 293: 2-(4-(6-((4-cyano-2-fluorobenzyl)oxy)pyridin-2-yl)-2,3,6-trifluorobenzyl)-1-(4,4-dimethyltetrahydrofuran-3-yl)-1H-benzo[d]imidazole-6-carboxylic acid 2-(4-(6-((4-cyano-2-fluorobenzyl)oxy)pyridin-2-yl)-2,3,6-trifluorobenzyl)-1-(4,4-dimethyltetrahydrofuran-3-yl)-1H-benzo[d]imidazole-6-carboxylic acid was prepared in a manner as described in Procedure 22, starting with Intermediates I-116 and I-25. 1H NMR (400 MHz, Methanol-d4) δ 8.85 (s, 1H), 8.11 (dd, J=8.6, 1.4 Hz, 1H), 7.89 (t, J=7.9 Hz, 1H), 7.82-7.66 (m, 3H), 7.66-7.50 (m, 3H), 7.01 (d, J=8.3 Hz, 1H), 5.64 (s, 2H), 5.17 (d, J=6.5 Hz, 1H), 4.85-4.50 (m, 4H), 4.00 (d, J=8.9 Hz, 1H), 3.87 (d, J=8.9 Hz, 1H), 1.48 (s, 3H), 0.82 (s, 3H). ES/MS m/z: 631.3 (M+H$^+$).

Example 294: 2-(4-(6-((6-chloro-4-methoxypyridin-3-yl)methoxy)pyridin-2-yl)-2,5-difluorobenzyl)-1-(4,4-dimethyltetrahydrofuran-3-yl)-1H-benzo[d]imidazole-6-carboxylic acid 2-(4-(6-((6-chloro-4-methoxypyridin-3-yl)methoxy)pyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 27, starting with Intermediate I-1199. 1H NMR (400 MHz, Methanol-d4) δ 8.88 (s, 1H), 8.28 (s, 1H), 8.16 (dd, J=8.6, 1.4 Hz, 1H), 7.93 (dd, J=10.8, 6.3 Hz, 1H), 7.85-7.72 (m, 2H), 7.58 (dd, J=7.4, 1.5 Hz, 1H), 7.39 (dd, J=11.2, 6.0 Hz, 1H), 7.18 (s, 1H), 6.91 (d, J=8.2 Hz, 1H), 5.51 (s, 2H), 5.13 (d, J=6.6 Hz, 1H), 4.76-4.58 (m, 3H), 4.53 (dd, J=11.6, 6.7 Hz, 1H), 4.00 (s, 4H), 3.84 (d, J=8.9 Hz, 1H), 1.42 (s, 3H), 0.76 (s, 3H). ES/MS m/z: 636.1 (M+H$^+$).

Example 295: 2-(4-(6-((6-chloro-4-fluoropyridin-3-yl)methoxy)pyridin-2-yl)-2,5-difluorobenzyl)-1-(4,4-dimethyltetrahydrofuran-3-yl)-1H-benzo[d]imidazole-6-carboxylic acid 2-(4-(6-((6-chloro-4-fluoropyridin-3-yl)methoxy)pyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 27, starting with Intermediate I-1199. 1H NMR (400 MHz, Methanol-d4) δ 8.91 (s, 1H), 8.57 (d, J=9.6 Hz, 1H), 8.19 (dd, J=8.6, 1.4 Hz, 1H), 7.95 (dd, J=10.8, 6.3 Hz, 1H), 7.89-7.75 (m, 2H), 7.59 (dd, J=7.5, 1.6 Hz, 1H), 7.41 (dd, J=10.1, 4.8 Hz, 2H), 6.93 (d, J=8.2 Hz, 1H), 5.60 (s, 2H), 5.15 (d, J=6.6 Hz, 1H), 4.81-4.61 (m, 3H), 4.53 (dd, J=11.6, 6.7 Hz, 1H), 4.00 (d, J=8.9 Hz, 1H), 3.85 (d, J=8.9 Hz, 1H), 1.42 (s, 3H), 0.77 (s, 3H). ES/MS m/z: 623.7 (M+H⁺).

Example 296: 2-(4-(6-((5-chloro-3-fluoropyridin-2-yl)methoxy)pyridin-2-yl)-2,5-difluorobenzyl)-1-(4,4-dimethyltetrahydrofuran-3-yl)-1H-benzo[d]imidazole-6-carboxylic acid 2-(4-(6-((5-chloro-3-fluoropyridin-2-yl)methoxy)pyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 27, starting with Intermediate I-1199. 1H NMR (400 MHz, Methanol-d4) δ 8.90 (s, 1H), 8.43 (d, J=1.9 Hz, 1H), 8.18 (dd, J=8.6, 1.4 Hz, 1H), 7.91 (dd, J=10.9, 6.3 Hz, 1H), 7.88-7.74 (m, 3H), 7.59 (dd, J=7.4, 1.5 Hz, 1H), 7.38 (dd, J=11.2, 6.1 Hz, 1H), 6.92 (d, J=8.2 Hz, 1H), 5.63 (d, J=1.9 Hz, 2H), 5.14 (d, J=6.6 Hz, 1H), 4.80-4.61 (m, 3H), 4.53 (dd, J=11.6, 6.7 Hz, 1H), 4.00 (d, J=8.9 Hz, 1H), 3.85 (d, J=8.9 Hz, 1H), 1.41 (s, 3H), 0.76 (s, 3H). ES/MS m/z: 623.7 (M+H⁺).

Example 297: (S)-2-((6-((4-chlorobenzyl)oxy)-5'-fluoro-2'-oxo-[2,4'-bipyridin]-1'(2'H)-yl)methyl)-1-(4,4-dimethyltetrahydrofuran-3-yl)-1H-benzo[d]imidazole-6-carboxylic acid (S)-2-((6-((4-chlorobenzyl)oxy)-5'-fluoro-2'-oxo-[2,4'-bipyridin]-1'(2'H)-yl)methyl)-1-(4,4-dimethyltetrahydrofuran-3-yl)-1H-benzo[d]imidazole-6-carboxylic acid was prepared in a manner as described in Procedure 35, starting with Intermediates I-1237 and I-1248. 1H NMR (400 MHz, DMSO) δ 8.48 (s, 1H), 8.24 (d, J=6.9 Hz, 1H), 7.92 (t, J=7.9 Hz, 1H), 7.81 (d, J=8.4 Hz, 1H), 7.66 (d, J=8.5 Hz, 1H), 7.57-7.49 (m, 3H), 7.45 (d, J=8.4 Hz, 2H), 7.06 (d, J=8.3 Hz, 1H), 6.97 (d, J=7.4 Hz, 1H), 5.55 (d, J=16.0 Hz, 1H), 5.46 (d, J=8.7 Hz, 3H), 5.10 (d, J=6.6 Hz, 1H), 4.61-4.39 (m, 2H), 3.83-3.69 (m, 2H), 1.38 (s, 3H), 0.66 (s, 3H). ES/MS m/z: 603.09 (M+H⁺).

Example 298: (S)-2-(4-(2-((4-cyano-2-fluorobenzyl)oxy)pyrimidin-4-yl)-2-fluorobenzyl)-1-(4,4-dimethyltetrahydrofuran-3-yl)-4-fluoro-1H-benzo[d]imidazole-6-carboxylic acid (S)-2-(4-(2-((4-cyano-2-fluorobenzyl)oxy)pyrimidin-4-yl)-2-fluorobenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1230 and I-94. 1H NMR (400 MHz, DMSO) δ 8.75 (d, J=5.2 Hz, 1H), 8.35 (s, 1H), 8.06 (d, J=9.4 Hz, 2H), 7.95 (dd, J=10.0, 1.5 Hz, 1H), 7.90-7.69 (m, 3H), 7.65-7.46 (m, 2H), 5.64 (s, 2H), 5.01 (d, J=6.5 Hz, 1H), 4.73-4.37 (m, 4H), 3.74 (q, J=8.7 Hz, 2H), 1.31 (s, 3H), 0.59 (s, 3H). ES/MS m/z: 614.38 (M+H⁺).

Example 299: (S)-2-(4-(6-((4-chlorobenzyl)oxy)-5-fluoropyridin-2-yl)-2,5-difluorobenzyl)-1-(4,4-dimethyltetrahydrofuran-3-yl)-1H-benzo[d]imidazole-6-carboxylic acid (S)-2-(4-(6-((4-chlorobenzyl)oxy)-5-fluoropyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 35, starting with Intermediates I-1246 and I-82. 1H NMR (400 MHz, DMSO) δ 8.49 (s, 1H), 8.10-7.72 (m, 3H), 7.72-7.40 (m, 8H), 5.57 (s, 2H), 5.02 (d, J=6.5 Hz, 1H), 4.82-4.27 (m, 4H), 3.85-3.64 (m, 2H), 1.34 (s, 3H), 0.61 (s, 3H). ES/MS m/z: 622.17 (M+H⁺).

Example 300: (S)-2-((6-((4-chlorobenzyl)oxy)-5,5'-difluoro-2'-oxo-[2,4'-bipyridin]-1'(2'H)-yl)methyl)-1-(4,4-dimethyltetrahydrofuran-3-yl)-1H-benzo[d]imidazole-6-carboxylic acid (S)-2-((6-((4-chlorobenzyl)oxy)-5,5'-difluoro-2'-oxo-[2,4'-bipyridin]-1'(2'H)-yl)methyl)-1-(4,4-dimethyltetrahydrofuran-3-yl)-1H-benzo[d]imidazole-6-carboxylic acid was prepared in a manner as described in Procedure 35, starting with Intermediates I-1237 and I-1246. 1H NMR (400 MHz, DMSO) δ 8.48 (s, 1H), 8.25 (d, J=7.1 Hz, 1H), 8.04-7.76 (m, 2H), 7.74-7.40 (m, 6H), 6.95 (d, J=7.5 Hz, 1H), 5.50 (d, J=28.8 Hz, 4H), 5.10 (d, J=6.7 Hz, 1H), 4.70-4.34 (m, 2H), 3.73 (d, J=8.6 Hz, 2H), 1.38 (s, 3H), 0.66 (s, 3H). ES/MS m/z: 621.09 (M+H⁺).

Example 301: (S)-2-(2-chloro-4-(2-((4-cyanobenzyl)oxy)pyrimidin-4-yl)-5-methylbenzyl)-1-(4,4-dimethyltetrahydrofuran-3-yl)-1H-benzo[d]imidazole-6-carboxylic acid (S)-2-(2-chloro-4-(2-((4-cyanobenzyl)oxy)pyrimidin-4-yl)-5-methylbenzyl)-1-(4,4-dimethyltetrahydrofuran-3-yl)-1H-benzo[d]imidazole-6-carboxylic acid was prepared in a manner as described in Procedure 35, starting with Intermediates I-1030 and I-1248. 1H NMR (400 MHz, DMSO) δ 8.75 (d, J=5.1 Hz, 1H), 8.50 (s, 1H), 8.00-7.74 (m, 3H), 7.74-7.53 (m, 4H), 7.53-7.28 (m, 2H), 5.57 (s, 2H), 5.02 (d, J=6.7 Hz, 1H), 4.66-4.29 (m, 4H), 3.93-3.59 (m, 2H), 2.33 (s, 3H), 1.34 (s, 3H), 0.66 (s, 3H). ES/MS m/z: 608.29 (M+H⁺).

Example 302: (S)-2-(4-(6-((4-chloro-2-fluorobenzyl)oxy)pyridin-2-yl)-2,6-difluorobenzyl)-1-(4,4-dimethyltetrahydrofuran-3-yl)-1H-benzo[d]imidazole-6-carboxylic acid (S)-2-(4-(6-((4-chloro-2-fluorobenzyl)oxy)pyridin-2-yl)-2,6-difluorobenzyl)-1-(4,4-dimethyltetrahydrofuran-3-yl)-1H-benzo[d]imidazole-6-carboxylic acid was prepared in a manner as described in Procedure 35, starting with Intermediates I-1233 and I-102. 1H NMR (400 MHz, DMSO) δ 8.49 (s, 1H), 7.88 (dd, J=8.2, 5.1 Hz, 3H), 7.82-7.71 (m, 2H), 7.71-7.44 (m, 4H), 7.34 (dd, J=8.2, 2.0 Hz, 1H), 6.95 (d, J=8.2 Hz, 1H), 5.55 (s, 2H), 5.09 (d, J=6.6 Hz, 1H), 4.58 (d, J=18.1 Hz, 2H), 4.47 (dd, J=11.2, 6.7 Hz, 1H), 4.32 (d, J=17.3 Hz, 1H), 3.86-3.71 (m, 2H), 1.38 (s, 3H), 0.66 (s, 3H). ES/MS m/z: 622.2 (M+H⁺).

Example 303: (S)-2-(4-(6-((4-chloro-2-fluorobenzyl)oxy)-5-fluoropyridin-2-yl)-2,6-difluorobenzyl)-1-(4,4-dimethyltetrahydrofuran-3-yl)-1H-benzo[d]imidazole-6-carboxylic acid (S)-2-(4-(6-((4-chloro-2-fluorobenzyl)oxy)-5-fluoropyridin-2-yl)-2,6-difluorobenzyl)-1-(4,4-dimethyltetrahydrofuran-3-yl)-1H-benzo[d]imidazole-6-carboxylic acid was prepared in a manner as described in Procedure 35, starting with Intermediates I-1233 and I-1036. 1H NMR (400 MHz, DMSO) δ 8.48 (s, 1H), 7.93-7.75 (m, 5H), 7.65 (t, J=8.2 Hz, 1H), 7.61-7.50 (m, 2H), 7.36 (dd, J=8.2, 2.1 Hz, 1H), 5.64 (s, 2H), 5.09 (d, J=6.6 Hz, 1H), 4.64-4.42 (m, 3H), 4.30 (d, J=17.3 Hz, 1H), 3.76 (t, J=6.4 Hz, 2H), 1.38 (s, 3H), 0.65 (s, 3H). ES/MS m/z: 640.13 (M+H⁺).

Example 305: (S)-2-(4-(6-((4-chloro-2-fluorobenzyl)oxy)pyridin-2-yl)-2,6-difluorobenzyl)-1-(4,4-dimethyltetrahydrofuran-3-yl)-4-fluoro-1H-benzo[d]imidazole-6-carboxylic acid (S)-2-(4-(6-((4-chloro-2-fluorobenzyl)oxy)pyridin-2-yl)-2,6-difluorobenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1234 and I-102. 1H NMR (400 MHz, DMSO) δ 8.35 (s, 1H), 7.89 (dd, J=9.8, 8.3 Hz, 3H), 7.76 (d, J=7.5 Hz, 1H), 7.63 (t, J=8.2 Hz, 1H), 7.55-7.43 (m, 2H), 7.33 (dd, J=8.2, 2.1 Hz, 1H), 6.94 (d, J=8.1 Hz, 1H), 5.55 (s, 2H), 5.11 (d, J=6.5 Hz, 1H), 4.71-4.49 (m, 2H), 4.46 (dd, J=11.3, 6.6 Hz, 1H), 4.32 (d, J=17.3 Hz, 1H), 3.76 (s, 2H), 1.39 (s, 3H), 0.66 (s, 3H). ES/MS m/z: 642.72 (M+H$^+$).

Example 306: (S)-2-(4-(6-((4-chloro-2-fluorobenzyl)oxy)-5-fluoropyridin-2-yl)-2,6-difluorobenzyl)-1-(4,4-dimethyltetrahydrofuran-3-yl)-4-fluoro-1H-benzo[d]imidazole-6-carboxylic acid (S)-2-(4-(6-((4-chloro-2-fluorobenzyl)oxy)-5-fluoropyridin-2-yl)-2,6-difluorobenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1234 and I-1036. 1H NMR (400 MHz, DMSO) δ 8.35 (s, 1H), 7.93-7.74 (m, 4H), 7.65 (t, J=8.2 Hz, 1H), 7.51 (ddd, J=11.1, 8.9, 1.6 Hz, 2H), 7.36 (dd, J=8.2, 2.1 Hz, 1H), 5.64 (s, 2H), 5.11 (d, J=6.5 Hz, 1H), 4.71-4.39 (m, 3H), 4.31 (d, J=17.4 Hz, 1H), 3.76 (s, 2H), 1.38 (s, 3H), 0.66 (s, 3H). ES/MS m/z: 658.85 (M+H$^+$).

Example 307: (S)-2-(4-(6-((4-cyano-2-fluorobenzyl)oxy)-5-fluoropyridin-2-yl)-2,6-difluorobenzyl)-1-(4,4-dimethyltetrahydrofuran-3-yl)-4-fluoro-1H-benzo[d]imidazole-6-carboxylic acid (S)-2-(4-(6-((4-cyano-2-fluorobenzyl)oxy)-5-fluoropyridin-2-yl)-2,6-difluorobenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1234 and I-109. 1H NMR (400 MHz, DMSO) δ 8.35 (s, 1H), 8.02-7.69 (m, 7H), 7.53-7.47 (m, 1H), 5.74 (s, 2H), 5.11 (d, J=6.4 Hz, 1H), 4.74-4.50 (m, 2H), 4.46 (dd, J=11.1, 6.6 Hz, 1H), 4.31 (d, J=17.3 Hz, 1H), 3.76 (s, 2H), 1.38 (s, 3H), 0.66 (s, 3H). ES/MS m/z: 649.36 (M+H$^+$).

Example 308: (S)-2-(4-(6-((4-cyanobenzyl)oxy)-5-fluoropyridin-2-yl)-2-fluorobenzyl)-1-(4,4-dimethyltetrahydrofuran-3-yl)-4-fluoro-1H-benzo[d]imidazole-6-carboxylic acid (S)-2-(4-(6-((4-cyanobenzyl)oxy)-5-fluoropyridin-2-yl)-2-fluorobenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1230 and I-1092. 1H NMR (400 MHz, DMSO) δ 8.35 (s, 1H), 7.98-7.79 (m, 6H), 7.72 (d, J=3.2 Hz, 1H), 7.60-7.42 (m, 2H), 7.19 (dd, J=8.2, 2.6 Hz, 3H), 5.69 (s, 2H), 5.01 (s, 1H), 4.67-4.27 (m, 4H), 1.30 (s, 3H), 0.58 (s, 3H). ES/MS m/z: 613.21 (M+H$^+$).

Example 309: (S)-1-(4,4-dimethyltetrahydrofuran-3-yl)-4-fluoro-2-(2-fluoro-4-(6-((5-methoxy-1,3,4-thiadiazol-2-yl)methoxy)pyridin-2-yl)benzyl)-1H-benzo[d]imidazole-6-carboxylic acid (S)-1-(4,4-dimethyltetrahydrofuran-3-yl)-4-fluoro-2-(2-fluoro-4-(6-((5-methoxy-1,3,4-thiadiazol-2-yl)methoxy)pyridin-2-yl)benzyl)-1H-benzo[d]imidazole-6-carboxylic acid was prepared in a manner as described in Procedure 35, starting with Intermediates I-1230 and I-1244. 1H NMR (400 MHz, DMSO) δ 8.18 (s, 1H), 8.00 (dd, J=15.7, 9.9 Hz, 2H), 7.89 (t, J=7.8 Hz, 1H), 7.74 (d, J=7.7 Hz, 1H), 7.48 (t, J=8.7 Hz, 2H), 6.92 (d, J=8.2 Hz, 1H), 5.75 (s, 2H), 4.93 (s, 1H), 4.63-4.22 (m, 2H), 4.09 (s, 3H), 3.84-3.65 (m, 2H), 1.26 (s, 3H), 0.56 (s, 3H). ES/MS m/z: 608.25 (M+H$^+$).

Example 310: (S)-2-(4-(6-((4-chlorobenzyl)oxy)-5-fluoropyridin-2-yl)-2,3,6-trifluorobenzyl)-1-(4,4-dimethyltetrahydrofuran-3-yl)-4-fluoro-1H-benzo[d]imidazole-6-carboxylic acid (S)-2-(4-(6-((4-chlorobenzyl)oxy)-5-fluoropyridin-2-yl)-2,3,6-trifluorobenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1232 and I-1246. 1H NMR (400 MHz, DMSO) δ 8.36 (s, 1H), 7.90 (dd, J=10.2, 8.2 Hz, 1H), 7.70 (td, J=6.3, 3.3 Hz, 1H), 7.64-7.45 (m, 6H), 5.58 (s, 2H), 5.11 (d, J=6.5 Hz, 1H), 4.67 (d, J=17.4 Hz, 1H), 4.61-4.30 (m, 3H), 3.76 (s, 2H), 1.39 (s, 3H), 0.67 (s, 3H). ES/MS m/z: 658.14 (M+H$^+$).

Example 311A: 2-[[4-[6-[(4-cyano-2-fluoro-phenyl)methoxy]-2-pyridyl]-2,5-difluoro-phenyl]methyl]-3-[4-methoxy-4-methyl-tetrahydrofuran-3-yl]benzimidazole-5-carboxylic acid Example 311B: 2-[[4-[6-[(4-cyano-2-fluoro-phenyl)methoxy]-2-pyridyl]-2,5-difluoro-phenyl]methyl]-3-[4-methoxy-4-methyl-tetrahydrofuran-3-yl]benzimidazole-5-carboxylic acid Procedure 39

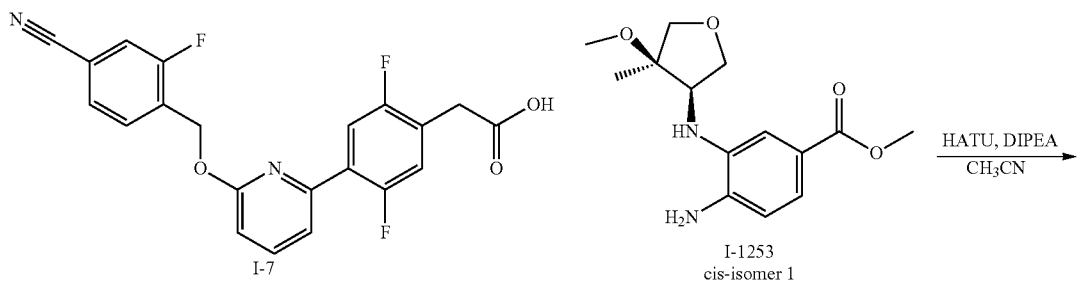

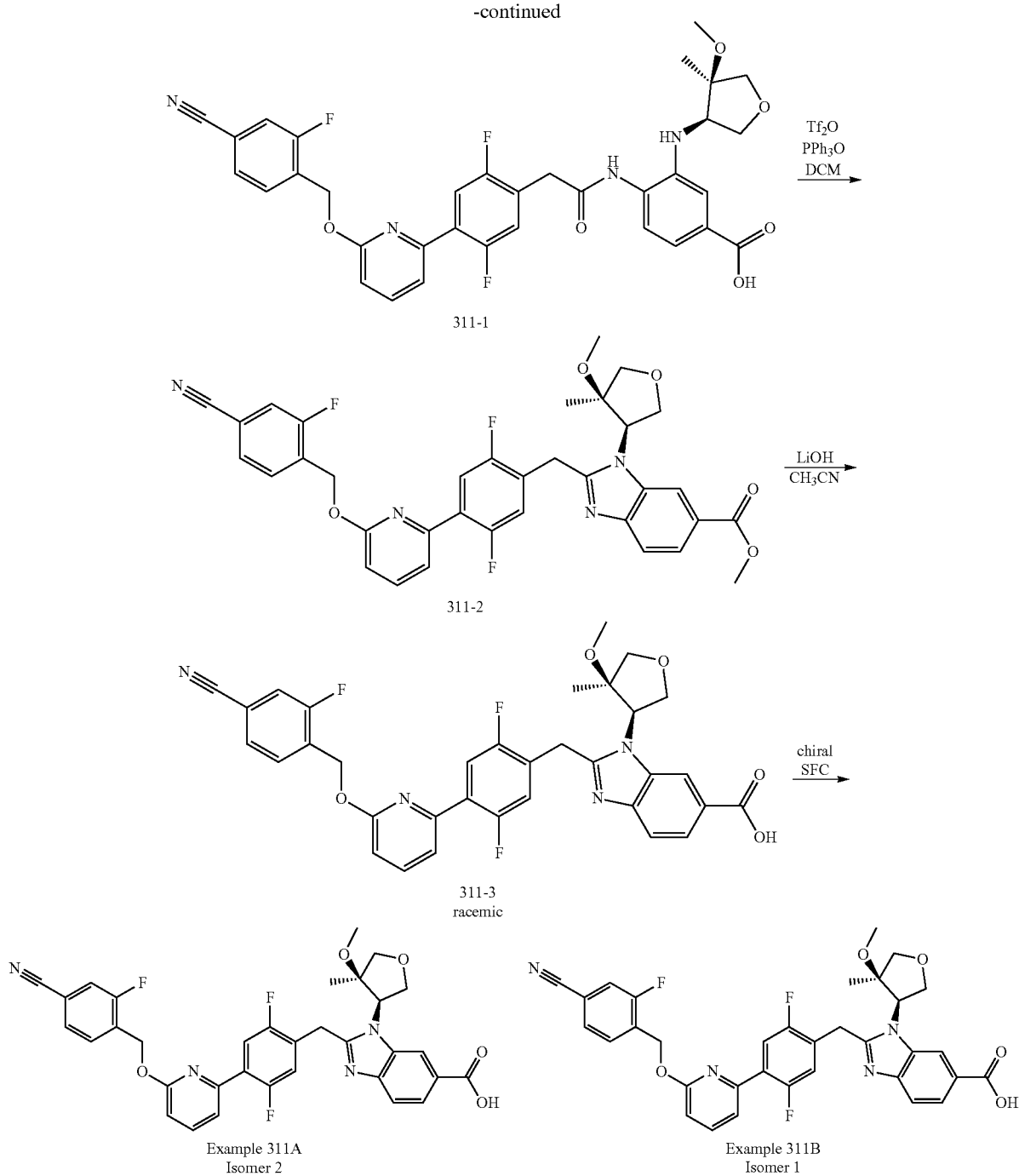

Example 311A
Isomer 2

Example 311B
Isomer 1

Methyl 4-[[2-[4-[6-[(4-cyano-2-fluoro-phenyl)methoxy]-2-pyridyl]-2,5-difluoro-phenyl]acetyl]amino]-3-[[4-methoxy-4-methyl-tetrahydrofuran-3-yl]amino]benzoate (311-1): A mixture of 2-[4-[6-[(4-cyano-2-fluoro-phenyl)methoxy]-2-pyridyl]-2,5-difluoro-phenyl]acetic acid (I-7, 145 mg, 0.365 mmol), racemic cis methyl 4-amino-3-[3-4-methoxy-4-methyl-tetrahydrofuran-3-yl]amino]benzoate (Intermediate I-1253 cis-isomer 1, 93 mg, 0.332 mmol), o-(7-Azabenzotriazol-1-yl)-N,N,N',N'-tetramethyluronium hexafluorophosphate (176 mg, 0.342 mmol) and N,N-diisopropylethylamine (0.28 mL, 1.62 mmol) in DMF (1.5 mL) and CAN (1.5 mL) was stirred at 25° C. for 5 h. The mixture was diluted in EtOAc and washed with brine, dried over sodium sulfate, concentrated, and purified by silica gel flash column chromatography (EtOAc/hexanes) to give the title compound. ES/MS: 661.26 (M+H+).

Methyl 2-[[4-[6-[(4-cyano-2-fluoro-phenyl)methoxy]-2-pyridyl]-2,5-difluoro-phenyl]methyl]-3-[4-methoxy-4-methyl-tetrahydrofuran-3-yl]benzimidazole-5-carboxylate (311-2): A mixture of methyl 4-[[2-[4-[6-[(4-cyano-2-fluoro-phenyl)methoxy]-2-pyridyl]-2,5-difluoro-phenyl]acetyl]amino]-3-[[3-4-methoxy-4-methyl-tetrahydrofuran-3-yl]amino]benzoate (311-1, 226 mg, 0.34 mmol), triphenylphosphine oxide (285 mg, 1.0 mmol) and triflic anhydride (0.086 mL, 0.51 mmol) in DCM (5.0 mL) was stirred at 0° C. for 10 min then warmed to 25° C. and stirred for 1 h. The mixture was diluted in EtOAc and washed with brine, dried over sodium sulfate, concentrated, and purified by silica gel flash column chromatography (EtOAc/hexanes) to give the title compound. ES/MS: 643.7 (M+H+).

2-[[4-[6-[(4-cyano-2-fluoro-phenyl)methoxy]-2-pyridyl]-2,5-difluoro-phenyl]methyl]-3-[4-methoxy-4-methyl-tetrahydrofuran-3-yl]benzimidazole-5-carboxylic acid (311-3): A mixture in 3 mL of methyl 2-[[4-[6-[(4-cyano-2-fluoro-phenyl)methoxy]-2-pyridyl]-2,5-difluoro-phenyl]methyl]-3-[4-methoxy-4-methyl-tetrahydrofuran-3-yl]benzimidazole-5-carboxylate (311-2, 114 mg, 0.177 mmol) in acetonitrile and 1 mL of water was added aqueous LiOH (1.8 mL, 0.53 mmol, 0.3 M). The mixture was then stirred at 100° C. for 5 min. Upon completion the mixture was cooled to rt, filtered through celite and concentrated. The crude material was purified by reverse phase chromatography (ACN/water with 0.1% TFA added) to yield the title compound as a racemic mixture. ES/MZ: 629.3 (M+H+). Relative stereochemistry was confirmed by . . . .

Racemic 311-3 was purified by preparative chiral SFC (Daicel Chiralpak AD-H column, EtOH—$NH_3$—$CO_2$) to yield Example 311A and Example 311B as separate stereoisomers.

Example 311A: 2-(4-(6-((4-cyano-2-fluorobenzyl)oxy) pyridin-2-yl)-2,5-difluorobenzyl)-1-((3R,4R)-4-methoxy-4-methyltetrahydrofuran-3-yl)-1H-benzo[d]imidazole-6-carboxylic acid was isolated as the later eluting of two stereoisomers. 1H NMR (400 MHz, DMSO) δ 8.44 (s, 1H), 7.98-7.84 (m, 2H), 7.77 (ddd, J=15.0, 8.4, 1.6 Hz, 5H), 7.68-7.48 (m, 3H), 7.37 (dd, J=11.5, 6.0 Hz, 1H), 7.00 (d, J=8.3 Hz, 1H), 5.61 (s, 2H), 5.29 (s, 1H), 4.61-4.33 (m, 3H), 4.28-4.14 (m, 2H), 2.96 (s, 3H), 1.43 (s, 3H). ES/MS m/z: 629.32 (M+H+).

Example 311B: was isolated as the earlier eluting of two stereoisomers. 1H NMR (400 MHz, DMSO) δ 8.44 (s, 1H), 7.98-7.84 (m, 2H), 7.77 (ddd, J=15.0, 8.4, 1.6 Hz, 5H), 7.68-7.48 (m, 3H), 7.37 (dd, J=11.5, 6.0 Hz, 1H), 7.00 (d, J=8.3 Hz, 1H), 5.61 (s, 2H), 5.29 (s, 1H), 4.61-4.33 (m, 3H), 4.28-4.14 (m, 2H), 2.96 (s, 3H), 1.43 (s, 3H). ES/MS m/z: 629.32 (M+H+).

Example 312: 2-(4-(6-((4-cyano-2-fluorobenzyl) oxy)pyridin-2-yl)-2,5-difluorobenzyl)-1-((3R,4S)-4-methoxy-4-methyltetrahydrofuran-3-yl)-1H-benzo [d]imidazole-6-carboxylic acid Example 313: 2-(4-(6-((4-cyano-2-fluorobenzyl) oxy)pyridin-2-yl)-2,5-difluorobenzyl)-1-((3R,4S)-4-methoxy-4-methyltetrahydrofuran-3-yl)-1H-benzo [d]imidazole-6-carboxylic acid Examples 312 and 313 were prepared in a manner as described in Procedure 39, starting with Intermediates I-7 and I-1253 trans-isomer 2, and using preparative chiral SFC (Daicel Chiralpak IG column, EtOH—$CO_2$) to yield Example 312 and Example 313 as separate stereoisomers.

Example 312: 2-(4-(6-((4-cyano-2-fluorobenzyl)oxy) pyridin-2-yl)-2,5-difluorobenzyl)-1-((3R,4S)-4-methoxy-4-methyltetrahydrofuran-3-yl)-1H-benzo[d]imidazole-6-carboxylic acid was isolated as the later eluting of two stereoisomers. 1H NMR (400 MHz, DMSO) δ 8.46 (s, 1H), 7.99-7.85 (m, 2H), 7.85-7.69 (m, 4H), 7.64 (d, J=8.5 Hz, 1H), 7.55 (d, J=7.3 Hz, 1H), 7.46 (dd, J=10.4, 7.1 Hz, 1H), 7.00 (d, J=8.3 Hz, 1H), 5.61 (s, 2H), 5.23 (d, J=6.8 Hz, 1H), 4.82-4.25 (m, 4H), 4.13 (d, J=10.1 Hz, 1H), 3.80 (d, J=10.1 Hz, 1H), 3.31 (s, 3H), 0.84 (s, 3H). ES/MS m/z: 629.32 (M+H+).

Example 313: 2-(4-(6-((4-cyano-2-fluorobenzyl)oxy) pyridin-2-yl)-2,5-difluorobenzyl)-1-((3R,4S)-4-methoxy-4-methyltetrahydrofuran-3-yl)-1H-benzo[d]imidazole-6-carboxylic acid was isolated as the earlier eluting of two stereoisomers. 1H NMR (400 MHz, DMSO) δ 8.46 (s, 1H), 7.99-7.85 (m, 2H), 7.85-7.69 (m, 4H), 7.64 (d, J=8.5 Hz, 1H), 7.55 (d, J=7.3 Hz, 1H), 7.46 (dd, J=10.4, 7.1 Hz, 1H), 7.00 (d, J=8.3 Hz, 1H), 5.61 (s, 2H), 5.23 (d, J=6.8 Hz, 1H), 4.82-4.25 (m, 4H), 4.13 (d, J=10.1 Hz, 1H), 3.80 (d, J=10.1 Hz, 1H), 3.31 (s, 3H), 0.84 (s, 3H). ES/MS m/z: 629.32 (M+H+).

Example 316: (S)-2-(4-(6-((4-cyanobenzyl)oxy)-5-fluoropyridin-2-yl)-2,3,6-trifluorobenzyl)-1-(4,4-dimethyltetrahydrofuran-3-yl)-4-fluoro-1H-benzo[d] imidazole-6-carboxylic acid (S)-2-(4-(6-((4-cyanobenzyl)oxy)-5-fluoropyridin-2-yl)-2,3,6-trifluorobenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1232 and I-1092. 1H NMR (400 MHz, DMSO) δ 8.36 (s, 1H), 7.92 (dd, J=19.4, 8.4 Hz, 3H), 7.72 (d, J=8.0 Hz, 2H), 7.68-7.56 (m, 2H), 7.51 (d, J=11.2 Hz, 1H), 5.68 (s, 2H), 5.11 (d, J=6.4 Hz, 1H), 4.82-4.31 (m, 3H), 3.76 (s, 2H), 0.66 (s, 3H). ES/MS m/z: 649.31 (M+H+).

Example 317: (S)-2-(2-chloro-4-(2-((4-chloro-2-fluorobenzyl)oxy)pyrimidin-4-yl)-5-methylbenzyl)-1-(4,4-dimethyltetrahydrofuran-3-yl)-4-fluoro-1H-benzo[d]imidazole-6-carboxylic acid (S)-2-(2-chloro-4-(2-((4-chloro-2-fluorobenzyl)oxy)pyrimidin-4-yl)-5-methylbenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1031 and I-1241. 1H NMR (400 MHz, DMSO) δ 8.74 (d, J=5.1 Hz, 1H), 8.36 (s, 1H), 7.69-7.57 (m, 2H), 7.57-7.45 (m, 3H), 7.41 (s, 1H), 7.35 (dd, J=8.3, 2.1 Hz, 1H), 5.02 (d, J=6.7 Hz, 1H), 4.64-4.31 (m, 4H), 3.81-3.67 (m, 2H), 1.33 (s, 3H), 0.66 (s, 3H). ES/MS m/z: 653.73 (M+H+).

Example 318: (S)-2-(2-chloro-4-(2-((4-chloro-2-fluorobenzyl)oxy)pyrimidin-4-yl)-5-methylbenzyl)-1-(4,4-dimethyltetrahydrofuran-3-yl)-1H-benzo[d] imidazole-6-carboxylic acid (S)-2-(2-chloro-4-(2-((4-chloro-2-fluorobenzyl)oxy)pyrimidin-4-yl)-5-methylbenzyl)-1-(4,4-dimethyltetrahydrofuran-3-yl)-1H-benzo[d]imidazole-6-carboxylic acid was prepared in a manner as described in Procedure 35, starting with Intermediates I-1030 and I-1241. 1H NMR (400 MHz, DMSO) δ 8.75 (d, J=5.1 Hz, 1H), 8.36 (s, 1H), 7.94 (d, J=10.0 Hz, 1H), 7.83-7.70 (m, 2H), 7.61 (s, 1H), 7.57-7.46 (m, 2H), 7.41 (s, 1H), 5.59 (s, 2H), 5.02 (d, J=6.6 Hz, 1H), 4.73-4.33 (m, 4H), 3.85-3.65 (m, 2H), 1.33 (s, 3H), 0.65 (s, 3H). ES/MS m/z: 636.25 (M+H+).

Example 319: (S)-2-(2-chloro-4-(2-((4-cyano-2-fluorobenzyl)oxy)pyrimidin-4-yl)-5-methylbenzyl)-1-(4,4-dimethyltetrahydrofuran-3-yl)-4-fluoro-1H-benzo[d]imidazole-6-carboxylic acid (S)-2-(2-chloro-4-(2-((4-cyano-2-fluorobenzyl)oxy)pyrimidin-4-yl)-5-methylbenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1031 and I-94. 1H NMR (400 MHz, DMSO) δ 8.75 (d, J=5.1 Hz, 1H), 8.36 (s, 1H), 7.94 (d, J=10.0 Hz, 1H), 7.83-7.70 (m, 2H), 7.61 (s, 1H), 7.57-7.46 (m, 2H), 7.41 (s, 1H), 5.59 (s, 2H), 5.02 (d, J=6.6 Hz, 1H), 4.73-4.33 (m, 4H), 3.85-3.65 (m, 2H), 1.33 (s, 3H), 0.65 (s, 3H). ES/MS m/z: 644.8 (M+H$^+$).

Example 320: (S)-2-(2-chloro-4-(2-((4-cyano-2-fluorobenzyl)oxy)pyrimidin-4-yl)-5-methylbenzyl)-1-(4,4-dimethyltetrahydrofuran-3-yl)-1H-benzo[d]imidazole-6-carboxylic acid (S)-2-(2-chloro-4-(2-((4-cyano-2-fluorobenzyl)oxy)pyrimidin-4-yl)-5-methylbenzyl)-1-(4,4-dimethyltetrahydrofuran-3-yl)-1H-benzo[d]imidazole-6-carboxylic acid was prepared in a manner as described in Procedure 35, starting with Intermediates I-1030 and I-94. 1H NMR (400 MHz, DMSO) δ 8.75 (d, J=5.1 Hz, 1H), 8.51 (s, 1H), 7.94 (d, J=10.0 Hz, 1H), 7.88-7.69 (m, 3H), 7.68-7.57 (m, 2H), 7.49 (d, J=5.1 Hz, 1H), 7.42 (s, 1H), 5.59 (s, 2H), 5.02 (d, J=6.8 Hz, 1H), 4.73-4.23 (m, 4H), 3.88-3.68 (m, 2H), 1.33 (s, 3H), 0.66 (s, 3H). ES/MS m/z: 626.81 (M+H$^+$).

Example 321: (S)-2-(4-(6-((4-cyano-2-fluorobenzyl)oxy)pyridin-2-yl)-2,6-difluorobenzyl)-1-(4,4-dimethyltetrahydrofuran-3-yl)-1H-benzo[d]imidazole-6-carboxylic acid (S)-2-(4-(6-((4-cyano-2-fluorobenzyl)oxy)pyridin-2-yl)-2,6-difluorobenzyl)-1-(4,4-dimethyltetrahydrofuran-3-yl)-1H-benzo[d]imidazole-6-carboxylic acid was prepared in a manner as described in Procedure 35, starting with Intermediates I-1233 and I-3. 1H NMR (400 MHz, DMSO) δ 8.48 (s, 1H), 7.98-7.70 (m, 9H), 7.57 (d, J=8.5 Hz, 1H), 6.99 (d, J=8.2 Hz, 1H), 5.65 (s, 2H), 5.09 (d, J=6.6 Hz, 1H), 4.57 (d, J=16.7 Hz, 2H), 4.47 (dd, J=11.1, 6.7 Hz, 1H), 4.31 (d, J=17.1 Hz, 1H), 3.86-3.69 (m, 2H), 1.38 (s, 3H), 0.65 (s, 3H). ES/MS m/z: 613.44 (M+H$^+$).

Example 322: (S)-2-(4-(6-((4-cyano-2-fluorobenzyl)oxy)-5-fluoropyridin-2-yl)-2,6-difluorobenzyl)-1-(4,4-dimethyltetrahydrofuran-3-yl)-1H-benzo[d]imidazole-6-carboxylic acid (S)-2-(4-(6-((4-cyano-2-fluorobenzyl)oxy)-5-fluoropyridin-2-yl)-2,6-difluorobenzyl)-1-(4,4-dimethyltetrahydrofuran-3-yl)-1H-benzo[d]imidazole-6-carboxylic acid was prepared in a manner as described in Procedure 35, starting with Intermediates I-1233 and I-109. 1H NMR (400 MHz, DMSO) δ 8.47 (s, 1H), 8.01-7.69 (m, 8H), 7.56 (d, J=8.5 Hz, 1H), 5.74 (s, 2H), 5.08 (d, J=6.7 Hz, 1H), 4.76-4.44 (m, 3H), 4.29 (d, J=17.1 Hz, 1H), 3.77 (d, J=3.8 Hz, 2H), 1.38 (s, 3H), 0.65 (s, 3H). ES/MS m/z: 631.32 (M+H$^+$).

Example 323: (S)-2-(2-chloro-4-(6-((6-chloro-4-methoxypyridin-3-yl)methoxy)-5-fluoropyridin-2-yl)-5-methylbenzyl)-1-(4,4-dimethyltetrahydrofuran-3-yl)-1H-benzo[d]imidazole-6-carboxylic acid (S)-2-(2-chloro-4-(6-((6-chloro-4-methoxypyridin-3-yl)methoxy)-5-fluoropyridin-2-yl)-5-methylbenzyl)-1-(4,4-dimethyltetrahydrofuran-3-yl)-1H-benzo[d]imidazole-6-carboxylic acid was prepared in a manner as described in Procedure 35, starting with Intermediates I-1030 and I-1243. 1H NMR (400 MHz, DMSO) δ 8.51 (s, 1H), 8.30 (s, 1H), 7.83 (dd, J=10.2, 8.2 Hz, 2H), 7.64 (d, J=8.4 Hz, 1H), 7.53 (s, 1H), 7.37 (s, 1H), 7.32-7.23 (m, 3H), 5.43 (s, 2H), 5.02 (d, J=6.8 Hz, 1H), 4.72-4.34 (m, 4H), 3.93 (s, 4H), 2.32 (s, 3H), 1.33 (s, 3H), 0.66 (s, 3H). ES/MS m/z: 666.25 (M+H$^+$).

Example 324: (S)-2-(4-(6-((6-chloro-4-methoxypyridin-3-yl)methoxy)-5-fluoropyridin-2-yl)-2-fluorobenzyl)-1-(4,4-dimethyltetrahydrofuran-3-yl)-4-fluoro-1H-benzo[d]imidazole-6-carboxylic acid (S)-2-(4-(6-((6-chloro-4-methoxypyridin-3-yl)methoxy)-5-fluoropyridin-2-yl)-2-fluorobenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1230 and I-1243. 1H NMR (400 MHz, DMSO) δ 8.36 (d, J=8.3 Hz, 2H), 7.96-7.87 (m, 2H), 7.81 (dd, J=10.2, 8.2 Hz, 1H), 7.70 (dd, J=8.2, 2.8 Hz, 1H), 7.57-7.46 (m, 2H), 7.27 (s, 1H), 5.54 (s, 2H), 5.01 (d, J=6.6 Hz, 1H), 4.64-4.32 (m, 5H), 3.96 (s, 3H), 1.31 (s, 3H), 0.59 (s, 3H). ES/MS m/z: 653.53 (M+H$^+$).

Example 325: (S)-2-(4-(6-((4-cyanobenzyl)oxy)-5-fluoropyridin-2-yl)-2,5-difluorobenzyl)-1-(4,4-dimethyltetrahydrofuran-3-yl)-4-fluoro-1H-benzo[d]imidazole-6-carboxylic acid (S)-2-(4-(6-((4-cyanobenzyl)oxy)-5-fluoropyridin-2-yl)-2,5-difluorobenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-108 and I-1092. 1H NMR (400 MHz, DMSO) δ 8.35 (s, 1H), 8.10-7.80 (m, 3H), 7.80-7.65 (m, 3H), 7.65-7.35 (m, 3H), 5.68 (s, 2H), 5.03 (d, J=6.6 Hz, 1H), 4.69-4.30 (m, 4H), 1.34 (s, 3H), 0.61 (s, 3H). ES/MS m/z: 631.17 (M+H$^+$).

Example 326: (S)-2-((5'-chloro-6-((4-cyano-2-fluorobenzyl)oxy)-2'-oxo-[2,4'-bipyridin]-1'(2'H)-yl)methyl)-1-(4,4-dimethyltetrahydrofuran-3-yl)-4-fluoro-1H-benzo[d]imidazole-6-carboxylic acid (S)-2-((5'-chloro-6-((4-cyano-2-fluorobenzyl)oxy)-2'-oxo-[2,4'-bipyridin]-1'(2'H)-yl)methyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1238 and I-3. 1H NMR (400 MHz, DMSO) δ 8.34 (d, J=20.1 Hz, 2H), 8.04-7.85 (m, 2H), 7.74 (d, J=4.7 Hz, 2H), 7.55 (dd, J=11.2, 1.2 Hz, 1H), 7.40 (d, J=7.3 Hz, 1H), 7.07 (d, J=8.3 Hz, 1H), 6.67 (s, 1H), 5.65-5.38 (m, 4H), 5.13 (d, J=6.5 Hz, 1H), 4.64-4.39 (m, 2H), 3.83-3.53 (m, 2H), 1.38 (s, 3H), 0.68 (s, 3H). ES/MS m/z: 646.34 (M+H$^+$).

Example 327: (S)-2-((5'-chloro-6-((4-chloro-2-fluorobenzyl)oxy)-2'-oxo-[2,4'-bipyridin]-1'(2'H)-yl)methyl)-1-(4,4-dimethyltetrahydrofuran-3-yl)-4-fluoro-1H-benzo[d]imidazole-6-carboxylic acid (S)-2-((5'-chloro-6-((4-chloro-2-fluorobenzyl)oxy)-2'-oxo-[2,4'-bipyridin]-1'(2'H)-yl)methyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1238 and I-102. 1H NMR (400 MHz, DMSO) δ 8.34 (d, J=16.2 Hz, 2H), 7.91 (dd, J=8.3, 7.3 Hz, 1H), 7.68-7.44 (m, 3H), 7.44-7.27 (m, 2H), 7.02 (d, J=8.3 Hz, 1H), 6.70 (s, 1H), 5.45 (s, 2H), 5.14 (d, J=6.6 Hz, 1H), 4.63-4.29 (m, 2H), 3.93-3.63 (m, 2H), 1.39 (s, 3H), 0.68 (s, 3H). ES/MS m/z: 655.53 (M+H⁺).

Example 328: (S)-2-((6-((4-cyano-2-fluorobenzyl)oxy)-5,5'-difluoro-2'-oxo-[2,4'-bipyridin]-1'(2'H)-yl)methyl)-1-(4,4-dimethyltetrahydrofuran-3-yl)-1H-benzo[d]imidazole-6-carboxylic acid (S)-2-((6-((4-cyano-2-fluorobenzyl)oxy)-5,5'-difluoro-2'-oxo-[2,4'-bipyridin]-1'(2'H)-yl)methyl)-1-(4,4-dimethyltetrahydrofuran-3-yl)-1H-benzo[d]imidazole-6-carboxylic acid was prepared in a manner as described in Procedure 35, starting with Intermediates I-1237 and I-109. 1H NMR (400 MHz, DMSO) δ 8.48 (s, 1H), 8.24 (d, J=7.0 Hz, 1H), 8.04-7.84 (m, 2H), 7.87-7.70 (m, 3H), 7.66 (d, J=8.5 Hz, 1H), 7.59 (dt, J=8.6, 2.0 Hz, 1H), 6.92 (d, J=7.6 Hz, 1H), 5.67 (s, 2H), 5.63-5.32 (m, 2H), 5.10 (d, J=6.6 Hz, 1H), 4.55 (d, J=11.1 Hz, 1H), 4.44 (dd, J=11.1, 6.8 Hz, 1H), 3.83-3.59 (m, 2H), 1.37 (s, 3H), 0.65 (s, 3H). ES/MS m/z: 630.22 (M+H⁺).

Example 329: (S)-2-(4-(6-((4-chloro-2-fluorobenzyl)oxy)pyridin-2-yl)-2-fluorobenzyl)-1-(4,4-dimethyltetrahydrofuran-3-yl)-4-fluoro-1H-benzo[d]imidazole-6-carboxylic acid (S)-2-(4-(6-((4-chloro-2-fluorobenzyl)oxy)pyridin-2-yl)-2-fluorobenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1230 and I-102. 1H NMR (400 MHz, DMSO) δ 8.35 (s, 1H), 8.10-7.90 (m, 2H), 7.85 (t, J=7.8 Hz, 1H), 7.74-7.57 (m, 2H), 7.57-7.44 (m, 3H), 7.32 (dd, J=8.2, 2.1 Hz, 1H), 6.89 (d, J=8.2 Hz, 1H), 5.53 (s, 2H), 5.01 (d, J=6.6 Hz, 1H), 4.66-4.23 (m, 4H), 1.30 (s, 3H), 0.58 (s, 3H). ES/MS m/z: 622.45 (M+H⁺).

Example 330: Methyl (S)-2-(4-(6-((4-cyano-2-fluorobenzyl)oxy)-5-fluoropyridin-2-yl)-2-fluorobenzyl)-1-(4,4-dimethyltetrahydrofuran-3-yl)-1H-benzo[d]imidazole-6-carboxylate

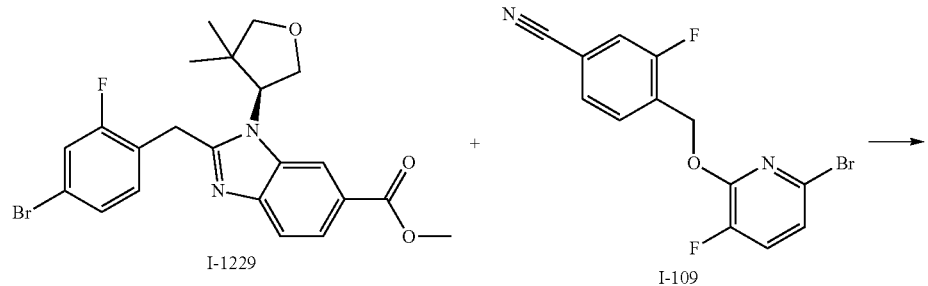

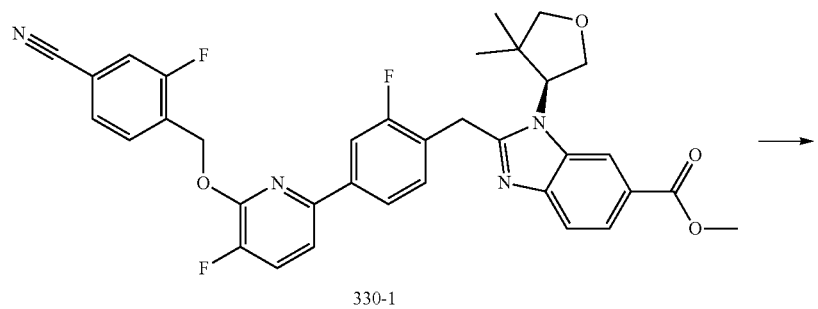

330-1

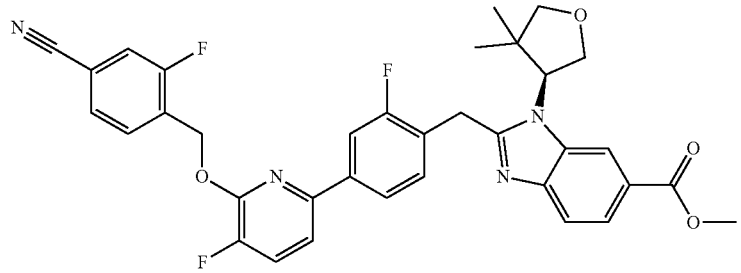

Example 330

The title compound was prepared in a manner similar to that described in Procedure 35, starting with Intermediates I-109 and I-1229.

Methyl (S)-2-(4-(6-((4-cyano-2-fluorobenzyl)oxy)-5-fluoropyridin-2-yl)-2-fluorobenzyl)-1-(4,4-dimethyltetrahydrofuran-3-yl)-1H-benzo[d]imidazole-6-carboxylate (330-1): ES/MS m/z: 627.7 (M+H$^+$).

Methyl (S)-2-(4-(6-((4-cyano-2-fluorobenzyl)oxy)-5-fluoropyridin-2-yl)-2-fluorobenzyl)-1-(4,4-dimethyltetrahydrofuran-3-yl)-1H-benzo[d]imidazole-6-carboxylate (Example 330): 1H NMR (400 MHz, DMSO) δ 8.49 (s, 1H), 8.05-7.68 (m, 9H), 7.62 (d, J=8.5 Hz, 1H), 7.49 (t, J=7.9 Hz, 1H), 5.72 (s, 2H), 4.99 (d, J=6.7 Hz, 1H), 4.60-4.29 (m, 3H), 3.88-3.67 (m, 2H), 1.30 (s, 3H), 0.58 (s, 3H). ES/MS m/z: 613.3 (M+H$^+$).

Example 331: (S)-2-(4-(6-((4-chloro-2-fluorobenzyl)oxy)pyridin-2-yl)-2-fluorobenzyl)-1-(4,4-dimethyltetrahydrofuran-3-yl)-1H-benzo[d]imidazole-6-carboxylic acid (S)-2-(4-(6-((4-chloro-2-fluorobenzyl)oxy)pyridin-2-yl)-2-fluorobenzyl)-1-(4,4-dimethyltetrahydrofuran-3-yl)-1H-benzo[d]imidazole-6-carboxylic acid was prepared in a manner as described in Procedure 35, starting with Intermediates I-1229 and I-1021H NMR (400 MHz, DMSO) δ 8.51 (s, 1H), 8.00-7.90 (m, 2H), 7.90-7.78 (m, 2H), 7.74-7.57 (m, 3H), 7.57-7.43 (m, 2H), 7.33 (dd, J=8.2, 2.1 Hz, 1H), 6.90 (d, J=8.2 Hz, 1H), 5.53 (s, 2H), 5.02 (d, J=6.6 Hz, 1H), 4.62-4.27 (m, 5H), 3.88-3.67 (m, 2H), 1.30 (s, 3H), 0.59 (s, 3H). ES/MS m/z: 604.3 (M+H$^+$).

Example 332: (S)-2-(4-(6-((4-chloro-2-fluorobenzyl)oxy)-5-fluoropyridin-2-yl)-2-fluorobenzyl)-1-(4,4-dimethyltetrahydrofuran-3-yl)-1H-benzo[d]imidazole-6-carboxylic acid (S)-2-(4-(6-((4-chloro-2-fluorobenzyl)oxy)-5-fluoropyridin-2-yl)-2-fluorobenzyl)-1-(4,4-dimethyltetrahydrofuran-3-yl)-1H-benzo[d]imidazole-6-carboxylic acid was prepared in a manner as described in Procedure 35, starting with Intermediates I-1229 and I-1036. 1H NMR (400 MHz, DMSO) δ 8.50 (s, 1H), 7.98-7.86 (m, 2H), 7.86-7.80 (m, 2H), 7.76-7.58 (m, 3H), 7.57-7.44 (m, 2H), 7.35 (dd, J=8.2, 2.1 Hz, 1H), 5.62 (s, 2H), 5.00 (d, J=6.6 Hz, 1H), 4.61-4.33 (m, 5H), 3.83-3.67 (m, 2H), 1.30 (s, 3H), 0.58 (s, 3H). ES/MS m/z: 622.16 (M+H$^+$).

Example 334: (S)-2-(2-chloro-4-(6-((4-chloro-2-fluorobenzyl)oxy)-5-fluoropyridin-2-yl)-5-methylbenzyl)-1-(4,4-dimethyltetrahydrofuran-3-yl)-4-fluoro-1H-benzo[d]imidazole-6-carboxylic acid (S)-2-(2-chloro-4-(6-((4-chloro-2-fluorobenzyl)oxy)-5-fluoropyridin-2-yl)-5-methylbenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1031 and I-1036. 1H NMR (400 MHz, DMSO) δ 8.36 (s, 1H), 7.83 (dd, J=10.5, 8.1 Hz, 1H), 7.59 (t, J=8.2 Hz, 1H), 7.55-7.45 (m, 3H), 7.41-7.22 (m, 3H), 5.51 (s, 2H), 5.02 (d, J=6.7 Hz, 1H), 4.59-4.47 (m, 1H), 4.47-4.32 (m, 2H), 3.88-3.60 (m, 2H), 2.31 (s, 3H), 1.33 (s, 3H), 0.65 (s, 3H). ES/MS m/z: 670.33 (M+H$^+$).

Example 335: (S)-2-(4-(6-((4-chloro-2-fluorobenzyl)oxy)-5-fluoropyridin-2-yl)-2,3,6-trifluorobenzyl)-1-(4,4-dimethyltetrahydrofuran-3-yl)-1H-benzo[d]imidazole-6-carboxylic acid (S)-2-(4-(6-((4-chloro-2-fluorobenzyl)oxy)-5-fluoropyridin-2-yl)-2,3,6-trifluorobenzyl)-1-(4,4-dimethyltetrahydrofuran-3-yl)-1H-benzo[d]imidazole-6-carboxylic acid was prepared in a manner as described in Procedure 35, starting with Intermediates I-1231 and I-1036. 1H NMR (400 MHz, DMSO) δ 8.48 (s, 1H), 7.91 (dd, J=10.2, 8.2 Hz, 1H), 7.78 (dd, J=8.4, 1.5 Hz, 1H), 7.75-7.69 (m, 1H), 7.69-7.48 (m, 4H), 7.36 (dd, J=8.4, 2.1 Hz, 1H), 5.61 (s, 2H), 5.09 (d, J=6.6 Hz, 1H), 4.76-4.27 (m, 4H), 3.92-3.69 (m, 2H), 1.39 (s, 3H), 0.65 (s, 3H). ES/MS m/z: 658.12 (M+H$^+$).

Example 336: (S)-2-(4-(6-((4-chloro-2-fluorobenzyl)oxy)-5-fluoropyridin-2-yl)-2,3,6-trifluorobenzyl)-1-(4,4-dimethyltetrahydrofuran-3-yl)-4-fluoro-1H-benzo[d]imidazole-6-carboxylic acid (S)-2-(4-(6-((4-chloro-2-fluorobenzyl)oxy)-5-fluoropyridin-2-yl)-2,3,6-trifluorobenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1232 and I-1036. 1H NMR (400 MHz, DMSO) δ 8.36 (s, 1H), 7.91 (dd, J=10.2, 8.2 Hz, 1H), 7.74 (ddd, J=10.5, 5.7, 2.0 Hz, 1H), 7.69-7.56 (m, 2H), 7.52 (ddd, J=11.1, 3.4, 1.6 Hz, 2H), 7.35 (dd, J=8.2, 2.1 Hz, 1H), 5.61 (s, 2H), 5.11 (d, J=6.5 Hz, 1H), 4.67 (d, J=17.4 Hz, 1H), 4.62-4.32 (m, 3H), 3.76 (s, 2H), 1.39 (s, 3H), 0.67 (s, 3H). ES/MS m/z: 676.38 (M+H$^+$).

Example 337: (S)-2-(4-(6-((4-cyano-2-fluorobenzyl)oxy)-5-fluoropyridin-2-yl)-2-fluorobenzyl)-1-(4,4-dimethyltetrahydrofuran-3-yl)-4-fluoro-1H-benzo[d]imidazole-6-carboxylic acid (S)-2-(4-(6-((4-cyano-2-fluorobenzyl)oxy)-5-fluoropyridin-2-yl)-2-fluorobenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1230 and I-109. 1H NMR (400 MHz, DMSO) δ 8.35 (s, 1H), 8.09-7.64 (m, 8H), 7.57-7.39 (m, 2H), 5.72 (s, 2H), 5.00 (d, J=6.6 Hz, 1H), 4.59-4.28 (m, 2H), 3.75-3.80 (m, 2H), 1.30 (s, 3H), 0.58 (s, 3H). ES/MS m/z: 630.35 (M+H$^+$).

Example 339: (S)-2-(4-(6-((6-chloro-4-methoxypyridin-3-yl)methoxy)-5-fluoropyridin-2-yl)-2,3,6-trifluorobenzyl)-1-(4,4-dimethyltetrahydrofuran-3-yl)-4-fluoro-1H-benzo[d]imidazole-6-carboxylic acid (S)-2-(4-(6-((6-chloro-4-methoxypyridin-3-yl)methoxy)-5-fluoropyridin-2-yl)-2,3,6-trifluorobenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1232 and I-1243. 1H NMR (400 MHz, DMSO) δ 8.36 (d, J=2.6 Hz, 2H), 7.90 (dd, J=10.2, 8.2 Hz, 1H), 7.75 (ddd, J=10.4, 5.8, 2.0 Hz, 1H), 7.61 (ddd, J=8.1, 2.9, 1.5 Hz, 1H), 7.51 (dd, J=11.2, 1.2 Hz, 1H), 7.27 (s, 1H), 5.53 (s, 2H), 5.11 (d, J=6.5 Hz, 1H), 4.67 (d, J=17.5 Hz, 1H), 4.61-4.31 (m, 3H), 3.95 (s, 3H), 3.76 (s, 2H), 1.39 (s, 3H), 0.67 (s, 3H). ES/MS m/z: 689.58 (M+H$^+$).

Example 340: (S)-2-(4-(6-((6-chloro-4-methoxypyridin-3-yl)methoxy)-5-fluoropyridin-2-yl)-2,5-difluorobenzyl)-1-(4,4-dimethyltetrahydrofuran-3-yl)-4-fluoro-1H-benzo[d]imidazole-6-carboxylic acid (S)-2-(4-(6-((6-chloro-4-methoxypyridin-3-yl)methoxy)-5-fluoropyridin-2-yl)-2,5-difluorobenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-108 and I-1243. 1H NMR (400 MHz, DMSO) δ 8.35 (s, 2H), 7.84 (ddd, J=10.2, 7.4, 4.4 Hz, 2H), 7.61-7.43 (m, 3H), 7.27 (s, 1H), 5.52 (s, 2H), 5.04 (d, J=6.6 Hz, 1H), 4.63-4.49 (m, 2H), 4.49-4.28 (m, 2H), 3.95 (s, 3H), 1.34 (s, 3H), 0.62 (s, 3H). ES/MS m/z: 671.6 (M+H$^+$).

Example 341: (S)-2-(4-(6-((6-chloro-4-methoxy-pyridin-3-yl)methoxy)-5-fluoropyridin-2-yl)-2,3,6-trifluorobenzyl)-1-(4,4-dimethyltetrahydrofuran-3-yl)-1H-benzo[d]imidazole-6-carboxylic acid (S)-2-(4-(6-((6-chloro-4-methoxypyridin-3-yl)methoxy)-5-fluoropyridin-2-yl)-2,3,6-trifluorobenzyl)-1-(4,4-dimethyltetrahydrofuran-3-yl)-1H-benzo[d]imidazole-6-carboxylic acid was prepared in a manner as described in Procedure 35, starting with Intermediates I-1231 and I-1243. 1H NMR (400 MHz, DMSO) δ 8.48 (s, 1H), 8.36 (s, 1H), 7.90 (dd, J=10.2, 8.2 Hz, 1H), 7.78 (dd, J=8.4, 1.5 Hz, 1H), 7.60 (dd, J=8.7, 3.3 Hz, 2H), 7.28 (s, 1H), 5.53 (s, 2H), 5.09 (d, J=6.5 Hz, 1H), 4.75-4.52 (m, 2H), 4.47 (dd, J=11.1, 6.7 Hz, 1H), 4.36 (d, J=17.4 Hz, 1H), 3.96 (s, 3H), 3.86-3.71 (m, 2H), 1.39 (s, 3H), 0.66 (s, 3H). ES/MS m/z: 671.51 (M+H$^+$).

Example 342: (S)-2-(4-(6-((6-chloro-4-methoxy-pyridin-3-yl)methoxy)-5-fluoropyridin-2-yl)-2,5-difluorobenzyl)-1-(4,4-dimethyltetrahydrofuran-3-yl)-1H-benzo[d]imidazole-6-carboxylic acid (S)-2-(4-(6-((6-chloro-4-methoxypyridin-3-yl)methoxy)-5-fluoropyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 35, starting with Intermediates I-82 and I-1243. 1H NMR (400 MHz, DMSO) δ 8.51 (s, 1H), 8.35 (s, 1H), 7.89-7.76 (m, 3H), 7.64 (d, J=8.5 Hz, 1H), 7.59-7.41 (m, 2H), 7.27 (s, 1H), 5.52 (s, 2H), 5.03 (d, J=6.7 Hz, 1H), 4.63-4.32 (m, 4H), 3.95 (s, 3H), 3.88-3.66 (m, 2H), 1.34 (s, 3H), 0.62 (s, 3H). ES/MS m/z: 653.76 (M+H$^+$).

Example 343: 2-(2-chloro-4-(2-((4-chloro-2-fluorobenzyl)oxy)pyrimidin-4-yl)-5-fluorobenzyl)-1-(4,4-dimethyltetrahydrofuran-3-yl)-4-fluoro-1H-benzo[d]imidazole-6-carboxylic acid 2-(2-chloro-4-(2-((4-chloro-2-fluorobenzyl)oxy)pyrimidin-4-yl)-5-fluorobenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1239 and I-1241. 1H NMR (400 MHz, DMSO) δ 8.79 (d, J=5.2 Hz, 1H), 8.36 (s, 1H), 8.17 (d, J=7.0 Hz, 1H), 7.70-7.45 (m, 5H), 7.35 (dd, J=8.2, 2.1 Hz, 1H), 5.54 (s, 2H), 5.04 (d, J=6.7 Hz, 1H), 4.67 (d, J=17.1 Hz, 1H), 4.59-4.37 (m, 3H), 3.84-3.66 (m, 2H), 1.36 (s, 3H), 0.67 (s, 3H). ES/MS m/z: 657.36 (M+H$^+$).

Example 344: 2-(2-chloro-4-(2-((4-(difluoromethyl)-2-fluorobenzyl)oxy)pyrimidin-4-yl)-5-fluorobenzyl)-1-(4,4-dimethyltetrahydrofuran-3-yl)-4-fluoro-1H-benzo[d]imidazole-6-carboxylic acid 2-(2-chloro-4-(2-((4-(difluoromethyl)-2-fluorobenzyl)oxy)pyrimidin-4-yl)-5-fluorobenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1239 and I-1242. 1H NMR (400 MHz, DMSO) δ 8.80 (d, J=5.2 Hz, 1H), 8.36 (s, 1H), 8.16 (d, J=7.0 Hz, 1H), 7.75 (t, J=7.6 Hz, 1H), 7.65 (dd, J=5.2, 1.8 Hz, 1H), 7.59 (d, J=11.7 Hz, 1H), 7.50 (dd, J=16.7, 9.4 Hz, 3H), 7.07 (t, J=55.6 Hz, 1H), 5.61 (s, 2H), 5.04 (d, J=6.6 Hz, 1H), 4.66 (d, J=17.1 Hz, 1H), 4.58-4.37 (m, 3H), 3.85-3.70 (m, 2H), 1.36 (s, 3H), 0.67 (s, 3H). ES/MS m/z: 673.175 (M+H$^+$).

Example 345: 2-(2-chloro-4-(6-((4-cyano-2-fluorobenzyl)oxy)-5-fluoropyridin-2-yl)-5-fluorobenzyl)-1-(4,4-dimethyltetrahydrofuran-3-yl)-1H-benzo[d]imidazole-6-carboxylic acid 2-(2-chloro-4-(6-((4-cyano-2-fluorobenzyl)oxy)-5-fluoropyridin-2-yl)-5-fluorobenzyl)-1-(4,4-dimethyltetrahydrofuran-3-yl)-1H-benzo[d]imidazole-6-carboxylic acid was prepared in a manner as described in Procedure 35, starting with Intermediates I-1240 and I-109. 1H NMR (400 MHz, DMSO) δ 8.49 (s, 1H), 8.00-7.83 (m, 3H), 7.83-7.71 (m, 3H), 7.65-7.43 (m, 3H), 5.69 (s, 2H), 5.01 (d, J=6.7 Hz, 1H), 4.69-4.49 (m, 2H), 4.49-4.35 (m, 2H), 3.80 (d, J=8.6 Hz, 1H), 3.73 (d, J=8.6 Hz, 1H), 1.35 (s, 3H), 0.66 (s, 3H). ES/MS m/z: 647.46 (M+H$^+$).

Example 346: 2-(2-chloro-4-(6-((4-cyano-2-fluorobenzyl)oxy)-5-fluoropyridin-2-yl)-5-fluorobenzyl)-1-(4,4-dimethyltetrahydrofuran-3-yl)-4-fluoro-1H-benzo[d]imidazole-6-carboxylic acid 2-(2-chloro-4-(6-((4-cyano-2-fluorobenzyl)oxy)-5-fluoropyridin-2-yl)-5-fluorobenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1239 and I-109. 1H NMR (400 MHz, DMSO) δ 8.36 (s, 1H), 8.00-7.83 (m, 3H), 7.83-7.70 (m, 2H), 7.60-7.43 (m, 3H), 5.70 (s, 2H), 5.03 (d, J=6.7 Hz, 1H), 4.62 (d, J=17.0 Hz, 1H), 4.53 (d, J=11.9 Hz, 1H), 4.47-4.36 (m, 2H), 3.83-3.69 (m, 2H), 1.35 (s, 3H), 0.66 (s, 3H). ES/MS m/z: 665.3 (M+H$^+$).

Example 347: 2-(4-(6-((4-chloro-2-fluorobenzyl)oxy)-5-fluoropyridin-2-yl)-2,5-difluorobenzyl)-1-(4,4-dimethyltetrahydrofuran-3-yl)-4-fluoro-1H-benzo[d]imidazole-6-carboxylic acid 2-(4-(6-((4-chloro-2-fluorobenzyl)oxy)-5-fluoropyridin-2-yl)-2,5-difluorobenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1041 and I-1036. 1H NMR (400 MHz, DMSO) δ 8.36 (s, 1H), 7.84 (ddd, J=11.9, 10.3, 7.4 Hz, 2H), 7.63 (t, J=8.1 Hz, 1H), 7.59-7.43 (m, 4H), 7.35 (dd, J=8.2, 2.0 Hz, 1H), 5.61 (s, 2H), 5.04 (d, J=6.6 Hz, 1H), 4.61-4.47 (m, 2H), 4.48-4.32 (m, 2H), 3.75 (q, J=8.7 Hz, 2H), 1.34 (s, 3H), 0.61 (s, 3H). ES/MS m/z: 658.8 (M+H$^+$).

Example 348: 2-(4-(4-((4-chloro-2-fluorobenzyl)oxy)pyrimidin-2-yl)-2,5-difluorobenzyl)-1-(4,4-dimethyltetrahydrofuran-3-yl)-4-fluoro-1H-benzo[d]imidazole-6-carboxylic acid 2-(4-(4-((4-chloro-2-fluorobenzyl)oxy)pyrimidin-2-yl)-2,5-difluorobenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1041 and I-1336. 1H NMR (400 MHz, MeOD) δ 8.60 (d, J=5.8 Hz, 1H), 8.55 (s, 1H), 7.90 (dd, J=10.3, 6.1 Hz, 1H), 7.66 (d, J=11.0 Hz, 1H), 7.56 (t, J=8.0 Hz, 1H), 7.35-7.13 (m, 3H), 6.91 (d, J=5.8 Hz, 1H), 5.59 (s, 2H), 4.91 (s, 8H), 4.65-4.55 (m, 1H), 4.55-4.42 (m, 3H), 3.93 (d, J=8.8 Hz, 1H), 3.79 (d, J=8.8 Hz, 1H), 3.33 (p, J=1.7 Hz, 5H), 1.36 (s, 3H), 0.67 (s, 3H). ES/MS m/z: 641.2 (M+H$^+$).

Example 349: 2-[[2,5-difluoro-4-[6-[(2-methoxycar-bonylisoindolin-5-yl)methoxy]-2-pyridyl]phenyl]methyl]-7-fluoro-3-[[(2S)-oxetan-2-yl]methyl]benzimidazole-5-carboxylic acid
Procedure 40
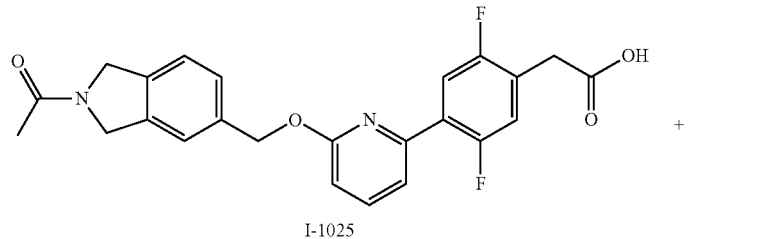
I-1025
+
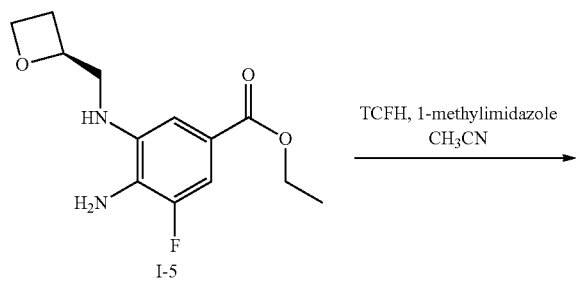
I-5
TCFH, 1-methylimidazole
CH₃CN
→
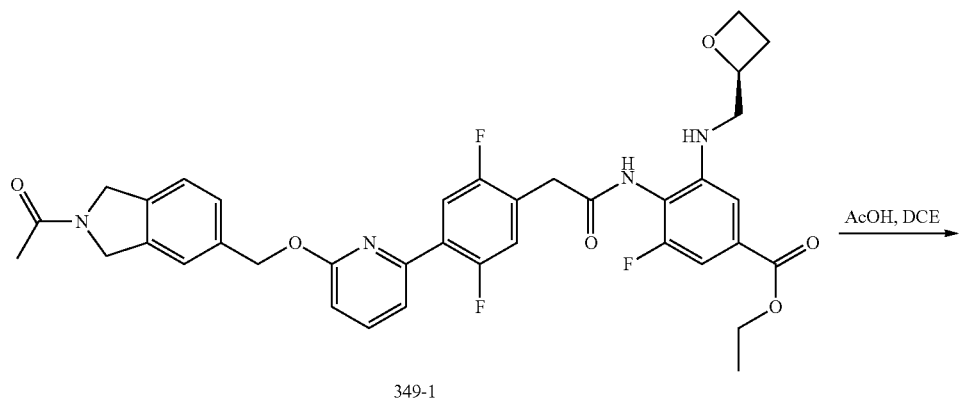
349-1
AcOH, DCE
→
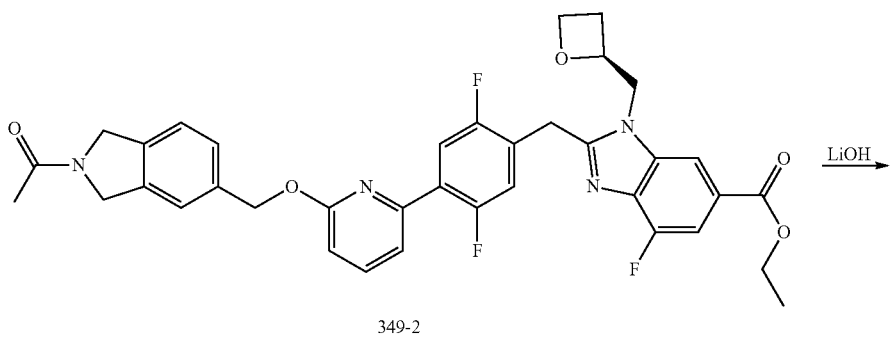
349-2
LiOH
→

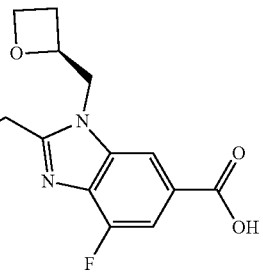

Example 349

Methyl 5-[[6-[4-[2-[4-ethoxycarbonyl-2-fluoro-6-[[(2S)-oxetan-2-yl]methylamino]anilino]-2-oxo-ethyl]-2,5-difluoro-phenyl]-2-pyridyl]oxymethyl]isoindoline-2-carboxylate (349-1). 1-Methylimidazole (0.0186 mL, 0.233 mmol) followed by TCFH (15.7 mg, 0.0559 mmol) was added to a solution of 2-[2,5-difluoro-4-[6-[(2-methoxycarbonylisoindolin-5-yl)methoxy]-2-pyridyl]phenyl]acetic acid (20.9 mg, 0.0460 mmol) and ethyl 4-amino-3-fluoro-5-[[(2S)-oxetan-2-yl]methylamino]benzoate (12.5 mg, 0.0466 mmol) in CH3CN (2 mL) at 0° C. The mixture was stirred for 1 hr., then diluted with EtOAc and washed with saturated NH4Cl, 1N NaOH, and brine. Dried over sodium sulfate, concentrated and carried onto next step below without purification. ES/MS: 706 (M+H+).

Ethyl 2-[[2,5-difluoro-4-[6-[(2-methoxycarbonylisoindolin-5-yl)methoxy]-2-pyridyl]phenyl]methyl]-7-fluoro-3-[[(2S)-oxetan-2-yl]methyl]benzimidazole-5-carboxylate (349-2): A solution of methyl 5-[[6-[4-[2-[4-ethoxycarbonyl-2-fluoro-6-[[(2S)-oxetan-2-yl]methylamino]anilino]-2-oxo-ethyl]-2,5-difluoro-phenyl]-2-pyridyl]oxymethyl]isoindoline-2-carboxylate (32.0 mg, 0.0454 mmol) and acetic acid (81.8 mg, 1.36 mmol) in DCE (4 mL) was heated at 60° C. overnight, then at 75° C. for 9 hr. The mixture was cooled to rt. Diluted with EtOAc and carefully neutralized with NaHCO3 (114 mg). Washed organic layer with brine and dried over sodium sulfate. The crude residue was purified by chromatography (eluent: EtOAc/hexanes) to give desired product. ES/MS: 687.2 (M+H+); NMR (400 MHz, Chloroform-d) δ 7.94 (s, 1H), 7.84 (dd, J=10.8, 6.3 Hz, 1H), 7.73-7.61 (m, 2H), 7.49 (dd, J=7.7, 1.5 Hz, 1H), 7.46-7.35 (m, 2H), 7.33 (s, 1H), 7.11 (dd, J=11.3, 6.1 Hz, 1H), 6.82 (d, J=8.3 Hz, 1H), 5.48 (s, 2H), 5.24-5.08 (m, 1H), 4.84-4.69 (m, 5H), 4.68-4.21 (m, 6H), 3.81 (s, 3H), 2.76 (dq, J=14.0, 7.5 Hz, 1H), 2.41 (dt, J=17.7, 7.9 Hz, 1H), 1.44 (t, J=7.1 Hz, 3H).

2-[[2,5-difluoro-4-[6-[(2-methoxycarbonylisoindolin-5-yl)methoxy]-2-pyridyl]phenyl]methyl]-7-fluoro-3-[[(2S)-oxetan-2-yl]methyl]benzimidazole-5-carboxylic acid (Example 349): A suspension of ethyl 2-[[2,5-difluoro-4-[6-[(2-methoxycarbonylisoindolin-5-yl)methoxy]-2-pyridyl]phenyl]methyl]-7-fluoro-3-[[(2S)-oxetan-2-yl]methyl]benzimidazole-5-carboxylate (10.0 mg, 0.0146 mmol) and lithium hydroxide, monohydrate (300 mmol/L, 0.146 mL, 0.0437 mmol) in CH3CN (3 mL) in a 40 ml glass vial was heated at 100° C. until completion. The mixture was then diluted with EtOAc and brine, followed by the addition of 0.090 mL 1M citric acid. The organic extract was dried over sodium sulfate, filtered and concentrated. The organic extract was then purified by RP-HPLC (eluent: MeCN/H2O). The resulting product fractions were diluted with EtOAc and neutralized with sodium bicarbonate solution. The organic extract was dried over sodium sulfate, filtered and concentrated to give title product. ES/MS: 659.2 (M+H+); 1H NMR (400 MHz, Methanol-d4) δ 8.16 (d, J=1.3 Hz, 1H), 7.82-7.77 (m, 1H), 7.75 (d, J=7.9 Hz, 1H), 7.65 (dd, J=11.2, 1.2 Hz, 1H), 7.50 (dd, J=7.4, 1.6 Hz, 1H), 7.44 (t, J=9.7 Hz, 2H), 7.31 (dd, J=11.5, 7.9 Hz, 1H), 7.17 (dd, J=11.5, 6.0 Hz, 1H), 6.86 (d, J=8.2 Hz, 1H), 5.49 (s, 2H), 5.16 (qd, J=7.1, 2.5 Hz, 1H), 4.77-4.50 (m, 10H), 4.50-4.35 (m, 1H), 3.78 (d, J=1.8 Hz, 3H), 2.88-2.69 (m, 1H), 2.53-2.40 (m, 1H).

Example 350: 2-(4-(6-((6-(1H-1,2,3-triazol-1-yl)pyridin-3-yl)methoxy)pyridin-2-yl)-2-chloro-5-fluorobenzyl)-4-fluoro-1-(2-methoxyethyl)-1H-benzo[d]imidazole-6-carboxylic acid 2-(4-(6-((6-(1H-1,2,3-triazol-1-yl)pyridin-3-yl)methoxy)pyridin-2-yl)-2-chloro-5-fluorobenzyl)-4-fluoro-1-(2-methoxyethyl)-1H-benzo[d]imidazole-6-carboxylic acid was prepared in a manner as described in Procedure 18, starting with Intermediates I-1268 and I-1278. 1H NMR (400 MHz, DMSO-d6) δ 8.88 (d, J=1.2 Hz, 1H), 8.75 (d, J=2.1 Hz, 1H), 8.25 (dd, J=8.4, 2.2 Hz, 1H), 8.17 (d, J=8.4 Hz, 1H), 8.10 (d, J=1.3 Hz, 1H), 8.05-7.97 (m, 2H), 7.91 (t, J=7.9 Hz, 1H), 7.58-7.48 (m, 2H), 7.45 (d, J=11.7 Hz, 1H), 7.01 (d, J=8.3 Hz, 1H), 5.61 (s, 2H), 4.63 (t, J=5.1 Hz, 2H), 4.53 (s, 2H), 3.70 (t, J=5.0 Hz, 2H), 3.22 (s, 3H). ES/MS m/z: 632.4 (M+H+).

Example 351: 2-(2-chloro-4-(6-((4-cyano-2-fluorobenzyl)oxy)pyridin-2-yl)-5-fluorobenzyl)-4-fluoro-1-(2-methoxyethyl)-1H-benzo[d]imidazole-6-carboxylic acid 2-(2-chloro-4-(6-((4-cyano-2-fluorobenzyl)oxy)pyridin-2-yl)-5-fluorobenzyl)-4-fluoro-1-(2-methoxyethyl)-1H-benzo[d]imidazole-6-carboxylic acid was prepared in a manner as described in Procedure 18, starting with Intermediates I-3 and I-1278. 1H NMR (400 MHz, DMSO-d6) δ 8.10 (d, J=1.2 Hz, 1H), 7.98-7.85 (m, 3H), 7.74 (d, J=5.4 Hz, 2H), 7.55-7.47 (m, 2H), 7.43 (d, J=11.8 Hz, 1H), 7.01 (d, J=8.2 Hz, 1H), 5.60 (s, 2H), 4.62 (t, J=5.1 Hz, 2H), 4.52 (s, 2H), 3.70 (t, J=5.0 Hz, 2H), 3.22 (s, 3H). ES/MS m/z: 607.6 (M+H+).

Example 352: (R)-2-(4-(6-((6-(1H-1,2,3-triazol-1-yl)pyridin-3-yl)methoxy)pyridin-2-yl)-2,5-difluorobenzyl)-4-fluoro-1-(2-methoxypropyl)-1H-benzo[d]imidazole-6-carboxylic acid (R)-2-(4-(6-((6-(1H-1,2,3-triazol-1-yl)pyridin-3-yl)methoxy)pyridin-2-yl)-2,5-difluorobenzyl)-4-fluoro-1-(2-methoxypropyl)-1H-benzo[d]imidazole-6-carboxylic acid was prepared in a manner as described in Procedure 18, starting with Intermediates I-1268 and I-1272. 1H NMR (400 MHz, DMSO-d6) δ 8.88 (d, J=1.2 Hz, 1H), 8.75 (d, J=2.1 Hz, 1H), 8.25 (dd, J=8.4, 2.2 Hz, 1H), 8.17 (d, J=8.5 Hz, 1H), 8.12 (d, J=1.3 Hz, 1H), 8.00 (d, J=1.2 Hz, 1H), 7.96-7.82 (m, 2H), 7.60-7.46 (m, 2H), 7.40 (dd, J=11.5, 6.1 Hz, 1H), 7.00 (d, J=8.2 Hz, 1H), 5.62 (s, 2H), 4.54 (dd, J=15.2, 3.1 Hz, 1H), 4.47 (s, 2H), 4.37 (dd, J=15.2, 8.8 Hz, 1H), 3.79-3.60 (m, 1H), 3.08 (s, 3H), 1.23 (d, J=6.1 Hz, 3H). ES/MS m/z: 630.2 (M+H+).

Example 353: (R)-2-(4-(6-((4-chloro-2,5-difluorobenzyl)oxy)pyridin-2-yl)-2,5-difluorobenzyl)-4-fluoro-1-(2-methoxypropyl)-1H-benzo[d]imidazole-6-carboxylic acid (R)-2-(4-(6-((4-chloro-2,5-difluorobenzyl)oxy)pyridin-2-yl)-2,5-difluorobenzyl)-4-fluoro-1-(2-methoxypropyl)-1H-benzo[d]imidazole-6-carboxylic acid was prepared in a manner as described in Procedure 18, starting with Intermediates I-1284 and I-1272. 1H NMR (400 MHz, DMSO-d6) δ 8.90 (d, J=1.2 Hz, 1H), 8.12 (d, J=1.3 Hz, 1H), 8.01 (d, J=1.2 Hz, 1H), 7.97-7.78 (m, 5H), 7.58-7.45 (m, 2H), 7.40 (dd, J=11.5, 6.0 Hz, 1H), 6.98 (d, J=8.2 Hz, 1H), 5.60 (s, 2H), 4.54 (dd, J=15.2, 3.1 Hz, 1H), 4.47 (s, 2H), 4.37 (dd, J=15.2, 8.8 Hz, 1H), 3.78-3.59 (m, 1H), 3.08 (s, 3H), 1.23 (d, J=6.1 Hz, 3H). ES/MS m/z: 647.2 (M+H+).

Example 354: (R)-2-(2,5-difluoro-4-(6-((2-fluoro-4-(1H-1,2,3-triazol-1-yl)benzyl)oxy)pyridin-2-yl)benzyl)-4-fluoro-1-(2-methoxypropyl)-1H-benzo[d]imidazole-6-carboxylic acid (R)-2-(2,5-difluoro-4-(6-((2-fluoro-4-(1H-1,2,3-triazol-1-yl)benzyl)oxy)pyridin-2-yl)benzyl)-4-fluoro-1-(2-methoxypropyl)-1H-benzo[d]imidazole-6-carboxylic acid was prepared in a manner as described in Procedure 18, starting with Intermediates I-1283 and I-1272. 1H NMR (400 MHz, DMSO-d6) δ 8.90 (d, J=1.2 Hz, 1H), 8.12 (d, J=1.3 Hz, 1H), 8.01 (d, J=1.2 Hz, 1H), 7.97-7.78 (m, 5H), 7.58-7.45 (m, 2H), 7.40 (dd, J=11.5, 6.0 Hz, 1H), 6.98 (d, J=8.2 Hz, 1H), 5.60 (s, 2H), 4.54 (dd, J=15.2, 3.1 Hz, 1H), 4.47 (s, 2H), 4.37 (dd, J=15.2, 8.8 Hz, 1H), 3.78-3.59 (m, 1H), 3.08 (s, 3H), 1.23 (d, J=6.1 Hz, 3H). ES/MS m/z: 647.2 (M+H+).

Example 355: (R)-2-(4-(6-((4-cyano-2-fluorobenzyl)oxy)pyridin-2-yl)-2,5-difluorobenzyl)-4-fluoro-1-(2-methoxypropyl)-1H-benzo[d]imidazole-6-carboxylic acid (R)-2-(4-(6-((4-cyano-2-fluorobenzyl)oxy)pyridin-2-yl)-2,5-difluorobenzyl)-4-fluoro-1-(2-methoxypropyl)-1H-benzo[d]imidazole-6-carboxylic acid was prepared in a manner as described in Procedure 18, starting with Intermediates I-3 and I-1272. 1H NMR (400 MHz, DMSO-d6) δ 8.12 (d, J=1.2 Hz, 1H), 7.97-7.85 (m, 2H), 7.82-7.70 (m, 3H), 7.58-7.46 (m, 2H), 7.39 (dd, J=11.5, 6.0 Hz, 1H), 6.99 (d, J=8.3 Hz, 1H), 5.61 (s, 2H), 4.53 (dd, J=15.2, 3.1 Hz, 1H), 4.46 (s, 2H), 4.36 (dd, J=15.2, 8.8 Hz, 1H), 3.68 (ddd, J=9.1, 6.1, 3.1 Hz, 1H), 3.08 (s, 3H), 1.23 (d, J=6.1 Hz, 3H). ES/MS m/z: 605.2 (M+H+).

Example 357: (S)-2-(4-(6-((4-(difluoromethyl)benzyl)oxy)pyridin-2-yl)-2,5-difluorobenzyl)-1-(4,4-dimethyltetrahydrofuran-3-yl)-1H-benzo[d]imidazole-6-carboxylic acid (S)-2-(4-(6-((4-(difluoromethyl)benzyl)oxy)pyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 27, starting with Intermediate I-1219 and 4-(difluoromethyl)benzyl bromide. 1H NMR (400 MHz, Methanol-d4) δ 8.87 (s, 1H), 8.15 (dd, J=8.7, 1.3 Hz, 1H), 7.99-7.71 (m, 3H), 7.71-7.45 (m, 5H), 7.37 (dd, J=11.2, 6.0 Hz, 1H), 7.03-6.86 (m, 1H),  5.56 (s, 2H), 5.12 (d, J=6.6 Hz, 1H), 4.78-4.61 (m, 3H), 4.52 (dd, J=11.6, 6.7 Hz, 1H), 3.99 (d, J=8.9 Hz, 1H), 3.84 (d, J=8.9 Hz, 1H),  1.40 (s, 3H), 0.75 (s, 3H). ES/MS m/z: 620.3 (M+H+).

Example 358: (S)-2-(2,5-difluoro-4-(6-((4-(trifluoromethyl)benzyl)oxy)pyridin-2-yl)benzyl)-1-(4,4-dimethyltetrahydrofuran-3-yl)-1H-benzo[d]imidazole-6-carboxylic acid (S)-2-(2,5-difluoro-4-(6-((4-(trifluoromethyl)benzyl)oxy)pyridin-2-yl)benzyl)-1-(4,4-dimethyltetrahydrofuran-3-yl)-1H-benzo[d]imidazole-6-carboxylic acid was prepared in a manner as described in Procedure 27, starting with Intermediate I-1219 and 4-(trifluoromethyl)benzyl bromide. 1H NMR (400 MHz, Methanol-d4) δ 8.96 (s, 1H), 8.24 (dd, J=8.6, 1.3 Hz, 1H), 7.83 (d, J=8.6 Hz, 1H), 7.78-7.67 (m, 2H), 7.58 (d, J=8.6 Hz, 2H), 7.46 (d, J=7.5 Hz, 1H), 7.19 (d, J=10.5 Hz, 1H), 7.02 (dd, J=9.0, 2.9 Hz, 1H), 5.51 (s, 2H), 5.19 (d, J=6.5 Hz, 1H), 4.83-4.62 (m, 3H), 4.52 (dd, J=11.8, 6.6 Hz, 1H), 4.01 (d, J=9.0 Hz, 1H), 3.84 (d, J=9.0 Hz, 1H), 2.21 (s, 3H), 1.36 (s, 3H), 0.73 (s, 3H). ES/MS m/z: 638.0 (M+H+).

Example 359: (S)-2-(4-(6-((4-cyano-2-fluorobenzyl)oxy)-3-fluoropyridin-2-yl)-2-fluoro-5-methylbenzyl)-1-(4,4-dimethyltetrahydrofuran-3-yl)-1H-benzo[d]imidazole-6-carboxylic acid ((S)-2-(4-(6-((4-cyano-2-fluorobenzyl)oxy)-3-fluoropyridin-2-yl)-2-fluoro-5-methylbenzyl)-1-(4,4-dimethyltetrahydrofuran-3-yl)-1H-benzo[d]imidazole-6-carboxylic acid was prepared in a manner as described in Procedure 35, starting with Intermediates I-1322 and I-1076. 1H NMR (400 MHz, Methanol-d4) δ 8.96 (s, 1H), 8.24 (dd, J=8.6, 1.3 Hz, 1H), 7.83 (d, J=8.6 Hz, 1H), 7.78-7.67 (m, 2H), 7.58 (d, J=8.6 Hz, 2H), 7.46 (d, J=7.5 Hz, 1H), 7.19 (d, J=10.5 Hz, 1H), 7.02 (dd, J=9.0, 2.9 Hz, 1H), 5.51 (s, 2H), 5.19 (d, J=6.5 Hz, 1H), 4.83-4.62 (m, 3H), 4.52 (dd, J=11.8, 6.6 Hz, 1H), 4.01 (d, J=9.0 Hz, 1H), 3.84 (d, J=9.0 Hz, 1H), 2.21 (s, 3H), 1.36 (s, 3H), 0.73 (s, 3H). ES/MS m/z: 627.0 (M+H+).

Example 360: (S)-2-(2,5-difluoro-4-(6-((4-fluorobenzyl)oxy)pyridin-2-yl)benzyl)-1-(4,4-dimethyltetrahydrofuran-3-yl)-1H-benzo[d]imidazole-6-carboxylic acid (S)-2-(2,5-difluoro-4-(6-((4-fluorobenzyl)oxy)pyridin-2-yl)benzyl)-1-(4,4-dimethyltetrahydrofuran-3-yl)-1H-benzo[d]imidazole-6-carboxylic acid was prepared in a manner as described in Procedure 27, starting with Intermediate I-1219 and 4-fluorobenzyl bromide. 1H NMR (400 MHz, Methanol-d4) δ 8.91 (s, 1H), 8.18 (dd, J=8.6, 1.3 Hz, 1H), 7.93 (dd, J=10.8, 6.2 Hz, 1H), 7.87-7.73 (m, 2H), 7.66-7.48 (m, 3H), 7.40 (dd, J=11.2, 6.0 Hz, 1H), 7.21-7.02 (m, 2H), 6.90 (d, J=8.2 Hz, 1H), 5.46 (s, 2H), 5.15 (d, J=6.5 Hz, 1H), 4.79-4.63 (m, 2H), 4.52 (dd, J=11.6, 6.7 Hz, 1H), 4.00 (d, J=8.9 Hz, 1H), 3.84 (d, J=8.9 Hz, 1H), 3.33 (p, J=1.7 Hz, 3H), 1.41 (s, 3H), 0.76 (s, 3H). ES/MS m/z: 588.5 (M+H+).

Example 361: (S)-2-(2,5-difluoro-4-(6-((4-methylbenzyl)oxy)pyridin-2-yl)benzyl)-1-(4,4-dimethyltetrahydrofuran-3-yl)-1H-benzo[d]imidazole-6-carboxylic acid (S)-2-(2,5-difluoro-4-(6-((4-methylbenzyl)oxy)pyridin-2-yl)benzyl)-1-(4,4-dimethyltetrahydrofuran-3-yl)-1H-benzo[d]imidazole-6-carboxylic acid was prepared in a manner as described in Procedure 27, starting with Intermediate I-1219 and 4-methylbenzyl bromide. 1H NMR (400 MHz, Methanol-d4) δ 8.89 (s, 1H), 8.17 (dd, J=8.6, 1.3 Hz, 1H), 7.93 (dd, J=10.9, 6.3 Hz, 1H), 7.88-7.72 (m, 2H), 7.54 (dd, J=7.5, 1.7 Hz, 1H), 7.38 (dd, J=14.9, 7.0 Hz, 3H), 7.19 (d, J=7.8 Hz, 2H), 6.88 (d, J=8.2 Hz, 1H), 5.44 (s, 2H), 5.14 (d, J=6.6 Hz, 1H), 4.77-4.61 (m, 3H), 4.53 (dd, J=11.6, 6.7 Hz, 1H), 4.00 (d, J=8.9 Hz, 1H), 3.84 (d, J=8.9 Hz, 1H), 2.34 (s, 3H), 1.42 (s, 3H), 0.76 (s, 3H). ES/MS m/z: 584.6 (M+H$^+$).

Example 362: (S)-2-(4-(6-((4-cyanobenzyl)oxy)pyridin-2-yl)-2,6-difluorobenzyl)-1-(4,4-dimethyltetrahydrofuran-3-yl)-1H-benzo[d]imidazole-6-carboxylic acid (S)-2-(4-(6-((4-cyanobenzyl)oxy)pyridin-2-yl)-2,6-difluorobenzyl)-1-(4,4-dimethyltetrahydrofuran-3-yl)-1H-benzo[d]imidazole-6-carboxylic acid was prepared in a manner as described in Procedure 35, starting with Intermediates I-114 and I-1233. 1H NMR (400 MHz, Methanol-d4) δ 8.99-8.75 (m, 1H), 8.15 (dd, J=8.6, 1.4 Hz, 1H), 7.95-7.66 (m, 8H), 7.61 (d, J=7.5 Hz, 1H), 6.97 (d, J=8.2 Hz, 1H), 5.62 (s, 2H), 5.17 (d, J=6.5 Hz, 1H), 4.81-4.46 (m, 4H), 4.00 (d, J=8.9 Hz, 1H), 3.86 (d, J=8.9 Hz, 1H), 1.45 (s, 3H), 0.79 (s, 3H). ES/MS m/z: 595.3 (M+H$^+$).

Example 363: (S)-2-(4-(6-(benzyloxy)pyridin-2-yl)-2,5-difluorobenzyl)-1-(4,4-dimethyltetrahydrofuran-3-yl)-1H-benzo[d]imidazole-6-carboxylic acid (S)-2-(4-(6-(benzyloxy)pyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 35, starting with Intermediates I-1324 and I-82. 1H NMR (400 MHz, Methanol-d4) δ 8.91 (s, 1H), 8.19 (dd, J=8.6, 1.4 Hz, 1H), 7.92 (dd, J=10.9, 6.3 Hz, 1H), 7.87-7.70 (m, 2H), 7.56 (dd, J=7.4, 1.7 Hz, 1H), 7.52-7.44 (m, 2H), 7.42-7.33 (m, 4H), 6.91 (d, J=8.2 Hz, 1H), 5.49 (s, 2H), 5.15 (d, J=6.5 Hz, 1H), 4.77-4.62 (m, 3H), 4.53 (dd, J=11.6, 6.7 Hz, 1H), 4.00 (d, J=8.9 Hz, 1H), 3.85 (d, J=8.9 Hz, 1H), 1.42 (s, 3H), 0.77 (s, 3H). ES/MS m/z: 570.6 (M+H$^+$).

Example 364: (S)-2-(4-(6-((4-cyano-2-fluorobenzyl)oxy)-3-fluoropyridin-2-yl)-2-fluorobenzyl)-1-(4,4-dimethyltetrahydrofuran-3-yl)-1H-benzo[d]imidazole-6-carboxylic acid (S)-2-(4-(6-((4-cyano-2-fluorobenzyl)oxy)-3-fluoropyridin-2-yl)-2-fluorobenzyl)-1-(4,4-dimethyltetrahydrofuran-3-yl)-1H-benzo[d]imidazole-6-carboxylic acid was prepared in a manner as described in Procedure 35, starting with Intermediates I-1322 and I-1229. 1H NMR (400 MHz, Methanol-d4) δ 8.89 (s, 1H), 8.17 (dd, J=8.6, 1.3 Hz, 1H), 7.91 (d, J=8.1 Hz, 1H), 7.87-7.66 (m, 5H), 7.63-7.54 (m, 3H), 6.97 (dd, J=8.9, 2.7 Hz, 1H), 5.61 (s, 2H), 5.12 (d, J=6.6 Hz, 1H), 4.76-4.61 (m, 3H), 4.60-4.49 (m, 1H), 4.00 (d, J=8.9 Hz, 1H), 3.83 (d, J=8.9 Hz, 1H), 1.37 (s, 3H), 0.73 (s, 3H). ES/MS m/z: 613.2 (M+H$^+$).

Example 365: (S)-2-(4-(6-((4-cyano-2-fluorobenzyl)oxy)-3-fluoropyridin-2-yl)-2,5-difluorobenzyl)-1-(4,4-dimethyltetrahydrofuran-3-yl)-4-fluoro-1H-benzo[d]imidazole-6-carboxylic acid (S)-2-(4-(6-((4-cyano-2-fluorobenzyl)oxy)-3-fluoropyridin-2-yl)-2,5-difluorobenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1322 and I-108. 1H NMR (400 MHz, Methanol-d4) δ 8.58 (s, 1H), 7.82-7.65 (m, 3H), 7.65-7.55 (m, 2H), 7.35 (dd, J=9.9, 5.7 Hz, 1H), 7.27 (dd, J=9.9, 6.0 Hz, 1H), 7.01 (dd, J=9.0, 2.9 Hz, 1H), 5.54 (s, 2H), 4.99 (d, J=6.7 Hz, 1H), 4.69-4.42 (m, 4H), 3.95 (d, J=8.8 Hz, 1H), 3.80 (d, J=8.8 Hz, 1H), 1.36 (s, 3H), 0.68 (s, 3H). ES/MS m/z: 649.2 (M+H$^+$).

Example 366: 2-(4-(6-((4-cyanobenzyl)oxy)-5-fluoropyridin-2-yl)-2,5-difluorobenzyl)-7-fluoro-1-(2-methoxyethyl)-1H-benzo[d]imidazole-6-carboxylic acid 2-(4-(6-((4-cyanobenzyl)oxy)-5-fluoropyridin-2-yl)-2,5-difluorobenzyl)-7-fluoro-1-(2-methoxyethyl)-1H-benzo[d]imidazole-6-carboxylic acid was prepared in a manner as described in Procedure 35, starting with Intermediates I-1247 and I-1325. 1H NMR (400 MHz, Chloroform-d) δ 8.00 (t, J=7.5 Hz, 1H), 7.80-7.68 (m, 3H), 7.68-7.57 (m, 3H), 7.56-7.36 (m, 2H), 7.15 (dd, J=11.1, 6.0 Hz, 1H), 5.60 (s, 2H), 4.67-4.55 (m, 4H), 3.82 (t, J=4.8 Hz, 2H), 3.33 (s, 3H). ES/MS m/z: 591.5 (M+H$^+$).

Example 367: (S)-2-(4-(6-((4-chlorobenzyl)oxy)pyridin-2-yl)-2,5-difluorobenzyl)-1-(4,4-dimethyltetrahydrofuran-3-yl)-4-fluoro-1H-benzo[d]imidazole-6-carboxylic acid (S)-2-(4-(6-((4-chlorobenzyl)oxy)pyridin-2-yl)-2,5-difluorobenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1248 and I-108. 1H NMR (400 MHz, Methanol-d4) δ 8.58 (s, 1H), 7.90-7.82 (m, 1H), 7.77 (t, J=7.9 Hz, 1H), 7.70 (dd, J=11.0, 1.2 Hz, 1H), 7.58-7.44 (m, 3H), 7.42-7.34 (m, 2H), 7.24 (dd, J=11.4, 6.0 Hz, 1H), 6.88 (d, J=8.2 Hz, 1H), 5.46 (s, 2H), 4.97 (d, J=6.7 Hz, 1H), 4.65-4.34 (m, 4H), 3.93 (d, J=8.8 Hz, 1H), 3.79 (d, J=8.8 Hz, 1H), 1.35 (s, 3H), 0.66 (s, 3H). ES/MS m/z: 622.8 (M+H$^+$).

Example 368: (R)-2-(4-(6-((4-cyano-2-fluorobenzyl)oxy)-5-fluoropyridin-2-yl)-2,5-difluorobenzyl)-4-fluoro-1-(2-methoxypropyl)-1H-benzo[d]imidazole-6-carboxylic acid (R)-2-(4-(6-((4-cyano-2-fluorobenzyl)oxy)-5-fluoropyridin-2-yl)-2,5-difluorobenzyl)-4-fluoro-1-(2-methoxypropyl)-1H-benzo[d]imidazole-6-carboxylic acid was prepared in a manner as described in Procedure 35, starting with Intermediates I-109 and I-1272. 1H NMR (400 MHz, Methanol-d4) δ 7.99 (d, J=1.2 Hz, 1H), 7.86-7.68 (m, 2H), 7.68-7.47 (m, 5H), 7.12 (dd, J=11.6, 6.1 Hz, 1H), 5.71 (s, 2H), 4.52 (d, J=16.6 Hz, 1H), 4.45-4.34 (m, 1H), 4.27 (dd, J=15.1, 8.9 Hz, 1H), 3.75 (ddd, J=9.2, 6.1, 3.1 Hz, 1H), 3.13 (s, 3H), 2.08-1.89 (m, 1H), 1.29 (d, J=6.2 Hz, 3H). ES/MS m/z: 623.3 (M+H$^+$).

Example 369: (S)-2-(4-(6-((4-cyano-2-fluorobenzyl)oxy)-5-fluoropyridin-2-yl)-3-fluorobenzyl)-1-(4,4-dimethyltetrahydrofuran-3-yl)-1H-benzo[d]imidazole-6-carboxylic acid (S)-2-(4-(6-((4-cyano-2-fluorobenzyl)oxy)-5-fluoropyridin-2-yl)-3-fluorobenzyl)-1-(4,4-dimethyltetrahydrofuran-3-yl)-1H-benzo[d]imidazole-6-carboxylic acid was prepared in a manner as described in Procedure 35, starting with Intermediates I-109 and I-1326. 1H NMR (400 MHz, Methanol-d4) δ 8.90 (s, 1H), 8.20 (dd, J=8.6, 1.4 Hz, 1H), 8.02 (t, J=8.3 Hz, 1H), 7.92-7.71 (m, 2H), 7.69-7.46 (m, 4H), 7.40-7.21 (m, 2H), 5.70 (s, 2H), 5.10 (d, J=6.5 Hz, 1H), 4.83-4.58 (m, 3H), 4.47 (dd, J=11.6, 6.7 Hz, 1H), 3.99 (d, J=8.9 Hz, 1H), 3.82 (d, J=8.9 Hz, 1H), 1.33 (s, 3H), 0.69 (s, 3H). ES/MS m/z: 613.6 (M+H$^+$).

Example 370: (S)-2-(4-(6-((4-cyanobenzyl)oxy)-5-fluoropyridin-2-yl)-2-fluorobenzyl)-1-(4,4-dimethyltetrahydrofuran-3-yl)-1H-benzo[d]imidazole-6-carboxylic acid (S)-2-(4-(6-((4-cyanobenzyl)oxy)-5-fluoropyridin-2-yl)-2-fluorobenzyl)-1-(4,4-dimethyltetrahydrofuran-3-yl)-1H-benzo[d]imidazole-6-carboxylic acid was prepared in a manner as described in Procedure 27, starting with Intermediate I-1327 and 4-cyanobenzyl bromide. 1H NMR (400 MHz, Methanol-d4) δ 8.86 (s, 1H), 8.15 (dd, J=8.6, 1.4 Hz, 1H), 7.96-7.82 (m, 2H), 7.78 (d, J=2.9 Hz, 1H), 7.77-7.70 (m, 3H), 7.70-7.56 (m, 3H), 7.56-7.42 (m, 1H), 5.69 (s, 2H), 5.09 (d, J=6.6 Hz, 1H), 4.74-4.58 (m, 3H), 4.49 (dd, J=11.5, 6.7 Hz, 1H), 4.18 (ddd, J=12.3, 9.0, 3.7 Hz, 1H), 3.99 (d, J=8.9 Hz, 1H), 3.82 (d, J=8.9 Hz, 1H), 3.76-3.72 (m, 1H), 3.56 (dt, J=11.8, 2.8 Hz, 1H), 1.36 (s, 3H), 0.71 (s, 3H). ES/MS m/z: 595.7 (M+H$^+$).

Example 371: (S)-2-(4-(6-((4-chlorobenzyl)oxy)pyridin-2-yl)-2-fluorobenzyl)-1-(4,4-dimethyltetrahydrofuran-3-yl)-1H-benzo[d]imidazole-6-carboxylic acid (S)-2-(4-(6-((4-chlorobenzyl)oxy)pyridin-2-yl)-2-fluorobenzyl)-1-(4,4-dimethyltetrahydrofuran-3-yl)-1H-benzo[d]imidazole-6-carboxylic acid was prepared in a manner as described in Procedure 27, starting with Intermediate I-1328 and 4-chlorobenzyl bromide. 1H NMR (400 MHz, Methanol-d4) δ 8.96 (s, 1H), 8.25 (dd, J=8.6, 1.4 Hz, 1H), 8.06-7.92 (m, 2H), 7.88-7.73 (m, 2H), 7.68-7.55 (m, 2H), 7.55-7.44 (m, 2H), 7.44-7.28 (m, 2H), 6.88 (d, J=8.2 Hz, 1H), 5.50 (s, 2H), 5.19 (d, J=6.4 Hz, 1H), 4.78 (d, J=7.2 Hz, 2H), 4.65 (dd, J=11.7, 1.3 Hz, 1H), 4.51 (dd, J=11.8, 6.6 Hz, 1H), 4.01 (d, J=9.0 Hz, 1H), 3.84 (d, J=9.0 Hz, 1H), 1.37 (s, 3H), 0.75 (s, 3H). ES/MS m/z: 587.0 (M+H$^+$).

Example 372: (S)-2-(4-(6-((4-cyanobenzyl)oxy)pyridin-2-yl)-2-fluorobenzyl)-1-(4,4-dimethyltetrahydrofuran-3-yl)-4-fluoro-1H-benzo[d]imidazole-6-carboxylic acid (S)-2-(4-(6-((4-cyanobenzyl)oxy)pyridin-2-yl)-2-fluorobenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-114 and I-1230. 1H NMR (400 MHz, Methanol-d4) δ 8.57 (s, 1H), 7.91-7.62 (m, 8H), 7.52 (d, J=7.5 Hz, 1H), 7.38 (t, J=7.8 Hz, 1H), 6.89 (d, J=8.2 Hz, 1H), 5.60 (s, 2H), 4.94 (s, 1H), 4.60-4.48 (m, 3H), 4.43 (dd, J=11.4, 6.8 Hz, 1H), 3.93 (d, J=8.9 Hz, 1H), 3.78 (d, J=8.8 Hz, 1H), 1.29 (s, 3H), 0.62 (s, 3H). ES/MS m/z: 595.7 (M+H$^+$).

Example 373: (S)-2-(4-(6-((4-cyanobenzyl)oxy)pyridin-2-yl)-2-fluorobenzyl)-1-(4,4-dimethyltetrahydrofuran-3-yl)-1H-benzo[d]imidazole-6-carboxylic acid (S)-2-(4-(6-((4-cyanobenzyl)oxy)pyridin-2-yl)-2-fluorobenzyl)-1-(4,4-dimethyltetrahydrofuran-3-yl)-1H-benzo[d]imidazole-6-carboxylic acid was prepared in a manner as described in Procedure 27, starting with Intermediate I-1328 and 4-cyanobenzyl bromide. 1H NMR (400 MHz, Methanol-d4) δ 8.92 (s, 1H), 8.21 (dd, J=8.6, 1.4 Hz, 1H), 8.00-7.87 (m, 2H), 7.87-7.79 (m, 2H), 7.74 (d, J=8.3 Hz, 2H), 7.67 (d, J=8.1 Hz, 2H), 7.61-7.46 (m, 2H), 6.93 (d, J=8.2 Hz, 1H), 5.61 (s, 2H), 5.15 (d, J=6.5 Hz, 1H), 4.73 (d, J=5.6 Hz, 2H), 4.64 (dd, J=11.7, 1.4 Hz, 1H), 4.50 (dd, J=11.7, 6.7 Hz, 1H), 4.00 (d, J=8.9 Hz, 1H), 3.83 (d, J=8.9 Hz, 1H), 1.36 (s, 3H), 0.73 (s, 3H). ES/MS m/z: 577.7 (M+H$^+$).

Example 374: 2-(2,5-difluoro-4-(6-((2-fluoro-4-(1H-1,2,3-triazol-1-yl)benzyl)oxy)pyridin-2-yl)benzyl)-7-fluoro-1-(2-methoxyethyl)-1H-benzo[d]imidazole-6-carboxylic acid 2-(2,5-difluoro-4-(6-((2-fluoro-4-(1H-1,2,3-triazol-1-yl)benzyl)oxy)pyridin-2-yl)benzyl)-7-fluoro-1-(2-methoxyethyl)-1H-benzo[d]imidazole-6-carboxylic acid was prepared in a manner as described in Procedure 27, starting with Intermediates I-1282 and I-1324. 1H NMR (400 MHz, DMSO-d6) δ 8.90 (d, J=1.2 Hz, 1H), 8.01 (d, J=1.2 Hz, 1H), 7.98-7.76 (m, 5H), 7.65 (dd, J=8.5, 6.8 Hz, 1H), 7.53 (dd, J=7.5, 1.7 Hz, 1H), 7.48-7.32 (m, 2H), 6.98 (d, J=8.3 Hz, 1H), 5.60 (s, 2H), 4.61 (t, J=5.2 Hz, 2H), 4.43 (s, 2H), 3.73 (t, J=5.2 Hz, 2H), 3.23 (s, 3H). ES/MS m/z: 633.3 (M+H$^+$).

Example 375: 2-(4-(6-((4-cyanobenzyl)oxy)pyridin-2-yl)-2,5-difluorobenzyl)-7-fluoro-1-(2-methoxyethyl)-1H-benzo[d]imidazole-6-carboxylic acid 2-(4-(6-((4-cyanobenzyl)oxy)pyridin-2-yl)-2,5-difluorobenzyl)-7-fluoro-1-(2-methoxyethyl)-1H-benzo[d]imidazole-6-carboxylic acid was prepared in a manner as described in Procedure 35, starting with Intermediates I-114 and I-1325. 1H NMR (400 MHz, Methanol-d4) δ 7.94 (dd, J=8.6, 6.6 Hz, 1H), 7.82 (t, J=7.8 Hz, 1H), 7.79-7.72 (m, 3H), 7.67 (d, J=8.1 Hz, 2H), 7.55 (dd, J=7.5, 1.6 Hz, 1H), 7.50 (d, J=8.6 Hz, 1H), 7.25 (dd, J=11.4, 6.0 Hz, 1H), 6.95 (d, J=8.2 Hz, 1H), 5.59 (s, 2H), 4.74 (t, J=5.0 Hz, 2H), 4.59 (s, 2H), 3.84 (t, J=4.9 Hz, 2H), 3.32 (s, 3H). ES/MS m/z: 573.3 (M+H$^+$).

Example 376: (S)-2-(4-(6-((4-cyanobenzyl)oxy)pyridin-2-yl)-2,5-difluorobenzyl)-1-(4,4-dimethyltetrahydrofuran-3-yl)-4-fluoro-1H-benzo[d]imidazole-6-carboxylic acid (S)-2-(4-(6-((4-cyanobenzyl)oxy)pyridin-2-yl)-2,5-difluorobenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-114 and I-108. 1H NMR (400 MHz, Methanol-d4) δ 8.58 (s, 1H), 7.86-7.72 (m, 4H), 7.71-7.63 (m, 3H), 7.54 (dd, J=7.5, 1.6 Hz, 1H), 7.23 (dd, J=11.4, 6.0 Hz, 1H), 6.93 (d, J=8.2 Hz, 1H), 5.58 (s, 2H), 4.97 (d, J=6.7 Hz, 1H), 4.65-4.41 (m, 4H), 3.94 (d, J=8.8 Hz, 1H), 3.80 (d, J=8.8 Hz, 1H), 1.35 (s, 3H), 0.66 (s, 3H). ES/MS m/z: 613.63 (M+H$^+$).

Example 377: 2-(4-(6-((4-chlorobenzyl)oxy)pyridin-2-yl)-2,3,6-trifluorobenzyl)-4-fluoro-1-(2-methoxyethyl)-1H-benzo[d]imidazole-6-carboxylic acid 2-(4-(6-((4-chlorobenzyl)oxy)pyridin-2-yl)-2,3,6-trifluorobenzyl)-4-fluoro-1-(2-methoxyethyl)-1H-benzo[d]imidazole-6-carboxylic acid was prepared in a manner as described in Procedure 27, starting with Intermediates I-1136 and 4-chlorobenzyl bromide. 1H NMR (400 MHz, Methanol-d4) δ 8.15 (d, J=1.2 Hz, 1H), 7.83 (dd, J=8.3, 7.5 Hz, 1H), 7.66 (ddd, J=11.3, 5.4, 1.8 Hz, 2H), 7.56 (dd, J=7.4, 1.7 Hz, 1H), 7.53-7.45 (m, 2H), 7.45-7.33 (m, 2H), 6.92 (d, J=8.3 Hz, 1H), 5.48 (s, 2H), 4.67 (t, J=5.0 Hz, 2H), 4.60 (s, 2H), 3.86-3.78 (m, 2H), 3.33 (s, 3H). ES/MS m/z: 600.4 (M+H$^+$).

Example 378: 2-(4-(6-((4-cyanobenzyl)oxy)pyridin-2-yl)-2,3,6-trifluorobenzyl)-4-fluoro-1-(2-methoxyethyl)-1H-benzo[d]imidazole-6-carboxylic acid 2-(4-(6-((4-cyanobenzyl)oxy)pyridin-2-yl)-2,3,6-trifluorobenzyl)-4-fluoro-1-(2-methoxyethyl)-1H-benzo[d]imidazole-6-carboxylic acid was prepared in a manner as described in Procedure 36, starting with Intermediates I-116 and I-1032. 1H NMR (400 MHz, Methanol-d4) δ 8.15 (d, J=1.3 Hz, 1H), 7.85 (t, J=7.9 Hz, 1H), 7.75 (d, J=8.3 Hz, 2H), 7.72-7.64 (m, 3H), 7.63-7.56 (m, 2H), 6.97 (d, J=8.3 Hz, 1H), 5.59 (s, 2H), 4.68 (d, J=5.0 Hz, 2H), 4.60 (s, 2H), 3.75 (dd, J=2.9, 1.7 Hz, 1H), 3.62-3.51 (m, 2H), 3.32 (s, 3H). ES/MS m/z: 591.6 (M+H$^+$).

Example 379: (R)-2-(4-(6-((4-cyano-2-fluorobenzyl)oxy)pyridin-2-yl)-2-fluorobenzyl)-1-(4,4-dimethyltetrahydrofuran-3-yl)-1H-benzo[d]imidazole-6-carboxylic acid Example 380: (S)-2-(4-(6-((4-cyano-2-fluorobenzyl)oxy)pyridin-2-yl)-2-fluorobenzyl)-1-(4,4-dimethyltetrahydrofuran-3-yl)-1H-benzo[d]imidazole-6-carboxylic acid Examples 379 and 380 were prepared via preparative chiral SFC (Lux Cellulose-2, EtOH/CO$_2$ eluent) of Example 384.

(R)-2-(4-(6-((4-cyano-2-fluorobenzyl)oxy)pyridin-2-yl)-2-fluorobenzyl)-1-(4,4-dimethyltetrahydrofuran-3-yl)-1H-benzo[d]imidazole-6-carboxylic acid (Example 379) was isolated as the later-eluting of two stereoisomers. NMR ES/MS m/z: 595.6 (M+H$^+$).

(S)-2-(4-(6-((4-cyano-2-fluorobenzyl)oxy)pyridin-2-yl)-2-fluorobenzyl)-1-(4,4-dimethyltetrahydrofuran-3-yl)-1H-benzo[d]imidazole-6-carboxylic acid (Example 379) was isolated as the earlier-eluting of two stereoisomers. NMR ES/MS m/z: 595.6 (M+H$^+$).

Example 381: (R)-2-(4-(6-((4-cyanobenzyl)oxy)pyridin-2-yl)-2,5-difluorobenzyl)-4-fluoro-1-(2-methoxypropyl)-1H-benzo[d]imidazole-6-carboxylic acid (R)-2-(4-(6-((4-cyanobenzyl)oxy)pyridin-2-yl)-2,5-difluorobenzyl)-4-fluoro-1-(2-methoxypropyl)-1H-benzo[d]imidazole-6-carboxylic acid was prepared in a manner as described in Procedure 35, starting with Intermediates I-114 and I-1033. 1H NMR (400 MHz, Methanol-d4) δ 8.17 (d, J=1.2 Hz, 1H), 7.83-7.59 (m, 8H), 7.50 (dd, J=7.5, 1.5 Hz, 1H), 7.19 (dd, J=11.5, 6.0 Hz, 1H), 6.91 (d, J=8.2 Hz, 1H), 5.55 (s, 2H), 4.61-4.45 (m, 3H), 4.37 (dd, J=15.2, 9.1 Hz, 1H), 3.72 (dqt, J=10.1, 6.9, 3.4 Hz, 1H), 3.15 (s, 3H), 1.30 (d, J=6.1 Hz, 3H). ES/MS m/z: 587.73 (M+H$^+$).

Example 382: 2-(4-(6-((4-cyanobenzyl)oxy)pyridin-2-yl)-2,5-difluorobenzyl)-4-fluoro-1-(2-methoxyethyl)-1H-benzo[d]imidazole-6-carboxylic acid 2-(4-(6-((4-cyanobenzyl)oxy)pyridin-2-yl)-2,5-difluorobenzyl)-4-fluoro-1-(2-methoxyethyl)-1H-benzo[d]imidazole-6-carboxylic acid was prepared in a manner as described in Procedure 27, starting with Intermediate I-1206 and 4-cyanobenzyl bromide. 1H NMR (400 MHz, Methanol-d4) δ 8.19 (s, 1H), 7.80 (d, J=7.8 Hz, 1H), 7.77-7.69 (m, 4H), 7.66 (d, J=8.3 Hz, 2H), 7.51 (dd, J=7.5, 1.6 Hz, 1H), 7.19 (dd, J=11.4, 6.0 Hz, 1H), 6.92 (d, J=8.2 Hz, 1H), 5.57 (s, 2H), 4.63 (t, J=5.0 Hz, 2H), 4.57 (s, 2H), 3.75 (t, J=4.9 Hz, 2H), 3.27 (s, 3H). ES/MS m/z: 573.6 (M+H$^+$).

Example 383A: (S)-2-(4-(6-((4-(difluoromethyl)-2-fluorobenzyl)oxy)pyridin-2-yl)-2,5-difluorobenzyl)-1-(4,4-dimethyltetrahydrofuran-3-yl)-1H-benzo[d]imidazole-6-carboxylic acid Example 383B: (R)-2-(4-(6-((4-(difluoromethyl)-2-fluorobenzyl)oxy)pyridin-2-yl)-2,5-difluorobenzyl)-1-(4,4-dimethyltetrahydrofuran-3-yl)-1H-benzo[d]imidazole-6-carboxylic acid Examples 383A and 383B were prepared via preparative chiral SFC (Daicel Chiralpak AD-H column, EtOH/CO$_2$ eluent) of Example 21.

(S)-2-(4-(6-((4-(difluoromethyl)-2-fluorobenzyl)oxy)pyridin-2-yl)-2,5-difluorobenzyl)-1-(4,4-dimethyltetrahydrofuran-3-yl)-1H-benzo[d]imidazole-6-carboxylic acid (Example 383A) was isolated as the later-eluting of two stereoisomers. 1H NMR (400 MHz, Methanol-d4) δ 8.79 (s, 1H), 8.07 (dd, J=8.5, 1.4 Hz, 1H), 7.97-7.77 (m, 2H), 7.69 (dd, J=24.1, 8.1 Hz, 2H), 7.55 (dd, J=7.5, 1.5 Hz, 1H), 7.43-7.20 (m, 3H), 6.97-6.86 (m, 1H), 5.59 (s, 2H), 5.04 (d, J=6.7 Hz, 1H), 4.67-4.44 (m, 4H), 3.97 (d, J=8.8 Hz, 1H), 3.82 (d, J=8.8 Hz, 1H), 3.75-3.61 (m, 2H), 1.39 (s, 3H), 0.71 (s, 3H). ES/MS m/z: 638.36 (M+H$^+$).

(R)-2-(4-(6-((4-(difluoromethyl)-2-fluorobenzyl)oxy)pyridin-2-yl)-2,5-difluorobenzyl)-1-(4,4-dimethyltetrahydrofuran-3-yl)-1H-benzo[d]imidazole-6-carboxylic acid (Example 383B): 1H NMR (400 MHz, Methanol-d4) δ 8.79 (s, 1H), 8.08 (dd, J=8.5, 1.5 Hz, 1H), 7.94-7.76 (m, 2H), 7.69 (dd, J=24.9, 8.1 Hz, 2H), 7.56 (dd, J=7.5, 1.6 Hz, 1H), 7.45-7.20 (m, 3H), 6.92 (d, J=8.4 Hz, 1H), 5.60 (s, 2H), 5.05 (d, J=6.7 Hz, 1H), 4.76-4.43 (m, 4H), 3.97 (d, J=8.8 Hz, 1H), 3.82 (d, J=8.8 Hz, 1H), 3.74-3.66 (m, 1H), 1.39 (s, 3H), 0.71 (s, 3H). ES/MS m/z: 638.3 (M+H$^+$).

Example 384: 2-(4-(6-((4-cyano-2-fluorobenzyl)oxy)pyridin-2-yl)-2-fluorobenzyl)-1-(4,4-dimethyltetrahydrofuran-3-yl)-1H-benzo[d]imidazole-6-carboxylic acid 2-(4-(6-((4-cyano-2-fluorobenzyl)oxy)pyridin-2-yl)-2-fluorobenzyl)-1-(4,4-dimethyltetrahydrofuran-3-yl)-1H-benzo[d]imidazole-6-carboxylic acid was prepared in a manner as described in Procedure 36, starting with Intermediates I-1329 and I-25. 1H NMR (400 MHz, Methanol-d4) δ 8.85 (s, 1H), 8.14 (dd, J=8.6, 1.4 Hz, 1H), 8.03-7.87 (m, 2H), 7.87-7.67 (m, 4H), 7.67-7.44 (m, 3H), 6.92 (d, J=8.2 Hz, 1H), 5.66 (s, 2H), 5.08 (d, J=6.6 Hz, 1H), 4.72-4.56 (m, 3H), 4.49 (dd, J=11.5, 6.8 Hz, 1H), 3.99 (d, J=8.9 Hz, 1H), 3.82 (d, J=8.8 Hz, 1H), 3.72-3.63 (m, 1H), 1.36 (s, 3H), 0.71 (s, 3H). ES/MS m/z: 595.6 (M+H$^+$).

Example 385A: (S)-2-(4-(6-((4-chlorobenzyl)oxy) pyridin-2-yl)-2,5-difluorobenzyl)-1-(4,4-dimethyltetrahydrofuran-3-yl)-1H-benzo[d]imidazole-6-carboxylic acid Example 385B: (R)-2-(4-(6-((4-chlorobenzyl)oxy) pyridin-2-yl)-2,5-difluorobenzyl)-1-(4,4-dimethyltetrahydrofuran-3-yl)-1H-benzo[d]imidazole-6-carboxylic acid Examples 385A and 385B were prepared via preparative chiral SFC (Daicel Chiralpak AD-H column, EtOH/CO$_2$ eluent) of Example 387.

(S)-2-(4-(6-((4-chlorobenzyl)oxy)pyridin-2-yl)-2,5-difluorobenzyl)-1-(4,4-dimethyltetrahydrofuran-3-yl)-1H-benzo[d]imidazole-6-carboxylic acid (Example 385A) was isolated as the later-eluting of two stereoisomers. 1H NMR (400 MHz, Methanol-d4) δ 8.84 (s, 1H), 8.13 (dd, J=8.5, 1.4 Hz, 1H), 8.00-7.70 (m, 3H), 7.55 (dd, J=7.5, 1.6 Hz, 1H), 7.48 (d, J=8.2 Hz, 2H), 7.44-7.23 (m, 3H), 6.91 (d, J=8.2 Hz, 1H), 5.48 (s, 2H), 5.18-5.02 (m, 1H), 4.75-4.48 (m, 4H), 3.99 (d, J=8.9 Hz, 1H), 3.85 (s, 1H), 3.74-3.61 (m, 1H), 1.40 (s, 3H), 0.74 (s, 3H). ES/MS m/z: 604.85 (M+H$^+$).

(R)-2-(4-(6-((4-chlorobenzyl)oxy)pyridin-2-yl)-2,5-difluorobenzyl)-1-(4,4-dimethyltetrahydrofuran-3-yl)-1H-benzo[d]imidazole-6-carboxylic acid (Example 385B) was isolated as the earlier-eluting of two stereoisomers. 1H NMR (400 MHz, Methanol-d4) δ 8.82 (s, 1H), 8.15-8.01 (m, 1H), 7.98-7.66 (m, 3H), 7.55 (dd, J=7.5, 1.6 Hz, 1H), 7.48 (d, J=8.2 Hz, 2H), 7.42-7.34 (m, 3H), 6.90 (d, J=8.2 Hz, 1H), 5.48 (s, 2H), 5.12-4.99 (m, 1H), 4.74-4.43 (m, 4H), 3.98 (d, J=8.9 Hz, 1H), 3.92-3.73 (m, 2H), 1.40 (s, 3H), 0.73 (s, 3H). ES/MS m/z: 604.8 (M+H$^+$).

Example 386: 2-(4-(6-((4-chlorobenzyl)oxy)pyridin-2-yl)-2,5-difluorobenzyl)-4-fluoro-1-(2-methoxyethyl)-1H-benzo[d]imidazole-6-carboxylic acid 2-(4-(6-((4-chlorobenzyl)oxy)pyridin-2-yl)-2,5-difluorobenzyl)-4-fluoro-1-(2-methoxyethyl)-1H-benzo[d]imidazole-6-carboxylic acid was prepared in a manner as described in Procedure 27, starting with Intermediate I-1206 and 4-chlorobenzyl bromide. 1H NMR (400 MHz, DMSO-d6) δ 8.10 (s, 1H), 7.97-7.73 (m, 2H), 7.60-7.31 (m, 7H), 6.95 (d, J=8.2 Hz, 1H), 5.47 (s, 2H), 4.62 (t, J=5.1 Hz, 2H), 4.46 (s, 2H), 3.68 (t, J=5.0 Hz, 2H), 3.66-3.51 (m, 1H), 3.21 (s, 3H). ES/MS m/z: 582.65 (M+H$^+$).

Example 387: 2-(4-(6-((4-chlorobenzyl)oxy)pyridin-2-yl)-2,5-difluorobenzyl)-1-(4,4-dimethyltetrahydrofuran-3-yl)-11H-benzo[d]imidazole-6-carboxylic acid 2-(4-(6-((4-chlorobenzyl)oxy)pyridin-2-yl)-2,5-difluorobenzyl)-1-(4,4-dimethyltetrahydrofuran-3-yl)-1H-benzo [d]imidazole-6-carboxylic acid was prepared in a manner as described in Procedure 27, starting with Intermediate I-1199 and 4-chlorobenzyl bromide. 1H NMR (400 MHz, Methanol-d4) δ 8.89 (s, 1H), 8.17 (dd, J=8.6, 1.4 Hz, 1H), 7.90 (dd, J=10.9, 6.3 Hz, 1H), 7.87-7.70 (m, 2H), 7.56 (dd, J=7.3, 1.6 Hz, 1H), 7.53-7.44 (m, 2H), 7.43-7.31 (m, 3H), 6.92 (d, J=8.2 Hz, 1H), 5.48 (s, 2H), 5.14 (d, J=6.5 Hz, 1H), 4.78-4.60 (m, 3H), 4.52 (dd, J=11.6, 6.7 Hz, 1H), 4.00 (d, J=8.9 Hz, 1H), 3.84 (d, J=8.9 Hz, 1H), 1.41 (s, 3H), 0.76 (s, 3H). ES/MS m/z: 605.25 (M+H$^+$).

Example 388: (S)-2-((3'-((4-chloro-6-(1H-1,2,3-triazol-1-yl)pyridin-3-yl)methoxy)-2,4',5-trifluoro-[1,1'-biphenyl]-4-yl)methyl)-1-(4,4-dimethyltetrahydrofuran-3-yl)-1H-benzo[d]imidazole-6-carboxylic acid (S)-2-((3'-((4-chloro-6-(1H-1,2,3-triazol-1-yl)pyridin-3-yl)methoxy)-2,4',5-trifluoro-[1,1'-biphenyl]-4-yl)methyl)-1-(4,4-dimethyltetrahydrofuran-3-yl)-1H-benzo[d]imidazole-6-carboxylic acid was prepared in a manner as described in Procedure 35, starting with Intermediates I-82 and I-1061. 1H NMR (400 MHz, DMSO-d6) δ 8.93 (d, J=1.2 Hz, 1H), 8.83 (s, 1H), 8.48 (s, 1H), 8.33 (s, 1H), 8.04 (d, J=1.3 Hz, 1H), 7.80 (dd, J=8.4, 1.4 Hz, 1H), 7.62 (t, J=8.2 Hz, 2H), 7.56 (dd, J=10.1, 6.5 Hz, 1H), 7.47-7.43 (m, 1H), 7.40 (dd, J=11.3, 8.6 Hz, 1H), 7.30-7.23 (m, 1H), 5.46 (s, 2H), 5.02 (d, J=6.6 Hz, 1H), 4.58-4.48 (m, 2H), 4.44 (dd, J=11.1, 6.8 Hz, 1H), 4.36 (d, J=16.8 Hz, 1H), 3.82-3.68 (m, 2H), 1.34 (s, 3H), 0.60 (s, 3H). ES/MS m/z: 689.1 (M+H$^+$).

Example 389: 2-(4-(2-((4-chloro-6-(1H-1,2,3-triazol-1-yl)pyridin-3-yl)methoxy)pyrimidin-4-yl)-2,5-difluorobenzyl)-1-(2-methoxyethyl)-1H-benzo[d]imidazole-6-carboxylic acid 2-(4-(2-((4-chloro-6-(1H-1,2,3-triazol-1-yl)pyridin-3-yl)methoxy)pyrimidin-4-yl)-2,5-difluorobenzyl)-1-(2-methoxyethyl)-1H-benzo[d]imidazole-6-carboxylic acid was prepared in a manner as described in Procedure 35, starting with Intermediates I-96 and I-1062. 1H NMR (400 MHz, DMSO-d6) δ 8.92 (d, J=1.3 Hz, 1H), 8.84 (s, 1H), 8.80 (d, J=5.2 Hz, 1H), 8.32 (s, 1H), 8.21 (s, 1H), 8.03 (d, J=1.2 Hz, 1H), 7.97 (dd, J=10.1, 6.3 Hz, 1H), 7.79 (dd, J=8.6, 1.5 Hz, 1H), 7.65 (dd, J=5.3, 1.8 Hz, 1H), 7.59 (d, J=8.4 Hz, 1H), 7.48 (dd, J=11.5, 5.8 Hz, 1H), 5.69 (s, 2H), 4.59 (d, J=5.5 Hz, 2H), 4.48 (s, 2H), 3.68 (t, J=5.0 Hz, 2H), 3.20 (s, 3H). ES/MS m/z: 633.1 (M+H$^+$).

Example 390: 2-((3'-((4-chloro-6-(1H-1,2,3-triazol-1-yl)pyridin-3-yl)methoxy)-2,4',5-trifluoro-[1,1'-biphenyl]-4-yl)methyl)-1-(2-methoxyethyl)-1H-benzo[d]imidazole-6-carboxylic acid 2-((3'-((4-chloro-6-(1H-1,2,3-triazol-1-yl)pyridin-3-yl)methoxy)-2,4',5-trifluoro-[1,1'-biphenyl]-4-yl)methyl)-1-(2-methoxyethyl)-1H-benzo[d]imidazole-6-carboxylic acid was prepared in a manner as described in Procedure 35, starting with Intermediates I-96 and I-1061. 1H NMR (400 MHz, DMSO-d6) δ 8.92 (d, J=1.3 Hz, 1H), 8.83 (s, 1H), 8.33 (s, 1H), 8.25 (d, J=1.5 Hz, 1H), 8.04 (d, J=1.3 Hz, 1H), 7.83 (dd, J=8.4, 1.5 Hz, 1H), 7.62 (dd, J=8.5, 3.5 Hz, 2H), 7.56 (dd, J=10.2, 6.5 Hz, 1H), 7.39 (dd, J=11.0, 7.5 Hz, 2H), 7.31-7.19 (m, 1H), 5.45 (s, 2H), 4.63 (t, J=5.2 Hz, 2H), 4.47 (s, 2H), 3.68 (d, J=5.3 Hz, 2H), 3.21 (s, 3H). ES/MS m/z: 649.1 (M+H$^+$).

Example 391: 2-(4-(6-((4-chloro-6-(1H-1,2,3-triazol-1-yl)pyridin-3-yl)methoxy)pyridin-2-yl)-2,3,6-trifluorobenzyl)-1-(2-methoxyethyl)-1H-benzo[d]imidazole-6-carboxylic acid 2-(4-(6-((4-chloro-6-(1H-1,2,3-triazol-1-yl)pyridin-3-yl)methoxy)pyridin-2-yl)-2,3,6-trifluorobenzyl)-1-(2- methoxyethyl)-1H-benzo[d]imidazole-6-carboxylic acid was prepared in a manner as described in Procedure 38, starting with Intermediates I-1186 and I-1049. 1H NMR (400 MHz, DMSO-d6) δ 8.90 (d, J=1.3 Hz, 1H), 8.83 (s, 1H), 8.31 (s, 1H), 8.21 (d, J=1.5 Hz, 1H), 8.03 (d, J=1.3 Hz, 1H), 7.96 (t, J=7.8 Hz, 1H), 7.82-7.73 (m, 2H), 7.58 (dd, J=13.1, 7.9 Hz, 2H), 7.06 (d, J=8.4 Hz, 1H), 5.67 (s, 2H), 4.65 (s, 2H), 4.53 (s, 2H), 3.72 (t, J=5.0 Hz, 2H), 3.24 (s, 3H). ES/MS m/z: 650.1 (M+H$^+$).

Example 392: 2-(4-(6-((4-chloro-6-(1H-1,2,3-triazol-1-yl)pyridin-3-yl)methoxy)-5-fluoropyridin-2-yl)-2,3,6-trifluorobenzyl)-1-(2-methoxyethyl)-1H-benzo[d]imidazole-6-carboxylic acid 2-(4-(6-((4-chloro-6-(1H-1,2,3-triazol-1-yl)pyridin-3-yl)methoxy)-5-fluoropyridin-2-yl)-2,3,6-trifluorobenzyl)-1-(2-methoxyethyl)-1H-benzo[d]imidazole-6-carboxylic acid was prepared in a manner as described in Procedure 38, starting with Intermediates I-1186 and I-1050. 1H NMR (400 MHz, DMSO-d6) δ 8.91 (d, J=1.3 Hz, 1H), 8.85 (s, 1H), 8.32 (s, 1H), 8.21 (s, 1H), 8.03 (d, J=1.3 Hz, 1H), 7.99-7.86 (m, 1H), 7.80-7.70 (m, 1H), 7.63 (d, J=8.5 Hz, 1H), 7.56 (d, J=8.4 Hz, 1H), 5.76 (s, 2H), 4.65 (s, 2H), 4.52 (s, 2H), 3.72 (t, J=4.9 Hz, 2H), 3.24 (s, 3H). ES/MS m/z: 668.1 (M+H$^+$).

Example 393: (S)-2-(4-(6-((3,4-dichlorobenzyl)oxy)pyridin-2-yl)-2,5-difluorobenzyl)-1-(4,4-dimethyltetrahydrofuran-3-yl)-1H-benzo[d]imidazole-6-carboxylic acid (S)-2-(4-(6-((3,4-dichlorobenzyl)oxy)pyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 35, starting with Intermediates I-82 and I-1060. 1H NMR (400 MHz, DMSO-d6) δ 8.48 (s, 1H), 7.89 (t, J=7.9 Hz, 1H), 7.80 (dt, J=10.4, 3.3 Hz, 3H), 7.63 (dd, J=16.7, 8.4 Hz, 2H), 7.57-7.41 (m, 3H), 6.98 (d, J=8.3 Hz, 1H), 5.48 (s, 2H), 5.01 (d, J=6.7 Hz, 1H), 4.58-4.48 (m, 2H), 4.48-4.31 (m, 2H), 3.81-3.71 (m, 2H), 1.33 (s, 3H), 0.60 (s, 3H). ES/MS m/z: 638.2 (M+H$^+$).

Example 394: (S)-2-(4-(6-((4-chloro-3-fluorobenzyl)oxy)pyridin-2-yl)-2,5-difluorobenzyl)-1-(4,4-dimethyltetrahydrofuran-3-yl)-1H-benzo[d]imidazole-6-carboxylic acid (S)-2-(4-(6-((4-chloro-3-fluorobenzyl)oxy)pyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 35, starting with Intermediates I-82 and I-1059. 1H NMR (400 MHz, DMSO-d6) δ 8.48 (s, 1H), 7.89 (t, J=7.9 Hz, 1H), 7.83-7.75 (m, 2H), 7.61 (dt, J=8.0, 3.8 Hz, 2H), 7.58-7.49 (m, 2H), 7.45 (dd, J=11.2, 6.2 Hz, 1H), 7.39-7.35 (m, 1H), 6.98 (d, J=8.2 Hz, 1H), 5.48 (s, 2H), 5.01 (d, J=6.5 Hz, 1H), 4.59-4.48 (m, 2H), 4.48-4.31 (m, 2H), 3.81-3.68 (m, 2H), 1.33 (s, 3H), 0.60 (s, 3H). ES/MS m/z: 622.2 (M+H$^+$).

Example 396: (S)-2-(4-(6-((4-cyanobenzyl)oxy)-5-fluoropyridin-2-yl)-2,5-difluorobenzyl)-3-(4,4-dimethyltetrahydrofuran-3-yl)-3H-imidazo[4,5-b]pyridine-5-carboxylic acid (S)-2-(4-(6-((4-cyanobenzyl)oxy)-5-fluoropyridin-2-yl)-2,5-difluorobenzyl)-3-(4,4-dimethyltetrahydrofuran-3-yl)-3H-imidazo[4,5-b]pyridine-5-carboxylic acid was prepared in a manner as described in Procedure 35, starting with Intermediates I-1247 and I-1167. 1H NMR (400 MHz, DMSO) δ 8.08 (d, J=8.6 Hz, 1H), 7.96 (d, J=8.3 Hz, 1H), 7.87 (dd, J=9.9, 8.3 Hz, 3H), 7.77-7.67 (m, 3H), 7.55 (dd, J=8.5, 2.4 Hz, 1H), 7.46 (dd, J=11.4, 6.0 Hz, 1H), 5.67 (s, 2H), 4.96 (dd, J=8.4, 5.3 Hz, 1H), 4.74 (dd, J=9.6, 5.1 Hz, 1H), 4.58 (d, J=17.1 Hz, 1H), 4.48 (d, J=17.1 Hz, 1H), 4.37 (dt, J=9.0, 5.0 Hz, 2H), 3.63 (d, J=7.9 Hz, 1H), 1.24 (s, 3H), 0.62 (s, 3H). ES/MS m/z: 614.0 (M+H$^+$).

Example 397: (S)-5-chloro-2-(4-(6-((4-cyanobenzyl)oxy)pyridin-2-yl)-2,5-difluorobenzyl)-1-(4,4-dimethyltetrahydrofuran-3-yl)-1H-benzo[d]imidazole-6-carboxylic acid (S)-5-chloro-2-(4-(6-((4-cyanobenzyl)oxy)pyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 35, starting with Intermediates I-114 and I-1107. 1H NMR (400 MHz, DMSO) δ 8.31 (s, 1H), 7.89 (dd, J=17.8, 8.0 Hz, 3H), 7.78-7.65 (m, 4H), 7.53 (d, J=7.4 Hz, 1H), 7.45 (t, J=8.7 Hz, 1H), 7.01 (d, J=8.2 Hz, 1H), 5.58 (s, 2H), 5.00 (d, J=6.5 Hz, 1H), 4.56-4.47 (m, 2H), 4.46-4.31 (m, 3H), 4.36 (s, 15H), 4.16 (s, 1H), 3.78-3.68 (m, 2H), 1.33 (s, 3H), 0.61 (s, 3H). ES/MS m/z: 629.0 (M+H$^+$).

Example 398: (S)-2-(4-(6-((2,4-dichlorobenzyl)oxy)-5-fluoropyridin-2-yl)-2,5-difluorobenzyl)-1-(4,4-dimethyltetrahydrofuran-3-yl)-1H-benzo[d]imidazole-6-carboxylic acid (S)-2-(4-(6-((2,4-dichlorobenzyl)oxy)-5-fluoropyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 35, starting with Intermediates I-1098 and I-82. 1H NMR (400 MHz, DMSO) δ 8.49 (s, 1H), 7.92-7.69 (m, 4H), 7.64 (dd, J=8.4, 6.1 Hz, 2H), 7.60-7.53 (m, 1H), 7.53-7.42 (m, 2H), 5.63 (s, 2H), 5.02 (d, J=6.6 Hz, 1H), 4.54 (dd, J=15.0, 2.5 Hz, 2H), 4.48-4.34 (m, 2H), 3.78 (d, J=8.7 Hz, 1H), 3.73 (d, J=8.6 Hz, 1H), 1.33 (s, 3H), 0.61 (s, 3H). ES/MS m/z: 656.0 (M+H$^+$).

Example 399: (S)-2-(4-(6-((2,4-dichlorobenzyl)oxy)pyridin-2-yl)-2,5-difluorobenzyl)-1-(4,4-dimethyltetrahydrofuran-3-yl)-1H-benzo[d]imidazole-6-carboxylic acid (S)-2-(4-(6-((2,4-dichlorobenzyl)oxy)pyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 35, starting with Intermediates I-1099 and I-82. 1H NMR (400 MHz, DMSO) δ 8.50 (s, 1H), 7.90 (t, J=7.9 Hz, 1H), 7.86-7.75 (m, 2H), 7.70 (d, J=2.1 Hz, 1H), 7.66-7.59 (m, 2H), 7.58-7.51 (m, 1H), 7.51-7.42 (m, 2H), 7.00 (d, J=8.2 Hz, 1H), 5.54 (s, 2H), 5.03 (d, J=6.7 Hz, 1H), 4.73 (s, 8H), 4.55 (d, J=17.4 Hz, 2H), 4.48-4.37 (m, 2H), 4.35 (s, 4H), 3.82-3.70 (m, 2H), 1.33 (s, 3H), 0.61 (s, 3H). ES/MS m/z: 638.0 (M+H$^+$).

Example 400: (S)-2-(4-(6-((4-chloro-2-fluorobenzyl)oxy)pyridin-2-yl)-2,5-difluorobenzyl)-1-(4,4-dimethyltetrahydrofuran-3-yl)-5-hydroxy-1H-benzo[d]imidazole-6-carboxylic acid (S)-2-(4-(6-((4-chloro-2-fluorobenzyl)oxy)pyridin-2-yl)-2,5-difluorobenzyl)-1-(4,4-dimethyltetrahydrofuran-3-yl)-

5-hydroxy-1H-benzo[d]imidazole-6-carboxylic acid was prepared in a manner as described in Procedure 35, starting with Intermediates I-102 and I-1106. 1H NMR (400 MHz, DMSO) δ 8.40 (s, 1H), 7.93-7.80 (m, 2H), 7.61 (t, J=8.1 Hz, 1H), 7.57-7.41 (m, 4H), 7.33 (dd, J=8.3, 1.9 Hz, 1H), 6.96 (d, J=8.3 Hz, 1H), 5.51 (s, 2H), 4.98 (d, J=6.6 Hz, 1H), 4.57-4.47 (m, 2H), 4.47-4.34 (m, 2H), 3.77 (d, J=8.7 Hz, 1H), 3.72 (d, J=8.6 Hz, 1H), 2.58 (s, 3H), 1.31 (s, 3H), 0.60 (s, 3H). ES/MS m/z: 636.0 (M+H$^+$).

Example 401: (S)-2-(4-(6-((4-cyanobenzyl)oxy)pyridin-2-yl)-2,5-difluorobenzyl)-1-(4,4-dimethyltetrahydrofuran-3-yl)-5-hydroxy-1H-benzo[d]imidazole-6-carboxylic acid (S)-2-(4-(6-((4-cyanobenzyl)oxy)pyridin-2-yl)-2,5-difluorobenzyl)-1-(4,4-dimethyltetrahydrofuran-3-yl)-5-hydroxy-1H-benzo[d]imidazole-6-carboxylic acid was prepared in a manner as described in Procedure 35, starting with Intermediates I-114 and I-1106. 1H NMR (400 MHz, DMSO) δ 8.40 (s, 1H), 7.95-7.83 (m, 3H), 7.74 (dd, J=10.4, 6.5 Hz, 1H), 7.68 (d, J=8.0 Hz, 2H), 7.53 (d, J=7.4 Hz, 1H), 7.45 (s, 1H), 7.50-7.40 (m, 1H), 7.01 (d, J=8.3 Hz, 1H), 5.58 (s, 2H), 4.97 (d, J=6.6 Hz, 1H), 4.52 (d, J=7.5 Hz, 1H), 4.49 (s, 1H), 4.47-4.33 (m, 2H), 3.80-3.68 (m, 2H), 2.58 (s, 3H), 1.31 (s, 3H), 0.59 (s, 3H). ES/MS m/z: 609 (M+H$^+$).

Example 402: (S)-5-chloro-2-(4-(6-((4-chloro-2-fluorobenzyl)oxy)pyridin-2-yl)-2,5-difluorobenzyl)-1-(4,4-dimethyltetrahydrofuran-3-yl)-1H-benzo[d]imidazole-6-carboxylic acid (S)-5-chloro-2-(4-(6-((4-chloro-2-fluorobenzyl)oxy)pyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 35, starting with Intermediates I-102 and I-1107. 1H NMR (400 MHz, DMSO) δ 8.32 (s, 1H), 7.93-7.79 (m, 2H), 7.73 (s, 1H), 7.61 (t, J=8.2 Hz, 1H), 7.59-7.41 (m, 3H), 7.33 (dd, J=8.3, 2.0 Hz, 1H), 6.96 (d, J=8.3 Hz, 1H), 5.51 (s, 2H), 5.00 (d, J=6.5 Hz, 1H), 4.57-4.47 (m, 2H), 4.46-4.32 (m, 2H), 3.78-3.68 (m, 2H), 1.33 (s, 3H), 0.61 (s, 3H). ES/MS m/z: 656.0 (M+H$^+$).

Example 403: 2-(4-(6-((2-chloro-4-(1H-1,2,3-triazol-1-yl)benzyl)oxy)pyridin-2-yl)-2,3,6-trifluorobenzyl)-1-(2-methoxyethyl)-1H-benzo[d]imidazole-6-carboxylic acid 2-(4-(6-((2-chloro-4-(1H-1,2,3-triazol-1-yl)benzyl)oxy)pyridin-2-yl)-2,3,6-trifluorobenzyl)-1-(2-methoxyethyl)-1H-benzo[d]imidazole-6-carboxylic acid was prepared in a manner as described in Procedure 38, starting with Intermediates I-1102 and I-1103. 1H NMR (400 MHz, DMSO) δ 8.92 (s, 1H), 8.22 (s, 1H), 8.16 (d, J=2.1 Hz, 1H), 8.03-7.92 (m, 3H), 7.87-7.75 (m, 2H), 7.75-7.67 (m, 1H), 7.58 (t, J=7.7 Hz, 2H), 7.08 (d, J=8.3 Hz, 1H), 5.63 (s, 2H), 4.65 (t, J=5.1 Hz, 2H), 4.53 (s, 2H), 3.73 (t, J=5.0 Hz, 2H), 3.24 (s, 3H), 2.56 (d, J=7.5 Hz, 1H). ES/MS m/z: 649.0 (M+H$^+$).

Example 404: (S)-2-(4-(2-((2,4-dichlorobenzyl)oxy)pyrimidin-4-yl)-2,5-difluorobenzyl)-1-(4,4-dimethyltetrahydrofuran-3-yl)-4-fluoro-1H-benzo[d]imidazole-6-carboxylic acid (S)-2-(4-(2-((2,4-dichlorobenzyl)oxy)pyrimidin-4-yl)-2,5-difluorobenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1099 and I-108. 1H NMR (400 MHz, Chloroform-d) δ 8.31 (d, J=5.1 Hz, 1H), 7.51 (t, J=8.1 Hz, 1H), 7.21 (d, J=5.2 Hz, 1H), 7.19-7.13 (m, 2H), 5.51-5.46 (m, 2H); 1H NMR (400 MHz, DMSO) δ 8.78 (d, J=5.1 Hz, 1H), 8.57 (d, J=1.5 Hz, 1H), 7.92 (ddt, J=10.3, 3.5, 1.7 Hz, 3H), 7.75 (dq, J=11.3, 8.2 Hz, 3H), 7.62 (dd, J=5.2, 1.8 Hz, 1H), 7.51 (dd, J=11.5, 6.0 Hz, 1H), 5.81-5.70 (m, 1H), 5.62 (s, 2H), 4.65 (s, 2H), 4.27 (dd, J=10.8, 7.9 Hz, 1H), 4.20 (dd, J=10.8, 3.3 Hz, 1H), 2.40 (dd, J=13.2, 9.4 Hz, 1H), 2.02 (dd, J=13.3, 6.9 Hz, 1H), 1.50 (s, 3H), 1.27 (s, 3H). ES/MS m/z: 658.2 (M+H$^+$).

Example 405: (S)-2-(4-(4-((4-chloro-2-fluorobenzyl)oxy)pyrimidin-2-yl)-2,5-difluorobenzyl)-1-(4,4-dimethyltetrahydrofuran-3-yl)-1H-benzo[d]imidazole-6-carboxylic acid (S)-2-(4-(4-((4-chloro-2-fluorobenzyl)oxy)pyrimidin-2-yl)-2,5-difluorobenzyl)-1-(4,4-dimethyltetrahydrofuran-3-yl)-1H-benzo[d]imidazole-6-carboxylic acid was prepared in a manner as described in Procedure 35, starting with Intermediates I-1338 and I-82. 1H NMR (400 MHz, DMSO-d6) δ 8.72 (d, J=5.8 Hz, 1H), 8.50 (s, 1H), 7.92 (dd, J=10.1, 6.2 Hz, 1H), 7.82 (dd, J=8.5, 1.5 Hz, 1H), 7.64 (dt, J=8.2, 4.0 Hz, 2H), 7.50 (ddd, J=16.8, 10.5, 4.0 Hz, 2H), 7.35 (dd, J=8.4, 2.1 Hz, 1H), 7.04 (d, J=5.8 Hz, 1H), 5.58 (s, 2H), 5.03 (d, J=6.6 Hz, 1H), 4.60-4.52 (m, 2H), 4.49-4.38 (m, 2H), 3.85-3.69 (m, 2H), 1.34 (s, 3H), 0.61 (s, 3H). ES/MS m/z: 623.0 (M+H$^+$).

Example 406: 1-(3-oxabicyclo[3.1.1]heptan-1-yl)-2-(4-(6-((4-chloro-2-fluorobenzyl)oxy)pyridin-2-yl)-2,5-difluorobenzyl)-1H-benzo[d]imidazole-6-carboxylic acid 1-(3-oxabicyclo[3.1.1]heptan-1-yl)-2-(4-(6-((4-chloro-2-fluorobenzyl)oxy)pyridin-2-yl)-2,5-difluorobenzyl)-1H-benzo[d]imidazole-6-carboxylic acid was prepared in a manner as described in Procedure 35, starting with Intermediates I-102 and I-1153. 1H NMR (400 MHz, DMSO-d6) δ 8.12 (d, J=1.4 Hz, 1H), 7.95-7.76 (m, 3H), 7.65-7.58 (m, 2H), 7.52 (ddd, J=12.1, 8.8, 1.9 Hz, 2H), 7.43 (dd, J=11.5, 6.1 Hz, 1H), 7.33 (dd, J=8.3, 2.1 Hz, 1H), 6.95 (d, J=8.3 Hz, 1H), 5.51 (s, 2H), 4.38 (s, 2H), 4.11 (s, 2H), 3.94 (d, J=2.1 Hz, 2H), 2.90-2.77 (m, 2H), 2.69 (ddd, J=12.3, 6.5, 3.7 Hz, 3H). ES/MS m/z: 620.0 (M+H$^+$).

Example 407: racemic 1-((4R)-2-oxabicyclo[3.1.1]heptan-4-yl)-2-(4-(6-((4-chloro-2-fluorobenzyl)oxy)pyridin-2-yl)-2,5-difluorobenzyl)-1H-benzo[d]imidazole-6-carboxylic acid Racemic 1-((4R)-2-oxabicyclo[3.1.1]heptan-4-yl)-2-(4-(6-((4-chloro-2-fluorobenzyl)oxy)pyridin-2-yl)-2,5-difluorobenzyl)-1H-benzo[d]imidazole-6-carboxylic acid was prepared in a manner as described in Procedure 35, starting with Intermediates I-102 and I-1342. 1H NMR (400 MHz, DMSO-d6) δ 8.71 (d, J=1.4 Hz, 1H), 7.92-7.81 (m, 3H), 7.67-7.58 (m, 2H), 7.55-7.43 (m, 3H), 7.34 (dd, J=8.2, 2.1 Hz, 1H), 6.96 (d, J=8.3 Hz, 1H), 5.51 (s, 2H), 5.46 (q, J=4.5, 3.8 Hz, 1H), 4.74-4.63 (m, 2H), 4.60-4.40 (m, 3H), 3.08 (p, J=5.5 Hz, 1H), 2.36 (ddd, J=11.0, 5.8, 3.6 Hz, 1H), 2.28 (dd, J=10.9, 9.2 Hz, 1H), 2.13-2.04 (m, 1H), 2.00 (dd, J=10.7, 9.2 Hz, 1H). ES/MS m/z: 620.0 (M+H$^+$).

Example 408: 2-(4-(6-((4-cyano-2-fluorobenzyl)oxy)pyridin-2-yl)-2,5-difluorobenzyl)-1-((3S,4R)-4-methoxytetrahydro-2H-pyran-3-yl)-1H-benzo[d]imidazole-6-carboxylic acid

Example 409: 2-(4-(6-((4-cyano-2-fluorobenzyl)oxy)pyridin-2-yl)-2,5-difluorobenzyl)-1-((3R,4S)-4-methoxytetrahydro-2H-pyran-3-yl)-1H-benzo[d]imidazole-6-carboxylic acid Example 408 and Example 409 were prepared via preparative chiral SFC (Daicel Chiralpak AD-H column, EtOH/CO₂ eluent) of Example 70.

2-(4-(6-((4-cyano-2-fluorobenzyl)oxy)pyridin-2-yl)-2,5-difluorobenzyl)-1-((3S,4R)-4-methoxytetrahydro-2H-pyran-3-yl)-1H-benzo[d]imidazole-6-carboxylic acid (Example 408) was isolated as the later-eluting of two stereoisomers. 1H NMR (400 MHz, DMSO-d6) δ 8.54 (s, 1H), 7.91 (t, J=9.9 Hz, 2H), 7.85-7.68 (m, 4H), 7.61 (d, J=8.4 Hz, 1H), 7.54 (d, J=7.3 Hz, 1H), 7.40 (dd, J=11.4, 6.0 Hz, 1H), 7.00 (d, J=8.2 Hz, 1H), 5.61 (s, 2H), 4.87 (dd, J=9.0, 4.7 Hz, 1H), 4.63 (d, J=16.9 Hz, 1H), 4.59-4.46 (m, 2H), 3.90 (dd, J=10.7, 4.6 Hz, 1H), 3.84-3.77 (m, 2H), 3.14 (s, 3H), 1.99 (q, J=4.6, 4.0 Hz, 3H). ES/MS m/z: 629.3 (M+H⁺).

2-(4-(6-((4-cyano-2-fluorobenzyl)oxy)pyridin-2-yl)-2,5-difluorobenzyl)-1-((3R,4S)-4-methoxytetrahydro-2H-pyran-3-yl)-1H-benzo[d]imidazole-6-carboxylic acid (Example 409) was isolated as the earlier-eluting of two stereoisomers. 1H NMR (400 MHz, DMSO-d6) δ 8.54 (s, 1H), 7.91 (t, J=9.9 Hz, 2H), 7.85-7.68 (m, 4H), 7.61 (d, J=8.4 Hz, 1H), 7.54 (d, J=7.3 Hz, 1H), 7.40 (dd, J=11.4, 6.0 Hz, 1H), 7.00 (d, J=8.2 Hz, 1H), 5.61 (s, 2H), 4.87 (dd, J=9.0, 4.7 Hz, 1H), 4.63 (d, J=16.9 Hz, 1H), 4.59-4.46 (m, 2H), 3.90 (dd, J=10.7, 4.6 Hz, 1H), 3.84-3.77 (m, 2H), 3.14 (s, 3H), 1.99 (q, J=4.6, 4.0 Hz, 3H). ES/MS m/z: 629.3 (M+H⁺).

Example 410: (S)-2-(4-(4-((4-chloro-2-fluorobenzyl)oxy)-5-fluoropyrimidin-2-yl)-2,5-difluorobenzyl)-1-(4,4-dimethyltetrahydrofuran-3-yl)-1H-benzo[d]imidazole-6-carboxylic acid (S)-2-(4-(4-((4-chloro-2-fluorobenzyl)oxy)-5-fluoropyrimidin-2-yl)-2,5-difluorobenzyl)-1-(4,4-dimethyltetrahydrofuran-3-yl)-1H-benzo[d]imidazole-6-carboxylic acid was prepared in a manner as described in Procedure 35, starting with Intermediates I-1154 and I-82. 1H NMR (400 MHz, DMSO-d6) δ 8.83 (d, J=2.8 Hz, 1H), 8.50 (s, 1H), 7.90 (dd, J=10.1, 6.2 Hz, 1H), 7.81 (dd, J=8.4, 1.5 Hz, 1H), 7.65 (q, J=8.3 Hz, 2H), 7.55 (dd, J=10.0, 2.0 Hz, 1H), 7.49 (dd, J=11.0, 6.0 Hz, 1H), 7.37 (dd, J=8.3, 2.0 Hz, 1H), 5.67 (s, 2H), 5.02 (d, J=6.6 Hz, 1H), 4.61-4.50 (m, 2H), 4.48-4.37 (m, 2H), 3.85-3.69 (m, 2H), 1.34 (s, 3H), 0.61 (s, 3H). ES/MS m/z: 641.0 (M+H⁺).

Example 411: racemic 2-(4-(6-((4-cyano-2-fluorobenzyl)oxy)pyridin-2-yl)-2,5-difluorobenzyl)-1-((3R,4R)-4-cyclopropoxytetrahydrofuran-3-yl)-1H-benzo[d]imidazole-6-carboxylic acid Racemic 2-(4-(6-((4-cyano-2-fluorobenzyl)oxy)pyridin-2-yl)-2,5-difluorobenzyl)-1-((3R,4R)-4-cyclopropoxytetrahydrofuran-3-yl)-1H-benzo[d]imidazole-6-carboxylic acid was prepared in a manner as described in Procedure 22, starting with Intermediates I-7 and I-1155. 1H NMR (400 MHz, DMSO-d6) δ 8.39 (d, J=1.5 Hz, 1H), 8.00-7.89 (m, 2H), 7.84-7.71 (m, 4H), 7.60 (d, J=8.4 Hz, 1H), 7.53 (d, J=7.2 Hz, 1H), 7.37 (dd, J=11.5, 6.0 Hz, 1H), 7.00 (d, J=8.3 Hz, 1H), 5.59 (d, J=14.5 Hz, 3H), 4.50 (s, 2H), 4.40 (ddd, J=13.3, 8.4, 4.9 Hz, 2H), 4.19-4.09 (m, 1H), 4.04 (dd, J=10.4, 8.2 Hz, 1H), 3.87 (dd, J=10.2, 4.6 Hz, 1H), 2.91 (tt, J=5.9, 2.9 Hz, 1H), 0.22 (dd, J=10.9, 5.2 Hz, 1H), 0.11 (ddd, J=12.6, 9.1, 5.0 Hz, 2H), −0.04−−0.40 (m, 1H). ES/MS m/z: 641.0 (M+H⁺).

Example 412: racemic 2-(4-(6-((4-cyano-2-fluorobenzyl)oxy)pyridin-2-yl)-2,5-difluorobenzyl)-1-((3R,4R)-4-(2,2-difluoroethoxy)tetrahydrofuran-3-yl)-1H-benzo[d]imidazole-6-carboxylic acid Racemic 2-(4-(6-((4-cyano-2-fluorobenzyl)oxy)pyridin-2-yl)-2,5-difluorobenzyl)-1-((3R,4R)-4-(2,2-difluoroethoxy)tetrahydrofuran-3-yl)-1H-benzo[d]imidazole-6-carboxylic acid was prepared in a manner as described in Procedure 22, starting with Intermediates I-7 and I-1156. 1H NMR (400 MHz, DMSO-d6) δ 8.43 (s, 1H), 8.03-7.86 (m, 2H), 7.85-7.67 (m, 4H), 7.60 (d, J=8.5 Hz, 1H), 7.53 (d, J=7.3 Hz, 1H), 7.34 (dd, J=11.5, 6.1 Hz, 1H), 7.00 (d, J=8.3 Hz, 1H), 5.87-5.45 (m, 3H), 4.54 (s, 2H), 4.51-4.41 (m, 2H), 4.14 (s, OH), 4.05 (dd, J=10.5, 8.3 Hz, 1H), 3.93-3.83 (m, 2H), 3.62-3.43 (m, 1H), 3.24-2.99 (m, 1H). ES/MS m/z: 665.0 (M+H⁺).

Example 413: (S)-2-(4-(6-((2-cyano-4-(trifluoromethyl)benzyl)oxy)pyridin-2-yl)-2,5-difluorobenzyl)-1-(4,4-dimethyltetrahydrofuran-3-yl)-1H-benzo[d]imidazole-6-carboxylic acid

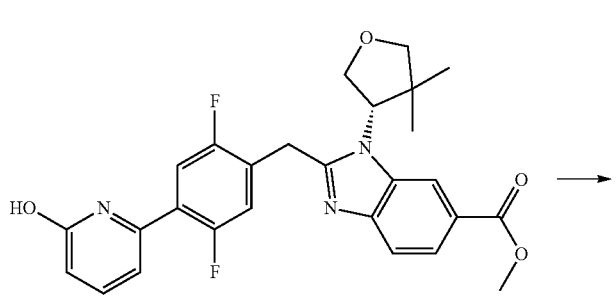

I-1219

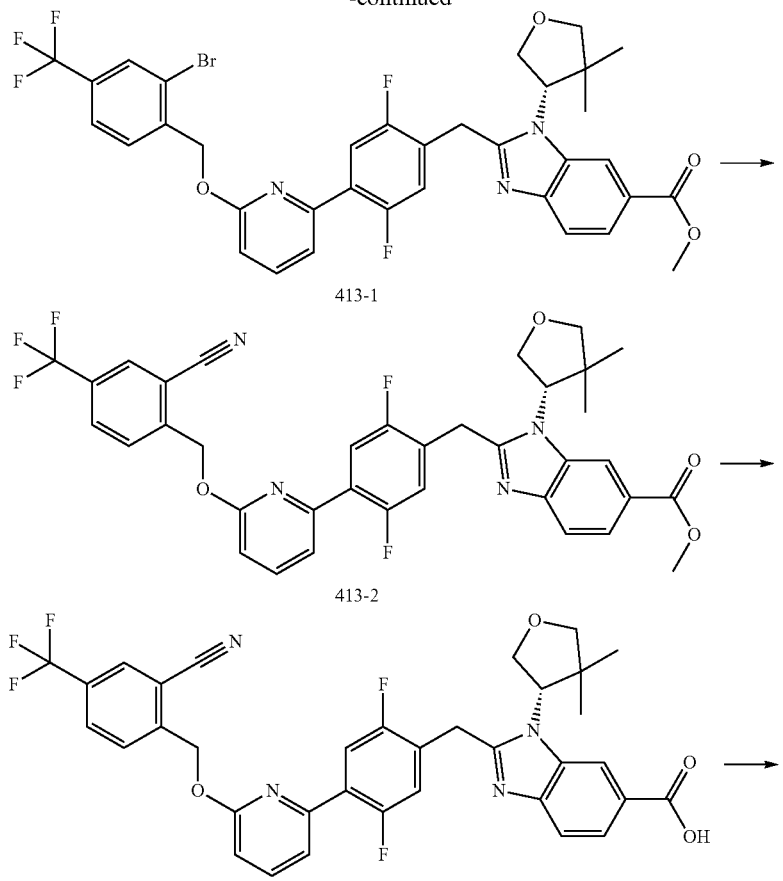

Example 413

Methyl (S)-2-(4-(6-((2-bromo-4-(trifluoromethyl)benzyl)oxy)pyridin-2-yl)-2,5-difluorobenzyl)-1-(4,4-dimethyltetrahydrofuran-3-yl)-1H-benzo[d]imidazole-6-carboxylate (413-1): A mixture of Intermediate I-1219 (44 mg, 1.0 equivalent), 2-bromo-1-(bromomethyl)-4-(trifluoromethyl)benzene (30 mg, 1.05 equivalent), cesium carbonate (47 mg, 1.6 equivalent) and acetonitrile (3 mL) was stirred at 50 C for 1 hr. The mixture was filtered, concentrated and purified by silica gel flash column chromatography (EtOAc/hexane) to yield the title compound. ES/MS m/z: 730.0 (M+H+).

Methyl (S)-2-(4-(6-((2-cyano-4-(trifluoromethyl)benzyl)oxy)pyridin-2-yl)-2,5-difluorobenzyl)-1-(4,4-dimethyltetrahydrofuran-3-yl)-1H-benzo[d]imidazole-6-carboxylate (413-2): A mixture of methyl (S)-2-(4-(6-((2-bromo-4-(trifluoromethyl)benzyl)oxy)pyridin-2-yl)-2,5-difluorobenzyl)-1-(4,4-dimethyltetrahydrofuran-3-yl)-1H-benzo[d]imidazole-6-carboxylate (413-1, 42 mg, 1.0 equivalent), zinc cyanide (20 mg, 3.0 equivalent), zinc(0) (38 mg, 1.0 equivalent), Pd(PPh3)4 (20 mg, 0.30 equivalent), and DMF (3.8 mL) was purged with argon for 1 min, then stirred at 100° C. for 5 hr. Silica gel flash column chromatography (EtOAc/hexane) yielded the title compound. ES/MS m/z: 677.0 (M+H+).

(S)-2-(4-(6-((2-cyano-4-(trifluoromethyl)benzyl)oxy)pyridin-2-yl)-2,5-difluorobenzyl)-1-(4,4-dimethyltetrahydrofuran-3-yl)-1H-benzo[d]imidazole-6-carboxylic acid (Example 413): A mixture of methyl (S)-2-(4-(6-((2-cyano-4-(trifluoromethyl)benzyl)oxy)pyridin-2-yl)-2,5-difluorobenzyl)-1-(4,4-dimethyltetrahydrofuran-3-yl)-1H-benzo[d]imidazole-6-carboxylate (413-2, 38 mg, 1.0 equivalent), lithium hydroxide (0.3 M in water, 0.56 mL, 3.0 equivalent) and acetonitrile (0.50 mL) was stirred at 105° C. for 6 min. The mixture was quenched with acetic acid and purified by reverse-phase preparative HPLC (MeCN/water, 0.1% TFA) to yield the title compound. 1H NMR (400 MHz, DMSO-d6) δ 8.49 (s, 1H), 8.43 (d, J=1.9 Hz, 1H), 8.12 (dd, J=8.3, 1.9 Hz, 1H), 7.99-7.88 (m, 2H), 7.81 (dd, J=8.5, 1.5 Hz, 1H), 7.72 (dd, J=10.4, 6.4 Hz, 1H), 7.63 (d, J=8.5 Hz, 1H), 7.57 (dd, J=7.5, 1.6 Hz, 1H), 7.46 (dd, J=11.4, 6.0 Hz, 1H), 7.04 (d, J=8.3 Hz, 1H), 5.75 (s, 2H), 5.02 (d, J=6.7 Hz, 1H), 4.59-4.50 (m, 2H), 4.48-4.35 (m, 2H), 3.83-3.67 (m, 2H), 1.33 (s, 3H), 0.60 (s, 3H). ES/MS m/z: 663.0 (M+H+).

Example 414: (S)-2-(4-(6-((6-(1H-1,2,3-triazol-1-yl)-4-(trifluoromethyl)pyridin-3-yl)methoxy)pyridin-2-yl)-2,5-difluorobenzyl)-1-(4,4-dimethyltetrahydrofuran-3-yl)-1H-benzo[d]imidazole-6-carboxylic acid (S)-2-(4-(6-((6-(1H-1,2,3-triazol-1-yl)-4-(trifluoromethyl)pyridin-3-yl)methoxy)pyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 27, starting with Intermediates I-1157 and I-1219. 1H NMR (400 MHz, DMSO-d6) δ 9.04 (s, 1H), 8.97 (d, J=1.3 Hz, 1H), 8.50 (s, 1H), 8.41 (s, 1H), 8.06 (d, J=1.2 Hz, 1H), 7.93 (t, J=7.9 Hz, 1H), 7.87-7.76 (m, 2H), 7.63 (d, J=8.4 Hz, 1H), 7.57 (dd, J=7.5, 1.6 Hz, 1H), 7.47 (dd, J=11.4, 6.1 Hz, 1H), 7.02 (d, J=8.3 Hz, 1H), 5.77

(s, 2H), 5.02 (d, J=6.7 Hz, 1H), 4.55 (d, J=17.2 Hz, 2H), 4.49-4.35 (m, 2H), 3.88-3.58 (m, 2H), 1.32 (s, 3H), 0.60 (s, 3H). ES/MS m/z: 706 (M+H$^+$).

Example 415: (S)-2-(4-(5-chloro-6-((4-cyanobenzyl)oxy)pyridin-2-yl)-2,3,6-trifluorobenzyl)-1-(4,4-dimethyltetrahydrofuran-3-yl)-1H-benzo[d]imidazole-6-carboxylic acid (S)-2-(4-(5-chloro-6-((4-cyanobenzyl)oxy)pyridin-2-yl)-2,3,6-trifluorobenzyl)-1-(4,4-dimethyltetrahydrofuran-3-yl)-1H-benzo[d]imidazole-6-carboxylic acid was prepared in a manner as described in Procedure 35, starting with Intermediates I-1158 and I-82. 1H NMR (400 MHz, DMSO-d6) δ 8.48 (s, 1H), 8.14 (d, J=8.1 Hz, 1H), 7.92-7.85 (m, 2H), 7.78 (dd, J=8.4, 1.5 Hz, 1H), 7.75-7.64 (m, 3H), 7.64-7.54 (m, 2H), 5.69 (s, 2H), 5.08 (d, J=6.6 Hz, 1H), 4.70-4.54 (m, 2H), 4.47 (dd, J=11.1, 6.7 Hz, 1H), 4.35 (d, J=17.3 Hz, 1H), 3.83-3.71 (m, 2H), 1.39 (s, 3H), 0.65 (s, 3H). ES/MS m/z: 647.0 (M+H$^+$).

Example 416: (S)-2-(4-(5-chloro-6-((4-cyano-2-fluorobenzyl)oxy)pyridin-2-yl)-2,3,6-trifluorobenzyl)-1-(4,4-dimethyltetrahydrofuran-3-yl)-1H-benzo[d]imidazole-6-carboxylic acid (S)-2-(4-(5-chloro-6-((4-cyano-2-fluorobenzyl)oxy)pyridin-2-yl)-2,3,6-trifluorobenzyl)-1-(4,4-dimethyltetrahydrofuran-3-yl)-1H-benzo[d]imidazole-6-carboxylic acid was prepared in a manner as described in Procedure 35, starting with Intermediates I-1159 and I-82. 1H NMR (400 MHz, DMSO-d6) δ 8.48 (s, 1H), 8.15 (d, J=8.0 Hz, 1H), 7.95 (d, J=10.0 Hz, 1H), 7.77 (dd, J=5.8, 2.7 Hz, 3H), 7.71 (dd, J=10.6, 5.4 Hz, 1H), 7.63 (d, J=8.0 Hz, 1H), 7.59 (d, J=8.5 Hz, 1H), 5.72 (s, 2H), 5.09 (d, J=6.5 Hz, 1H), 4.65 (d, J=17.3 Hz, 1H), 4.57 (d, J=11.1 Hz, 1H), 4.47 (dd, J=11.1, 6.8 Hz, 1H), 4.35 (d, J=17.2 Hz, 1H), 3.85-3.75 (m, 2H), 1.39 (s, 3H), 0.66 (s, 3H). ES/MS m/z: 665.0 (M+H$^+$).

Example 417: (S)-2-(4-(6-((4-chloro-2-fluorobenzyl)oxy)pyridin-2-yl)-2,5-difluorobenzyl)-1-(4,4-dimethyltetrahydrofuran-3-yl)-5-fluoro-1H-benzo[d]imidazole-6-carboxylic acid (S)-2-(4-(6-((4-chloro-2-fluorobenzyl)oxy)pyridin-2-yl)-2,5-difluorobenzyl)-1-(4,4-dimethyltetrahydrofuran-3-yl)-5-fluoro-1H-benzo[d]imidazole-6-carboxylic acid was prepared in a manner as described in Procedure 35, starting with Intermediates I-1161 and I-102. 1H NMR (400 MHz, DMSO-d6) δ 8.38 (d, J=6.5 Hz, 1H), 7.89 (t, J=7.8 Hz, 1H), 7.83 (dd, J=9.8, 7.0 Hz, 1H), 7.62 (d, J=8.2 Hz, 1H), 7.56-7.47 (m, 3H), 7.47-7.42 (m, 1H), 7.33 (dd, J=8.2, 2.0 Hz, 1H), 6.96 (d, J=8.3 Hz, 1H), 5.51 (s, 2H), 5.00 (d, J=6.5 Hz, 1H), 4.52 (d, J=17.4 Hz, 2H), 4.47-4.30 (m, 2H), 3.82-3.67 (m, 2H), 1.34 (s, 3H), 0.61 (s, 3H). ES/MS m/z: 640.0 (M+H$^+$).

Example 418: (S)-2-(4-(6-((4-cyanobenzyl)oxy)pyridin-2-yl)-2,5-difluorobenzyl)-1-(4,4-dimethyltetrahydrofuran-3-yl)-5-fluoro-1H-benzo[d]imidazole-6-carboxylic acid (S)-2-(4-(6-((4-cyanobenzyl)oxy)pyridin-2-yl)-2,5-difluorobenzyl)-1-(4,4-dimethyltetrahydrofuran-3-yl)-5-fluoro-1H-benzo[d]imidazole-6-carboxylic acid was prepared in a manner as described in Procedure 35, starting with Intermediates I-114 and I-1161. 1H NMR (400 MHz, DMSO-d6) δ 8.38 (d, J=6.5 Hz, 1H), 7.96-7.83 (m, 3H), 7.77-7.65 (m, 3H), 7.53 (d, J=7.4 Hz, 1H), 7.45 (dd, J=10.2, 7.0 Hz, 2H), 7.01 (d, J=8.2 Hz, 1H), 5.58 (s, 2H), 5.00 (d, J=6.5 Hz, 1H), 4.51 (d, J=15.7 Hz, 2H), 4.47-4.30 (m, 2H), 3.81-3.69 (m, 2H), 1.33 (s, 3H), 0.61 (s, 3H). ES/MS m/z: 613.0 (M+H$^+$).

Example 419: (S)-2-(4-(6-((4-cyano-2-fluorobenzyl)oxy)pyridin-2-yl)-2,5-difluorobenzyl)-1-(4,4-dimethyltetrahydrofuran-3-yl)-5-fluoro-1H-benzo[d]imidazole-6-carboxylic acid (S)-2-(4-(6-((4-cyano-2-fluorobenzyl)oxy)pyridin-2-yl)-2,5-difluorobenzyl)-1-(4,4-dimethyltetrahydrofuran-3-yl)-5-fluoro-1H-benzo[d]imidazole-6-carboxylic acid was prepared in a manner as described in Procedure 35, starting with Intermediates I-3 and I-1161. 1H NMR (400 MHz, DMSO-d6) δ 8.38 (d, J=6.4 Hz, 1H), 7.98-7.85 (m, 2H), 7.83-7.69 (m, 3H), 7.54 (d, J=7.3 Hz, 1H), 7.46 (dd, J=10.8, 7.4 Hz, 2H), 7.00 (d, J=8.3 Hz, 1H), 5.61 (s, 2H), 5.00 (d, J=6.5 Hz, 1H), 4.52 (d, J=17.0 Hz, 2H), 4.47-4.31 (m, 2H), 3.82-3.69 (m, 2H), 1.33 (s, 3H), 0.61 (s, 3H). ES/MS m/z: 631.0 (M+H$^+$).

Example 420: (S)-2-(4-(6-((6-(difluoromethyl)pyridin-3-yl)methoxy)pyridin-2-yl)-2,5-difluorobenzyl)-1-(4,4-dimethyltetrahydrofuran-3-yl)-1H-benzo[d]imidazole-6-carboxylic acid (S)-2-(4-(6-((6-(difluoromethyl)pyridin-3-yl)methoxy)pyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 27, starting with Intermediate I-1219. 1H NMR (400 MHz, DMSO-d6) δ 8.83 (d, J=2.0 Hz, 1H), 8.50 (s, 1H), 8.12 (dd, J=8.1, 2.0 Hz, 1H), 7.91 (t, J=7.9 Hz, 1H), 7.88-7.78 (m, 2H), 7.74 (d, J=8.0 Hz, 1H), 7.63 (d, J=8.5 Hz, 1H), 7.55 (d, J=7.3 Hz, 1H), 7.47 (dd, J=10.9, 6.6 Hz, 1H), 7.16-6.78 (m, 2H), 5.61 (s, 2H), 5.03 (d, J=6.7 Hz, 1H), 4.55 (d, J=16.8 Hz, 2H), 4.50-4.32 (m, 2H), 3.95-3.65 (m, 2H), 1.34 (s, 3H), 0.61 (s, 3H). ES/MS m/z: 621.0 (M+H$^+$).

Example 421: (S)-2-(4-(6-((4-cyanobenzyl)oxy)pyridin-2-yl)-2,5-difluorobenzyl)-1-(4,4-dimethyltetrahydrofuran-3-yl)-1H-imidazo[4,5-c]pyridine-6-carboxylic acid (S)-2-(4-(6-((4-cyanobenzyl)oxy)pyridin-2-yl)-2,5-difluorobenzyl)-1-(4,4-dimethyltetrahydrofuran-3-yl)-1H-imidazo[4,5-c]pyridine-6-carboxylic acid was prepared in a manner as described in Procedure 35, starting with Intermediates I-114 and I-1162. 1H NMR (400 MHz, DMSO-d6) δ 9.03 (s, 1H), 8.62 (s, 1H), 7.97-7.83 (m, 3H), 7.75 (dd, J=10.2, 6.5 Hz, 1H), 7.69 (d, J=8.1 Hz, 2H), 7.54 (d, J=7.3 Hz, 1H), 7.50 (dd, J=11.2, 6.3 Hz, 1H), 7.02 (d, J=8.3 Hz, 1H), 5.59 (s, 2H), 5.09 (d, J=6.3 Hz, 1H), 4.62 (d, J=17.3 Hz, 1H), 4.54 (d, J=11.2 Hz, 1H), 4.49-4.37 (m, 2H), 3.80-3.71 (m, 2H), 1.37 (s, 3H), 0.63 (s, 3H). ES/MS m/z: 596.0 (M+H$^+$).

Example 422: (S)-2-(4-(6-((4-cyano-2-fluorobenzyl)oxy)pyridin-2-yl)-2,5-difluorobenzyl)-1-(4,4-dimethyltetrahydrofuran-3-yl)-1H-imidazo[4,5-c]pyridine-6-carboxylic acid (S)-2-(4-(6-((4-cyano-2-fluorobenzyl)oxy)pyridin-2-yl)-2,5-difluorobenzyl)-1-(4,4-dimethyltetrahydrofuran-3-yl)-

1H-imidazo[4,5-c]pyridine-6-carboxylic acid was prepared in a manner as described in Procedure 35, starting with Intermediates I-3 and I-1162. 1H NMR (400 MHz, DMSO-d6) δ 9.02 (s, 1H), 8.61 (s, 1H), 7.98-7.88 (m, 2H), 7.84-7.71 (m, 3H), 7.55 (d, J=7.4 Hz, 1H), 7.50 (dd, J=11.0, 6.4 Hz, 1H), 7.01 (d, J=8.2 Hz, 1H), 5.61 (s, 2H), 5.09 (d, J=6.1 Hz, 1H), 4.62 (d, J=17.3 Hz, 1H), 4.54 (d, J=11.2 Hz, 1H), 4.50-4.36 (m, 2H), 3.80-3.74 (m, 2H), 1.37 (s, 3H), 0.63 (s, 3H). ES/MS m/z: 614.0 (M+H$^+$).

Example 423: (S)-2-(4-(6-((4-chloro-2-fluorobenzyl)oxy)pyridin-2-yl)-2,5-difluorobenzyl)-1-(4,4-dimethyltetrahydrofuran-3-yl)-1H-imidazo[4,5-c]pyridine-6-carboxylic acid (S)-2-(4-(6-((4-chloro-2-fluorobenzyl)oxy)pyridin-2-yl)-2,5-difluorobenzyl)-1-(4,4-dimethyltetrahydrofuran-3-yl)-1H-imidazo[4,5-c]pyridine-6-carboxylic acid was prepared in a manner as described in Procedure 35, starting with Intermediates I-102 and I-1162. 1H NMR (400 MHz, DMSO-d6) δ 9.01 (s, 1H), 8.61 (s, 1H), 7.96-7.80 (m, 2H), 7.61 (t, J=8.2 Hz, 1H), 7.58-7.45 (m, 3H), 7.34 (dd, J=8.2, 1.9 Hz, 1H), 6.97 (dd, J=8.2 Hz, 1H), 5.52 (s, 2H), 5.09 (d, J=6.2 Hz, 1H), 4.62 (d, J=17.1 Hz, 1H), 4.54 (d, J=11.2 Hz, 1H), 4.50-4.38 (m, 2H), 3.79-3.73 (m, 2H), 1.37 (s, 3H), 0.63 (s, 3H). ES/MS m/z: 623.0 (M+H$^+$).

Example 424: (S)-2-(2,5-difluoro-4-(6-((6-(2,2,2-trifluoroethoxy)pyridin-3-yl)methoxy)pyridin-2-yl)benzyl)-1-(4,4-dimethyltetrahydrofuran-3-yl)-1H-benzo[d]imidazole-6-carboxylic acid (S)-2-(2,5-difluoro-4-(6-((6-(2,2,2-trifluoroethoxy)pyridin-3-yl)methoxy)pyridin-2-yl)benzyl)-1-(4,4-dimethyltetrahydrofuran-3-yl)-1H-benzo[d]imidazole-6-carboxylic acid was prepared in a manner as described in Procedure 27, starting with Intermediate I-1219. 1H NMR (400 MHz, DMSO-d6) δ 8.49 (s, 1H), 8.36 (d, J=2.2 Hz, 1H), 7.95 (dd, J=8.5, 2.4 Hz, 1H), 7.88 (td, J=8.9, 7.9, 4.5 Hz, 2H), 7.84-7.77 (m, 1H), 7.62 (d, J=8.5 Hz, 1H), 7.53 (d, J=7.3 Hz, 1H), 7.47 (dd, J=10.8, 6.8 Hz, 1H), 7.02 (d, J=8.5 Hz, 1H), 6.93 (d, J=8.2 Hz, 1H), 5.47 (s, 2H), 5.00 (q, J=8.8 Hz, 3H), 4.60-4.48 (m, 2H), 4.48-4.32 (m, 2H), 3.83-3.71 (m, 2H), 1.34 (s, 3H), 0.61 (s, 3H). ES/MS m/z: 669.0 (M+H$^+$).

Example 425: (S)-2-(2,5-difluoro-4-(6-((6-(trifluoromethyl)pyridin-3-yl)methoxy)pyridin-2-yl)benzyl)-1-(4,4-dimethyltetrahydrofuran-3-yl)-1H-benzo[d]imidazole-6-carboxylic acid (S)-2-(2,5-difluoro-4-(6-((6-(trifluoromethyl)pyridin-3-yl)methoxy)pyridin-2-yl)benzyl)-1-(4,4-dimethyltetrahydrofuran-3-yl)-1H-benzo[d]imidazole-6-carboxylic acid was prepared in a manner as described in Procedure 27, starting with Intermediate I-1219. 1H NMR (400 MHz, DMSO-d6) δ 8.92 (d, J=2.0 Hz, 1H), 8.49 (s, 1H), 8.20 (d, J=8.1 Hz, 1H), 7.93 (dd, J=17.1, 8.2 Hz, 2H), 7.79 (dd, J=9.3, 7.5 Hz, 2H), 7.62 (d, J=8.5 Hz, 1H), 7.55 (d, J=7.4 Hz, 1H), 7.46 (dd, J=10.7, 6.8 Hz, 1H), 7.02 (d, J=8.3 Hz, 1H), 5.65 (s, 2H), 5.02 (d, J=6.7 Hz, 1H), 4.58-4.49 (m, 2H), 4.49-4.30 (m, 2H), 3.85-3.71 (m, 2H), 1.33 (s, 3H), 0.60 (s, 3H). ES/MS m/z: 639.0 (M+H$^+$).

Example 426: (S)-2-(2,5-difluoro-4-(6-((1-methyl-2-oxo-1,2-dihydropyridin-3-yl)methoxy)pyridin-2-yl)benzyl)-1-(4,4-dimethyltetrahydrofuran-3-yl)-1H-benzo[d]imidazole-6-carboxylic acid (S)-2-(2,5-difluoro-4-(6-((1-methyl-2-oxo-1,2-dihydropyridin-3-yl)methoxy)pyridin-2-yl)benzyl)-1-(4,4-dimethyltetrahydrofuran-3-yl)-1H-benzo[d]imidazole-6-carboxylic acid was prepared in a manner as described in Procedure 35, starting with Intermediates I-1164 and I-82. 1H NMR (400 MHz, DMSO-d6) δ 8.50 (s, 1H), 7.92-7.79 (m, 3H), 7.71 (dd, J=6.8, 2.0 Hz, 1H), 7.65 (d, J=8.4 Hz, 1H), 7.57-7.50 (m, 2H), 7.46 (dd, J=11.3, 6.1 Hz, 1H), 6.95 (d, J=8.3 Hz, 1H), 6.25 (t, J=6.8 Hz, 1H), 5.29 (s, 2H), 5.03 (d, J=6.6 Hz, 1H), 4.61-4.52 (m, 2H), 4.48-4.36 (m, 2H), 3.86-3.68 (m, 2H), 3.48 (s, 3H), 1.34 (s, 3H), 0.61 (d, J=3.4 Hz, 3H). ES/MS m/z: 601.0 (M+H$^+$).

Example 427: (S)-2-(2,5-difluoro-4-(6-((1-methyl-2-oxo-1,2-dihydropyridin-4-yl)methoxy)pyridin-2-yl)benzyl)-1-(4,4-dimethyltetrahydrofuran-3-yl)-1H-benzo[d]imidazole-6-carboxylic acid (S)-2-(2,5-difluoro-4-(6-((1-methyl-2-oxo-1,2-dihydropyridin-4-yl)methoxy)pyridin-2-yl)benzyl)-1-(4,4-dimethyltetrahydrofuran-3-yl)-1H-benzo[d]imidazole-6-carboxylic acid was prepared in a manner as described in Procedure 35, starting with Intermediates I-1165 and I-82. 1H NMR (400 MHz, DMSO-d6) δ 8.50 (s, 1H), 7.91 (t, J=7.9 Hz, 1H), 7.80 (dd, J=9.3, 7.8 Hz, 2H), 7.68 (d, J=7.0 Hz, 1H), 7.63 (d, J=8.5 Hz, 1H), 7.54 (d, J=7.4 Hz, 1H), 7.46 (dd, J=10.1, 7.4 Hz, 1H), 7.02 (d, J=8.3 Hz, 1H), 6.42 (s, 1H), 6.29 (dd, J=7.0, 1.8 Hz, 1H), 5.34 (s, 2H), 5.02 (d, J=6.7 Hz, 1H), 4.58-4.50 (m, 2H), 4.48-4.35 (m, 2H), 3.85-3.66 (m, 2H), 3.40 (s, 3H), 1.34 (s, 3H), 0.61 (s, 3H). ES/MS m/z: 601.0 (M+H$^+$).

Example 428: (S)-2-(4-(6-((4-cyano-2-fluorobenzyl)oxy)-5-fluoropyridin-2-yl)-2,5-difluorobenzyl)-3-(4,4-dimethyltetrahydrofuran-3-yl)-3H-imidazo[4,5-b]pyridine-5-carboxylic acid (S)-2-(4-(6-((4-cyano-2-fluorobenzyl)oxy)-5-fluoropyridin-2-yl)-2,5-difluorobenzyl)-3-(4,4-dimethyltetrahydrofuran-3-yl)-3H-imidazo[4,5-b]pyridine-5-carboxylic acid was prepared in a manner as described in Procedure 35, starting with Intermediates I-109 and I-1167. 1H NMR (400 MHz, DMSO-d6) δ 8.09 (d, J=8.3 Hz, 1H), 7.95 (dd, J=9.3, 7.6 Hz, 2H), 7.88 (dd, J=10.2, 8.2 Hz, 1H), 7.81-7.70 (m, 3H), 7.59-7.53 (m, 1H), 7.47 (dd, J=11.4, 6.1 Hz, 1H), 5.70 (s, 2H), 4.96 (dd, J=8.5, 5.3 Hz, 1H), 4.74 (dd, J=9.6, 5.2 Hz, 1H), 4.65-4.44 (m, 2H), 4.37 (dt, J=8.9, 5.1 Hz, 2H), 3.63 (d, J=7.9 Hz, 1H), 1.24 (s, 3H), 0.62 (s, 3H). ES/MS m/z: 632.0 (M+H$^+$).

Example 429: (S)-2-(2,5-difluoro-4-(6-((3-fluoropyridin-4-yl)methoxy)pyridin-2-yl)benzyl)-1-(4,4-dimethyltetrahydrofuran-3-yl)-1H-benzo[d]imidazole-6-carboxylic acid (S)-2-(2,5-difluoro-4-(6-((3-fluoropyridin-4-yl)methoxy)pyridin-2-yl)benzyl)-1-(4,4-dimethyltetrahydrofuran-3-yl)-1H-benzo[d]imidazole-6-carboxylic acid was prepared in a manner as described in Procedure 35, starting with Intermediates I-1168 and I-82. 1H NMR (400 MHz, DMSO-d6) δ 8.61 (d, J=1.7 Hz, 1H), 8.50 (s, 1H), 8.45 (d, J=4.9 Hz, 1H), 7.92 (t, J=7.9 Hz, 1H), 7.82 (dd, J=8.4, 1.4 Hz, 1H), 7.74 (dd, J=10.5, 6.4 Hz, 1H), 7.64 (d, J=8.5 Hz, 1H), 7.61-7.53 (m, 2H), 7.46 (dd, J=11.4, 6.1 Hz, 1H), 7.03 (d, J=8.2 Hz, 1H), 5.62 (s, 2H), 5.03 (d, J=6.7 Hz, 1H), 4.55 (d, J=16.4 Hz, 2H), 4.51-4.35 (m, 2H), 3.83-3.71 (m, 2H), 1.33 (s, 3H), 0.61 (s, 3H). ES/MS m/z: 589.0 (M+H$^+$).

Example 430: (S)-2-(2,5-difluoro-4-(6-((3-methoxypyridin-4-yl)methoxy)pyridin-2-yl)benzyl)-1-(4,4-dimethyltetrahydrofuran-3-yl)-1H-benzo[d]imidazole-6-carboxylic acid (S)-2-(2,5-difluoro-4-(6-((3-methoxypyridin-4-yl)methoxy)pyridin-2-yl)benzyl)-1-(4,4-dimethyltetrahydrofuran-3-yl)-1H-benzo[d]imidazole-6-carboxylic acid was prepared in a manner as described in Procedure 35, starting with Intermediates I-1169 and I-82. 1H NMR (400 MHz, DMSO-d6) δ 8.61 (s, 1H), 8.49 (s, 1H), 8.44 (d, J=5.3 Hz, 1H), 7.94 (t, J=7.9 Hz, 1H), 7.81 (dd, J=8.5, 1.4 Hz, 1H), 7.75 (d, J=5.4 Hz, 1H), 7.67 (t, J=8.4 Hz, 1H), 7.62 (d, J=8.4 Hz, 1H), 7.56 (d, J=7.4 Hz, 1H), 7.46 (t, J=8.7 Hz, 1H), 7.09 (d, J=8.3 Hz, 1H), 5.63 (s, 2H), 5.02 (d, J=6.6 Hz, 1H), 4.60-4.48 (m, 2H), 4.48-4.31 (m, 2H), 4.05 (s, 3H), 3.87-3.65 (m, 2H), 1.33 (s, 3H), 0.61 (s, 3H). ES/MS m/z: 601.1 (M+H$^+$).

Example 431: (S)-2-(4-(6-((4-cyclopropylbenzyl)oxy)pyridin-2-yl)-2,5-difluorobenzyl)-1-(4,4-dimethyltetrahydrofuran-3-yl)-1H-benzo[d]imidazole-6-carboxylic acid (S)-2-(4-(6-((4-cyclopropylbenzyl)oxy)pyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 35, starting with Intermediates I-1170 and I-82. 1H NMR (400 MHz, DMSO-d6) δ 8.50 (s, 1H), 7.94-7.75 (m, 3H), 7.64 (d, J=8.4 Hz, 1H), 7.58-7.41 (m, 2H), 7.36 (d, J=7.8 Hz, 2H), 7.09 (d, J=7.8 Hz, 2H), 6.92 (d, J=8.2 Hz, 1H), 5.41 (s, 2H), 5.03 (d, J=6.7 Hz, 1H), 4.55 (d, J=16.6 Hz, 2H), 4.50-4.33 (m, 2H), 3.86-3.67 (m, 2H), 1.91 (tt, J=8.7, 5.0 Hz, 1H), 1.34 (s, 3H), 0.99-0.85 (m, 2H), 0.66 (dt, J=6.5, 4.6 Hz, 2H), 0.61 (s, 3H). ES/MS m/z: 610.0 (M+H$^+$).

Example 432: (S)-2-(4-(5-chloro-6-((4-cyanobenzyl)oxy)pyridin-2-yl)-2,5-difluorobenzyl)-1-(4,4-dimethyltetrahydrofuran-3-yl)-1H-benzo[d]imidazole-6-carboxylic acid (S)-2-(4-(5-chloro-6-((4-cyanobenzyl)oxy)pyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 35, starting with Intermediates I-1158 and I-82. 1H NMR (400 MHz, DMSO-d6) δ 8.49 (s, 1H), 8.09 (d, J=8.0 Hz, 1H), 7.90 (d, J=8.2 Hz, 2H), 7.82-7.74 (m, 2H), 7.70 (d, J=8.0 Hz, 2H), 7.62 (d, J=8.4 Hz, 1H), 7.60-7.52 (m, 1H), 7.48 (dd, J=11.4, 6.1 Hz, 1H), 5.69 (s, 2H), 5.02 (d, J=6.6 Hz, 1H), 4.59-4.51 (m, 2H), 4.51-4.34 (m, 2H), 3.82-3.67 (m, 2H), 1.34 (s, 3H), 0.61 (s, 3H). ES/MS m/z: 629.0 (M+H$^+$).

Example 433: (S)-2-(4-(5-chloro-6-((4-chlorobenzyl)oxy)pyridin-2-yl)-2,5-difluorobenzyl)-1-(4,4-dimethyltetrahydrofuran-3-yl)-1H-benzo[d]imidazole-6-carboxylic acid (S)-2-(4-(5-chloro-6-((4-chlorobenzyl)oxy)pyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 35, starting with Intermediates I-1172 and I-82. 1H NMR (400 MHz, DMSO-d6) δ 8.49 (s, 1H), 8.07 (d, J=8.0 Hz, 1H), 7.88-7.78 (m, 2H), 7.62 (d, J=8.5 Hz, 1H), 7.58-7.51 (m, 3H), 7.51-7.41 (m, 3H), 5.58 (s, 2H), 5.02 (d, J=6.6 Hz, 1H), 4.57-4.50 (m, 2H), 4.49-4.33 (m, 2H), 3.83-3.68 (m, 2H), 1.34 (s, 3H), 0.61 (s, 3H). ES/MS m/z: 638.0 (M+H$^+$).

Example 434: (S)-2-(4-(5-chloro-6-((4-cyano-2-fluorobenzyl)oxy)pyridin-2-yl)-2,5-difluorobenzyl)-1-(4,4-dimethyltetrahydrofuran-3-yl)-1H-benzo[d]imidazole-6-carboxylic acid (S)-2-(4-(5-chloro-6-((4-cyano-2-fluorobenzyl)oxy)pyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 35, starting with Intermediates I-1158 and I-82. 1H NMR (400 MHz, DMSO-d6) δ 8.49 (s, 1H), 8.10 (d, J=8.0 Hz, 1H), 7.95 (d, J=10.0 Hz, 1H), 7.83-7.74 (m, 4H), 7.62 (d, J=8.5 Hz, 1H), 7.58 (dd, J=8.1, 1.4 Hz, 1H), 7.48 (dd, J=11.4, 6.1 Hz, 1H), 5.71 (s, 2H), 5.02 (d, J=6.6 Hz, 1H), 4.59-4.49 (m, 2H), 4.48-4.34 (m, 2H), 3.83-3.68 (m, 2H), 1.34 (s, 3H), 0.61 (s, 3H). ES/MS m/z: 647.0 (M+H$^+$).

Example 435: 2-(4-(6-((4-cyano-2-fluorobenzyl)oxy)pyridin-2-yl)-2,5-difluorobenzyl)-1-((3S,4S)-4-(hydroxymethyl)tetrahydrofuran-3-yl)-1H-benzo[d]imidazole-6-carboxylic acid

Example 436: 2-(4-(6-((4-cyano-2-fluorobenzyl)oxy)pyridin-2-yl)-2,5-difluorobenzyl)-1-((3R,4R)-4-(hydroxymethyl)tetrahydrofuran-3-yl)-1H-benzo[d]imidazole-6-carboxylic acid Example 435 and Example 436 were prepared via preparative chiral SFC (Daicel Chiralpak AD-H column, MeOH—CO$_2$ eluent) of Example 216.

2-(4-(6-((4-cyano-2-fluorobenzyl)oxy)pyridin-2-yl)-2,5-difluorobenzyl)-1-((3S,4S)-4-(hydroxymethyl)tetrahydrofuran-3-yl)-1H-benzo[d]imidazole-6-carboxylic acid (Example 435) was isolated as the later-eluting of two stereoisomers. 1H NMR (400 MHz, DMSO-d6) δ 8.55 (s, 1H), 7.98-7.85 (m, 2H), 7.85-7.70 (m, 4H), 7.61 (d, J=8.4 Hz, 1H), 7.54 (d, J=7.3 Hz, 1H), 7.37 (dd, J=11.5, 6.0 Hz, 1H), 7.00 (d, J=8.3 Hz, 1H), 5.61 (s, 2H), 5.53 (d, J=7.6 Hz, 1H), 4.55 (s, 2H), 4.50 (d, J=10.8 Hz, 1H), 4.21 (dd, J=10.9, 6.5 Hz, 1H), 4.06 (t, J=8.7 Hz, 1H), 3.80 (t, J=8.3 Hz, 1H), 3.18-3.09 (m, 1H), 3.00 (q, J=7.8 Hz, 1H), 2.75 (t, J=9.5 Hz, 1H). ES/MS m/z: 615.0 (M+H$^+$).

2-(4-(6-((4-cyano-2-fluorobenzyl)oxy)pyridin-2-yl)-2,5-difluorobenzyl)-1-((3R,4R)-4-(hydroxymethyl)tetrahydrofuran-3-yl)-1H-benzo[d]imidazole-6-carboxylic acid (Example 436) was isolated as the earlier-eluting of two stereoisomers. 1H NMR (400 MHz, DMSO-d6) δ 8.55 (s, 1H), 7.98-7.85 (m, 2H), 7.85-7.70 (m, 4H), 7.61 (d, J=8.4 Hz, 1H), 7.54 (d, J=7.3 Hz, 1H), 7.37 (dd, J=11.5, 6.0 Hz, 1H), 7.00 (d, J=8.3 Hz, 1H), 5.61 (s, 2H), 5.53 (d, J=7.6 Hz, 1H), 4.55 (s, 2H), 4.50 (d, J=10.8 Hz, 1H), 4.21 (dd, J=10.9, 6.5 Hz, 1H), 4.06 (t, J=8.7 Hz, 1H), 3.80 (t, J=8.3 Hz, 1H), 3.18-3.09 (m, 1H), 3.00 (q, J=7.8 Hz, 1H), 2.75 (t, J=9.5 Hz, 1H). ES/MS m/z: 615.0 (M+H$^+$).

Example 437: (S)-2-(4-(6-((4-chloro-2-fluorobenzyl)oxy)pyridin-2-yl)-2,5-difluorobenzyl)-3-(4,4-dimethyltetrahydrofuran-3-yl)-3H-imidazo[4,5-b]pyridine-5-carboxylic acid (S)-2-(4-(6-((4-chloro-2-fluorobenzyl)oxy)pyridin-2-yl)-2,5-difluorobenzyl)-3-(4,4-dimethyltetrahydrofuran-3-yl)-3H-imidazo[4,5-b]pyridine-5-carboxylic acid was prepared in a manner as described in Procedure 35, starting with Intermediates 102 and I-1167. 1H NMR (400 MHz, DMSO-d6) δ 8.10 (d, J=8.3 Hz, 1H), 7.96 (d, J=8.3 Hz, 1H), 7.92-7.80 (m, 2H), 7.60 (t, J=8.2 Hz, 1H), 7.57-7.44 (m, 3H), 7.33 (dd, J=8.2, 2.0 Hz, 1H), 6.96 (d, J=8.3 Hz, 1H), 5.51 (s, 2H), 4.97 (dd, J=8.4, 5.3 Hz, 1H), 4.74 (dd, J=9.6, 5.2 Hz, 1H), 4.64-4.47 (m, 2H), 4.37 (dt, J=8.9, 5.1 Hz, 2H), 3.63 (d, J=7.9 Hz, 1H), 1.24 (s, 3H), 0.62 (s, 3H). ES/MS m/z: 623.0 (M+H$^+$).

Example 438: (S)-2-(4-(6-((4-chlorobenzyl)oxy)pyridin-2-yl)-2,5-difluorobenzyl)-3-(4,4-dimethyltetrahydrofuran-3-yl)-3H-imidazo[4,5-b]pyridine-5-carboxylic acid (S)-2-(4-(6-((4-chlorobenzyl)oxy)pyridin-2-yl)-2,5-difluorobenzyl)-3-(4,4-dimethyltetrahydrofuran-3-yl)-3H-imidazo[4,5-b]pyridine-5-carboxylic acid was prepared in a manner as described in Procedure 35, starting with Intermediates I-1248 and I-1167. 1H NMR (400 MHz, DMSO-d6) δ 8.09 (d, J=8.3 Hz, 1H), 7.96 (d, J=8.3 Hz, 1H), 7.88 (t, J=7.9 Hz, 1H), 7.82 (dd, J=10.3, 6.6 Hz, 1H), 7.58-7.40 (m, 6H), 6.96 (d, J=8.3 Hz, 1H), 5.47 (s, 2H), 4.97 (dd, J=8.4, 5.3 Hz, 1H), 4.75 (dd, J=9.6, 5.2 Hz, 1H), 4.65-4.45 (m, 2H), 4.37 (dt, J=8.9, 5.1 Hz, 2H), 3.63 (d, J=7.9 Hz, 1H), 1.24 (s, 3H), 0.63 (s, 3H). ES/MS m/z: 605.0 (M+H$^+$).

Example 439: (S)-2-(4-(6-((4-cyano-2-fluorobenzyl)oxy)pyridin-2-yl)-2,5-difluorobenzyl)-3-(4,4-dimethyltetrahydrofuran-3-yl)-3H-imidazo[4,5-b]pyridine-5-carboxylic acid (S)-2-(4-(6-((4-cyano-2-fluorobenzyl)oxy)pyridin-2-yl)-2,5-difluorobenzyl)-3-(4,4-dimethyltetrahydrofuran-3-yl)-3H-imidazo[4,5-b]pyridine-5-carboxylic acid was prepared in a manner as described in Procedure 35, starting with Intermediates I-3 and I-1167. 1H NMR (400 MHz, DMSO-d6) δ 8.09 (d, J=8.3 Hz, 1H), 8.00-7.85 (m, 3H), 7.84-7.68 (m, 3H), 7.58-7.52 (m, 1H), 7.46 (dd, J=11.3, 6.2 Hz, 1H), 7.00 (d, J=8.3 Hz, 1H), 5.61 (s, 2H), 4.96 (dd, J=8.4, 5.3 Hz, 1H), 4.74 (dd, J=9.6, 5.1 Hz, 1H), 4.64-4.46 (m, 2H), 4.37 (dt, J=8.9, 5.1 Hz, 2H), 3.63 (d, J=7.9 Hz, 1H), 1.23 (s, 3H), 0.62 (s, 3H). ES/MS m/z: 614.0 (M+H$^+$).

Example 440: (S)-2-(4-(6-((4-cyanobenzyl)oxy)pyridin-2-yl)-2,5-difluorobenzyl)-3-(4,4-dimethyltetrahydrofuran-3-yl)-3H-imidazo[4,5-b]pyridine-5-carboxylic acid (S)-2-(4-(6-((4-cyanobenzyl)oxy)pyridin-2-yl)-2,5-difluorobenzyl)-3-(4,4-dimethyltetrahydrofuran-3-yl)-3H-imidazo[4,5-b]pyridine-5-carboxylic acid was prepared in a manner as described in Procedure 35, starting with Intermediates I-114 and I-1167. 1H NMR (400 MHz, DMSO-d6) δ 8.09 (d, J=8.3 Hz, 1H), 7.96 (d, J=8.3 Hz, 1H), 7.93-7.83 (m, 3H), 7.74 (dd, J=10.2, 6.6 Hz, 1H), 7.68 (d, J=8.0 Hz, 2H), 7.58-7.51 (m, 1H), 7.46 (dd, J=11.2, 6.3 Hz, 1H), 7.01 (d, J=8.3 Hz, 1H), 5.58 (s, 2H), 4.96 (dd, J=8.5, 5.2 Hz, 1H), 4.74 (dd, J=9.6, 5.1 Hz, 1H), 4.64-4.44 (m, 2H), 4.37 (dt, J=9.0, 5.1 Hz, 2H), 3.63 (d, J=7.9 Hz, 1H), 1.24 (s, 3H), 0.62 (s, 3H). ES/MS m/z: 596.0 (M+H$^+$).

Example 441: (S)-4-chloro-2-(4-(6-((4-chlorobenzyl)oxy)-5-fluoropyridin-2-yl)-2,5-difluorobenzyl)-1-(4,4-dimethyltetrahydrofuran-3-yl)-1H-benzo[d]imidazole-6-carboxylic acid (S)-4-chloro-2-(4-(6-((4-chlorobenzyl)oxy)-5-fluoropyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 35, starting with Intermediates I-1246 and I-1037. 1H NMR (400 MHz, DMSO-d6) δ 8.47 (s, 1H), 7.96-7.74 (m, 3H), 7.55 (d, J=8.3 Hz, 3H), 7.51-7.39 (m, 3H), 5.57 (s, 2H), 5.03 (d, J=6.5 Hz, 1H), 4.54 (t, J=13.8 Hz, 2H), 4.47-4.36 (m, 2H), 3.84-3.68 (m, 2H), 1.32 (s, 3H), 0.60 (s, 3H). ES/MS m/z: 656.0 (M+H$^+$).

Example 442: (S)-2-(2,5-difluoro-4-(6-((2-fluoro-4-(1-methyl-1H-1,2,3-triazol-4-yl)benzyl)oxy)pyridin-2-yl)benzyl)-1-(4,4-dimethyltetrahydrofuran-3-yl)-1H-benzo[d]imidazole-6-carboxylic acid Procedure 41

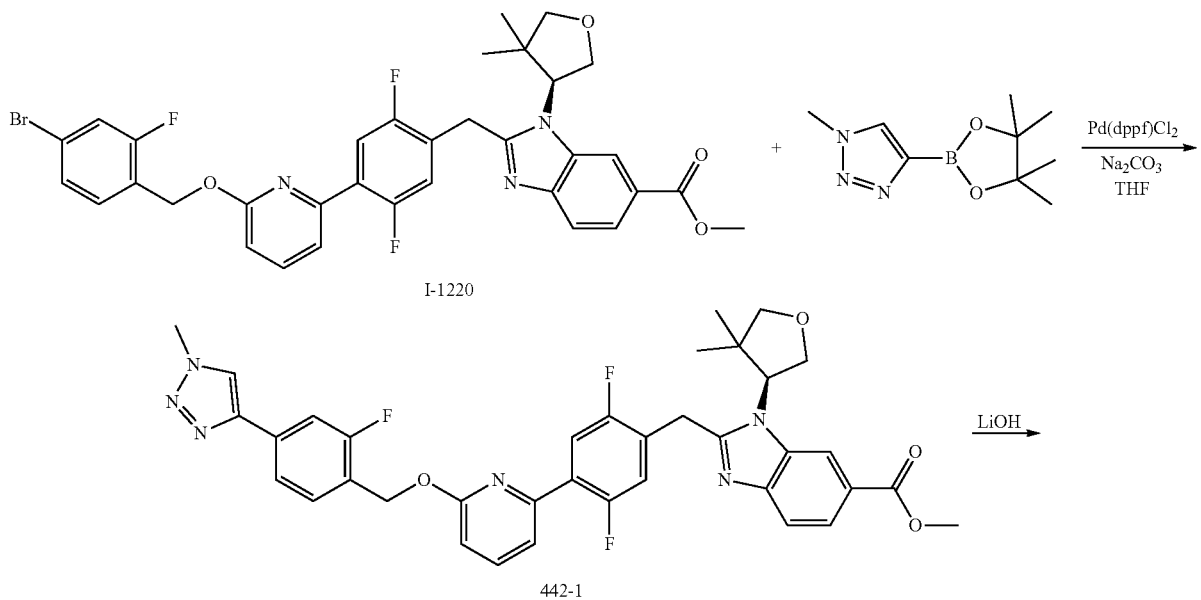

-continued

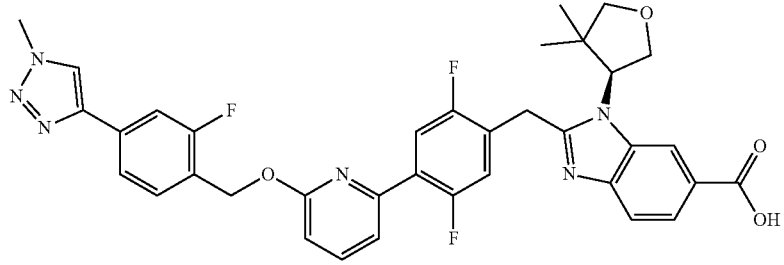

Example 442

Methyl (S)-2-(2,5-difluoro-4-(6-((2-fluoro-4-(1-methyl-1H-1,2,3-triazol-4-yl)benzyl)oxy)pyridin-2-yl)benzyl)-1-(4,4-dimethyltetrahydrofuran-3-yl)-1H-benzo[d]imidazole-6-carboxylate (442-1): A mixture of methyl (S)-2-(4-(6-((4-bromo-2-fluorobenzyl)oxy)pyridin-2-yl)-2,5-difluorobenzyl)-1-(4,4-dimethyltetrahydrofuran-3-yl)-1H-benzo[d]imidazole-6-carboxylate (I-1220, 50 mg, 1.0 equivalent), 1-methyl-4-(4,4,5,5-tetramethyl-1,3,2-dioxaborolan-2-yl)triazole (31 mg, 2.0 equivalent), sodium carbonate (2 M in water, 74 µL, 2.0 equivalent), Pd(dppf)Cl$_2$ (5.2 mg, 0.10 equivalent), and 1,4-dioxane (1 mL) was degassed with argon, then stirred at 120 C for 1 hr. The mixture was filtered and then concentrated in vacuo. For this particular example the crude was carried forward without further purification. However, other examples could be purified by preparative HPLC (MeCN in water with 0.1% TFA), or by silica gel flash column chromatography (EtOAc/hexane) to yield the title compound.

(S)-2-(2,5-difluoro-4-(6-((2-fluoro-4-(1-methyl-1H-1,2,3-triazol-4-yl)benzyl)oxy)pyridin-2-yl)benzyl)-1-(4,4-dimethyltetrahydrofuran-3-yl)-1H-benzo[d]imidazole-6-carboxylic acid (Example 442): Crude methyl (S)-2-(2,5-difluoro-4-(6-((2-fluoro-4-(1-methyl-1H-1,2,3-triazol-4-yl)benzyl)oxy)pyridin-2-yl)benzyl)-1-(4,4-dimethyltetrahydrofuran-3-yl)-1H-benzo[d]imidazole-6-carboxylate (442-1) (30 mg, 1.0 equivalent) was mixed with 1 mL of MeCN and 0.3 mL of 2 N aqueous lithium hydroxide. The mixture was heated to 80° C. for 30 minutes. Then 0.3 mL of acetic acid was added to the mixture. The mixture was filtered and purified by reverse phase preparative HPLC (eluent: water/MeCN 0.1% TFA) to give title compound. 1H NMR (400 MHz, Methanol-d4) δ 8.89 (s, 1H), 8.17 (dd, J=8.6, 1.4 Hz, 1H), 7.96-7.81 (m, 3H), 7.81-7.67 (m, 2H), 7.59 (dd, J=7.3, 1.6 Hz, 1H), 7.49-7.35 (m, 3H), 7.06-6.75 (m, 1H), 5.64 (s, 2H), 5.14 (d, J=6.5 Hz, 1H), 4.80-4.61 (m, 3H), 4.52 (dd, J=11.6, 6.7 Hz, 1H), 4.13 (s, 3H), 4.00 (d, J=8.9 Hz, 1H), 3.84 (d, J=8.9 Hz, 1H), 1.41 (s, 3H), 0.76 (s, 3H).

Example 443: (S)-2-(4-(6-((4-(1-(difluoromethyl)-1H-pyrazol-4-yl)-2-fluorobenzyl)oxy)pyridin-2-yl)-2,5-difluorobenzyl)-1-(4,4-dimethyltetrahydrofuran-3-yl)-1H-benzo[d]imidazole-6-carboxylic acid (S)-2-(4-(6-((4-(1-(difluoromethyl)-1H-pyrazol-4-yl)-2-fluorobenzyl)oxy)pyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 41, starting with Intermediate I-1220 and 1-(difluoromethyl)-4-(4,4,5,5-tetramethyl-1,3,2-dioxaborolan-2-yl)pyrazole. 1H NMR (400 MHz, Methanol-d4) δ 8.93 (s, 1H), 8.49 (d, J=0.7 Hz, 1H), 8.21 (dd, J=8.7, 1.4 Hz, 1H), 8.11 (s, 1H), 7.95 (dd, J=10.9, 6.3 Hz, 1H), 7.89-7.72 (m, 2H), 7.71-7.31 (m, 6H), 6.93 (dd, J=8.3, 0.7 Hz, 1H), 5.57 (s, 2H), 5.17 (d, J=6.4 Hz, 1H), 4.81-4.57 (m, 3H), 4.53 (dd, J=11.7, 6.7 Hz, 1H), 4.00 (d, J=8.9 Hz, 1H), 3.84 (d, J=8.9 Hz, 1H), 1.41 (s, 3H), 0.77 (s, 3H). ES/MS m/z: 704.1 (M+H$^+$).

Example 444: (S)-2-(2,5-difluoro-4-(6-((2-fluoro-4-(2-methylthiazol-5-yl)benzyl)oxy)pyridin-2-yl)benzyl)-1-(4,4-dimethyltetrahydrofuran-3-yl)-1H-benzo[d]imidazole-6-carboxylic acid (S)-2-(2,5-difluoro-4-(6-((2-fluoro-4-(2-methylthiazol-5-yl)benzyl)oxy)pyridin-2-yl)benzyl)-1-(4,4-dimethyltetrahydrofuran-3-yl)-1H-benzo[d]imidazole-6-carboxylic acid was prepared in a manner as described in Procedure 41, starting with Intermediates I-1220 and 2-methyl-5-(4,4,5,5-tetramethyl-1,3,2-dioxaborolan-2-yl)thiazole. 1H NMR (400 MHz, Methanol-d4) δ 8.93 (s, 1H), 8.21 (dd, J=8.6, 1.4 Hz, 1H), 8.01-7.90 (m, 2H), 7.90-7.75 (m, 2H), 7.59 (ddd, J=8.2, 5.0, 3.4 Hz, 2H), 7.51-7.32 (m, 3H), 7.02-6.87 (m, 1H), 5.58 (s, 2H), 5.17 (d, J=6.5 Hz, 1H), 4.83-4.61 (m, 3H), 4.52 (dd, J=11.7, 6.7 Hz, 1H), 4.00 (d, J=9.0 Hz, 1H), 3.84 (d, J=8.9 Hz, 1H), 2.74 (s, 3H), 1.41 (s, 3H), 0.77 (s, 3H). ES/MS m/z: 685.1 (M+H$^+$).

Example 445: (S)-2-(2,5-difluoro-4-(6-((2-fluoro-4-(2-methyloxazol-5-yl)benzyl)oxy)pyridin-2-yl)benzyl)-1-(4,4-dimethyltetrahydrofuran-3-yl)-1H-benzo[d]imidazole-6-carboxylic acid (S)-2-(2,5-difluoro-4-(6-((2-fluoro-4-(2-methyloxazol-5-yl)benzyl)oxy)pyridin-2-yl)benzyl)-1-(4,4-dimethyltetrahydrofuran-3-yl)-1H-benzo[d]imidazole-6-carboxylic acid was prepared in a manner as described in Procedure 41, starting with Intermediates I-1220 and 2-methyl-5-(4,4,5,5-tetramethyl-1,3,2-dioxaborolan-2-yl)oxazole. 1H NMR (400 MHz, Methanol-d4) δ 8.93 (s, 1H), 8.21 (dd, J=8.6, 1.4 Hz, 1H), 7.94 (dd, J=10.9, 6.3 Hz, 1H), 7.90-7.76 (m, 2H), 7.67-7.53 (m, 2H), 7.54-7.37 (m, 4H), 6.93 (d, J=8.2 Hz, 1H), 5.57 (s, 2H), 5.17 (d, J=6.4 Hz, 1H), 4.83-4.61 (m, 3H), 4.53 (dd, J=11.7, 6.7 Hz, 1H), 4.00 (d, J=8.9 Hz, 1H), 3.84 (d, J=8.9 Hz, 1H), 2.53 (s, 3H), 1.41 (s, 3H), 0.77 (s, 3H). ES/MS m/z: 669.2 (M+H$^+$).

Example 446: (S)-2-(4-(6-((2-cyanobenzyl)oxy)pyridin-2-yl)-2,5-difluorobenzyl)-1-(4,4-dimethyltetrahydrofuran-3-yl)-1H-benzo[d]imidazole-6-carboxylic acid (S)-2-(4-(6-((2-cyanobenzyl)oxy)pyridin-2-yl)-2,5-difluorobenzyl)-1-(4,4-dimethyltetrahydrofuran-3-yl)-1H- benzo[d]imidazole-6-carboxylic acid was prepared in a manner as described in Procedure 27, starting with Intermediate I-1219 and 2-(chloromethyl)benzonitrile. 1H NMR (400 MHz, Methanol-d4) δ 8.91 (s, 1H), 8.19 (dd, J=8.6, 1.4 Hz, 1H), 7.94-7.80 (m, 2H), 7.79 (d, J=8.1 Hz, 2H), 7.75-7.66 (m, 2H), 7.58 (dd, J=7.5, 1.6 Hz, 1H), 7.51 (qd, J=7.6, 1.6 Hz, 1H), 7.40 (dd, J=11.2, 6.0 Hz, 1H), 6.96 (d, J=8.3 Hz, 1H), 5.68 (s, 2H), 5.15 (d, J=6.5 Hz, 1H), 4.79-4.60 (m, 3H), 4.53 (dd, J=11.7, 6.7 Hz, 1H), 4.00 (d, J=8.9 Hz, 1H), 3.84 (d, J=8.9 Hz, 1H), 1.41 (s, 3H), 0.76 (s, 3H). ES/MS m/z: 595.3 (M+H$^+$).

Example 447: (S)-2-(4-(6-((4-chloro-2-fluorobenzyl)oxy)-4-(difluoromethyl)pyridin-2-yl)-2,5-difluorobenzyl)-1-(4,4-dimethyltetrahydrofuran-3-yl)-1H-benzo[d]imidazole-6-carboxylic acid (S)-2-(4-(6-((4-chloro-2-fluorobenzyl)oxy)-4-(difluoromethyl)pyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 35, starting with Intermediates I-1222 and I-82. 1H NMR (400 MHz, Methanol-d4) δ 8.88 (s, 1H), 8.16 (dd, J=8.6, 1.4 Hz, 1H), 7.96 (dd, J=10.7, 6.3 Hz, 1H), 7.77 (d, J=8.6 Hz, 1H), 7.70 (s, 1H), 7.56 (t, J=8.0 Hz, 1H), 7.43 (dd, J=11.3, 6.0 Hz, 1H), 7.31-7.19 (m, 2H), 7.07 (s, 1H), 6.88 (t, J=55.4 Hz, 1H), 5.58 (s, 2H), 5.13 (d, J=6.6 Hz, 1H), 4.79-4.59 (m, 3H), 4.53 (dd, J=11.6, 6.7 Hz, 1H), 4.00 (d, J=8.9 Hz, 1H), 3.84 (d, J=8.9 Hz, 1H), 1.42 (s, 3H), 0.76 (s, 3H). ES/MS m/z: 672.2 (M+H$^+$).

Example 448: (S)-2-(4-(6-((4-(1H-1,2,4-triazol-1-yl)benzyl)oxy)pyridin-2-yl)-2,5-difluorobenzyl)-1-(4,4-dimethyltetrahydrofuran-3-yl)-1H-benzo[d]imidazole-6-carboxylic acid (S)-2-(4-(6-((4-(1H-1,2,4-triazol-1-yl)benzyl)oxy)pyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 27, starting with Intermediates I-1219 and 1-[4-(bromomethyl)phenyl]-1,2,4-triazole. 1H NMR (400 MHz, Methanol-d4) δ 9.10 (s, 1H), 8.90 (s, 1H), 8.23-8.08 (m, 2H), 7.91 (dd, J=10.9, 6.3 Hz, 1H), 7.88-7.81 (m, 3H), 7.78 (d, J=8.6 Hz, 1H), 7.68 (d, J=8.5 Hz, 2H), 7.58 (dd, J=7.5, 1.6 Hz, 1H), 7.40 (dd, J=11.2, 6.0 Hz, 1H), 6.95 (d, J=8.3 Hz, 1H), 5.58 (s, 2H), 5.14 (d, J=6.6 Hz, 1H), 4.79-4.57 (m, 3H), 4.52 (dd, J=11.6, 6.7 Hz, 1H), 4.00 (d, J=8.9 Hz, 1H), 3.84 (d, J=8.9 Hz, 1H), 1.40 (s, 3H), 0.75 (s, 3H). ES/MS m/z: 637.0 (M+H$^+$).

Example 449: (S)-2-(4-(6-((4-chloro-2-cyanobenzyl)oxy)pyridin-2-yl)-2,5-difluorobenzyl)-1-(4,4-dimethyltetrahydrofuran-3-yl)-1H-benzo[d]imidazole-6-carboxylic acid (S)-2-(4-(6-((4-chloro-2-cyanobenzyl)oxy)pyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 27, starting with Intermediates I-1219 and 2-(bromomethyl)-5-chloro-benzonitrile. 1H NMR (400 MHz, Methanol-d4) δ 8.89 (s, 1H), 8.17 (dd, J=8.6, 1.5 Hz, 1H), 7.93-7.81 (m, 3H), 7.78 (d, J=8.6 Hz, 1H), 7.71 (d, J=1.6 Hz, 2H), 7.59 (d, J=7.4, 1.6 Hz, 1H), 7.38 (dd, J=11.0, 6.0 Hz, 1H), 6.97 (d, J=8.2 Hz, 1H), 5.66 (s, 2H), 5.13 (d, J=6.6 Hz, 1H), 4.81-4.60 (m, 3H), 4.52 (dd, J=11.6, 6.7 Hz, 1H), 4.00 (d, J=8.9 Hz, 1H), 3.84 (d, J=8.8 Hz, 1H), 1.41 (s, 3H), 0.76 (s, 3H). ES/MS m/z: 629.2 (M+H$^+$).

Example 450: (S)-2-(4-(6-((4-chloro-2-fluoro-5-methylbenzyl)oxy)pyridin-2-yl)-2,5-difluorobenzyl)-1-(4,4-dimethyltetrahydrofuran-3-yl)-1H-benzo[d]imidazole-6-carboxylic acid (S)-2-(4-(6-((4-chloro-2-fluoro-5-methylbenzyl)oxy)pyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 27, starting with Intermediates I-1219 and 1-(bromomethyl)-4-chloro-2-fluoro-5-methyl-benzene. 1H NMR (400 MHz, Methanol-d4) δ 8.89 (s, 1H), 8.17 (dd, J=8.6, 1.3 Hz, 1H), 7.94 (dd, J=10.9, 6.3 Hz, 1H), 7.90-7.73 (m, 2H), 7.58 (d, J=7.5 Hz, 1H), 7.48 (d, J=7.8 Hz, 1H), 7.39 (dd, J=11.2, 6.0 Hz, 1H), 7.22 (d, J=9.7 Hz, 1H), 6.91 (d, J=8.3 Hz, 1H), 5.50 (s, 2H), 5.14 (d, J=6.3 Hz, 1H), 4.81-4.61 (m, 3H), 4.53 (dd, J=11.6, 6.7 Hz, 1H), 4.00 (d, J=8.9 Hz, 1H), 3.85 (d, J=8.9 Hz, 1H), 2.34 (s, 3H), 1.42 (s, 3H), 0.76 (s, 3H). ES/MS m/z: 636.3 (M+H$^+$).

Example 451: (S)-2-(2,5-difluoro-4-(6-((2,3,4-trifluorobenzyl)oxy)pyridin-2-yl)benzyl)-1-(4,4-dimethyltetrahydrofuran-3-yl)-1H-benzo[d]imidazole-6-carboxylic acid (S)-2-(2,5-difluoro-4-(6-((2,3,4-trifluorobenzyl)oxy)pyridin-2-yl)benzyl)-1-(4,4-dimethyltetrahydrofuran-3-yl)-1H-benzo[d]imidazole-6-carboxylic acid was prepared in a manner as described in Procedure 27, starting with Intermediates I-1219 and 1-(bromomethyl)-2,3,4-trifluoro-benzene. 1H NMR (400 MHz, Methanol-d4) δ 8.92 (s, 1H), 8.20 (dd, J=8.6, 1.4 Hz, 1H), 7.94 (dd, J=10.8, 6.3 Hz, 1H), 7.89-7.74 (m, 2H), 7.59 (dd, J=7.5, 1.6 Hz, 1H), 7.48-7.31 (m, 2H), 7.13 (tdd, J=9.2, 7.1, 2.1 Hz, 1H), 6.91 (d, J=8.2 Hz, 1H), 5.55 (s, 2H), 5.16 (d, J=6.6 Hz, 1H), 4.83-4.60 (m, 3H), 4.53 (dd, J=11.7, 6.7 Hz, 1H), 4.01 (d, J=8.9 Hz, 1H), 3.85 (d, J=8.9 Hz, 1H), 1.42 (s, 3H), 0.77 (s, 3H). ES/MS m/z: 624.3 (M+H$^+$).

Example 452: (S)-2-(4-(6-((3-chloro-4-methylbenzyl)oxy)pyridin-2-yl)-2,5-difluorobenzyl)-1-(4,4-dimethyltetrahydrofuran-3-yl)-1H-benzo[d]imidazole-6-carboxylic acid (S)-2-(4-(6-((3-chloro-4-methylbenzyl)oxy)pyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 27, starting with Intermediates I-1219 and 2-chloro-4-(chloromethyl)-1-methyl-benzene. 1H NMR (400 MHz, Methanol-d4) δ 8.93 (s, 1H), 8.21 (d, J=8.5 Hz, 1H), 7.90 (ddd, J=11.1, 6.5, 4.8 Hz, 1H), 7.87-7.77 (m, 2H), 7.64-7.53 (m, 1H), 7.47-7.39 (m, 2H), 7.38-7.12 (m, 2H), 7.02-6.78 (m, 1H), 5.66-5.39 (m, 2H), 5.17 (d, J=6.5 Hz, 1H), 4.81-4.60 (m, 3H), 4.53 (dd, J=11.7, 6.7 Hz, 1H), 4.01 (d, J=8.9 Hz, 1H), 3.85 (d, J=8.9 Hz, 1H), 2.52-2.31 (m, 3H), 1.42 (s, 3H), 0.77 (s, 3H). ES/MS m/z: 618.1 (M+H$^+$).

Example 453: (S)-2-(4-(6-((4-chloro-2,6-difluorobenzyl)oxy)pyridin-2-yl)-2,5-difluorobenzyl)-1-(4,4-dimethyltetrahydrofuran-3-yl)-1H-benzo[d]imidazole-6-carboxylic acid (S)-2-(4-(6-((4-chloro-2,6-difluorobenzyl)oxy)pyridin-2-yl)-2,5-difluorobenzyl)-1-(4,4-dimethyltetrahydrofuran-3- yl)-1H-benzo[d]imidazole-6-carboxylic acid was prepared in a manner as described in Procedure 27, starting with Intermediates I-1219 and 2-(bromomethyl)-5-chloro-1,3-difluoro-benzene. 1H NMR (400 MHz, Methanol-d4) δ 8.89 (s, 1H), 8.18 (dd, J=8.6, 1.3 Hz, 1H), 8.04 (dd, J=10.9, 6.3 Hz, 1H), 7.91-7.65 (m, 2H), 7.67-7.44 (m, 1H), 7.40 (dd, J=11.2, 6.0 Hz, 1H), 7.17 (d, J=7.3 Hz, 2H), 6.85 (d, J=8.3 Hz, 1H), 5.55 (s, 2H), 5.14 (d, J=6.6 Hz, 1H), 4.81-4.60 (m, 3H), 4.53 (dd, J=11.6, 6.7 Hz, 1H), 4.00 (d, J=8.9 Hz, 1H), 3.85 (d, J=8.9 Hz, 1H), 1.42 (s, 3H), 0.77 (s, 3H). ES/MS m/z: 640.2 (M+H$^+$).

Example 454: (S)-2-(4-(6-((2-chloro-4,5-difluorobenzyl)oxy)pyridin-2-yl)-2,5-difluorobenzyl)-1-(4,4-dimethyltetrahydrofuran-3-yl)-1H-benzo[d]imidazole-6-carboxylic acid (S)-2-(4-(6-((2-chloro-4,5-difluorobenzyl)oxy)pyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 27, starting with Intermediates I-1219 and 1-(bromomethyl)-2-chloro-4,5-difluoro-benzene. 1H NMR (400 MHz, Methanol-d4) δ 8.86 (s, 1H), 8.15 (dd, J=8.6, 1.4 Hz, 1H), 7.91-7.79 (m, 2H), 7.76 (d, J=8.5 Hz, 1H), 7.60 (dd, J=7.5, 1.6 Hz, 1H), 7.56-7.44 (m, 2H), 7.37 (dd, J=11.2, 6.0 Hz, 1H), 6.98 (d, J=8.2 Hz, 1H), 5.55 (s, 2H), 5.11 (d, J=6.5 Hz, 1H), 4.76-4.60 (m, 3H), 4.52 (dd, J=11.6, 6.8 Hz, 1H), 3.99 (d, J=8.9 Hz, 1H), 3.84 (d, J=8.8 Hz, 1H), 1.41 (s, 3H), 0.75 (s, 3H). ES/MS m/z: 640.3 (M+H$^+$).

Example 455: (S)-2-(2,5-difluoro-4-(6-((2,4,5-trifluorobenzyl)oxy)pyridin-2-yl)benzyl)-1-(4,4-dimethyltetrahydrofuran-3-yl)-1H-benzo[d]imidazole-6-carboxylic acid (S)-2-(2,5-difluoro-4-(6-((2,4,5-trifluorobenzyl)oxy)pyridin-2-yl)benzyl)-1-(4,4-dimethyltetrahydrofuran-3-yl)-1H-benzo[d]imidazole-6-carboxylic acid was prepared in a manner as described in Procedure 27, starting with Intermediates I-1219 and 1-(chloromethyl)-2,4,5-trifluoro-benzene. 1H NMR (400 MHz, Methanol-d4) δ 8.88 (s, 1H), 8.16 (dd, J=8.6, 1.4 Hz, 1H), 7.93 (dd, J=10.8, 6.3 Hz, 1H), 7.83 (t, J=7.9 Hz, 1H), 7.77 (d, J=8.6 Hz, 1H), 7.59 (dd, J=7.4, 1.6 Hz, 1H), 7.49 (ddd, J=10.8, 8.9, 6.6 Hz, 1H), 7.38 (dd, J=11.2, 6.0 Hz, 1H), 7.22 (td, J=10.1, 6.6 Hz, 1H), 6.93 (d, J=8.2 Hz, 1H), 5.52 (s, 2H), 5.21-5.06 (m, 1H), 4.78-4.58 (m, 3H), 4.53 (dd, J=11.5, 6.7 Hz, 1H), 4.00 (d, J=8.9 Hz, 1H), 3.84 (d, J=8.9 Hz, 1H), 1.41 (s, 3H), 0.75 (s, 3H). ES/MS m/z: 624.1 (M+H$^+$).

Example 456: (S)-2-(4-(6-((2,5-difluoro-4-methylbenzyl)oxy)pyridin-2-yl)-2,5-difluorobenzyl)-1-(4,4-dimethyltetrahydrofuran-3-yl)-1H-benzo[d]imidazole-6-carboxylic acid (S)-2-(4-(6-((2,5-difluoro-4-methylbenzyl)oxy)pyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 27, starting with Intermediates I-1219 and 1-(bromomethyl)-2,5-difluoro-4-methyl-benzene. 1H NMR (400 MHz, Methanol-d4) δ 8.90 (s, 1H), 8.18 (dd, J=8.6, 1.4 Hz, 1H), 7.93 (dd, J=10.9, 6.3 Hz, 1H), 7.89-7.73 (m, 2H), 7.58 (dd, J=7.5, 1.5 Hz, 1H), 7.39 (dd, J=11.2, 6.0 Hz, 1H), 7.20 (dd, J=9.7, 6.0 Hz, 1H), 7.04 (dd, J=10.1, 6.1 Hz, 1H), 6.92 (d, J=8.3 Hz, 1H), 5.50 (s, 2H), 5.14 (d, J=6.6 Hz, 1H), 4.81-4.60 (m, 3H), 4.53 (dd, J=11.7, 6.7 Hz, 1H), 4.00 (d, J=8.9 Hz, 1H), 3.84 (d, J=8.9 Hz, 1H), 2.26 (d, J=1.9 Hz, 3H), 1.41 (s, 3H), 0.76 (s, 3H). ES/MS m/z: 620.3 (M+H$^+$).

Example 457: (S)-2-(4-(6-((3,4-difluorobenzyl)oxy)pyridin-2-yl)-2,5-difluorobenzyl)-1-(4,4-dimethyltetrahydrofuran-3-yl)-1H-benzo[d]imidazole-6-carboxylic acid (S)-2-(4-(6-((3,4-difluorobenzyl)oxy)pyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 27, starting with Intermediates I-1219 and 4-(chloromethyl)-1,2-difluoro-benzene. 1H NMR (400 MHz, Methanol-d4) δ 8.88 (s, 1H), 8.16 (dd, J=8.6, 1.4 Hz, 1H), 7.91 (dd, J=10.8, 6.3 Hz, 1H), 7.87-7.73 (m, 2H), 7.57 (dd, J=7.4, 1.6 Hz, 1H), 7.46-7.35 (m, 2H), 7.35-7.17 (m, 2H), 6.93 (d, J=8.3 Hz, 1H), 5.47 (s, 2H), 5.13 (d, J=6.5 Hz, 1H), 4.82-4.60 (m, 3H), 4.52 (dd, J=11.6, 6.7 Hz, 1H), 4.00 (d, J=8.9 Hz, 1H), 3.84 (d, J=8.9 Hz, 1H), 1.41 (s, 3H), 0.75 (s, 3H). ES/MS m/z: 606.2 (M+H$^+$).

Example 458: (S)-2-(2,5-difluoro-4-(6-((2,4,6-trifluorobenzyl)oxy)pyridin-2-yl)benzyl)-1-(4,4-dimethyltetrahydrofuran-3-yl)-1H-benzo[d]imidazole-6-carboxylic acid (S)-2-(2,5-difluoro-4-(6-((2,4,6-trifluorobenzyl)oxy)pyridin-2-yl)benzyl)-1-(4,4-dimethyltetrahydrofuran-3-yl)-1H-benzo[d]imidazole-6-carboxylic acid was prepared in a manner as described in Procedure 27, starting with Intermediates I-1219 and 2-(bromomethyl)-1,3,5-trifluoro-benzene. 1H NMR (400 MHz, Methanol-d4) δ 8.89 (s, 1H), 8.17 (dd, J=8.7, 1.4 Hz, 1H), 8.05 (dd, J=10.9, 6.3 Hz, 1H), 7.88-7.75 (m, 2H), 7.59 (dd, J=7.5, 1.6 Hz, 1H), 7.40 (dd, J=11.3, 6.0 Hz, 1H), 7.01-6.89 (m, 2H), 6.84 (d, J=8.3 Hz, 1H), 5.54 (s, 2H), 5.14 (d, J=7.1 Hz, 1H), 4.81-4.60 (m, 3H), 4.53 (dd, J=11.6, 6.7 Hz, 1H), 4.00 (d, J=8.9 Hz, 1H), 3.85 (d, J=8.9 Hz, 1H), 1.42 (s, 3H), 0.76 (s, 3H). ES/MS m/z: 624.3 (M+H$^+$).

Example 459: (S)-2-(4-(6-((5-chloro-2-fluoro-4-methylbenzyl)oxy)pyridin-2-yl)-2,5-difluorobenzyl)-1-(4,4-dimethyltetrahydrofuran-3-yl)-1H-benzo[d]imidazole-6-carboxylic acid (S)-2-(4-(6-((5-chloro-2-fluoro-4-methylbenzyl)oxy)pyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 27, starting with Intermediates I-1219 and 1-chloro-5-(chloromethyl)-4-fluoro-2-methyl-benzene. 1H NMR (400 MHz, Methanol-d4) δ 8.86 (s, 1H), 8.14 (dd, J=8.6, 1.4 Hz, 1H), 7.92 (dd, J=10.8, 6.3 Hz, 1H), 7.86-7.73 (m, 2H), 7.57 (dd, J=7.5, 1.6 Hz, 1H), 7.53 (d, J=6.7 Hz, 1H), 7.36 (dd, J=11.2, 6.0 Hz, 1H), 7.12 (d, J=10.4 Hz, 1H), 6.92 (d, J=8.3 Hz, 1H), 5.50 (s, 2H), 5.11 (d, J=6.5 Hz, 1H), 4.79-4.58 (m, 3H), 4.52 (dd, J=11.5, 6.7 Hz, 1H), 3.99 (d, J=8.9 Hz, 1H), 3.84 (d, J=8.8 Hz, 1H), 2.37 (s, 3H), 1.41 (s, 3H), 0.75 (s, 3H). ES/MS m/z: 636.2 (M+H$^+$).

Example 460: (S)-2-(4-(6-((2-chloro-4-cyanobenzyl)oxy)pyridin-2-yl)-2,5-difluorobenzyl)-1-(4,4-dimethyltetrahydrofuran-3-yl)-1H-benzo[d]imidazole-6-carboxylic acid (S)-2-(4-(6-((2-chloro-4-cyanobenzyl)oxy)pyridin-2-yl)-2,5-difluorobenzyl)-1-(4,4-dimethyltetrahydrofuran-3-yl)-

1H-benzo[d]imidazole-6-carboxylic acid was prepared in a manner as described in Procedure 27, starting with Intermediates I-1219 and 4-(bromomethyl)-3-chloro-benzonitrile. 1H NMR (400 MHz, Methanol-d4) δ 8.88 (s, 1H), 8.16 (d, J=8.6 Hz, 1H), 7.98-7.83 (m, 2H), 7.83-7.66 (m, 4H), 7.60 (d, J=7.4 Hz, 1H), 7.37 (dd, J=11.2, 6.0 Hz, 1H), 7.01 (d, J=8.3 Hz, 1H), 5.67 (s, 2H), 5.12 (d, J=6.4 Hz, 1H), 4.74-4.58 (m, 3H), 4.52 (dd, J=11.6, 6.7 Hz, 1H), 3.99 (d, J=8.9 Hz, 1H), 3.84 (d, J=8.9 Hz, 1H), 1.40 (s, 3H), 0.75 (s, 3H). ES/MS m/z: 629.15 (M+H$^+$).

Example 461: (S)-2-(4-(6-((4-cyano-2-methoxybenzyl)oxy)pyridin-2-yl)-2,5-difluorobenzyl)-1-(4,4-dimethyltetrahydrofuran-3-yl)-1H-benzo[d]imidazole-6-carboxylic acid (S)-2-(4-(6-((4-cyano-2-methoxybenzyl)oxy)pyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 27, starting with Intermediates I-1219 and 4-(bromomethyl)-3-methoxy-benzonitrile. 1H NMR (400 MHz, Methanol-d4) δ 8.84 (s, 1H), 8.12 (dd, J=8.6, 1.4 Hz, 1H), 7.89-7.77 (m, 2H), 7.75 (d, J=8.6 Hz, 1H), 7.58 (d, J=7.7 Hz, 2H), 7.38 (d, J=1.4 Hz, 1H), 7.37-7.26 (m, 2H), 6.96 (d, J=8.3 Hz, 1H), 5.58 (s, 2H), 5.08 (d, J=6.6 Hz, 1H), 4.74-4.47 (m, 4H), 3.97 (d, J=2.4 Hz, 4H), 3.84 (d, J=8.9 Hz, 1H), 1.40 (s, 3H), 0.74 (s, 3H). ES/MS m/z: 625.2 (M+H$^+$).

Example 462: (S)-2-(4-(6-((4-chloro-2-methoxybenzyl)oxy)pyridin-2-yl)-2,5-difluorobenzyl)-1-(4,4-dimethyltetrahydrofuran-3-yl)-1H-benzo[d]imidazole-6-carboxylic acid (S)-2-(4-(6-((4-chloro-2-methoxybenzyl)oxy)pyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 27, starting with Intermediates I-1219 and 1-(bromomethyl)-4-chloro-2-methoxy-benzene. 1H NMR (400 MHz, Methanol-d4) δ 8.77 (s, 1H), 8.10-8.01 (m, 1H), 7.88 (dd, J=10.9, 6.3 Hz, 1H), 7.79 (t, J=7.9 Hz, 1H), 7.72 (d, J=8.5 Hz, 1H), 7.55 (dd, J=7.5, 1.5 Hz, 1H), 7.39 (d, J=8.1 Hz, 1H), 7.27 (dd, J=11.3, 6.1 Hz, 1H), 7.05 (d, J=1.9 Hz, 1H), 6.95 (dd, J=8.1, 2.0 Hz, 1H), 6.88 (d, J=8.2 Hz, 1H), 5.48 (s, 2H), 5.02 (d, J=6.7 Hz, 1H), 4.69-4.46 (m, 4H), 3.97 (d, J=8.8 Hz, 1H), 3.91 (s, 3H), 3.82 (d, J=8.8 Hz, 1H), 1.39 (s, 3H), 0.71 (s, 3H). ES/MS m/z: 634.3 (M+H$^+$).

Example 463: (S)-2-(2,5-difluoro-4-(6-((2-fluoro-4-methylbenzyl)oxy)pyridin-2-yl)benzyl)-1-(4,4-dimethyltetrahydrofuran-3-yl)-1H-benzo[d]imidazole-6-carboxylic acid (S)-2-(2,5-difluoro-4-(6-((2-fluoro-4-methylbenzyl)oxy)pyridin-2-yl)benzyl)-1-(4,4-dimethyltetrahydrofuran-3-yl)-1H-benzo[d]imidazole-6-carboxylic acid was prepared in a manner as described in Procedure 27, starting with Intermediates I-1219 and 1-(bromomethyl)-2-fluoro-4-methyl-benzene. 1H NMR (400 MHz, Methanol-d4) δ 8.96 (s, 1H), 8.23 (dd, J=8.6, 1.4 Hz, 1H), 7.96 (dd, J=10.9, 6.3 Hz, 1H), 7.89-7.74 (m, 2H), 7.56 (dd, J=7.5, 1.6 Hz, 1H), 7.51-7.33 (m, 2H), 6.97 (dd, J=14.8, 9.5 Hz, 1H), 6.88 (d, J=8.2 Hz, 1H), 5.49 (s, 2H), 5.20 (d, J=6.4 Hz, 1H), 4.89-4.60 (m, 3H), 4.53 (dd, J=11.8, 6.6 Hz, 1H), 4.01 (d, J=9.0 Hz, 1H), 3.85 (d, J=8.9 Hz, 1H), 2.34 (s, 3H), 1.42 (s, 3H), 0.78 (s, 3H). ES/MS m/z: 602.3 (M+H$^+$).

Example 464: (S)-2-(4-(6-((2-chloro-4-fluorobenzyl)oxy)pyridin-2-yl)-2,5-difluorobenzyl)-1-(4,4-dimethyltetrahydrofuran-3-yl)-1H-benzo[d]imidazole-6-carboxylic acid (S)-2-(4-(6-((2-chloro-4-fluorobenzyl)oxy)pyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 27, starting with Intermediates I-1219 and 1-(bromomethyl)-2-chloro-4-fluorobenzene. 1H NMR (400 MHz, Methanol-d4) δ 8.94 (s, 1H), 8.21 (dd, J=8.7, 1.4 Hz, 1H), 7.91 (dd, J=10.9, 6.3 Hz, 1H), 7.88-7.73 (m, 2H), 7.68-7.54 (m, 2H), 7.43 (dd, J=11.1, 6.1 Hz, 1H), 7.28 (dd, J=8.6, 2.6 Hz, 1H), 7.10 (td, J=8.5, 2.6 Hz, 1H), 6.94 (d, J=8.3 Hz, 1H), 5.56 (s, 2H), 5.18 (d, J=6.5 Hz, 1H), 4.85-4.60 (m, 3H), 4.53 (dd, J=11.7, 6.7 Hz, 1H), 4.00 (d, J=8.9 Hz, 1H), 3.85 (d, J=8.9 Hz, 1H), 1.42 (s, 3H), 0.77 (s, 3H). ES/MS m/z: 622.2 (M+H$^+$).

Example 465: (S)-2-(2,5-difluoro-4-(6-((4-fluoro-2-methylbenzyl)oxy)pyridin-2-yl)benzyl)-1-(4,4-dimethyltetrahydrofuran-3-yl)-1H-benzo[d]imidazole-6-carboxylic acid (S)-2-(2,5-difluoro-4-(6-((4-fluoro-2-methylbenzyl)oxy)pyridin-2-yl)benzyl)-1-(4,4-dimethyltetrahydrofuran-3-yl)-1H-benzo[d]imidazole-6-carboxylic acid was prepared in a manner as described in Procedure 27, starting with Intermediates I-1219 and 1-(bromomethyl)-4-fluoro-2-methylbenzene. 1H NMR (400 MHz, Methanol-d4) δ 8.92 (s, 1H), 8.20 (dd, J=8.6, 1.4 Hz, 1H), 7.95 (dd, J=10.8, 6.4 Hz, 1H), 7.85-7.70 (m, 2H), 7.56 (dd, J=7.4, 1.7 Hz, 1H), 7.43 (td, J=10.9, 9.7, 5.9 Hz, 2H), 6.99 (dd, J=9.9, 2.8 Hz, 1H), 6.90 (dd, J=11.5, 8.4 Hz, 2H), 5.47 (s, 2H), 5.16 (d, J=6.4 Hz, 1H), 4.83-4.61 (m, 3H), 4.53 (dd, J=11.7, 6.7 Hz, 1H), 4.01 (d, J=8.9 Hz, 1H), 3.85 (d, J=8.9 Hz, 1H), 2.43 (s, 3H), 1.42 (s, 3H), 0.77 (s, 3H). ES/MS m/z: 602.3 (M+H$^+$).

Example 466: (S)-2-(4-(6-((2,4-difluorobenzyl)oxy)pyridin-2-yl)-2,5-difluorobenzyl)-1-(4,4-dimethyltetrahydrofuran-3-yl)-1H-benzo[d]imidazole-6-carboxylic acid (S)-2-(4-(6-((2,4-difluorobenzyl)oxy)pyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 27, starting with Intermediates I-1219 and 1-(bromomethyl)-2,4-difluoro-benzene. 1H NMR (400 MHz, Methanol-d4) δ 8.91 (s, 1H), 8.19 (dd, J=8.6, 1.4 Hz, 1H), 7.96 (dd, J=10.8, 6.3 Hz, 1H), 7.89-7.70 (m, 2H), 7.65-7.52 (m, 2H), 7.41 (dd, J=11.2, 6.0 Hz, 1H), 7.10-6.94 (m, 2H), 6.90 (d, J=8.2 Hz, 1H), 5.52 (s, 2H), 5.16 (d, J=6.4 Hz, 1H), 4.82-4.60 (m, 3H), 4.53 (dd, J=11.6, 6.7 Hz, 1H), 4.00 (d, J=8.9 Hz, 1H), 3.85 (d, J=8.9 Hz, 1H), 1.42 (s, 3H), 0.77 (s, 3H). ES/MS m/z: 606.3 (M+H$^+$).

Example 467: 2-(4-(6-((4-cyanobenzyl)oxy)-5-fluoropyridin-2-yl)-2,5-difluorobenzyl)-1-((3S,4S)-4-(methoxymethyl)tetrahydrofuran-3-yl)-1H-benzo[d]imidazole-6-carboxylic acid 2-(4-(6-((4-cyanobenzyl)oxy)-5-fluoropyridin-2-yl)-2,5-difluorobenzyl)-1-((3S,4S)-4-(methoxymethyl)tetrahydrofuran-3-yl)-1H-benzo[d]imidazole-6-carboxylic acid was prepared in a manner as described in Procedure 35, starting with Intermediates I-1267 and I-1092. 1H NMR (400 MHz, DMSO) δ 7.89 (dd, J=16.6, 8.2 Hz, 3H), 7.70 (dd, J=12.0, 7.3 Hz, 2H), 7.52 (d, J=7.4 Hz, 1H), 7.39-7.30 (m, 1H), 7.01 (d, J=8.2 Hz, 1H), 5.58 (s, 2H), 5.49 (s, 1H), 4.48 (t, J=13.9 Hz, 2H), 4.35 (t, J=5.1 Hz, 1H), 4.26-4.14 (m, 1H), 2.92 (s, 3H), 2.08 (s, 2H). ES/MS m/z: 629.1 (M+H$^+$).

Example 468: 2-(4-(6-((4-cyanobenzyl)oxy)pyridin-2-yl)-2,5-difluorobenzyl)-1-((3S,4S)-4-(methoxymethyl)tetrahydrofuran-3-yl)-1H-benzo[d]imidazole-6-carboxylic acid 2-(4-(6-((4-cyanobenzyl)oxy)pyridin-2-yl)-2,5-difluorobenzyl)-1-((3 S,4S)-4-(methoxymethyl)tetrahydrofuran-3-yl)-1H-benzo[d]imidazole-6-carboxylic acid was prepared in a manner as described in Procedure 35, starting with Intermediates I-1267 and I-114. 1H NMR (400 MHz, DMSO) δ 7.89 (dd, J=16.6, 8.2 Hz, 3H), 7.70 (dd, J=12.0, 7.3 Hz, 2H), 7.52 (d, J=7.4 Hz, 1H), 7.40-7.29 (m, 1H), 7.01 (d, J=8.2 Hz, 1H), 5.58 (s, 2H), 5.49 (s, 1H), 4.48 (t, J=13.9 Hz, 2H), 4.35 (t, J=5.1 Hz, 1H), 4.29-4.16 (m, 1H), 2.92 (s, 3H), 2.08 (s, 2H). ES/MS m/z: 611.2 (M+H$^+$).

Example 469: (S)-2-(4-(6-((4-chloro-2-(trifluoromethyl)benzyl)oxy)pyridin-2-yl)-2,5-difluorobenzyl)-1-(4,4-dimethyltetrahydrofuran-3-yl)-1H-benzo[d]imidazole-6-carboxylic acid (S)-2-(4-(6-((4-chloro-2-(trifluoromethyl)benzyl)oxy)pyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 35, starting with Intermediates I-82 and I-1260. 1H NMR (400 MHz, DMSO) δ 8.48 (s, 1H), 7.97-7.85 (m, 2H), 7.85-7.73 (m, 3H), 7.70 (dd, J=10.5, 6.4 Hz, 1H), 7.62 (d, J=8.5 Hz, 1H), 7.55 (d, J=7.3 Hz, 1H), 7.44 (dd, J=11.4, 6.1 Hz, 1H), 7.01 (d, J=8.3 Hz, 1H), 5.64 (s, 2H), 5.00 (d, J=6.7 Hz, 1H), 4.63-4.47 (m, 2H), 4.47-4.31 (m, 2H), 3.80-3.66 (m, 2H), 2.55 (s, 3H), 1.32 (s, 3H), 0.59 (s, 3H). ES/MS m/z: 672.1 (M+H$^+$).

Example 470: (S)-2-(2,5-difluoro-4-(6-((6-(trifluoromethyl)pyridazin-3-yl)methoxy)pyridin-2-yl)benzyl)-1-(4,4-dimethyltetrahydrofuran-3-yl)-1H-benzo[d]imidazole-6-carboxylic acid (S)-2-(2,5-difluoro-4-(6-((6-(trifluoromethyl)pyridazin-3-yl)methoxy)pyridin-2-yl)benzyl)-1-(4,4-dimethyltetrahydrofuran-3-yl)-1H-benzo[d]imidazole-6-carboxylic acid was prepared in a manner as described in Procedure 35, starting with Intermediates I-82 and I-1261. 1H NMR (400 MHz, DMSO) δ 8.51 (s, 1H), 8.29 (d, J=8.8 Hz, 1H), 8.10 (d, J=8.8 Hz, 1H), 7.94 (t, J=7.9 Hz, 1H), 7.83 (dd, J=8.5, 1.5 Hz, 1H), 7.73-7.51 (m, 3H), 7.45 (dd, J=11.4, 6.1 Hz, 1H), 7.09 (d, J=8.3 Hz, 1H), 5.90 (s, 2H), 5.03 (d, J=6.7 Hz, 1H), 4.63-4.31 (m, 4H), 3.85-3.65 (m, 2H), 1.32 (s, 3H), 0.60 (s, 3H). ES/MS m/z: 640.0 (M+H$^+$).

Example 471: 2-(4-(6-((4-chloro-2-fluorobenzyl)oxy)-5-fluoropyridin-2-yl)-2,5-difluorobenzyl)-1-((3S,4R)-4-methyltetrahydrofuran-3-yl)-1H-benzo[d]imidazole-6-carboxylic acid 2-(4-(6-((4-chloro-2-fluorobenzyl)oxy)-5-fluoropyridin-2-yl)-2,5-difluorobenzyl)-1-((3S,4R)-4-methyltetrahydrofuran-3-yl)-1H-benzo[d]imidazole-6-carboxylic acid was prepared in a manner as described in Procedure 39, starting with Intermediates I-1256 and I-1292. 1H NMR (400 MHz, DMSO) δ 8.50 (s, 1H), 7.97-7.73 (m, 3H), 7.71-7.50 (m, 4H), 7.45 (dd, J=11.2, 6.0 Hz, 1H), 7.35 (d, J=8.2 Hz, 1H), 5.60 (s, 2H), 5.43 (s, 1H), 4.66-4.40 (m, 3H), 4.31-4.18 (m, 1H), 4.18-4.09 (m, 1H), 3.59 (d, J=8.8 Hz, 4H), 0.53 (d, J=7.0 Hz, 3H). ES/MS m/z: 626.0 (M+H$^+$).

Example 472: 2-(4-(6-((4-chloro-2-fluorobenzyl)oxy)pyridin-2-yl)-2,5-difluorobenzyl)-1-((3S,4R)-4-methyltetrahydrofuran-3-yl)-1H-benzo[d]imidazole-6-carboxylic acid 2-(4-(6-((4-chloro-2-fluorobenzyl)oxy)pyridin-2-yl)-2,5-difluorobenzyl)-1-((3 S,4R)-4-methyltetrahydrofuran-3-yl)-1H-benzo[d]imidazole-6-carboxylic acid was prepared in a manner as described in Procedure 39, starting with Intermediates I-1255 and I-1292. 1H NMR (400 MHz, DMSO) δ 8.51 (s, 1H), 7.97-7.75 (m, 3H), 7.62 (d, J=8.7 Hz, 2H), 7.56-7.42 (m, 3H), 7.35-7.31 (m, 1H), 6.95 (d, J=8.3 Hz, 1H), 5.51 (s, 2H), 5.44 (t, J=7.2 Hz, 1H), 4.57-4.39 (m, 3H), 4.24 (dd, J=10.9, 6.7 Hz, 1H), 4.13 (t, J=8.5 Hz, 1H), 3.60 (t, J=8.5 Hz, 1H), 0.53 (d, J=7.0 Hz, 3H). ES/MS m/z: 608.0 (M+H$^+$).

Example 473: 2-(4-(6-((4-chloro-2-fluorobenzyl)oxy)pyridin-2-yl)-2,5-difluorobenzyl)-1-((3R,4R)-4-methoxy-4-methyltetrahydrofuran-3-yl)-1H-benzo[d]imidazole-6-carboxylic acid, isomer 1 (absolute stereochemistry not known)

2-(4-(6-((4-chloro-2-fluorobenzyl)oxy)pyridin-2-yl)-2,5-difluorobenzyl)-1-((3R,4R)-4-methoxy-4-methyltetrahydrofuran-3-yl)-1H-benzo[d]imidazole-6-carboxylic acid, isomer 1 (absolute stereochemistry not known) was prepared in a manner as described in Procedure 39, starting with Intermediates I-1255 and I-1258. 1H NMR (400 MHz, DMSO) δ 8.47 (s, 1H), 7.98-7.70 (m, 3H), 7.61 (t, J=8.3 Hz, 2H), 7.57-7.46 (m, 2H), 7.39 (dd, J=11.5, 6.0 Hz, 1H), 7.33 (dd, J=8.3, 2.1 Hz, 1H), 6.96 (d, J=8.3 Hz, 1H), 5.51 (s, 2H), 5.33 (d, J=8.2 Hz, 1H), 4.73-4.38 (m, 4H), 4.30-4.11 (m, 2H), 3.63 (d, J=10.0 Hz, 1H), 2.97 (s, 3H), 1.43 (s, 3H). ES/MS m/z: 638.0 (M+H$^+$).

Example 474: 2-(4-(6-((4-chloro-2-fluorobenzyl)oxy)pyridin-2-yl)-2,5-difluorobenzyl)-1-((3R,4R)-4-methoxy-4-methyltetrahydrofuran-3-yl)-1H-benzo[d]imidazole-6-carboxylic acid, isomer 2 (absolute stereochemistry not known)

2-(4-(6-((4-chloro-2-fluorobenzyl)oxy)pyridin-2-yl)-2,5-difluorobenzyl)-1-((3R,4R)-4-methoxy-4-methyltetrahydrofuran-3-yl)-1H-benzo[d]imidazole-6-carboxylic acid, isomer 2 (absolute stereochemistry not known) was prepared in a manner as described in Procedure 39 starting with Intermediates I-1255 and I-1257. 1H NMR (400 MHz, DMSO) δ 8.45 (s, 1H), 7.95-7.76 (m, 3H), 7.67-7.56 (m, 2H), 7.56-7.47 (m, 2H), 7.43-7.30 (m, 2H), 6.95 (d, J=8.3 Hz, 1H), 5.51 (s, 2H), 5.31 (s, 1H), 4.64-4.35 (m, 3H), 4.29-4.14 (m, 2H), 3.63 (d, J=10.1 Hz, 1H), 2.96 (s, 3H), 1.43 (s, 3H). ES/MS m/z: 638.0 (M+H$^+$).

Example 475: (S)-2-(4-(6-((2,6-difluorobenzyl)oxy)-5-fluoropyridin-2-yl)-2,5-difluorobenzyl)-1-(4,4-dimethyltetrahydrofuran-3-yl)-1H-benzo[d]imidazole-6-carboxylic acid (S)-2-(4-(6-((2,6-difluorobenzyl)oxy)-5-fluoropyridin-2-yl)-2,5-difluorobenzyl)-1-(4,4-dimethyltetrahydrofuran-3- yl)-1H-benzo[d]imidazole-6-carboxylic acid was prepared in a manner as described in Procedure 35, starting with Intermediates I-82 and I-1262. 1H NMR (400 MHz, DMSO) δ 8.51 (s, 1H), 7.96-7.77 (m, 3H), 7.65 (d, J=8.4 Hz, 1H), 7.60-7.38 (m, 3H), 7.19 (t, J=8.0 Hz, 2H), 5.63 (s, 2H), 5.04 (d, J=6.6 Hz, 1H), 4.67-4.29 (m, 4H), 3.85-3.69 (m, 2H), 1.34 (s, 3H), 0.62 (s, 3H). ES/MS m/z: 624.2 (M+H$^+$).

Example 476: (S)-2-(4-(6-((2,6-difluorobenzyl)oxy) pyridin-2-yl)-2,5-difluorobenzyl)-1-(4,4-dimethyltetrahydrofuran-3-yl)-1H-benzo[d]imidazole-6-carboxylic acid (S)-2-(4-(6-((2,6-difluorobenzyl)oxy)pyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 35, starting with Intermediates I-82 and I-1263. 1H NMR (400 MHz, DMSO) δ 8.51 (s, 1H), 8.00-7.79 (m, 3H), 7.65 (d, J=8.4 Hz, 1H), 7.60-7.38 (m, 3H), 7.18 (t, J=7.9 Hz, 2H), 6.91 (d, J=8.3 Hz, 1H), 5.53 (s, 2H), 5.04 (d, J=6.6 Hz, 1H), 4.67-4.32 (m, 4H), 3.87-3.70 (m, 2H), 1.34 (s, 3H), 0.62 (s, 3H). ES/MS m/z: 606.2 (M+H$^+$).

Example 477: (S)-2-(2,5-difluoro-4-(5-fluoro-6-((2-fluorobenzyl)oxy)pyridin-2-yl)benzyl)-1-(4,4-dimethyltetrahydrofuran-3-yl)-1H-benzo[d]imidazole-6-carboxylic acid (S)-2-(2,5-difluoro-4-(5-fluoro-6-((2-fluorobenzyl)oxy) pyridin-2-yl)benzyl)-1-(4,4-dimethyltetrahydrofuran-3-yl)-1H-benzo[d]imidazole-6-carboxylic acid was prepared in a manner as described in Procedure 35, starting with Intermediates I-82 and I-1264. 1H NMR (400 MHz, DMSO) δ 8.50 (s, 1H), 8.03-7.79 (m, 3H), 7.75-7.51 (m, 3H), 7.46 (dq, J=13.9, 7.0, 6.5 Hz, 2H), 7.26 (q, J=9.3, 7.7 Hz, 2H), 5.62 (s, 2H), 5.03 (d, J=6.7 Hz, 1H), 4.66-4.28 (m, 4H), 3.83-3.66 (m, 2H), 1.34 (s, 3H), 0.61 (s, 3H). ES/MS m/z: 606.2 (M+H$^+$).

Example 478: (S)-2-(2,5-difluoro-4-(6-((2-fluorobenzyl)oxy)pyridin-2-yl)benzyl)-1-(4,4-dimethyltetrahydrofuran-3-yl)-1H-benzo[d]imidazole-6-carboxylic acid (S)-2-(2,5-difluoro-4-(6-((2-fluorobenzyl)oxy)pyridin-2-yl)benzyl)-1-(4,4-dimethyltetrahydrofuran-3-yl)-1H-benzo [d]imidazole-6-carboxylic acid was prepared in a manner as described in Procedure 35, starting with Intermediates I-82 and I-1265. 1H NMR (400 MHz, DMSO) δ 8.52 (s, 1H), 7.98-7.77 (m, 3H), 7.78-7.36 (m, 5H), 7.36-7.13 (m, 2H), 6.96 (d, J=8.3 Hz, 1H), 5.53 (s, 2H), 5.05 (d, J=6.6 Hz, 1H), 4.72-4.37 (m, 4H), 3.90-3.66 (m, 2H), 1.34 (s, 3H), 0.62 (s, 3H). ES/MS m/z: 588.3 (M+H$^+$).

Example 479: (S)-2-(4-(6-((4-cyano-2-fluorobenzyl) oxy)-5-fluoropyridin-2-yl)-2,3,6-trifluorobenzyl)-1-(4,4-dimethyltetrahydrofuran-3-yl)-4-fluoro-1H-benzo[d]imidazole-6-carboxylic acid (S)-2-(4-(6-((4-cyano-2-fluorobenzyl)oxy)-5-fluoropyridin-2-yl)-2,3,6-trifluorobenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-82 and I-109. 1H NMR (400 MHz, Acetonitrile-d3) δ 8.42 (s, 1H), 7.73 (t, J=7.7 Hz, 1H), 7.68-7.51 (m, 6H), 5.68 (s, 2H), 4.93 (d, J=6.6 Hz, 1H), 4.59 (dd, J=11.3, 1.5 Hz, 1H), 4.53-4.40 (m, 2H), 4.32 (d, J=17.2 Hz, 1H), 3.85 (d, J=8.7 Hz, 1H), 3.78 (d, J=8.7 Hz, 1H), 1.41 (s, 3H), 0.72 (s, 3H). ES/MS m/z: 667.2 (M+H$^+$).

Example 480: 2-(4-(6-((4-cyanobenzyl)oxy)-5-fluoropyridin-2-yl)-2,5-difluorobenzyl)-1-((3S,4R)-4-methyltetrahydrofuran-3-yl)-1H-benzo[d]imidazole-6-carboxylic acid 2-(4-(6-((4-cyanobenzyl)oxy)-5-fluoropyridin-2-yl)-2,5-difluorobenzyl)-1-((3S,4R)-4-methyltetrahydrofuran-3-yl)-1H-benzo[d]imidazole-6-carboxylic acid was prepared in a manner as described in Procedure 35, starting with Intermediates I-1287 and I-1292. 1H NMR (400 MHz, Acetonitrile-d3) δ 8.57 (s, 1H), 7.86 (dd, J=8.4, 1.5 Hz, 1H), 7.78-7.68 (m, 3H), 7.65 (d, J=8.1 Hz, 2H), 7.62-7.54 (m, 2H), 7.52 (ddd, J=8.3, 3.1, 1.4 Hz, 1H), 7.20 (dd, J=11.6, 6.1 Hz, 1H), 5.63 (s, 2H), 5.24 (t, J=7.2 Hz, 1H), 4.55 (dd, J=11.0, 1.4 Hz, 1H), 4.37 (s, 2H), 4.23 (dd, J=11.0, 6.7 Hz, 1H), 4.13 (t, J=8.5 Hz, 1H), 3.67 (t, J=8.4 Hz, 1H), 2.88 (hept, J=7.6 Hz, 1H), 0.57 (d, J=7.0 Hz, 3H). ES/MS m/z: 599.3 (M+H$^+$).

Example 481: 2-(4-(6-((4-cyano-2,5-difluorobenzyl) oxy)-5-fluoropyridin-2-yl)-2,5-difluorobenzyl)-1-((3S,4R)-4-methyltetrahydrofuran-3-yl)-1H-benzo [d]imidazole-6-carboxylic acid 2-(4-(6-((4-cyano-2,5-difluorobenzyl)oxy)-5-fluoropyridin-2-yl)-2,5-difluorobenzyl)-1-((3S,4R)-4-methyltetrahydrofuran-3-yl)-1H-benzo[d]imidazole-6-carboxylic acid was prepared in a manner as described in Procedure 35, starting with Intermediates I-1294 and I-1292. 1H NMR (400 MHz, Acetonitrile-d3) δ 8.56 (s, 1H), 7.87 (dd, J=8.5, 1.5 Hz, 1H), 7.70 (dd, J=10.7, 6.5 Hz, 1H), 7.65-7.48 (m, 5H), 7.20 (dd, J=11.6, 6.1 Hz, 1H), 5.65 (s, 2H), 5.23 (t, J=7.3 Hz, 1H), 4.56 (dd, J=10.9, 1.4 Hz, 1H), 4.37 (s, 2H), 4.23 (dd, J=10.9, 6.7 Hz, 1H), 4.13 (t, J=8.5 Hz, 1H), 3.68 (t, J=8.3 Hz, 1H), 2.87 (hept, J=7.7 Hz, 1H), 0.57 (d, J=7.0 Hz, 3H). ES/MS m/z: 635.2 (M+H$^+$).

Example 482: (S)-2-(4-(6-((4-cyano-2-fluorobenzyl) oxy)-5-fluoropyridin-2-yl)-2,3,6-trifluorobenzyl)-1-(4,4-dimethyltetrahydrofuran-3-yl)-1H-benzo[d] imidazole-6-carboxylic acid (S)-2-(4-(6-((4-cyano-2-fluorobenzyl)oxy)-5-fluoropyridin-2-yl)-2,3,6-trifluorobenzyl)-1-(4,4-dimethyltetrahydrofuran-3-yl)-1H-benzo[d]imidazole-6-carboxylic acid was prepared in a manner as described in Procedure 35, starting with Intermediates I-109 and I-1231. 1H NMR (400 MHz, Acetonitrile-d$_3$) δ 8.54 (s, 1H), 7.83 (dd, J=8.5, 1.5 Hz, 1H), 7.72 (t, J=7.7 Hz, 1H), 7.66-7.45 (m, 6H), 5.66 (s, 2H), 4.92 (d, J=6.7 Hz, 1H), 4.60 (dd, J=11.2, 1.5 Hz, 1H), 4.53-4.40 (m, 2H), 4.31 (d, J=17.1 Hz, 1H), 3.86 (d, J=8.7 Hz, 1H), 3.77 (d, J=8.7 Hz, 1H), 1.41 (s, 3H), 0.70 (s, 3H). ES/MS m/z: 649.2 (M+H$^+$).

Example 483: (S)-2-(4-(6-((4-cyano-2,5-difluorobenzyl)oxy)-5-fluoropyridin-2-yl)-2,5-difluorobenzyl)-1-(4,4-dimethyltetrahydrofuran-3-yl)-4-fluoro-1H-benzo[d]imidazole-6-carboxylic acid (S)-2-(4-(6-((4-cyano-2,5-difluorobenzyl)oxy)-5-fluoropyridin-2-yl)-2,5-difluorobenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1294 and I-108. 1H NMR (400 MHz, Acetonitrile-$d_3$) δ 8.41 (s, 1H), 7.72 (dd, J=10.7, 6.4 Hz, 1H), 7.67-7.49 (m, 5H), 7.23 (dd, J=11.5, 6.1 Hz, 1H), 5.66 (s, 2H), 4.85 (d, J=6.7 Hz, 1H), 4.54 (dd, J=11.3, 1.5 Hz, 1H), 4.43 (dd, J=11.3, 6.8 Hz, 1H), 4.39-4.27 (m, 2H), 3.84 (d, J=8.8 Hz, 1H), 3.75 (d, J=8.8 Hz, 1H), 1.35 (s, 3H), 0.67 (s, 3H). ES/MS m/z: 667.2 (M+H$^+$).

Example 484: 2-(4-(2-((4-chloro-2-fluorobenzyl) oxy)pyrimidin-4-yl)-2,5-difluorobenzyl)-1-((3S,4R)-4-methyltetrahydrofuran-3-yl)-1H-benzo[d]imidazole-6-carboxylic acid 2-(4-(2-((4-chloro-2-fluorobenzyl)oxy)pyrimidin-4-yl)-2,5-difluorobenzyl)-1-((3S,4R)-4-methyltetrahydrofuran-3-yl)-1H-benzo[d]imidazole-6-carboxylic acid was prepared in a manner as described in Procedure 35, starting with Intermediates I-105 and I-1241. 1H NMR (400 MHz, Acetonitrile-$d_3$) δ 8.63 (d, J=5.1 Hz, 1H), 8.57 (s, 1H), 7.94 (dd, J=10.5, 6.3 Hz, 1H), 7.86 (dd, J=8.5, 1.5 Hz, 1H), 7.62-7.52 (m, 3H), 7.31-7.19 (m, 3H), 5.53 (s, 2H), 5.24 (t, J=7.2 Hz, 1H), 4.55 (dd, J=11.0, 1.4 Hz, 1H), 4.40 (s, 2H), 4.23 (dd, J=11.0, 6.7 Hz, 1H), 4.13 (t, J=8.5 Hz, 1H), 3.67 (t, J=8.4 Hz, 1H), 2.89 (hept, J=7.5 Hz, 1H), 0.57 (d, J=7.1 Hz, 3H). ES/MS m/z: 609.2 (M+H$^+$).

Example 485: 2-(4-(6-((4-chloro-2-fluorobenzyl) oxy)-5-fluoropyridin-2-yl)-2,3,6-trifluorobenzyl)-4-fluoro-1-(2-methoxyethyl)-1H-benzo[d]imidazole-6-carboxylic acid 2-(4-(6-((4-chloro-2-fluorobenzyl)oxy)-5-fluoropyridin-2-yl)-2,3,6-trifluorobenzyl)-4-fluoro-1-(2-methoxyethyl)-1H-benzo[d]imidazole-6-carboxylic acid was prepared in a manner as described in Procedure 35, starting with Intermediates I-1135 and I-1036. 1H NMR (400 MHz, Acetonitrile-$d_3$) δ 8.03 (d, J=1.3 Hz, 1H), 7.69-7.64 (m, 1H), 7.64-7.50 (m, 4H), 7.31-7.22 (m, 2H), 5.59 (s, 2H), 4.53 (t, J=5.0 Hz, 2H), 4.46 (s, 2H), 3.75 (t, J=5.0 Hz, 2H), 3.27 (s, 3H). ES/MS m/z: 636.2 (M+H$^+$).

Example 486: 2-(4-(6-((4-cyano-2-fluorobenzyl) oxy)-5-fluoropyridin-2-yl)-2,5-difluorobenzyl)-1-((3S,4R)-4-methyltetrahydrofuran-3-yl)-1H-benzo [d]imidazole-6-carboxylic acid 2-(4-(6-((4-cyano-2-fluorobenzyl)oxy)-5-fluoropyridin-2-yl)-2,5-difluorobenzyl)-1-((3S,4R)-4-methyltetrahydrofuran-3-yl)-1H-benzo[d]imidazole-6-carboxylic acid was prepared in a manner as described in Procedure 35, starting with Intermediates I-109 and I-1292. 1H NMR (400 MHz, Acetonitrile-$d_3$) δ 8.57 (d, J=1.5 Hz, 1H), 7.86 (dd, J=8.5, 1.6 Hz, 1H), 7.75-7.68 (m, 2H), 7.62-7.53 (m, 4H), 7.51 (ddd, J=8.2, 3.1, 1.4 Hz, 1H), 7.20 (dd, J=11.6, 6.1 Hz, 1H), 5.66 (s, 2H), 5.24 (t, J=7.2 Hz, 1H), 4.54 (dd, J=11.0, 1.4 Hz, 1H), 4.37 (s, 2H), 4.23 (dd, J=11.0, 6.7 Hz, 1H), 4.13 (t, J=8.5 Hz, 1H), 3.67 (t, J=8.4 Hz, 1H), 2.87 (dq, J=15.2, 7.6 Hz, 1H), 0.57 (d, J=7.1 Hz, 3H). "ES/MS m/z: 617.2 (M+H$^+$).

Example 487: (S)-2-(4-(6-((4-cyano-2,5-difluorobenzyl)oxy)pyridin-2-yl)-2,5-difluorobenzyl)-1-(4, 4-dimethyltetrahydrofuran-3-yl)-1H-benzo[d]imidazole-6-carboxylic acid (S)-2-(4-(6-((4-cyano-2,5-difluorobenzyl)oxy)pyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 35, starting with Intermediates I-1295 and I-82. 1H NMR (400 MHz, Acetonitrile-$d_3$) δ 8.55 (s, 1H), 7.86 (dd, J=8.5, 1.5 Hz, 1H), 7.83-7.78 (m, 1H), 7.75 (dd, J=10.7, 6.4 Hz, 1H), 7.62-7.57 (m, 1H), 7.53 (ddt, J=10.5, 9.2, 4.8 Hz, 3H), 7.22 (dd, J=11.5, 6.1 Hz, 1H), 6.92 (dd, J=8.3, 0.7 Hz, 1H), 5.58 (s, 2H), 4.84 (d, J=6.6 Hz, 1H), 4.56 (dd, J=11.2, 1.6 Hz, 1H), 4.42 (dd, J=11.2, 6.9 Hz, 1H), 4.36 (d, J=6.3 Hz, 2H), 3.85 (d, J=8.7 Hz, 1H), 3.75 (d, J=8.7 Hz, 1H), 1.34 (s, 3H), 0.65 (s, 3H). ES/MS m/z: 631.2 (M+H$^+$).

Example 488: (S)-2-(4-(6-((4-chloro-2,3-difluorobenzyl)oxy)pyridin-2-yl)-2,5-difluorobenzyl)-1-(4, 4-dimethyltetrahydrofuran-3-yl)-1H-benzo[d]imidazole-6-carboxylic acid (S)-2-(4-(6-((4-chloro-2,3-difluorobenzyl)oxy)pyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 35, starting with Intermediates I-1296 and I-82. 1H NMR (400 MHz, Acetonitrile-d3) δ 8.69 (s, 1H), 8.01 (dd, J=8.6, 1.5 Hz, 1H), 7.85 (dd, J=10.8, 6.4 Hz, 1H), 7.77 (dd, J=8.2, 7.5 Hz, 1H), 7.72 (d, J=8.5 Hz, 1H), 7.50 (dd, J=7.5, 1.7 Hz, 1H), 7.36-7.22 (m, 3H), 6.86 (d, J=8.2 Hz, 1H), 5.53 (d, J=1.3 Hz, 2H), 4.93 (d, J=6.6 Hz, 1H), 4.62-4.50 (m, 3H), 4.43 (dd, J=11.6, 6.8 Hz, 1H), 3.89 (d, J=8.9 Hz, 1H), 3.76 (d, J=8.9 Hz, 1H), 1.34 (s, 3H), 0.68 (s, 3H). ES/MS m/z: 640.2 (M+H$^+$).

Example 489: (S)-2-(4-(6-((4-chloro-2,6-difluorobenzyl)oxy)pyridin-2-yl)-2,5-difluorobenzyl)-1-(4, 4-dimethyltetrahydrofuran-3-yl)-1H-benzo[d]imidazole-6-carboxylic acid (S)-2-(4-(6-((4-chloro-2,6-difluorobenzyl)oxy)pyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 35, starting with Intermediates I-1297 and I-82. 1H NMR (400 MHz, Acetonitrile-d3) δ 8.62 (s, 1H), 7.98-7.89 (m, 2H), 7.75 (t, J=7.9 Hz, 1H), 7.65 (d, J=8.5 Hz, 1H), 7.50 (dd, J=7.5, 1.7 Hz, 1H), 7.26 (dd, J=11.5, 6.1 Hz, 1H), 7.14 (d, J=7.4 Hz, 2H), 6.78 (d, J=8.2 Hz, 1H), 5.51 (s, 2H), 4.89 (d, J=6.7 Hz, 1H), 4.55 (dd, J=11.4, 1.5 Hz, 1H), 4.49-4.37 (m, 3H), 3.87 (d, J=8.8 Hz, 1H), 3.75 (d, J=8.8 Hz, 1H), 1.34 (s, 3H), 0.67 (s, 3H). ES/MS m/z: 640.2 (M+H$^+$).

Example 490: (S)-2-(4-(6-((4-chloro-2,5-difluorobenzyl)oxy)pyridin-2-yl)-2,5-difluorobenzyl)-1-(4, 4-dimethyltetrahydrofuran-3-yl)-1H-benzo[d]imidazole-6-carboxylic acid (S)-2-(4-(6-((4-chloro-2,5-difluorobenzyl)oxy)pyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 35, starting with Intermediates I-1298 and I-82. 1H NMR (400 MHz, Acetonitrile-d3) δ 8.56 (s, 1H), 7.88 (dd, J=8.5, 1.5 Hz, 1H), 7.85-7.73 (m, 2H), 7.60 (d, J=8.5 Hz, 1H), 7.54-7.48 (m, 1H), 7.44 (dd, J=9.5, 6.3 Hz, 1H), 7.35 (dd, J=9.2, 6.1 Hz, 1H), 7.22 (dd, J=11.5, 6.1 Hz, 1H), 6.87 (d, J=8.2 Hz, 1H), 5.50 (s, 2H), 4.85 (d, J=6.7 Hz, 1H), 4.55 (dd, J=11.2, 1.5 Hz, 1H), 4.42 (dd, J=11.1, 6.9 Hz, 1H), 4.38 (d, J=6.0 Hz, 2H), 3.86 (d, J=8.7 Hz, 1H), 3.75 (d, J=8.7 Hz, 1H), 1.34 (s, 3H), 0.65 (s, 3H). ES/MS m/z: 640.2 (M+H$^+$).

Example 491: (S)-2-(4-(6-((4-cyano-2,5-difluorobenzyl)oxy)-5-fluoropyridin-2-yl)-2,5-difluorobenzyl)-1-(4,4-dimethyltetrahydrofuran-3-yl)-1H-benzo[d]imidazole-6-carboxylic acid (S)-2-(4-(6-((4-cyano-2,5-difluorobenzyl)oxy)-5-fluoropyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 35, starting with Intermediates I-1294 and I-82. 1H NMR (400 MHz, Acetonitrile-d3) δ 8.59 (s, 1H), 7.90 (dd, J=8.5, 1.5 Hz, 1H), 7.74 (dd, J=10.7, 6.5 Hz, 1H), 7.66-7.49 (m, 5H), 7.25 (dd, J=11.6, 6.1 Hz, 1H), 5.68 (s, 2H), 4.87 (d, J=6.8 Hz, 1H), 4.59 (dd, J=11.2, 1.5 Hz, 1H), 4.46 (dd, J=11.1, 6.8 Hz, 1H), 4.39 (d, J=6.7 Hz, 2H), 3.89 (d, J=8.7 Hz, 1H), 3.78 (d, J=8.7 Hz, 1H), 1.37 (s, 3H), 0.68 (s, 3H). ES/MS m/z: 649.2 (M+H$^+$).

Example 492: (S)-2-(4-(6-((4-cyano-2,3-difluorobenzyl)oxy)pyridin-2-yl)-2,5-difluorobenzyl)-1-(4,4-dimethyltetrahydrofuran-3-yl)-1H-benzo[d]imidazole-6-carboxylic acid (S)-2-(4-(6-((4-cyano-2,3-difluorobenzyl)oxy)pyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 35, starting with Intermediates I-1300 and I-82. 1H NMR (400 MHz, Acetonitrile-d3) δ 8.70 (s, 1H), 8.02 (dd, J=8.6, 1.5 Hz, 1H), 7.83 (d, J=7.5 Hz, 1H), 7.81-7.75 (m, 1H), 7.72 (d, J=8.5 Hz, 1H), 7.57-7.51 (m, 2H), 7.51-7.44 (m, 1H), 7.29 (dd, J=11.4, 6.1 Hz, 1H), 6.92 (d, J=8.3 Hz, 1H), 5.62 (s, 2H), 4.93 (d, J=6.6 Hz, 1H), 4.62-4.54 (m, 1H), 4.51 (d, J=8.4 Hz, 2H), 4.44 (dd, J=11.5, 6.7 Hz, 1H), 3.90 (d, J=8.9 Hz, 1H), 3.77 (d, J=8.9 Hz, 1H), 1.35 (s, 3H), 0.69 (s, 3H). ES/MS m/z: 631.25 (M+H$^+$).

Example 493: (S)-2-(4-(6-((4-cyano-2,6-difluorobenzyl)oxy)pyridin-2-yl)-2,5-difluorobenzyl)-1-(4,4-dimethyltetrahydrofuran-3-yl)-1H-benzo[d]imidazole-6-carboxylic acid (S)-2-(4-(6-((4-cyano-2,6-difluorobenzyl)oxy)pyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 35, starting with Intermediates I-1301 and I-82. 1H NMR (400 MHz, Acetonitrile-d3) δ 8.60 (s, 1H), 7.95-7.88 (m, 2H), 7.81 (t, J=7.8 Hz, 1H), 7.64 (d, J=8.5 Hz, 1H), 7.58 (dd, J=7.3, 1.6 Hz, 1H), 7.48 (d, J=6.7 Hz, 2H), 7.26 (dd, J=11.6, 6.0 Hz, 1H), 6.84 (d, J=8.2 Hz, 1H), 5.63 (s, 2H), 4.88 (d, J=6.9 Hz, 1H), 4.60 (dd, J=11.3, 1.4 Hz, 1H), 4.46 (dd, J=11.3, 6.8 Hz, 1H), 4.41 (d, J=5.9 Hz, 2H), 3.89 (d, J=8.7 Hz, 1H), 3.78 (d, J=8.6 Hz, 1H), 1.38 (s, 3H), 0.69 (s, 3H). ES/MS m/z: 631.3 (M+H$^+$).

Example 494: 2-(4-(6-((4-cyano-2-fluorobenzyl)oxy)pyridin-2-yl)-2,5-difluorobenzyl)-1-((3S,4R)-4-methyltetrahydrofuran-3-yl)-1H-benzo[d]imidazole-6-carboxylic acid 2-(4-(6-((4-cyano-2-fluorobenzyl)oxy)pyridin-2-yl)-2,5-difluorobenzyl)-1-((3S,4R)-4-methyltetrahydrofuran-3-yl)-1H-benzo[d]imidazole-6-carboxylic acid was prepared in a manner as described in Procedure 35, starting with Intermediates I-3 and I-1292. 1H NMR (400 MHz, Acetonitrile-d3) δ 8.60 (d, J=1.5 Hz, 1H), 7.89 (dd, J=8.5, 1.6 Hz, 1H), 7.84-7.75 (m, 2H), 7.72 (t, J=7.5 Hz, 1H), 7.62 (d, J=8.5 Hz, 1H), 7.58 (d, J=8.7 Hz, 2H), 7.54 (dd, J=7.5, 1.8 Hz, 1H), 7.23 (dd, J=11.5, 6.1 Hz, 1H), 6.91 (d, J=8.2 Hz, 1H), 5.62 (s, 2H), 5.27 (t, J=7.2 Hz, 1H), 4.57 (dd, J=10.9, 1.4 Hz, 1H), 4.41 (s, 2H), 4.26 (dd, J=11.0, 6.7 Hz, 1H), 4.16 (t, J=8.5 Hz, 1H), 3.70 (t, J=8.4 Hz, 1H), 2.91 (hept, J=7.1 Hz, 1H), 0.59 (d, J=7.1 Hz, 3H). ES/MS m/z: 599.3 (M+H$^+$).

Example 495: (S)-2-(4-(6-((4-chloro-2-fluorobenzyl)oxy)-5-fluoropyridin-2-yl)-2,5-difluorobenzyl)-1-(4,4-dimethyltetrahydrofuran-3-yl)-4-fluoro-1H-benzo[d]imidazole-6-carboxylic acid (S)-2-(4-(6-((4-chloro-2-fluorobenzyl)oxy)-5-fluoropyridin-2-yl)-2,5-difluorobenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1036 and I-108. 1H NMR (400 MHz, Acetonitrile-d3) δ 8.41 (s, 1H), 7.81 (dd, J=10.7, 6.5 Hz, 1H), 7.63-7.50 (m, 4H), 7.30-7.19 (m, 3H), 5.59 (d, J=1.1 Hz, 2H), 4.85 (d, J=6.6 Hz, 1H), 4.54 (dd, J=11.3, 1.6 Hz, 1H), 4.43 (dd, J=11.3, 6.8 Hz, 1H), 4.37 (d, J=7.1 Hz, 2H), 3.84 (d, J=8.8 Hz, 1H), 3.75 (d, J=8.7 Hz, 1H), 1.35 (s, 3H), 0.67 (s, 3H). ES/MS m/z: 658.2 (M+H$^+$).

Example 496: (S)-2-(4-(6-((4-cyano-2-fluorobenzyl)oxy)-5-fluoropyridin-2-yl)-2,5-difluorobenzyl)-1-(4,4-dimethyltetrahydrofuran-3-yl)-1H-benzo[d]imidazole-6-carboxylic acid (S)-2-(4-(6-((4-cyano-2-fluorobenzyl)oxy)-5-fluoropyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 35, starting with Intermediates I-109 and I-82. 1H NMR (400 MHz, Acetonitrile-d3) δ 8.58 (s, 1H), 7.89 (dd, J=8.5, 1.5 Hz, 1H), 7.79-7.71 (m, 2H), 7.65-7.52 (m, 5H), 7.24 (dd, J=11.6, 6.1 Hz, 1H), 5.70 (s, 2H), 4.86 (d, J=6.6 Hz, 1H), 4.59 (dd, J=11.2, 1.6 Hz, 1H), 4.45 (dd, J=11.3, 7.0 Hz, 1H), 4.38 (d, J=6.4 Hz, 2H), 3.88 (d, J=8.7 Hz, 1H), 3.78 (d, J=8.7 Hz, 1H), 1.37 (s, 3H), 0.68 (s, 3H). ES/MS m/z: 631.3 (M+H$^+$).

Example 497: (S)-2-(4-(6-((4-chloro-2-fluorobenzyl)oxy)-5-fluoropyridin-2-yl)-2,5-difluorobenzyl)-1-(4,4-dimethyltetrahydrofuran-3-yl)-1H-benzo[d]imidazole-6-carboxylic acid (S)-2-(4-(6-((4-chloro-2-fluorobenzyl)oxy)-5-fluoropyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 35, starting with Intermediates I-1036 and I-82. 1H NMR (400 MHz, Acetonitrile-d3) δ 8.56 (s, 1H), 7.87 (dd, J=8.5, 1.5 Hz, 1H), 7.80 (dd, J=10.8, 6.5 Hz, 1H), 7.64-7.47 (m, 4H), 7.32-7.16 (m, 3H), 5.59 (s, 2H), 4.85 (d, J=6.8 Hz, 1H), 4.56 (dd, J=11.1, 1.6 Hz, 1H), 4.48-4.42 (m, 1H), 4.42-4.30 (m, 2H), 3.86 (d, J=8.7 Hz, 1H), 3.75 (d, J=8.7 Hz, 1H), 1.34 (s, 3H), 0.65 (s, 3H). ES/MS m/z: 640.232 (M+H$^+$).

Example 498: (S)-2-(4-(6-((4-cyano-2,6-difluorobenzyl)oxy)pyridin-2-yl)-2,5-difluorobenzyl)-1-(4,4-dimethyltetrahydrofuran-3-yl)-4-fluoro-1H-benzo[d]imidazole-6-carboxylic acid (S)-2-(4-(6-((4-cyano-2,6-difluorobenzyl)oxy)pyridin-2-yl)-2,5-difluorobenzyl)-1-(4,4-dimethyltetrahydrofuran-3- yl)-4-fluoro-1H-benzo[d]imidazole-6-carboxylic acid was prepared in a manner as described in Procedure 35, starting with Intermediates I-1301 and I-108. 1H NMR (400 MHz, Acetonitrile-d3) δ 8.46 (s, 1H), 7.90 (dd, J=10.8, 6.4 Hz, 1H), 7.78 (t, J=7.9 Hz, 1H), 7.63 (dd, J=11.2, 1.2 Hz, 1H), 7.55 (dd, J=7.5, 1.8 Hz, 1H), 7.45 (d, J=6.7 Hz, 2H), 7.26 (dd, J=11.4, 6.1 Hz, 1H), 6.81 (d, J=8.2 Hz, 1H), 5.60 (s, 2H), 4.89 (d, J=6.7 Hz, 1H), 4.55 (dd, J=11.4, 1.5 Hz, 1H), 4.50-4.37 (m, 3H), 3.86 (d, J=8.8 Hz, 1H), 3.76 (d, J=8.8 Hz, 1H), 1.36 (s, 3H), 0.69 (s, 3H). ES/MS m/z: 649.2 (M+H$^+$).

Example 499: 2-(4-(6-((4-chloro-2,6-difluorobenzyl)oxy)pyridin-2-yl)-2,5-difluorobenzyl)-1-(4,4-dimethyltetrahydrofuran-3-yl)-4-fluoro-1H-benzo[d]imidazole-6-carboxylic acid 2-(4-(6-((4-chloro-2,6-difluorobenzyl)oxy)pyridin-2-yl)-2,5-difluorobenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1297 and I-1336. 1H NMR (400 MHz, DMSO-d6) δ 13.08 (s, 1H), 8.35 (s, 1H), 7.92 (dd, J=10.4, 6.4 Hz, 1H), 7.87 (t, J=7.9 Hz, 1H), 7.58-7.40 (m, 5H), 6.91 (d, J=8.2 Hz, 1H), 5.50 (s, 2H), 5.03 (d, J=6.6 Hz, 1H), 4.59-4.47 (m, 2H), 4.47-4.36 (m, 2H), 3.74 (q, J=8.7 Hz, 2H), 1.34 (s, 3H), 0.61 (s, 3H). ES/MS m/z: 658.1 (M+H$^+$).

Example 500: (S)-2-(4-(6-((4-cyano-2,3-difluorobenzyl)oxy)pyridin-2-yl)-2,5-difluorobenzyl)-1-(4,4-dimethyltetrahydrofuran-3-yl)-4-fluoro-1H-benzo[d]imidazole-6-carboxylic acid (S)-2-(4-(6-((4-cyano-2,3-difluorobenzyl)oxy)pyridin-2-yl)-2,5-difluorobenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1300 and I-108. 1H NMR (400 MHz, Acetonitrile-d$_3$) δ 8.48 (s, 1H), 7.83-7.72 (m, 2H), 7.65 (dd, J=11.1, 1.2 Hz, 1H), 7.56-7.44 (m, 3H), 7.25 (dd, J=11.5, 6.1 Hz, 1H), 6.90 (d, J=8.2 Hz, 1H), 5.61 (d, J=1.3 Hz, 2H), 4.91 (d, J=6.6 Hz, 1H), 4.54 (dd, J=11.5, 1.4 Hz, 1H), 4.48-4.37 (m, 3H), 3.86 (d, J=8.8 Hz, 1H), 3.76 (d, J=8.9 Hz, 1H), 1.35 (s, 3H), 0.69 (s, 3H). ES/MS m/z: 649.2 (M+H$^+$).

Example 501: 2-(4-(6-((4-chloro-2,5-difluorobenzyl)oxy)pyridin-2-yl)-2,5-difluorobenzyl)-1-(4,4-dimethyltetrahydrofuran-3-yl)-4-fluoro-1H-benzo[d]imidazole-6-carboxylic acid 2-(4-(6-((4-chloro-2,5-difluorobenzyl)oxy)pyridin-2-yl)-2,5-difluorobenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1284 and I-1336. 1H NMR (400 MHz, Acetonitrile-d$_3$) δ 8.49 (s, 1H), 7.82 (dd, J=10.8, 6.4 Hz, 1H), 7.76 (dd, J=8.3, 7.4 Hz, 1H), 7.67 (dd, J=11.0, 1.2 Hz, 1H), 7.50-7.39 (m, 2H), 7.33 (dd, J=9.2, 6.1 Hz, 1H), 7.25 (dd, J=11.5, 6.1 Hz, 1H), 6.87 (dd, J=8.3, 0.6 Hz, 1H), 5.47 (s, 2H), 4.93 (d, J=6.6 Hz, 1H), 4.57-4.46 (m, 3H), 4.47-4.37 (m, 1H), 3.85 (d, J=8.9 Hz, 1H), 3.76 (d, J=8.9 Hz, 1H), 1.34 (s, 3H), 0.69 (s, 3H). ES/MS m/z: 658.1 (M+H$^+$).

Example 502A: (S)-2-(4-(6-((4-(difluoromethyl)-2-fluorobenzyl)oxy)pyridin-2-yl)-2,5-difluorobenzyl)-1-(4,4-dimethyltetrahydrofuran-3-yl)-4-fluoro-1H-benzo[d]imidazole-6-carboxylic acid Example 502B: (R)-2-(4-(6-((4-(difluoromethyl)-2-fluorobenzyl)oxy)pyridin-2-yl)-2,5-difluorobenzyl)-1-(4,4-dimethyltetrahydrofuran-3-yl)-4-fluoro-1H-benzo[d]imidazole-6-carboxylic acid Example 502A and Example 502B were obtained from preparative chiral SFC (Daicel Chiraltek AD-H column, EtOH/CO$_2$ eluent) of Example 506.

(S)-2-(4-(6-((4-(difluoromethyl)-2-fluorobenzyl)oxy)pyridin-2-yl)-2,5-difluorobenzyl)-1-(4,4-dimethyltetrahydrofuran-3-yl)-4-fluoro-1H-benzo[d]imidazole-6-carboxylic acid (Example 502A) was isolated as the later-eluting of two stereoisomers. 1H NMR (400 MHz, Acetonitrile-d3) δ 8.49 (s, 1H), 7.89-7.81 (m, 1H), 7.79 (d, J=7.9 Hz, 1H), 7.70-7.62 (m, 2H), 7.54 (dd, J=7.4, 1.7 Hz, 1H), 7.40-7.33 (m, 2H), 7.25 (dd, J=11.4, 6.1 Hz, 1H), 6.89 (d, J=8.2 Hz, 1H), 6.78 (t, J=55.9 Hz, 1H), 5.59 (s, 2H), 4.90 (d, J=6.6 Hz, 1H), 4.55 (dd, J=11.5, 1.4 Hz, 1H), 4.48-4.38 (m, 3H), 3.86 (d, J=8.8 Hz, 1H), 3.76 (d, J=8.8 Hz, 1H), 1.35 (s, 3H), 0.69 (s, 3H). ES/MS m/z: 656.1 (M+H$^+$).

(R)-2-(4-(6-((4-(difluoromethyl)-2-fluorobenzyl)oxy)pyridin-2-yl)-2,5-difluorobenzyl)-1-(4,4-dimethyltetrahydrofuran-3-yl)-4-fluoro-1H-benzo[d]imidazole-6-carboxylic acid (Example 502B) was isolated as the earlier-eluting of two stereoisomers. 1H NMR (400 MHz, Acetonitrile-d3) δ 8.44 (s, 1H), 7.91-7.77 (m, 2H), 7.70 (t, J=7.7 Hz, 1H), 7.60 (dd, J=11.3, 1.2 Hz, 1H), 7.57 (dd, J=7.5, 1.8 Hz, 1H), 7.44-7.34 (m, 2H), 7.26 (dd, J=11.5, 6.1 Hz, 1H), 6.98-6.88 (m, 1H), 6.74 (d, J=55.9 Hz, 1H), 5.62 (s, 2H), 4.88 (d, J=6.5 Hz, 1H), 4.57 (dd, J=11.2, 1.5 Hz, 1H), 4.50-4.32 (m, 3H), 3.87 (d, J=8.7 Hz, 1H), 3.77 (d, J=8.8 Hz, 1H), 1.38 (s, 3H), 0.69 (s, 3H). ES/MS m/z: 656.2 (M+H$^+$).

Example 503: 2-(2,5-difluoro-4-(5-fluoro-6-((2-fluoro-4-(trifluoromethyl)benzyl)oxy)pyridin-2-yl)benzyl)-1-(4,4-dimethyltetrahydrofuran-3-yl)-4-fluoro-1H-benzo[d]imidazole-6-carboxylic acid 2-(2,5-difluoro-4-(5-fluoro-6-((2-fluoro-4-(trifluoromethyl)benzyl)oxy)pyridin-2-yl)benzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1302 and I-1336. 1H NMR (400 MHz, Acetonitrile-d3) δ 8.41 (s, 1H), 7.80-7.72 (m, 2H), 7.63-7.48 (m, 5H), 7.23 (dd, J=11.5, 6.1 Hz, 1H), 5.69 (s, 2H), 4.85 (d, J=6.7 Hz, 1H), 4.55 (d, J=11.2 Hz, 1H), 4.45 (d, J=8.1 Hz, 1H), 4.42-4.29 (m, 2H), 3.84 (d, J=8.8 Hz, 1H), 3.75 (d, J=8.9 Hz, 1H), 1.35 (s, 3H), 0.66 (s, 3H). ES/MS m/z: 692.1 (M+H$^+$).

Example 504: 2-(4-(2-((4-(difluoromethyl)-2-fluorobenzyl)oxy)pyrimidin-4-yl)-2,5-difluorobenzyl)-1-(4,4-dimethyltetrahydrofuran-3-yl)-4-fluoro-1H-benzo[d]imidazole-6-carboxylic acid 2-(4-(2-((4-(difluoromethyl)-2-fluorobenzyl)oxy)pyrimidin-4-yl)-2,5-difluorobenzyl)-1-(4,4-dimethyltetrahydrofuran-3-yl)-4-fluoro-1H-benzo[d]imidazole-6-carboxylic acid was prepared in a manner as described in Procedure 35, starting with Intermediates I-1303 and I-1336. 1H NMR (400 MHz, Acetonitrile-d3) δ 8.65 (d, J=5.2 Hz, 1H), 8.45 (s, 1H), 7.95 (dd, J=10.4, 6.2 Hz, 1H), 7.69 (t, J=7.6 Hz, 1H), 7.62 (dd, J=11.1, 1.2 Hz, 1H), 7.58 (dd, J=5.2, 1.8 Hz, 1H), 7.42-7.35 (m, 2H), 7.30 (dd, J=11.5, 5.9 Hz, 1H), 6.79 (t, J=55.9 Hz, 1H), 5.61 (s, 2H), 4.88 (d, J=6.7 Hz, 1H), 4.55 (d, J=11.4 Hz, 1H), 4.50-4.36 (m, 3H), 3.85 (d, J=8.8 Hz, 1H), 3.76 (d, J=8.8 Hz, 1H), 1.35 (s, 3H), 0.68 (s, 3H). ES/MS m/z: 657.1 (M+H$^+$).

Example 505: racemic 2-(4-(6-((4-cyano-2-fluorobenzyl)oxy)pyridin-2-yl)-2,5-difluorobenzyl)-1-((3R,4S)-4-methyltetrahydrofuran-3-yl)-1H-benzo[d]imidazole-6-carboxylic acid Racemic 2-(4-(6-((4-cyano-2-fluorobenzyl)oxy)pyridin-2-yl)-2,5-difluorobenzyl)-1-((3R,4S)-4-methyltetrahydrofuran-3-yl)-1H-benzo[d]imidazole-6-carboxylic acid was prepared in a manner as described in Procedure 36, starting with Intermediates I-7 and I-1289. 1H NMR (400 MHz, DMSO-d6) δ 8.50 (s, 1H), 7.94-7.87 (m, 2H), 7.81-7.71 (m, 3H), 7.61 (d, J=8.4 Hz, 1H), 7.54 (d, J=7.2 Hz, 1H), 7.44 (dd, J=11.4, 6.3 Hz, 2H), 6.99 (d, J=8.2 Hz, 1H), 5.60 (s, 2H), 5.42 (t, J=7.1 Hz, 1H), 4.56-4.39 (m, 3H), 4.26-4.17 (m, 1H), 4.12 (t, J=8.5 Hz, 1H), 3.59 (t, J=8.5 Hz, 1H), 2.92-2.82 (m, 1H), 0.52 (d, J=7.0 Hz, 3H). ES/MS m/z: 599.2 (M+H$^+$).

Example 506: 2-(4-(6-((4-(difluoromethyl)-2-fluorobenzyl)oxy)pyridin-2-yl)-2,5-difluorobenzyl)-1-(4,4-dimethyltetrahydrofuran-3-yl)-4-fluoro-1H-benzo[d]imidazole-6-carboxylic acid 2-(4-(6-((4-(difluoromethyl)-2-fluorobenzyl)oxy)pyridin-2-yl)-2,5-difluorobenzyl)-1-(4,4-dimethyltetrahydrofuran-3-yl)-4-fluoro-1H-benzo[d]imidazole-6-carboxylic acid was prepared in a manner as described in Procedure 36, starting with Intermediates I-1305 and I-1336. 1H NMR (400 MHz, Acetonitrile-d3) δ 8.41 (s, 1H), 7.88-7.77 (m, 2H), 7.67 (t, J=7.7 Hz, 1H), 7.62 (d, J=11.0 Hz, 1H), 7.58-7.51 (m, 1H), 7.41-7.32 (m, 2H), 7.23 (dd, J=11.5, 6.1 Hz, 1H), 6.94-6.61 (m, 3H), 5.60 (s, 2H), 4.87 (d, J=6.7 Hz, 1H), 4.57 (d, J=11.4 Hz, 1H), 4.52-4.45 (m, 1H), 4.45-4.32 (m, 2H), 3.85 (d, J=8.8 Hz, 1H), 3.83-3.74 (m, 1H), 1.35 (s, 3H), 0.67 (s, 3H). ES/MS m/z: 656.1 (M+H$^+$).

Example 507: 2-(4-(6-((4-chloro-2-fluorobenzyl)oxy)pyridin-2-yl)-2,5-difluorobenzyl)-1-(3-methoxy-3-methylbutan-2-yl)-1H-benzo[d]imidazole-6-carboxylic acid 2-(4-(6-((4-chloro-2-fluorobenzyl)oxy)pyridin-2-yl)-2,5-difluorobenzyl)-1-(3-methoxy-3-methylbutan-2-yl)-1H-benzo[d]imidazole-6-carboxylic acid was prepared in a manner as described in Procedure 35, starting with Intermediates I-102 and I-1307. 1H NMR (400 MHz, Acetonitrile-d3) δ 8.58 (dd, J=1.6, 0.6 Hz, 1H), 7.87-7.77 (m, 2H), 7.77-7.72 (m, 1H), 7.59-7.47 (m, 3H), 7.28-7.20 (m, 2H), 7.16 (dd, J=11.5, 6.1 Hz, 1H), 6.84 (dd, J=8.3, 0.7 Hz, 1H), 5.51 (d, J=1.0 Hz, 2H), 4.55 (q, J=7.1 Hz, 1H), 4.38 (d, J=2.4 Hz, 2H), 3.18 (s, 2H), 1.64 (d, J=7.1 Hz, 3H), 1.34 (s, 3H), 1.02 (s, 3H). ES/MS m/z: 624.1 (M+H$^+$).

Example 508: (S)-2-((3'-((4-chloro-2-fluorobenzyl)oxy)-2,5-difluoro-[1,1'-biphenyl]-4-yl)methyl)-1-(4,4-dimethyltetrahydrofuran-3-yl)-1H-benzo[d]imidazole-6-carboxylic acid (S)-2-((3'-((4-chloro-2-fluorobenzyl)oxy)-2,5-difluoro-[1,1'-biphenyl]-4-yl)methyl)-1-(4,4-dimethyltetrahydrofuran-3-yl)-1H-benzo[d]imidazole-6-carboxylic acid was prepared in a manner as described in Procedure 35, starting with Intermediates I-1308 and I-82. 1H NMR (400 MHz, Acetonitrile-d$_3$) δ 8.55 (s, 1H), 7.87 (dd, J=8.5, 1.5 Hz, 1H), 7.60 (d, J=8.5 Hz, 1H), 7.53 (t, J=8.2 Hz, 1H), 7.39 (t, J=7.9 Hz, 1H), 7.32 (dd, J=10.2, 6.4 Hz, 1H), 7.31-7.13 (m, 5H), 7.04 (ddd, J=8.4, 2.6, 1.0 Hz, 1H), 5.16 (s, 2H), 4.84 (dd, J=6.9, 1.6 Hz, 1H), 4.55 (dd, J=11.2, 1.6 Hz, 1H), 4.43 (dd, J=11.2, 6.9 Hz, 1H), 4.35 (d, J=6.5 Hz, 2H), 3.85 (d, J=8.7 Hz, 1H), 3.75 (d, J=8.7 Hz, 1H), 1.34 (s, 3H), 0.65 (s, 3H). ES/MS m/z: 621.2 (M+H$^+$).

Example 509: (S)-2-((3'-((4-chloro-2-fluorobenzyl)oxy)-2,4',5-trifluoro-[1,1'-biphenyl]-4-yl)methyl)-1-(4,4-dimethyltetrahydrofuran-3-yl)-1H-benzo[d]imidazole-6-carboxylic acid (S)-2-((3'-((4-chloro-2-fluorobenzyl)oxy)-2,4',5-trifluoro-[1,1'-biphenyl]-4-yl)methyl)-1-(4,4-dimethyltetrahydrofuran-3-yl)-1H-benzo[d]imidazole-6-carboxylic acid was prepared in a manner as described in Procedure 35, starting with Intermediates I-1309 and I-82. 1H NMR (400 MHz, Acetonitrile-d3) δ 8.55 (s, 1H), 7.87 (dd, J=8.5, 1.5 Hz, 1H), 7.60 (d, J=8.5 Hz, 1H), 7.53 (t, J=8.2 Hz, 1H), 7.39-7.10 (m, 7H), 5.19 (s, 2H), 4.84 (dd, J=6.9, 1.6 Hz, 1H), 4.55 (dd, J=11.2, 1.6 Hz, 1H), 4.42 (dd, J=11.1, 6.8 Hz, 1H), 4.35 (d, J=6.6 Hz, 2H), 3.85 (d, J=8.7 Hz, 1H), 3.74 (d, J=8.7 Hz, 1H), 1.34 (s, 3H), 0.64 (s, 3H). ES/MS m/z: 639.2 (M+H$^+$).

Example 510: 2-(4-(6-((4-chloro-2-fluorobenzyl)oxy)pyridin-2-yl)-2,5-difluorobenzyl)-1-(2-methoxy-2-methylpropyl)-1H-benzo[d]imidazole-6-carboxylic acid 2-(4-(6-((4-chloro-2-fluorobenzyl)oxy)pyridin-2-yl)-2,5-difluorobenzyl)-1-(2-methoxy-2-methylpropyl)-1H-benzo[d]imidazole-6-carboxylic acid was prepared in a manner as described in Procedure 35, starting with Intermediates I-102 and I-1311. 1H NMR (400 MHz, Acetonitrile-d3) δ 8.24 (s, 1H), 7.91-7.73 (m, 3H), 7.61-7.48 (m, 3H), 7.29-7.13 (m, 3H), 6.84 (d, J=8.2 Hz, 1H), 5.52 (s, 2H), 4.44 (s, 2H), 4.30 (s, 2H), 3.14 (s, 3H), 1.22 (s, 6H). ES/MS m/z: 610.2 (M+H$^+$).

Example 511: 2-(4-(6-((4-cyanobenzyl)oxy)pyridin-2-yl)-2,5-difluorobenzyl)-1-(2-methoxyethyl)-1H-benzo[d]imidazole-6-carboxylic acid 2-(4-(6-((4-cyanobenzyl)oxy)pyridin-2-yl)-2,5-difluorobenzyl)-1-(2-methoxyethyl)-1H-benzo[d]imidazole-6-carboxylic acid was prepared in a manner as described in Procedure 6, starting with Intermediates I-17 and 4-(bromomethyl)benzonitrile. 1H NMR (400 MHz, Methanol-d4) δ 8.25 (s, 1H), 7.97 (dd, J=8.5, 1.5 Hz, 1H), 7.78 (t, J=7.9 Hz, 1H), 7.75-7.60 (m, 6H), 7.51 (d, J=7.4 Hz, 1H), 7.12 (dd, J=11.6, 6.0 Hz, 1H), 6.90 (d, J=8.3 Hz, 1H), 5.57 (s, 2H), 4.55 (t, J=5.1 Hz, 2H), 4.47 (s, 2H), 3.72 (t, J=5.0 Hz, 2H), 3.25 (s, 3H). ES/MS m/z: 555.3 (M+H$^+$).

Example 512: (S)-2-(2,5-difluoro-4-(6-((1-methyl-1H-benzo[d][1,2,3]triazol-5-yl)methoxy)pyridin-2-yl)benzyl)-1-(4,4-dimethyltetrahydrofuran-3-yl)-1H-benzo[d]imidazole-6-carboxylic acid (S)-2-(2,5-difluoro-4-(6-((1-methyl-1H-benzo[d][1,2,3]triazol-5-yl)methoxy)pyridin-2-yl)benzyl)-1-(4,4-dimethyltetrahydrofuran-3-yl)-1H-benzo[d]imidazole-6-carboxylic acid was prepared in a manner as described in Procedure 35, starting with Intermediates I-1035 and I-82. 1H NMR (400 MHz, DMSO-d6) δ 8.50 (s, 1H), 8.15 (s, 1H), 7.96-7.83 (m, 3H), 7.82 (dd, J=8.5, 1.5 Hz, 1H), 7.71 (dd, J=8.6, 1.4 Hz, 1H), 7.63 (d, J=8.4 Hz, 1H), 7.53 (dd, J=7.5, 1.5 Hz, 1H), 7.47 (dd, J=11.1, 6.4 Hz, 1H), 6.99 (d, J=8.3 Hz, 1H), 5.65 (s, 2H), 5.03 (d, J=6.6 Hz, 1H), 4.63-4.54 (m, 1H), 4.53 (s, 1H), 4.49-4.35 (m, 2H), 4.31 (s, 3H), 3.81-3.70 (m, 2H), 1.34 (s, 3H), 0.61 (s, 3H). ES/MS m/z: 624.6 (M+H$^+$).

Example 513: (S)-2-(2,5-difluoro-4-(6-((1-methyl-1H-benzo[d][1,2,3]triazol-6-yl)methoxy)pyridin-2-yl)benzyl)-1-(4,4-dimethyltetrahydrofuran-3-yl)-1H-benzo[d]imidazole-6-carboxylic acid (S)-2-(2,5-difluoro-4-(6-((1-methyl-1H-benzo[d][1,2,3]triazol-6-yl)methoxy)pyridin-2-yl)benzyl)-1-(4,4-dimethyltetrahydrofuran-3-yl)-1H-benzo[d]imidazole-6-carboxylic acid was prepared in a manner as described in Procedure 35, starting with Intermediates I-1034 and I-82. 1H NMR (400 MHz, DMSO-d6) δ 8.49 (s, 1H), 8.04 (d, J=8.6 Hz, 1H), 8.01 (s, 1H), 7.90 (t, J=7.9 Hz, 1H), 7.87-7.78 (m, 2H), 7.62 (d, J=8.5 Hz, 1H), 7.54 (ddd, J=7.6, 5.1, 1.4 Hz, 2H), 7.46 (dd, J=11.4, 6.2 Hz, 1H), 7.00 (d, J=8.2 Hz, 1H), 5.67 (s, 2H), 5.02 (d, J=6.6 Hz, 1H), 4.64-4.48 (m, 2H), 4.48-4.32 (m, 2H), 4.30 (s, 3H), 3.82-3.72 (m, 2H), 1.34 (s, 3H), 0.61 (s, 3H). ES/MS m/z: 624.6 (M+H$^+$).

Example 514: 2-(2,5-difluoro-4-(6-((2-(methylsulfonyl)isoindolin-5-yl)methoxy)pyridin-2-yl)benzyl)-4-fluoro-1-(2-methoxyethyl)-1H-benzo[d]imidazole-6-carboxylic acid 2-(2,5-difluoro-4-(6-((2-(methylsulfonyl)isoindolin-5-yl)methoxy)pyridin-2-yl)benzyl)-4-fluoro-1-(2-methoxyethyl)-1H-benzo[d]imidazole-6-carboxylic acid was prepared in a manner as described in Procedure 35, starting with Intermediates I-1022 and I-1033. 1H NMR (400 MHz, DMSO-d6) δ 8.10 (d, J=1.3 Hz, 1H), 7.91-7.78 (m, 2H), 7.54-7.42 (m, 3H), 7.39 (dd, J=11.6, 6.1 Hz, 1H), 7.35 (d, J=7.8 Hz, 1H), 6.93 (d, J=8.2 Hz, 1H), 5.48 (s, 2H), 4.71-4.53 (m, 6H), 4.46 (s, 2H), 3.68 (t, J=5.0 Hz, 2H), 3.21 (s, 3H), 2.96 (s, 3H). ES/MS m/z: 666.6 (M+H$^+$).

Example 515: (S)-2-(2,5-difluoro-4-(5-fluoro-6-((2-(methoxycarbonyl)isoindolin-5-yl)methoxy)pyridin-2-yl)benzyl)-4-fluoro-1-(oxetan-2-ylmethyl)-1H-benzo[d]imidazole-6-carboxylic acid (S)-2-(2,5-difluoro-4-(5-fluoro-6-((2-(methoxycarbonyl)isoindolin-5-yl)methoxy)pyridin-2-yl)benzyl)-4-fluoro-1-(oxetan-2-ylmethyl)-1H-benzo[d]imidazole-6-carboxylic acid was prepared in a manner as described in Procedure 40, starting with Intermediates I-1029 and I-5. 1H NMR (400 MHz, Methanol-d4) δ 8.15 (d, J=1.3 Hz, 1H), 7.75 (dd, J=10.8, 6.4 Hz, 1H), 7.66 (d, J=11.3 Hz, 1H), 7.59 (dd, J=9.9, 8.2 Hz, 1H), 7.55-7.42 (m, 3H), 7.39-7.30 (m, 1H), 7.18 (dd, J=11.5, 6.0 Hz, 1H), 5.58 (s, 2H), 5.18 (d, J=7.5 Hz, 1H), 4.78-4.65 (m, 6H), 4.65-4.31 (m, 4H), 3.78 (d, J=1.7 Hz, 3H), 2.90-2.60 (m, 1H), 2.56-2.36 (m, 1H). ES/MS m/z: 676.6 (M+H$^+$).

Example 516: (S)-2-(2,5-difluoro-4-(5-fluoro-6-((2-(methoxycarbonyl)isoindolin-5-yl)methoxy)pyridin-2-yl)benzyl)-1-(oxetan-2-ylmethyl)-1H-benzo[d]imidazole-6-carboxylic acid (S)-2-(2,5-difluoro-4-(5-fluoro-6-((2-(methoxycarbonyl)isoindolin-5-yl)methoxy)pyridin-2-yl)benzyl)-1-(oxetan-2-ylmethyl)-1H-benzo[d]imidazole-6-carboxylic acid was prepared in a manner as described in Procedure 22, starting with Intermediates I-1029 and I-4. 1H NMR (400 MHz, Methanol-d4) δ 8.27 (s, 1H), 8.02-7.92 (m, 1H), 7.75 (dd, J=10.7, 6.2 Hz, 1H), 7.67-7.54 (m, 2H), 7.54-7.43 (m, 3H), 7.33 (d, J=8.1 Hz, 0H), 7.17 (dd, J=11.5, 6.0 Hz, 1H), 5.59 (s, 2H), 5.20 (d, J=10.9 Hz, 1H), 4.73 (s, 5H), 4.68-4.50 (m, 3H), 4.50-4.36 (m, 1H), 3.78 (d, J=1.9 Hz, 3H), 2.78 (s, 1H), 2.51 (s, 1H). ES/MS m/z: 658.6 (M+H$^+$).

Example 517: (S)-2-(2,5-difluoro-4-(6-((2-(methylsulfonyl)isoindolin-5-yl)methoxy)pyridin-2-yl)benzyl)-4-fluoro-1-(oxetan-2-ylmethyl)-1H-benzo[d]imidazole-6-carboxylic acid (S)-2-(2,5-difluoro-4-(6-((2-(methylsulfonyl)isoindolin-5-yl)methoxy)pyridin-2-yl)benzyl)-4-fluoro-1-(oxetan-2-ylmethyl)-1H-benzo[d]imidazole-6-carboxylic acid was prepared in a manner as described in Procedure 40, starting with Intermediates I-1027 and I-5. 1H NMR (400 MHz, Methanol-d4) δ 8.15 (s, 1H), 7.84-7.71 (m, 2H), 7.67 (d, J=11.3 Hz, 1H), 7.54-7.40 (m, 3H), 7.33 (d, J=7.9 Hz, 1H), 7.18 (dd, J=11.5, 6.1 Hz, 1H), 6.87 (d, J=8.2 Hz, 1H), 5.51 (s, 2H), 5.17 (d, J=8.1 Hz, 1H), 4.70 (d, J=4.3 Hz, 5H), 4.66-4.48 (m, 4H), 4.45 (dt, J=9.0, 5.9 Hz, 1H), 2.91 (s, 3H), 2.79 (s, 1H), 2.55-2.41 (m, 1H). ES/MS m/z: 678.6 (M+H$^+$).

Example 518: (S)-2-(4-(6-((4-cyano-2-fluorobenzyl)oxy)pyridin-2-yl)-2,5-difluorobenzyl)-4-fluoro-1-(2-methoxypropyl)-1H-benzo[d]imidazole-6-carboxylic acid (S)-2-(4-(6-((4-cyano-2-fluorobenzyl)oxy)pyridin-2-yl)-2,5-difluorobenzyl)-4-fluoro-1-(2-methoxypropyl)-1H-benzo[d]imidazole-6-carboxylic acid was prepared in a manner as described in Procedure 40, starting with Intermediates I-7 and I-1270. 1H NMR (400 MHz, DMSO-d6) δ 8.12 (d, J=1.3 Hz, 1H), 7.97-7.85 (m, 2H), 7.75 (ddd, J=9.7, 7.8, 6.5 Hz, 3H), 7.58-7.44 (m, 2H), 7.39 (dd, J=11.5, 6.1 Hz, 1H), 6.99 (d, J=8.3 Hz, 1H), 5.60 (s, 2H), 4.53 (dd, J=15.2, 3.2 Hz, 1H), 4.46 (s, 2H), 4.36 (dd, J=15.2, 8.8 Hz, 1H), 3.76-3.61 (m, 1H), 3.08 (s, 3H), 1.23 (d, J=6.2 Hz, 3H). ES/MS m/z: 605.5 (M+H$^+$).

Example 519: (S)-2-(2,5-difluoro-4-(6-((2-(methylsulfonyl)isoindolin-5-yl)methoxy)pyridin-2-yl)benzyl)-1-(oxetan-2-ylmethyl)-1H-benzo[d]imidazole-6-carboxylic acid (S)-2-(2,5-difluoro-4-(6-((2-(methylsulfonyl)isoindolin-5-yl)methoxy)pyridin-2-yl)benzyl)-1-(oxetan-2-ylmethyl)-1H-benzo[d]imidazole-6-carboxylic acid was prepared in a manner as described in Procedure 35, starting with Intermediates I-1022 and I-8. 1H NMR (400 MHz, Methanol-d4) δ 8.30 (s, 1H), 7.99 (dd, J=8.5, 1.5 Hz, 1H), 7.86-7.73 (m, 2H), 7.66 (d, J=8.5 Hz, 1H), 7.56-7.49 (m, 1H), 7.46 (d, J=10.9 Hz, 2H), 7.33 (d, J=7.8 Hz, 1H), 7.18 (dd, J=11.6, 6.0 Hz, 1H), 6.87 (d, J=8.2 Hz, 1H), 5.51 (s, 2H), 5.21 (d, J=8.8 Hz, 1H), 4.79-4.65 (m, 5H), 4.65-4.35 (m, 4H), 2.91 (s, 3H), 2.87-2.69 (m, 1H), 2.51 (d, J=11.2 Hz, 0H). ES/MS m/z: 661.2 (M+H$^+$).

Example 520: (S)-2-(4-(6-((2-(cyclopropanecarbonyl)isoindolin-5-yl)methoxy)pyridin-2-yl)-2,5-difluorobenzyl)-1-(oxetan-2-ylmethyl)-1H-benzo[d]imidazole-6-carboxylic acid (S)-2-(4-(6-((2-(cyclopropanecarbonyl)isoindolin-5-yl)methoxy)pyridin-2-yl)-2,5-difluorobenzyl)-1-(oxetan-2-ylmethyl)-1H-benzo[d]imidazole-6-carboxylic acid was prepared in a manner as described in Procedure 35, starting with Intermediates I-1021 and I-8. 1H NMR (400 MHz, Methanol-d4) δ 8.31 (d, J=1.4 Hz, 1H), 7.99 (dd, J=8.5, 1.5 Hz, 1H), 7.85-7.72 (m, 2H), 7.67 (d, J=8.5 Hz, 1H), 7.56-7.43 (m, 3H), 7.36 (dd, J=7.9, 3.8 Hz, 1H), 7.24-7.09 (m, 1H), 6.87 (d, J=8.2 Hz, 1H), 5.52 (d, J=2.5 Hz, 2H), 5.19 (td, J=7.2, 2.5 Hz, 1H), 5.08 (d, J=4.3 Hz, 2H), 4.77 (d, J=6.9 Hz, 2H), 4.73-4.37 (m, 6H), 2.88-2.67 (m, 1H), 2.50 (dq, J=11.4, 7.7 Hz, 1H), 1.97-1.84 (m, 1H), 0.97 (dq, J=6.0, 3.1 Hz, 2H), 0.91 (ddt, J=8.8, 6.0, 2.8 Hz, 2H). ES/MS m/z: 651.2 (M+H$^+$).

Example 521: (S)-2-(2,5-difluoro-4-(6-((2-(methoxycarbonyl)isoindolin-5-yl)methoxy)pyridin-2-yl)benzyl)-1-(oxetan-2-ylmethyl)-1H-benzo[d]imidazole-6-carboxylic acid (S)-2-(2,5-difluoro-4-(6-((2-(methoxycarbonyl)isoindolin-5-yl)methoxy)pyridin-2-yl)benzyl)-1-(oxetan-2-ylmethyl)-1H-benzo[d]imidazole-6-carboxylic acid was prepared in a manner as described in Procedure 35, starting with Intermediates I-1016 and I-8. 1H NMR (400 MHz, Methanol-d4) δ 8.31 (s, 1H), 7.99 (dd, J=8.5, 1.5 Hz, 1H), 7.86-7.70 (m, 2H), 7.67 (d, J=8.5 Hz, 1H), 7.53-7.41 (m, 3H), 7.36-7.25 (m, 1H), 7.17 (dd, J=11.4, 6.0 Hz, 1H), 6.87 (d, J=8.3 Hz, 1H), 5.50 (s, 2H), 5.20 (d, J=7.2 Hz, 1H), 4.72 (q, J=3.8, 3.2 Hz, 6H), 4.66-4.34 (m, 4H), 3.78 (d, J=1.9 Hz, 3H), 2.91-2.74 (m, 1H), 2.50 (dt, J=17.5, 7.8 Hz, 1H). ES/MS m/z: 641.2 (M+H$^+$).

Example 522: (S)-2-(4-(6-((2-acetylisoindolin-5-yl)methoxy)pyridin-2-yl)-2,5-difluorobenzyl)-1-(oxetan-2-ylmethyl)-1H-benzo[d]imidazole-6-carboxylic acid (S)-2-(4-(6-((2-acetylisoindolin-5-yl)methoxy)pyridin-2-yl)-2,5-difluorobenzyl)-1-(oxetan-2-ylmethyl)-1H-benzo[d]imidazole-6-carboxylic acid was prepared in a manner as described in Procedure 35, starting with Intermediates I-1015 and I-8. 1H NMR (400 MHz, Methanol-d4) δ 8.31 (s, 1H), 7.99 (dd, J=8.5, 1.5 Hz, 1H), 7.79 (q, J=8.7, 7.8 Hz, 2H), 7.67 (d, J=8.5 Hz, 1H), 7.58-7.42 (m, 3H), 7.42-7.27 (m, 1H), 7.26-7.13 (m, 1H), 6.87 (d, J=8.3 Hz, 1H), 5.52 (s, 2H), 5.30-5.12 (m, 1H), 4.73 (dd, J=16.6, 7.0 Hz, 3H), 4.66-4.37 (m, 5H), 2.91-2.65 (m, 1H), 2.60-2.39 (m, 1H), 2.18 (d, J=5.9 Hz, 3H). ES/MS m/z: 625.2 (M+H$^+$).

Example 523: (S)-2-(2,5-difluoro-4-(6-((1-methyl-1H-benzo[d][1,2,3]triazol-5-yl)methoxy)pyridin-2-yl)benzyl)-1-(oxetan-2-ylmethyl)-1H-benzo[d]imidazole-6-carboxylic acid (S)-2-(2,5-difluoro-4-(6-((1-methyl-1H-benzo[d][1,2,3]triazol-5-yl)methoxy)pyridin-2-yl)benzyl)-1-(oxetan-2-ylmethyl)-1H-benzo[d]imidazole-6-carboxylic acid was prepared in a manner as described in Procedure 27, starting with Intermediate I-9 and 5-(bromomethyl)-1-methyl-benzotriazole. 1H NMR (400 MHz, Methanol-d4) δ 8.32 (s, 1H), 8.10 (s, 1H), 8.00 (dd, J=8.5, 1.5 Hz, 1H), 7.89-7.71 (m, 4H), 7.66 (s, 1H), 7.53 (d, J=7.4 Hz, 1H), 7.18 (dd, J=11.4, 6.0 Hz, 1H), 6.92 (d, J=8.3 Hz, 1H), 5.68 (s, 2H), 5.20 (q, J=6.8 Hz, 1H), 4.74 (dd, J=15.7, 6.9 Hz, 1H), 4.68-4.47 (m, 4H), 4.45 (dt, J=9.3, 5.9 Hz, 1H), 4.35 (d, J=1.0 Hz, 3H), 2.80 (dt, J=15.9, 7.7 Hz, 1H), 2.58-2.38 (m, 1H). ES/MS m/z: 597.2 (M+H$^+$).

Example 524: (S)-2-(2,5-difluoro-4-(6-((1-methyl-1H-indazol-6-yl)methoxy)pyridin-2-yl)benzyl)-1-(oxetan-2-ylmethyl)-1H-benzo[d]imidazole-6-carboxylic acid (S)-2-(2,5-difluoro-4-(6-((1-methyl-1H-indazol-6-yl)methoxy)pyridin-2-yl)benzyl)-1-(oxetan-2-ylmethyl)-1H-benzo[d]imidazole-6-carboxylic acid was prepared in a manner as described in Procedure 27, starting with Intermediate I-9 and 6-(bromomethyl)-1-methyl-indazole. 1H NMR (400 MHz, Methanol-d4) δ 8.31 (d, J=1.5 Hz, 1H), 8.02-7.93 (m, 2H), 7.87-7.72 (m, 4H), 7.71-7.61 (m, 2H), 7.52 (dd, J=7.5, 1.6 Hz, 1H), 7.32 (dd, J=8.4, 1.2 Hz, 1H), 7.17 (dd, J=11.5, 6.0 Hz, 1H), 6.91 (d, J=8.2 Hz, 1H), 5.64 (s, 2H), 5.19 (qd, J=7.1, 2.5 Hz, 1H), 4.72 (dd, J=15.7, 6.9 Hz, 1H), 4.67-4.48 (m, 5H), 4.48-4.34 (m, 1H), 4.06 (s, 3H), 2.91-2.65 (m, 1H), 2.58-2.40 (m, 1H). ES/MS m/z: 596.2 (M+H$^+$).

Example 525: (S)-2-(2,5-difluoro-4-(6-((1-methyl-1H-benzo[d][1,2,3]triazol-6-yl)methoxy)pyridin-2-yl)benzyl)-1-(oxetan-2-ylmethyl)-1H-benzo[d]imidazole-6-carboxylic acid (S)-2-(2,5-difluoro-4-(6-((1-methyl-1H-benzo[d][1,2,3]triazol-6-yl)methoxy)pyridin-2-yl)benzyl)-1-(oxetan-2-ylmethyl)-1H-benzo[d]imidazole-6-carboxylic acid was prepared in a manner as described in Procedure 27, starting with Intermediate I-9 and I-1014. 1H NMR (400 MHz, Methanol-d4) δ 8.31 (d, J=1.4 Hz, 1H), 8.00 (d, J=2.1 Hz, 1H), 7.98 (d, J=2.2 Hz, 1H), 7.92 (s, 1H), 7.86-7.73 (m, 2H), 7.66 (d, J=8.5 Hz, 1H), 7.60 (dd, J=8.7, 1.3 Hz, 1H), 7.53 (dd, J=7.5, 1.5 Hz, 1H), 7.18 (dd, J=11.4, 6.0 Hz, 1H), 6.93 (d, J=8.2 Hz, 1H), 5.70 (s, 2H), 5.19 (dd, J=7.2, 2.5 Hz, 1H), 4.72 (dd, J=15.7, 6.9 Hz, 1H), 4.67-4.49 (m, 4H), 4.48-4.36 (m, 1H), 4.33 (s, 3H), 2.79 (ddt, J=14.2, 11.6, 6.8 Hz, 1H), 2.56-2.41 (m, 1H). ES/MS m/z: 597.2 (M+H$^+$).

Example 526: (S)-2-(2,5-difluoro-4-(6-((1-methyl-1H-indazol-5-yl)methoxy)pyridin-2-yl)benzyl)-1-(oxetan-2-ylmethyl)-1H-benzo[d]imidazole-6-carboxylic acid (S)-2-(2,5-difluoro-4-(6-((1-methyl-1H-indazol-5-yl)methoxy)pyridin-2-yl)benzyl)-1-(oxetan-2-ylmethyl)-1H-benzo[d]imidazole-6-carboxylic acid was prepared in a manner as described in Procedure 27, starting with Intermediates I-9 and 5-(bromomethyl)-1-methyl-indazole. 1H NMR (400 MHz, Methanol-d4) δ 8.31 (d, J=1.4 Hz, 1H), 7.99 (d, J=9.1 Hz, 2H), 7.91-7.81 (m, 2H), 7.76 (q, J=6.7, 5.5 Hz, 1H), 7.67 (d, J=8.5 Hz, 1H), 7.63-7.53 (m, 2H), 7.51 (dd, J=7.5, 1.6 Hz, 1H), 7.18 (dd, J=11.4, 6.0 Hz, 1H), 6.86 (d, J=8.2 Hz, 1H), 5.59 (s, 2H), 5.20 (qd, J=7.2, 2.5 Hz, 1H), 4.81-4.67 (m, 1H), 4.67-4.49 (m, 4H), 4.49-4.35 (m, 1H), 4.07 (d, J=0.9 Hz, 3H), 2.89-2.71 (m, 1H), 2.64-2.38 (m, 1H). ES/MS m/z: 596.2 (M+H$^+$).

Example 527: (S)-2-(4-(6-(benzo[c][1,2,5]thiadiazol-5-ylmethoxy)pyridin-2-yl)-2,5-difluorobenzyl)-1-(oxetan-2-ylmethyl)-1H-benzo[d]imidazole-6-carboxylic acid (S)-2-(4-(6-(benzo[c][1,2,5]thiadiazol-5-ylmethoxy)pyridin-2-yl)-2,5-difluorobenzyl)-1-(oxetan-2-ylmethyl)-1H-benzo[d]imidazole-6-carboxylic acid was prepared in a manner as described in Procedure 27, starting with Intermediates I-9 and 5-(bromomethyl)-2,1,3-benzothiadiazole.

1H NMR (400 MHz, Methanol-d4) δ 8.29 (s, 1H), 8.11 (s, 1H), 8.04 (d, J=9.0 Hz, 1H), 7.98 (dd, J=8.5, 1.5 Hz, 1H), 7.86-7.72 (m, 3H), 7.65 (d, J=8.5 Hz, 1H), 7.55 (d, J=7.5 Hz, 1H), 7.16 (dd, J=11.5, 6.1 Hz, 1H), 6.97 (d, J=8.2 Hz, 1H), 5.71 (s, 2H), 5.19 (d, J=7.3 Hz, 1H), 4.72 (dd, J=15.7, 6.9 Hz, 1H), 4.67-4.34 (m, 5H), 2.79 (t, J=9.1 Hz, 1H), 2.59-2.41 (m, 1H). ES/MS m/z: 600.2 (M+H$^+$).

Example 528: (S)-4-chloro-2-(4-(6-((4-chloro-6-(1H-1,2,3-triazol-1-yl)pyridin-3-yl)methoxy)pyridin-2-yl)-2,5-difluorobenzyl)-1-(4,4-dimethyltetrahydrofuran-3-yl)-1H-benzo[d]imidazole-6-carboxylic acid (S)-4-chloro-2-(4-(6-((4-chloro-6-(1H-1,2,3-triazol-1-yl)pyridin-3-yl)methoxy)pyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 35, starting with Intermediates I-112 and I-1037. 1H NMR (400 MHz, DMSO) δ 8.89 (s, 1H), 8.82 (s, 1H), 8.47 (s, 1H), 8.30 (s, 1H), 8.03 (s, 1H), 7.98-7.85 (m, 2H), 7.81 (s, 1H), 7.57 (d, J=7.3 Hz, 1H), 7.46 (dd, J=11.4, 6.1 Hz, 1H), 7.01 (d, J=8.2 Hz, 1H), 5.68 (s, 2H), 5.03 (d, J=6.6 Hz, 1H), 4.67-4.29 (m, 4H), 3.84-3.68 (m, 2H), 1.31 (s, 3H), 0.59 (s, 3H). ES/MS m/z: 706.0 (M+H$^+$).

Example 529: (S)-2-(2,5-difluoro-4-(6-((2-(methoxycarbonyl)isoindolin-5-yl)methoxy)pyridin-2-yl)benzyl)-1-(4,4-dimethyltetrahydrofuran-3-yl)-1H-benzo[d]imidazole-6-carboxylic acid (S)-2-(2,5-difluoro-4-(6-((2-(methoxycarbonyl)isoindolin-5-yl)methoxy)pyridin-2-yl)benzyl)-1-(4,4-dimethyltetrahydrofuran-3-yl)-1H-benzo[d]imidazole-6-carboxylic acid was prepared in a manner as described in Procedure 35, starting with Intermediates I-1016 and I-82. 1H NMR (400 MHz, DMSO) δ 8.49 (s, 1H), 7.91-7.77 (m, 3H), 7.55-7.39 (m, 5H), 7.34 (dd, J=10.6, 7.8 Hz, 1H), 6.94 (d, J=8.3 Hz, 1H), 5.47 (s, 2H), 5.02 (d, J=6.6 Hz, 1H), 4.64 (t, J=6.9 Hz, 4H), 4.58-4.50 (m, 2H), 4.44 (dd, J=11.2, 6.8 Hz, 1H), 4.39 (d, J=16.9 Hz, 1H), 3.81-3.71 (m, 2H), 3.67 (s, 3H), 1.34 (s, 3H), 0.61 (s, 3H). ES/MS m/z: 669.6 (M+H$^+$).

Example 530: (S)-2-(4-(6-(benzo[d]thiazol-6-ylmethoxy)pyridin-2-yl)-2,5-difluorobenzyl)-1-(oxetan-2-ylmethyl)-1H-benzo[d]imidazole-6-carboxylic acid (S)-2-(4-(6-(benzo[d]thiazol-6-ylmethoxy)pyridin-2-yl)-2,5-difluorobenzyl)-1-(oxetan-2-ylmethyl)-1H-benzo[d]imidazole-6-carboxylic acid was prepared in a manner as described in Procedure 27, starting with Intermediates I-9 and I-1346. 1H NMR (400 MHz, Methanol-d4) δ 9.21 (s, 1H), 8.52 (d, J=1.4 Hz, 1H), 8.20 (dd, J=8.6, 1.4 Hz, 2H), 8.08 (d, J=8.4 Hz, 1H), 7.87 (dd, J=10.8, 6.3 Hz, 1H), 7.83-7.73 (m, 2H), 7.69 (dd, J=8.5, 1.6 Hz, 1H), 7.55 (dd, J=7.5, 1.6 Hz, 1H), 7.31 (dd, J=11.1, 6.0 Hz, 1H), 6.93 (d, J=8.2 Hz, 1H), 5.66 (s, 2H), 5.24 (tt, J=7.3, 3.8 Hz, 1H), 4.93 (dd, J=15.5, 7.5 Hz, 1H), 4.83-4.63 (m, 4H), 4.54 (dt, J=9.1, 6.0 Hz, 1H), 2.98-2.75 (m, 1H), 2.67-2.50 (m, 1H). ES/MS m/z: 599.1 (M+H$^+$).

Example 531: (S)-2-(2,5-difluoro-4-(6-((3-methyl-2-oxo-2,3-dihydrobenzo[d]thiazol-6-yl)methoxy)pyridin-2-yl)benzyl)-1-(oxetan-2-ylmethyl)-1H-benzo[d]imidazole-6-carboxylic acid (S)-2-(2,5-difluoro-4-(6-((3-methyl-2-oxo-2,3-dihydrobenzo[d]thiazol-6-yl)methoxy)pyridin-2-yl)benzyl)-1-(oxetan-2-ylmethyl)-1H-benzo[d]imidazole-6-carboxylic acid was prepared in a manner as described in Procedure 27, starting with Intermediates I-9 and 5-(bromomethyl)-3-methyl-1,3-benzothiazol-2-one. 1H NMR (400 MHz, Methanol-d4) δ 8.57 (d, J=1.3 Hz, 1H), 8.21 (dd, J=8.6, 1.4 Hz, 1H), 7.90 (dd, J=10.8, 6.3 Hz, 1H), 7.85-7.74 (m, 2H), 7.69 (d, J=1.6 Hz, 1H), 7.54 (ddd, J=8.3, 6.4, 1.7 Hz, 2H), 7.37 (dd, J=11.2, 6.1 Hz, 1H), 7.26 (d, J=8.3 Hz, 1H), 6.91 (d, J=8.2 Hz, 1H), 5.52 (s, 2H), 5.26 (qd, J=7.4, 2.4 Hz, 1H), 4.98 (dd, J=15.5, 7.5 Hz, 1H), 4.86-4.64 (m, 4H), 4.54 (dt, J=9.1, 6.0 Hz, 1H), 3.47 (s, 3H), 2.88 (dtd, J=11.5, 8.2, 6.1 Hz, 1H), 2.58 (ddt, J=11.5, 9.1, 7.2 Hz, 1H). ES/MS m/z: 629.2 (M+H$^+$).

Example 532: (S)-methyl 2-(4-(6-((4-chloro-2-fluorobenzyl)oxy)pyridin-2-yl)-2,5-difluorobenzyl)-1-(4,4-dimethyltetrahydrofuran-3-yl)-1H-benzo[d]imidazole-6-carboxylate (S)-methyl 2-(4-(6-((4-chloro-2-fluorobenzyl)oxy)pyridin-2-yl)-2,5-difluorobenzyl)-1-(4,4-dimethyltetrahydrofuran-3-yl)-1H-benzo[d]imidazole-6-carboxylate was prepared and described previously as Intermediate I-103. 1H NMR (400 MHz, Chloroform-d) δ 8.55 (s, 1H), 8.01 (dd, J=8.5, 1.5 Hz, 1H), 7.88 (dd, J=10.8, 6.3 Hz, 1H), 7.79 (d, J=8.5 Hz, 1H), 7.66 (t, J=7.9 Hz, 1H), 7.54-7.41 (m, 3H), 7.14 (dt, J=9.8, 2.3 Hz, 2H), 7.08 (dd, J=11.3, 6.0 Hz, 1H), 6.79 (d, J=8.2 Hz, 1H), 5.49 (s, 2H), 4.65 (d, J=7.0 Hz, 1H), 4.57 (dd, J=11.0, 1.8 Hz, 1H), 4.47-4.30 (m, 3H), 3.96-3.92 (m, 4H), 3.79 (d, J=8.8 Hz, 1H), 1.34 (s, 3H), 0.66 (s, 3H). ES/MS m/z: 636.3 (M+H$^+$).

Example 533: 2-(4-(6-((4-chloro-2-fluorobenzyl)oxy)pyridin-2-yl)-2,5-difluorobenzyl)-1-((3R,4R)-4-methoxytetrahydrofuran-3-yl)-1H-benzo[d]imidazole-6-carboxylic acid 2-(4-(6-((4-chloro-2-fluorobenzyl)oxy)pyridin-2-yl)-2,5-difluorobenzyl)-1-((3R,4R)-4-methoxytetrahydrofuran-3-yl)-1H-benzo[d]imidazole-6-carboxylic acid was prepared in a manner as described in Procedure 39, starting with Intermediates I-1255 and I-1351. 1H NMR (400 MHz, DMSO) δ 8.43 (d, J=1.5 Hz, 1H), 7.91-7.75 (m, 3H), 7.67-7.57 (m, 2H), 7.53 (ddd, J=10.1, 7.3, 2.5 Hz, 2H), 7.43-7.28 (m, 2H), 5.60 (s, 2H), 4.54 (s, 2H), 4.42 (dd, J=10.4, 3.6 Hz, 1H), 4.19-4.07 (m, 2H), 4.02 (dd, J=10.5, 8.2 Hz, 1H), 3.80 (dd, J=10.5, 4.7 Hz, 1H), 2.88 (s, 3H). ES/MS m/z: 624.1 (M+H$^+$).

Example 534: 2-(4-(6-((4-chloro-2-fluorobenzyl)oxy)-5-fluoropyridin-2-yl)-2,5-difluorobenzyl)-1-((3R,4R)-4-methoxytetrahydrofuran-3-yl)-1H-benzo[d]imidazole-6-carboxylic acid 2-(4-(6-((4-chloro-2-fluorobenzyl)oxy)-5-fluoropyridin-2-yl)-2,5-difluorobenzyl)-1-((3R,4R)-4-methoxytetrahydrofuran-3-yl)-1H-benzo[d]imidazole-6-carboxylic acid was prepared in a manner as described in Procedure 39, starting with Intermediates I-1256 and I-1351. 1H NMR (400 MHz, DMSO) δ 1H NMR (400 MHz, DMSO) δ 8.45 (d, J=1.6 Hz, 1H), 7.94-7.77 (m, 3H), 7.68-7.55 (m, 2H), 7.55-7.46 (m, 2H), 7.39-7.27 (m, 2H), 6.96 (d, J=8.2 Hz, 1H), 5.65-5.54 (m, 1H), 5.50 (s, 2H), 4.57 (s, 2H), 4.43 (dd, J=10.4, 3.6 Hz, 1H), 4.13 (dt, J=8.5, 2.1 Hz, 2H), 4.02 (dd, J=10.6, 8.2 Hz, 1H), 3.79 (dd, J=10.8, 4.9 Hz, 1H), 2.88 (s, 3H). ES/MS m/z: 642.2 (M+H$^+$).

Example 535: (S)-2-(2,5-difluoro-4-(6-((2-fluoro-4-(1-methyl-1H-pyrazol-4-yl)benzyl)oxy)pyridin-2-yl)benzyl)-1-(4,4-dimethyltetrahydrofuran-3-yl)-1H-benzo[d]imidazole-6-carboxylic acid (S)-2-(2,5-difluoro-4-(6-((2-fluoro-4-(1-methyl-1H-pyrazol-4-yl)benzyl)oxy)pyridin-2-yl)benzyl)-1-(4,4-dimethyltetrahydrofuran-3-yl)-1H-benzo[d]imidazole-6-carboxylic acid was prepared in a manner as described in Procedure 41, starting with Intermediate I-1220 and (1-methylpyrazol-4-yl)boronic acid. 1H NMR (400 MHz, Methanol-d4) δ 8.92 (s, 1H), 8.20 (dd, J=8.6, 1.4 Hz, 1H), 8.10-7.92 (m, 2H), 7.91-7.73 (m, 3H), 7.58 (dd, J=7.4, 1.6 Hz, 1H), 7.51 (t, J=7.8 Hz, 1H), 7.46-7.28 (m, 3H), 6.91 (d, J=8.2 Hz, 1H), 5.54 (s, 2H), 5.15 (d, J=6.4 Hz, 1H), 4.80-4.61 (m, 3H), 4.52 (dd, J=11.7, 6.7 Hz, 1H), 4.00 (d, J=8.9 Hz, 1H), 3.93 (s, 3H), 3.84 (d, J=8.9 Hz, 1H), 1.41 (s, 3H), 0.76 (s, 3H). ES/MS m/z: 668.2 (M+H$^+$).

Example 536: (S)-2-(2,5-difluoro-4-(5-fluoro-6-((4-(trifluoromethyl)benzyl)oxy)pyridin-2-yl)benzyl)-1-(4,4-dimethyltetrahydrofuran-3-yl)-1H-benzo[d]imidazole-6-carboxylic acid (S)-2-(2,5-difluoro-4-(5-fluoro-6-((4-(trifluoromethyl)benzyl)oxy)pyridin-2-yl)benzyl)-1-(4,4-dimethyltetrahydrofuran-3-yl)-1H-benzo[d]imidazole-6-carboxylic acid was prepared in a manner as described in Procedure 35, starting with Intermediates I-1383 and I-82. 1H NMR (400 MHz, DMSO-d6) δ 8.49 (s, 1H), 7.87 (dd, J=10.3, 8.2 Hz, 1H), 7.84-7.69 (m, 6H), 7.62 (d, J=8.4 Hz, 1H), 7.55 (ddd, J=8.2, 2.9, 1.4 Hz, 1H), 7.46 (dd, J=11.5, 6.1 Hz, 1H), 5.68 (s, 2H), 5.02 (d, J=6.7 Hz, 1H), 4.55-4.48 (m, 2H), 4.47-4.32 (m, 2H), 3.82-3.69 (m, 2H), 1.33 (s, 3H), 0.60 (s, 3H). ES/MS m/z: 656.0 (M+H$^+$).

Example 537: (S)-2-(2,5-difluoro-4-(2-((4-(trifluoromethyl)benzyl)oxy)pyrimidin-4-yl)benzyl)-1-(4,4-dimethyltetrahydrofuran-3-yl)-1H-benzo[d]imidazole-6-carboxylic acid (S)-2-(2,5-difluoro-4-(2-((4-(trifluoromethyl)benzyl)oxy)pyrimidin-4-yl)benzyl)-1-(4,4-dimethyltetrahydrofuran-3-yl)-1H-benzo[d]imidazole-6-carboxylic acid was prepared in a manner as described in Procedure 35, starting with Intermediates I-1384 and I-82. 1H NMR (400 MHz, DMSO-d6) δ 8.79 (d, J=5.2 Hz, 1H), 8.48 (s, 1H), 7.91 (dd, J=10.2, 6.3 Hz, 1H), 7.83-7.75 (m, 3H), 7.73 (d, J=8.2 Hz, 2H), 7.64 (dd, J=5.2, 1.9 Hz, 1H), 7.61 (d, J=8.5 Hz, 1H), 7.55 (dd, J=11.5, 5.9 Hz, 1H), 5.63 (s, 2H), 5.02 (d, J=6.6 Hz, 1H), 4.61-4.49 (m, 2H), 4.49-4.36 (m, 2H), 3.82-3.67 (m, 2H), 1.34 (s, 3H), 0.61 (s, 3H). ES/MS m/z: 639.0 (M+H$^+$).

Example 538: 2-(2,5-difluoro-4-(5-fluoro-6-((4-(trifluoromethyl)benzyl)oxy)pyridin-2-yl)benzyl)-1-((3S,4S)-4-(methoxymethyl)tetrahydrofuran-3-yl)-1H-benzo[d]imidazole-6-carboxylic acid 2-(2,5-difluoro-4-(5-fluoro-6-((4-(trifluoromethyl)benzyl)oxy)pyridin-2-yl)benzyl)-1-((3S,4S)-4-(methoxymethyl)tetrahydrofuran-3-yl)-1H-benzo[d]imidazole-6-carboxylic acid was prepared in a manner as described in Procedure 35 starting with Intermediates I-1383 and I-1267. 1H NMR (400 MHz, DMSO-d6) δ 8.55 (s, 1H), 7.87 (dd, J=10.3, 8.2 Hz, 1H), 7.80 (dd, J=9.7, 8.3 Hz, 3H), 7.76-7.68 (m, 3H), 7.61 (d, J=8.5 Hz, 1H), 7.55 (ddd, J=8.2, 2.9, 1.5 Hz, 1H), 7.39 (dd, J=11.3, 6.2 Hz, 1H), 5.68 (s, 2H), 5.52 (t, J=7.3 Hz, 1H), 4.57-4.41 (m, 3H), 4.20 (dd, J=10.9, 6.5 Hz, 1H), 4.08 (t, J=8.7 Hz, 1H), 3.77 (t, J=8.2 Hz, 1H), 3.19-3.01 (m, 2H), 2.91 (s, 3H), 2.60 (t, J=8.8 Hz, 1H). ES/MS m/z: 672.0 (M+H$^+$).

Example 539: racemic 2-(4-(6-((4-cyano-2-fluorobenzyl)oxy)pyridin-2-yl)-2,5-difluorobenzyl)-1-((3R,4R)-4-(2,2-difluoroethoxy)tetrahydrofuran-3-yl)-1H-benzo[d]imidazole-6-carboxylic acid Racemic 2-(4-(6-((4-cyano-2-fluorobenzyl)oxy)pyridin-2-yl)-2,5-difluorobenzyl)-1-((3R,4R)-4-(2,2-difluoroethoxy)tetrahydrofuran-3-yl)-1H-benzo[d]imidazole-6-carboxylic acid was prepared in a manner as described in Procedure 3, starting with Intermediates I-7 and I-1386. 1H NMR (400 MHz, DMSO-d6) δ 8.43 (s, 1H), 8.03-7.86 (m, 2H), 7.85-7.67 (m, 4H), 7.60 (d, J=8.5 Hz, 1H), 7.53 (d, J=7.3 Hz, 1H), 7.34 (dd, J=11.5, 6.1 Hz, 1H), 7.00 (d, J=8.3 Hz, 1H), 5.87-5.45 (m, 3H), 4.54 (s, 2H), 4.51-4.41 (m, 2H), 4.14 (s, OH), 4.05 (dd, J=10.5, 8.3 Hz, 1H), 3.93-3.83 (m, 2H), 3.62-3.43 (m, 1H), 3.24-2.99 (m, 1H). ES/MS m/z: 665.0 (M+H$^+$).

Example 540: 2-(4-(6-((4-cyano-2-fluorobenzyl)oxy)pyridin-2-yl)-2,5-difluorobenzyl)-1-((3R,4R)-4-(2,2-difluoroethoxy)tetrahydrofuran-3-yl)-1H-benzo[d]imidazole-6-carboxylic acid

Example 541: 2-(4-(6-((4-cyano-2-fluorobenzyl)oxy)pyridin-2-yl)-2,5-difluorobenzyl)-1-((3S,4S)-4-(2,2-difluoroethoxy)tetrahydrofuran-3-yl)-1H-benzo[d]imidazole-6-carboxylic acid Examples 540 and 541: -(4-(6-((4-cyano-2-fluorobenzyl)oxy)pyridin-2-yl)-2,5-difluorobenzyl)-1-((3R,4R)-4-(2,2-difluoroethoxy)tetrahydrofuran-3-yl)-1H-benzo[d]imidazole-6-carboxylic acid (Example 540) and 2-(4-(6-((4-cyano-2-fluorobenzyl)oxy)pyridin-2-yl)-2,5-difluorobenzyl)-1-((3S,4S)-4-(2,2-difluoroethoxy)tetrahydrofuran-3-yl)-1H-benzo[d]imidazole-6-carboxylic acid (Example 541) were prepared via preparative chiral SFC (Chiralpak OJ-H column, MeOH/CO$_2$ eluent) of Example 539.

Example 542: 2-(4-(6-((4-chloro-2-fluorobenzyl)oxy)pyridin-2-yl)-2,5-difluorobenzyl)-1-((3S,4S)-4-(methoxymethyl)tetrahydrofuran-3-yl)-1H-benzo[d]imidazole-6-carboxylic acid 2-(4-(6-((4-chloro-2-fluorobenzyl)oxy)pyridin-2-yl)-2,5-difluorobenzyl)-1-((3S,4S)-4-(methoxymethyl)tetrahydrofuran-3-yl)-1H-benzo[d]imidazole-6-carboxylic acid was prepared in a manner as described in Procedure 35, starting with Intermediates I-102 and I-1267. 1H NMR (400 MHz, MeOD) δ 8.71 (s, 1H), 7.95 (dd, J=8.5, 1.5 Hz, 1H), 7.82 (dd, J=10.8, 6.4 Hz, 1H), 7.73 (t, J=7.9 Hz, 1H), 7.62 (d, J=8.5 Hz, 1H), 7.49 (t, J=8.0 Hz, 2H), 7.28-7.04 (m, 3H), 6.82 (d, J=8.2 Hz, 1H), 5.46 (d, J=14.0 Hz, 3H), 4.60-4.41 (m, 3H), 4.23 (dd, J=10.9, 6.6 Hz, 1H), 4.15-4.06 (m, 1H), 3.89 (dd, J=9.0, 7.0 Hz, 1H), 3.35 (s, OH), 3.21-3.04 (m, 2H), 2.92 (s, 3H), 2.57 (t, J=8.9 Hz, 1H). ES/MS m/z: 638.1 (M+H$^+$).

Example 543: 2-(4-(6-((4-chloro-2-fluorobenzyl)oxy)-5-fluoropyridin-2-yl)-2,5-difluorobenzyl)-1-((3S,4S)-4-(methoxymethyl)tetrahydrofuran-3-yl)-1H-benzo[d]imidazole-6-carboxylic acid 2-(4-(6-((4-chloro-2-fluorobenzyl)oxy)-5-fluoropyridin-2-yl)-2,5-difluorobenzyl)-1-((3S,4S)-4-(methoxymethyl)

tetrahydrofuran-3-yl)-1H-benzo[d]imidazole-6-carboxylic acid was prepared in a manner as described in Procedure 35, starting with Intermediates I-1036 and I-1267. 1H NMR (400 MHz, MeOD) δ 8.72 (s, 1H), 7.94 (dd, J=8.5, 1.5 Hz, 1H), 7.76 (dd, J=10.7, 6.4 Hz, 1H), 7.70-7.44 (m, 4H), 7.26 (dd, J=8.6, 2.6 Hz, 1H), 7.23-7.03 (m, 2H), 5.59 (s, 2H), 5.45 (t, J=7.2 Hz, 1H), 4.65-4.46 (m, 3H), 4.24 (dd, J=10.9, 6.6 Hz, 1H), 4.11 (t, J=8.9 Hz, 1H), 3.89 (dd, J=9.0, 7.0 Hz, 1H), 3.22-3.06 (m, 2H), 2.92 (s, 3H). ES/MS m/z: 656.1 (M+H$^+$).

Example 544: 2-(4-(6-((4-chlorobenzyl)oxy)pyridin-2-yl)-2,5-difluorobenzyl)-1-((3S,4S)-4-(methoxymethyl)tetrahydrofuran-3-yl)-1H-benzo[d]imidazole-6-carboxylic acid 2-(4-(6-((4-chlorobenzyl)oxy)pyridin-2-yl)-2,5-difluorobenzyl)-1-((3S,4S)-4-(methoxymethyl)tetrahydrofuran-3-yl)-1H-benzo[d]imidazole-6-carboxylic acid was prepared in a manner as described in Procedure 35, starting with Intermediates I-1248 and I-1267. 1H NMR (400 MHz, MeOD) δ 8.72 (s, 1H), 7.95 (dd, J=8.4, 1.5 Hz, 1H), 7.80 (dd, J=10.8, 6.3 Hz, 1H), 7.74 (t, J=7.8 Hz, 1H), 7.64 (d, J=8.5 Hz, 1H), 7.49 (dd, J=7.5, 1.7 Hz, 1H), 7.45 (d, J=8.5 Hz, 2H), 7.36-7.33 (m, 2H), 7.14 (dd, J=11.5, 6.0 Hz, 1H), 6.84 (d, J=8.2 Hz, 1H), 5.44 (s, 3H), 4.61-4.38 (m, 3H), 4.24 (dd, J=10.9, 6.6 Hz, 1H), 4.19-4.04 (m, 1H), 3.90 (dd, J=9.0, 7.0 Hz, 1H), 2.93 (s, 3H). ES/MS m/z: 620.2 (M+H$^+$).

Example 545: 2-(4-(6-((4-chlorobenzyl)oxy)-5-fluoropyridin-2-yl)-2,5-difluorobenzyl)-1-((3S,4S)-4-(methoxymethyl)tetrahydrofuran-3-yl)-1H-benzo[d]imidazole-6-carboxylic acid 2-(4-(6-((4-chlorobenzyl)oxy)-5-fluoropyridin-2-yl)-2,5-difluorobenzyl)-1-((3S,4S)-4-(methoxymethyl)tetrahydrofuran-3-yl)-1H-benzo[d]imidazole-6-carboxylic acid was prepared in a manner as described in Procedure 35, starting with Intermediates I-1246 and I-1267. 1H NMR (400 MHz, MeOD) δ 8.73 (s, 1H), 7.95 (dd, J=8.5, 1.5 Hz, 1H), 7.81-7.75 (m, 1H), 7.64 (d, J=8.5 Hz, 1H), 7.58 (dd, J=9.8, 8.2 Hz, 1H), 7.54-7.46 (m, 3H), 7.42-7.33 (m, 2H), 7.15 (dd, J=11.5, 6.1 Hz, 1H), 5.59-5.36 (m, 3H), 4.63-4.41 (m, 3H), 4.26 (dd, J=10.9, 6.6 Hz, 1H), 4.13 (t, J=8.9 Hz, 1H), 3.91 (dd, J=9.0, 7.0 Hz, 1H), 2.93 (s, 3H). ES/MS m/z: 638.1 (M+H$^+$).

Example 546: 2-(4-(6-((4-chloro-2-fluorobenzyl)oxy)pyridin-2-yl)-2,5-difluorobenzyl)-1-((3S,4S)-4-(methoxymethyl)-4-methyltetrahydrofuran-3-yl)-1H-benzo[d]imidazole-6-carboxylic acid, isomer 1 (relative stereochemistry shown)

2-(4-(6-((4-chloro-2-fluorobenzyl)oxy)pyridin-2-yl)-2,5-difluorobenzyl)-1-((3S,4S)-4-(methoxymethyl)-4-methyltetrahydrofuran-3-yl)-1H-benzo[d]imidazole-6-carboxylic acid, isomer 1 (relative stereochemistry shown) was prepared in a manner as described in Procedure 35, starting with Intermediates I-102 and I-1377. 1H NMR (400 MHz, MeOD) δ 8.73 (s, 1H), 7.95 (dd, J=8.5, 1.5 Hz, 1H), 7.83 (dd, J=10.7, 6.3 Hz, 1H), 7.74 (t, J=7.9 Hz, 1H), 7.64 (d, J=8.5 Hz, 1H), 7.55-7.47 (m, 2H), 7.24-7.16 (m, 2H), 7.12 (dd, J=11.5, 6.0 Hz, 1H), 6.83 (d, J=8.2 Hz, 1H), 5.49 (s, 2H), 4.96 (d, J=6.5 Hz, 1H), 4.61-4.46 (m, 2H), 4.46-4.34 (m, 2H), 3.98 (d, J=9.1 Hz, 1H), 3.73 (d, J=9.0 Hz, 1H), 3.03 (d, J=9.4 Hz, 1H), 2.88 (s, 3H), 2.69 (d, J=9.4 Hz, 1H), 1.45 (s, 3H). ES/MS m/z: 652.2 (M+H$^+$).

Example 547: 2-(4-(6-((4-chloro-2-fluorobenzyl)oxy)pyridin-2-yl)-2,5-difluorobenzyl)-1-((3S,4S)-4-(methoxymethyl)-4-methyltetrahydrofuran-3-yl)-1H-benzo[d]imidazole-6-carboxylic acid, isomer 2 (relative stereochemistry shown)

2-(4-(6-((4-chloro-2-fluorobenzyl)oxy)pyridin-2-yl)-2,5-difluorobenzyl)-1-((3S,4S)-4-(methoxymethyl)-4-methyltetrahydrofuran-3-yl)-1H-benzo[d]imidazole-6-carboxylic acid, isomer 2 (relative stereochemistry shown) was prepared in a manner as described in Procedure 35, starting with Intermediates I-102 and I-1378. 1H NMR (400 MHz, MeOD) δ 8.74 (s, 1H), 7.96 (dd, J=8.5, 1.5 Hz, 1H), 7.84 (dd, J=10.8, 6.4 Hz, 1H), 7.77 (t, J=7.9 Hz, 1H), 7.65 (d, J=8.5 Hz, 1H), 7.53 (t, J=8.0 Hz, 2H), 7.30-7.17 (m, 2H), 7.13 (dd, J=11.5, 6.0 Hz, 1H), 6.85 (d, J=8.2 Hz, 1H), 5.51 (s, 2H), 4.97 (d, J=6.5 Hz, 1H), 4.58 (d, J=17.2 Hz, 2H), 4.51-4.34 (m, 2H), 3.99 (d, J=9.0 Hz, 1H), 3.74 (d, J=9.1 Hz, 1H), 3.05 (d, J=9.4 Hz, 1H), 2.89 (s, 3H), 2.70 (d, J=9.2 Hz, 1H), 1.46 (s, 3H). ES/MS m/z: 652.2 (M+H$^+$).

Example 548 (prophetic example): 2-(4-(6-((4-chloro-2-fluorobenzyl)oxy)pyridin-2-yl)-2,5-difluorobenzyl)-1-((3R,4S)-4-(methoxymethyl)-4-methyltetrahydrofuran-3-yl)-1H-benzo[d]imidazole-6-carboxylic acid (Isomer 1, relative stereochemistry shown)

2-(4-(6-((4-chloro-2-fluorobenzyl)oxy)pyridin-2-yl)-2,5-difluorobenzyl)-1-((3R,4S)-4-(methoxymethyl)-4-methyltetrahydrofuran-3-yl)-1H-benzo[d]imidazole-6-carboxylic acid (Isomer 1, relative stereochemistry shown) was prepared in a manner as described in Procedure 35, starting with Intermediates I-102 and I-1379.

Example 549: 2-(4-(6-((4-chloro-2-fluorobenzyl)oxy)pyridin-2-yl)-2,5-difluorobenzyl)-1-((3R,4S)-4-(methoxymethyl)-4-methyltetrahydrofuran-3-yl)-1H-benzo[d]imidazole-6-carboxylic acid (Isomer 2, relative stereochemistry shown)

2-(4-(6-((4-chloro-2-fluorobenzyl)oxy)pyridin-2-yl)-2,5-difluorobenzyl)-1-((3R,4S)-4-(methoxymethyl)-4-methyltetrahydrofuran-3-yl)-1H-benzo[d]imidazole-6-carboxylic acid (Isomer 2, relative stereochemistry shown) was prepared in a manner as described in Procedure 35, starting with Intermediates I-102 and I-1380. 1H NMR (400 MHz, MeOD) δ 8.75 (s, 1H), 7.99 (dd, J=8.5, 1.5 Hz, 1H), 7.86 (dd, J=10.7, 6.4 Hz, 1H), 7.79 (t, J=7.9 Hz, 1H), 7.68 (d, J=8.5 Hz, 1H), 7.61-7.49 (m, 2H), 7.25 (ddd, J=12.2, 8.9, 2.1 Hz, 2H), 7.10 (dd, J=11.5, 6.0 Hz, 1H), 6.88 (d, J=8.2 Hz, 1H), 5.54 (s, 2H), 5.23 (d, J=7.0 Hz, 1H), 4.69-4.38 (m, 3H), 4.33 (dd, J=11.0, 7.1 Hz, 1H), 3.97 (d, J=9.2 Hz, 1H), 3.85 (d, J=9.2 Hz, 1H), 3.50 (s, 3H), 0.72 (s, 3H). ES/MS m/z: 652.2 (M+H$^+$).

Example 550: (S)-2-(2,5-difluoro-4-(6-((6-(1-methyl-1H-1,2,3-triazol-4-yl)pyridin-3-yl)methoxy)pyridin-2-yl)benzyl)-1-(4,4-dimethyltetrahydrofuran-3-yl)-1H-benzo[d]imidazole-6-carboxylic acid (S)-2-(2,5-difluoro-4-(6-((6-(1-methyl-1H-1,2,3-triazol-4-yl)pyridin-3-yl)methoxy)pyridin-2-yl)benzyl)-1-(4,4-dimethyltetrahydrofuran-3-yl)-1H-benzo[d]imidazole-6-carboxylic acid was prepared in a manner as described in Procedure 41, starting with Intermediate I-1350 and 1-methyl-4-(4,4,5,5-tetramethyl-1,3,2-dioxaborolan-2-yl) triazole. NMR ES/MS m/z: 652.2 (M+H$^+$).

Example 551: (S)-2-(4-(6-((4-(1-(difluoromethyl)-1H-pyrazol-4-yl)benzyl)oxy)pyridin-2-yl)-2,5-difluorobenzyl)-1-(4,4-dimethyltetrahydrofuran-3-yl)-1H-benzo[d]imidazole-6-carboxylic acid (S)-2-(4-(6-((4-(1-(difluoromethyl)-1H-pyrazol-4-yl)benzyl)oxy)pyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 41, starting with Intermediate I-1349 and 1-(difluoromethyl)-4-(4,4,5,5-tetramethyl-1,3,2-dioxaborolan-2-yl)pyrazole. 1H NMR (400 MHz, Methanol-d4) δ 8.90 (s, 1H), 8.52-8.01 (m, 2H), 7.91 (ddd, J=10.9, 6.3, 2.0 Hz, 1H), 7.87-7.71 (m, 2H), 7.71-7.23 (m, 7H), 6.91 (dd, J=8.3, 5.7 Hz, 1H), 5.50 (d, J=8.5 Hz, 2H), 5.14 (s, 1H), 4.79-4.60 (m, 3H), 4.52 (ddd, J=11.6, 6.7, 3.2 Hz, 1H), 3.99 (dd, J=8.9, 3.2 Hz, 1H), 3.84 (dd, J=8.9, 4.1 Hz, 1H), 1.41 (d, J=5.4 Hz, 3H), 0.76 (d, J=4.4 Hz, 3H). ES/MS m/z: 686.2 (M+H$^+$).

Example 552: (S)-2-(4-(6-((4-chloro-6-(1-(difluoromethyl)-1H-pyrazol-4-yl)pyridin-3-yl)methoxy)pyridin-2-yl)-2,5-difluorobenzyl)-1-(4,4-dimethyltetrahydrofuran-3-yl)-1H-benzo[d]imidazole-6-carboxylic acid (S)-2-(4-(6-((4-chloro-6-(1-(difluoromethyl)-1H-pyrazol-4-yl)pyridin-3-yl)methoxy)pyridin-2-yl)-2,5-difluorobenzyl)-1-(4,4-dimethyltetrahydrofuran-3-yl)-1H-benzo[d]imidazole-6-carboxylic acid was prepared in a manner as described in Procedure 41, starting with Intermediate I-1348 and 1-(difluoromethyl)-4-(4,4,5,5-tetramethyl-1,3,2-dioxaborolan-2-yl)pyrazole. 1H NMR (400 MHz, Methanol-d4) δ 8.89 (s, 1H), 8.80-8.63 (m, 2H), 8.29 (s, 1H), 8.17 (dd, J=8.6, 1.4 Hz, 1H), 8.05-7.89 (m, 2H), 7.90-7.74 (m, 2H), 7.74-7.35 (m, 3H), 6.96 (dd, J=8.3, 0.7 Hz, 1H), 5.67 (s, 2H), 5.13 (d, J=6.5 Hz, 1H), 4.79-4.59 (m, 3H), 4.52 (dd, J=11.6, 6.7 Hz, 1H), 3.99 (d, J=8.9 Hz, 1H), 3.83 (d, J=8.9 Hz, 1H), 1.40 (s, 3H), 0.75 (s, 3H). ES/MS m/z: 721.2 (M+H$^+$).

Example 553: (S)-2-(2,5-difluoro-4-(6-((2-fluoro-4-(2-methyl-2H-1,2,3-triazol-4-yl)benzyl)oxy)pyridin-2-yl)benzyl)-1-(4,4-dimethyltetrahydrofuran-3-yl)-1H-benzo[d]imidazole-6-carboxylic acid (S)-2-(2,5-difluoro-4-(6-((2-fluoro-4-(2-methyl-2H-1,2,3-triazol-4-yl)benzyl)oxy)pyridin-2-yl)benzyl)-1-(4,4-dimethyltetrahydrofuran-3-yl)-1H-benzo[d]imidazole-6-carboxylic acid was prepared in a manner as described in Procedure 41, starting with Intermediate I-1220 and 2-methyl-4-(4,4,5,5-tetramethyl-1,3,2-dioxaborolan-2-yl)triazole. 1H NMR (400 MHz, Methanol-d4) δ 8.90 (s, 1H), 8.18 (dd, J=8.6, 1.4 Hz, 1H), 8.02 (s, 1H), 7.94 (dd, J=10.9, 6.3 Hz, 1H), 7.89-7.72 (m, 2H), 7.71-7.50 (m, 4H), 7.39 (dd, J=11.2, 6.0 Hz, 1H), 6.93 (d, J=8.2 Hz, 1H), 5.58 (s, 2H), 5.14 (d, J=6.5 Hz, 1H), 4.80-4.59 (m, 3H), 4.52 (dd, J=11.6, 6.7 Hz, 1H), 4.22 (s, 3H), 3.99 (d, J=8.9 Hz, 1H), 3.83 (d, J=8.9 Hz, 1H), 1.40 (s, 3H), 0.75 (s, 3H). ES/MS m/z: 669.1 (M+H$^+$).

Example 554: (S)-2-(2,5-difluoro-4-(6-((2-fluoro-4-(1-methyl-1H-1,2,3-triazol-5-yl)benzyl)oxy)pyridin-2-yl)benzyl)-1-(4,4-dimethyltetrahydrofuran-3-yl)-1H-benzo[d]imidazole-6-carboxylic acid (S)-2-(2,5-difluoro-4-(6-((2-fluoro-4-(1-methyl-1H-1,2,3-triazol-5-yl)benzyl)oxy)pyridin-2-yl)benzyl)-1-(4,4-dimethyltetrahydrofuran-3-yl)-1H-benzo[d]imidazole-6-carboxylic acid was prepared in a manner as described in Procedure 41, starting with Intermediate I-1220 and 1-methyl-5-(4,4,5,5-tetramethyl-1,3,2-dioxaborolan-2-yl)triazole. 1H NMR (400 MHz, Methanol-d4) δ 8.88 (s, 1H), 8.16 (dd, J=8.6, 1.4 Hz, 1H), 7.97-7.86 (m, 2H), 7.84 (dd, J=8.3, 7.5 Hz, 1H), 7.80-7.68 (m, 2H), 7.59 (dd, J=7.2, 1.6 Hz, 1H), 7.49-7.33 (m, 3H), 6.95 (dd, J=8.3, 0.6 Hz, 1H), 5.64 (s, 2H), 5.13 (d, J=6.6 Hz, 1H), 4.81-4.57 (m, 3H), 4.52 (dd, J=11.6, 6.7 Hz, 1H), 4.13 (s, 3H), 3.99 (d, J=8.9 Hz, 1H), 3.84 (d, J=8.9 Hz, 1H), 1.41 (s, 3H), 0.75 (s, 3H). ES/MS m/z: 669.1 (M+H$^+$).

Example 555: (S)-2-(2,5-difluoro-4-(6-((4-fluoro-6-(1-methyl-11H-1,2,3-triazol-4-yl)pyridin-3-yl)methoxy)pyridin-2-yl)benzyl)-1-(4,4-dimethyltetrahydrofuran-3-yl)-1H-benzo[d]imidazole-6-carboxylic acid (S)-2-(2,5-difluoro-4-(6-((4-fluoro-6-(1-methyl-1H-1,2,3-triazol-4-yl)pyridin-3-yl)methoxy)pyridin-2-yl)benzyl)-1-(4,4-dimethyltetrahydrofuran-3-yl)-1H-benzo[d]imidazole-6-carboxylic acid was prepared in a manner as described in Procedure 41, starting with Intermediate I-1347 and 1-methyl-4-(4,4,5,5-tetramethyl-1,3,2-dioxaborolan-2-yl)triazole. 1H NMR (400 MHz, Methanol-d4) δ 8.89 (d, J=9.8 Hz, 1H), 8.83 (s, 1H), 8.23 (s, 1H), 8.12 (dd, J=8.6, 1.4 Hz, 1H), 8.03-7.90 (m, 1H), 7.88-7.69 (m, 3H), 7.65-7.51 (m, 1H), 7.36 (dd, J=11.2, 6.1 Hz, 1H), 6.94 (dd, J=8.2, 0.7 Hz, 1H), 5.68 (s, 2H), 5.09 (d, J=6.4 Hz, 1H), 4.76-4.56 (m, 3H), 4.52 (dd, J=11.5, 6.7 Hz, 1H), 4.40 (s, 3H), 3.99 (d, J=8.9 Hz, 1H), 3.83 (d, J=8.9 Hz, 1H), 1.40 (s, 3H), 0.74 (s, 3H). ES/MS m/z: 670.1 (M+H$^+$).

Example 556: 2-(2,5-difluoro-4-(6-((4-(trifluoromethyl)benzyl)oxy)pyridin-2-yl)benzyl)-1-((3S,4S)-4-(methoxymethyl)tetrahydrofuran-3-yl)-1H-benzo[d]imidazole-6-carboxylic acid 2-(2,5-difluoro-4-(6-((4-(trifluoromethyl)benzyl)oxy)pyridin-2-yl)benzyl)-1-((3S,4S)-4-(methoxymethyl)tetrahydrofuran-3-yl)-1H-benzo[d]imidazole-6-carboxylic acid was prepared in a manner as described in Procedure 35, starting with Intermediates I-1382 and I-1267. 1H NMR (400 MHz, DMSO-d6) δ 8.54 (s, 1H), 7.94-7.88 (m, 1H), 7.81 (dd, J=8.5, 1.5 Hz, 1H), 7.78-7.69 (m, 5H), 7.61 (d, J=8.4 Hz, 1H), 7.53 (dd, J=7.5, 1.7 Hz, 1H), 7.38 (dd, J=11.4, 6.1 Hz, 1H), 7.01 (d, J=8.3 Hz, 1H), 5.59 (s, 2H), 5.52 (s, 1H), 4.58-4.40 (m, 3H), 4.21 (dd, J=10.8, 6.5 Hz, 1H), 4.08 (t, J=8.8 Hz, 1H), 3.82-3.72 (m, 2H), 3.18-2.99 (m, 2H), 2.91 (s, 3H). ES/MS m/z: 654.0 (M+H$^+$).

Example 557: (S)-2-(2,5-difluoro-4-(5-fluoro-6-((4-fluorobenzyl)oxy)pyridin-2-yl)benzyl)-1-(4,4-dimethyltetrahydrofuran-3-yl)-1H-benzo[d]imidazole-6-carboxylic acid (S)-2-(2,5-difluoro-4-(5-fluoro-6-((4-fluorobenzyl)oxy)pyridin-2-yl)benzyl)-1-(4,4-dimethyltetrahydrofuran-3-yl)-1H-benzo[d]imidazole-6-carboxylic acid was prepared in a manner as described in Procedure 35, starting with Intermediates I-1381 and I-82. 1H NMR (400 MHz, DMSO-d6) δ 8.50 (s, 1H), 7.89-7.77 (m, 3H), 7.63 (d, J=8.5 Hz, 1H), 7.61-7.52 (m, 3H), 7.48 (dd, J=11.5, 6.1 Hz, 1H), 7.30-7.17 (m, 2H), 5.55 (s, 2H), 5.03 (d, J=6.6 Hz, 1H), 4.62-4.55 (m, 1H), 4.53 (d, J=1.5 Hz, 1H), 4.48-4.35 (m, 2H), 3.84-3.68 (m, 2H), 1.34 (s, 3H), 0.61 (s, 3H). ES/MS m/z: 606.0 (M+H⁺).

Example 558: (S)-1-(4,4-dimethyltetrahydrofuran-3-yl)-2-(2,3,6-trifluoro-4-(5-fluoro-6-((4-fluorobenzyl)oxy)pyridin-2-yl)benzyl)-1H-benzo[d]imidazole-6-carboxylic acid (S)-1-(4,4-dimethyltetrahydrofuran-3-yl)-2-(2,3,6-trifluoro-4-(5-fluoro-6-((4-fluorobenzyl)oxy)pyridin-2-yl)benzyl)-1H-benzo[d]imidazole-6-carboxylic acid was prepared in a manner as described in Procedure 35, starting with Intermediates I-1381 and I-1231. 1H NMR (400 MHz, DMSO-d6) δ 8.48 (s, 1H), 7.90 (dd, J=10.3, 8.2 Hz, 1H), 7.78 (dd, J=8.5, 1.5 Hz, 1H), 7.76-7.67 (m, 1H), 7.63-7.53 (m, 4H), 7.31-7.20 (m, 2H), 5.56 (s, 2H), 5.09 (d, J=6.6 Hz, 1H), 4.73-4.52 (m, 2H), 4.47 (dd, J=11.2, 6.7 Hz, 1H), 4.35 (d, J=17.4 Hz, 1H), 3.84-3.70 (m, 2H), 1.39 (s, 3H), 0.66 (s, 3H). ES/MS m/z: 624.0 (M+H⁺).

Example 559: 2-((3'-((4-chloro-2-fluorobenzyl)oxy)-2,4',5-trifluoro-[1,1'-biphenyl]-4-yl)methyl)-1-((3S,4S)-4-(methoxymethyl)tetrahydrofuran-3-yl)-1H-benzo[d]imidazole-6-carboxylic acid 2-((3'-((4-chloro-2-fluorobenzyl)oxy)-2,4',5-trifluoro-[1,1'-biphenyl]-4-yl)methyl)-1-((3S,4S)-4-(methoxymethyl)tetrahydrofuran-3-yl)-1H-benzo[d]imidazole-6-carboxylic acid was prepared in a manner as described in Procedure 35, starting with Intermediates I-1309 and I-1267. 1H NMR (400 MHz, MeOD) δ 8.74 (s, 1H), 7.97 (dd, J=8.5, 1.5 Hz, 1H), 7.69-7.62 (m, 1H), 7.62-7.52 (m, 1H), 7.41-7.29 (m, 2H), 7.29-7.22 (m, 2H), 7.22-7.10 (m, 2H), 5.49 (t, J=7.3 Hz, 1H), 5.27-5.17 (m, 2H), 4.65-4.47 (m, 3H), 4.33-4.22 (m, 1H), 4.00-3.87 (m, 1H), 2.96 (s, 3H). ES/MS m/z: 655.2 (M+H⁺).

Example 560: 2-(4-(6-((4-chloro-6-(1H-1,2,3-triazol-1-yl)pyridin-3-yl)methoxy)pyridin-2-yl)-2,5-difluorobenzyl)-1-(2-(difluoromethoxy)ethyl)-1H-benzo[d]imidazole-6-carboxylic acid 2-(4-(6-((4-chloro-6-(1H-1,2,3-triazol-1-yl)pyridin-3-yl)methoxy)pyridin-2-yl)-2,5-difluorobenzyl)-1-(2-(difluoromethoxy)ethyl)-1H-benzo[d]imidazole-6-carboxylic acid was prepared in a manner as described in Procedure 22, starting with Intermediates I-1355 and I-1352. 1H NMR (400 MHz, DMSO-d6) δ 8.90 (d, J=1.3 Hz, 1H), 8.82 (s, 1H), 8.30 (s, 1H), 8.25 (d, J=1.5 Hz, 1H), 8.02 (d, J=1.3 Hz, 1H), 7.94-7.85 (m, 2H), 7.80 (dd, J=8.4, 1.6 Hz, 1H), 7.61 (d, J=8.5 Hz, 1H), 7.57-7.52 (m, 1H), 7.40 (dd, J=11.5, 6.0 Hz, 1H), 7.00 (d, J=8.2 Hz, 1H), 6.64 (t, J=75.4 Hz, 1H), 5.67 (s, 2H), 4.72 (t, J=5.1 Hz, 2H), 4.44 (s, 2H), 4.20 (t, J=5.0 Hz, 2H). ES/MS m/z: 668.0 (M+H⁺).

Example 561: 2-(4-(6-((4-chloro-6-(1H-1,2,3-triazol-1-yl)pyridin-3-yl)methoxy)pyridin-2-yl)-2,5-difluorobenzyl)-1-(2-isopropoxyethyl)-1H-benzo[d]imidazole-6-carboxylic acid 2-(4-(6-((4-chloro-6-(1H-1,2,3-triazol-1-yl)pyridin-3-yl)methoxy)pyridin-2-yl)-2,5-difluorobenzyl)-1-(2-isopropoxyethyl)-1H-benzo[d]imidazole-6-carboxylic acid was prepared in a manner as described in Procedure 22, starting with Intermediates I-1356 and I-1352. 1H NMR (400 MHz, DMSO-d6) δ 8.90 (d, J=1.3 Hz, 1H), 8.82 (s, 1H), 8.30 (s, 1H), 8.27 (d, J=1.5 Hz, 1H), 8.02 (d, J=1.2 Hz, 1H), 7.94-7.86 (m, 2H), 7.83 (dd, J=8.4, 1.5 Hz, 1H), 7.62 (d, J=8.4 Hz, 1H), 7.54 (dd, J=7.4, 1.7 Hz, 1H), 7.40 (dd, J=11.4, 6.1 Hz, 1H), 5.66 (s, 2H), 4.58 (t, J=5.1 Hz, 2H), 4.52 (s, 2H), 3.71 (t, J=5.0 Hz, 2H), 3.45 (p, J=6.0 Hz, 1H), 0.95 (s, 3H), 0.93 (s, 3H). ES/MS m/z: 660.0 (M+H⁺).

Example 562: 2-(4-(6-((4-chloro-6-(1H-1,2,3-triazol-1-yl)pyridin-3-yl)methoxy)pyridin-2-yl)-2,5-difluorobenzyl)-1-(2-cyclopropoxyethyl)-1H-benzo[d]imidazole-6-carboxylic acid 2-(4-(6-((4-chloro-6-(1H-1,2,3-triazol-1-yl)pyridin-3-yl)methoxy)pyridin-2-yl)-2,5-difluorobenzyl)-1-(2-cyclopropoxyethyl)-1H-benzo[d]imidazole-6-carboxylic acid was prepared in a manner as described in Procedure 22, starting with Intermediates I-1357 and I-1352. 1H NMR (400 MHz, DMSO-d6) δ 8.90 (d, J=1.3 Hz, 1H), 8.83 (s, 1H), 8.31 (s, 1H), 8.26 (d, J=1.5 Hz, 1H), 8.03 (d, J=1.3 Hz, 1H), 7.96-7.86 (m, 2H), 7.84 (dd, J=8.5, 1.6 Hz, 1H), 7.63 (d, J=8.4 Hz, 1H), 7.55 (dd, J=7.5, 1.7 Hz, 1H), 7.40 (dd, J=11.5, 6.1 Hz, 1H), 7.01 (d, J=8.3 Hz, 1H), 5.67 (s, 2H), 4.60 (t, J=5.1 Hz, 2H), 4.46 (s, 2H), 3.79 (t, J=5.0 Hz, 2H), 3.25 (tt, J=6.1, 3.0 Hz, 1H), 0.31 (ddd, J=13.8, 6.6, 2.7 Hz, 2H), 0.24 (tt, J=6.3, 3.2 Hz, 2H). ES/MS m/z: 658.1 (M+H⁺).

Example 563: 2-(4-(6-((4-chloro-6-(1H-1,2,3-triazol-1-yl)pyridin-3-yl)methoxy)pyridin-2-yl)-2,5-difluorobenzyl)-1-(2-methoxy-2-methylpropyl)-1H-benzo[d]imidazole-6-carboxylic acid 2-(4-(6-((4-chloro-6-(1H-1,2,3-triazol-1-yl)pyridin-3-yl)methoxy)pyridin-2-yl)-2,5-difluorobenzyl)-1-(2-methoxy-2-methylpropyl)-1H-benzo[d]imidazole-6-carboxylic acid was prepared in a manner as described in Procedure 35, starting with Intermediates I-1366 and I-1049. 1H NMR (400 MHz, DMSO-d6) δ 8.89 (d, J=1.2 Hz, 1H), 8.81 (s, 1H), 8.39 (d, J=1.5 Hz, 1H), 8.30 (s, 1H), 8.03 (d, J=1.3 Hz, 1H), 7.93-7.86 (m, 2H), 7.84 (dd, J=8.5, 1.3 Hz, 1H), 7.62 (d, J=8.4 Hz, 1H), 7.55 (dd, J=7.4, 1.7 Hz, 1H), 7.41 (dd, J=11.5, 6.1 Hz, 1H), 7.00 (d, J=8.2 Hz, 1H), 5.66 (s, 2H), 4.55 (s, 2H), 4.50 (s, 2H), 3.10 (s, 3H), 1.21 (s, 6H). ES/MS m/z: 660.2 (M+H⁺).

Example 564: 2-(4-(6-((4-chloro-2-fluorobenzyl)oxy)pyridin-2-yl)-2,5-difluorobenzyl)-1-((2S,3S)-3-methoxybutan-2-yl)-1H-benzo[d]imidazole-6-carboxylic acid 2-(4-(6-((4-chloro-2-fluorobenzyl)oxy)pyridin-2-yl)-2,5-difluorobenzyl)-1-((2S,3S)-3-methoxybutan-2-yl)-1H-benzo[d]imidazole-6-carboxylic acid was prepared in a manner as described in Procedure 35, starting with Intermediates I-1364 and I-102. 1H NMR (400 MHz, DMSO-d6) δ 8.32 (d, J=1.5 Hz, 1H), 7.90-7.85 (m, 1H), 7.85-7.78 (m, 2H), 7.64-7.57 (m, 2H), 7.53-7.47 (m, 2H), 7.38 (dd, J=11.5, 6.1 Hz, 1H), 7.32 (dd, J=8.2, 2.1 Hz, 1H), 6.94 (d, J=8.2 Hz, 1H), 5.50 (s, 2H), 4.70 (s, 1H), 4.45 (q, J=16.8 Hz, 2H), 3.93-3.81 (m, 1H), 3.00 (s, 3H), 1.62 (d, J=7.1 Hz, 3H), 1.21 (d, J=6.1 Hz, 3H). ES/MS m/z: 610.2 (M+H⁺).

Example 565: 2-(4-(6-((4-chloro-2-fluorobenzyl)oxy)pyridin-2-yl)-2,5-difluorobenzyl)-1-((2R,3R)-3-methoxybutan-2-yl)-1H-benzo[d]imidazole-6-carboxylic acid 2-(4-(6-((4-chloro-2-fluorobenzyl)oxy)pyridin-2-yl)-2,5-difluorobenzyl)-1-((2R,3R)-3-methoxybutan-2-yl)-1H- benzo[d]imidazole-6-carboxylic acid was prepared in a manner as described in Procedure 35, starting with Intermediates I-1362 and I-102. 1H NMR (400 MHz, DMSO-d6) δ 8.33 (d, J=1.5 Hz, 1H), 7.91-7.85 (m, 1H), 7.85-7.79 (m, 2H), 7.63 (d, J=8.3 Hz, 1H), 7.59 (d, J=8.2 Hz, 1H), 7.50 (td, J=10.0, 9.3, 1.9 Hz, 2H), 7.39 (dd, J=11.5, 6.1 Hz, 1H), 7.32 (dd, J=8.3, 2.1 Hz, 1H), 6.94 (d, J=8.2 Hz, 1H), 5.50 (s, 2H), 4.71 (s, 1H), 4.46 (q, J=16.8 Hz, 2H), 3.88 (dd, J=8.1, 6.1 Hz, 1H), 3.00 (s, 3H), 1.62 (d, J=7.1 Hz, 3H), 1.21 (d, J=6.1 Hz, 3H). ES/MS m/z: 610.2 (M+H$^+$).

Example 566: 2-(4-(6-((4-chloro-2-fluorobenzyl)oxy)pyridin-2-yl)-2,5-difluorobenzyl)-1-(2-isobutoxyethyl)-1H-benzo[d]imidazole-6-carboxylic acid -(4-(6-((4-chloro-2-fluorobenzyl)oxy)pyridin-2-yl)-2,5-difluorobenzyl)-1-(2-isobutoxyethyl)-1H-benzo[d]imidazole-6-carboxylic acid was prepared in a manner as described in Procedure 22, starting with Intermediates I-1358 and I-1255. 1H NMR (400 MHz, DMSO-d6) δ 8.26 (d, J=1.5 Hz, 1H), 7.91-7.85 (m, 1H), 7.84-7.82 (m, 1H), 7.81 (d, J=1.5 Hz, 1H), 7.66-7.56 (m, 1H), 7.61 (d, J=3.2 Hz, 1H), 7.54-7.46 (m, 2H), 7.37 (dd, J=11.5, 6.1 Hz, 1H), 7.33 (dd, J=8.4, 2.1 Hz, 1H), 6.95 (d, J=8.2 Hz, 1H), 5.50 (s, 2H), 4.61 (t, J=5.1 Hz, 2H), 4.50 (s, 2H), 3.71 (t, J=5.0 Hz, 2H), 3.10 (d, J=6.5 Hz, 2H), 1.66 (hept, J=6.7 Hz, 1H), 0.72 (s, 3H), 0.70 (s, 3H). ES/MS m/z: 624.3 (M+H$^+$).

Example 567: 2-(4-(6-((4-chloro-6-(4,5,6,7-tetrahydro-2H-benzo[d][1,2,3]triazol-2-yl)pyridin-3-yl)methoxy)pyridin-2-yl)-2,5-difluorobenzyl)-1-(2-methoxyethyl)-1H-benzo[d]imidazole-6-carboxylic acid 2-(4-(6-((4-chloro-6-(4,5,6,7-tetrahydro-2H-benzo[d][1,2,3]triazol-2-yl)pyridin-3-yl)methoxy)pyridin-2-yl)-2,5-difluorobenzyl)-1-(2-methoxyethyl)-1H-benzo[d]imidazole-6-carboxylic acid was prepared in a manner as described in Procedure 38, starting with Intermediates I-1359 and I-1354. 1H NMR (400 MHz, DMSO-d6) δ 8.73 (s, 1H), 8.26 (d, J=1.5 Hz, 1H), 8.04 (s, 1H), 7.93-7.86 (m, 2H), 7.84 (dd, J=8.4, 1.5 Hz, 1H), 7.64 (d, J=8.5 Hz, 1H), 7.54 (dd, J=7.5, 1.7 Hz, 1H), 7.41 (dd, J=11.5, 6.1 Hz, 1H), 6.99 (d, J=8.2 Hz, 1H), 5.62 (s, 2H), 4.63 (t, J=5.1 Hz, 2H), 4.50 (s, 2H), 3.69 (t, J=5.0 Hz, 2H), 3.21 (s, 3H), 2.77 (d, J=5.5 Hz, 4H), 1.83 (q, J=3.3 Hz, 4H). ES/MS m/z: 686.3 (M+H$^+$).

Example 568: 2-(4-(6-((4-chloro-6-(4,5,6,7-tetrahydro-1H-benzo[d][1,2,3]triazol-1-yl)pyridin-3-yl)methoxy)pyridin-2-yl)-2,5-difluorobenzyl)-1-(2-methoxyethyl)-1H-benzo[d]imidazole-6-carboxylic acid 2-(4-(6-((4-chloro-6-(4,5,6,7-tetrahydro-1H-benzo[d][1,2,3]triazol-1-yl)pyridin-3-yl)methoxy)pyridin-2-yl)-2,5-difluorobenzyl)-1-(2-methoxyethyl)-1H-benzo[d]imidazole-6-carboxylic acid was prepared in a manner as described in Procedure 38, starting with Intermediates I-1359 and I-1353. 1H NMR (400 MHz, DMSO-d6) δ 8.79 (s, 1H), 8.24 (d, J=1.5 Hz, 1H), 8.20 (s, 1H), 7.91 (t, J=7.9 Hz, 1H), 7.88-7.79 (m, 2H), 7.62 (d, J=8.4 Hz, 1H), 7.54 (dd, J=7.5, 1.7 Hz, 1H), 7.40 (dd, J=11.5, 6.0 Hz, 1H), 7.00 (d, J=8.2 Hz, 1H), 5.64 (s, 2H), 4.62 (t, J=5.2 Hz, 2H), 4.48 (s, 2H), 3.68 (t, J=5.1 Hz, 2H), 3.21 (s, 3H), 3.03 (s, 2H), 2.71 (s, 2H), 1.82-1.71 (m, 4H). ES/MS m/z: 686.1 (M+H$^+$).

Example 569: 2-(4-(6-((4-chloro-6-(1H-1,2,3-triazol-1-yl)pyridin-3-yl)methoxy)pyridin-2-yl)-2,5-difluorobenzyl)-1-(2-isobutoxyethyl)-1H-benzo[d]imidazole-6-carboxylic acid 2-(4-(6-((4-chloro-6-(1H-1,2,3-triazol-1-yl)pyridin-3-yl)methoxy)pyridin-2-yl)-2,5-difluorobenzyl)-1-(2-isobutoxyethyl)-1H-benzo[d]imidazole-6-carboxylic acid was prepared in a manner as described in Procedure 22, starting with Intermediates I-1358 and I-1352. 1H NMR (400 MHz, DMSO-d6) δ 8.89 (d, J=1.3 Hz, 1H), 8.82 (s, 1H), 8.30 (s, 1H), 8.28 (d, J=1.5 Hz, 1H), 8.02 (d, J=1.3 Hz, 1H), 7.94-7.90 (m, 1H), 7.90-7.86 (m, 1H), 7.84 (dd, J=8.4, 1.5 Hz, 1H), 7.63 (d, J=8.5 Hz, 1H), 7.54 (dd, J=7.3, 1.7 Hz, 1H), 7.39 (dd, J=11.4, 6.1 Hz, 1H), 7.00 (dd, J=8.3, 0.6 Hz, 1H), 5.66 (s, 2H), 4.63 (t, J=5.0 Hz, 2H), 4.53 (s, 2H), 3.71 (t, J=4.9 Hz, 2H), 3.10 (d, J=6.5 Hz, 2H), 1.65 (hept, J=6.7 Hz, 1H), 0.72 (s, 3H), 0.70 (s, 3H). ES/MS m/z: 674.1 (M+H$^+$).

Example 570: 2-(4-(6-((4-chloro-2-fluorobenzyl)oxy)pyridin-2-yl)-2,5-difluorobenzyl)-1-((3R,4R)-4-isopropoxytetrahydrofuran-3-yl)-1H-benzo[d]imidazole-6-carboxylic acid 2-(4-(6-((4-chloro-2-fluorobenzyl)oxy)pyridin-2-yl)-2,5-difluorobenzyl)-1-((3R,4R)-4-isopropoxytetrahydrofuran-3-yl)-1H-benzo[d]imidazole-6-carboxylic acid was prepared in a manner as described in Procedure 37, starting with Intermediates I-1346 and I-1368. 1H NMR (400 MHz, DMSO) δ 8.36 (d, J=1.5 Hz, 1H), 7.93-7.79 (m, 3H), 7.71 (d, J=8.5 Hz, 1H), 7.60 (t, J=8.2 Hz, 1H), 7.56-7.46 (m, 2H), 7.46-7.26 (m, 2H), 6.95 (d, J=8.3 Hz, 1H), 5.50 (s, 2H), 5.29 (dt, J=7.4, 3.5 Hz, 1H), 4.67-4.13 (m, 6H), 3.78-3.59 (m, 1H), 3.37 (m, J=7.0 Hz, 1H), 1.00 (d, J=7.0 Hz, 6H). ES/MS m/z: 652.2 (M+H$^+$).

Example 571: 2-(4-(6-((4-chloro-2-fluorobenzyl)oxy)pyridin-2-yl)-2,5-difluorobenzyl)-1-((3R,4R)-4-ethoxytetrahydrofuran-3-yl)-1H-benzo[d]imidazole-6-carboxylic acid 2-(4-(6-((4-chloro-2-fluorobenzyl)oxy)pyridin-2-yl)-2,5-difluorobenzyl)-1-((3R,4R)-4-ethoxytetrahydrofuran-3-yl)-1H-benzo[d]imidazole-6-carboxylic acid was prepared in a manner as described in Procedure 37, starting with Intermediates I-1346 and I-1367. 1H NMR (400 MHz, DMSO) δ 8.34 (d, J=1.5 Hz, 1H), 7.93-7.79 (m, 3H), 7.69 (d, J=8.5 Hz, 1H), 7.60 (t, J=8.2 Hz, 1H), 7.50 (ddd, J=8.6, 5.6, 2.0 Hz, 2H), 7.45-7.27 (m, 2H), 6.95 (d, J=8.2 Hz, 1H), 5.50 (s, 2H), 5.39-5.18 (m, 1H), 4.64-4.46 (m, 2H), 4.46-4.34 (m, 2H), 4.34-4.12 (m, 2H), 3.71 (h, J=5.2 Hz, 1H), 3.45-3.30 (m, 2H), 1.00 (t, J=7.0 Hz, 3H). ES/MS m/z: 638.1 (M+H$^+$).

Example 572: (R)-1-(2-oxabicyclo[3.1.1]heptan-4-yl)-2-(4-(6-((4-chloro-2-fluorobenzyl)oxy)pyridin-2-yl)-2,5-difluorobenzyl)-1H-benzo[d]imidazole-6-carboxylic acid Example 573: (S)-1-(2-oxabicyclo[3.1.1]heptan-4-yl)-2-(4-(6-((4-chloro-2-fluorobenzyl)oxy)pyridin-2-yl)-2,5-difluorobenzyl)-1H-benzo[d]imidazole-6-carboxylic acid Examples 572 and 572: (R)-1-(2-oxabicyclo[3.1.1]heptan-4-yl)-2-(4-(6-((4-chloro-2-fluorobenzyl)oxy)pyridin-2-yl)-2,5-difluorobenzyl)-1H-benzo[d]imidazole-6-carboxylic acid (Example 572) and (S)-1-(2-oxabicyclo[3.1.1]heptan-4-yl)-2-(4-(6-((4-chloro-2-fluorobenzyl)oxy)pyridin-2-yl)-2,5-difluorobenzyl)-1H-benzo[d]imidazole-6-carboxylic acid (Example 573) were prepared via preparative chiral SFC (Chiralpak OJ-H column, MeOH/CO₂ eluent) of Example 407.

Example 574: (S)-1-(4,4-dimethyltetrahydrofuran-3-yl)-2-(2,3,6-trifluoro-4-(2-((4-fluorobenzyl)oxy)pyrimidin-4-yl)benzyl)-1H-benzo[d]imidazole-6-carboxylic acid (S)-1-(4,4-dimethyltetrahydrofuran-3-yl)-2-(2,3,6-trifluoro-4-(2-((4-fluorobenzyl)oxy)pyrimidin-4-yl)benzyl)-1H-benzo[d]imidazole-6-carboxylic acid was prepared in a manner as described in Procedure 35, starting with Intermediates I-1387 and I-1231. 1H NMR (400 MHz, DMSO) δ 8.84 (d, J=5.1 Hz, 1H), 8.48 (s, 1H), 7.84 (ddd, J=9.9, 5.6, 2.0 Hz, 1H), 7.78 (dd, J=8.4, 1.5 Hz, 1H), 7.68 (dd, J=5.1, 1.8 Hz, 1H), 7.63-7.53 (m, 3H), 7.30-7.20 (m, 2H), 5.50 (s, 2H), 5.13-5.04 (m, 1H), 4.68 (d, J=17.3 Hz, 1H), 4.57 (d, J=11.5 Hz, 1H), 4.51-4.34 (m, 2H), 3.79-3.74 (m, 2H), 1.39 (s, 3H), 0.66 (s, 3H). ES/MS m/z: 607.0 (M+H⁺).

Example 575: (S)-2-(2,5-difluoro-4-(2-((4-fluorobenzyl)oxy)pyrimidin-4-yl)benzyl)-1-(4,4-dimethyltetrahydrofuran-3-yl)-1H-benzo[d]imidazole-6-carboxylic acid (S)-2-(2,5-difluoro-4-(2-((4-fluorobenzyl)oxy)pyrimidin-4-yl)benzyl)-1-(4,4-dimethyltetrahydrofuran-3-yl)-1H-benzo[d]imidazole-6-carboxylic acid was prepared in a manner as described in Procedure 35, starting with Intermediates I-1387 and I-82. 1H NMR (400 MHz, DMSO) δ 8.78 (d, J=5.2 Hz, 1H), 8.48 (s, 1H), 7.94 (dd, J=10.2, 6.3 Hz, 1H), 7.80 (dd, J=8.4, 1.5 Hz, 1H), 7.70-7.50 (m, 5H), 7.29-7.19 (m, 2H), 5.49 (s, 2H), 5.02 (d, J=6.7 Hz, 1H), 4.61-4.50 (m, 2H), 4.49-4.36 (m, 2H), 3.81-3.70 (m, 2H), 1.34 (s, 3H), 0.61 (s, 3H). ES/MS m/z: 589.1 (M+H⁺).

Example 576: (5-methyl-2-oxo-1,3-dioxol-4-yl)methyl (S)-2-(4-(6-((4-chloro-2-fluorobenzyl)oxy)pyridin-2-yl)-2,5-difluorobenzyl)-1-(4,4-dimethyltetrahydrofuran-3-yl)-1H-benzo[d]imidazole-6-carboxylate Procedure 42

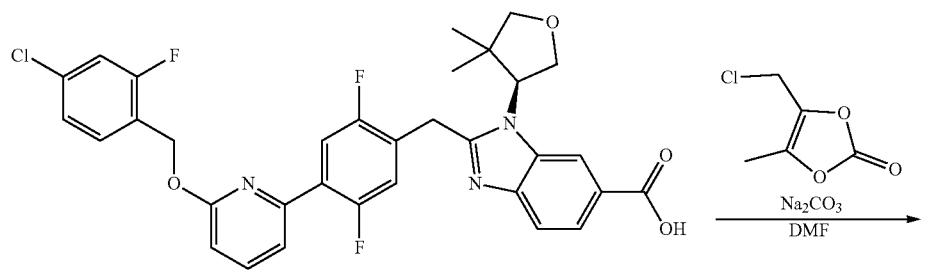

Example 115

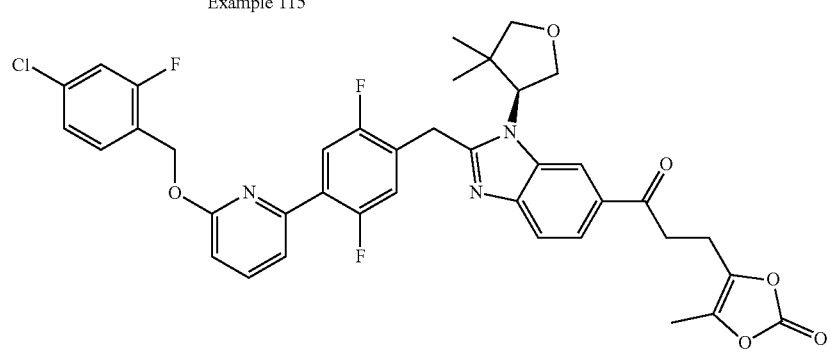

Example 576

(5-methyl-2-oxo-1,3-dioxol-4-yl)methyl (S)-2-(4-(6-((4-chloro-2-fluorobenzyl)oxy)pyridin-2-yl)-2,5-difluorobenzyl)-1-(4,4-dimethyltetrahydrofuran-3-yl)-1H-benzo[d]imidazole-6-carboxylate: Na₂CO₃ (17 mg, 0.16 mmol) followed by 4-(chloromethyl)-5-methyl-1,3-dioxol-2-one (0.018 mL, 0.16 mmol) were added to a mixture of (S)-2-(4-(6-((4-chloro-2-fluorobenzyl)oxy)pyridin-2-yl)-2,5-difluorobenzyl)-1-(4,4-dimethyltetrahydrofuran-3-yl)-1H-benzo[d]imidazole-6-carboxylic acid (Example 115, 50 mg, 0.08 mmol) in DMF (1.0 mL). The resulting mixture was stirred at rt overnight. The mixture was diluted with EtOAc and washed with water then 10% LiCl. Organic phase was dried over MgSO₄, filtered, concentrated, and purified by silica gel flash column chromatography (EtOAc in Hex) to yield the title compound. 1H NMR (400 MHz, DMSO-d6) δ 8.52 (s, 1H), 7.88 (dd, J=8.2, 7.5 Hz, 1H), 7.85-7.79 (m, 2H), 7.65 (d, J=8.6 Hz, 1H), 7.60 (t, J=8.2 Hz, 1H), 7.55-7.51 (m, 1H), 7.49 (dd, J=10.1, 2.1 Hz, 1H), 7.47-7.42 (m, 1H), 7.33 (dd, J=8.3, 2.1 Hz, 1H), 6.95 (d, J=8.2 Hz, 1H), 5.50 (s, 2H), 5.23 (s, 2H), 5.02 (d, J=6.6 Hz, 1H), 4.53 (d, J=13.9 Hz, 2H), 4.48-4.30 (m, 2H), 3.80-3.68 (m, 2H), 2.23 (s, 3H), 1.34 (s, 3H), 1.21 (d, J=16.9 Hz, 1H), 0.59 (s, 3H). ES/MS m/z: 734.0 (M+H$^+$).

Example 577: (phosphonooxy)methyl (S)-2-(4-(6-((4-chloro-2-fluorobenzyl)oxy)pyridin-2-yl)-2,5-difluorobenzyl)-1-(4,4-dimethyltetrahydrofuran-3-yl)-1H-benzo[d]imidazole-6-carboxylate Procedure 43

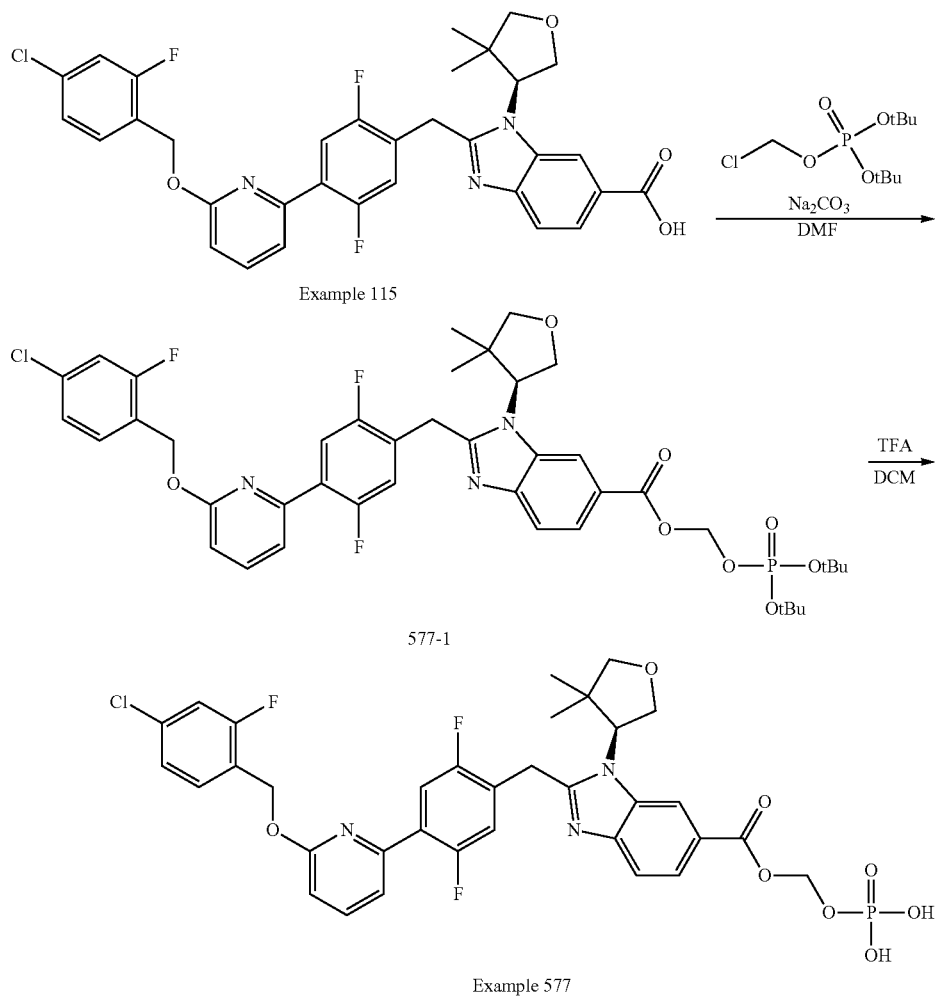

((di-tert-butoxyphosphoryl)oxy)methyl (S)-2-(4-(6-((4-chloro-2-fluorobenzyl)oxy)pyridin-2-yl)-2,5-difluorobenzyl)-1-(4,4-dimethyltetrahydrofuran-3-yl)-1H-benzo[d]imidazole-6-carboxylate (577-1): Na$_2$CO$_3$ (17 mg, 0.16 mmol) followed by di-tert-butyl (chloromethyl) phosphate (41 mg, 0.161 mmol) were added to a mixture of (S)-2-(4-(6-((4-chloro-2-fluorobenzyl)oxy)pyridin-2-yl)-2,5-difluorobenzyl)-1-(4,4-dimethyltetrahydrofuran-3-yl)-1H-benzo[d]imidazole-6-carboxylic acid (Example 115, 50 mg, 0.08 mmol) in DMF (1.0 mL)> The resulting mixture was stirred at rt overnight. The mixture was diluted with EtOAc and washed with water then 10% LiCl. Nest, the organic phase was dried over MgSO$_4$, filtered, concentrated, and purified by silica gel flash column chromatography (EtOAc in Hex) to yield the title compound. ES/MS: 844.1 (M+H$^+$).

(phosphonooxy)methyl (S)-2-(4-(6-((4-chloro-2-fluorobenzyl)oxy)pyridin-2-yl)-2,5-difluorobenzyl)-1-(4,4-dimethyltetrahydrofuran-3-yl)-1H-benzo[d]imidazole-6-carboxylate (Example 577): A mixture of ((di-tert-butoxyphosphoryl)oxy)methyl (S)-2-(4-(6-((4-chloro-2-fluorobenzyl)oxy)pyridin-2-yl)-2,5-difluorobenzyl)-1-(4,4-dimethyltetrahydrofuran-3-yl)-1H-benzo[d]imidazole-6-carboxylate (577-1, 68 mg, 0.0805 mmol) in DCM (2 mL) and TFA (0.5 mL) was stirred at rt for 30 min. Solvent was evaporated to give the title compound. 1H NMR (400 MHz, DMSO-d6) δ 8.54 (s, 1H), 7.92-7.80 (m, 3H), 7.68 (d, J=8.5 Hz, 1H), 7.60 (t, J=8.2 Hz, 1H), 7.53 (dd, J=7.5, 1.6 Hz, 1H), 7.49 (dd, J=10.0, 2.1 Hz, 1H), 7.47-7.43 (m, 1H), 7.33 (dd, J=8.4, 2.1 Hz, 1H), 6.95 (d, J=8.4 Hz, 1H), 5.82-5.68 (m, 2H), 5.51 (s, 2H), 5.03 (d, J=6.7 Hz, 1H), 4.60-4.55 (m, 1H), 4.53 (s, 1H), 4.48-4.35 (m, 2H), 3.79 (d, J=8.7 Hz, 1H), 3.73 (d, J=8.6 Hz, 1H), 1.34 (s, 3H), 0.60 (s, 3H). ES/MS m/z: 731.9 (M+H$^+$).

Example 578: (isobutyryloxy)methyl (S)-2-(4-(6-((4-chloro-2-fluorobenzyl)oxy)pyridin-2-yl)-2,5-difluorobenzyl)-1-(4,4-dimethyltetrahydrofuran-3-yl)-1H-benzo[d]imidazole-6-carboxylate (isobutyryloxy)methyl (S)-2-(4-(6-((4-chloro-2-fluorobenzyl)oxy)pyridin-2-yl)-2,5-difluorobenzyl)-1-(4,4-dimethyltetrahydrofuran-3-yl)-1H-benzo[d]imidazole-6-carboxylate was prepared in a manner as described in Procedure 42, using Example 115 and chloromethyl isobutyrate. ES/MS m/z: 722.1 (M+H$^+$).

Comparative Example 1 (CE-1)

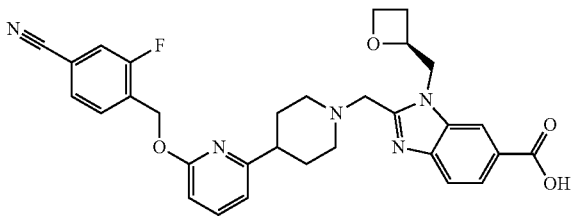

CE-1

(S)-2-((4-(6-((4-cyano-2-fluorobenzyl)oxy)pyridin-2-yl)piperidin-1-yl)methyl)-1-(oxetan-2-ylmethyl)-1H-benzo[d]imidazole-6-carboxylic acid: (S)-2-((4-(6-((4-cyano-2-fluorobenzyl)oxy)pyridin-2-yl)piperidin-1-yl)methyl)-1-(oxetan-2-ylmethyl)-1H-benzo[d]imidazole-6-carboxylic acid was prepared in a manner as described in Patent Application WO2018/109607 (see Example 4A-01) and references therein.

Comparative Example 2 (CE-2)

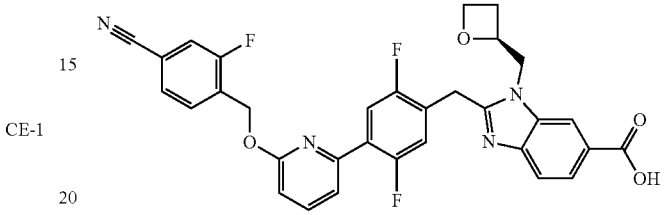

CE-2

(S)-2-(4-(6-((4-cyano-2-fluorobenzyl)oxy)pyridin-2-yl)-2,5-difluorobenzyl)-1-(oxetan-2-ylmethyl)-1H-benzo[d]imidazole-6-carboxylic acid (Comparative Example 2): (S)-2-(4-(6-((4-cyano-2-fluorobenzyl)oxy)pyridin-2-yl)-2,5-difluorobenzyl)-1-(oxetan-2-ylmethyl)-1H-benzo[d]imidazole-6-carboxylic acid was prepared in a manner as described in Patent Application WO2021/081207 (see Example 444) and references therein.

TABLE 2
Compounds
| Ex. | Structure | Procedure | ES/MS m/z | ¹H NMR |
|---|---|---|---|---|
| 1 | 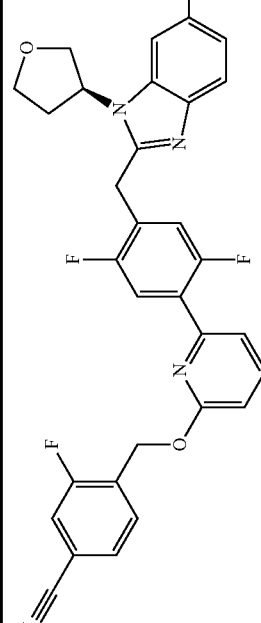 | 1 | 585.3 | 1H NMR (400 MHz, DMSO-d6) δ 8.43 (d, J = 1.4 Hz, 1H), 7.97-7.85 (m, 3H), 7.83-7.71 (m, 3H), 7.68 (d, J = 8.5 Hz, 1H), 7.53 (dd, J = 7.5, 1.7 Hz, 1H), 7.40 (dd, J = 11.5, 6.1 Hz, 1H), 7.00 (d, J = 8.2 Hz, 1H), 5.60 (s, 2H), 5.58-5.49 (m, 1H), 4.58 (s, 2H), 4.31 (td, J = 8.7, 2.8 Hz, 1H), 4.22 (dd, J = 10.4, 2.8 Hz, 1H), 3.97 (dd, J = 10.5, 7.7 Hz, 1H), 3.72 (td, J = 9.3, 7.0 Hz, 1H), 2.23-2.06 (m, 1H). |
| 2 | 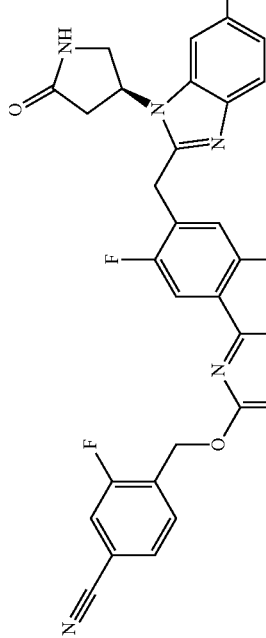 | 1 | 598.2 | 1H NMR (400 MHz, DMSO) δ 8.22 (s, 1H), 8.09 (d, J = 1.4 Hz, 1H), 7.97-7.82 (m, 3H), 7.81-7.71 (m, 3H), 7.68 (d, J = 8.4 Hz, 1H), 7.54 (dd, J = 7.5, 1.7 Hz, 1H), 7.38 (dd, J = 11.5, 6.1 Hz, 1H), 7.00 (d, J = 8.3 Hz, 1H), 5.68 (tt, J = 10.0, 5.2 Hz, 1H), 5.60 (s, 2H), 4.51 (s, 2H), 3.89 (t, J = 10.1 Hz, 1H), 3.62 (dd, J = 10.9, 4.6 Hz, 1H), 2.86 (dd, J = 17.9, 10.4 Hz, 1H), 2.62 (dd, J = 17.8, 5.7 Hz, 1H). |

TABLE 2-continued

Compounds

| Ex. | Structure | Procedure | ES/MS m/z | 1H NMR |
|---|---|---|---|---|
| 3 | 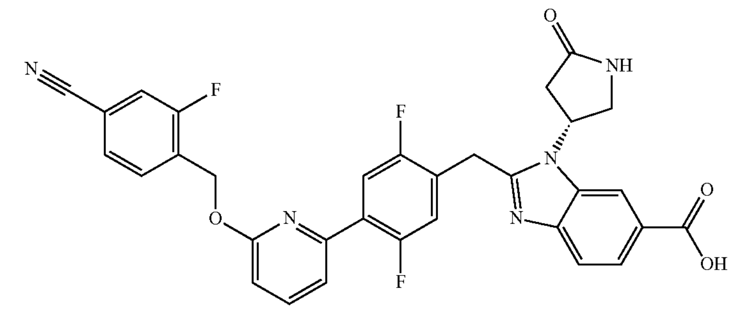 [SMILES: N#Cc1ccc(COc2cccc(-c3cc(F)c(Cc4nc5ccc(C(=O)O)cc5n4[C@H]4CNC(=O)C4)cc3F)n2)c(F)c1] | 1 | 598.3 | 1H NMR (400 MHz, DMSO) δ 8.22 (s, 1H), 8.09 (d, J = 1.5 Hz, 1H), 7.96-7.82 (m, 3H), 7.81-7.71 (m, 3H), 7.68 (d, J = 8.5 Hz, 1H), 7.54 (dd, J = 7.6, 1.7 Hz, 1H), 7.38 (dd, J = 11.4, 6.1 Hz, 1H), 7.00 (d, J = 8.2 Hz, 1H), 5.68 (tt, J = 10.1, 5.2 Hz, 1H), 5.60 (s, 2H), 4.51 (s, 2H), 3.89 (t, J = 10.1 Hz, 1H), 3.61 (dd, J = 11.0, 4.6 Hz, 1H), 2.86 (dd, J = 17.9, 10.4 Hz, 1H), 2.62 (dd, J = 17.9, 5.7 Hz, 1H). |
| 4 | 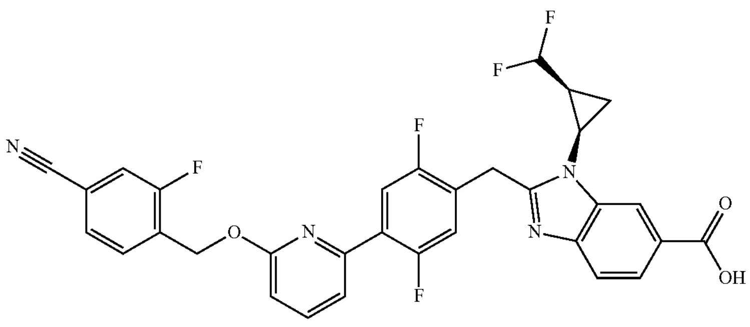 [SMILES: N#Cc1ccc(COc2cccc(-c3cc(F)c(Cc4nc5ccc(C(=O)O)cc5n4[C@@H]4C[C@@H]4C(F)F)cc3F)n2)c(F)c1] | 1 | 605.3 | 1H NMR (400 MHz, Methanol-d4) δ 8.64-8.45 (m, 1H), 8.15 (td, J = 9.0, 1.5 Hz, 1H), 7.91-7.78 (m, 2H), 7.78-7.66 (m, 2H), 7.66-7.48 (m, 3H), 7.33 (ddd, J = 17.3, 11.2, 6.1 Hz, 1H), 7.09-6.83 (m, 1H), 6.16 (td, J = 56.2, 4.3 Hz, 1H), 5.67-5.59 (m, 2H), 4.72 (d, J = 3.1 Hz, 2H), 3.91 (q, J = 5.4, 4.0 Hz, 1H), 2.36 (d, J = 57.4 Hz, 1H), 1.94 (d, J = 9.4 Hz, 1H), 1.86-1.75 (m, 1H). |
| 5 | 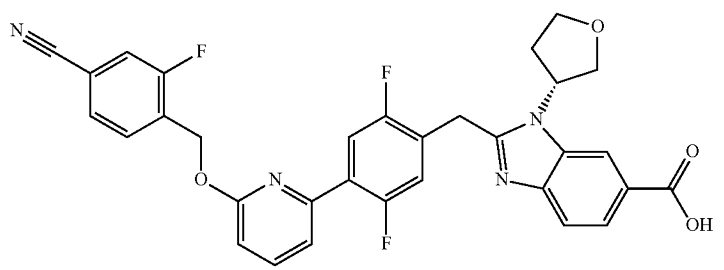 [SMILES: N#Cc1ccc(COc2cccc(-c3cc(F)c(Cc4nc5ccc(C(=O)O)cc5n4[C@@H]4CCOC4)cc3F)n2)c(F)c1] | 1 | 585.5 | 1H NMR (400 MHz, DMSO-d6) δ 8.43 (d, J = 1.4 Hz, 1H), 7.97-7.85 (m, 3H), 7.83-7.71 (m, 3H), 7.68 (d, J = 8.5 Hz, 1H), 7.53 (dd, J = 7.5, 1.7 Hz, 1H), 7.40 (dd, J = 11.5, 6.1 Hz, 1H), 7.00 (d, J = 8.2 Hz, 1H), 5.60 (s, 2H), 5.58-5.49 (m, 1H), 4.58 (s, 2H), 4.31 (td, J = 8.7, 2.8 Hz, 1H), 4.22 (dd, J = 10.4, 2.8 Hz, 1H), 3.97 (dd, J = 10.5, 7.7 Hz, 1H), 3.72 (td, J = 9.3, 7.0 Hz, 1H), 2.23-2.06 (m, 1H). |

TABLE 2-continued

Compounds

| Ex. | Structure | Procedure | ES/MS m/z | ¹H NMR |
|---|---|---|---|---|
| 6 | 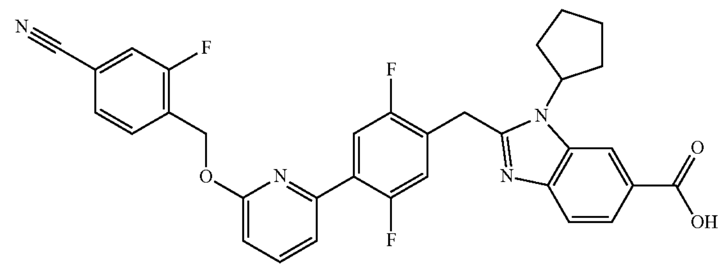 [SMILES: N#Cc1ccc(COc2cccc(-c3cc(F)c(Cc4nc5ccc(C(=O)O)cc5n4C4CCCC4)cc3F)n2)c(F)c1] | 1 | 583.6 | 1H NMR (400 MHz, DMSO-d6) δ 8.18 (d, J = 1.4 Hz, 1H), 7.97-7.85 (m, 3H), 7.83-7.68 (m, 4H), 7.53 (dd, J = 7.5, 1.7 Hz, 1H), 7.41 (dd, J = 11.5, 6.1 Hz, 1H), 7.00 (d, J = 8.2 Hz, 1H), 5.60 (s, 2H), 5.16 (p, J = 8.8 Hz, 1H), 4.58 (s, 2H), 2.22-2.08 (m, 4H), 2.06-1.94 (m, 2H), 1.89-1.69 (m, 2H). |
| 7 | 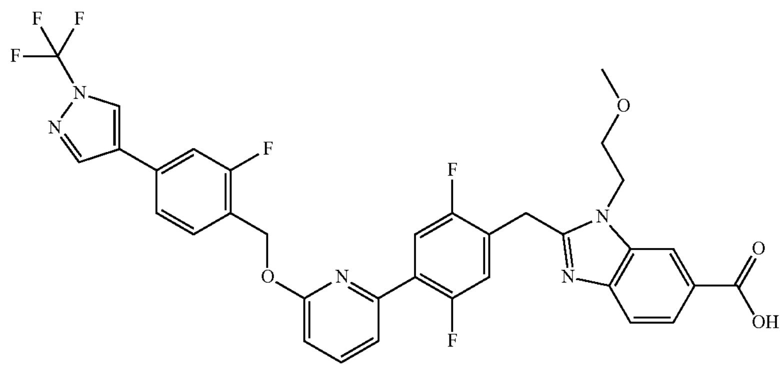 [SMILES: COCCn1c(Cc2cc(F)c(-c3cccc(OCc4ccc(-c5cnn(C(F)(F)F)c5)cc4F)n3)cc2F)nc2ccc(C(=O)O)cc21] | 2 | MH+ 682.2 | 1H NMR (400 MHz, DMSO-d6) δ 9.08 (s, 1H), 8.54 (s, 1H), 8.20 (s, 1H), 7.91-7.82 (m, 2H), 7.79 (dd, J = 8.4, 1.6 Hz, 1H), 7.73 (d, J = 11.5 Hz, 1H), 7.67-7.54 (m, 3H), 7.52 (d, J = 7.3 Hz, 1H), 7.38 (dd, J = 11.7, 6.1 Hz, 1H), 6.96 (d, J = 8.2 Hz, 1H), 6.53 (s, 1H), 5.53 (s, 2H), 4.59 (t, J = 5.1 Hz, 2H), 4.44 (s, 2H), 3.68 (t, J = 5.1 Hz, 2H), 3.21 (s, 3H). |
| 8 | 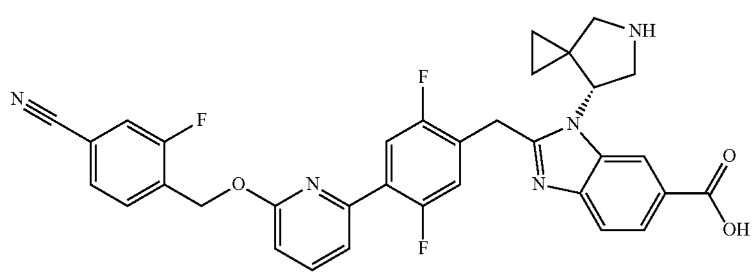 [SMILES: N#Cc1ccc(COc2cccc(-c3cc(F)c(Cc4nc5ccc(C(=O)O)cc5n4[C@H]4CNCC45CC5)cc3F)n2)c(F)c1] | 3 | (MH+) 610.2 | 1H NMR (400 MHz, DMSO-d6) δ 8.42 (s, 1H), 7.97-7.85 (m, 2H), 7.82-7.67 (m, 4H), 7.63 (dd, J = 8.4, 1.6 Hz, 1H), 7.53 (dd, J = 7.7, 1.6 Hz, 1H), 7.31 (dd, J = 11.5, 6.2 Hz, 1H), 7.00 (d, J = 8.3 Hz, 1H), 5.60 (s, 2H), 5.07 (s, 1H), 4.41 (s, 2H), 3.68 (t, J = 10.4 Hz, 2H), 3.14 (d, J = 11.0 Hz, 2H), 0.83 (d, J = 23.4 Hz, 2H), 0.58 (m, 2H). |

TABLE 2-continued

Compounds

| Ex. | Structure | Procedure | ES/MS m/z | ¹H NMR |
|---|---|---|---|---|
| 9 | 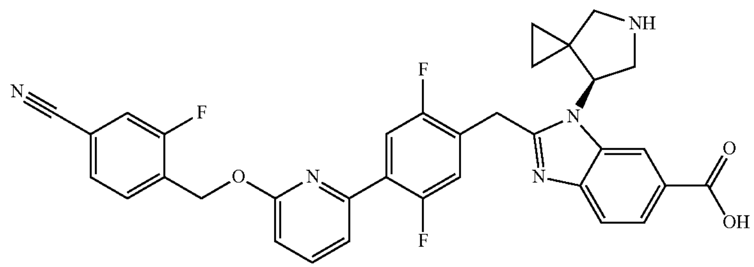 [SMILES: N#Cc1ccc(COc2cccc(-c3cc(F)c(Cc4nc5ccc(C(=O)O)cc5n4[C@@H]4CNCC45CC5)cc3F)n2)c(F)c1] | 3 | (MH+) 610.2 | 1H NMR (400 MHz, DMSO-d6) δ 8.48 (s, 1H), 7.98-7.81 (m, 2H), 7.77 (ddd, J = 16.8, 8.1, 1.5 Hz, 5H), 7.62 (d, J = 8.5 Hz, 1H), 7.57-7.45 (m, 1H), 7.30 (d, J = 10.5 Hz, 1H), 6.99 (d, J = 8.3 Hz, 1H), 6.54 (s, 0H), 5.60 (s, 2H), 5.40 (s, 0H), 5.01 (s, 1H), 4.40 (s, 2H), 3.60 (s, 1H), 3.11-2.99 (m, 1H), 0.76 (d, J = 8.8 Hz, 1H), 0.58 (s, 3H), −0.06 (s, 1H). |
| 10 | 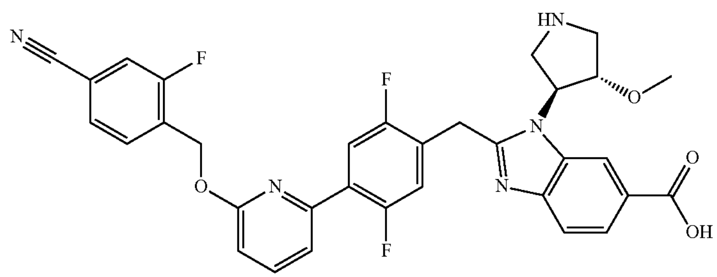 [SMILES: CO[C@H]1CNC[C@@H]1n1c(Cc2cc(F)c(-c3cccc(OCc4ccc(C#N)cc4F)n3)cc2F)nc2ccc(C(=O)O)cc21] | 3 | 614.2 | 1H NMR (400 MHz, DMSO-d6) δ 9.34 (s, 2H), 8.27 (d, J = 1.4 Hz, 1H), 7.99-7.84 (m, 4H), 7.83-7.67 (m, 5H), 7.53 (dd, J = 7.5, 1.7 Hz, 1H), 7.01 (d, J = 8.3 Hz, 1H), 5.60 (s, 2H), 5.28 (td, J = 10.2, 7.9 Hz, 1H), 4.68 (q, J = 7.0 Hz, 1H), 4.56-4.34 (m, 2H), 3.34 (d, J = 11.4 Hz, 1H), 3.15 (s, 3H). |
| 11 | 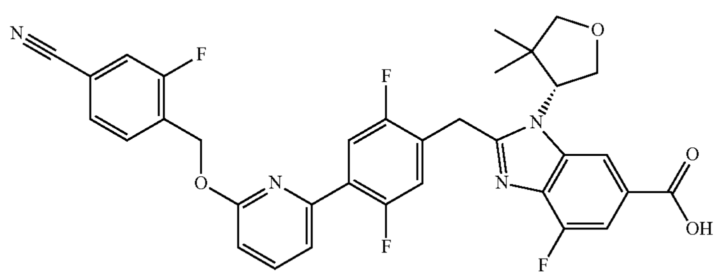 [SMILES: CC1(C)COC[C@@H]1n1c(Cc2cc(F)c(-c3cccc(OCc4ccc(C#N)cc4F)n3)cc2F)nc2c(F)cc(C(=O)O)cc21] | 3 | 631.2 | 1H NMR (400 MHz, DMSO) δ 13.09 (s, 1H), 8.35 (s, 1H), 7.96-7.86 (m, 2H), 7.83-7.70 (m, 3H), 7.59-7.42 (m, 3H), 7.00 (d, J = 8.2 Hz, 1H), 5.61 (s, 2H), 5.03 (d, J = 6.6 Hz, 1H), 4.59-4.49 (m, 2H), 4.48-4.35 (m, 2H), 3.75 (q, J = 8.7 Hz, 2H), 1.34 (s, 3H), 0.61 (s, 3H). |

TABLE 2-continued

Compounds

| Ex. | Structure | Procedure | ES/MS m/z | ¹H NMR |
|---|---|---|---|---|
| 12 | 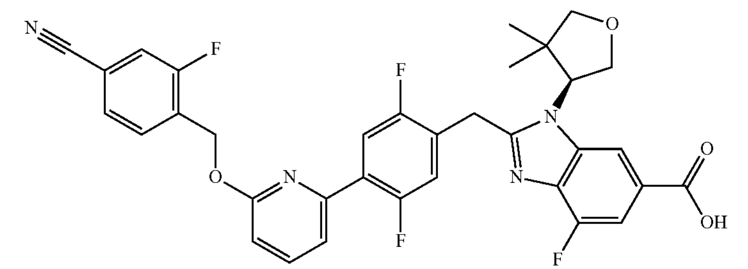 [SMILES: CC1(C)COC[C@H]1n1c(Cc2cc(F)c(-c3cccc(OCc4ccc(C#N)cc4F)n3)cc2F)nc2c(F)cc(C(=O)O)cc21] | 3 | 631.2 | 1H NMR (400 MHz, DMSO) δ 13.10 (s, 1H), 8.35 (s, 1H), 7.96-7.86 (m, 2H), 7.83-7.70 (m, 3H), 7.59-7.48 (m, 2H), 7.46 (dd, J = 11.4, 6.1 Hz, 1H), 7.00 (d, J = 8.2 Hz, 1H), 5.61 (s, 2H), 5.03 (d, J = 6.5 Hz, 1H), 4.59-4.49 (m, 2H), 4.48-4.35 (m, 2H), 3.75 (q, J = 8.7 Hz, 2H), 1.33 (s, 3H), 0.61 (s, 3H). |
| 13 | 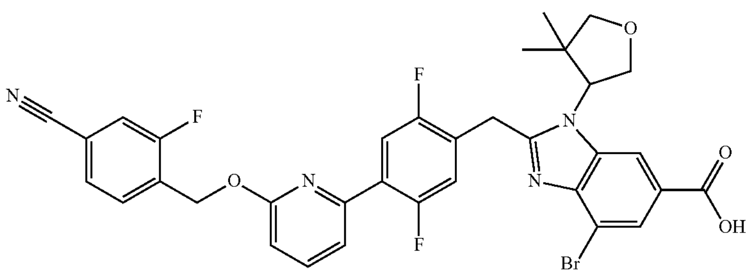 [SMILES: CC1(C)COCC1n1c(Cc2cc(F)c(-c3cccc(OCc4ccc(C#N)cc4F)n3)cc2F)nc2c(Br)cc(C(=O)O)cc21] | 3 | 693.19 | 1H NMR (400 MHz, Methanol-d4) δ 8.71 (s, 1H), 8.17 (d, J = 1.2 Hz, 1H), 7.90-7.67 (m, 3H), 7.66-7.47 (m, 3H), 7.19 (dd, J = 11.5, 6.0 Hz, 1H), 6.92 (d, J = 8.2 Hz, 1H), 5.63 (s, 2H), 4.55 (dd, J = 11.4, 1.9 Hz, 3H), 4.44 (dd, J = 11.3, 6.8 Hz, 1H), 3.93 (d, J = 8.9 Hz, 1H), 3.78 (d, J = 8.8 Hz, 1H), 3.37-3.34 (m, 2H), 1.30 (s, 3H), 0.61 (s, 3H). |
| 14 | 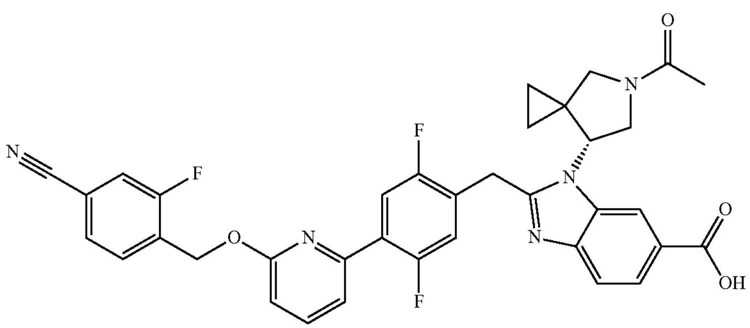 [SMILES: CC(=O)N1C[C@H](n2c(Cc3cc(F)c(-c4cccc(OCc5ccc(C#N)cc5F)n4)cc3F)nc3ccc(C(=O)O)cc32)C2(CC2)C1] | 4 | (MH+) 652.2 | 1H NMR (400 MHz, DMSO-d6) δ 8.06 (s, 1H), 7.96-7.86 (m, 2H), 7.83-7.67 (m, 4H), 7.64-7.55 (m, 1H), 7.54 (dd, J = 7.5, 1.6 Hz, 1H), 7.40 (dd, J = 11.5, 6.1 Hz, 1H), 7.00 (d, J = 8.3 Hz, 1H), 5.34 (s, 1H), 5.19 (d, J = 8.0 Hz, 1H), 4.35 (dt, J = 28.0, 16.9 Hz, 3H), 4.23-4.07 (m, 1H), 4.07-3.82 (m, 2H), 3.82-3.53 (m, 1H), 2.10 (s, 2H), 2.03 (s, 1H), 1.07-0.78 (m, 2H), 0.78-0.53 (m, 1H), 0.29-0.04 (m, 1H). |

TABLE 2-continued

Compounds

| Ex. | Structure | Procedure | ES/MS m/z | ¹H NMR |
|---|---|---|---|---|
| 15 | 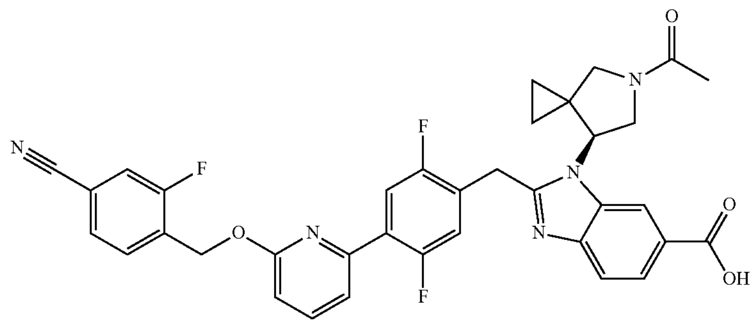 [SMILES: CC(=O)N1C[C@@H](n2c(Cc3cc(F)c(-c4cccc(OCc5ccc(C#N)cc5F)n4)cc3F)nc3ccc(C(=O)O)cc32)C2(CC2)C1] | 4 | (MH+) 652.2 | 1H NMR (400 MHz, DMSO-d6) δ 12.79 (s, 1H), 8.12 (s, 0H), 8.06 (d, J = 1.4 Hz, 1H), 7.96-7.84 (m, 2H), 7.83-7.66 (m, 4H), 7.63 (dd, J = 8.5, 3.3 Hz, 1H), 7.54 (dd, J = 7.5, 1.6 Hz, 1H), 7.40 (dd, J = 11.5, 6.1 Hz, 1H), 7.00 (d, J = 8.2 Hz, 1H), 5.60 (s, 2H), 5.34 (s, 0H), 5.19 (d, J = 8.0 Hz, 1H), 4.63-4.22 (m, 3H), 4.19-4.05 (m, 1H), 3.99 (dd, J = 13.5, 3.3 Hz, 1H), 3.92 (d, J = 10.7 Hz, 1H), 3.82-3.46 (m, 2H), 2.10 (s, 2H), 2.03 (s, 1H), 1.08-0.75 (m, 2H), 0.71 (dd, J = 10.2, 5.3 Hz, 1H), 0.17 (ddt, J = 16.4, 11.2, 5.8 Hz, 1H). |
| 16 | 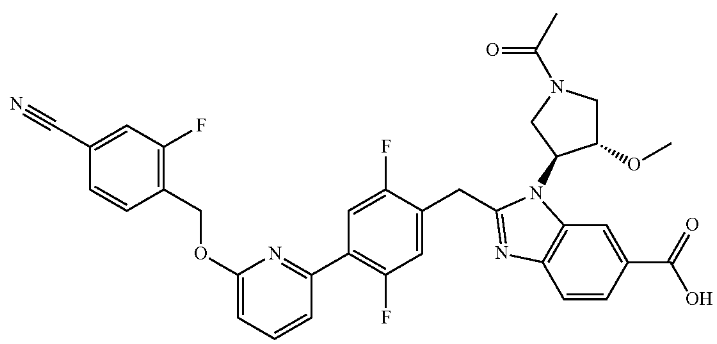 [SMILES: CO[C@H]1CN(C(C)=O)C[C@@H]1n1c(Cc2cc(F)c(-c3cccc(OCc4ccc(C#N)cc4F)n3)cc2F)nc2ccc(C(=O)O)cc21] | 4 | 656.2 | 1H NMR (400 MHz, DMSO-d6) δ 8.12 (dd, J = 37.9, 1.4 Hz, 1H), 7.96-7.81 (m, 3H), 7.79-7.71 (m, 3H), 7.68 (d, J = 8.5 Hz, 1H), 7.56-7.51 (m, 1H), 7.43-7.33 (m, 1H), 7.00 (d, J = 8.3 Hz, 1H), 5.60 (s, 2H), 5.33 (dq, J = 27.6, 8.0 Hz, 1H), 4.55 (dd, J = 13.1, 6.1 Hz, 2H), 4.43 (dd, J = 16.8, 5.7 Hz, 1H), 4.24-4.07 (m, 1H), 4.07-3.93 (m, 1H), 3.41 (ddd, J = 84.8, 11.4, 6.6 Hz, 1H), 3.17 (d, J = 5.9 Hz, 3H), 2.05 (d, J = 24.1 Hz, 3H). |

TABLE 2-continued

Compounds

| Ex. | Structure | Procedure | ES/MS m/z | ¹H NMR |
|---|---|---|---|---|
| 17 | 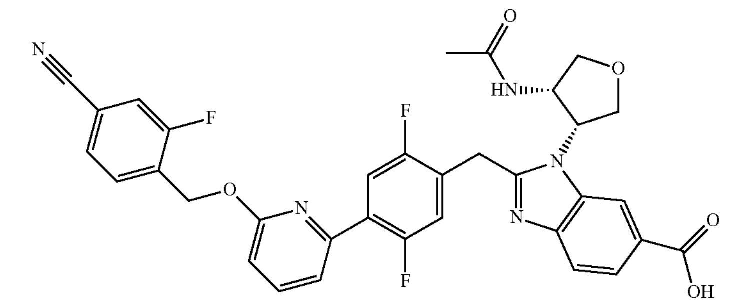 [SMILES: CC(=O)N[C@@H]1COC[C@@H]1n1c(Cc2cc(F)c(-c3cccc(OCc4ccc(C#N)cc4F)n3)cc2F)nc2ccc(C(=O)O)cc21] | 4 | 642.2 | 1H NMR (400 MHz, DMSO-d6) δ 8.25 (s, 1H), 8.00 (s, 1H), 7.97-7.86 (m, 4H), 7.76 (m, 3H), 7.54 (d, J = 8.4 Hz, 2H), 6.99 (d, J = 8.2 Hz, 2H), 5 .64 (s, 2H), 4.64 (d, J = 17.2 Hz, 5H), 4.53 (d, J = 16.0 Hz, 3H). |
| 18 | 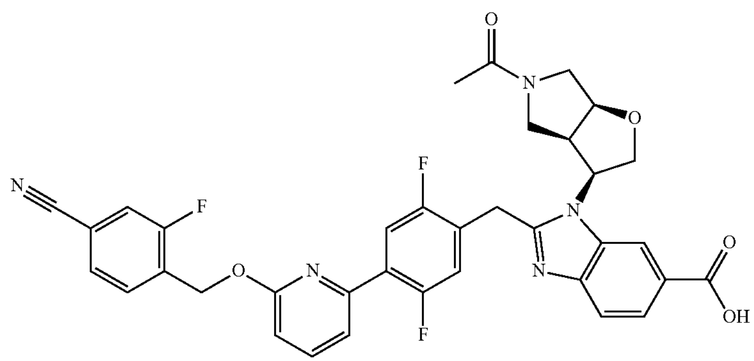 [SMILES: CC(=O)N1C[C@@H]2[C@H](n3c(Cc4cc(F)c(-c5cccc(OCc6ccc(C#N)cc6F)n5)cc4F)nc4ccc(C(=O)O)cc43)CO[C@@H]2C1] | 4 | 668.2 | 1H NMR (400 MHz, DMSO-d6) δ 8.57 (dd, J = 15.4, 1.4 Hz, 1H), 7.95-7.85 (m, 2H), 7.84-7.68 (m, 4H), 7.63 (dd, J = 8.5, 7.0 Hz, 1H), 7.54 (dt, J = 7.5, 1.9 Hz, 1H), 7.44 (dt, J = 11.3, 5.4 Hz, 1H), 7.00 (dd, J = 8.3, 1.9 Hz, 1H), 5.66-5.52 (m, 3H), 4.76-4.57 (m, 2H), 4.57-4.45 (m, 3H), 4.13-4.05 (m, 2H), 4.00 (d, J = 13.2 Hz, 0H), 3.89 (d, J = 12.4 Hz, 1H), 3.55 (dd, J = 12.5, 4.6 Hz, 1H), 3.40 (d, J = 9.1 Hz, 0H), 3.28 (t, J = 9.9 Hz, 0H), 3.21-3.06 (m, 1H), 2.76 (dd, J = 12.9, 9.8 Hz, 1H), 2.70-2.57 (m, 1H), 2.42-2.31 (m, 3H), 1.74 (s, 3H), 0.89 (s, 1H). |

TABLE 2-continued

Compounds

| Ex. | Structure | Procedure | ES/MS m/z | ¹H NMR |
|---|---|---|---|---|
| 19 | 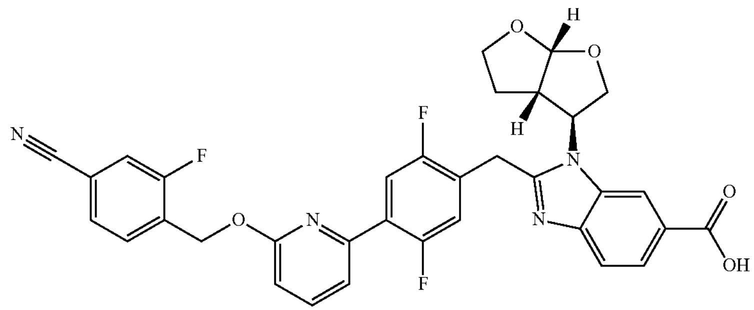 [SMILES: N#Cc1ccc(COc2cccc(-c3cc(F)c(Cc4nc5ccc(C(=O)O)cc5n4[C@@H]4CO[C@H]5OCC[C@H]54)cc3F)n2)c(F)c1] | 5 | MH+ 627.2 | 1H NMR (400 MHz, DMSO-d6) δ 12.78 (s, 1H), 8.51 (d, J = 1.4 Hz, 1H), 7.97-7.85 (m, 2H), 7.84-7.68 (m, 5H), 7.64 (d, J = 8.5 Hz, 1H), 7.54 (dd, J = 7.3, 1.6 Hz, 1H), 7.41 (dd, J = 11.4, 6.1 Hz, 1H), 7.00 (d, J = 8.2 Hz, 1H), 5.80 (d, J = 5.3 Hz, 1H), 5.60 (s, 2H), 5.48-5.30 (m, 1H), 4.71 (dd, J = 11.1, 2.5 Hz, 1H), 4.65-4.30 (m, 2H), 4.16 (dd, J = 11.1, 7.0 Hz, 1H), 3.82-3.62 (m, 1H), 3.57-3.45 (m, 1H), 3.30 (s, 1H), 1.73-1.56 (m, 1H). |
| 20 | 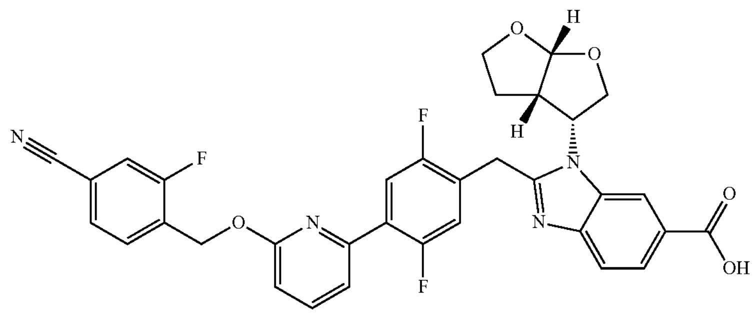 [SMILES: N#Cc1ccc(COc2cccc(-c3cc(F)c(Cc4nc5ccc(C(=O)O)cc5n4[C@H]4CO[C@H]5OCC[C@H]54)cc3F)n2)c(F)c1] | 5 | MH+ 627.2 | 1H NMR (400 MHz, DMSO-d6) δ 12.78 (s, 1H), 8.51 (d, J = 1.4 Hz, 1H), 7.98-7.84 (m, 2H), 7.84-7.68 (m, 4H), 7.64 (d, J = 8.4 Hz, 1H), 7.54 (dd, J = 7.5, 1.6 Hz, 1H), 7.41 (dd, J = 11.4, 6.1 Hz, 1H), 7.00 (d, J = 8.3 Hz, 1H), 5.80 (d, J = 5.3 Hz, 1H), 5.60 (s, 2H), 5.40 (ddd, J = 9.5, 7.0, 2.6 Hz, 1H), 4.72 (dd, J = 11.0, 2.6 Hz, 1H), 4.58-4.27 (m, 2H), 4.16 (dd, J = 11.1, 6.9 Hz, 1H), 3.72 (td, J = 8.6, 2.2 Hz, 1H), 3.62-3.42 (m, 1H), 1.61 (dtd, J = 13.2, 10.7, 8.7 Hz, 1H), 0.77 (dd, J = 13.3, 6.3 Hz, 1H). |

TABLE 2-continued

Compounds

| Ex. | Structure | Procedure | ES/MS m/z | ¹H NMR |
|---|---|---|---|---|
| 21 | 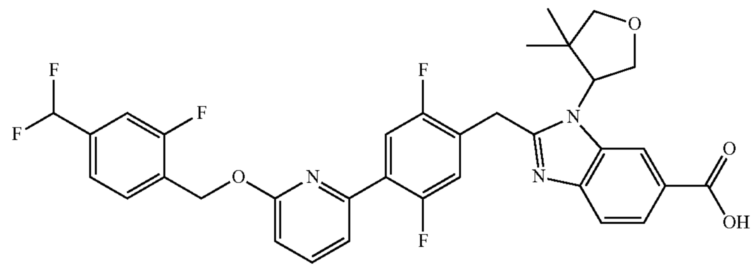 [SMILES: CC1(C)COCC1n1c(Cc2cc(F)c(-c3cccc(OCc4ccc(C(F)F)cc4F)n3)cc2F)nc2ccc(C(=O)O)cc21] | 5 | 638.4 | 1H NMR (400 MHz, Methanol-d4) δ 8.85 (s, 1H), 8.13 (dd, J = 8.6, 1.4 Hz, 1H), 8.00-7.81 (m, 2H), 7.81-7.73 (m, 1H), 7.68 (t, J = 7.5 Hz, 1H), 7.58 (dd, J = 7.4, 1.6 Hz, 1H), 7.46-7.30 (m, 3H), 7.01-6.85 (m, 1H), 6.79 (s, 1H), 5.61 (s, 2H), 5.09 (d, J = 6.6 Hz, 1H), 4.70-4.61 (m, 3H), 4.52 (dd, J = 11.5, 6.7 Hz, 1H), 3.99 (d, J = 8.9 Hz, 1H), 3.84 (d, J = 8.9 Hz, 1H), 1.40 (s, 3H), 0.74 (s, 3H). |
| 22 | 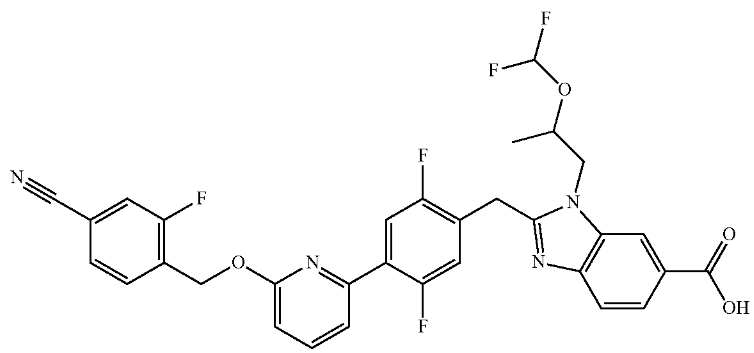 [SMILES: CC(Cn1c(Cc2cc(F)c(-c3cccc(OCc4ccc(C#N)cc4F)n3)cc2F)nc2ccc(C(=O)O)cc21)OC(F)F] | 5 | 623.3 | 1H NMR (400 MHz, Methanol-d4) δ 8.53 (t, J = 0.9 Hz, 1H), 8.19 (dd, J = 8.6, 1.4 Hz, 1H), 7.90-7.79 (m, 2H), 7.79-7.67 (m, 2H), 7.60 (ddt, J = 9.3, 8.0, 1.5 Hz, 3H), 7.37 (dd, J = 11.2, 6.0 Hz, 1H), 6.96 (d, J = 8.2 Hz, 1H), 6.26 (t, J = 74.2 Hz, 1H), 5.64 (s, 2H), 4.82-4.62 (m, 5H), 1.54 (d, J = 5.1 Hz, 3H). |
| 23 | 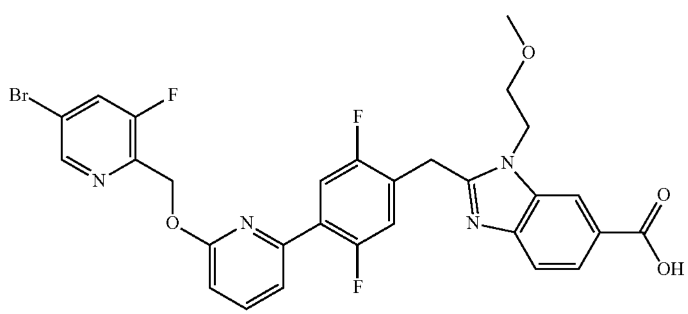 [SMILES: COCCn1c(Cc2cc(F)c(-c3cccc(OCc4ncc(Br)cc4F)n3)cc2F)nc2ccc(C(=O)O)cc21] | 6 | 628 | 1H NMR (400 MHz, DMSO-d6) δ 8.59 (t, J = 1.3 Hz, 1H), 8.30 (d, J = 1.5 Hz, 1H), 8.25 (dd, J = 9.5, 1.9 Hz, 1H), 7.94-7.84 (m, 2H), 7.74 (dd, J = 10.6, 6.4 Hz, 1H), 7.66 (d, J = 8.5 Hz, 1H), 7.52 (dd, J = 7.5, 1.6 Hz, 1H), 7.41 (dd, J = 11.5, 6.1 Hz, 1H), 6.96 (d, J = 8.2 Hz, 1H), 5.58 (d, J = 1.8 Hz, 2H), 4.66 (t, J = 5.1 Hz, 2H), 4.52 (s, 2H), 3.72-3.68 (m, 2H), 3.21 (s, 3H). |

TABLE 2-continued

Compounds

| Ex. | Structure | Procedure | ES/MS m/z | ¹H NMR |
|---|---|---|---|---|
| 24 | (structure) | 6 | 566 | 1H NMR (400 MHz, DMSO-d6) δ 8.82 (d, J = 1.3 Hz, 1H), 8.68 (d, J = 1.3 Hz, 1H), 8.27 (d, J = 1.5 Hz, 1H), 7.91 (t, J = 7.9 Hz, 1H), 7.85 (dd, J = 8.5, 1.5 Hz, 1H), 7.71 (dd, J = 10.5, 6.4 Hz, 1H), 7.64 (d, J = 8.4 Hz, 1H), 7.53 (dd, J = 7.5, 1.6 Hz, 1H), 7.39 (dd, J = 11.5, 6.1 Hz, 1H), 7.03 (d, J = 8.3 Hz, 1H), 5.63 (s, 2H), 4.63 (t, J = 5.1 Hz, 2H), 4.49 (s, 2H), 3.69 (t, J = 5.0 Hz, 2H), 3.21 (s, 3H). |
| 25 | (structure) | 6 | 559.4 | 1H NMR (400 MHz, Methanol-d4) δ 8.56-8.44 (m, 2H), 8.17 (dt, J = 8.6, 1.4 Hz, 1H), 7.91-7.80 (m, 2H), 7.73 (dd, J = 14.4, 8.3 Hz, 2H), 7.56 (dd, J = 7.5, 1.6 Hz, 1H), 7.33 (dd, J = 11.2, 6.1 Hz, 1H), 6.96 (d, J = 8.2 Hz, 1H), 5.65 (s, 2H), 4.76 (t, J = 5.0 Hz, 2H), 4.71 (s, 2H), 3.81 (t, J = 4.9 Hz, 2H), 3.30 (s, 3H), 2.83 (s, 3H), 2.74 (s, 3H). |
| 26 | (structure) | 6 | 566.4 | 1H NMR (400 MHz, Methanol-d4) δ 8.32 (dd, J = 1.5, 0.7 Hz, 1H), 8.12 (dd, J = 8.6, 1.5 Hz, 1H), 7.83 (dd, J = 10.7, 6.3 Hz, 1H), 7.78-7.69 (m, 2H), 7.56-7.47 (m, 1H), 7.22 (ddd, J = 8.7, 5.6, 3.2 Hz, 1H), 7.18-7.13 (m, 1H), 7.13-7.04 (m, 1H), 7.04-6.94 (m, 1H), 6.86 (dd, J = 8.3, 0.7 Hz, 1H), 5.50 (d, J = 1.2 Hz, 2H), 4.63-4.55 (m, 4H), 3.76 (t, J = 5.0 Hz, 2H), 3.29 (s, 3H). |

TABLE 2-continued

Compounds

| Ex. | Structure | Procedure | ES/MS m/z | ¹H NMR |
|---|---|---|---|---|
| 27 | 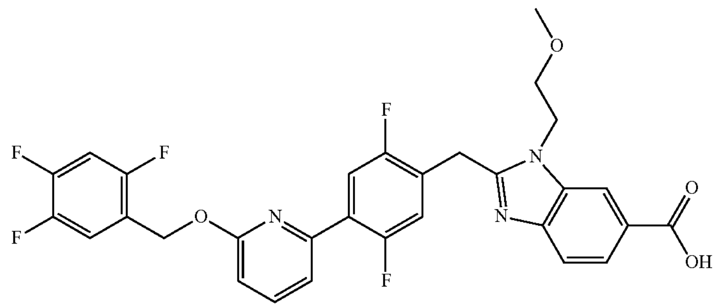 [SMILES: COCCn1c(Cc2cc(F)c(-c3cccc(OCc4cc(F)c(F)cc4F)n3)cc2F)nc2ccc(C(=O)O)cc21] | 6 | 584.4 | 1H NMR (400 MHz, Methanol-d4) δ 8.46 (d, J = 1.3 Hz, 1H), 8.15 (dd, J = 8.6, 1.5 Hz, 1H), 7.89 (dd, J = 10.8, 6.3 Hz, 1H), 7.81 (t, J = 7.9 Hz, 1H), 7.74 (d, J = 8.5 Hz, 1H), 7.56 (dd, J = 7.4, 1.6 Hz, 1H), 7.48 (ddd, J = 10.8, 8.9, 6.6 Hz, 1H), 7.30 (dd, J = 11.3, 6.0 Hz, 1H), 7.22 (td, J = 10.0, 6.5 Hz, 1H), 6.91 (d, J = 8.2 Hz, 1H), 5.50 (s, 2H), 4.74 (t, J = 5.0 Hz, 2H), 4.68 (s, 2H), 3.81 (t, J = 4.9 Hz, 2H), 3.30 (s, 3H). |
| 28 | 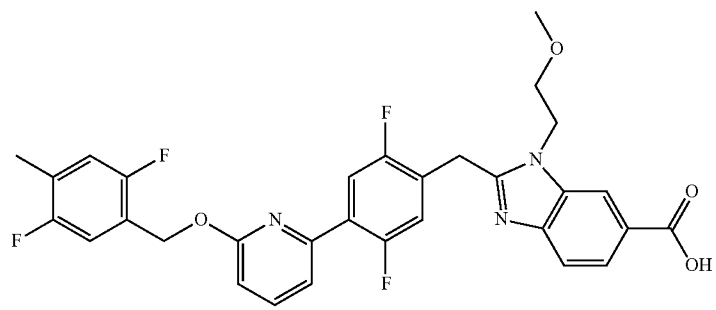 [SMILES: COCCn1c(Cc2cc(F)c(-c3cccc(OCc4cc(F)c(C)cc4F)n3)cc2F)nc2ccc(C(=O)O)cc21] | 6 | 580.4 | 1H NMR (400 MHz, Methanol-d4) δ 8.37 (d, J = 1.4 Hz, 1H), 8.14 (dd, J = 8.6, 1.5 Hz, 1H), 7.87 (dd, J = 10.8, 6.3 Hz, 1H), 7.78-7.71 (m, 2H), 7.52 (dd, J = 7.3, 1.6 Hz, 1H), 7.27-7.10 (m, 2H), 6.96 (dd, J = 10.0, 6.1 Hz, 1H), 6.86 (d, J = 8.1 Hz, 1H), 5.46 (s, 2H), 4.65 (t, J = 5.0 Hz, 2H), 4.62 (s, 2H), 3.84-3.70 (m, 2H), 3.30 (s, 3H), 2.25 (d, J = 2.0 Hz, 3H). |
| 29 | 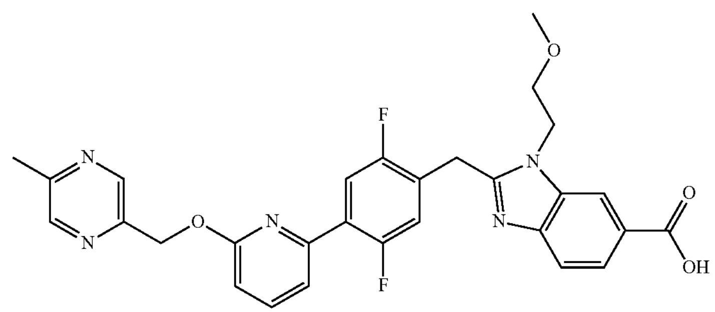 [SMILES: COCCn1c(Cc2cc(F)c(-c3cccc(OCc4cnc(C)cn4)n3)cc2F)nc2ccc(C(=O)O)cc21] | 6 | 546.4 | 1H NMR (400 MHz, Methanol-d4) δ 8.65 (d, J = 1.4 Hz, 1H), 8.58 (t, J = 1.0 Hz, 1H), 8.53 (d, J = 1.4 Hz, 1H), 8.25 (dd, J = 8.6, 1.4 Hz, 1H), 7.85 (d, J = 7.7 Hz, 1H), 7.82 (t, J = 3.2 Hz, 1H), 7.79 (d, J = 8.6 Hz, 1H), 7.58 (dd, J = 11.2, 6.1 Hz, 1H), 7.37 (dd, J = 8.1 Hz, 1H), 6.98 (d, J = 8.1 Hz, 1H), 5.61 (s, 2H), 4.84 (d, J = 5.0 Hz, 2H), 4.78 (s, 2H), 3.91-3.79 (m, 2H), 3.32 (s, 3H), 2.56 (s, 3H). |

TABLE 2-continued

Compounds

| Ex. | Structure | Procedure | ES/MS m/z | ¹H NMR |
|---|---|---|---|---|
| 30 | 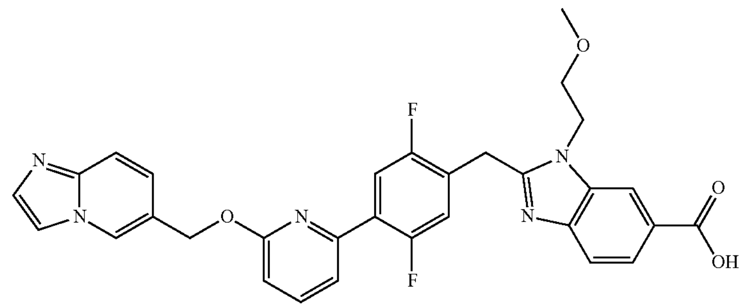 [SMILES: COCCn1c(Cc2cc(F)c(-c3cccc(OCc4ccc5nccn5c4)n3)cc2F)nc2ccc(C(=O)O)cc21] | 6 | 570.2 | 1H NMR (400 MHz, Methanol-d4) δ 8.99 (t, J = 1.3 Hz, 1H), 8.49 (d, J = 1.5 Hz, 1H), 8.29-8.22 (m, 1H), 8.15 (td, J = 8.6, 1.5 Hz, 2H), 8.06 (d, J = 2.2 Hz, 1H), 8.00-7.83 (m, 3H), 7.75 (d, J = 8.5 Hz, 1H), 7.60 (dd, J = 7.4, 1.6 Hz, 1H), 7.34 (dd, J = 11.3, 6.0 Hz, 1H), 6.99 (d, J = 8.2 Hz, 1H), 5.69 (d, J = 1.1 Hz, 2H), 4.76 (t, J = 5.0 Hz, 2H), 4.70 (s, 2H), 3.88-3.73 (m, 2H), 3.31 (s, 3H). |
| 31 | 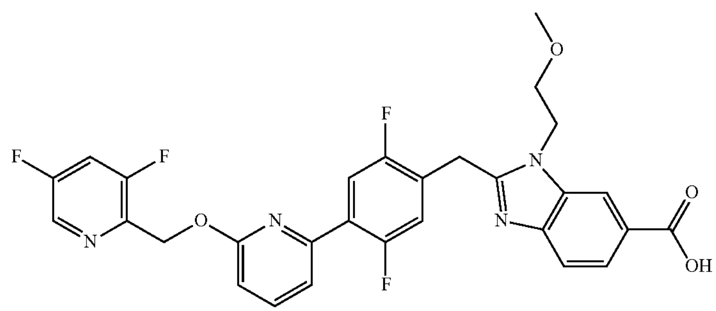 [SMILES: COCCn1c(Cc2cc(F)c(-c3cccc(OCc4ncc(F)cc4F)n3)cc2F)nc2ccc(C(=O)O)cc21] | 6 | 567.3 | 1H NMR (400 MHz, Methanol-d4) δ 8.56 (t, J = 1.0 Hz, 1H), 8.39 (d, J = 2.4 Hz, 1H), 8.23 (dd, J = 8.6, 1.4 Hz, 1H), 7.94 (dd, J = 10.9, 6.3 Hz, 1H), 7.88-7.74 (m, 2H), 7.66 (ddd, J = 9.7, 8.5, 2.4 Hz, 1H), 7.58 (dd, J = 7.3, 1.6 Hz, 1H), 7.36 (dd, J = 11.2, 6.1 Hz, 1H), 6.91 (dd, J = 8.3, 0.6 Hz, 1H), 5.62 (d, J = 2.0 Hz, 2H), 4.83 (t, J = 5.0 Hz, 2H), 4.77 (s, 2H), 3.85 (dd, J = 5.4, 4.4 Hz, 2H), 3.33 (s, 3H). |
| 32 | 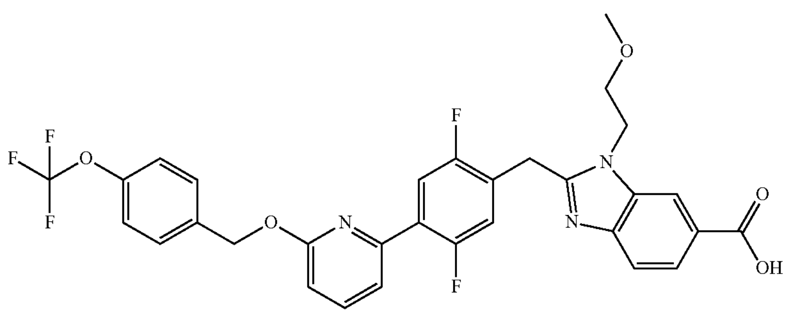 [SMILES: COCCn1c(Cc2cc(F)c(-c3cccc(OCc4ccc(OC(F)(F)F)cc4)n3)cc2F)nc2ccc(C(=O)O)cc21] | 6 | 614.52 | 1H NMR (400 MHz, Methanol-d4) δ 8.50 (d, J = 1.4 Hz, 1H), 8.18 (dd, J = 8.5, 1.5 Hz, 1H), 7.92-7.68 (m, 3H), 7.66-7.46 (m, 3H), 7.40-7.20 (m, 3H), 6.92 (d, J = 8.3 Hz, 1H), 5.52 (s, 2H), 4.77 (t, J = 5.0 Hz, 2H), 4.71 (s, 2H), 3.82 (t, J = 4.9 Hz, 2H), 3.31 (s, 3H). |

TABLE 2-continued

Compounds

| Ex. | Structure | Procedure | ES/MS m/z | ¹H NMR |
|---|---|---|---|---|
| 33 | 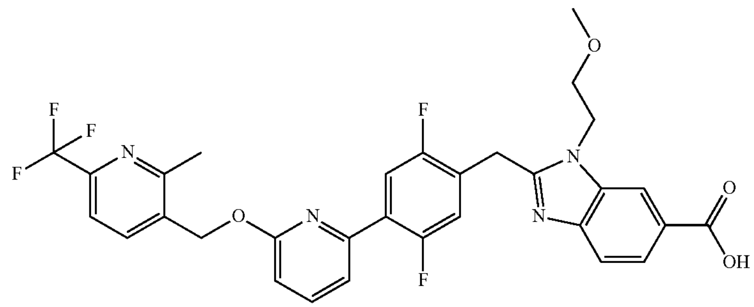 [SMILES: COCCn1c(Cc2cc(F)c(-c3cccc(OCc4ccc(C(F)(F)F)nc4C)n3)cc2F)nc2ccc(C(=O)O)cc21] | 6 | 613.45 | 1H NMR (400 MHz, Methanol-d4) δ 8.53 (d, J = 1.3 Hz, 1H), 8.20 (dd, J = 8.6, 1.4 Hz, 1H), 8.05 (d, J = 7.9 Hz, 1H), 7.91-7.70 (m, 3H), 7.64 (d, J = 7.9 Hz, 1H), 7.57 (dd, J = 7.4, 1.6 Hz, 1H), 7.35 (dd, J = 11.2, 6.1 Hz, 1H), 6.98 (d, J = 8.2 Hz, 1H), 5.62 (s, 2H), 4.83-4.64 (m, 4H), 3.88-3.78 (m, 2H), 3.32 (s, 3H), 2.69 (s, 3H). |
| 34 | 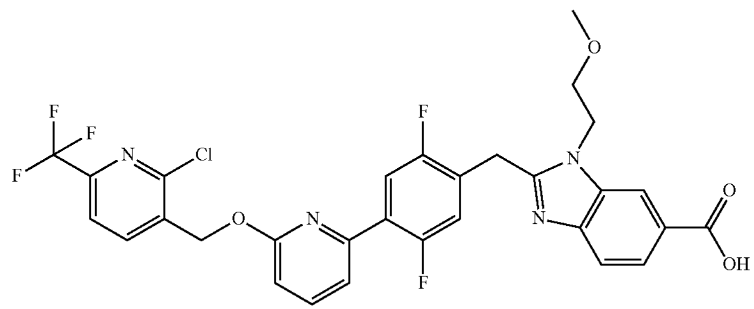 [SMILES: COCCn1c(Cc2cc(F)c(-c3cccc(OCc4ccc(C(F)(F)F)nc4Cl)n3)cc2F)nc2ccc(C(=O)O)cc21] | 6 | 633.58 | 1H NMR (400 MHz, Chloroform-d) δ 8.24 (t, J = 0.9 Hz, 1H), 8.13 (dd, J = 8.6, 1.4 Hz, 1H), 8.10-8.03 (m, 1H), 7.99 (d, J = 8.6 Hz, 1H), 7.82-7.69 (m, 2H), 7.65 (d, J = 7.8 Hz, 1H), 7.56 (dd, J = 7.5, 1.3 Hz, 1H), 7.35-7.32 (m, 1H), 6.92 (dd, J = 8.2, 0.7 Hz, 1H), 5.63 (s, 2H), 4.74 (s, 2H), 4.57 (t, J = 4.9 Hz, 2H), 3.78 (t, J = 4.8 Hz, 2H), 3.32 (s, 3H). |
| 35 | 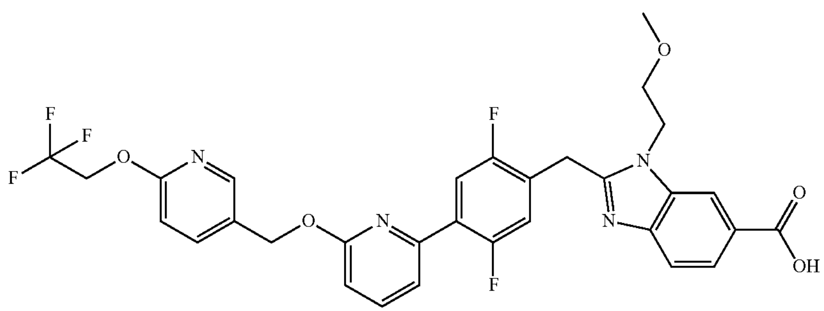 [SMILES: COCCn1c(Cc2cc(F)c(-c3cccc(OCc4ccc(OCC(F)(F)F)nc4)n3)cc2F)nc2ccc(C(=O)O)cc21] | 6 | 629.29 | 1H NMR (400 MHz, Chloroform-d) δ 8.24 (d, J = 19.5 Hz, 2H), 8.09 (d, J = 8.5 Hz, 1H), 7.96 (d, J = 8.4 Hz, 1H), 7.91-7.73 (m, 2H), 7.68 (t, J = 8.0 Hz, 1H), 7.50 (d, J = 7.5 Hz, 1H), 6.90 (d, J = 8.4 Hz, 1H), 6.79 (d, J = 8.2 Hz, 1H), 5.42 (s, 2H), 4.78 (dd, J = 16.8, 8.5 Hz, 4H), 4.56 (s, 2H), 3.78 (d, J = 5.2 Hz, 2H), 3.33 (s, 3H). |

TABLE 2-continued

Compounds

| Ex. | Structure | Procedure | ES/MS m/z | 1H NMR |
|---|---|---|---|---|
| 36 | (structure) | 7 | 648.2 | 1H NMR (400 MHz, DMSO-d6) δ 9.13 (d, J = 1.5 Hz, 1H), 8.98 (s, 1H), 8.78 (d, J = 1.4 Hz, 1H), 8.45 (s, 1H), 8.26 (d, J = 1.5 Hz, 1H), 8.09-7.71 (m, 4H), 7.63 (d, J = 8.4 Hz, 1H), 7.53 (dd, J = 7.6, 1.7 Hz, 1H), 7.39 (dd, J = 11.5, 6.1 Hz, 1H), 7.03 (d, J = 8.3 Hz, 1H), 5.62 (s, 2H), 4.63 (t, J = 5.1 Hz, 2H), 4.48 (s, 2H), 3.69 (t, J = 5.1 Hz, 2H), 3.20 (s, 3H). |
| 37 | (structure) | 7 | 613.2 | 1H NMR (400 MHz, DMSO-d6) δ 9.19 (d, J = 1.5 Hz, 1H), 8.94 (d, J = 1.4 Hz, 1H), 8.45 (s, 1H), 8.28 (d, J = 1.5 Hz, 1H), 7.92 (t, J = 7.9 Hz, 1H), 7.86 (dd, J = 8.4, 1.5 Hz, 1H), 7.72 (dd, J = 10.5, 6.4 Hz, 1H), 7.64 (d, J = 8.5 Hz, 1H), 7.54 (dd, J = 7.5, 1.7 Hz, 1H), 7.40 (dd, J = 11.5, 6.1 Hz, 1H), 7.05 (d, J = 8.3 Hz, 1H), 5.69 (s, 2H), 4.64 (t, J = 5.1 Hz, 2H), 4.49 (s, 2H), 4.31 (s, 3H), 3.69 (t, J = 5.0 Hz, 2H), 3.20 (s, 3H). |
| 38 | (structure) | 7 | 612.2 | 1H NMR (400 MHz, DMSO-d6) δ 8.97 (d, J = 1.5 Hz, 1H), 8.70 (d, J = 1.4 Hz, 1H), 8.41 (s, 1H), 8.28 (d, J = 1.5 Hz, 1H), 8.10 (s, 1H), 7.90 (t, J = 7.9 Hz, 1H), 7.86 (dd, J = 8.4, 1.5 Hz, 1H), 7.78 (dd, J = 10.5, 6.4 Hz, 1H), 7.65 (d, J = 8.4 Hz, 1H), 7.53 (dd, J = 7.5, 1.7 Hz, 1H), 7.40 (dd, J = 11.5, 6.1 Hz, 1H), 7.01 (d, J = 8.2 Hz, 1H), 5.58 (s, 2H), 4.65 (t, J = 5.2 Hz, 2H), 4.51 (s, 2H), 3.90 (s, 3H), 3.69 (t, J = 5.0 Hz, 2H), 3.21 (s, 3H). |

TABLE 2-continued

Compounds

| Ex. | Structure | Procedure | ES/MS m/z | ¹H NMR |
|---|---|---|---|---|
| 39 | 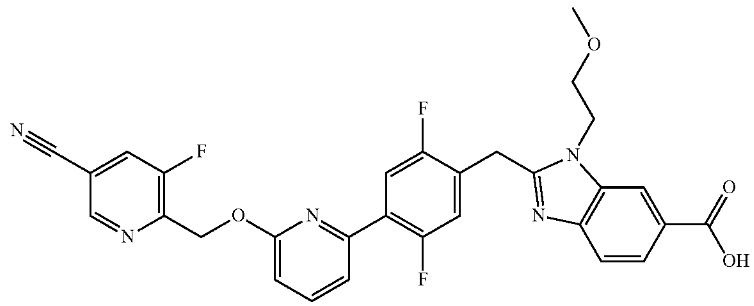 [SMILES: COCCn1c(Cc2cc(F)c(-c3cccc(OCc4ncc(C#N)cc4F)n3)cc2F)nc2ccc(C(=O)O)cc21] | 8 | 574.2 | 1H NMR (400 MHz, DMSO-d6) δ 8.89 (t, J = 1.2 Hz, 1H), 8.48 (dd, J = 9.9, 1.7 Hz, 1H), 8.29 (d, J = 1.5 Hz, 1H), 7.93-7.82 (m, 2H), 7.66 (d, J = 8.5 Hz, 1H), 7.61 (dd, J = 10.6, 6.4 Hz, 1H), 7.51 (dd, J = 7.5, 1.6 Hz, 1H), 7.39 (dd, J = 11.6, 6.1 Hz, 1H), 6.99 (d, J = 8.3 Hz, 1H), 5.69 (d, J = 1.7 Hz, 2H), 4.65 (t, J = 5.1 Hz, 2H), 4.51 (s, 2H), 3.69 (t, J = 5.0 Hz, 2H), 3.21 (s, 3H). |
| 40 | 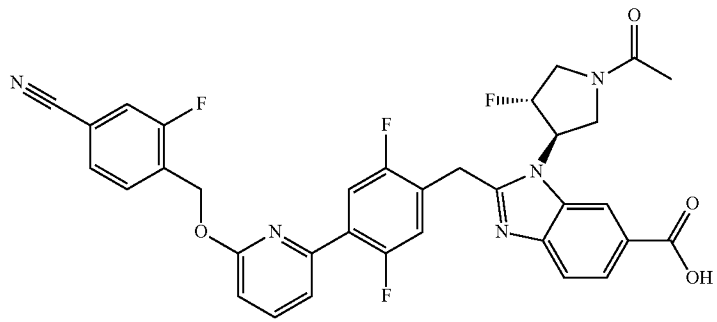 [SMILES: CC(=O)N1C[C@@H](F)[C@H](n2c(Cc3cc(F)c(-c4cccc(OCc5ccc(C#N)cc5F)n4)cc3F)nc3ccc(C(=O)O)cc32)C1] | 9 | 644.4 | 1H NMR (400 MHz, DMSO) δ 8.06 (dd, J = 43.2, 1.5 Hz, 1H), 7.95-7.87 (m, 2H), 7.84 (dt, J = 8.4, 1.9 Hz, 1H), 7.81-7.71 (m, 4H), 7.68 (d, J = 8.5 Hz, 1H), 7.54 (dd, J = 7.5, 1.7 Hz, 1H), 7.45-7.36 (m, 1H), 7.00 (d, J = 8.3 Hz, 1H), 5.83-5.62 (m, 1H), 5.62 (s, 2H), 4.63-4.39 (m, 2H), 4.32-4.06 (m, 2H), 4.02-3.86 (m, 1H), 2.09 (d, J = 13.4 Hz, 3H). |

TABLE 2-continued

Compounds

| Ex. | Structure | Procedure | ES/MS m/z | ¹H NMR |
|---|---|---|---|---|
| 41 | 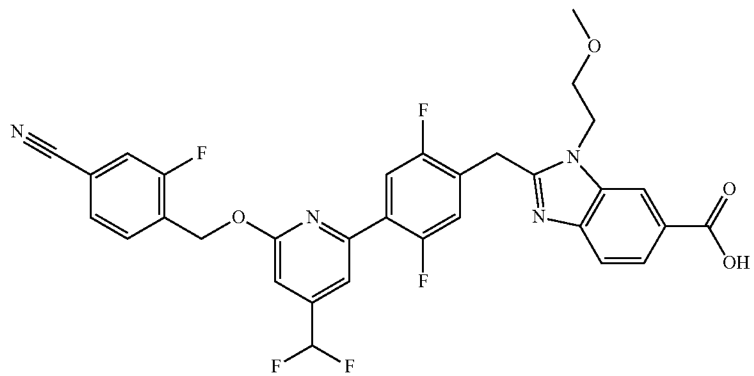 [SMILES: COCCn1c(Cc2cc(F)c(-c3cc(C(F)F)cc(OCc4ccc(C#N)cc4F)n3)cc2F)nc2ccc(C(=O)O)cc21] | 10 | 623.4 | 1H NMR (400 MHz, Methanol-d4) δ 8.30 (d, J = 1.1 Hz, 1H), 8.10 (dd, J = 8.5, 1.5 Hz, 1H), 7.77 (dd, J = 10.6, 6.3 Hz, 1H), 7.72 (d, J = 8.8 Hz, 1H), 7.68 (d, J = 7.5 Hz, 1H), 7.63 (s, 1H), 7.55-7.44 (m, 2H), 7.17 (dd, J = 11.2, 6.0 Hz, 1H), 7.02 (s, 1H), 6.73 (t, J = 55.5 Hz, 1H), 5.62 (s, 2H), 4.57 (d, J = 6.4 Hz, 4H), 3.76 (t, J = 4.9 Hz, 2H), 3.29 (s, 3H). |
| 42 | 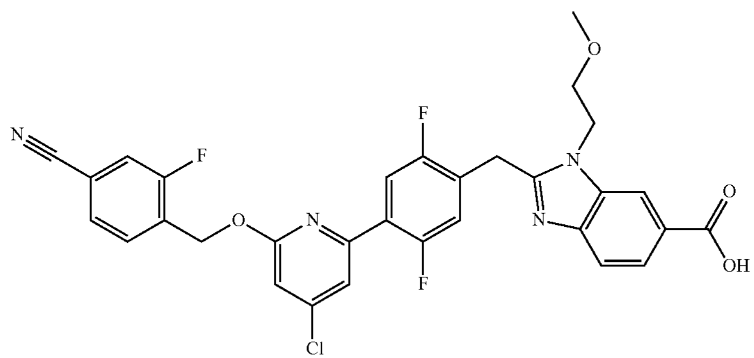 [SMILES: COCCn1c(Cc2cc(F)c(-c3cc(Cl)cc(OCc4ccc(C#N)cc4F)n3)cc2F)nc2ccc(C(=O)O)cc21] | 10 | 607.6 | 1H NMR (400 MHz, Methanol-d4) δ 8.33 (d, J = 1.4 Hz, 1H), 8.12 (dd, J = 8.6, 1.5 Hz, 1H), 7.80-7.65 (m, 3H), 7.58-7.48 (m, 3H), 7.19 (dd, J = 11.3, 6.0 Hz, 1H), 6.94 (d, J = 1.4 Hz, 1H), 5.60 (s, 2H), 4.64-4.56 (m, 4H), 3.77 (t, J = 5.0 Hz, 2H), 3.29 (s, 3H). |

TABLE 2-continued

Compounds

| Ex. | Structure | Procedure | ES/MS m/z | ¹H NMR |
|---|---|---|---|---|
| 43 | 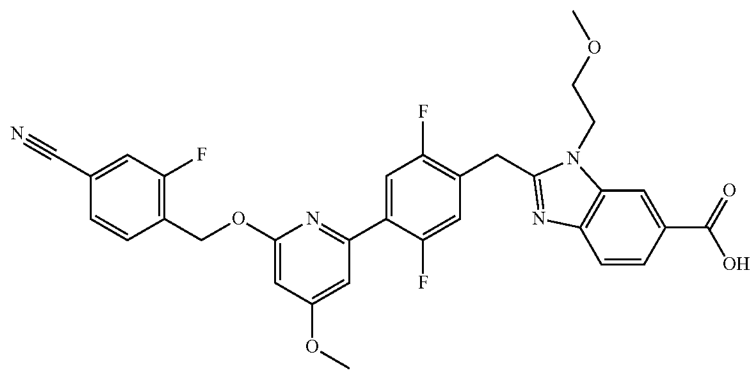 [SMILES: COCCn1c(Cc2cc(F)c(-c3cc(OC)cc(OCc4ccc(C#N)cc4F)n3)cc2F)nc2ccc(C(=O)O)cc21] | 10 | 603.5 | 1H NMR (400 MHz, DMSO-d6) δ 8.29 (d, J = 1.5 Hz, 1H), 7.97-7.89 (m, 1H),7.86 (dd, J = 8.4, 1.5 Hz, 1H), 7.81-7.70 (m, 3H), 7.65 (d, J = 8.4 Hz, 1H), 7.40 (dd, J = 11.5, 6.1 Hz, 1H), 7.08 (t, J = 1.5 Hz, 1H), 6.57 (d, J = 1.9 Hz, 1H), 5.58 (s, 2H), 4.65 (t, J = 5.1 Hz, 2H), 4.51 (s, 2H), 3.87 (s, 3H), 3.70 (t, J = 5.0 Hz, 2H), 3.21 (s, 3H). |
| 44 | 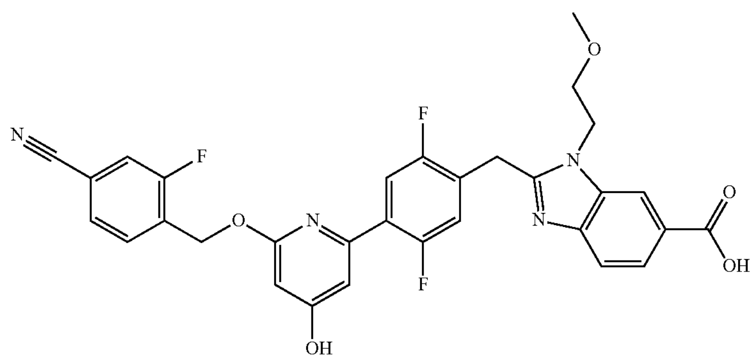 [SMILES: COCCn1c(Cc2cc(F)c(-c3cc(O)cc(OCc4ccc(C#N)cc4F)n3)cc2F)nc2ccc(C(=O)O)cc21] | 10 | 589.3 | 1H NMR (400 MHz, Methanol-d4) δ 8.52 (d, J = 1.2 Hz, 1H), 8.19 (dd, J = 8.6, 1.5 Hz, 1H), 7.83-7.74 (m, 2H), 7.68 (dt, J = 12.8, 6.7 Hz, 1H), 7.63-7.52 (m, 2H), 7.30 (dd, J = 11.3, 6.1 Hz, 1H), 7.07 (t, J = 1.6 Hz, 1H), 6.29 (d, J = 1.8 Hz, 1H), 5.58 (s, 2H), 4.78 (t, J = 5.0 Hz, 2H), 4.71 (s, 2H), 3.82 (t, J = 4.9 Hz, 2H). |

TABLE 2-continued

Compounds

| Ex. | Structure | Procedure | ES/MS m/z | ¹H NMR |
|---|---|---|---|---|
| 45 | (structure) | 10 | 589.2 | 1H NMR (400 MHz, DMSO-d6) δ 8.25 (s, 1H), 7.92 (d, J = 10.0 Hz, 1H), 7.87-7.78 (m, 2H), 7.74 (s, 2H), 7.62 (d, J = 8.5 Hz, 1H), 7.38 (dd, J = 11.7,6.0 Hz, 1H), 7.26 (s, 2H), 6.71 (d, J = 1.4 Hz, 1H), 5.50 (s, 2H), 4.61 (t, J = 5.1 Hz, 2H), 4.47 (s, 2H), 3.68 (t, J = 5.1 Hz, 2H), 3.20 (s, 3H). |
| 46 | (structure) | 11 | 537.4 | 1H NMR (400 MHz, Methanol-d4) δ 8.74 (t, J = 1.5 Hz, 1H), 8.52 (t, J =1.0 Hz, 1H), 8.19 (dd, J = 8.6, 1.5 Hz, 1H), 8.12-8.00 (m, 2H), 7.80 (t, J = 7.7 Hz, 1H), 7.75 (dd, J = 8.6, 0.7 Hz 1H), 7.70 (t, J = 2.1 Hz, 1H), 7.67-7.60 (m, 3H), 7.50 (t, J = 8.0 Hz, 1H), 7.21 (ddd, J = 8.3, 2.6, 0.9 Hz, 1H), 5.35 (s, 2H), 4.81 (t, J = 4.9 Hz, 2H), 4.77 (s, 2H), 3.84 (t, J = 4.9 Hz, 2H), 3.32 (s, 3H). |

TABLE 2-continued

Compounds

| Ex. | Structure | Procedure | ES/MS m/z | ¹H NMR |
|---|---|---|---|---|
| 47 | 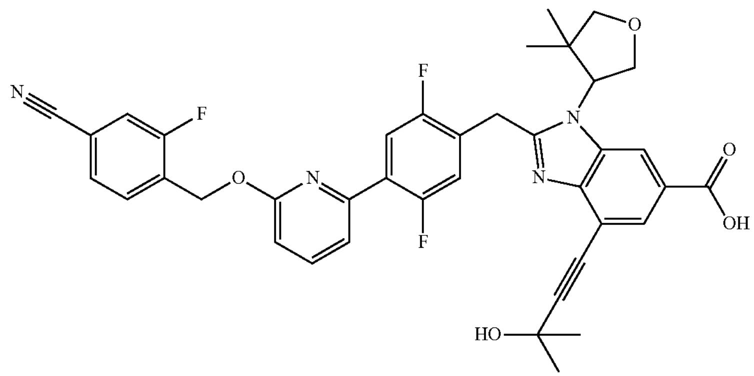 [SMILES: CC(C)(O)C#Cc1cc(C(=O)O)cc2c1nc(Cc1cc(F)c(-c3cccc(OCc4ccc(C#N)cc4F)n3)cc1F)n2C1COCC1(C)C] | 12 | 695.29 | 1H NMR (400 MHz, Methanol-d4) δ 8.69 (s, 1H), 8.04 (d, J = 1.4 Hz, 1H), 7.93-7.67 (m, 3H), 7.67-7.48 (m, 3H), 7.15 (dd, J = 11.0, 6.7 Hz, 1H), 7.00-6.85 (m, 1H), 5.63 (s, 2H), 5.00-4.92 (m, 1H), 4.64-4.39 (m, 4H), 3.93 (d, J = 8.9 Hz, 1H), 3.78 (d, J = 8.9 Hz, 1H), 2.00 (d, J = 39.2 Hz, 1H), 1.64 (s, 6H), 1.30 (s, 3H), 0.61 (s, 3H). |
| 48 | 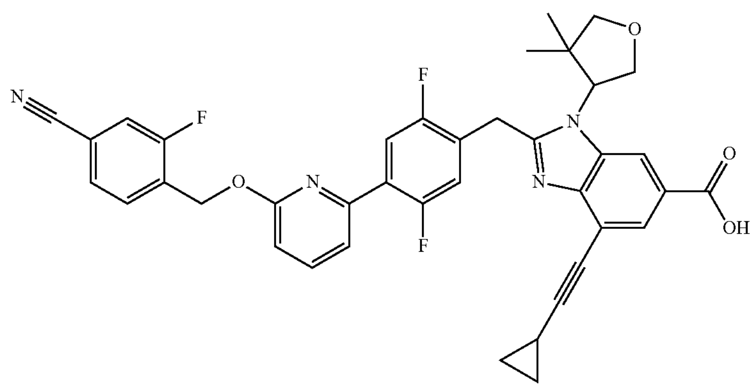 [SMILES: CC1(C)COCC1n1c(Cc2cc(F)c(-c3cccc(OCc4ccc(C#N)cc4F)n3)cc2F)nc2c(C#CC3CC3)cc(C(=O)O)cc21] | 12 | 677.32 | 1H NMR (400 MHz, Methanol-d4) δ 8.67 (s, 1H), 8.01 (d, J = 1.4 Hz, 1H), 7.90-7.69 (m, 3H), 7.69-7.47 (m, 3H), 7.19 (dd, J = 11.3, 6.0 Hz, 1H), 6.93 (d, J = 8.2 Hz, 1H), 5.63 (s, 2H), 5.00-4.90 (m, 2H), 4.56 (dd, J = 19.4, 8.0 Hz, 3H), 4.43 (dd, J = 11.4, 6.8 Hz, 1H), 3.94 (d, J = 8.9 Hz, 1H), 3.78 (d, J = 8.9 Hz, 1H), 1.61 (ddd, J = 12.8, 8.3, 5.1 Hz, 1H), 1.28 (s, 3H), 1.02-0.84 (m, 4H), 0.61 (s, 3H). |

TABLE 2-continued

Compounds

| Ex. | Structure | Procedure | ES/MS m/z | ¹H NMR |
|---|---|---|---|---|
| 49 | 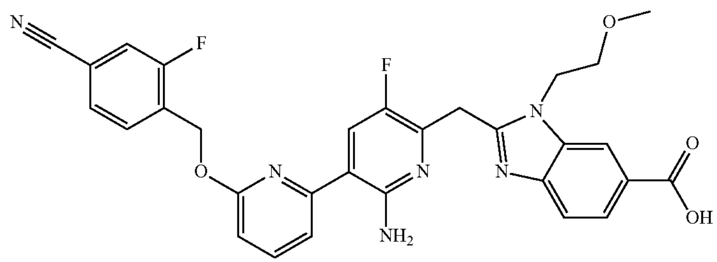 [SMILES: COCCn1c(Cc2nc(N)c(-c3cccc(OCc4ccc(C#N)cc4F)n3)cc2F)nc2ccc(C(=O)O)cc21] | 13 | 571.3 | ¹H NMR (400 MHz, Methanol-d₄) δ 8.60 (t, J = 1.0 Hz, 1H), 8.28 (dd, J = 8.6, 1.4 Hz, 1H), 7.91-7.81 (m, 3H), 7.70 (t, J = 7.5 Hz, 1H), 7.63-7.55 (m, 2H), 7.48 (d, J = 7.5 Hz, 1H), 6.95 (d, J = 8.3 Hz, 1H), 5.56 (s, 2H), 4.87-4.82 (m, 4H), 3.96-3.71 (m, 2H), 3.30 (s, 3H). |
| 50 | 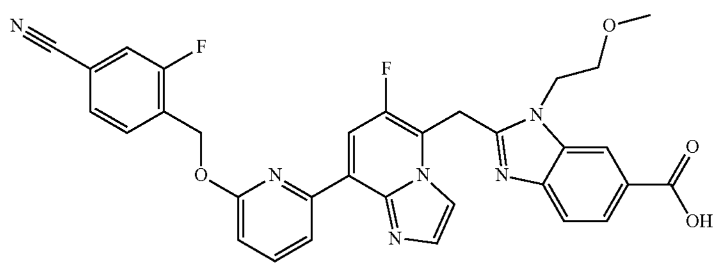 | 14 | 595.3 | 1H NMR (400 MHz, Methanol-d4) δ 8.57 (d, J = 9.5 Hz, 1H), 8.35 (d, J = 1.4 Hz, 1H), 8.18 (s, 2H), 8.07 (dd, J = 8.4, 7.5 Hz, 1H), 7.96 (dd, J = 8.5, 1.5 Hz, 1H), 7.85 (d, J = 7.4 Hz, 1H), 7.79 (t, J = 7.6 Hz, 1H), 7.66-7.55 (m, 2H), 7.50 (d, J = 8.5 Hz, 1H), 7.19 (d, J = 8.3 Hz, 1H), 5.73 (s, 2H), 5.22 (dd, J = 6.9, 2.1 Hz, 1H), 4.78 (t, J = 4.8 Hz, 2H), 3.96-3.83 (m, 2H), 3.41 (s, 3H). |
| 51 | 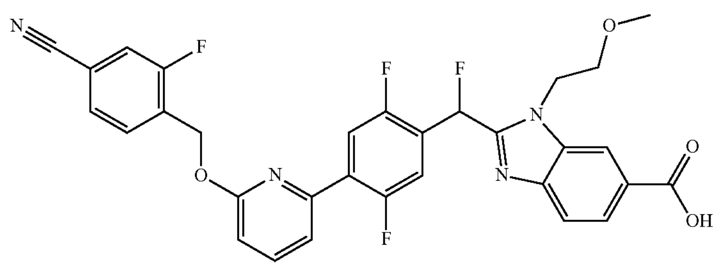 [SMILES: COCCn1c(C(F)c2cc(F)c(-c3cccc(OCc4ccc(C#N)cc4F)n3)cc2F)nc2ccc(C(=O)O)cc21] | 15 | 591.2 | 1H NMR (400 MHz, Methanol-d4) δ 8.38 (d, J = 1.4 Hz, 1H), 8.02 (dd, J = 8.6, 1.5 Hz, 1H), 7.88-7.63 (m, 4H), 7.41 (d, J = 45.5 Hz, 4H), 6.93 (d, J = 8.2 Hz, 1H), 5.60 (s, 2H), 4.79-4.62 (m, 2H), 3.89-3.67 (m, 2H), 3.25 (s, 3H). 19F NMR (376 MHz, Methanol-d4) δ -78.14, -117.82 (dd, J = 9.6, 7.2 Hz), -121.92 (ddd, J = 17.8, 11.2, 6.2 Hz), -124.47 (ddd, J = 17.3, 11.0, 5.8 Hz), -179.57 (d, J = 45.4 Hz). |

TABLE 2-continued

Compounds

| Ex. | Structure | Procedure | ES/MS m/z | 1H NMR |
|---|---|---|---|---|
| 52 | 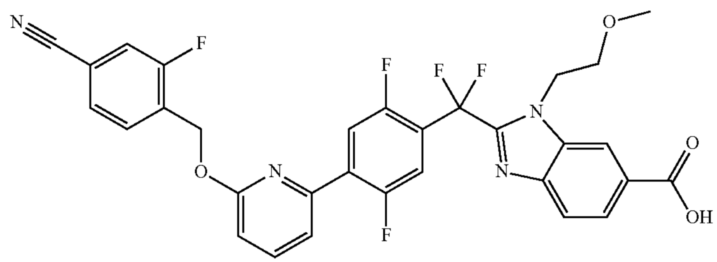 [SMILES: COCCn1c(C(F)(F)c2cc(F)c(-c3cccc(OCc4ccc(C#N)cc4F)n3)cc2F)nc2ccc(C(=O)O)cc21] | 15 | 609.3 | 1H NMR (400 MHz, Methanol-d4) δ 8.47-8.20 (m, 1H), 8.16-7.83 (m, 1H), 7.83-7.71 (m, 2H), 7.71-7.33 (m, 6H), 6.99-6.80 (m, 1H), 5.60-5.35 (m, 2H), 4.71-4.56 (m, 2H), 3.86-3.66 (m, 2H), 3.22 (s, 3H). 19F NMR (376 MHz, Methanol-d4) δ −78.33 (d, J = 11.0 Hz), −91.17 (t, J = 11.0 Hz), −117.83 (d, J = 9.4 Hz), −120.07, −121.85. |
| 53 | 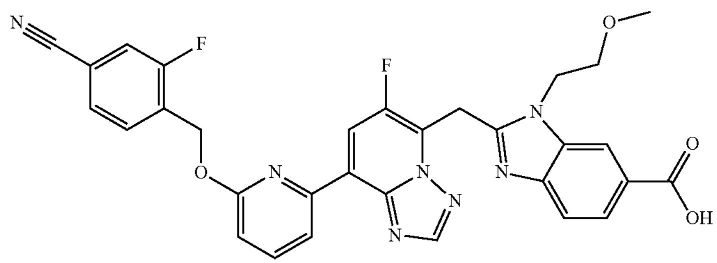 [SMILES: COCCn1c(Cc2c(F)cc(-c3cccc(OCc4ccc(C#N)cc4F)n3)c3ncnn23)nc2ccc(C(=O)O)cc21] | 16 | 596.7 | 1H NMR (400 MHz, Methanol-d4) δ 8.78 (d, J = 7.5 Hz, 1H), 8.59 (d, J = 10.5 Hz, 1H), 8.53 (d, J = 6.9 Hz, 1H), 8.48 (s, 1H), 8.22-8.08 (m, 1H), 7.94 (t, J = 7.9 Hz, 1H), 7.78 (t, J = 7.6 Hz, 1H), 7.74-7.55 (m, 3H), 7.05 (d, J = 8.3 Hz, 1H), 5.72 (s, 2H), 5.37-5.25 (m, 2H), 4.92 (t, J = 4.9 Hz, 2H), 3.89 (t, J = 4.9 Hz, 2H), 3.28 (s, 3H). |
| 54 | 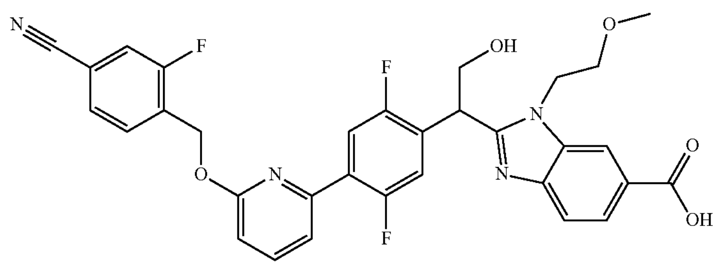 [SMILES: COCCn1c(C(CO)c2cc(F)c(-c3cccc(OCc4ccc(C#N)cc4F)n3)cc2F)nc2ccc(C(=O)O)cc21] | 17 | 603.3 | 1H NMR (400 MHz, Methanol-d4) δ 8.49 (t, J = 1.0 Hz, 1H), 8.20 (dd, J = 8.6, 1.4 Hz, 1H), 7.86 (d, J = 8.6 Hz, 1H), 7.84-7.75 (m, 2H), 7.72 (t, J = 7.5 Hz, 1H), 7.66-7.50 (m, 4H), 7.42 (dd, J = 11.8, 6.0 Hz, 1H), 6.95 (d, J = 8.2 Hz, 1H), 5.62 (s, 2H), 5.25 (t, J = 6.1 Hz, 1H), 4.82-4.73 (m, 1H), 4.67 (ddd, J = 15.3, 7.2, 3.5 Hz, 1H), 4.40 (dd, J = 11.0, 6.5 Hz, 1H), 4.32 (dd, J = 11.0, 5.7 Hz, 1H), 3.85-3.66 (m, 2H), 3.21 (s, 3H). |

TABLE 2-continued

Compounds

| Ex. | Structure | Procedure | ES/MS m/z | ¹H NMR |
|---|---|---|---|---|
| 55 | | 18 | 651.3 | 1H NMR (400 MHz, Acetonitrile-d3) δ 8.32 (d, J = 1.4 Hz, 1H), 8.21 (d, J = 1.4 Hz, 1H), 7.99 (s, 2H), 7.88-7.77 (m, 2H), 7.73 (t, J = 7.5 Hz, 1H), 7.64-7.51 (m, 3H), 7.21 (dd, J = 11.7, 6.1 Hz, 1H), 6.92 (d, J = 8.3 Hz, 1H), 5.63 (s, 2H), 4.56 (t, J = 5.0 Hz, 2H), 4.49 (s, 2H), 3.74 (t, J = 5.0 Hz, 2H), 3.25 (s, 3H). |
| 56 | | 18 | 752.2 | 1H NMR (400 MHz, Acetonitrile-d3) δ 8.53 (s, 1H), 8.33 (d, J = 0.7 Hz, 1H), 8.16 (d, J = 1.5 Hz, 1H), 8.12 (d, J = 1.5 Hz, 1H), 7.88-7.76 (m, 2H), 7.73 (t, J = 7.6 Hz, 1H), 7.64-7.50 (m, 3H), 7.24 (dd, J = 11.7, 6.1 Hz, 1H), 6.92 (dd, J = 8.3, 0.6 Hz, 1H), 5.63 (s, 2H), 4.61 (t, J = 5.8 Hz, 2H), 4.55-4.43 (m, 4H), 3.88 (s, 8H), 3.72 (t, J = 5.0 Hz, 2H), 3.63 (t, J = 5.8 Hz, 2H), 3.23 (s, 3H). |

TABLE 2-continued

Compounds

| Ex. | Structure | Procedure | ES/MS m/z | ¹H NMR |
|---|---|---|---|---|
| 57 | 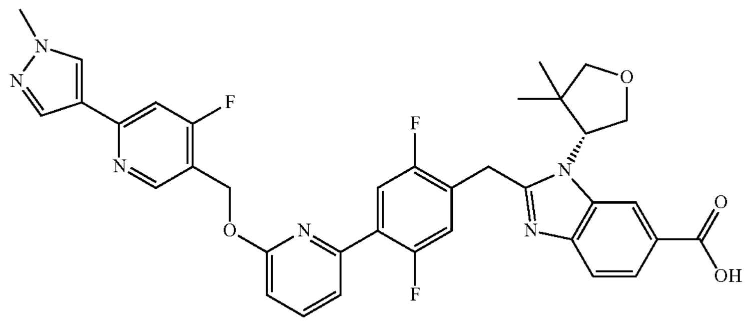 [SMILES: Cn1cc(-c2cc(F)c(COc3cccc(-c4cc(F)c(Cc5nc6ccc(C(=O)O)cc6n5[C@H]5COCC5(C)C)cc4F)n3)cn2)cn1] | 19 | 669.6 | 1H NMR (400 MHz, DMSO-d6) δ 8.69 (d, J = 10.4 Hz, 1H), 8.51 (s, 1H), 8.35 (s, 1H), 8.06 (s, 1H), 8.00-7.86 (m, 2H), 7.83 (dd, J = 8.4, 1.5 Hz, 1H), 7.73-7.61 (m, 2H), 7.55 (dd, J = 7.5, 1.6 Hz, 1H), 7.48 (dd, J = 11.2, 6.3 Hz, 1H), 6.95 (d, J = 8.3 Hz, 1H), 5.55 (s, 2H), 5.04 (d, J = 6.6 Hz, 1H), 4.49-4.36 (m, 2H), 3.89 (s, 3H), 3.79 (d, J = 8.7 Hz, 1H), 3.74 (d, J = 8.6 Hz, 1H), 1.34 (s, 3H), 0.62 (s, 3H). |
| 58 | 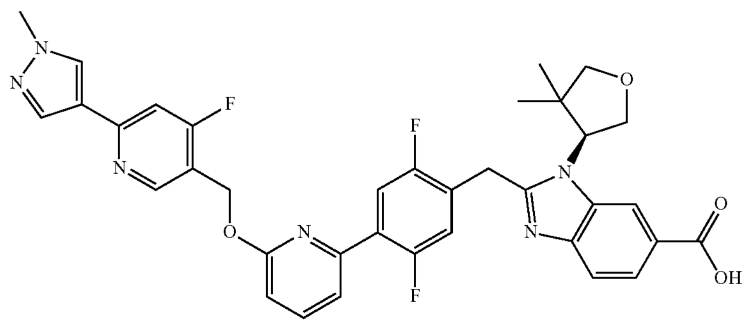 | 19 | 669.6 | 1H NMR (400 MHz, DMSO-d6) δ 8.69 (d, J = 10.4 Hz, 1H), 8.51 (s, 1H), 8.35 (s, 1H), 8.06 (s, 1H), 8.00-7.86 (m, 2H), 7.83 (dd, J = 8.4, 1.5 Hz, 1H), 7.73-7.61 (m, 2H), 7.55 (dd, J = 7.5, 1.6 Hz, 1H), 7.48 (dd, J = 11.2, 6.3 Hz, 1H), 6.95 (d, J = 8.3 Hz, 1H), 5.55 (s, 2H), 5.04 (d, J = 6.6 Hz, 1H), 4.65-4.51 (m, 2H), 3.89 (s, 3H), 3.79 (d, J = 8.7 Hz, 1H), 3.74 (d, J = 8.6 Hz, 1H), 1.34 (s, 3H), 0.62 (s, 3H). |

TABLE 2-continued

Compounds

| Ex. | Structure | Procedure | ES/MS m/z | ¹H NMR |
|---|---|---|---|---|
| 59 | 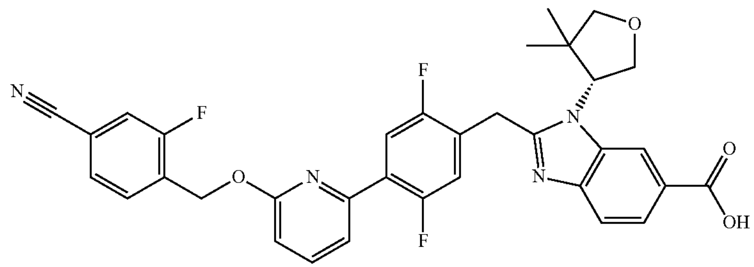 [SMILES: CC1(C)COC[C@@H]1n1c(Cc2cc(F)c(-c3cccc(OCc4ccc(C#N)cc4F)n3)cc2F)nc2ccc(C(=O)O)cc21] | 20 | 613.2 | 1H NMR (400 MHz, DMSO-d6) δ 12.77 (s, 1H), 8.48 (s, 1H), 7.96-7.86 (m, 2H), 7.83-7.70 (m, 4H), 7.61 (d, J = 8.5 Hz, 1H), 7.55 (dd, J = 7.5, 1.6 Hz, 1H), 7.45 (dd, J = 11.3, 6.2 Hz, 1H), 7.00 (d, J = 8.2 Hz, 1H), 5.61 (s, 2H), 5.01 (d, J = 6.7 Hz, 1H), 4.58-4.47 (m, 2H), 4.44 (dd, J = 11.1, 6.8 Hz, 1H), 4.36 (d, J = 16.9 Hz, 1H), 3.82-3.70 (m, 2H), 1.33 (s, 3H), 1.24 (s, 1H), 0.60 (s, 3H). |
| 60 | 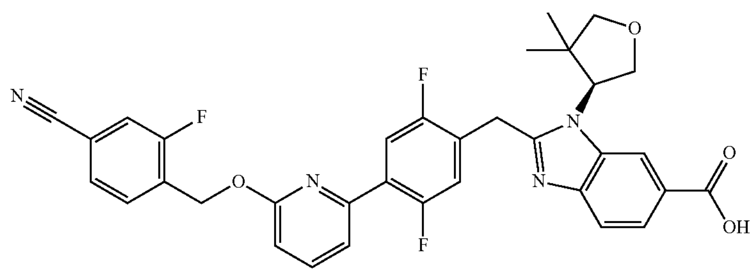 [SMILES: CC1(C)COC[C@H]1n1c(Cc2cc(F)c(-c3cccc(OCc4ccc(C#N)cc4F)n3)cc2F)nc2ccc(C(=O)O)cc21] | 20 | 613.2 | 1H NMR (400 MHz, DMSO-d6) δ 8.49 (s, 1H), 7.96-7.85 (m, 2H), 7.85-7.68 (m, 4H), 7.63 (d, J = 8.5 Hz, 1H), 7.55 (dd, J = 7.5, 1.6 Hz, 1H), 7.46 (dd, J = 11.3, 6.2 Hz, 1H), 7.00 (d, J = 8.3 Hz, 1H), 5.02 (d, J = 6.6 Hz, 1H), 4.58-4.49 (m, 2H), 4.49-4.34 (m, 2H), 3.82-3.70 (m, 2H), 1.33 (s, 3H), 0.61 (s, 3H). |
| 61 | 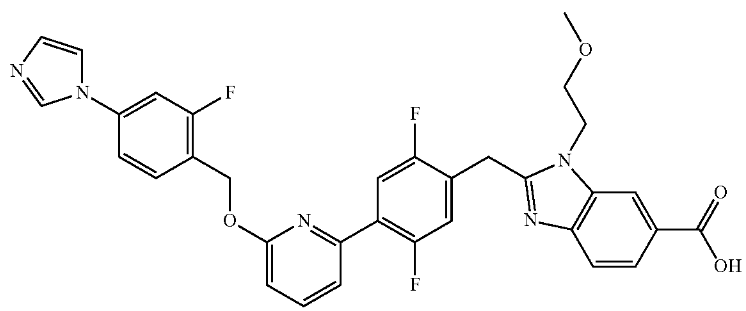 [SMILES: COCCn1c(Cc2cc(F)c(-c3cccc(OCc4ccc(-n5ccnc5)cc4F)n3)cc2F)nc2ccc(C(=O)O)cc21] | 21 | 614.1 | 1H NMR (400 MHz, DMSO-d6) δ 12.81 (s, 1H), 9.32 (s, 1H), 8.25-8.16 (m, 2H), 7.94-7.77 (m, 5H), 7.73-7.64 (m, 2H), 7.60 (d, 1H), 7.54 (dd, 1H), 7.40 (dd, 1H), 6.97 (d, 1H), 5.60 (s, 2H), 4.61 (t, 2H), 4.46 (s, 2H), 3.69 (t, 2H), 3.22 (s, 3H). |

TABLE 2-continued

Compounds

| Ex. | Structure | Procedure | ES/MS m/z | ¹H NMR |
|---|---|---|---|---|
| 62 | 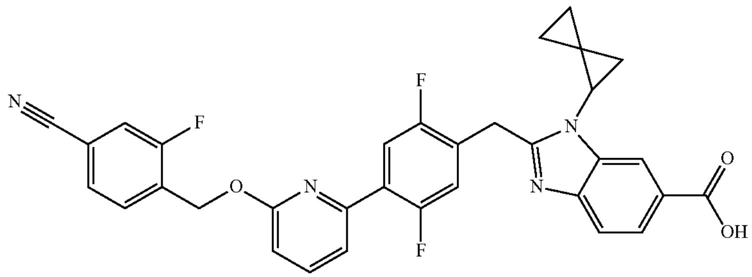 [SMILES: N#Cc1ccc(COc2cccc(-c3cc(F)c(Cc4nc5ccc(C(=O)O)cc5n4C4CC45CC5)cc3F)n2)c(F)c1] | 22 | (M + H+) 581.2 | 1H NMR (400 MHz, DMSO-d6) δ 7.94 (s, 1H), 7.92-7.87 (m, 2H), 7.80-7.65 (m, 4H), 7.61 (d, J = 8.5 Hz, 1H), 7.53 (d, J = 7.3 Hz, 1H), 7.44 (dd, J = 11.5, 6.0 Hz, 1H), 6.99 (d, J = 8.2 Hz, 1H), 5.60 (s, 2H), 4.34 (s, 2H), 3.91 (dd, J = 7.2, 4.0 Hz, 1H), 1.94-1.77 (m, 2H), 1.36 (s, 1H), 1.08 (td, J = 9.2, 4.6 Hz, 2H), 0.90 (m, 1H). |
| 63 | 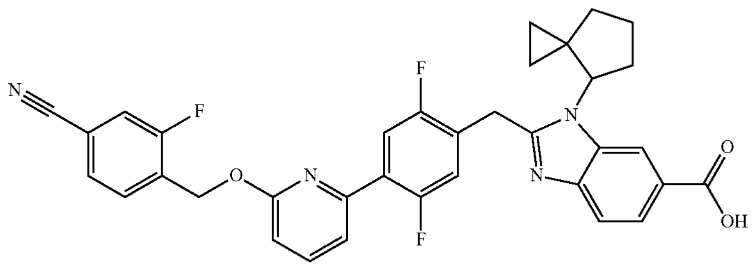 [SMILES: N#Cc1ccc(COc2cccc(-c3cc(F)c(Cc4nc5ccc(C(=O)O)cc5n4C4CCCC45CC5)cc3F)n2)c(F)c1] | 22 | (M + H+) 609.2 | 1H NMR (400 MHz, DMSO-d6) δ 8.24 (d, J = 1.4 Hz, 1H), 8.00-7.82 (m, 2H), 7.82-7.67 (m, 4H), 7.62 (d, J = 8.4 Hz, 1H), 7.53 (dd, J = 7.5, 1.6 Hz, 1H), 7.31 (dd, J = 11.4, 6.1 Hz, 1H), 6.99 (d, J = 8.2 Hz, 1H), 5.60 (s, 2H), 4.97 (t, J = 8.4 Hz, 1H), 4.38 (s, 2H), 2.26 (ddt, J = 30.5, 18.5, 6.2 Hz, 3H), 2.04 (d, J = 7.1 Hz, 1H), 1.87 (dq, J = 11.9, 6.6, 5.8 Hz, 1H), 1.77-1.57 (m, 1H), 0.83-0.61 (m, 1H), 0.55 (dt, J = 9.3, 5.1 Hz, 1H), 0.48 (dd, J = 9.2, 3.2 Hz, 1H), −0.09 (dd, J = 10.0, 4.9 Hz, 1H). |
| 64 | 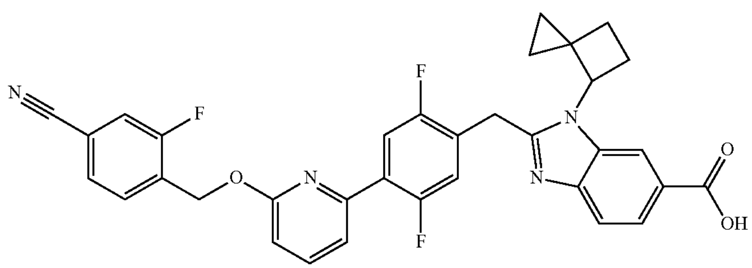 [SMILES: N#Cc1ccc(COc2cccc(-c3cc(F)c(Cc4nc5ccc(C(=O)O)cc5n4C4CCC45CC5)cc3F)n2)c(F)c1] | 22 | (M + H+) 595.1 | 1H NMR (400 MHz, DMSO-d6) δ 12.84 (s, 1H), 8.50 (d, J = 1.5 Hz, 1H), 7.99-7.84 (m, 2H), 7.82 (dd, J = 8.4, 1.5 Hz, 1H), 7.78-7.70 (m, 3H), 7.64 (d, J = 8.2 Hz, 1H), 7.51 (dd, J = 7.5, 1.7 Hz, 1H), 7.22 (dd, J = 11.5, 6.0 Hz, 1H), 6.99 (d, J = 8.2 Hz, 1H), 5.60 (s, 2H), 5.37 (dd, J = 9.1, 7.0 Hz, 1H), 4.40 (s, 2H), 2.99-2.78 (m, 1H), 2.76-2.52 (m, 1H), 2.45-2.15 (m, |

TABLE 2-continued

Compounds

| Ex. | Structure | Procedure | ES/MS m/z | ¹H NMR |
|---|---|---|---|---|
| 65 | 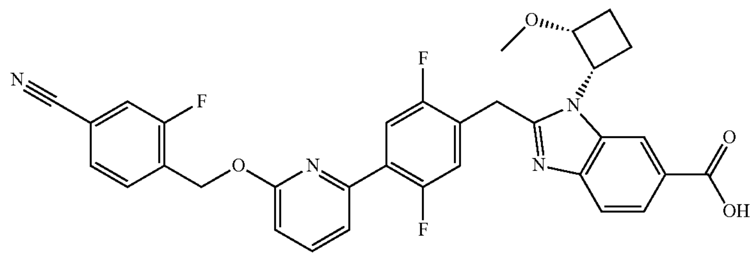 [SMILES: CO[C@@H]1CC[C@@H]1n1c(Cc2cc(F)c(-c3cccc(OCc4ccc(C#N)cc4F)n3)cc2F)nc2ccc(C(=O)O)cc21] | 22 | 599.2 | 1H NMR (400 MHz, DMSO-d6) δ 8.45 (d, J = 1.4 Hz, 1H), 7.95-7.86 (m, 2H), 7.82 (dd, J = 8.5, 1.5 Hz, 1H), 7.79-7.69 (m, 3H), 7.63 (d, J = 8.5 Hz, 1H), 7.53 (dd, J = 7.5, 1.7 Hz, 1H), 7.34 (dd, J = 11.5, 6.1 Hz, 1H), 7.00 (d, J = 8.2 Hz, 1H), 5.60 (s, 2H), 5.48-5.32 (m, 1H), 4.59-4.42 (m, 2H), 4.30 (dd, J = 5.9, 3.2 Hz, 1H), 3.22-3.07 (m, 1H), 2.95 (s, 3H), 2.63 (pd, J = 9.7, 8.8, 3.3 Hz, 1H), 2.24 (ddd, J = 14.2, 9.1, 5.5 Hz, 1H), 2.12 (t, J = 11.7 Hz, 1H), 2H), 0.59 (td, J = 7.4, 6.7, 4.3 Hz, 2H), 0.44-0.22 (m, 1H), 0.22-0.05 (m, 1H). |
| 66 | 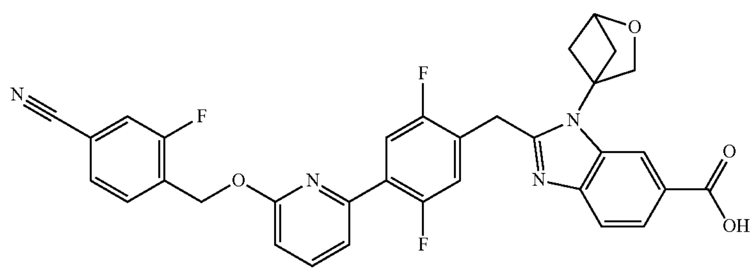 [SMILES: N#Cc1ccc(COc2cccc(-c3cc(F)c(Cc4nc5ccc(C(=O)O)cc5n4C45COC(C4)C5)cc3F)n2)c(F)c1] | 22 | 597.2 | 1H NMR (400 MHz, DMSO-d6) δ 8.08 (d, J = 1.4 Hz, 1H), 7.94-7.88 (m, 2H), 7.84-7.71 (m, 4H), 7.64 (d, J = 8.4 Hz, 1H), 7.55 (dd, J = 7.5, 1.6 Hz, 1H), 7.41 (dd, J = 11.4, 6.1 Hz, 1H), 7.00 (d, J = 8.2 Hz, 1H), 5.61 (s, 2H), 4.77 (s, 1H), 4.40 (s, 2H), 3.94 (s, 2H), 2.61 (t, J = 1.7 Hz, 4H). |
| 67 | 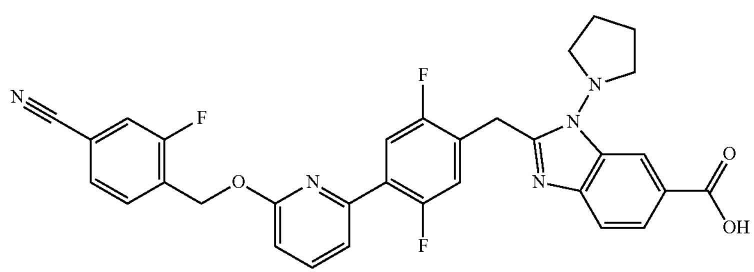 [SMILES: N#Cc1ccc(COc2cccc(-c3cc(F)c(Cc4nc5ccc(C(=O)O)cc5n4N4CCCC4)cc3F)n2)c(F)c1] | 22 | 584.2 | 1H NMR (400 MHz, DMSO-d6) δ 8.10 (d, J = 1.4 Hz, 1H), 7.94-7.86 (m, 2H), 7.84 (dd, J = 8.5, 1.5 Hz, 1H), 7.78-7.71 (m, 3H), 7.69 (d, J = 8.5 Hz, 1H), 7.52 (d, J = 7.6, 1.6 Hz, 1H), 7.38 (dd, J = 11.6, 6.0 Hz, 1H), 6.99 (d, J = 8.3 Hz, 1H), 5.59 (s, 2H), 4.39 (s, 2H), 3.38-3.25 (m, 4H), 2.13-1.94 (m, 4H). |

TABLE 2-continued

Compounds

| Ex. | Structure | Procedure | ES/MS m/z | ¹H NMR |
|---|---|---|---|---|
| 68 | 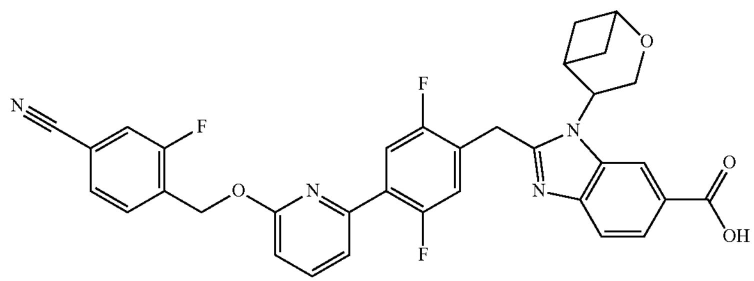 [SMILES: N#Cc1ccc(COc2cccc(-c3cc(F)c(Cc4nc5ccc(C(=O)O)cc5n4C4COC5CC4C5)cc3F)n2)c(F)c1] | 22 | 611.2 | 1H NMR (400 MHz, DMSO-d6) δ 8.68 (d, J = 1.4 Hz, 1H), 7.96-7.86 (m, 2H), 7.82 (dd, J = 8.5, 1.5 Hz, 1H), 7.80-7.70 (m, 3H), 7.63 (d, J = 8.5 Hz, 1H), 7.54 (dd, J = 7.5, 1.6 Hz, 1H), 7.44 (dd, J = 11.4, 6.1 Hz, 1H), 7.00 (d, J = 8.3 Hz, 1H), 5.61 (s, 2H), 5.50-5.36 (m, 1H), 4.73-4.61 (m, 2H), 4.58-4.37 (m, 3H), 3.07 (p, J = 5.6 Hz, 1H), 2.36 (ddd, J = 9.6, 5.7, 3.5 Hz, 1H), 2.27 (t, J = 10.0 Hz, 1H), 2.09 (q, J = 5.3, 4.3 Hz, 1H), 2.04-1.96 (m, 1H). |
| 69 | 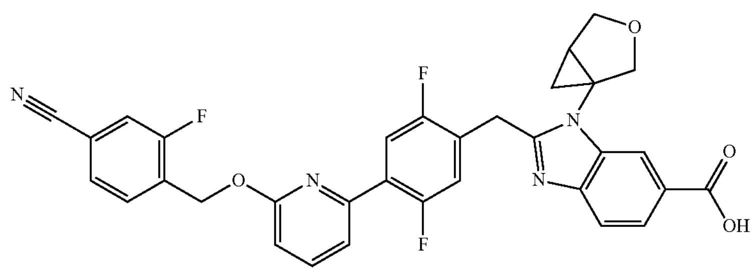 [SMILES: N#Cc1ccc(COc2cccc(-c3cc(F)c(Cc4nc5ccc(C(=O)O)cc5n4C45COCC4C5)cc3F)n2)c(F)c1] | 22 | 597.2 | 1H NMR (400 MHz, DMSO-d6) δ 7.95-7.88 (m, 2H), 7.83 (dd, J = 8.4, 1.5 Hz, 1H), 7.82-7.71 (m, 4H), 7.65 (d, J = 8.6 Hz, 1H), 7.58-7.52 (m, 1H), 7.46 (s, 1H), 7.00 (d, J = 8.3 Hz, 1H), 5.61 (s, 2H), 4.49 (d, J = 7.5 Hz, 2H), 4.21 (dd, J = 8.9, 2.8 Hz, 1H), 4.03-3.91 (m, 3H), 3.79-3.70 (m, 1H), 1.83-1.54 (m, 1H), 1.42 (s, 1H). |
| 70 | 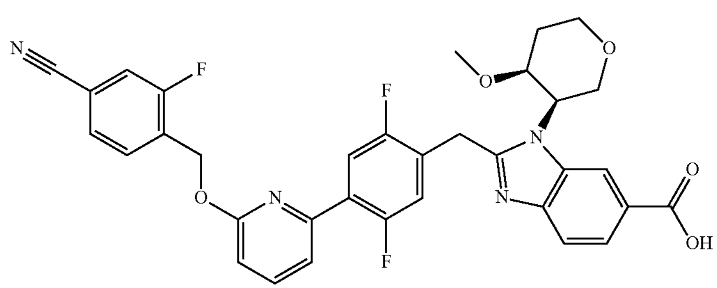 [SMILES: CO[C@H]1CCOC[C@H]1n1c(Cc2cc(F)c(-c3cccc(OCc4ccc(C#N)cc4F)n3)cc2F)nc2ccc(C(=O)O)cc21] | 22 | 629.3 | 1H NMR (400 MHz, DMSO-d6) δ 8.54 (s, 1H), 7.91 (t, J = 9.9 Hz, 2H), 7.85-7.68 (m, 4H), 7.61 (d, J = 8.4 Hz, 1H), 7.54 (d, J = 7.3 Hz, 1H), 7.40 (dd, J = 11.4, 6.0 Hz, 1H), 7.00 (d, J = 8.2 Hz, 1H), 5.61 (s, 2H), 4.87 (dd, J = 9.0, 4.7 Hz, 1H), 4.63 (d, J = 16.9 Hz, 1H), 4.59-4.46 (m, 2H), 3.90 (dd, J = 10.7, 4.6 Hz, 1H), 3.84-3.77 (m, 2H), 3.14 (s, 3H), 1.99 (q, J = 4.6, 4.0 Hz, 3H). |

TABLE 2-continued

Compounds

| Ex. | Structure | Procedure | ES/MS m/z | ¹H NMR |
|---|---|---|---|---|
| 71 | 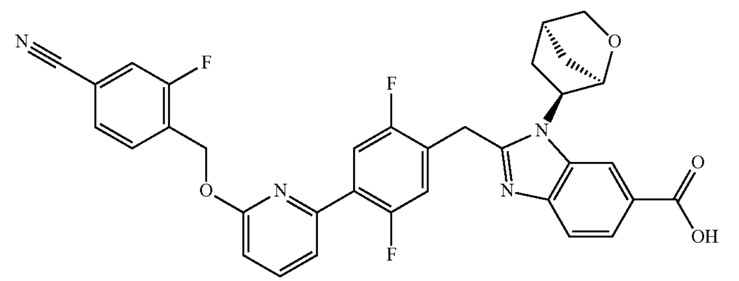 [SMILES: N#Cc1ccc(COc2cccc(-c3cc(F)c(Cc4nc5ccc(C(=O)O)cc5n4[C@H]4C[C@H]5CO[C@@H]4C5)cc3F)n2)c(F)c1] | 22 | 611.2 | 1H NMR (400 MHz, DMSO-d6) δ 8.49 (s, 1H), 7.96-7.87 (m, 2H), 7.83 (d, J = 8.5 Hz, 1H), 7.81-7.70 (m, 3H), 7.63 (d, J = 8.4 Hz, 1H), 7.59-7.48 (m, 1H), 7.41 (dd, J = 11.5, 6.0 Hz, 1H), 7.00 (d, J = 8.2 Hz, 1H), 5.61 (s, 2H), 5.07 (dd, J = 11.5, 5.6 Hz, 1H), 4.54 (d, J = 12.8 Hz, 3H), 4.06 (d, J = 7.1 Hz, 1H), 3.95-3.83 (m, 1H), 2.81 (t, J = 3.1 Hz, 1H), 2.40 (t, J = 13.9 Hz, 1H), 2.18-1.95 (m, 2H), 1.83 (d, J = 10.4 Hz, 1H). |
| 72 | 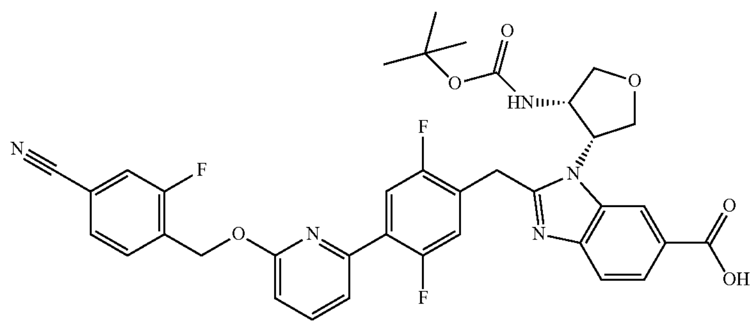 [SMILES: CC(C)(C)OC(=O)N[C@@H]1COC[C@@H]1n1c(Cc2cc(F)c(-c3cccc(OCc4ccc(C#N)cc4F)n3)cc2F)nc2ccc(C(=O)O)cc21] | 22 | 700.2 | 1H NMR (400 MHz, DMSO-d6) δ 8.44 (s, 1H), 7.94-7.86 (m, 2H), 7.81-7.70 (m, 4H), 7.54 (dd, J = 11.0, 7.7 Hz, 2H), 7.30 (dd, J = 11.2, 6.4 Hz, 1H), 7.09 (s, 1H), 7.00 (d, J = 8.3 Hz, 1H), 5.62 (s, 2H), 5.40 (s, 1H), 4.63-4.43 (m, 4H), 4.30 (d, J = 17.0 Hz, 1H), 4.20 (dd, J = 10.9, 7.0 Hz, 1H), 4.08-3.89 (m, 3H), 1.12 (s, 9H). |
| 73 | 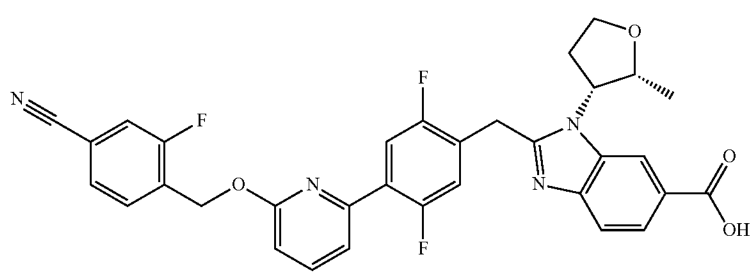 [SMILES: C[C@H]1OCC[C@H]1n1c(Cc2cc(F)c(-c3cccc(OCc4ccc(C#N)cc4F)n3)cc2F)nc2ccc(C(=O)O)cc21] | 22 | 599.2 | 1H NMR (400 MHz, DMSO-d6) δ 8.32 (d, J = 1.4 Hz, 1H), 7.94-7.87 (m, 2H), 7.83 (dd, J = 8.5, 1.5 Hz, 1H), 7.80-7.71 (m, 3H), 7.65 (d, J = 8.5 Hz, 1H), 7.54 (dd, J = 7.5, 1.5 Hz, 1H), 7.43 (dd, J = 11.4, 6.1 Hz, 1H), 7.00 (d, J = 8.3 Hz, 1H), 4.54 (d, J = 5.8 Hz, 4H), 4.38-4.32 (m, 2H), 4.00 (p, J = 6.2 Hz, 1H), 3.73 (q, J = 9.0 Hz, 1H), 0.80 (d, J = 6.3 Hz, 3H). |

US 11,858,918 B2

TABLE 2-continued

| Ex. | Structure | Procedure | ES/MS m/z | ¹H NMR |
|---|---|---|---|---|
| 74 | 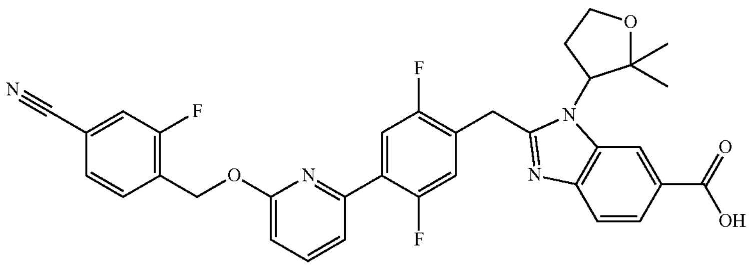 [SMILES: CC1(C)OCCC1n1c(Cc2cc(F)c(-c3cccc(OCc4ccc(C#N)cc4F)n3)cc2F)nc2ccc(C(=O)O)cc21] | 22 | 613.2 | 1H NMR (400 MHz, DMSO-d6) δ 8.25 (d, J = 1.5 Hz, 1H), 7.96-7.87 (m, 2H), 7.82-7.69 (m, 4H), 7.63 (d, J = 8.4 Hz, 1H), 7.54 (d, J = 6.7 Hz, 1H), 7.43 (dd, J = 11.4, 6.4 Hz, 2H), 7.00 (d, J = 8.2 Hz, 1H), 5.60 (s, 2H), 5.01 (s, 2H), 4.48 (t, J = 14.0 Hz, 3H), 4.29 (d, J = 3.5 Hz, 2H), 3.99 (d, J = 8.4 Hz, 2H), 1.29 (s, 3H), 0.77 (s, 3H). |
| 75 | 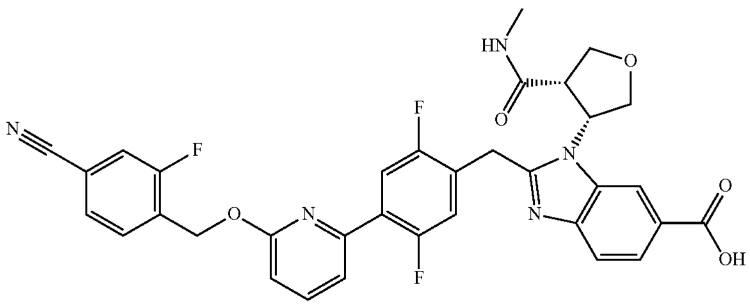 [SMILES: CNC(=O)[C@@H]1COC[C@@H]1n1c(Cc2cc(F)c(-c3cccc(OCc4ccc(C#N)cc4F)n3)cc2F)nc2ccc(C(=O)O)cc21] | 22 | 642.2 | 1H NMR (400 MHz, DMSO-d6) δ 8.37 (d, J = 1.4 Hz, 1H), 7.99 (q, J = 4.6 Hz, 1H), 7.96-7.82 (m, 3H), 7.82-7.71 (m, 3H), 7.68 (d, J = 8.4 Hz, 1H), 7.52 (dd, J = 7.6, 1.7 Hz, 1H), 7.23 (dd, J = 11.5, 6.0 Hz, 1H), 7.00 (d, J = 8.2 Hz, 1H), 5.71 (td, J = 7.1, 3.3 Hz, 1H), 5.60 (s, 2H), 4.59-4.48 (m, 2H), 4.48-4.42 (m, 1H), 4.27 (dd, J = 10.3, 3.4 Hz, 1H), 4.13 (dd, J =10.5, 8.3 Hz, 1H), 3.65 (t, J = 9.4 Hz, 1H), 3.45 (ddd, J = 9.9, 8.0, 6.2 Hz, 1H), 2.50 (s, 3H). |
| 76 | 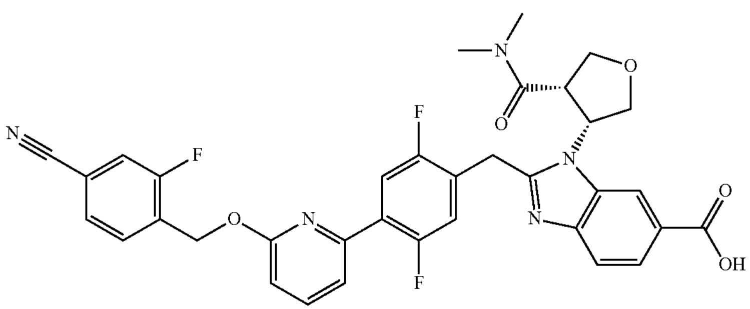 [SMILES: CN(C)C(=O)[C@@H]1COC[C@@H]1n1c(Cc2cc(F)c(-c3cccc(OCc4ccc(C#N)cc4F)n3)cc2F)nc2ccc(C(=O)O)cc21] | 22 | 656.2 | 1H NMR (400 MHz, DMSO-d6) δ 8.53 (d, J = 1.5 Hz, 0H), 8.46 (d, J = 1.5 Hz, 1H), 7.97-7.83 (m, 5H), 7.83-7.63 (m, 7H), 7.61-7.46 (m, 2H), 7.37 (dd, J = 11.5, 6.1 Hz, 0H), 7.21 (dd, J = 11.6, 6.1Hz, 1H), 7.00 (dd, J = 8.3, 2.0 Hz, 2H), 5.87 (s, 1H), 5.82 (s, 1H), 5.61 (d, J = 8.6 Hz, 0H), 4.69 (t, J = 2.3 Hz, 3H), 4.61-4.42 (m, 3H), 4.40-4.31 (m, 2H), 4.31-4.20 (m, 1H), 4.20-4.05 (m, 2H), 3.77 (d, J = 8.8, |

TABLE 2-continued

Compounds

| Ex. | Structure | Procedure | ES/MS m/z | ¹H NMR |
|---|---|---|---|---|
| 77 | 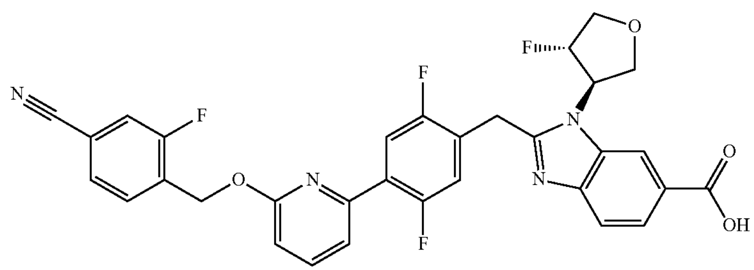 | | | 5.6 Hz, 1H), 3.57 (t, J = 9.1 Hz, 1H), 3.02 (s, 1H), 2.78 (s, 3H), 2.72 (s, 3H). |
| 78 | 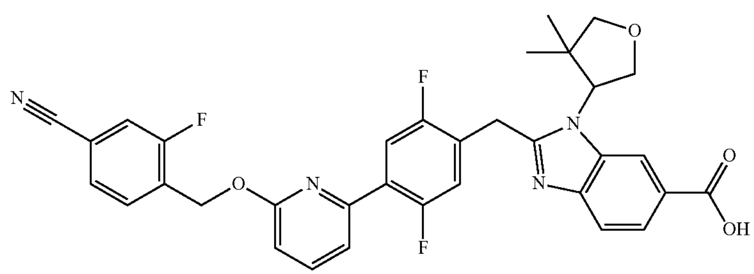 [SMILES: CC1(C)COCC1n1c(Cc2cc(F)c(-c3cccc(OCc4ccc(C#N)cc4F)n3)cc2F)nc2ccc(C(=O)O)cc21] | 22 | 603.2 | 1H NMR (400 MHz, DMSO-d6) δ 8.29 (d, J = 1.4 Hz, 1H), 7.96-7.89 (m, 2H), 7.89-7.82 (m, 1H), 7.82-7.71 (m, 3H), 7.68 (d, J = 8.5 Hz, 1H), 7.53 (dd, J = 7.5, 1.7 Hz, 1H), 7.41 (dd, J = 11.5, 6.1 Hz, 1H), 7.00 (d, J = 8.2 Hz, 1H), 5.66 (dq, J = 5.0, 2.3 Hz, 1H), 5.60 (s, 2H), 5.54 (q, J = 5.3, 3.7 Hz, 1H), 4.55 (q, J = 16.8 Hz, 2H), 4.46-4.24 (m, 3H), 4.08 (ddd, J = 24.6, 11.4, 3.1 Hz, 1H). |
| 79 | 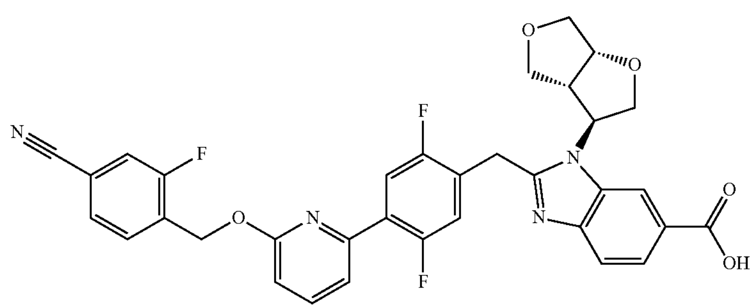 [SMILES: N#Cc1ccc(COc2cccc(-c3cc(F)c(Cc4nc5ccc(C(=O)O)cc5n4[C@@H]4CO[C@H]5COC[C@H]54)cc3F)n2)c(F)c1] | 22 | 613.2 | 1H NMR (400 MHz, DMSO-d6) δ 8.50 (s, 1H), 7.96-7.87 (m, 2H), 7.86-7.71 (m, 5H), 7.63 (d, J = 8.5 Hz, 1H), 7.55 (dd, J = 7.5, 1.6 Hz, 1H), 7.46 (dd, J = 11.3, 6.2 Hz, 1H), 7.00 (d, J = 8.3 Hz, 1H), 5.61 (s, 2H), 5.03 (d, J = 6.6 Hz, 1H), 4.60-4.49 (m, 2H), 4.49-4.33 (m, 2H), 3.83-3.68 (m, 2H), 1.33 (s, 3H), 0.61 (s, 3H)." |
|  |  | 22 | 627.2 | 1H NMR (400 MHz, DMSO-d6) δ 8.47 (d, J = 1.4 Hz, 1H), 7.96-7.85 (m, 3H), 7.85-7.65 (m, 5H), 7.53 (dd, J = 7.5, 1.6 Hz, 1H), 7.40 (dd, J = 11.5, 6.1 Hz, 1H), 7.00 (d, J = 8.3 Hz, 1H), 5.60 (s, 2H), 5.25 (td, J = 5.2, 2.6 Hz, 1H), 5.09 (dd, J = 7.0, 4.1 Hz, 1H), 4.60 (s, 2H), 4.23 (d, J = 5.1 Hz, 2H), 3.96 (dd, J = 12.2, 9.2 Hz, 2H), 3.58-3.48 (m, 2H), 3.18 (ddt, J = 6.9, 4.5, 2.3 Hz, 1H). |

TABLE 2-continued

Compounds

| Ex. | Structure | Procedure | ES/MS m/z | ¹H NMR |
|---|---|---|---|---|
| 80 | 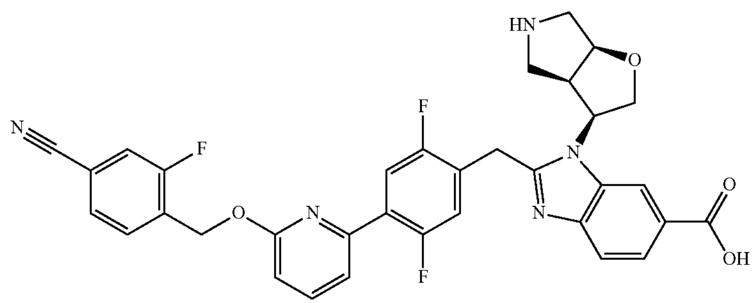 [SMILES: N#Cc1ccc(COc2cccc(-c3cc(F)c(Cc4nc5ccc(C(=O)O)cc5n4[C@@H]4CO[C@@H]5CNC[C@H]45)cc3F)n2)c(F)c1] | 22 | 626.2 | 1H NMR (400 MHz, DMSO-d6) δ 8.50 (d, J = 1.4 Hz, 1H), 7.98-7.87 (m, 2H), 7.84 (dd, J = 8.4, 1.5 Hz, 1H), 7.81-7.70 (m, 3H), 7.66 (d, J = 8.5 Hz, 1H), 7.55 (dd, J = 7.5, 1.6 Hz, 1H), 7.43 (dd, J = 11.5, 6.1 Hz, 1H), 7.01 (d, J = 8.3 Hz, 1H), 5.61 (s, 3H), 4.86 (dd, J = 11.1, 2.3 Hz, 1H), 4.76 (td, J = 6.0, 2.5 Hz, 1H), 4.55-4.36 (m, 2H), 4.23 (dd, J = 11.1, 7.3 Hz, 1H), 3.71-3.48 (m, 2H), 3.46-3.29 (m, 1H), 3.04 (s, 1H), 2.46-2.29 (m, 2H). |
| 81 | 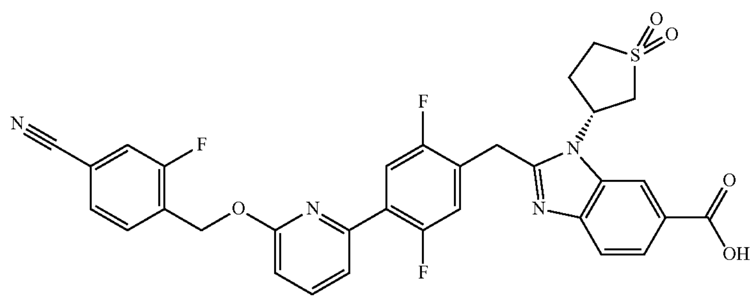 [SMILES: N#Cc1ccc(COc2cccc(-c3cc(F)c(Cc4nc5ccc(C(=O)O)cc5n4[C@@H]4CCS(=O)(=O)C4)cc3F)n2)c(F)c1] | 22 | 633.2 | 1H NMR (400 MHz, DMSO-d6) δ 8.41 (d, J = 1.3 Hz, 1H), 7.94-7.88 (m, 2H), 7.86 (dd, J = 8.5, 1.4 Hz, 1H), 7.81-7.71 (m, 3H), 7.68 (d, J = 8.4 Hz, 1H), 7.54 (dd, J = 7.4, 1.6 Hz, 1H), 7.38 (dd, J = 11.4, 6.1 Hz, 1H), 7.00 (d, J = 8.2 Hz, 1H), 5.73 (ddd, J = 18.8, 10.9, 7.8 Hz, 1H), 5.61 (s, 2H), 4.53 (s, 2H), 3.78 (dd, J = 14.3, 10.6 Hz, 1H), 3.70-3.53 (m, 2H), 3.32 (td, J = 13.1, 6.8 Hz, 1H), 2.86-2.60 (m, 2H). |

TABLE 2-continued

Compounds

| Ex. | Structure | Procedure | ES/MS m/z | ¹H NMR |
|---|---|---|---|---|
| 82 | (structure) | 22 | 625.2 | 1H NMR (400 MHz, DMSO-d6) δ 8.28 (d, J = 1.4 Hz, 1H), 7.96-7.86 (m, 2H), 7.81-7.70 (m, 4H), 7.61 (d, J = 8.4 Hz, 1H), 7.54 (dd, J = 7.6, 1.7 Hz, 1H), 7.48 (dd, J = 11.4, 6.0 Hz, 1H), 7.00 (d, J = 8.3 Hz, 1H), 5.61 (s, 2H), 5.27-5.19 (m, 1H), 4.55 (d, J = 16.8 Hz, 1H), 4.37 (d, J = 16.8 Hz, 1H), 4.22 (d, J = 11.5 Hz, 1H), 4.00 (dd, J = 11.8, 2.1 Hz, 1H), 3.79-3.68 (m, 1H), 3.19 (d, J = 11.7 Hz, 1H), 2.89 (td, J = 12.5, 11.5, 4.5 Hz, 1H), 2.05 (d, J = 11.6 Hz, 1H), 0.61 (dt, J = 10.1, 5.2 Hz, 1H), 0.40 (s, 1H), 0.22 (dt, J = 10.2, 5.3 Hz, 1H). |
| 83 | (structure) | 22 | 627.2 | 1H NMR (400 MHz, DMSO-d6) δ 8.30 (s, 1H), 7.96-7.86 (m, 2H), 7.86-7.70 (m, 5H), 7.61 (d, J = 8.4 Hz, 1H), 7.55 (dd, J = 7.5, 1.7 Hz, 1H), 7.46 (dd, J = 11.5, 6.1 Hz, 1H), 7.00 (d, J = 8.3 Hz, 1H), 5.61 (s, 2H), 4.75 (dd, J = 12.6, 3.9 Hz, 1H), 4.63 (d, J = 16.9 Hz, 1H), 4.42 (d, J = 16.9 Hz, 1H), 4.19-4.11 (m, 1H), 3.63-3.53 (m, 2H), 3.47 (d, J = 11.4 Hz, 1H), 2.91 (dt, J = 12.7, 5.8 Hz, 1H), 1.75 (d, J = 10.8 Hz, 1H), 1.20 (s, 3H), 0.91 (s, 3H). |

TABLE 2-continued

Compounds

| Ex. | Structure | Procedure | ES/MS m/z | ¹H NMR |
|---|---|---|---|---|
| 84 | | 23 | 650.3 | 1H NMR (400 MHz, Acetonitrile-d3) δ 8.83 (s, 1H), 8.75 (d, J = 6.4 Hz, 2H), 8.54 (s, 1H), 8.43 (s, 1H), 7.90-7.75 (m, 3H), 7.72 (t, J = 7.4 Hz, 1H), 7.57 (t, J = 8.1 Hz, 3H), 7.26 (dd, J = 11.6, 6.0 Hz, 1H), 6.94 (d, J = 8.3 Hz, 1H), 5.63 (s, 2H), 4.77-4.41 (m, 4H), 3.75 (t, J = 5.0 Hz, 2H), 3.23 (s, 3H). |
| 85 | | 24 | 672.2 | ¹H NMR (400 MHz, DMSO-d₆) δ 8.26 (d, J = 5.2 Hz, 1H), 7.99-7.87 (m, 2H), 7.83-7.71 (m, 4H), 7.60 (d, J = 8.4 Hz, 1H), 7.54 (d, J = 7.3 Hz, 1H), 7.34 (dd, J = 11.5, 6.0 Hz, 1H), 7.00 (d, J = 8.3 Hz, 1H), 5.61 (s, 2H), 5.49 (d, J = 5.7 Hz, 1H), 4.62-4.43 (m, 2H), 4.15 (d, J = 8.8 Hz, 2H), 3.88 (t, J = 9.9 Hz, 1H), 3.69 (d, J = 4.8 Hz, 3H), 3.10 (s, 3H) (note: 3 protons hidden by solvent). |

TABLE 2-continued

Compounds

| Ex. | Structure | Procedure | ES/MS m/z | ¹H NMR |
|---|---|---|---|---|
| 86 | 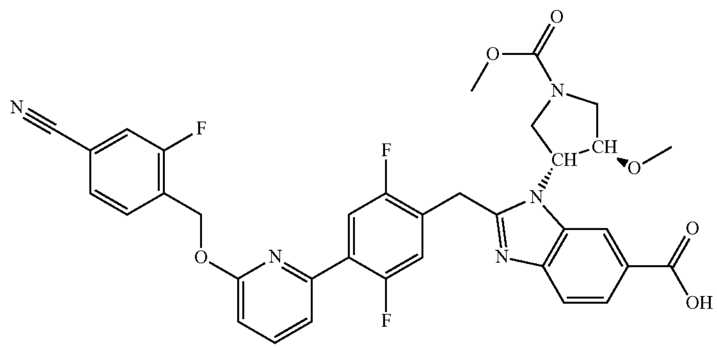 [SMILES: COC(=O)N1C[C@@H](n2c(Cc3cc(F)c(-c4cccc(OCc5ccc(C#N)cc5F)n4)cc3F)nc3ccc(C(=O)O)cc32)[C@H](OC)C1] | 24 | 672.2 | 1H NMR (400 MHz, DMSO-d6) δ 8.12 (s, 1H), 7.99-7.87 (m, 2H), 7.84 (dd, J = 8.4, 1.4 Hz, 1H), 7.79-7.72 (m, 3H), 7.67 (d, J = 8.4 Hz, 1H), 7.53 (dd, J = 7.5, 1.7 Hz, 1H), 7.38 (dd, J = 11.5, 6.1 Hz, 1H), 7.00 (d, J = 8.3 Hz, 1H), 5.60 (s, 2H), 5.33 (s, 1H), 4.63-4.37 (m, 3H), 3.68 (s, 4H), 3.36 (d, J = 9.4 Hz, 1H), 3.17 (s, 3H). |
| 87 | 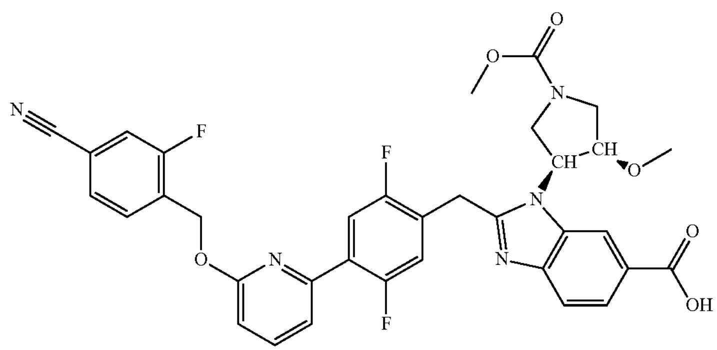 [SMILES: COC(=O)N1C[C@@H](OC)[C@@H](n2c(Cc3cc(F)c(-c4cccc(OCc5ccc(C#N)cc5F)n4)cc3F)nc3ccc(C(=O)O)cc32)C1] | 24 | 672.2 | 1H NMR (400 MHz, DMSO-d6) δ 8.27 (d, J = 5.9 Hz, 1H), 7.97-7.87 (m, 2H), 7.84-7.58 (m, 4H), 7.54 (dd, J = 7.6, 1.7 Hz, 1H), 7.35 (dd, J = 11.5, 6.1 Hz, 1H), 7.00 (d, J = 8.3 Hz, 1H), 5.61 (s, 2H), 5.55-5.42 (m, 1H), 4.62-4.43 (m, 2H), 4.16 (d, J = 9.1 Hz, 2H), 3.88 (t, J = 9.9 Hz, 1H), 3.10 (s, 3H). |

TABLE 2-continued

Compounds

| Ex. | Structure | Procedure | ES/MS m/z | ¹H NMR |
|---|---|---|---|---|
| 88 | 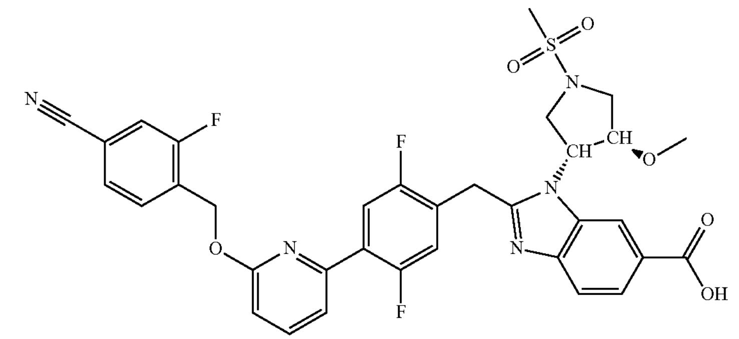 [SMILES: CO[C@@H]1CN(S(C)(=O)=O)C[C@H]1n1c(Cc2cc(F)c(-c3cccc(OCc4ccc(C#N)cc4F)n3)cc2F)nc2ccc(C(=O)O)cc21] | 25 | 692.2 | 1H NMR (400 MHz, DMSO-d6) δ 8.27 (d, J = 1.5 Hz, 1H), 7.96-7.83 (m, 3H), 7.80-7.73 (m, 3H), 7.68 (d, J = 8.4 Hz, 1H), 7.53 (dd, J = 7.4, 1.7 Hz, 1H), 7.38 (dd, J = 11.5, 6.1 Hz, 1H), 7.00 (d, J = 8.3 Hz, 1H), 5.60 (s, 2H), 5.34 (dt, J = 9.6, 6.6 Hz, 1H), 4.61-4.38 (m, 3H), 4.06-3.92 (m, 2H), 3.30 (dd, J = 10.1, 6.9 Hz, 1H), 3.18 (s, 3H), 3.13 (s, 3H). |
| 89 | 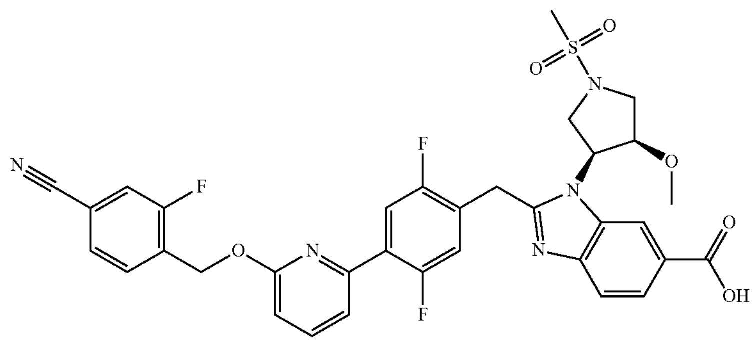 [SMILES: CO[C@@H]1CN(S(C)(=O)=O)C[C@@H]1n1c(Cc2cc(F)c(-c3cccc(OCc4ccc(C#N)cc4F)n3)cc2F)nc2ccc(C(=O)O)cc21] | 25 | 692.2 | 1H NMR (400 MHz, DMSO-d6) δ 8.41 (s, 1H), 7.97-7.87 (m, 2H), 7.82-7.71 (m, 4H),7.60 (d, J = 8.4 Hz, 1H), 7.56-7.52 (m, 1H), 7.34 (dd, J = 11.4, 6.1 Hz, 1H), 7.00 (d, J = 8.3 Hz, 1H), 5.61 (s, 2H), 5.53 (td, J = 8.6, 5.1 Hz, 1H), 4.62-4.46 (m, 2H), 4.19 (q, J = 4.6, 3.7 Hz, 1H), 4.05 (dd, J = 10.3, 8.2 Hz, 1H), 3.84 (t, J = 9.7 Hz, 1H), 3.10 (s, 3H), 3.08 (s, 3H). |

TABLE 2-continued

Compounds

| Ex. | Structure | Procedure | ES/MS m/z | ¹H NMR |
|---|---|---|---|---|
| 90 | 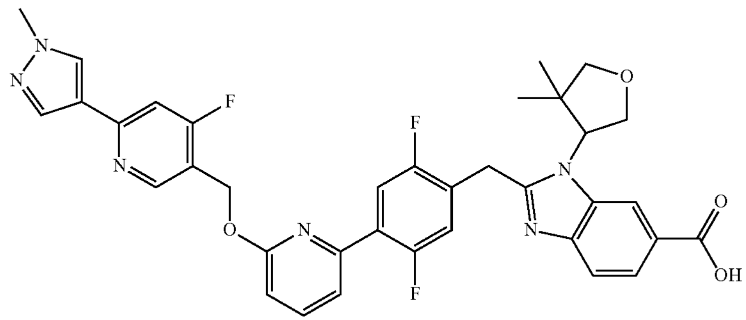 | 26 | 669.6 | 1H NMR (400 MHz, DMSO-d6) δ 8.69 (d, J = 10.4 Hz, 1H), 8.51 (s, 1H), 8.35 (s, 1H), 8.06 (s, 1H), 8.00-7.86 (m, 2H), 7.83 (dd, J = 8.4, 1.5 Hz, 1H), 7.73-7.61 (m, 2H), 7.55 (dd, J = 7.5, 1.6 Hz, 1H), 7.48 (dd, J = 11.2, 6.3 Hz, 1H), 6.95 (d, J = 8.3 Hz, 1H), 5.55 (s, 2H), 5.04 (d, J = 6.6 Hz, 1H), 4.65-4.51 (m, 2H), 3.89 (s, 3H), 3.79 (d, J = 8.7 Hz, 1H), 3.74 (d, J = 8.6 Hz, 1H), 1.34 (s, 3H), 0.62 (s, 3H). |
| 91 | 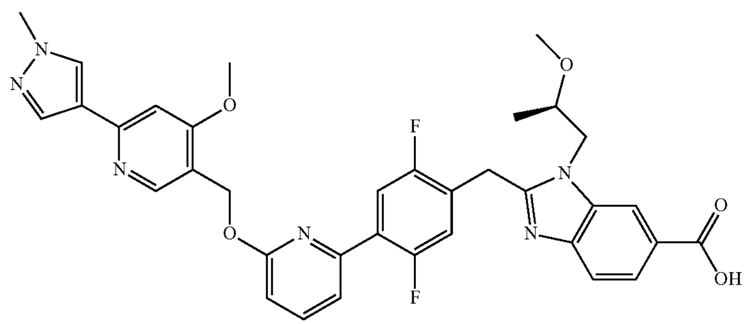 [SMILES: COc1cc(-c2cnn(C)c2)ncc1COc1cccc(-c2cc(F)c(Cc3nc4ccc(C(=O)O)cc4n3C[C@@H](C)OC)cc2F)n1] | 26 | 655.3 | 1H NMR (400 MHz, DMSO-d6) δ 8.65 (s, 1H), 8.60 (s, 1H), 8.32 (s, 1H), 8.27 (d, J = 1.5 Hz, 1H), 7.96-7.79 (m, 3H), 7.75 (s, 1H), 7.62 (d, J = 8.4 Hz, 1H), 7.55 (dd, J = 7.5, 1.6 Hz, 1H), 7.42 (dd, J = 11.5, 6.1 Hz, 1H), 6.97 (d, J = 8.3 Hz, 1H), 5.50 (s, 2H), 4.54 (dd, J = 15.2, 3.2 Hz, 1H), 4.49 (s, 2H), 4.38 (dd, J = 15.2, 8.8 Hz, 1H), 4.16 (s, 3H), 3.97 (s, 3H), 3.71 (ddd, J = 9.3, 6.2, 3.2 Hz, 1H), 3.09 (s, 3H), 1.24 (d, J = 6.1 Hz, 3H). |
| 92 | 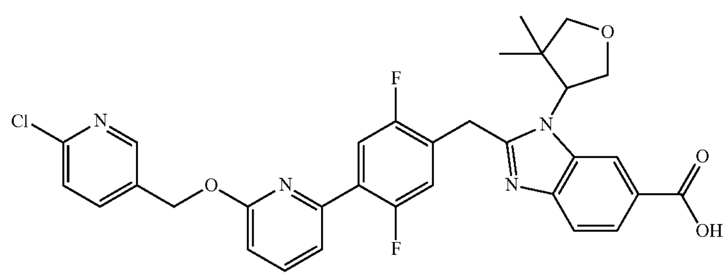 [SMILES: CC1(C)COCC1n1c(Cc2cc(F)c(-c3cccc(OCc4ccc(Cl)nc4)n3)cc2F)nc2ccc(C(=O)O)cc21] | 27 | 605.86 | 1H NMR (400 MHz, Methanol-d4) δ 8.89 (s, 1H), 8.51 (d, J = 2.4 Hz, 1H), 8.17 (dd, J = 8.6, 1.3 Hz, 1H), 8.05-7.88 (m, 2H), 7.88-7.72 (m, 2H), 7.58 (dd, J = 7.5, 1.6 Hz, 1H), 7.48 (d, J = 8.2 Hz, 1H), 7.40 (d, J = 11.1, 6.1 Hz, 1H), 6.94 (d, J = 8.3 Hz, 1H), 5.55 (s, 2H), 5.14 (d, J = 6.6 Hz, 1H), 4.78-4.61 (m, 3H), 4.52 (dd, J = 11.6, |

TABLE 2-continued

Compounds

| Ex. | Structure | Procedure | ES/MS m/z | ¹H NMR |
|---|---|---|---|---|
| 93 | 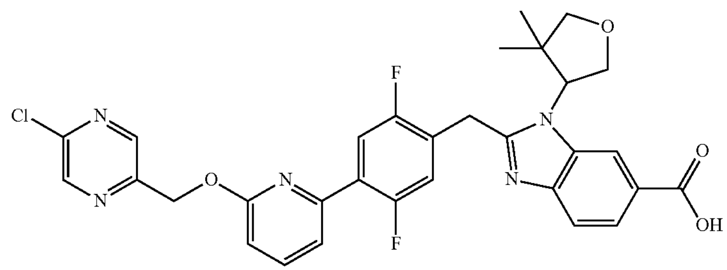 [SMILES: CC1(C)COCC1n1c(Cc2cc(F)c(-c3cccc(OCc4cnc(Cl)cn4)n3)cc2F)nc2ccc(C(=O)O)cc21] | 27 | 606.77 | 1H NMR (400 MHz, Methanol-d4) δ 8.92 (s, 1H), 8.66 (d, J = 1.4 Hz, 1H), 8.59 (d, J = 1.3 Hz, 1H), 8.20 (d, J = 8.6 Hz, 1H), 7.94-7.72 (m, 3H), 7.60 (dd, J = 7.5, 1.6 Hz, 1H), 7.41 (dd, J = 11.2, 6.0 Hz, 1H), 7.01 (d, J = 8.3 Hz, 1H), 5.64 (s, 2H), 5.15 (d, J = 6.6 Hz, 1H), 4.79-4.59 (m, 3H), 4.53 (dd, J = 11.7, 6.7 Hz, 1H), 4.00 (d, J = 8.9 Hz, 1H), 3.85 (d, J = 8.9 Hz, 1H), 1.41 (s, 3H), 0.76 (s, 3H). |
| 94 | 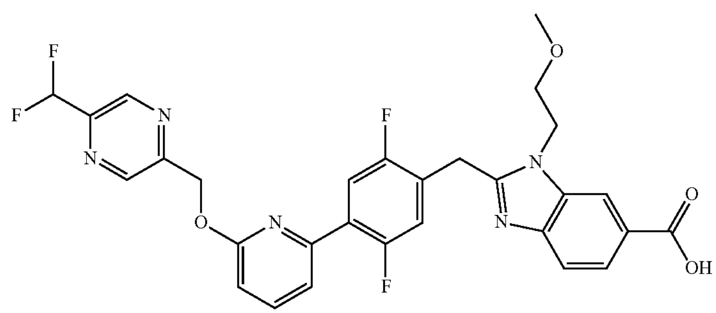 [SMILES: COCCn1c(Cc2cc(F)c(-c3cccc(OCc4cnc(C(F)F)cn4)n3)cc2F)nc2ccc(C(=O)O)cc21] | 28 | 582.2 | 1H NMR (400 MHz, DMSO-d6) δ 8.97 (s, 1H), 8.93 (d, J = 1.4 Hz, 1H), 8.25 (d, J = 1.5 Hz, 1H), 7.92 (t, J = 7.9 Hz, 1H), 7.84 (dd, J = 8.4, 1.5 Hz, 1H), 7.68-7.59 (m, 2H), 7.53 (dd, J = 7.6, 1.6 Hz, 1H), 7.38 (dd, J = 11.5, 6.1Hz, 1H), 7.29-6.93 (m, 2H), 5.71 (s, 2H), 4.62 (t, J = 5.1 Hz, 2H), 4.47 (s, 2H), 3.69 (t, J = 5.1 Hz, 2H), 3.21 (s, 3H). |

TABLE 2-continued

Compounds

| Ex. | Structure | Procedure | ES/MS m/z (M + H+) | 1H NMR |
|---|---|---|---|---|
| 95 | 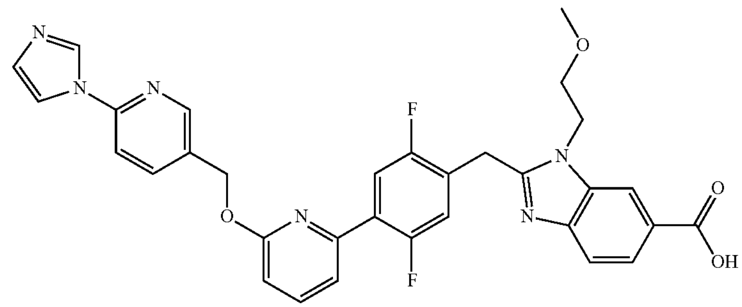 [SMILES: COCCn1c(Cc2cc(F)c(-c3cccc(OCc4ccc(-n5ccnc5)nc4)n3)cc2F)nc2ccc(C(=O)O)cc21] | 28 | 597.2 | 1H NMR (400 MHz, DMSO-d6) δ 8.65 (d, J = 2.2 Hz, 1H), 8.55 (s, 1H), 8.20 (d, J = 1.4 Hz, 1H), 8.14 (dd, J = 8.4, 2.3 Hz, 1H), 7.97 (s, 1H), 7.92-7.83 (m, 3H), 7.79 (dd, J = 8.4, 1.5 Hz, 1H), 7.60 (d, J = 8.5 Hz, 1H), 7.53 (d, J = 7.1 Hz, 1H), 7.39 (dd, J = 11.5, 6.1 Hz, 1H), 7.13 (s, 1H), 6.97 (d, J = 8.3 Hz, 1H), 5.56 (s, 2H), 5.40 (s, 1H), 4.59 (d, J = 5.6 Hz, 2H), 4.44 (s, 2H), 3.69 (t, J = 5.0 Hz, 2H), 3.22 (s, 3H). |
| 96 | 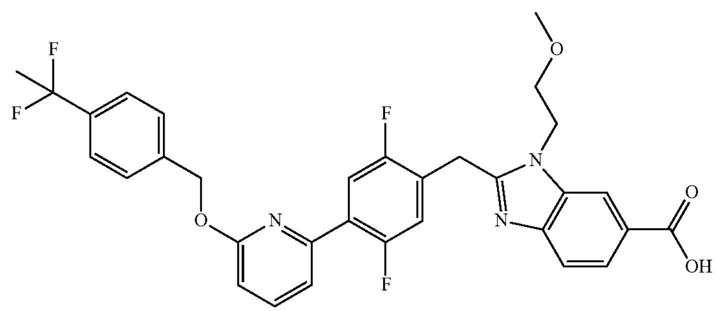 [SMILES: COCCn1c(Cc2cc(F)c(-c3cccc(OCc4ccc(C(C)(F)F)cc4)n3)cc2F)nc2ccc(C(=O)O)cc21] | 28 | 594.4 | 1H NMR (400 MHz, DMSO-d6) δ 12.84 (s, 1H), 8.32 (d, 1H), 7.93-7.84 (m, 2H), 7.79 (dd, 1H), 7.70-7.59 (m, 1H), 7.59 (d, 4H), 7.51 (dd, 1H), 7.43 (dd, 1H), 6.97 (d, 1H), 5.53 (s, 2H), 4.67 (t, 2H), 3.70 (t, 2H), 3.21 (s, 3H), 2.49 (s, 0H), 1.96 (t, 3H). |
| 97 | 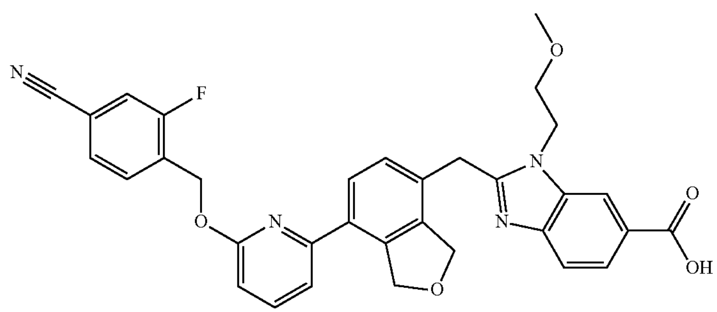 [SMILES: COCCn1c(Cc2ccc(-c3cccc(OCc4ccc(C#N)cc4F)n3)c3c2COC3)nc2ccc(C(=O)O)cc21] | 29 | 579.2 | 1H NMR (400 MHz, DMSO) δ 8.26 (s, 1H), 7.98-7.92 (m, 1H), 7.91-7.81 (m, 3H), 7.78-7.68 (m, 2H), 7.65 (d, J = 8.4 Hz, 1H), 7.59 (d, J = 7.6 Hz, 1H), 7.27 (d, J = 8.0 Hz, 1H), 6.93 (d, J = 8.2 Hz, 1H), 5.58 (s, 2H), 5.36 (s, 2H), 4.99 (s, 2H), 4.58 (t, J = 5.3 Hz, 2H), 4.42 (s, 2H), 3.63 (t, J = 5.1 Hz, 2H), 3.20 (s, 3H). |

TABLE 2-continued

Compounds

| Ex. | Structure | Procedure | ES/MS m/z | ¹H NMR |
|---|---|---|---|---|
| 98 | 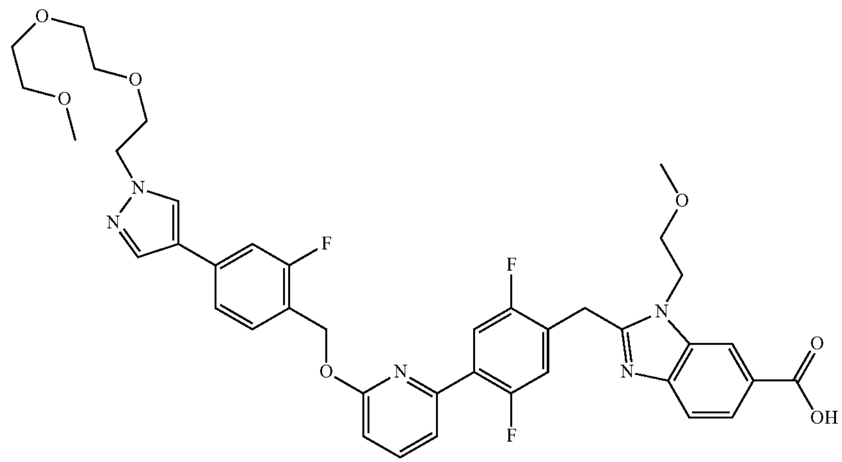 [SMILES: COCCOCCOCCn1cc(-c2ccc(COc3cccc(-c4cc(F)c(Cc5nc6ccc(C(=O)O)cc6n5CCOC)cc4F)n3)c(F)c2)cn1] | 30 | 760.4 | 1H NMR (400 MHz, DMSO-d6) δ 8.25 (d, 1H), 7.96 (s, 1H), 7.93-7.79 (m, 2H), 7.63 (d, 1H), 7.59-7.35 (m, 4H), 6.94 (d, 1H), 5.50 (s, 1H), 4.63 (d, OH), 4.62 (s, 1H), 4.48 (s, 1H), 4.26 (d, 1H), 3.79 (s, 1H), 3.48 (dt, 5H), 3.36 (q, 2H), 3.19 (dd, 4H) (note: multiple protons hidden under water peak). |
| 99 | 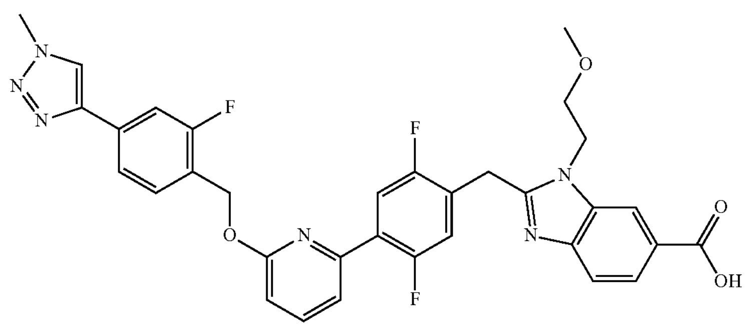 [SMILES: COCCn1c(Cc2cc(F)c(-c3cccc(OCc4ccc(-c5cn(C)nn5)cc4F)n3)cc2F)nc2ccc(C(=O)O)cc21] | 30 | 629.1 | ¹H NMR (400 MHz, DMSO-d₆) δ 8.29 (d, 1H), 7.99 (s, 1H), 7.92-7.82 (m, 3H), 7.73 (t, 1H), 7.65 (d, 1H), 7.62 (dd, 1H), 7.53 (dd, 1H), 7.50 (dd, 1H), 7.42 (dd, 1H), 6.98 (dd, 1H), 5.59 (s, 2H), 4.65 (t, 2H), 4.52 (s, 2H), 4.11 (s, 3H), 3.70 (t, 2H), 3.22 (s, 3H). |

TABLE 2-continued

Compounds

| Ex. | Structure | Procedure | ES/MS m/z | ¹H NMR |
|---|---|---|---|---|
| 100 | 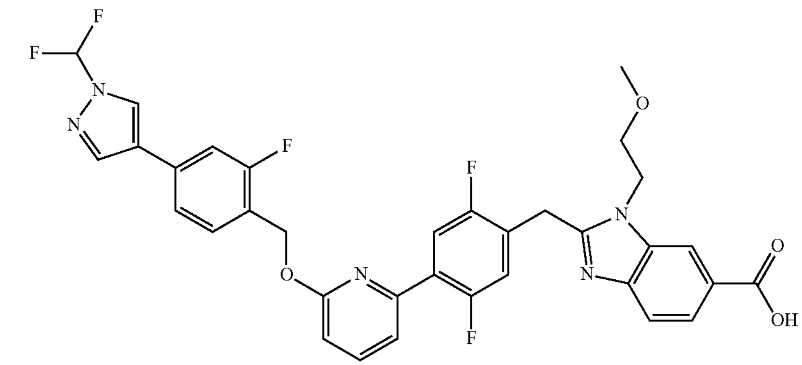 [SMILES: COCCn1c(Cc2cc(F)c(-c3cccc(OCc4ccc(-c5cnn(C(F)F)c5)cc4F)n3)cc2F)nc2ccc(C(=O)O)cc21] | 30 | 664.2 | ¹H NMR (400 MHz, DMSO-d₆) δ 12.87 (s, 1H), 8.82 (s, 1H), 8.35 (s, 1H), 8.29 (d, 1H), 7.95-7.82 (m, 4H), 7.72-7.54 (m, 5H), 7.52 (dd, 1H), 7.42 (dd, 1H), 6.96 (d, 1H), 5.52 (s, 2H), 4.65 (t, 2H), 4.52 (s, 2H), 3.70 (t, 2H), 3.22 (s, 3H). |
| 101 | 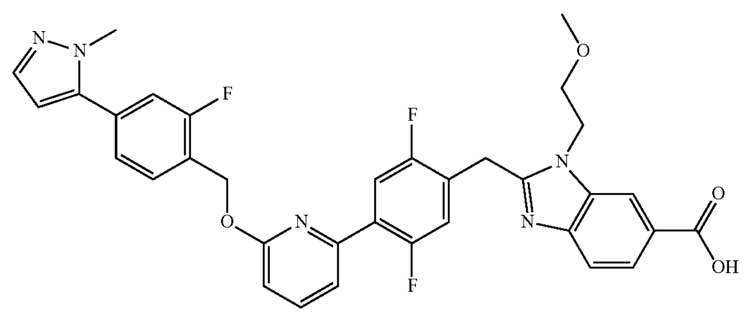 [SMILES: COCCn1c(Cc2cc(F)c(-c3cccc(OCc4ccc(-c5ccnn5C)cc4F)n3)cc2F)nc2ccc(C(=O)O)cc21] | 30 | 628.3 | ¹H NMR (400 MHz, DMSO-d₆) δ 12.86 (s, 1H), 8.29 (d, 1H), 7.94-7.81 (m, 3H), 7.73-7.62 (m, 2H), 7.57-7.45 (m, 3H), 7.47-7.38 (m, 2H), 6.98 (d, 1H), 6.49 (d, 1H), 5.58 (s, 2H), 4.66 (t, 2H), 4.52 (s, 2H), 3.88 (s, 3H), 3.70 (t, 2H), 3.22 (s, 3H). |
| 102 | 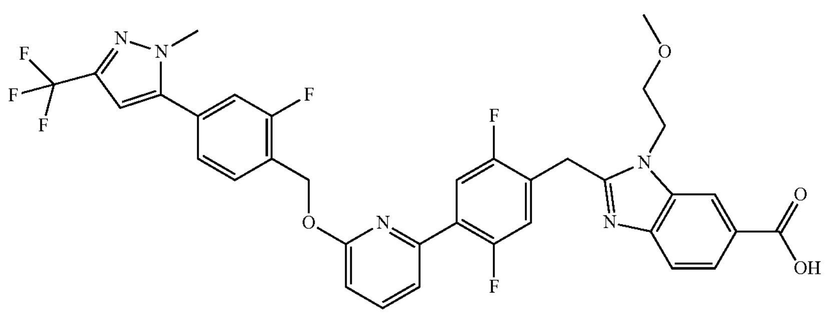 [SMILES: COCCn1c(Cc2cc(F)c(-c3cccc(OCc4ccc(-c5cc(C(F)(F)F)nn5C)cc4F)n3)cc2F)nc2ccc(C(=O)O)cc21] | 30 | 696.2 | ¹H NMR (400 MHz, DMSO-d₆) δ 8.27 (d, 1H), 7.94-7.80 (m, 3H), 7.73 (t, 1H), 7.67-7.37 (m, 5H), 7.03-6.95 (m, 2H), 5.59 (s, 2H), 4.64 (t, 2H), 4.50 (s, 2H), 3.70 (t, 2H), 3.21 (s, 3H). |

TABLE 2-continued

Compounds

| Ex. | Structure | Procedure | ES/MS m/z | ¹H NMR |
|---|---|---|---|---|
| 103 | 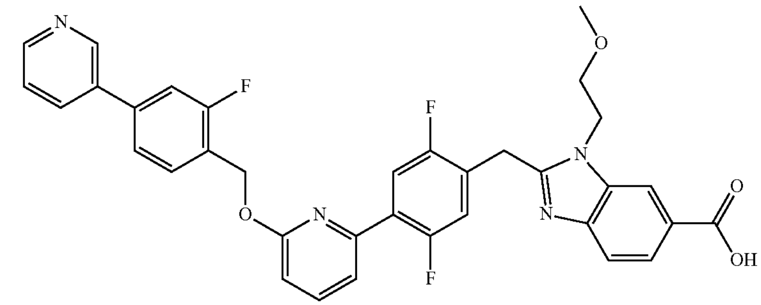 [SMILES: COCCn1c(Cc2cc(F)c(-c3cccc(OCc4ccc(-c5cccnc5)cc4F)n3)cc2F)nc2ccc(C(=O)O)cc21] | 30 | 625.2 | ¹H NMR (400 MHz, DMSO-d₆) δ 9.05 (d, 1H), 8.69 (dd, 1H), 8.35 (dt, 1H), 8.27 (d, 1H), 7.94-7.80 (m, 3H), 7.80-7.60 (m, 5H), 7.53 (dd, 1H), 7.42 (dd, 1H), 6.98 (d, 1H), 5.59 (s, 2H), 4.64 (t, 2H), 4.50 (s, 2H), 3.70 (t, 2H), 3.21 (s, 3H). |
| 104 | 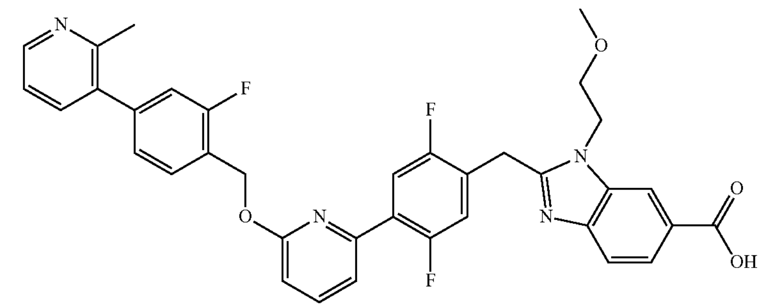 [SMILES: COCCn1c(Cc2cc(F)c(-c3cccc(OCc4ccc(-c5cccnc5C)cc4F)n3)cc2F)nc2ccc(C(=O)O)cc21] | 30 | 639.3 | ¹H NMR (400 MHz, DMSO-d₆) δ 8.74 (dd, 1H), 8.27 (d, 1H), 8.20 (d, 1H), 7.95-7.80 (m, 3H), 7.75 (dt, 2H), 7.63 (d, 1H), 7.57-7.32 (m, 4H), 6.99 (d, 1H), 5.60 (s, 2H), 4.64 (t, 2H), 4.50 (s, 2H), 3.70 (t, 2H), 3.22 (s, 3H), 2.59 (s, 3H). |
| 105 | 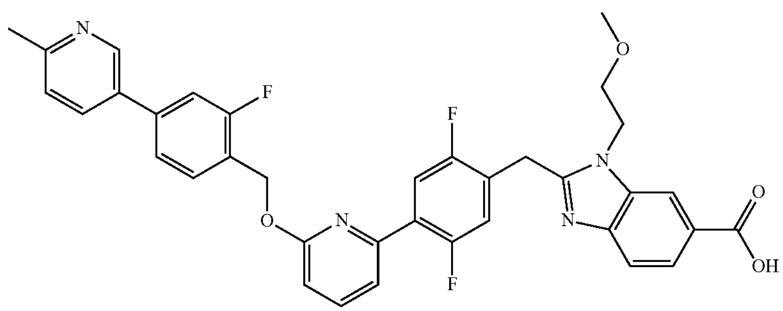 [SMILES: COCCn1c(Cc2cc(F)c(-c3cccc(OCc4ccc(-c5ccc(C)nc5)cc4F)n3)cc2F)nc2ccc(C(=O)O)cc21] | 30 | 639.3 | ¹H NMR (400 MHz, DMSO-d₆) δ 12.88 (s, 1H), 9.03 (d, 1H), 8.51 (dd, 1H), 8.27 (d, 1H), 7.94-7.65 (m, 7H), 7.63 (d, 1H), 7.53 (dd, 1H), 7.42 (dd, 1H), 6.97 (d, 1H), 5.59 (s, 2H), 4.64 (t, 2H), 3.70 (t, 2H), 3.21 (s, 3H), 2.66 (s, 3H). |

TABLE 2-continued

Compounds

| Ex. | Structure | Procedure | ES/MS m/z | ¹H NMR |
|---|---|---|---|---|
| 106 | 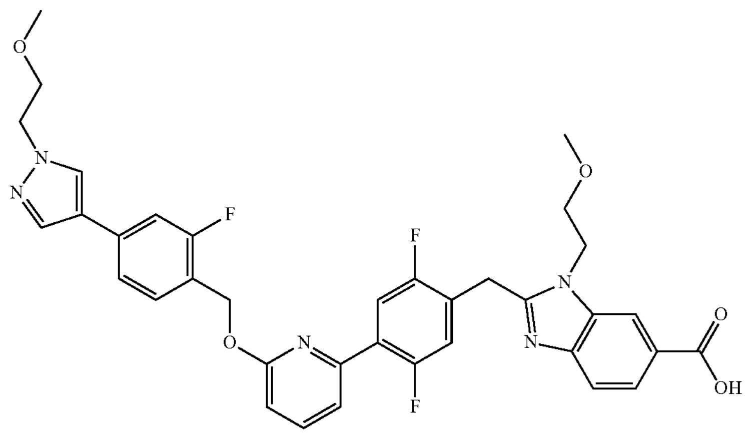 [SMILES: COCCn1cc(-c2ccc(COc3cccc(-c4cc(F)c(Cc5nc6ccc(C(=O)O)cc6n5CCOC)cc4F)n3)c(F)c2)cn1] | 30 | 672.2 | ¹H NMR (400 MHz, DMSO-d₆) δ 8.28-8.21 (m, 4H), 7.96 (s, 2H), 7.92-7.79 (m, 6H), 7.63 (d, 2H), 7.57-7.47 (m, 7H), 7.45 (d, 1H), 7.43 (s, 1H), 6.94 (d, 2H), 5.49 (s, 4H), 4.63 (t, 4H), 4.49 (s, 4H), 4.27 (t, 4H), 3.70 (dt, 9H), 3.24 (s, 6H), 3.22 (s, 6H). |
| 107 | 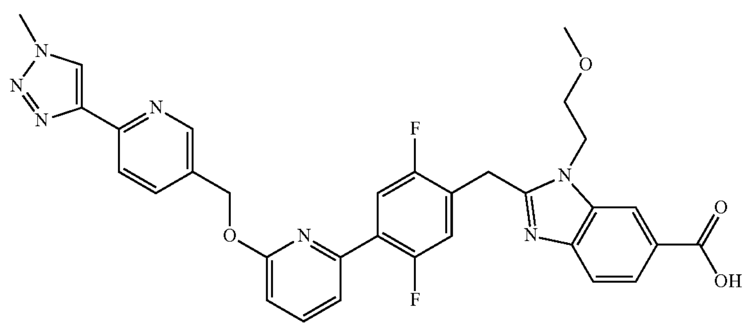 [SMILES: COCCn1c(Cc2cc(F)c(-c3cccc(OCc4ccc(-c5cnn(C)c5)nc4)n3)cc2F)nc2ccc(C(=O)O)cc21] | 30 | 612.1 | ¹H NMR (400 MHz, Acetonitrile-d₃) δ 8.85 (d, 1H), 8.34 (s, 1H), 8.09-7.98 (m, 3H), 7.93-7.70 (m, 4H), 7.56 (dd, 1H), 7.27 (dd, 1H), 6.96-6.89 (m, 1H), 5.60 (s, 2H), 4.57 (dd, 4H), 4.35 (s, 3H), 3.75 (t, 2H), 3.26 (s, 3H). |

TABLE 2-continued

Compounds

| Ex. | Structure | Procedure | ES/MS m/z | ¹H NMR |
|---|---|---|---|---|
| 108 | 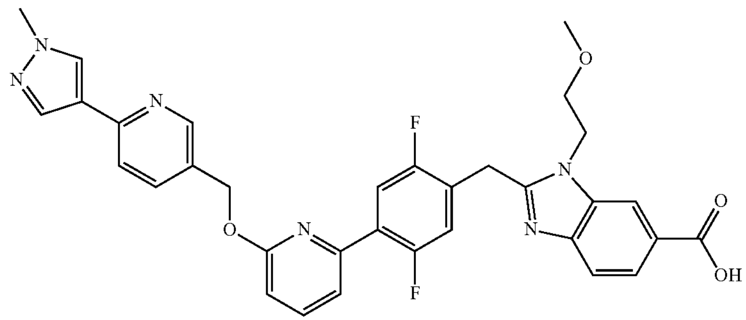 | 30 | 611.2 | ¹H NMR (400 MHz, Acetonitrile-d₃) δ 8.80 (d, 1H), 8.43-8.30 (m, 3H), 8.16 (d, 1H), 8.08 (dd, 1H), 7.98-7.77 (m, 3H), 7.76 (d, 1H), 7.54 (dd, 1H), 7.29 (dd, 1H), 6.92 (d, 1H), 5.60 (s, 2H), 4.65 (d, 1H), 4.63 (s, 3H), 3.95 (s, 3H), 3.78 (t, 2H), 3.28 (s, 3H). |
| 109 | 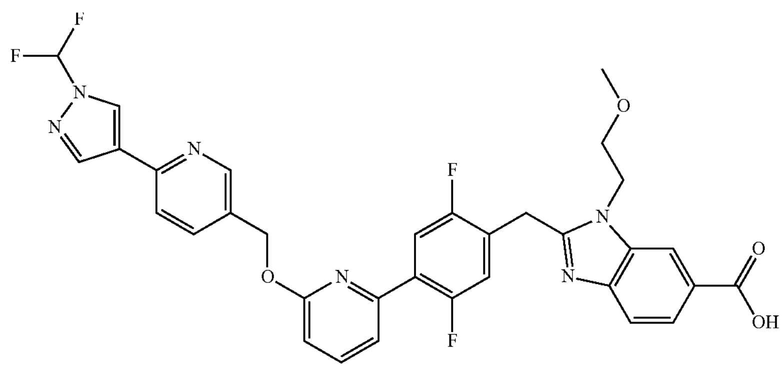 [SMILES: COCCn1c(Cc2cc(F)c(-c3cccc(OCc4ccc(-c5cnn(C(F)F)c5)nc4)n3)cc2F)nc2ccc(C(=O)O)cc21] | 30 | 647.2 | ¹H NMR (400 MHz, Acetonitrile-d₃) δ 8.79 (d, 1H), 8.63 (s, 1H), 8.45-8.40 (m, 1H), 8.31 (s, 1H), 8.11 (ddd, 2H), 7.97-7.87 (m, 1H), 7.87-7.76 (m, 3H), 7.62-7.52 (m, 1H), 7.45 (s, 0H), 7.35-7.26 (m, 1H), 6.92 (d, 1H), 5.59 (s, 2H), 4.65 (t, 2H), 3.78 (t, 2H), 3.27 (s, 3H), 1.97-1.86 (m, 1H). |
| 110 | 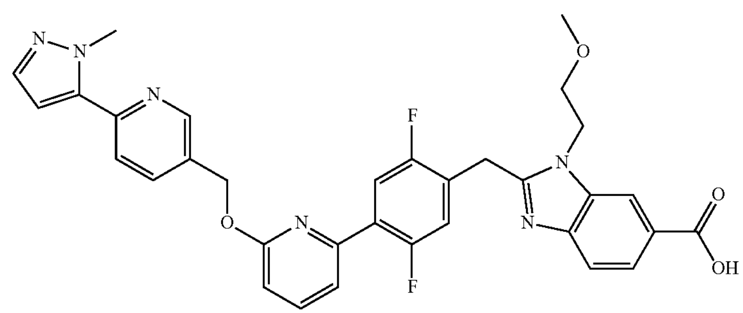 [SMILES: COCCn1c(Cc2cc(F)c(-c3cccc(OCc4ccc(-c5ccnn5C)nc4)n3)cc2F)nc2ccc(C(=O)O)cc21] | 30 | 611.2 | ¹H NMR (400 MHz, Acetonitrile-d₃) δ 8.81 (d, 1H), 8.39 (s, 1H), 8.08 (dd, 1H), 7.97 (dd, 1H), 7.91 (dd, 1H), 7.85-7.75 (m, 2H), 7.72 (d, 1H), 7.56 (dd, 1H), 7.47 (d, 1H), 7.30 (dd, 1H), 6.93 (d, 1H), 6.69 (d, 1H), 5.58 (s, 2H), 4.62 (s, 3H), 4.62 (d, 1H), 4.16 (s, 3H), 3.76 (t, 2H), 3.26 (s, 3H). |

TABLE 2-continued

Compounds

| Ex. | Structure | Procedure | ES/MS m/z | ¹H NMR |
|---|---|---|---|---|
| 111 | 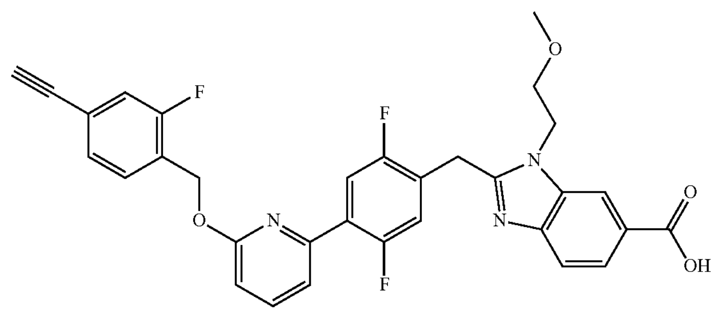 [SMILES: C#Cc1ccc(COc2cccc(-c3cc(F)c(Cc4nc5ccc(C(=O)O)cc5n4CCOC)cc3F)n2)c(F)c1] | 31 | 572.4 | 1H NMR (400 MHz, DMSO-d6) δ 8.28 (d, J = 1.4 Hz, 1H), 7.93-7.84 (m, 2H), 7.81 (dd, J = 10.5, 6.5 Hz, 1H), 7.65 (d, J = 8.4 Hz, 1H), 7.57 (t, J = 7.8 Hz, 1H), 7.52 (dd, J = 7.5, 1.7 Hz, 1H), 7.41 (ddd, J = 11.4, 4.4, 2.8 Hz, 2H), 7.35 (dd, J = 7.8, 1.6 Hz, 1H), 6.96 (d, J = 8.3 Hz, 1H), 5.53 (s, 2H), 4.65 (t, J = 5.1 Hz, 2H), 4.51 (s, 2H), 4.34 (s, 1H), 3.70 (t, J = 5.0 Hz, 2H), 3.22 (s, 3H). |
| 112 | 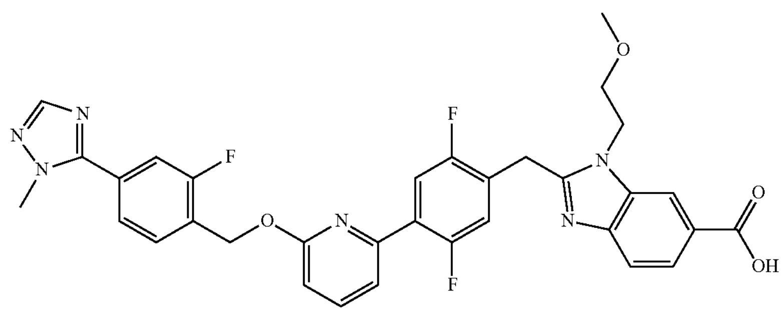 [SMILES: COCCn1c(Cc2cc(F)c(-c3cccc(OCc4ccc(-c5ncnn5C)cc4F)n3)cc2F)nc2ccc(C(=O)O)cc21] | 32 | 629.2 | 1H NMR (400 MHz, DMSO-d6) δ 8.31 (d, J = 1.4 Hz, 1H), 8.03 (s, 1H), 7.92-7.82 (m, 3H), 7.79-7.61 (m, 4H), 7.54 (dd, J = 7.6, 1.7 Hz, 1H), 7.43 (dd, J = 11.5, 6.1 Hz, 1H), 6.99 (d, J = 8.2 Hz, 1H), 5.61 (s, 2H), 4.67 (t, J = 5.1 Hz, 2H), 4.54 (s, 2H), 4.00 (s, 3H), 3.70 (d, J = 5.0 Hz, 2H), 3.21 (s, 3H). |
| 113 | 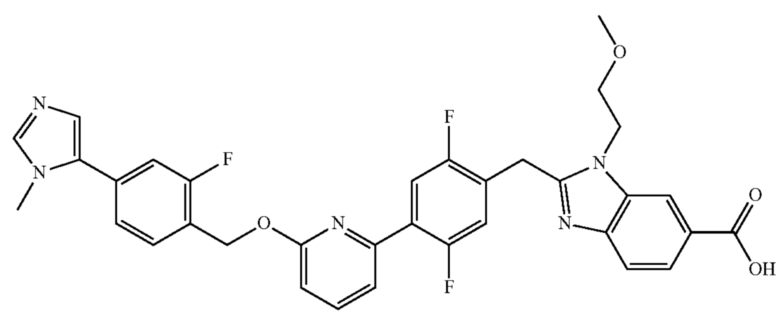 [SMILES: COCCn1c(Cc2cc(F)c(-c3cccc(OCc4ccc(-c5cncn5C)cc4F)n3)cc2F)nc2ccc(C(=O)O)cc21] | 33 | 628.2 | 1H NMR (400 MHz, DMSO-d6) δ 9.18 (d, J = 1.4 Hz, 1H), 8.25 (d, J = 1.4 Hz, 1H), 7.97-7.80 (m, 4H), 7.76 (t, J = 7.8 Hz, 1H), 7.65-7.57 (m, 2H), 7.52 (ddd, J = 15.7, 7.7, 1.7 Hz, 2H), 7.41 (dd, J = 11.5, 6.0 Hz, 1H), 6.98 (d, J = 8.2 Hz, 1H), 5.61 (s, 2H), 4.63 (t, J = 5.1 Hz, 2H), 4.48 (s, 2H), 3.88 (s, 3H), 3.70 (s, 3H), 3.22 (s, 3H). |

TABLE 2-continued

Compounds

| Ex. | Structure | Procedure | ES/MS m/z | ¹H NMR |
|---|---|---|---|---|
| 114 | 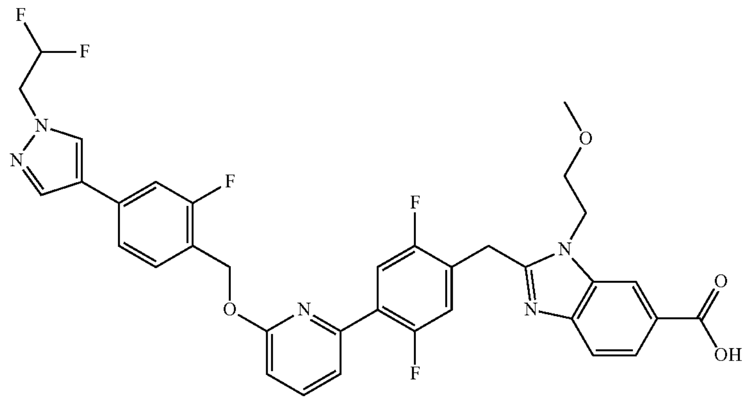 [SMILES: COCCn1c(Cc2cc(F)c(-c3cccc(OCc4ccc(-c5cnn(CC(F)F)c5)cc4F)n3)cc2F)nc2ccc(C(=O)O)cc21] | 34 | 678.2 | ¹H NMR (400 MHz, Acetonitrile-d₃) δ 8.28 (s, 1H), 8.00 (s, 1H), 7.96 (s, 0H), 7.93-7.88 (m, 2H), 7.80 (t, 1H), 7.69 (d, 1H), 7.56 (t, 3H), 7.42-7.35 (m, 2H), 7.23 (dd, 1H), 6.87 (d, 2H), 6.24 (tt, 1H), 5.56 (s, 2H), 4.55-4.51 (m, 2H), 4.49 (s, 2H), 3.73 (t, 2H), 3.25 (s, 3H). |
| 115 | 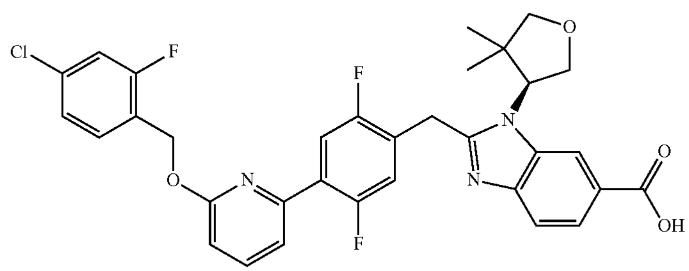 [SMILES: CC1(C)COC[C@H]1n1c(Cc2cc(F)c(-c3cccc(OCc4ccc(Cl)cc4F)n3)cc2F)nc2ccc(C(=O)O)cc21] | 22 | 622.2 | 1H NMR (400 MHz, DMSO-d6) δ 8.50 (s, 1H), 7.94-7.76 (m, 3H), 7.62 (dd, J = 12.6, 8.3 Hz, 2H), 7.57-7.42 (m, 3H), 7.33 (dd, J = 8.2, 2.0 Hz, 1H), 6.96 (d, J = 8.2 Hz, 1H), 5.51 (s, 2H), 5.02 (d, J = 6.6 Hz, 1H), 4.54 (dd, J = 14.1, 2.9 Hz, 2H), 4.49-4.33 (m, 2H), 3.82-3.72 (m, 2H), 1.34 (s, 3H), 0.61 (s, 3H). |
| 116 | 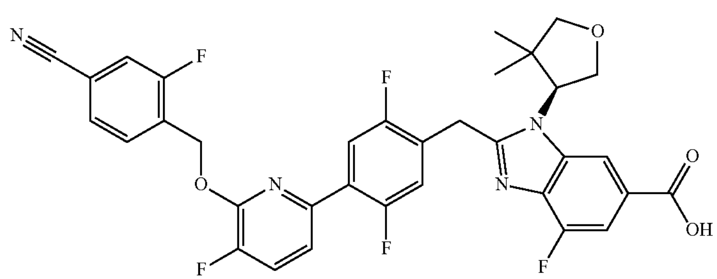 [SMILES: CC1(C)COC[C@H]1n1c(Cc2cc(F)c(-c3ccc(F)c(OCc4ccc(C#N)cc4F)n3)cc2F)nc2c(F)cc(C(=O)O)cc21] | 22 | 648.6 | 1H NMR (400 MHz, DMSO) δ 13.12 (s, 1H), 8.79 (d, J = 5.2 Hz, 1H), 8.36 (s, 1H), 7.96 (dd, J = 10.2, 6.2 Hz, 1H), 7.68-7.60 (m, 2H), 7.60-7.51 (m, 2H), 7.51 (d, J = 2.1 Hz, 1H), 7.35 (dd, J = 8.2, 2.0 Hz, 1H), 5.54 (s, 2H), 5.04 (d, J = 6.6 Hz, 1H), 4.58 (d, J = 17.0 Hz, 1H), 4.53 (d, J = 11.8 Hz, 1H), 4.48-4.38 (m, 2H), 3.76 (s, 10H), 3.76 (d, J = 16.5 Hz, 2H), 1.34 (s, 3H), 0.62 (s, 3H). |

TABLE 2-continued

Compounds

| Ex. | Structure | Procedure | ES/MS m/z | ¹H NMR |
|---|---|---|---|---|
| 117 | 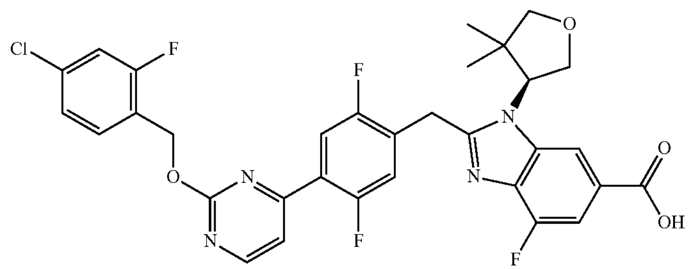 [SMILES: CC1(C)COC[C@H]1n1c(Cc2cc(F)c(-c3ccnc(OCc4ccc(Cl)cc4F)n3)cc2F)nc2c(F)cc(C(=O)O)cc21] | 22 | 642.0 | ¹H NMR (400 MHz, DMSO) δ 8.79 (d, J = 5.2 Hz, 1H), 8.36 (s, 1H), 7.96 (dd, J = 10.2, 6.2 Hz, 1H), 7.68-7.48 (m, 5H), 7.35 (dd, J = 8.3, 2.1 Hz, 1H), 5.54 (s, 2H), 5.04 (d, J = 6.5 Hz, 1H), 4.59 (d, J = 17.0 Hz, 1H), 4.53 (d, J = 11.8 Hz, 1H), 4.48-4.38 (m, 2H), 3.75 (q, J = 8.7 Hz, 2H), 1.34 (s, 3H), 0.62 (s, 3H). |
| 118 | 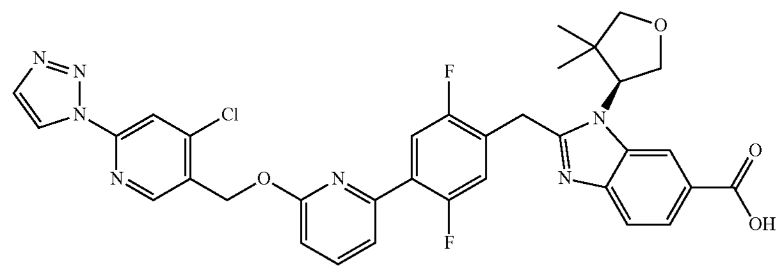 [SMILES: CC1(C)COC[C@H]1n1c(Cc2cc(F)c(-c3cccc(OCc4cnc(-n5ccnn5)cc4Cl)n3)cc2F)nc2ccc(C(=O)O)cc21] | 22 | 672.1 | 1H NMR (400 MHz, DMSO-d6) δ 8.89 (d, J = 1.3 Hz, 1H), 8.82 (s, 1H), 8.47 (s, 1H), 8.30 (s, 1H), 8.02 (d, J = 1.3 Hz, 1H), 7.97-7.84 (m, 2H), 7.79 (dd, J = 8.5, 1.5 Hz, 1H), 7.61 (d, J = 8.5 Hz, 1H), 7.56 (d, J = 7.2 Hz, 1H), 7.46 (dd, J = 8.3, 6.4 Hz, 1H), 7.01 (d, J = 11.1, 6.4 Hz, 1H), 5.67 (s, 2H), 5.01 (d, J = 6.7 Hz, 1H), 4.57-4.48 (m, 2H), 4.46-4.33 (m, 2H), 3.79-3.70 (m, 2H), 1.33 (s, 3H), 0.60 (s, 3H). |
| 119 | 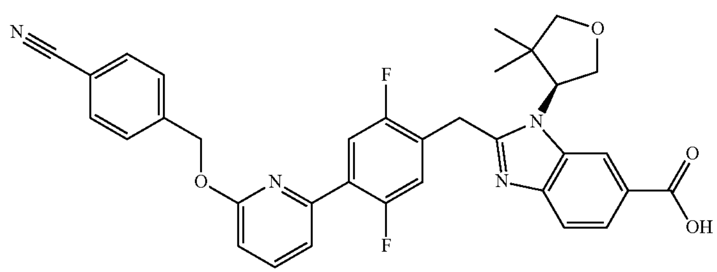 [SMILES: CC1(C)COC[C@H]1n1c(Cc2cc(F)c(-c3cccc(OCc4ccc(C#N)cc4)n3)cc2F)nc2ccc(C(=O)O)cc21] | 22 | 595.6 | 1H NMR (400 MHz, Methanol-d4) δ 8.87 (s, 1H), 8.16 (dd, J = 8.6, 1.4 Hz, 1H), 7.91-7.72 (m, 5H), 7.66 (d, J = 8.4 Hz, 2H), 7.58 (dd, J = 7.5, 1.6 Hz, 1H), 7.37 (dd, J = 11.2, 6.1 Hz, 1H), 6.97 (d, J = 8.2 Hz, 1H), 5.59 (s, 2H), 5.12 (d, J = 6.6 Hz, 1H), 4.76-4.60 (m, 3H), 4.52 (dd, J = 11.6, 6.7 Hz, 1H), 3.99 (d, J = 8.9 Hz, 1H), 3.84 (d, J = 8.9 Hz, 1H), 1.40 (s, 3H), 0.75 (s, 3H). |

TABLE 2-continued

Compounds

| Ex. | Structure | Procedure | ES/MS m/z | ¹H NMR |
|---|---|---|---|---|
| 120 | 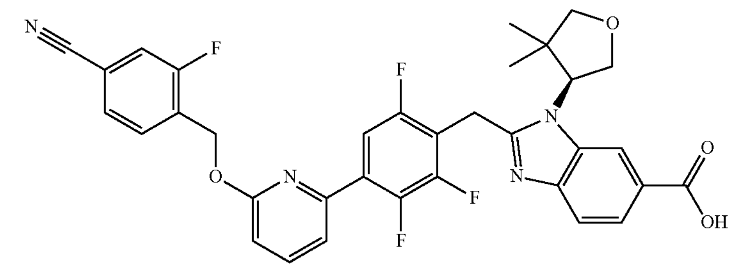 [SMILES: CC1(C)COC[C@H]1n1c(Cc2c(F)cc(-c3cccc(OCc4ccc(C#N)cc4F)n3)c(F)c2F)nc2ccc(C(=O)O)cc21] | 22 | 631.2 | 1H NMR (400 MHz, Methanol-d4) δ 8.85 (s, 1H), 8.11 (dd, J = 8.6, 1.4 Hz, 1H), 7.89 (t, J = 7.9 Hz, 1H), 7.81-7.66 (m, 3H), 7.66-7.55 (m, 3H), 7.01 (d, J = 8.3 Hz, 1H), 5.65 (s, 2H), 5.17 (d, J = 6.6 Hz, 1H), 4.84-4.68 (m, 2H), 4.68-4.49 (m, 2H), 4.00 (d, J = 8.8 Hz, 1H), 3.87 (d, J = 8.8 Hz, 1H), 1.48 (s, 3H), 0.82 (s, 3H). |
| 121 | 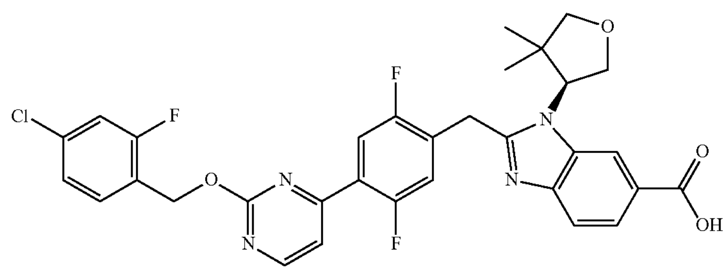 [SMILES: CC1(C)COC[C@H]1n1c(Cc2cc(F)c(-c3ccnc(OCc4ccc(Cl)cc4F)n3)cc2F)nc2ccc(C(=O)O)cc21] | 22 | 623.5 | 1H NMR (400 MHz, Methanol-d4) δ 8.86 (s, 1H), 8.72 (d, J = 5.2 Hz, 1H), 8.14 (dd, J = 8.6, 1.4 Hz, 1H), 8.06 (dd, J = 10.4, 6.1 Hz, 1H), 7.75 (d, J = 8.6 Hz, 1H), 7.68 (dd, J = 5.2, 1.6 Hz, 1H), 7.60 (t, J = 8.1 Hz, 1H), 7.46 (dd, J = 11.2, 5.9 Hz, 1H), 7.32-7.22 (m, 2H), 5.61 (s, 2H), 5.12 (d, J = 6.6 Hz, 1H), 4.81-4.58 (m, 3H), 4.53 (dd, J = 11.5, 6.8 Hz, 1H), 3.99 (d, J = 8.9 Hz, 1H), 3.84 (d, J = 8.9 Hz, 1H), 1.42 (s, 3H), 0.76 (s, 3H). |
| 122 | 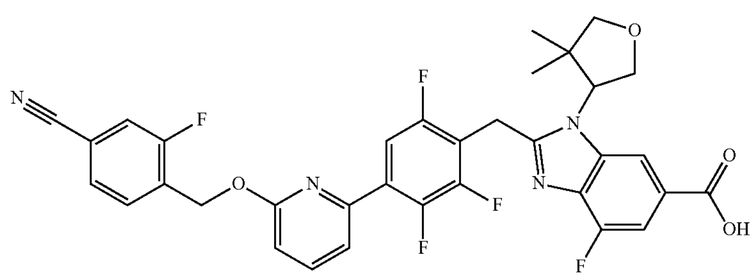 [SMILES: CC1(C)COCC1n1c(Cc2c(F)cc(-c3cccc(OCc4ccc(C#N)cc4F)n3)c(F)c2F)nc2c(F)cc(C(=O)O)cc21] | 22 | 649.7 | 1H NMR (400 MHz, Methanol-d4) δ 8.57 (s, 1H), 7.86 (t, J = 7.9 Hz, 1H), 7.74 (t, J = 7.5 Hz, 1H), 7.69-7.50 (m, 5H), 6.98 (d, J = 8.2 Hz, 1H), 5.64 (s, 2H), 5.10 (d, J = 6.6 Hz, 1H), 4.75-4.61 (m, 2H), 4.55 (dd, J = 11.4, 6.8 Hz, 1H), 4.45 (d, J = 17.2 Hz, 1H), 3.95 (d, J = 8.8 Hz, 1H), 3.84 (d, J = 8.8 Hz, 1H), 1.46 (s, 3H), 0.78 (s, 3H). |

TABLE 2-continued

Compounds

| Ex. | Structure | Procedure | ES/MS m/z | 1H NMR |
|---|---|---|---|---|
| 123 | 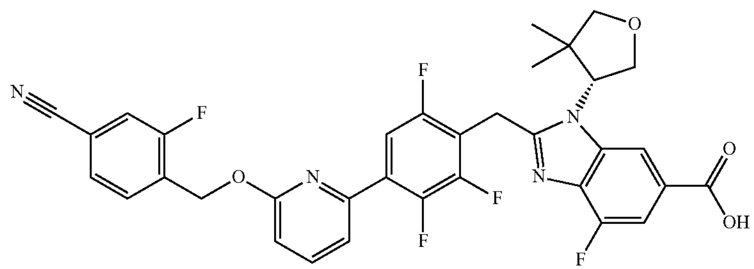 [SMILES: CC1(C)COC[C@@H]1n1c(Cc2c(F)cc(-c3cccc(OCc4ccc(C#N)cc4F)n3)c(F)c2F)nc2c(F)cc(C(=O)O)cc21] | 30 | 649.6 | 1H NMR (400 MHz, Methanol-d4) δ 8.56 (s, 1H), 7.87 (t, J = 7.9 Hz, 1H), 7.75 (t, J = 7.5 Hz, 1H), 7.69-7.53 (m, 5H), 6.98 (d, J = 8.3 Hz, 1H), 5.64 (s, 2H), 5.10 (d, J = 6.6 Hz, 1H), 4.78-4.60 (m, 2H), 4.55 (dd, J = 11.3, 6.8 Hz, 1H), 4.44 (d, J = 17.1 Hz, 1H), 3.95 (d, J = 8.8 Hz, 1H), 3.84 (d, J = 8.8 Hz, 1H), 1.46 (s, 3H), 0.78 (s, 3H) |
| 124 | 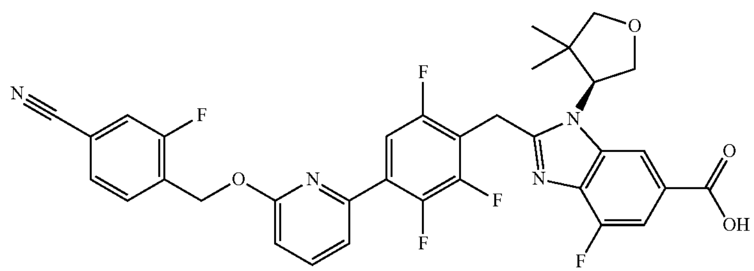 [SMILES: CC1(C)COC[C@H]1n1c(Cc2c(F)cc(-c3cccc(OCc4ccc(C#N)cc4F)n3)c(F)c2F)nc2c(F)cc(C(=O)O)cc21] | 30 | 649.5 | 1H NMR (400 MHz, Methanol-d4) δ 8.56 (s, 1H), 7.87 (t, J = 7.9 Hz, 1H), 7.75 (t, J = 7.5 Hz, 1H), 7.69-7.53 (m, 5H), 6.98 (d, J = 8.3 Hz, 1H), 5.64 (s, 2H), 5.10 (d, J = 6.6 Hz, 1H), 4.78-4.60 (m, 2H), 4.55 (dd, J = 11.3, 6.8 Hz, 1H), 4.44 (d, J = 17.1 Hz, 1H), 3.95 (d, J = 8.8 Hz, 1H), 3.84 (d, J = 8.8 Hz, 1H), 1.46 (s, 3H), 0.78 (s, 3H). |
| 125 | 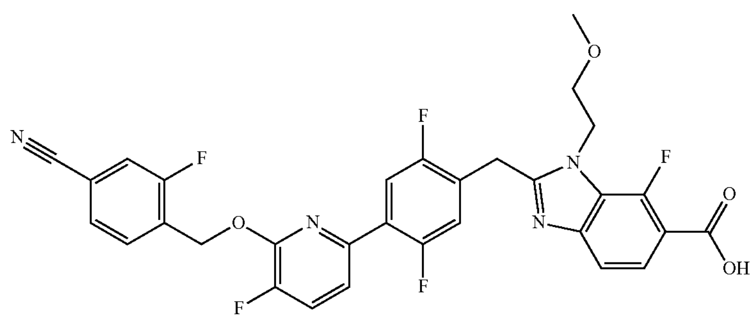 [SMILES: COCCn1c(Cc2cc(F)c(-c3ccc(F)c(OCc4ccc(C#N)cc4F)n3)cc2F)nc2ccc(C(=O)O)c(F)c21] | 1 (step 2) | 609.5 | 1H NMR (400 MHz, Chloroform-d) δ 8.03 (dd, J = 8.7, 6.6 Hz, 1H), 7.82-7.63 (m, 3H), 7.60-7.37 (m, 4H), 7.18 (dd, J = 11.1, 6.0 Hz, 1H), 5.66 (s, 2H), 5.32 (s, 1H), 4.64 (d, J = 6.9 Hz, 4H), 3.83 (t, J = 4.8 Hz, 2H), 3.34 (s, 3H). |

TABLE 2-continued

Compounds

| Ex. | Structure | Procedure | ES/MS m/z | ¹H NMR |
|---|---|---|---|---|
| 126 | 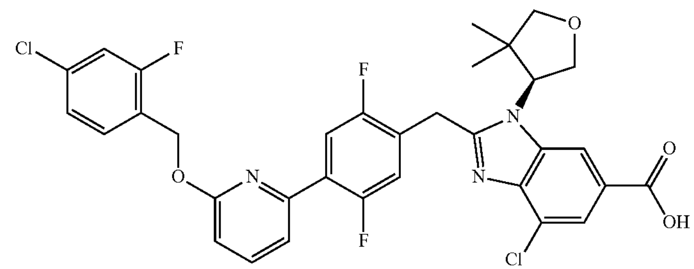 [SMILES: CC1(C)COC[C@H]1n1c(Cc2cc(F)c(-c3cccc(OCc4ccc(Cl)cc4F)n3)cc2F)nc2c(Cl)cc(C(=O)O)cc21] | 35 | (M+) 656.0 | 1H NMR (400 MHz, DMSO-d6) δ 8.47 (s, 1H), 7.95-7.83 (m, 2H), 7.81 (d, J = 1.3 Hz, 1H), 7.61 (t, J = 8.2 Hz, 1H), 7.54 (dd, J = 7.6, 1.6 Hz, 1H), 7.47 (ddd, J = 17.2, 10.7, 4.1 Hz, 2H), 7.33 (dd, J = 8.2, 2.0 Hz, 1H), 6.95 (d, J = 8.2 Hz, 1H), 5.51 (s, 2H), 5.03 (d, J = 6.6 Hz, 1H), 4.69-4.25 (m, 4H), 3.88-3.67 (m, 2H), 1.32 (s, 3H), 0.60 (s, 3H). |
| 127 | 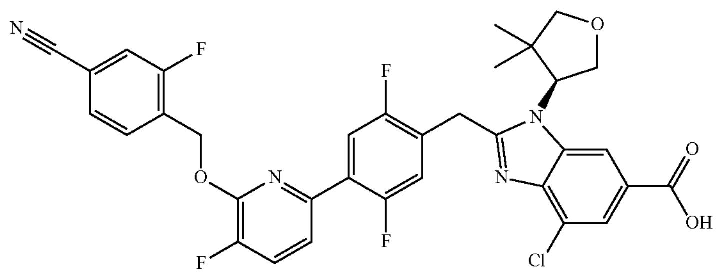 [SMILES: CC1(C)COC[C@H]1n1c(Cc2cc(F)c(-c3ccc(F)c(OCc4ccc(C#N)cc4F)n3)cc2F)nc2c(Cl)cc(C(=O)O)cc21] | 35 | (M+) 665.0 | 1H NMR (400 MHz, DMSO-d6) δ 8.46 (s, 1H), 7.94 (dd, J = 10.0, 1.4 Hz, 1H), 7.88 (dd, J = 10.2, 8.2 Hz, 1H), 7.84-7.67 (m, 4H), 7.63-7.49 (m, 1H), 7.45 (dd, J = 11.4, 6.2 Hz, 1H), 5.70 (s, 2H), 5.03 (d, J = 6.6 Hz, 1H), 4.61-4.34 (m, 4H), 3.79-3.72 (m, 2H), 3.17 (s, 1H), 1.32 (s, 3H), 0.59 (s, 3H). |
| 129 | 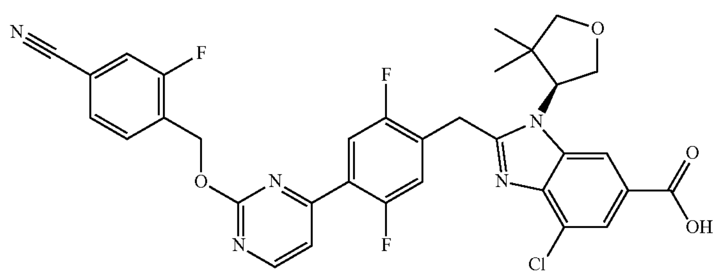 [SMILES: CC1(C)COC[C@H]1n1c(Cc2cc(F)c(-c3cccc(OCc4ccc(C#N)cc4F)n3)cc2F)nc2c(Cl)cc(C(=O)O)cc21] | 35 | (M+) 648.0 | 1H NMR (400 MHz, DMSO-d6) δ 13.12 (s, 1H), 8.79 (d, J = 5.2 Hz, 1H), 8.47 (s, 1H), 7.95 (dt, J = 10.5, 3.2 Hz, 2H), 7.83-7.72 (m, 3H), 7.66 (dd, J = 5.2, 1.7 Hz, 1H), 7.55 (dd, J = 11.5, 5.9 Hz, 1H), 5.64 (s, 2H), 5.03 (d, J = 6.6 Hz, 1H), 4.66-4.35 (m, 5H), 3.75 (q, J = 8.7 Hz, 2H), 1.32 (s, 3H), 0.60 (s, 3H). |

TABLE 2-continued

Compounds

| Ex. | Structure | Procedure | ES/MS m/z | ¹H NMR |
|---|---|---|---|---|
| 130 | 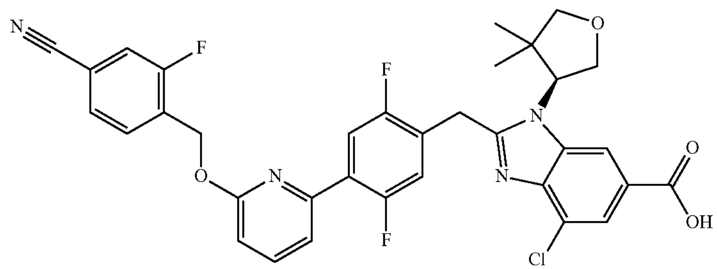 | 35 | (M+) 647.0 | 1H NMR (400 MHz, DMSO-d6) δ 8.47 (s, 1H), 8.02-7.84 (m, 2H), 7.86-7.79 (m, 2H), 7.79-7.70 (m, 2H), 7.55 (dd, J = 7.6, 1.6 Hz, 1H), 7.45 (dd, J = 11.4, 6.1 Hz, 1H), 7.00 (d, J = 8.3 Hz, 1H), 5.61 (s, 2H), 5.03 (d, J = 6.6 Hz, 1H), 4.70-4.28 (m, 4H), 3.88-3.56 (m, 3H), 1.32 (s, 3H), 0.59 (s, 3H). |
| 131 | 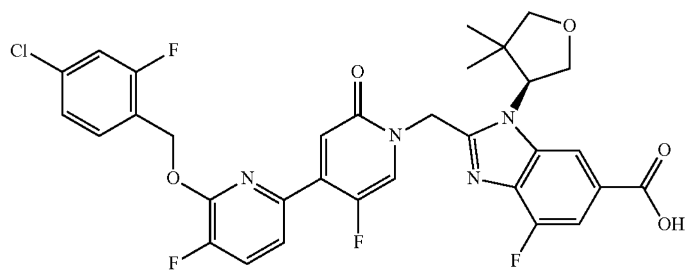 [SMILES: CC1(C)COC[C@H]1n1c(Cn2cc(F)c(-c3ccc(F)c(OCc4ccc(Cl)cc4F)n3)cc2=O)nc2c(F)cc(C(=O)O)cc21] | 35 | (M+) 657.0 | 1H NMR (400 MHz, DMSO-d6) δ 8.36 (s, 1H), 8.27 (d, J = 7.0 Hz, 1H), 7.90 (dd, J = 10.2, 8.2 Hz, 1H), 7.67-7.48 (m, 4H), 7.35 (dd, J = 8.3, 2.0 Hz, 1H), 6.98 (d, J = 7.6 Hz, 1H), 5.64-5.35 (m, 4H), 5.14 (d, J = 6.5 Hz, 1H), 4.54 (dd, J = 11.3 Hz, 1H), 4.43 (dd, J = 11.3, 6.7 Hz, 1H), 3.93-3.69 (m, 2H), 1.38 (s, 3H), 0.67 (s, 3H). |
| 132 | 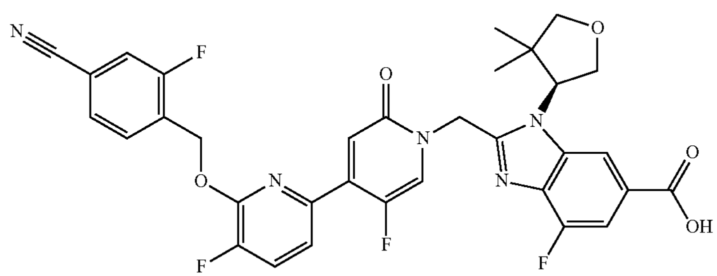 [SMILES: CC1(C)COC[C@H]1n1c(Cn2cc(F)c(-c3ccc(F)c(OCc4ccc(C#N)cc4F)n3)cc2=O)nc2c(F)cc(C(=O)O)cc21] | 35 | (M+) 648.0 | 1H NMR (400 MHz, DMSO-d6) δ 8.36 (s, 1H), 8.27 (d, J = 7.0 Hz, 1H), 8.03-7.85 (m, 2H), 7.85-7.69 (m, 2H), 7.62-7.57 (m, 1H), 7.55 (d, J = 11.2 Hz, 1H), 6.93 (d, J = 7.6 Hz, 1H), 5.68 (s, 2H), 5.14 (d, J = 6.6 Hz, 1H), 4.61-4.45 (m, 1H), 4.45-4.28 (m, 1H), 3.89-3.68 (m, 2H), 1.38 (s, 3H), 0.67 (s, 3H). |

TABLE 2-continued

Compounds

| Ex. | Structure | Procedure | ES/MS m/z | ¹H NMR |
|---|---|---|---|---|
| 133 | 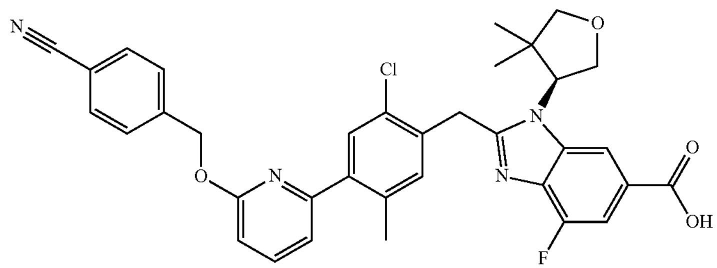 [SMILES: Cc1cc(Cc2nc3c(F)cc(C(=O)O)cc3n2[C@@H]2COCC2(C)C)c(Cl)cc1-c1cccc(OCc2ccc(C#N)cc2)n1] | 35 | (M+) 625.3 | 1H NMR (400 MHz, DMSO-d6) δ 8.36 (s, 1H), 7.92-7.82 (m, 3H), 7.64 (d, J = 8.0 Hz, 2H), 7.51 (d, J = 11.2 Hz, 1H), 7.43 (s, 1H), 7.33 (s, 1H), 7.25 (d, J = 7.3 Hz, 1H), 6.98 (d, J = 8.3 Hz, 1H), 5.51 (s, 2H), 5.02 (d, J = 6.6 Hz, 1H), 4.62-4.44 (m, 2H), 4.44-4.27 (m, 2H), 3.91-3.64 (m, 2H), 2.23 (s, 3H), 1.33 (s, 3H). |
| 134 | 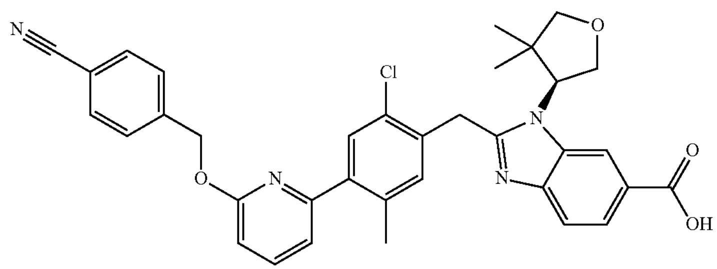 [SMILES: Cc1cc(Cc2nc3ccc(C(=O)O)cc3n2[C@@H]2COCC2(C)C)c(Cl)cc1-c1cccc(OCc2ccc(C#N)cc2)n1] | 35 | (M+) 607.5 | 1H NMR (400 MHz, DMSO-d6) δ 8.50 (s, 1H), 7.83 (m, 4H), 7.81 (dd, J = 8.5, 1.5 Hz, 1H), 7.63 (t, J = 8.2 Hz, 3H), 7.42 (s, 1H), 7.33 (s, 1H), 7.25 (d, J = 7.3 Hz, 1H), 6.98 (d, J = 8.2 Hz, 1H), 5.51 (s, 2H), 5.01 (d, J = 6.7 Hz, 1H), 4.66-4.46 (m, 2H), 4.46-4.27 (m, 2H), 2.23 (s, 3H), 1.33 (s, 3H), 0.65 (s, 3H). |
| 135 | 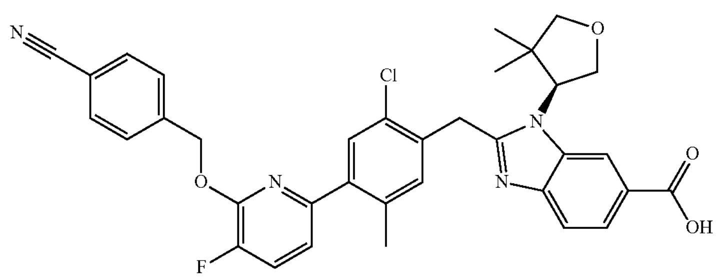 | 35 | (M+) 624.6 | 1H NMR (400 MHz, DMSO-d6) δ 8.49 (s, 1H), 8.01-7.83 (m, 2H), 7.83-7.73 (m, 1H), 7.66 (d, J = 8.1 Hz, 2H), 7.61 (d, J = 8.5 Hz, 1H), 7.43 (s, 1H), 7.34 (s, 1H), 7.29 (dd, J = 8.1, 2.8 Hz, 1H), 5.59 (s, 2H), 5.00 (d, J = 6.7 Hz, 1H), 4.61-4.48 (m, 2H), 4.48-4.27 (m, 2H), 3.80 (d, J = 8.6 Hz, 1H), 3.73 (d, J = 8.6 Hz, 1H), 2.23 (s, 2H), 1.33 (s, 3H), 0.65 (s, 3H). |

TABLE 2-continued

Compounds

| Ex. | Structure | Procedure | ES/MS m/z | ¹H NMR |
|---|---|---|---|---|
| 136 | 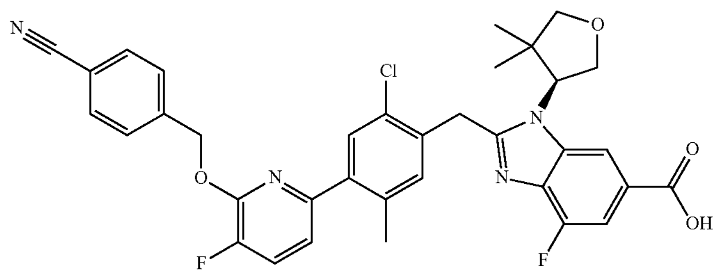 [SMILES: Cc1cc(Cc2nc3c(F)cc(C(=O)O)cc3n2[C@@H]2COCC2(C)C)c(Cl)cc1-c1ccc(F)c(OCc2ccc(C#N)cc2)n1] | 35 | (M+) 642.6 | 1H NMR (400 MHz, DMSO-d6) δ 8.36 (s, 1H), 7.95-7.78 (m, 3H), 7.66 (d, J = 8.1 Hz, 2H), 7.51 (d, J = 11.2 Hz, 1H), 7.43 (s, 1H), 7.34 (s, 1H), 7.29 (dd, J = 8.1, 2.8 Hz, 1H), 5.59 (s, 2H), 5.02 (d, J = 6.7 Hz, 1H), 4.64-4.45 (m, 2H), 4.45-4.26 (m, 2H), 3.88-3.69 (m, 2H), 2.23 (s, 3H), 1.33 (s, 4H), 0.65 (s, 3H). |
| 137 | 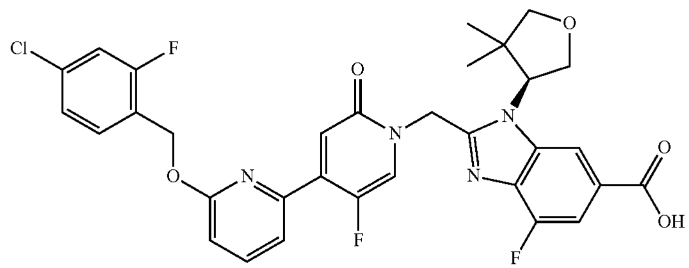 [SMILES: CC1(C)COC[C@H]1n1c(Cn2cc(F)c(-c3cccc(OCc4ccc(Cl)cc4F)n3)cc2=O)nc2c(F)cc(C(=O)O)cc21] | 35 | (M+) 638.6 | 1H NMR (400 MHz, DMSO-d6) δ 8.36 (s, 1H), 8.26 (d, J = 6.9 Hz, 1H), 7.99-7.88 (m, 1H), 7.61 (t, J = 8.2 Hz, 1H), 7.57-7.51 (m, 2H), 7.49 (dd, J = 10.0, 2.1 Hz, 1H), 7.33 (dd, J = 8.2, 2.0 Hz, 1H), 7.05 (d, J = 8.3 Hz, 1H), 7.00 (d, J = 7.5 Hz, 1H), 5.64-5.40 (m, 4H), 5.14 (d, J = 6.6 Hz, 1H), 4.54 (d, J = 11.3 Hz, 1H), 4.43 (dd, J = 11.3, 6.8 Hz, 1H), 3.79-3.67 (m, 2H), 1.38 (s, 3H), 0.67 (s, 3H). |
| 138 | 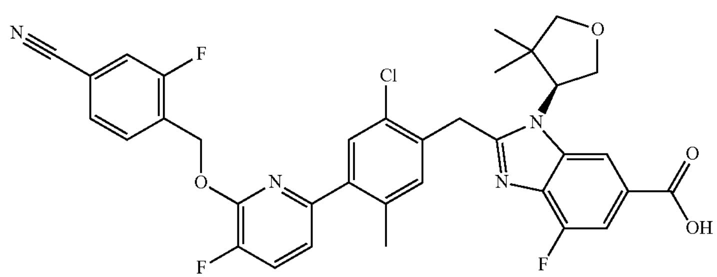 | 35 | (M+) 660.6 | 1H NMR (400 MHz, DMSO-d6) δ 8.36 (s, 1H), 7.97-7.89 (m, 1H), 7.85 (dd, J = 10.5, 8.1Hz, 1H), 7.74 (dd, J = 3.6, 1.9 Hz, 2H), 7.51 (dd, J = 11.3, 1.2 Hz, 1H), 7.45 (s, 1H), 7.38-7.29 (m, 2H), 5.62 (s, 2H), 5.01 (d, J = 6.7 Hz, 1H), 4.63-4.45 (m, 2H), 4.45-4.34 (m, 2H), 3.79 (d, J = 8.7 Hz, 1H), 3.72 (d, J = 8.6 Hz, 1H), 2.27 (s, 3H), 1.33 (s, 3H), 0.65 (s, 3H). |

TABLE 2-continued

Compounds

| Ex. | Structure | Procedure | ES/MS m/z | ¹H NMR |
|---|---|---|---|---|
| 139 | 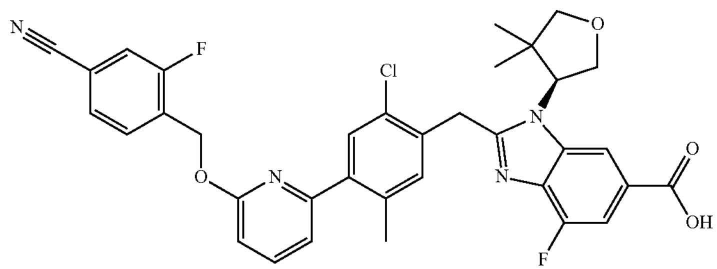 [SMILES: Cc1cc(Cc2nc3c(F)cc(C(=O)O)cc3n2[C@@H]2COCC2(C)C)c(Cl)cc1-c1cccc(OCc2ccc(C#N)cc2F)n1] | 35 | (M+) 642.6 | 1H NMR (400 MHz, DMSO-d6) δ 8.36 (s, 1H), 7.96-7.82 (m, 2H), 7.72 (d, J = 5.8 Hz, 2H), 7.53-7.48 (m, 1H), 7.44 (s, 1H), 7.34 (s, 1H), 7.28 (d, J = 7.3 Hz, 1H), 6.97 (d, J = 8.3 Hz, 1H), 5.53 (s, 2H), 5.01 (d, J = 6.7 Hz, 1H), 4.62-4.48 (m, 2H), 4.44-4.33 (m, 2H), 3.79 (d, J = 8.7 Hz, 1H), 3.72 (d, J = 8.7 Hz, 1H), 2.27 (s, 3H), 1.32 (s, 3H), 0.65 (s, 3H). |
| 140 | 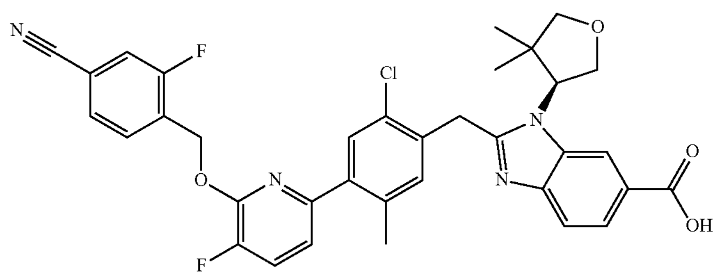 [SMILES: Cc1cc(Cc2nc3ccc(C(=O)O)cc3n2[C@@H]2COCC2(C)C)c(Cl)cc1-c1ccc(F)c(OCc2ccc(C#N)cc2F)n1] | 35 | (M+) 642.6 | 1H NMR (400 MHz, DMSO-d6) δ 8.50 (s, 1H), 7.96-7.90 (m, 1H), 7.90-7.79 (m, 2H), 7.74 (d, J = 5.6 Hz, 2H), 7.63 (d, J = 8.5 Hz, 1H), 7.45 (s, 1H), 7.35 (s, 1H), 7.31 (dd, J = 8.1, 2.8 Hz, 1H), 5.61 (s, 2H), 5.01 (d, J = 6.7 Hz, 1H), 4.64-4.46 (m, 2H), 4.46-4.26 (m, 2H), 3.74 (m, 2H), 2.26 (s, 3H), 1.33 (s, 3H), 0.65 (s, 3H). |
| 141 | 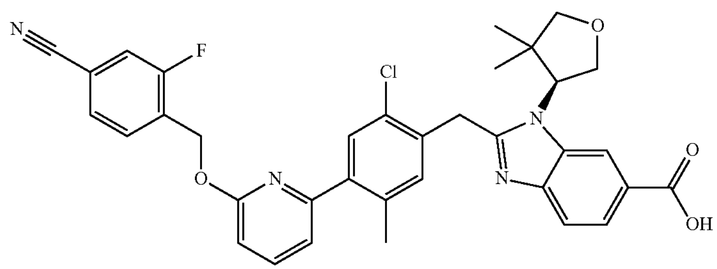 [SMILES: Cc1cc(Cc2nc3ccc(C(=O)O)cc3n2[C@@H]2COCC2(C)C)c(Cl)cc1-c1cccc(OCc2ccc(C#N)cc2F)n1] | 35 | (M+) 624.6 | 1H NMR (400 MHz, DMSO-d6) δ 8.50 (s, 1H), 7.96-7.85 (m, 2H), 7.81 (d, J = 8.6 Hz, 1H), 7.78-7.66 (m, 2H), 7.63 (d, J = 8.5 Hz, 1H), 7.44 (s, 1H), 7.35 (s, 1H), 7.27 (d, J = 7.3 Hz, 1H), 6.98 (d, J = 8.3 Hz, 1H), 5.53 (s, 2H), 5.01 (d, J = 6.7 Hz, 1H), 4.63-4.47 (m, 2H), 3.74 (m, 2H), 2.26 (s, 3H), 1.32 (s, 3H), 0.65 (s, 3H). |

TABLE 2-continued

Compounds

| Ex. | Structure | Procedure | ES/MS m/z | ¹H NMR |
|---|---|---|---|---|
| 142 | 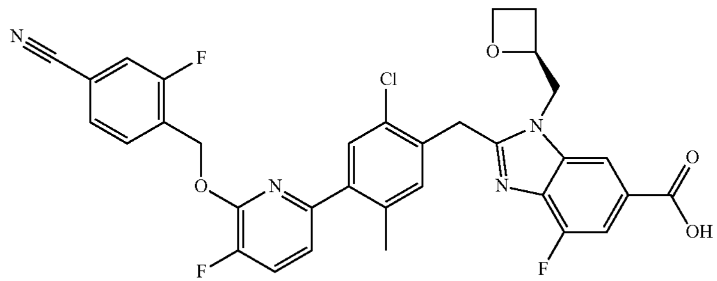 [SMILES: Cc1cc(Cc2nc3c(F)cc(C(=O)O)cc3n2C[C@@H]2CCO2)c(Cl)cc1-c1ccc(F)c(OCc2ccc(C#N)cc2F)n1] | 35 | (M+) 633.0 | 1H NMR (400 MHz, DMSO-d6) δ 13.14 (s, 1H), 8.36 (s, 1H), 8.26 (d, J = 6.9 Hz, 1H), 7.92 (t, J = 9.0 Hz, 2H), 7.80-7.67 (m, 2H), 7.62-7.48 (m, 2H), 7.10 (d, J = 8.3 Hz, 1H), 6.95 (d, J = 7.4 Hz, 1H), 5.69-5.30 (m, 4H), 5.14 (d, J = 6.7 Hz, 1H), 4.54 (d, J = 11.2 Hz, 1H), 4.43 (dd, J = 11.3, 6.7 Hz, 1H), 3.92-3.61 (m, 2H), 1.38 (s, 3H), 0.67 (s, 3H). |
| 143 | 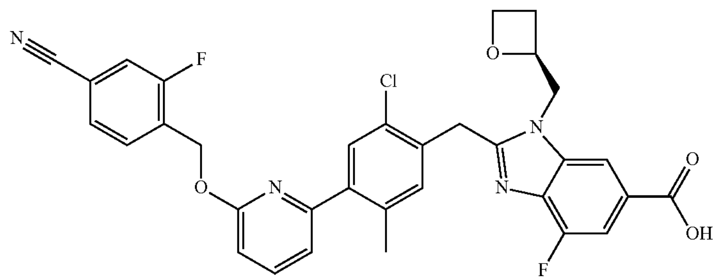 [SMILES: Cc1cc(Cc2nc3c(F)cc(C(=O)O)cc3n2C[C@@H]2CCO2)c(Cl)cc1-c1cccc(OCc2ccc(C#N)cc2F)n1] | 35 | (M+) 615.0 | 1H NMR (400 MHz, Methanol-d4) δ 8.16 (d, J = 1.3 Hz, 1H), 7.81 (dd, J = 8.3, 7.3 Hz, 1H), 7.72-7.60 (m, 2H), 7.60-7.49 (m, 2H), 7.41 (s, 1H), 7.19-7.10 (m, 2H), 6.91 (d, J = 8.3 Hz, 1H), 5.54 (s, 2H), 5.12 (dd, J = 7.4, 2.4 Hz, 1H), 4.76-4.59 (m, 3H), 4.59-4.35 (m, 3H), 2.77 (dtd, J = 11.4, 8.2, 6.1 Hz, 1H), 2.48 (ddt, J = 11.5, 9.1, 7.2 Hz, 1H), 2.24 (s, 3H). |
| 144 | 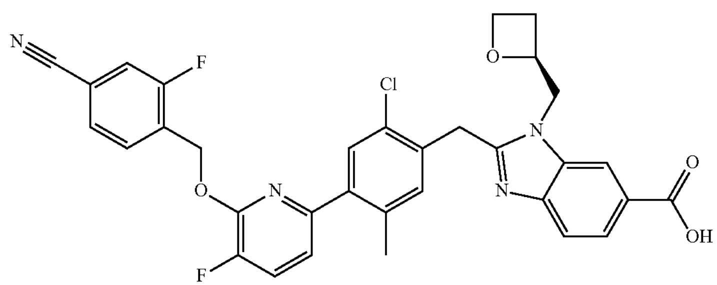 [SMILES: Cc1cc(Cc2nc3ccc(C(=O)O)cc3n2C[C@@H]2CCO2)c(Cl)cc1-c1ccc(F)c(OCc2ccc(C#N)cc2F)n1] | 35 | (M+) 615.0 | 1H NMR (400 MHz, Methanol-d4) δ 8.31 (d, J = 1.4 Hz, 1H), 7.98 (dd, J = 8.5, 1.5 Hz, 1H), 7.72 (t, J = 7.6 Hz, 1H), 7.68-7.64 (m, 1H), 7.64-7.55 (m, 3H), 7.42 (s, 1H), 7.19 (s, 1H), 7.15 (dd, J = 8.1, 2.8 Hz, 1H), 5.63 (s, 2H), 5.17 (qd, J = 7.1, 2.6 Hz, 1H), 4.76-4.39 (m, 6H), 2.95-2.66 (m, 1H), 2.50 (ddt, J = 11.5, 9.1, 7.2 Hz, 1H), 2.25 (s, 3H). |

TABLE 2-continued

Compounds

| Ex. | Structure | Procedure | ES/MS m/z | ¹H NMR |
|---|---|---|---|---|
| 145 | 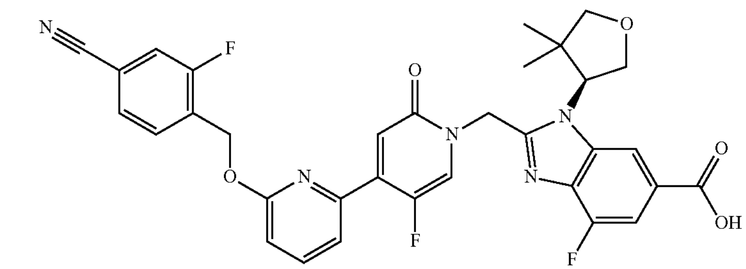 [SMILES: CC1(C)COC[C@H]1n1c(Cn2cc(F)c(-c3cccc(OCc4ccc(C#N)cc4F)n3)cc2=O)nc2c(F)cc(C(=O)O)cc21] | 35 | (MH+) 630.2 | 1H NMR (400 MHz, DMSO-d6) δ 13.14 (s, 1H), 8.36 (s, 1H), 8.26 (d, J = 6.9 Hz, 1H), 7.92 (t, J = 9.0 Hz, 2H), 7.80-7.67 (m, 2H), 7.62-7.48 (m, 2H), 7.10 (d, J = 8.3 Hz, 1H), 6.95 (d, J = 7.4 Hz, 1H), 5.69-5.30 (m, 4H), 5.14 (d, J = 6.7 Hz, 1H), 4.54 (d, J = 11.2 Hz, 1H), 4.43 (dd, J = 11.3, 6.7 Hz, 1H), 3.92-3.61 (m, 2H), 1.38 (s, 3H), 0.67 (s, 3H). |
| 146 | 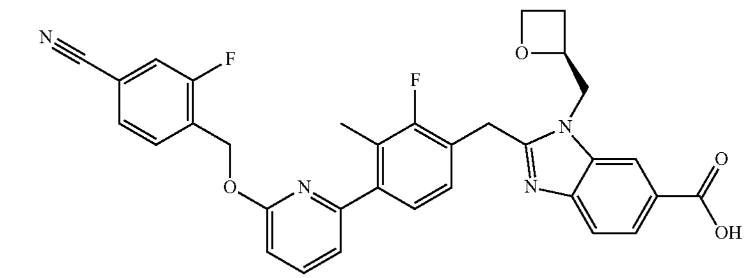 [SMILES: Cc1c(-c2cccc(OCc3ccc(C#N)cc3F)n2)ccc(Cc2nc3ccc(C(=O)O)cc3n2C[C@@H]2CCO2)c1F] | 35 | (M+) 581.2 | 1H NMR (400 MHz, Methanol-d4) δ 8.31 (d, J = 1.4 Hz, 1H), 7.98 (dd, J = 8.5, 1.5 Hz, 1H), 7.81 (dd, J = 8.3, 7.3 Hz, 1H), 7.73-7.63 (m, 2H), 7.63-7.51 (m, 2H), 7.21-7.09 (m, 3H), 6.91 (d, J = 8.2 Hz, 1H), 5.56 (s, 2H), 5.15 (qd, J = 7.1, 2.5 Hz, 1H), 4.70 (dd, J = 15.7, 7.0 Hz, 1H), 4.66-4.39 (m, 6H), 2.77 (dtd, J = 11.4, 8.2, 6.1 Hz, 1H), 2.56-2.38 (m, 1H), 2.22 (d, J = 2.6 Hz, 3H). |
| 147 | 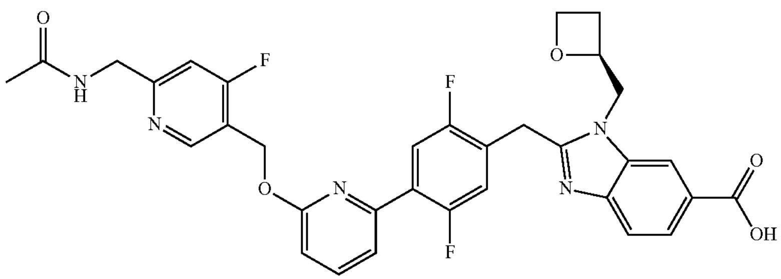 [SMILES: CC(=O)NCc1cc(F)c(COc2cccc(-c3cc(F)c(Cc4nc5ccc(C(=O)O)cc5n4C[C@@H]4CCO4)cc3F)n2)cn1] | 35 | (M + H+) 632.2 | 1H NMR (400 MHz, Methanol-d4) δ 8.67 (d, J = 9.6 Hz, 1H), 8.56 (s, OH), 8.32 (d, J = 1.4 Hz, 1H), 7.99 (dd, J = 8.5, 1.5 Hz, 1H), 7.88 (dd, J = 10.7, 6.3 Hz, 1H), 7.79 (t, J = 7.9 Hz, 1H), 7.68 (d, J = 8.5 Hz, 1H), 7.54 (dd, J = 7.6, 1.6 Hz, 1H), 7.20 (dd, J = 11.2, 6.0 Hz, 2H), 6.87 (d, J = 8.1 Hz, 1H), 5.61 (s, 2H), 5.21 (tt, J = 7.3, 3.6 Hz, 1H), 4.80-4.35 (m, 9H), 2.89-2.65 (m, 1H), 2.61-2.35 (m, 1H), 2.04 (s, 3H). |

TABLE 2-continued

Compounds

| Ex. | Structure | Procedure | ES/MS m/z | ¹H NMR |
|---|---|---|---|---|
| 148 | 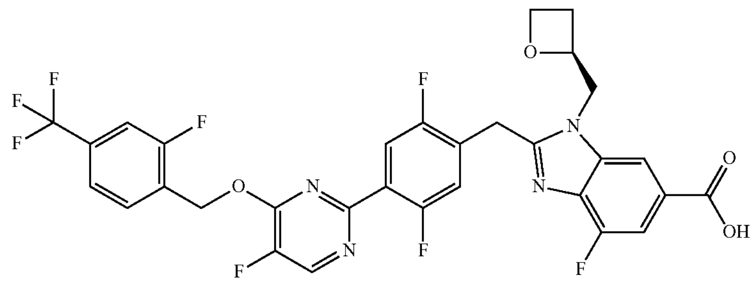 [SMILES: O=C(O)c1cc(F)c2nc(Cc3cc(F)c(-c4ncc(F)c(OCc5ccc(C(F)(F)F)cc5F)n4)cc3F)n(C[C@@H]3CCO3)c2c1] | 35 | (M + H+) 665.0 | 1H NMR (400 MHz, DMSO-d6) δ 8.84 (d, J = 2.8 Hz, 1H), 8.14 (s, 1H), 7.86 (dd, J = 9.6, 6.3 Hz, 2H), 7.81-7.73 (m, 1H), 7.72-7.63 (m, 1H), 7.50 (dd, J = 11.4, 1.2 Hz, 1H), 7.42 (dd, J = 11.1, 6.0 Hz, 1H), 5.77 (s, 2H), 5.18-4.94 (m, 1H), 4.78 (dd, J = 15.5, 7.1 Hz, 1H), 4.69-4.40 (m, 4H), 4.35 (dt, J = 8.9, 5.9 Hz, 1H), 2.70 (ddd, J = 16.1, 6.3, 2.8 Hz, 1H), 2.43-2.26 (m, 1H). |
| 149 | 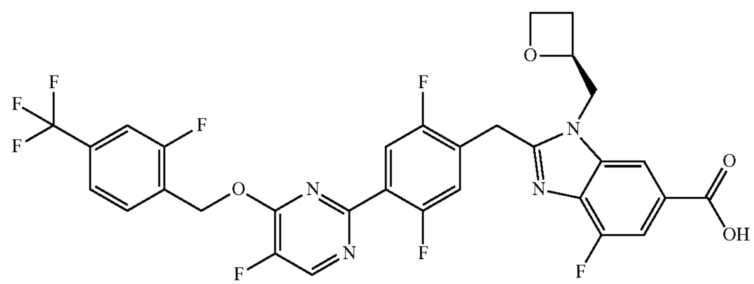 [SMILES: O=C(O)c1cc(F)c2nc(Cc3cc(F)c(-c4ncc(F)c(OCc5ccc(C(F)(F)F)cc5F)n4)cc3F)n(C[C@@H]3CCO3)c2c1] | 35 | (M + H+) 647.0 | 1H NMR (400 MHz, DMSO-d6) δ 8.73 (d, J = 5.8 Hz, 1H), 8.12 (s, 1H), 7.88 (dd, J = 10.2, 6.2 Hz, 1H), 7.83 (t, J = 7.6 Hz, 1H), 7.77 (dd, J = 9.9, 1.6 Hz, 1H), 7.65 (d, J = 8.0 Hz, 1H), 7.50 (dd, J = 11.5, 1.2 Hz, 1H), 7.41 (dd, J = 11.1, 6.0 Hz, 1H), 7.07 (d, J = 5.8 Hz, 1H), 5.68 (s, 2H), 5.07 (qd, J = 6.9, 2.8 Hz, 1H), 4.78 (dd, J = 15.6, 7.1 Hz, 1H), 4.70-4.42 (m, 4H), 4.35 (dt, J = 9.1, 6.0 Hz, 1H), 2.86-2.64 (m, 1H), 2.44-2.25 (m, 1H). |

TABLE 2-continued

Compounds

| Ex. | Structure | Procedure | ES/MS m/z | 1H NMR |
|---|---|---|---|---|
| 150 | 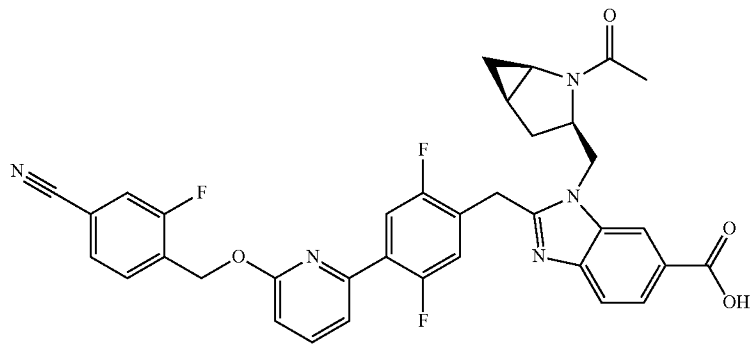 [SMILES: CC(=O)N1[C@@H](Cn2c(Cc3cc(F)c(-c4cccc(OCc5ccc(C#N)cc5F)n4)cc3F)nc3ccc(C(=O)O)cc32)C[C@H]2C[C@H]21] | 4 | (MH+) 652.2 | 1H NMR (400 MHz, DMSO-d6) δ 8.37 (s, 1H), 7.98-7.85 (m, 2H), 7.83 (dd, J = 8.4, 1.5 Hz, 1H), 7.75 (q, J = 5.4 Hz, 3H), 7.62 (d, J = 8.4 Hz, 1H), 7.53 (dd, J = 7.5, 1.7 Hz, 1H), 7.46 (dd, J = 11.5, 6.0 Hz, 1H), 7.00 (d, J = 8.2 Hz, 1H), 5.60 (s, 2H), 4.69 (s, 1H), 4.62-4.44 (m, 4H), 4.31 (dd, J = 14.4, 8.5 Hz, 1H), 2.26 (d, J = 14.1 Hz, 1H), 2.11 (s, 2H), 1.80 (dd, J = 15.7, 13.0 Hz, 1H), 1.65 (d, J = 7.0 Hz, 1H), 0.96-0.80 (m, 2H). |
| 151 | 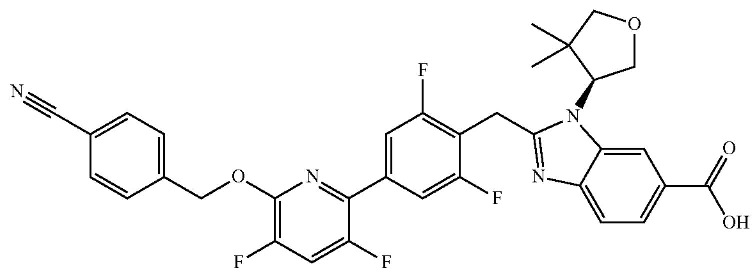 [SMILES: CC1(C)COC[C@H]1n1c(Cc2c(F)cc(-c3nc(OCc4ccc(C#N)cc4)c(F)cc3F)cc2F)nc2ccc(C(=O)O)cc21] | 35 | (M + H+) 631.2 | 1H NMR (400 MHz, DMSO-d6) δ 8.46 (s, 1H), 8.20 (t, J = 9.9 Hz, 1H), 7.89 (d, J = 8.2 Hz, 2H), 7.78-7.73 (m, 1H), 7.71 (d, J = 8.1 Hz, 2H), 7.61 (d, J = 8.4 Hz, 2H), 7.56 (d, J = 8.5 Hz, 1H), 5.67 (s, 2H), 5.08 (d, J = 6.6 Hz, 1H), 4.57 (d, J = 17.7 Hz, 2H), 4.46 (dd, J = 11.1, 6.6 Hz, 1H), 4.29 (d, J = 16.8 Hz, 1H), 3.80-3.71 (m, 2H), 1.37 (s, 3H), 0.64 (s, 3H). |
| 152 | 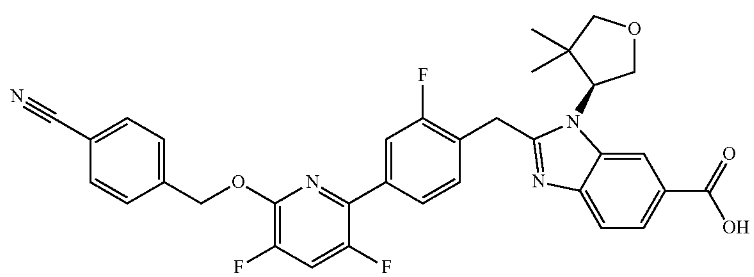 [SMILES: CC1(C)COC[C@H]1n1c(Cc2ccc(-c3nc(OCc4ccc(C#N)cc4)c(F)cc3F)cc2F)nc2ccc(C(=O)O)cc21] | 35 | (M + H+) 613.3 | 1H NMR (400 MHz, DMSO-d6) δ 8.49 (s, 1H), 8.15 (t, J = 9.9 Hz, 1H), 7.88 (d, J = 8.1 Hz, 2H), 7.81 (dd, J = 8.5, 1.4 Hz, 1H), 7.75-7.65 (m, 4H), 7.62 (d, J = 8.5 Hz, 1H), 7.53 (t, J = 8.0 Hz, 1H), 5.65 (s, 2H), 5.00 (d, J = 6.6 Hz, 1H), 4.57-4.48 (m, 2H), 4.48-4.36 (m, 2H), 3.78 (d, J = 8.6 Hz, 1H), 3.72 (d, J = 8.6 Hz, 1H), 1.30 (s, 3H), 0.58 (s, 3H). |

TABLE 2-continued

Compounds

| Ex. | Structure | Procedure | ES/MS m/z | ¹H NMR |
|---|---|---|---|---|
| 153 | 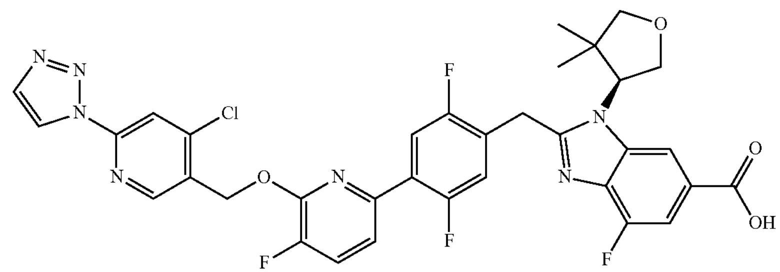 [SMILES: CC1(C)COC[C@H]1n1c(Cc2cc(F)c(-c3ccc(F)c(OCc4cnc(-n5ccnn5)cc4Cl)n3)cc2F)nc2c(F)cc(C(=O)O)cc21] | 35 | (M + H+) 708.0 | 1H NMR (400 MHz, DMSO-d6) δ 8.90 (d, J = 1.3 Hz, 1H), 8.84 (s, 1H), 8.35 (s, 1H), 8.32 (s, 1H), 8.03 (d, J = 1.3 Hz, 1H), 7.88 (ddd, J = 11.3, 7.4, 4.3 Hz, 2H), 7.64-7.55 (m, 1H), 7.55-7.44 (m, 2H), 5.76 (s, 2H), 5.03 (d, J = 6.5 Hz, 1H), 4.59-4.47 (m, 2H), 4.47-4.35 (m, 2H), 3.74 (q, J = 8.7 Hz, 2H), 1.33 (s, 3H), 0.60 (s, 3H). |
| 154 | 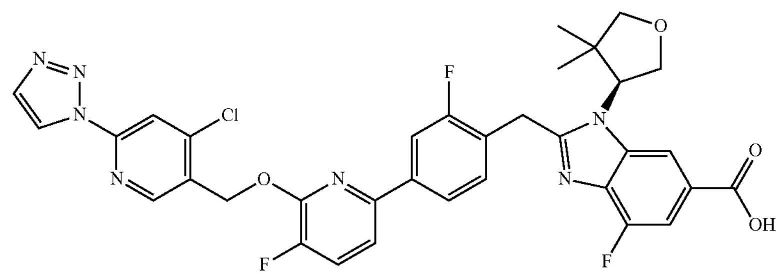 [SMILES: CC1(C)COC[C@H]1n1c(Cc2ccc(-c3ccc(F)c(OCc4cnc(-n5ccnn5)cc4Cl)n3)cc2F)nc2c(F)cc(C(=O)O)cc21] | 35 | (M + H+) 690.0 | 1H NMR (400 MHz, DMSO-d6) δ 8.89 (d, J = 1.3 Hz, 1H), 8.86 (s, 1H), 8.34 (s, 1H), 8.32 (s, 1H), 8.02 (d, J = 1.3 Hz, 1H), 7.99-7.91 (m, 2H),7.85 (dd, J = 10.2, 8.2 Hz, 1H), 7.73 (dd, J = 8.3, 2.8 Hz, 1H), 7.50 (dd, J = 9.7, 6.9 Hz, 2H), 5.78 (s, 2H), 5.00 (d, J = 6.7 Hz, 1H), 4.50 (dd, J = 14.1, 8.4 Hz, 2H), 4.46-4.34 (m, 2H), 3.79-3.66 (m, 2H), 1.29 (s, 3H), 0.57 (s, 3H). |
| 155 | 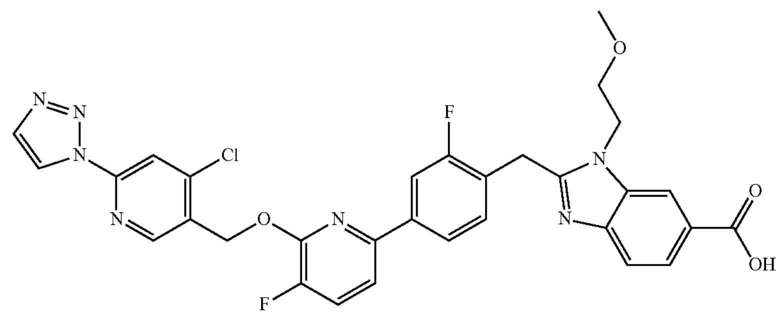 [SMILES: COCCn1c(Cc2ccc(-c3ccc(F)c(OCc4cnc(-n5ccnn5)cc4Cl)n3)cc2F)nc2ccc(C(=O)O)cc21] | 35 | (M + H+) 632.2 | 1H NMR (400 MHz, DMSO-d6) δ 8.90 (d, J = 1.3 Hz, 1H), 8.86 (s, 1H), 8.32 (s, 1H), 8.23 (s, 1H), 8.02 (d, J = 1.3 Hz, 1H), 7.97-7.88 (m, 2H), 7.88-7.79 (m, 2H), 7.72 (dd, J = 8.2, 2.7 Hz, 1H), 7.60 (d, J = 8.4 Hz, 1H), 7.45 (t, J = 8.0 Hz, 1H), 5.77 (s, 2H), 4.59 (s, 2H), 4.47 (t, J = 5.0 Hz, 2H), 3.66 (t, J = 5.0 Hz, 2H), 3.20 (s, 3H). |

TABLE 2-continued

Compounds

| Ex. | Structure | Procedure | ES/MS m/z | ¹H NMR |
|---|---|---|---|---|
| 156 | 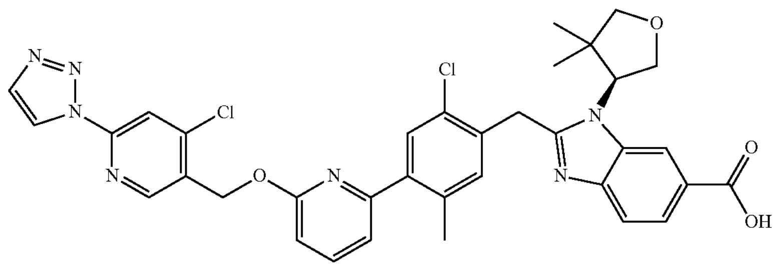 | 35 | (M + H+) 684.2 | 1H NMR (400 MHz, DMSO-d6) δ 8.89 (d, J = 1.3 Hz, 1H), 8.76 (s, 1H), 8.49 (s, 1H), 8.29 (s, 1H), 8.03 (d, J = 1.2 Hz, 1H), 7.89 (t, J = 7.8 Hz, 1H), 7.80 (dd, J = 8.5, 1.5 Hz, 1H), 7.62 (d, J = 8.5 Hz, 1H), 7.52 (s, 1H), 7.36 (s, 1H), 7.29 (d, J = 7.3 Hz, 1H), 6.98 (d, J = 8.3 Hz, 1H), 5.58 (s, 2H), 5.00 (d, J = 6.8 Hz, 1H), 4.61-4.48 (m, 2H), 4.46-4.33 (m, 2H), 3.84-3.69 (m, 2H), 2.33 (s, 3H), 1.32 (s, 3H), 0.64 (s, 3H). |
| 157 | 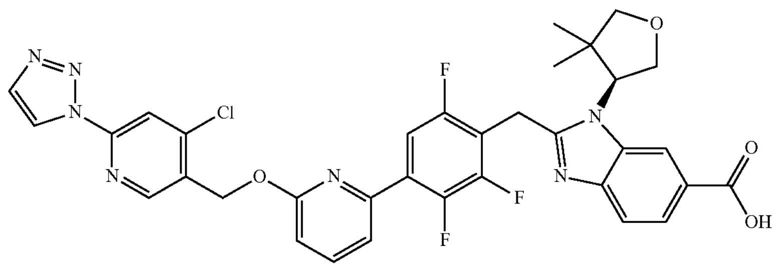 [SMILES: CC1(C)COC[C@H]1n1c(Cc2c(F)cc(-c3cccc(OCc4cnc(-n5ccnn5)cc4Cl)n3)c(F)c2F)nc2ccc(C(=O)O)cc21] | 35 | (M + H+) 690.1 | 1H NMR (400 MHz, DMSO-d6) δ 8.90 (s, 1H), 8.83 (s, 1H), 8.47 (s, 1H), 8.31 (s, 1H), 8.03 (d, J = 1.3 Hz, 1H), 7.96 (t, J = 7.9 Hz, 1H), 7.77 (d, J = 8.2 Hz, 1H), 7.60 (dd, J = 10.7, 7.7 Hz, 2H), 7.06 (d, J = 8.3 Hz, 1H), 5.68 (s, 2H), 5.08 (d, J = 6.5 Hz, 1H), 4.68-4.53 (m, 2H), 4.46 (dd, J = 11.3, 6.9 Hz, 1H), 4.35 (d, J = 17.2 Hz, 1H), 3.76 (d, J = 2.8 Hz, 2H), 1.38 (s, 3H), 0.65 (s, 3H). |
| 158 | 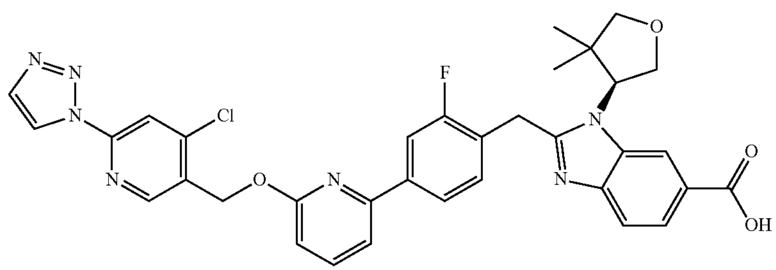 [SMILES: CC1(C)COC[C@H]1n1c(Cc2ccc(-c3cccc(OCc4cnc(-n5ccnn5)cc4Cl)n3)cc2F)nc2ccc(C(=O)O)cc21] | 35 | (M + H+) 654.2 | 1H NMR (400 MHz, DMSO-d6) δ 8.89 (d, J = 1.3 Hz, 1H), 8.83 (s, 1H), 8.47 (s, 1H), 8.30 (s, 1H), 8.02 (d, J = 1.3 Hz, 1H), 8.00-7.93 (m, 2H), 7.88 (t, J = 7.9 Hz, 1H), 7.80 (dd, J = 8.4, 1.5 Hz, 1H), 7.70 (d, J = 7.5 Hz, 1H), 7.61 (d, J = 8.5 Hz, 1H), 7.50 (t, J = 8.1 Hz, 1H), 6.95 (d, J = 8.2 Hz, 1H), 5.69 (s, 2H), 4.98 (d, J = 6.8 Hz, 1H), 4.54-4.47 (m, 2H), 4.47-4.35 (m, 2H), 3.81-3.68 (m, 2H), 1.29 (s, 3H), 0.57 (s, 3H). |

TABLE 2-continued

Compounds

| Ex. | Structure | Procedure | ES/MS m/z | ¹H NMR |
|---|---|---|---|---|
| 159 | 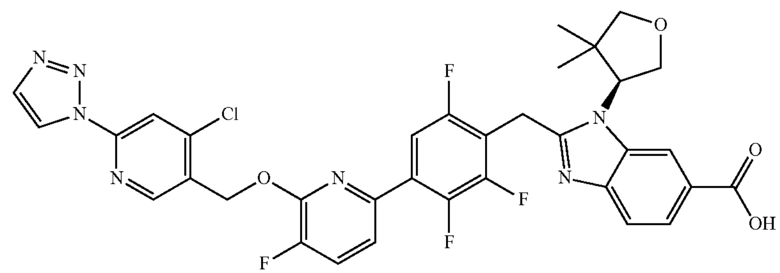 [SMILES: CC1(C)COC[C@H]1n1c(Cc2c(F)cc(-c3ccc(F)c(OCc4cnc(-n5ccnn5)cc4Cl)n3)c(F)c2F)nc2ccc(C(=O)O)cc21] | 35 | (M + H+) 708.1 | 1H NMR (400 MHz, DMSO-d6) δ 8.91 (d, J = 1.3 Hz, 1H), 8.85 (s, 1H), 8.47 (s, 1H), 8.33 (s, 1H), 8.03 (d, J = 1.2 Hz, 1H), 7.99-7.87 (m, 1H), 7.77 (d, J = 8.6 Hz, 2H), 7.64 (d, J = 8.4 Hz, 1H), 7.58 (d, J = 8.4 Hz, 1H), 5.77 (s, 2H), 5.08 (d, J = 6.7 Hz, 1H), 4.64 (d, J = 17.5 Hz, 1H), 4.57 (d, J = 11.3 Hz, 1H), 4.51 -4.42 (m, 1H), 4.35 (d, J = 17.6 Hz, 1H), 3.76 (d, J = 2.5 Hz, 2H), 1.38 (s, 3H), 0.65 (s, 3H). |
| 160 | 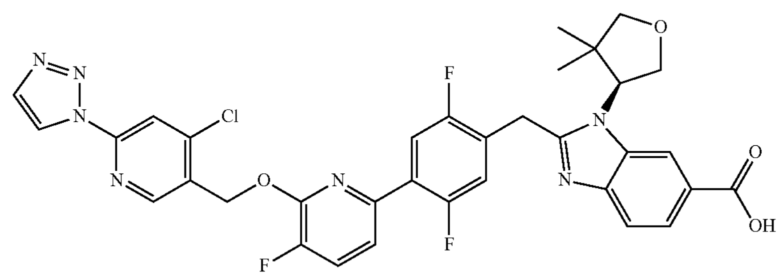 [SMILES: CC1(C)COC[C@H]1n1c(Cc2cc(F)c(-c3ccc(F)c(OCc4cnc(-n5ccnn5)cc4Cl)n3)cc2F)nc2ccc(C(=O)O)cc21] | 35 | (M + H+) 690.1 | 1H NMR (400 MHz, DMSO-d6) δ 8.90 (d, J = 1.3 Hz, 1H), 8.84 (s, 1H), 8.47 (s, 1H), 8.32 (s, 1H), 8.03 (d, J = 1.2 Hz, 1H), 7.87 (td, J = 9.7, 9.1, 7.4 Hz, 2H), 7.82-7.75 (m, 1H), 7.60 (t, J = 9.5 Hz, 2H), 7.47 (dd, J = 11.6, 6.1 Hz, 1H), 5.76 (s, 2H), 5.01 (d, J = 6.8 Hz, 1H), 4.58-4.47 (m, 2H), 4.48-4.32 (m, 2H), 3.80-3.68 (m, 2H), 1.33 (s, 3H), 0.60 (s, 3H). |
| 161 | 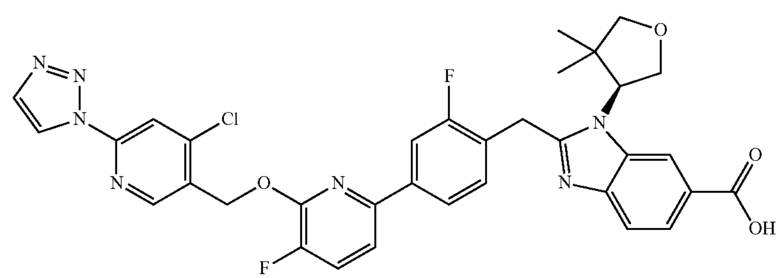 | 35 | (M + H+) 672.2 | 1H NMR (400 MHz, DMSO-d6) δ 8.90 (d, J = 1.3 Hz, 1H), 8.86 (s, 1H), 8.48 (s, 1H), 8.32 (s, 1H), 8.02 (d, J = 1.3 Hz, 1H), 7.94 (t, J = 8.5 Hz, 2H), 7.85 (dd, J = 10.2, 8.3 Hz, 1H), 7.82-7.77 (m, 1H), 7.73 (dd, J = 8.3, 2.7 Hz, 1H), 7.61 (d, J = 8.4 Hz, 1H), 7.50 (t, J = 8.1 Hz, 1H), 5.78 (s, 2H), 4.99 (d, J = 6.6 Hz, 1H), 4.54-4.47 (m, 2H), 4.46-4.35 (m, 2H), 3.81-3.69 (m, 2H), 1.29 (s, 3H), 0.57 (s, 3H). |

TABLE 2-continued

Compounds

| Ex. | Structure | Procedure | ES/MS m/z | 1H NMR |
|---|---|---|---|---|
| 162 | 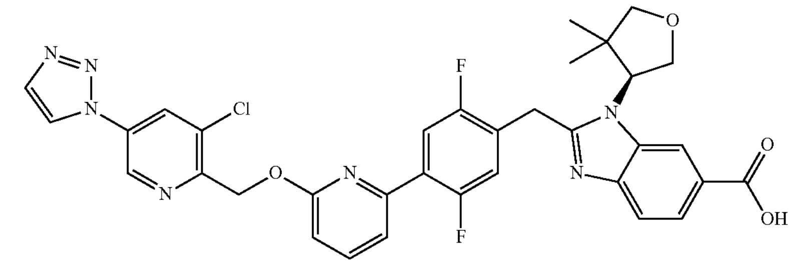 [SMILES: CC1(C)COC[C@H]1n1c(Cc2cc(F)c(-c3cccc(OCc4ncc(-n5ccnn5)cc4Cl)n3)cc2F)nc2ccc(C(=O)O)cc21] | 35 | (M + H+) 672.2 | 1H NMR (400 MHz, DMSO-d6) δ 9.12 (d, J = 2.2 Hz, 1H), 8.95 (d, J = 1.2 Hz, 1H), 8.62 (s, 1H), 8.04 (d, J = 1.2 Hz, 1H), 7.89 (dd, J = 7.9 Hz, 1H), 7.79 (dd, J = 8.5, 1.4 Hz, 1H), 7.73 (dd, J = 10.6, 6.4 Hz, 1H), 7.60 (d, J = 8.4 Hz, 1H), 7.53 (d, J = 7.3 Hz, 1H), 7.42 (dd, J = 11.5, 6.0 Hz, 1H), 7.01 (d, J = 8.3 Hz, 1H), 5.73 (s, 2H), 5.02-4.95 (m, 1H), 4.56-4.45 (m, 2H), 4.46-4.30 (m, 2H), 3.82-3.67 (m, 2H), 1.30 (s, 3H), 0.58 (s, 3H). |
| 163 | 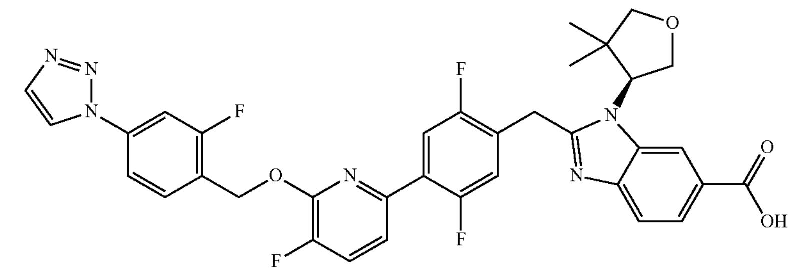 | 35 | (M + H+) 673.2 | 1H NMR (400 MHz, DMSO-d6) δ 8.89 (d, J = 1.2 Hz, 1H), 8.48 (s, 1H), 8.00 (d, J = 1.1 Hz, 1H), 7.95 (dd, J = 10.8, 2.0 Hz, 1H), 7.88-7.83 (m, 3H), 7.91-7.76 (m, 2H), 7.61 (d, J = 8.5 Hz, 1H), 7.59-7.53 (m, 1H), 7.46 (dd, J = 11.4, 6.1Hz, 1H), 5.68 (s, 2H), 5.01 (d, J = 6.8 Hz, 1H), 4.57-4.48 (m, 2H), 4.48-4.30 (m, 2H), 3.82-3.69 (m, 2H), 1.33 (s, 3H), 0.60 (s, 3H). |
| 164 | 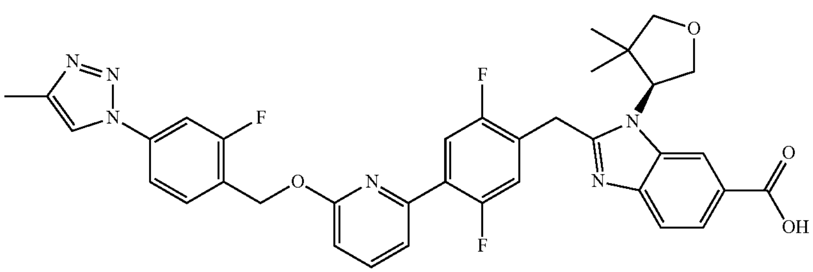 [SMILES: Cc1cn(-c2ccc(COc3cccc(-c4cc(F)c(Cc5nc6ccc(C(=O)O)cc6n5[C@@H]5COCC5(C)C)cc4F)n3)c(F)c2)nn1] | 35 | (M + H+) 669.2 | 1H NMR (400 MHz, DMSO-d6) δ 8.60 (s, 1H), 8.48 (s, 1H), 7.92-7.81 (m, 3H), 7.81-7.75 (m, 3H), 7.61 (d, J = 8.4 Hz, 1H), 7.57-7.51 (m, 1H), 7.45 (dd, J = 11.3, 6.2 Hz, 1H), 6.98 (s, 2H), 5.58 (s, 2H), 5.01 (d, J = 6.7 Hz, 1H), 4.59-4.48 (m, 2H), 4.50-4.34 (m, 2H), 3.83-3.70 (m, 2H), 2.33 (s, 3H), 1.33 (s, 3H), 0.60 (s, 3H). |

TABLE 2-continued

Compounds

| Ex. | Structure | Procedure | ES/MS m/z | ¹H NMR |
|---|---|---|---|---|
| 165 | 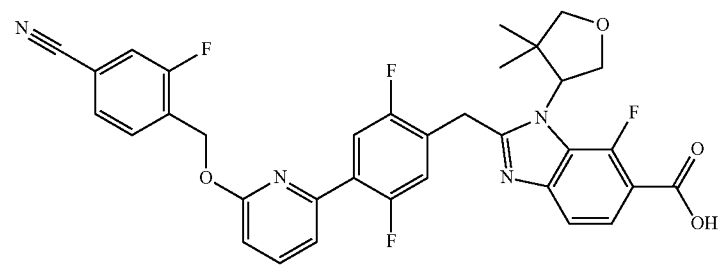 [SMILES: CC1(C)COCC1n1c(Cc2cc(F)c(-c3cccc(OCc4ccc(C#N)cc4F)n3)cc2F)nc2ccc(C(=O)O)c(F)c21] | 35 | (M + H+) 631.1 | 1H NMR (400 MHz, DMSO-d6) δ 7.94-7.86 (m, 2H), 7.80-7.71 (m, 3H), 7.66 (d, J = 7.7 Hz, 1H), 7.54 (d, J = 7.4 Hz, 1H), 7.41 (p, J = 11.0,9.8 Hz, 2H), 6.99 (d, J = 8.2 Hz, 1H), 5.60 (s, 2H), 5.22 (d, J = 112.0 Hz, 1H), 4.54 (d, J = 24.0 Hz, 2H), 4.47-4.14 (m, 2H), 3.94-3.58 (m, 2H), 1.29 (d, J = 21.9 Hz, 3H), 0.72 (d, J = 14.3 Hz, 3H). |
| 166 | 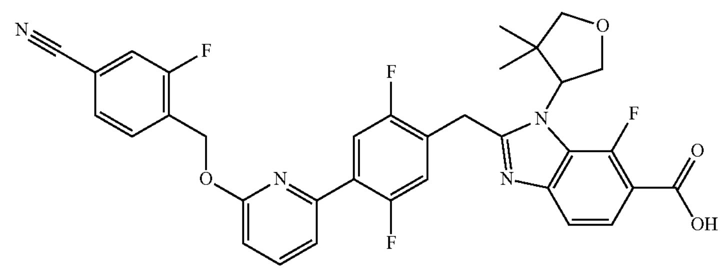 [SMILES: CC1(C)COCC1n1c(Cc2cc(F)c(-c3cccc(OCc4ccc(C#N)cc4F)n3)cc2F)nc2ccc(C(=O)O)c(F)c21] | 35 | (M + H+) 631.2 | 1H NMR (400 MHz, DMSO-d6) δ 7.95-7.86 (m, 2H), 7.79-7.71 (m, 3H), 7.66 (t, J = 7.6 Hz, 1H), 7.54 (d, J = 7.3 Hz, 1H), 7.43 (q, J = 10.6, 7.8 Hz, 2H), 6.99 (d, J = 8.3 Hz, 2H), 5.60 (s, 2H), 5.22 (d, J = 111.9 Hz, 1H), 4.54 (d, J = 24.1 Hz, 2H), 4.37 (d, J = 18.0 Hz, 1H), 3.92-3.67 (m, 1H), 1.29 (d, J = 21.9 Hz, 3H), 0.72 (d, J = 14.2 Hz, 3H). |
| 167 | 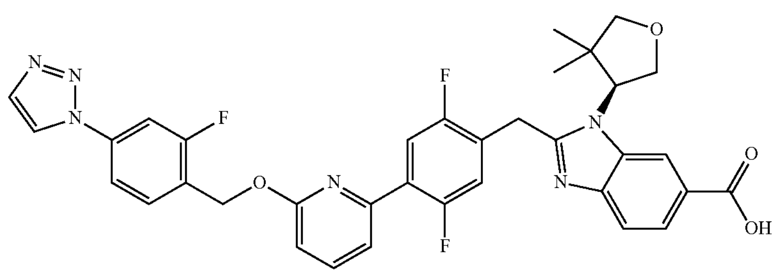 [SMILES: CC1(C)COC[C@H]1n1c(Cc2cc(F)c(-c3cccc(OCc4ccc(-n5ccnn5)cc4F)n3)cc2F)nc2ccc(C(=O)O)cc21] | 35 | (M + H+) 655.2 | 1H NMR (400 MHz, DMSO-d6) δ 8.89 (s, 1H), 8.48 (s, 1H), 8.00 (s, 1H), 7.95-7.87 (m, 3H), 7.87-7.81 (m, 2H), 7.79 (dd, J = 8.3, 1.7 Hz, 2H), 7.61 (d, J = 8.5 Hz, 1H), 7.54 (d, J = 7.3 Hz, 1H), 7.46 (dd, J = 11.3, 6.1 Hz, 1H), 6.98 (d, J = 8.3 Hz, 1H), 5.59 (s, 2H), 5.01 (d, J = 6.7 Hz, 1H), 4.58-4.47 (m, 2H), 4.47-4.28 (m, 2H), 3.81-3.63 (m, 2H), 1.33 (s, 3H), 0.60 (s, 3H). |

TABLE 2-continued

Compounds

| Ex. | Structure | Procedure | ES/MS m/z | ¹H NMR |
|---|---|---|---|---|
| 168 | 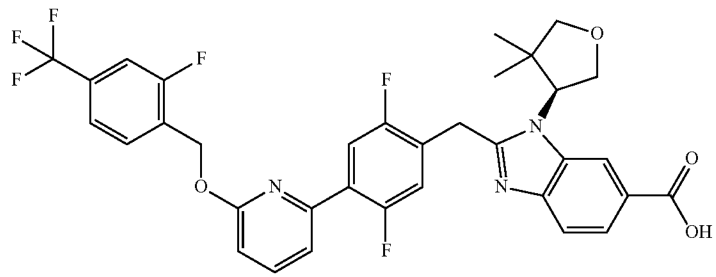 [SMILES: CC1(C)COC[C@H]1n1c(Cc2cc(F)c(-c3cccc(OCc4ccc(C(F)(F)F)cc4F)n3)cc2F)nc2ccc(C(=O)O)cc21] | 35 | (M + H+) 656.2 | 1H NMR (400 MHz, DMSO-d6) δ 8.47 (s, 1H), 7.90 (t, J = 7.9 Hz, 1H), 7.83-7.70 (m, 4H), 7.62 (t, J = 7.8 Hz, 2H), 7.54 (d, J = 7.3 Hz, 1H), 7.44 (dd, J = 11.3, 6.1 Hz, 1H), 6.99 (d, J = 8.3 Hz, 1H), 5.61 (s, 2H), 5.00 (d, J = 6.6 Hz, 1H), 4.57-4.47 (m, 2H), 4.43 (dd, J = 11.1, 6.8 Hz, 1H), 4.36 (d, J = 17.0 Hz, 1H), 3.83-3.69 (m, 2H), 1.32 (s, 3H), 0.59 (s, 3H). |
| 169 | 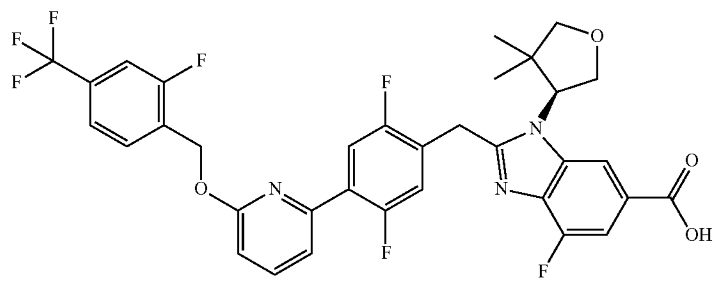 [SMILES: CC1(C)COC[C@H]1n1c(Cc2cc(F)c(-c3cccc(OCc4ccc(C(F)(F)F)cc4F)n3)cc2F)nc2c(F)cc(C(=O)O)cc21] | 35 | (M + H+) 674.1 | 1H NMR (400 MHz, DMSO-d6) δ 8.35 (s, 1H), 7.90 (t, J = 7.8 Hz, 1H), 7.81-7.71 (m, 3H), 7.62 (d, J = 8.0 Hz, 1H), 7.53 (dd, J = 12.7, 9.2 Hz, 2H), 7.45 (dd, J = 11.4, 6.1 Hz, 1H), 6.99 (d, J = 8.3 Hz, 1H), 5.61 (s, 2H), 5.02 (d, J = 6.6 Hz, 1H), 4.59-4.47 (m, 2H), 4.47-4.34 (m, 2H), 3.74 (q, J = 8.7 Hz, 2H), 1.33 (s, 3H), 0.60 (s, 3H). |
| 170 | 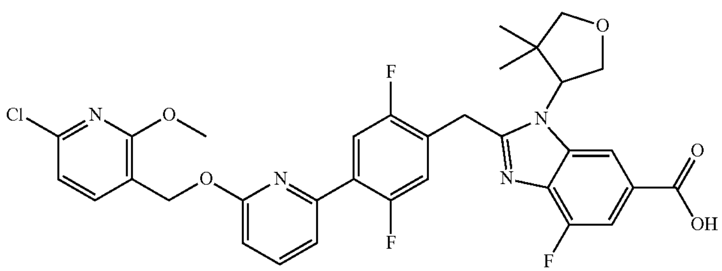 [SMILES: COc1nc(Cl)ccc1COc1cccc(-c2cc(F)c(Cc3nc4c(F)cc(C(=O)O)cc4n3C3COCC3(C)C)cc2F)n1] | 35 | (M + H+) 653.2 | 1H NMR (400 MHz, DMSO-d6) δ 8.35 (s, 1H), 7.92-7.81 (m, 2H), 7.79 (dd, J = 10.3, 6.5 Hz, 1H), 7.56-7.49 (m, 2H), 7.46 (dd, J = 11.3, 6.2 Hz, 1H), 7.12 (d, J = 7.7 Hz, 1H), 6.96 (d, J = 8.2 Hz, 1H), 5.41 (s, 2H), 5.02 (d, J = 6.6 Hz, 1H), 4.60-4.47 (m, 2H), 4.47-4.33 (m, 2H), 3.93 (s, 3H), 3.74 (q, J = 8.7 Hz, 2H), 3.10 (qd, J = 7.3, 4.8 Hz, 1H), 1.33 (s, 3H), 0.60 (s, 3H). |

TABLE 2-continued

Compounds

| Ex. | Structure | Procedure | ES/MS m/z | ¹H NMR |
|---|---|---|---|---|
| 171 | 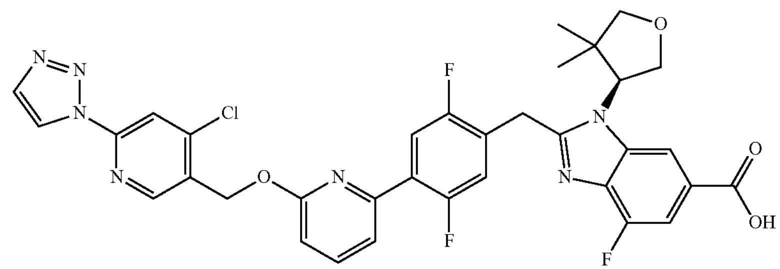 [SMILES: CC1(C)COC[C@H]1n1c(Cc2cc(F)c(-c3cccc(OCc4cnc(-n5ccnn5)cc4Cl)n3)cc2F)nc2c(F)cc(C(=O)O)cc21] | 35 | (M + H+) 690.1 | 1H NMR (400 MHz, DMSO-d6) δ 8.89 (d, J = 1.4 Hz, 1H), 8.82 (s, 1H), 8.35 (s, 1H), 8.30 (s, 1H), 8.02 (d, J = 1.4 Hz, 1H), 7.92 (d, J = 7.7 Hz, 1H), 7.90-7.86 (m, 1H), 7.57 (dd, J = 7.6, 1.5 Hz, 1H), 7.51 (d, J = 11.4 Hz, 1H), 7.47 (dd, J = 11.4, 6.4 Hz, 1H), 7.00 (d, J = 8.2 Hz, 1H), 5.67 (s, 2H), 5.03 (d, J = 6.6 Hz, 1H), 4.58-4.47 (m, 2H), 4.47-4.31 (m, 2H), 3.74 (q, J = 8.7 Hz, 2H), 1.33 (s, 3H), 0.60 (s, 3H). |
| 172 | 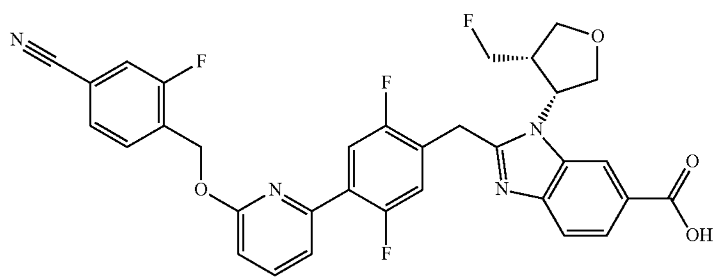 [SMILES: N#Cc1ccc(COc2cccc(-c3cc(F)c(Cc4nc5ccc(C(=O)O)cc5n4[C@H]4COC[C@H]4CF)cc3F)n2)c(F)c1] | 36 | (M + H+) 617.3 | 1H NMR (400 MHz, DMSO-d6) δ 8.53 (s, 1H), 7.94-7.90 (m, 1H), 7.89 (d, J = 8.0 Hz, 1H), 7.81 (dd, J = 8.4, 1.5 Hz, 1H), 7.79-7.70 (m, 3H), 7.62 (d, J = 8.4 Hz, 1H), 7.53 (dd, J = 7.5, 1.7 Hz, 1H), 7.39 (dd, J = 11.4, 6.1 Hz, 1H), 6.99 (d, J = 8.3 Hz, 1H), 5.61 (d, J = 9.4 Hz, 3H), 4.56 (s, 1H), 4.52 (s, 1H), 4.42 (d, J = 17.0 Hz, 1H), 4.34-4.10 (m, 2H), 4.06 (td, J = 9.0, 1.7 Hz, 1H), 3.97-3.77 (m, 2H), 3.31 (dq, J = 15.6, 7.6 Hz, 1H). |
| 173 | 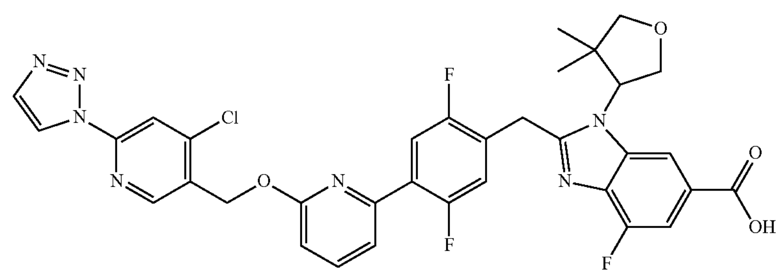 [SMILES: CC1(C)COCC1n1c(Cc2cc(F)c(-c3cccc(OCc4cnc(-n5ccnn5)cc4Cl)n3)cc2F)nc2c(F)cc(C(=O)O)cc21] | 35 | (M + H+) 690.0 | 1H NMR (400 MHz, DMSO-d6) δ 8.89 (d, J = 1.3 Hz, 1H), 8.82 (s, 1H), 8.35 (s, 1H), 8.30 (s, 1H), 8.02 (d, J = 1.2 Hz, 1H), 7.94-7.91 (m, 1H), 7.90-7.87 (m, 1H), 7.57 (dd, J = 7.6, 1.6 Hz, 1H), 7.52 (dd, J = 11.2, 1.2 Hz, 1H), 7.47 (dd, J = 11.4, 6.5 Hz, 1H), 7.01 (d, J = 8.3 Hz, 1H), 5.67 (s, 2H), 5.03 (d, J = 6.6 Hz, 1H), 4.53 (dd, J = 14.2, 11.9 Hz, 2H), 4.47-4.35 (m, |

TABLE 2-continued

Compounds

| Ex. | Structure | Procedure | ES/MS m/z | ¹H NMR |
|---|---|---|---|---|
| | | | | 2H), 3.74 (q, J = 8.7 Hz, 2H), 1.33 (s, 3H), 0.60 (s, 3H). |
| 174 | 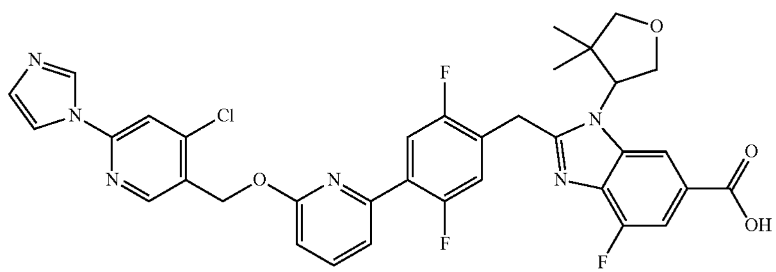 [SMILES: CC1(C)COCC1n1c(Cc2cc(F)c(-c3cccc(OCc4cnc(-n5ccnc5)cc4Cl)n3)cc2F)nc2c(F)cc(C(=O)O)cc21] | 35 | (M + H+) 689.4 | 1H NMR (400 MHz, DMSO-d6) δ 9.33 (s, 1H), 8.78 (s, 1H), 8.35 (s, 1H), 8.30 (s, 1H), 8.27 (t, J = 1.6 Hz, 1H), 7.92 (d, J = 7.9 Hz, 1H), 7.89 (t, J = 3.3 Hz, 1H), 7.57 (dt, J = 4.4, 1.7 Hz, 2H), 7.52 (dd, J = 11.2, 1.2 Hz, 1H), 7.49-7.43 (m, 1H), 6.99 (d, J = 8.3 Hz, 1H), 5.66 (s, 2H), 5.03 (d, J = 6.5 Hz, 1H), 4.59-4.49 (m, 2H), 4.47-4.35 (m, 2H), 3.74 (q, J = 8.7 Hz, 2H), 1.33 (s, 3H), 0.61 (s, 3H). |
| 175 | 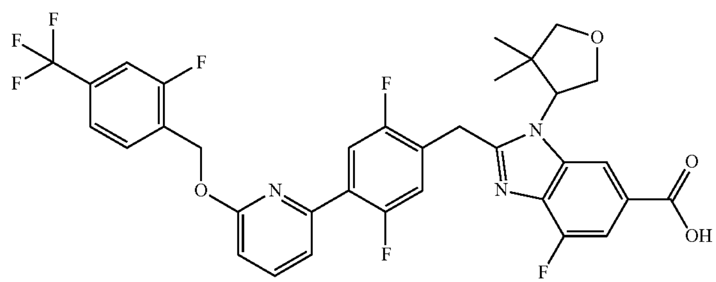 | 35 | (M + H+) 674.1 | 1H NMR (400 MHz, DMSO-d6) δ 8.35 (s, 1H), 7.90 (t, J = 7.9 Hz, 1H), 7.83-7.77 (m, 2H), 7.74 (dd, J = 10.4, 1.9 Hz, 1H), 7.64-7.60 (m, 1H), 7.57-7.49 (m, 2H), 7.46 (dd, J = 11.4, 6.1 Hz, 1H), 6.99 (d, J = 8.2 Hz, 1H), 5.61 (s, 2H), 5.02 (d, J = 6.6 Hz, 1H), 4.61-4.47 (m, 2H), 4.47-4.34 (m, 2H), 3.74 (q, J = 8.7 Hz, 2H), 1.33 (s, 3H), 0.60 (s, 3H). |

TABLE 2-continued

Compounds

| Ex. | Structure | Procedure | ES/MS m/z | ¹H NMR |
|---|---|---|---|---|
| 176 A | 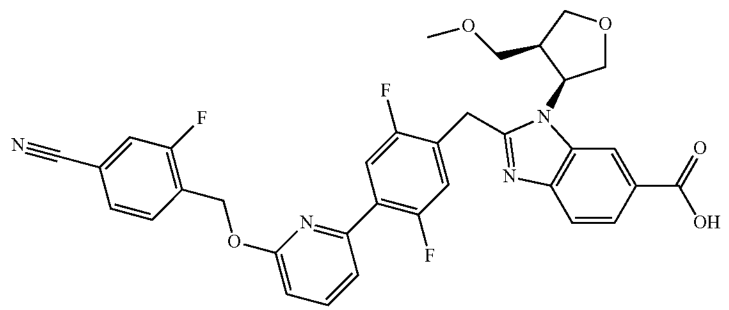 [SMILES: COC[C@H]1COC[C@H]1n1c(Cc2cc(F)c(-c3cccc(OCc4ccc(C#N)cc4F)n3)cc2F)nc2ccc(C(=O)O)cc21] | 22 | 629.0 | 1H NMR (400 MHz, DMSO) δ 8.45 (s, 1H), 7.96-7.86 (m, 4H), 7.80-7.71 (m, 2H), 7.53 (d, J = 8.2 Hz, 2H), 7.35 (dd, J = 11.0, 5.7 Hz, 1H), 7.00 (d, J = 8.3 Hz, 1H), 5.61 (s, 2H), 5.48 (s, 1H), 4.49 (d, J = 11.9 Hz, 2H), 4.42 (d, J = 17.2 Hz, 1H), 4.21 (dd, J = 10.8, 6.8 Hz, 1H), 4.16-4.03 (m, 1H), 3.78 (s, 1H), 3.09 (s, 2H), 3.07-2.99 (m, 1H), 2.92 (s, 3H), 2.59 (s, 1H). |
| 176 B | 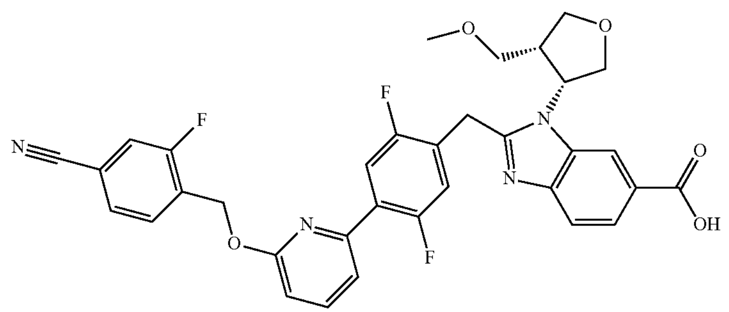 [SMILES: COC[C@@H]1COC[C@@H]1n1c(Cc2cc(F)c(-c3cccc(OCc4ccc(C#N)cc4F)n3)cc2F)nc2ccc(C(=O)O)cc21] | 22 | 629.0 | 1H NMR (400 MHz, DMSO) δ 8.51 (s, 1H), 7.96-7.86 (m, 2H), 7.82-7.71 (m, 4H), 7.62-7.51 (m, 2H), 7.36 (dd, J = 11.4, 6.1 Hz, 1H), 7.00 (d, J = 8.3 Hz, 1H), 5.61 (s, 2H), 5.50 (s, 1H), 4.56-4.47 (m, 2H), 4.43 (d, J = 16.8 Hz, 1H), 4.21 (dd, J = 10.9, 6.6 Hz, 1H), 4.08 (t, J = 8.7 Hz, 1H), 3.77 (t, J = 8.2 Hz, 1H), 3.14-3.00 (m, 2H), 2.92 (s, 3H), 2.63-2.52 (m, 1H), 1.24 (s, 1H). |
| 177 | 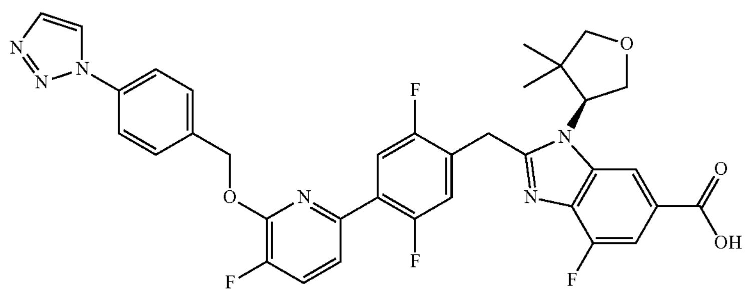 [SMILES: CC1(C)COC[C@H]1n1c(Cc2cc(F)c(-c3ccc(F)c(OCc4ccc(-n5ccnn5)cc4)n3)cc2F)nc2c(F)cc(C(=O)O)cc21] | 35 | 673.0 | 1H NMR (400 MHz, DMSO) δ 13.05 (s, 1H), 8.84 (d, J = 1.1 Hz, 1H), 8.35 (s, 1H), 8.01-7.93 (m, 3H), 7.85 (ddd, J = 13.3, 10.3, 7.4 Hz, 2H), 7.75 (d, J = 8.3 Hz, 2H), 7.60-7.43 (m, 3H), 5.66 (s, 2H), 5.03 (d, J = 6.5 Hz, 1H), 4.59-4.49 (m, 2H), 4.47-4.34 (m, 2H), 3.75 (q, J = 8.7 Hz, 2H), 1.34 (s, 3H), 0.61 (s, 3H). |

TABLE 2-continued

Compounds

| Ex. | Structure | Procedure | ES/MS m/z | ¹H NMR |
|---|---|---|---|---|
| 178 | 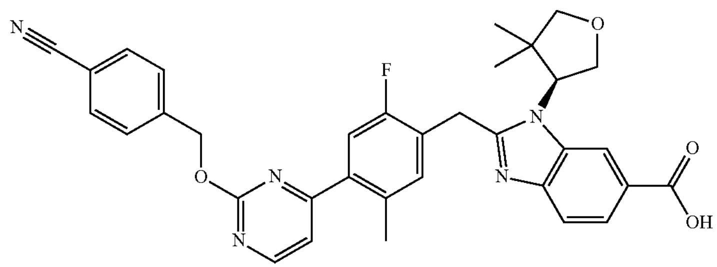 [SMILES: Cc1cc(Cc2nc3ccc(C(=O)O)cc3n2[C@@H]2COCC2(C)C)c(F)cc1-c1ccnc(OCc2ccc(C#N)cc2)n1] | 35 | 592 | 1H NMR (400 MHz, DMSO) δ 8.74 (d, 1H), 8.49 (s, 1H) 7.80-7.90 (m, 3H), 7.70-7.60 (m, 3H), 7.46-7.36 (m, 3H), 5.56 (s, 2H), 5.02 (d, 1H), 4.53-4.43 (m, 4H), 3.82-3.72 (m, 2H), 2.33 (s, 3H), 1.32 (s, 3H), 0.60 (s, 3H). |
| 179 | 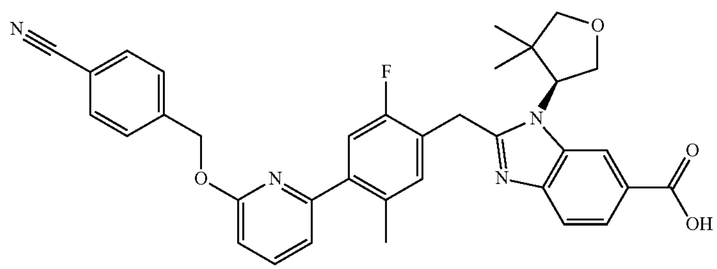 [SMILES: Cc1cc(Cc2nc3ccc(C(=O)O)cc3n2[C@@H]2COCC2(C)C)c(F)cc1-c1cccc(OCc2ccc(C#N)cc2)n1] | 35 | 591.2 | 1H NMR (400 MHz, DMSO) δ 8.49 (s, 1H), 7.92-7.78 (m, 4H), 7.63 (dd, J = 8.3, 4.5 Hz, 3H), 7.33-7.20 (m, 3H), 5.51 (s, 2H), 4.56-4.38 (m, 3H), 3.82-3.70 (m, 2H), 3.74 (s, 21H), 2.22 (s, 3H), 1.31 (s, 3H), 0.60 (s, 3H). |
| 180 | 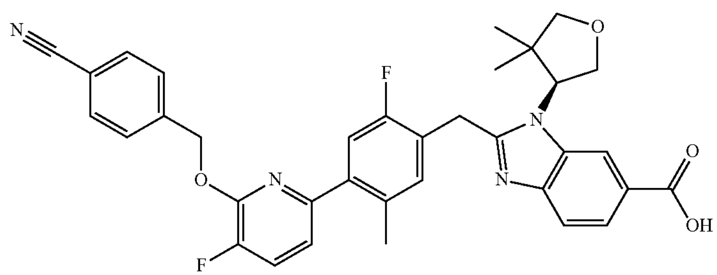 [SMILES: Cc1cc(Cc2nc3ccc(C(=O)O)cc3n2[C@@H]2COCC2(C)C)c(F)cc1-c1ccc(F)c(OCc2ccc(C#N)cc2)n1] | 35 | 609.0 | 1H NMR (400 MHz, DMSO) δ 8.49 (s, 1H), 7.90-7.78 (m, 4H), 7.64 (dd, J = 12.6, 8.3 Hz, 3H), 7.33-7.21 (m, 3H), 5.59 (s, 2H), 5.02 (d, J = 6.6 Hz, 1H), 4.56-4.38 (m, 3H), 4.33 (d, J = 16.9 Hz, 1H), 3.79 (d, J = 8.6 Hz, 1H), 3.73 (d, J = 8.6 Hz, 1H), 2.22 (s, 3H), 1.31 (s, 3H), 0.60 (s, 3H). |

TABLE 2-continued

Compounds

| Ex. | Structure | Procedure | ES/MS m/z | ¹H NMR |
|---|---|---|---|---|
| 181 | 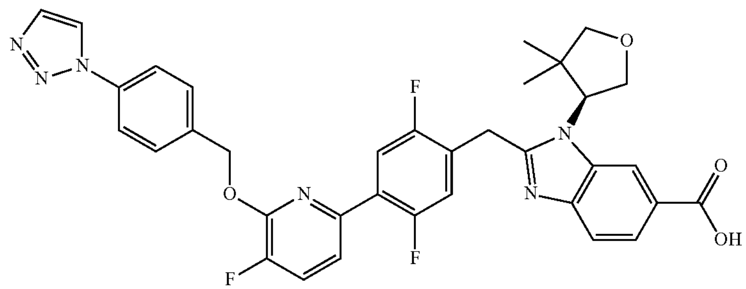 [SMILES: CC1(C)COC[C@H]1n1c(Cc2cc(F)c(-c3ccc(F)c(OCc4ccc(-n5ccnn5)cc4)n3)cc2F)nc2ccc(C(=O)O)cc21] | 35 | 655.2 | 1H NMR (400 MHz, DMSO) δ 8.84 (d, J = 1.2 Hz, 1H), 8.51 (s, 1H), 8.01-7.93 (m, 3H), 7.91-7.83 (m, 1H), 7.87-7.79 (m, 2H), 7.78-7.71 (m, 2H), 7.64 (d, J = 8.4 Hz, 1H), 7.60-7.52 (m, 1H), 7.48 (dd, J = 11.4, 6.1 Hz, 1H), 5.66 (s, 2H), 5.04 (d, J = 6.6 Hz, 1H), 4.60-4.51 (m, 2H), 4.48-4.37 (m, 2H), 3.79 (d, J = 8.6 Hz, 1H), 3.73 (d, J = 8.6 Hz, 1H), 1.33 (s, 3H), 0.61 (s, 3H). |
| 182 | 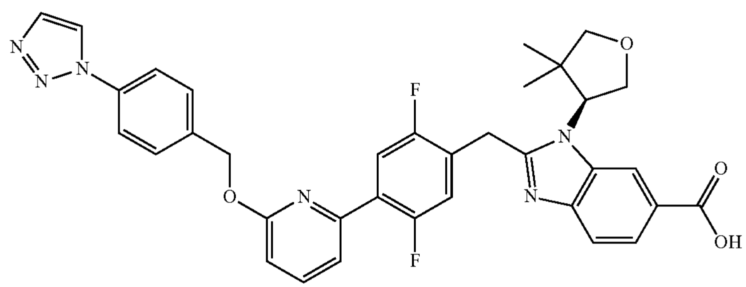 | 35 | 638.3 | 1H NMR (400 MHz, DMSO) δ 8.87-8.77 (m, 2H), 8.50 (s, 1H), 8.01-7.92 (m, 4H), 7.82 (dd, J = 8.5, 1.5 Hz, 1H), 7.74 (d, J = 8.4 Hz, 2H), 7.67-7.60 (m, 2H), 7.56 (dd, J = 11.4, 5.9 Hz, 1H), 5.60 (s, 2H), 5.21 (s, 15H), 5.03 (d, J = 6.6 Hz, 1H), 4.59 (d, J = 17.1Hz, 1H), 4.55 (d, J = 11.7 Hz, 1H), 4.48-4.38 (m, 2H), 3.78 (d, J = 8.6 Hz, 1H), 3.73 (d, J = 8.6 Hz, 1H), 1.34 (s, 3H), 0.62 (s, 3H). |
| 183 | 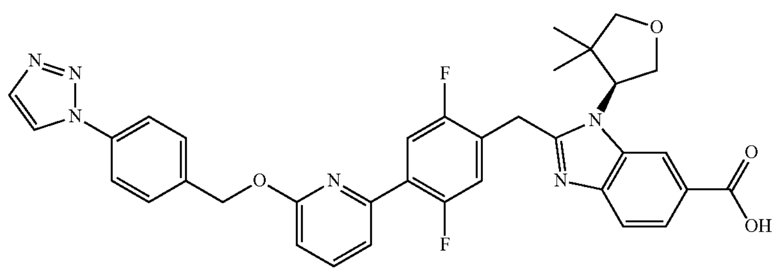 [SMILES: CC1(C)COC[C@H]1n1c(Cc2cc(F)c(-c3cccc(OCc4ccc(-n5ccnn5)cc4)n3)cc2F)nc2ccc(C(=O)O)cc21] | 35 | 636.6 | 1H NMR (400 MHz, DMSO) δ 8.83 (d, J = 1.2 Hz, 1H), 8.50 (s, 1H), 7.98 (d, J = 1.2 Hz, 1H), 7.91 (m, 2H), 7.90 (t, J = 7.8 Hz, 1H), 7.86 (dd, J = 10.3, 6.6 Hz, 1H), 7.82 (dd, J = 8.4, 1.5 Hz, 1H), 7.76-7.69 (m, 2H), 7.63 (d, J = 8.4 Hz, 1H), 7.54 (dd, J = 7.6, 1.6 Hz, 1H), 7.47 (dd, J = 11.2, 6.3 Hz, 1H), 7.00 (d, J = 8.2 Hz, 1H), 5.57 (s, 2H), 5.03 (d, J = 6.6 Hz, 1H), 4.59-4.54 (m, 1H), 4.53 (s, 1H), 4.48-4.35 (m, 2H), 4.03 (s, 21H), 3.78 (d, J = 8.7 Hz, |

TABLE 2-continued

Compounds

| Ex. | Structure | Procedure | ES/MS m/z | ¹H NMR |
|---|---|---|---|---|
| 184 | 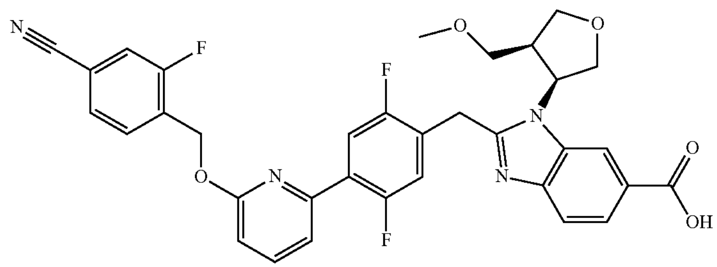 [SMILES: COC[C@H]1COC[C@H]1n1c(Cc2cc(F)c(-c3cccc(OCc4ccc(C#N)cc4F)n3)cc2F)nc2ccc(C(=O)O)cc21] | 22 | 628.2 | 1H NMR (400 MHz, DMSO) δ 12.76 (s, 1H), 8.55 (s, 1H), 7.96-7.86 (m, 2H), 7.81 (dd, J = 8.3, 1.5 Hz, 1H), 7.81-7.68 (m, 3H), 7.62 (d, J = 8.5 Hz, 1H), 7.54 (dd, J = 7.6, 1.7 Hz, 1H), 7.38 (dd, J = 11.4, 6.1 Hz, 1H), 7.00 (d, J = 8.3 Hz, 1H), 5.61 (s, 2H), 5.52 (s, 1H), 4.58-4.41 (m, 3H), 4.21 (dd, J = 10.8, 6.5 Hz, 1H), 4.08 (t, J = 8.7 Hz, 1H), 3.77 (t, J = 8.1 Hz, 1H), 3.17-3.01 (m, 2H), 2.91 (s, 3H), 2.60 (t, J = 8.7 Hz, 1H), 1H), 3.73 (d, J = 8.6 Hz, 1H), 1.33 (s, 3H), 0.61 (s, 3H). |
| 185 | 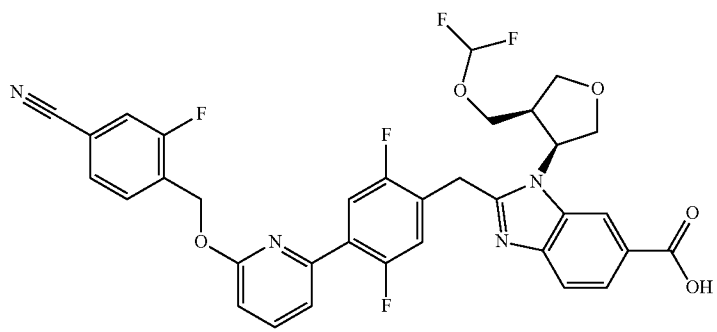 [SMILES: N#Cc1ccc(COc2cccc(-c3cc(F)c(Cc4nc5ccc(C(=O)O)cc5n4[C@@H]4COC[C@@H]4COC(F)F)cc3F)n2)c(F)c1] | 22 | 664.6 | 1H NMR (400 MHz, DMSO) δ 8.53 (s, 1H), 7.96-7.86 (m, 2H), 7.81 (dd, J = 8.4, 1.5 Hz, 1H), 7.81-7.70 (m, 3H), 7.66-7.50 (m, 2H), 7.38 (dd, J = 11.4, 6.1 Hz, 1H), 7.00 (d, J = 8.2 Hz, 1H), 6.6-6.25 (m, 1H), 5.61 (s, 2H), 4.56 (d, J = 16.9 Hz, 1H), 4.50 (d, J = 10.9 Hz, 1H), 4.42 (d, J = 17.0 Hz, 1H), 4.19 (dd, J = 10.9, 6.7 Hz, 1H), 4.09 (t, J = 8.6 Hz, 1H), 3.93-3.86 (m, 1H), 3.61-3.51 (m, 1H). |

TABLE 2-continued

Compounds

| Ex. | Structure | Procedure | ES/MS m/z | ¹H NMR |
|---|---|---|---|---|
| 186 | 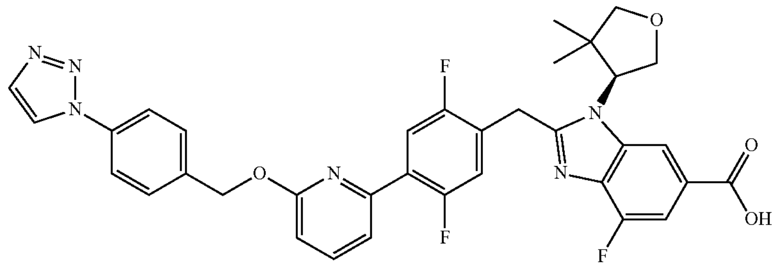 [SMILES: CC1(C)COC[C@H]1n1c(Cc2cc(F)c(-c3cccc(OCc4ccc(-n5ccnn5)cc4)n3)cc2F)nc2c(F)cc(C(=O)O)cc21] | 35 | 654.6 | 1H NMR (400 MHz, DMSO) δ 13.14 (s, 1H), 8.83 (d, J = 1.2 Hz, 1H), 8.36 (s, 1H), 8.00-7.82 (m, 5H), 7.73 (d, J = 8.2 Hz, 2H), 7.58-7.49 (m, 2H), 7.47 (dd, J = 11.2, 6.2 Hz, 1H), 7.00 (d, J = 8.2 Hz, 1H), 5.58 (s, 2H), 5.04 (d, J = 6.5 Hz, 1H), 4.59-4.49 (m, 2H), 4.48-4.35 (m, 2H), 4.26 (s, 13H), 3.75 (q, J = 8.7 Hz, 2H), 2.55 (s, 1H), 1.34 (s, 3H), 0.61 (s, 3H). |
| 187 | 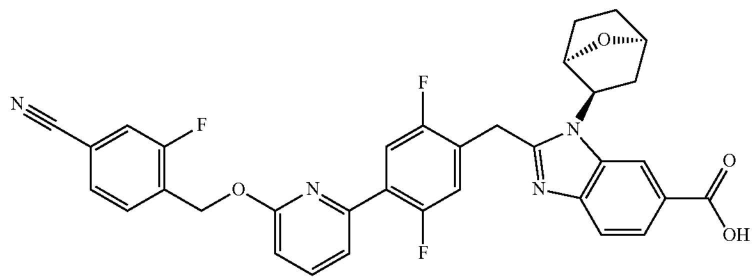 [SMILES: N#Cc1ccc(COc2cccc(-c3cc(F)c(Cc4nc5ccc(C(=O)O)cc5n4[C@@H]4C[C@@H]5CC[C@H]4O5)cc3F)n2)c(F)c1] | 36 | 610.6 | 1H NMR (400 MHz, DMSO) δ 12.98 (s, 1H), 8.31 (d, J = 1.5 Hz, 1H), 7.96-7.86 (m, 2H), 7.82 (dd, J = 8.5, 1.3 Hz, 1H), 7.82-7.70 (m, 3H), 7.66 (d, J = 8.4 Hz, 1H), 7.55 (dd, J = 7.5, 1.7 Hz, 1H), 7.41 (dd, J = 11.3, 6.1 Hz, 1H), 7.00 (d, J = 8.2 Hz, 1H), 5.61 (s, 2H), 5.02 (dt, J = 11.1, 5.0 Hz, 1H), 4.85 (dt, J = 12.8, 4.2 Hz, 2H), 4.58 (d, J = 17.0 Hz, 1H), 4.47 (d, J = 17.0 Hz, 1H), 2.37 (d, J = 10.9 Hz, 1H), 2.10-1.96 (m, 1H), 1.90 (d, J = 10.3 Hz, 1H), 1.68 (q, J = 5.3 Hz, 2H). |
| 188 | 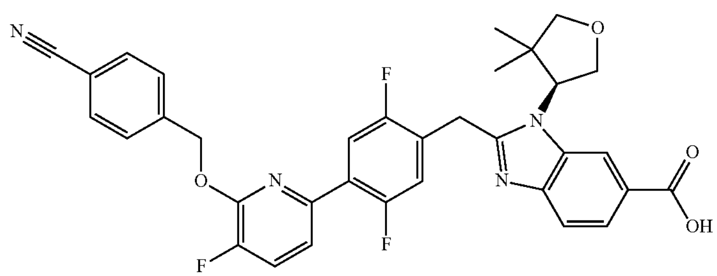 | 35 | 612.6 | 1H NMR (400 MHz, DMSO) δ 8.49 (s, 1H), 7.92-7.77 (m, 4H), 7.72 (t, J = 8.8 Hz, 3H), 7.62 (d, J = 8.5 Hz, 1H), 7.59-7.52 (m, 1H), 7.46 (dd, J = 11.4, 6.1 Hz, 1H), 5.67 (s, 2H), 5.02 (d, J = 6.7 Hz, 1H),4.58-4.49 (m, 2H), 4.44 (dd, J = 11.2, 6.8 Hz, 1H), 4.38 (d, J = 16.9 Hz, 1H), 3.82-3.70 (m, 2H), 1.34 (s, 3H), 0.61 (s, 3H). |

TABLE 2-continued

Compounds

| Ex. | Structure | Procedure | ES/MS m/z | ¹H NMR |
|---|---|---|---|---|
| 189 | 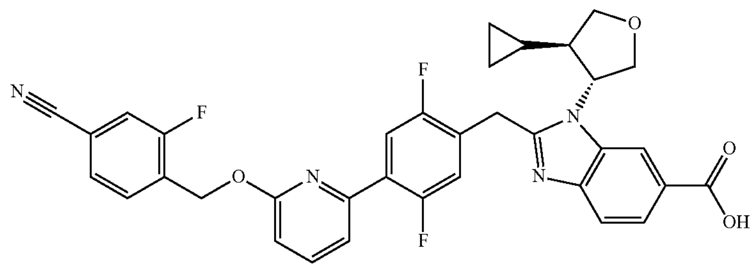 [SMILES: N#Cc1ccc(COc2cccc(-c3cc(F)c(Cc4nc5ccc(C(=O)O)cc5n4[C@H]4COC[C@@H]4C4CC4)cc3F)n2)c(F)c1] | 36 | 624.6 | 1H NMR (400 MHz, DMSO) δ 8.56 (s, 1H), 8.22 (s, 1H), 7.96-7.87 (m, 2H), 7.82-7.70 (m, 4H), 7.60 (d, J = 8.4 Hz, 1H), 7.55 (dd, J = 7.5, 1.7 Hz, 1H), 7.41 (dd, J = 11.4, 6.1 Hz, 1H), 7.04-6.95 (m, 1H), 5.61 (s, 2H), 5.48 (t, J = 7.2 Hz, 1H), 4.63-4.53 (m, 2H), 4.47 (d, J = 17.0 Hz, 1H), 4.23 (dd, J = 10.9, 6.6 Hz, 1H), 4.12 (t, J = 8.5 Hz, 1H), 3.82 (t, J = 8.4 Hz, 1H), 3.02-2.87 (m, 1H), 2.18 (p, J = 8.4 Hz, 1H), 1.24 (s, 1H), 1.16 (t, J = 7.3 Hz, 2H), 0.24 (s, 2H), 0.11 (d, J = 7.1 Hz, 2H), −0.12 (s, 1H). |
| 190 | 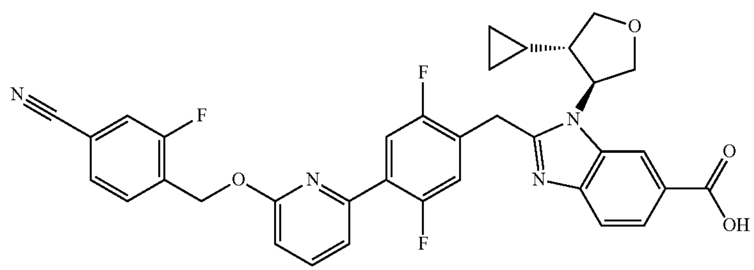 [SMILES: N#Cc1ccc(COc2cccc(-c3cc(F)c(Cc4nc5ccc(C(=O)O)cc5n4[C@@H]4COC[C@H]4C4CC4)cc3F)n2)c(F)c1] | 36 | 624.6 | 1H NMR (400 MHz, DMSO) δ 12.74 (s, 1H), 8.55 (s, 1H), 7.96-7.87 (m, 2H), 7.81-7.70 (m, 4H), 7.63-7.51 (m, 2H), 7.41 (dd, J = 11.3, 6.1 Hz, 1H), 7.00 (d, J = 8.2 Hz, 1H), 5.61 (s, 2H), 5.47 (t, J = 7.2 Hz, 1H), 4.62-4.52 (m, 2H), 4.46 (d, J = 16.9 Hz, 1H), 4.23 (dd, J = 10.8, 6.7 Hz, 1H), 4.12 (t, J = 8.5 Hz, 1H), 3.81 (t, J = 8.4 Hz, 1H), 2.17 (p, J = 8.5 Hz, 1H), 1.24 (s, 1H), 0.23 (s, 2H), 0.11 (s, 1H), −0.13 (s, 1H). |

TABLE 2-continued

Compounds

| Ex. | Structure | Procedure | ES/MS m/z | ¹H NMR |
|---|---|---|---|---|
| 191 | 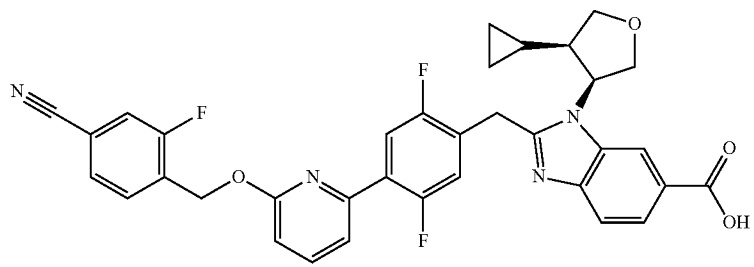 | 36 | 624.6 | 1H NMR (400 MHz, DMSO) δ 8.28 (s, 1H), 7.96-7.86 (m, 2H), 7.84-7.72 (m, 4H), 7.62 (d, J = 8.4 Hz, 1H), 7.54 (d, J = 7.4 Hz, 1H), 7.41 (dd, J = 11.4, 6.0 Hz, 1H), 7.00 (d, J = 8.3 Hz, 1H), 5.61 (s, 2H), 5.31 (s, 1H), 4.76-4.42 (m, 2H), 4.35 (t, J = 8.2 Hz, 1H), 4.31-4.12 (m, 2H), 3.58 (t, J = 9.6 Hz, 1H), 2.89 (d, J = 7.4 Hz, 1H), 2.68 (s, 1H), 2.34 (s, 1H), 1.92 (s, 0H), 1.24 (s, 2H), 1.14 (t, J = 7.2 Hz, 2H), 1.04-0.78 (m, 2H), 0.38 (d, J = 9.7 Hz, 2H), 0.11 (s, 1H), −0.38 (d, J = 5.2 Hz, 1H). |
| 192 | 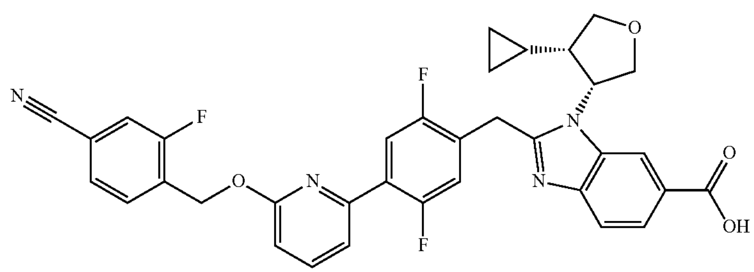 [SMILES: N#Cc1ccc(COc2cccc(-c3cc(F)c(Cc4nc5ccc(C(=O)O)cc5n4[C@H]4COC[C@H]4C4CC4)cc3F)n2)c(F)c1] | 36 | 624.6 | 1H NMR (400 MHz, DMSO) δ 12.79 (s, 1H), 8.28 (s, 1H), 8.00-7.84 (m, 2H), 7.77 (dd,J= 15.6, 7.3 Hz, 3H), 7.63 (d, J = 8.5 Hz, 1H), 7.54 (d, J = 7.3 Hz, 1H), 7.41 (dd, J = 11.5, 6.0 Hz, 1H), 7.00 (d, J = 8.3 Hz, 1H), 5.61 (s, 2H), 5.32 (s, 1H), 4.62-4.42 (m, 2H), 4.40-4.09 (m, 2H), 3.58 (t, J = 9.6 Hz, 1H), 1.92 (d, J = 8.1 Hz, 0H), 1.02-0.82 (m, 1H), 0.37 (d, J = 13.0 Hz, 1H), 0.10 (d, J = 5.4 Hz, 1H), −0.37 (d, J = 4.9 Hz, 1H). |

TABLE 2-continued

Compounds

| Ex. | Structure | Procedure | ES/MS m/z | ¹H NMR |
|---|---|---|---|---|
| 193 | 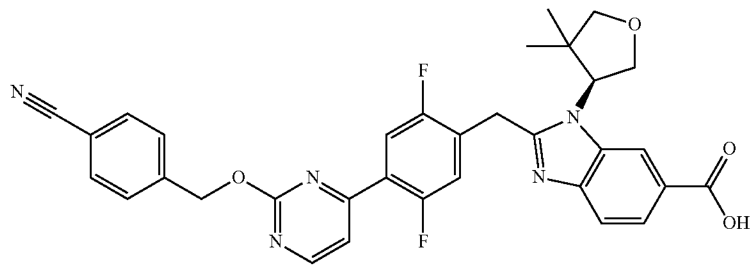 [SMILES: CC1(C)COC[C@H]1n1c(Cc2cc(F)c(-c3ccnc(OCc4ccc(C#N)cc4)n3)cc2F)nc2ccc(C(=O)O)cc21] | 35 | 595.6 | 1H NMR (400 MHz, DMSO) δ 8.79 (d, J = 5.2 Hz, 1H), 8.36 (s, 1H), 7.91 (dd, J = 17.7, 7.2 Hz, 3H), 7.70 (d, J = 8.2 Hz, 2H), 7.65 (dd, J = 5.2, 1.8 Hz, 1H), 7.60-7.48 (m, 2H), 5.62 (s, 2H), 5.04 (d, J = 6.6 Hz, 1H), 4.58 (d, J = 17.1 Hz, 1H), 4.53 (d, J = 11.8 Hz, 1H), 4.48-4.37 (m, 2H), 3.75 (q, J = 8.7 Hz, 2H), 1.34 (s, 3H), 0.62 (s, 3H). |
| 194 | 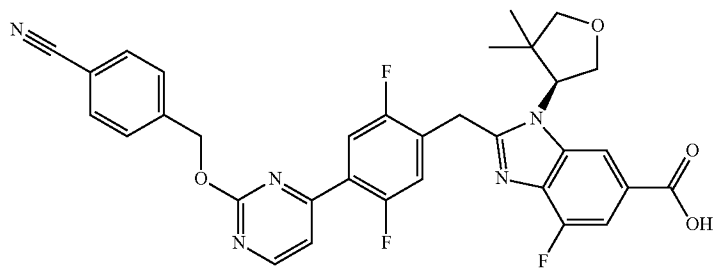 [SMILES: CC1(C)COC[C@H]1n1c(Cc2cc(F)c(-c3ccnc(OCc4ccc(C#N)cc4)n3)cc2F)nc2c(F)cc(C(=O)O)cc21] | 35 | 613.6 | 1H NMR (400 MHz, DMSO) δ 8.79 (d, J = 5.2 Hz, 1H), 8.36 (s, 1H), 7.91 (dd, J = 17.7, 7.2 Hz, 3H), 7.70 (d, J = 8.2 Hz, 2H), 7.65 (dd, J = 5.2, 1.8 Hz, 1H), 7.60-7.48 (m, 2H), 5.62 (s, 2H), 5.04 (d, J = 6.6 Hz, 1H), 4.58 (d, J = 17.1 Hz, 1H), 4.53 (d, J = 11.8 Hz, 1H), 4.48-4.37 (m, 2H), 3.75 (q, J = 8.7 Hz, 2H), 1.34 (s, 3H), 0.62 (s, 3H). |
| 195 | 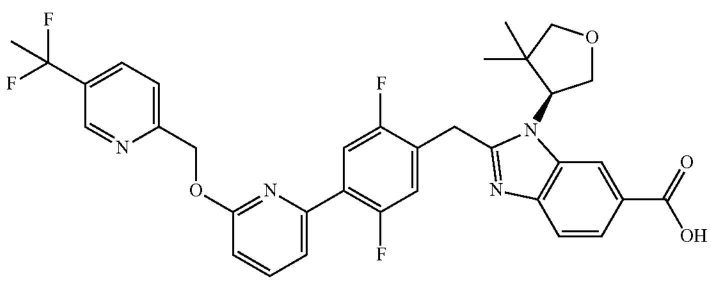 [SMILES: CC(F)(F)c1ccc(COc2cccc(-c3cc(F)c(Cc4nc5ccc(C(=O)O)cc5n4[C@@H]4COCC4(C)C)cc3F)n2)nc1] | 35 | 634.6 | 1H NMR (400 MHz, DMSO) δ 13.08 (s, 1H), 8.49 (d, J = 1.3 Hz, 1H), 8.35 (s, 1H), 7.93 (dd, J = 10.2, 8.3 Hz, 1H), 7.82 (dd, J = 10.2, 6.7 Hz, 1H), 7.66-7.59 (m, 1H), 7.56-7.43 (m, 2H), 5.98 (s, 2H), 5.03 (d, J = 6.6 Hz, 1H), 4.59 - 4.48 (m, 2H), 4.47-4.35 (m, 2H), 3.84 (s, 14H), 3.74 (q, J = 8.7 Hz, 2H), 1.33 (s, 3H), 0.60 (s, 3H). |

TABLE 2-continued

Compounds

| Ex. | Structure | Procedure | ES/MS m/z | ¹H NMR |
|---|---|---|---|---|
| 196 | 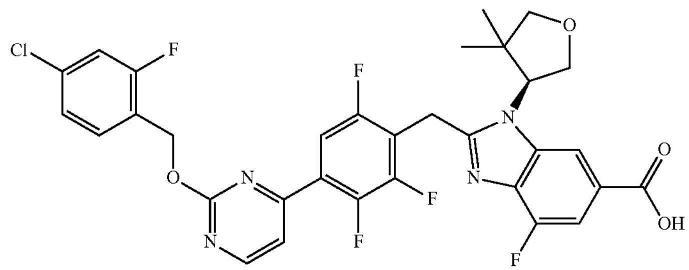 [SMILES: CC1(C)COC[C@H]1n1c(Cc2c(F)cc(-c3ccnc(OCc4ccc(Cl)cc4F)n3)c(F)c2F)nc2c(F)cc(C(=O)O)cc21] | 35 | 658.6 | 1H NMR (400 MHz, DMSO) δ 13.08 (s, 1H), 8.49 (d, J = 1.3 Hz, 1H), 8.35 (s, 1H), 7.93 (dd, J = 10.2, 8.3 Hz, 1H), 7.82 (dd, J = 10.2, 6.7 Hz, 1H), 7.66-7.59 (m, 1H), 7.56-7.43 (m, 2H), 5.98 (s, 2H), 5.03 (d, J = 6.6 Hz, 1H), 4.59 -4.48 (m, 2H), 4.47-4.35 (m, 2H), 3.84 (s, 14H), 3.74 (q, J = 8.7 Hz, 2H), 1.33 (s, 3H), 0.60 (s, 3H). |
| 197 | 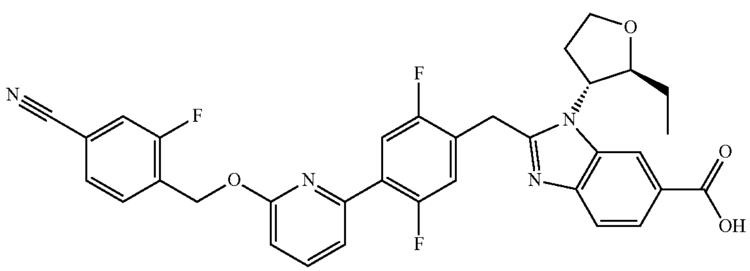 [SMILES: CC[C@@H]1OCC[C@H]1n1c(Cc2cc(F)c(-c3cccc(OCc4ccc(C#N)cc4F)n3)cc2F)nc2ccc(C(=O)O)cc21] | 36 | 612.6 | 1H NMR (400 MHz, DMSO) δ 8.32 (d, J = 1.5 Hz, 1H), 7.96-7.64 (m, 7H), 7.53 (dd, J = 7.5, 1.7 Hz, 1H), 7.42 (dd, J = 11.5, 6.1 Hz, 1H), 7.00 (d, J = 8.3 Hz, 1H), 5.60 (s, 2H), 5.09-4.99 (m, 1H), 4.60-4.44 (m, 2H), 4.23 (ddt, J = 13.1, 8.7, 3.6 Hz, 2H), 4.00 (q, J = 8.0 Hz, 1H), 2.39-2.26 (m, 1H), 1.66-1.47 (m, 2H), 0.86 (t, J = 7.4 Hz, 3H). |
| 198 | 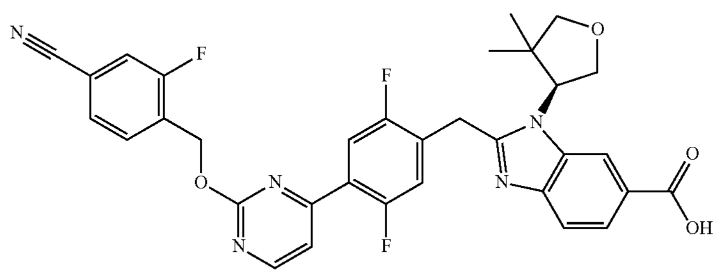 [SMILES: CC1(C)COC[C@H]1n1c(Cc2cc(F)c(-c3ccnc(OCc4ccc(C#N)cc4F)n3)cc2F)nc2ccc(C(=O)O)cc21] | 35 | 614.5 | 1H NMR (400 MHz, DMSO) δ 8.79 (d, J = 5.2 Hz, 1H), 8.49 (s, 1H), 7.98-7.88 (m, 2H), 7.84-7.72 (m, 3H), 7.69-7.59 (m, 2H), 7.55 (dd, J = 11.4, 5.9 Hz, 1H), 5.64 (s, 2H), 5.02 (d, J = 6.6 Hz, 1H), 4.62-4.50 (m, 2H), 4.48-4.37 (m, 2H), 3.82-3.70 (m, 2H), 1.34 (s, 3H), 0.61 (s, 3H). |

TABLE 2-continued

Compounds

| Ex. | Structure | Procedure | ES/MS m/z | 1H NMR |
|---|---|---|---|---|
| 199 | 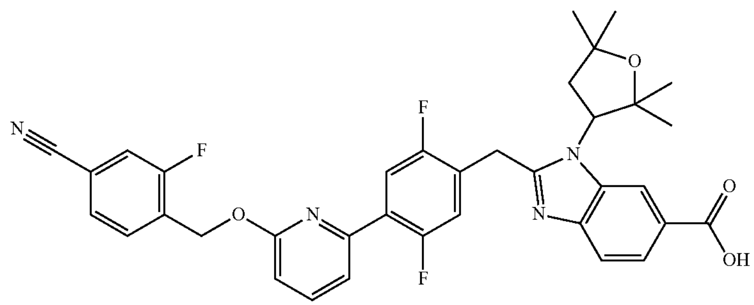 [SMILES: CC1(C)CC(n2c(Cc3cc(F)c(-c4cccc(OCc5ccc(C#N)cc5F)n4)cc3F)nc3ccc(C(=O)O)cc32)C(C)(C)O1] | 36 | 641.2 | 1H NMR (400 MHz, DMSO) δ 8.37 (d, J = 1.5 Hz, 1H), 7.95-7.63 (m, 7H), 7.54 (dd, J = 7.5, 1.7 Hz, 1H), 7.44 (dd, J = 11.5, 6.0 Hz, 1H), 7.00 (d, J = 8.3 Hz, 1H), 5.60 (s, 2H), 5.23 (dd, J = 10.7, 8.3 Hz, 1H), 4.67 (d, J = 17.0 Hz, 1H), 4.44 (d, J = 16.9 Hz, 1H), 3.00-2.90 (m, 1H), 2.39 (dd, J = 12.7, 8.2 Hz, 1H), 1.50 (s, 3H), 1.39 (d, J = 17.9 Hz, 6H), 1.07 (s, 3H). |
| 200 | 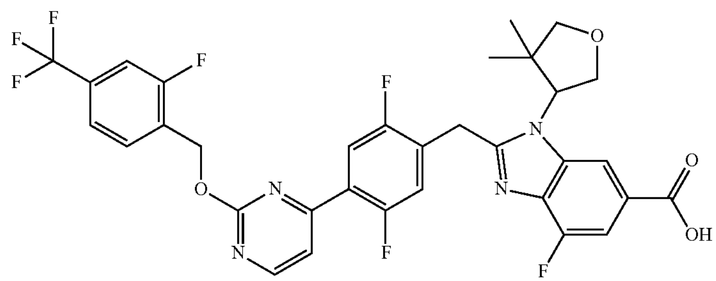 [SMILES: CC1(C)COCC1n1c(Cc2cc(F)c(-c3ccnc(OCc4ccc(C(F)(F)F)cc4F)n3)cc2F)nc2c(F)cc(C(=O)O)cc21] | 35 | 675 | 1H NMR (400 MHz, DMSO) δ 13.09 (s, 1H), 8.80 (d, J = 5.1 Hz, 1H), 8.36 (s, 1H), 7.93 (dd, J = 10.2, 6.2 Hz, 1H), 7.87-7.73 (m, 2H), 7.66 (dt, J = 5.2, 2.6 Hz, 2H), 7.60-7.48 (m, 2H), 5.65 (s, 2H), 5.04 (d, J = 6.6 Hz, 1H), 4.58 (d, J = 17.1 Hz, 1H), 4.53 (d, J = 11.9 Hz, 1H), 4.48-4.38 (m, 2H), 4.11 (s, 7H), 3.75 (q, J = 8.7 Hz, 2H), 1.34 (s, 3H), 0.62 (s, 3H). |
| 201 | 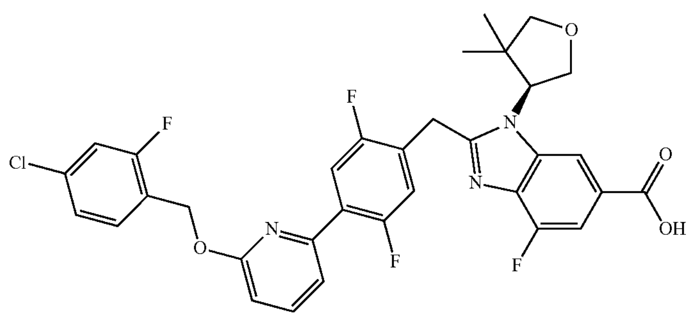 [SMILES: CC1(C)COC[C@H]1n1c(Cc2cc(F)c(-c3cccc(OCc4ccc(Cl)cc4F)n3)cc2F)nc2c(F)cc(C(=O)O)cc21] | 35 | 640.2 | 1H NMR (400 MHz, DMSO) δ 13.07 (s, 1H), 8.36 (s, 1H), 7.93-7.81 (m, 2H), 7.65-7.42 (m, 5H), 7.33 (dd, J = 8.2, 2.1 Hz, 1H), 6.95 (d, J = 8.3 Hz, 1H), 5.51 (s, 2H), 5.04 (d, J = 6.5 Hz, 1H), 4.59-4.49 (m, 2H), 4.48-4.35 (m, 2H), 3.75 (q, J = 8.6 Hz, 2H), 1.34 (s, 3H), 0.61 (s, 3H). |

TABLE 2-continued

Compounds

| Ex. | Structure | Procedure | ES/MS m/z | ¹H NMR |
|---|---|---|---|---|
| 202 | 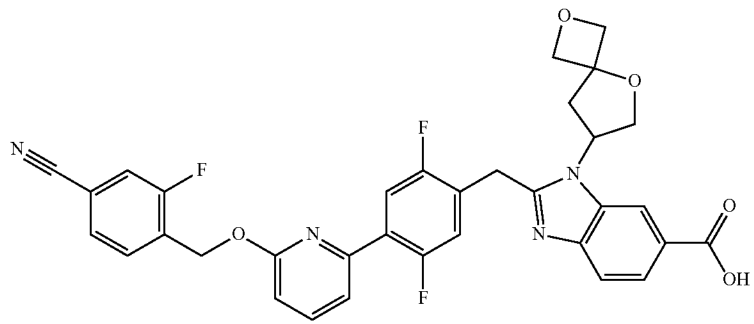 [SMILES: N#Cc1ccc(COc2cccc(-c3cc(F)c(Cc4nc5ccc(C(=O)O)cc5n4C4COC5(COC5)C4)cc3F)n2)c(F)c1] | 22 | 627.2 | 1H NMR (400 MHz, DMSO) δ8.20 (s, 1H), 7.96-7.86 (m, 2H), 7.83-7.70 (m, 4H), 7.61 (d, J = 8.4 Hz, 1H), 7.53 (d, J = 7.0 Hz, 1H), 7.34 (dd, J = 11.5, 6.1 Hz, 1H), 7.00 (d, J = 8.2 Hz, 1H), 5.60 (s, 2H), 5.53 (s, 1H), 4.89 (d, J = 7.0 Hz, 1H), 4.75 (d, J = 7.1 Hz, 1H), 4.63 (q, J = 6.8 Hz, 2H), 4.47 (s, 2H), 4.25 (dd, J = 10.4, 3.4 Hz, 1H),4.16 (dd, J = 10.4, 7.6 Hz, 1H), 3.31 (s, 1H), 2.93 (dd, J = 14.0, 9.1 Hz, 1H), 2.51-2.39 (m, 1H), 1.24 (s, 1H). |
| 203 | 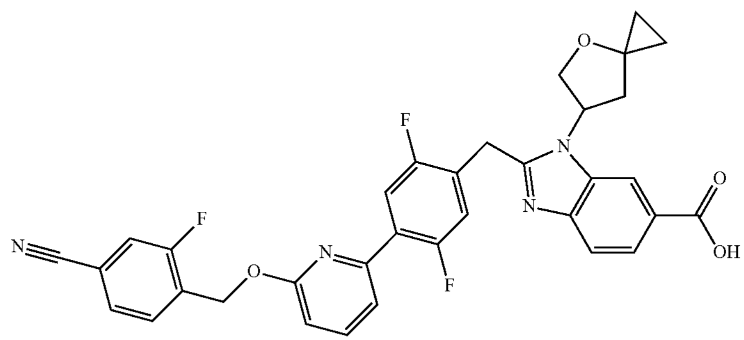 [SMILES: N#Cc1ccc(COc2cccc(-c3cc(F)c(Cc4nc5ccc(C(=O)O)cc5n4C4COC5(CC5)C4)cc3F)n2)c(F)c1] | 22 | 611.2 | 1H NMR (400 MHz, DMSO) δ 12.95 (s, 1H), 8.60 (d, J = 1.5 Hz, 1H), 7.96-7.86 (m, 3H), 7.82-7.66 (m, 4H), 7.53 (dd, J = 7.5, 1.7 Hz, 1H), 7.42 (dd, J = 11.5, 6.1Hz, 1H), 7.00 (d, J = 8.2 Hz, 1H), 5.73 (qd, J = 7.6, 3.6 Hz, 1H), 5.60 (s, 2H), 4.61 (s, 2H), 4.17 (qd, J = 10.2, 5.5 Hz, 2H), 2.51-2.40 (m, 2H), 1.20-1.09 (m, 1H), 0.82 (td, J = 10.4, 6.0 Hz, 2H), 0.65-0.54 (m, 1H). |

TABLE 2-continued

Compounds

| Ex. | Structure | Procedure | ES/MS m/z | ¹H NMR |
|---|---|---|---|---|
| 204 | 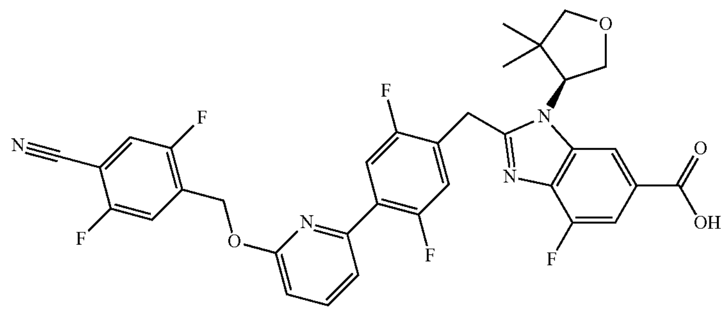 [SMILES: CC1(C)COC[C@H]1n1c(Cc2cc(F)c(-c3cccc(OCc4cc(F)c(C#N)cc4F)n3)cc2F)nc2c(F)cc(C(=O)O)cc21] | 35 | 649.2 | 1H NMR (400 MHz, DMSO) δ 8.36 (s, 1H), 8.05 (dd, J = 9.2, 5.2 Hz, 1H), 7.92 (t, J = 7.9 Hz, 1H), 7.77 (ddd, J = 12.5, 9.8, 6.1Hz, 2H), 7.60-7.42 (m, 3H), 7.02 (d, J = 8.3 Hz, 1H), 5.60 (s, 2H), 5.04 (d, J = 6.6 Hz, 1H), 4.59-4.49 (m, 2H), 4.48-4.35 (m, 2H), 3.75 (q, J = 8.7 Hz, 3H), 1.34 (s, 3H), 0.61 (s, 3H). |
| 205 | 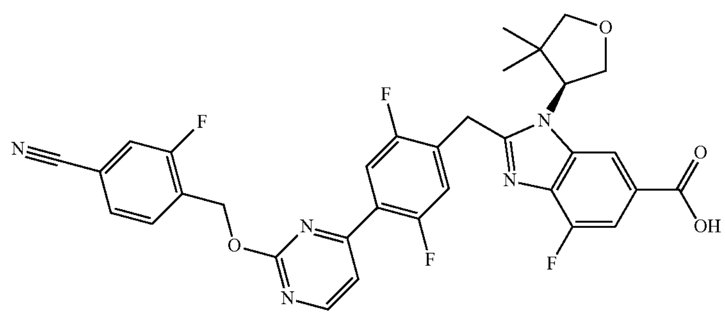 [SMILES: CC1(C)COC[C@H]1n1c(Cc2cc(F)c(-c3ccnc(OCc4ccc(C#N)cc4F)n3)cc2F)nc2c(F)cc(C(=O)O)cc21] | 35 | 632.2 | 1H NMR (400 MHz, DMSO) δ 8.79 (d, J = 5.1 Hz, 1H), 8.36 (s, 1H), 7.98-7.89 (m, 2H), 7.83-7.72 (m, 2H), 7.65-7.67 (m, 1H), 7.60-7.48 (m, 2H), 5.64 (s, 2H), 5.04-5.02 (m, 1H), 4.63-4.49 (m, 2H), 4.48-4.37 (m, 2H), 3.75 (q, J = 8.7 Hz, 2H), 1.34 (s, 3H), 0.62 (s, 3H). |
| 206 | 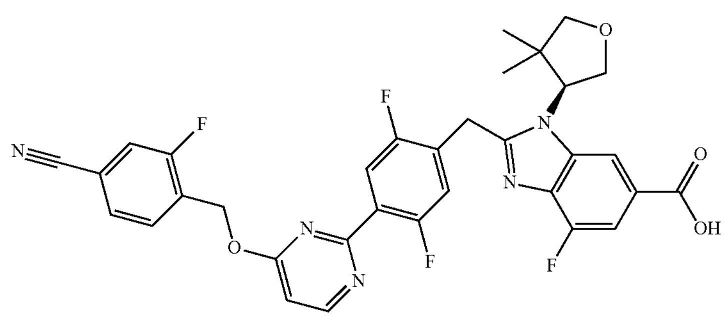 [SMILES: CC1(C)COC[C@H]1n1c(Cc2cc(F)c(-c3nccc(OCc4ccc(C#N)cc4F)n3)cc2F)nc2c(F)cc(C(=O)O)cc21] | 35 | 632.2 | 1H NMR (400 MHz, DMSO) δ 8.82-8.71 (m, 1H), 8.36 (s, 1H), 7.98-7.85 (m, 2H), 7.83-7.72 (m, 2H), 7.60-7.43 (m, 2H), 7.08 (d, J = 5.8 Hz, 1H), 5.66 (d, J = 13.7 Hz, 2H), 5.03 (d, J = 6.6 Hz, 1H), 4.63-4.49 (m, 2H), 4.48-4.37 (m, 2H), 3.75 (q, J = 8.7 Hz, 2H), 1.34 (d, J = 2.8 Hz, 3H), 0.62 (d, J = 2.7 Hz, 3H). |

TABLE 2-continued

Compounds

| Ex. | Structure | Procedure | ES/MS m/z | ¹H NMR |
|---|---|---|---|---|
| 207 | 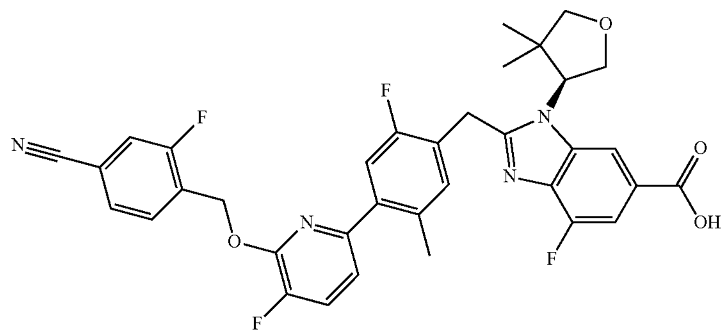 [SMILES: Cc1cc(Cc2nc3c(F)cc(C(=O)O)cc3n2[C@@H]2COCC2(C)C)c(F)cc1-c1ccc(F)c(OCc2ccc(C#N)cc2F)n1] | 35 | 645.2 | 1H NMR (400 MHz, DMSO) δ 13.06 (s, 1H), 8.35 (s, 1H), 7.96-7.89 (m, 1H), 7.85 (dd, J = 10.5, 8.1 Hz, 1H), 7.74 (dd, J = 3.5, 1.6 Hz, 2H), 7.52 (dd, J = 11.2, 1.2 Hz, 1H), 7.34-7.24 (m, 3H), 5.61 (s, 2H), 5.02 (d, J = 6.6 Hz, 1H), 4.55-4.38 (m, 3H), 4.34 (d, J = 16.8 Hz, 1H), 3.80-3.69 (m, 2H), 2.26 (s, 3H), 1.31 (s, 3H), 0.60 (s, 3H). |
| 208 | 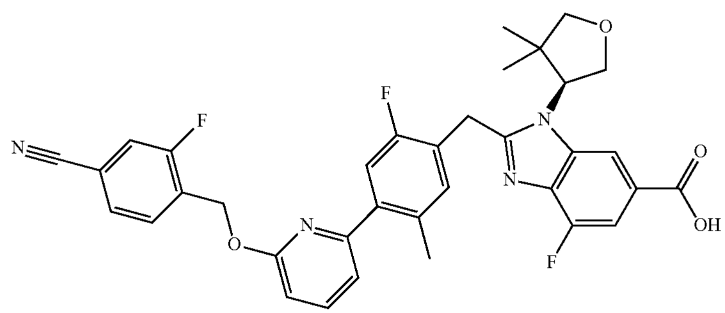 | 35 | 627.2 | 1H NMR (400 MHz, DMSO) δ 8.35 (s, 1H), 7.94-7.86 (m, 2H), 7.75-7.70 (m, 2H), 7.52 (d, 1H), 7.34-7.22 (m, 3H), 6.96 (d, 1H), 5.53 (s, 2H), 5.02 (d, 1H), 4.53-4.41 (m, 3H), 4.34 (d, 1H), 3.77-3.69 (dd, 2H), 2.26 (s, 3H), 1.31 (s, 3H), 0.59 (s, 3H), |
| 209 | 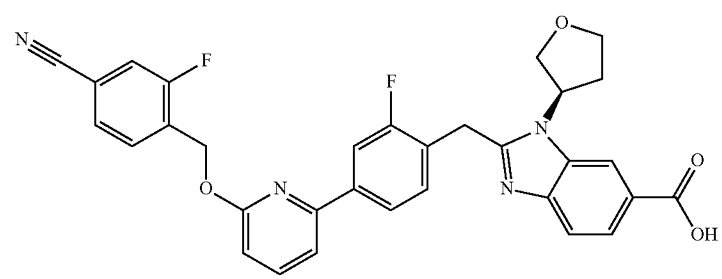 [SMILES: N#Cc1ccc(COc2cccc(-c3ccc(Cc4nc5ccc(C(=O)O)cc5n4[C@@H]4CCOC4)c(F)c3)n2)c(F)c1] | 22 | 567.378 | 1H NMR (400 MHz, MeOD) δ 8.81 (d, J = 1.4 Hz, 1H), 8.22 (dd, J = 8.6, 1.4 Hz, 1H), 7.97-7.86 (m, 2H), 7.86-7.79 (m, 2H), 7.73 (t, J = 7.6 Hz, 1H), 7.61 (dd, J = 9.7, 1.5 Hz, 1H), 7.57 (dd, J = 7.7, 1.7 Hz, 2H), 7.50 (t, J = 7.9 Hz, 1H), 6.92 (d, J = 8.3 Hz, 1H), 5.65 (s, 2H), 4.78 (t, J = 8.8 Hz, 2H), 4.48 (d, J = 2.6 Hz, 1H), 4.40-4.32 (m, 1H), 4.04 (dd, J = 11.0, 7.5 Hz, 1H), 3.80 (td, J = 9.7, 6.9 Hz, 1H), 2.54 (dt, J = 14.3, 7.3 Hz, 1H), 2.35-2.20 (m, |

TABLE 2-continued

Compounds

| Ex. | Structure | Procedure | ES/MS m/z | ¹H NMR |
|---|---|---|---|---|
| 210 | (structure) | 22 | 567.287 | 1H NMR (400 MHz, MeOD) δ 8.84 (d, J = 4.2 Hz, 1H), 8.25 (dd, J = 8.5, 4.2 Hz, 1H), 8.01-7.87 (m, 2H), 7.82 (t, J = 7.7 Hz, 2H), 7.73 (t, J = 7.6 Hz, 1H), 7.64-7.49 (m, 4H), 6.93 (d, J = 8.2 Hz, 1H), 5.65 (s, 2H), 4.81 (s, 2H), 4.53-4.45 (m, 1H), 4.38 (d, J = 11.1Hz, 1H), 4.06 (dd, J = 11.1,7.5 Hz, 1H), 3.81 (td, J = 9.7, 6.7 Hz, 1H), 2.56 (q, J = 12.0, 10.2 Hz, 1H), 2.29 (d, J = 13.8 Hz, 1H). |
| 211 | (structure) | 35 | 619.3 | 1H NMR (400 MHz, DMSO-d6) δ 8.73 (d, J = 5.0 Hz, 1H), 8.35 (s, 1H), 7.56-7.39 (m, 7H), 7.38 (d, J = 7.5 Hz, 1H), 5.46 (s, 2H), 5.03 (d, J = 6.6 Hz, 1H), 4.57-4.31 (m, 4H), 3.75 (q, J = 8.7 Hz, 2H), 2.36 (s, 3H), 1.32 (s, 3H), 0.61 (s, 3H). |
| 212 | (structure) | 35 | 635 | 1H NMR (400 MHz, DMSO-d6) δ 8.74 (d, J = 5.1 Hz, 1H), 8.36 (s, 1H), 7.63 (s, 1H), 7.55-7.43 (m, 6H), 7.41 (s, 1H), 5.46 (s, 2H), 5.02 (d, J = 6.7 Hz, 1H), 4.59 (d, J = 17.1 Hz, 1H), 4.52 (d, J = 11.1 Hz, 1H), 4.47-4.36 (m, 2H), 3.85-3.68 (m, 2H), 2.37 (s, 3H), 1.34 (s, 3H), 0.66 (s, 3H). |

TABLE 2-continued

Compounds

| Ex. | Structure | Procedure | ES/MS m/z | ¹H NMR |
|---|---|---|---|---|
| 213 | 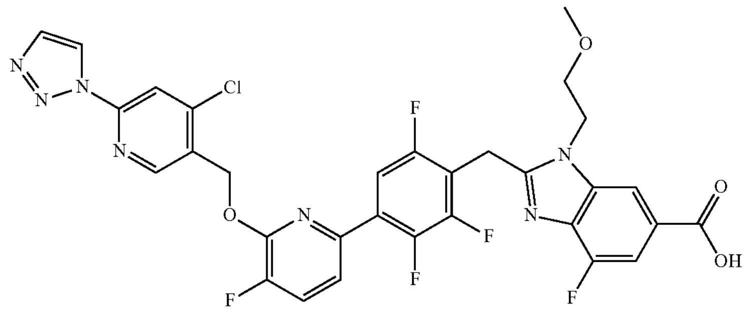 [SMILES: COCCn1c(Cc2c(F)cc(-c3ccc(F)c(OCc4cnc(-n5ccnn5)cc4Cl)n3)c(F)c2F)nc2c(F)cc(C(=O)O)cc21] | 29 | 686 | 1H NMR (400 MHz, DMSO-d6) δ 8.92 (d, J = 1.3 Hz, 1H), 8.86 (s, 1H), 8.33 (s, 1H), 8.11 (d, J = 1.3 Hz, 1H), 8.04 (d, J = 1.2 Hz, 1H), 7.94 (dd, J = 10.2, 8.2 Hz, 1H), 7.77 (dd, J = 10.4, 5.7 Hz, 1H), 7.69-7.60 (m, 1H), 7.54-7.46 (m, 1H), 5.77 (s, 2H), 4.68 (t, J = 5.1 Hz, 2H), 4.55 (s, 2H), 3.73 (t, J = 4.9 Hz, 2H), 3.25 (s, 3H). |
| 214 | 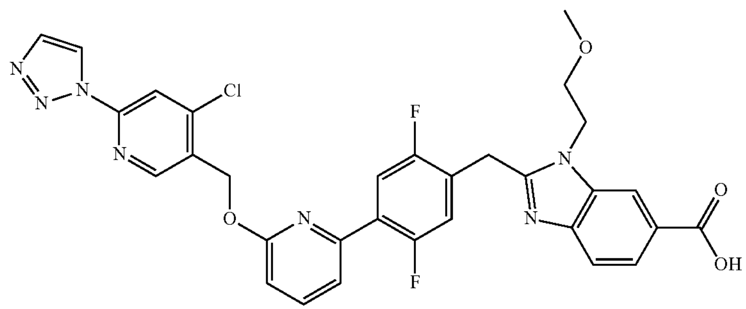 | 35 | 632 | 1H NMR (400 MHz, DMSO-d6) δ 8.91 (s, 1H), 8.83 (s, 1H), 8.31 (s, 1H), 8.22 (s, 1H), 8.03 (s, 1H), 7.95-7.84 (m, 2H), 7.80 (d, J = 8.7 Hz, 1H), 7.62 (s, 1H), 7.55 (d, J = 7.7 Hz, 1H), 7.40 (dd, J = 11.6, 6.2 Hz, 1H), 7.01 (d, J = 8.4 Hz, 1H), 5.67 (s, 2H), 4.60 (s, 2H), 4.46 (s, 2H), 3.69 (t, J = 5.0 Hz, 2H), 3.21 (s, 3H). |
| 215 | 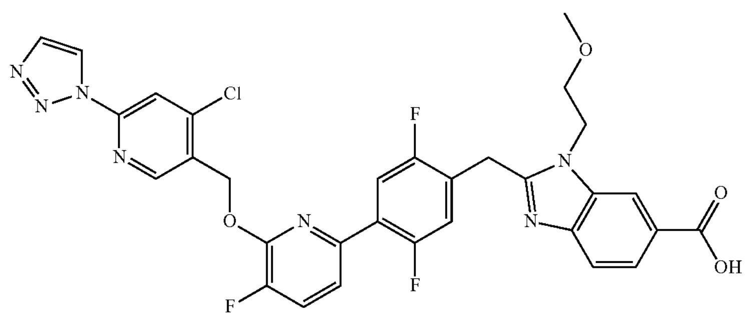 [SMILES: COCCn1c(Cc2cc(F)c(-c3ccc(F)c(OCc4cnc(-n5ccnn5)cc4Cl)n3)cc2F)nc2ccc(C(=O)O)cc21] | 35 | 650 | 1H NMR (400 MHz, DMSO-d6) δ 8.91 (d, J = 1.3 Hz, 1H), 8.85 (s, 1H), 8.33 (s, 1H), 8.22 (s, 1H), 8.04 (d, J = 1.3 Hz, 1H), 7.93-7.83 (m, 2H), 7.83-7.78 (m, 2H), 7.61 (d, J = 8.4 Hz, 1H), 7.57 (d, J = 8.9 Hz, 1H), 7.41 (dd, J = 10.9, 6.5 Hz, 1H), 5.76 (s, 2H), 4.60 (d, J = 5.7 Hz, 2H), 4.46 (s, 2H), 3.69 (t, J = 5.0 Hz, 2H), 3.21 (s, 3H). |

TABLE 2-continued

Compounds

| Ex. | Structure | Procedure | ES/MS m/z | ¹H NMR |
|---|---|---|---|---|
| 216 | 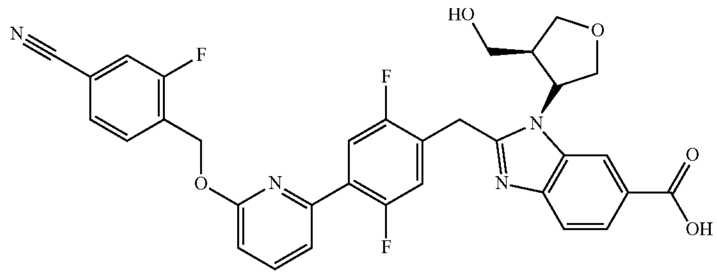 | 5 | 615 | 1H NMR (400 MHz, DMSO-d6) δ 8.55 (s, 1H), 7.98-7.85 (m, 2H), 7.85-7.70 (m, 4H), 7.61 (d, J = 8.4 Hz, 1H), 7.54 (d, J = 7.3 Hz, 1H), 7.37 (dd, J = 11.5, 6.0 Hz, 1H), 7.00 (d, J = 8.3 Hz, 1H), 5.61 (s, 2H), 5.53 (d, J = 7.6 Hz, 1H), 4.55 (s, 2H), 4.50 (d, J = 10.8 Hz, 1H), 4.21 (dd, J = 10.9, 6.5 Hz, 1H), 4.06 (t, J = 8.7 Hz, 1H), 3.80 (t, J = 8.3 Hz, 1H), 3.18-3.09 (m, 1H), 3.00 (q, J = 7.8 Hz, 1H), 2.75 (t, J = 9.5 Hz, 1H). |
| 217 | 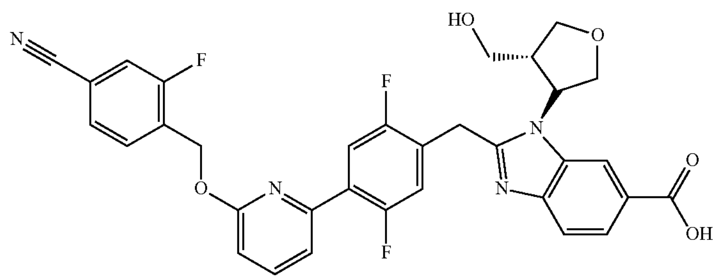 | 5 | 615 | 1H NMR (400 MHz, DMSO-d6) δ 8.42 (s, 1H), 7.96-7.86 (m, 2H), 7.84 (dd, J = 8.5, 1.5 Hz, 1H), 7.77 (t, J = 8.8, 4.8 Hz, 3H), 7.65 (d, J = 8.5 Hz, 1H), 7.54 (d, J = 7.3 Hz, 1H), 7.39 (dd, J = 11.5, 6.1 Hz, 1H), 7.00 (d, J = 8.3 Hz, 1H), 5.61 (s, 2H), 5.26 (s, 1H), 4.65-4.46 (m, 2H), 4.37 (t, J = 8.5 Hz, 1H), 4.21 (dd, J = 10.5, 3.2 Hz, 1H), 4.08 (dd, J = 10.4, 7.9 Hz, 1H), 3.62-3.46 (m, 3H), 2.76 (d, J = 7.3 Hz, 1H). |
| 218 | 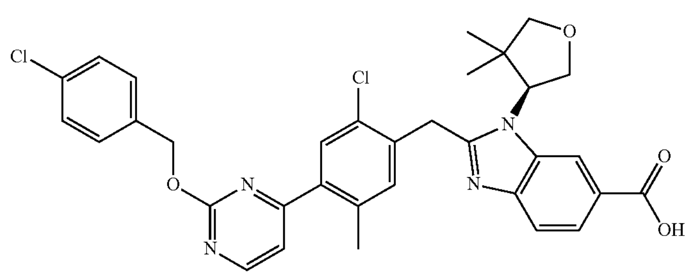 | 35 | 618 | 1H NMR (400 MHz, DMSO-d6) δ 8.74 (d, J = 5.0 Hz, 1H), 8.50 (s, 1H), 7.81 (dd, J = 8.4, 1.5 Hz, 1H), 7.62 (t, J = 4.2 Hz, 2H), 7.55-7.42 (m, 5H), 7.41 (s, 1H), 5.46 (s, 2H), 5.01 (d, J = 6.7 Hz, 1H), 4.56 (dd, J = 22.6, 14.0 Hz, 2H), 3.81 (d, J = 8.7 Hz, 1H), 3.73 (d, J = 8.6 Hz, 1H), 2.36 (s, 3H), 1.34 (s, 3H), 0.66 (s, 3H). |

TABLE 2-continued

Compounds

| Ex. | Structure | Procedure | ES/MS m/z | ¹H NMR |
|---|---|---|---|---|
| 219 | 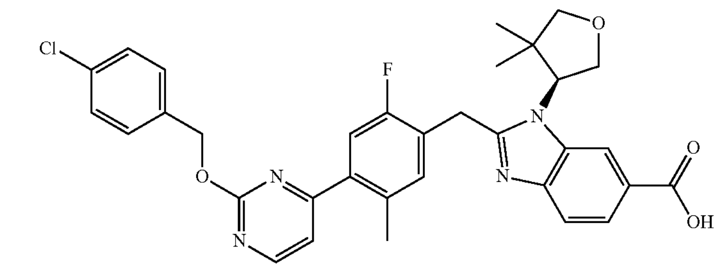 [SMILES: Cc1cc(Cc2nc3ccc(C(=O)O)cc3n2[C@@H]2COCC2(C)C)c(F)cc1-c1ccnc(OCc2ccc(Cl)cc2)n1] | 35 | 601 | 1H NMR (400 MHz, DMSO-d6) δ 8.73 (d, J = 5.1 Hz, 1H), 8.49 (s, 1H), 7.81 (dd, J = 8.5, 1.5 Hz, 1H), 7.62 (d, J = 8.5 Hz, 1H), 7.54-7.45 (m, 4H), 7.44-7.33 (m, 3H), 5.45 (s, 2H), 5.01 (d, J = 6.7 Hz, 1H), 4.58-4.29 (m, 4H), 3.82-3.67 (m, 2H), 2.36 (s, 3H), 1.32 (s, 3H), 0.60 (s, 3H). |
| 220 | 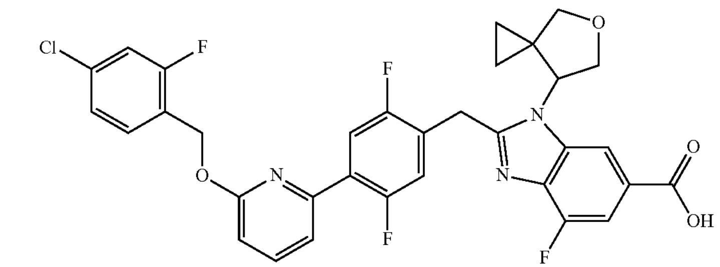 [SMILES: O=C(O)c1cc(F)c2nc(Cc3cc(F)c(-c4cccc(OCc5ccc(Cl)cc5F)n4)cc3F)n(C3COCC34CC4)c2c1] | 35 | 638 | 1H NMR (400 MHz, DMSO-d6) δ 8.39 (s, 1H), 7.92-7.79 (m, 2H), 7.61 (t, J = 8.2 Hz, 1H), 7.57-7.45 (m, 3H), 7.43-7.26 (m, 2H), 6.95 (d, J = 8.3 Hz, 1H), 5.51 (s, 2H), 5.24 (s, 1H), 4.42 (s, 2H), 4.35-4.23 (m, 2H), 4.03 (d, J = 8.9 Hz, 1H), 3.90 (d, J = 8.9 Hz, 1H), 1.00-0.44 (m, 3H), −0.11 (s, 1H). |
| 221 | 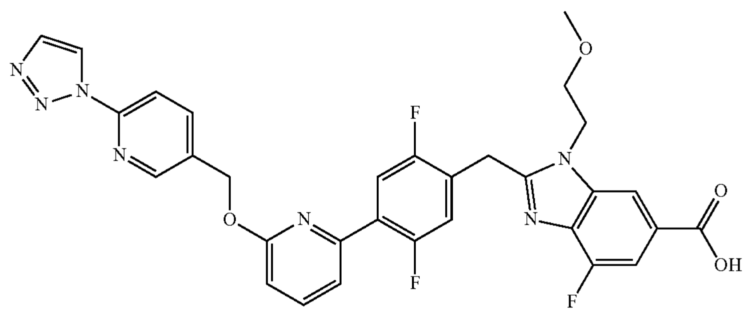 [SMILES: COCCn1c(Cc2cc(F)c(-c3cccc(OCc4ccc(-n5ccnn5)nc4)n3)cc2F)nc2c(F)cc(C(=O)O)cc21] | 35 | 616 | 1H NMR (400 MHz, DMSO-d6) δ 8.88 (d, J = 1.2 Hz, 1H), 8.76 (d, J = 2.1 Hz, 1H), 8.25 (dd, J = 8.3, 2.2 Hz, 1H), 8.17 (d, J = 8.4 Hz, 1H), 8.10 (d, J = 1.3 Hz, 1H), 8.00 (d, J = 1.2 Hz, 1H), 7.95-7.80 (m, 2H), 7.57-7.47 (m, 2H), 7.40 (dd, J = 11.5, 6.1 Hz, 1H), 7.00 (d, J = 8.2 Hz, 1H), 5.63 (s, 2H), 4.62 (t, J = 5.1 Hz, 2H), 4.47 (s, 2H), 3.68 (t, J = 5.0 Hz, 2H), 3.21 (s, 3H). |

TABLE 2-continued

Compounds

| Ex. | Structure | Procedure | ES/MS m/z | ¹H NMR |
|---|---|---|---|---|
| 222 | | 35 | 633 | 1H NMR (400 MHz, DMSO-d6) δ 8.84 (d, J = 1.2 Hz, 1H), 8.11 (d, J = 1.3 Hz, 1H), 8.04-7.89 (m, 4H), 7.73 (d, J = 8.5 Hz, 3H), 7.63-7.55 (m, 1H), 7.53-7.44 (m, 1H), 7.05 (d, J = 8.3 Hz, 1H), 5.58 (s, 2H), 4.68 (t, J = 5.2 Hz, 2H), 4.55 (s, 2H), 3.73 (t, J = 4.9 Hz, 2H), 3.24 (s, 3H). |
| 223 | | 35 | 651 | 1H NMR (400 MHz, DMSO-d6) δ 8.84 (d, J = 1.2 Hz, 1H), 8.11 (d, J = 1.3 Hz, 1H), 8.02-7.86 (m, 4H), 7.73 (dd, J = 18.0, 8.6 Hz, 3H), 7.65-7.56 (m, 1H), 7.50 (dd, J = 11.4, 1.3 Hz, 1H), 5.67 (s, 2H), 4.68 (t, J = 5.0 Hz, 2H), 4.54 (s, 2H), 3.73 (t, J = 5.0 Hz, 2H), 3.24 (s, 3H). |
| 224 | | 35 | 647 | 1H NMR (400 MHz, DMSO-d6) δ 8.39 (s, 1H), 8.01-7.93 (m, 1H), 7.87 (dd, J = 10.2, 8.2 Hz, 1H), 7.84-7.70 (m, 3H), 7.54 (dd, J = 14.2, 10.3 Hz, 2H), 7.37(dd, J = 11.2, 6.3 Hz, 1H), 5.70 (s, 2H), 5.24 (s, 1H),4.41 (s, 2H), 4.35-4.24 (m, 2H), 4.02 (d, J = 8.9 Hz, 1H), 3.90 (d, J = 8.9 Hz, 1H), 0.93-0.50 (m, 3H), −0.11 (s, 1H). |

TABLE 2-continued

Compounds

| Ex. | Structure | Procedure | ES/MS m/z | ¹H NMR |
|---|---|---|---|---|
| 225 | 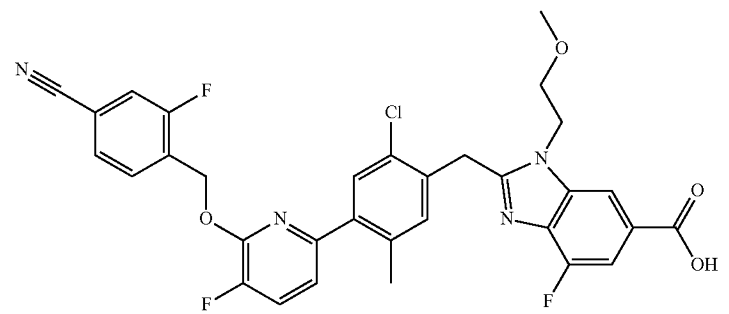 [SMILES: COCCn1c(Cc2cc(C)c(-c3ccc(F)c(OCc4ccc(C#N)cc4F)n3)cc2Cl)nc2c(F)cc(C(=O)O)cc21] | 35 | 621 | 1H NMR (400 MHz, DMSO-d6) δ 8.09 (d, J = 1.2 Hz, 1H), 7.96-7.91 (m, 1H), 7.85 (dd, J = 10.5, 8.1 Hz, 1H), 7.74 (d, J = 4.7 Hz, 2H), 7.55-7.47 (m, 1H), 7.43 (s, 1H), 7.31 (d, J = 9.4 Hz, 2H), 5.61 (s, 2H), 4.61 (t, J = 5.1 Hz, 2H), 4.47 (s, 2H), 3.69 (t, J = 5.0 Hz, 2H), 3.22 (s, 3H), 2.25 (s, 3H). |
| 226 | 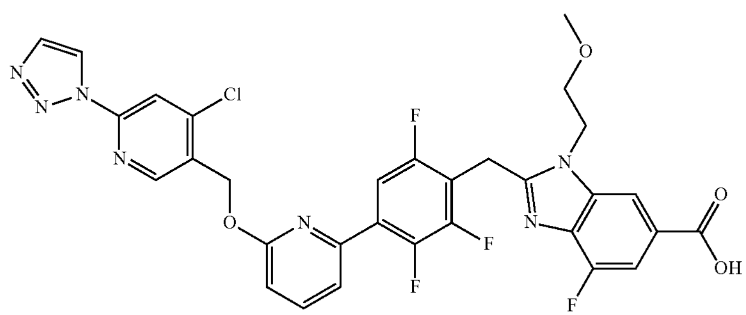 [SMILES: COCCn1c(Cc2c(F)cc(-c3cccc(OCc4cnc(-n5ccnn5)cc4Cl)n3)c(F)c2F)nc2c(F)cc(C(=O)O)cc21] | 35 | 668 | 1H NMR (400 MHz, DMSO-d6) δ 8.91 (d, J = 1.3 Hz, 1H), 8.84 (s, 1H), 8.31 (s, 1H), 8.11 (d, J = 1.3 Hz, 1H), 8.03 (d, J = 1.3 Hz, 1H), 7.96 (t, J = 7.9 Hz, 1H), 7.84-7.74 (m, 1H), 7.61 (d, J = 7.3 Hz, 1H), 7.50 (d, J = 11.4 Hz, 1H), 7.06 (d, J = 8.3 Hz, 1H), 5.68 (s, 2H), 4.68 (t, J = 5.1 Hz, 2H), 4.56 (s, 2H), 3.73 (t, J = 5.0 Hz, 2H), 3.25 (s, 3H). |
| 227 | 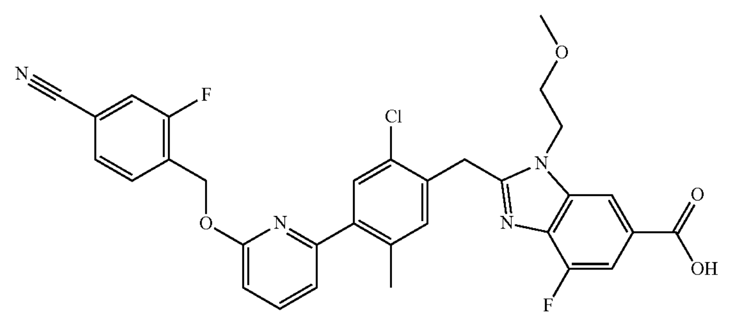 [SMILES: COCCn1c(Cc2cc(C)c(-c3cccc(OCc4ccc(C#N)cc4F)n3)cc2Cl)nc2c(F)cc(C(=O)O)cc21] | 35 | 603 | 1H NMR (400 MHz, DMSO-d6) δ 8.09 (d, J = 1.3 Hz, 1H), 7.95-7.84 (m, 2H), 7.72 (d, J = 5.8 Hz, 2H), 7.50 (dd, J = 11.4, 1.3 Hz, 1H), 7.43 (s, 1H), 7.29 (s, 1H), 7.27 (d, J = 7.3 Hz, 1H), 6.96 (d, J = 8.3 Hz, 1H), 5.52 (s, 2H), 4.60 (t, J = 5.1 Hz, 2H), 4.47 (s, 2H), 3.68 (t, J = 5.0 Hz, 2H), 3.22 (s, 3H), 2.25 (s, 3H). |

TABLE 2-continued

Compounds

| Ex. | Structure | Procedure | ES/MS m/z | ¹H NMR |
|---|---|---|---|---|
| 228 | 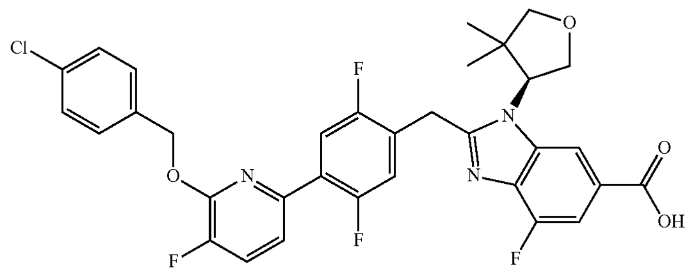 | 35 | 640.1 | 1H NMR (400 MHz, DMSO-d6) δ 8.35 (s, 1H), 7.83 (ddd, J = 20.6, 10.3, 7.3 Hz, 2H), 7.59-7.50 (m, 4H), 7.50-7.43 (m, 3H), 5.57 (s, 2H), 5.04 (d, J = 6.8 Hz, 1H), 4.64-4.49 (m, 2H), 4.49-4.33 (m, 2H), 3.75 (q, J = 8.7 Hz, 2H), 1.34 (s, 3H), 0.62 (s, 3H). |
| 229 | 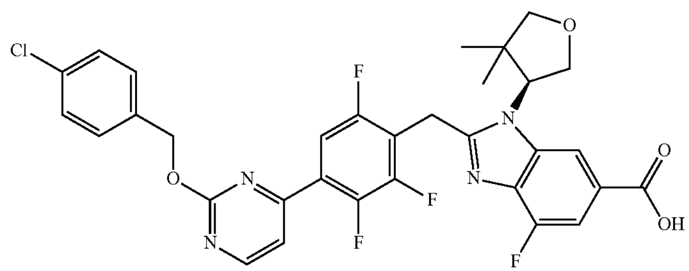 [SMILES: CC1(C)COC[C@H]1n1c(Cc2c(F)cc(-c3ccnc(OCc4ccc(Cl)cc4)n3)c(F)c2F)nc2c(F)cc(C(=O)O)cc21] | 35 | 641.6 | 1H NMR (400 MHz, DMSO-d6) δ 8.84 (d, J = 5.1 Hz, 1H), 8.36 (s, 1H), 7.90-7.79 (m, 1H), 7.69 (dd, J = 5.1, 1.7 Hz, 1H), 7.60-7.41 (m, 5H), 5.52 (s, 2H), 5.11 (d, J = 6.5 Hz, 1H), 4.70 (d, J = 17.4 Hz, 1H), 4.56 (d, J = 11.5 Hz, 1H), 4.52-4.31 (m, 2H), 3.76 (s, 2H), 1.40 (s, 3H), 0.67 (s, 3H). |
| 230 | 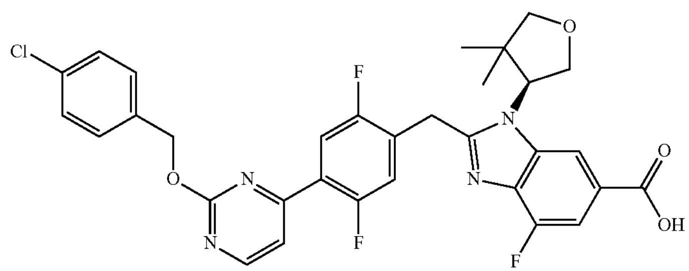 [SMILES: CC1(C)COC[C@H]1n1c(Cc2cc(F)c(-c3ccnc(OCc4ccc(Cl)cc4)n3)cc2F)nc2c(F)cc(C(=O)O)cc21] | 35 | 623.6 | 1H NMR (400 MHz, DMSO-d6) δ 8.78 (d, J = 5.1 Hz, 1H), 8.36 (s, 1H), 7.95 (dd, J = 10.2, 6.2 Hz, 1H), 7.63 (dd, J = 5.3, 1.8 Hz, 1H), 7.59-7.49 (m, 4H), 7.47 (d, J = 8.4 Hz, 2H), 5.51 (s, 2H), 5.04 (d, J = 6.5 Hz, 1H), 4.56 (dd, J = 22.4, 14.1 Hz, 2H), 4.49-4.35 (m, 2H), 3.75 (q, J = 8.6 Hz, 2H), 1.34 (s, 3H), 0.62 (s, 3H). |

TABLE 2-continued

Compounds

| Ex. | Structure | Procedure | ES/MS m/z | ¹H NMR |
|---|---|---|---|---|
| 231 | 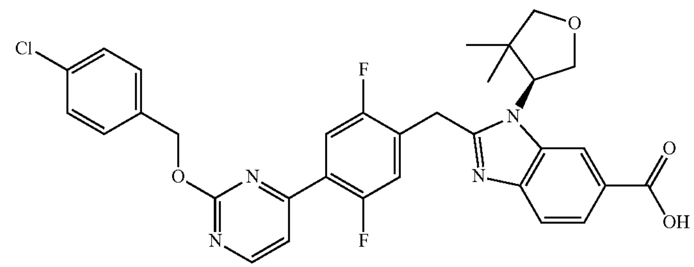 [SMILES: CC1(C)COC[C@H]1n1c(Cc2cc(F)c(-c3ccnc(OCc4ccc(Cl)cc4)n3)cc2F)nc2ccc(C(=O)O)cc21] | 35 | 606.6 | 1H NMR (400 MHz, DMSO-d6) δ 8.78 (d, J = 5.2 Hz, 1H), 8.48 (s, 1H), 7.93 (dd, J = 10.2, 6.2 Hz, 1H), 7.79 (dd, J = 8.5, 1.4 Hz, 1H), 7.65-7.59 (m, 2H), 7.59-7.51 (m, 3H), 7.47 (d, J = 8.5 Hz, 2H), 5.51 (s, 2H), 5.01 (d, J = 6.5 Hz, 1H), 4.61-4.49 (m, 2H), 4.49-4.34 (m, 2H), 3.76 (q, J = 8.6 Hz, 2H), 1.34 (s, 3H), 0.61 (s, 3H). |
| 232 | 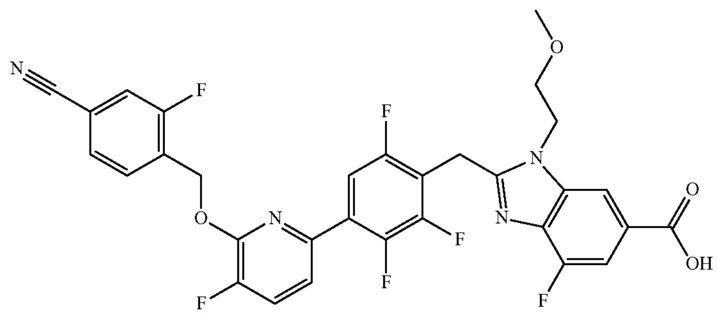 [SMILES: COCCn1c(Cc2c(F)cc(-c3ccc(F)c(OCc4ccc(C#N)cc4F)n3)c(F)c2F)nc2c(F)cc(C(=O)O)cc21] | 35 | 626.6 | 1H NMR (400 MHz, DMSO-d6) δ 8.11 (d, J = 1.3 Hz, 1H), 7.97-7.86 (m, 2H), 7.83-7.74 (m, 2H), 7.64 (ddt, J = 16.9, 8.4, 1.7 Hz, 2H), 7.50 (dd, J = 11.4, 1.3 Hz, 1H), 5.70 (s, 2H), 4.68 (t, J = 5.1 Hz, 2H), 4.54 (s, 2H), 3.73 (t, J = 5.0 Hz, 2H), 3.24 (s, 3H). |
| 233 | 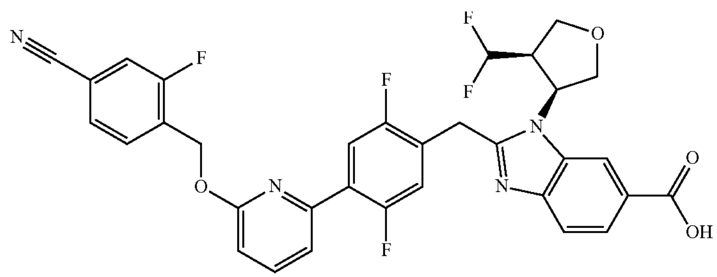 [SMILES: N#Cc1ccc(COc2cccc(-c3cc(F)c(Cc4nc5ccc(C(=O)O)cc5n4[C@@H]4COC[C@@H]4C(F)F)cc3F)n2)c(F)c1] | 35 with Chiral separation peak 2 | 634.6 | 1H NMR (400 MHz, DMSO-d6) δ 8.55 (s, 1H), 7.97-7.87 (m, 2H), 7.84-7.71 (m, 4H),7.61 (d, J = 8.5 Hz, 1H), 7.54 (dd, J = 7.5, 1.7 Hz, 1H), 7.39 (dd, J = 11.4, 6.1 Hz, 1H), 7.00 (d, J = 8.3 Hz, 1H), 5.82-5.40 (m, 3H), 4.62-4.49 (m, 2H), 4.40 (d, J = 17.0 Hz, 1H), 4.29-4.13 (m, 2H), 4.09 (t, J = 9.1 Hz, 1H), 3.58-3.49 (m, 2H). |

TABLE 2-continued

Compounds

| Ex. | Structure | Procedure | ES/MS m/z | ¹H NMR |
|---|---|---|---|---|
| 234 | 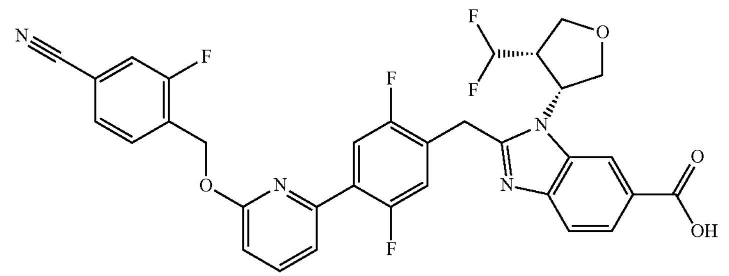 [SMILES: N#Cc1ccc(COc2cccc(-c3cc(F)c(Cc4nc5ccc(C(=O)O)cc5n4[C@H]4COC[C@H]4C(F)F)cc3F)n2)c(F)c1] | 35 with Chiral separation peak 1 | 634.6 | 1H NMR (400 MHz, DMSO-d6) δ 8.55 (s, 1H), 7.97-7.87 (m, 2H), 7.84-7.71 (m, 4H), 7.61 (d, J = 8.5 Hz, 1H), 7.54 (dd, J = 7.5, 1.7 Hz, 1H), 7.39 (dd, J = 11.4, 6.1 Hz, 1H), 7.00 (d, J = 8.3 Hz, 1H), 5.82-5.40 (m, 3H), 4.62-4.49 (m, 2H), 4.40 (d, J = 17.0 Hz, 1H), 4.29-4.13 (m, 2H), 4.09 (t, J = 9.1 Hz, 1H), 3.58-3.49 (m, 2H). |
| 235 | 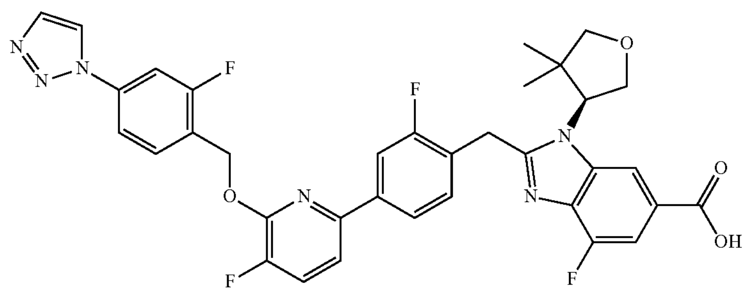 [SMILES: CC1(C)COC[C@H]1n1c(Cc2ccc(-c3ccc(F)c(OCc4ccc(-n5ccnn5)cc4F)n3)cc2F)nc2c(F)cc(C(=O)O)cc21] | 35 | 673.3 | 1H NMR (400 MHz, DMSO-d6) δ 8.90 (d, J = 1.2 Hz, 1H), 8.35 (s, 1H), 8.01 (d, J = 1.2 Hz, 1H), 7.99-7.90 (m, 3H), 7.90-7.79 (m, 3H), 7.72 (dd, J = 8.3, 2.8 Hz, 1H), 7.56-7.46 (m, 2H), 5.71 (s, 2H), 5.01 (d, J = 6.5 Hz, 1H), 4.59-4.46 (m, 2H), 4.46-4.34 (m, 2H), 3.82-3.69 (m, 2H), 1.30 (s, 3H), 0.58 (s, 3H). |
| 236 | 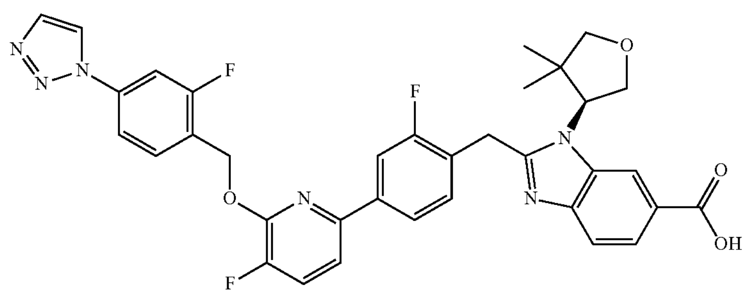 [SMILES: CC1(C)COC[C@H]1n1c(Cc2ccc(-c3ccc(F)c(OCc4ccc(-n5ccnn5)cc4F)n3)cc2F)nc2ccc(C(=O)O)cc21] | 35 | 655.4 | 1H NMR (400 MHz, DMSO-d6) δ 8.90 (d, J = 1.3 Hz, 1H), 8.50 (s, 1H), 8.01 (d, J = 1.2 Hz, 1H), 7.99-7.90 (m, 3H), 7.90-7.81 (m, 4H), 7.72 (dd, J = 8.2, 2.7 Hz, 1H), 7.63 (t, J = 8.1 Hz, 1H), 7.51 (s, 2H), 5.01 (d, J = 6.7 Hz, 1H), 4.63-4.49 (m, 2H), 4.49-4.37 (m, 2H), 3.83-3.67 (m, 2H), 1.30 (s, 3H), 0.58 (s, 3H). |

TABLE 2-continued

Compounds

| Ex. | Structure | Procedure | ES/MS m/z | ¹H NMR |
|---|---|---|---|---|
| 237 | 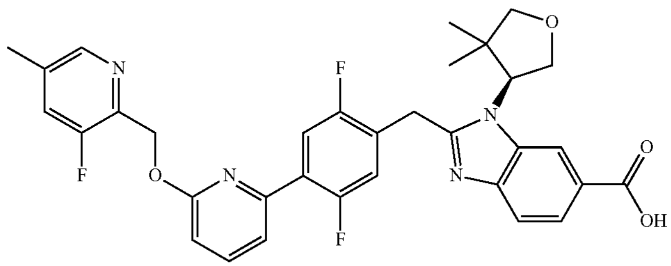 [SMILES: Cc1cnc(COc2cccc(-c3cc(F)c(Cc4nc5ccc(C(=O)O)cc5n4[C@@H]4COCC4(C)C)cc3F)n2)c(F)c1] | 35 | 603.4 | 1H NMR (400 MHz, DMSO-d6) δ 8.51 (s, 1H), 8.29 (s, 1H), 7.93-7.79 (m, 3H), 7.63 (dd, J = 11.7, 9.4 Hz, 2H), 7.53 (dd, J = 7.5, 1.6 Hz, 1H), 7.46 (dd, J = 11.5, 6.0 Hz, 1H), 6.94 (d, J = 8.3 Hz, 1H), 5.56 (d, J = 1.8 Hz, 2H), 5.04 (d, J = 6.6 Hz, 1H), 4.61-4.50 (m, 2H), 4.49-4.36 (m, 2H), 3.86-3.57 (m, 2H), 2.34 (s, 3H), 1.33 (s, 3H), 0.61 (s, 3H). |
| 238 | 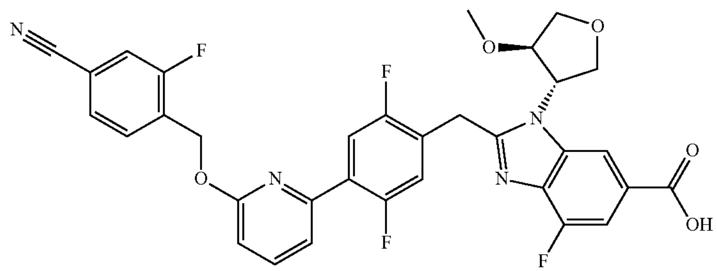 [SMILES: CO[C@H]1COC[C@@H]1n1c(Cc2cc(F)c(-c3cccc(OCc4ccc(C#N)cc4F)n3)cc2F)nc2c(F)cc(C(=O)O)cc21] | 3 | 633.0 | 1H NMR (400 MHz, DMSO-d6) δ 8.27 (d, J = 1.3 Hz, 1H), 7.99-7.83 (m, 2H), 7.83-7.68 (m, 3H), 7.53 (dd, J = 7.5, 1.7 Hz, 1H), 7.49 (dd, J = 11.2, 1.3 Hz, 1H), 7.31 (dd, J = 11.5, 6.1 Hz, 1H), 7.00 (d, J = 8.2 Hz, 1H), 5.73-5.47 (m, 3H), 4.53 (s, 2H), 4.40 (dd, J = 10.7, 3.4 Hz, 1H), 4.17-4.09 (m, 2H), 4.01 (dd, J = 10.6, 8.2 Hz, 1H), 3.78 (dd, J = 10.5, 4.6 Hz, 1H), 2.87 (s, 3H). |
| 239 | 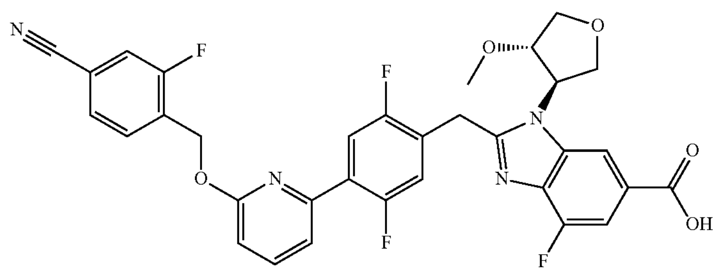 [SMILES: CO[C@@H]1COC[C@H]1n1c(Cc2cc(F)c(-c3cccc(OCc4ccc(C#N)cc4F)n3)cc2F)nc2c(F)cc(C(=O)O)cc21] | 3 | 633.0 | 1H NMR (400 MHz, DMSO-d6) δ 8.27 (d, J = 1.3 Hz, 1H), 7.99-7.83 (m, 2H), 7.83-7.68 (m, 3H), 7.53 (dd, J = 7.5, 1.7 Hz, 1H), 7.49 (dd, J = 11.2, 1.3 Hz, 1H), 7.31 (dd, J = 11.5, 6.1 Hz, 1H), 7.00 (d, J = 8.2 Hz, 1H), 5.73-5.47 (m, 3H), 4.53 (s, 2H), 4.40 (dd, J = 10.7, 3.4 Hz, 1H), 4.17-4.09 (m, 2H), 4.01 (dd, J = 10.6, 8.2 Hz, 1H), 3.78 (dd, J = 10.5, 4.6 Hz, 1H), 2.87 (s, 3H). |

TABLE 2-continued

Compounds

| Ex. | Structure | Procedure | ES/MS m/z | ¹H NMR |
|---|---|---|---|---|
| 240 | 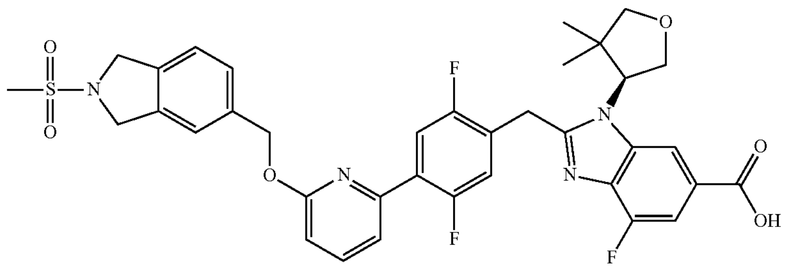 [SMILES: CC1(C)COC[C@H]1n1c(Cc2cc(F)c(-c3cccc(OCc4ccc5c(c4)CN(S(C)(=O)=O)C5)n3)cc2F)nc2c(F)cc(C(=O)O)cc21] | 35 | 706.6 | 1H NMR (400 MHz, DMSO-d6) δ 8.36 (s, 1H), 7.94-7.78 (m, 2H), 7.55-7.42 (m, 5H), 7.35 (d, J = 7.8 Hz, 1H), 6.94 (d, J = 8.3 Hz, 1H), 5.49 (s, 2H), 5.04 (d, J = 6.5 Hz, 1H), 4.64 (d, J = 3.4 Hz, 4H), 4.60-4.34 (m, 4H), 3.75 (q, J = 8.7 Hz, 2H), 2.96 (s, 3H), 1.34 (s, 3H), 0.62 (s, 3H). |
| 241 | 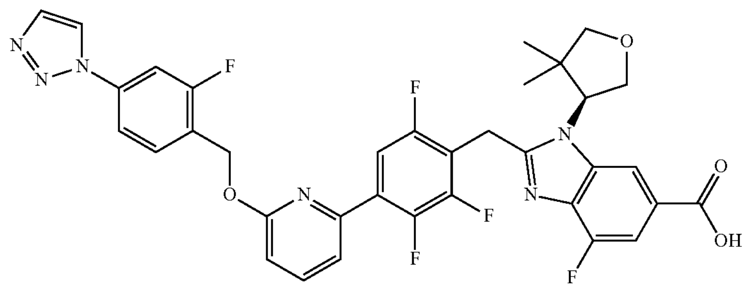 [SMILES: CC1(C)COC[C@H]1n1c(Cc2c(F)cc(-c3cccc(OCc4ccc(-n5ccnn5)cc4F)n3)c(F)c2F)nc2c(F)cc(C(=O)O)cc21] | 35 | 690.6 | 1H NMR (400 MHz, DMSO-d6) δ 8.90 (d, J = 1.2 Hz, 1H), 8.36 (s, 1H), 8.01 (d, J = 1.2 Hz, 1H), 7.97-7.89 (m, 2H), 7.89-7.74 (m, 3H), 7.64-7.58 (m, 1H), 7.51 (dd, J = 11.2, 1.2 Hz, 1H), 7.04 (d, J = 8.3 Hz, 1H), 5.61 (s, 2H), 5.11 (d, J = 6.4 Hz, 1H), 4.67 (dd, J = 17.4 Hz, 1H), 4.56 (d, J = 11.3, 6.6 Hz, 1H), 4.38 (d, J = 17.5 Hz, 1H), 3.76 (s, 2H), 1.39 (s, 3H), 0.67 (s, 3H). |
| 242 | 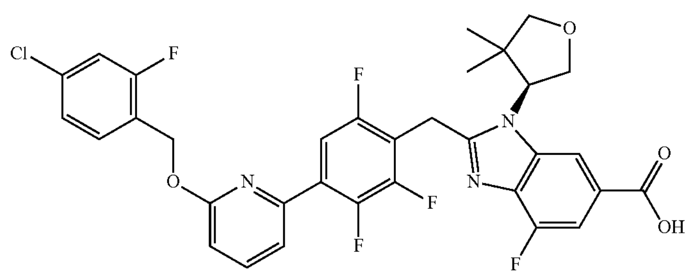 [SMILES: CC1(C)COC[C@H]1n1c(Cc2c(F)cc(-c3cccc(OCc4ccc(Cl)cc4F)n3)c(F)c2F)nc2c(F)cc(C(=O)O)cc21] | 35 | 659.5 | 1H NMR (400 MHz, DMSO-d6) δ 8.36 (s, 1H), 7.93 (t, J = 7.9 Hz, 1H), 7.76 (ddd, J = 10.4, 5.7, 2.0 Hz, 1H), 7.65-7.57 (m, 2H), 7.51 (ddd, J = 10.0, 5.3, 1.6 Hz, 2H), 7.33 (dd, J = 8.3, 2.0 Hz, 1H), 7.01 (d, J = 8.3 Hz, 1H), 5.52 (s, 2H), 5.11 (d, J = 6.4 Hz, 1H), 4.67 (d, J = 17.4 Hz, 1H), 4.56 (dd, J = 11.3, 6.7 Hz, 1H), 4.46 (dd, J = 17.4 Hz, 1H), 4.38 (d, J = 17.4 Hz, 1H), 3.76 (s, 2H), 1.39 (s, 3H), 0.67 (s, 3H). |

TABLE 2-continued

Compounds

| Ex. | Structure | Procedure | ES/MS m/z | ¹H NMR |
|---|---|---|---|---|
| 243 | 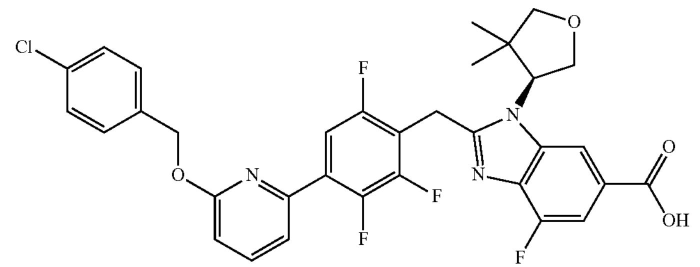 [SMILES: CC1(C)COC[C@H]1n1c(Cc2c(F)cc(-c3cccc(OCc4ccc(Cl)cc4)n3)c(F)c2F)nc2c(F)cc(C(=O)O)cc21] | 35 | 641.6 | 1H NMR (400 MHz, DMSO-d6) δ 8.36 (s, 1H), 7.93 (t, J = 7.9 Hz, 1H), 7.73 (ddd, J = 10.7, 5.6, 1.9 Hz, 1H), 7.57 (dd, J = 7.4, 1.7 Hz, 1H), 7.55-7.49 (m, 3H), 7.46 (d, J = 8.5 Hz, 2H), 7.01 (d, J = 8.3 Hz, 1H), 5.49 (s, 2H), 5.11 (d, J = 6.5 Hz, 1H), 4.67 (d, J = 17.4 Hz, 1H), 4.56 (d, J = 11.2 Hz, 1H), 4.46 (dd, J = 11.3, 6.6 Hz, 1H), 4.37 (d, J = 17.4 Hz, 1H), 3.76 (s, 2H), 1.39 (s, 3H), 0.67 (s, 3H). |
| 244 | 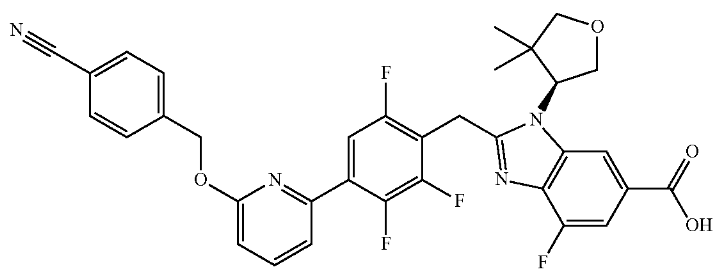 [SMILES: CC1(C)COC[C@H]1n1c(Cc2c(F)cc(-c3cccc(OCc4ccc(C#N)cc4)n3)c(F)c2F)nc2c(F)cc(C(=O)O)cc21] | 35 | 630.6 | 1H NMR (400 MHz, DMSO-d6) δ 8.36 (s, 1H), 7.96 (d, J = 7.7 Hz, 1H), 7.92-7.85 (m, 2H), 7.74-7.62 (m, 3H), 7.61-7.56 (m, 1H), 7.54-7.46 (m, 1H), 7.06 (d, J = 8.3 Hz, 1H), 5.60 (s, 2H), 5.11 (d, J = 6.5 Hz, 1H), 4.66 (d, J = 17.4 Hz, 1H), 4.55 (d, J = 11.2 Hz, 1H), 4.46 (dd, J = 11.3, 6.6 Hz, 1H), 4.37 (d, J = 17.4 Hz, 1H), 3.76 (s, 2H), 1.39 (s, 3H), 0.66 (s, 3H). |
| 245 | 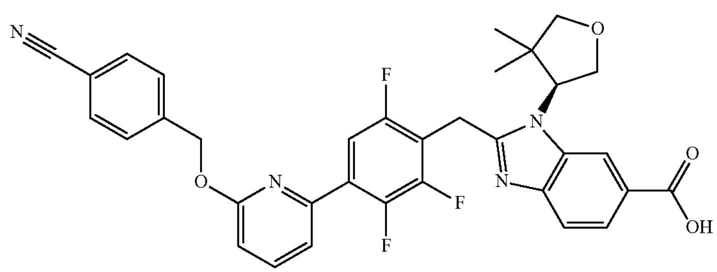 [SMILES: CC1(C)COC[C@H]1n1c(Cc2c(F)cc(-c3cccc(OCc4ccc(C#N)cc4)n3)c(F)c2F)nc2ccc(C(=O)O)cc21] | 35 | 612.6 | 1H NMR (400 MHz, DMSO-d6) δ 8.48 (s, 1H), 7.95 (t, J = 7.9 Hz, 1H), 7.88 (d, J = 8.2 Hz, 2H), 7.78 (dd, J = 8.4, 1.4 Hz, 1H), 7.69 (d, J = 8.0 Hz, 2H), 7.68-7.61 (m, 1H), 7.58 (dd, J = 8.2, 2.9 Hz, 2H), 7.07 (d, J = 8.3 Hz, 1H), 5.59 (s, 2H), 5.09 (d, J = 6.6 Hz, 1H), 4.64 (d, J = 17.4 Hz, 1H), 4.57 (dd, J = 11.1, 6.8 Hz, 1H), 4.47 (dd, J = 11.2, 6.8 Hz, 1H), 4.35 (d, J = 17.3 Hz, 1H), 3.82-3.72 (m, 2H), 1.39 (s, 3H), 0.66 (s, 3H). |

TABLE 2-continued

Compounds

| Ex. | Structure | Procedure | ES/MS m/z | ¹H NMR |
|---|---|---|---|---|
| 246 | 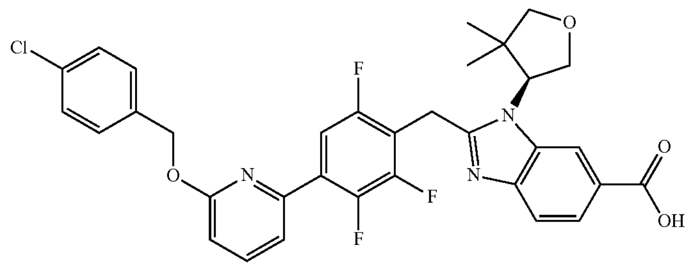 [SMILES: CC1(C)COC[C@H]1n1c(Cc2c(F)cc(-c3cccc(OCc4ccc(Cl)cc4)n3)c(F)c2F)nc2ccc(C(=O)O)cc21] | 35 | 623.6 | 1H NMR (400 MHz, DMSO-d6) δ 8.48 (s, 1H), 7.93 (t, J = 7.9 Hz, 1H), 7.78 (dd, J = 8.4, 1.5 Hz, 1H), 7.71 (ddd, J = 10.4, 5.6, 2.0 Hz, 1H), 7.63-7.50 (m, 4H), 7.46 (d, J = 8.4 Hz, 2H), 7.02 (d, J = 8.3 Hz, 1H), 5.49 (s, 2H), 5.09 (d, J = 6.6 Hz, 1H), 4.64 (d, J = 17.3 Hz, 1H), 4.57 (d, J = 11.1 Hz, 1H), 4.47 (dd, J = 11.2, 6.7 Hz, 1H), 4.35 (d, J = 17.3 Hz, 1H), 3.83-3.73 (m, 2H), 1.39 (s, 3H), 0.66 (s, 3H). |
| 247 | 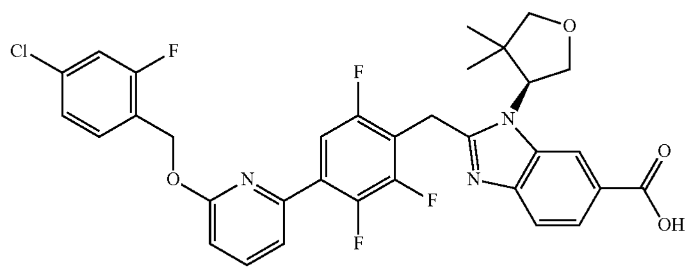 [SMILES: CC1(C)COC[C@H]1n1c(Cc2c(F)cc(-c3cccc(OCc4ccc(Cl)cc4F)n3)c(F)c2F)nc2ccc(C(=O)O)cc21] | 35 | 641.6 | 1H NMR (400 MHz, DMSO-d6) δ 8.49 (s, 1H), 7.93 (t, J = 7.9 Hz, 1H), 7.79 (dd, J = 8.5, 1.4 Hz, 1H), 7.77-7.71 (m, 1H), 7.65-7.56 (m, 3H), 7.50 (dd, J = 10.0, 2.0 Hz, 1H), 7.34 (dd, J = 8.3, 2.0 Hz, 1H), 7.01 (d, J = 8.3 Hz, 1H), 5.52 (s, 2H), 5.10 (d, J = 6.6 Hz, 1H), 4.66 (d, J = 17.3 Hz, 1H), 4.58 (d, J = 11.1 Hz, 1H), 4.47 (dd, J = 11.2, 6.7 Hz, 1H), 4.37 (d, J = 17.3 Hz, 1H), 3.84-3.69 (m, 2H), 1.39 (s, 3H), 0.66 (s, 3H). |
| 248 | 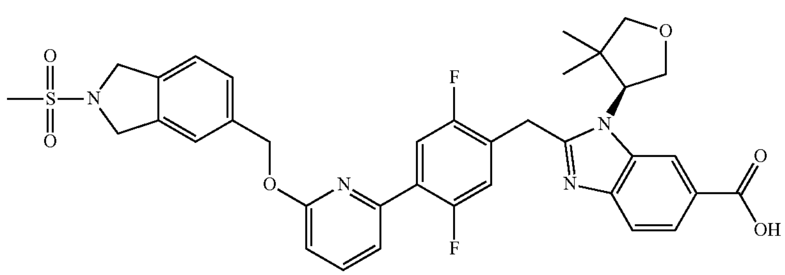 [SMILES: CC1(C)COC[C@H]1n1c(Cc2cc(F)c(-c3cccc(OCc4ccc5c(c4)CN(S(C)(=O)=O)C5)n3)cc2F)nc2ccc(C(=O)O)cc21] | 35 | 688.6 | 1H NMR (400 MHz, DMSO-d6) δ 8.50 (s, 1H), 7.92-7.78 (m, 3H), 7.63 (d, J = 8.5 Hz, 1H), 7.56-7.41 (m, 4H), 7.35 (d, J = 7.8 Hz, 1H), 6.95 (d, J = 8.3 Hz, 1H), 5.48 (s, 2H), 5.03 (d, J = 6.7 Hz, 1H), 4.64 (q, J = 2.5 Hz, 4H), 4.58-4.51 (m, 2H), 4.49-4.36 (m, 2H), 3.84-3.68 (m, 2H), 2.96 (s, 3H), 1.34 (s, 3H), 0.62 (s, 3H). |

TABLE 2-continued

Compounds

| Ex. | Structure | Procedure | ES/MS m/z | ¹H NMR |
|---|---|---|---|---|
| 249 | 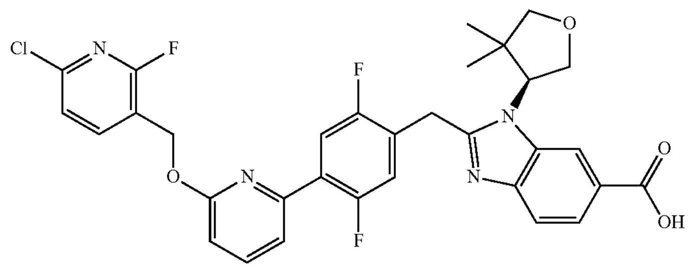 [SMILES: CC1(C)COC[C@H]1n1c(Cc2cc(F)c(-c3cccc(OCc4ccc(Cl)nc4F)n3)cc2F)nc2ccc(C(=O)O)cc21] | 27 | 624.6 | 1H NMR (400 MHz, DMSO-d6) δ 8.50 (s, 1H), 8.18 (dd, J = 9.6, 7.8 Hz 1H), 7.90 (t, J = 7.9 Hz, 1H), 7.87-7.78 (m, 2H), 7.63 (d, J = 8.5 Hz, 1H), 7.55 (dd, J = 7.8, 2.5 Hz, 2H), 7.47 (dd, J = 11.2, 6.3 Hz, 1H), 6.98 (d, J = 8.3 Hz, 1H), 5.53 (s, 2H), 5.02 (d, J = 6.6 Hz, 1H), 4.59-4.50 (m, 2H), 4.49-4.35 (m, 2H), 3.83-3.70 (m, 2H), 1.34 (s, 3H), 0.61 (s, 3H). |
| 250 | 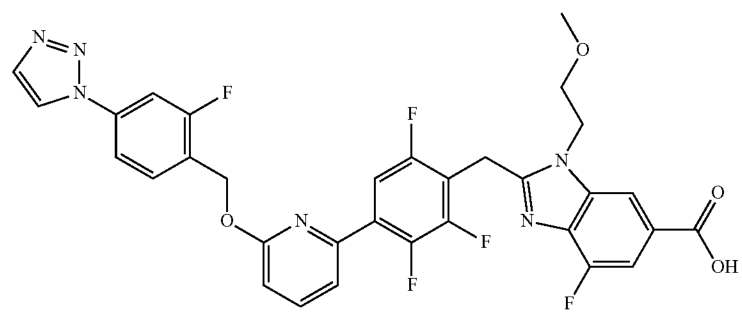 [SMILES: COCCn1c(Cc2c(F)cc(-c3cccc(OCc4ccc(-n5ccnn5)cc4F)n3)c(F)c2F)nc2c(F)cc(C(=O)O)cc21] | 27 | 650.6 | 1H NMR (400 MHz, DMSO-d6) δ 8.90 (d, J = 1.3 Hz, 1H), 8.11 (d, J = 1.3 Hz, 1H), 8.03-7.90 (m, 3H), 7.89-7.73 (m, 3H), 7.59 (d, J = 7.3 Hz, 1H), 7.50 (d, J = 11.3 Hz, 1H), 7.03 (d, J = 8.3 Hz, 1H), 5.60 (s, 2H), 4.68 (t, J = 5.1 Hz, 2H), 4.55 (s, 2H), 3.73 (t, J = 4.9 Hz, 2H), 3.24 (s, 3H). |
| 251 | 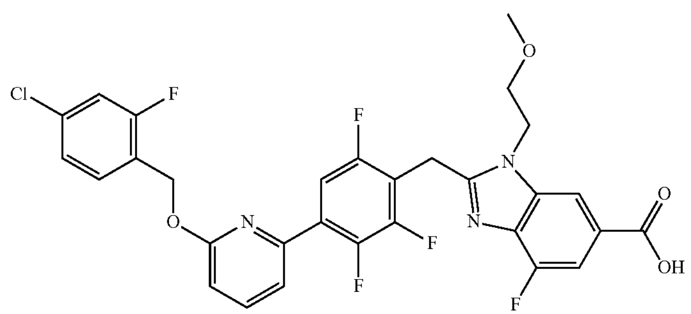 [SMILES: COCCn1c(Cc2c(F)cc(-c3cccc(OCc4ccc(Cl)cc4F)n3)c(F)c2F)nc2c(F)cc(C(=O)O)cc21] | 27 | 617.6 | 1H NMR (400 MHz, DMSO-d6) δ 8.11 (d, J = 1.3 Hz, 1H), 7.93 (t, J = 7.9 Hz, 1H), 7.77-7.69 (m, 1H), 7.64-7.56 (m, 2H), 7.54-7.46 (m, 2H), 7.33 (dd, J = 8.2, 2.0 Hz, 1H), 7.00 (d, J = 8.3 Hz, 1H), 5.52 (s, 2H), 4.68 (t, J = 5.1 Hz, 2H), 4.55 (s, 2H), 3.73 (t, J = 5.0 Hz, 2H), 3.24 (s, 3H). |

TABLE 2-continued

Compounds

| Ex. | Structure | Procedure | ES/MS m/z | ¹H NMR |
|---|---|---|---|---|
| 252 | 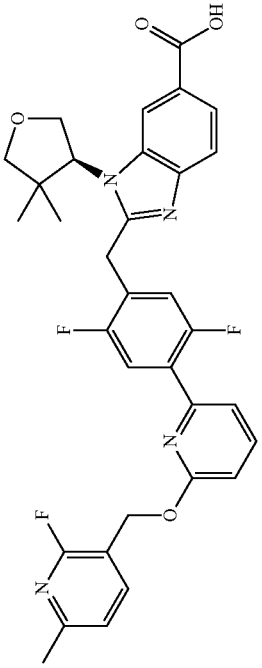 | 37 | 602.6 | 1H NMR (400 MHz, DMSO-d6) δ 8.50 (s, 1H), 7.99 (dd, J = 10.1, 7.5 Hz, 1H), 7.94-7.78 (m, 3H), 7.64 (d, J = 8.4 Hz, 1H), 7.54 (dd, J = 7.5, 1.7 Hz, 1H), 7.47 (dd, J = 11.3, 6.2 Hz, 1H), 7.24 (dd, J = 7.6, 1.9 Hz, 1H), 6.96 (d, J = 8.2 Hz, 1H), 5.48 (s, 2H), 5.03 (d, J = 6.6 Hz, 1H), 4.62-4.51 (m, 2H), 4.51-4.35 (m, 2H), 3.81-3.69 (m, 2H), 2.43 (s, 3H), 1.34 (s, 3H), 0.61 (s, 3H). |
| 253 | 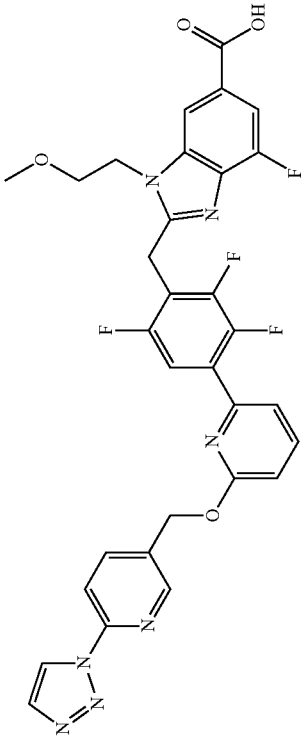 | 27 | 633.6 | 1H NMR (400 MHz, DMSO-d6) δ 8.88 (d, J = 1.3 Hz, 1H), 8.76 (d, J = 2.2 Hz, 1H), 8.26 (dd, J = 8.4, 2.2 Hz, 1H), 8.18 (d, J = 8.4 Hz, 1H), 8.11 (d, J = 1.3 Hz, 1H), 8.03-7.91 (m, 2H), 7.81-7.72 (m, 1H), 7.59 (dd, J = 7.5, 1.8 Hz, 1H), 7.54-7.46 (m, 1H), 7.05 (d, J = 8.3 Hz, 1H), 5.63 (s, 2H), 4.68 (t, J = 5.1 Hz, 2H), 4.55 (s, 2H), 3.73 (t, J = 5.0 Hz, 2H), 3.25 (s, 3H). |
| 254 | 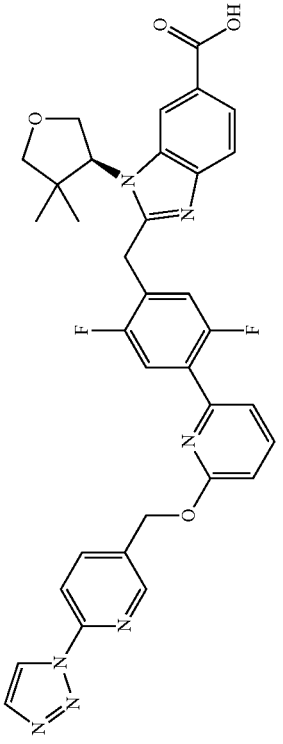 | 35 | 638.2 | 1H NMR (400 MHz, DMSO-d6) δ 8.88 (d, J = 1.2 Hz, 1H), 8.76 (d, J = 2.1 Hz, 1H), 8.49 (s, 1H), 8.26 (dd, J = 8.4, 2.2 Hz, 1H), 8.17 (d, J = 8.4 Hz, 1H), 8.00 (d, J = 1.2 Hz, 1H), 7.96-7.85 (m, 2H), 7.81 (dd, J = 8.4, 1.4 Hz, 1H), 7.62 (d, J = 8.5 Hz, 1H), 7.55 (d, J = 7.4 Hz, 1H), 7.47 (dd, J = 10.4, 7.2 Hz, 1H), 7.01 (d, J = 8.3 Hz, 1H), 5.63 (s, 2H), 5.02 (d, J = 6.7 Hz, 1H), 4.59-4.49 (m, 2H), 4.49-4.30 (m, |

TABLE 2-continued

Compounds

| Ex. | Structure | Procedure | ES/MS m/z | ¹H NMR |
|---|---|---|---|---|
| 255 | (structure) | 35 | 598 | 2H), 3.78 (d, J = 8.7 Hz, 1H), 3.73 (d, J = 8.6 Hz, 1H), 1.34 (s, 3H), 0.61 (s, 3H). 1H NMR (400 MHz, DMSO-d6) δ 8.10 (d, J = 1.3 Hz, 1H), 7.98 (d, J = 7.2 Hz, 1H), 7.88 (t, J = 7.9 Hz, 1H), 7.55-7.48 (m, 4H), 7.48-7.42 (m, 3H), 6.97 (d, J = 8.2 Hz, 1H), 5.46 (s, 2H), 4.63 (t, J = 5.1 Hz, 2H), 4.52 (s, 2H), 3.70 (t, J = 5.0 Hz, 2H), 3.22 (s, 3H). |
| 256 | (structure) | 35 | 633 | 1H NMR (400 MHz, DMSO-d6) δ 8.27 (d, J = 1.3 Hz, 1H), 7.95-7.86 (m, 2H), 7.75 (tdd, J = 9.4, 7.2, 3.0 Hz, 3H), 7.53 (dd, J = 7.5, 1.7 Hz, 1H), 7.48 (dd, J = 11.2, 1.3 Hz, 1H), 7.31 (dd, J = 11.5, 6.1 Hz, 1H), 6.99 (d, J = 8.2 Hz, 1H), 5.64-5.51 (m, 3H), 4.53 (s, 2H), 4.40 (dd, J = 10.6, 3.4 Hz, 1H), 4.13 (td, J = 8.8, 7.6, 3.7 Hz, 2H), 4.00 (dd, J = 10.6, 8.2 Hz, 1H), 3.78 (dd, J = 10.4, 4.6 Hz, 1H), 2.87 (s, 3H). |

TABLE 2-continued

Compounds

| Ex. | Structure | Procedure | ES/MS m/z | ¹H NMR |
|---|---|---|---|---|
| 257 | 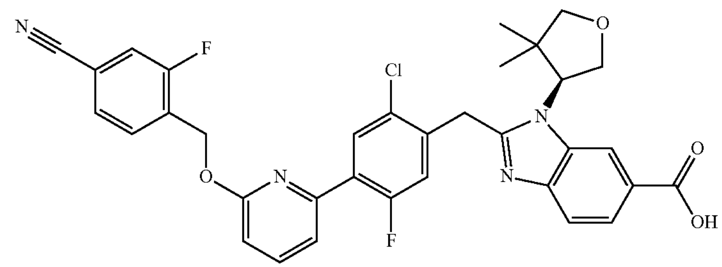 [SMILES: CC1(C)COC[C@H]1n1c(Cc2cc(F)c(-c3cccc(OCc4ccc(C#N)cc4F)n3)cc2Cl)nc2ccc(C(=O)O)cc21] | 35 | 629 | 1H NMR (400 MHz, DMSO-d6) δ 8.51 (s, 1H), 7.97-7.87 (m, 3H), 7.82 (dd, J = 8.5, 1.5 Hz, 1H), 7.78-7.70 (m, 2H), 7.63 (d, J = 8.5 Hz, 1H), 7.58-7.45 (m, 2H), 7.02 (d, J = 8.2 Hz, 1H), 5.60 (s, 2H), 5.02 (d, J = 6.7 Hz, 1H), 4.63 (d, J = 17.1 Hz, 1H), 4.55 (d, J = 11.7 Hz, 1H), 4.49-4.36 (m, 2H), 3.81 (d, J = 8.6 Hz, 1H), 3.73 (d, J = 8.6 Hz, 1H), 1.35 (s, 3H), 0.66 (s, 3H). |
| 258 | 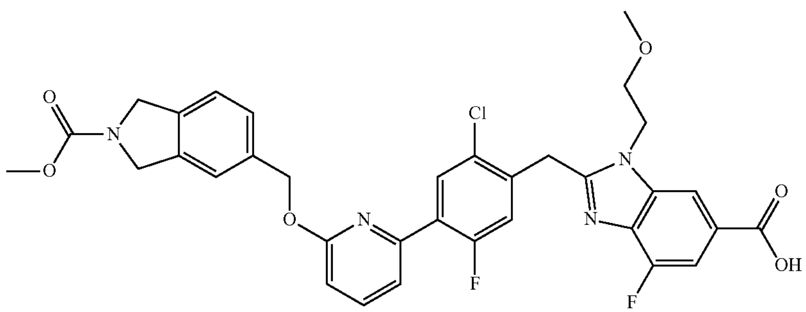 [SMILES: COCCn1c(Cc2cc(F)c(-c3cccc(OCc4ccc5c(c4)CN(C(=O)OC)C5)n3)cc2Cl)nc2c(F)cc(C(=O)O)cc21] | 35 | 663 | 1H NMR (400 MHz, DMSO-d6) δ 8.10 (s, 1H), 8.01 (d, J = 7.1 Hz, 1H), 7.87 (t, J = 7.9 Hz, 1H), 7.56-7.39 (m, 5H), 7.38-7.30 (m, 1H), 6.95 (d, J = 8.3 Hz, 1H), 5.47 (s, 2H), 4.64(t, J = 7.8 Hz, 6H), 4.53 (s, 2H), 3.70 (t, J = 5.1 Hz, 2H), 3.66 (d, J = 2.4 Hz, 3H), 3.22 (s, 3H). |
| 259 | 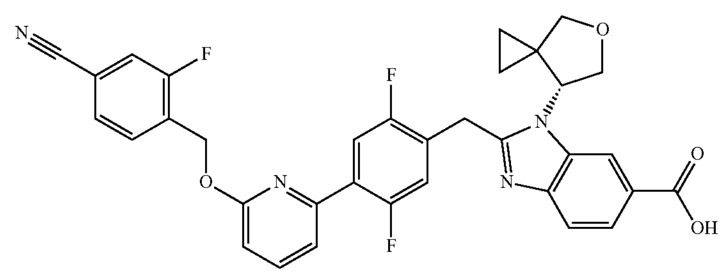 [SMILES: N#Cc1ccc(COc2cccc(-c3cc(F)c(Cc4nc5ccc(C(=O)O)cc5n4[C@H]4COCC45CC5)cc3F)n2)c(F)c1] | chiral separation Peak 2 | 610.6 | 1H NMR (400 MHz, DMSO-d6) δ 8.57 (s, 1H), 7.98-7.83 (m, 3H), 7.81-7.71 (m, 3H),7.67 (d, J = 8.5 Hz, 1H), 7.53 (dd, J = 7.5, 1.6 Hz, 1H), 7.40 (dd, J = 11.4, 6.1 Hz, 1H), 7.00 (d, J = 8.3 Hz, 1H), 5.60 (s, 2H), 5.27 (s, 1H), 4.47 (s, 2H), 4.37-4.23 (m, 2H), 4.05 (d, J = 8.9 Hz, 1H), 3.91 (d, J = 8.9 Hz, 1H), 0.75 (dd, J = 24.6, 17.1 Hz, 3H), −0.07 (s, 1H). |

TABLE 2-continued

Compounds

| Ex. | Structure | Procedure | ES/MS m/z | ¹H NMR |
|---|---|---|---|---|
| 260 | 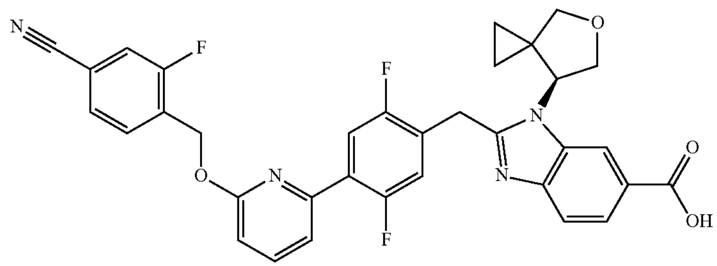 [SMILES: N#Cc1ccc(COc2cccc(-c3cc(F)c(Cc4nc5ccc(C(=O)O)cc5n4[C@@H]4COCC45CC5)cc3F)n2)c(F)c1] | chiral separation Peak 1 | 610.6 | 1H NMR (400 MHz, DMSO-d6) δ 8.57 (s, 1H), 7.98-7.83 (m, 3H), 7.81-7.71 (m, 3H), 7.67 (d, J = 8.5 Hz, 1H), 7.53 (dd, J = 7.5, 1.6 Hz, 1H), 7.40 (dd, J = 11.4, 6.1 Hz, 1H), 7.00 (d, J = 8.3 Hz, 1H), 5.60 (s, 2H), 5.27 (s, 1H), 4.47 (s, 2H), 4.37-4.23 (m, 2H), 4.05 (d, J = 8.9 Hz, 1H), 3.91 (d, J = 8.9 Hz, 1H), 0.75 (dd, J = 24.6, 17.1 Hz, 3H), −0.07 (s, 1H). |
| 261 | 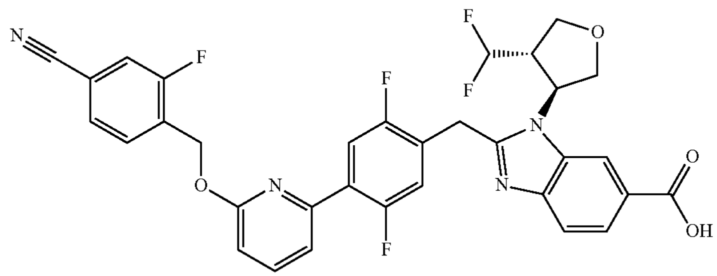 [SMILES: N#Cc1ccc(COc2cccc(-c3cc(F)c(Cc4nc5ccc(C(=O)O)cc5n4[C@@H]4COC[C@H]4C(F)F)cc3F)n2)c(F)c1] | chiral separation Peak 1 | 635.2 | 1H NMR (400 MHz, DMSO-d6) δ 8.38 (d, J = 1.4 Hz, 1H), 7.96-7.82 (m, 3H), 7.82-7.70 (m, 3H), 7.67 (d, J = 8.5 Hz, 1H), 7.54 (dd, J = 7.5, 1.6 Hz, 1H), 7.41 (dd, J = 11.5, 6.0 Hz, 1H), 7.00 (d, J = 8.3 Hz, 1H), 6.41 (td, J = 55.8, 4.9 Hz, 1H), 5.65-5.50 (m, 3H), 4.59 (d, J = 17.0 Hz, 1H), 4.49 (t, J = 8.9 Hz, 1H), 4.41 (d, J = 16.9 Hz, 1H), 4.28 (dd, J = 10.5, 3.3 Hz, 1H), 4.15 (dd, J = 10.5, 7.9 Hz, 1H), 3.81 (t, J = 9.2 Hz, 1H), 3.25 (d, J = 14.7 Hz, 1H). |
| 262 | 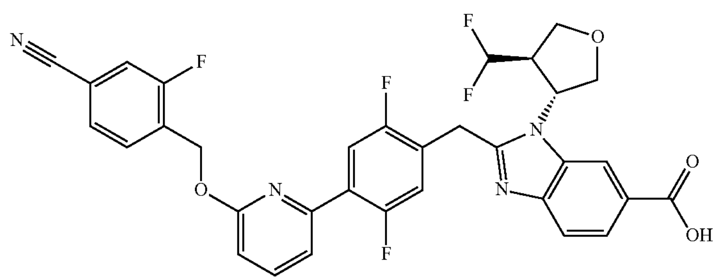 [SMILES: N#Cc1ccc(COc2cccc(-c3cc(F)c(Cc4nc5ccc(C(=O)O)cc5n4[C@H]4COC[C@@H]4C(F)F)cc3F)n2)c(F)c1] | chiral separation Peak 2 | 635.2 | 1H NMR (400 MHz, DMSO-d6) δ 8.38 (d, J = 1.4 Hz, 1H), 7.96-7.82 (m, 3H), 7.82-7.70 (m, 3H), 7.67 (d, J = 8.5 Hz, 1H), 7.54 (dd, J = 7.5, 1.6 Hz, 1H), 7.41 (dd, J = 11.5, 6.0 Hz, 1H), 7.00 (d, J = 8.3 Hz, 1H), 6.41 (td, J = 55.8, 4.9 Hz, 1H), 5.65-5.50 (m, 3H), 4.59 (d, J = 17.0 Hz, 1H), 4.49 (t, J = 8.9 Hz, 1H), 4.41 (d, J = 16.9 Hz, 1H), 4.28 (dd, J = 10.5, 3.3 Hz, 1H), 4.15 (dd, J = 10.5, 7.9 |

TABLE 2-continued

Compounds

| Ex. | Structure | Procedure | ES/MS m/z | ¹H NMR |
|---|---|---|---|---|
| 263 | 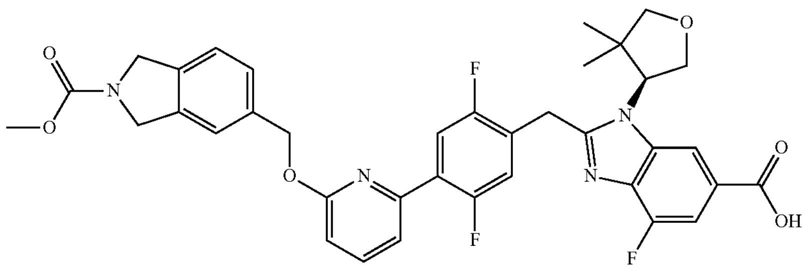 [SMILES: COC(=O)N1Cc2ccc(COc3cccc(-c4cc(F)c(Cc5nc6c(F)cc(C(=O)O)cc6n5[C@@H]5COCC5(C)C)cc4F)n3)cc2C1] | 35 | 687.2 | 1H NMR (400 MHz, DMSO-d6) δ 8.36 (s, 1H), 7.92-7.76 (m, 2H), 7.57-7.40 (m, 5H), 7.34 (dd, J = 10.8, 7.9 Hz, 1H), 6.94 (d, J = 8.3 Hz, 1H), 5.48 (s, 2H), 5.04 (d, J = 6.6 Hz, 1H), 4.69-4.60 (m, 4H),4.59-4.49 (m, 2H), 4.48-4.35 (m, 2H), 3.75 (q, J = 8.7 Hz, 2H), 3.66 (d, J = 3.3 Hz, 3H), 1.34 (s, 3H), 0.62 (s, 3H). |
| 264 | 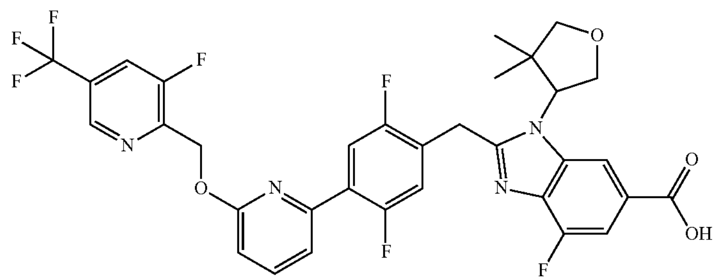 [SMILES: CC1(C)COCC1n1c(Cc2cc(F)c(-c3cccc(OCc4ncc(C(F)(F)F)cc4F)n3)cc2F)nc2c(F)cc(C(=O)O)cc21] | 35 | 675.2 | 1H NMR (400 MHz, DMSO-d6) δ 8.85 (s, 1H), 8.37 (d, J = 11.1 Hz, 2H), 7.89 (t, J = 7.9 Hz, 1H), 7.60 (dd, J = 10.6, 6.4 Hz, 1H), 7.56-7.48 (m, 2H), 7.44 (dd, J = 11.5, 6.0 Hz, 1H), 7.00 (d, J = 8.2 Hz, 1H), 5.71 (s, 2H), 5.02 (d, J = 6.6 Hz, 1H), 4.58-4.48 (m, 2H), 4.46-4.33 (m, 2H), 3.74 (q, J = 8.7 Hz, 2H), 1.32 (s, 3H), 0.60 (s, 3H). |
| 265 | 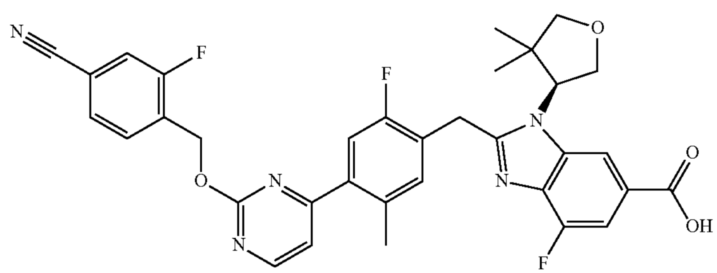 [SMILES: Cc1cc(Cc2nc3c(F)cc(C(=O)O)cc3n2[C@@H]2COCC2(C)C)c(F)cc1-c1ccnc(OCc2ccc(C#N)cc2F)n1] | 35 | 628.2 | 1H NMR (400 MHz, DMSO-d6) δ 8.75 (d, J = 5.1 Hz, 1H), 8.35 (s, 1H), 7.94 (d, J = 10.0 Hz, 1H), 7.80-7.70 (m, 2H), 7.52 (dd, J = 11.3, 1.2 Hz, 1H), 7.48 (d, J = 5.1 Hz, 1H), 7.42 (d, J = 10.5 Hz, 1H), 7.38 (d, J = 7.5 Hz, 1H), 5.59 (s, 2H), 5.02 (d, J = 6.6 Hz, 1H), 4.56-4.46 (m, 2H), 4.42 (dd, J = 11.3, 6.7 Hz, 1H), 4.36 (d, J = 16.9 Hz, 1H), 3.77 (d, J = 8.7 Hz, 1H), 3.72 (d, J = 8.6 Hz, 1H), 2.36 (s, 3H), 1.32 (s, 3H), 0.61 (s, 3H). |

TABLE 2-continued

Compounds

| Ex. | Structure | Procedure | ES/MS m/z | ¹H NMR |
|---|---|---|---|---|
| 266 | 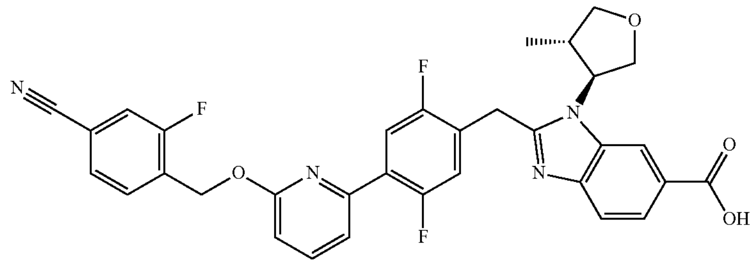 [SMILES: C[C@@H]1COC[C@H]1n1c(Cc2cc(F)c(-c3cccc(OCc4ccc(C#N)cc4F)n3)cc2F)nc2ccc(C(=O)O)cc21] | 22 | 599.2 | 1H NMR (400 MHz, DMSO-d6) δ 8.39 (d, J = 1.5 Hz, 1H), 7.96-7.81 (m, 3H), 7.68 (d, J = 8.5 Hz, 1H), 7.53 (dd, J = 7.5, 1.6 Hz, 1H), 7.44 (dd, J = 11.5, 6.1 Hz, 1H), 7.00 (d, J = 8.2 Hz, 1H), 5.60 (s, 2H), 5.06 (td, J = 7.6, 3.6 Hz, 1H), 4.56 (d, J = 16.9 Hz, 1H), 4.48 (d, J = 16.8 Hz, 1H), 4.37 (t, J = 8.2 Hz, 1H), 4.22 (dd, J = 10.5, 3.6 Hz, 1H), 4.13 (dd, J = 10.5, 8.1 Hz, 1H), 3.38 (t, J = 9.4 Hz, 1H), 2.68 (dq, J = 9.7, 6.7 Hz, 1H), 1.06 (d, J = 6.7 Hz, 3H). |
| 267 | 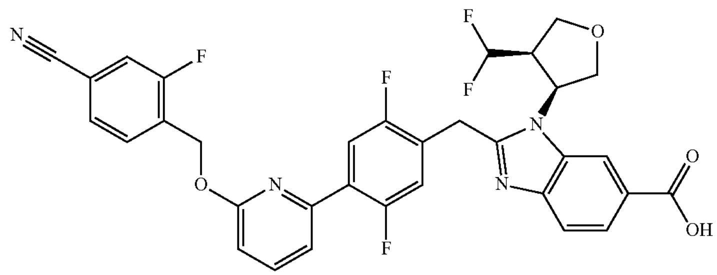 [SMILES: N#Cc1ccc(COc2cccc(-c3cc(F)c(Cc4nc5ccc(C(=O)O)cc5n4[C@@H]4COC[C@@H]4C(F)F)cc3F)n2)c(F)c1] | 22 | 635.2 | 1H NMR (400 MHz, DMSO-d6) δ 8.55 (s, 1H), 7.97-7.87 (m, 2H), 7.84-7.67 (m, 4H), 7.61 (d, J = 8.4 Hz, 1H), 7.54 (dd, J = 7.4, 1.7 Hz, 1H), 7.39 (dd, J = 11.4, 6.1Hz, 1H), 7.00 (d, J = 8.3 Hz, 1H), 5.80-5.56 (m, 3H), 4.55 (d, J = 12.6 Hz, 2H), 4.39 (d, J = 17.0 Hz, 1H), 4.27-4.12 (m, 2H), 4.09 (t, J = 9.2 Hz, 1H), 3.62-3.39 (m, 2H). |
| 268 | 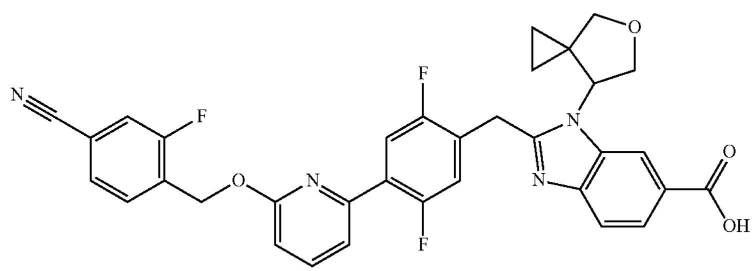 [SMILES: N#Cc1ccc(COc2cccc(-c3cc(F)c(Cc4nc5ccc(C(=O)O)cc5n4C4COCC45CC5)cc3F)n2)c(F)c1] | 22 | 611.2 | 1H NMR (400 MHz, DMSO-d6) δ 8.57 (s, 1H), 7.98-7.83 (m, 3H), 7.81-7.71 (m, 3H), 7.67 (d, J = 8.5 Hz, 1H), 7.53 (dd, J = 7.5, 1.6 Hz, 1H), 7.40 (dd, J = 11.4, 6.1 Hz, 1H), 7.00 (d, J = 8.3 Hz, 1H), 5.60 (s, 2H), 5.27 (s, 1H), 4.47 (s, 2H), 4.37-4.23 (m, 2H), 4.05 (d, J = 8.9 Hz, 1H), 3.91 (d, J = 8.9 Hz, 1H), 0.75 (dd, J = 24.6, 17.1 Hz, 3H), -0.07 (s, 1H). |

TABLE 2-continued

Compounds

| Ex. | Structure | Procedure | ES/MS m/z | ¹H NMR |
|---|---|---|---|---|
| 269 | 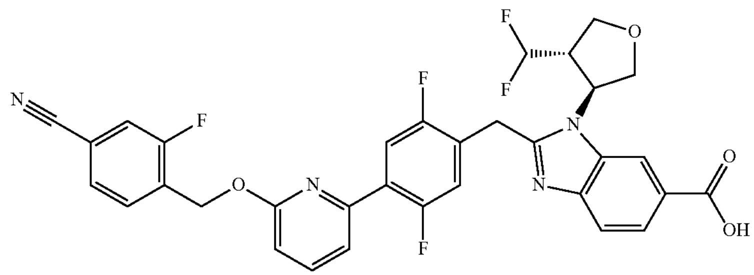 [SMILES: N#Cc1ccc(COc2cccc(-c3cc(F)c(Cc4nc5ccc(C(=O)O)cc5n4[C@@H]4COC[C@H]4C(F)F)cc3F)n2)c(F)c1] | 22 | 635.2 | 1H NMR (400 MHz, DMSO-d6) δ 8.38 (d, J = 1.4 Hz, 1H), 7.96-7.82 (m, 3H), 7.67 (d, J = 8.5 Hz, 1H), 7.54 (dd, J = 7.5, 1.6 Hz, 1H), 7.41 (dd, J = 11.5, 6.0 Hz, 1H), 7.00 (d, J = 8.3 Hz, 1H), 6.41 (td, J = 55.8, 4.9 Hz, 1H), 5.65-5.50 (m, 3H), 4.59 (d, J = 17.0 Hz, 1H), 4.49 (t, J = 8.9 Hz, 1H), 4.41 (dd, J = 16.9 Hz, 1H), 4.28 (dd, J = 10.5, 3.3 Hz, 1H), 4.15 (dd, J = 10.5, 7.9 Hz, 1H), 3.81 (t, J = 9.2 Hz, 1H), 3.25 (d, J = 14.7 Hz, 1H). |
| 270 | 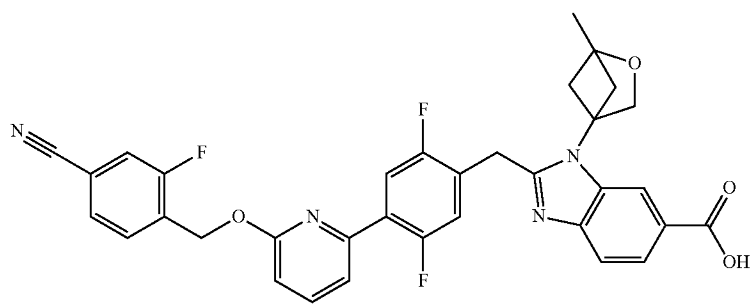 [SMILES: CC12CC(n3c(Cc4cc(F)c(-c5cccc(OCc6ccc(C#N)cc6F)n5)cc4F)nc4ccc(C(=O)O)cc43)(CO1)C2] | 22 | 611.2 | 1H NMR (400 MHz, DMSO-d6) δ 8.09 (d, J = 1.4 Hz, 1H), 7.95-7.87 (m, 2H), 7.84-7.74 (m, 4H), 7.64 (d, J = 8.4 Hz, 1H), 7.54 (dd, J = 7.5, 1.6 Hz, 1H), 7.38 (dd, J = 11.5, 6.1 Hz, 1H), 7.00 (d, J = 8.2 Hz, 1H), 5.61 (s, 2H), 4.39 (s, 2H), 3.99 (s, 2H), 2.63-2.55 (m, 2H), 1.51 (s, 3H). |

TABLE 2-continued

Compounds

| Ex. | Structure | Procedure | ES/MS m/z | ¹H NMR |
|---|---|---|---|---|
| 271 | 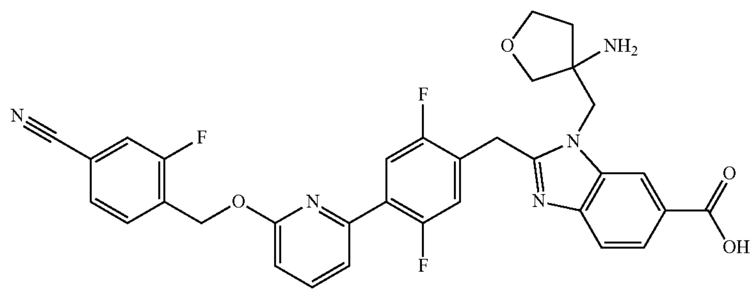 [SMILES: N#Cc1ccc(COc2cccc(-c3cc(F)c(Cc4nc5ccc(C(=O)O)cc5n4CC4(N)CCOC4)cc3F)n2)c(F)c1] | 3 | 614.2 | 1H NMR (400 MHz, DMSO-d6) δ 8.40 (s, 3H), 8.37 (s, 1H), 7.96-7.88 (m, 2H), 7.84 (dd, J = 8.5, 1.4 Hz, 1H), 7.79-7.71 (m, 3H), 7.66 (d, J = 8.4 Hz, 1H), 7.56-7.50 (m, 1H), 7.46 (dd, J = 11.6, 6.1 Hz, 1H), 7.01 (d, J = 8.3 Hz, 1H), 5.60 (s, 2H), 4.80 (s, 2H), 4.41 (s, 2H), 4.00 (q, J = 7.9 Hz, 1H), 3.97-3.88 (m, 1H), 3.88-3.79 (m, 2H), 2.37-2.12 (m, 2H). |
| 272 | 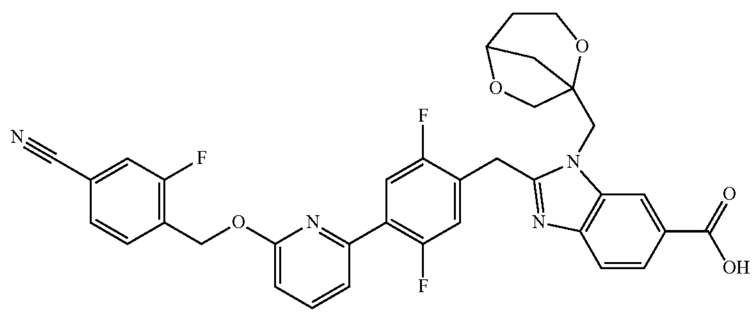 [SMILES: N#Cc1ccc(COc2cccc(-c3cc(F)c(Cc4nc5ccc(C(=O)O)cc5n4CC45COC(CCO4)C5)cc3F)n2)c(F)c1] | 5 | 641.2 | 1H NMR (400 MHz, DMSO-d6) δ 8.38 (d, J = 1.5 Hz, 1H), 7.94-7.88 (m, 2H), 7.84 (dd, J = 8.5, 1.5 Hz, 1H), 7.80-7.70 (m, 3H), 7.63 (d, J = 8.4 Hz, 1H), 7.53 (dd, J = 7.6, 1.7 Hz, 1H), 7.39 (dd, J = 11.5, 6.1 Hz, 1H), 7.00 (d, J = 8.2 Hz, 1H), 5.60 (s, 2H), 4.86-4.65 (m, 2H), 4.52 (d, J = 4.7 Hz, 3H), 3.98 (d, J = 9.3 Hz, 1H), 3.91 (d, J = 9.3 Hz, 1H), 2.13 (dd, J = 11.0, 6.4 Hz, 1H), 1.64-1.38 (m, 4H). |

TABLE 2-continued

Compounds

| Ex. | Structure | Procedure | ES/MS m/z | ¹H NMR |
|---|---|---|---|---|
| 273 | 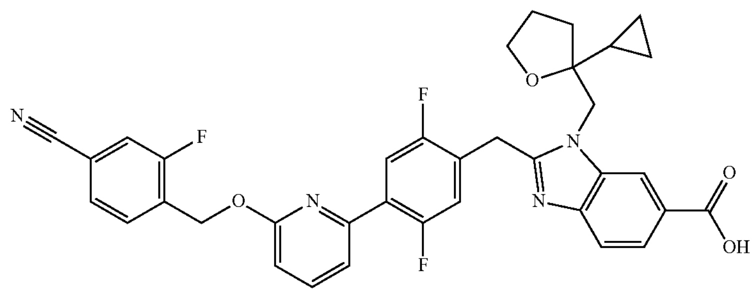 [SMILES: N#Cc1ccc(COc2cccc(-c3cc(F)c(Cc4nc5ccc(C(=O)O)cc5n4CC4(C5CC5)CCCO4)cc3F)n2)c(F)c1] | 5 | 639.2 | 1H NMR (400 MHz, DMSO-d6) δ 8.43 (d, J = 1.5 Hz, 1H), 7.95-7.83 (m, 3H), 7.80-7.71 (m, 3H), 7.64 (d, J = 8.4 Hz, 1H), 7.53 (dd, J = 7.5, 1.7 Hz, 1H), 7.43 (dd, J = 11.5, 6.1 Hz, 1H), 7.00 (d, J = 8.2 Hz, 1H), 5.60 (s, 2H), 4.62 (s, 2H), 4.57 (s, 2H), 3.75-3.58 (m, 2H), 1.99-1.86 (m, 2H), 1.86-1.72 (m, 1H), 1.66-1.51 (m, 1H), 1.12 (qd, J = 8.1, 5.2 Hz, 1H), 0.31 (dq, J = 9.1, 4.4, 3.9 Hz, 1H), 0.26-0.15 (m, 1H), 0.10--0.12 (m, 2H). |
| 274 | 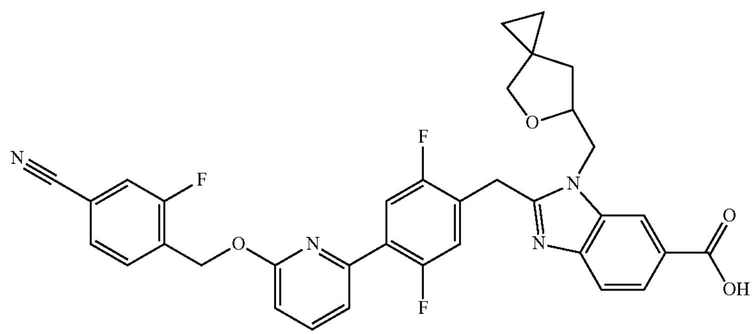 [SMILES: N#Cc1ccc(COc2cccc(-c3cc(F)c(Cc4nc5ccc(C(=O)O)cc5n4CC4CC5(CC5)CO4)cc3F)n2)c(F)c1] | 5 | 625.2 | 1H NMR (400 MHz, DMSO-d6) δ 8.32 (d, J = 1.5 Hz, 1H), 7.95-7.83 (m, 3H), 7.80-7.71 (m, 3H), 7.65 (d, J = 8.4 Hz, 1H), 7.53 (dd, J = 7.5, 1.7 Hz, 1H), 7.43 (dd, J = 11.5, 6.1 Hz, 1H), 7.00 (d, J = 8.2 Hz, 1H), 5.60 (s, 2H), 4.67 (dd, J = 15.2, 2.9 Hz, 1H), 4.62-4.46 (m, 3H), 4.40 (qd, J = 7.1, 2.9 Hz, 1H), 3.67 (d, J = 8.0 Hz, 1H), 3.51 (d, J = 8.0 Hz, 1H), 2.03 (dd, J = 12.4, 6.6 Hz, 1H), 1.78 (dd, J = 12.3, 7.0 Hz, 1H), 0.70-0.45 (m, 4H). |

TABLE 2-continued

Compounds

| Ex. | Structure | Procedure | ES/MS m/z | ¹H NMR |
|---|---|---|---|---|
| 275 | 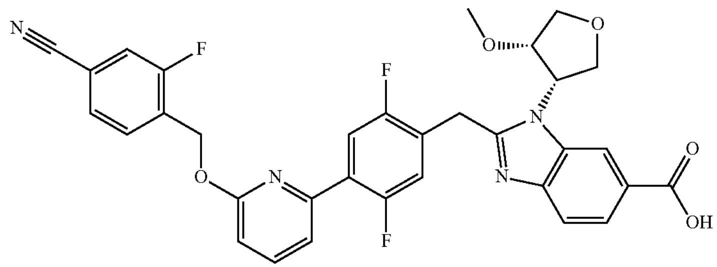 [SMILES: CO[C@@H]1COC[C@@H]1n1c(Cc2cc(F)c(-c3cccc(OCc4ccc(C#N)cc4F)n3)cc2F)nc2ccc(C(=O)O)cc21] | chiral separation Peak 2 | 615.2 | 1H NMR (400 MHz, DMSO-d6) δ 8.38 (s, 1H), 7.97-7.86 (m, 2H), 7.75 (dt, J = 6.5, 5.2 Hz, 4H), 7.60-7.43 (m, 2H), 7.29 (dd, J = 11.4, 6.1 Hz, 1H), 6.99 (d, J = 8.2 Hz, 1H), 5.60 (s, 2H), 5.53 (d, J = 10.2 Hz, 1H), 4.49 (s, 2H), 4.42 (dd, J = 10.3, 3.8 Hz, 1H), 4.17-4.06 (m, 2H), 4.02 (dd, J = 10.3, 8.3 Hz, 1H), 3.82 (dd, J = 10.1, 4.5 Hz, 1H), 2.87 (s, 3H). |
| 276 | 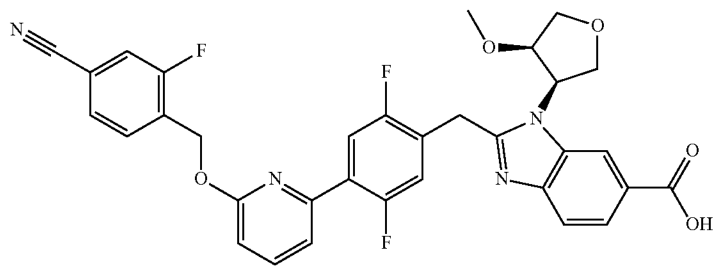 [SMILES: CO[C@H]1COC[C@H]1n1c(Cc2cc(F)c(-c3cccc(OCc4ccc(C#N)cc4F)n3)cc2F)nc2ccc(C(=O)O)cc21] | chiral separation Peak 1 | 615.2 | 1H NMR (400 MHz, DMSO-d6) δ 8.39 (d, J = 1.5 Hz, 1H), 7.98-7.84 (m, 2H), 7.80-7.68 (m, 4H), 7.58 (d, J = 8.4 Hz, 1H), 7.53 (d, J = 6.8 Hz, 1H), 7.29 (dd, J = 11.6, 6.0 Hz, 1H), 6.99 (d, J = 8.3 Hz, 1H), 5.60 (s, 2H), 5.54 (t, J = 9.6 Hz, 1H), 4.50 (s, 2H), 4.42 (dd, J = 10.4, 3.7 Hz, 1H), 4.19-4.08 (m, 2H), 4.02 (t, J = 9.4 Hz, 1H), 3.82 (dd, J = 10.3, 4.5 Hz, 1H), 2.87 (s, 3H); 1H NMR (400 MHz, DMSO-d6) δ 8.38 (s, 1H), 7.97-7.86 (m, 2H), 7.75 (dt, J = 6.5, 5.2 Hz, 4H), 7.60-7.43 (m, 2H), 7.29 (dd, J = 11.4, 6.1 Hz, 1H), 6.99 (d, J = 8.2 Hz, 1H), 5.60 (s, 2H), 5.53 (d, J = 10.2 Hz, 1H), 4.49 (s, 2H), 4.42 (dd, J = 10.3, 3.8 Hz, 1H), 4.17-4.06 (m, 2H), 4.02 (dd, J = 10.3, 8.3 Hz, 1H), 3.82 (dd, J = 10.1, 4.5 Hz, 1H), 2.87 (s, 3H). |

TABLE 2-continued

Compounds

| Ex. | Structure | Procedure | ES/MS m/z | 1H NMR |
|---|---|---|---|---|
| 277 | 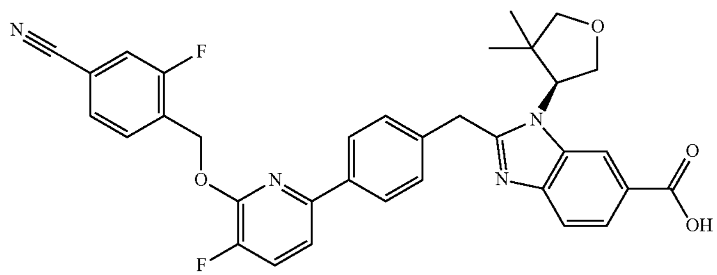 [SMILES: CC1(C)COC[C@H]1n1c(Cc2ccc(-c3ccc(F)c(OCc4ccc(C#N)cc4F)n3)cc2)nc2ccc(C(=O)O)cc21] | 35 | 595.2 | 1H NMR (400 MHz, Methanol-d4) δ 8.90 (s, 1H), 8.21 (dd, J = 8.6, 1.4 Hz, 1H), 8.06 (d, J = 8.2 Hz, 2H), 7.83 (d, J = 8.6 Hz, 1H), 7.77 (t, J = 7.5 Hz, 1H), 7.68-7.52 (m, 4H), 7.49 (d, J = 8.1 Hz, 2H), 5.73 (s, 2H), 5.10 (d, J = 6.2 Hz, 1H), 4.80-4.62 (m, 2H), 4.62-4.53 (m, 1H), 4.45 (dd, J = 11.6, 6.7 Hz, 1H), 3.99 (d, J = 9.0 Hz, 1H), 3.80 (d, J = 8.9 Hz, 1H), 1.28 (s, 3H), 0.65 (s, 3H). |
| 278 | 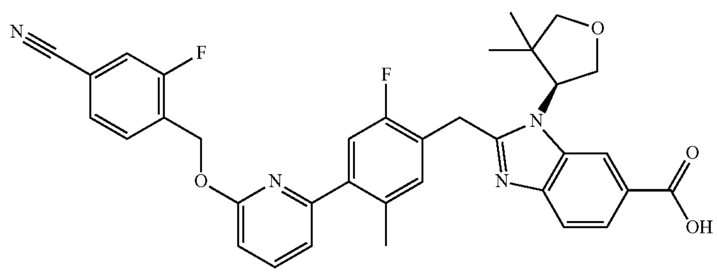 [SMILES: Cc1cc(Cc2nc3ccc(C(=O)O)cc3n2[C@@H]2COCC2(C)C)c(F)cc1-c1cccc(OCc2ccc(C#N)cc2F)n1] | 35 | 609.3 | 1H NMR (400 MHz, Methanol-d4) δ 8.92 (s, 1H), 8.21 (dd, J = 8.6, 1.4 Hz, 1H), 7.93-7.78 (m, 2H), 7.70 (t, J = 7.6 Hz, 1H), 7.61-7.53 (m, 2H), 7.38 (d, J = 7.6 Hz, 1H), 7.25 (d, J = 10.8 Hz, 1H), 7.17 (d, J = 7.4 Hz, 1H), 6.95 (d, J = 8.3 Hz, 1H), 5.57 (s, 2H), 5.15 (d, J = 6.5 Hz, 1H), 4.79-4.62 (m, 3H), 4.52 (dd, J = 11.7, 6.6 Hz, 1H), 4.01 (d, J = 8.9 Hz, 1H), 3.84 (d, J = 8.9 Hz, 1H), 2.31 (s, 3H), 1.37 (s, 3H), 0.73 (s, 3H). |
| 279 | 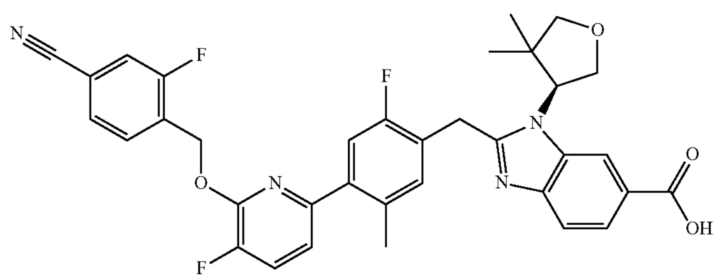 [SMILES: Cc1cc(Cc2nc3ccc(C(=O)O)cc3n2[C@@H]2COCC2(C)C)c(F)cc1-c1ccc(F)c(OCc2ccc(C#N)cc2F)n1] | 35 | 627.26 | 1H NMR (400 MHz, Methanol-d4) δ 8.91 (s, 1H), 8.19 (dd, J = 8.6, 1.4 Hz, 1H), 7.80 (d, J = 8.6 Hz, 1H), 7.73 (t, J = 7.6 Hz, 1H), 7.66 (dd, J = 10.1, 8.1 Hz, 1H), 7.64-7.58 (m, 2H), 131 (d, J = 7.6 Hz, 1H), 7.26 (d, J = 10.8 Hz, 1H), 7.19 (dd, J = 8.1, 2.8 Hz, 1H), 5.64 (s, 2H), 5.13 (d, J = 6.4 Hz, 1H), 4.77-4.59 (m, 3H), 4.51 (dd, J = 11.6, 6.7 Hz, 1H), 4.00 (d, J = 9.0 |

TABLE 2-continued
Compounds
| Ex. | Structure | Procedure | ES/MS m/z | ¹H NMR |
|---|---|---|---|---|
| 280 | 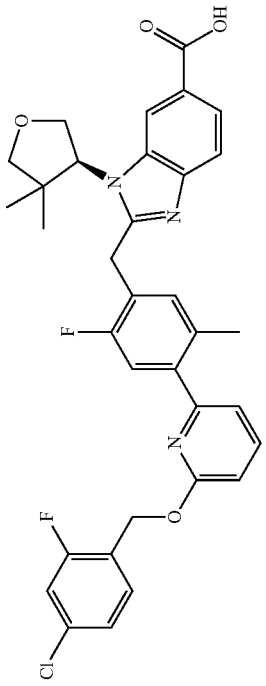 | 35 | 618.25 | 1H NMR (400 MHz, Methanol-d4) δ 8.94 (s, 1H), 8.23 (dd, J = 8.6, 1.4 Hz, 1H), 7.83 (t, J = 8.0 Hz, 2H), 7.51 (t, J = 8.3 Hz, 1H), 7.41 (d, J = 7.6 Hz, 1H), 7.30 (d, J = 10.8 Hz, 1H), 7.28-7.19 (m, 2H), 7.16 (d, J = 7.3 Hz, 1H), 6.91 (d, J = 8.3 Hz, 1H), 5.46 (s, 2H), 5.17 (d, J = 7.0 Hz, 1H), 4.81-4.58 (m, 3H), 4.52 (dd, J = 11.7, 6.7 Hz, 1H), 4.01 (d, J = 8.9 Hz, 1H), 3.85 (d, J = 9.0 Hz, 1H), 2.36 (s, 3H), 1.38 (s, 3H), 0.74 (s, 3H). Hz, 1H), 3.84 (d, J = 8.9 Hz, 1H), 2.31 (s, 3H), 1.37 (s, 3H), 0.72 (s, 3H). |
| 281 | 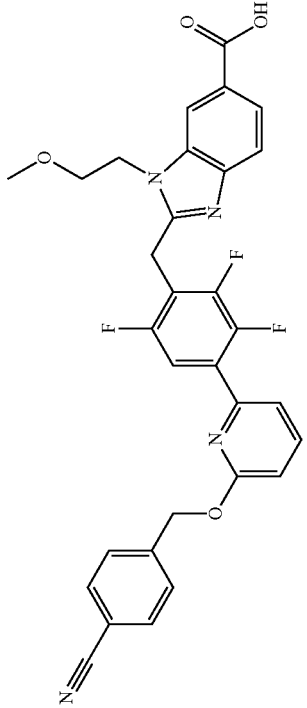 | 38 | 573.6 | 1H NMR (400 MHz, Methanol-d4) δ 8.67 (s, 1H), 7.95 (dd, J = 8.6, 1.5 Hz, 1H), 7.82-7.64 (m, 3H), 7.59 (d, J = 8.5 Hz, 1H), 5.82 (s, 2H), 5.08 (d, J = 6.8 Hz, 1H), 4.72 (d, J= 11.0 Hz, 1H), 4.68-4.51 (m, 4H), 4.42 (d, J = 17.1 Hz, 1H), 3.99 (d, J = 8.7 Hz, 1H), 3.84 (d, J = 8.7 Hz, 1H), 1.50-1.40 (m, 6H), 0.77 (s, 3H). |

TABLE 2-continued

Compounds

| Ex. | Structure | Procedure | ES/MS m/z | ¹H NMR |
|---|---|---|---|---|
| 282 | 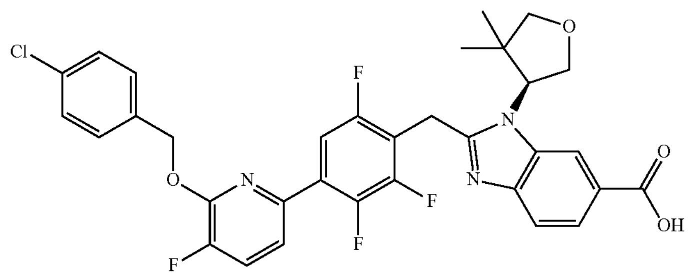 [SMILES: CC1(C)COC[C@H]1n1c(Cc2c(F)cc(-c3ccc(F)c(OCc4ccc(Cl)cc4)n3)c(F)c2F)nc2ccc(C(=O)O)cc21] | 35 | 640.5 | 1H NMR (400 MHz, Methanol-d4) δ 8.83 (s, 1H), 8.09 (dd, J = 8.5, 1.4 Hz, 1H), 7.73-7.64 (m, 3H), 7.64-7.55 (m, 1H), 7.51 (d, J = 8.4 Hz, 2H), 7.47-7.20 (m, 2H), 5.57 (s, 2H), 5.16 (d, J = 6.6 Hz, 1H), 4.81-4.63 (m, 2H), 4.57 (dd, J = 11.5, 6.7 Hz, 2H), 3.99 (d, J = 8.8 Hz, 1H), 3.86 (d, J = 8.8 Hz, 1H), 1.48 (s, 3H), 0.81 (s, 3H). |
| 283 | 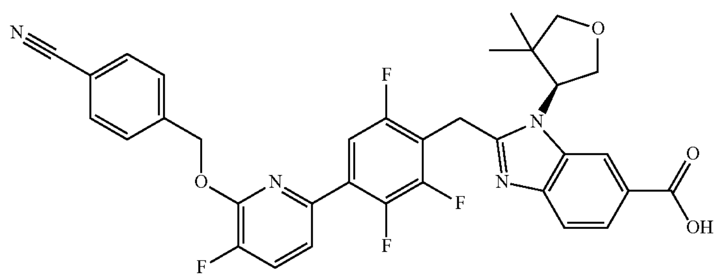 [SMILES: CC1(C)COC[C@H]1n1c(Cc2c(F)cc(-c3ccc(F)c(OCc4ccc(C#N)cc4)n3)c(F)c2F)nc2ccc(C(=O)O)cc21] | 35 | 631.5 | 1H NMR (400 MHz, Methanol-d4) δ 8.83 (s, 1H), 8.09 (dd, J = 8.6, 1.4 Hz, 1H), 7.84-7.74 (m, 2H), 7.74-7.66 (m, 4H), 7.51 (m, 2H), 5.68 (s, 2H), 5.16 (d, J = 6.6 Hz, 1H), 4.80-4.66 (m, 2H), 4.57 (dd, J = 11.6, 6.7 Hz, 2H), 3.99 (d, J = 8.9 Hz, 1H), 3.86 (d, J = 8.9 Hz, 1H), 1.48 (s, 3H), 0.81 (s, 3H). |
| 284 | 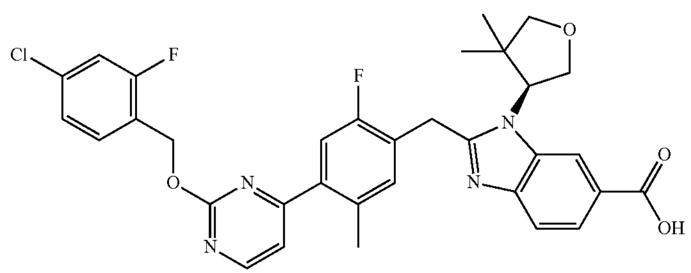 | 35 | 619.2 | 1H NMR (400 MHz, Methanol-d4) δ 8.91 (s, 1H), 8.71 (d, J = 5.1 Hz, 1H), 8.19 (dd, J = 8.6, 1.4 Hz, 1H), 7.79 (d, J = 8.6 Hz, 1H), 7.58 (t, J = 8.2 Hz, 1H), 7.44 (dd, J = 14.0, 9.0 Hz, 2H), 7.34 (d, J = 5.1 Hz, 1H), 7.31-7.20 (m, 2H), 5.57 (s, 2H), 5.15 (d, J = 6.2 Hz, 1H), 4.79-4.58 (m, 3H), 4.52 (dd, J = 11.6, 6.7 Hz, 1H), 4.00 (d, J = 8.9 Hz, 1H), 3.84 (d, J = 8.9 Hz, 1H), 2.43 (s, 3H), 1.39 (s, 3H), 0.75 (s, 3H). |

TABLE 2-continued

Compounds

| Ex. | Structure | Procedure | ES/MS m/z | ¹H NMR |
|---|---|---|---|---|
| 285 | 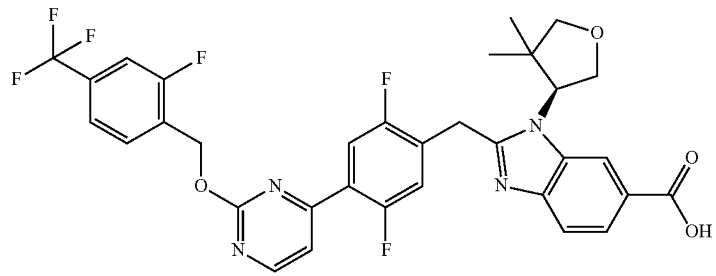 [SMILES: CC1(C)COC[C@H]1n1c(Cc2cc(F)c(-c3ccnc(OCc4ccc(C(F)(F)F)cc4F)n3)cc2F)nc2ccc(C(=O)O)cc21] | 35 | 657.3 | 1H NMR (400 MHz, Methanol-d4) δ 8.85 (s, 1H), 8.73 (d, J = 5.2 Hz, 1H), 8.13 (dd, J = 8.5, 1.4 Hz, 1H), 8.03 (dd, J = 10.4, 6.1 Hz, 1H), 7.82 (t, J = 7.5 Hz, 1H), 7.74 (d, J = 8.6 Hz, 1H), 7.69 (dd, J = 5.2, 1.7 Hz, 1H), 7.56 (d, J = 7.9 Hz, 2H), 7.45 (dd, J = 11.2, 5.9 Hz, 1H), 5.71 (s, 2H), 5.11 (d, J = 6.6 Hz, 1H), 4.79-4.58 (m, 3H), 4.52 (dd, J = 11.5, 6.8 Hz, 1H), 3.99 (d, J = 8.9 Hz, 1H), 3.84 (d, J = 8.9 Hz, 1H), 1.42 (s, 3H), 0.76 (s, 3H). |
| 286 | 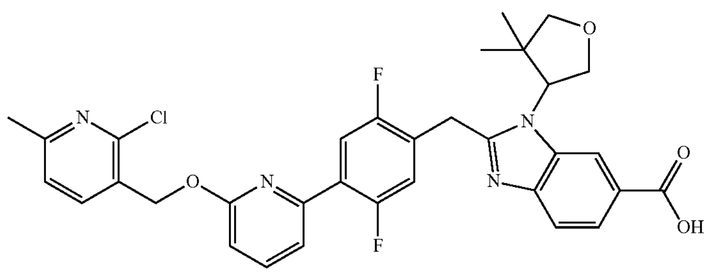 [SMILES: Cc1ccc(COc2cccc(-c3cc(F)c(Cc4nc5ccc(C(=O)O)cc5n4C4COCC4(C)C)cc3F)n2)c(Cl)n1] | 27 | 619.4 | 1H NMR (400 MHz, Methanol-d4) δ 8.91 (s, 1H), 8.19 (dd, J = 8.6, 1.4 Hz, 1H), 7.93-7.80 (m, 3H), 7.78 (d, J = 8.6 Hz, 1H), 7.59 (dd, J = 7.4, 1.6 Hz, 1H), 7.40 (dd, J = 11.2, 6.0 Hz, 1H), 7.27 (d, J = 7.8 Hz, 1H), 6.98 (d, J = 8.2 Hz, 1H), 5.57 (s, 2H), 5.15 (d, J = 6.4 Hz, 1H), 4.75 (d, J = 17.3 Hz, 1H), 4.71-4.62 (m, 2H), 4.53 (dd, J = 11.7, 6.7 Hz, 1H), 4.00 (d, J = 8.9 Hz, 1H), 3.85 (d, J = 8.9 Hz, 1H), 2.51 (s, 3H), 1.41 (s, 3H), 0.76 (s, 3H). |

TABLE 2-continued

Compounds

| Ex. | Structure | Procedure | ES/MS m/z | ¹H NMR |
|---|---|---|---|---|
| 287 | 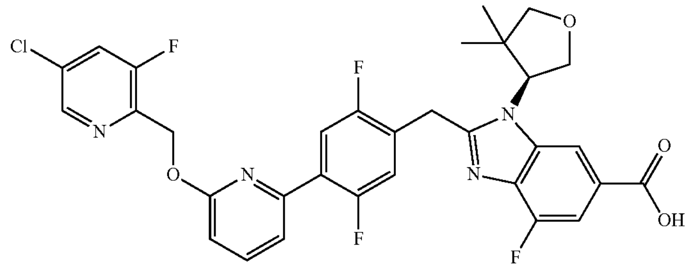 [SMILES: CC1(C)COC[C@H]1n1c(Cc2cc(F)c(-c3cccc(OCc4ncc(Cl)cc4F)n3)cc2F)nc2c(F)cc(C(=O)O)cc21] | 35 | 641.3 | 1H NMR (400 MHz, Methanol-d4) δ 8.56 (s, 1H), 8.43 (d, J = 1.9 Hz, 1H), 7.93-7.74 (m, 3H), 7.68 (dd, J = 11.1, 1.2 Hz, 1H), 7.60-7.50 (m, 1H), 7.21 (dd, J = 11.5, 6.0 Hz, 1H), 6.89 (d, J = 8.2 Hz, 1H), 5.63 (d, J = 1.9 Hz, 2H), 4.95 (d, J = 7.3 Hz, 1H), 4.62-4.44 (m, 4H), 3.94 (d, J = 8.8 Hz, 1H), 3.80 (d, J = 8.8 Hz, 1H), 1.35 (s, 3H), 0.66 (s, 3H). |
| 288 | 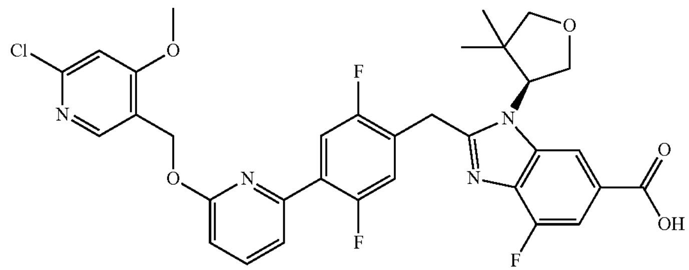 [SMILES: COc1cc(Cl)ncc1COc1cccc(-c2cc(F)c(Cc3nc4c(F)cc(C(=O)O)cc4n3[C@@H]3COCC3(C)C)cc2F)n1] | 35 | 653.5 | 1H NMR (400 MHz, Methanol-d4) δ 8.58 (s, 1H), 8.29 (s, 1H), 7.88 (dd, J = 10.8, 6.3 Hz, 1H), 7.84-7.75 (m, 1H), 7.70 (dd, J = 11.0, 1.2 Hz, 1H), 7.58-7.50 (m, 1H), 7.29-7.23 (m, 1H), 7.22 (d, J = 11.4 Hz, 1H), 6.89 (dd, J = 8.3, 0.7 Hz, 1H), 5.58-5.44 (m, 2H), 4.98 (d, J = 6.7 Hz, 1H), 4.66-4.35 (m, 4H), 4.02 (s, 3H), 3.94 (d, J = 8.8 Hz, 1H), 3.80 (d, J = 8.8 Hz, 1H), 1.36 (s, 3H), 0.68 (s, 3H). |
| 289 A | 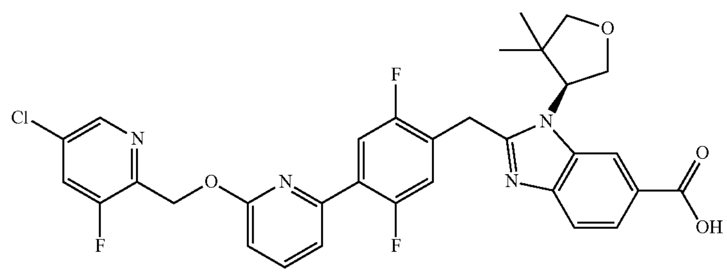 [SMILES: CC1(C)COC[C@H]1n1c(Cc2cc(F)c(-c3cccc(OCc4ncc(Cl)cc4F)n3)cc2F)nc2ccc(C(=O)O)cc21] | chiral separation Peak 2 | 623.7 | 1H NMR (400 MHz, Methanol-d4) δ 8.81 (s, 1H), 8.43 (d, J = 1.9 Hz, 1H), 8.09 (dd, J = 8.6, 1.4 Hz, 1H), 7.95-7.78 (m, 3H), 7.74 (d, J = 8.6 Hz, 1H), 7.58 (dd, J = 7.6, 1.5 Hz, 1H), 7.31 (dd, J = 11.4, 6.0 Hz, 1H), 6.91 (d, J = 8.3 Hz, 1H), 5.63 (d, J = 1.9 Hz, 2H), 5.06 (d, J = 6.6 Hz, 1H), 4.74-4.43 (m, 4H), 3.98 (d, J = 8.8 Hz, 1H), 3.83 (d, J = 8.8 Hz, 1H), 1.40 (s, 3H), 0.72 (s, 3H). |

TABLE 2-continued

Compounds

| Ex. | Structure | Procedure | ES/MS m/z | ¹H NMR |
|---|---|---|---|---|
| 289 B | 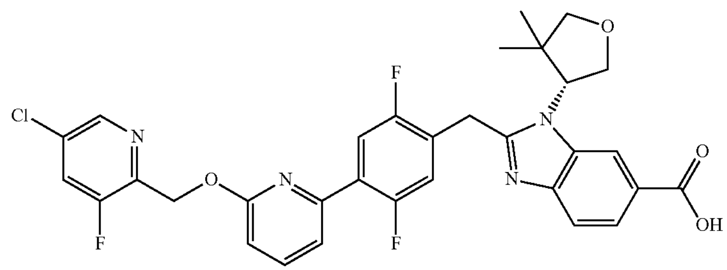 | chiral separation Peak 1 | 623.7 | 1H NMR (400 MHz, Methanol-d4) δ 8.90 (s, 1H), 8.43 (d, J = 1.9 Hz, 1H), 8.18 (dd, J = 8.6, 1.4 Hz, 1H), 7.91 (dd, J = 10.9, 6.3 Hz, 1H), 7.88-7.74 (m, 3H), 7.59 (dd, J = 7.4, 1.5 Hz, 1H), 7.38 (dd, J = 11.2, 6.1 Hz, 1H), 6.92 (d, J = 8.2 Hz, 1H), 5.63 (d, J = 1.9 Hz, 2H), 5.14 (d, J = 6.6 Hz, 1H), 4.80-4.61 (m, 3H), 4.53 (dd, J = 11.6, 6.7 Hz, 1H), 4.00 (d, J = 8.9 Hz, 1H), 3.85 (d, J = 8.9 Hz, 1H), 1.41 (s, 3H), 0.76 (s, 3H). |
| 290 A | 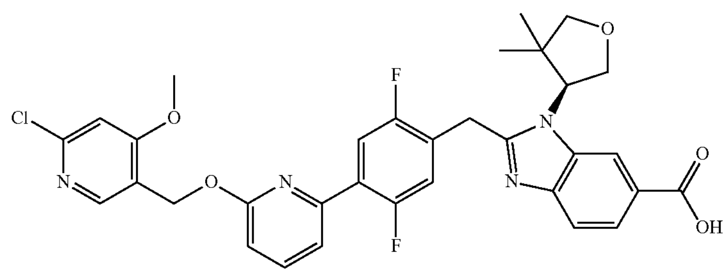 [SMILES: COc1cc(Cl)ncc1COc1cccc(-c2cc(F)c(Cc3nc4ccc(C(=O)O)cc4n3[C@@H]3COCC3(C)C)cc2F)n1] | chiral separation Peak 2 | 636.1 | 1H NMR (400 MHz, Methanol-d4) δ 8.88 (s, 1H), 8.28 (s, 1H), 8.16 (dd, J = 8.6, 1.4 Hz, 1H), 7.93 (dd, J = 10.8, 6.3 Hz, 1H), 7.85-7.72 (m, 2H), 7.58 (dd, J = 7.4, 1.5 Hz, 1H), 7.39 (dd, J = 11.2, 6.0 Hz, 1H), 7.18 (s, 1H), 6.91 (d, J = 8.2 Hz, 1H), 5.51 (s, 2H), 5.13 (d, J = 6.6 Hz, 1H), 4.76-4.58 (m, 3H), 4.53 (dd, J = 11.6, 6.7 Hz, 1H), 4.00 (s, 4H), 3.84 (d, J = 8.9 Hz, 1H), 1.42 (s, 3H), 0.76 (s, 3H). |
| 290 B | 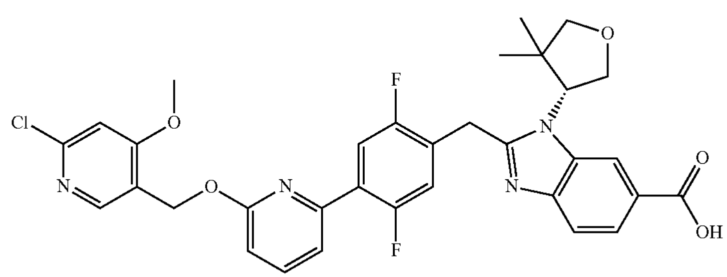 [SMILES: COc1cc(Cl)ncc1COc1cccc(-c2cc(F)c(Cc3nc4ccc(C(=O)O)cc4n3[C@H]3COCC3(C)C)cc2F)n1] | chiral separation Peak 1 | 636.1 | 1H NMR (400 MHz, Methanol-d4) δ 8.88 (s, 1H), 8.28 (s, 1H), 8.16 (dd, J = 8.6, 1.4 Hz, 1H), 7.93 (dd, J = 10.8, 6.3 Hz, 1H), 7.85-7.72 (m, 2H), 7.58 (dd, J = 7.4, 1.5 Hz, 1H), 7.39 (dd, J = 11.2, 6.0 Hz, 1H), 7.18 (s, 1H), 6.91 (d, J = 8.2 Hz, 1H), 5.51 (s, 2H), 5.13 (d, J = 6.6 Hz, 1H), 4.76-4.58 (m, 3H), 4.53 (dd, J = 11.6, 6.7 Hz, 1H), 4.00 (s, 4H), 3.84 (d, J = 8.9 Hz, 1H), 1.42 (s, 3H), 0.76 (s, 3H). |

TABLE 2-continued

Compounds

| Ex. | Structure | Procedure | ES/MS m/z | ¹H NMR |
|---|---|---|---|---|
| 291 | 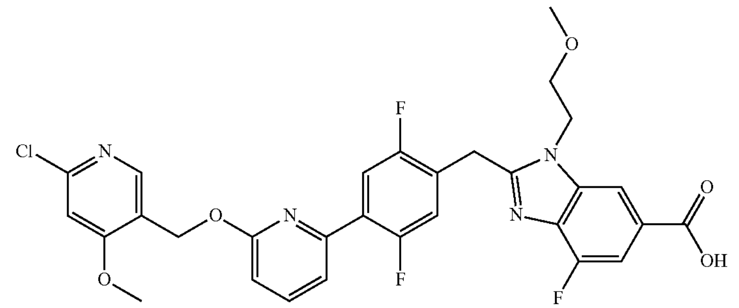 [SMILES: COCCn1c(Cc2cc(F)c(-c3cccc(OCc4cnc(Cl)cc4OC)n3)cc2F)nc2c(F)cc(C(=O)O)cc21] | 37 | 613.4 | 1H NMR (400 MHz, Methanol-d4) δ 8.28 (s, 1H), 8.19 (d, J = 1.2 Hz, 1H), 7.86 (dd, J = 10.8, 6.3 Hz, 1H), 7.79 (t, J = 7.9 Hz, 1H), 7.72 (dd, J = 11.1, 1.2 Hz, 1H), 7.54 (dd, J = 7.5, 1.6 Hz, 1H), 7.20 (q, J = 6.2 Hz, 2H), 6.88 (d, J = 8.2 Hz, 1H), 5.50 (s, 2H), 4.63 (t, J = 5.0 Hz, 2H), 4.57 (s, 2H), 4.01 (s, 3H), 3.75 (t, J = 4.9 Hz, 2H), 3.28 (s, 3H). |
| 292 | 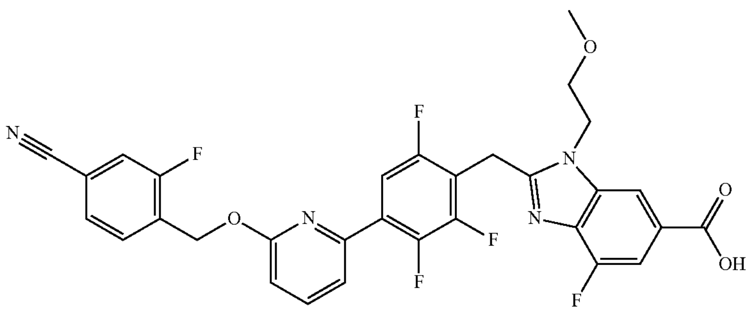 [SMILES: COCCn1c(Cc2c(F)cc(-c3cccc(OCc4ccc(C#N)cc4F)n3)c(F)c2F)nc2c(F)cc(C(=O)O)cc21] | 22 | 609.3 | 1H NMR (400 MHz, Methanol-d4) δ 8.15 (d, J = 1.3 Hz, 1H), 7.86 (t, J = 7.9 Hz, 1H), 7.75 (t, J = 7.5 Hz, 1H), 7.70-7.56 (m, 5H), 6.97 (d, J = 8.3 Hz, 1H), 5.64 (s, 2H), 4.67 (t, J = 5.0 Hz, 2H), 4.60 (s, 2H), 3.81 (t, J = 4.9 Hz, 2H). |
| 293 | 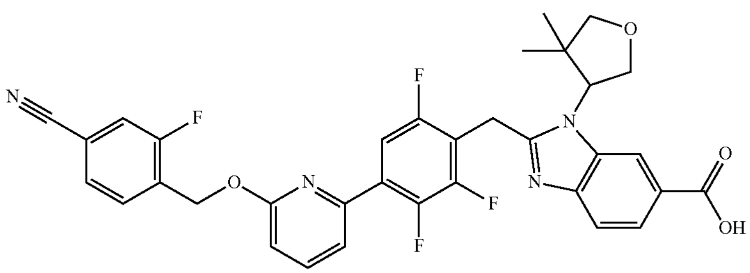 [SMILES: CC1(C)COCC1n1c(Cc2c(F)cc(-c3cccc(OCc4ccc(C#N)cc4F)n3)c(F)c2F)nc2ccc(C(=O)O)cc21] | 22 | 631.3 | 1H NMR (400 MHz, Methanol-d4) δ 8.85 (s, 1H), 8.11 (dd, J = 8.6, 1.4 Hz 1H), 7.89 (t, J = 7.9 Hz, 1H), 7.82-7.66 (m, 3H), 7.66-7.50 (m, 3H), 7.01 (d, J = 8.3 Hz, 1H), 5.64 (s, 2H), 5.17 (d, J = 6.5 Hz, 1H), 4.85-4.50 (m, 4H), 4.00 (d, J = 8.9 Hz, 1H), 3.87 (d, J = 8.9 Hz, 1H), 1.48 (s, 3H), 0.82 (s, 3H). |

TABLE 2-continued

Compounds

| Ex. | Structure | Procedure | ES/MS m/z | ¹H NMR |
|---|---|---|---|---|
| 294 | 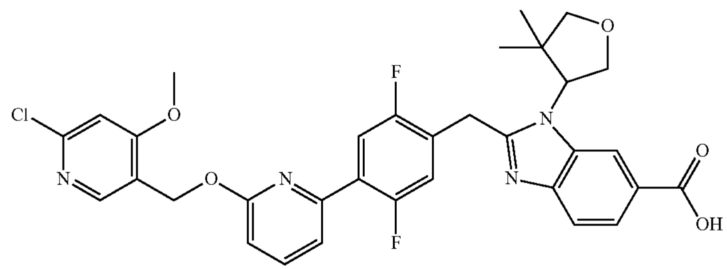 [SMILES: COc1cc(Cl)ncc1COc1cccc(-c2cc(F)c(Cc3nc4ccc(C(=O)O)cc4n3C3COCC3(C)C)cc2F)n1] | 27 | 636.1 | 1H NMR (400 MHz, Methanol-d4) δ 8.88 (s, 1H), 8.28 (s, 1H), 8.16 (dd, J = 8.6, 1.4 Hz, 1H), 7.93 (dd, J = 10.8, 6.3 Hz, 1H), 7.85-7.72 (m, 2H), 7.58 (dd, J = 7.4, 1.5 Hz, 1H), 7.39 (dd, J = 11.2, 6.0 Hz, 1H), 7.18 (s, 1H), 6.91 (d, J = 8.2 Hz, 1H), 5.51 (s, 2H), 5.13 (d, J = 6.6 Hz, 1H), 4.76-4.58 (m, 3H), 4.53 (dd, J = 11.6, 6.7 Hz, 1H), 4.00 (s, 4H), 3.84 (d, J = 8.9 Hz, 1H), 1.42 (s, 3H), 0.76 (s, 3H). |
| 295 | 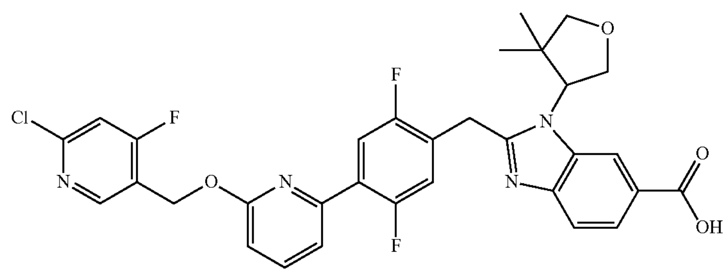 [SMILES: CC1(C)COCC1n1c(Cc2cc(F)c(-c3cccc(OCc4cnc(Cl)cc4F)n3)cc2F)nc2ccc(C(=O)O)cc21] | 27 | 623.7 | 1H NMR (400 MHz, Methanol-d4) δ 8.91 (s, 1H), 8.57 (d, J = 9.6 Hz, 1H), 8.19 (dd, J = 8.6, 1.4 Hz, 1H), 7.95 (dd, J = 10.8, 6.3 Hz, 1H), 7.89-7.75 (m, 2H), 7.59 (dd, J = 7.5, 1.6 Hz, 1H), 7.41 (dd, J = 10.1, 4.8 Hz, 2H), 6.93 (d, J = 8.2 Hz, 1H), 5.60 (s, 2H), 5.15 (d, J = 6.6 Hz, 1H), 4.81-4.61 (m, 3H), 4.53 (dd, J = 11.6, 6.7 Hz, 1H), 4.00 (d, J = 8.9 Hz, 1H), 3.85 (d, J = 8.9 Hz, 1H), 1.42 (s, 3H), 0.77 (s, 3H). |
| 296 | 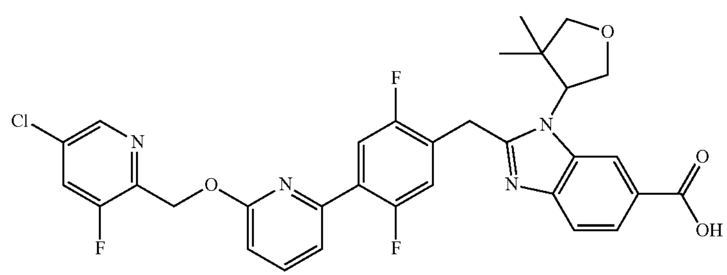 [SMILES: CC1(C)COCC1n1c(Cc2cc(F)c(-c3cccc(OCc4ncc(Cl)cc4F)n3)cc2F)nc2ccc(C(=O)O)cc21] | 27 | 623.7 | 1H NMR (400 MHz, Methanol-d4) δ 8.90 (s, 1H), 8.43 (d, J = 1.9 Hz, 1H), 8.18 (dd, J = 8.6, 1.4 Hz, 1H), 7.91 (dd, J = 10.9, 6.3 Hz, 1H), 7.88-7.74 (m, 3H), 7.59 (dd, J = 7.4, 1.5 Hz, 1H), 7.38 (dd, J = 11.2, 6.1 Hz, 1H), 6.92 (d, J = 8.2 Hz, 1H), 5.63 (d, J = 1.9 Hz, 2H), 5.14 (d, J = 6.6 Hz, 1H), 4.80-4.61 (m, 3H), 4.53 (dd, J = 11.6, 6.7 Hz, 1H), 4.00 (d, J = 8.9 Hz, |

TABLE 2-continued

Compounds

| Ex. | Structure | Procedure | ES/MS m/z | ¹H NMR |
|---|---|---|---|---|
| 297 | 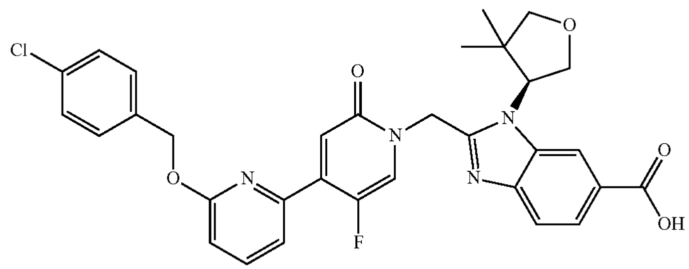 [SMILES: CC1(C)COC[C@H]1n1c(Cn2cc(F)c(-c3cccc(OCc4ccc(Cl)cc4)n3)cc2=O)nc2ccc(C(=O)O)cc21] | 35 | 603.09 | 1H NMR (400 MHz, DMSO) δ 8.48 (s, 1H), 8.24 (d, J = 6.9 Hz, 1H), 7.92 (t, J = 7.9 Hz, 1H), 7.81 (d, J = 8.4 Hz, 1H), 7.66 (d, J = 8.5 Hz, 1H), 7.57-7.49 (m, 3H), 7.45 (d, J = 8.4 Hz, 2H), 7.06 (d, J = 8.3 Hz, 1H), 6.97 (d, J = 7.4 Hz, 1H), 5.55 (d, J = 16.0 Hz, 1H), 5.46 (d, J = 8.7 Hz, 3H), 5.10 (d, J = 6.6 Hz, 1H), 4.61-4.39 (m, 2H), 3.83-3.69 (m, 2H), 1.38 (s, 3H), 0.66 (s, 3H). |
| 298 | 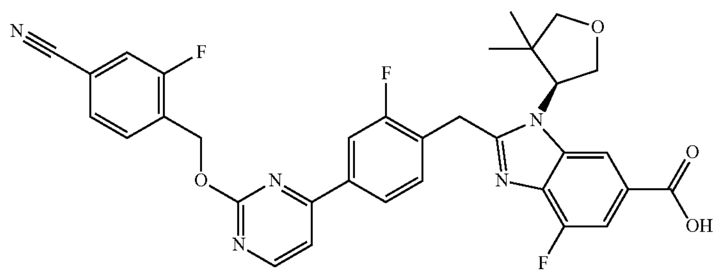 [SMILES: CC1(C)COC[C@H]1n1c(Cc2ccc(-c3ccnc(OCc4ccc(C#N)cc4F)n3)cc2F)nc2c(F)cc(C(=O)O)cc21] | 35 | 614.38 | 1H NMR (400 MHz, DMSO) δ 8.75 (d, J = 5.2 Hz, 1H), 8.35 (s, 1H), 8.06 (d, J = 9.4 Hz, 2H), 7.95 (dd, J = 10.0, 1.5 Hz, 1H), 7.90-7.69 (m, 3H), 7.65-7.46 (m, 2H), 5.64 (s, 2H), 5.01 (d, J = 6.5 Hz, 1H), 4.73-4.37 (m, 4H), 3.74 (q, J = 8.7 Hz, 2H), 1.31 (s, 3H), 0.59 (s, 3H). |
| 299 | 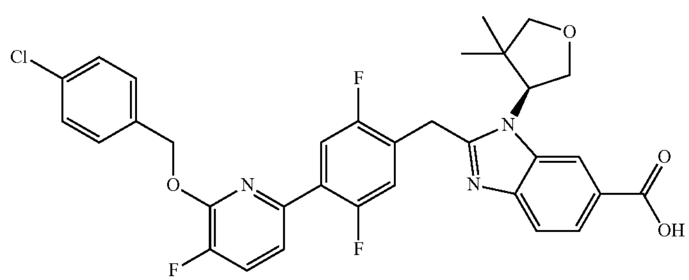 [SMILES: CC1(C)COC[C@H]1n1c(Cc2cc(F)c(-c3ccc(F)c(OCc4ccc(Cl)cc4)n3)cc2F)nc2ccc(C(=O)O)cc21] | 35 | 622.17 | 1H NMR (400 MHz, DMSO) δ 8.49 (s, 1H), 8.10-7.72 (m, 3H), 7.72-7.40 (m, 8H), 5.57 (s, 2H), 5.02 (d, J = 6.5 Hz, 1H), 4.82-4.27 (m, 4H), 3.85-3.64 (m, 2H), 1.34 (s, 3H), 0.61 (s, 3H). |

TABLE 2-continued

Compounds

| Ex. | Structure | Procedure | ES/MS m/z | ¹H NMR |
|---|---|---|---|---|
| 300 | (structure) | 35 | 621.09 | 1H NMR (400 MHz, DMSO) δ 8.48 (s, 1H), 8.25 (d, J = 7.1 Hz, 1H), 8.04-7.76 (m, 2H), 7.74-7.40 (m, 6H), 6.95 (d, J = 7.5 Hz, 1H), 5.50 (d, J = 28.8 Hz, 4H), 5.10 (d, J = 6.7 Hz, 1H), 4.70-4.34 (m, 2H), 3.73 (d, J = 8.6 Hz, 2H), 1.38 (s, 3H), 0.66 (s, 3H). |
| 301 | (structure) | 35 | 608.29 | 1H NMR (400 MHz, DMSO) δ 8.75 (d, J = 5.1 Hz, 1H), 8.50 (s, 1H), 8.00-7.74 (m, 3H), 7.74-7.53 (m, 4H), 7.53-7.28 (m, 2H), 5.57 (s, 2H), 5.02 (d, J = 6.7 Hz, 1H), 4.66-4.29 (m, 4H), 3.93-3.59 (m, 2H), 2.33 (s, 3H), 1.34 (s, 3H), 0.66 (s, 3H). |
| 302 | (structure) | 35 | 622.21 | 1H NMR (400 MHz, DMSO) δ 8.49 (s, 1H), 7.88 (dd, J = 8.2, 5.1 Hz, 3H), 7.82-7.71 (m, 2H), 7.71-7.44 (m, 4H), 7.34 (dd, J = 8.2, 2.0 Hz, 1H), 6.95 (d, J = 8.2 Hz, 1H), 5.55 (s, 2H), 5.09 (d, J = 6.6 Hz, 1H), 4.58 (d, J = 18.1 Hz, 2H), 4.47 (dd, J = 11.2, 6.7 Hz, 1H), 4.32 (d, J = 17.3 Hz, 1H), 3.86-3.71 (m, 2H), 1.38 (s, 3H), 0.66 (s, 3H). |

TABLE 2-continued

Compounds

| Ex. | Structure | Procedure | ES/MS m/z | 1H NMR |
|---|---|---|---|---|
| 303 | | 35 | 640.13 | 1H NMR (400 MHz, DMSO) δ 8.48 (s, 1H), 7.93-7.75 (m, 5H), 7.65 (t, J = 8.2 Hz, 1H), 7.61-7.50 (m, 2H), 7.36 (dd, J = 8.2, 2.1 Hz, 1H), 5.64 (s, 2H), 5.09 (d, J = 6.6 Hz, 1H), 4.64-4.42 (m, 3H), 4.30 (d, J = 17.3 Hz, 1H), 3.76 (t, J = 6.4 Hz, 2H), 1.38 (s, 3H), 0.65 (s, 3H). |
| 305 | | 35 | 642.72 | 1H NMR (400 MHz, DMSO) δ 8.35 (s, 1H), 7.89 (dd, J = 9.8, 8.3 Hz, 3H), 7.76 (d, J = 7.5 Hz, 1H), 7.63 (t, J = 8.2 Hz, 1H), 7.55-7.43 (m, 2H), 7.33 (dd, J = 8.2, 2.1 Hz, 1H), 6.94 (d, J = 8.1 Hz, 1H), 5.55 (s, 2H), 5.11 (d, J = 6.5 Hz, 1H), 4.71-4.49 (m, 2H), 4.46 (dd, J = 11.3, 6.6 Hz, 1H), 4.32 (d, J = 17.3 Hz, 1H), 3.76 (s, 2H), 1.39 (s, 3H), 0.66 (s, 3H). |
| 306 | | 35 | 658.85 | 1H NMR (400 MHz, DMSO) δ 8.35 (s, 1H), 7.93-7.74 (m, 4H), 7.65 (t, J = 8.2 Hz, 1H), 7.51 (ddd, J = 11.1, 8.9, 1.6 Hz, 2H), 7.36 (dd, J = 8.2, 2.1 Hz, 1H), 5.64 (s, 2H), 5.11 (d, J = 6.5 Hz, 1H), 4.71-4.39 (m, 3H), 4.31 (d, J = 17.4 Hz, 1H), 3.76 (s, 2H), 1.38 (s, 3H), 0.66 (s, 3H). |

TABLE 2-continued

Compounds

| Ex. | Structure | Procedure | ES/MS m/z | ¹H NMR |
|---|---|---|---|---|
| 307 | 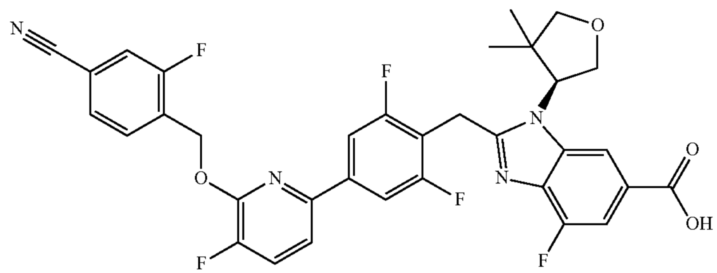 [SMILES: CC1(C)COC[C@H]1n1c(Cc2c(F)cc(-c3ccc(F)c(OCc4ccc(C#N)cc4F)n3)cc2F)nc2c(F)cc(C(=O)O)cc21] | 35 | 649.36 | 1H NMR (400 MHz, DMSO) δ 8.35 (s, 1H), 8.02-7.69 (m, 7H), 7.53-7.47 (m, 1H), 5.74 (s, 2H), 5.11 (d, J = 6.4 Hz, 1H), 4.74-4.50 (m, 2H), 4.46 (dd, J = 11.1, 6.6 Hz, 1H), 4.31 (d, J = 17.3 Hz, 1H), 3.76 (s, 2H), 1.38 (s, 3H), 0.66 (s, 3H). |
| 308 | 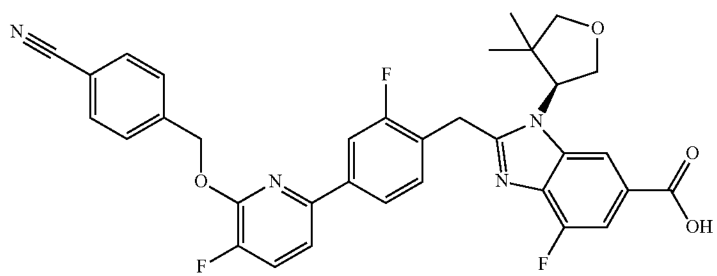 [SMILES: CC1(C)COC[C@H]1n1c(Cc2ccc(-c3ccc(F)c(OCc4ccc(C#N)cc4)n3)cc2F)nc2c(F)cc(C(=O)O)cc21] | 35 | 613.21 | 1H NMR (400 MHz, DMSO) δ 8.35 (s, 1H), 7.98-7.79 (m, 6H), 7.72 (d, J = 3.2 Hz, 1H), 7.60-7.42 (m, 2H), 7.19 (dd, J = 8.2, 2.6 Hz, 3H), 5.69 (s, 2H), 5.01 (s, 1H), 4.67-4.27 (m, 4H), 1.30 (s, 3H), 0.58 (s, 3H). |
| 309 | 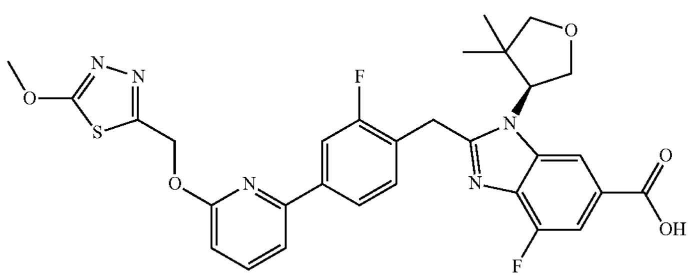 [SMILES: COc1nnc(COc2cccc(-c3ccc(Cc4nc5c(F)cc(C(=O)O)cc5n4[C@@H]4COCC4(C)C)c(F)c3)n2)s1] | 35 | 608.25 | 1H NMR (400 MHz, DMSO) δ 8.18 (s, 1H), 8.00 (dd, J = 15.7, 9.9 Hz, 2H), 7.89 (t, J = 7.8 Hz, 1H), 7.74 (d, J = 7.7 Hz, 1H), 7.48 (t, J = 8.7 Hz, 2H), 6.92 (d, J = 8.2 Hz, 2H), 5.75 (s, 2H), 4.93 (s, 1H), 4.63-4.22 (m, 2H), 4.09 (s, 3H), 3.84-3.65 (m, 2H), 1.26 (s, 3H), 0.56 (s, 3H). |

TABLE 2-continued

Compounds

| Ex. | Structure | Procedure | ES/MS m/z | ¹H NMR |
|---|---|---|---|---|
| 310 | 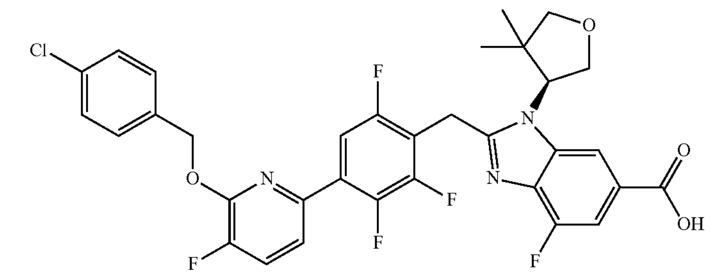 [SMILES: CC1(C)COC[C@H]1n1c(Cc2c(F)cc(-c3ccc(F)c(OCc4ccc(Cl)cc4)n3)c(F)c2F)nc2c(F)cc(C(=O)O)cc21] | 35 | 658.14 | 1H NMR (400 MHz, DMSO) δ 8.36 (s, 1H), 7.90 (dd, J = 10.2, 8.2 Hz, 1H), 7.70 (td, J = 6.3, 3.3 Hz, 1H), 7.64-7.45 (m, 6H), 5.58 (s, 2H), 5.11 (d, J = 6.5 Hz, 2H), 4.67 (d, J = 17.4 Hz, 1H), 4.61-4.30 (m, 3H), 3.76 (s, 2H), 1.39 (s, 3H), 0.67 (s, 3H). |
| 311 A | 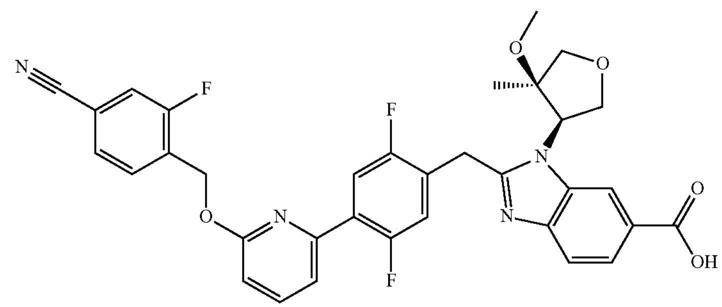 [SMILES: CO[C@@]1(C)COC[C@H]1n1c(Cc2cc(F)c(-c3cccc(OCc4ccc(C#N)cc4F)n3)cc2F)nc2ccc(C(=O)O)cc21] | 39 | 629.32 | 1H NMR (400 MHz, DMSO) δ 8.44 (s, 1H), 7.98-7.84 (m, 2H), 7.77 (ddd, J = 15.0, 8.4, 1.6 Hz, 5H), 7.68-7.48 (m, 3H), 7.37 (dd, J = 11.5, 6.0 Hz, 1H), 7.00 (d, J = 8.3 Hz, 1H), 5.61 (s, 2H), 5.29 (s, 1H), 4.61-4.33 (m, 3H), 4.28-4.14 (m, 2H), 2.96 (s, 3H), 1.43 (s, 3H). |
| 311 B | 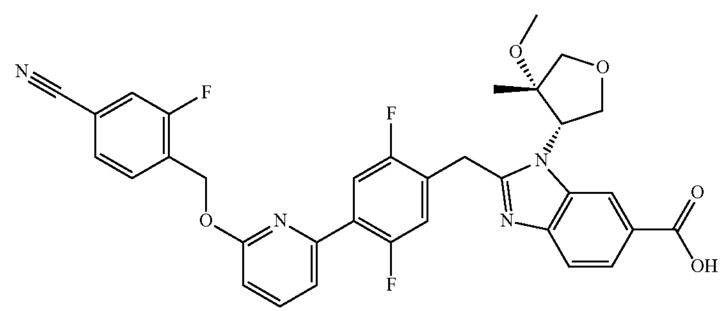 [SMILES: CO[C@]1(C)COC[C@@H]1n1c(Cc2cc(F)c(-c3cccc(OCc4ccc(C#N)cc4F)n3)cc2F)nc2ccc(C(=O)O)cc21] | 39 | 629.32 | 1H NMR (400 MHz, DMSO) δ 8.44 (s, 1H), 7.98-7.84 (m, 2H), 7.77 (ddd, J = 15.0, 8.4, 1.6 Hz, 5H), 7.68-7.48 (m, 3H), 7.37 (dd, J = 11.5, 6.0 Hz, 1H), 7.00 (d, J = 8.3 Hz, 1H), 5.61 (s, 2H), 5.29 (s, 1H), 4.61-4.33 (m, 3H), 4.28-4.14 (m, 2H), 2.96 (s, 3H), 1.43 (s, 3H). |

TABLE 2-continued

Compounds

| Ex. | Structure | Procedure | ES/MS m/z | ¹H NMR |
|---|---|---|---|---|
| 312 | 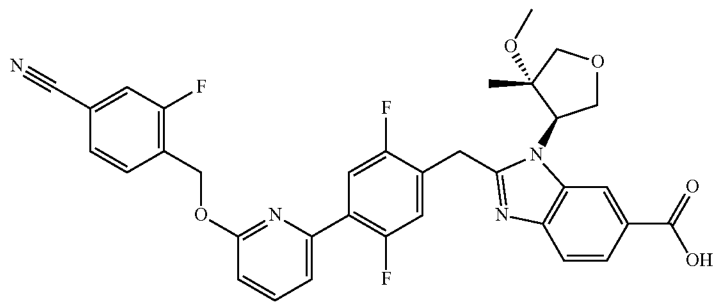 [SMILES: CO[C@]1(C)COC[C@H]1n1c(Cc2cc(F)c(-c3cccc(OCc4ccc(C#N)cc4F)n3)cc2F)nc2ccc(C(=O)O)cc21] | 39 | 629.32 | 1H NMR (400 MHz, DMSO) δ 8.46 (s, 1H), 7.99-7.85 (m, 2H), 7.85-7.69 (m, 4H), 7.64 (d, J = 8.5 Hz, 1H), 7.55 (d, J = 7.3 Hz, 1H), 7.46 (dd, J = 10.4, 7.1 Hz, 1H), 7.00 (d, J = 8.3 Hz, 1H), 5.61 (s, 2H), 5.23 (d, J = 6.8 Hz, 1H), 4.82-4.25 (m, 4H), 4.13 (d, J = 10.1 Hz, 1H), 3.80 (d, J = 10.1 Hz, 1H), 3.31 (s, 3H), 0.84 (s, 3H). |
| 313 | 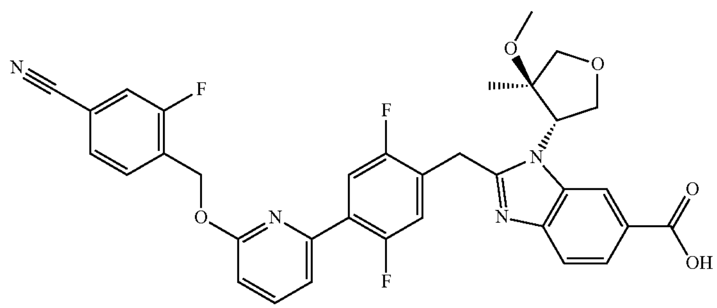 [SMILES: CO[C@@]1(C)COC[C@@H]1n1c(Cc2cc(F)c(-c3cccc(OCc4ccc(C#N)cc4F)n3)cc2F)nc2ccc(C(=O)O)cc21] | 39 | 629.32 | 1H NMR (400 MHz, DMSO) δ 8.46 (s, 1H), 7.99-7.85 (m, 2H), 7.85-7.69 (m, 4H), 7.64 (d, J = 8.5 Hz, 1H), 7.55 (d, J = 7.3 Hz, 1H), 7.46 (dd, J = 10.4, 7.1 Hz, 1H), 7.00 (d, J = 8.3 Hz, 1H), 5.61 (s, 2H), 5.23 (d, J = 6.8 Hz, 1H), 4.82-4.25 (m, 4H), 4.13 (d, J = 10.1 Hz, 1H), 3.80 (d, J = 10.1 Hz, 1H), 3.31 (s, 3H), 0.84 (s, 3H). |
| 316 | 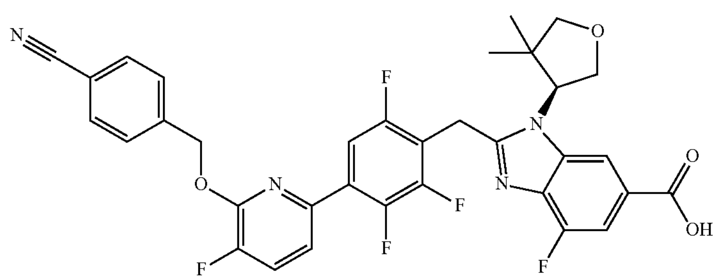 [SMILES: CC1(C)COC[C@H]1n1c(Cc2c(F)cc(-c3ccc(F)c(OCc4ccc(C#N)cc4)n3)c(F)c2F)nc2c(F)cc(C(=O)O)cc21] | 35 | 649.31 | 1H NMR (400 MHz, DMSO) δ 8.36 (s, 1H), 7.92 (dd, J = 19.4, 8.4 Hz, 3H), 7.72 (d, J = 8.0 Hz, 2H), 7.68-7.56 (m, 2H), 7.51 (d, J = 11.2 Hz, 1H), 5.68 (s, 2H), 5.11 (d, J = 6.4 Hz, 1H), 4.82-4.31 (m, 3H), 3.76 (s, 2H), 0.66 (s, 3H). |

TABLE 2-continued

Compounds

| Ex. | Structure | Procedure | ES/MS m/z | ¹H NMR |
|---|---|---|---|---|
| 317 | 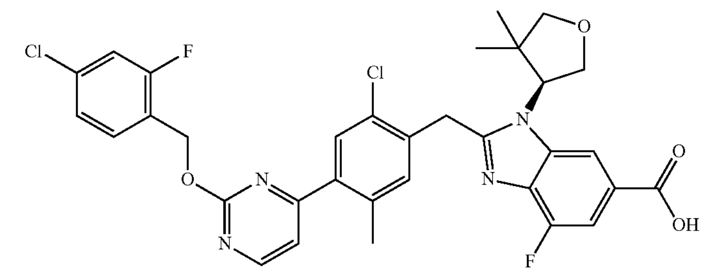 | 35 | 649.31 | 1H NMR (400 MHz, DMSO) δ 8.74 (d, J = 5.1 Hz, 1H), 8.36(s, 1H), 7.69-7.57 (m, 2H), 7.57-7.45 (m, 3H), 7.41 (s, 1H), 7.35 (dd, J = 8.3, 2.1 Hz, 1H), 5.02 (d, J = 6.7 Hz, 1H), 4.64-4.31 (m, 4H), 3.81-3.67 (m, 2H), 1.33 (s, 3H), 0.66 (s, 3H). |
| 318 | 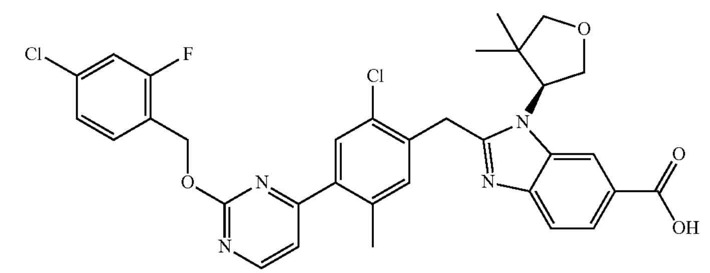 [SMILES: Cc1cc(Cc2nc3ccc(C(=O)O)cc3n2[C@@H]2COCC2(C)C)c(Cl)cc1-c1ccnc(OCc2ccc(Cl)cc2F)n1] | 35 | 636.25 | 1H NMR (400 MHz, DMSO) δ 8.75 (d, J = 5.1 Hz, 1H), 8.36 (s, 1H), 7.94 (d, J = 10.0 Hz, 1H), 7.83-7.70 (m, 2H), 7.61 (s, 1H), 7.57-7.46 (m, 2H), 7.41 (s, 1H), 5.59 (s, 2H), 5.02 (d, J = 6.6 Hz, 1H), 4.73-4.33 (m, 4H), 3.85-3.65 (m, 2H), 1.33 (s, 3H), 0.65 (s, 3H). |
| 319 | 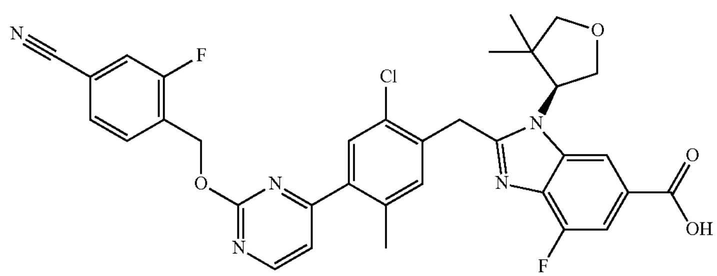 [SMILES: Cc1cc(Cc2nc3c(F)cc(C(=O)O)cc3n2[C@@H]2COCC2(C)C)c(Cl)cc1-c1ccnc(OCc2ccc(C#N)cc2F)n1] | 35 | 644.8 | 1H NMR (400 MHz, DMSO) δ 8.75 (d, J = 5.1 Hz, 1H), 8.36 (s, 1H), 7.94 (d, J = 10.0 Hz, 1H), 7.83-7.70 (m, 2H), 7.61 (s, 1H), 7.57-7.46 (m, 2H), 7.41 (s, 1H), 5.59 (s, 2H), 5.02 (d, J = 6.6 Hz, 1H), 4.73-4.33 (m, 4H), 3.85-3.65 (m, 2H), 1.33 (s, 3H), 0.65 (s, 3H). |

TABLE 2-continued

Compounds

| Ex. | Structure | Procedure | ES/MS m/z | ¹H NMR |
|---|---|---|---|---|
| 320 | 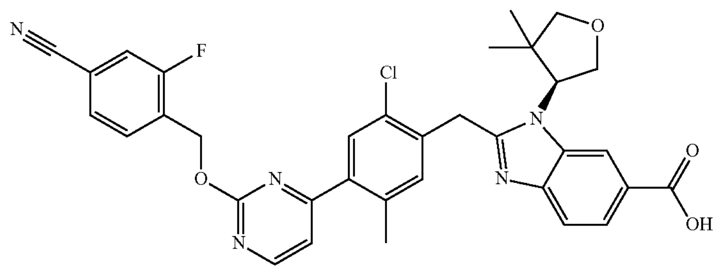 [SMILES: Cc1cc(Cc2nc3ccc(C(=O)O)cc3n2[C@@H]2COCC2(C)C)c(Cl)cc1-c1ccnc(OCc2ccc(C#N)cc2F)n1] | 35 | 626.81 | 1H NMR (400 MHz, DMSO) δ 8.75 (d, J = 5.1 Hz, 1H), 8.51 (s, 1H), 7.94 (d, J = 10.0 Hz, 1H), 7.88-7.57 (m, 3H), 7.68-7.57 (m, 2H), 7.49 (d, J = 5.1 Hz, 1H), 7.42 (s, 1H), 5.59 (s, 2H), 5.02 (d, J = 6.8 Hz, 1H), 4.73-4.23 (m, 4H), 3.88-3.68 (m, 2H), 1.33 (s, 3H), 0.66 (s, 3H). |
| 321 | 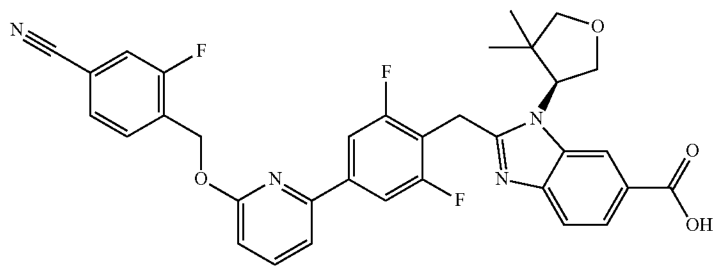 [SMILES: CC1(C)COC[C@H]1n1c(Cc2c(F)cc(-c3cccc(OCc4ccc(C#N)cc4F)n3)cc2F)nc2ccc(C(=O)O)cc21] | 35 | 613.44 | 1H NMR (400 MHz, DMSO) δ 8.48 (s, 1H), 7.98-7.70 (m, 9H), 7.57 (d, J = 8.5 Hz, 1H), 6.99 (d, J = 8.2 Hz, 1H), 5.65 (s, 2H), 5.09 (d, J = 6.6 Hz, 1H), 4.57 (d, J = 16.7 Hz, 2H), 4.47 (dd, J = 11.1, 6.7 Hz, 1H), 4.31 (d, J = 17.1 Hz, 1H), 3.86-3.69 (m, 2H), 1.38 (s, 3H), 0.65 (s, 3H). |
| 322 | 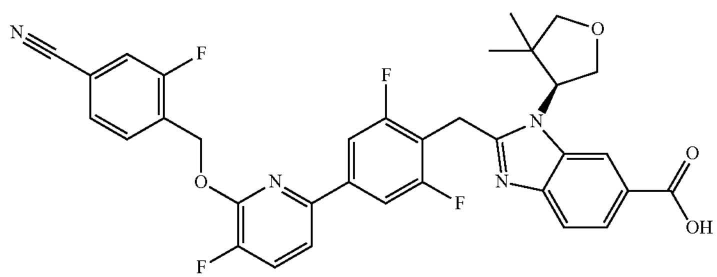 [SMILES: CC1(C)COC[C@H]1n1c(Cc2c(F)cc(-c3ccc(F)c(OCc4ccc(C#N)cc4F)n3)cc2F)nc2ccc(C(=O)O)cc21] | 35 | 631.32 | 1H NMR (400 MHz, DMSO) δ 8.47 (s, 1H), 8.01-7.69 (m, 8H), 7.56 (d, J = 8.5 Hz, 1H), 5.74 (s, 2H), 5.08 (d, J = 6.7 Hz, 1H), 4.76-4.44 (m, 3H), 4.29 (d, J = 17.1 Hz, 1H), 3.77 (d, J = 3.8 Hz, 2H), 1.38 (s, 3H), 0.65 (s, 3H). |

TABLE 2-continued

Compounds

| Ex. | Structure | Procedure | ES/MS m/z | ¹H NMR |
|---|---|---|---|---|
| 323 | 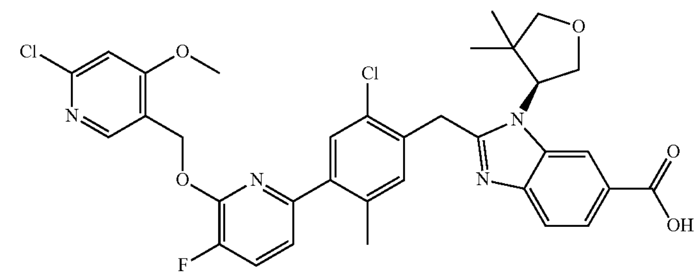 | 35 | 666.25 | 1H NMR (400 MHz, DMSO) δ 8.51 (s, 1H), 8.30 (s, 1H), 7.83 (dd, J = 10.2, 8.2 Hz, 2H), 7.64 (d, J = 8.4 Hz, 1H), 7.53 (s, 1H), 7.37 (s, 1H), 7.32-7.23 (m, 3H), 5.43 (s, 2H), 5.02 (d, J = 6.8 Hz, 1H), 4.72-4.34 (m, 4H), 3.93 (s, 4H), 2.32 (s, 3H), 1.33 (s, 3H), 0.66 (s, 3H). |
| 324 | 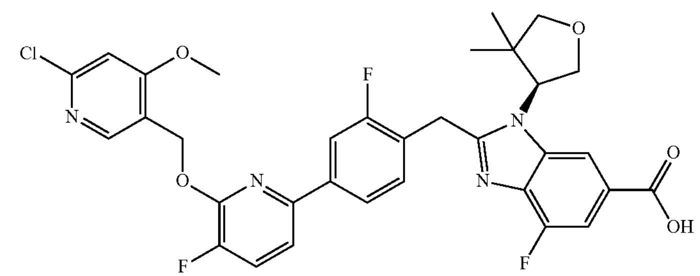 [SMILES: COc1cc(Cl)ncc1COc1nc(-c2ccc(Cc3nc4c(F)cc(C(=O)O)cc4n3[C@@H]3COCC3(C)C)c(F)c2)ccc1F] | 35 | 653.53 | 1H NMR (400 MHz, DMSO) δ 8.36 (d, J = 8.3 Hz, 2H), 7.96-7.87 (m, 2H), 7.81 (dd, J = 10.2, 8.2 Hz, 1H), 7.70 (dd, J = 8.2, 2.8 Hz, 1H), 7.57-7.46 (m, 2H), 7.27 (s, 1H), 5.54 (s, 2H), 5.01 (d, J = 6.6 Hz, 1H), 4.64-4.32 (m, 5H), 3.96 (s, 3H), 1.31 (s, 3H), 0.59 (s, 3H). |
| 325 | 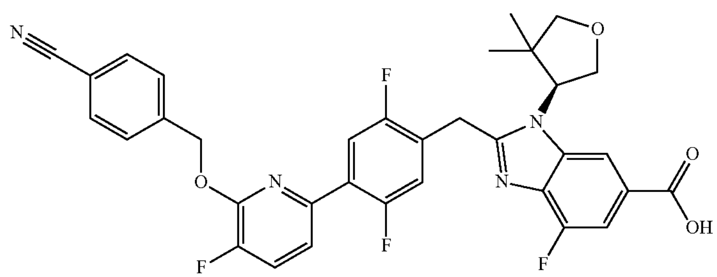 [SMILES: CC1(C)COC[C@H]1n1c(Cc2cc(F)c(-c3ccc(F)c(OCc4ccc(C#N)cc4)n3)cc2F)nc2c(F)cc(C(=O)O)cc21] | 35 | 631.17 | 1H NMR (400 MHz, DMSO) δ 8.35 (s, 1H), 8.10-7.80 (m, 3H), 7.80-7.65 (m, 3H), 7.65-7.35 (m, 3H), 5.68 (s, 2H), 5.03 (d, J = 6.6 Hz, 1H), 4.69-4.30 (m, 4H), 1.34 (s, 3H), 0.61 (s, 3H). |

TABLE 2-continued

Compounds

| Ex. | Structure | Procedure | ES/MS m/z | ¹H NMR |
|---|---|---|---|---|
| 326 | (structure) | 35 | 646.34 | 1H NMR (400 MHz, DMSO) δ 8.34 (d, J = 20.1 Hz, 2H), 8.04-7.85 (m, 2H), 7.74 (d, J = 4.7 Hz, 2H), 7.55 (dd, J = 11.2, 1.2 Hz, 1H), 7.40 (d, J = 7.3 Hz, 1H), 7.07 (d, J = 8.3 Hz, 1H), 6.67 (s, 1H), 5.65-5.38 (m, 4H), 5.13 (d, J = 6.5 Hz, 1H), 4.64-4.39 (m, 2H), 3.83-3.53 (m, 2H), 1.38 (s, 3H), 0.68 (s, 3H). |
| 327 | (structure) | 35 | 655.53 | 1H NMR (400 MHz, DMSO) δ 8.34 (d, J = 16.2 Hz, 2H), 7.91 (dd, J = 8.3, 7.3 Hz, 1H), 7.68-7.44 (m, 3H), 7.44-7.27 (m, 2H), 7.02 (d, J = 8.3 Hz, 1H), 6.70 (s, 1H), 5.45 (s, 2H), 5.14 (d, J = 6.6 Hz, 1H), 4.63-4.29 (m, 2H), 3.93-3.63 (m, 2H), 1.39 (s, 3H), 0.68 (s, 3H). |
| 328 | (structure) | 35 | 630.22 | 1H NMR (400 MHz, DMSO) δ 8.48 (s, 1H), 8.24 (d, J = 7.0 Hz, 1H), 8.04-7.84 (m, 2H), 7.87-7.70 (m, 3H), 7.66 (d, J = 8.5 Hz, 1H), 7.59 (dt, J = 8.6, 2.0 Hz, 1H), 6.92 (d, J = 7.6 Hz, 1H), 5.67 (s, 2H), 5.63-5.32 (m, 2H), 5.10 (d, J = 6.6 Hz, 1H), 4.55 (d, J = 11.1 Hz, 1H), 4.44 (dd, J = 11.1, 6.8 Hz, 1H), 3.83-3.59 (m, 2H), 1.37 (s, 3H), 0.65 (s, 3H). |

TABLE 2-continued

Compounds

| Ex. | Structure | Procedure | ES/MS m/z | ¹H NMR |
|---|---|---|---|---|
| 329 | 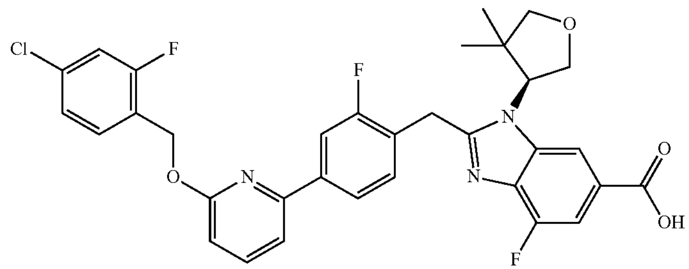 [SMILES: CC1(C)COC[C@H]1n1c(Cc2ccc(-c3cccc(OCc4ccc(Cl)cc4F)n3)cc2F)nc2c(F)cc(C(=O)O)cc21] | 35 | 622.45 | 1H NMR (400 MHz, DMSO) δ 8.35 (s, 1H), 8.10-7.90 (m, 2H), 7.85 (t, J = 7.8 Hz, 1H), 7.74-7.57 (m, 2H), 7.57-7.44 (m, 3H), 7.32 (dd, J = 8.2, 2.1 Hz, 1H), 6.89 (d, J = 8.2 Hz, 1H), 5.53 (s, 2H), 5.01 (d, J = 6.6 Hz, 1H), 4.66-4.23 (m, 4H), 1.30 (s, 3H), 0.58 (s, 3H). |
| 330 | 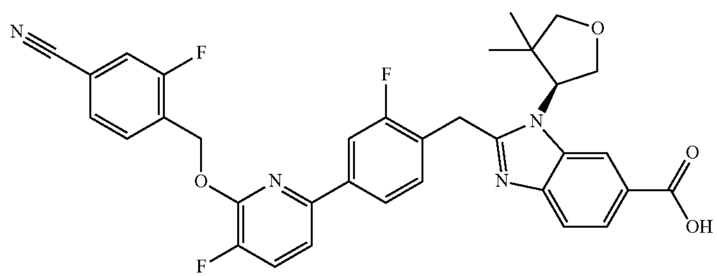 [SMILES: CC1(C)COC[C@H]1n1c(Cc2ccc(-c3ccc(F)c(OCc4ccc(C#N)cc4F)n3)cc2F)nc2ccc(C(=O)O)cc21] | 35 | 613.26 | 1H NMR (400 MHz, DMSO) δ 8.49 (s, 1H), 8.05-7.68 (m, 9H), 7.62 (d, J = 8.5 Hz, 1H), 7.49 (t, J = 7.9 Hz, 1H), 5.72 (s, 2H), 4.99 (d, J = 6.7 Hz, 1H), 4.60-4.29 (m, 2H), 3.88-3.67 (m, 2H), 1.30 (s, 3H), 0.58 (s, 3H). |
| 331 | 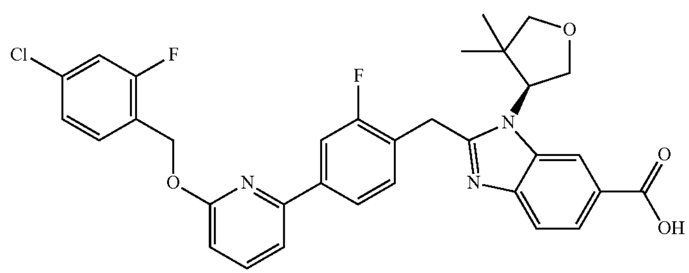 [SMILES: CC1(C)COC[C@H]1n1c(Cc2ccc(-c3cccc(OCc4ccc(Cl)cc4F)n3)cc2F)nc2ccc(C(=O)O)cc21] | 35 | 604.28 | 1H NMR (400 MHz, DMSO) δ 8.51 (s, 1H), 8.00-7.90 (m, 2H), 7.90-7.78 (m, 2H), 7.74-7.57 (m, 3H), 7.57-7.43 (m, 2H), 7.33 (dd, J = 8.2, 2.1 Hz, 1H), 6.90 (d, J = 8.2 Hz, 1H), 5.53 (s, 2H), 5.02 (d, J = 6.6 Hz, 1H), 4.62-4.27 (m, 5H), 3.88-3.67 (m, 2H), 1.30 (s, 3H), 0.59 (s, 3H). |

TABLE 2-continued

Compounds

| Ex. | Structure | Procedure | ES/MS m/z | ¹H NMR |
|---|---|---|---|---|
| 332 | 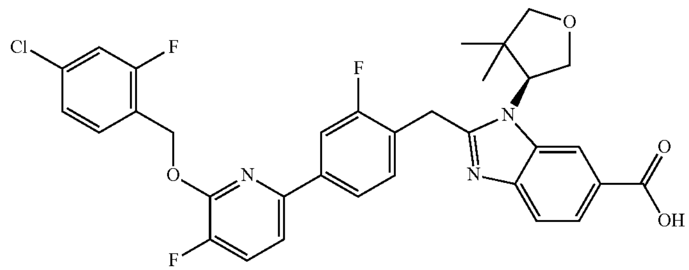 [SMILES: CC1(C)COC[C@H]1n1c(Cc2ccc(-c3ccc(F)c(OCc4ccc(Cl)cc4F)n3)cc2F)nc2ccc(C(=O)O)cc21] | 35 | 622.16 | 1H NMR (400 MHz, DMSO) δ 8.50 (s, 1H), 7.98-7.86 (m, 2H), 7.86-7.80 (m, 2H), 7.76-7.58 (m, 3H), 7.57-7.44 (m, 2H), 7.35 (dd, J = 8.2, 2.1 Hz, 1H), 5.62 (s, 2H), 5.00 (d, J = 6.6 Hz, 1H), 4.61-4.33 (m, 5H), 1.30 (s, 3H), 0.58 (s, 3H). |
| 334 | 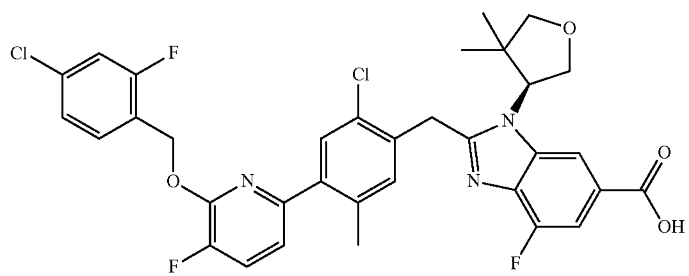 [SMILES: Cc1cc(Cc2nc3c(F)cc(C(=O)O)cc3n2[C@@H]2COCC2(C)C)c(Cl)cc1-c1ccc(F)c(OCc2ccc(Cl)cc2F)n1] | 35 | 670.33 | 1H NMR (400 MHz, DMSO) δ 8.48 (s, 1H), 7.91 (dd, J = 10.2, 8.2 Hz, 1H), 7.78 (dd, J = 8.4, 1.5 Hz, 1H), 7.75-7.69 (m, 1H), 7.69-7.48 (m, 4H), 7.36 (dd, J = 8.4, 2.1 Hz, 1H), 5.61 (s, 2H), 5.09 (d, J = 6.6 Hz, 1H), 4.76-4.27 (m, 4H), 3.92-3.69 (m, 2H), 1.39 (s, 3H), 0.65 (s, 3H). |
| 335 | 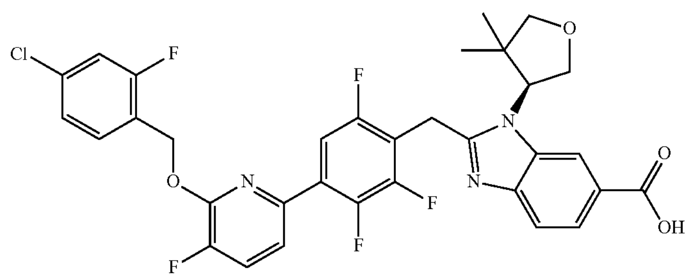 [SMILES: CC1(C)COC[C@H]1n1c(Cc2c(F)cc(-c3ccc(F)c(OCc4ccc(Cl)cc4F)n3)c(F)c2F)nc2ccc(C(=O)O)cc21] | 35 | 658.12 | 1H NMR (400 MHz, DMSO) δ 8.48 (s, 1H), 7.91 (dd, J = 10.2, 8.2 Hz, 1H), 7.78 (dd, J = 8.4, 1.5 Hz, 1H), 7.75-7.69 (m, 1H), 7.69-7.48 (m, 4H), 7.36 (dd, J = 8.4, 2.1 Hz, 1H), 5.61 (s, 2H), 5.09 (d, J = 6.6 Hz, 1H), 4.76-4.27 (m, 4H), 3.92-3.69 (m, 2H), 1.39 (s, 3H), 0.65 (s, 3H). |

TABLE 2-continued

Compounds

| Ex. | Structure | Procedure | ES/MS m/z | 1H NMR |
|---|---|---|---|---|
| 336 | 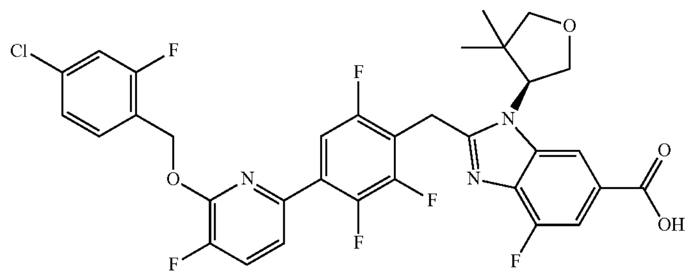 [SMILES: CC1(C)COC[C@H]1n1c(Cc2c(F)cc(-c3ccc(F)c(OCc4ccc(Cl)cc4F)n3)c(F)c2F)nc2c(F)cc(C(=O)O)cc21] | 35 | 676.38 | 1H NMR (400 MHz, DMSO) δ 8.36 (s, 1H), 7.91 (dd, J = 10.2, 8.2 Hz, 1H), 7.74 (ddd, J = 10.5, 5.7,2.0 Hz, 1H), 7.69-7.56 (m, 2H), 7.52 (ddd, J = 11.1, 3.4, 1.6 Hz, 2H), 7.35 (dd, J = 8.2, 2.1 Hz, 1H), 5.61 (s, 2H), 5.11 (d, J = 6.5 Hz, 1H), 4.67 (d, J = 17.4 Hz, 1H), 4.62-4.32 (m, 3H), 3.76 (s, 2H), 1.39 (s, 3H), 0.67 (s, 3H). |
| 337 | 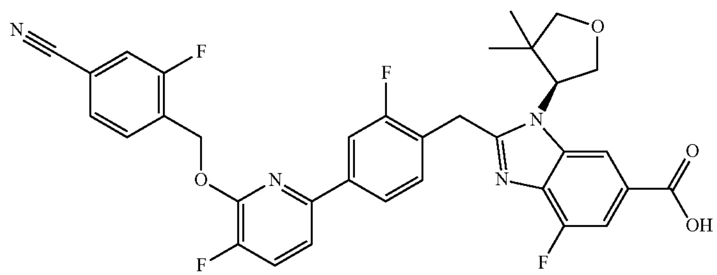 [SMILES: CC1(C)COC[C@H]1n1c(Cc2ccc(-c3ccc(F)c(OCc4ccc(C#N)cc4F)n3)cc2F)nc2c(F)cc(C(=O)O)cc21] | 35 | 630.35 | 1H NMR (400 MHz, DMSO) δ 8.35 (s, 1H), 8.09-7.64 (m, 8H), 7.57-7.39 (m, 2H), 5.72 (s, 2H), 5.00 (d, J = 6.6 Hz, 1H), 4.59-4.28 (m, 2H), 3.75-3.80 (m, 2H), 1.30 (s, 3H), 0.58 (s, 3H). |
| 339 | 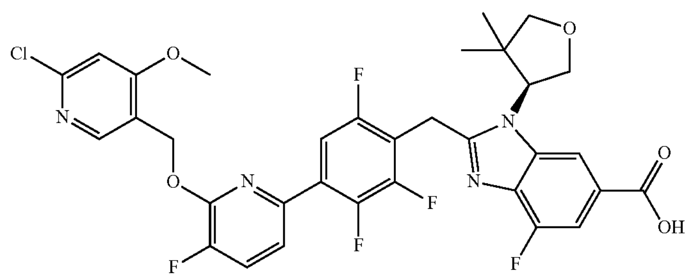 [SMILES: COc1cc(Cl)ncc1COc1nc(-c2cc(F)c(Cc3nc4c(F)cc(C(=O)O)cc4n3[C@@H]3COCC3(C)C)c(F)c2F)ccc1F] | 35 | 689.58 | 1H NMR (400 MHz, DMSO) δ 8.36 (d, J = 2.6 Hz, 2H), 7.90 (dd, J = 10.2, 8.2 Hz, 1H), 7.75 (ddd, J = 10.4, 5.8, 2.0 Hz, 1H), 7.61 (ddd, J = 8.1, 2.9, 1.5 Hz, 1H), 7.51 (dd, J = 11.2, 1.2 Hz, 1H), 7.27 (s, 1H),5.53 (s, 2H), 5.11 (d, J = 6.5 Hz, 1H), 4.67 (d, J = 17.5 Hz, 1H), 4.61-4.31 (m, 3H), 3.95 (s, 3H), 3.76 (s, 2H), 1.39 (s, 3H), 0.67 (s, 3H). |

TABLE 2-continued

Compounds

| Ex. | Structure | Procedure | ES/MS m/z | ¹H NMR |
|---|---|---|---|---|
| 340 | 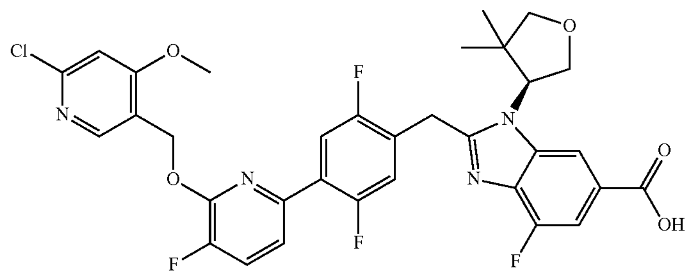 [SMILES: COc1cc(Cl)ncc1COc1nc(-c2cc(F)c(Cc3nc4c(F)cc(C(=O)O)cc4n3[C@@H]3COCC3(C)C)cc2F)ccc1F] | 35 | 671.6 | 1H NMR (400 MHz, DMSO) δ 8.35 (s, 2H), 7.84 (ddd, J = 10.2, 7.4, 4.4 Hz, 2H), 7.61-7.43 (m, 3H), 7.27 (s, 1H), 5.52 (s, 2H), 5.04 (d, J = 6.6 Hz, 1H), 4.63-4.49 (m, 2H), 4.49-4.28 (m, 2H), 3.95 (s, 3H), 1.34 (s, 3H), 0.62 (s, 3H). |
| 341 | 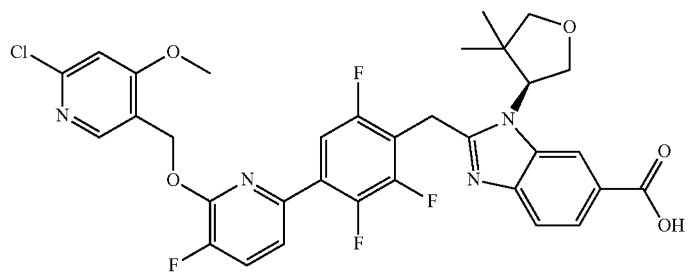 | 35 | 671.51 | 1H NMR (400 MHz, DMSO) δ 8.48 (s, 1H), 8.36 (s, 1H), 7.90 (dd, J = 10.2, 8.2 Hz, 1H), 7.78 (dd, J = 8.4, 1.5 Hz, 1H), 7.60 (dd, J = 8.7, 3.3 Hz, 2H), 7.28 (s, 1H), 5.53 (s, 2H), 5.09 (d, J = 6.5 Hz, 1H), 4.75-4.52 (m, 2H), 4.47 (dd, J = 11.1, 6.7 Hz, 1H), 4.36 (d, J = 17.4 Hz, 1H), 3.96 (s, 3H), 3.86-3.71 (m, 2H), 1.39 (s, 3H), 0.66 (s, 3H). |
| 342 | 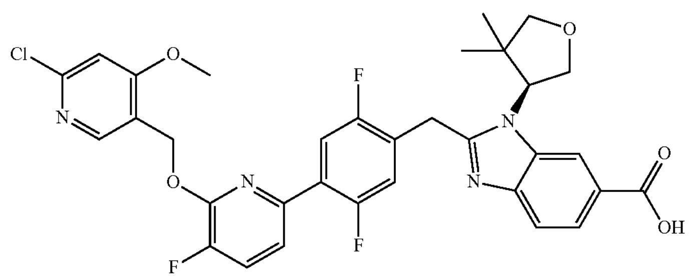 | 35 | 653.76 | 1H NMR (400 MHz, DMSO) δ 8.51 (s, 1H), 8.35 (s, 1H), 7.89-7.76 (m, 3H), 7.64 (d, J = 8.5 Hz, 1H), 7.59-7.41 (m, 2H), 7.27 (s, 1H), 5.52 (s, 2H), 5.03 (d, J = 6.7 Hz, 1H), 4.63-4.32 (m, 4H), 3.95 (s, 3H), 3.88-3.66 (m, 2H), 1.34 (s, 3H), 0.62 (s, 3H). |

TABLE 2-continued

Compounds

| Ex. | Structure | Procedure | ES/MS m/z | ¹H NMR |
|---|---|---|---|---|
| 343 | 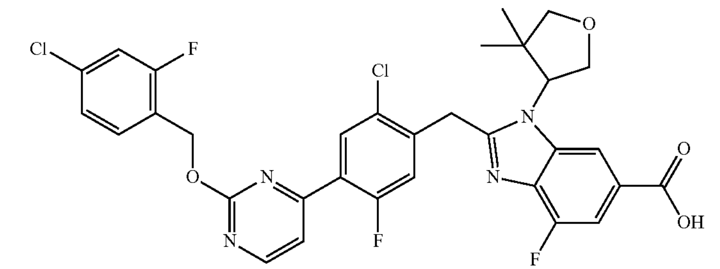 [SMILES: CC1(C)COCC1n1c(Cc2cc(F)c(-c3ccnc(OCc4ccc(Cl)cc4F)n3)cc2Cl)nc2c(F)cc(C(=O)O)cc21] | 35 | 657.36 | 1H NMR (400 MHz, DMSO) δ 8.79 (d, J = 5.2 Hz, 1H), 8.36 (s, 1H), 8.17 (d, J = 7.0 Hz, 1H), 7.70-7.45 (m, 5H), 7.35 (dd, J = 8.2, 2.1 Hz, 1H), 5.54 (s, 2H), 5.04 (d, J = 6.7 Hz, 1H), 4.67 (d, J = 17.1 Hz, 1H), 4.59-4.37 (m, 3H), 3.84-3.66 (m, 2H), 1.36 (s, 3H), 0.67 (s, 3H). |
| 344 | 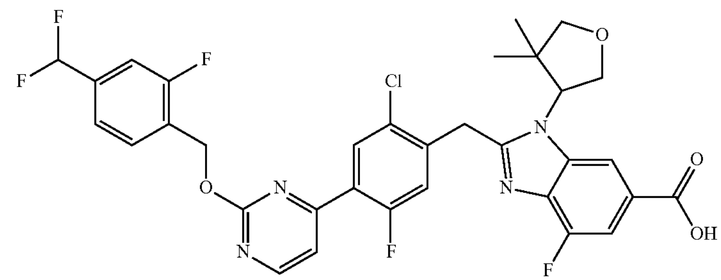 [SMILES: CC1(C)COCC1n1c(Cc2cc(F)c(-c3ccnc(OCc4ccc(C(F)F)cc4F)n3)cc2Cl)nc2c(F)cc(C(=O)O)cc21] | 35 | 673.175 | 1H NMR (400 MHz, DMSO) δ 8.80 (d, J = 5.2 Hz, 1H), 8.36 (s, 1H), 8.16 (d, J = 7.0 Hz, 1H), 7.75 (t, J = 7.6 Hz, 1H), 7.65 (dd, J = 5.2, 1.8 Hz, 1H), 7.59 (d, J = 11.7 Hz, 1H), 7.50 (dd, J = 16.7, 9.4 Hz, 3H), 7.07 (t, J = 55.6 Hz, 1H), 5.61 (s, 2H), 5.04 (d, J = 6.6 Hz, 1H), 4.66 (d, J = 17.1 Hz, 1H), 4.58-4.37 (m, 3H), 3.85-3.70 (m, 2H), 1.36 (s, 3H), 0.67 (s, 3H). |
| 345 | 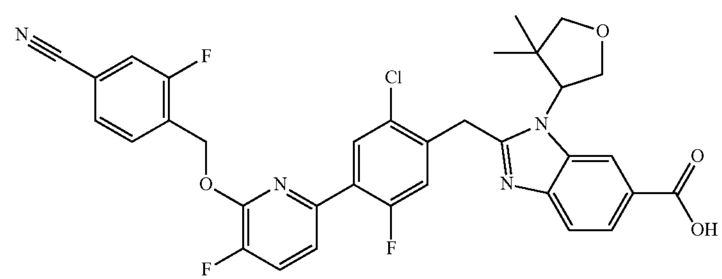 [SMILES: CC1(C)COCC1n1c(Cc2cc(F)c(-c3ccc(F)c(OCc4ccc(C#N)cc4F)n3)cc2Cl)nc2ccc(C(=O)O)cc21] | 35 | 647.46 | 1H NMR (400 MHz, DMSO) δ 8.49 (s, 1H), 8.00-7.83 (m, 3H), 7.83-7.71 (m, 3H), 7.65-7.43 (m, 3H), 5.69 (s, 2H), 5.01 (d, J = 6.7 Hz, 1H), 4.69-4.49 (m, 2H), 4.49-4.35 (m, 2H), 3.80 (d, J = 8.6 Hz, 1H), 3.73 (d, J = 8.6 Hz, 1H), 1.35 (s, 3H), 0.66 (s, 3H). |

TABLE 2-continued

Compounds

| Ex. | Structure | Procedure | ES/MS m/z | ¹H NMR |
|---|---|---|---|---|
| 346 | 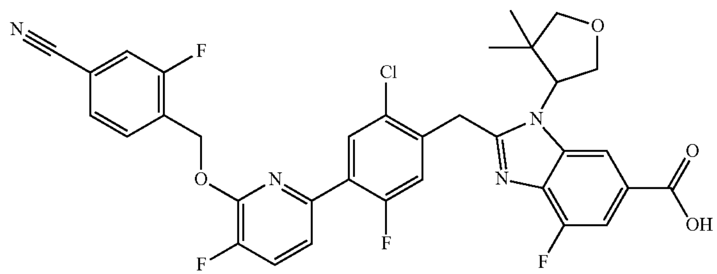 [SMILES: CC1(C)COCC1n1c(Cc2cc(F)c(-c3ccc(F)c(OCc4ccc(C#N)cc4F)n3)cc2Cl)nc2c(F)cc(C(=O)O)cc21] | 35 | 665.284 | 1H NMR (400 MHz, DMSO) δ 8.36 (s, 1H), 8.00-7.83 (m, 3H), 7.83-7.70 (m, 2H), 7.60-7.43 (m, 3H), 5.70 (s, 2H), 5.03 (d, J = 6.7 Hz, 1H), 4.62 (d, J = 17.0 Hz, 1H), 4.53 (d, J = 11.9 Hz, 1H), 4.47-4.36 (m, 2H), 3.83-3.69 (m, 2H), 1.35 (s, 3H), 0.66 (s, 3H). |
| 347 | 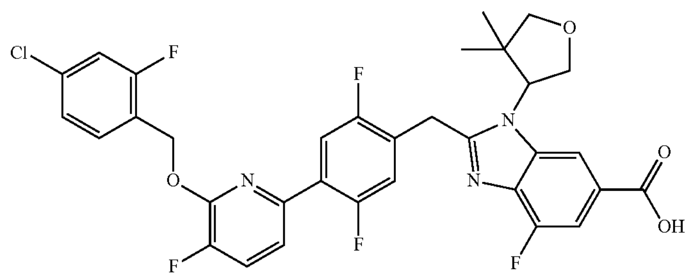 [SMILES: CC1(C)COCC1n1c(Cc2cc(F)c(-c3ccc(F)c(OCc4ccc(Cl)cc4F)n3)cc2F)nc2c(F)cc(C(=O)O)cc21] | 35 | 658.8 | 1H NMR (400 MHz, DMSO) δ 8.36 (s, 1H), 7.84 (ddd, J = 11.9, 10.3, 7.4 Hz, 2H), 7.63 (t, J = 8.1 Hz, 1H), 7.59-7.43 (m, 4H), 7.35 (dd, J = 8.2, 2.0 Hz, 1H), 5.61 (s, 2H), 5.04 (d, J = 6.6 Hz, 1H), 4.61-4.47 (m, 2H), 4.48-4.32 (m, 2H), 3.75 (q, J = 8.7 Hz, 2H), 1.34 (s, 3H), 0.61 (s, 3H). |
| 348 | 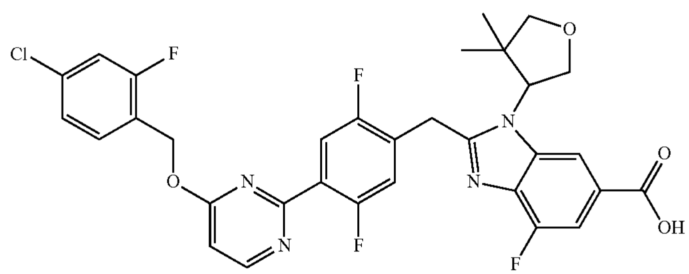 [SMILES: CC1(C)COCC1n1c(Cc2cc(F)c(-c3nccc(OCc4ccc(Cl)cc4F)n3)cc2F)nc2c(F)cc(C(=O)O)cc21] | 35 | 641.2 | 1H NMR (400 MHz, MeOD) δ 8.60 (d, J = 5.8 Hz, 1H), 8.55 (s, 1H), 7.90 (dd, J = 10.3, 6.1 Hz, 1H), 7.66 (d, J = 11.0 Hz, 1H), 7.56 (t, J = 8.0 Hz, 1H), 7.35-7.13 (m, 3H), 6.91 (d, J = 5.8 Hz, 1H), 5.59 (s, 2H), 4.91 (s, 8H), 4.65-4.55 (m, 1H), 4.55-4.42 (m, 3H), 3.93 (d, J = 8.8 Hz, 1H), 3.79 (d, J = 8.8 Hz, 1H), 3.33 (p, J = 1.7 Hz, 5H), 1.36 (s, 3H), 0.67 (s, 3H). |

TABLE 2-continued

Compounds

| Ex. | Structure | Procedure | ES/MS m/z | ¹H NMR |
|---|---|---|---|---|
| 349 | 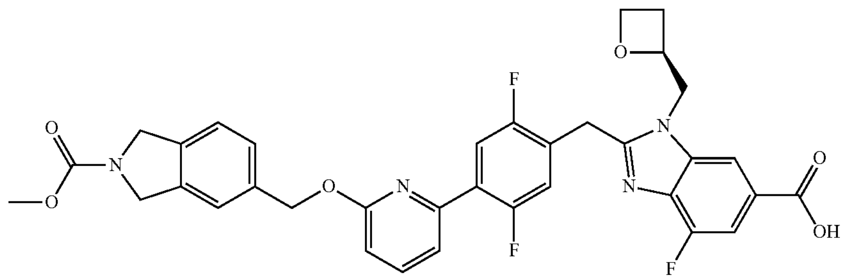 [SMILES: COC(=O)N1Cc2ccc(COc3cccc(-c4cc(F)c(Cc5nc6c(F)cc(C(=O)O)cc6n5C[C@@H]5CCO5)cc4F)n3)cc2C1] | 40 | (M+) 659.2 | 1H NMR (400 MHz, Methanol-d4) δ 8.16 (d, J = 1.3 Hz, 1H), 7.82-7.77 (m, 1H), 7.75 (d, J = 7.9 Hz, 1H), 7.65 (dd, J = 11.2, 1.2 Hz, 1H), 7.50 (dd, J = 7.4, 1.6 Hz, 1H), 7.44 (t, J = 9.7 Hz, 2H), 7.31 (dd, J = 11.5, 7.9 Hz, 1H), 7.17 (dd, J = 11.5, 6.0 Hz, 1H), 6.86 (d, J = 8.2 Hz, 1H), 5.49 (s, 2H), 5.16 (qd, J = 7.1, 2.5 Hz, 1H), 4.77-4.50 (m, 10H), 4.50-4.35 (m, 1H), 3.78 (d, J = 1.8 Hz, 3H), 2.88-2.69 (m, 1H), 2.53-2.40 (m, 1H). |
| 350 | 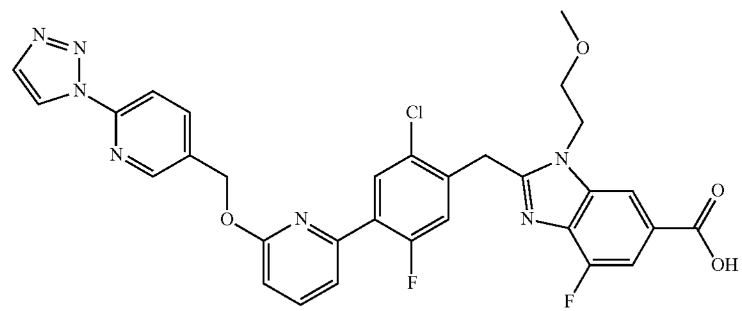 [SMILES: COCCn1c(Cc2cc(F)c(-c3cccc(OCc4ccc(-n5ccnn5)nc4)n3)cc2Cl)nc2c(F)cc(C(=O)O)cc21] | 18 | 632.4 | 1H NMR (400 MHz, DMSO-d6) δ 8.88 (d, J = 1.2 Hz, 1H), 8.75 (d, J = 2.1 Hz, 1H), 8.25 (dd, J = 8.4, 2.2 Hz, 1H), 8.17 (d, J = 8.4 Hz, 1H), 8.10 (d, J = 1.3 Hz, 1H), 8.05-7.97 (m, 2H), 7.91 (t, J = 7.9 Hz, 1H), 7.58-7.48 (m, 2H), 7.45 (d, J = 11.7 Hz, 1H), 7.01 (d, J = 8.3 Hz, 1H), 5.61 (s, 2H), 4.63 (t, J = 5.1 Hz, 2H), 4.53 (s, 2H), 3.70 (t, J = 5.0 Hz, 2H), 3.22 (s, 3H). |
| 351 | 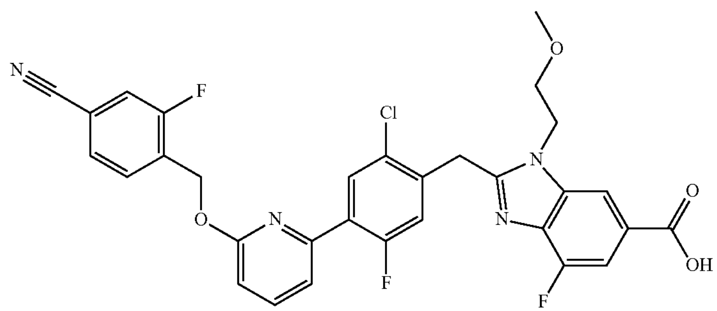 [SMILES: COCCn1c(Cc2cc(F)c(-c3cccc(OCc4ccc(C#N)cc4F)n3)cc2Cl)nc2c(F)cc(C(=O)O)cc21] | 18 | 607.6 | 1H NMR (400 MHz, DMSO-d6) δ 8.10 (d, J = 1.2 Hz, 1H), 7.98-7.85 (m, 3H), 7.74 (d, J = 5.4 Hz, 2H), 7.55-7.47 (m, 2H), 7.43 (d, J = 11.8 Hz, 1H), 7.01 (d, J = 8.2 Hz, 1H), 5.60 (s, 2H), 4.62 (t, J = 5.1 Hz, 2H), 4.52 (s, 2H), 3.70 (t, J = 5.0 Hz, 2H), 3.22 (s, 3H). |

TABLE 2-continued

Compounds

| Ex. | Structure | Procedure | ES/MS m/z | ¹H NMR |
|---|---|---|---|---|
| 352 | 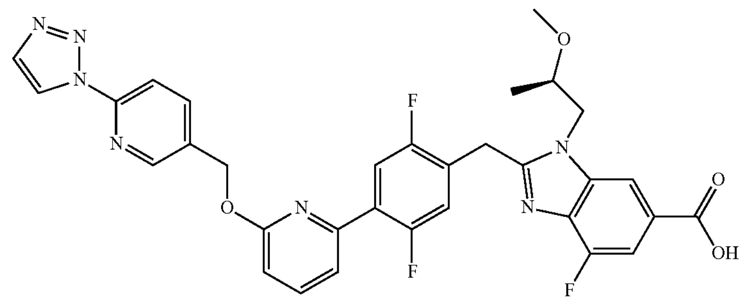 [SMILES: CO[C@H](C)Cn1c(Cc2cc(F)c(-c3cccc(OCc4ccc(-n5ccnn5)nc4)n3)cc2F)nc2c(F)cc(C(=O)O)cc21] | 18 | 630.2 | 1H NMR (400 MHz, DMSO-d6) δ 8.88 (d, J = 1.2 Hz, 1H), 8.75 (d, J = 2.1 Hz, 1H), 8.25 (dd, J = 8.4, 2.2 Hz, 1H), 8.17 (d, J = 8.5 Hz, 1H), 8.12 (d, J = 1.3 Hz, 1H), 8.00 (d, J = 1.2 Hz, 1H), 7.96-7.82 (m, 2H), 7.60-7.46 (m, 2H), 7.40 (dd, J = 11.5, 6.1 Hz, 1H), 7.00 (d, J = 8.2 Hz, 1H), 5.62 (s, 2H), 4.54 (dd, J = 15.2, 3.1 Hz, 1H), 4.47 (s, 2H), 4.37 (dd, J = 15.2, 8.8 Hz, 1H), 3.79-3.60 (m, 1H), 3.08 (s, 3H), 1.23 (d, J = 6.1 Hz, 3H). |
| 353 | 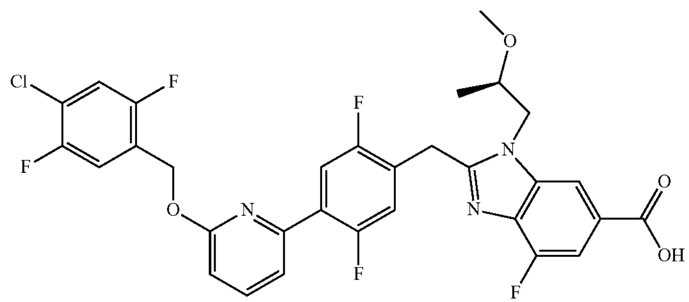 [SMILES: CO[C@H](C)Cn1c(Cc2cc(F)c(-c3cccc(OCc4cc(F)c(Cl)cc4F)n3)cc2F)nc2c(F)cc(C(=O)O)cc21] | 18 | 632.5 | 1H NMR (400 MHz, DMSO-d6) δ 8.90 (d, J = 1.2 Hz, 1H), 8.12 (d, J = 1.3 Hz, 1H), 8.01 (d, J = 1.2 Hz, 1H), 7.97-7.78 (m, 5H), 7.58-7.45 (m, 2H), 7.40 (dd, J = 11.5, 6.0 Hz, 1H), 6.98 (d, J = 8.2 Hz, 1H), 5.60 (s, 2H), 4.54 (dd, J = 15.2, 3.1 Hz, 1H), 4.47 (s, 2H), 4.37 (dd, J = 15.2, 8.8 Hz, 1H), 3.78-3.59 (m, 1H), 3.08 (s, 3H), 1.23 (d, J = 6.1 Hz, 3H). |
| 354 | 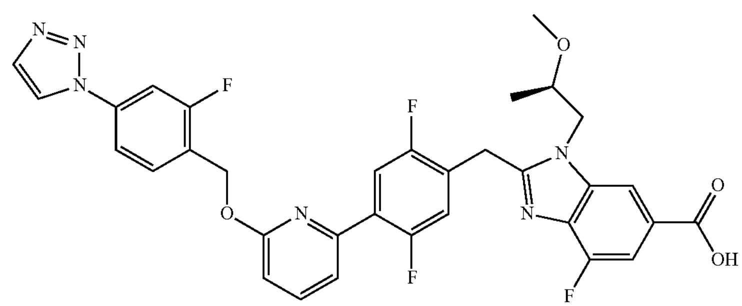 [SMILES: CO[C@H](C)Cn1c(Cc2cc(F)c(-c3cccc(OCc4ccc(-n5ccnn5)cc4F)n3)cc2F)nc2c(F)cc(C(=O)O)cc21] | 18 | 647.2 | 1H NMR (400 MHz, DMSO-d6) δ 8.90 (d, J = 1.2 Hz, 1H), 8.12 (d, J = 1.3 Hz, 1H), 8.01 (d, J = 1.2 Hz, 1H), 7.97-7.78 (m, 5H), 7.58-7.45 (m, 2H), 7.40 (dd, J = 11.5, 6.0 Hz, 1H), 6.98 (d, J = 8.2 Hz, 1H), 5.60 (s, 2H), 4.54 (dd, J = 15.2, 3.1 Hz, 1H), 4.47 (s, 2H), 4.37 (dd, J = 15.2, 8.8 Hz, 1H), 3.78-3.59 (m, 1H), 3.08 (s, 3H), 1.23 (d, J = 6.1 Hz, 3H). |

TABLE 2-continued

Compounds

| Ex. | Structure | Procedure | ES/MS m/z | 1H NMR |
|---|---|---|---|---|
| 355 | 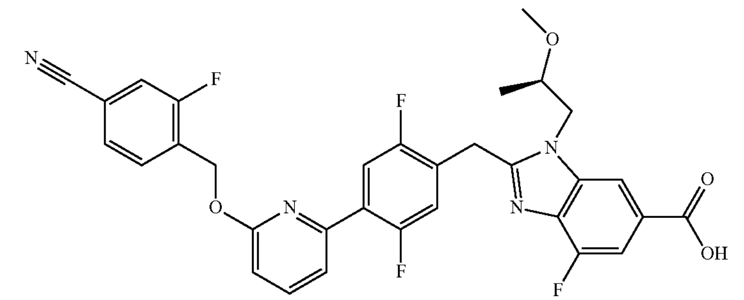 [SMILES: CO[C@H](C)Cn1c(Cc2cc(F)c(-c3cccc(OCc4ccc(C#N)cc4F)n3)cc2F)nc2c(F)cc(C(=O)O)cc21] | 18 | 605.2 | 1H NMR (400 MHz, DMSO-d6) δ 8.12 (d, J = 1.2 Hz, 1H), 7.97-7.85 (m, 2H), 7.82-7.70 (m, 3H), 7.58-7.46 (m, 2H), 7.39 (dd, J = 11.5, 6.0 Hz, 1H), 6.99 (d, J = 8.3 Hz, 1H), 5.61 (s, 2H), 4.53 (dd, J = 15.2, 3.1 Hz, 1H), 4.46 (s, 2H), 4.36 (dd, J = 15.2, 8.8 Hz, 1H), 3.68 (ddd, J = 9.1, 6.1, 3.1 Hz, 1H), 3.08 (s, 3H), 1.23 (d, J = 6.1 Hz, 3H). |
| 357 | 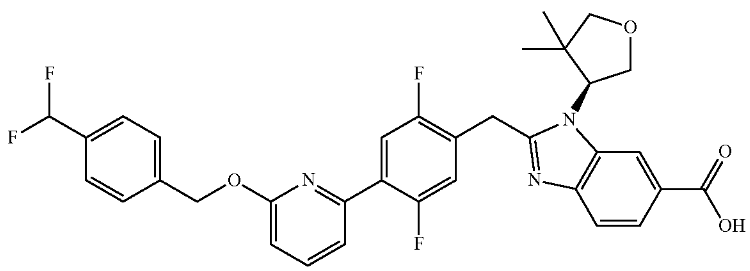 [SMILES: CC1(C)COC[C@H]1n1c(Cc2cc(F)c(-c3cccc(OCc4ccc(C(F)F)cc4)n3)cc2F)nc2ccc(C(=O)O)cc21] | 27 | 620.3 | 1H NMR (400 MHz, Methanol-d4) δ 8.87 (s, 1H), 8.15 (dd, J = 8.7, 1.3 Hz, 1H), 7.99-7.71 (m, 3H), 7.71-7.45 (m, 5H), 7.37 (dd, J = 11.2, 6.0 Hz, 1H), 7.03-6.86 (m, 1H),  5.56 (s, 2H), 5.12 (d, J = 6.6 Hz, 1H), 4.78-4.61 (m, 3H), 4.52 (dd, J = 11.6, 6.7 Hz, 1H), 3.99 (d, J = 8.9 Hz, 1H), 3.84 (d, J = 8.9 Hz, 1H),  1.40 (s, 3H), 0.75 (s, 3H). |
| 358 | 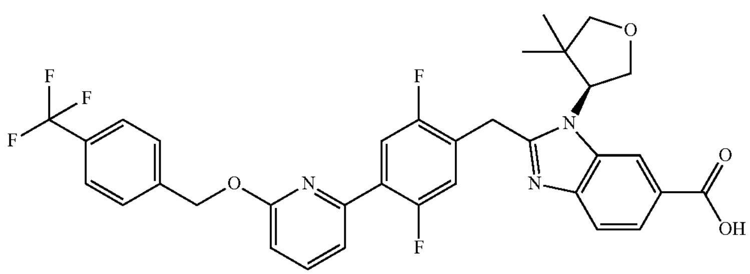 [SMILES: CC1(C)COC[C@H]1n1c(Cc2cc(F)c(-c3cccc(OCc4ccc(C(F)(F)F)cc4)n3)cc2F)nc2ccc(C(=O)O)cc21] | 27 | 638.0 | 1H NMR (400 MHz, Methanol-d4) δ 8.96 (s, 1H), 8.24 (dd, J = 8.6, 1.3 Hz, 1H), 7.83 (d, J = 8.6 Hz, 1H), 7.78-7.67 (m, 2H), 7.58 (d, J = 8.6 Hz, 2H), 7.46 (d, J = 7.5 Hz, 1H), 7.19 (d, J =10.5 Hz, 1H), 7.02 (dd, J = 9.0, 2.9 Hz, 1H), 5.51 (s, 2H), 5.19 (d, J = 6.5 Hz, 1H), 4.83-4.62 (m, 3H),4.52 (dd, J = 11.8, 6.6 Hz, 1H), 4.01 (d, J = 9.0 Hz, 1H), 3.84 (d, J = 9.0 Hz, 1H), 2.21 (s, 3H), 1.36 (s, 3H), 0.73 (s, 3H). |

TABLE 2-continued

Compounds

| Ex. | Structure | Procedure | ES/MS m/z | ¹H NMR |
|---|---|---|---|---|
| 359 | 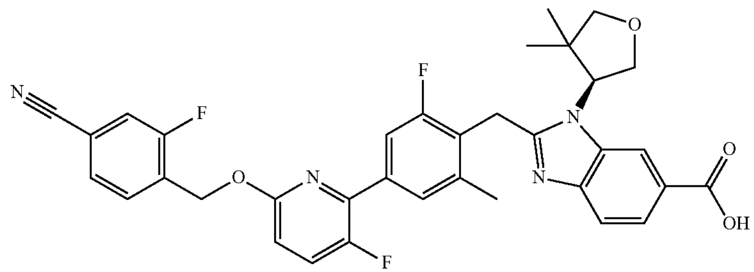 [SMILES: Cc1cc(-c2nc(OCc3ccc(C#N)cc3F)ccc2F)cc(F)c1Cc1nc2ccc(C(=O)O)cc2n1[C@@H]1COCC1(C)C] | 35 | 627.0 | 1H NMR (400 MHz, Methanol-d4) δ 8.96 (s, 1H), 8.24 (dd, J = 8.6, 1.3 Hz, 1H), 7.83 (d, J = 8.6 Hz, 1H), 7.78-7.67 (m, 2H), 7.58 (d, J = 8.6 Hz, 2H), 7.46 (d, J = 7.5 Hz, 1H), 7.19 (d, J = 10.5 Hz, 1H), 7.02 (dd, J = 9.0, 2.9 Hz, 1H), 5.51 (s, 2H), 5.19 (d, J = 6.5 Hz, 1H), 4.83-4.62 (m, 3H), 4.52 (dd, J = 11.8, 6.6 Hz, 1H), 4.01 (d, J = 9.0 Hz, 1H), 3.84 (d, J = 9.0 Hz, 1H), 2.21 (s, 3H), 1.36 (s, 3H), 0.73 (s, 3H). |
| 360 | 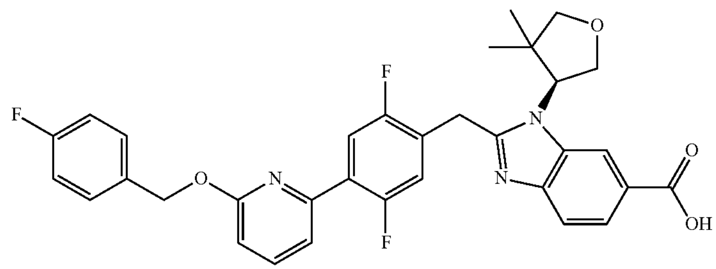 [SMILES: CC1(C)COC[C@H]1n1c(Cc2cc(F)c(-c3cccc(OCc4ccc(F)cc4)n3)cc2F)nc2ccc(C(=O)O)cc21] | 27 | 588.5 | 1H NMR (400 MHz, Methanol-d4) δ 8.91 (s, 1H), 8.18 (dd, J = 8.6, 1.3 Hz, 1H), 7.93 (dd, J = 10.8, 6.2 Hz, 1H), 7.87-7.73 (m, 2H), 7.66-7.48 (m, 3H), 7.40 (dd, J = 11.2, 6.0 Hz, 1H), 7.21-7.02 (m, 2H), 6.90 (d, J = 8.2 Hz, 1H), 5.46 (s, 2H), 5.15 (d, J = 6.5 Hz, 1H), 4.79-4.63 (m, 2H), 4.52 (dd, J = 11.6, 6.7 Hz, 1H), 4.00 (d, J = 8.9 Hz, 1H), 3.84 (d, J = 8.9 Hz, 1H), 3.33 (p, J = 1.7 Hz, 3H), 1.41 (s, 3H), 0.76 (s, 3H). |
| 361 | 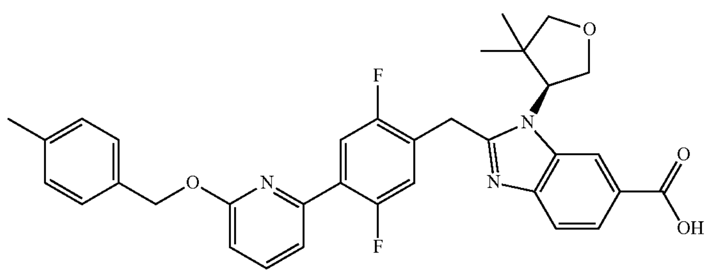 [SMILES: Cc1ccc(COc2cccc(-c3cc(F)c(Cc4nc5ccc(C(=O)O)cc5n4[C@@H]4COCC4(C)C)cc3F)n2)cc1] | 27 | 584.6 | 1H NMR (400 MHz, Methanol-d4) δ 8.89 (s, 1H), 8.17 (dd, J = 8.6, 1.3 Hz, 1H), 7.93 (dd, J = 10.9, 6.3 Hz, 1H), 7.88-7.72 (m, 2H), 7.54 (dd, J = 7.5, 1.7 Hz, 1H), 7.38 (dd, J = 14.9, 7.0 Hz, 3H), 7.19 (d, J = 7.8 Hz, 2H), 6.88 (d, J = 8.2 Hz, 1H), 5.44 (s, 2H), 5.14 (d, J = 6.6 Hz, 1H), 4.77-4.61 (m, 3H), 4.53 (dd, J = 11.6, 6.7 Hz, 1H), 4.00 (d, J = 8.9 Hz, 1H), 3.84 (d, J = 8.9 Hz, |

TABLE 2-continued

| Ex. | Structure | Procedure | ES/MS m/z | ¹H NMR |
|---|---|---|---|---|
| 362 | 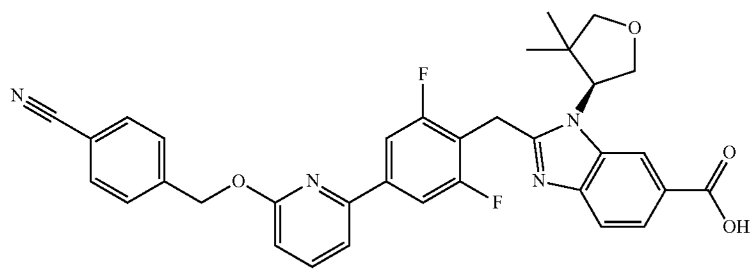 [SMILES: CC1(C)COC[C@H]1n1c(Cc2c(F)cc(-c3cccc(OCc4ccc(C#N)cc4)n3)cc2F)nc2ccc(C(=O)O)cc21] | 35 | 595.3 | 1H NMR (400 MHz, Methanol-d4) δ 8.99-8.75 (m, 1H), 8.15 (dd, J = 8.6, 1.4 Hz, 1H), 7.95-7.66 (m, 8H), 7.61 (d, J = 7.5 Hz, 1H), 6.97 (d, J = 8.2 Hz, 1H), 5.62 (s, 2H), 5.17 (d, J = 6.5 Hz, 1H), 4.81-4.46 (m, 4H), 4.00 (d, J = 8.9 Hz, 1H), 3.86 (d, J = 8.9 Hz, 1H), 1.45 (s, 3H), 0.79 (s, 3H). |
| 363 | 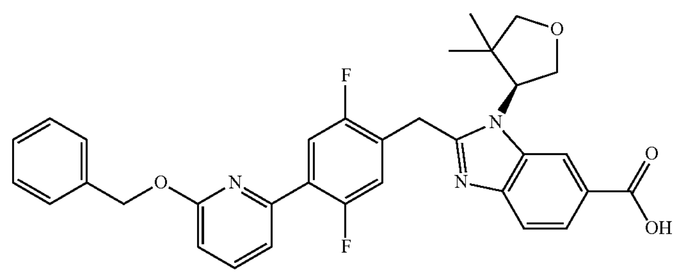 [SMILES: CC1(C)COC[C@H]1n1c(Cc2cc(F)c(-c3cccc(OCc4ccccc4)n3)cc2F)nc2ccc(C(=O)O)cc21] | 35 | 570.6 | 1H NMR (400 MHz, Methanol-d4) δ 8.91 (s, 1H), 8.19 (dd, J = 8.6, 1.4 Hz, 1H), 7.92 (dd, J = 10.9, 6.3 Hz, 1H), 7.87-7.70 (m, 2H), 7.56 (dd, J = 7.4, 1.7 Hz, 1H), 7.52-7.44 (m, 2H), 7.42-7.33 (m, 4H), 6.91 (d, J = 8.2 Hz, 1H), 5.49 (s, 2H), 5.15 (d, J = 6.5 Hz, 1H), 4.77-4.62 (m, 3H), 4.53 (dd, J = 11.6, 6.7 Hz, 1H), 4.00 (d, J = 8.9 Hz, 1H), 3.85 (d, J = 8.9 Hz, 1H), 1.42 (s, 3H), 0.77 (s, 3H). |
| 364 | 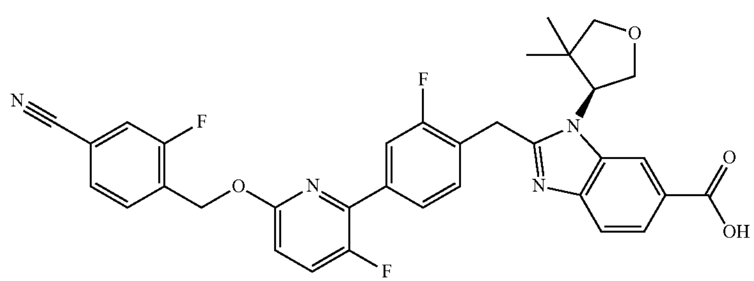 [SMILES: CC1(C)COC[C@H]1n1c(Cc2ccc(-c3nc(OCc4ccc(C#N)cc4F)ccc3F)cc2F)nc2ccc(C(=O)O)cc21] | 35 | 613.2 | 1H NMR (400 MHz, Methanol-d4) δ 8.89 (s, 1H), 8.17 (dd, J = 8.6, 1.3 Hz, 1H), 7.91 (d, J = 8.1 Hz, 1H), 7.87-7.66 (m, 5H), 7.63-7.54 (m, 3H), 6.97 (dd, J = 8.9, 2.7 Hz, 1H), 5.61 (s, 2H), 5.12 (d, J = 6.6 Hz, 1H), 4.76-4.61 (m, 3H), 4.60-4.49 (m, 1H), 4.00 (d, J = 8.9 Hz, 1H), 3.83 (d, J = 8.9 Hz, 1H), 1.37 (s, 3H), 0.73 (s, 3H). |

TABLE 2-continued

Compounds

| Ex. | Structure | Procedure | ES/MS m/z | ¹H NMR |
|---|---|---|---|---|
| 365 | 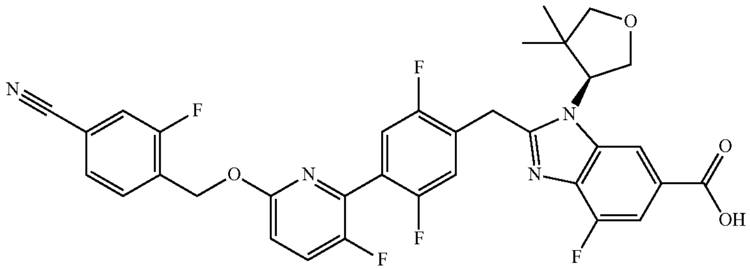 [SMILES: CC1(C)COC[C@H]1n1c(Cc2cc(F)c(-c3nc(OCc4ccc(C#N)cc4F)ccc3F)cc2F)nc2c(F)cc(C(=O)O)cc21] | 35 | 649.2 | 1H NMR (400 MHz, Methanol-d4) δ 8.58 (s, 1H), 7.82-7.65 (m, 3H), 7.65-7.55 (m, 2H), 7.35 (dd, J = 9.9, 5.7 Hz, 1H), 7.27 (dd, J = 9.9, 6.0 Hz, 1H), 7.01 (dd, J = 9.0, 2.9 Hz, 1H), 5.54 (s, 2H), 4.99 (d, J = 6.7 Hz, 1H), 4.69-4.42 (m, 4H), 3.95 (d, J = 8.8 Hz, 1H), 3.80 (d, J = 8.8 Hz, 1H), 1.36 (s, 3H), 0.68 (s, 3H). |
| 366 | 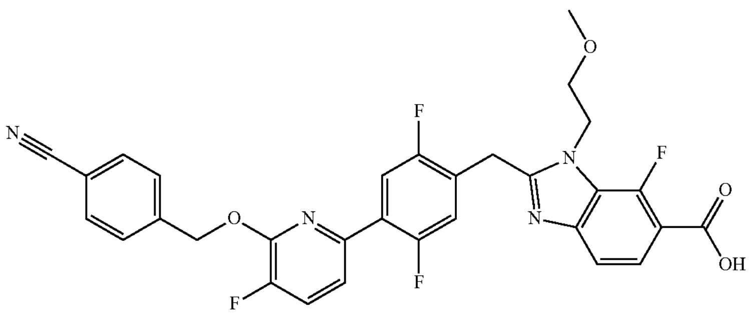 [SMILES: COCCn1c(Cc2cc(F)c(-c3ccc(F)c(OCc4ccc(C#N)cc4)n3)cc2F)nc2ccc(C(=O)O)c(F)c21] | 35 | 591.5 | 1H NMR (400 MHz, Chloroform-d) δ 8.00 (t, J = 7.5 Hz, 1H), 7.80-7.68 (m, 3H), 7.68-7.57 (m, 3H), 7.56-7.36 (m, 2H), 7.15 (dd, J = 11.1, 6.0 Hz, 1H), 5.60 (s, 2H), 4.67-4.55 (m, 4H), 3.82 (t, J = 4.8 Hz, 2H), 3.33 (s, 3H). |
| 367 | 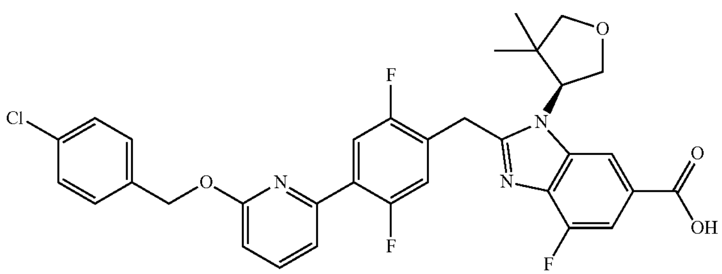 [SMILES: CC1(C)COC[C@H]1n1c(Cc2cc(F)c(-c3cccc(OCc4ccc(Cl)cc4)n3)cc2F)nc2c(F)cc(C(=O)O)cc21] | 35 | 622.8 | 1H NMR (400 MHz, Methanol-d4) δ 8.58 (s, 1H), 7.90-7.82 (m, 1H), 7.77 (t, J = 7.9 Hz, 1H), 7.70 (dd, J = 11.0, 1.2 Hz, 1H), 7.58-7.44 (m, 3H), 7.42-7.34 (m, 2H), 7.24 (dd, J = 11.4, 6.0 Hz, 1H), 6.88 (d, J = 8.2 Hz, 1H), 5.46 (s, 2H), 4.97 (d, J = 6.7 Hz, 1H), 4.65-4.34 (m, 4H), 3.93 (d, J = 8.8 Hz, 1H), 3.79 (d, J = 8.8 Hz, 1H), 1.35 (s, 3H), 0.66 (s, 3H). |

TABLE 2-continued

Compounds

| Ex. | Structure | Procedure | ES/MS m/z | ¹H NMR |
|---|---|---|---|---|
| 368 | 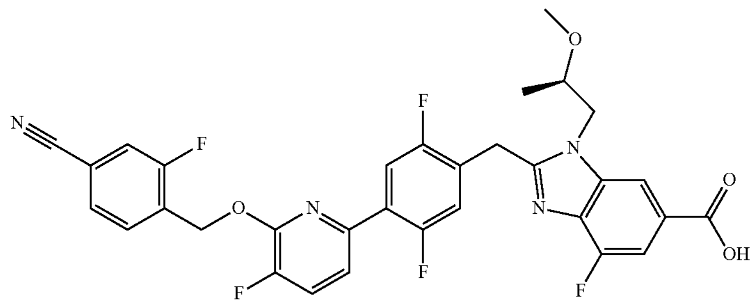 [SMILES: CO[C@H](C)Cn1c(Cc2cc(F)c(-c3ccc(F)c(OCc4ccc(C#N)cc4F)n3)cc2F)nc2c(F)cc(C(=O)O)cc21] | 35 | 623.3 | 1H NMR (400 MHz, Methanol-d4) δ 7.99 (d, J = 1.2 Hz, 1H), 7.86-7.68 (m, 2H), 7.68-7.47 (m, 5H), 7.12 (dd, J = 11.6, 6.1 Hz, 1H), 5.71 (s, 2H),4.52 (d, J = 16.6 Hz, 1H), 4.45-4.34 (m, 1H), 4.27 (dd, J = 15.1, 8.9 Hz, 1H), 3.75 (ddd, J = 9.2, 6.1, 3.1 Hz, 1H), 3.13 (s, 3H), 2.08-1.89 (m, 1H), 1.29 (d, J = 6.2 Hz, 3H). |
| 369 | 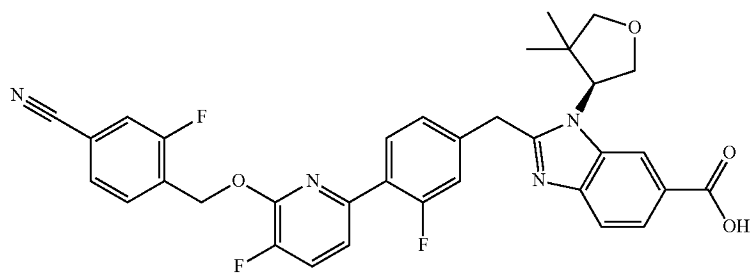 [SMILES: CC1(C)COC[C@H]1n1c(Cc2ccc(-c3ccc(F)c(OCc4ccc(C#N)cc4F)n3)c(F)c2)nc2ccc(C(=O)O)cc21] | 35 | 613.6 | 1H NMR (400 MHz, Methanol-d4) δ 8.90 (s, 1H), 8.20 (dd, J = 8.6, 1.4 Hz, 1H), 8.02 (t, J = 8.3 Hz, 1H), 7.92-7.71 (m, 2H), 7.69-7.46 (m, 4H), 7.40-7.21 (m, 2H), 5.70 (s, 2H), 5.10 (d, J = 6.5 Hz, 1H), 4.83-4.58 (m, 3H), 4.47 (dd, J = 11.6, 6.7 Hz, 1H), 3.99 (d, J = 8.9 Hz, 1H), 3.82 (d, J = 8.9 Hz, 1H), 1.33 (s, 3H), 0.69 (s, 3H). |
| 370 | 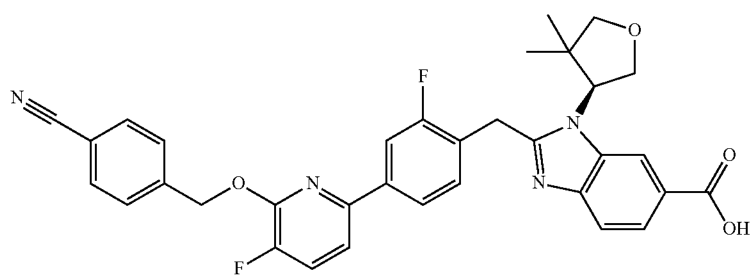 [SMILES: CC1(C)COC[C@H]1n1c(Cc2ccc(-c3ccc(F)c(OCc4ccc(C#N)cc4)n3)cc2F)nc2ccc(C(=O)O)cc21] | 27 | 595.7 | 1H NMR (400 MHz, Methanol-d4) δ 8.86 (s, 1H), 8.15 (dd, J = 8.6, 1.4 Hz, 1H), 7.96-7.82 (m, 2H), 7.78 (d, J = 2.9 Hz, 1H), 7.77-7.70 (m, 3H), 7.70-7.56 (m, 3H), 7.56-7.42 (m, 1H), 5.69 (s, 2H), 5.09 (d, J = 6.6 Hz, 1H), 4.74-4.58 (m, 3H), 4.49 (dd, J = 11.5, 6.7 Hz, 1H), 4.18 (ddd, J = 12.3, 9.0, 3.7 Hz, 1H), 3.99 (d, J = 8.9 Hz, 1H), 3.82 (d, J = 8.9 Hz, 1H), 3.76-3.72 (m, 1H), 3.56 (dt, J = 11.8, 2.8 Hz, 1H), 1.36 (s, 3H), 0.71 (s, 3H). |

TABLE 2-continued

Compounds

| Ex. | Structure | Procedure | ES/MS m/z | ¹H NMR |
|---|---|---|---|---|
| 371 | 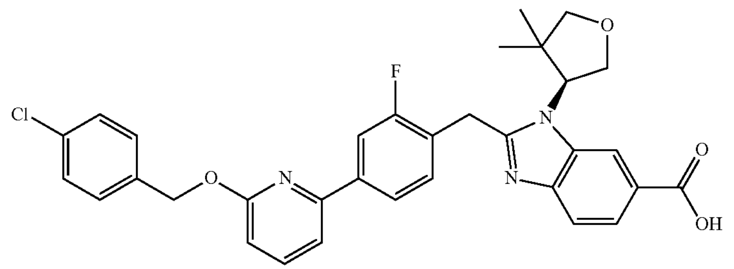 [SMILES: CC1(C)COC[C@H]1n1c(Cc2ccc(-c3cccc(OCc4ccc(Cl)cc4)n3)cc2F)nc2ccc(C(=O)O)cc21] | 24 | 587.0 | 1H NMR (400 MHz, Methanol-d4) δ 8.96 (s, 1H), 8.25 (dd, J = 8.6, 1.4 Hz, 1H), 8.06-7.92 (m, 2H), 7.88-7.73 (m, 2H), 7.68-7.55 (m, 2H), 7.55-7.44 (m, 2H), 7.44-7.28 (m, 2H), 6.88 (d, J = 8.2 Hz, 1H), 5.50 (s, 2H), 5.19 (d, J = 6.4 Hz, 1H), 4.78 (d, J = 7.2 Hz, 2H), 4.65 (dd, J = 11.7, 1.3 Hz, 1H), 4.51 (dd, J = 11.8, 6.6 Hz, 1H), 4.01 (d, J = 9.0 Hz, 1H), 3.84 (d, J = 9.0 Hz, 1H), 1.37 (s, 3H), 0.75 (s, 3H). |
| 372 | 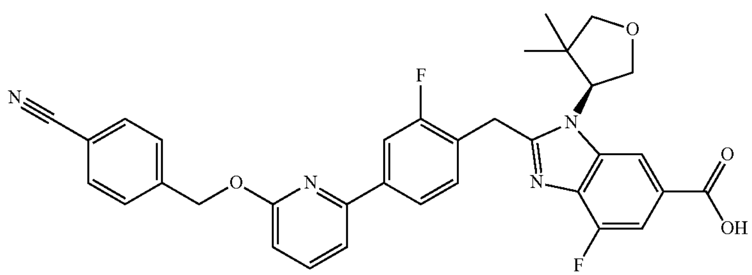 [SMILES: CC1(C)COC[C@H]1n1c(Cc2ccc(-c3cccc(OCc4ccc(C#N)cc4)n3)cc2F)nc2c(F)cc(C(=O)O)cc21] | 35 | 595.7 | 1H NMR (400 MHz, Methanol-d4) δ 8.57 (s, 1H), 7.91-7.62 (m, 8H), 7.52 (d, J = 7.5 Hz, 1H), 7.38 (t, J = 7.8 Hz, 1H), 6.89 (d, J = 8.2 Hz, 1H), 5.60 (s, 2H), 4.94 (s, 1H), 4.60-4.48 (m, 3H), 4.43 (dd, J = 11.4, 6.8 Hz, 1H), 3.93 (d, J = 8.9 Hz, 1H), 3.78 (d, J = 8.8 Hz, 1H), 1.29 (s, 3H), 0.62 (s, 3H). |
| 373 | 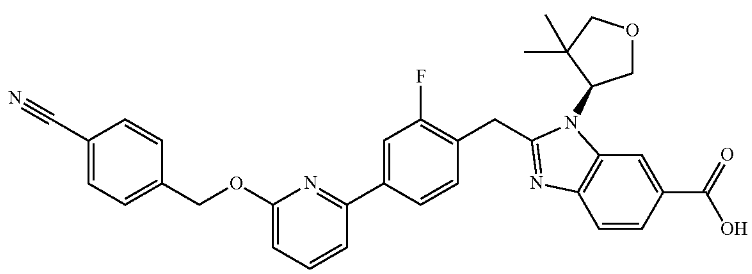 [SMILES: CC1(C)COC[C@H]1n1c(Cc2ccc(-c3cccc(OCc4ccc(C#N)cc4)n3)cc2F)nc2ccc(C(=O)O)cc21] | 27 | 577.7 | 1H NMR (400 MHz, Methanol-d4) δ 8.92 (s, 1H), 8.21 (dd, J = 8.6, 1.4 Hz, 1H), 8.00-7.87 (m, 2H), 7.87-7.79 (m, 2H), 7.74 (d, J = 8.3 Hz, 2H), 7.67 (d, J = 8.1 Hz, 2H), 7.61-7.46 (m, 2H), 6.93 (d, J = 8.2 Hz, 1H), 5.61 (s, 2H), 5.15 (d, J = 6.5 Hz, 1H), 4.73 (d, J = 5.6 Hz, 2H), 4.64 (dd, J = 11.7, 1.4 Hz, 1H), 4.50 (dd, J = 11.7, 6.7 Hz, 1H), 4.00 (d, J = 8.9 Hz, 1H), 3.83 (d, J = 8.9 Hz, 1H), 1.36 (s, 3H), 0.73 (s, 3H). |

TABLE 2-continued

Compounds

| Ex. | Structure | Procedure | ES/MS m/z | ¹H NMR |
|---|---|---|---|---|
| 374 | 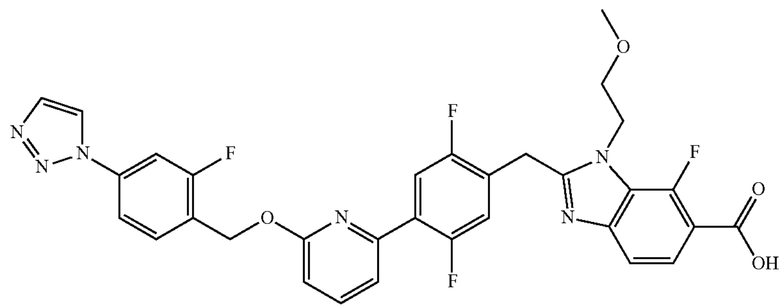 [SMILES: COCCn1c(Cc2cc(F)c(-c3cccc(OCc4ccc(-n5ccnn5)cc4F)n3)cc2F)nc2ccc(C(=O)O)c(F)c21] | 27 | 633.3 | 1H NMR (400 MHz, DMSO-d6) δ 8.90 (d, J = 1.2 Hz, 1H), 8.01 (d, J = 1.2 Hz, 1H), 7.98-7.76 (m, 5H), 7.65 (dd, J = 8.5, 6.8 Hz, 1H), 7.53 (dd, J = 7.5, 1.7 Hz, 1H), 7.48-7.32 (m, 2H), 6.98 (d, J = 8.3 Hz, 1H), 5.60 (s, 2H), 4.61 (t, J = 5.2 Hz, 2H), 4.43 (s, 2H), 3.73 (t, J = 5.2 Hz, 2H), 3.23 (s, 3H). |
| 375 | 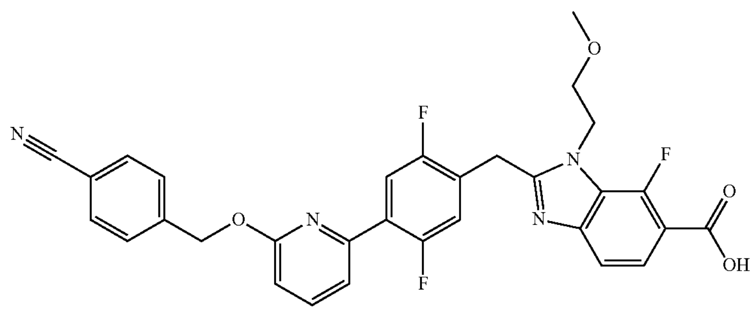 [SMILES: COCCn1c(Cc2cc(F)c(-c3cccc(OCc4ccc(C#N)cc4)n3)cc2F)nc2ccc(C(=O)O)c(F)c21] | 35 | 573.3 | 1H NMR (400 MHz, Methanol-d4) δ 7.94 (dd, J = 8.6, 6.6 Hz, 1H), 7.82 (t, J = 7.8 Hz, 1H), 7.79-7.72 (m, 3H), 7.67 (d, J = 8.1 Hz, 2H), 7.55 (dd, J = 7.5, 1.6 Hz, 1H), 7.50 (d, J = 8.6 Hz, 1H), 7.25 (dd, J = 11.4, 6.0 Hz, 1H), 6.95 (d, J = 8.2 Hz, 1H), 5.59 (s, 2H), 4.74 (t, J = 5.0 Hz, 2H), 4.59 (s, 2H), 3.84 (t, J = 4.9 Hz, 2H), 3.32 (s, 3H). |
| 376 | 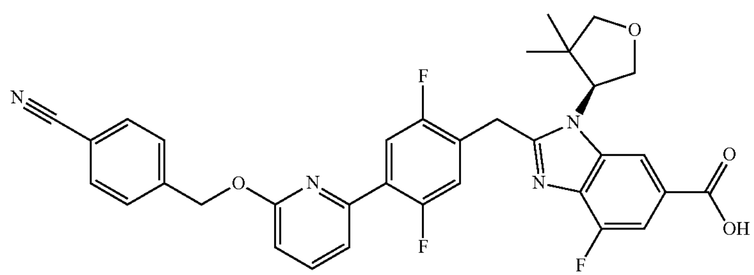 [SMILES: CC1(C)COC[C@H]1n1c(Cc2cc(F)c(-c3cccc(OCc4ccc(C#N)cc4)n3)cc2F)nc2c(F)cc(C(=O)O)cc21] | 35 | 613.63 | 1H NMR (400 MHz, Methanol-d4) δ 8.58 (s, 1H), 7.86-7.72 (m, 4H), 7.71-7.63 (m, 3H), 7.54 (dd, J = 7.5, 1.6 Hz, 1H), 7.23 (dd, J = 11.4, 6.0 Hz, 1H), 6.93 (d, J = 8.2 Hz, 1H), 5.58 (s, 2H), 4.97 (d, J = 6.7 Hz, 1H), 4.65-4.41 (m, 4H), 3.94 (d, J = 8.8 Hz, 1H), 3.80 (d, J = 8.8 Hz, 1H), 1.35 (s, 3H), 0.66 (s, 3H). |

TABLE 2-continued

Compounds

| Ex. | Structure | Procedure | ES/MS m/z | ¹H NMR |
|---|---|---|---|---|
| 377 | 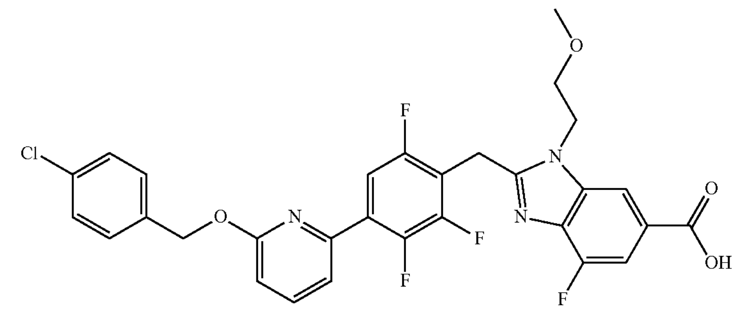 [SMILES: COCCn1c(Cc2c(F)cc(-c3cccc(OCc4ccc(Cl)cc4)n3)c(F)c2F)nc2c(F)cc(C(=O)O)cc21] | 27 | 600.4 | 1H NMR (400 MHz, Methanol-d4) δ 8.15 (d, J = 1.2 Hz, 1H), 7.83 (dd, J = 8.3, 7.5 Hz, 1H), 7.66 (ddd, J = 11.3, 5.4, 1.8 Hz, 2H), 7.56 (dd, J = 7.4, 1.7 Hz, 1H), 7.53-7.45 (m, 2H), 7.45 - 7.33 (m, 2H), 6.92 (d, J = 8.3 Hz, 1H), 5.48 (s, 2H), 4.67 (t, J = 5.0 Hz, 2H), 4.60 (s, 2H), 3.86- 3.78 (m, 2H), 3.33 (s, 3H). |
| 378 | 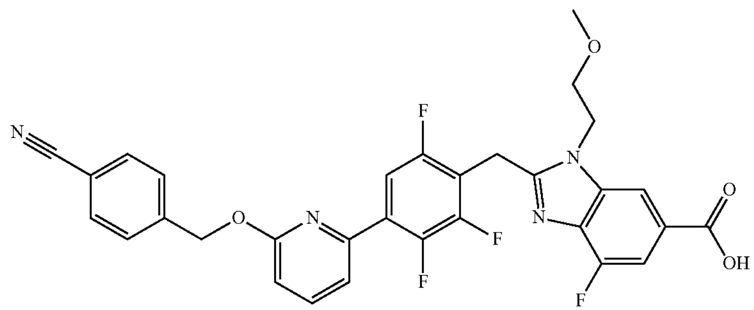 [SMILES: COCCn1c(Cc2c(F)cc(-c3cccc(OCc4ccc(C#N)cc4)n3)c(F)c2F)nc2c(F)cc(C(=O)O)cc21] | 36 | 591.6 | 1H NMR (400 MHz, Methanol-d4) δ 8.15 (d, J = 1.3 Hz, 1H), 7.85 (t, J = 7.9 Hz, 1H), 7.75 (d, J = 8.3 Hz, 2H), 7.72-7.64 (m, 3H), 7.63-7.56 (m, 2H), 6.97 (d, J = 8.3 Hz, 1H), 5.59 (s, 2H), 4.68 (d, J = 5.0 Hz, 2H), 4.60 (s, 2H), 3.75 (dd, J = 2.9, 1.7 Hz, 1H), 3.62-3.51 (m, 2H), 3.32 (s, , 3H). |
| 379 | 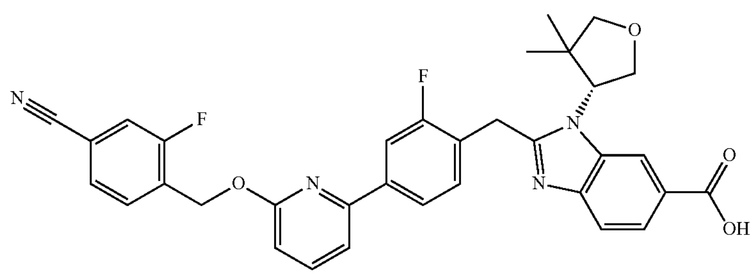 [SMILES: CC1(C)COC[C@@H]1n1c(Cc2ccc(-c3cccc(OCc4ccc(C#N)cc4F)n3)cc2F)nc2ccc(C(=O)O)cc21] | chiral separation Peak 2 | 595.6 | 1H NMR (400 MHz, Methanol-d4) δ 8.88 (s, 1H), 8.29-8.11 (m, 1H), 8.04-7.89 (m, 2H), 7.89-7.69 (m, 3H), 7.67-7.42 (m, 4H), 6.92 (d, J = 8.1 Hz, 1H), 5.66 (s, 2H), 5.17-5.06 (m, 1H), 4.79-4.60 (m, 3H), 4.50 (dd, J = 11.5, 6.7 Hz, 1H), 4.32-4.14 (m, 1H), 3.99 (d, J = 8.9 Hz, 1H), 3.56 (dq, J = 9.8, 2.9 Hz, 1H), 1.36 (s, 3H), 0.72 (s, 3H). |

TABLE 2-continued

Compounds

| Ex. | Structure | Procedure | ES/MS m/z | ¹H NMR |
|---|---|---|---|---|
| 380 | 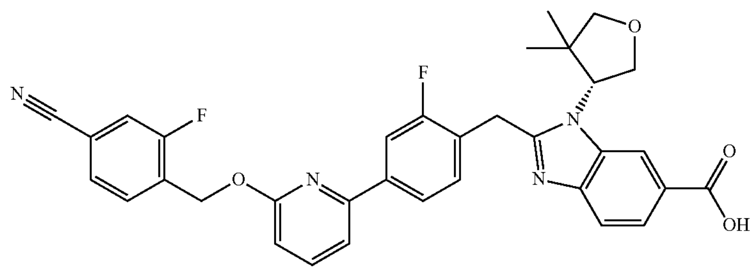 [SMILES: CC1(C)COC[C@@H]1n1c(Cc2ccc(-c3cccc(OCc4ccc(C#N)cc4F)n3)cc2F)nc2ccc(C(=O)O)cc21] | chiral separation Peak 1 | 595.6 | 1H NMR (400 MHz, Methanol-d4) δ 8.91 (s, 1H), 8.28-8.12 (m, 1H), 8.06-7.89 (m, 2H), 7.89-7.70 (m, 3H), 7.68-7.43 (m, 4H), 6.93 (d, J = 8.2 Hz, 1H), 5.66 (s, 2H), 5.20-5.11 (m, 1H), 4.81-4.61 (m, 3H), 4.61-4.49 (m, 1H), 4.28-4.11 (m, 1H), 4.00 (d, J = 8.9 Hz, 1H), 3.59-3.46 (m, 1H), 1.37 (s, 3H), 0.73 (s, 3H). |
| 381 | 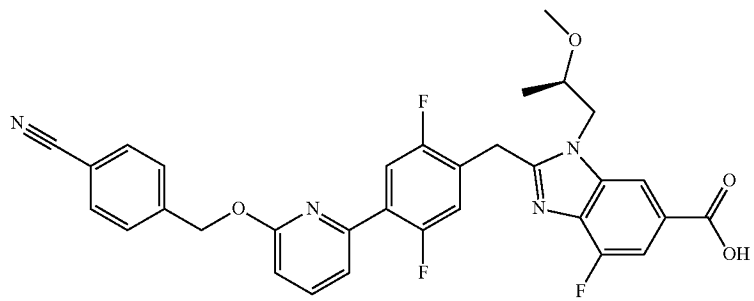 [SMILES: CO[C@H](C)Cn1c(Cc2cc(F)c(-c3cccc(OCc4ccc(C#N)cc4)n3)cc2F)nc2c(F)cc(C(=O)O)cc21] | 35 | 587.73 | 1H NMR (400 MHz, Methanol-d4) δ 8.17 (d, J = 1.2 Hz, 1H), 7.83-7.59 (m, 8H), 7.50 (dd, J = 7.5, 1.5 Hz, 1H), 7.19 (dd, J = 11.5, 6.0 Hz, 1H), 6.91 (d, J = 8.2 Hz, 1H), 5.55 (s, 2H), 4.61-4.45 (m, 3H), 4.37 (dd, J = 15.2, 9.1 Hz, 1H), 3.72 (dqt, J = 10.1,6.9, 3.4 Hz, 1H), 3.15 (s, 3H), 1.30 (d, J = 6.1 Hz, 3H). |
| 382 | 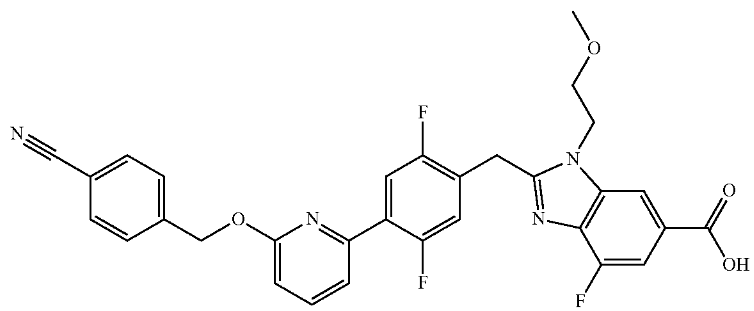 [SMILES: COCCn1c(Cc2cc(F)c(-c3cccc(OCc4ccc(C#N)cc4)n3)cc2F)nc2c(F)cc(C(=O)O)cc21] | 27 | 573.6 | 1H NMR (400 MHz, Methanol-d4) δ 8.19 (s, 1H), 7.80 (d, J = 7.8 Hz, 1H), 7.777-7.69 (m, 4H), 7.66 (d, J = 8.3 Hz, 2H), 7.51 (dd, J = 7.5, 1.6 Hz, 1H), 7.19 (dd, J = 11.4, 6.0 Hz, 1H), 6.92 (d, J = 8.2 Hz, 1H), 5.57 (s, 2H), 4.63 (t, J = 5.0 Hz, 2H), 4.57 (s, 2H), 3.75 (t, J = 4.9 Hz, 2H), 3.27 (s, 3H). |

TABLE 2-continued

Compounds

| Ex. | Structure | Procedure | ES/MS m/z | ¹H NMR |
|---|---|---|---|---|
| 383 A | 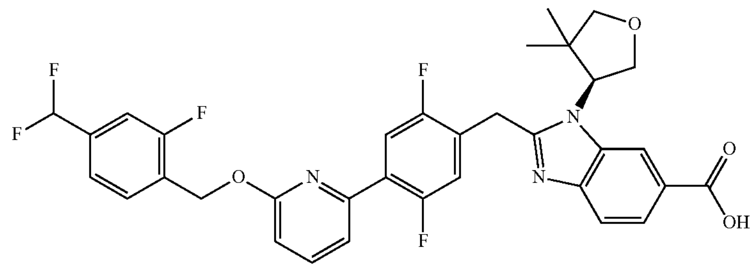 [SMILES: CC1(C)COC[C@H]1n1c(Cc2cc(F)c(-c3cccc(OCc4ccc(C(F)F)cc4F)n3)cc2F)nc2ccc(C(=O)O)cc21] | chiral separation Peak 2 | 638.36 | 1H NMR (400 MHz, Methanol-d4) δ 8.79 (s, 1H), 8.07 (dd, J = 8.5, 1.4 Hz, 1H), 7.97-7.77 (m, 2H), 7.69 (dd, J = 24.1, 8.1 Hz, 2H), 7.55 (dd, J = 7.5, 1.5 Hz, 1H), 7.43-7.20 (m, 3H), 6.97-6.86 (m, 1H), 5.59 (s, 2H), 5.04 (d, J = 6.7 Hz, 1H), 4.67-4.44 (m, 4H), 3.97 (d, J = 8.8 Hz, 1H), 3.82 (d, J = 8.8 Hz, 1H), 3.75-3.61 (m, 2H), 1.39 (s, 3H), 0.71 (s, 3H). |
| 383 B | 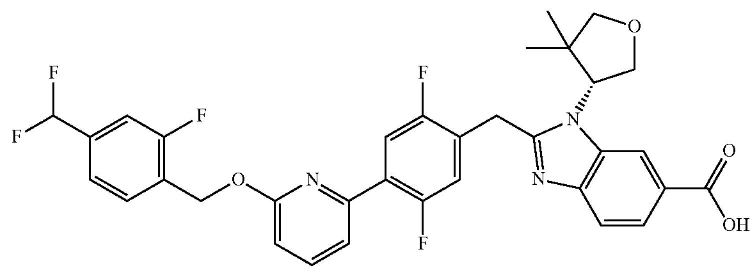 [SMILES: CC1(C)COC[C@@H]1n1c(Cc2cc(F)c(-c3cccc(OCc4ccc(C(F)F)cc4F)n3)cc2F)nc2ccc(C(=O)O)cc21] | chiral separation Peak 1 | 638.3 | 1H NMR (400 MHz, Methanol-d4) δ 8.79 (s, 1H), 8.08 (dd, J = 8.5, 1.5 Hz, 1H), 7.94-7.76 (m, 2H), 7.69 (dd, J = 24.9, 8.1 Hz, 2H), 7.56 (dd, J = 7.5, 1.6 Hz, 1H), 7.45-7.20 (m, 3H), 6.92 (d, J = 8.4 Hz, 1H), 5.60 (s, 2H), 5.05 (d, J = 6.7 Hz, 1H), 4.76-4.43 (m, 4H), 3.97 (d, J = 8.8 Hz, 1H), 3.82 (d, J = 8.8 Hz, 1H), 3.74-3.66 (m, 1H), 1.39 (s, 3H), 0.71 (s, 3H). |
| 384 | 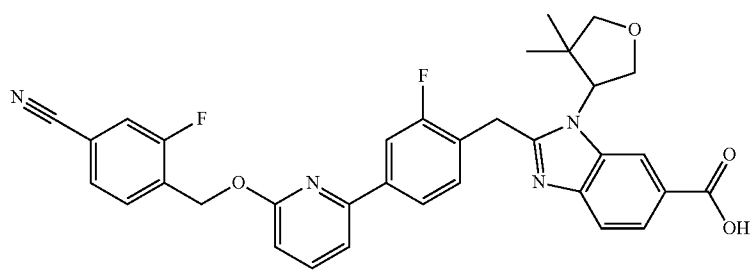 [SMILES: CC1(C)COCC1n1c(Cc2ccc(-c3cccc(OCc4ccc(C#N)cc4F)n3)cc2F)nc2ccc(C(=O)O)cc21] | 36 | 595.6 | 1H NMR (400 MHz, Methanol-d4) δ 8.85 (s, 1H), 8.14 (dd, J = 8.6, 1.4 Hz, 1H), 8.03-7.87 (m, 2H), 7.87-7.67 (m, 4H), 7.67-7.44 (m, 3H), 6.92 (d, J = 8.2 Hz, 1H), 5.66 (s, 2H), 5.08 (d, J = 6.6 Hz, 1H), 4.72-4.56 (m, 3H), 4.49 (dd, J = 11.5, 6.8 Hz, 1H), 3.99 (d, J = 8.9 Hz, 1H), 3.82 (d, J = 8.8 Hz, 1H), 3.72-3.63 (m, 1H), 1.36 (s, 3H), 0.71 (s, 3H). |

TABLE 2-continued

Compounds

| Ex. | Structure | Procedure | ES/MS m/z | ¹H NMR |
|---|---|---|---|---|
| 385 A | 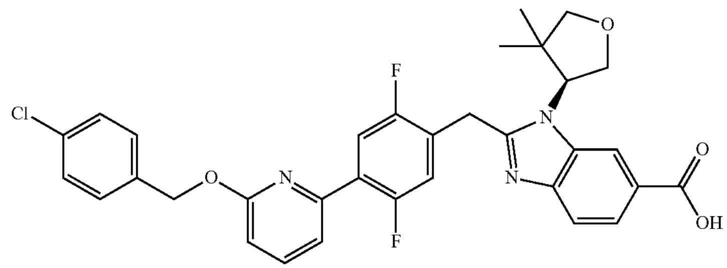 [SMILES: CC1(C)COC[C@H]1n1c(Cc2cc(F)c(-c3cccc(OCc4ccc(Cl)cc4)n3)cc2F)nc2ccc(C(=O)O)cc21] | chiral separation Peak 2 | 604.85 | 1H NMR (400 MHz, Methanol-d4) δ 8.84 (s, 1H), 8.13 (dd, J = 8.5, 1.4 Hz, 1H), 8.00-7.70 (m, 3H), 7.55 (dd, J = 7.5, 1.6 Hz, 1H), 7.48 (d, J = 8.2 Hz, 2H), 7.44-7.23 (m, 3H), 6.91 (d, J = 8.2 Hz, 1H), 5.48 (s, 2H), 5.18-5.02 (m, 1H), 4.75-4.48 (m, 4H), 3.99 (d, J = 8.9 Hz, 1H), 3.85 (s, 1H), 3.74-3.61 (m, 1H), 1.40 (s, 3H), 0.74 (s, 3H). |
| 385 B | 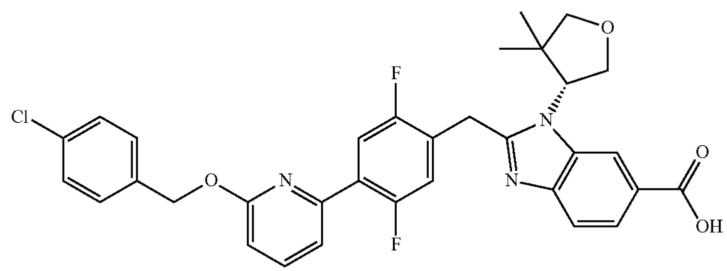 [SMILES: CC1(C)COC[C@@H]1n1c(Cc2cc(F)c(-c3cccc(OCc4ccc(Cl)cc4)n3)cc2F)nc2ccc(C(=O)O)cc21] | chiral separation Peak 1 | 604.8 | 1H NMR (400 MHz, Methanol-d4) δ 8.82 (s, 1H), 8.15-8.01 (m, 1H), 7.98-7.66 (m, 3H), 7.55 (dd, J = 7.5, 1.6 Hz, 1H), 7.48 (d, J = 8.2 Hz, 2H), 7.42-7.34 (m, 3H), 6.90 (d, J = 8.2 Hz, 1H), 5.48 (s, 2H), 5.12-4.99 (m, 4H), 3.98 (d, J = 8.9 Hz, 1H), 3.92-3.73 (m, 2H), 1.40 (s, 3H), 0.73 (s, 3H). |
| 386 | 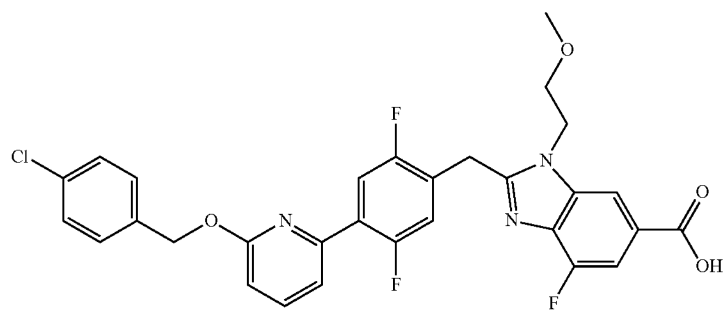 [SMILES: COCCn1c(Cc2cc(F)c(-c3cccc(OCc4ccc(Cl)cc4)n3)cc2F)nc2c(F)cc(C(=O)O)cc21] | 27 | 582.65 | 1H NMR (400 MHz, DMSO-d6) δ 8.10 (s, 1H), 7.97-7.73 (m, 2H), 7.60-7.31 (m, 7H), 6.95 (d, J = 8.2 Hz, 1H), 5.47 (s, 2H), 4.62 (t, J = 5.1 Hz, 2H), 4.46 (s, 2H), 3.68 (t, J = 5.0 Hz, 2H), 3.66-3.51 (m, 1H), 3.21 (s, 3H). |

TABLE 2-continued

Compounds

| Ex. | Structure | Procedure | ES/MS m/z | ¹H NMR |
|---|---|---|---|---|
| 387 | 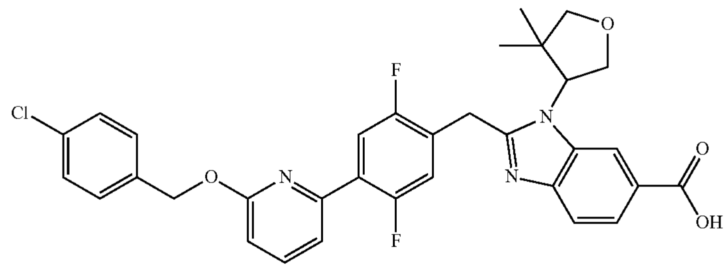 [SMILES: CC1(C)COCC1n1c(Cc2cc(F)c(-c3cccc(OCc4ccc(Cl)cc4)n3)cc2F)nc2ccc(C(=O)O)cc21] | 27 | 605.25 | 1H NMR (400 MHz, Methanol-d4) δ 8.89 (s, 1H), 8.17 (dd, J = 8.6, 1.4 Hz, 1H), 7.90 (dd, J = 10.9, 6.3 Hz, 1H), 7.87-7.70 (m, 2H), 7.56 (dd, J = 7.3, 1.6 Hz, 1H), 7.53-7.44 (m, 2H), 7.43-7.31 (m, 3H), 6.92 (d, J = 8.2 Hz, 1H), 5.48 (s, 2H), 5.14 (d, J = 6.5 Hz, 1H), 4.78-4.60 (m, 3H), 4.52 (dd, J = 11.6, 6.7 Hz, 1H), 4.00 (d, J = 8.9 Hz, 1H), 3.84 (d, J = 8.9 Hz, 1H), 1.41 (s, 3H), 0.76 (s, 3H). |
| 388 | 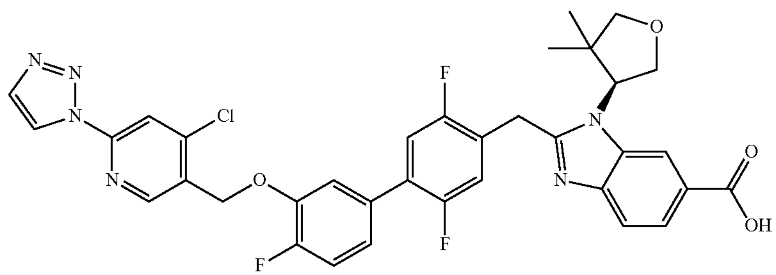 [SMILES: CC1(C)COC[C@H]1n1c(Cc2cc(F)c(-c3ccc(F)c(OCc4cnc(-n5ccnn5)cc4Cl)c3)cc2F)nc2ccc(C(=O)O)cc21] | 35 | 689.1 | 1H NMR (400 MHz, DMSO-d6) δ 8.93 (d, J = 1.2 Hz, 1H), 8.83 (s, 1H), 8.48 (s, 1H), 8.33 (s, 1H), 8.04 (d, J = 1.3 Hz, 1H), 7.80 (dd, J = 8.4, 1.4 Hz, 1H), 7.62 (t, J = 8.2 Hz, 2H), 7.56 (dd, J = 10.1, 6.5 Hz, 1H), 7.47-7.43 (m, 1H), 7.40 (dd, J = 11.3, 8.6 Hz, 1H), 7.30-7.23 (m, 1H), 5.46 (s, 2H), 5.02 (d, J = 6.6 Hz, 1H), 4.58-4.48 (m, 2H), 4.44 (dd, J = 11.1, 6.8 Hz, 1H), 4.36 (d, J = 16.8 Hz, 1H), 3.82-3.68 (m, 2H), 1.34 (s, 3H), 0.60 (s, 3H). |

TABLE 2-continued

Compounds

| Ex. | Structure | Procedure | ES/MS m/z | ¹H NMR |
|---|---|---|---|---|
| 389 | 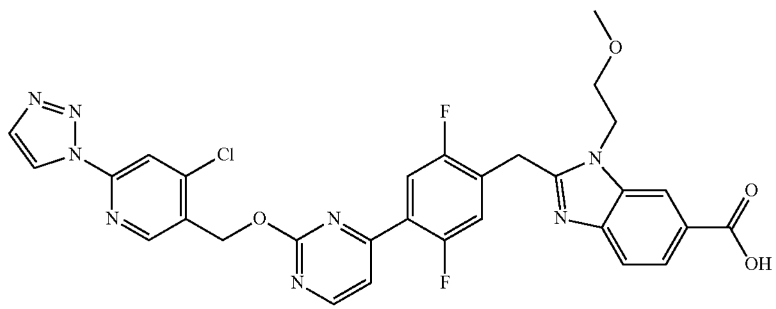 [SMILES: COCCn1c(Cc2cc(F)c(-c3ccnc(OCc4cnc(-n5ccnn5)cc4Cl)n3)cc2F)nc2ccc(C(=O)O)cc21] | 35 | 633.1 | 1H NMR (400 MHz, DMSO-d6) δ 8.92 (d, J = 1.3 Hz, 1H), 8.84 (s, 1H), 8.80 (d, J = 5.2 Hz, 1H), 8.32 (s, 1H), 8.21 (s, 1H), 8.03 (d, J = 1.2 Hz, 1H), 7.97 (dd, J = 10.1, 6.3 Hz, 1H), 7.79 (dd, J = 8.6, 1.5 Hz, 1H), 7.65 (dd, J = 5.3, 1.8 Hz, 1H), 7.59 (d, J = 8.4 Hz, 1H), 7.48 (dd, J = 11.5, 5.8 Hz, 1H), 5.69 (s, 2H), 4.59 (d, J = 5.5 Hz, 2H), 4.48 (s, 2H), 3.68 (t, J = 5.0 Hz, 2H), 3.20 (s, 3H). |
| 390 | 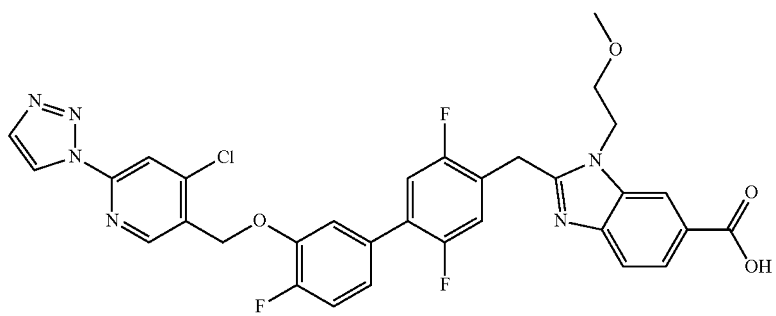 [SMILES: COCCn1c(Cc2cc(F)c(-c3ccc(F)c(OCc4cnc(-n5ccnn5)cc4Cl)c3)cc2F)nc2ccc(C(=O)O)cc21] | 35 | 649.1 | 1H NMR (400 MHz, DMSO-d6) δ 8.92 (d, J = 1.3 Hz, 1H), 8.83 (s, 1H), 8.33 (s, 1H), 8.25 (d, J = 1.5 Hz, 1H), 8.04 (d, J = 1.3 Hz, 1H), 7.83 (dd, J = 8.4, 1.5 Hz, 1H), 7.62 (dd, J = 8.5, 3.5 Hz, 2H), 7.56 (dd, J = 10.2, 6.5 Hz, 1H), 7.39 (dd, J = 11.0, 7.5 Hz, 2H), 7.31-7.19 (m, 1H), 5.45 (s, 2H), 4.63 (t, J = 5.2 Hz, 2H), 4.47 (s, 2H), 3.68 (t, J = 5.3 Hz, 2H), 3.21 (s, 3H). |
| 391 | 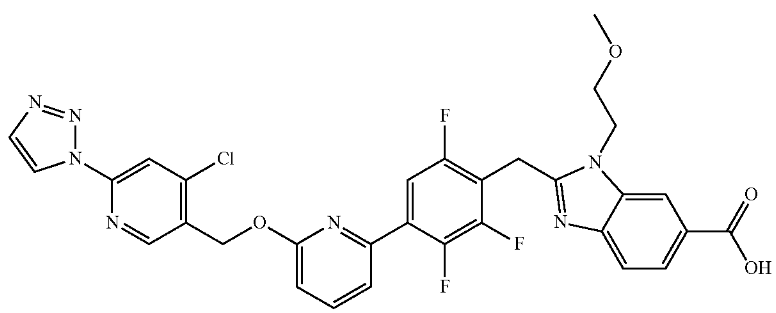 [SMILES: COCCn1c(Cc2c(F)cc(-c3cccc(OCc4cnc(-n5ccnn5)cc4Cl)n3)c(F)c2F)nc2ccc(C(=O)O)cc21] | 38 | 650.1 | 1H NMR (400 MHz, DMSO-d6) δ 8.90 (d, J = 1.3 Hz, 1H), 8.83 (s, 1H), 8.31 (s, 1H), 8.21 (d, J = 1.5 Hz, 1H), 8.03 (d, J = 1.3 Hz, 1H), 7.96 (t, J = 7.8 Hz, 1H), 7.82-7.73 (m, 2H), 7.58 (dd, J = 13.1, 7.9 Hz, 2H), 7.06 (d, J = 8.4 Hz, 1H), 5.67 (s, 2H), 4.65 (s, 2H), 4.53 (s, 2H), 3.72 (t, J = 5.0 Hz, 2H), 3.24 (s, 3H). |

TABLE 2-continued

Compounds

| Ex. | Structure | Procedure | ES/MS m/z | ¹H NMR |
|---|---|---|---|---|
| 392 | 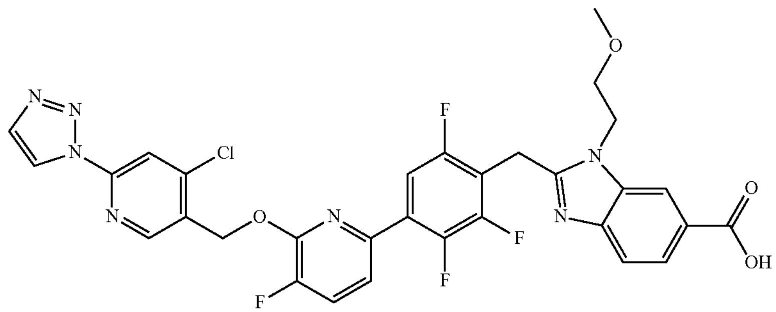 [SMILES: COCCn1c(Cc2c(F)cc(-c3ccc(F)c(OCc4cnc(-n5ccnn5)cc4Cl)n3)c(F)c2F)nc2ccc(C(=O)O)cc21] | 38 | 668.1 | 1H NMR (400 MHz, DMSO-d6) δ 8.91 (d, J = 1.3 Hz, 1H), 8.85 (s, 1H), 8.32 (s, 1H), 8.21 (s, 1H), 8.03 (d, J = 1.3 Hz, 1H), 7.99-7.86 (m, 1H), 7.80-7.70 (m, 1H), 7.63 (d, J = 8.5 Hz, 1H), 7.56 (d, J = 8.4 Hz, 1H), 5.76 (s, 2H), 4.65 (s, 2H), 4.52 (s, 2H), 3.72 (t, J = 4.9 Hz, 2H), 3.24 (s, 3H). |
| 393 | 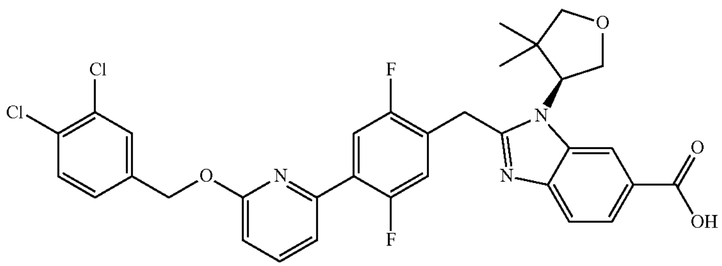 [SMILES: CC1(C)COC[C@H]1n1c(Cc2cc(F)c(-c3cccc(OCc4ccc(Cl)c(Cl)c4)n3)cc2F)nc2ccc(C(=O)O)cc21] | 35 | 638.2 | 1H NMR (400 MHz, DMSO-d6) δ 8.48 (s, 1H), 7.89 (t, J = 7.9 Hz, 1H), 7.80 (dt, J = 10.4, 3.3 Hz, 3H), 7.63 (dd, J = 16.7, 8.4 Hz, 2H), 7.57-7.41 (m, 3H), 6.98 (d, J = 8.3 Hz, 1H), 5.48 (s, 2H), 5.01 (d, J = 6.7 Hz, 1H), 4.58-4.48 (m, 2H), 4.48-4.31 (m, 2H), 3.81-3.71 (m, 2H), 1.33 (s, 3H), 0.60 (s, 3H). |
| 394 | 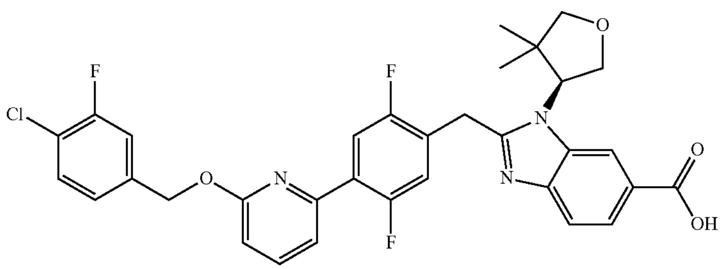 [SMILES: CC1(C)COC[C@H]1n1c(Cc2cc(F)c(-c3cccc(OCc4ccc(Cl)c(F)c4)n3)cc2F)nc2ccc(C(=O)O)cc21] | 35 | 622.2 | 1H NMR (400 MHz, DMSO-d6) δ 8.48 (s, 1H), 7.89 (t, J = 7.9 Hz, 1H), 7.83-7.75 (m, 2H), 7.61 (dt, J = 8.0, 3.8 Hz, 2H), 7.58-7.49 (m, 2H), 7.45 (dd, J = 11.2, 6.2 Hz, 1H), 7.39-7.35 (m, 1H), 6.98 (d, J = 8.2 Hz, 1H), 5.48 (s, 2H), 5.01 (d, J = 6.5 Hz, 1H), 4.59-4.48 (m, 2H), 4.48-4.31 (m, 2H), 3.81-3.68 (m, 2H), 1.33 (s, 3H), 0.60 (s, 3H). |

TABLE 2-continued

Compounds

| Ex. | Structure | Procedure | ES/MS m/z | ¹H NMR |
|---|---|---|---|---|
| 396 | 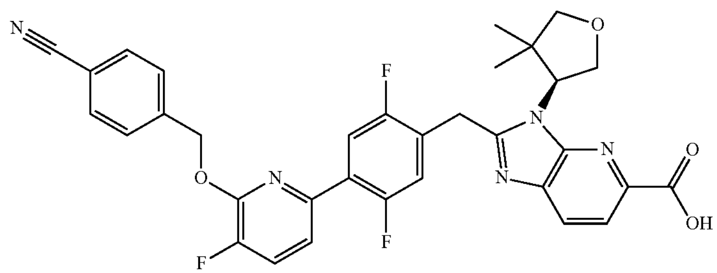 [SMILES: CC1(C)COC[C@H]1n1c(Cc2cc(F)c(-c3ccc(F)c(OCc4ccc(C#N)cc4)n3)cc2F)nc2ccc(C(=O)O)nc21] | 35 | 614.0 | 1H NMR (400 MHz, DMSO) δ 8.08 (d, J = 8.6 Hz, 1H), 7.96 (d, J = 8.3 Hz, 1H), 7.87 (dd, J = 9.9, 8.3 Hz, 3H), 7.77-7.67 (m, 3H), 7.55 (dd, J = 8.5, 2.4 Hz, 1H), 7.46 (dd, J = 11.4, 6.0 Hz, 1H), 5.67 (s, 2H), 4.96 (dd, J = 8.4, 5.3 Hz, 1H), 4.74 (dd, J = 9.6, 5.1 Hz, 1H), 4.58 (d, J = 17.1 Hz, 1H), 4.48 (d, J = 17.1 Hz, 1H), 4.37 (dt, J = 9.0, 5.0 Hz, 2H), 3.63 (d, J = 7.9 Hz, 1H), 1.24 (s, 3H), 0.62 (s, 3H). |
| 397 | 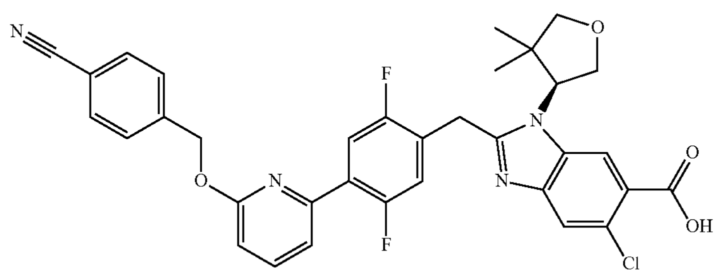 [SMILES: CC1(C)COC[C@H]1n1c(Cc2cc(F)c(-c3cccc(OCc4ccc(C#N)cc4)n3)cc2F)nc2cc(Cl)c(C(=O)O)cc21] | 35 | 629.0 | 1H NMR (400 MHz, DMSO) δ 8.31 (s, 1H), 7.89 (dd, J = 17.8, 8.0 Hz, 3H), 7.78-7.65 (m, 4H), 7.53 (d, J = 7.4 Hz, 1H), 7.45 (t, J = 8.7 Hz, 1H), 7.01 (d, J = 8.2 Hz, 1H), 5.58 (s, 2H), 5.00 (d, J = 6.5 Hz, 1H), 4.56-4.47 (m, 2H), 4.46-4.31 (m, 3H), 4.36 (s, 15H), 4.16 (s, 1H), 3.78-3.68 (m, 2H), 1.33 (s, 3H), 0.61 (s, 3H). |
| 398 | 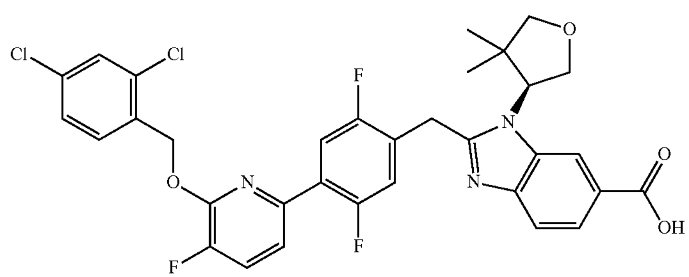 [SMILES: CC1(C)COC[C@H]1n1c(Cc2cc(F)c(-c3ccc(F)c(OCc4ccc(Cl)cc4Cl)n3)cc2F)nc2ccc(C(=O)O)cc21] | 35 | 656.0 | 1H NMR (400 MHz, DMSO) δ 8.49 (s, 1H), 7.92-7.69 (m, 4H), 7.64 (dd, J = 8.4, 6.1 Hz, 2H), 7.60-7.53 (m, 1H), 7.53-7.42 (m, 2H), 5.63 (s, 2H), 5.02 (d, J = 6.6 Hz, 1H), 4.54 (dd, J = 15.0, 2.5 Hz, 2H), 4.48-4.34 (m, 2H), 3.78 (d, J = 8.7 Hz, 1H), 3.73 (d, J = 8.6 Hz, 1H), 1.33 (s, 3H), 0.61 (s, 3H). |

TABLE 2-continued

Compounds

| Ex. | Structure | Procedure | ES/MS m/z | ¹H NMR |
|---|---|---|---|---|
| 399 | 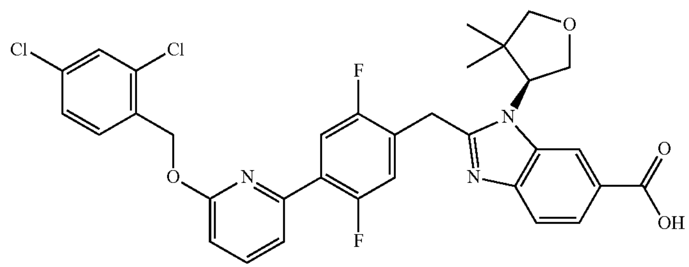 | 35 | 638.0 | 1H NMR (400 MHz, DMSO) δ 8.50 (s, 1H), 7.90 (t, J = 7.9 Hz, 1H), 7.86-7.75 (m, 2H), 7.70 (d, J = 2.1 Hz, 1H), 7.66-7.59 (m, 2H), 7.58-7.51 (m, 1H), 7.51-7.42 (m, 2H), 7.00 (d, J = 8.2 Hz, 1H), 5.54 (s, 2H), 5.03 (d, J = 6.7 Hz, 1H), 4.73 (s, 8H), 4.55 (d, J = 17.4 Hz, 2H), 4.48-4.37 (m, 2H), 4.35 (s, 4H), 3.82-3.70 (m, 2H), 1.33 (s, 3H), 0.61 (s, 3H). |
| 400 | 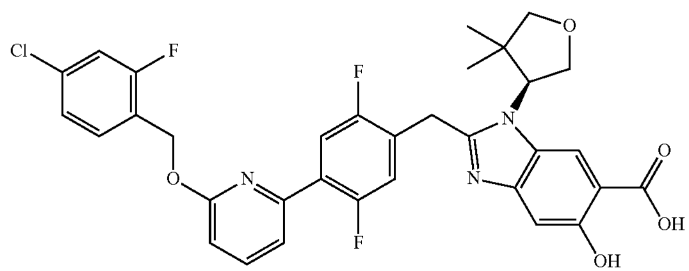 [SMILES: CC1(C)COC[C@H]1n1c(Cc2cc(F)c(-c3cccc(OCc4ccc(Cl)cc4F)n3)cc2F)nc2cc(O)c(C(=O)O)cc21] | 35 | 636.0 | 1H NMR (400 MHz, DMSO) δ 8.40 (s, 1H), 7.93-7.80 (m, 2H), 7.61 (t, J = 8.1 Hz, 1H), 7.57-7.41 (m, 4H), 7.33 (dd, J = 8.3, 1.9 Hz, 1H), 6.96 (d, J = 8.3 Hz, 1H), 5.51 (s, 2H), 4.98 (d, J = 6.6 Hz, 1H), 4.57-4.47 (m, 2H), 4.47-4.34 (m, 2H), 3.77 (d, J = 8.7 Hz, 1H), 3.72 (d, J = 8.6 Hz, 1H), 2.58 (s, 3H), 1.31 (s, 3H), 0.60 (s, 3H). |
| 401 | 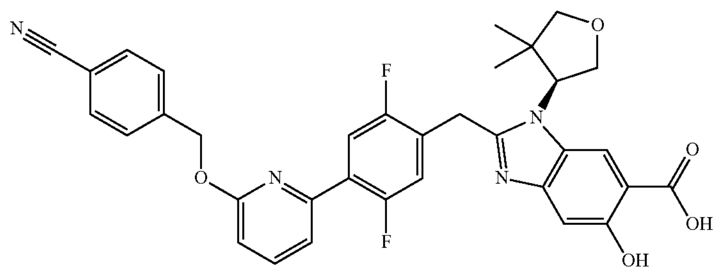 | 35 | 609 | .1H NMR (400 MHz, DMSO) δ 8.40 (s, 1H), 7.95-7.83 (m, 3H), 7.74 (dd, J = 10.4, 6.5 Hz, 1H), 7.68 (d, J = 8.0 Hz, 2H), 7.53 (d, J = 7.4 Hz, 1H), 7.45 (s, 1H), 7.50-7.40 (m, 1H), 7.01 (d, J = 8.3 Hz, 1H), 5.58 (s, 2H), 4.97 (d, J = 6.6 Hz, 1H), 4.52 (d, J = 7.5 Hz, 1H), 4.49 (s, 1H), 4.47-4.33 (m, 2H), 3.80-3.68 (m, 2H), 2.58 (s, 3H), 1.31 (s, 3H), 0.59 (s, 3H). |

TABLE 2-continued

Compounds

| Ex. | Structure | Procedure | ES/MS m/z | ¹H NMR |
|---|---|---|---|---|
| 402 | 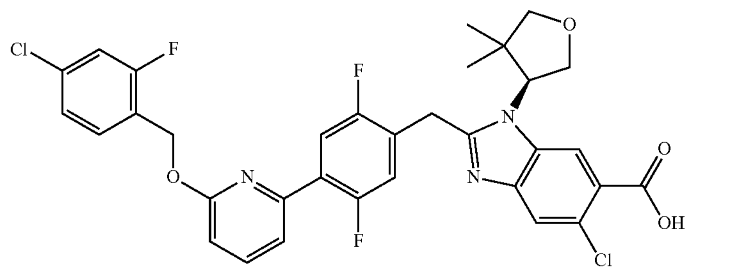 [SMILES: CC1(C)COC[C@H]1n1c(Cc2cc(F)c(-c3cccc(OCc4ccc(Cl)cc4F)n3)cc2F)nc2cc(Cl)c(C(=O)O)cc21] | 35 | 656 | 1H NMR (400 MHz, DMSO) δ 8.32 (s, 1H), 7.93-7.79 (m, 2H), 7.73 (s, 1H), 7.61 (t, J = 8.2 Hz, 1H), 7.59-7.41 (m, 3H), 7.33 (dd, J = 8.3, 2.0 Hz, 1H), 6.96 (d, J = 8.3 Hz, 1H), 5.51 (s, 2H), 5.00 (d, J = 6.5 Hz, 1H), 4.57-4.47 (m, 2H), 4.46-4.32 (m, 2H), 3.78-3.68 (m, 2H), 1.33 (s, 3H), 0.61 (s, 3H). |
| 403 | 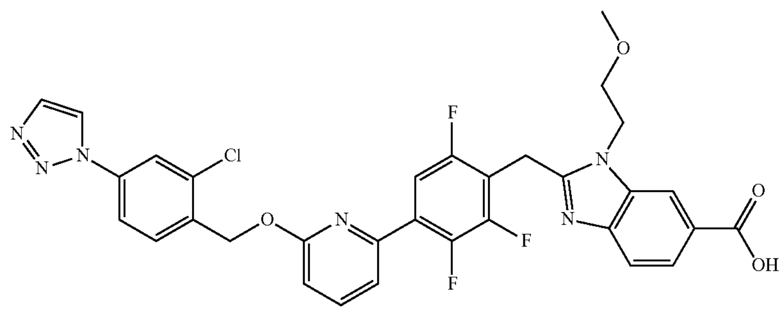 [SMILES: COCCn1c(Cc2c(F)cc(-c3cccc(OCc4ccc(-n5ccnn5)cc4Cl)n3)c(F)c2F)nc2ccc(C(=O)O)cc21] | 38 | 649.0 | 1H NMR (400 MHz, DMSO) δ 8.92 (s, 1H), 8.22 (s, 1H), 8.16 (d, J = 2.1 Hz, 1H), 8.03-7.92 (m, 3H), 7.87-7.75 (m, 2H), 7.75-7.67 (m, 1H), 7.58 (t, J = 7.7 Hz, 2H), 7.08 (d, J = 8.3 Hz, 1H), 5.63 (s, 2H), 4.65 (t, J = 5.1 Hz, 2H), 4.53 (s, 2H), 3.73 (t, J = 5.0 Hz, 2H), 3.24 (s, 3H), 2.56 (d, J = 7.5 Hz, 1H). |
| 404 | 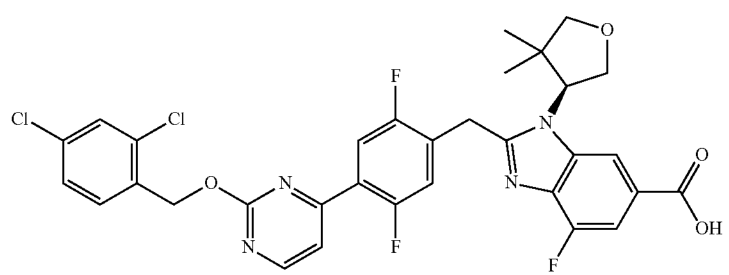 [SMILES: CC1(C)COC[C@H]1n1c(Cc2cc(F)c(-c3ccnc(OCc4ccc(Cl)cc4Cl)n3)cc2F)nc2c(F)cc(C(=O)O)cc21] | 35 | 658.2 | 1H NMR (400 MHz, Chloroform-d) δ 8.31 (d, J = 5.1 Hz, 1H), 7.51 (t, J = 8.1 Hz, 1H), 7.21 (d, J = 5.2 Hz, 1H), 7.19-7.13 (m, 2H), 5.51-5.46 (m, 2H), ;1H NMR (400 MHz, DMSO) δ 8.78 (d, J = 5.1 Hz, 1H), 8.57 (d, J = 1.5 Hz, 1H), 7.92 (ddt, J = 10.3, 3.5, 1.7 Hz, 3H), 7.75 (dq, J = 11.3, 8.2 Hz, 3H), 7.62 (dd, J = 5.2, 1.8 Hz, 1H), 7.51 (dd, J = 11.5, 6.0 Hz, 1H), 5.81-5.70 (m, 1H), 5.62 (s, 2H), 4.65 (s, 2H), 4.27 (dd, J = 10.8, 7.9 Hz, 1H), 4.20 (dd, J = 10.8, 3.3 Hz, 1H), 2.40 |

TABLE 2-continued

Compounds

| Ex. | Structure | Procedure | ES/MS m/z | ¹H NMR |
|---|---|---|---|---|
| | | | | (dd, J = 13.2, 9.4 Hz, 1H), 2.02 (dd, J = 13.3, 6.9 Hz, 1H), 1.50 (s, 3H), 1.27 (s, 3H). |
| 405 | 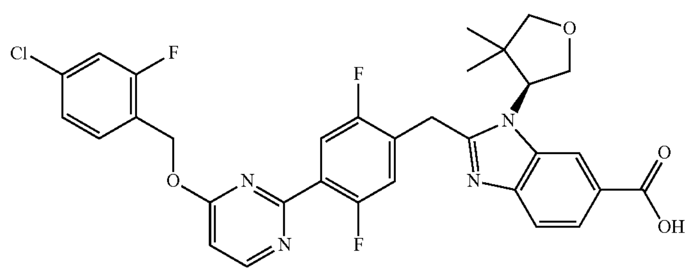 [SMILES: CC1(C)COC[C@H]1n1c(Cc2cc(F)c(-c3nccc(OCc4ccc(Cl)cc4F)n3)cc2F)nc2ccc(C(=O)O)cc21] | 35 | 623.0 | 1H NMR (400 MHz, DMSO-d6) δ 8.72 (d, J = 5.8 Hz, 1H), 8.50 (s, 1H), 7.92 (dd, J = 10.1, 6.2 Hz, 1H), 7.82 (dd, J = 8.5, 1.5 Hz, 1H), 7.64 (dt, J = 8.2, 4.0 Hz, 2H), 7.50 (ddd, J = 16.8, 10.5, 4.0 Hz, 2H), 7.35 (dd, J = 8.4, 2.1 Hz, 1H), 7.04 (d, J = 5.8 Hz, 1H), 5.58 (s, 2H), 5.03 (d, J = 6.6 Hz, 1H), 4.60-4.52 (m, 2H), 4.49-4.38 (m, 2H), 3.85-3.69 (m, 2H), 1.34 (s, 3H), 0.61 (s, 3H). |
| 406 | 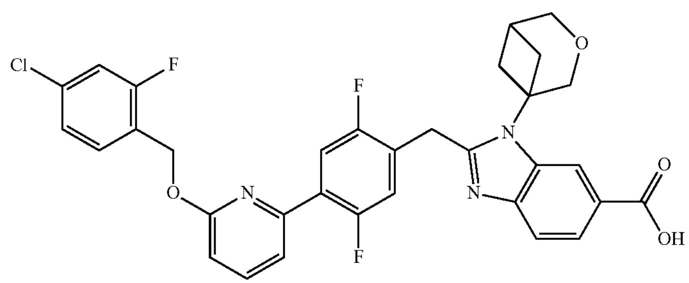 [SMILES: O=C(O)c1ccc2nc(Cc3cc(F)c(-c4cccc(OCc5ccc(Cl)cc5F)n4)cc3F)n(C34COCC(C3)C4)c2c1] | 35 | 620.0 | 1H NMR (400 MHz, DMSO-d6) δ 8.12 (d, J = 1.4 Hz, 1H), 7.95-7.76 (m, 3H), 7.65-7.58 (m, 2H), 7.52 (ddd, J = 12.1, 8.8, 1.9 Hz, 2H), 7.43 (dd, J = 11.5, 6.1 Hz, 1H), 7.33 (dd, J = 8.3, 2.1 Hz, 1H), 6.95 (d, J = 8.3 Hz, 1H), 5.51 (s, 2H), 4.38 (s, 2H), 4.11 (s, 2H), 3.94 (d, J = 2.1 Hz, 2H), 2.90-2.77 (m, 2H), 2.69 (ddd, J = 12.3, 6.5, 3.7 Hz, 3H). |

TABLE 2-continued

Compounds

| Ex. | Structure | Procedure | ES/MS m/z | ¹H NMR |
|---|---|---|---|---|
| 407 | 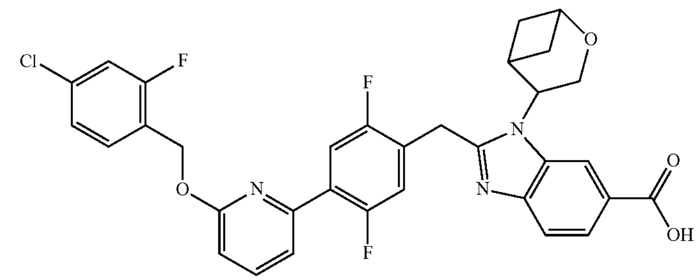 [SMILES: O=C(O)c1ccc2nc(Cc3cc(F)c(-c4cccc(OCc5ccc(Cl)cc5F)n4)cc3F)n(C3COC4CC3C4)c2c1] | 35 | 620.0 | 1H NMR (400 MHz, DMSO-d6) δ 8.71 (d, J = 1.4 Hz, 1H), 7.92-7.81 (m, 3H), 7.67-7.58 (m, 2H), 7.55-7.43 (m, 3H), 7.34 (dd, J = 8.2, 2.1 Hz, 1H), 6.96 (d, J = 8.3 Hz, 1H), 5.51 (s, 2H), 5.46 (q, J = 4.5, 3.8 Hz, 1H), 4.74-4.63 (m, 2H), 4.60-4.40 (m, 3H), 3.08 (p, J = 5.5 Hz, 1H), 2.36 (ddd, J = 11.0, 5.8, 3.6 Hz, 1H), 2.28 (dd, J = 10.9, 9.2 Hz, 1H), 2.13-2.04 (m, 1H), 2.00 (dd, J = 10.7, 9.2 Hz, 1H). |
| 408 | 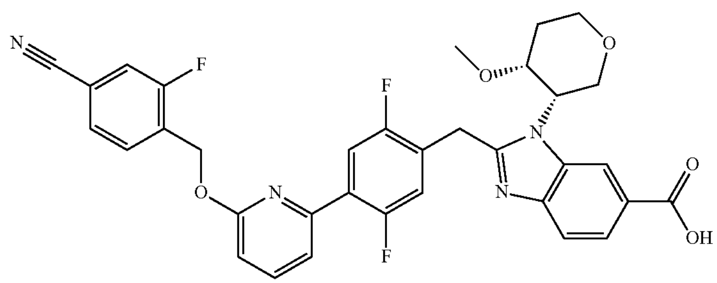 [SMILES: CO[C@@H]1CCOC[C@@H]1n1c(Cc2cc(F)c(-c3cccc(OCc4ccc(C#N)cc4F)n3)cc2F)nc2ccc(C(=O)O)cc21] | chiral separation Peak 2 | 629.3 | 1H NMR (400 MHz, DMSO-d6) δ 8.54 (s, 1H), 7.91 (t, J = 9.9 Hz, 2H), 7.85-7.68 (m, 4H), 7.61 (d, J = 8.4 Hz, 1H), 7.54 (d, J = 7.3 Hz, 1H), 7.40 (dd, J = 11.4, 6.0 Hz, 1H), 7.00 (d, J = 8.2 Hz, 1H), 5.61 (s, 2H), 4.87 (dd, J = 9.0, 4.7 Hz, 1H), 4.63 (d, J = 16.9 Hz, 1H), 4.59-4.46 (m, 2H), 3.90 (dd, J = 10.7, 4.6 Hz, 1H), 3.84-3.77 (m, 2H), 3.14 (s, 3H), 1.99 (q, J = 4.6, 4.0 Hz, 3H). |
| 409 | 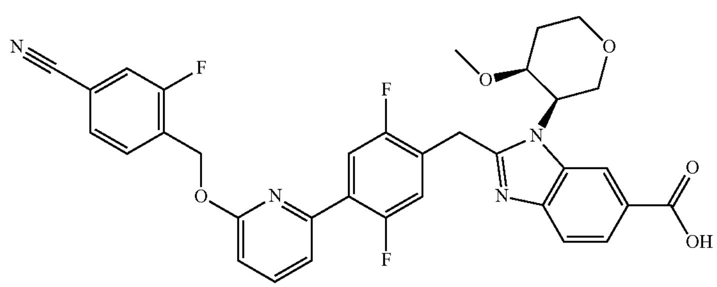 [SMILES: CO[C@H]1CCOC[C@H]1n1c(Cc2cc(F)c(-c3cccc(OCc4ccc(C#N)cc4F)n3)cc2F)nc2ccc(C(=O)O)cc21] | chiral separation Peak 1 | 629.3 | 1H NMR (400 MHz, DMSO-d6) δ 8.54 (s, 1H), 7.91 (t, J = 9.9 Hz, 2H), 7.85-7.68 (m, 4H), 7.61 (d, J = 8.4 Hz, 1H), 7.54 (d, J = 7.3 Hz, 1H), 7.40 (dd, J = 11.4, 6.0 Hz, 1H), 7.00 (d, J = 8.2 Hz, 1H), 5.61 (s, 2H), 4.87 (dd, J = 9.0, 4.7 Hz, 1H), 4.63 (d, J = 16.9 Hz, 1H), 4.59-4.46 (m, 2H), 3.90 (dd, J = 10.7, 4.6 Hz, 1H), 3.84-3.77 (m, 2H), 3.14 (s, 3H), 1.99 (q, J = 4.6, 4.0 Hz, 3H). |

TABLE 2-continued

Compounds

| Ex. | Structure | Procedure | ES/MS m/z | ¹H NMR |
|---|---|---|---|---|
| 410 | 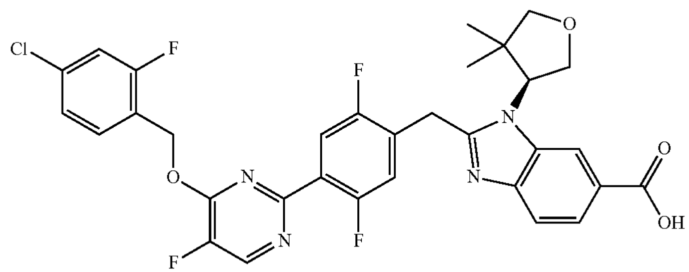 [SMILES: CC1(C)COC[C@H]1n1c(Cc2cc(F)c(-c3ncc(F)c(OCc4ccc(Cl)cc4F)n3)cc2F)nc2ccc(C(=O)O)cc21] | 35 | 641 | 1H NMR (400 MHz, DMSO-d6) δ 8.83 (d, J = 2.8 Hz, 1H), 8.50 (s, 1H), 7.90 (dd, J = 10.1, 6.2 Hz, 1H), 7.81 (dd, J = 8.4, 1.5 Hz, 1H), 7.65 (q, J = 8.3 Hz, 2H), 7.55 (dd, J = 10.0, 2.0 Hz, 1H), 7.49 (dd, J = 11.0, 6.0 Hz, 1H), 131 (dd, J = 8.3, 2.0 Hz, 1H), 5.67 (s, 2H), 5.02 (d, J = 6.6 Hz, 1H), 4.61-4.50 (m, 2H), 4.48-4.37 (m, 2H), 3.85-3.69 (m, 2H), 1.34 (s, 3H), 0.61 (s, 3H). |
| 411 | 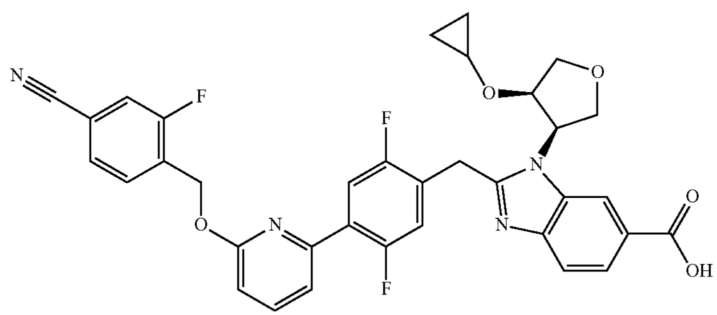 [SMILES: N#Cc1ccc(COc2cccc(-c3cc(F)c(Cc4nc5ccc(C(=O)O)cc5n4[C@@H]4COC[C@@H]4OC4CC4)cc3F)n2)c(F)c1] | 22 | 641 | 1H NMR (400 MHz, DMSO-d6) δ 8.39 (d, J = 1.5 Hz, 1H), 8.00-7.89 (m, 2H), 7.84-7.71 (m, 4H), 7.60 (d, J = 8.4 Hz, 1H), 7.53 (d, J = 7.2 Hz, 1H), 7.37 (dd, J = 11.5, 6.0 Hz, 1H), 7.00 (d, J = 8.3 Hz, 1H), 5.59 (d, J = 14.5 Hz, 3H), 4.50 (s, 2H), 4.40 (ddd, J = 13.3, 8.4, 4.9 Hz, 2H), 4.19-4.09 (m, 1H), 4.04 (dd, J = 10.4, 8.2 Hz, 1H), 3.87 (dd, J = 10.2, 4.6 Hz, 1H), 2.91 (tt, J = 5.9, 2.9 Hz, 1H), 0.22 (dd, J = 10.9, 5.2 Hz, 1H), 0.11 (ddd, J = 12.6, 9.1, 5.0 Hz, 2H), −0.04−−0.40 (m, 1H). |

TABLE 2-continued

Compounds

| Ex. | Structure | Procedure | ES/MS m/z | ¹H NMR |
|---|---|---|---|---|
| 412 | 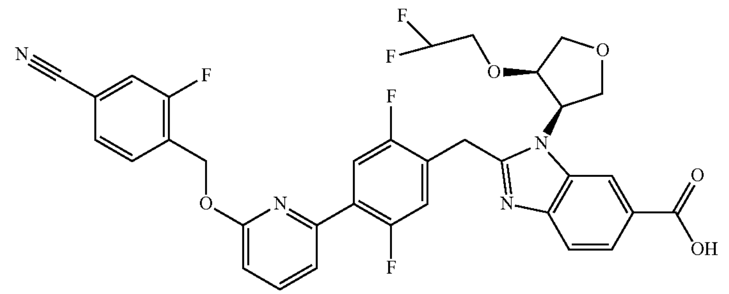 [SMILES: N#Cc1ccc(COc2cccc(-c3cc(F)c(Cc4nc5ccc(C(=O)O)cc5n4[C@@H]4COC[C@@H]4OCC(F)F)cc3F)n2)c(F)c1] | 22 | 665 | 1H NMR (400 MHz, DMSO-d6) δ 8.43 (s, 1H), 8.03-7.86 (m, 2H), 7.85-7.67 (m, 4H), 7.60 (d, J = 8.5 Hz, 1H), 7.53 (d, J = 7.3 Hz, 1H), 7.34 (dd, J = 11.5, 6.1Hz, 1H), 7.00 (d, J = 8.3 Hz, 1H), 5.87-5.45 (m, 3H), 4.54 (s, 2H), 4.51-4.41 (m, 2H), 4.14 (s, 0H), 4.05 (dd, J = 10.5, 8.3 Hz, 1H), 3.93-3.83 (m, 2H), 3.62-3.43 (m, 1H), 3.24-2.99 (m, 1H). |
| 413 | 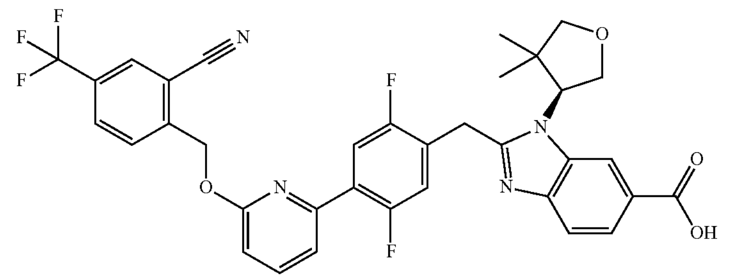 [SMILES: CC1(C)COC[C@H]1n1c(Cc2cc(F)c(-c3cccc(OCc4ccc(C(F)(F)F)cc4C#N)n3)cc2F)nc2ccc(C(=O)O)cc21] | 27 | 663 | 1H NMR (400 MHz, DMSO-d6) δ 8.49 (s, 1H), 8.43 (d, J = 1.9 Hz, 1H), 8.12 (dd, J = 8.3, 1.9 Hz, 1H), 7.99-7.88 (m, 2H), 7.81 (dd, J = 8.5, 1.5 Hz, 1H), 7.72 (dd, J = 10.4, 6.4 Hz, 1H), 7.63 (d, J = 8.5 Hz, 1H), 7.57 (dd, J = 7.5, 1.6 Hz, 1H), 7.46 (dd, J = 11.4, 6.0 Hz, 1H), 7.04 (d, J = 8.3 Hz, 1H), 5.75 (s, 2H), 5.02 (d, J = 6.7 Hz, 1H), 4.59-4.50 (m, 2H), 4.48-4.35 (m, 2H), 3.83-3.67 (m, 2H), 1.33 (s, 3H), 0.60 (s, 3H). |
| 414 | 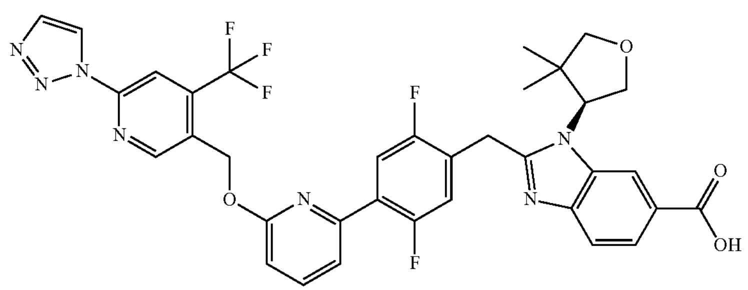 [SMILES: CC1(C)COC[C@H]1n1c(Cc2cc(F)c(-c3cccc(OCc4cnc(-n5ccnn5)cc4C(F)(F)F)n3)cc2F)nc2ccc(C(=O)O)cc21] | 27 | 706 | 1H NMR (400 MHz, DMSO-d6) δ 9.04 (s, 1H), 8.97 (d, J = 1.3 Hz, 1H), 8.50 (s, 1H), 8.41 (s, 1H), 8.06 (d, J = 1.2 Hz, 1H), 7.93 (t, J = 7.9 Hz, 1H), 7.87-7.76 (m, 2H), 7.63 (d, J = 8.4 Hz, 1H), 7.57 (dd, J = 7.5, 1.6 Hz, 1H), 7.47 (dd, J = 11.4, 6.1 Hz, 1H), 7.02 (d, J = 8.3 Hz, 1H), 5.77 (s, 2H), 5.02 (d, J = 6.7 Hz, 1H), 4.55 (d, J = 17.2 Hz, 2H), 4.49-4.35 (m, 2H), 3.88-3.58 (m, 2H), 1.32 (s, 3H), 0.60 (s, 3H). |

TABLE 2-continued

Compounds

| Ex. | Structure | Procedure | ES/MS m/z | ¹H NMR |
|---|---|---|---|---|
| 415 | 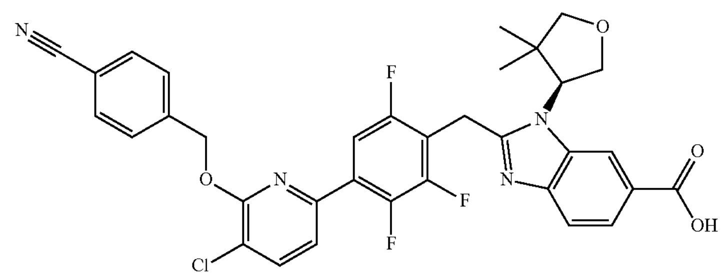 [SMILES: CC1(C)COC[C@H]1n1c(Cc2c(F)cc(-c3ccc(Cl)c(OCc4ccc(C#N)cc4)n3)c(F)c2F)nc2ccc(C(=O)O)cc21] | 35 | 647 | 1H NMR (400 MHz, DMSO-d6) δ 8.48 (s, 1H), 8.14 (d, J = 8.1 Hz, 1H), 7.92-7.85 (m, 2H), 7.78 (dd, J = 8.4, 1.5 Hz, 1H), 7.75-7.64 (m, 3H), 7.64-7.54 (m, 2H), 5.69 (s, 2H), 5.08 (d, J = 6.6 Hz, 1H), 4.70-4.54 (m, 2H), 4.47 (dd, J = 11.1, 6.7 Hz, 1H), 4.35 (d, J = 17.3 Hz, 1H), 3.83-3.71 (m, 2H), 1.39 (s, 3H), 0.65 (s, 3H). |
| 416 | 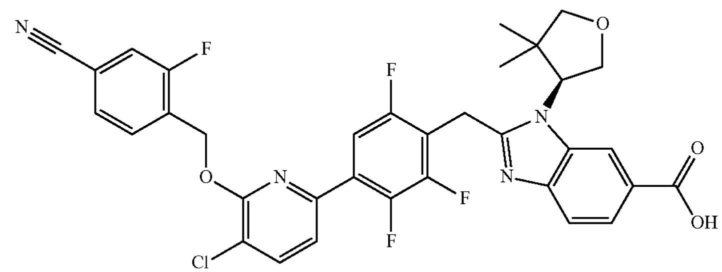 [SMILES: CC1(C)COC[C@H]1n1c(Cc2c(F)cc(-c3ccc(Cl)c(OCc4ccc(C#N)cc4F)n3)c(F)c2F)nc2ccc(C(=O)O)cc21] | 35 | 665 | 1H NMR (400 MHz, DMSO-d6) δ 8.48 (s, 1H), 8.15 (d, J = 8.0 Hz, 1H), 7.95 (d, J = 10.0 Hz, 1H), 7.77 (dd, J = 5.8, 2.7 Hz, 3H), 7.71 (dd, J = 10.6, 5.4 Hz, 1H), 7.63 (d, J = 8.0 Hz, 1H), 7.59 (d, J = 8.5 Hz, 1H), 5.72 (s, 2H), 5.09 (d, J = 6.5 Hz, 1H), 4.65 (d, J = 17.3 Hz, 1H), 4.57 (d, J = 11.1 Hz, 1H), 4.47 (dd, J = 11.1, 6.8 Hz, 1H), 4.35 (d, J = 17.2 Hz, 1H), 3.85-3.75 (m, 2H), 1.39 (s, 3H), 0.66 (s, 3H). |
| 417 | 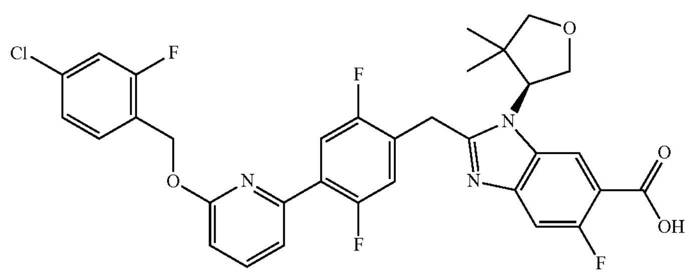 [SMILES: CC1(C)COC[C@H]1n1c(Cc2cc(F)c(-c3cccc(OCc4ccc(Cl)cc4F)n3)cc2F)nc2cc(F)c(C(=O)O)cc21] | 35 | 640 | 1H NMR (400 MHz, DMSO-d6) δ 8.38 (d, J = 6.5 Hz, 1H), 7.89 (t, J = 7.8 Hz, 1H), 7.83 (dd, J = 9.8, 7.0 Hz, 1H), 7.62 (d, J = 8.2 Hz, 1H), 7.56-7.47 (m, 3H), 7.47-7.42 (m, 1H), 7.33 (dd, J = 8.2, 2.0 Hz, 1H), 6.96 (d, J = 8.3 Hz, 1H), 5.51 (s, 2H), 5.00 (d, J = 6.5 Hz, 1H), 4.52 (d, J = 17.4 Hz, 2H), 4.47-4.30 (m, 2H), 3.82-3.67 (m, 3H), 1.34 (s, 3H), 0.61 (s, 3H). |

TABLE 2-continued

Compounds

| Ex. | Structure | Procedure | ES/MS m/z | ¹H NMR |
|---|---|---|---|---|
| 418 | 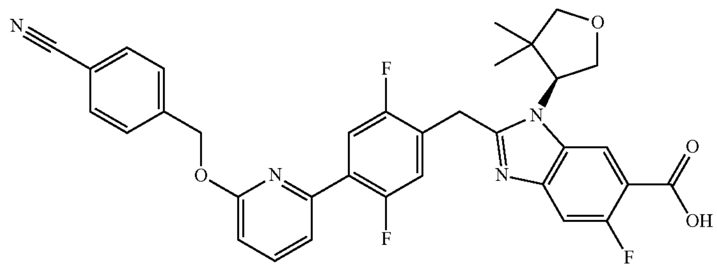 [SMILES: CC1(C)COC[C@H]1n1c(Cc2cc(F)c(-c3cccc(OCc4ccc(C#N)cc4)n3)cc2F)nc2cc(F)c(C(=O)O)cc21] | 35 | 613 | 1H NMR (400 MHz, DMSO-d6) δ 8.38 (d, J = 6.5 Hz, 1H), 7.96-7.83 (m, 3H), 7.77-7.65 (m, 3H), 7.53 (d, J = 7.4 Hz, 1H), 7.45 (dd, J = 10.2, 7.0 Hz, 2H), 7.01 (d, J = 8.2 Hz, 1H), 5.58 (s, 2H), 5.00 (d, J = 6.5 Hz, 1H), 4.51 (d, J = 15.7 Hz, 2H), 4.47-4.30 (m, 2H), 3.81-3.69 (m, 2H), 1.33 (s, 3H), 0.61 (s, 3H). |
| 419 | 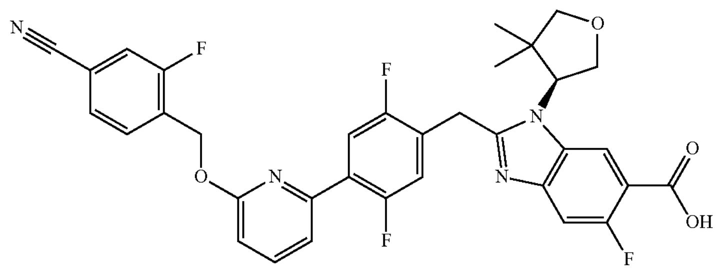 [SMILES: CC1(C)COC[C@H]1n1c(Cc2cc(F)c(-c3cccc(OCc4ccc(C#N)cc4F)n3)cc2F)nc2cc(F)c(C(=O)O)cc21] | 35 | 631 | 1H NMR (400 MHz, DMSO-d6) δ 8.38 (d, J = 6.4 Hz, 1H), 7.98-7.85 (m, 2H), 7.83-7.69 (m, 3H), 7.54 (d, J = 7.3 Hz, 1H), 7.46 (dd, J = 10.8, 7.4 Hz, 2H), 7.00 (d, J = 8.3 Hz, 1H), 5.61 (s, 2H), 5.00 (d, J = 6.5 Hz, 1H), 4.52 (d, J = 17.0 Hz, 2H), 4.47-4.31 (m, 2H), 1.33 (s, 3H), 0.61 (s, 3H). |
| 420 | 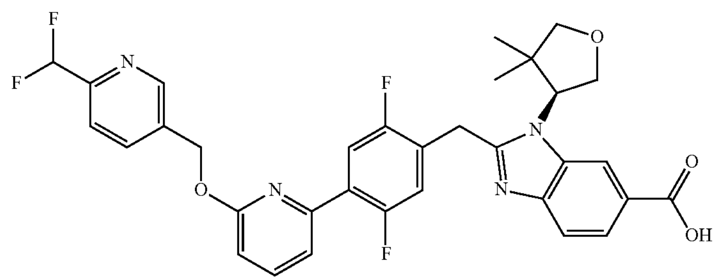 [SMILES: CC1(C)COC[C@H]1n1c(Cc2cc(F)c(-c3cccc(OCc4ccc(C(F)F)nc4)n3)cc2F)nc2ccc(C(=O)O)cc21] | 27 | 621 | 1H NMR (400 MHz, DMSO-d6) δ 8.83 (d, J = 2.0 Hz, 1H), 8.50 (s, 1H), 8.12 (dd, J = 8.1, 2.0 Hz, 1H), 7.91 (t, J = 7.9 Hz, 1H), 7.88-7.78 (m, 2H), 7.74 (d, J = 8.0 Hz, 1H), 7.63 (d, J = 8.5 Hz, 1H), 7.55 (d, J = 7.3 Hz, 1H), 7.47 (dd, J = 10.9, 6.6 Hz, 1H), 7.16-6.78 (m, 2H), 5.61 (s, 2H), 5.03 (d, J = 6.7 Hz, 1H), 4.55 (d, J = 16.8 Hz, 2H), 4.50-4.32 (m, 2H), 3.95-3.65 (m, 2H), 1.34 (s, 3H), 0.61 (s, 3H). |

TABLE 2-continued

Compounds

| Ex. | Structure | Procedure | ES/MS m/z | ¹H NMR |
|---|---|---|---|---|
| 421 | 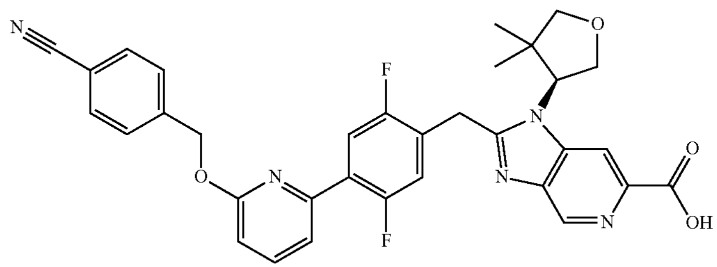 [SMILES: CC1(C)COC[C@H]1n1c(Cc2cc(F)c(-c3cccc(OCc4ccc(C#N)cc4)n3)cc2F)nc2cnc(C(=O)O)cc21] | 35 | 596 | 1H NMR (400 MHz, DMSO-d6) δ 9.03 (s, 1H), 8.62 (s, 1H), 7.97-7.83 (m, 3H), 7.75 (dd, J = 10.2, 6.5 Hz, 1H), 7.69 (d, J = 8.1 Hz, 2H), 7.54 (d, J = 7.3 Hz, 1H), 7.50 (dd, J = 11.2, 6.3 Hz, 1H), 7.02 (d, J = 8.3 Hz, 1H), 5.59 (s, 2H), 5.09 (d, J = 6.3 Hz, 1H), 4.62 (d, J = 17.3 Hz, 1H), 4.54 (d, J = 11.2 Hz, 1H), 4.49-4.37 (m, 2H), 3.80-3.71 (m, 2H), 1.37 (s, 3H), 0.63 (s, 3H). |
| 422 | 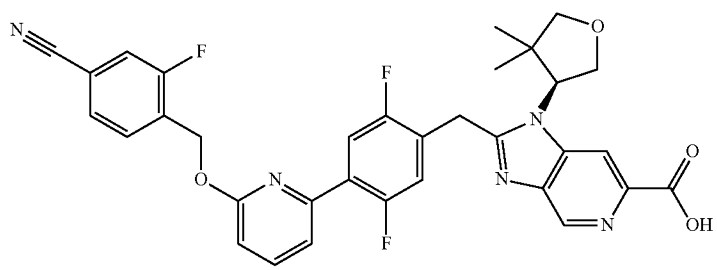 [SMILES: CC1(C)COC[C@H]1n1c(Cc2cc(F)c(-c3cccc(OCc4ccc(C#N)cc4F)n3)cc2F)nc2cnc(C(=O)O)cc21] | 35 | 614 | 1H NMR (400 MHz, DMSO-d6) δ 9.02 (s, 1H), 8.61 (s, 1H), 7.98-7.88 (m, 2H), 7.84-7.71 (m, 3H), 7.55 (d, J = 7.4 Hz, 1H), 7.50 (dd, J = 11.0, 6.4 Hz, 1H), 7.01 (d, J = 8.2 Hz, 1H), 5.61 (s, 2H), 5.09 (d, J = 6.1 Hz, 1H), 4.62 (d, J = 17.3 Hz, 1H), 4.54 (d, J = 11.2 Hz, 1H), 4.50-4.36 (m, 2H), 3.80-3.74 (m, 2H), 1.37 (s, 3H), 0.63 (s, 3H). |
| 423 | 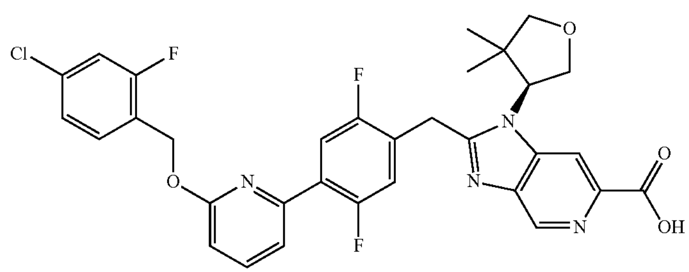 [SMILES: CC1(C)COC[C@H]1n1c(Cc2cc(F)c(-c3cccc(OCc4ccc(Cl)cc4F)n3)cc2F)nc2cnc(C(=O)O)cc21] | 35 | 623 | 1H NMR (400 MHz, DMSO-d6) δ 9.01 (s, 1H), 8.61 (s, 1H), 7.96-7.80 (m, 2H), 7.61 (t, J = 8.2 Hz, 1H), 7.58-7.45 (m, 3H), 7.34 (dd, J = 8.2, 1.9 Hz, 1H), 6.97 (d, J = 8.2 Hz, 1H), 5.52 (s, 2H), 5.09 (d, J = 6.2 Hz, 1H), 4.62 (d, J = 17.1 Hz, 1H), 4.54 (d, J = 11.2 Hz, 1H), 4.50-4.38 (m, 2H), 3.79-3.73 (m, 2H), 1.37 (s, 3H), 0.63 (s, 3H). |

TABLE 2-continued

| Ex. | Structure | Procedure | ES/MS m/z | $^1$H NMR |
|---|---|---|---|---|
| 424 | 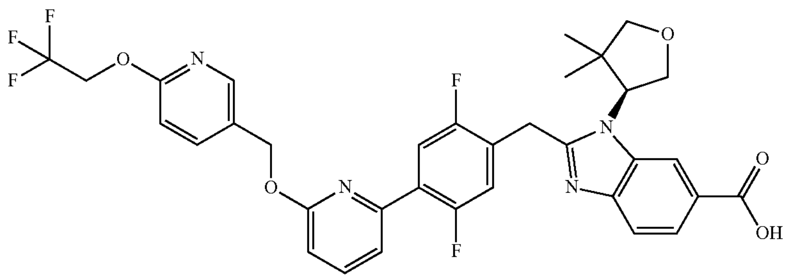 [SMILES: CC1(C)COC[C@H]1n1c(Cc2cc(F)c(-c3cccc(OCc4ccc(OCC(F)(F)F)nc4)n3)cc2F)nc2ccc(C(=O)O)cc21] | 27 | 669 | 1H NMR (400 MHz, DMSO-d6) δ 8.49 (s, 1H), 8.36 (d, J = 2.2 Hz, 1H), 7.95 (dd, J = 8.5, 2.4 Hz, 1H), 7.88 (td, J = 8.9, 7.9, 4.5 Hz, 2H), 7.84-7.77 (m, 1H), 7.62 (d, J = 8.5 Hz, 1H), 7.53 (d, J = 7.3 Hz, 1H), 7.47 (dd, J = 10.8, 6.8 Hz, 1H), 7.02 (d, J = 8.5 Hz, 1H), 6.93 (d, J = 8.2 Hz, 1H), 5.47 (s, 2H), 5.00 (q, J = 8.8 Hz, 3H), 4.60-4.48 (m, 2H), 4.48-4.32 (m, 2H), 3.83-3.71 (m, 2H), 1.34 (s, 3H), 0.61 (s, 3H). |
| 425 | 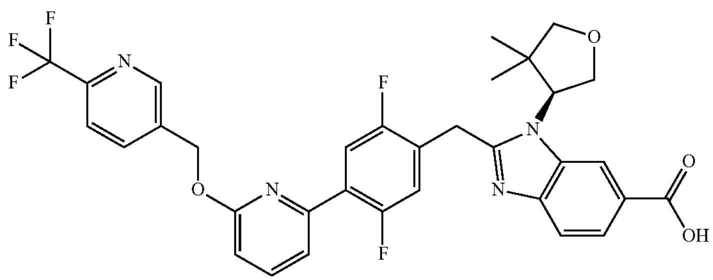 [SMILES: CC1(C)COC[C@H]1n1c(Cc2cc(F)c(-c3cccc(OCc4ccc(C(F)(F)F)nc4)n3)cc2F)nc2ccc(C(=O)O)cc21] | 27 | 639 | 1H NMR (400 MHz, DMSO-d6) δ 8.92 (d, J = 2.0 Hz, 1H), 8.49 (s, 1H), 8.20 (d, J = 8.1 Hz, 1H), 7.93 (dd, J = 17.1, 8.2 Hz, 2H), 7.79 (dd, J = 9.3, 7.5 Hz, 2H), 7.62 (d, J = 8.5 Hz, 1H), 7.55 (d, J = 7.4 Hz, 1H), 7.46 (dd, J = 10.7, 6.8 Hz, 1H), 7.02 (d, J = 8.3 Hz, 1H), 5.65 (s, 2H), 5.02 (d, J = 6.7 Hz, 1H), 4.58-4.49 (m, 2H), 4.49-4.30 (m, 2H), 3.85-3.71 (m, 2H), 1.33 (s, 3H), 0.60 (s, 3H). |
| 426 | 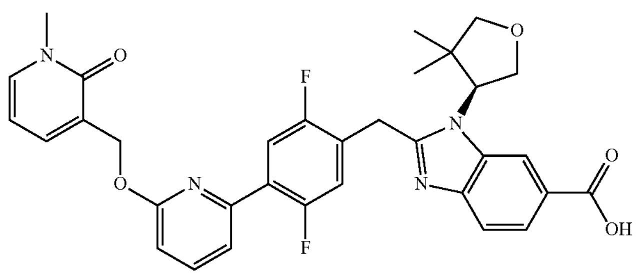 [SMILES: Cn1cccc(COc2cccc(-c3cc(F)c(Cc4nc5ccc(C(=O)O)cc5n4[C@@H]4COCC4(C)C)cc3F)n2)c1=O] | 35 | 601.0 | 1H NMR (400 MHz, DMSO-d6) δ 8.50 (s, 1H), 7.92-7.79 (m, 3H), 7.71 (dd, J = 6.8, 2.0 Hz, 1H), 7.65 (d, J = 8.4 Hz, 1H), 7.57-7.50 (m, 2H), 7.46 (dd, J = 11.3, 6.1 Hz, 1H), 6.95 (d, J = 8.3 Hz, 1H), 6.25 (t, J = 6.8 Hz, 1H), 5.29 (s, 2H), 5.03 (d, J = 6.6 Hz, 1H), 4.61-4.52 (m, 2H), 4.48-4.36 (m, 2H), 3.86-3.68 (m, 2H), 3.48 (s, 3H), 1.34 (s, 3H), 0.61 (d, J = 3.4 Hz, 3H). |

TABLE 2-continued

Compounds

| Ex. | Structure | Procedure | ES/MS m/z | ¹H NMR |
|---|---|---|---|---|
| 427 | 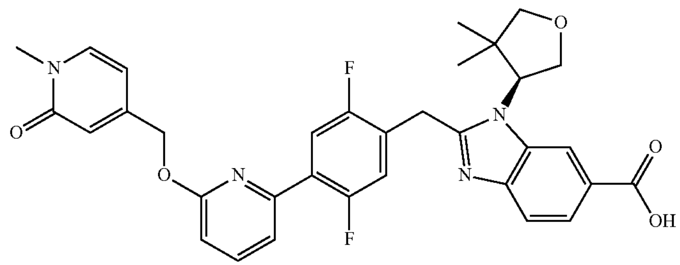 [SMILES: Cn1ccc(COc2cccc(-c3cc(F)c(Cc4nc5ccc(C(=O)O)cc5n4[C@@H]4COCC4(C)C)cc3F)n2)cc1=O] | 35 | 601.0 | 1H NMR (400 MHz, DMSO-d6) δ 8.50 (s, 1H), 7.91 (t, J = 7.9 Hz, 1H), 7.80 (dd, J = 9.3, 7.8 Hz, 2H), 7.68 (d, J = 7.0 Hz, 1H), 7.63 (d, J = 8.5 Hz, 1H), 7.54 (d, J = 7.4 Hz, 1H), 7.46 (dd, J = 10.1, 7.4 Hz, 1H), 7.02 (d, J = 8.3 Hz, 1H), 6.42 (s, 1H), 6.29 (dd, J = 7.0, 1.8 Hz, 1H), 5.34 (s, 2H), 5.02 (d, J = 6.7 Hz, 1H), 4.58-4.50 (m, 2H), 4.48-4.35 (m, 2H), 3.85-3.66 (m, 2H), 3.40 (s, 3H), 1.34 (s, 3H), 0.61 (s, 3H) |
| 428 | 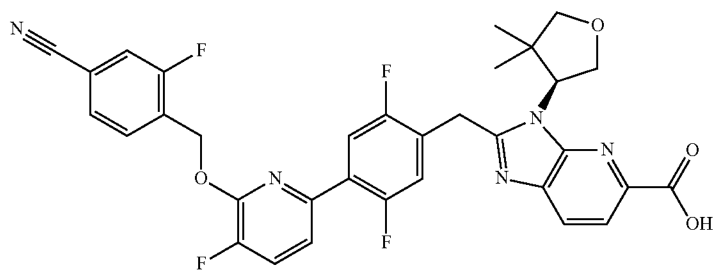 | 35 | 632.0 | 1H NMR (400 MHz, DMSO-d6) δ 8.09 (d, J = 8.3 Hz, 1H), 7.95 (dd, J = 9.3, 7.6 Hz, 2H), 7.88 (dd, J = 10.2, 8.2 Hz, 1H), 7.81-7.70 (m, 3H), 7.59-7.53 (m, 1H), 7.47 (dd, J = 11.4, 6.1 Hz, 1H), 5.70 (s, 2H), 4.96 (dd, J = 8.5, 5.3 Hz, 1H), 4.74 (dd, J = 9.6, 5.2 Hz, 1H), 4.65-4.44 (m, 2H), 4.37 (dt, J = 8.9, 5.1 Hz, 2H), 3.63 (d, J = 7.9 Hz, 1H), 1.24 (s, 3H), 0.62 (s, 3H). |
| 429 | 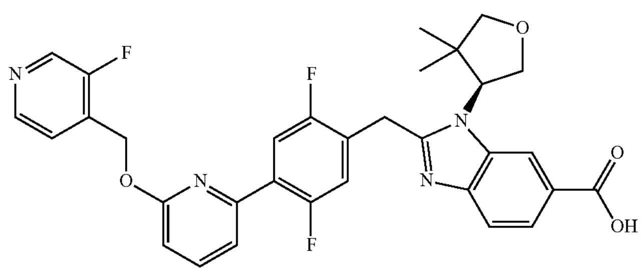 [SMILES: CC1(C)COC[C@H]1n1c(Cc2cc(F)c(-c3cccc(OCc4ccncc4F)n3)cc2F)nc2ccc(C(=O)O)cc21] | 35 | 589.0 | .1H NMR (400 MHz, DMSO-d6) δ 8.61 (d, J = 1.7 Hz, 1H), 8.50 (s, 1H), 8.45 (d, J = 4.9 Hz, 1H), 7.92 (t, J = 7.9 Hz, 1H), 7.82 (dd, J = 8.4, 1.4 Hz, 1H), 7.74 (dd, J = 10.5, 6.4 Hz, 1H), 7.64 (d, J = 8.5 Hz, 1H), 7.61-7.53 (m, 2H), 7.46 (dd, J = 11.4, 6.1 Hz, 1H), 7.03 (d, J = 8.2 Hz, 1H), 5.62 (s, 2H), 5.03 (d, J = 6.7 Hz, 1H), 4.55 (d, J = -16.4 Hz, 2H), 4.51-4.35 (m, 2H), 3.83-3.71 (m, 2H), 1.33 (s, 3H), 0.61 (s, 3H). |

TABLE 2-continued

Compounds

| Ex. | Structure | Procedure | ES/MS m/z | ¹H NMR |
|---|---|---|---|---|
| 430 | 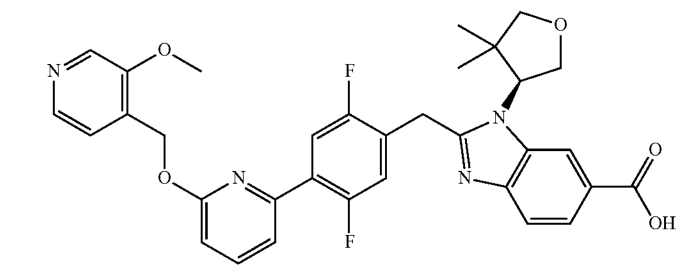 [SMILES: COc1cnccc1COc1cccc(-c2cc(F)c(Cc3nc4ccc(C(=O)O)cc4n3[C@@H]3COCC3(C)C)cc2F)n1] | 35 | 601.1 | 1H NMR (400 MHz, DMSO-d6) δ 8.61 (s, 1H), 8.49 (s, 1H), 8.44 (d, J = 5.3 Hz, 1H), 7.94 (t, J = 7.9 Hz, 1H), 7.81 (dd, J = 8.5, 1.4 Hz, 1H), 7.75 (d, J = 5.4 Hz, 1H), 7.67 (t, J = 8.4 Hz, 1H), 7.62 (d, J = 8.4 Hz, 1H), 7.56 (d, J = 7.4 Hz, 1H), 7.46 (t, J = 8.7 Hz, 1H), 7.09 (d, J = 8.3 Hz, 1H), 5.63 (s, 2H), 5.02 (d, J = 6.6 Hz, 1H), 4.60-4.48 (m, 2H), 4.48-4.31 (m, 2H), 4.05 (s, 3H), 3.87-3.65 (m, 2H), 1.33 (s, 3H), 0.61 (s, 3H). |
| 431 | 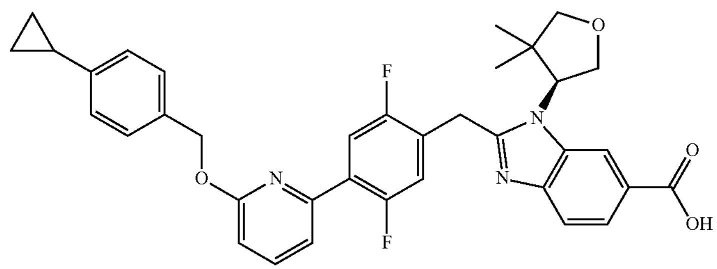 [SMILES: CC1(C)COC[C@H]1n1c(Cc2cc(F)c(-c3cccc(OCc4ccc(C5CC5)cc4)n3)cc2F)nc2ccc(C(=O)O)cc21] | 35 | 610.0 | 1H NMR (400 MHz, DMSO-d6) δ 8.50 (s, 1H), 7.94-7.75 (m, 3H), 7.64 (d, J = 8.4 Hz, 1H), 7.58-7.41 (m, 2H), 7.36 (d, J = 7.8 Hz, 2H), 7.09 (d, J = 7.8 Hz, 2H), 6.92 (d, J = 8.2 Hz, 1H), 5.41 (s, 2H), 5.03 (d, J = 6.7 Hz, 1H), 4.55 (d, J = 16.6 Hz, 2H), 4.50-4.33 (m, 2H), 3.86-3.67 (m, 2H), 1.91 (tt, J = 8.7, 5.0 Hz, 1H), 1.34 (s, 3H), 0.99-0.85 (m, 2H), 0.66 (dt, J = 6.5, 4.6 Hz, 2H), 0.61 (s, 3H). |

TABLE 2-continued

Compounds

| Ex. | Structure | Procedure | ES/MS m/z | ¹H NMR |
|---|---|---|---|---|
| 432 | 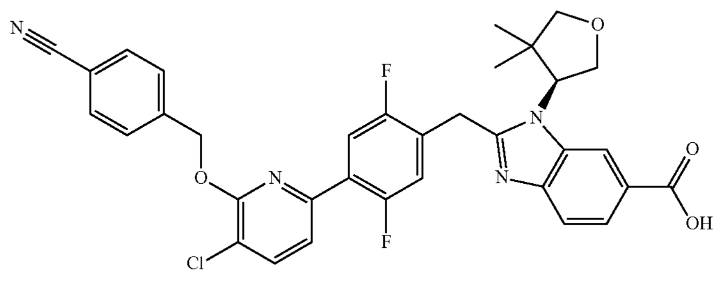 | 35 | 629.0 | 1H NMR (400 MHz, DMSO-d6) δ 8.49 (s, 1H), 8.09 (d, J = 8.0 Hz, 1H), 7.90 (d, J = 8.2 Hz, 2H), 7.82-7.74 (m, 2H), 7.70 (d, J = 8.0 Hz, 2H), 7.62 (d, J = 8.4 Hz, 1H), 7.48 (dd, J = 11.4, 6.1 Hz, 1H), 5.69 (s, 2H), 5.02 (d, J = 6.6 Hz, 1H), 4.59-4.51 (m, 2H), 4.51-4.34 (m, 2H), 3.82-3.67 (m, 2H), 1.34 (s, 3H), 0.61 (s, 3H). |
| 433 | 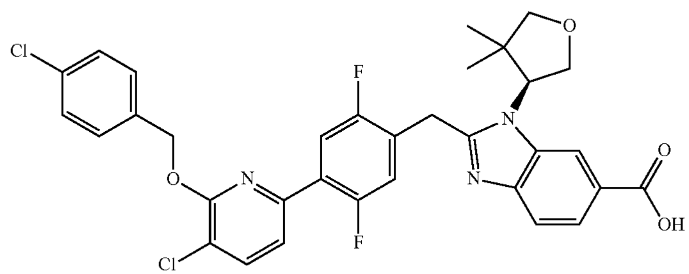 [SMILES: CC1(C)COC[C@H]1n1c(Cc2cc(F)c(-c3ccc(Cl)c(OCc4ccc(Cl)cc4)n3)cc2F)nc2ccc(C(=O)O)cc21] | 35 | 638.0 | 1H NMR (400 MHz, DMSO-d6) δ 8.49 (s, 1H), 8.07 (d, J = 8.0 Hz, 1H), 7.88-7.78 (m, 2H), 7.62 (d, J = 8.5 Hz, 1H), 7.58-7.51 (m, 3H), 7.51-7.41 (m, 3H), 5.58 (s, 2H), 5.02 (d, J = 6.6 Hz, 1H), 4.57-4.50 (m, 2H), 4.49-4.33 (m, 2H), 3.83-3.68 (m, 2H), 1.34 (s, 3H), 0.61 (s, 3H). |
| 434 | 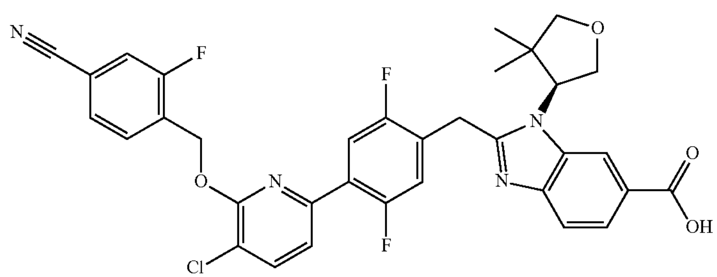 [SMILES: CC1(C)COC[C@H]1n1c(Cc2cc(F)c(-c3ccc(Cl)c(OCc4ccc(C#N)cc4F)n3)cc2F)nc2ccc(C(=O)O)cc21] | 35 | 647.0 | 1H NMR (400 MHz, DMSO-d6) δ 8.49 (s, 1H), 8.10 (d, J = 8.0 Hz, 1H), 7.95 (d, J = 10.0 Hz, 1H), 7.83-7.74 (m, 4H), 7.62 (d, J = 8.5 Hz, 1H), 7.58 (dd, J = 8.1, 1.4 Hz, 1H), 7.48 (dd, J = 11.4, 6.1 Hz, 1H), 5.71 (s, 2H), 5.02 (d, J = 6.6 Hz, 1H), 4.59-4.49 (m, 2H), 4.48-4.34 (m, 2H), 3.83-3.68 (m, 2H), 1.34 (s, 3H), 0.61 (s, 3H). |

TABLE 2-continued

Compounds

| Ex. | Structure | Procedure | ES/MS m/z | ¹H NMR |
|---|---|---|---|---|
| 435 | | chiral separation Peak 2 | 615.0 | 1H NMR (400 MHz, DMSO-d6) δ 8.55 (s, 1H), 7.98-7.85 (m, 2H), 7.85-7.70 (m, 4H), 7.61 (d, J = 8.4 Hz, 1H), 7.54 (d, J = 7.3 Hz, 1H), 7.37 (dd, J = 11.5, 6.0 Hz, 1H), 7.00 (d, J = 8.3 Hz, 1H), 5.61 (s, 2H), 5.53 (d, J = 7.6 Hz, 1H), 4.55 (s, 2H), 4.50 (d, J = 10.8 Hz, 1H), 4.21 (dd, J = 10.9, 6.5 Hz, 1H), 4.06 (t, J = 8.7 Hz, 1H), 3.80 (t, J = 8.3 Hz, 1H), 3.18-3.09 (m, 1H), 3.00 (q, J = 7.8 Hz, 1H), 2.75 (t, J = 9.5 Hz, 1H). |
| 436 | | chiral separation Peak 1 | 615.0 | 1H NMR (400 MHz, DMSO-d6) δ 8.55 (s, 1H), 7.98-7.85 (m, 2H), 7.85-7.70 (m, 4H), 7.61 (d, J = 8.4 Hz, 1H), 7.54 (d, J = 7.3 Hz, 1H), 7.37 (dd, J = 11.5, 6.0 Hz, 1H), 7.00 (d, J = 8.3 Hz, 1H), 5.61 (s, 2H), 5.53 (d, J = 7.6 Hz, 1H), 4.55 (s, 2H), 4.50 (d, J = 10.8 Hz, 1H), 4.21 (dd, J = 10.9, 6.5 Hz, 1H), 4.06 (t, J = 8.7 Hz, 1H), 3.80 (t, J = 8.3 Hz, 1H), 3.18-3.09 (m, 1H), 3.00 (q, J = 7.8 Hz, 1H), 2.75 (t, J = 9.5 Hz, 1H). |
| 437 | | 35 | 623.0 | 1H NMR (400 MHz, DMSO-d6) δ 8.10 (d, J = 8.3 Hz, 1H), 7.96 (d, J = 8.3 Hz, 1H), 7.92-7.80 (m, 2H), 7.60 (t, J = 8.2 Hz, 1H), 7.57-7.44 (m, 3H), 7.33 (dd, J = 8.2, 2.0 Hz, 1H), 6.96 (d, J = 8.3 Hz, 1H), 5.51 (s, 2H), 4.97 (dd, J = 8.4, 5.3 Hz, 1H), 4.74 (dd, J = 9.6, 5.2 Hz, 1H), 4.64-4.47 (m, 2H), 4.37 (dt, J = 8.9, 5.1 Hz, 2H), 3.63 (d, J = 7.9 Hz, 1H), 1.24 (s, 3H), 0.62 (s, 3H). |

TABLE 2-continued

Compounds

| Ex. | Structure | Procedure | ES/MS m/z | ¹H NMR |
|---|---|---|---|---|
| 438 | 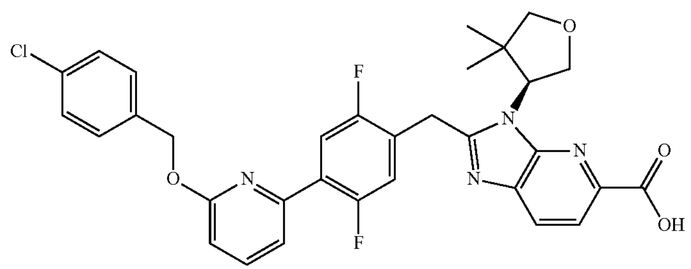 [SMILES: CC1(C)COC[C@H]1n1c(Cc2cc(F)c(-c3cccc(OCc4ccc(Cl)cc4)n3)cc2F)nc2ccc(C(=O)O)nc21] | 35 | 605.0 | 1H NMR (400 MHz, DMSO-d6) δ 8.09 (d, J = 8.3 Hz, 1H), 7.96 (d, J = 8.3 Hz, 1H), 7.88 (t, J = 7.9 Hz, 1H), 7.82 (dd, J = 10.3, 6.6 Hz, 1H), 7.58-7.40 (m, 6H), 6.96 (d, J = 8.3 Hz, 1H), 5.47 (s, 2H), 4.97 (dd, J = 8.4, 5.3 Hz, 1H), 4.75 (dd, J = 9.6, 5.2 Hz, 1H), 4.65-4.45 (m, 2H), 4.37 (dt, J = 8.9, 5.1 Hz, 2H), 3.63 (d, J = 7.9 Hz, 1H), 1.24 (s, 3H), 0.63 (s, 3H). |
| 439 | 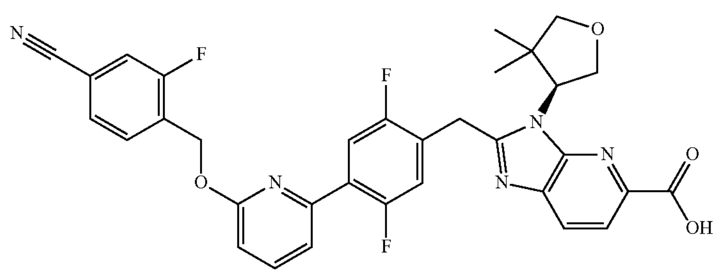 [SMILES: CC1(C)COC[C@H]1n1c(Cc2cc(F)c(-c3cccc(OCc4ccc(C#N)cc4F)n3)cc2F)nc2ccc(C(=O)O)nc21] | 35 | 614.0 | 1H NMR (400 MHz, DMSO-d6) δ 8.09 (d, J = 8.3 Hz, 1H), 8.00-7.85 (m, 3H), 7.84-7.68 (m, 3H), 7.58-7.52 (m, 1H), 7.46 (dd, J = 11.3, 6.2 Hz, 1H), 7.00 (d, J = 8.3 Hz, 1H), 5.61 (s, 2H), 4.96 (dd, J = 8.4, 5.3 Hz, 1H), 4.74 (dd, J = 9.6, 5.1 Hz, 1H), 4.64-4.46 (m, 2H), 4.37 (dt, J = 8.9, 5.1 Hz, 2H), 3.63 (d, J = 7.9 Hz, 1H), 1.23 (s, 3H), 0.62 (s, 3H). |
| 440 | 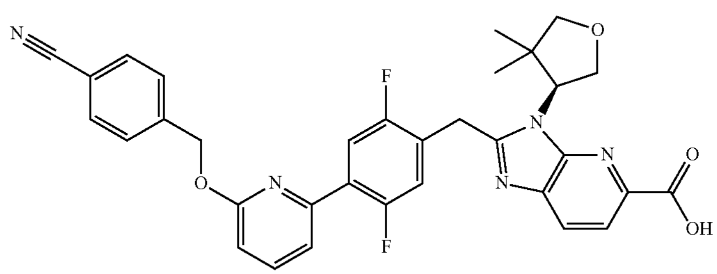 [SMILES: CC1(C)COC[C@H]1n1c(Cc2cc(F)c(-c3cccc(OCc4ccc(C#N)cc4)n3)cc2F)nc2ccc(C(=O)O)nc21] | 35 | 596.0 | 1H NMR (400 MHz, DMSO-d6) δ 8.09 (d, J = 8.3 Hz, 1H), 7.96 (d, J = 8.3 Hz, 1H), 7.93-7.83 (m, 3H), 7.74 (dd, J = 10.2, 6.6 Hz, 1H), 7.68 (d, J = 8.0 Hz, 2H), 7.58-7.51 (m, 1H), 7.46 (dd, J = 11.2, 6.3 Hz, 1H), 7.01 (d, J = 8.3 Hz, 1H), 5.58 (s, 2H), 4.96 (dd, J = 8.5, 5.2 Hz, 1H), 4.74 (dd, J = 9.6, 5.1 Hz, 1H), 4.64-4.44 (m, 2H), 4.37 (dt, J = 9.0, 5.1 Hz, 2H), 3.63 (d, J = 7.9 Hz, 1H), 1.24 (s, 3H), 0.62 (s, 3H). |

TABLE 2-continued

Compounds

| Ex. | Structure | Procedure | ES/MS m/z | ¹H NMR |
|---|---|---|---|---|
| 441 | 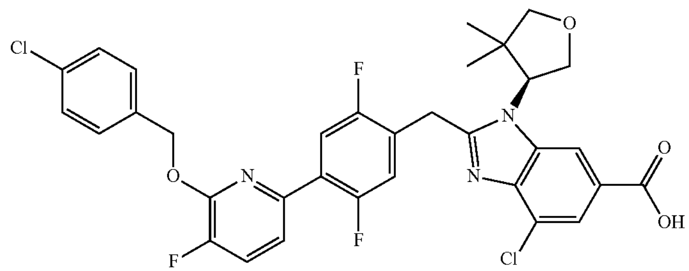 [SMILES: CC1(C)COC[C@H]1n1c(Cc2cc(F)c(-c3ccc(F)c(OCc4ccc(Cl)cc4)n3)cc2F)nc2c(Cl)cc(C(=O)O)cc21] | 35 | 656.0 | 1H NMR (400 MHz, DMSO-d6) δ 8.47 (s, 1H), 7.96-7.74 (m, 3H), 7.55 (d, J = 8.3 Hz, 3H), 7.51-7.39 (m, 3H), 5.57 (s, 2H), 5.03 (d, J = 6.5 Hz, 1H), 4.54 (t, J = 13.8 Hz, 2H), 4.47-4.36 (m, 2H), 3.84-3.68 (m, 2H), 1.32 (s, 3H), 0.60 (s, 3H), |
| 442 | 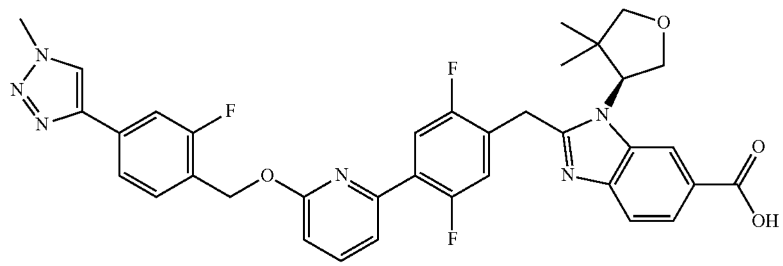 [SMILES: Cn1cc(-c2ccc(COc3cccc(-c4cc(F)c(Cc5nc6ccc(C(=O)O)cc6n5[C@@H]5COCC5(C)C)cc4F)n3)c(F)c2)nn1] | 41 | 669.2 | 1H NMR (400 MHz, Methanol-d4) δ 8.89 (s, 1H), 8.17 (dd, J = 8.6, 1.4 Hz, 1H), 7.96-7.81 (m, 3H), 7.81-7.67 (m, 2H), 7.59 (dd, J = 7.3, 1.6 Hz, 1H), 7.49-7.35 (m, 3H), 7.06-6.75 (m, 1H), 5.64 (s, 2H), 5.14 (d, J = 6.5 Hz, 1H), 4.80-4.61 (m, 3H), 4.52 (dd, J = 11.6, 6.7 Hz, 1H), 4.13 (s, 3H), 4.00 (d, J = 8.9 Hz, 1H), 3.84 (d, J = 8.9 Hz, 1H), 1.41 (s, 3H), 0.76 (s, 3H). |
| 443 | 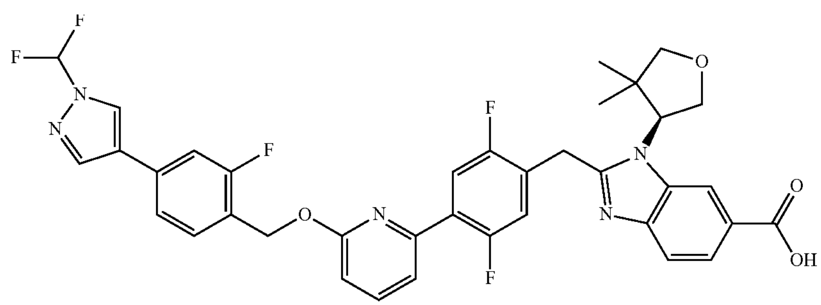 [SMILES: CC1(C)COC[C@H]1n1c(Cc2cc(F)c(-c3cccc(OCc4ccc(-c5cnn(C(F)F)c5)cc4F)n3)cc2F)nc2ccc(C(=O)O)cc21] | 41 | 704.1 | 1H NMR (400 MHz, Methanol-d4) δ 8.93 (s, 1H), 8.49 (d, J = 0.7 Hz, 1H), 8.21 (dd, J = 8.7, 1.4 Hz, 1H), 8.11 (s, 1H), 7.95 (dd, J = 10.9, 6.3 Hz, 1H), 7.89-7.72 (m, 2H), 7.71-7.31 (m, 6H), 6.93 (dd, J = 8.3, 0.7 Hz, 1H), 5.57 (s, 2H), 5.17 (d, J = 6.4 Hz, 1H), 4.81-4.57 (m, 3H), 4.53 (dd, J = 11.7, 6.7 Hz, 1H), 4.00 (d, J = 8.9 Hz, 1H), 3.84 (d, J = 8.9 Hz, 1H), 1.41 (s, 3H), 0.77 (s, 3H). |

TABLE 2-continued

Compounds

| Ex. | Structure | Procedure | ES/MS m/z | ¹H NMR |
|---|---|---|---|---|
| 444 | 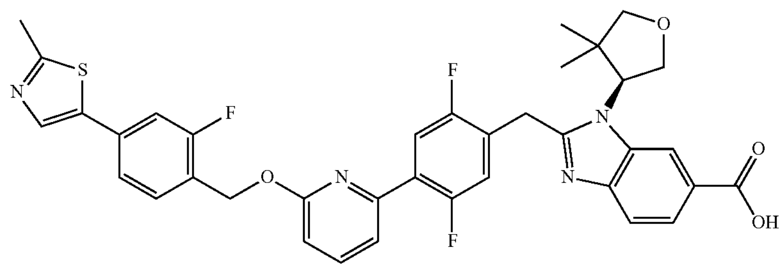 | 41 | 685.1 | 1H NMR (400 MHz, Methanol-d4) δ 8.93 (s, 1H), 8.21 (dd, J = 8.6, 1.4 Hz, 1H), 8.01-7.90 (m, 2H), 7.59 (ddd, J = 8.2, 5.0, 3.4 Hz, 2H), 7.51-7.32 (m, 3H), 7.02-6.87 (m, 1H), 5.58 (s, 2H), 5.17 (d, J = 6.5 Hz, 1H), 4.83-4.61 (m, 3H), 4.52 (dd, J = 11.7, 6.7 Hz, 1H), 4.00 (d, J = 9.0 Hz, 1H), 3.84 (d, J = 8.9 Hz, 1H), 2.74 (s, 3H), 1.41 (s, 3H), 0.77 (s, 3H). |
| 445 | 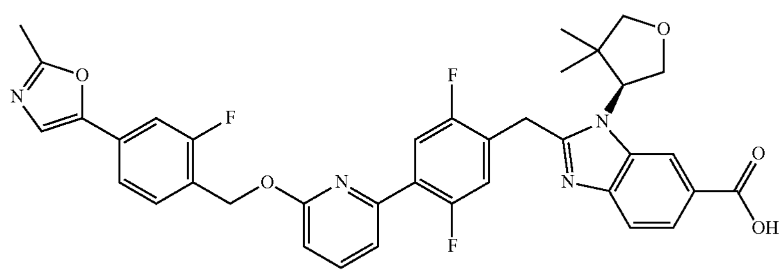 [SMILES: Cc1ncc(-c2ccc(COc3cccc(-c4cc(F)c(Cc5nc6ccc(C(=O)O)cc6n5[C@@H]5COCC5(C)C)cc4F)n3)c(F)c2)s1] | 41 | 669.2 | 1H NMR (400 MHz, Methanol-d4) δ 8.93 (s, 1H), 8.21 (dd, J = 8.6, 1.4 Hz, 1H), 7.94 (dd, J = 10.9, 6.3 Hz, 1H), 7.90-7.76 (m, 2H), 7.67-7.53 (m, 2H), 7.54-7.37 (m, 4H), 6.93 (d, J = 8.2 Hz, 1H), 5.57 (s, 2H), 5.17 (d, J = 6.4 Hz, 1H), 4.83-4.61 (m, 3H), 4.53 (dd, J = 11.7, 6.7 Hz, 1H), 4.00 (d, J = 8.9 Hz, 1H), 3.84 (d, J = 8.9 Hz, 1H), 2.53 (s, 3H), 1.41 (s, 3H), 0.77 (s, 3H). |
| 446 | 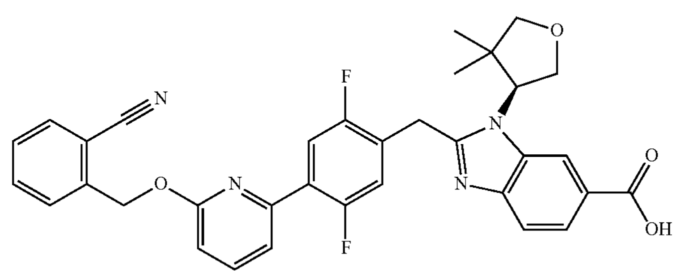 [SMILES: CC1(C)COC[C@H]1n1c(Cc2cc(F)c(-c3cccc(OCc4ccccc4C#N)n3)cc2F)nc2ccc(C(=O)O)cc21] | 27 | 595.3 | 1H NMR (400 MHz, Methanol-d4) δ 8.91 (s, 1H), 8.19 (dd, J = 8.6, 1.4 Hz, 1H), 7.94-7.80 (m, 2H), 7.79 (d, J = 8.1 Hz, 2H), 7.75-7.66 (m, 2H), 7.58 (dd, J = 7.5, 1.6 Hz, 1H), 7.51 (qd, J = 7.6, 1.6 Hz, 1H), 7.40 (dd, J = 11.2, 6.0 Hz, 1H), 6.96 (d, J = 8.3 Hz, 1H), 5.68 (s, 2H), 5.15 (d, J = 6.5 Hz, 1H), 4.79-4.60 (m, 3H), 4.53 (dd, J = 11.7, 6.7 Hz, 1H), 4.00 (d, J = 8.9 Hz, 1H), 3.84 (d, J = 8.9 Hz, 1H), 1.41 (s, 3H), 0.76 (s, 3H). |

TABLE 2-continued

Compounds

| Ex. | Structure | Procedure | ES/MS m/z | ¹H NMR |
|---|---|---|---|---|
| 447 | 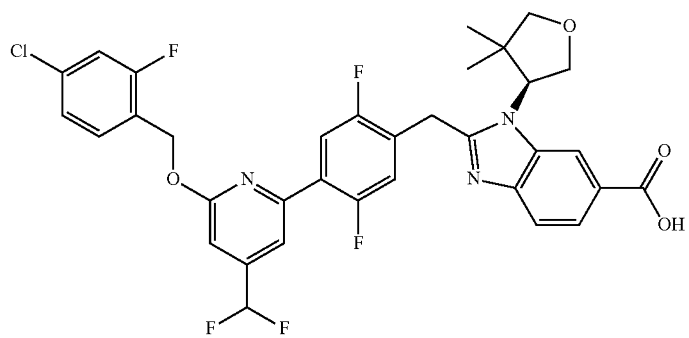 [SMILES: CC1(C)COC[C@H]1n1c(Cc2cc(F)c(-c3cc(C(F)F)cc(OCc4ccc(Cl)cc4F)n3)cc2F)nc2ccc(C(=O)O)cc21] | 35 | 672.2 | 1H NMR (400 MHz, Methanol-d4) δ 8.88 (s, 1H), 8.16 (dd, J = 8.6, 1.4 Hz, 1H), 7.96 (dd, J = 10.7, 6.3 Hz, 1H), 7.77 (d, J = 8.6 Hz, 1H), 7.70 (s, 1H), 7.56 (t, J = 8.0 Hz, 1H), 7.43 (dd, J = 11.3, 6.0 Hz, 1H), 7.31-7.19 (m, 2H), 7.07 (s, 1H), 6.88 (t, J = 55.4 Hz, 1H), 5.58 (s, 2H), 5.13 (d, J = 6.6 Hz, 1H), 4.79-4.59 (m, 3H), 4.53 (dd, J = 11.6, 6.7 Hz, 1H), 4.00 (d, J = 8.9 Hz, 1H), 3.84 (d, J = 8.9 Hz, 1H), 1.42 (s, 3H), 0.76 (s, 3H). |
| 448 | 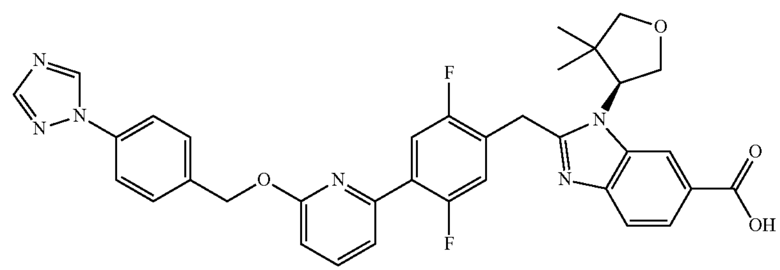 [SMILES: CC1(C)COC[C@H]1n1c(Cc2cc(F)c(-c3cccc(OCc4ccc(-n5cncn5)cc4)n3)cc2F)nc2ccc(C(=O)O)cc21] | 27 | 637 | 1H NMR (400 MHz, Methanol-d4) δ 9.10 (s, 1H), 8.90 (s, 1H), 8.23-8.08 (m, 2H), 7.91 (dd, J = 10.9, 6.3 Hz, 1H), 7.88-7.81 (m, 3H), 7.78 (d, J = 8.6 Hz, 1H), 7.68 (d, J = 8.5 Hz, 2H), 7.58 (dd, J = 7.5, 1.6 Hz, 1H), 7.40 (dd, J = 11.2, 6.0 Hz, 1H), 6.95 (d, J = 8.3 Hz, 1H), 5.58 (s, 2H), 5.14 (d, J = 6.6 Hz, 1H), 4.79-4.57 (m, 3H), 4.52 (dd, J = 11.6, 6.7 Hz, 1H), 4.00 (d, J = 8.9 Hz, 1H), 3.84 (d, J = 8.9 Hz, 1H), 1.40 (s, 3H), 0.75 (s, 3H). |

TABLE 2-continued

Compounds

| Ex. | Structure | Procedure | ES/MS m/z | ¹H NMR |
|---|---|---|---|---|
| 449 | 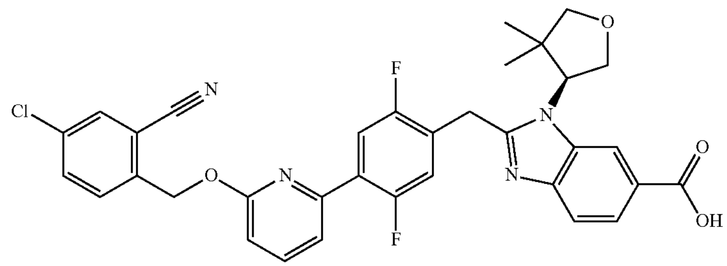 [SMILES: CC1(C)COC[C@H]1n1c(Cc2cc(F)c(-c3cccc(OCc4ccc(Cl)cc4C#N)n3)cc2F)nc2ccc(C(=O)O)cc21] | 27 | 629.2 | 1H NMR (400 MHz, Methanol-d4) δ 8.89 (s, 1H), 8.17 (dd, J = 8.6, 1.5 Hz, 1H), 7.93-7.81 (m, 3H), 7.78 (d, J = 8.6 Hz, 1H), 7.71 (d, J = 1.6 Hz, 2H), 7.59 (dd, J = 7.4, 1.6 Hz, 1H), 7.38 (dd, J = 11.1, 6.0 Hz, 1H), 6.97 (d, J = 8.2 Hz, 1H), 5.66 (s, 2H), 5.13 (d, J = 6.6 Hz, 1H), 4.81-4.60 (m, 3H), 4.52 (dd, J = 11.6, 6.7 Hz, 1H), 4.00 (d, J = 8.9 Hz, 1H), 3.84 (d, J = 8.8 Hz, 1H), 1.41 (s, 3H), 0.76 (s, 3H). |
| 450 | 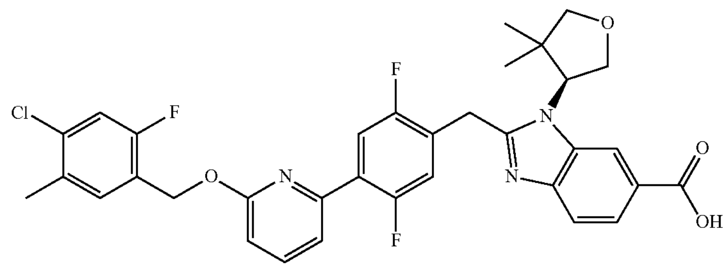 [SMILES: Cc1cc(COc2cccc(-c3cc(F)c(Cc4nc5ccc(C(=O)O)cc5n4[C@@H]4COCC4(C)C)cc3F)n2)c(F)cc1Cl] | 27 | 636.3 | 1H NMR (400 MHz, Methanol-d4) δ 8.89 (s, 1H), 8.17 (dd, J = 8.6, 1.3 Hz, 1H), 7.94 (dd, J = 10.9, 6.3 Hz, 1H), 7.90-7.73 (m, 2H), 7.58 (d, J = 7.5 Hz, 1H), 7.48 (d, J = 7.8 Hz, 1H), 7.39 (dd, J = 11.2, 6.0 Hz, 1H), 7.22 (d, J = 9.7 Hz, 1H), 6.91 (d, J = 8.3 Hz, 1H), 5.50 (s, 2H), 5.14 (d, J = 6.3 Hz, 1H), 4.81-4.61 (m, 3H), 4.53 (dd, J = 11.6, 6.7 Hz, 1H), 4.00 (d, J = 8.9 Hz, 1H), 3.85 (d, J = 8.9 Hz, 1H), 2.34 (s, 3H), 1.42 (s, 3H), 0.76 (s, 3H). |
| 451 | 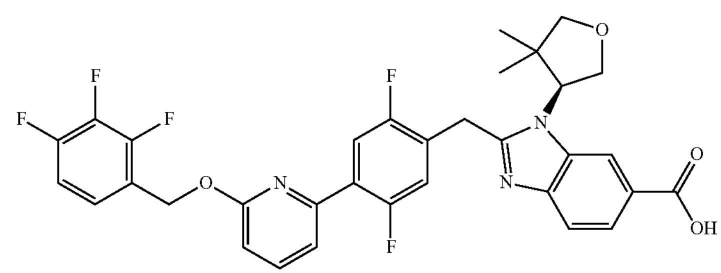 [SMILES: CC1(C)COC[C@H]1n1c(Cc2cc(F)c(-c3cccc(OCc4ccc(F)c(F)c4F)n3)cc2F)nc2ccc(C(=O)O)cc21] | 27 | 624.3 | 1H NMR (400 MHz, Methanol-d4) δ 8.92 (s, 1H), 8.20 (dd, J = 8.6, 1.4 Hz, 1H), 7.94 (dd, J = 10.8, 6.3 Hz, 1H), 7.89-7.74 (m, 2H), 7.59 (dd, J = 7.5, 1.6 Hz, 1H), 7.48-7.31 (m, 2H), 7.13 (tdd, J = 9.2, 7.1, 2.1 Hz, 1H), 6.91 (d, J = 8.2 Hz, 1H), 5.55 (s, 2H), 5.16 (d, J = 6.6 Hz, 1H), 4.83-4.60 (m, 3H), 4.53 (dd, J = 11.7, 6.7 Hz, 1H), 4.01 (d, |

TABLE 2-continued

Compounds

| Ex. | Structure | Procedure | ES/MS m/z | ¹H NMR |
|---|---|---|---|---|
| 452 | 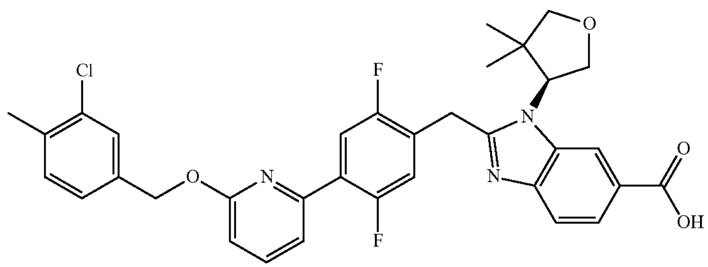 [SMILES: Cc1ccc(COc2cccc(-c3cc(F)c(Cc4nc5ccc(C(=O)O)cc5n4[C@@H]4COCC4(C)C)cc3F)n2)cc1Cl] | 27 | 618.1 | 1H NMR (400 MHz, Methanol-d4) δ 8.93 (s, 1H), 8.21 (d, J = 8.5 Hz, 1H), 7.90 (ddd, J = 11.1, 6.5, 4.8 Hz, 1H), 7.87-7.77 (m, 2H), 7.64-7.53 (m, 1H), 7.47-7.39 (m, 2H), 7.38-7.12 (m, 2H), 7.02-6.78 (m, 1H), 5.66-5.39 (m, 2H), 5.17 (d, J = 6.5 Hz, 1H), 4.81-4.60 (m, 3H), 4.53 (dd, J =11.7, 6.7 Hz, 1H), 4.01 (d, J = 8.9 Hz, 1H), 3.85 (d, J = 8.9 Hz, 1H), 2.52-2.31 (m, 3H), 1.42 (s, 3H), 0.77 (s, 3H). |
| | | | | J = 8.9 Hz, 1H), 3.85 (d, J = 8.9 Hz, 1H), 1.42 (s, 3H), 0.77 (s, 3H). |
| 453 | 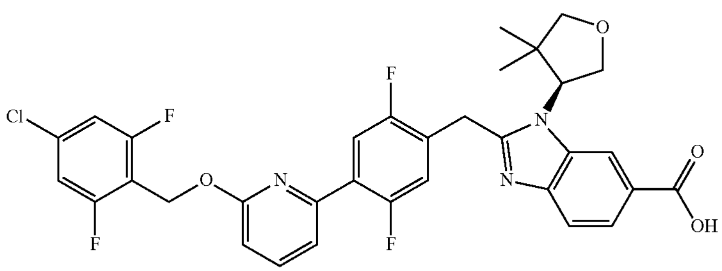 [SMILES: CC1(C)COC[C@H]1n1c(Cc2cc(F)c(-c3cccc(OCc4c(F)cc(Cl)cc4F)n3)cc2F)nc2ccc(C(=O)O)cc21] | 27 | 640.2 | 1H NMR (400 MHz, Methanol-d4) δ 8.89 (s, 1H), 8.18 (dd, J = 8.6, 1.3 Hz, 1H), 8.04 (dd, J = 10.9, 6.3 Hz, 1H), 7.91-7.65 (m, 2H), 7.67-7.44 (m, 1H), 7.40 (dd, J = 11.2, 6.0 Hz, 1H), 7.17 (d, J = 7.3 Hz, 2H), 6.85 (d, J = 8.3 Hz, 1H), 5.55 (s, 2H), 5.14 (d, J = 6.6 Hz, 1H), 4.81-4.60 (m, 3H), 4.53 (dd, J = 11.6, 6.7 Hz, 1H), 4.00 (d, J = 8.9 Hz, 1H), 3.85 (d, J = 8.9 Hz, 1H), 1.42 (s, 3H), 0.77 (s, 3H). |

TABLE 2-continued

Compounds

| Ex. | Structure | Procedure | ES/MS m/z | $^1$H NMR |
|---|---|---|---|---|
| 454 | 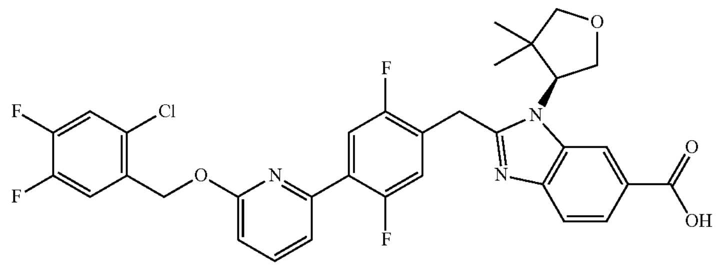 [SMILES: CC1(C)COC[C@H]1n1c(Cc2cc(F)c(-c3cccc(OCc4cc(F)c(F)cc4Cl)n3)cc2F)nc2ccc(C(=O)O)cc21] | 27 | 640.3 | 1H NMR (400 MHz, Methanol-d4) δ 8.86 (s, 1H), 8.15 (dd, J = 8.6, 1.4 Hz, 1H), 7.91-7.79 (m, 2H), 7.76 (d, J = 8.5 Hz, 1H), 7.60 (dd, J = 7.5, 1.6 Hz, 1H), 7.56-7.44 (m, 2H), 7.37 (dd, J = 11.2, 6.0 Hz, 1H), 6.98 (d, J = 8.2 Hz, 1H), 5.55 (s, 2H), 5.11 (d, J = 6.5 Hz, 1H), 4.76-4.60 (m, 3H), 4.52 (dd, J = 11.6, 6.8 Hz, 1H), 3.99 (d, J = 8.9 Hz, 1H), 3.84 (d, J = 8.8 Hz, 1H), 1.41 (s, 3H), 0.75 (s, 3H). |
| 455 | 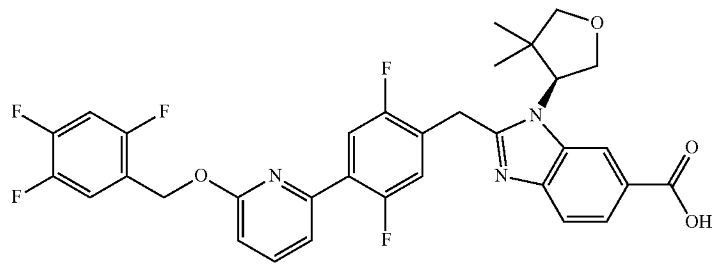 | 27 | 624.1 | 1H NMR (400 MHz, Methanol-d4) δ 8.88 (s, 1H), 8.16 (dd, J = 8.6, 1.4 Hz, 1H), 7.93 (dd, J = 10.8, 6.3 Hz, 1H), 7.83 (t, J = 7.9 Hz, 1H), 7.77 (d, J = 8.6 Hz, 1H), 7.59 (dd, J = 7.4, 1.6 Hz, 1H), 7.49 (ddd, J = 10.8, 8.9, 6.6 Hz, 1H), 7.38 (dd, J = 11.2, 6.0 Hz, 1H), 7.22 (td, J = 10.1, 6.6 Hz, 1H), 6.93 (d, J = 8.2 Hz, 1H), 5.52 (s, 2H), 5.21-5.06 (m, 1H), 4.78-4.58 (m, 3H), 4.53 (dd, J = 11.5, 6.7 Hz, 1H), 4.00 (d, J = 8.9 Hz, 1H), 3.84 (d, J = 8.9 Hz, 1H), 1.41 (s, 3H), 0.75 (s, 3H). |

TABLE 2-continued

Compounds

| Ex. | Structure | Procedure | ES/MS m/z | ¹H NMR |
|---|---|---|---|---|
| 456 | 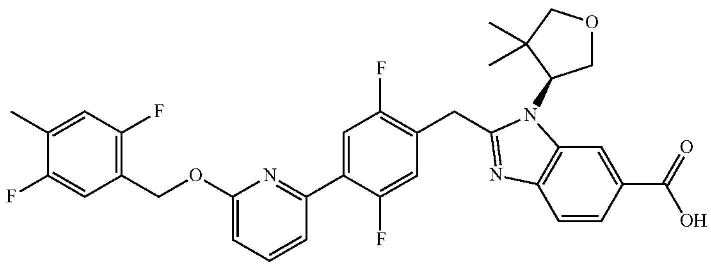 [SMILES: Cc1cc(F)c(COc2cccc(-c3cc(F)c(Cc4nc5ccc(C(=O)O)cc5n4[C@@H]4COCC4(C)C)cc3F)n2)cc1F] | | 620.3 | 1H NMR (400 MHz, Methanol-d4) δ 8.90 (s, 1H), 8.18 (dd, J = 8.6, 1.4 Hz, 1H), 7.93 (dd, J = 10.9, 6.3 Hz, 1H), 7.89-7.73 (m, 2H), 7.58 (dd, J = 7.5, 1.5 Hz, 1H), 7.39 (dd, J = 11.2, 6.0 Hz, 1H), 7.20 (dd, J = 9.7, 6.0 Hz, 1H), 7.04 (dd, J = 10.1, 6.1 Hz, 1H), 6.92 (d, J = 8.3 Hz, 1H), 5.50 (s, 2H), 5.14 (d, J = 6.6 Hz, 1H), 4.81-4.60 (m, 3H), 4.53 (dd, J = 11.7, 6.7 Hz, 1H), 4.00 (d, J = 8.9 Hz, 1H), 3.84 (d, J = 8.9 Hz, 1H), 2.26 (d, J = 1.9 Hz, 3H), 1.41 (s, 3H), 0.76 (s, 3H). |
| 457 | 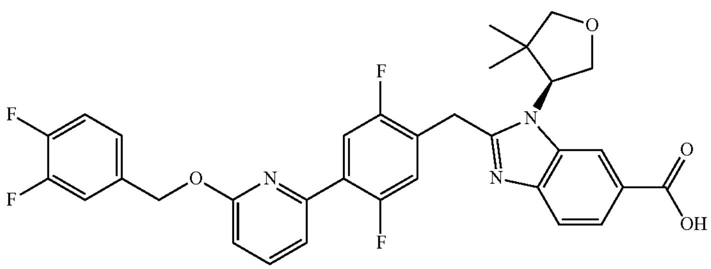 [SMILES: CC1(C)COC[C@H]1n1c(Cc2cc(F)c(-c3cccc(OCc4ccc(F)c(F)c4)n3)cc2F)nc2ccc(C(=O)O)cc21] | 27 | 606.2 | 1H NMR (400 MHz, Methanol-d4) δ 8.88 (s, 1H), 8.16 (dd, J = 8.6, 1.4 Hz, 1H), 7.91 (dd, J = 10.8, 6.3 Hz, 1H), 7.87-7.73 (m, 2H), 7.57 (dd, J = 7.4, 1.6 Hz, 1H), 7.46-7.35 (m, 2H), 7.35-7.17 (m, 2H), 6.93 (d, J = 8.3 Hz, 1H), 5.47 (s, 2H), 5.13 (d, J = 6.5 Hz, 1H), 4.82-4.60 (m, 3H), 4.52 (dd, J = 11.6, 6.7 Hz, 1H), 4.00 (d, J = 8.9 Hz, 1H), 3.84 (d, J = 8.9 Hz, 1H), 1.41 (s, 3H), 0.75 (s, 3H). |

TABLE 2-continued

Compounds

| Ex. | Structure | Procedure | ES/MS m/z | ¹H NMR |
|---|---|---|---|---|
| 458 | 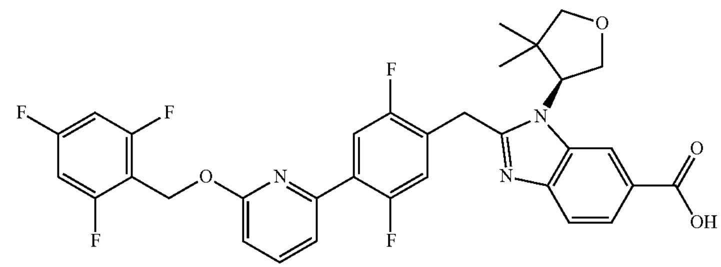 [SMILES: CC1(C)COC[C@H]1n1c(Cc2cc(F)c(-c3cccc(OCc4c(F)cc(F)cc4F)n3)cc2F)nc2ccc(C(=O)O)cc21] | 27 | 624.3 | 1H NMR (400 MHz, Methanol-d4) δ 8.89 (s, 1H), 8.17 (dd, J = 8.7, 1.4 Hz, 1H), 8.05 (dd, J = 10.9, 6.3 Hz, 1H), 7.88-7.75 (m, 2H), 7.59 (dd, J = 7.5, 1.6 Hz, 1H), 7.40 (dd, J = 11.3, 6.0 Hz, 1H), 7.01-6.89 (m, 2H), 6.84 (d, J = 8.3 Hz, 1H), 5.54 (s, 2H), 5.14 (d, J = 7.1 Hz, 1H), 4.81-4.60 (m, 3H), 4.53 (dd, J = 11.6, 6.7 Hz, 1H), 4.00 (d, J = 8.9 Hz, 1H), 3.85 (d, J = 8.9 Hz, 1H), 1.42 (s, 3H), 0.76 (s, 3H). |
| 459 | 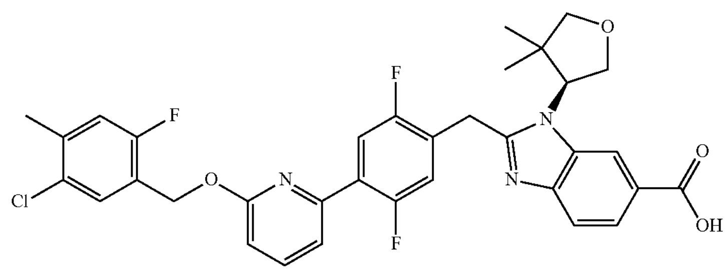 [SMILES: Cc1cc(F)c(COc2cccc(-c3cc(F)c(Cc4nc5ccc(C(=O)O)cc5n4[C@@H]4COCC4(C)C)cc3F)n2)cc1Cl] | 27 | 636.2 | 1H NMR (400 MHz, Methanol-d4) δ 8.86 (s, 1H), 8.14 (dd, J = 8.6, 1.4 Hz, 1H), 7.92 (dd, J = 10.8, 6.3 Hz, 1H), 7.86-7.73 (m, 2H), 7.57 (dd, J = 7.5, 1.6 Hz, 1H), 7.53 (d, J = 6.7 Hz, 1H), 7.36 (dd, J = 11.2, 6.0 Hz, 1H), 7.12 (d, J = 10.4 Hz, 1H), 6.92 (d, J = 8.3 Hz, 1H), 5.50 (s, 2H), 5.11 (d, J = 6.5 Hz, 1H), 4.79-4.58 (m, 3H), 4.52 (dd, J = 11.5, 6.7 Hz, 1H), 3.99 (d, J = 8.9 Hz, 1H), 3.84 (d, J = 8.8 Hz, 1H), 2.37 (s, 3H), 1.41 (s, 3H), 0.75 (s, 3H). |
| 460 | 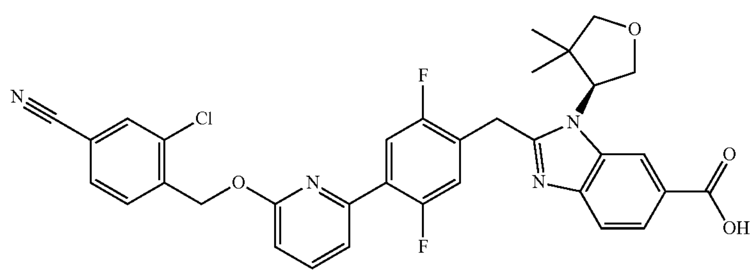 [SMILES: CC1(C)COC[C@H]1n1c(Cc2cc(F)c(-c3cccc(OCc4ccc(C#N)cc4Cl)n3)cc2F)nc2ccc(C(=O)O)cc21] | 27 | 629.15 | 1H NMR (400 MHz, Methanol-d4) δ 8.88 (s, 1H), 8.16 (d, J = 8.6 Hz, 1H), 7.98-7.83 (m, 2H), 7.83-7.66 (m, 4H), 7.60 (d, J = 7.4 Hz, 1H), 7.37 (dd, J = 11.2, 6.0 Hz, 1H), 7.01 (d, J = 8.3 Hz, 1H), 5.67 (s, 2H), 5.12 (d, J = 6.4 Hz, 1H), 4.74-4.58 (m, 3H), 4.52 (dd, J = 11.6, 6.7 Hz, 1H), 3.99 (d, J = 8.9 Hz, 1H), 3.84 (d, J = 8.9 Hz, 1H), 1.40 (s, 3H), 0.75 (s, 3H). |

TABLE 2-continued

Compounds

| Ex. | Structure | Procedure | ES/MS m/z | 1H NMR |
|---|---|---|---|---|
| 461 | (structure) | 27 | 625.2 | 1H NMR (400 MHz, Methanol-d4) δ 8.84 (s, 1H), 8.12 (dd, J = 8.6, 1.4 Hz, 1H), 7.89-7.77 (m, 2H), 7.75 (d, J = 8.6 Hz, 1H), 7.58 (d, J = 7.7 Hz, 2H), 7.38 (d, J = 1.4 Hz, 1H), 7.37-7.26 (m, 2H), 6.96 (d, J = 8.3 Hz, 1H), 5.58 (s, 2H), 5.08 (d, J = 6.6 Hz, 1H), 4.74-4.47 (m, 4H), 3.97 (d, J = 2.4 Hz, 4H), 3.84 (d, J = 8.9 Hz, 1H), 1.40 (s, 3H), 0.74 (s, 3H). |
| 462 | (structure) | 27 | 634.3 | 1H NMR (400 MHz, Methanol-d4) δ 8.77 (s, 1H), 8.10-8.01 (m, 1H), 7.88 (dd, J = 10.9, 6.3 Hz, 1H), 7.79 (t, J = 7.9 Hz, 1H), 7.72 (d, J = 8.5 Hz, 1H), 7.55 (dd, J = 7.5, 1.5 Hz, 1H), 7.39 (d, J = 8.1 Hz, 1H), 7.27 (dd, J = 11.3, 6.1 Hz, 1H), 7.05 (d, J = 1.9 Hz, 1H), 6.95 (dd, J = 8.1, 2.0 Hz, 1H), 6.88 (d, J = 8.2 Hz, 1H), 5.48 (s, 2H), 5.02 (d, J = 6.7 Hz, 1H), 4.69-4.46 (m, 4H), 3.97 (d, J = 8.8 Hz, 1H), 3.91 (s, 3H), 3.82 (d, J = 8.8 Hz, 1H), 1.39 (s, 3H), 0.71 (s, 3H). |
| 463 | (structure) | 27 | 602.3 | 1H NMR (400 MHz, Methanol-d4) δ 8.96 (s, 1H), 8.23 (dd, J = 8.6, 1.4 Hz, 1H), 7.96 (dd, J = 10.9, 6.3 Hz, 1H), 7.89-7.74 (m, 2H), 7.56 (dd, J = 7.5, 1.6 Hz, 1H), 7.51-7.33 (m, 2H), 6.97 (dd, J = 14.8, 9.5 Hz, 2H), 6.88 (d, J = 8.2 Hz, 1H), 5.49 (s, 2H), 5.20 (d, J = 6.4 Hz, 1H), 4.89-4.60 (m, 3H), 4.53 (dd, J = 11.8, 6.6 Hz, 1H), 4.01 (d, J = 9.0 |

TABLE 2-continued

Compounds

| Ex. | Structure | Procedure | ES/MS m/z | 1H NMR |
|---|---|---|---|---|
| | | | | Hz, 1H), 3.85 (d, J = 8.9 Hz, 1H), 2.34 (s, 3H), 1.42 (s, 3H), 0.78 (s, 3H). |
| 464 | 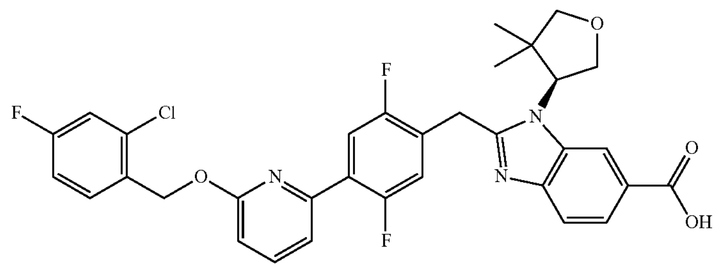 [SMILES: CC1(C)COC[C@H]1n1c(Cc2cc(F)c(-c3cccc(OCc4ccc(F)cc4Cl)n3)cc2F)nc2ccc(C(=O)O)cc21] | 27 | 622.2 | 1H NMR (400 MHz, Methanol-d4) δ 8.94 (s, 1H), 8.21 (dd, J = 8.7, 1.4 Hz, 1H), 7.91 (dd, J = 10.9, 6.3 Hz, 1H), 7.88-7.73 (m, 2H), 7.68-7.54 (m, 2H), 7.43 (dd, J = 11.1, 6.1 Hz, 1H), 7.28 (dd, J = 8.6, 2.6 Hz, 1H), 7.10 (td, J = 8.5, 2.6 Hz, 1H), 6.94 (d, J = 8.3 Hz, 1H), 5.56 (s, 2H), 5.18 (d, J = 6.5 Hz, 1H), 4.85-4.60 (m, 3H), 4.53 (dd, J = 11.7, 6.7 Hz, 1H), 4.00 (d, J = 8.9 Hz, 1H), 3.85 (d, J = 8.9 Hz, 1H), 1.42 (s, 3H), 0.77 (s, 3H). |
| 465 | 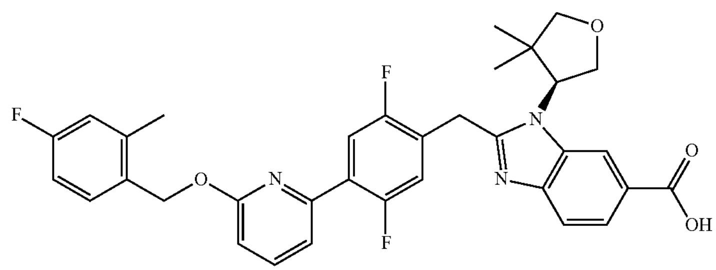 [SMILES: Cc1cc(F)ccc1COc1cccc(-c2cc(F)c(Cc3nc4ccc(C(=O)O)cc4n3[C@@H]3COCC3(C)C)cc2F)n1] | 27 | 602.3 | 1H NMR (400 MHz, Methanol-d4) δ 8.92 (s, 1H), 8.20 (dd, J = 8.6, 1.4 Hz, 1H), 7.95 (dd, J = 10.8, 6.4 Hz, 1H), 7.85-7.70 (m, 2H), 7.56 (dd, J = 7.4, 1.7 Hz, 1H), 7.43 (td, J = 10.9, 9.7, 5.9 Hz, 2H), 6.99 (dd, J = 9.9, 2.8 Hz, 1H), 6.90 (dd, J = 11.5, 8.4 Hz, 2H), 5.47 (s, 2H), 5.16 (d, J = 6.4 Hz, 1H), 4.83-4.61 (m, 3H), 4.53 (dd, J = 11.7, 6.7 Hz, 1H), 4.01 (d, J = 8.9 Hz, 1H), 3.85 (d, J = 8.9 Hz, 1H), 2.43 (s, 3H), 1.42 (s, 3H), 0.77 (s, 3H). |

TABLE 2-continued

Compounds

| Ex. | Structure | Procedure | ES/MS m/z | ¹H NMR |
|---|---|---|---|---|
| 466 | 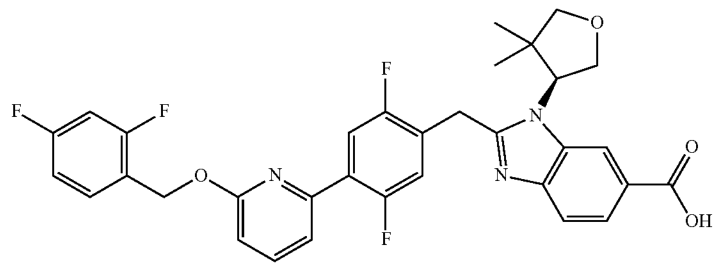 | 27 | 606.3 | 1H NMR (400 MHz, Methanol-d4) δ 8.91 (s, 1H), 8.19 (dd, J = 8.6, 1.4 Hz, 1H), 7.96 (dd, J = 10.8, 6.3 Hz, 1H), 7.89-7.70 (m, 2H), 7.65-7.52 (m, 2H), 7.41 (dd, J = 11.2, 6.0 Hz, 1H), 7.10-6.94 (m, 2H), 6.90 (d, J = 8.2 Hz, 1H), 5.52 (s, 2H), 5.16 (d, J = 6.4 Hz, 1H), 4.82-4.60 (m, 3H), 4.53 (dd, J = 11.6, 6.7 Hz, 1H), 4.00 (d, J = 8.9 Hz, 1H), 3.85 (d, J = 8.9 Hz, 1H), 1.42 (s, 3H), 0.77 (s, 3H). |
| 467 | 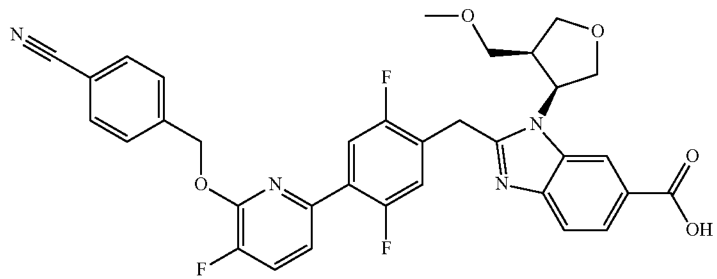 [SMILES: COC[C@H]1COC[C@H]1n1c(Cc2cc(F)c(-c3ccc(F)c(OCc4ccc(C#N)cc4)n3)cc2F)nc2ccc(C(=O)O)cc21] | 35 | 629.1 | 1H NMR (400 MHz, DMSO) δ 7.89 (dd, J = 16.6, 8.2 Hz, 3H), 7.70 (dd, J = 12.0, 7.3 Hz, 2H), 7.52 (d, J = 7.4 Hz, 1H), 7.39-7.30 (m, 1H), 7.01 (d, J = 8.2 Hz, 1H), 5.58 (s, 2H), 5.49 (s, 1H), 4.48 (t, J = 13.9 Hz, 2H), 4.35 (t, J = 5.1 Hz, 1H), 4.26-4.14 (m, 1H), 2.92 (s, 3H), 2.08 (s, 2H). |
| 468 | 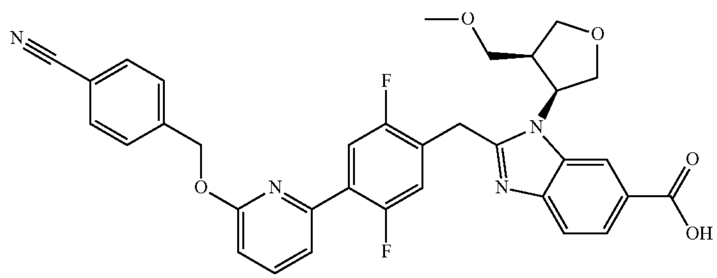 [SMILES: COC[C@H]1COC[C@H]1n1c(Cc2cc(F)c(-c3cccc(OCc4ccc(C#N)cc4)n3)cc2F)nc2ccc(C(=O)O)cc21] | 35 | 611.2 | 1H NMR (400 MHz, DMSO) δ 7.89 (dd, J = 16.6, 8.2 Hz, 3H), 7.70 (dd, J = 12.0, 7.3 Hz, 2H), 7.52 (d, J = 7.4 Hz, 1H), 7.40-7.29 (m, 1H), 7.01 (d, J = 8.2 Hz, 1H), 5.58 (s, 2H), 5.49 (s, 1H), 4.48 (t, J = 13.9 Hz, 2H), 4.35 (t, J = 5.1 Hz, 1H), 4.29-4.16 (m, 1H), 2.92 (s, 3H), 2.08 (s, 2H). |

TABLE 2-continued

Compounds

| Ex. | Structure | Procedure | ES/MS m/z | ¹H NMR |
|---|---|---|---|---|
| 469 | 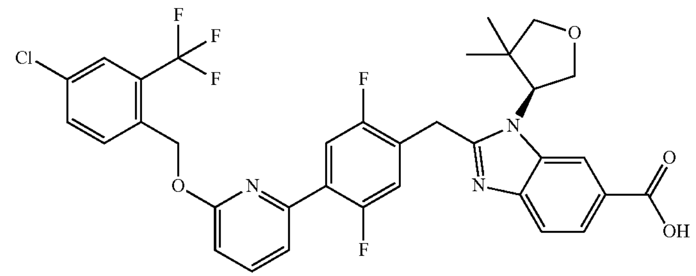 [SMILES: CC1(C)COC[C@H]1n1c(Cc2cc(F)c(-c3cccc(OCc4ccc(Cl)cc4C(F)(F)F)n3)cc2F)nc2ccc(C(=O)O)cc21] | 35 | 672.1 | 1H NMR (400 MHz, DMSO) δ 8.48 (s, 1H), 7.97-7.85 (m, 2H), 7.85-7.73 (m, 3H), 7.70 (dd, J = 10.5, 6.4 Hz, 1H), 7.62 (d, J = 8.5 Hz, 1H), 7.55 (d, J = 7.3 Hz, 1H), 7.44 (dd, J = 11.4, 6.1 Hz, 1H), 7.01 (d, J = 8.3 Hz, 1H), 5.64 (s, 2H), 5.00 (d, J = 6.7 Hz, 1H), 4.63-4.47 (m, 2H), 4.47-4.31 (m, 2H), 3.80-3.66 (m, 2H), 2.55 (s, 3H), 1.32 (s, 3H), 0.59 (s, 3H). |
| 470 | 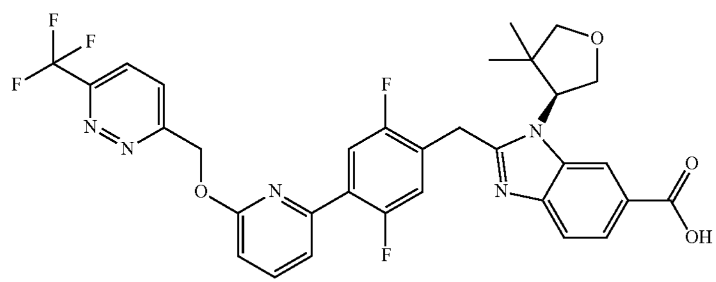 [SMILES: CC1(C)COC[C@H]1n1c(Cc2cc(F)c(-c3cccc(OCc4ccc(C(F)(F)F)nn4)n3)cc2F)nc2ccc(C(=O)O)cc21] | 35 | 640.0 | 1H NMR (400 MHz, DMSO) δ 8.51 (s, 1H), 8.29 (d, J = 8.8 Hz, 1H), 8.10 (d, J = 8.8 Hz, 1H), 7.94 (t, J = 7.9 Hz, 1H), 7.83 (dd, J = 8.5, 1.5 Hz, 1H), 7.73-7.51 (m, 3H), 7.45 (dd, J = 11.4, 6.1 Hz, 1H), 7.09 (d, J = 8.3 Hz, 1H), 5.90 (s, 2H), 5.03 (d, J = 6.7 Hz, 1H), 4.63-4.31 (m, 4H), 3.85-3.65 (m, 2H), 1.32 (s, 3H), 0.60 (s, 3H). |
| 471 | 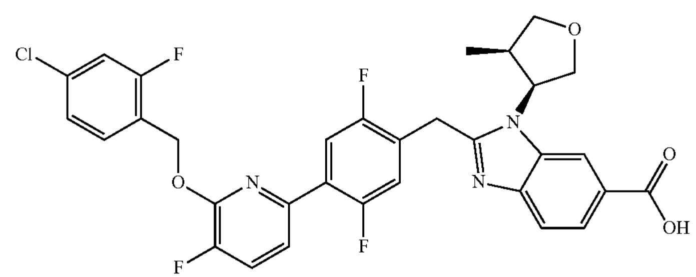 [SMILES: C[C@H]1COC[C@H]1n1c(Cc2cc(F)c(-c3ccc(F)c(OCc4ccc(Cl)cc4F)n3)cc2F)nc2ccc(C(=O)O)cc21] | 39 | 626.0 | 1H NMR (400 MHz, DMSO) δ 8.50 (s, 1H), 7.97-7.73 (m, 3H), 7.71-7.50 (m, 4H), 7.45 (dd, J = 11.2, 6.0 Hz, 1H), 7.35 (d, J = 8.2 Hz, 1H), 5.60 (s, 2H), 5.43 (s, 1H), 4.66-4.40 (m, 3H), 4.31-4.18 (m, 1H), 4.18-4.09 (m, 1H), 3.59 (d, J = 8.8 Hz, 4H), 0.53 (d, J = 7.0 Hz, 3H). |

TABLE 2-continued

Compounds

| Ex. | Structure | Procedure | ES/MS m/z | ¹H NMR |
|---|---|---|---|---|
| 472 | 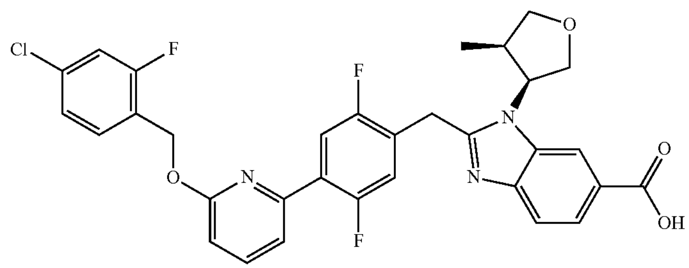 [SMILES: C[C@H]1COC[C@H]1n1c(Cc2cc(F)c(-c3cccc(OCc4ccc(Cl)cc4F)n3)cc2F)nc2ccc(C(=O)O)cc21] | 39 | 608.0 | 1H NMR (400 MHz, DMSO) δ 8.51 (s, 1H), 7.97-7.75 (m, 3H), 7.62 (d, J = 8.7 Hz, 2H), 7.56-7.42 (m, 3H), 7.35-7.31 (m, 1H), 6.95 (d, J = 8.3 Hz, 1H), 5.51 (s, 2H), 5.44 (t, J = 7.2 Hz, 1H), 4.57-4.39 (m, 3H), 4.24 (dd, J = 10.9, 6.7 Hz, 1H), 4.13 (t, J = 8.5 Hz, 1H), 3.60 (t, J = 8.5 Hz, 1H), 0.53 (d, J = 7.0 Hz, 3H). |
| 473 | 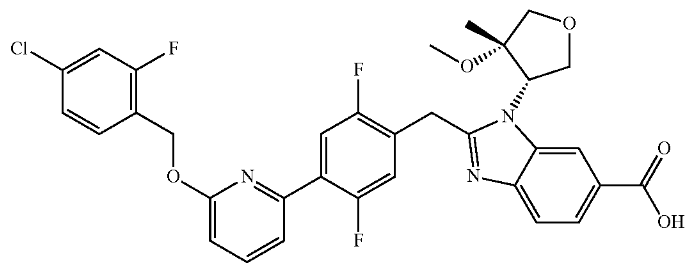 [SMILES: CO[C@]1(C)COC[C@@H]1n1c(Cc2cc(F)c(-c3cccc(OCc4ccc(Cl)cc4F)n3)cc2F)nc2ccc(C(=O)O)cc21] | 39 | 638.0 | 1H NMR (400 MHz, DMSO) δ 8.47 (s, 1H), 7.98-7.70 (m, 3H), 7.61 (t, J = 8.3 Hz, 2H), 7.57-7.46 (m, 2H), 7.39 (dd, J = 11.5, 6.0 Hz, 1H), 7.33 (dd, J = 8.3, 2.1 Hz, 1H), 6.96 (d, J = 8.3 Hz, 1H), 5.51 (s, 2H), 5.33 (d, J = 8.2 Hz, 1H), 4.73-4.38 (m, 4H), 4.30-4.11 (m, 2H), 3.63 (d, J = 10.0 Hz, 1H), 2.97 (s, 3H), 1.43 (s, 3H). |
| 474 | 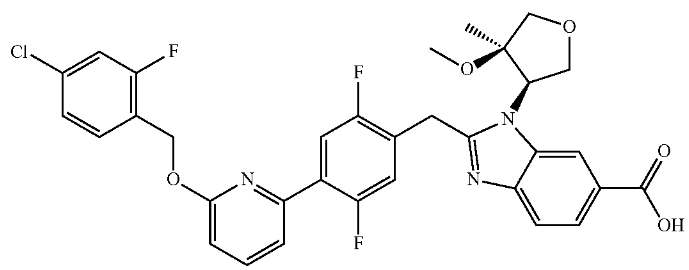 [SMILES: CO[C@@]1(C)COC[C@H]1n1c(Cc2cc(F)c(-c3cccc(OCc4ccc(Cl)cc4F)n3)cc2F)nc2ccc(C(=O)O)cc21] | 39 | 638.0 | 1H NMR (400 MHz, DMSO) δ 8.45 (s, 1H), 7.95-7.67 (m, 3H), 7.56-7.47 (m, 2H), 7.43-7.30 (m, 2H), 6.95 (d, J = 8.3 Hz, 1H), 5.51 (s, 2H), 5.31 (s, 1H), 4.64-4.35 (m, 3H), 4.29-4.14 (m, 2H), 3.63 (d, J = 10.1 Hz, 1H), 2.96 (s, 3H), 1.43 (s, 3H). |

TABLE 2-continued

Compounds

| Ex. | Structure | Procedure | ES/MS m/z | ¹H NMR |
|---|---|---|---|---|
| 475 | 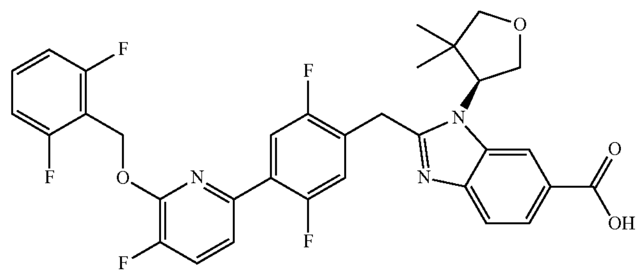 [SMILES: CC1(C)COC[C@H]1n1c(Cc2cc(F)c(-c3ccc(F)c(OCc4c(F)cccc4F)n3)cc2F)nc2ccc(C(=O)O)cc21] | 35 | 624.2 | 1H NMR (400 MHz, DMSO) δ 8.51 (s, 1H), 7.96-7.77 (m, 3H), 7.65 (d, J = 8.4 Hz, 1H), 7.60-7.38 (m, 3H), 7.19 (t, J = 8.0 Hz, 2H), 5.63 (s, 2H), 5.04 (d, J = 6.6 Hz, 1H), 4.67-4.29 (m, 4H), 3.85-3.69 (m, 2H), 1.34 (s, 3H), 0.62 (s, 3H). |
| 476 | 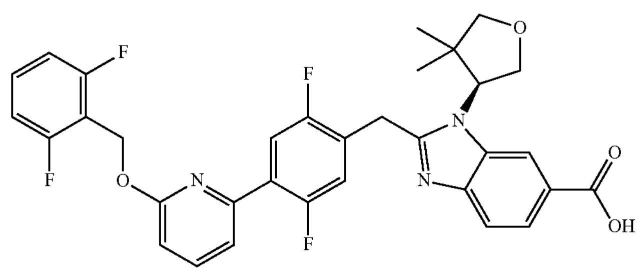 | 35 | 606.2 | 1H NMR (400 MHz, DMSO) δ 8.51 (s, 1H), 7.96-7.77 (m, 3H), 7.65 (d, J = 8.4 Hz, 1H), 7.60-7.38 (m, 3H), 7.19 (t, J = 8.0 Hz, 2H), 5.63 (s, 2H), 5.04 (d, J = 6.6 Hz, 1H), 4.67-4.29 (m, 4H), 3.85-3.69 (m, 2H), 1.34 (s, 3H), 0.62 (s, 3H). |
| 477 | 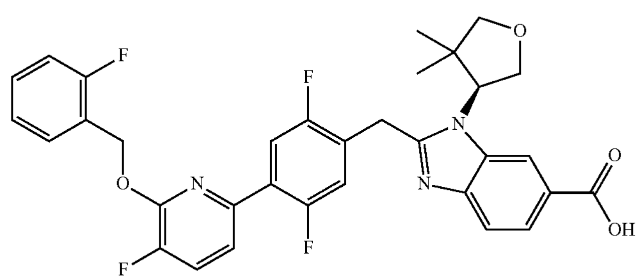 [SMILES: CC1(C)COC[C@H]1n1c(Cc2cc(F)c(-c3ccc(F)c(OCc4ccccc4F)n3)cc2F)nc2ccc(C(=O)O)cc21] | 35 | 606.2 | 1H NMR (400 MHz, DMSO) δ 8.50 (s, 1H), 8.03-7.79 (m, 3H), 7.75-7.51 (m, 3H), 7.46 (dq, J = 13.9, 7.0, 6.5 Hz, 2H), 7.26 (q, J = 9.3, 7.7 Hz, 2H), 5.62 (s, 2H), 5.03 (d, J = 6.7 Hz, 1H), 4.66-4.28 (m, 4H), 3.83-3.66 (m, 2H), 1.34 (s, 3H), 0.61 (s, 3H). |

TABLE 2-continued

Compounds

| Ex. | Structure | Procedure | ES/MS m/z | ¹H NMR |
|---|---|---|---|---|
| 478 | 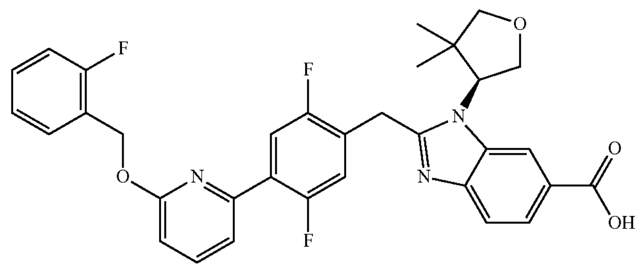 [SMILES: CC1(C)COC[C@H]1n1c(Cc2cc(F)c(-c3cccc(OCc4ccccc4F)n3)cc2F)nc2ccc(C(=O)O)cc21] | 35 | 588.3 | 1H NMR (400 MHz, DMSO) δ 8.52 (s, 1H), 7.98-7.77 (m, 3H), 7.78-7.36 (m, 5H), 7.36-7.13 (m, 2H), 6.96 (d, J = 8.3 Hz, 1H), 5.53 (s, 2H), 5.05 (d, J = 6.6 Hz, 1H), 4.72-4.37 (m, 4H), 3.90-3.66 (m, 2H), 1.34 (s, 3H), 0.62 (s, 3H). |
| 479 | 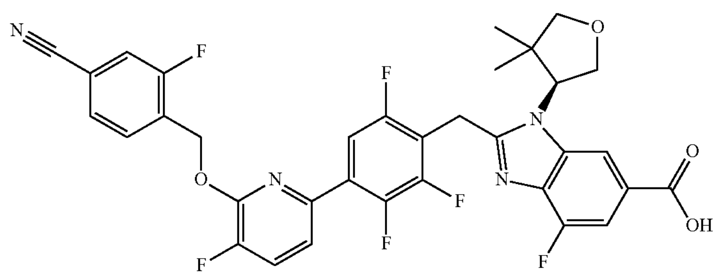 [SMILES: CC1(C)COC[C@H]1n1c(Cc2c(F)cc(-c3ccc(F)c(OCc4ccc(C#N)cc4F)n3)c(F)c2F)nc2c(F)cc(C(=O)O)cc21] | 35 | 667.2 | 1H NMR (400 MHz, Acetonitrile-d3) δ 8.42 (s, 1H), 7.73 (t, J = 7.7 Hz, 1H), 7.68-7.51 (m, 6H), 5.68 (s, 2H), 4.93 (d, J = 6.6 Hz, 1H), 4.59 (dd, J = 11.3, 1.5 Hz, 1H), 4.53-4.40 (m, 2H), 4.32 (d, J = 17.2 Hz, 1H), 3.85 (d, J = 8.7 Hz, 1H), 3.78 (d, J = 8.7 Hz, 1H), 1.41 (s, 3H), 0.72 (s, 3H). |
| 480 | 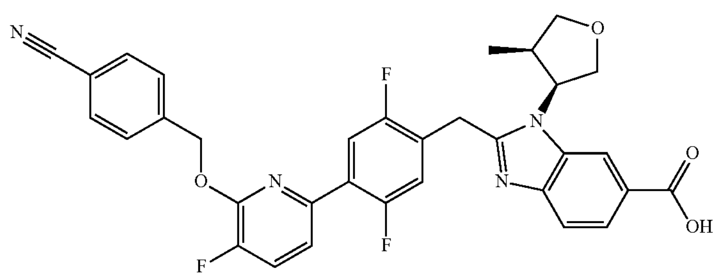 [SMILES: C[C@H]1COC[C@H]1n1c(Cc2cc(F)c(-c3ccc(F)c(OCc4ccc(C#N)cc4)n3)cc2F)nc2ccc(C(=O)O)cc21] | 35 | 599.3 | 1H NMR (400 MHz, Acetonitrile-d3) δ 8.57 (s, 1H), 7.86 (dd, J = 8.4, 1.5 Hz, 1H), 7.78-7.68 (m, 3H), 7.65 (d, J = 8.1 Hz, 2H), 7.62-7.54 (m, 2H), 7.52 (ddd, J = 8.3, 3.1, 1.4 Hz, 1H), 7.20 (dd, J = 11.6, 6.1 Hz, 1H), 5.63 (s, 2H), 5.24 (t, J = 7.2 Hz, 1H), 4.55 (dd, J = 11.0, 1.4 Hz, 1H), 4.37 (s, 2H), 4.23 (dd, J = 11.0, 6.7 Hz, 1H), 4.13 (t, J = 8.5 Hz, 1H), 3.67 (dd, J = 8.4 Hz, 1H), 2.88 (hept, J = 7.6 Hz, 1H), 0.57 (d, J = 7.0 Hz, 3H). |

TABLE 2-continued

Compounds

| Ex. | Structure | Procedure | ES/MS m/z | ¹H NMR |
|---|---|---|---|---|
| 481 | 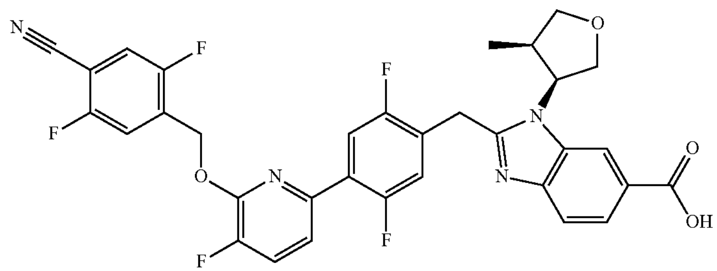 [SMILES: C[C@H]1COC[C@H]1n1c(Cc2cc(F)c(-c3ccc(F)c(OCc4cc(F)c(C#N)cc4F)n3)cc2F)nc2ccc(C(=O)O)cc21] | 35 | 635.2 | 1H NMR (400 MHz, Acetonitrile-d3) δ 8.56 (s, 1H), 7.87 (dd, J = 8.5, 1.5 Hz, 1H), 7.70 (dd, J = 10.7, 6.5 Hz, 1H), 7.65-7.48 (m, 5H), 7.20 (dd, J = 11.6, 6.1 Hz, 1H), 5.65 (s, 2H), 5.23 (t, J = 7.3 Hz, 1H), 4.56 (dd, J = 10.9, 1.4 Hz, 1H), 4.37 (s, 2H), 4.23 (dd, J = 10.9, 6.7 Hz, 1H), 3.68 (t, J = 8.5 Hz, 1H), 2.87 (hept, J = 7.7 Hz, 1H), 0.57 (d, J = 7.0 Hz, 3H). |
| 482 | 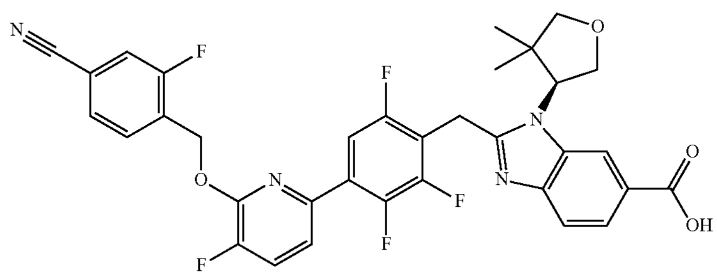 | 35 | 649.2 | 1H NMR (400 MHz, Acetonitrile-d3) δ 8.54 (s, 1H), 7.83 (dd, J = 8.5, 1.5 Hz, 1H), 7.72 (t, J = 7.7 Hz, 1H), 7.66-7.45 (m, 6H), 5.66 (s, 2H), 4.92 (d, J = 6.7 Hz, 1H), 4.60 (dd, J = 11.2, 1.5 Hz, 1H), 4.53-4.40 (m, 2H), 4.31 (d, J = 17.1Hz, 1H), 3.86 (d, J = 8.7 Hz, 1H), 3.77 (d, J = 8.7 Hz, 1H), 1.41 (s, 3H), 0.70 (s, 3H). |
| 483 | 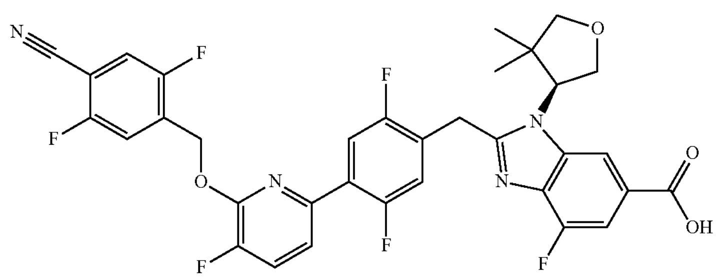 [SMILES: CC1(C)COC[C@H]1n1c(Cc2cc(F)c(-c3ccc(F)c(OCc4cc(F)c(C#N)cc4F)n3)cc2F)nc2c(F)cc(C(=O)O)cc21] | 35 | 667.2 | 1H NMR (400 MHz, Acetonitrile-d3) δ 8.41 (s, 1H), 7.72 (dd, J = 10.7, 6.4 Hz, 1H), 7.67-7.49 (m, 5H), 7.23 (dd, J = 11.5, 6.1 Hz, 1H), 5.66 (s, 2H), 4.85 (d, J = 6.7 Hz, 1H), 4.54 (dd, J = 11.3, 1.5 Hz, 1H), 4.43 (dd, J = 11.3, 6.8 Hz, 1H), 4.39-4.27 (m, 2H), 3.84 (d, J = 8.8 Hz, 1H), 3.75 (d, J = 8.8 Hz, 1H), 1.35 (s, 3H), 0.67 (s, 3H). |

TABLE 2-continued

Compounds

| Ex. | Structure | Procedure | ES/MS m/z | ¹H NMR |
|---|---|---|---|---|
| 484 | 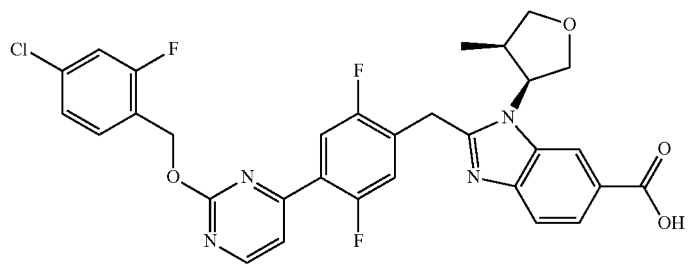 [SMILES: C[C@H]1COC[C@H]1n1c(Cc2cc(F)c(-c3ccnc(OCc4ccc(Cl)cc4F)n3)cc2F)nc2ccc(C(=O)O)cc21] | 35 | 609.2 | 1H NMR (400 MHz, Acetonitrile-d3) δ 8.63 (d, J = 5.1 Hz, 1H), 8.57 (s, 1H), 7.94 (dd, J = 10.5, 6.3 Hz, 1H), 7.86 (dd, J = 8.5, 1.5 Hz, 1H), 7.62-7.52 (m, 3H), 7.31-7.19 (m, 3H), 5.53 (s, 2H), 5.24 (t, J = 7.2 Hz, 1H), 4.55 (dd, J = 11.0, 1.4 Hz, 1H), 4.40 (s, 2H), 4.23 (dd, J = 11.0, 6.7 Hz, 1H), 4.13 (t, J = 8.5 Hz, 1H), 3.67 (t, J = 8.4 Hz, 1H), 2.89 (hept, J = 7.5 Hz, 1H), 0.57 (d, J = 7.1 Hz, 3H). |
| 485 | 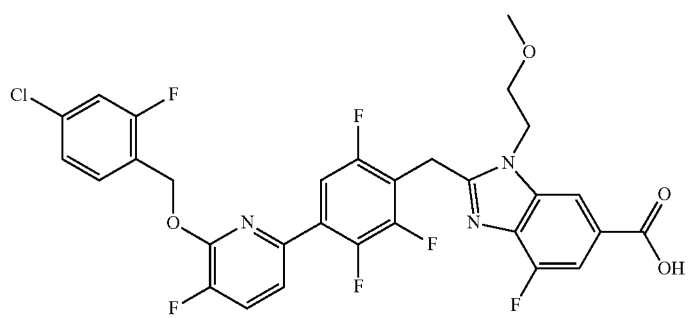 [SMILES: COCCn1c(Cc2c(F)cc(-c3ccc(F)c(OCc4ccc(Cl)cc4F)n3)c(F)c2F)nc2c(F)cc(C(=O)O)cc21] | 35 | 636.2 | 1H NMR (400 MHz, Acetonitrile-d3) δ 8.03 (d, J = 1.3 Hz, 1H), 7.69-7.64 (m, 1H), 7.64-7.50 (m, 4H), 7.31-7.22 (m, 2H), 5.59 (s, 2H), 4.53 (t, J = 5.0 Hz, 2H), 4.46 (s, 2H), 3.75 (t, J = 5.0 Hz, 2H), 3.27 (s, 3H). |
| 486 | 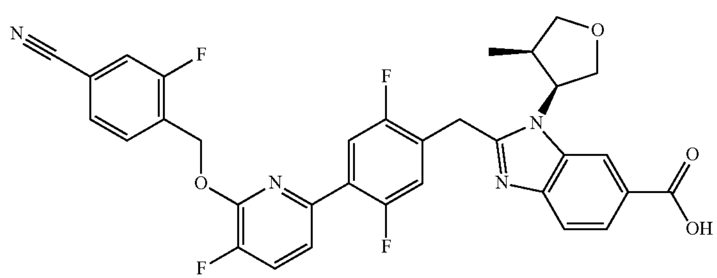 [SMILES: C[C@H]1COC[C@H]1n1c(Cc2cc(F)c(-c3ccc(F)c(OCc4ccc(C#N)cc4F)n3)cc2F)nc2ccc(C(=O)O)cc21] | 35 | 617.2 | 1H NMR (400 MHz, Acetonitrile-d3) δ 8.57 (d, J = 1.5 Hz, 1H), 7.86 (dd, J = 8.5, 1.6 Hz, 1H), 7.75-7.68 (m, 2H), 7.62-7.53 (m, 4H), 7.51 (ddd, J = 8.2, 3.1, 1.4 Hz, 1H), 7.20 (dd, J = 11.6, 6.1 Hz, 1H), 5.66 (s, 2H), 5.24 (t, J = 7.2 Hz, 1H), 4.54 (dd, J = 11.0, 1.4 Hz, 1H), 4.37 (s, 2H), 4.23 (dd, J = 11.0, 6.7 Hz, 1H), 4.13 (t, J = 8.5 Hz, 1H), 3.67 (t, J = 8.4 Hz, 1H), 2.87 (dq, J = 15.2, 7.6 Hz, 1H), 0.57 (d, J = 7.1 Hz, 3H). |

TABLE 2-continued

Compounds

| Ex. | Structure | Procedure | ES/MS m/z | ¹H NMR |
|---|---|---|---|---|
| 487 | 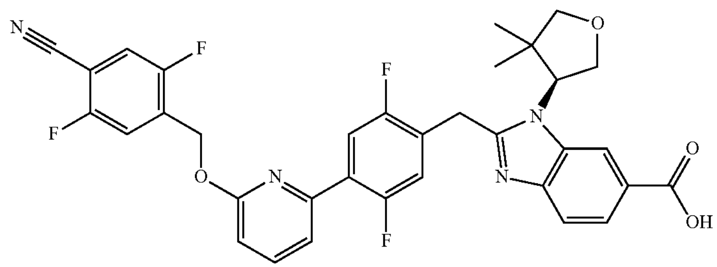 [SMILES: CC1(C)COC[C@H]1n1c(Cc2cc(F)c(-c3cccc(OCc4cc(F)c(C#N)cc4F)n3)cc2F)nc2ccc(C(=O)O)cc21] | 35 | 631.2 | 1H NMR (400 MHz, Acetonitrile-d3) δ 8.55 (s, 1H), 7.86 (dd, J = 8.5, 1.5 Hz, 1H), 7.83-7.78 (m, 1H), 7.75 (dd, J = 10.7, 6.4 Hz, 1H), 7.62-7.57 (m, 1H), 7.53 (ddt, J = 10.5, 9.2, 4.8 Hz, 3H), 7.22 (dd, J = 11.5, 6.1 Hz, 1H), 6.92 (dd, J = 8.3, 0.7 Hz, 1H), 5.58 (s, 2H), 4.84 (d, J = 6.6 Hz, 1H), 4.56 (dd, J = 11.2, 6.9 Hz, 1H), 4.36 (d, J = 6.3 Hz, 2H), 3.85 (d, J = 8.7 Hz, 1H), 3.75 (d, J = 8.7 Hz, 1H), 1.34 (s, 3H), 0.65 (s, 3H). |
| 488 | 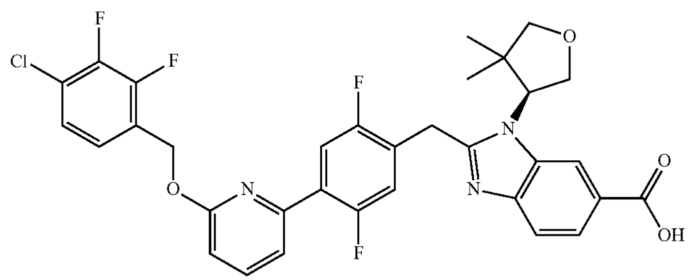 [SMILES: CC1(C)COC[C@H]1n1c(Cc2cc(F)c(-c3cccc(OCc4ccc(Cl)c(F)c4F)n3)cc2F)nc2ccc(C(=O)O)cc21] | 35 | 640.2 | 1H NMR (400 MHz, Acetonitrile-d3) δ 8.69 (s, 1H), 8.01 (dd, J = 8.6, 1.5 Hz, 1H), 7.85 (dd, J = 10.8, 6.4 Hz, 1H), 7.77 (dd, J = 8.2, 7.5 Hz, 1H), 7.72 (d, J = 8.5 Hz, 1H), 7.50 (dd, J = 7.5, 1.7 Hz, 1H), 7.36-7.22 (m, 3H), 6.86 (d, J = 8.2 Hz, 1H), 5.53 (d, J = 1.3 Hz, 2H), 4.93 (d, J = 6.6 Hz, 1H), 4.62-4.50 (m, 3H), 4.43 (dd, J = 11.6, 6.8 Hz, 1H), 3.89 (d, J = 8.9 Hz, 1H), 3.76 (d, J = 8.9 Hz, 1H), 1.34 (s, 3H), 0.68 (s, 3H). |

TABLE 2-continued

Compounds

| Ex. | Structure | Procedure | ES/MS m/z | ¹H NMR |
|---|---|---|---|---|
| 489 | 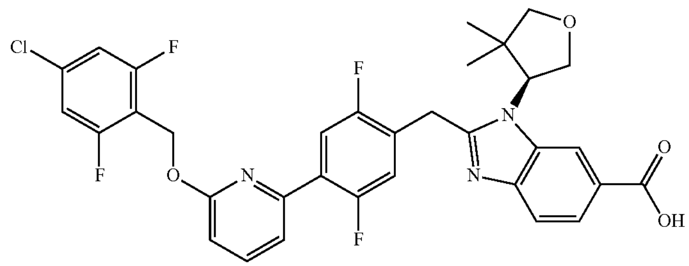 [SMILES: CC1(C)COC[C@H]1n1c(Cc2cc(F)c(-c3cccc(OCc4c(F)cc(Cl)cc4F)n3)cc2F)nc2ccc(C(=O)O)cc21] | 35 | 640.2 | 1H NMR (400 MHz, Acetonitrile-d3) δ 8.62 (s, 1H), 7.98-7.89 (m, 2H), 7.75 (t, J = 7.9 Hz, 1H), 7.65 (d, J = 8.5 Hz, 1H), 7.50 (dd, J = 7.5, 1.7 Hz, 1H), 7.26 (dd, J = 11.5, 6.1 Hz, 1H), 7.14 (d, J = 7.4 Hz, 2H), 6.78 (d, J = 8.2 Hz, 1H), 5.51 (s, 2H), 4.89 (d, J = 6.7 Hz, 1H), 4.55 (dd, J = 11.4, 1.5 Hz, 1H), 4.49-4.37 (m, 3H), 3.87 (d, J = 8.8 Hz, 1H), 3.75 (d, J = 8.8 Hz, 1H), 1.34 (s, 3H), 0.67 (s, 3H). |
| 490 | 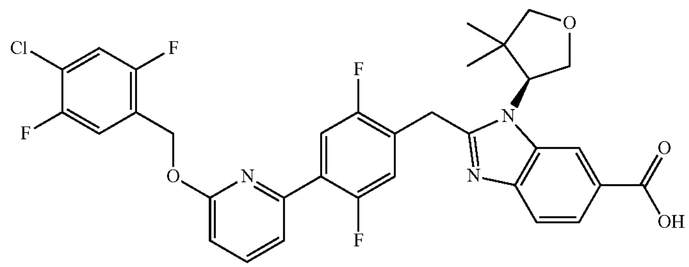 [SMILES: CC1(C)COC[C@H]1n1c(Cc2cc(F)c(-c3cccc(OCc4cc(F)c(Cl)cc4F)n3)cc2F)nc2ccc(C(=O)O)cc21] | | 640.2 | 1H NMR (400 MHz, Acetonitrile-d3) δ 8.56 (s, 1H), 7.88 (dd, J = 8.5, 1.5 Hz, 1H), 7.85-7.73 (m, 2H), 7.60 (d, J = 8.5 Hz, 1H), 7.54-7.48 (m, 1H), 7.44 (dd, J = 9.5, 6.3 Hz, 1H), 7.35 (dd, J = 9.2, 6.1 Hz, 1H), 7.22 (dd, J = 11.5, 6.1 Hz, 1H), 6.87 (d, J = 8.2 Hz, 1H), 5.50 (s, 2H), 4.85 (d, J = 6.7 Hz, 1H), 4.55 (dd, J = 11.2, 1.5 Hz, 1H), 4.42 (dd, J = 11.1, 6.9 Hz, 1H), 4.38 (d, J = 6.0 Hz, 2H), 3.86 (d, J = 8.7 Hz, 1H), 3.75 (d, J = 8.7 Hz, 1H), 1.34 (s, 3H), 0.65 (s, 3H). |

TABLE 2-continued

Compounds

| Ex. | Structure | Procedure | ES/MS m/z | 1H NMR |
|---|---|---|---|---|
| 491 | 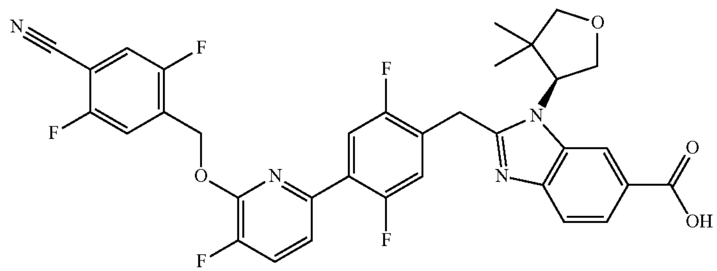 [SMILES: CC1(C)COC[C@H]1n1c(Cc2cc(F)c(-c3ccc(F)c(OCc4cc(F)c(C#N)cc4F)n3)cc2F)nc2ccc(C(=O)O)cc21] | 35 | 649.2 | 1H NMR (400 MHz, Acetonitrile-d3) δ 8.59 (s, 1H), 7.90 (dd, J = 8.5, 1.5 Hz, 1H), 7.74 (dd, J = 10.7, 6.5 Hz, 1H), 7.66-7.49 (m, 5H), 7.25 (dd, J = 11.6, 6.1 Hz, 1H), 5.68 (s, 2H), 4.87 (d, J = 6.8 Hz, 1H), 4.59 (dd, J = 11.2, 1.5 Hz, 1H), 4.46 (dd, J = 11.1, 6.8 Hz, 1H), 4.39 (d, J = 6.7 Hz, 2H), 3.89 (d, J = 8.7 Hz, 1H), 3.78 (d, J = 8.7 Hz, 1H), 1.37 (s, 3H), 0.68 (s, 3H). |
| 492 | 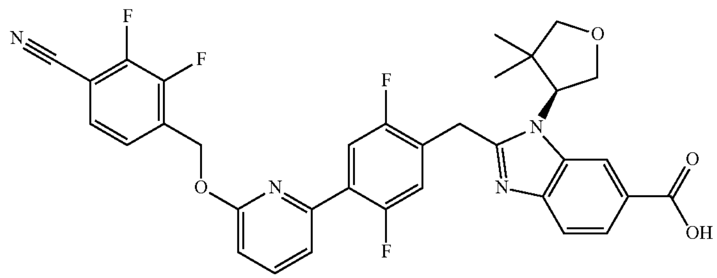 [SMILES: CC1(C)COC[C@H]1n1c(Cc2cc(F)c(-c3cccc(OCc4ccc(C#N)c(F)c4F)n3)cc2F)nc2ccc(C(=O)O)cc21] | 35 | 631.3 | 1H NMR (400 MHz, Acetonitrile-d3) δ 8.70 (s, 1H), 8.02 (dd, J = 8.6, 1.5 Hz, 1H),7.83 (d, J = 7.5 Hz, 1H), 7.81-7.75 (m, 1H), 7.72 (d, J = 8.5 Hz, 1H), 7.57-7.51 (m, 2H), 7.51-7.44 (m, 1H), 7.29 (dd, J = 11.4, 6.1 Hz, 1H), 6.92 (d, J = 8.3 Hz, 1H), 5.62 (s, 2H), 4.93 (d, J = 6.6 Hz, 1H), 4.62-4.54 (m, 1H), 4.51 (d, J = 8.4 Hz, 2H), 4.44 (dd, J = 11.5, 6.7 Hz, 1H), 3.90 (d, J = 8.9 Hz, 1H), 3.77 (d, J = 8.9 Hz, 1H), 1.35 (s, 3H), 0.69 (s, 3H). |
| 493 | 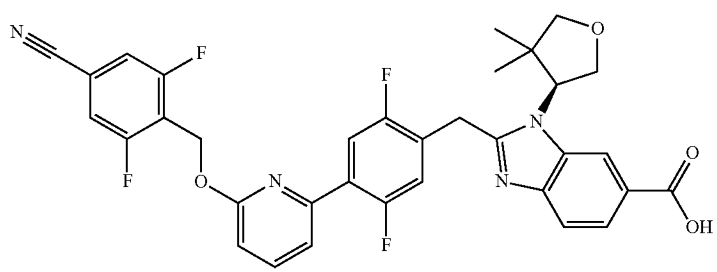 [SMILES: CC1(C)COC[C@H]1n1c(Cc2cc(F)c(-c3cccc(OCc4c(F)cc(C#N)cc4F)n3)cc2F)nc2ccc(C(=O)O)cc21] | 35 | 631.3 | 1H NMR (400 MHz, Acetonitrile-d3) δ 8.60 (s, 1H), 7.95-7.88 (m, 2H), 7.81 (t, J = 7.8 Hz, 1H), 7.64 (d, J = 8.5 Hz, 1H), 7.58 (dd, J = 7.3, 1.6 Hz, 1H), 7.48 (d, J = 6.7 Hz, 2H), 7.26 (dd, J = 11.6, 6.0 Hz, 1H), 6.84 (d, J = 8.2 Hz, 1H), 5.63 (s, 2H), 4.88 (d, J = 6.9 Hz, 1H), 4.60 (dd, J = 11.3, 1.4 Hz, 1H), 4.46 (dd, J = 5.9 6.8 Hz, 1H), 4.41 (d, J = 5.9 Hz, 2H), 3.89 (d, J = 8.7 Hz, |

TABLE 2-continued

Compounds

| Ex. | Structure | Procedure | ES/MS m/z | ¹H NMR |
|---|---|---|---|---|
| 494 | 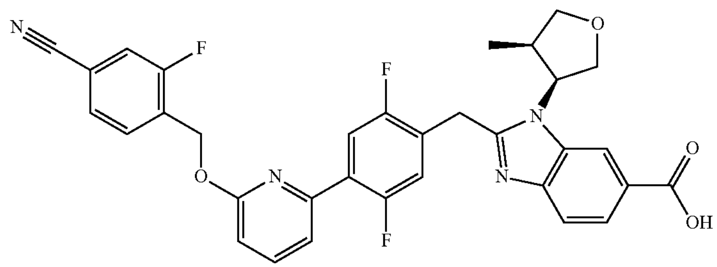 [SMILES: C[C@H]1COC[C@H]1n1c(Cc2cc(F)c(-c3cccc(OCc4ccc(C#N)cc4F)n3)cc2F)nc2ccc(C(=O)O)cc21] | 35 | 599.3 | 1H NMR (400 MHz, Acetonitrile-d3) δ 8.60 (d, J = 1.5 Hz, 1H), 7.89 (dd, J = 8.5, 1.6 Hz, 1H), 7.84-7.75 (m, 2H), 7.72 (t, J = 7.5 Hz, 1H), 7.62 (d, J = 8.5 Hz, 1H), 7.58 (d, J = 8.7 Hz, 2H), 7.54 (dd, J = 7.5, 1.8 Hz, 1H), 7.23 (dd, J = 11.5, 6.1 Hz, 1H), 6.91 (d, J = 8.2 Hz, 1H), 5.62 (s, 2H), 5.27 (t, J = 7.2 Hz, 1H), 4.57 (dd, J = 10.9, 1.4 Hz, 1H),4.41 (s, 2H), 4.26 (dd, J = 11.0, 6.7 Hz, 1H), 4.16 (t, J = 8.5 Hz, 1H), 3.70 (t, J = 8.4 Hz, 1H), 2.91 (hept, J = 7.1 Hz, 1H), 0.59 (d, J = 7.1 Hz, 3H). |
| 495 | 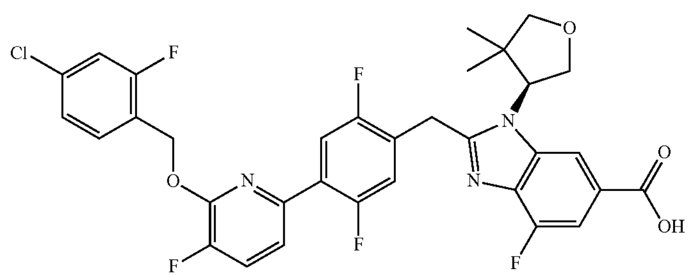 [SMILES: CC1(C)COC[C@H]1n1c(Cc2cc(F)c(-c3ccc(F)c(OCc4ccc(Cl)cc4F)n3)cc2F)nc2c(F)cc(C(=O)O)cc21] | 35 | 658.2 | 1H NMR (400 MHz, Acetonitrile-d3) δ 8.41 (s, 1H), 7.81 (dd, J = 10.7, 6.5 Hz, 1H), 7.63-7.50 (m, 4H), 7.30-7.19 (m, 3H), 5.59 (d, J = 1.1 Hz, 2H), 4.85 (d, J = 6.6 Hz, 1H), 4.54 (dd, J = 11.3, 1.6 Hz, 1H), 4.43 (dd, J = 11.3, 6.8 Hz, 1H), 4.37 (d, J = 7.1 Hz, 2H), 3.84 (d, J = 8.8 Hz, 1H), 3.75 (d, J = 8.7 Hz, 1H), 1.35 (s, 3H), 0.67 (s, 3H). |

TABLE 2-continued

Compounds

| Ex. | Structure | Procedure | ES/MS m/z | ¹H NMR |
|---|---|---|---|---|
| 496 | 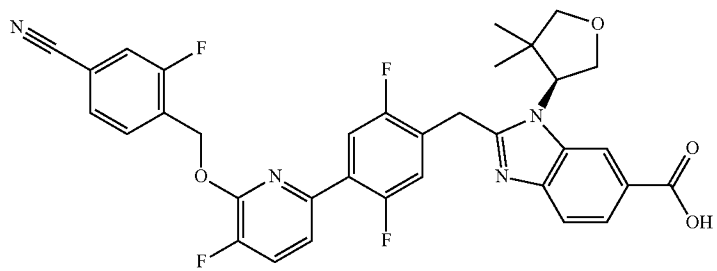 [SMILES: CC1(C)COC[C@H]1n1c(Cc2cc(F)c(-c3ccc(F)c(OCc4ccc(C#N)cc4F)n3)cc2F)nc2ccc(C(=O)O)cc21] | 35 | 631.3 | 1H NMR (400 MHz, Acetonitrile-d3) δ 8.58 (s, 1H), 7.89 (dd, J = 8.5, 1.5 Hz, 1H), 7.79-7.71 (m, 2H), 7.65-7.52 (m, 5H), 7.24 (dd, J = 11.6, 6.1 Hz, 1H), 5.70 (s, 2H), 4.86 (d, J = 6.6 Hz, 1H), 4.59 (dd, J = 11.2, 1.6 Hz, 1H), 4.45 (dd, J = 11.3, 7.0 Hz, 1H) 4.38 (d, J = 6.4 Hz, 2H), 3.88 (d, J = 8.7 Hz, 1H), 3.78 (d, J = 8.7 Hz, 1H), 1.37 (s, 3H), 0.68 (s, 3H). |
| 497 | 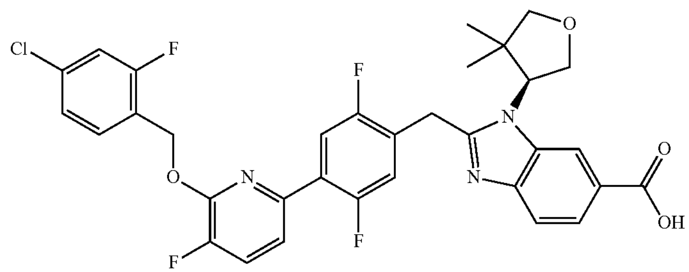 [SMILES: CC1(C)COC[C@H]1n1c(Cc2cc(F)c(-c3ccc(F)c(OCc4ccc(Cl)cc4F)n3)cc2F)nc2ccc(C(=O)O)cc21] | 35 | 640.2 | 1H NMR (400 MHz, Acetonitrile-d3) δ 8.56 (s, 1H), 7.87 (dd, J = 8.5, 1.5 Hz, 1H), 7.80 (dd, J = 10.8, 6.5 Hz, 1H), 7.64-7.47 (m, 4H), 7.32-7.16 (m, 3H), 5.59 (s, 2H), 4.85 (d, J = 6.8 Hz, 1H), 4.56 (dd, J = 11.1, 1.6 Hz, 1H), 4.48-4.42 (m, 1H), 4.42-4.30 (m, 2H), 3.86 (d, J = 8.7 Hz, 1H), 3.75 (d, J = 8.7 Hz, 1H), 1.34 (s, 3H), 0.65 (s, 3H). |
| 498 | 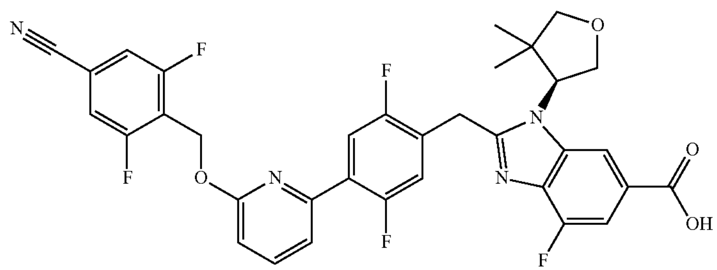 [SMILES: CC1(C)COC[C@H]1n1c(Cc2cc(F)c(-c3cccc(OCc4c(F)cc(C#N)cc4F)n3)cc2F)nc2c(F)cc(C(=O)O)cc21] | 35 | 649.2 | 1H NMR (400 MHz, Acetonitrile-d3) δ 8.46 (s, 1H), 7.90 (dd, J = 10.8, 6.4 Hz, 1H), 7.78 (t, J = 7.9 Hz, 1H), 7.63 (dd, J = 11.2, 1.2 Hz, 1H), 7.55 (dd, J = 7.5, 1.8 Hz, 1H), 7.45 (d, J = 6.7 Hz, 2H), 7.26 (dd, J = 11.4, 6.1 Hz, 1H), 6.81 (d, J = 8.2 Hz, 1H), 5.60 (s, 2H), 4.89 (d, J = 6.7 Hz, 1H), 4.55 (dd, J = 11.4, 1.5 Hz, 1H), 4.50-4.37 (m, 3H), 3.86 (d, J = 8.8 Hz, 1H), 3.76 (d, J = 8.8 Hz, 1H), 1.36 (s, 3H), 0.69 (s, 3H). |

TABLE 2-continued

Compounds

| Ex. | Structure | Procedure | ES/MS m/z | ¹H NMR |
|---|---|---|---|---|
| 499 | 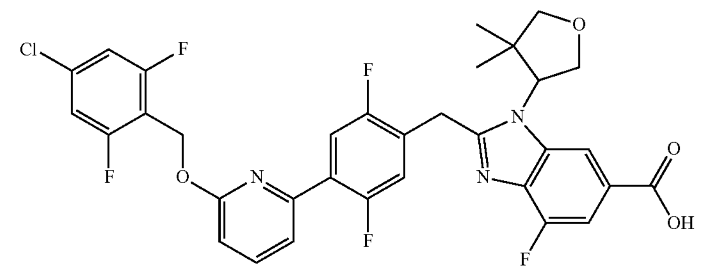 [SMILES: CC1(C)COCC1n1c(Cc2cc(F)c(-c3cccc(OCc4c(F)cc(Cl)cc4F)n3)cc2F)nc2c(F)cc(C(=O)O)cc21] | 35 | 658.1 | 1H NMR (400 MHz, DMSO-d6) δ 13.08 (s, 1H), 8.35 (s, 1H), 7.92 (dd, J = 10.4, 6.4 Hz, 1H), 7.87 (t, J = 7.9 Hz, 1H), 7.58-7.40 (m, 5H), 6.91 (d, J = 8.2 Hz, 1H), 5.50 (s, 2H), 5.03 (d, J = 6.6 Hz, 1H), 4.59-4.47 (m, 2H), 4.47-4.36 (m, 2H), 3.74 (q, J = 8.7 Hz, 2H), 1.34 (s, 3H), 0.61 (s, 3H). |
| 500 | 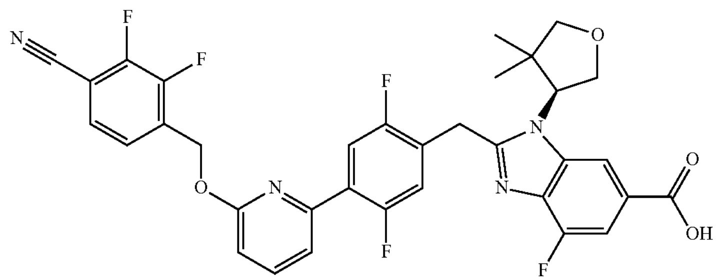 [SMILES: CC1(C)COC[C@H]1n1c(Cc2cc(F)c(-c3cccc(OCc4ccc(C#N)c(F)c4F)n3)cc2F)nc2c(F)cc(C(=O)O)cc21] | 35 | 649.2 | 1H NMR (400 MHz, Acetonitrile-d3) δ 8.48 (s, 1H), 7.83-7.72 (m, 2H), 7.65 (dd, J = 11.1, 1.2 Hz, 1H), 7.56-7.44 (m, 3H), 7.25 (dd, J =11.5, 6.1Hz, 1H), 6.90 (d, J = 8.2 Hz, 1H), 5.61 (d, J = 1.3 Hz, 1H), 4.91 (d, J = 6.6 Hz, 2H), 4.54 (dd, J = 11.5, 1.4 Hz, 1H), 4.48-4.37 (m, 3H), 3.86 (d, J = 8.8 Hz, 1H), 3.76 (d, J = 8.9 Hz, 1H), 1.35 (s, 3H), 0.69 (s, 3H). |
| 501 | 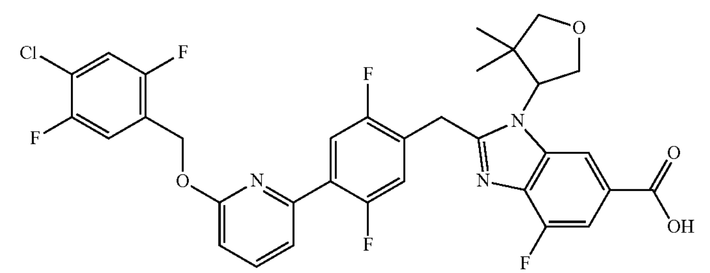 [SMILES: CC1(C)COCC1n1c(Cc2cc(F)c(-c3cccc(OCc4cc(F)c(Cl)cc4F)n3)cc2F)nc2c(F)cc(C(=O)O)cc21] | 35 | 658.1 | 1H NMR (400 MHz, Acetonitrile-d3) δ 8.49 (s, 1H), 7.82 (dd, J = 10.8, 6.4 Hz, 1H), 7.76 (dd, J = 8.3, 7.4 Hz, 1H), 7.67 (dd, J = 11.0, 1.2 Hz, 2H), 7.50-7.39 (m, 2H), 7.33 (dd, J = 9.2, 6.1 Hz, 1H), 7.25 (dd, J = 11.5, 6.1Hz, 1H), 6.87 (dd, J = 8.3, 0.6 Hz, 1H), 5.47 (s, 2H), 4.93 (d, J = 6.6 Hz, 1H), 4.57-4.46 (m, 3H), 4.47-4.37 (m, 1H), 3.85 (d, J = 8.9 Hz, 1H), 3.76 (d, J = 8.9 Hz, 1H), 1.34 (s, 3H), 0.69 (s, 3H). |

TABLE 2-continued

Compounds

| Ex. | Structure | Procedure | ES/MS m/z | 1H NMR |
|---|---|---|---|---|
| 502 A | 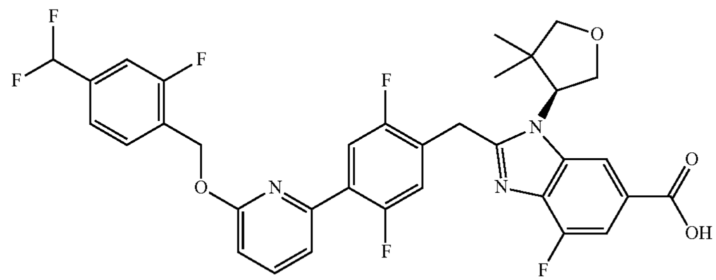 [SMILES: CC1(C)COC[C@H]1n1c(Cc2cc(F)c(-c3cccc(OCc4ccc(C(F)F)cc4F)n3)cc2F)nc2c(F)cc(C(=O)O)cc21] | chiral separation Peak 2 | 656.1 | 1H NMR (400 MHz, Acetonitrile-d3) δ 8.49 (s, 1H), 7.89-7.81 (m, 1H), 7.79 (d, J = 7.9 Hz, 1H), 7.70-7.62 (m, 2H), 7.54 (dd, J = 7.4, 1.7 Hz, 1H), 7.40-7.33 (m, 2H), 7.25 (dd, J = 11.4, 6.1 Hz, 1H), 6.89 (d, J = 8.2 Hz, 1H), 6.78 (t, J = 55.9 Hz, 1H), 5.59 (s, 2H), 4.90 (d, J = 6.6 Hz, 1H), 4.55 (dd, J = 11.5, 1.4 Hz, 1H), 4.48-4.38 (m, 3H), 3.86 (d, J = 8.8 Hz, 1H), 3.76 (d, J = 8.8 Hz, 1H), 1.35 (s, 3H), 0.69 (s, 3H). |
| 502 B | 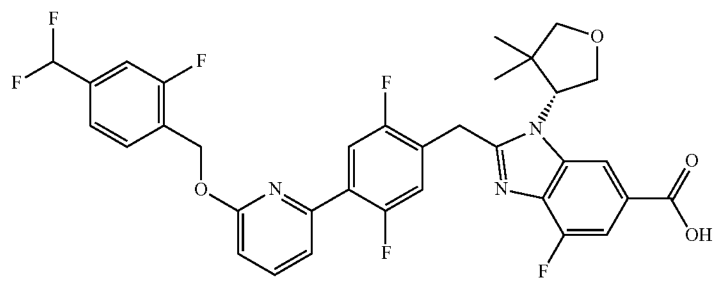 [SMILES: CC1(C)COC[C@@H]1n1c(Cc2cc(F)c(-c3cccc(OCc4ccc(C(F)F)cc4F)n3)cc2F)nc2c(F)cc(C(=O)O)cc21] | chiral separation Peak 1 | 656.2 | 1H NMR (400 MHz, Acetonitrile-d3) δ 8.44 (s, 1H), 7.91-7.77 (m, 2H), 7.70 (t, J = 7.7 Hz, 1H), 7.60 (dd, J = 11.3, 1.2 Hz, 1H), 7.57 (dd, J = 7.5, 1.8 Hz, 1H), 7.44-7.34 (m, 2H), 7.26 (dd, J =11.5, 6.1Hz, 1H), 6.98-6.88 (m, 1H), 6.74 (d, J = 55.9 Hz, 1H), 5.62 (s, 2H), 4.88 (d, J = 6.5 Hz, 1H), 4.57 (dd, J = 11.2, 1.5 Hz, 1H), 4.50-4.32 (m, 3H), 3.87 (d, J = 8.7 Hz, 1H), 3.77 (d, J = 8.8 Hz, 1H), 1.38 (s, 3H), 0.69 (s, 3H). |

TABLE 2-continued

Compounds

| Ex. | Structure | Procedure | ES/MS m/z | ¹H NMR |
|---|---|---|---|---|
| 503 | 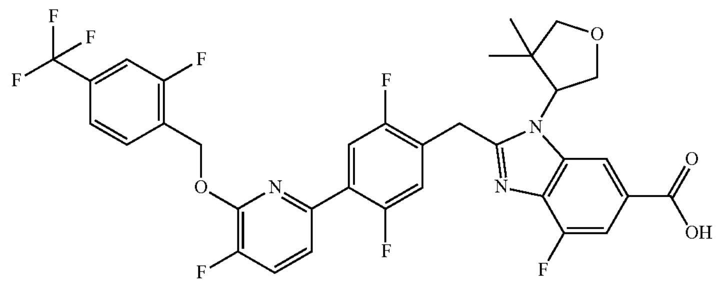 [SMILES: CC1(C)COCC1n1c(Cc2cc(F)c(-c3ccc(F)c(OCc4ccc(C(F)(F)F)cc4F)n3)cc2F)nc2c(F)cc(C(=O)O)cc21] | 35 | 692.1 | 1H NMR (400 MHz, Acetonitrile-d3) δ 8.41 (s, 1H), 7.80-7.72 (m, 2H), 7.63-7.48 (m, 5H), 7.23 (dd, J = 11.5, 6.1 Hz, 1H), 5.69 (s, 2H), 4.85 (d, J = 6.7 Hz, 1H), 4.55 (d, J = 11.2 Hz, 1H), 4.45 (d, J = 8.1 Hz, 1H), 4.42-4.29 (m, 2H), 3.84 (d, J = 8.8 Hz, 1H), 3.75 (d, J = 8.9 Hz, 1H), 1.35 (s, 3H), 0.66 (s, 3H). |
| 504 | 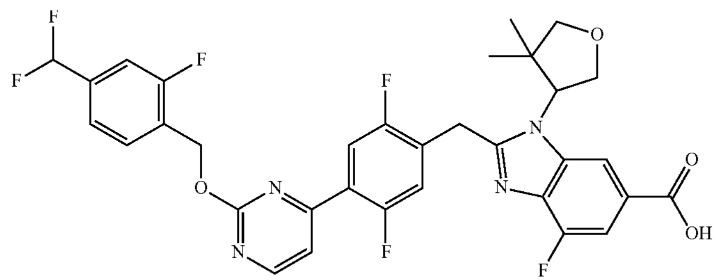 [SMILES: CC1(C)COCC1n1c(Cc2cc(F)c(-c3ccnc(OCc4ccc(C(F)F)cc4F)n3)cc2F)nc2c(F)cc(C(=O)O)cc21] | 35 | 657.1 | 1H NMR (400 MHz, Acetonitrile-d3) δ 8.65 (d, J = 5.2 Hz, 1H), 8.45 (s, 1H), 7.95 (dd, J = 10.4, 6.2 Hz, 1H), 7.69 (t, J = 7.6 Hz, 1H), 7.62 (dd, J = 11.1, 1.2 Hz, 1H), 7.58 (dd, J = 5.2, 1.8 Hz, 1H), 7.42-7.35 (m, 2H), 7.30 (dd, J = 11.5, 5.9 Hz, 1H), 6.79 (t, J = 55.9 Hz, 1H), 5.61 (s, 2H), 4.88 (d, J = 6.7 Hz, 1H), 4.55 (d, J = 11.4 Hz, 1H), 4.50-4.36 (m, 3H), 3.85 (d, J = 8.8 Hz, 1H), 3.76 (d, J = 8.8 Hz, 1H), 1.35 (s, 3H), 0.68 (s, 3H). |
| 505 | 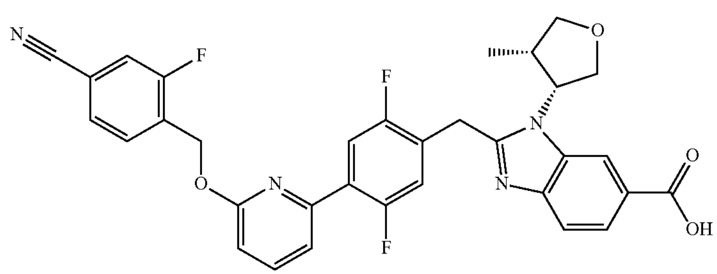 [SMILES: C[C@@H]1COC[C@@H]1n1c(Cc2cc(F)c(-c3cccc(OCc4ccc(C#N)cc4F)n3)cc2F)nc2ccc(C(=O)O)cc21] | 35 | 599.2 | 1H NMR (400 MHz, DMSO-d6) δ 8.50 (s, 1H), 7.94-7.87 (m, 2H), 7.81-7.71 (m, 3H), 7.61 (d, J = 8.4 Hz, 1H), 7.54 (d, J = 7.2 Hz, 1H), 7.44 (dd, J = 11.4, 6.3 Hz, 2H), 6.99 (d, J = 8.2 Hz, 1H), 5.60 (s, 2H), 5.42 (t, J = 7.1 Hz, 1H), 4.56-4.39 (m, 3H), 4.26-4.17 (m, 1H), 4.12 (t, J = 8.5 Hz, 1H), 3.59 (t, J = 8.5 Hz, 1H), 2.92-2.82 (m, 1H), 0.52 (d, J = 7.0 Hz, 3H). |

TABLE 2-continued

Compounds

| Ex. | Structure | Procedure | ES/MS m/z | ¹H NMR |
|---|---|---|---|---|
| 506 | 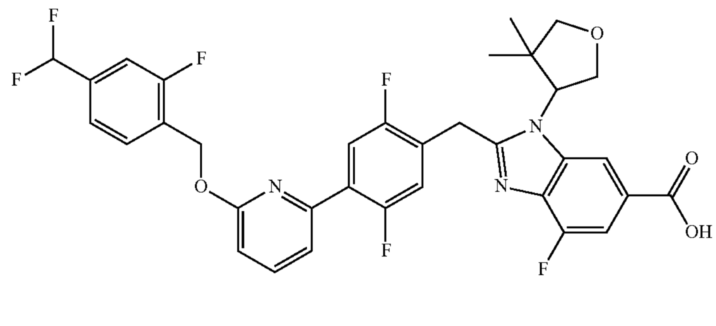 [SMILES: CC1(C)COCC1n1c(Cc2cc(F)c(-c3cccc(OCc4ccc(C(F)F)cc4F)n3)cc2F)nc2c(F)cc(C(=O)O)cc21] | 35 | 656.1 | 1H NMR (400 MHz, Acetonitrile-d3) δ 8.41 (s, 1H), 7.88-7.77 (m, 2H), 7.67 (t, J = 7.7 Hz, 1H), 7.62 (d, J = 11.0 Hz, 1H), 7.58-7.51 (m, 1H), 7.41-7.32 (m, 2H), 7.23 (dd, J = 11.5, 6.1 Hz, 1H), 6.94-6.61 (m, 3H), 5.60 (s, 2H),4.87 (d, J = 6.7 Hz, 1H), 4.57 (d, J = 11.4 Hz, 1H), 4.52-4.45 (m, 1H), 4.45-4.32 (m, 2H), 3.85 (d, J = 8.8 Hz, 1H), 3.83-3.74 (m, 1H), 1.35 (s, 3H), 0.67 (s, 3H). |
| 507 | 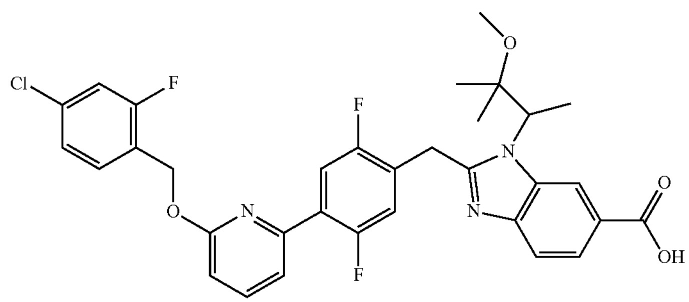 [SMILES: COC(C)(C)C(C)n1c(Cc2cc(F)c(-c3cccc(OCc4ccc(Cl)cc4F)n3)cc2F)nc2ccc(C(=O)O)cc21] | 35 | 624.1 | 1H NMR (400 MHz, Acetonitrile-d3) δ 8.58 (dd, J = 1.6, 0.6 Hz, 1H), 7.87-7.77 (m, 2H), 7.59-7.47 (m, 3H), 7.28-7.20 (m, 2H), 7.16 (dd, J = 11.5, 6.1Hz, 1H), 6.84 (dd, J = 8.3, 0.7 Hz, 1H), 5.51 (d, J = 1.0 Hz, 2H), 4.55 (q, J = 7.1 Hz, 1H), 4.38 (d, J = 2.4 Hz, 2H), 3.18 (s, 2H), 1.64 (d, J = 7.1 Hz, 3H), 1.34 (s, 3H), 1.02 (s, 3H). |
| 508 | 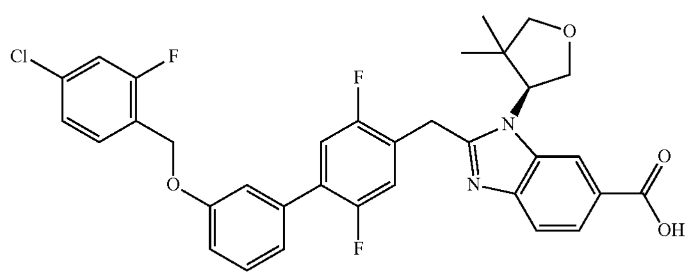 [SMILES: CC1(C)COC[C@H]1n1c(Cc2cc(F)c(-c3cccc(OCc4ccc(Cl)cc4F)c3)cc2F)nc2ccc(C(=O)O)cc21] | 35 | 621.2 | 1H NMR (400 MHz, Acetonitrile-d3) δ 8.55 (s, 1H), 7.87 (dd, J = 8.5, 1.5 Hz, 1H), 7.60 (d, J = 8.5 Hz, 1H), 7.53 (t, J = 8.2 Hz, 1H), 7.39 (t, J = 7.9 Hz, 1H), 7.32 (dd, J = 10.2, 6.4 Hz, 1H), 7.31-7.13 (m, 5H), 7.04 (ddd, J = 8.4, 2.6, 1.0 Hz, 1H), 5.16 (s, 2H), 4.84 (dd, J = 6.9, 1.6 Hz, 1H), 4.55 (dd, J = 11.2, 1.6 Hz, 1H), 4.43 (dd, J = 11.2, 6.9 Hz, 2H), 4.35 (d, J = 6.5 Hz, 2H), 3.85 (d, J = 8.7 Hz, 1H), 3.75 (d, J = 8.7 Hz, 1H), 1.34 (s, 3H), 0.65 (s, 3H). |

TABLE 2-continued

Compounds

| Ex. | Structure | Procedure | ES/MS m/z | ¹H NMR |
|---|---|---|---|---|
| 509 | 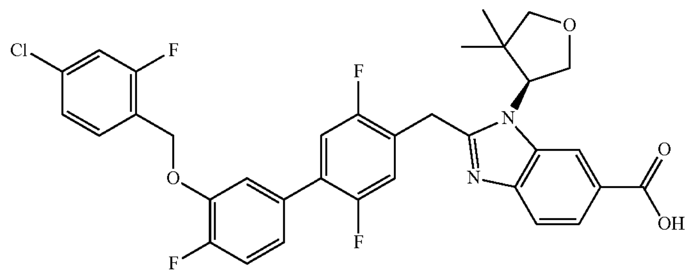 [SMILES: CC1(C)COC[C@H]1n1c(Cc2cc(F)c(-c3ccc(F)c(OCc4ccc(Cl)cc4F)c3)cc2F)nc2ccc(C(=O)O)cc21] | 35 | 639.2 | 1H NMR (400 MHz, Acetonitrile-d3) δ 8.55 (s, 1H), 7.87 (dd, J = 8.5, 1.5 Hz, 1H), 7.60 (d, J = 8.5 Hz, 1H), 7.53 (t, J = 8.2 Hz, 1H), 7.39-7.10 (m, 7H), 5.19 (s, 2H), 4.84 (dd, J = 6.9, 1.6 Hz, 1H), 4.55 (dd, J = 11.2, 1.6 Hz, 1H), 4.42 (dd, J = 11.1, 6.8 Hz, 1H), 4.35 (d, J = 6.6 Hz, 2H), 3.85 (d, J = 8.7 Hz, 1H), 3.74 (d, J = 8.7 Hz, 1H), 1.34 (s, 3H), 0.64 (s, 3H). |
| 510 | 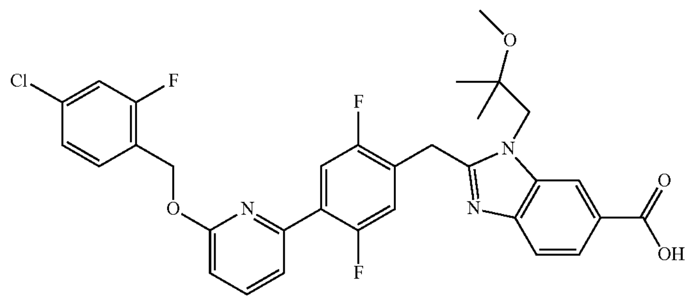 [SMILES: COC(C)(C)Cn1c(Cc2cc(F)c(-c3cccc(OCc4ccc(Cl)cc4F)n3)cc2F)nc2ccc(C(=O)O)cc21] | 35 | 610.2 | 1H NMR (400 MHz, Acetonitrile-d3) δ 8.24 (s, 1H), 7.91-7.73 (m, 3H), 7.61-7.48 (m, 3H), 7.29-7.13 (m, 3H), 6.84 (d, J = 8.2 Hz, 1H), 5.52 (s, 2H), 4.44 (s, 2H), 4.30 (s, 2H), 3.14 (s, 3H), 1.22 (s, 6H). |
| 511 | 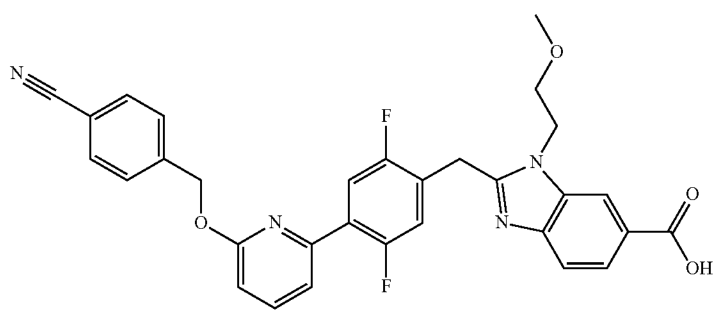 [SMILES: COCCn1c(Cc2cc(F)c(-c3cccc(OCc4ccc(C#N)cc4)n3)cc2F)nc2ccc(C(=O)O)cc21] | 6 | 555.3 | 1H NMR (400 MHz, Methanol-d4) δ 8.25 (s, 1H), 7.97 (dd, J = 8.5, 1.5 Hz 1H), 7.78 (t, J = 7.9 Hz, 1H), 7.75-7.60 (m, 6H), 7.51 (d, J = 7.4 Hz, 1H), 7.12 (dd, J = 11.6, 6.0 Hz, 1H), 6.90 (d, J = 8.3 Hz, 1H), 5.57 (s, 2H), 4.55 (t, J = 5.1 Hz, 2H), 4.47 (s, 2H), 3.72 (t, J = 5.0 Hz, 2H), 3.25 (s, 3H). |

TABLE 2-continued

Compounds

| Ex. | Structure | Procedure | ES/MS m/z | ¹H NMR |
|---|---|---|---|---|
| 512 | 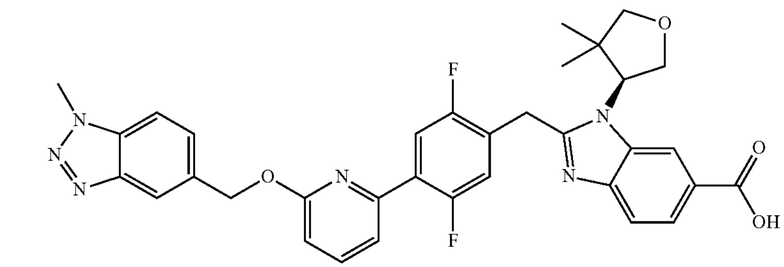 [SMILES: Cn1nnc2cc(COc3cccc(-c4cc(F)c(Cc5nc6ccc(C(=O)O)cc6n5[C@@H]5COCC5(C)C)cc4F)n3)ccc21] | 35 | (M+) 624.6 | 1H NMR (400 MHz, DMSO-d6) δ 8.50 (s, 1H), 8.15 (s, 1H), 7.96-7.83 (m, 3H), 7.82 (dd, J = 8.5, 1.5 Hz, 1H), 7.71 (dd, J = 8.6, 1.4 Hz, 1H), 7.63 (d, J = 8.4 Hz, 1H), 7.53 (dd, J = 7.5, 1.5 Hz, 1H), 7.47 (dd, J = 11.1, 6.4 Hz, 1H), 6.99 (d, J = 8.3 Hz, 1H), 5.65 (s, 2H), 5.03 (d, J = 6.6 Hz, 1H), 4.63-4.54 (m, 1H), 4.53 (s, 1H), 4.49-4.35 (m, 2H), 4.31 (s, 3H), 3.81-3.70 (m, 2H), 1.34 (s, 3H), 0.61 (s, 3H). |
| 513 | 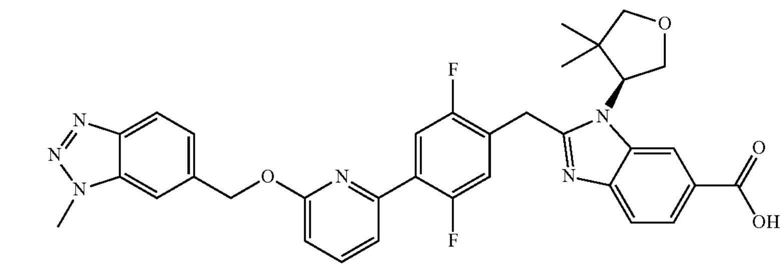 [SMILES: Cn1nnc2ccc(COc3cccc(-c4cc(F)c(Cc5nc6ccc(C(=O)O)cc6n5[C@@H]5COCC5(C)C)cc4F)n3)cc21] | 35 | (M+) 624.6 | 1H NMR (400 MHz, DMSO-d6) δ 8.49 (s, 1H), 8.04 (d, J = 8.6 Hz, 1H), 8.01 (s, 1H), 7.90 (t, J = 7.9 Hz, 1H), 7.87-7.78 (m, 2H), 7.62 (d, J = 8.5 Hz, 1H), 7.54 (ddd, J = 7.6, 5.1, 1.4 Hz, 2H), 7.46 (dd, J = 11.4, 6.2 Hz, 1H), 7.00 (d, J = 8.2 Hz, 1H), 5.67 (s, 2H), 5.02 (d, J = 6.6 Hz, 1H), 4.64-4.48 (m, 2H), 4.48-4.32 (m, 2H), 4.30 (s, 3H), 3.82-3.72 (m, 2H), 1.34 (s, 3H), 0.61 (s, 3H). |
| 514 | 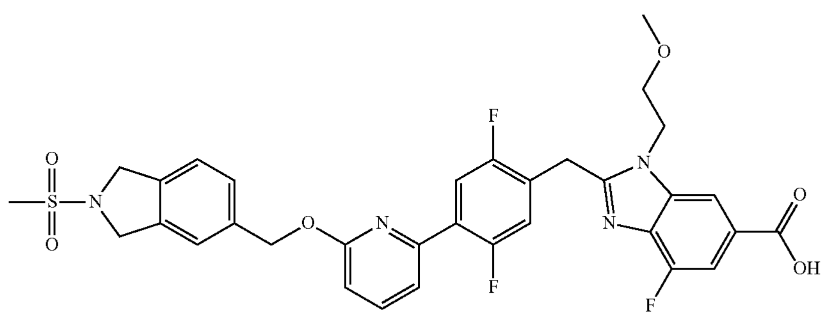 [SMILES: COCCn1c(Cc2cc(F)c(-c3cccc(OCc4ccc5c(c4)CN(S(C)(=O)=O)C5)n3)cc2F)nc2c(F)cc(C(=O)O)cc21] | 35 | (M+) 666.6 | 1H NMR (400 MHz, DMSO-d6) δ 8.10 (d, J = 1.3 Hz, 1H), 7.91-7.78 (m, 2H), 7.54-7.42 (m, 3H), 7.39 (dd, J = 11.6, 6.1 Hz, 1H), 7.35 (d, J = 7.8 Hz, 1H), 6.93 (d, J = 8.2 Hz, 1H), 5.48 (s, 2H), 4.71-4.53 (m, 6H), 4.46 (s, 2H), 3.68 (t, J = 5.0 Hz, 2H), 3.21 (s, 3H), 2.96 (s, 3H). |

TABLE 2-continued

Compounds

| Ex. | Structure | Procedure | ES/MS m/z | ¹H NMR |
|---|---|---|---|---|
| 515 | 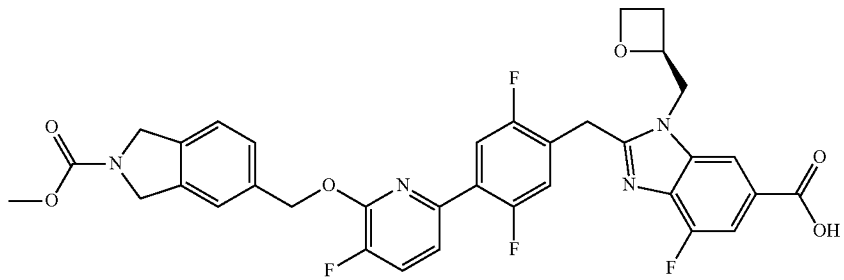 [SMILES: COC(=O)N1Cc2ccc(COc3nc(-c4cc(F)c(Cc5nc6c(F)cc(C(=O)O)cc6n5C[C@@H]5CCO5)cc4F)ccc3F)cc2C1] | 40 | (M+) 676.6 | 1H NMR (400 MHz, Methanol-d4) δ 8.15 (d, J = 1.3 Hz, 1H), 7.75 (dd, J = 10.8, 6.4 Hz, 1H), 7.66 (d, J = 11.3 Hz, 1H), 7.59 (dd, J = 9.9, 8.2 Hz, 1H), 7.55-7.42 (m, 3H), 7.39-7.30 (m, 1H), 7.18 (dd, J = 11.5, 6.0 Hz, 1H), 5.58 (s, 2H), 5.18 (d, J = 7.5 Hz, 1H), 4.78-4.65 (m, 6H), 4.65-4.31 (m, 4H), 3.78 (d, J = 1.7 Hz, 3H), 2.90-2.60 (m, 1H), 2.56-2.36 (m, 1H). |
| 516 | 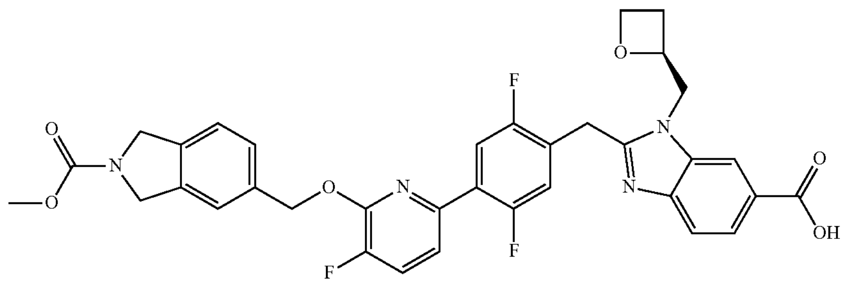 [SMILES: COC(=O)N1Cc2ccc(COc3nc(-c4cc(F)c(Cc5nc6ccc(C(=O)O)cc6n5C[C@@H]5CCO5)cc4F)ccc3F)cc2C1] | 22 | (M+) 658.6 | 1H NMR (400 MHz, Methanol-d4) δ 8.27 (s, 1H), 8.02-7.92 (m, 1H), 7.75 (dd, J = 10.7, 6.2 Hz, 1H), 7.67-7.54 (m, 2H), 7.54-7.43 (m, 3H), 7.33 (d, J = 8.1 Hz, 0H), 7.17 (dd, J = 11.5, 6.0 Hz, 1H), 5.59 (s, 2H), 5.20 (d, J = 10.9 Hz, 1H), 4.73 (s, 5H),4.68-4.50 (m, 3H), 4.50-4.36 (m, 1H), 3.78 (d, J = 1.9 Hz, 3H), 2.78 (s, 1H), 2.51 (s, 1H). |
| 517 | 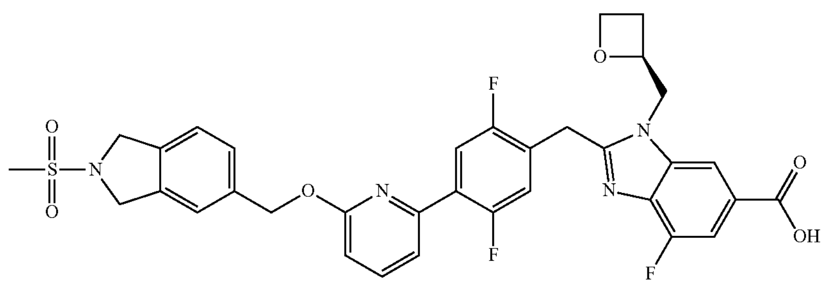 [SMILES: CS(=O)(=O)N1Cc2ccc(COc3cccc(-c4cc(F)c(Cc5nc6c(F)cc(C(=O)O)cc6n5C[C@@H]5CCO5)cc4F)n3)cc2C1] | 40 | (M+) 678.6 | 1H NMR (400 MHz, Methanol-d4) δ 8.15 (s, 1H), 7.84-7.71 (m, 2H), 7.67 (d, J = 11.3 Hz, 1H), 7.54-7.40 (m, 3H), 7.33 (d, J = 7.9 Hz, 1H), 7.18 (dd, J = 11.5, 6.1 Hz, 1H), 6.87 (d, J = 8.2 Hz, 1H), 5.51 (s, 2H), 5.17 (d, J = 8.1 Hz, 1H), 4.70 (d, J = 4.3 Hz, 5H), 4.66-4.48 (m, 4H), 4.45 (dt, J = 9.0, 5.9 Hz, 1H), 2.91 (s, 3H), 2.79 (s, 1H), 2.55-2.41 (m, 1H). |

TABLE 2-continued

Compounds

| Ex. | Structure | Procedure | ES/MS m/z | ¹H NMR |
|---|---|---|---|---|
| 518 | 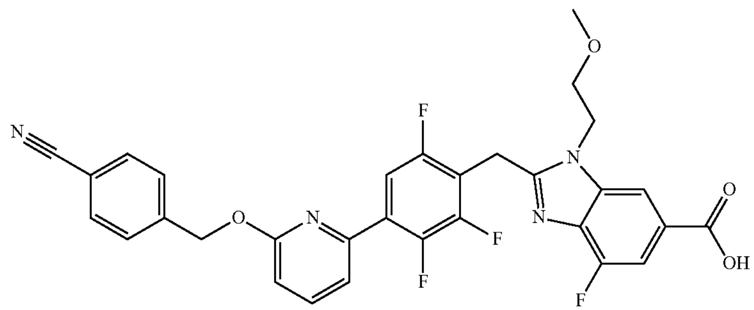 [SMILES: COCCn1c(Cc2c(F)cc(-c3cccc(OCc4ccc(C#N)cc4)n3)c(F)c2F)nc2c(F)cc(C(=O)O)cc21] | 40 | 605.5 | 1H NMR (400 MHz, DMSO-d6) δ 8.12 (d, J = 1.3 Hz, 1H), 7.97-7.85 (m, 2H), 7.75 (ddd, J = 9.7, 7.8, 6.5 Hz, 3H), 7.58-7.44 (m, 2H), 7.39 (dd, J = 11.5, 6.1 Hz, 1H), 6.99 (d, J = 8.3 Hz, 1H), 5.60 (s, 2H), 4.53 (dd, J = 15.2, 3.2 Hz, 1H), 4.46 (s, 2H), 4.36 (dd, J = 15.2, 8.8 Hz, 1H), 3.76-3.61 (m, 1H), 3.08 (s, 3H), 1.23 (d, J = 6.2 Hz, 3H). |
| 519 | 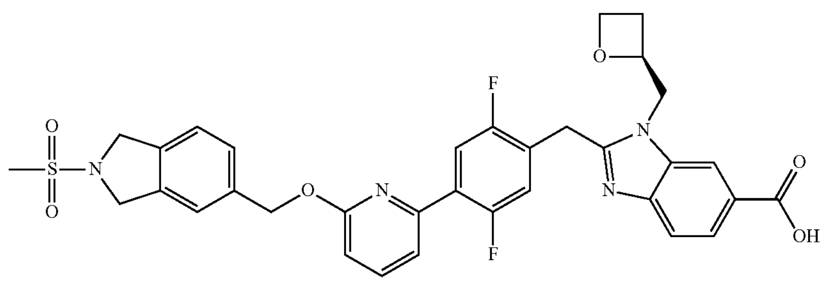 [SMILES: CS(=O)(=O)N1Cc2ccc(COc3cccc(-c4cc(F)c(Cc5nc6ccc(C(=O)O)cc6n5C[C@@H]5CCO5)cc4F)n3)cc2C1] | 35 | (M+) 661.2 | 1H NMR (400 MHz, Methanol-d4) δ 8.30 (s, 1H), 7.99 (dd, J = 8.5, 1.5 Hz, 1H), 7.86-7.73 (m, 2H), 7.66 (d, J = 8.5 Hz, 1H), 7.56-7.49 (m, 1H), 7.46 (d, J = 10.9 Hz, 2H), 7.33 (d, J = 7.8 Hz, 1H), 7.18 (dd, J = 11.6, 6.0 Hz, 1H), 6.87 (d, J = 8.2 Hz, 1H), 5.51 (s, 2H), 5.21 (d, J = 8.8 Hz, 1H), 4.79-4.65 (m, 5H), 4.65-4.35 (m, 4H), 2.91 (s, 3H), 2.87-2.69 (m, 1H), 2.51 (d, J = 11.2 Hz, 0H). |
| 520 | 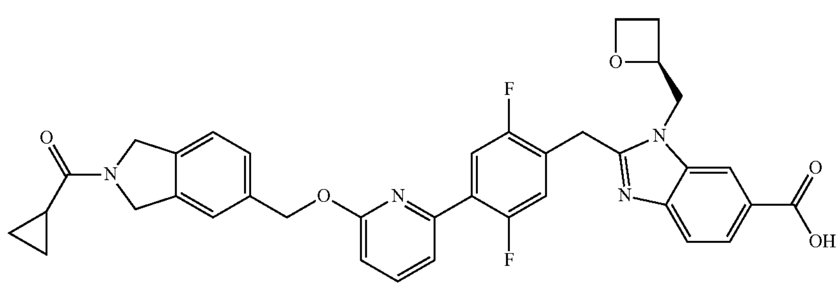 [SMILES: O=C(O)c1ccc2nc(Cc3cc(F)c(-c4cccc(OCc5ccc6c(c5)CN(C(=O)C5CC5)C6)n4)cc3F)n(C[C@@H]3CCO3)c2c1] | 35 | (M+) 651.2 | 1H NMR (400 MHz, Methanol-d4) δ 8.31 (d, J = 1.4 Hz, 1H), 7.99 (dd, J = 8.5, 1.5 Hz, 1H), 7.85-7.72 (m, 2H), 7.67 (d, J = 8.5 Hz, 1H), 7.56-7.43 (m, 3H), 7.36 (dd, J = 7.9, 3.8 Hz, 1H), 7.24-7.09 (m, 1H), 6.87 (d, J = 8.2 Hz, 1H), 5.52 (d, J = 2.5 Hz, 2H), 5.19 (td, J = 7.2, 2.5 Hz, 1H), 5.08 (d, J = 4.3 Hz, 2H), 4.77 (d, J = 6.9 Hz, 2H), 4.73-4.37 (m, 6H), 2.88-2.67 (m, 1H), 2.50 (dq, J = 11.4, 7.7 Hz, 1H), 1.97-1.84 (m, 1H), 0.97 |

TABLE 2-continued

Compounds

| Ex. | Structure | Procedure | ES/MS m/z | ¹H NMR |
|---|---|---|---|---|
| 521 | 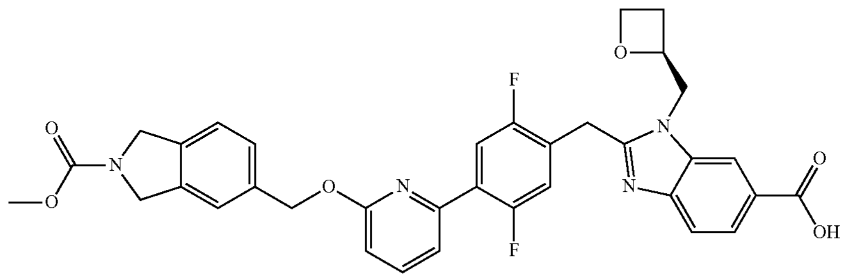 [SMILES: COC(=O)N1Cc2ccc(COc3cccc(-c4cc(F)c(Cc5nc6ccc(C(=O)O)cc6n5C[C@@H]5CCO5)cc4F)n3)cc2C1] | 35 | (M+) 641.2 | 1H NMR (400 MHz, Methanol-d4) δ 8.31 (s, 1H), 7.99 (dd, J = 8.5, 1.5 Hz, 1H), 7.86-7.70 (m, 2H), 7.67 (d, J = 8.5 Hz, 1H), 7.53-7.41 (m, 3H), 7.36-7.25 (m, 1H), 7.17 (dd, J = 11.4, 6.0 Hz, 1H), 6.87 (d, J = 8.3 Hz, 1H), 5.50 (s, 2H), 5.20 (d, J = 7.2 Hz, 1H), 4.72 (q, J = 3.8, 3.2 Hz, 6H), 4.66-4.34 (m, 4H), 3.78 (d, J = 1.9 Hz, 3H), 2.91-2.74 (m, 1H), 2.50 (dt, J = 17.5, 7.8 Hz, 1H). (dq, J = 6.0, 3.1 Hz, 2H), 0.91 (ddt, J = 8.8, 6.0, 2.8 Hz, 2H). |
| 522 | 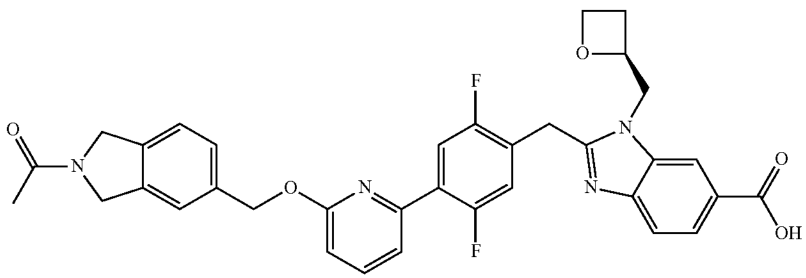 [SMILES: CC(=O)N1Cc2ccc(COc3cccc(-c4cc(F)c(Cc5nc6ccc(C(=O)O)cc6n5C[C@@H]5CCO5)cc4F)n3)cc2C1] | 35 | (M+) 625.2 | 1H NMR (400 MHz, Methanol-d4) δ 8.31 (s, 1H), 7.99 (dd, J = 8.5, 1.5 Hz, 1H), 7.79 (q, J = 8.7, 7.8 Hz, 2H), 7.67 (d, J = 8.5 Hz, 1H), 7.58-7.42 (m, 3H), 7.42-7.27 (m, 1H), 7.26-7.13 (m, 1H), 6.87 (d, J = 8.3 Hz, 1H), 5.52 (s, 2H), 5.30-5.12 (m, 1H), 4.73 (dd, J = 16.6, 7.0 Hz, 3H), 4.66-4.37 (m, 5H), 2.91-2.65 (m, 1H), 2.60-2.39 (m, 1H), 2.18 (d, J = 5.9 Hz, 3H). |

TABLE 2-continued

Compounds

| Ex. | Structure | Procedure | ES/MS m/z | ¹H NMR |
|---|---|---|---|---|
| 523 | 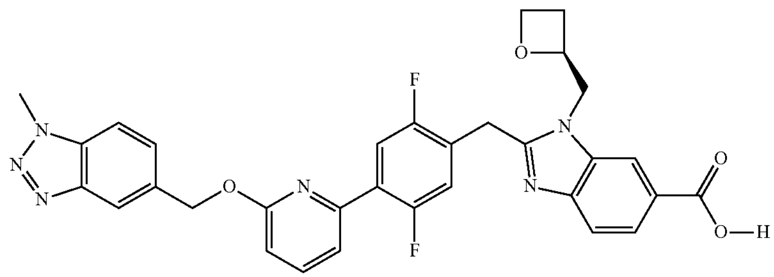 [SMILES: Cn1nnc2cc(COc3cccc(-c4cc(F)c(Cc5nc6ccc(C(=O)O)cc6n5C[C@@H]5CCO5)cc4F)n3)ccc21] | 27 | (M+) 597.2 | 1H NMR (400 MHz, Methanol-d4) δ 8.32 (s, 1H), 8.10 (s, 1H), 8.00 (dd, J = 8.5, 1.5 Hz, 1H), 7.89-7.71 (m, 4H), 7.66 (s, 1H), 7.53 (d, J = 7.4 Hz, 1H), 7.18 (dd, J = 11.4, 6.0 Hz, 1H), 6.92 (d, J = 8.3 Hz, 1H), 5.68 (s, 2H), 5.20 (q, J = 6.8 Hz, 1H), 4.74 (dd, J = 15.7, 6.9 Hz, 1H), 4.68-4.47 (m, 4H), 4.45 (dt, J = 9.3, 5.9 Hz, 1H), 4.35 (d, J = 1.0 Hz, 3H), 2.80 (dt, J = 15.9, 7.7 Hz, 1H), 2.58-2.38 (m, 1H). |
| 524 | 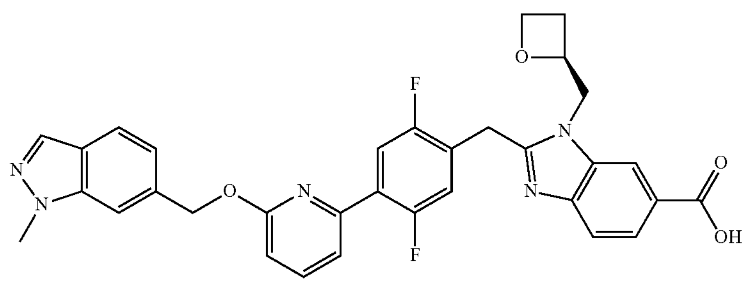 | 27 | (M+) 596.2 | 1H NMR (400 MHz, Methanol-d4) δ 8.31 (d, J = 1.5 Hz, 1H), 8.02-7.93 (m, 2H), 7.87-7.72 (m, 4H), 7.71-7.61 (m, 2H), 7.52 (dd, J = 7.5, 1.6 Hz, 1H), 7.32 (dd, J = 8.4, 1.2 Hz, 1H), 7.17 (dd, J = 11.5, 6.0 Hz, 1H), 6.91 (d, J = 8.2 Hz, 1H), 5.64 (s, 2H), 5.19 (qd, J = 7.1, 2.5 Hz, 1H), 4.72 (dd, J = 15.7, 6.9 Hz, 1H), 4.67-4.48 (m, 5H), 4.48-4.34 (m, 1H), 4.06 (s, 3H), 2.91-2.65 (m, 1H), 2.58-2.40 (m, 1H). |
| 525 | 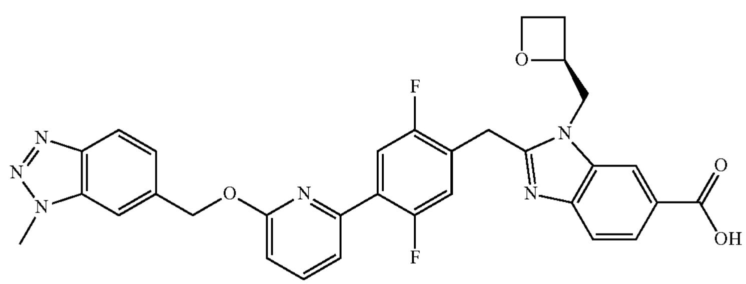 [SMILES: Cn1ncc2ccc(COc3cccc(-c4cc(F)c(Cc5nc6ccc(C(=O)O)cc6n5C[C@@H]5CCO5)cc4F)n3)cc21] | 27 | (M+) 597.2 | 1H NMR (400 MHz, Methanol-d4) δ 8.31 (d, J = 1.4 Hz, 1H), 8.00 (d, J = 2.1 Hz, 1H), 7.98 (d, J = 2.2 Hz, 1H), 7.92 (s, 1H), 7.86-7.73 (m, 2H), 7.66 (d, J = 8.5 Hz, 1H), 7.60 (dd, J = 8.7, 1.3 Hz, 1H), 7.53 (dd, J = 7.5, 1.5 Hz, 1H), 7.18 (dd, J = 11.4, 6.0 Hz, 1H), 6.93 (d, J = 8.2 Hz, 1H), 5.70 (s, 2H), 5.19 (dd, J = 7.2, 2.5 Hz, 1H), 4.72 (dd, J = 15.7, 6.9 Hz, 1H), 4.67-4.49 (m, 4H), 4.48-4.36 (m, 1H), |

TABLE 2-continued

Compounds

| Ex. | Structure | Procedure | ES/MS m/z | ¹H NMR |
|---|---|---|---|---|
| 526 | (structure) | 27 | (M+) 596.2 | 1H NMR (400 MHz, Methanol-d4) δ 8.31 (d, J = 1.4 Hz, 1H), 7.99 (d, J = 9.1 Hz, 2H), 7.91-7.81 (m, 2H), 7.76 (q, J = 6.7, 5.5 Hz, 1H), 7.67 (d, J = 8.5 Hz, 1H), 7.63-7.53 (m, 2H), 7.51 (dd, J = 7.5, 1.6 Hz, 1H), 7.18 (dd, J = 11.4, 6.0 Hz, 1H), 6.86 (d, J = 8.2 Hz, 1H), 5.59 (s, 2H), 5.20 (qd, J = 7.2, 2.5 Hz, 1H), 4.81-4.67 (m, 1H), 4.67-4.49 (m, 4H), 4.49-4.35 (m, 1H), 4.07 (d, J = 0.9 Hz, 3H), 2.89-2.71 (m, 1H), 2.64-2.38 (m, 1H). 4.33 (s, 3H), 2.79 (ddt, J = 14.2, 11.6, 6.8 Hz, 1H), 2.56-2.41 (m, 1H). |
| 527 | (structure) | 27 | (M+) 600.2 | 1H NMR (400 MHz, Methanol-d4) δ 8.29 (s, 1H), 8.11 (s, 1H), 8.04 (d, J = 9.0 Hz, 1H), 7.98 (dd, J = 8.5, 1.5 Hz, 1H), 7.86-7.72 (m, 3H), 7.65 (d, J = 8.5 Hz, 1H), 7.55 (d, J = 7.5 Hz, 1H), 7.16 (dd, J = 11.5, 6.1 Hz, 1H), 6.97 (d, J = 8.2 Hz, 1H), 5.71 (s, 2H), 5.19 (d, J = 7.3 Hz, 1H), 4.72 (dd, J = 15.7, 6.9 Hz, 1H), 4.67-4.34 (m, 5H), 2.79 (t, J = 9.1 Hz, 1H), 2.59-2.41 (m, 1H). |

TABLE 2-continued

Compounds

| Ex. | Structure | Procedure | ES/MS m/z | ¹H NMR |
|---|---|---|---|---|
| 528 | 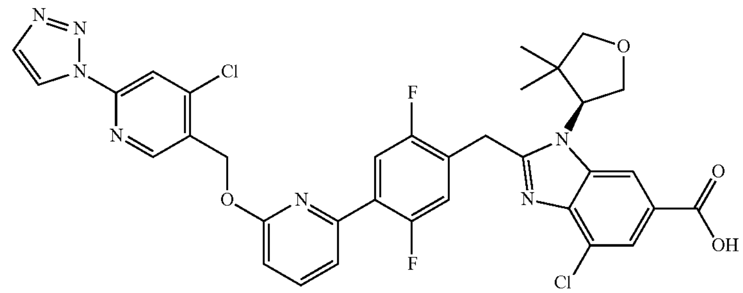 [SMILES: CC1(C)COC[C@H]1n1c(Cc2cc(F)c(-c3cccc(OCc4cnc(-n5ccnn5)cc4Cl)n3)cc2F)nc2c(Cl)cc(C(=O)O)cc21] | 35 | (M+) 706.0 | 1H NMR (400 MHz, DMSO) δ 8.89 (s, 1H), 8.82 (s, 1H), 8.47 (s, 1H), 8.30 (s, 1H), 8.03 (s, 1H), 7.98-7.85 (m, 2H), 7.81 (s, 1H), 7.57 (d, J = 7.3 Hz, 1H), 7.46 (dd, J = 11.4, 6.1Hz, 1H), 7.01 (d, J = 8.2 Hz, 1H), 5.68 (s, 2H), 5.03 (d, J = 6.6 Hz, 1H), 4.67-4.29 (m, 4H), 3.84-3.68 (m, 2H), 1.31 (s, 3H), 0.59 (s, 3H). |
| 529 | 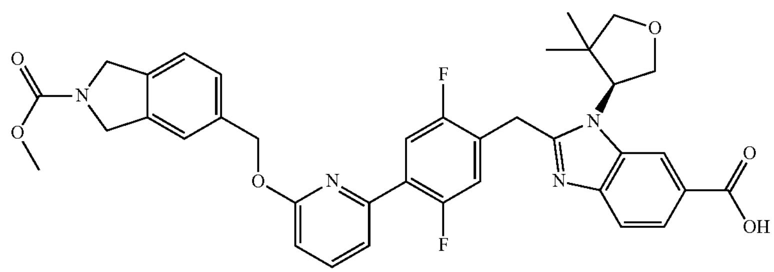 [SMILES: COC(=O)N1Cc2ccc(COc3cccc(-c4cc(F)c(Cc5nc6ccc(C(=O)O)cc6n5[C@@H]5COCC5(C)C)cc4F)n3)cc2C1] | 35 | 669.6 | 1H NMR (400 MHz, DMSO) δ 8.49 (s, 1H), 7.91-7.77 (m, 3H), 7.55-7.39 (m, 5H), 7.34 (dd, J = 10.6, 7.8 Hz, 1H), 6.94 (d, J = 8.3 Hz, 1H), 5.47 (s, 2H), 5.02 (d, J = 6.6 Hz, 1H), 4.64 (t, J = 6.9 Hz, 4H), 4.58-4.50 (m, 2H), 4.44 (dd, J = 11.2, 6.8 Hz, 1H), 4.39 (d, J = 16.9 Hz, 1H), 3.81-3.71 (m, 2H), 3.67 (s, 3H), 1.34 (s, 3H), 0.61 (s, 3H). |
| 530 | 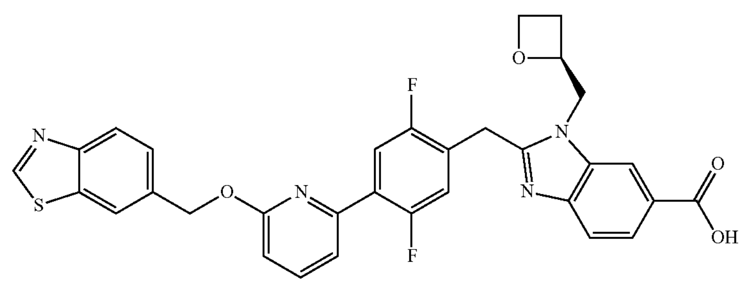 [SMILES: O=C(O)c1ccc2nc(Cc3cc(F)c(-c4cccc(OCc5ccc6ncsc6c5)n4)cc3F)n(C[C@@H]3CCO3)c2c1] | 27 | 599.1 | 1H NMR (400 MHz, Methanol-d4) δ 9.21 (s, 1H), 8.52 (d, J = 1.4 Hz, 1H), 8.20 (dd, J = 8.6, 1.4 Hz, 2H), 8.08 (d, J = 8.4 Hz, 1H), 7.87 (dd, J = 10.8, 6.3 Hz, 1H), 7.83-7.73 (m, 2H), 7.69 (dd, J = 8.5, 1.6 Hz, 1H), 7.55 (dd, J = 7.5, 1.6 Hz, 1H), 7.31 (dd, J = 11.1, 6.0 Hz, 1H), 6.93 (d, J = 8.2 Hz, 1H), 5.66 (s, 2H), 5.24 (tt, J = 7.3, 3.8 Hz, 1H), 4.93 (dd, J = 15.5, 7.5 Hz, 1H), 4.83-4.63 (m, 4H), 4.54 (dt, J = 9.1, 6.0 Hz, 1H), 2.98-2.75 (m, 1H), 2.67-2.50 (m, 1H). |

TABLE 2-continued

Compounds

| Ex. | Structure | Procedure | ES/MS m/z | ¹H NMR |
|---|---|---|---|---|
| 531 | 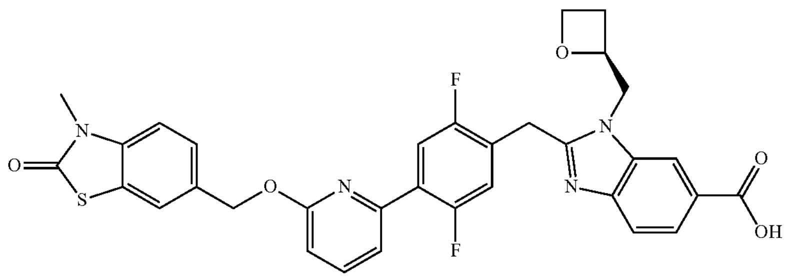 [SMILES: Cn1c(=O)sc2cc(COc3cccc(-c4cc(F)c(Cc5nc6ccc(C(=O)O)cc6n5C[C@@H]5CCO5)cc4F)n3)ccc21] | 27 | 629.2 | 1H NMR (400 MHz, Methanol-d4) δ 8.57 (d, J = 1.3 Hz, 1H), 8.21 (dd, J = 8.6, 1.4 Hz, 1H), 7.90 (dd, J = 10.8, 6.3 Hz, 1H), 7.85-7.74 (m, 2H), 7.69 (d, J = 1.6 Hz, 1H), 7.54 (ddd, J = 8.3, 6.4, 1.7 Hz, 2H), 7.37 (dd, J = 11.2, 6.1 Hz, 1H), 7.26 (d, J = 8.3 Hz, 1H), 6.91 (d, J = 8.2 Hz, 1H), 5.52 (s, 2H), 5.26 (qd, J = 7.4, 2.4 Hz, 1H), 4.98 (dd, J = 15.5, 7.5 Hz, 1H), 4.86-4.64 (m, 4H), 4.54 (dt, J = 9.1, 6.0 Hz, 1H), 3.47 (s, 3H), 2.88 (dtd, J = 11.5, 8.2, 6.1 Hz, 1H), 2.58 (ddt, J = 11.5, 9.1, 7.2 Hz, 1H). |
| 532 | 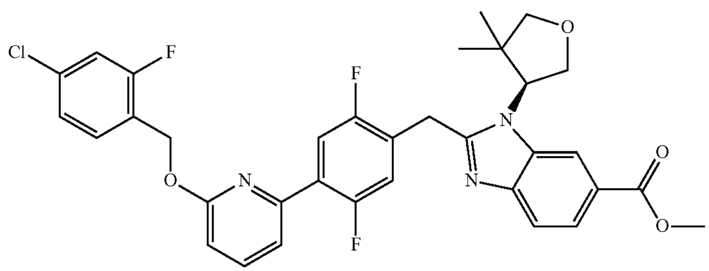 [SMILES: COC(=O)c1ccc2nc(Cc3cc(F)c(-c4cccc(OCc5ccc(Cl)cc5F)n4)cc3F)n([C@@H]3COCC3(C)C)c2c1] | | 636.3 | 1H NMR (400 MHz, Chloroform-d) δ 8.55 (s, 1H), 8.01 (dd, J = 8.5, 1.5 Hz, 1H), 7.88 (dd, J = 10.8, 6.3 Hz, 1H), 7.79 (d, J = 8.5 Hz, 1H), 7.66 (t, J = 7.9 Hz, 1H), 7.54-7.41 (m, 3H), 7.14 (dt, J = 9.8, 2.3 Hz, 2H), 7.08 (dd, J = 11.3, 6.0 Hz, 1H), 6.79 (d, J = 8.2 Hz, 1H), 5.49 (s, 2H), 4.65 (d, J = 7.0 Hz, 1H), 4.57 (dd, J = 11.0, 1.8 Hz, 1H), 4.47-4.30 (m, 3H), 3.96-3.92 (m, 4H), 3.79 (d, J = 8.8 Hz, 1H), 1.34 (s, 3H), 0.66 (s, 3H). |

TABLE 2-continued

Compounds

| Ex. | Structure | Procedure | ES/MS m/z | ¹H NMR |
|---|---|---|---|---|
| 533 | 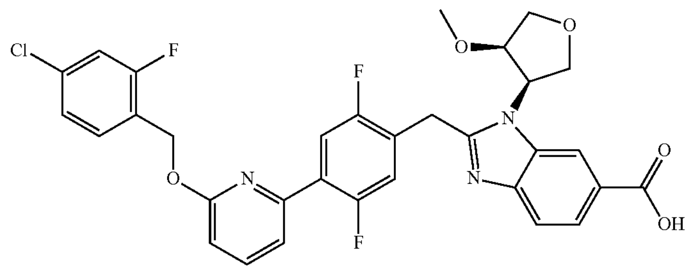 [SMILES: CO[C@H]1COC[C@H]1n1c(Cc2cc(F)c(-c3cccc(OCc4ccc(Cl)cc4F)n3)cc2F)nc2ccc(C(=O)O)cc21] | 39 | 624.1 | 1H NMR (400 MHz, DMSO) δ 8.43 (d, J = 1.5 Hz, 1H), 7.91-7.75 (m, 3H), 7.67-7.57 (m, 2H), 7.53 (ddd, J = 10.1, 7.3, 2.5 Hz, 2H), 7.43-7.28 (m, 2H), 5.60 (s, 2H), 4.54 (s, 2H), 4.42 (dd, J = 10.4, 3.6 Hz, 1H), 4.19-4.07 (m, 2H), 4.02 (dd, J = 10.5, 8.2 Hz, 1H), 3.80 (dd, J = 10.5, 4.7 Hz, 1H), 2.88 (s, 3H). |
| 534 | 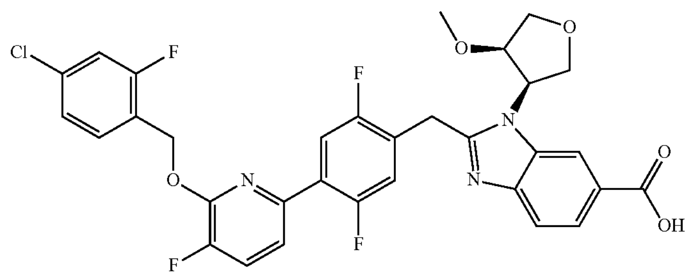 [SMILES: CO[C@H]1COC[C@H]1n1c(Cc2cc(F)c(-c3ccc(F)c(OCc4ccc(Cl)cc4F)n3)cc2F)nc2ccc(C(=O)O)cc21] | 39 | 642.2 | 1H NMR (400 MHz, DMSO) δ 1H NMR (400 MHz, DMSO) δ 8.45 (d, J = 1.6 Hz, 1H), 7.94-7.77 (m, 3H), 7.68-7.55 (m, 2H), 7.55-7.46 (m, 2H), 7.39-7.27 (m, 2H), 6.96 (d, J = 8.2 Hz, 1H), 5.65-5.54 (m, 1H), 5.50 (s, 2H), 4.57 (s, 2H), 4.43 (dd, J = 10.4, 3.6 Hz, 1H), 4.13 (dt, J = 8.5, 2.1 Hz, 2H), 4.02 (dd, J = 10.6, 8.2 Hz, 1H), 3.79 (dd, J = 10.8, 4.9 Hz, 1H), 2.88 (s, 3H). |
| 535 | 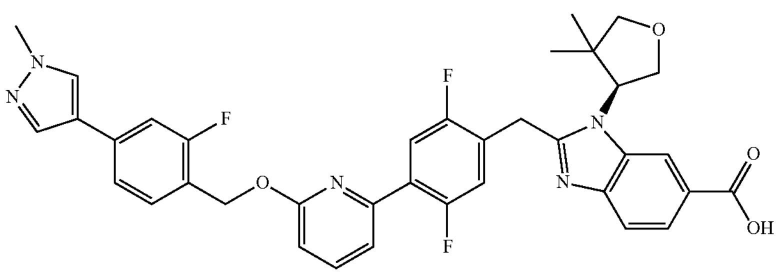 [SMILES: Cn1cc(-c2ccc(COc3cccc(-c4cc(F)c(Cc5nc6ccc(C(=O)O)cc6n5[C@@H]5COCC5(C)C)cc4F)n3)c(F)c2)cn1] | 41 | 668.2 | 1H NMR (400 MHz, Methanol-d4) δ 8.92 (s, 1H), 8.20 (dd, J = 8.6, 1.4 Hz, 1H), 8.10-7.92 (m, 2H), 7.91-7.73 (m, 3H), 7.58 (dd, J = 7.4, 1.6 Hz, 1H), 7.51 (t, J = 7.8 Hz, 1H), 7.46-7.28 (m, 3H), 6.91 (d, J = 8.2 Hz, 1H), 5.54 (s, 2H), 5.15 (d, J = 6.4 Hz, 1H), 4.80-4.61 (m, 3H), 4.52 (dd, J = 11.7, 6.7 Hz, 1H), 4.00 (d, J = 8.9 Hz, 1H), 3.93 (s, 3H), 3.84 (d, J = 8.9 Hz, 1H), 1.41 (s, 3H), 0.76 (s, 3H). |

TABLE 2-continued

Compounds

| Ex. | Structure | Procedure | ES/MS m/z | ¹H NMR |
|---|---|---|---|---|
| 536 | 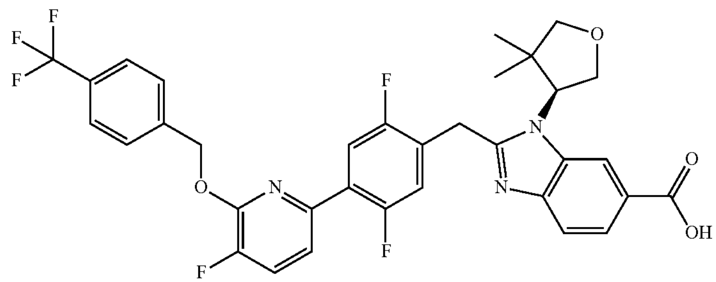 [SMILES: CC1(C)COC[C@H]1n1c(Cc2cc(F)c(-c3ccc(F)c(OCc4ccc(C(F)(F)F)cc4)n3)cc2F)nc2ccc(C(=O)O)cc21] | 35 | 656.0 | 1H NMR (400 MHz, DMSO-d6) δ 8.49 (s, 1H), 7.87 (dd, J = 10.3, 8.2 Hz, 1H), 7.84-7.69 (m, 6H), 7.62 (d, J = 8.4 Hz, 1H), 7.55 (ddd, J = 8.2, 2.9, 1.4 Hz, 1H), 7.46 (dd, J = 11.5, 6.1Hz, 1H), 5.68 (s, 2H), 5.02 (d, J = 6.7 Hz, 1H), 4.55-4.48 (m, 2H), 4.47-4.32 (m, 2H), 3.82-3.69 (m, 2H), 1.33 (s, 3H), 0.60 (s, 3H). |
| 537 | 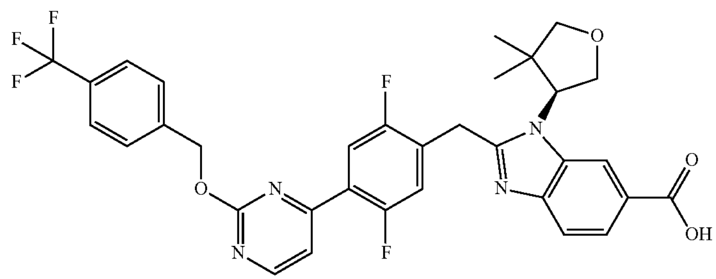 [SMILES: CC1(C)COC[C@H]1n1c(Cc2cc(F)c(-c3ccnc(OCc4ccc(C(F)(F)F)cc4)n3)cc2F)nc2ccc(C(=O)O)cc21] | 35 | 639.0 | 1H NMR (400 MHz, DMSO-d6) δ 8.79 (d, J = 5.2 Hz, 1H), 8.48 (s, 1H), 7.91 (dd, J = 10.2, 6.3 Hz, 1H), 7.83-7.75 (m, 3H), 7.73 (d, J = 8.2 Hz, 2H), 7.64 (dd, J = 5.2, 1.9 Hz, 1H), 7.61 (d, J = 8.5 Hz, 1H), 7.55 (dd, J = 11.5, 5.9 Hz, 1H), 5.63 (s, 2H), 5.02 (d, J = 6.6 Hz, 1H), 4.61-4.49 (m, 2H), 4.49-4.36 (m, 2H), 3.82-3.67 (m, 2H), 1.34 (s, 3H), 0.61 (s, 3H). |
| 538 | 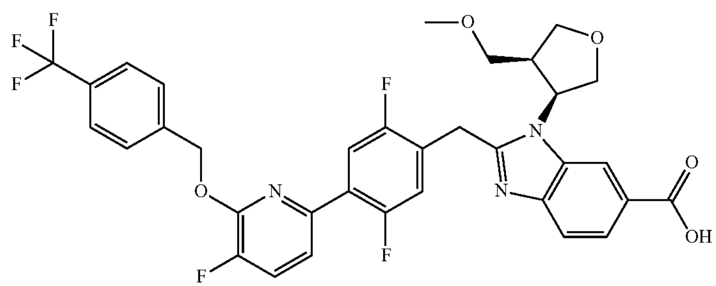 [SMILES: COC[C@H]1COC[C@H]1n1c(Cc2cc(F)c(-c3ccc(F)c(OCc4ccc(C(F)(F)F)cc4)n3)cc2F)nc2ccc(C(=O)O)cc21] | 35 | 672.0 | 1H NMR (400 MHz, DMSO-d6) δ 8.55 (s, 1H), 7.87 (dd, J = 10.3, 8.2 Hz, 1H), 7.80 (dd, J = 9.7, 8.3 Hz, 3H), 7.76-7.68 (m, 3H), 7.61 (d, J = 8.5 Hz, 1H), 7.55 (ddd, J = 8.2, 2.9, 1.5 Hz, 1H), 7.39 (dd, J = 11.3, 6.2 Hz, 1H), 5.68 (s, 2H), 5.52 (t, J = 7.3 Hz, 1H), 4.57-4.41 (m, 3H), 4.20 (dd, J = 10.9, 6.5 Hz, 1H), 4.08 (t, J = 8.7 Hz, 1H), 3.77 (t, J = 8.2 Hz, 1H), 3.19-3.01 (m, 2H), 2.91 (s, 3H), 2.60 (t, J = 8.8 Hz, 1H). |

TABLE 2-continued

Compounds

| Ex. | Structure | Procedure | ES/MS m/z | ¹H NMR |
|---|---|---|---|---|
| 539 | 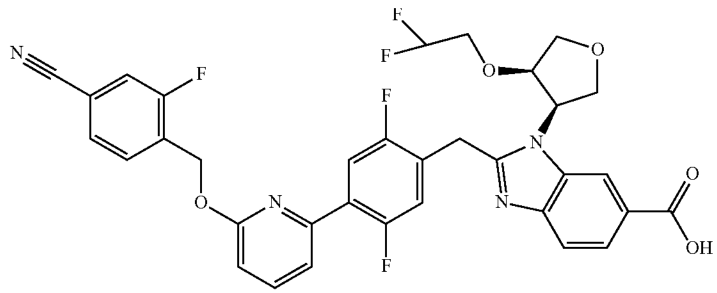 [SMILES: N#Cc1ccc(COc2cccc(-c3cc(F)c(Cc4nc5ccc(C(=O)O)cc5n4[C@@H]4COC[C@@H]4OCC(F)F)cc3F)n2)c(F)c1] | 3 | 665.0 | 1H NMR (400 MHz, DMSO-d6) δ 8.43 (s, 1H), 8.03-7.86 (m, 2H), 7.85-7.67 (m, 4H), 7.60 (d, J = 8.5 Hz, 1H), 7.53 (d, J = 7.3 Hz, 1H), 7.34 (dd, J = 11.5, 6.1 Hz, 1H), 7.00 (d, J = 8.3 Hz, 1H), 5.87-5.45 (m, 3H), 4.54 (s, 2H), 4.51-4.41 (m, 2H), 4.14 (s, 0H), 4.05 (dd, J = 10.5, 8.3 Hz, 1H), 3.93-3.83 (m, 2H), 3.62-3.43 (m, 1H), 3.24-2.99 (m, 1H). |
| 540 | 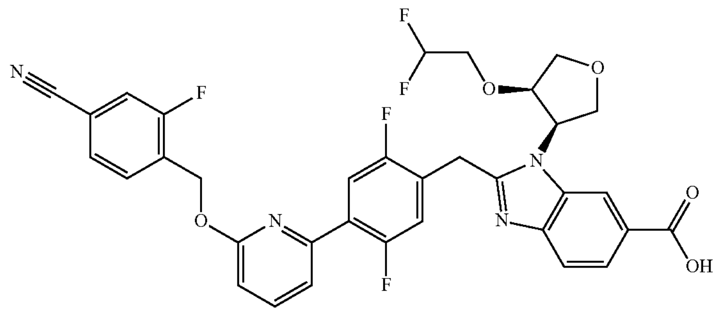 [SMILES: N#Cc1ccc(COc2cccc(-c3cc(F)c(Cc4nc5ccc(C(=O)O)cc5n4[C@@H]4COC[C@@H]4OCC(F)F)cc3F)n2)c(F)c1] | 35 | 665.0 | 1H NMR (400 MHz, DMSO-d6) δ 8.43 (s, 1H), 8.03-7.86 (m, 2H), 7.85-7.67 (m, 4H), 7.60 (d, J = 8.5 Hz, 1H), 7.53 (d, J = 7.3 Hz, 1H), 7.34 (dd, J = 11.5, 6.1 Hz, 1H), 7.00 (d, J = 8.3 Hz, 1H), 5.87-5.45 (m, 3H), 4.54 (s, 2H), 4.51-4.41 (m, 2H), 4.14 (s, 0H), 4.05 (dd, J = 10.5, 8.3 Hz, 1H), 3.93-3.83 (m, 2H), 3.62-3.43 (m, 1H), 3.24-2.99 (m, 1H). |
| 541 | 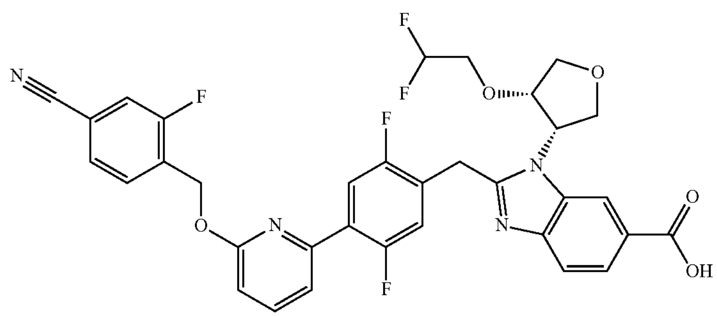 [SMILES: N#Cc1ccc(COc2cccc(-c3cc(F)c(Cc4nc5ccc(C(=O)O)cc5n4[C@H]4COC[C@H]4OCC(F)F)cc3F)n2)c(F)c1] | 35 | 665.0 | 1H NMR (400 MHz, DMSO-d6) δ 8.43 (s, 1H), 8.03-7.86 (m, 2H), 7.85-7.67 (m, 4H), 7.60 (d, J = 8.5 Hz, 1H), 7.53 (d, J = 7.3 Hz, 1H), 7.34 (dd, J = 11.5, 6.1Hz, 1H), 7.00 (d, J = 8.3 Hz, 1H), 5.87-5.45 (m, 3H), 4.54 (s, 2H), 4.51-4.41 (m, 2H), 4.14 (s, 0H), 4.05 (dd, J = 10.5, 8.3 Hz, 1H), 3.93-3.83 (m, 2H), 3.62-3.43 (m, 1H), 3.24-2.99 (m, 1H). |

TABLE 2-continued

Compounds

| Ex. | Structure | Procedure | ES/MS m/z | ¹H NMR |
|---|---|---|---|---|
| 542 | 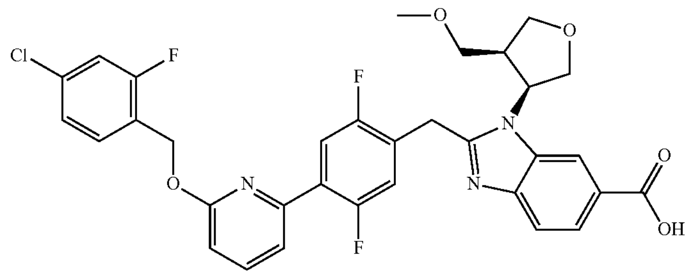 [SMILES: COC[C@H]1COC[C@H]1n1c(Cc2cc(F)c(-c3cccc(OCc4ccc(Cl)cc4F)n3)cc2F)nc2ccc(C(=O)O)cc21] | 35 | 638.1 | 1H NMR (400 MHz, MeOD) δ 8.71 (s, 1H), 7.95 (dd, J = 8.5, 1.5 Hz, 1H), 7.82 (dd, J = 10.8, 6.4 Hz, 1H), 7.73 (t, J = 7.9 Hz, 1H), 7.62 (d, J = 8.5 Hz, 1H), 7.49 (t, J = 8.0 Hz, 2H), 7.28-7.04 (m, 3H), 6.82 (d, J = 8.2 Hz, 1H), 5.46 (d, J = 14.0 Hz, 3H), 4.60-4.41 (m, 3H), 4.23 (dd, J = 10.9, 6.6 Hz, 1H), 3.89 (dd, J = 9.0, 7.0 Hz, 1H), 3.35 (s, 0H), 3.21-3.04 (m, 2H), 2.92 (s, 3H), 2.57 (t, J = 8.9 Hz, 1H). |
| 543 | 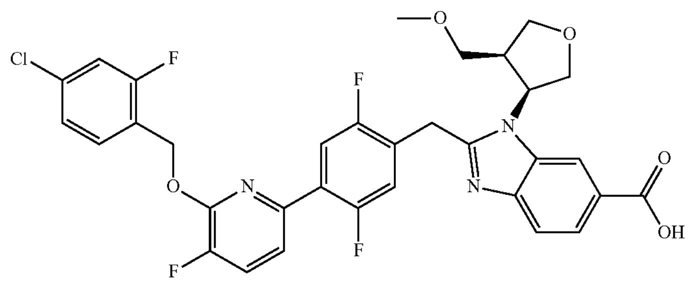 [SMILES: COC[C@H]1COC[C@H]1n1c(Cc2cc(F)c(-c3ccc(F)c(OCc4ccc(Cl)cc4F)n3)cc2F)nc2ccc(C(=O)O)cc21] | 35 | 656.1 | 1H NMR (400 MHz, MeOD) δ 8.72 (s, 1H), 7.94 (dd, J = 8.5, 1.5 Hz, 1H), 7.76 (dd, J = 10.7, 6.4 Hz, 1H), 7.70-7.44 (m, 4H), 7.26 (dd, J = 8.6, 2.6 Hz, 1H), 7.23-7.03 (m, 2H), 5.59 (s, 2H), 5.45 (t, J = 7.2 Hz, 1H), 4.65-4.46 (m, 3H), 4.24 (dd, J = 10.9, 6.6 Hz, 1H), 4.11 (t, J = 8.9 Hz, 1H), 3.89 (dd, J = 9.0, 7.0 Hz, 1H), 3.22-3.06 (m, 2H), 2.92 (s, 3H). |
| 544 | 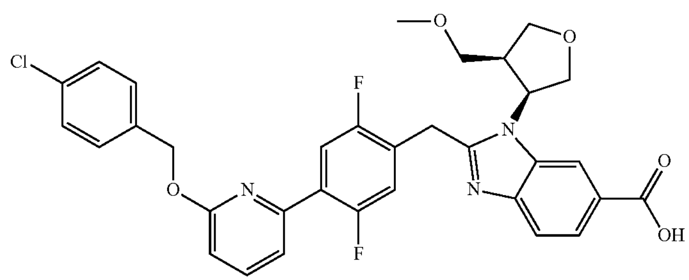 [SMILES: COC[C@H]1COC[C@H]1n1c(Cc2cc(F)c(-c3cccc(OCc4ccc(Cl)cc4)n3)cc2F)nc2ccc(C(=O)O)cc21] | 35 | 620.2 | 1H NMR (400 MHz, MeOD) δ 8.72 (s, 1H), 7.95 (dd, J = 8.4, 1.5 Hz, 1H), 7.80 (dd, J = 10.8, 6.3 Hz, 1H), 7.74 (t, J = 7.8 Hz, 1H), 7.64 (dd, J = 8.5 Hz, 1H), 7.49 (dd, J = 7.5, 1.7 Hz, 1H), 7.45 (d, J = 8.5 Hz, 1H), 7.36-7.33 (m, 2H), 7.14 (dd, J = 11.5, 6.0 Hz, 1H), 6.84 (d, J = 8.2 Hz, 1H), 5.44 (s, 3H), 4.61-4.38 (m, 3H), 4.24 (dd, J = 10.9, 6.6 Hz, 1H), 4.19-4.04 (m, 1H), 3.90 (dd, J = 9.0, 7.0 Hz, 1H), 2.93 (s, 3H). |

TABLE 2-continued

Compounds

| Ex. | Structure | Procedure | ES/MS m/z | ¹H NMR |
|---|---|---|---|---|
| 545 | 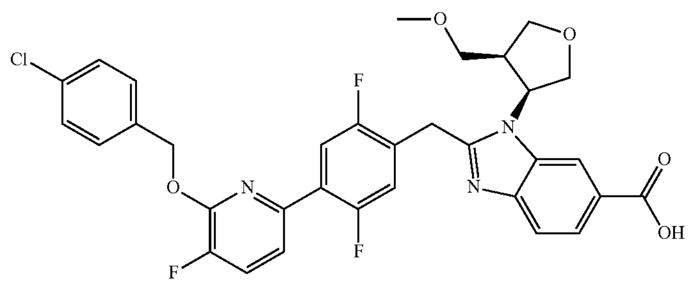 [SMILES: COC[C@H]1COC[C@H]1n1c(Cc2cc(F)c(-c3ccc(F)c(OCc4ccc(Cl)cc4)n3)cc2F)nc2ccc(C(=O)O)cc21] | 35 | 638.1 | 1H NMR (400 MHz, MeOD) δ 8.73 (s, 1H), 7.95 (dd, J = 8.5, 1.5 Hz, 1H), 7.81-7.75 (m, 1H), 7.64 (d, J = 8.5 Hz, 1H), 7.58 (dd, J = 9.8, 8.2 Hz, 1H), 7.54-7.46 (m, 3H), 7.42-7.33 (m, 2H), 7.15 (dd, J = 11.5, 6.1 Hz, 1H), 5.59-5.36 (m, 3H), 4.63-4.41 (m, 3H), 4.26 (dd, J = 10.9, 6.6 Hz, 1H), 4.13 (t, J = 8.9 Hz, 1H), 3.91 (dd, J = 9.0, 7.0 Hz, 1H), 2.93 (s, 3H). |
| 546 | Isomer 1 | 35 | 652.2 | 1H NMR (400 MHz, MeOD) δ 8.73 (s, 1H), 7.95 (dd, J = 8.5, 1.5 Hz, 1H), 7.83 (dd, J = 10.7, 6.3 Hz, 1H), 7.74 (t, J = 7.9 Hz, 1H), 7.64 (d, J = 8.5 Hz, 1H), 7.55-7.47 (m, 2H), 7.24-7.16 (m, 2H), 7.12 (dd, J = 11.5, 6.0 Hz, 1H), 6.83 (d, J = 8.2 Hz, 1H), 5.49 (s, 2H), 4.96 (d, J = 6.5 Hz, 1H), 4.61-4.46 (m, 2H), 4.46-4.34 (m, 2H), 3.98 (d, J = 9.1 Hz, 1H), 3.73 (d, J = 9.0 Hz, 1H), 3.03 (d, J = 9.4 Hz, 1H), 2.88 (s, 3H), 2.69 (d, J = 9.4 Hz, 1H), 1.45 (s, 3H). |

TABLE 2-continued

Compounds

| Ex. | Structure | Procedure | ES/MS m/z | ¹H NMR |
|---|---|---|---|---|
| 547 | Isomer 2 | 35 | 652.2 | 1H NMR (400 MHz, MeOD) δ 8.74 (s, 1H), 7.96 (dd, J = 8.5, 1.5 Hz, 1H), 7.84 (dd, J = 10.8, 6.4 Hz, 1H), 7.77 (t, J = 7.9 Hz, 1H), 7.65 (d, J = 8.5 Hz, 1H), 7.53 (t, J = 8.0 Hz, 2H), 7.30-7.17 (m, 2H), 7.13 (dd, J = 11.5, 6.0 Hz, 1H), 6.85 (d, J = 8.2 Hz, 1H), 5.51 (s, 2H), 4.97 (d, J = 6.5 Hz, 1H), 4.58 (d, J = 17.2 Hz, 2H), 4.51-4.34 (m, 2H), 3.99 (d, J = 9.0 Hz, 1H), 3.74 (d, J = 9.1 Hz, 1H), 3.05 (d, J = 9.4 Hz, 1H), 2.89 (s, 3H), 2.70 (d, J = 9.2 Hz, 1H), 1.46 (s, 3H). |
| 549 | Isomer 2 | 35 | 652.2 | 1H NMR (400 MHz, MeOD) δ 8.75 (s, 1H), 7.99 (dd, J = 8.5, 1.5 Hz, 1H), 7.86 (dd, J = 10.7, 6.4 Hz, 1H), 7.79 (t, J = 7.9 Hz, 1H), 7.68 (d, J = 8.5 Hz, 1H), 7.61-7.49 (m, 2H), 7.25 (ddd, J = 12.2, 8.9, 2.1 Hz, 2H), 7.10 (dd, J = 11.5, 6.0 Hz, 1H), 6.88 (d, J = 8.2 Hz, 1H), 5.54 (s, 2H), 5.23 (d, J = 7.0 Hz, 1H), 4.69-4.38 (m, 3H), 4.33 (dd, J = 11.0, 7.1 Hz, 1H), 3.97 (d, J = 9.2 Hz, 1H), 3.85 (d, J = 9.2 Hz, 1H), 3.50 (s, 3H), 0.72 (s, 3H). |

TABLE 2-continued

Compounds

| Ex. | Structure | Procedure | ES/MS m/z | ¹H NMR |
|---|---|---|---|---|
| 550 | 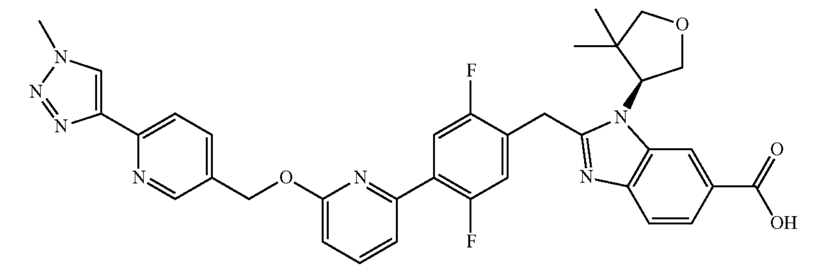 [SMILES: Cn1cc(-c2ccc(COc3cccc(-c4cc(F)c(Cc5nc6ccc(C(=O)O)cc6n5[C@@H]5COCC5(C)C)cc4F)n3)cn2)nn1] | 41 | 652.2 | 1H NMR (400 MHz, Methanol-d4) δ 8.95-8.82 (m, 2H), 8.21-8.12 (m, 2H), 8.06 (dd, J = 8.2, 2.3 Hz, 1H), 7.95-7.81 (m, 3H), 7.76 (dd, J = 8.6, 0.6 Hz, 1H), 7.63-7.49 (m, 1H), 7.38 (dd, J = 11.1, 6.1 Hz, 1H), 6.96 (dd, J = 8.3, 0.7 Hz, 1H), 5.63 (s, 2H), 5.12 (d, J = 6.5 Hz, 1H), 4.75-4.59 (m, 3H) 4.59-4.45 (m, 1H), 4.39 (s, 3H), 3.99 (d, J = 8.9 Hz, 1H), 3.83 (d, J = 8.9 Hz, 1H), 1.40 (s, 3H), 0.75 (s, 3H). |
| 551 | 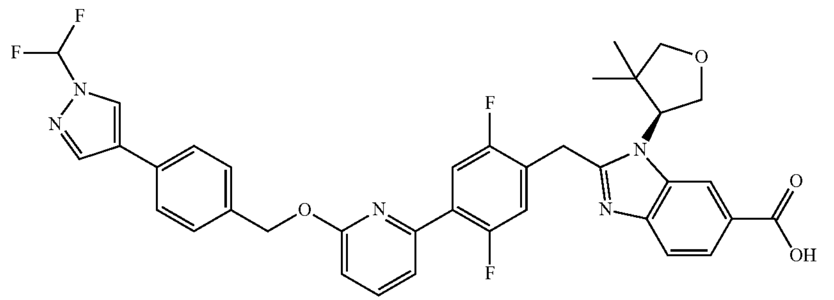 [SMILES: CC1(C)COC[C@H]1n1c(Cc2cc(F)c(-c3cccc(OCc4ccc(-c5cnn(C(F)F)c5)cc4)n3)cc2F)nc2ccc(C(=O)O)cc21] | 41 | 686.2 | 1H NMR (400 MHz, Methanol-d4) δ 8.90 (s, 1H), 8.52-8.01 (m, 2H), 7.91 (ddd, J = 10.9, 6.3, 2.0 Hz, 1H), 7.87-7.71 (m, 2H), 7.71-7.23 (m, 7H), 6.91 (dd, J = 8.3, 5.7 Hz, 1H), 5.50 (d, J = 8.5 Hz, 2H), 5.14 (s, 1H), 4.79-4.60 (m, 3H), 4.52 (ddd, J = 11.6, 6.7, 3.2 Hz, 1H), 3.99 (dd, J = 8.9, 3.2 Hz, 1H), 3.84 (dd, J = 8.9, 4.1 Hz, 1H), 1.41 (d, J = 5.4 Hz, 3H), 0.76 (d, J = 4.4 Hz, 3H). |
| 552 | 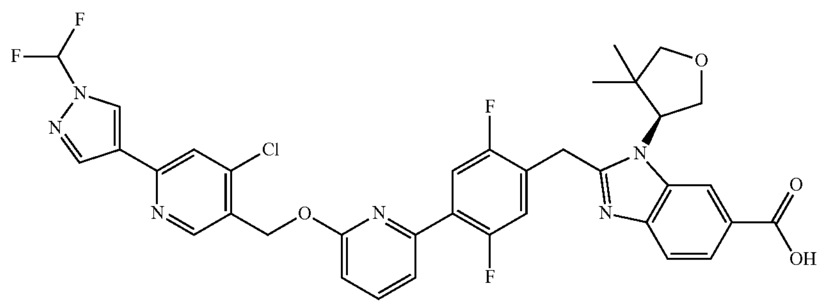 [SMILES: CC1(C)COC[C@H]1n1c(Cc2cc(F)c(-c3cccc(OCc4cnc(-c5cnn(C(F)F)c5)cc4Cl)n3)cc2F)nc2ccc(C(=O)O)cc21] | 41 | 721.2 | 1H NMR (400 MHz, Methanol-d4) δ 8.89 (s, 1H), 8.80- 8.63 (m, 2H), 8.29 (s, 1H), 8.17 (dd, J = 8.6, 1.4 Hz, 1H), 8.05-7.89 (m, 2H), 7.90-7.74 (m, 3H), 6.96 (dd, J = 8.3, 0.7 Hz, 1H), 5.67 (s, 2H), 5.13 (d, J = 6.5 Hz, 1H), 4.79-4.59 (m, 3H), 4.52 (dd, J = 11.6, 6.7 Hz, 1H), 3.99 (d, J = 8.9 Hz, 1H), 3.83 (d, J = 8.9 Hz, 1H), 1.40 (s, 3H), 0.75 (s, 3H). |

TABLE 2-continued

Compounds

| Ex. | Structure | Procedure | ES/MS m/z | 1H NMR |
|---|---|---|---|---|
| 553 | 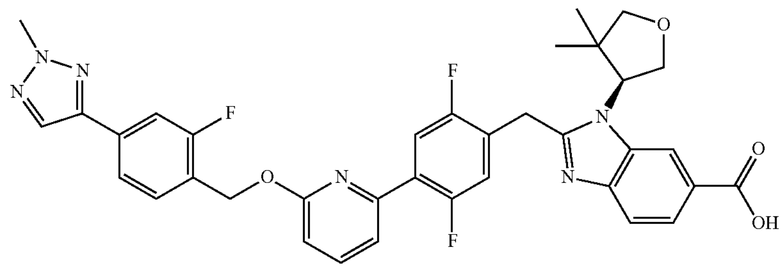 [SMILES: Cn1ncc(-c2ccc(COc3cccc(-c4cc(F)c(Cc5nc6ccc(C(=O)O)cc6n5[C@@H]5COCC5(C)C)cc4F)n3)c(F)c2)n1] | 41 | 669.1 | 1H NMR (400 MHz, Methanol-d4) δ 8.90 (s, 1H), 8.18 (dd, J = 8.6, 1.4 Hz, 1H), 8.02 (s, 1H), 7.94 (dd, J = 10.9, 6.3 Hz, 1H), 7.89-7.72 (m, 4H), 7.71-7.50 (m, 4H), 7.39 (dd, J = 11.2, 6.0 Hz, 1H), 6.93 (d, J = 8.2 Hz, 1H), 5.58 (s, 2H), 5.14 (d, J = 6.5 Hz, 1H), 4.80-4.59 (m, 3H), 4.52 (dd, J = 11.6, 6.7 Hz, 1H), 4.22 (s, 3H), 3.99 (d, J = 8.9 Hz, 1H), 3.83 (d, J = 8.9 Hz, 1H), 1.40 (s, 3H), 0.75 (s, 3H). |
| 554 | 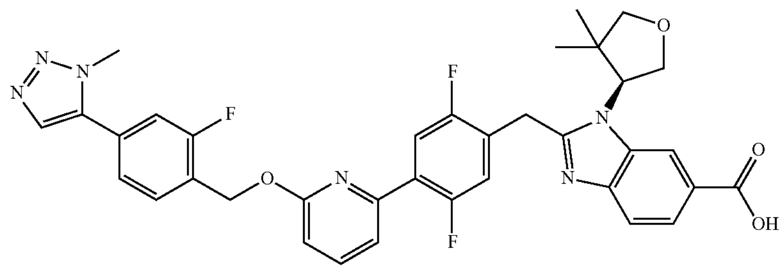 [SMILES: Cn1nncc1-c1ccc(COc2cccc(-c3cc(F)c(Cc4nc5ccc(C(=O)O)cc5n4[C@@H]4COCC4(C)C)cc3F)n2)c(F)c1] | 41 | 669.1 | 1H NMR (400 MHz, Methanol-d4) δ 8.88 (s, 1H), 8.16 (dd, J = 8.6, 1.4 Hz, 1H), 7.97-7.86 (m, 2H), 7.84 (dd, J = 8.3, 7.5 Hz, 1H), 7.80-7.68 (m, 2H), 7.59 (dd, J = 7.2, 1.6 Hz, 1H), 7.49-7.33 (m, 3H), 6.95 (dd, J = 8.3, 0.6 Hz, 1H), 5.64 (s, 2H), 5.13 (d, J = 6.6 Hz, 1H), 4.81-4.57 (m, 3H), 4.52 (dd, J = 11.6, 6.7 Hz, 1H), 4.13 (s, 3H), 3.99 (d, J = 8.9 Hz, 1H), 3.84 (d, J = 8.9 Hz, 1H), 1.41 (s, 3H), 0.75 (s, 3H). |
| 555 | 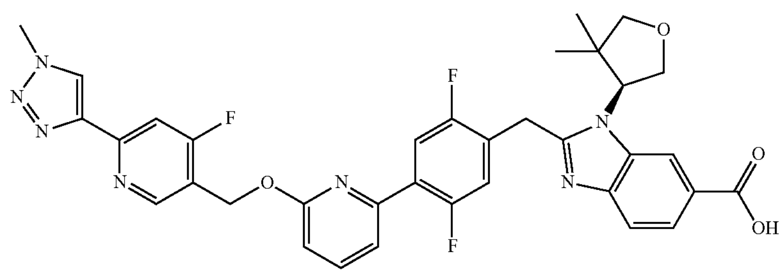 [SMILES: Cn1cc(-c2cc(F)c(COc3cccc(-c4cc(F)c(Cc5nc6ccc(C(=O)O)cc6n5[C@@H]5COCC5(C)C)cc4F)n3)cn2)nn1] | 41 | 670.1 | 1H NMR (400 MHz, Methanol-d4) δ 8.89 (d, J = 9.8 Hz, 1H), 8.83 (s, 1H), 8.23 (s, 1H), 8.12 (dd, J = 8.6, 1.4 Hz, 1H), 8.03-7.90 (m, 1H), 7.88-7.69 (m, 3H), 7.65-7.51 (m, 1H), 7.36 (dd, J=11.2, 6.1 Hz, 1H), 6.94 (dd, J = 8.2, 0.7 Hz, 1H), 5.68 (s, 2H), 5.09 (d, J = 6.4 Hz, 1H), 4.76-4.56 (m, 3H), 4.52 (dd, J = 11.5, 6.7 Hz, 1H), 4.40 (s, |

TABLE 2-continued

Compounds

| Ex. | Structure | Procedure | ES/MS m/z | ¹H NMR |
|---|---|---|---|---|
| | | | | 3H), 3.99 (d, J = 8.9 Hz, 1H), 3.83 (d, J = 8.9 Hz, 1H), 1.40 (s, 3H), 0.74 (s, 3H). |
| 556 | (structure) | 35 | 654.0 | 1H NMR (400 MHz, DMSO-d6) δ 8.54 (s, 1H), 7.94-7.88 (m, 1H), 7.81 (dd, J = 8.5, 1.5 Hz, 1H), 7.78-7.69 (m, 5H), 7.61 (d, J = 8.4 Hz, 1H), 7.53 (dd, J = 7.5, 1.7 Hz, 1H), 7.38 (dd, J = 11.4, 6.1 Hz, 1H), 7.01 (d, J = 8.3 Hz, 1H), 5.59 (s, 2H), 5.52 (s, 1H), 4.58-4.40 (m, 3H), 4.21 (dd, J = 10.8, 6.5 Hz, 1H), 4.08 (t, J = 8.8 Hz, 1H), 3.82-3.72 (m, 2H), 3.18-2.99 (m, 2H), 2.91 (s, 3H). |
| 557 | (structure) | 35 | 606.0 | 1H NMR (400 MHz, DMSO-d6) δ 8.50 (s, 1H), 7.89-7.77 (m, 3H), 7.63 (d, J = 8.5 Hz, 1H), 7.61-7.52 (m, 3H), 7.48 (dd, J = 11.5, 6.1 Hz, 1H), 7.30-7.17 (m, 2H), 5.55 (s, 2H), 5.03 (d, J = 6.6 Hz, 1H), 4.62-4.55 (m, 1H), 4.53 (d, J = 1.5 Hz, 1H), 4.48-4.35 (m, 2H), 3.84-3.68 (m, 2H), 1.34 (s, 3H), 0.61 (s, 3H). |
| 558 | (structure) | 35 | 624.0 | 1H NMR (400 MHz, DMSO-d6) δ 8.48 (s, 1H), 7.90 (dd, J = 10.3, 8.2 Hz, 1H), 7.78 (dd, J = 8.5, 1.5 Hz, 1H), 7.76-7.67 (m, 1H), 7.63-7.53 (m, 4H), 7.31-7.20 (m, 2H), 5.56 (s, 2H), 5.09 (d, J = 6.6 Hz, 1H), 4.73-4.52 (m, 2H), 4.47 (dd, J = 11.2, 6.7 Hz, 1H), 4.35 (d, J = 17.4 Hz, 1H), 3.84-3.70 (m, 2H), 1.39 (s, 3H), 0.66 (s, 3H). |

TABLE 2-continued

Compounds

| Ex. | Structure | Procedure | ES/MS m/z | ¹H NMR |
|---|---|---|---|---|
| 559 | 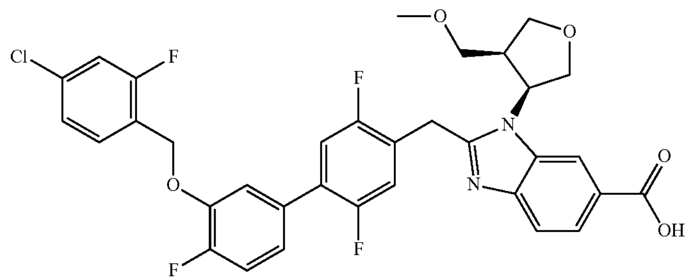 | 35 | 655.2 | 1H NMR (400 MHz, MeOD) δ 8.74 (s, 1H), 7.97 (dd, J = 8.5, 1.5 Hz, 1H), 7.69-7.62 (m, 1H), 7.62-7.52 (m, 2H), 7.41-7.29 (m, 2H), 7.29-7.22 (m, 2H), 7.22-7.10 (m, 2H), 5.49 (t, J = 7.3 Hz, 1H), 5.27-5.17 (m, 2H), 4.65-4.47 (m, 3H), 4.33-4.22 (m, 1H), 4.00-3.87 (m, 1H), 2.96 (s, 3H). |
| 560 | 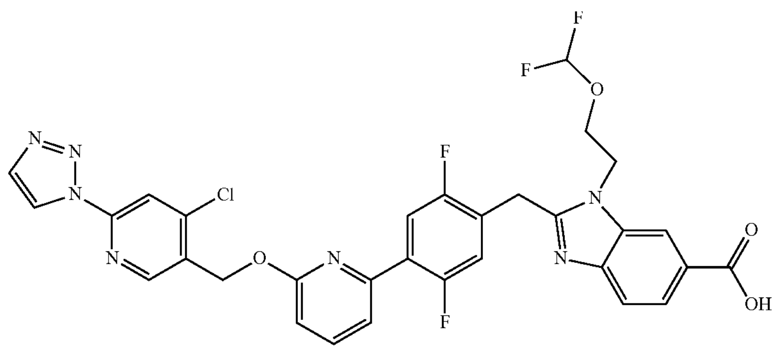 [SMILES: O=C(O)c1ccc2nc(Cc3cc(F)c(-c4cccc(OCc5cnc(-n6ccnn6)cc5Cl)n4)cc3F)n(CCOC(F)F)c2c1] | 22 | 668.0 | 1H NMR (400 MHz, DMSO-d6) δ 8.90 (d, J = 1.3 Hz, 1H), 8.82 (s, 1H), 8.30 (s, 1H), 8.25 (d, J = 1.5 Hz, 1H), 8.02 (d, J = 1.3 Hz, 1H), 7.94-7.85 (m, 2H), 7.80 (dd, J = 8.4, 1.6 Hz, 1H), 7.61 (d, J = 8.5 Hz, 1H), 7.57-7.52 (m, 1H), 7.40 (dd, J = 11.5, 6.0 Hz, 1H), 7.00 (d, J = 8.2 Hz, 1H), 6.64 (t, J = 75.4 Hz, 1H), 5.67 (s, 2H), 4.72 (t, J = 5.1 Hz, 2H), 4.44 (s, 2H), 4.20 (t, J = 5.0 Hz, 2H). |
| 561 | 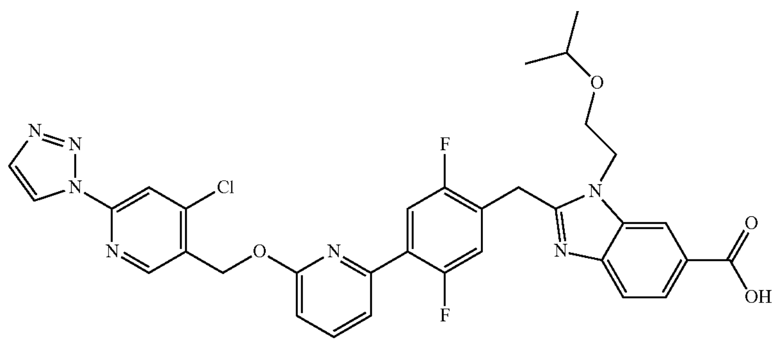 [SMILES: CC(C)OCCn1c(Cc2cc(F)c(-c3cccc(OCc4cnc(-n5ccnn5)cc4Cl)n3)cc2F)nc2ccc(C(=O)O)cc21] | 22 | 660.0 | 1H NMR (400 MHz, DMSO-d6) δ 8.90 (d, J = 1.3 Hz, 1H), 8.82 (s, 1H), 8.30 (s, 1H), 8.27 (d, J = 1.5 Hz, 1H), 8.02 (d, J = 1.2 Hz, 1H), 7.94-7.86 (m, 2H), 7.83 (dd, J = 8.4, 1.5 Hz, 1H), 7.62 (d, J = 8.4 Hz, 1H), 7.54 (dd, J = 7.4, 1.7 Hz, 1H), 7.40 (dd, J = 11.4, 6.1 Hz, 1H), 5.66 (s, 2H), 4.58 (t, J = 5.1 Hz, 2H), 4.52 (s, 2H), 3.71 (t, J = 5.0 Hz, 2H), 3.45 (p, J = 6.0 Hz, 1H), 0.95 (s, 3H), 0.93 (s, 3H |

TABLE 2-continued

Compounds

| Ex. | Structure | Procedure | ES/MS m/z | ¹H NMR |
|---|---|---|---|---|
| 562 | 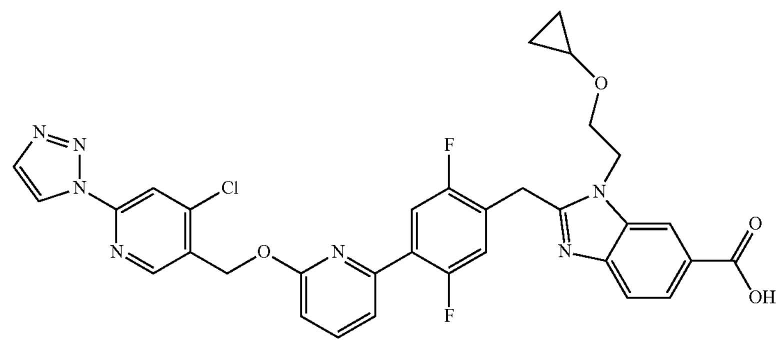 [SMILES: O=C(O)c1ccc2nc(Cc3cc(F)c(-c4cccc(OCc5cnc(-n6ccnn6)cc5Cl)n4)cc3F)n(CCOC3CC3)c2c1] | 22 | 658.1 | 1H NMR (400 MHz, DMSO-d6) δ 8.90 (d, J = 1.3 Hz, 1H), 8.83 (s, 1H), 8.31 (s, 1H), 8.26 (d, J = 1.5 Hz, 1H), 8.03 (d, J = 1.3 Hz, 1H), 7.96-7.86 (m, 2H), 7.84 (dd, J = 8.5, 1.6 Hz, 1H), 7.63 (d, J = 8.4 Hz, 1H), 7.55 (dd, J = 7.5, 1.7 Hz, 1H), 7.40 (dd, J = 11.5, 6.1 Hz, 1H), 7.01 (d, J = 8.3 Hz, 1H), 5.67 (s, 2H), 4.60 (t, J = 5.1 Hz, 2H), 4.46 (s, 2H), 3.79 (t, J = 5.0 Hz, 2H), 3.25 (tt, J = 6.1, 3.0 Hz, 1H), 0.31 (ddd, J = 13.8, 6.6, 2.7 Hz, 2H), 0.24 (tt, J = 6.3, 3.2 Hz, 2H). |
| 563 | 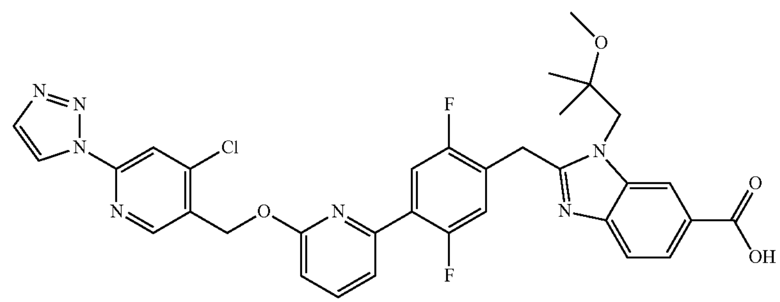 [SMILES: COC(C)(C)Cn1c(Cc2cc(F)c(-c3cccc(OCc4cnc(-n5ccnn5)cc4Cl)n3)cc2F)nc2ccc(C(=O)O)cc21] | 35 | 660.2 | 1H NMR (400 MHz, DMSO-d6) δ 8.89 (d, J = 1.2 Hz, 1H), 8.81 (s, 1H), 8.39 (d, J = 1.5 Hz, 1H), 8.30 (s, 1H), 8.03 (d, J = 1.3 Hz, 1H), 7.93-7.86 (m, 2H), 7.84 (dd, J = 8.5, 1.3 Hz, 1H), 7.62 (d, J = 8.4 Hz, 1H), 7.55 (dd, J = 7.4, 1.7 Hz, 1H), 7.41 (dd, J = 11.5, 6.1 Hz, 1H), 7.00 (d, J = 8.2 Hz, 1H), 5.66 (s, 2H), 4.55 (s, 2H), 4.50 (s, 2H), 3.10 (s, 3H), 1.21 (s, 6H). |
| 564 | 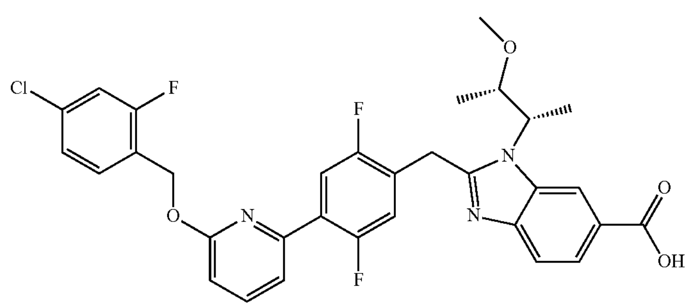 [SMILES: CO[C@@H](C)[C@H](C)n1c(Cc2cc(F)c(-c3cccc(OCc4ccc(Cl)cc4F)n3)cc2F)nc2ccc(C(=O)O)cc21] | 35 | 601.2 | 1H NMR (400 MHz, DMSO-d6) δ 8.32 (d, J = 1.5 Hz, 1H), 7.90-7.85 (m, 1H), 7.85-7.78 (m, 2H), 7.64-7.57 (m, 2H), 7.53-7.47 (m, 2H), 7.38 (dd, J = 11.5, 6.1 Hz, 1H), 7.32 (dd, J = 8.2, 2.1 Hz, 1H), 6.94 (d, J = 8.2 Hz, 1H), 5.50 (s, 2H), 4.70 (s, 1H), 4.45 (q, J = 16.8 Hz, 2H), 3.93-3.81 (m, 1H), 3.00 (s, 3H), 1.62 (d, J = 7.1 Hz, 3H), 1.21 (d, J = 6.1 Hz, 3H). |

TABLE 2-continued

Compounds

| Ex. | Structure | Procedure | ES/MS m/z | ¹H NMR |
|---|---|---|---|---|
| 565 | 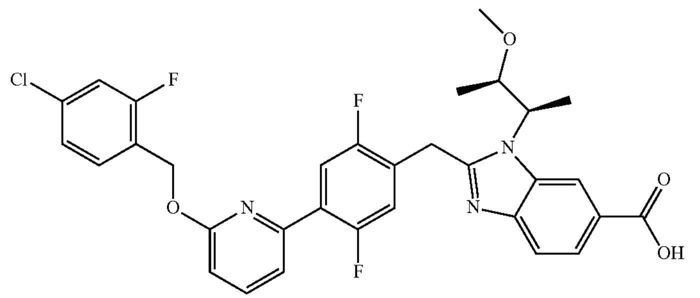 [SMILES: CO[C@H](C)[C@@H](C)n1c(Cc2cc(F)c(-c3cccc(OCc4ccc(Cl)cc4F)n3)cc2F)nc2ccc(C(=O)O)cc21] | 35 | 610.2 | 1H NMR (400 MHz, DMSO-d6) δ 8.33 (d, J = 1.5 Hz, 1H), 7.91-7.85 (m, 1H), 7.85-7.79 (m, 2H), 7.63 (d, J = 8.3 Hz, 1H), 7.59 (d, J = 8.2 Hz, 1H), 7.50 (td, J = 10.0, 9.3, 1.9 Hz, 2H), 7.39 (dd, J = 11.5, 6.1 Hz, 1H), 7.32 (dd, J = 8.3, 2.1 Hz, 1H), 6.94 (d, J = 8.2 Hz, 1H), 5.50 (s, 2H), 4.71 (s, 1H), 4.46 (q, J = 16.8 Hz, 2H), 3.88 (dd, J = 8.1, 6.1 Hz, 1H), 3.00 (s, 3H), 1.62 (d, J = 7.1 Hz, 3H), 1.21 (d, J = 6.1 Hz, 3H). |
| 566 | 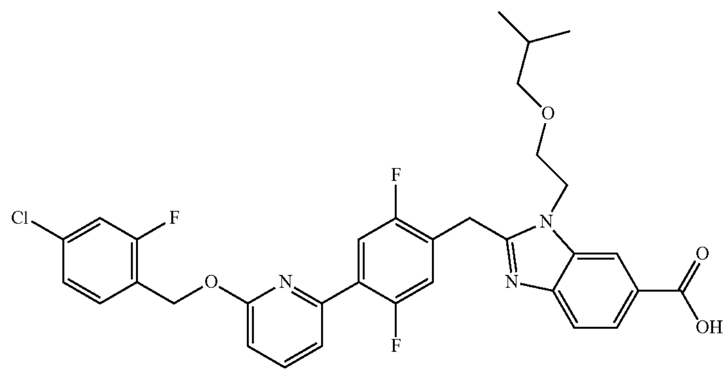 [SMILES: CC(C)COCCn1c(Cc2cc(F)c(-c3cccc(OCc4ccc(Cl)cc4F)n3)cc2F)nc2ccc(C(=O)O)cc21] | 22 | 624.3 | 1H NMR (400 MHz, DMSO-d6) δ 8.26 (d, J = 1.5 Hz, 1H), 7.91-7.85 (m, 1H), 7.84-7.82 (m, 1H), 7.81 (d, J = 1.5 Hz, 1H), 7.66-7.56 (m, 1H), 7.61 (d, J = 3.2 Hz, 1H), 7.54-7.46 (m, 2H), 7.37 (dd, J = 11.5, 6.1 Hz, 1H), 7.33 (dd, J = 8.4, 2.1 Hz, 1H), 6.95 (d, J = 8.2 Hz, 1H), 5.50 (s, 2H), 4.61 (t, J = 5.1 Hz, 2H), 4.50 (s, 2H), 3.71 (t, J = 5.0 Hz, 2H), 3.10 (d, J = 6.5 Hz, 2H), 1.66 (hept, J = 6.7 Hz, 1H), 0.72 (s, 3H), 0.70 (s, 3H). |

TABLE 2-continued

Compounds

| Ex. | Structure | Procedure | ES/MS m/z | ¹H NMR |
|---|---|---|---|---|
| 567 | 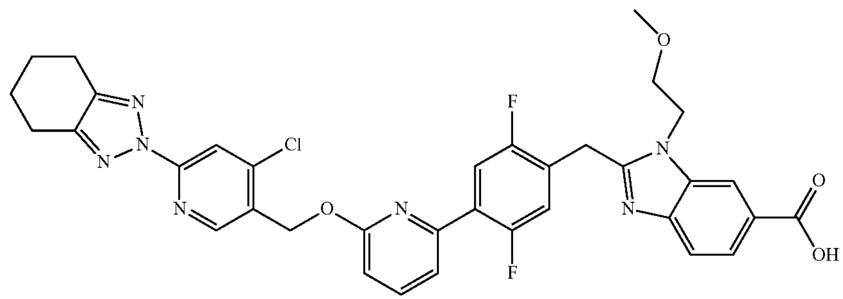 [SMILES: COCCn1c(Cc2cc(F)c(-c3cccc(OCc4cnc(-n5nc6c(n5)CCCC6)cc4Cl)n3)cc2F)nc2ccc(C(=O)O)cc21] | 38 | 686.3 | 1H NMR (400 MHz, DMSO-d6) δ 8.73 (s, 1H), 8.26 (d, J = 1.5 Hz, 1H), 8.04 (s, 1H), 7.93-7.86 (m, 2H), 7.84 (dd, J = 8.4, 1.5 Hz, 1H), 7.64 (d, J = 8.5 Hz, 1H), 7.54 (dd, J = 7.5, 1.7 Hz, 1H), 7.41 (dd, J = 11.5, 6.1 Hz, 1H), 6.99 (d, J = 8.2 Hz, 1H), 5.62 (s, 2H), 4.63 (t, J = 5.1 Hz, 2H), 4.50 (s, 2H), 3.69 (t, J = 5.0 Hz, 2H), 3.21 (s, 3H), 2.77 (d, J = 5.5 Hz, 4H), 1.83 (q, J = 3.3 Hz, 4H). |
| 568 | 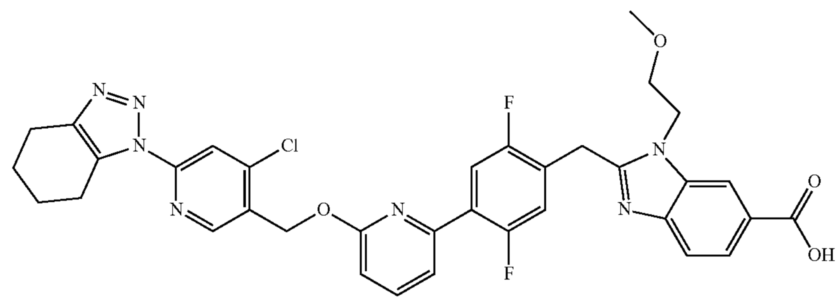 [SMILES: COCCn1c(Cc2cc(F)c(-c3cccc(OCc4cnc(-n5nnc6c5CCCC6)cc4Cl)n3)cc2F)nc2ccc(C(=O)O)cc21] | 38 | 686.1 | 1H NMR (400 MHz, DMSO-d6) δ 8.79 (s, 1H), 8.24 (d, J = 1.5 Hz, 1H), 8.20 (s, 1H), 7.91 (t, J = 7.9 Hz, 1H), 7.88-7.79 (m, 2H), 7.62 (d, J = 8.4 Hz, 1H), 7.54 (dd, J = 7.5, 1.7 Hz, 1H), 7.40 (dd, J = 11.5, 6.0 Hz, 1H), 7.00 (d, J = 8.2 Hz, 1H), 5.64 (s, 2H), 4.62 (t, J = 5.2 Hz, 2H), 4.48 (s, 2H), 3.68 (t, J = 5.1 Hz, 2H), 3.21 (s, 3H), 3.03 (s, 2H), 2.71 (s, 2H), 1.82-1.71 (m, 4H). |

TABLE 2-continued

Compounds

| Ex. | Structure | Procedure | ES/MS m/z | ¹H NMR |
|---|---|---|---|---|
| 569 | 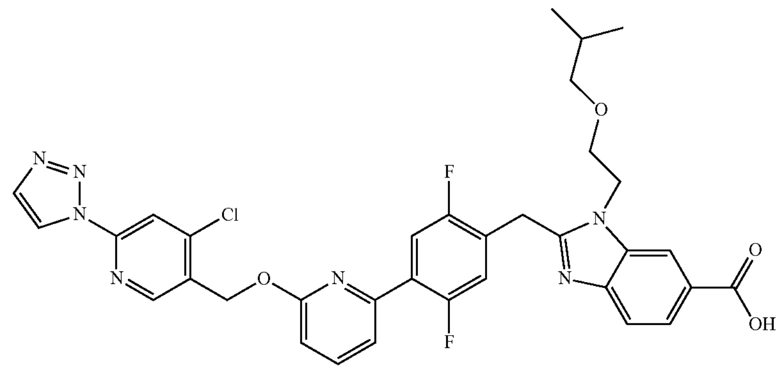 [SMILES: CC(C)COCCn1c(Cc2cc(F)c(-c3cccc(OCc4cnc(-n5ccnn5)cc4Cl)n3)cc2F)nc2ccc(C(=O)O)cc21] | 22 | 674.1 | 1H NMR (400 MHz, DMSO-d6) δ 8.89 (d, J = 1.3 Hz, 1H), 8.82 (s, 1H), 8.30 (s, 1H), 8.28 (d, J = 1.5 Hz, 1H), 8.02 (d, J = 1.3 Hz, 1H), 7.94-7.90 (m, 1H), 7.90-7.86 (m, 1H), 7.84 (dd, J = 8.4, 1.5 Hz, 1H), 7.63 (d, J = 8.5 Hz, 1H), 7.54 (dd, J = 7.3, 1.7 Hz, 1H), 7.39 (dd, J = 11.4, 6.1 Hz, 1H), 7.00 (dd, J = 8.3, 0.6 Hz, 1H), 5.66 (s, 2H), 4.63 (t, J = 5.0 Hz, 2H), 4.53 (s, 2H), 3.71 (t, J = 4.9 Hz, 2H), 3.10 (d, J = 6.5 Hz, 2H), 1.65 (hept, J = 6.7 Hz, 1H), 0.72 (s, 3H), 0.70 (s, 3H). |
| 570 | 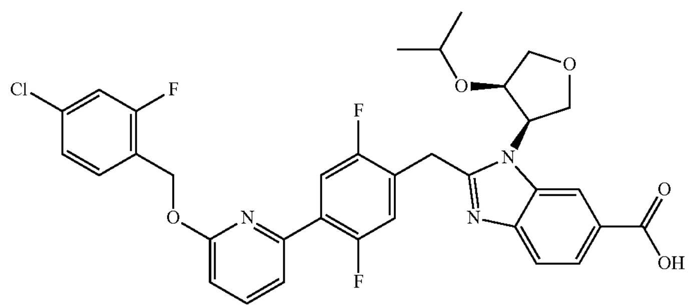 [SMILES: CC(C)O[C@H]1COC[C@H]1n1c(Cc2cc(F)c(-c3cccc(OCc4ccc(Cl)cc4F)n3)cc2F)nc2ccc(C(=O)O)cc21] | 37 | 652.2 | 1H NMR (400 MHz, DMSO) δ 8.36 (d, J = 1.5 Hz, 1H), 7.93-7.79 (m, 3H), 7.71 (d, J = 8.5 Hz, 1H), 7.60 (t, J = 8.2 Hz, 1H), 7.56-7.46 (m, 2H), 7.46-7.26 (m, 2H), 6.95 (d, J = 8.3 Hz, 1H), 5.50 (s, 2H), 5.29 (dt, J = 7.4, 3.5 Hz, 1H), 4.67-4.13 (m, 6H), 3.78-3.59 (m, 1H), 3.37 (m, J = 7.0 Hz, 1H), 1.00 (d, J = 7.0 Hz, 6H). |

TABLE 2-continued

Compounds

| Ex. | Structure | Procedure | ES/MS m/z | ¹H NMR |
|---|---|---|---|---|
| 571 | 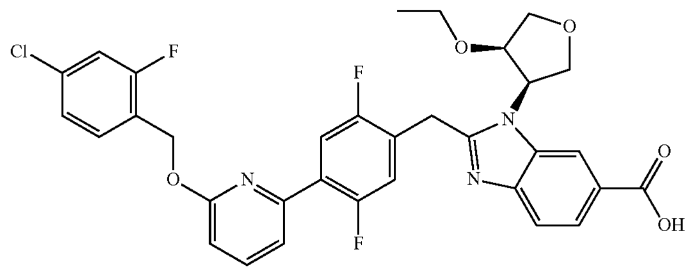 [SMILES: CCO[C@H]1COC[C@H]1n1c(Cc2cc(F)c(-c3cccc(OCc4ccc(Cl)cc4F)n3)cc2F)nc2ccc(C(=O)O)cc21] | 37 | 638.1 | 1H NMR (400 MHz, DMSO) δ 8.34 (d, J = 1.5 Hz, 1H), 7.93-7.79 (m, 3H), 7.69 (d, J = 8.5 Hz, 1H), 7.60 (t, J = 8.2 Hz, 1H), 7.50 (ddd, J = 8.6, 5.6, 2.0 Hz, 2H), 7.45-7.27 (m, 2H), 6.95 (d, J = 8.2 Hz, 1H), 5.50 (s, 2H), 5.39-5.18 (m, 1H), 4.64-4.46 (m, 2H), 4.34-4.12 (m, 2H), 3.71 (h, J = 5.2 Hz, 1H), 3.45-3.30 (m, 2H), 1.00 (t, J = 7.0 Hz, 3H). |
| 572 | 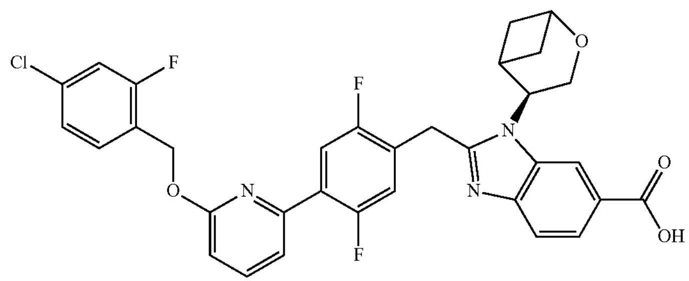 [SMILES: O=C(O)c1ccc2nc(Cc3cc(F)c(-c4cccc(OCc5ccc(Cl)cc5F)n4)cc3F)n([C@@H]3COC4CC3C4)c2c1] | 35 | 620.0 | 1H NMR (400 MHz, DMSO-d6) δ 8.71 (d, J = 1.4 Hz, 1H), 7.92-7.81 (m, 3H), 7.67-7.58 (m, 2H), 7.55-7.43 (m, 3H), 7.34 (dd, J = 8.2, 2.1 Hz, 1H), 6.96 (d, J = 8.3 Hz, 1H), 5.51 (s, 2H), 5.46 (q, J = 4.5, 3.8 Hz, 1H), 4.74-4.63 (m, 2H), 4.60-4.40 (m, 3H), 3.08 (p, J = 5.5 Hz, 1H), 2.36 (ddd, J = 11.0, 5.8, 3.6 Hz, 1H), 2.28 (dd, J = 10.9, 9.2 Hz, 1H), 2.13-2.04 (m, 1H), 2.00 (dd, J = 10.7, 9.2 Hz, 1H). |
| 573 | 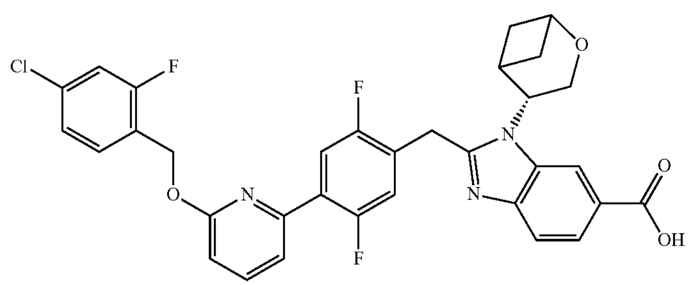 [SMILES: O=C(O)c1ccc2nc(Cc3cc(F)c(-c4cccc(OCc5ccc(Cl)cc5F)n4)cc3F)n([C@H]3COC4CC3C4)c2c1] | 35 | 620.0 | 1H NMR (400 MHz, DMSO-d6) δ 8.71 (d, J = 1.4 Hz, 1H), 7.92-7.81 (m, 3H), 7.67-7.58 (m, 2H), 7.55-7.43 (m, 3H), 7.34 (dd, J = 8.2, 2.1Hz, 1H), 6.96 (d, J = 8.3 Hz, 1H), 5.51 (s, 2H), 5.46 (q, J = 4.5, 3.8 Hz, 1H), 4.74-4.63 (m, 2H), 4.60-4.40 (m, 3H), 3.08 (p, J = 5.5 Hz, 1H), 2.36 (ddd, J = 11.0, 5.8, 3.6 Hz, 1H), 2.28 (dd, J = 10.9, 9.2 Hz, 1H), 2.13-2.04 (m, 1H), 2.00 (dd, J = 10.7, 9.2 Hz, 1H). |

TABLE 2-continued

Compounds

| Ex. | Structure | Procedure | ES/MS m/z | ¹H NMR |
|---|---|---|---|---|
| 574 | 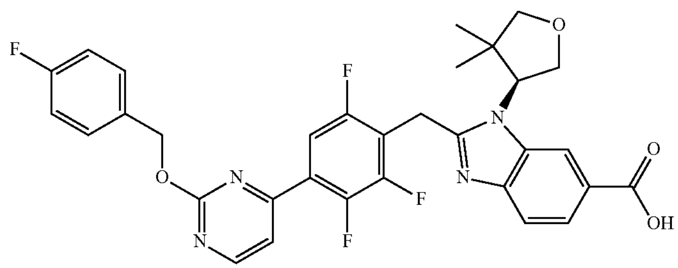 [SMILES: CC1(C)COC[C@H]1n1c(Cc2c(F)cc(-c3ccnc(OCc4ccc(F)cc4)n3)c(F)c2F)nc2ccc(C(=O)O)cc21] | 35 | 607.0 | 1H NMR (400 MHz, DMSO) δ 8.84 (d, J = 5.1 Hz, 1H), 8.48 (s, 1H), 7.84 (ddd, J = 9.9, 5.6, 2.0 Hz, 1H), 7.78 (dd, J = 8.4, 1.5 Hz, 1H), 7.68 (dd, J = 5.1, 1.8 Hz, 1H), 7.63-7.53 (m, 3H), 7.30-7.20 (m, 2H), 5.50 (s, 2H), 5.13-5.04 (m, 1H), 4.68 (d, J = 17.3 Hz, 1H), 4.57 (d, J = 11.5 Hz, 1H), 4.51-4.34 (m, 2H), 3.79-3.74 (m, 2H), 1.39 (s, 3H), 0.66 (s, 3H). |
| 575 | 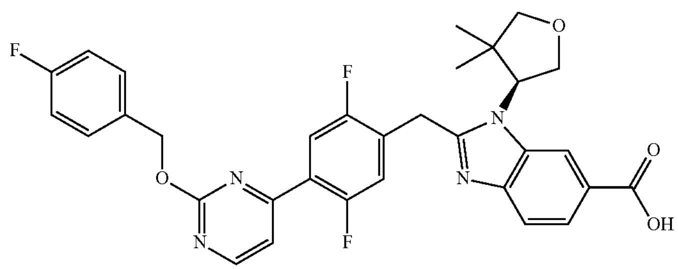 [SMILES: CC1(C)COC[C@H]1n1c(Cc2cc(F)c(-c3ccnc(OCc4ccc(F)cc4)n3)cc2F)nc2ccc(C(=O)O)cc21] | 35 | 589.1 | 1H NMR (400 MHz, DMSO) δ 8.78 (d, J = 5.2 Hz, 1H), 8.48 (s, 1H), 7.94 (dd, J = 10.2, 6.3 Hz, 1H), 7.80 (dd, J = 8.4, 1.5 Hz, 1H), 7.70-7.50 (m, 5H), 7.29-7.19 (m, 2H), 5.49 (s, 2H), 5.02 (d, J = 6.7 Hz, 1H), 4.61-4.50 (m, 2H), 4.49-4.36 (m, 2H), 3.81-3.70 (m, 2H), 1.34 (s, 3H), 0.61 (s, 3H) |
| 576 | 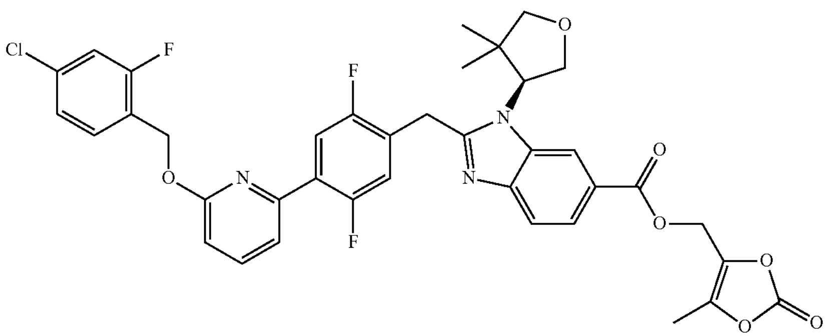 [SMILES: Cc1oc(=O)oc1COC(=O)c1ccc2nc(Cc3cc(F)c(-c4cccc(OCc5ccc(Cl)cc5F)n4)cc3F)n([C@@H]3COCC3(C)C)c2c1] | 42 | 734.0 | 1H NMR (400 MHz, DMSO-d6) δ 8.52 (s, 1H), 7.88 (dd, J = 8.2, 7.5 Hz, 1H), 7.85-7.79 (m, 2H), 7.65 (d, J = 8.6 Hz, 1H), 7.60 (t, J = 8.2 Hz, 1H), 7.55-7.51 (m, 1H), 7.49 (dd, J = 10.1, 2.1 Hz, 1H), 7.47-7.42 (m, 1H), 7.33 (dd, J = 8.3, 2.1 Hz, 1H), 6.95 (d, J = 8.2 Hz, 1H), 5.50 (s, 2H), 5.23 (s, 2H), 5.02 (d, J = 6.6 Hz, 1H), 4.53 (d, J = 13.9 Hz, 1H), 4.48-4.30 (m, 2H), 3.80-3.68 (m, 2H), 2.23 (s, 3H), 1.34 (s, 3H), 1.21 (d, J = 16.9 Hz, 1H), 0.59 (s, 3H |

TABLE 2-continued

Compounds

| Ex. | Structure | Procedure | ES/MS m/z | ¹H NMR |
|---|---|---|---|---|
| 577 | 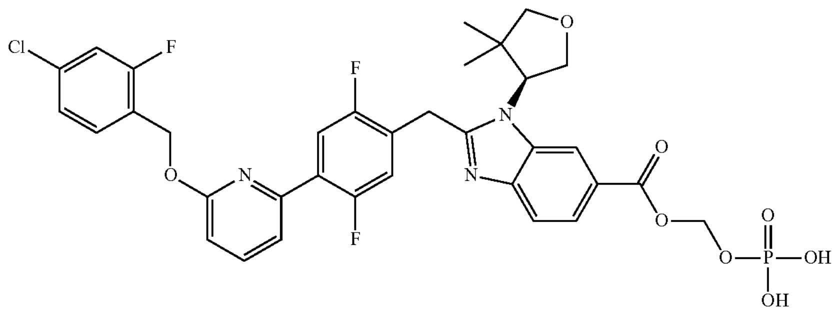 [SMILES: CC1(C)COC[C@H]1n1c(Cc2cc(F)c(-c3cccc(OCc4ccc(Cl)cc4F)n3)cc2F)nc2ccc(C(=O)OCOP(=O)(O)O)cc21] | 43 | 731.9 | 1H NMR (400 MHz, DMSO-d6) δ 8.54 (s, 1H), 7.92-7.80 (m, 3H), 7.68 (d, J = 8.5 Hz, 1H), 7.60 (t, J = 8.2 Hz, 1H), 7.53 (dd, J = 7.5, 1.6 Hz, 1H), 7.49 (dd, J = 10.0, 2.1 Hz, 1H), 7.47-7.43 (m, 1H), 7.33 (dd, J = 8.4, 2.1 Hz, 1H), 6.95 (d, J = 8.4 Hz, 1H), 5.82-5.68 (m, 2H), 5.51 (s, 2H), 5.03 (d, J = 6.7 Hz, 1H), 4.60-4.55 (m, 1H), 4.53 (s, 1H), 4.48-4.35 (m, 2H), 3.79 (d, J = 8.7 Hz, 1H), 3.73 (d, J = 8.6 Hz, 1H), 1.34 (s, 3H), 0.60 (s, 3H). |
| 578 | 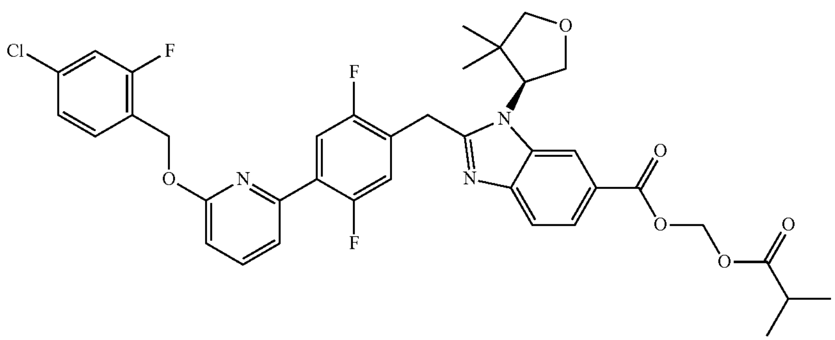 [SMILES: CC(C)C(=O)OCOC(=O)c1ccc2nc(Cc3cc(F)c(-c4cccc(OCc5ccc(Cl)cc5F)n4)cc3F)n([C@@H]3COCC3(C)C)c2c1] | 42 | 722.1 | |

C. Biological Data

GLP-1R Activation—cAMP Assay 1

GLP-1R activation by compounds of the present disclosure were quantified by measuring cAMP increase in CHO cells stably expressing GLP-1R (MultiSpan product #$C_{1267}$-1a). The cells were harvested and plated in growth medium (DMEM/F-12 (Corning product #10-090-CV) supplemented with 10% FBS (HyClone product #SH30071-03), penicillin/streptomycin (Corning product #30-002CI) and 10 g/ml puromycin (Gibco product #A11138-03)) at 1,000 cells/well in a 384-well plate (Greiner product #781080). The cells were then incubated overnight at 37° C., 5% $CO_2$. The next day, the medium was removed and the cells were washed with DPBS (Corning product #21-031-CM) before adding the assay medium (HBSS, Corning product #21-023-CV) with 20 mM Hepes (Gibco product #15630-080) and 0.1% BSA (Rockland Immunochemicals product #BSA-1000)). Following the medium change, the cells were incubated for 1 hour at 37° C., 5% $CO_2$. The tested GLP-1 compound was added to the cells in a 10-point dose response followed by a 30 minutes incubation at 37° C., 5% $CO_2$. cAMP concentration increase was then detected using Cisbio's cAMP Gs Dynamic Kit (product #62AM4PEC) according to the manufacturer's protocol. The response was plotted against the log of the agonist concentration and fitted to a sigmoidal equation to determine the $EC_{50}$.

GLP-1R Activation—cAMP Assay 2

GLP-1R activation by small molecule agonists was quantified by measuring cAMP increase in CHO cells stably expressing GLP-1R (MultiSpan product #$C_{1267-1}$a). 50 nL of agonists were pre-spotted in a 10-point dose response onto 384-well plate (Corning product #CL3826) using the Labcyte Echo System. The cells were harvested and plated in assay buffer (HIBSS (Corning product #21-023-CV) with 20 mM Hepes (Gibco product #15630-080) and 0.100 BSA (Rockland Immunochemicals product #BSA-1000) at 1,000 cells/well, 10 μL/well, onto the pre-spotted plates. The cells are then incubated for 30 minutes at 37° C., 500 $CO_2$. cAMP concentration increase was then detected using Cisbio's cAMP Gs Dynamic Kit (product #62AM4PEC) according to the manufacturer's protocol. The response was plotted against the log of the agonist concentration and fitted to a sigmoidal equation to determine the $EC_{50}$.

All compounds were run on one of the two GLP-1R Activation cAMP assays and the result are listed in Table 3, below.

TABLE 3

| Example No. | Activity GLP-1R Activation - Assay EC50 (nM) |
|---|---|
| 1 | 1.12 |
| 2 | 155.78 |
| 3 | 11.53 |
| 4 | 2.65 |
| 5 | 0.77 |
| 6 | 8.49 |
| 7 | 0.60 |
| 8 | 21.24 |
| 9 | 7.88 |
| 10 | 952.92 |
| 11 | 0.26 |
| 12 | 0.03 |
| 13 | 0.19 |
| 14 | 78.66 |
| 15 | 70.99 |
| 16 | 4800.27 |
| 17 | 5.61 |
| 18 | 49.19 |
| 19 | 0.60 |
| 20 | 0.35 |
| 21 | 0.11 |
| 22 | 0.72 |
| 23 | 4.57 |
| 24 | 9.96 |
| 25 | 7.55 |
| 26 | 18.68 |
| 27 | 13.08 |
| 28 | 1.46 |
| 29 | 35.98 |
| 30 | 49.90 |
| 31 | 30.43 |
| 32 | 3.43 |
| 33 | 2.58 |
| 34 | 3.25 |
| 35 | 2.67 |
| 36 | 1.04 |
| 37 | 1.97 |
| 38 | 4.02 |
| 39 | 8.98 |
| 40 | 154.83 |
| 41 | 4.88 |
| 42 | 4.25 |
| 43 | 20.80 |
| 44 | 0.81 |
| 45 | 16.73 |
| 46 | 20.95 |
| 47 | 0.78 |
| 48 | 0.21 |
| 49 | 45.59 |
| 50 | 5.24 |
| 51 | 0.83 |
| 52 | 21.27 |
| 53 | 5.11 |
| 54 | 31.60 |
| 55 | 25.84 |
| 56 | 902.70 |
| 57 | 2.06 |
| 58 | 0.58 |
| 59 | 0.32 |
| 60 | 0.04 |
| 61 | 0.83 |
| 62 | 7.32 |
| 63 | 2.55 |
| 64 | 1.28 |
| 65 | 5.05 |
| 66 | 12.86 |
| 67 | 7.25 |
| 68 | 0.33 |
| 69 | 13.84 |
| 70 | 0.26 |
| 71 | 1.19 |
| 72 | 37.00 |
| 73 | 2.40 |
| 74 | 4.38 |
| 75 | 15.63 |
| 76 | 100.00 |
| 77 | 1.91 |
| 78 | 0.36 |
| 79 | 5.62 |
| 80 | 4.91 |
| 81 | 40.86 |
| 82 | 1.60 |
| 83 | 0.62 |
| 84 | 1.34 |
| 85 | 1443.11 |
| 86 | 140.28 |
| 87 | 22.53 |
| 88 | 136.08 |
| 89 | 15.33 |
| 90 | 0.70 |

TABLE 3-continued

Activity

| Example No. | GLP-1R Activation - Assay EC50 (nM) |
|---|---|
| 91 | 2.06 |
| 92 | 0.13 |
| 93 | 0.35 |
| 94 | 23.95 |
| 95 | 0.97 |
| 96 | 0.98 |
| 97 | 21.22 |
| 98 | 1.43 |
| 99 | 0.60 |
| 100 | 0.45 |
| 101 | 1.46 |
| 102 | 22.79 |
| 103 | 1.23 |
| 104 | 41.30 |
| 105 | 1.55 |
| 106 | 2.22 |
| 107 | 1.40 |
| 108 | 3.28 |
| 109 | 2.51 |
| 110 | 4.93 |
| 111 | 1.46 |
| 112 | 23.03 |
| 113 | 11.00 |
| 114 | 5.99 |
| 115 | 0.122 |
| 116 | 0.005 |
| 117 | 0.044 |
| 118 | 0.053 |
| 119 | 0.031 |
| 120 | 0.101 |
| 121 | 0.083 |
| 122 | 0.031 |
| 123 | 0.528 |
| 124 | 0.027 |
| 125 | 0.112 |
| 126 | 0.332 |
| 127 | 0.353 |
| 129 | 0.271 |
| 130 | 0.038 |
| 131 | 0.145 |
| 132 | 0.043 |
| 133 | 0.021 |
| 134 | 0.077 |
| 135 | 0.361 |
| 136 | 0.312 |
| 137 | 0.039 |
| 138 | 0.136 |
| 139 | 0.023 |
| 140 | 0.158 |
| 141 | 0.079 |
| 142 | 0.894 |
| 143 | 0.614 |
| 144 | 1.084 |
| 145 | 0.022 |
| 146 | 0.379 |
| 147 | 0.233 |
| 148 | 0.174 |
| 149 | 0.082 |
| 150 | 0.063 |
| 151 | 0.234 |
| 152 | 0.115 |
| 153 | 0.011 |
| 154 | 0.034 |
| 155 | 0.416 |
| 156 | 0.064 |
| 157 | 0.081 |
| 158 | 0.032 |
| 159 | 0.043 |
| 160 | 0.035 |
| 161 | 0.015 |
| 162 | 0.187 |
| 163 | 0.039 |
| 164 | 0.085 |
| 165 | 0.553 |
| 166 | 0.222 |
| 167 | 0.027 |
| 168 | 0.388 |
| 169 | 0.171 |
| 170 | 0.227 |
| 171 | 0.05 |
| 172 | 0.129 |
| 173 | 0.018 |
| 174 | 0.051 |
| 175 | 0.106 |
| 176A | 0.085 |
| 176B | 0.748 |
| 177 | 0.021 |
| 178 | 0.499 |
| 179 | 0.064 |
| 180 | 0.089 |
| 181 | 0.025 |
| 182 | 0.178 |
| 183 | 0.129 |
| 184 | 0.157 |
| 185 | 0.594 |
| 186 | 0.018 |
| 187 | 0.391 |
| 188 | 0.032 |
| 189 | 0.149 |
| 190 | 0.061 |
| 191 | 0.353 |
| 192 | 0.444 |
| 193 | 0.132 |
| 194 | 0.265 |
| 195 | 0.539 |
| 196 | 0.508 |
| 197 | 6.62 |
| 198 | 0.508 |
| 199 | 90.91 |
| 200 | 0.508 |
| 201 | 0.028 |
| 202 | 4.006 |
| 203 | 38.299 |
| 204 | 0.09 |
| 205 | 0.097 |
| 206 | 0.191 |
| 207 | 0.168 |
| 208 | 0.249 |
| 209 | 12.329 |
| 210 | 14.11 |
| 211 | 0.258 |
| 212 | 0.379 |
| 213 | 0.042 |
| 214 | 0.299 |
| 215 | 0.21 |
| 216 | 0.056 |
| 217 | 1.106 |
| 218 | 0.279 |
| 219 | 0.189 |
| 220 | 0.216 |
| 221 | 0.508 |
| 222 | 0.136 |
| 223 | 0.126 |
| 224 | 0.515 |
| 225 | 7.141 |
| 226 | 0.022 |
| 227 | 4.799 |
| 228 | 0.047 |
| 229 | 0.135 |
| 230 | 0.034 |
| 231 | 0.049 |
| 232 | 0.118 |
| 233 | 3.108 |
| 234 | 0.448 |
| 235 | 0.191 |
| 236 | 0.203 |
| 237 | 0.52 |
| 238 | 0.1 |
| 239 | 0.04 |
| 240 | 0.127 |

TABLE 3-continued

| Example No. | Activity GLP-1R Activation - Assay EC50 (nM) |
|---|---|
| 241 | 0.013 |
| 242 | 0.02 |
| 243 | 0.022 |
| 244 | 0.015 |
| 245 | 0.051 |
| 246 | 0.065 |
| 247 | 0.151 |
| 248 | 0.186 |
| 249 | 0.137 |
| 250 | 0.048 |
| 251 | 0.079 |
| 252 | 0.059 |
| 253 | 0.071 |
| 254 | 0.088 |
| 255 | 0.108 |
| 256 | 0.117 |
| 257 | 0.064 |
| 258 | 0.24 |
| 259 | 0.578 |
| 260 | 0.411 |
| 261 | 4.079 |
| 262 | 1.073 |
| 263 | 0.709 |
| 264 | 0.155 |
| 265 | 0.171 |
| 266 | 0.363 |
| 267 | 0.055 |
| 268 | 0.175 |
| 269 | 0.164 |
| 270 | 6094.51 |
| 271 | 0.717 |
| 272 | 2.11 |
| 273 | 0.942 |
| 274 | 0.643 |
| 275 | 0.168 |
| 276 | 0.108 |
| 277 | 0.34 |
| 278 | 0.085 |
| 279 | 0.195 |
| 280 | 0.165 |
| 281 | 0.655 |
| 282 | 0.192 |
| 283 | 0.477 |
| 284 | 0.135 |
| 285 | 0.096 |
| 286 | 0.099 |
| 287 | 0.051 |
| 288 | 0.041 |
| 289A | 0.122 |
| 289B | 0.931 |
| 290A | 0.063 |
| 290B | 0.764 |
| 291 | 0.076 |
| 292 | 0.133 |
| 293 | 0.04 |
| 294 | 0.021 |
| 295 | 0.042 |
| 296 | 0.066 |
| 297 | 0.151 |
| 298 | 0.663 |
| 299 | 0.342 |
| 300 | 0.268 |
| 301 | 0.714 |
| 302 | 0.181 |
| 303 | 0.17 |
| 305 | 0.125 |
| 306 | 0.123 |
| 307 | 0.508 |
| 308 | 0.18 |
| 309 | 0.368 |
| 310 | 0.032 |
| 311A | 0.064 |
| 311B | 0.159 |
| 312 | 0.397 |
| 313 | 1.142 |
| 316 | 0.14 |
| 317 | 0.451 |
| 318 | 0.745 |
| 319 | 0.346 |
| 320 | 0.827 |
| 321 | 0.083 |
| 322 | 0.346 |
| 323 | 0.734 |
| 324 | 0.049 |
| 325 | 0.155 |
| 326 | 0.236 |
| 327 | 0.266 |
| 328 | 0.555 |
| 329 | 0.062 |
| 330 | 0.011 |
| 331 | 0.218 |
| 332 | 0.159 |
| 334 | 0.067 |
| 335 | 0.306 |
| 336 | 0.016 |
| 337 | 0.025 |
| 339 | 0.013 |
| 340 | 0.005 |
| 341 | 0.024 |
| 342 | 0.012 |
| 343 | 0.113 |
| 344 | 0.147 |
| 345 | 0.197 |
| 346 | 0.075 |
| 347 | 0.132 |
| 348 | 0.55 |
| 349 | 0.042 |
| 350 | 0.171 |
| 351 | 0.074 |
| 352 | 0.535 |
| 353 | 1.179 |
| 354 | 0.528 |
| 355 | 1.212 |
| 357 | 0.171 |
| 358 | 0.124 |
| 359 | 0.068 |
| 360 | 0.079 |
| 361 | 0.131 |
| 362 | 0.266 |
| 363 | 0.369 |
| 364 | 0.158 |
| 365 | 0.124 |
| 366 | 1.171 |
| 367 | 0.274 |
| 368 | 0.562 |
| 369 | 0.364 |
| 370 | 0.042 |
| 371 | 0.127 |
| 372 | 0.163 |
| 373 | 0.294 |
| 374 | 0.571 |
| 375 | 0.272 |
| 376 | 0.056 |
| 377 | 0.188 |
| 378 | 0.321 |
| 379 | 0.574 |
| 380 | 0.096 |
| 381 | 0.267 |
| 382 | 0.604 |
| 383A | 0.747 |
| 383B | 0.971 |
| 384 | 0.205 |
| 385A | 0.089 |
| 385B | 1.117 |
| 386 | 0.093 |
| 387 | 0.043 |
| 388 | 0.053 |
| 389 | 0.55 |
| 390 | 3.117 |
| 391 | 0.107 |

TABLE 3-continued

| Example No. | Activity GLP-1R Activation - Assay EC50 (nM) |
|---|---|
| 392 | 0.036 |
| 393 | 0.652 |
| 394 | 0.243 |
| 396 | 0.157 |
| 397 | 0.546 |
| 398 | 0.217 |
| 399 | 0.124 |
| 400 | 0.44 |
| 401 | 0.247 |
| 402 | 0.561 |
| 403 | 0.081 |
| 404 | 0.068 |
| 405 | 0.337 |
| 406 | 10.829 |
| 407 | 0.421 |
| 408 | 0.633 |
| 409 | 0.291 |
| 410 | 0.349 |
| 411 | 1.331 |
| 412 | 0.462 |
| 413 | 0.281 |
| 414 | 0.261 |
| 415 | 0.491 |
| 416 | 0.235 |
| 417 | 0.19 |
| 418 | 0.199 |
| 419 | 0.112 |
| 420 | 0.413 |
| 421 | 3.021 |
| 422 | 3.157 |
| 423 | 2.544 |
| 424 | 0.59 |
| 425 | 0.494 |
| 426 | 1.48 |
| 427 | 0.501 |
| 428 | 0.105 |
| 429 | 0.139 |
| 430 | 0.02 |
| 431 | 0.377 |
| 432 | 0.114 |
| 433 | 0.209 |
| 434 | 0.058 |
| 435 | 0.06 |
| 436 | 0.993 |
| 437 | 0.644 |
| 438 | 0.519 |
| 439 | 0.171 |
| 440 | 0.956 |
| 441 | 0.722 |
| 442 | 0.042 |
| 443 | 0.21 |
| 444 | 0.365 |
| 445 | 0.279 |
| 446 | 0.2 |
| 447 | 1.386 |
| 448 | 0.352 |
| 449 | 0.021 |
| 450 | 1.039 |
| 451 | 0.621 |
| 452 | 0.564 |
| 453 | 0.527 |
| 454 | 0.477 |
| 455 | 0.126 |
| 456 | 0.332 |
| 457 | 0.157 |
| 458 | 0.315 |
| 459 | 0.8 |
| 460 | 0.096 |
| 461 | 0.067 |
| 462 | 0.141 |
| 463 | 0.209 |
| 464 | 0.172 |
| 465 | 0.18 |
| 466 | 0.124 |
| 467 | 0.077 |
| 468 | 0.118 |
| 469 | 1.599 |
| 470 | 1.609 |
| 471 | 0.041 |
| 472 | 0.069 |
| 473 | 0.092 |
| 474 | 0.181 |
| 475 | 0.601 |
| 476 | 0.614 |
| 477 | 0.171 |
| 478 | 0.25 |
| 479 | 0.249 |
| 480 | 0.223 |
| 481 | 0.883 |
| 482 | 0.011 |
| 483 | 0.022 |
| 484 | 0.155 |
| 485 | 0.203 |
| 486 | 0.054 |
| 487 | 0.159 |
| 488 | 0.282 |
| 489 | 0.342 |
| 490 | 0.182 |
| 491 | 0.079 |
| 492 | 0.191 |
| 493 | 0.278 |
| 494 | 0.051 |
| 495 | 0.144 |
| 496 | 0.026 |
| 497 | 0.206 |
| 498 | 0.508 |
| 499 | 0.508 |
| 500 | 0.203 |
| 501 | 0.508 |
| 502A | 0.281 |
| 502B | 0.939 |
| 503 | 0.081 |
| 504 | 0.148 |
| 505 | 0.043 |
| 506 | 0.242 |
| 507 | 0.351 |
| 508 | 0.302 |
| 509 | 0.144 |
| 510 | 0.509 |
| 511 | 0.588 |
| 512 | 0.515 |
| 513 | 0.208 |
| 514 | 0.152 |
| 515 | 0.074 |
| 516 | 0.088 |
| 517 | 0.024 |
| 518 | 0.887 |
| 519 | 0.102 |
| 520 | 0.27 |
| 521 | 0.111 |
| 522 | 0.165 |
| 523 | 0.362 |
| 524 | 0.605 |
| 525 | 0.429 |
| 526 | 0.509 |
| 527 | 0.184 |
| 528 | 0.047 |
| 529 | 0.598 |
| 530 | 0.392 |
| 531 | 0.396 |
| 532 | 3678.8 |
| 533 | 0.5 |
| 534 | 0.353 |
| 535 | 0.099 |
| 536 | 0.083 |
| 537 | 0.121 |
| 538 | 0.109 |
| 539 | 0.462 |
| 540 | 0.052 |
| 541 | 0.434 |

TABLE 3-continued

| Example No. | GLP-1R Activation - Assay EC50 (nM) |
|---|---|
| 542 | 0.033 |
| 543 | 0.038 |
| 544 | 0.048 |
| 545 | 0.044 |
| 546 | 0.706 |
| 547 | 0.024 |
| 549 | 0.727 |
| 550 | 0.066 |
| 551 | 0.11 |
| 552 | 0.99 |
| 553 | 0.132 |
| 554 | 0.026 |
| 555 | 0.047 |
| 556 | 0.262 |
| 557 | 0.031 |
| 558 | 0.132 |
| 559 | 0.195 |
| 560 | 0.192 |
| 561 | 0.558 |
| 562 | 0.207 |
| 563 | 0.041 |
| 564 | 2.293 |
| 565 | 0.194 |
| 566 | 4.087 |
| 567 | 100 |
| 568 | 1.564 |
| 569 | 0.987 |
| 570 | 0.955 |
| 571 | 1.266 |
| 572 | 0.322 |
| 573 | 0.188 |
| 574 | 0.457 |
| 575 | 0.186 |

Pharmacokinetic (PK) Studies

Test Articles:

Examples 60, 115, 117, and 119 were tested along with comparative examples CE-1 and CE-2.

Dose Formulation Preparation

Compounds CE-2, Example 60, Example 115, Example 117, and Example 119 were combined with a mixture of 1000 NMP (v:v) and 9000 PEG300 (v:v), and the mixture was stirred until a homogeneous solution was obtained.

Compound CE-1 was combined with a mixture of 15% 2-hydroxypropyl-β-cyclodextrin (w:v) and 85% Mili-Q water (v:v), and the mixture was stirred until a homogeneous solution was obtained.

Study Design

Young adult non-naive Cynomolgus monkeys with weight about 2.5-5 kg (n=1-3/test article/route) were fasted overnight and then dosed with either CE-1, CE2, Example 60, Example 115, Example 117 or Example 119. Food was supplied approximately 4 hours post dose and animals were provided with free access to water all the time. Animals were restrained at designated time points for blood sampling. Approximately 500 µL of blood samples was taken via cephalic or saphenous vein into EDTA-K2 tubes. For oral administration (PO): blood samples were generally collected pre-dose, and at 15 min, 30 min, 1 hr., 2 hr., 4 hr., 8 hr., 12 hr., and 24 hr. time points after dosing. Blood was be maintained on wet ice, in chilled cryoracks, or at approximately 5° C. prior to centrifugation to obtain plasma. Centrifugation was conducted within 1 hour of collection. Plasma (approximately 200 µL) was placed into a micronic tubes containing 4 µL of formic acid (the final concentration of formic acid in plasma was approximately 2%) and samples were vortex mixed. Samples were maintained on dry ice prior to storage at approximately −70° C.

Bioanalytical Analysis

LC-MS/MS assays were utilized to quantify the concentration of the test articles in plasma as follows.

Sample Preparation

50 µL plasma sample was mixed with 350 µL of ACN combined with an internal standard. The mixture was then vortexed for about 1-5 min, and centrifuged at about 4,000-5,800 rpm for about 10-15 mm. An aliquot of 1 µL supernatant was used for LC-MS/MS analysis.

LC-MS/MS Method

MS conditions: A Sciex API 6500 equipped with electrospray ionization in the positive ion selected reaction monitoring mode was used for detection.

HPLC conditions

Mobile Phase A: $H_2O$-0.11% Formic Acid

Mobile Phase B: ACN-0.1% Formic Acid

| Time (min) | Mobile Phase B (%) |
|---|---|
| 0.10 | 35 |
| 0.55 | 50 |
| 1.10 | 95 |
| 1.22 | 95 |
| 1.26 | 35 |
| 1.50 | stop |

Column: Phenomenex Kinetex XBC18 (2.1×50 mm, 2.6 µm) with a flow rate of 1.20 mL/min Column temperature: 60° C.

Retention time: approximately between 0.85 to 1.05 min

Pharmacokinetics (PK) Parameters

Pharmacokinetics parameters, including area under the curve ($AUC_{0-24}$), maximum plasma concentration ($C_{max}$), time to reach maximum plasma concentration ($T_{max}$), oral bioavailability (F %), etc., were calculated using Dotmatics software in non-compartmental model.

The results of the pharmacokinetics studies are presented in FIG. 1 and Table 4. As is apparent in FIG. 1 CE-1 demonstrates low exposures (<10 nM plasma concentrations) over a period of 12 h after a single oral dose of 1 mg/kg that subsequently drop to below the detection limit. In comparison, CE-2 achieves disproportionately higher exposures 2 mg/kg at a 2-fold higher dose than CE-1 and has sustained exposures over 24 h after a single oral dose. However, the oral bioavailability for CE-1 and CE-2 is low, 2.5% and 27.4%, respectively.

Figure 2:
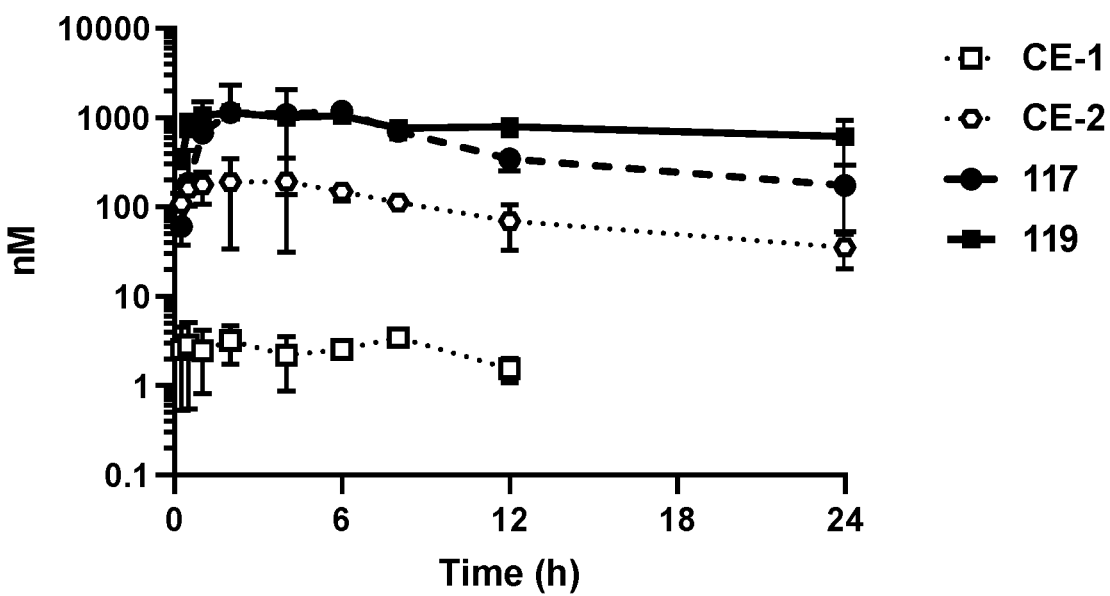
FIG. 2: Graph depicting plasma concentration as a function of time of in cynomolgus monkey.

In contrast, as illustrated in FIGS. 1 & 2 the plasma concentrations of orally-administered Examples 60, 115, 117, and 119 at the same dose level as CE-2 (i.e., 2 mg/kg) were higher than CE-1 (117-407-fold higher $AUC_{0-24}$ despite only 2-fold higher dose), and CE-2 (2-7-fold higher $AUC_{0-24}$ for the same dose) over 24 hours after oral dosing. Further, the oral bioavailability of Examples 60, 115, 117 and were higher than that of CE-1 and CE-2. These data show that compounds disclosed herein can provide prolonged exposures and/or higher oral bioavailability at least within 24 h following a single oral dose administration of compound.

TABLE 4

| | | In vivo Monkey Oral PK Profiles | | | |
|---|---|---|---|---|---|
| Compound No. | Oral dose (Arbitrary unit) | Cmax (Arbitrary unit) | Tmax (hr) | AUC$_{0-24}$ (Arbitrary units) | F % |
| Example 60  | 2 mg/kg | 385 ± 82   | 1.5 ± 0.9 | 5570 ± 2190  | 47.6 ± 12.3 |
| Example 115 | 2 mg/kg | 1540 ± 166 | 2.7 ± 1.2 | 17900 ± 2040 | 42.0 ± 16.5 |
| Example 117 | 2 mg/kg | 1600 ± 832 | 4.7 ± 2.3 | 12800 ± 4010 | 52.2 ± 16.3 |
| Example 119 | 2 mg/kg | 1190 ± 137 | 1.7± 0.6  | 19400 ± 3310 | 47.6 ± 8.1 |
| Compound CE-1 | 1 mg/kg | 4.5 ± 0.8 | 2.2 ± 1.8 | 47.7 ± 13.3 | 2.5 ± 0.2 |
| Compound CE-2 | 2 mg/kg | 224 ± 130 | 4.0 ± 2.0 | 2810 ± 1330 | 27.4 ± 12.9 |

Although the foregoing has been described in some detail by way of illustration and Example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A compound of Formula (II):

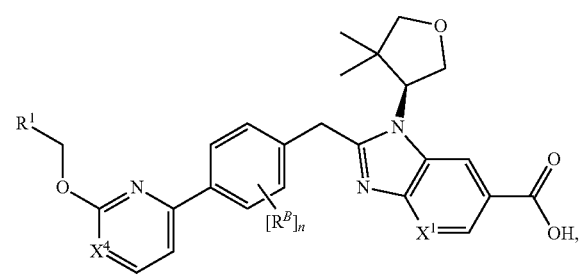

or a pharmaceutically acceptable salt thereof, wherein
R$^1$ is a phenyl or 6 membered heteroaryl optionally substituted with 1, 2, or 3 R$^4$;
X$^1$ is —C(H)= or —C(R$^8$)=;
X$^4$ is —C(H)=, —C(R$^8$)=, or N;
each R$^4$ is independently halogen or —CN;
each R$^B$ is independently C$_{1-9}$ alkyl, C$_{1-8}$ haloalkyl, or halogen;
each R$^8$ is independently halogen; and
n is 0, 1, 2, or 3.

2. The compound of claim 1, or a pharmaceutically acceptable salt thereof, wherein
R$^1$ is phenyl, substituted with 1, 2, or 3 halogen or —CN.

3. The compound of claim 1, or a pharmaceutically acceptable salt thereof, wherein
R$^1$ is

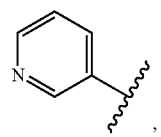

substituted with 1, 2, or 3 halogen or —CN.

4. The compound of claim 1, or a pharmaceutically acceptable salt thereof, wherein R$^1$ is

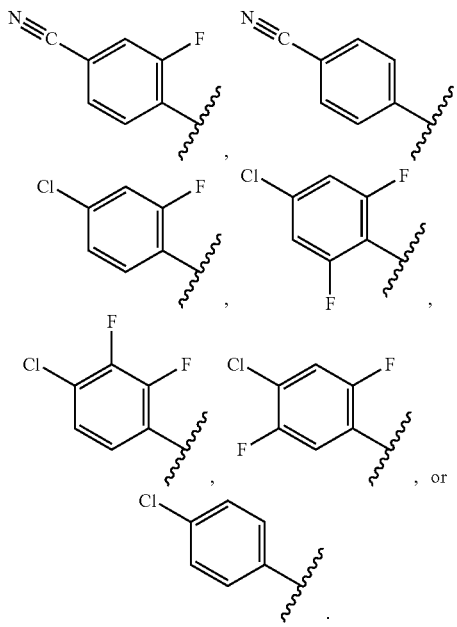

5. The compound of claim 1, or a pharmaceutically acceptable salt thereof, wherein R$^8$ is F or Cl.

6. A pharmaceutical composition comprising a pharmaceutically effective amount of a compound of claim 1, or a pharmaceutically acceptable salt thereof, and a pharmaceutically acceptable carrier or excipient.

7. The pharmaceutical composition of claim 6 further comprising one or more additional therapeutic agents.

8. The pharmaceutical composition of claim 7, wherein the additional therapeutic agent comprises an anti-obesity agent selected from peptide YY, a neuropeptide Y receptor type 2 (NPYR2) agonist, a NPYR1 agonist, an NPYR5 antagonist, a cannabinoid receptor type 1 (CB1 R) antagonist, a lipase inhibitor, a human proislet peptide (HIP), a melanocortin receptor 4 agonist (MC4R), a melanin concentrating hormone receptor 1 antagonist, a farnesoid X receptor (FXR) agonist, apoptotic signal-regulating kinase (ASK-1) inhibitor, zonisamide, phentermine (alone or in combination with topiramate), a norepinephrine/dopamine reuptake inhibitor, an opioid receptor antagonist, a combination of norepinephrine/dopamine reuptake inhibitor and opioid receptor antagonist, a GDF-15 analog, sibutramine, a cholecystokinin agonist, amylin, leptin, a serotonergic agent, a methionine aminopeptidase 2 (MetAP2) inhibitor, phendimetrazine, diethylpropion, benzphetamine, an SGLT2 inhibitor, an SGLTL1 inhibitor, a dual SGLT2/SGLT1 inhibitor, a fibroblast growth factor receptor (FGFR) modulator, an AMP-activated protein kinase (AMPK) activator, biotin, a MAS receptor modulator, or a glucagon receptor agonist (alone or in combination with another GLP-1 R agonist, a peroxisome proliferator-activated receptor alpha (PPARα) agonist, fish oil, an acetyl-coA carboxylase (ACC) inhibitor, a TGFβ antagonist, GFRAL agonist, and/or a pharmaceutically acceptable salt thereof.

9. The compound of claim 1, or a pharmaceutically acceptable salt thereof, wherein the compound is selected from:

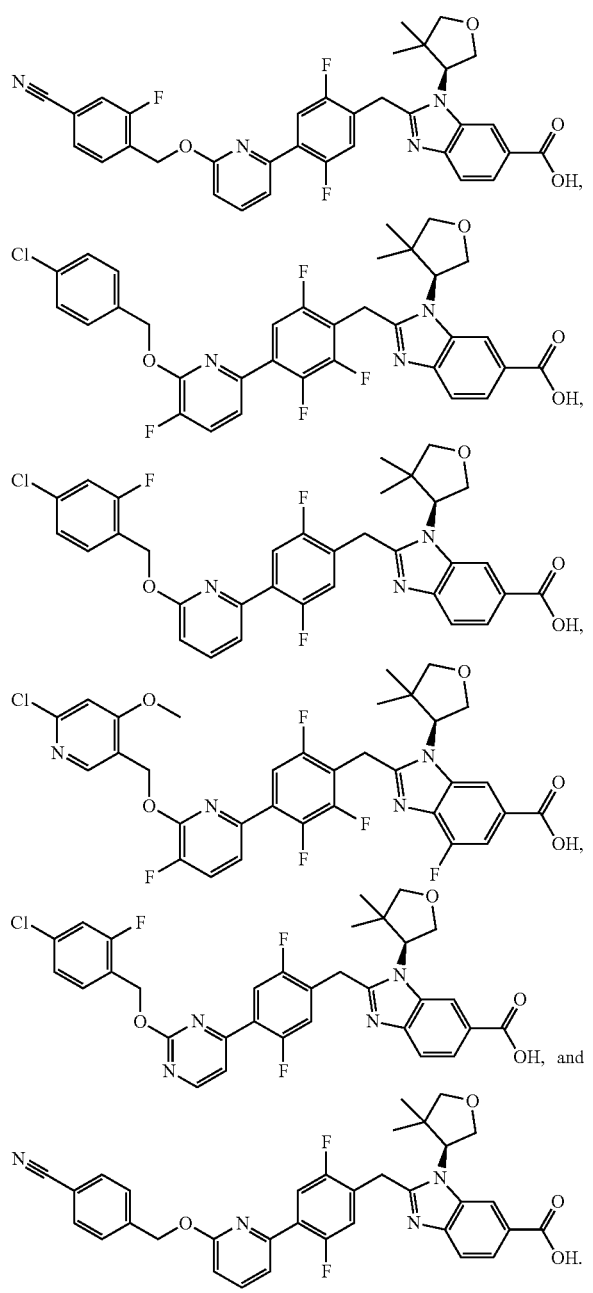

10. A compound, or a pharmaceutically acceptable salt thereof, wherein the compound is

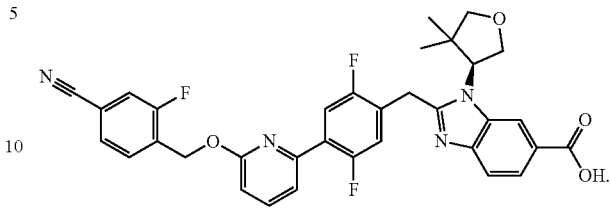

11. A pharmaceutical composition comprising a compound of claim 10, or a pharmaceutically acceptable salt thereof, and a pharmaceutically acceptable carrier or excipient.

12. The pharmaceutical composition of claim 11, further comprising one or more additional therapeutic agents.

13. A compound, or a pharmaceutically acceptable salt thereof, wherein the compound is

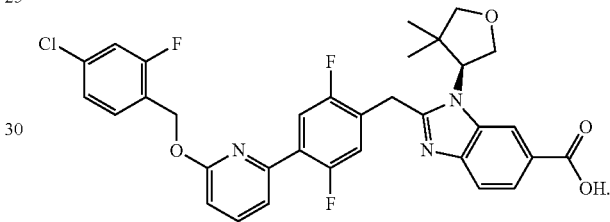

14. A pharmaceutical composition comprising a compound of claim 13, or a pharmaceutically acceptable salt thereof, and a pharmaceutically acceptable carrier or excipient.

15. The pharmaceutical composition of claim 14 further comprising one or more additional therapeutic agents.

16. A compound, or a pharmaceutically acceptable salt thereof, wherein the compound is

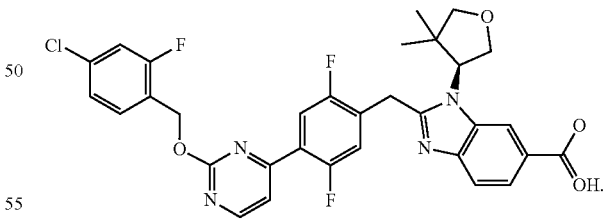

17. A pharmaceutical composition comprising a compound of claim 16, or a pharmaceutically acceptable salt thereof, and a pharmaceutically acceptable carrier or excipient.

18. The pharmaceutical composition of claim 17, further comprising one or more additional therapeutic agents.

* * * * *